US012152026B2

(12) United States Patent
Campbell et al.

(10) Patent No.: US 12,152,026 B2
(45) Date of Patent: *Nov. 26, 2024

(54) TRANSGLUTAMINASE 2 (TG2) INHIBITORS

(71) Applicant: Sitari Pharma, Inc., La Jolla, CA (US)

(72) Inventors: David Campbell, La Jolla, CA (US); Justin Chapman, La Jolla, CA (US); Mui Cheung, Collegeville, PA (US); Thomas R. Diraimondo, La Jolla, CA (US); Sergio G. Duron, La Jolla, CA (US)

(73) Assignee: Sitari Pharma, Inc., Wilmington, DE (US)

( * ) Notice: Subject to any disclaimer, the term of this patent is extended or adjusted under 35 U.S.C. 154(b) by 848 days.

This patent is subject to a terminal disclaimer.

(21) Appl. No.: 17/267,110

(22) PCT Filed: Aug. 9, 2019

(86) PCT No.: PCT/US2019/045827

§ 371 (c)(1),
(2) Date: Feb. 9, 2021

(87) PCT Pub. No.: WO2020/033784

PCT Pub. Date: Feb. 13, 2020

(65) Prior Publication Data

US 2021/0163480 A1 Jun. 3, 2021

Related U.S. Application Data

(60) Provisional application No. 62/717,697, filed on Aug. 10, 2018, provisional application No. 62/845,229, filed on May 8, 2019.

(51) Int. Cl.
*C07D 471/04* (2006.01)

(52) U.S. Cl.
CPC .................................. *C07D 471/04* (2013.01)

(58) Field of Classification Search
CPC .. C07D 471/04; C07D 401/06; C07D 405/14; C07D 473/00; C07D 473/30; C07D 473/34; C07K 5/06034; C07K 5/06104; C07K 5/06139
USPC .......................................................... 514/300
See application file for complete search history.

(56) References Cited

U.S. PATENT DOCUMENTS

| | | | |
|---|---|---|---|
| 5,021,440 A | 6/1991 | Remy et al. | |
| 8,471,063 B2 | 6/2013 | Oertel | |
| 8,889,716 B2 | 11/2014 | Prime et al. | |
| 9,434,763 B2 | 9/2016 | Buchold et al. | |
| 9,496,533 B2 | 11/2016 | Kwon et al. | |
| 9,526,801 B2 | 12/2016 | McDonald et al. | |
| 9,732,085 B2 | 8/2017 | Courtney et al. | |
| 11,548,892 B1 * | 1/2023 | Campbell | C07K 5/06139 |
| 2006/0052308 A1 | 3/2006 | Khosla et al. | |
| 2006/0183759 A1 | 8/2006 | Stein et al. | |
| 2012/0302539 A1 | 11/2012 | Prime et al. | |
| 2013/0236480 A1 | 9/2013 | Tharaux et al. | |
| 2013/0281324 A1 | 10/2013 | Gouliaev et al. | |
| 2015/0203535 A1 * | 7/2015 | Buchold | A61P 25/28 530/331 |
| 2015/0232420 A1 | 8/2015 | Dominguez et al. | |

FOREIGN PATENT DOCUMENTS

| | | |
|---|---|---|
| RU | 97120551 A | 10/1999 |
| WO | WO96/34890 | 11/1996 |
| WO | 2007/025247 A | 3/2007 |
| WO | 2012/078519 A | 12/2012 |
| WO | 2018/122419 | 7/2018 |

OTHER PUBLICATIONS

Siegel et al, (2007), Pharmacology & Therapeutics, vol. 115, p. 232-245 (Year: 2007).*
Szondy et al, (2017), BioMedicine, vol. 7, No. 3, Article 15, p. 1-13 (Year: 2017).*
Keillor et al., (2016), Expert Opinion on Therapeutic Patents, vol. 26, Issue. 1, p. 49-63 (Year: 2016).*
Tong et al, (2011), Clinical & Experimental Ophthalmology, p. 1-12 (Year: 2011).*
PCT/US2019/045827 International Search Report and Written Opinion of the International Searching Authority date Feb. 13, 2020.
Siegel, M., & Khosla, C. (2007). Transglutaminase 2 inhibitors and their therapeutic role in disease states. Pharmacology & Therapeutics, 115(2), 232-245. doi:10.1016/j.pharmthera.2007.05.003.

* cited by examiner

*Primary Examiner* — Yih-Horng Shiao
*Assistant Examiner* — Jaret J Crews
(74) *Attorney, Agent, or Firm* — Nora L. Stein

(57) ABSTRACT

Described herein are compounds and pharmaceutical compositions containing such compounds which inhibit transglutaminase 2 (TG2). Also described herein are methods for using such TG2 inhibitors, alone or in combination with other compounds, for treating diseases or conditions that would benefit from TG2 inhibition.

27 Claims, No Drawings

TRANSGLUTAMINASE 2 (TG2) INHIBITORS

This application is a § 371 of International Application No. PCT/US2019/045827, filed 9 Aug. 2019, which claims the benefit of U.S. application 62/717,697, filed 10 Aug. 2018 and U.S. 62/845,229, filed 8 May 2019.

BACKGROUND OF THE INVENTION

Transglutaminase 2 (TG2) is a member of the human transglutaminase family of enzymes, which is abundantly expressed in various tissues and is found in both intra- and extracellular locations. It possesses the catalytic activity of crosslinking of glutamine sidechains on substrate peptides or proteins with biogenic small molecule or protein-bound amines, which is subject to elaborate posttranslational regulation. TG2 has been implicated in the pathogenesis of a broad range of human diseases, particularly inflammatory disorders.

SUMMARY OF THE INVENTION

Described herein are inhibitors of transglutaminase 2 (TG2). Also disclosed herein are methods for synthesizing such TG2 inhibitors and methods for using such TG2 inhibitors in the treatment of diseases wherein TG2 inhibition provides therapeutic benefit to the patient having the disease. Further described are pharmaceutical formulations that include a TG2 inhibitor.

In another aspect is a compound having the structure of Formula (Q):

Formula (Q)

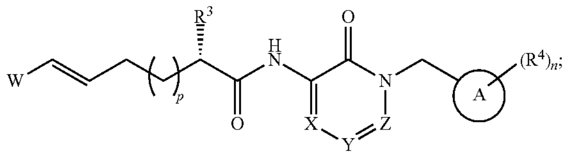

wherein:

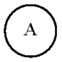

is a 9-membered bicyclic heteroaryl ring;

X, Y, and Z are selected from $=C(R^{11})-$ and $=N-$, wherein at least two of X, Y, and Z are $=C(R^{11})-$;

W is $-C(O)NR^1R^2$ or $-S(O)_2R^{12}$;

$R^1$ and $R^2$ are independently selected from H, $C_{1-6}$alkyl, and $-C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from $-N(H)C(O)OR^5$, $-OC(O)NR^6R^7$, $-N(H)C(O)NR^6R^7$, and $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, $-C_{1-6}$alkyl-$C_{3-12}$cycloalkyl, $-C_{2-6}$alkenyl-$C_{3-12}$cycloalkyl, phenyl, $-C_{1-6}$alkyl-phenyl, $-C_{2-6}$alkenyl-phenyl, $C_{2-9}$heterocycloalkyl, and $C_{2-9}$heteroaryl, wherein phenyl, $-C_{1-6}$alkyl-phenyl, $-C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, $-C_{1-6}$alkyl-OH, $-C_{1-6}$alkyl-O$-C_{1-6}$alkyl, $-C_{1-6}$alkyl-O$-C(O)C_{1-6}$alkyl, $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl, wherein $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, $-C_{1-6}$alkyl-OH, $-C_{1-6}$alkyl-O$-C_{1-6}$alkyl, and $-C_{1-6}$ alkyl-$N(C_{1-6}alkyl)_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, $-C_{1-6}$alkyl-OH, $-C_{1-6}$alkyl-O$-C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, $-C_{1-6}$alkyl-$C_{3-12}$cycloalkyl, phenyl, $-C_{1-6}$alkyl-phenyl, and $C_{2-9}$heteroaryl, wherein phenyl, $-C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, $-C_{1-6}$alkyl-$C_{3-12}$cycloalkyl, phenyl, $-C_{1-6}$alkyl-phenyl, and $C_{2-9}$heteroaryl, wherein phenyl, $-C_{1-6}$alkyl-phenyl, and $C_{2-9}$heteroaryl are optionally substituted with one or two groups independently selected from halogen and $C_{1-6}$alkyl;

each $R^{11}$ is independently selected from H, halogen, $C_{1-6}$alkyl, and $C_{1-6}$haloalkyl;

$R^{12}$ is $C_{1-6}$alkyl;

n is 0, 1, 2, 3, or 4; and p is 0, 1, or 2;

or a pharmaceutically acceptable salt or solvate thereof.

In one aspect is a compound having the structure of Formula (I):

Formula (I)

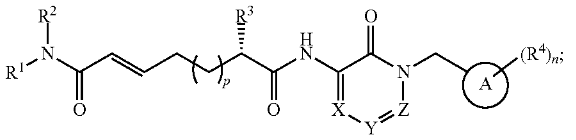

wherein:

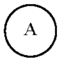

is a 9-membered bicyclic heteroaryl ring;

X, Y, and Z are selected from =C($R^{11}$)— and =N—, wherein at least two of X, Y, and Z are =C($R^{11}$)—;

$R^1$ and $R^2$ are independently selected from H and optionally substituted alkyl; or $R^1$ and $R^2$, together with the nitrogen to which they are attached, form an optionally substituted 3-, 4-, 5- or 6-membered heterocycloalkyl ring;

$R^3$ is —N(H)C(O)O$R^5$, —OC(O)N$R^6R^7$, —N(H)C(O)N$R^6R^7$, or —N(H)C(O)$R^8$;

each $R^4$ is independently selected from halogen, —CN, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^9$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, optionally substituted alkyl, optionally substituted alkenyl, optionally substituted alkynyl, optionally substituted cycloalkyl, optionally substituted phenyl, and optionally substituted heteroaryl;

$R^5$ is selected from optionally substituted alkyl, optionally substituted heterocycloalkyl, optionally substituted phenyl, and optionally substituted heteroaryl;

$R^6$ and $R^7$ are independently selected from H and optionally substituted alkyl; or $R^6$ and $R^7$, together with the nitrogen to which they are attached, form an optionally substituted 5- or 6-membered heterocycloalkyl ring;

$R^8$ is selected from optionally substituted alkyl, optionally substituted cycloalkyl, optionally substituted phenyl, optionally substituted heterocycloalkyl, and optionally substituted heteroaryl;

each $R^9$ is independently selected from optionally substituted alkyl, optionally substituted cycloalkyl, optionally substituted phenyl, and optionally substituted heteroaryl;

each $R^{10}$ is independently selected from H, optionally substituted alkyl, optionally substituted cycloalkyl, optionally substituted phenyl, and optionally substituted heteroaryl;

each $R^{11}$ is independently selected from H, halogen, and optionally substituted alkyl;

n is 0, 1, 2, 3, or 4; and p is 0, 1, or 2;

or a pharmaceutically acceptable salt or solvate thereof.

In another aspect is a compound having the structure of Formula (II):

Formula (II)

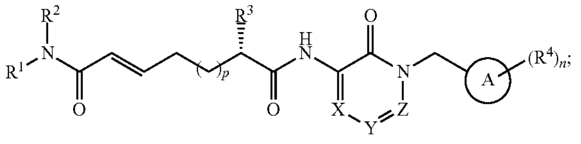

wherein:

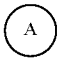

is a 9-membered bicyclic heteroaryl ring;

X, Y, and Z are selected from =C($R^{11}$)— and =N—, wherein at least two of X, Y, and Z are =C($R^{11}$)—;

$R^1$ and $R^2$ are independently selected from H, $C_{1-6}$alkyl, and —$C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from —N(H)C(O)O$R^5$, —OC(O)N$R^6R^7$, —N(H)C(O)N$R^6R^7$, and —N(H)C(O)$R^8$;

each $R^4$ is independently selected from halogen, —CN, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^9$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^1$C(O)O$R^9$, $C_{1-10}$alkyl, $C_{1-10}$alkyl-OH, $C_{1-10}$alkyl-O$R^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, —$C_{2-6}$alkenyl-$C_{3-12}$cycloalkyl, phenyl, —$C_{1-6}$alkyl-phenyl, —$C_{2-6}$alkenyl-phenyl, $C_{2-9}$heterocycloalkyl, and $C_{2-9}$heteroaryl, wherein phenyl, —$C_{1-6}$alkyl-phenyl, —$C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, —$C_{1-6}$alkyl-OH, —$C_{1-6}$alkyl-O—$C_{1-6}$alkyl, —$C_{1-6}$alkyl-O—C(O)$C_{1-6}$alkyl, $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl, wherein $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{11}$ is independently selected from H, halogen, $C_{1-6}$alkyl, and $C_{1-6}$haloalkyl;

n is 0, 1, 2, 3, or 4; and p is 0, 1, or 2;

or a pharmaceutically acceptable salt or solvate thereof.

In some embodiments is a compound of Formula (Q), (I), or (II), or a pharmaceutically acceptable salt or solvate thereof, wherein $R^1$ and $R^2$ are independently selected from H and $C_{1-6}$alkyl. In some embodiments is a compound of Formula (Q), (I), or (II), or a pharmaceutically acceptable salt or solvate thereof, wherein $R^1$ and $R^2$ are each H. In some embodiments is a compound of Formula (Q), (I), or (II), or a pharmaceutically acceptable salt or solvate thereof, wherein $R^1$ and $R^2$ are each $C_{1-6}$alkyl. In some embodiments is a compound of Formula (Q), (I), or (II), or a pharmaceutically acceptable salt or solvate thereof, wherein $R^1$ and $R^2$ are each —$CH_3$. In some embodiments is a compound of Formula (Q), (I), or (II), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (Q), (I), or (II), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (Q), (I), or (II), or a pharmaceutically acceptable salt or solvate thereof, wherein $R^3$ is —N(H)C(O)$OR^5$. In some embodiments is a compound of Formula (Q), (I), or (II), or a pharmaceutically acceptable salt or solvate thereof, wherein $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$ alkyl-$C_{2-9}$heterocycloalkyl, —$C_{1-6}$alkyl-phenyl, and $C_{2-9}$heteroaryl. In some embodiments is a compound of Formula (Q), (I), or (II), or a pharmaceutically acceptable salt or solvate thereof, wherein $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (Q), (I), or (II), or a pharmaceutically acceptable salt or solvate thereof, wherein $R^5$ is $C_{1-6}$alkyl. In some embodiments is a compound of Formula (Q), (I), or (II), or a pharmaceutically acceptable salt or solvate thereof, wherein $R^5$ is —$CH_3$. In some embodiments is a compound of Formula (Q), (I), or (II), or a pharmaceutically acceptable salt or solvate thereof, wherein $R^5$ is —$C_{1-6}$alkyl-OH. In some embodiments is a compound of Formula (Q), (I), or (II), or a pharmaceutically acceptable salt or solvate thereof, wherein $R^5$ is —$C_{1-6}$alkyl-O—$C_{1-6}$alkyl. In some embodiments is a compound of Formula (Q), (I), or (II), or a pharmaceutically acceptable salt or solvate thereof, wherein $R^5$ is —$C_{1-6}$alkyl-$C_{2-9}$heterocycloalkyl. In some embodiments is a compound of Formula (Q), (I), or (II), or a pharmaceutically acceptable salt or solvate thereof, wherein $R^5$ is —$C_{1-6}$alkyl-phenyl. In some embodiments is a compound of Formula (Q), (I), or (II), or a pharmaceutically acceptable salt or solvate thereof, wherein $R^5$ is —$CH_2$-phenyl. In some embodiments is a compound of Formula (Q), (I), or (II), or a pharmaceutically acceptable salt or solvate thereof, wherein $R^3$ is —OC(O)$NR^6R^7$. In some embodiments is a compound of Formula (Q), (I), or (II), or a pharmaceutically acceptable salt or solvate thereof, wherein $R^3$ is —N(H)C(O)$NR^6R^7$. In some embodiments is a compound of Formula (Q), (I), or (II), or a pharmaceutically acceptable salt or solvate thereof, wherein $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (Q), (I), or (II), or a pharmaceutically acceptable salt or solvate thereof, wherein $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (Q), (I), or (II), or a pharmaceutically acceptable salt or solvate thereof, wherein $R^6$ and $R^7$ are independently selected from $C_{1-6}$alkyl. In some embodiments is a compound of Formula (Q), (I), or (II), or a pharmaceutically acceptable salt or solvate thereof, wherein $R^6$ and $R^7$ are each —$CH_3$. In some embodiments is a compound of Formula (Q), (I), or (II), or a pharmaceutically acceptable salt or solvate thereof, wherein $R^3$ is —N(H)C(O)$R^8$. In some embodiments is a compound of Formula (Q), (I), or (II), or a pharmaceutically acceptable salt or solvate thereof, wherein $R^8$ is —$C_{1-6}$alkyl-OH. In some embodiments is a compound of Formula (Q), (I), or (II), or a pharmaceutically acceptable salt or solvate thereof, wherein $R^8$ is —$C_{1-6}$alkyl-O—$C_{1-6}$alkyl. In some embodiments is a compound of Formula (Q), (I), or (II), or a pharmaceutically acceptable salt or solvate thereof, wherein $R^8$ is phenyl optionally substituted with one or two groups independently selected from halogen and $C_{1-6}$alkyl. In some embodiments is a compound of Formula (Q), (I), or (II), or a pharmaceutically acceptable salt or solvate thereof, wherein $R^8$ is $C_{2-9}$heteroaryl optionally substituted with one or two groups independently selected from halogen and $C_{1-6}$alkyl. In some embodiments is a compound of Formula (Q), (I), or (II), or a pharmaceutically acceptable salt or solvate thereof, wherein each $R^4$ is independently selected from halogen, —$OR^9$, —C(O)$OR^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (Q), (I), or (II), or a pharmaceutically acceptable salt or solvate thereof, wherein each $R^4$ is independently selected from halogen, —$OR^9$, —C(O)$OR^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (Q), (I), or (II), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$ alkyl-phenyl are optionally substituted with one or two groups independently selected from halogen and $C_{1-6}$alkyl. In some embodiments is a compound of Formula (Q), (I), or (II), or a pharmaceutically acceptable salt or solvate thereof, wherein

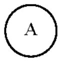

is selected from

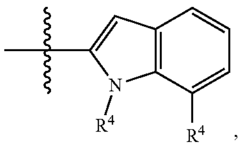
,
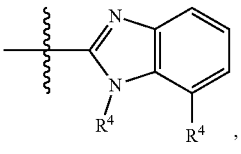
,

-continued

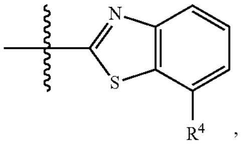,
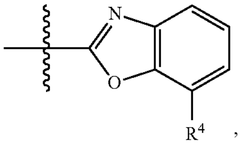,
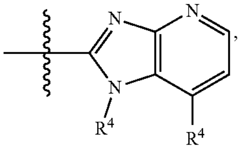,
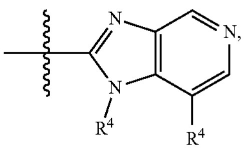
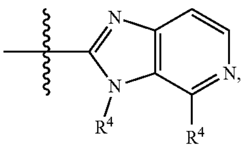 and 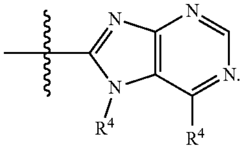

In some embodiments is a compound of Formula (Q), (I), or (II), or a pharmaceutically acceptable salt or solvate thereof, wherein

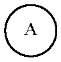

is selected from

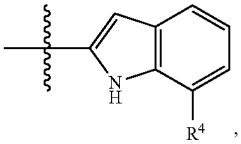,
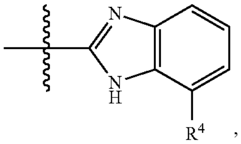,
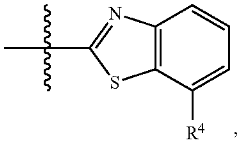,
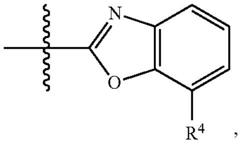,
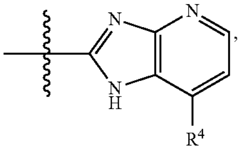,
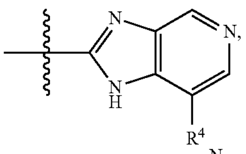
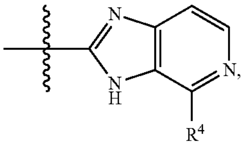 and 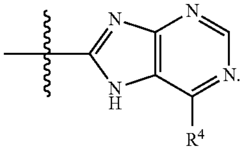

In some embodiments is a compound of Formula (Q), (I), or (II), or a pharmaceutically acceptable salt or solvate thereof, wherein

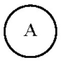 is 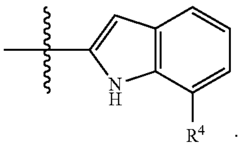

In some embodiments is a compound of Formula (Q), (I), or (II), or a pharmaceutically acceptable salt or solvate thereof, wherein

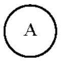 is 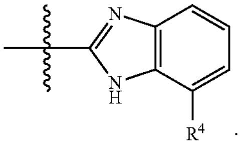

In some embodiments is a compound of Formula (Q), (I), or (II), or a pharmaceutically acceptable salt or solvate thereof, wherein

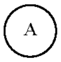 is 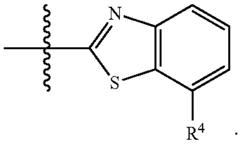

In some embodiments is a compound of Formula (Q), (I), or (II), or a pharmaceutically acceptable salt or solvate thereof, wherein

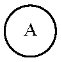 is 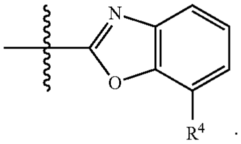

In some embodiments is a compound of Formula (Q), (I), or (II), or a pharmaceutically acceptable salt or solvate thereof, wherein

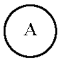 is 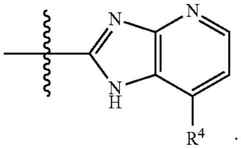

In some embodiments is a compound of Formula (Q), (I), or (II), or a pharmaceutically acceptable salt or solvate thereof, wherein

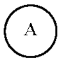 is 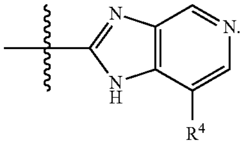

In some embodiments is a compound of Formula (Q), (I), or (II), or a pharmaceutically acceptable salt or solvate thereof, wherein

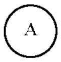 is 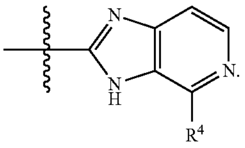

In some embodiments is a compound of Formula (Q), (I), or (II), or a pharmaceutically acceptable salt or solvate thereof, wherein

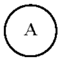 is 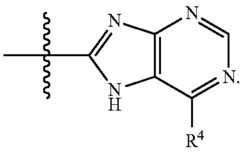

In some embodiments is a compound of Formula (Q), (I), or (II), or a pharmaceutically acceptable salt or solvate thereof, wherein $R^4$ is $C_{1-10}$alkyl. In some embodiments is a compound of Formula (Q), (I), or (II), or a pharmaceutically acceptable salt or solvate thereof, wherein $R^4$ is $C_{1-10}$haloalkyl. In some embodiments is a compound of Formula (Q), (I), or (II), or a pharmaceutically acceptable salt or solvate thereof, wherein $R^4$ is —$OR^9$. In some embodiments is a compound of Formula (Q), (I), or (II), or a pharmaceutically acceptable salt or solvate thereof, wherein $R^4$ is —$OR^9$ and $R^9$ is —$C_{1-6}$alkyl-phenyl optionally substituted with one or two halogens. In some embodiments is a compound of Formula (Q), (I), or (II), or a pharmaceutically acceptable salt or solvate thereof, wherein

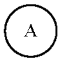

is selected from

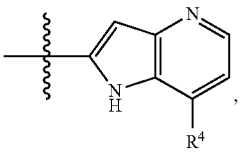,

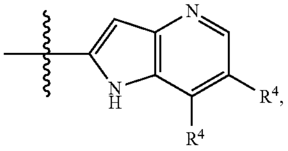

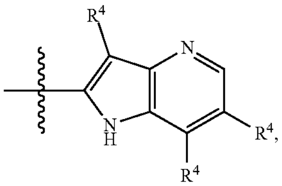

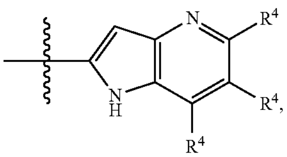

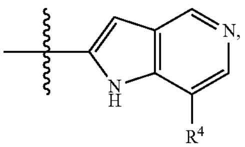

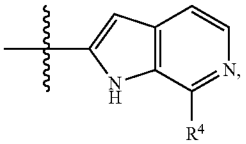

-continued

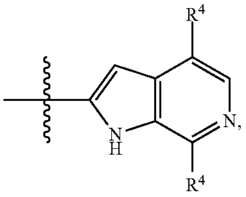

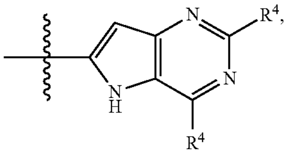

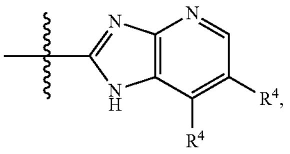

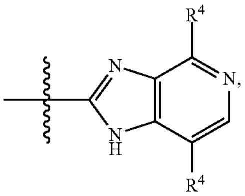

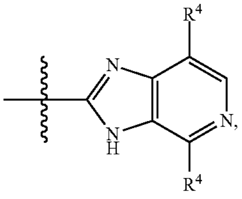 and

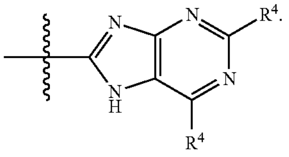

In some embodiments is a compound of Formula (Q), (I), or (II), or a pharmaceutically acceptable salt or solvate thereof, wherein

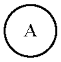 is 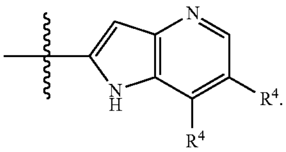

In some embodiments is a compound of Formula (Q), (I), or (II), or a pharmaceutically acceptable salt or solvate thereof, wherein

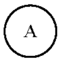 is 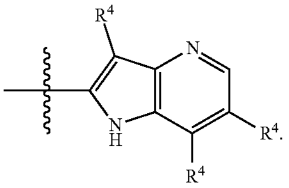

In some embodiments is a compound of Formula (Q), (I), (II), or a pharmaceutically acceptable salt or solvate thereof, wherein

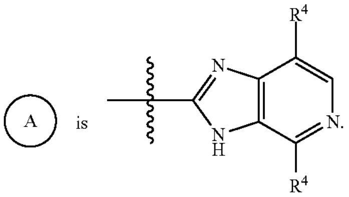

In some embodiments is a compound of Formula (Q), (I), or (II), or a pharmaceutically acceptable salt or solvate thereof, wherein each $R^4$ is independently selected from halogen and $C_{1-10}$alkyl. In some embodiments is a compound of Formula (Q), (I), or (II), or a pharmaceutically acceptable salt or solvate thereof, wherein p is 0. In some embodiments is a compound of Formula (Q), (I), or (II), or a pharmaceutically acceptable salt or solvate thereof, wherein p is 1. In some embodiments is a compound of Formula (Q), (I), or (II), or a pharmaceutically acceptable salt or solvate thereof, wherein p is 2. In some embodiments is a compound of Formula (Q), (I), or (II), or a pharmaceutically acceptable salt or solvate thereof, wherein X, Y, and Z are each $=C(R^{11})-$. In some embodiments is a compound of Formula (Q), (I), or (II), or a pharmaceutically acceptable salt or solvate thereof, wherein X is $=N-$, Y is $=C(R^{11})-$, and Z is $=C(R^{11})-$. In some embodiments is a compound of Formula (Q), (I), or (II), or a pharmaceutically acceptable salt or solvate thereof, wherein X is $=C(R^{11})-$, Y is $=C(R^{11})-$, and Z is $=N-$. In some embodiments is a compound of Formula (Q), (I), or (II), or a pharmaceutically acceptable salt or solvate thereof, wherein X is $=C(R^{11})-$, Y is $=N-$, and Z is $=C(R^{11})-$. In some embodiments is a compound of Formula (Q), (I), or (II), or a pharmaceutically acceptable salt or solvate thereof, wherein each $R^{11}$ is H. In some embodiments is a compound of Formula (Q), (I), or (II), or a pharmaceutically acceptable salt or solvate thereof, wherein X is $=C(H)-$, Y is $=C(H)-$, and Z is $=C(Cl)-$. In some embodiments is a compound of Formula (Q), (I), or (II), or a pharmaceutically acceptable salt or solvate thereof, wherein X is $=C(H)-$, Y is $=C(H)-$, and Z is $=C(CH_3)-$.

In another aspect described herein is a pharmaceutical composition comprising a compound of Formula (Q), (I), or (II), or a pharmaceutically acceptable salt or solvate thereof, and at least one pharmaceutically acceptable excipient.

In another aspect is a method of treating a transglutaminase 2 mediated disease or disorder in a patient in need thereof comprising administering to the patient a therapeutically effective amount of a compound of Formula (Q), (I), or (II), or pharmaceutically acceptable salt or solvate thereof, and a pharmaceutically acceptable excipient.

Another aspect of this invention relates to a method of treating a transglutaminase 2 mediated disease or disorder in a patient in need thereof, wherein disease or disorder is celiac disease, neurodegenerative disease, ocular disease, cancer, or fibrosis.

In another aspect is a method of treating cancer in a patient in need thereof comprising administering to the patient a therapeutically effective amount of the compound of Formula (Q), (I), or (II), or pharmaceutically acceptable salt or solvate thereof, or the pharmaceutical composition comprising a compound of Formula (Q), (I), or (II), or pharmaceutically acceptable salt or solvate thereof.

Also described herein is a method of treating celiac disease in a patient in need thereof, comprising administering to the patient a therapeutically effective amount of a compound of Formula (Q), (I), or (II), or a pharmaceutically acceptable salt or solvate thereof. In some embodiments, is a method of treating kidney fibrosis in a patient in need thereof, comprising administering to the patient a therapeutically effective amount of a compound of Formula (Q), (I), or (II), or a pharmaceutically acceptable salt or solvate thereof.

Also described herein is a method of treating a neurodegenerative disease in a patient in need thereof, comprising administering to the patient a therapeutically effective amount of a compound of Formula (Q), (I), or (II), or a pharmaceutically acceptable salt or solvate thereof. In some embodiments is a method of treating a neurodegenerative disease in a patient in need thereof, comprising administering to the patient a therapeutically effective amount of a compound of Formula (Q), (I), or (II), or a pharmaceutically acceptable salt or solvate thereof, wherein the neurodegenerative disease is selected from Parkinson's disease, Huntington's disease, and Alzheimer's disease.

In some embodiments, is a method of treating an ocular disease in a patient in need thereof, comprising administering to the patient a therapeutically effective amount of a compound of Formula (Q), (I), or (II), or a pharmaceutically acceptable salt or solvate thereof. In some embodiments is a method of treating an ocular disease in a patient in need thereof, comprising administering to the patient a therapeutically effective amount of a compound of Formula (Q), (I), or (II), or a pharmaceutically acceptable salt or solvate thereof, wherein the ocular disease is selected from macular degeneration, glaucoma, cataracts, and uveitis.

In some embodiments, is a method of treating cancer in a patient in need thereof, comprising administering to the patient a therapeutically effective amount of a compound of Formula (Q), (I), or (II), or a pharmaceutically acceptable salt or solvate thereof. In some embodiments is a method of treating cancer in a patient in need thereof, comprising administering to the patient a therapeutically effective amount of a compound of Formula (Q), (I), or (II), or a pharmaceutically acceptable salt or solvate thereof, wherein the cancer is selected from melanoma, glioblastoma, meningioma, pancreatic cancer, renal cell carcinoma, and breast cancer.

In some embodiments, is a method of treating fibrosis in a patient in need thereof, comprising administering to the patient a therapeutically effective amount of a compound of Formula (Q), (I), or (II), or a pharmaceutically acceptable salt or solvate thereof.

In some embodiments, is a method of treating kidney fibrosis in a patient in need thereof, comprising administering to the patient a therapeutically effective amount of a compound of Formula (Q), (I), or (II), or a pharmaceutically acceptable salt or solvate thereof.

In some embodiments, is a method of treating idiopathic pulmonary fibrosis in a patient in need thereof, comprising administering to the patient a therapeutically effective amount of a compound of Formula (Q), (I), or (II), or a pharmaceutically acceptable salt or solvate thereof.

In some embodiments, is a method of treating liver fibrosis in a patient in need thereof, comprising administering to the patient a therapeutically effective amount of a compound of Formula (Q), (I), or (II), or a pharmaceutically acceptable salt or solvate thereof.

Also described herein is a method of reducing transglutaminase 2 (TG2) activation in an individual comprising administering to the individual a compound of Formula (Q), (I), or (II), or a pharmaceutically acceptable salt or solvate thereof, in a dose effective to provide for a reduction in TG2 activity.

In another aspect is a compound of Formula (Q), (I), or (II) or a pharmaceutically acceptable salt thereof for use in therapy.

In another aspect is a compound of Formula (Q), (I), or (II), or a pharmaceutically acceptable salt or solvate thereof, for the use of in the treatment of celiac disease, neurodegenerative disease, ocular disease, cancer, or fibrosis.

In another aspect is a compound of Formula (Q), (I), or (II), or a pharmaceutically acceptable salt or solvate thereof, for use in treating celiac disease.

In another aspect is a compound of Formula (Q), (I), or (II), or a pharmaceutically acceptable salt or solvate thereof, for use in treating a neurodegenerative disease.

In another aspect is a compound of Formula (Q), (I), or (II), or a pharmaceutically acceptable salt or solvate thereof, for use in treating a neurodegenerative disease, wherein the neurodegenerative disease is selected from Parkinson's disease, Huntington's disease, and Alzheimer's disease In another aspect is a compound of Formula (Q), (I), or (II), or a pharmaceutically acceptable salt or solvate thereof, for use in treating an ocular disease.

In another aspect is a compound of Formula (Q), (I), or (II), or a pharmaceutically acceptable salt or solvate thereof, for use in treating an ocular disease, wherein the ocular disease is selected from macular degeneration, glaucoma, cataracts, and uveitis.

In another aspect is a compound of Formula (Q), (I), or (II), or a pharmaceutically acceptable salt or solvate thereof, for use in treating cancer.

In another aspect is a compound of Formula (Q), (I), or (II), or a pharmaceutically acceptable salt or solvate thereof, for use in treating cancer, wherein the cancer is selected from melanoma, glioblastoma, meningioma, pancreatic cancer, renal cell carcinoma, and breast cancer.

In another aspect is a compound of Formula (Q), (I), or (II), or a pharmaceutically acceptable salt or solvate thereof, for use in treating fibrosis.

In another aspect is a compound of Formula (Q), (I), or (II), or a pharmaceutically acceptable salt or solvate thereof, for use in treating kidney fibrosis.

In another aspect is a compound of Formula (Q), (I), or (II), or a pharmaceutically acceptable salt or solvate thereof, for use in treating idiopathic pulmonary fibrosis.

In another aspect is a compound of Formula (Q), (I), or (II), or a pharmaceutically acceptable salt or solvate thereof, for use in treating liver fibrosis.

In another aspect is a compound of Formula (Q), (I), or (II), or a pharmaceutically acceptable salt or solvate thereof, for use in reducing transglutaminase 2 (TG2) activation.

In another aspect, there is provided the use of a compound of Formula (Q), (I), or (II), or a pharmaceutically acceptable salt or solvate thereof, in the manufacture of a medicament for use in the treatment of a disease or disorder mediated by transglutaminase 2 (TG2).

In some embodiments is the use of a compound of Formula (Q), (I), or (II), or pharmaceutically acceptable salt or solvate thereof, in the manufacture of a medicament for use in the treatment of a disease or disorder mediated by transglutaminase 2, wherein the disease or disorder is celiac disease, neurodegenerative disease, ocular disease, cancer, or fibrosis.

In some embodiments is the use of a compound of Formula (Q), (I), or (II), or a pharmaceutically acceptable salt or solvate thereof, in the manufacture of a medicament for the use in the treatment of celiac disease. In some embodiments, is the use of a compound of Formula (Q), (I), or (II), or a pharmaceutically acceptable salt or solvate thereof, in the manufacture of a medicament for the use in the treatment of neurodegenerative disease. In some embodiments, is the use of a compound of Formula (Q), (I), or (II), or a pharmaceutically acceptable salt or solvate thereof, in the manufacture of a medicament for the use in the treatment of ocular disease. In some embodiments is the use of a compound of Formula (Q), (I), or (II), or a pharmaceutically acceptable salt or solvate thereof, in the manufacture of a medicament for the use in the treatment of cancer. In some embodiments, is the use of a compound of Formula (Q), (I), or (II), or a pharmaceutically acceptable salt or solvate thereof, in the manufacture of a medicament for the use in the treatment of fibrosis.

In some embodiments is the use of a compound of Formula (Q), (I), or (II), or a pharmaceutically acceptable salt or solvate thereof, in the manufacture of a medicament for the use in the treatment of kidney fibrosis. In some embodiments is the use of a compound of Formula (Q), (I), or (II), or a pharmaceutically acceptable salt or solvate thereof, in the manufacture of a medicament for the use in the treatment of idiopathic pulmonary fibrosis. In some embodiments, is the use of a compound of Formula (Q), (I), or (II), or a pharmaceutically acceptable salt or solvate thereof, in the manufacture of a medicament for the use in the treatment of liver fibrosis.

DETAILED DESCRIPTION OF THE INVENTION

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

As used in the specification and appended claims, unless specified to the contrary, the following terms have the meaning indicated below.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

"Amino" refers to the $—NH_2$ radical.

"Cyano" refers to the —CN radical.

"Nitro" refers to the $—NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to ten carbon atoms (e.g., $C_1$-$C_{10}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In other embodiments, an alkenyl comprises two to ten carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —$C(O)R^a$, —$C(O)OR^a$, —$C(O)N(R^a)_2$, —$N(R^a)C(O)OR^f$, —OC(O)-$nR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to ten carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, $C(O)R^a$, —$C(O)OR^a$, —$C(O)N(R^a)_2$, —$N(R^a)C(O)OR^f$, —OC(O)—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond.

Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl,
heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro, or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl,
heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) t-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Illustrative examples of heteroaryls useful in the present invention include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Examples of 5-membered "heteroaryl" groups include furanyl, thienyl, pyrrolyl, imidazolyl, pyrazolyl, triazolyl, tetrazolyl, thiazolyl, oxazolyl, isoxazolyl, oxadiazolyl, thiadiazolyl, and isothiazolyl. Examples of 6-membered "heteroaryl" groups include oxopyridyl, pyridinyl, pyridazinyl, pyrazinyl, and pyrimidinyl. Examples of 6,6-fused "heteroaryl" groups include quinolinyl, isoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Examples of 6,5-fused "heteroaryl" groups include benzofuranyl, benzothienyl, benzimidazolyl, benzthiazolyl, indolizinyl, indolyl, isoindolyl, and indazolyl. Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tOR^a$ (where t is 1 or 2), $—R^b—S(O)_tR^a$ (where t is 1 or 2) and $—R^b—S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain. As used herein, "9-membered bicyclic heteroaryl ring" represents a group or moiety comprising an aromatic bicyclic radical, containing 9 ring atoms, including at least one carbon atom and heteroatoms independently selected from nitrogen, oxygen, and sulfur. Illustrative examples of 9-membered bicyclic heteroaryl rings include, but are not limited to benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, and triazolopyrazinyl.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —R-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula $—O—R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

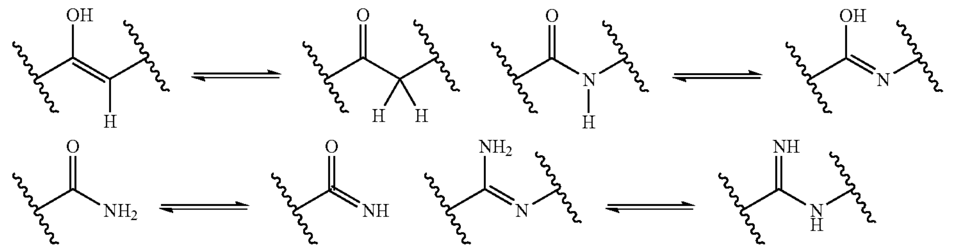

-continued

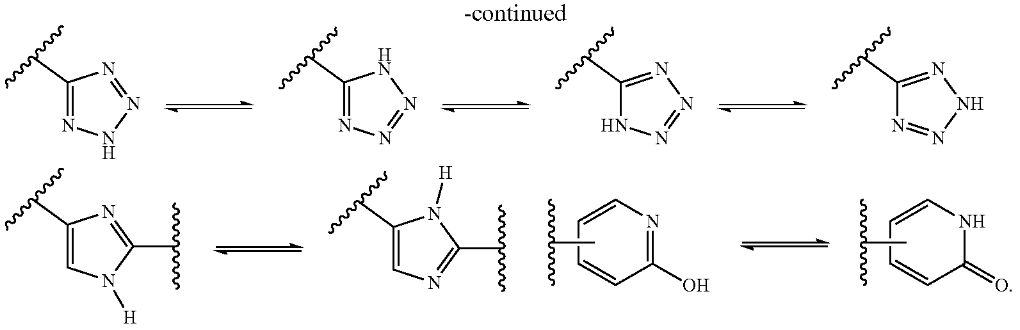

"Optional" or "optionally" means that a subsequently described event or circumstance may or may not occur and that the description includes instances when the event or circumstance occurs and instances in which it does not. The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(=O)—, —S—, —S(=O)—, —$S(=O)_2$—, —NH—, —NHC(O)—, —C(O)NH—, $S(=O)_2NH$—, —$NHS(=O)_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, and heterocycloalkyl.

The term "independently" means that where more than one substituent is selected from a number of possible substituents, those substituents may be the same or different. The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts. As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I) or Formula (II), as well as salts thereof, may be administered as the raw chemical. Additionally, the active ingredient may be presented as a pharmaceutical composition.

The term "patient" means a human or an animal.

The term "individual" means a human or an animal.

Compounds

The compounds of Formula (Q), (I), (II), (IIa), (IIb), (IIc), (IId), or (IIe) described herein are inhibitors of TG2. In some embodiments, the compounds of Formula (Q), (I), (II), (IIa), (IIb), (IIc), (IId), or (IIe) described herein, and pharmaceutical compositions comprising these compounds, are useful for the treatment of celiac disease, neurodegenerative diseases, ocular disease, cancer, or fibrositic diseases.

In some embodiments is a compound of Formula (I):

Formula (I)

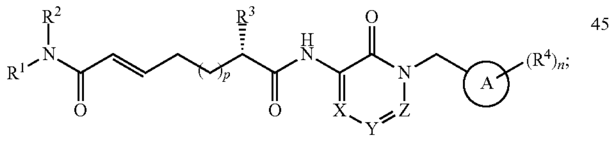

wherein:

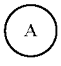

is a 9-membered bicyclic heteroaryl ring;

X, Y, and Z are selected from $=C(R^{11})—$ and $=N—$, wherein at least two of X, Y, and Z are $=C(R^{11})—$;

$R^1$ and $R^2$ are independently selected from H and optionally substituted alkyl; or $R^1$ and $R^2$, together with the nitrogen to which they are attached, form an optionally substituted 3-, 4-, 5- or 6-membered heterocycloalkyl ring;

$R^3$ is $—N(H)C(O)OR^5$, $—OC(O)NR^6R^7$, $—N(H)C(O)NR^6R^7$, or $—N(H)C(O)R^8$;

each $R^4$ is independently selected from halogen, —CN, $—OR^9$, $—SR^9$, $—N(R^{10})_2$, $—S(O)R^9$, $—S(O)_2R^9$, $—NHS(O)_2R^9$, $—S(O)_2N(R^{10})_2$, $—C(O)R^9$, $—C(O)OR^9$, $—OC(O)R^9$, $—C(O)N(R^{10})_2$, $—OC(O)N(R^{10})_2$, $—NR^{10}C(O)N(R^{10})_2$, $—NR^{10}C(O)R^9$, $—NR^{10}C(O)OR^9$, optionally substituted alkyl, optionally substituted alkenyl, optionally substituted alkynyl, optionally substituted cycloalkyl, optionally substituted phenyl, and optionally substituted heteroaryl;

$R^5$ is selected from optionally substituted alkyl, optionally substituted heterocycloalkyl, optionally substituted phenyl, and optionally substituted heteroaryl;

$R^6$ and $R^7$ are independently selected from H and optionally substituted alkyl; or $R^6$ and $R^7$, together with the nitrogen to which they are attached, form an optionally substituted 5- or 6-membered heterocycloalkyl ring;

$R^8$ is selected from optionally substituted alkyl, optionally substituted cycloalkyl, optionally substituted phenyl, optionally substituted heterocycloalkyl, and optionally substituted heteroaryl;

each $R^9$ is independently selected from optionally substituted alkyl, optionally substituted cycloalkyl, optionally substituted phenyl, and optionally substituted heteroaryl;

each $R^{10}$ is independently selected from H, optionally substituted alkyl, optionally substituted cycloalkyl, optionally substituted phenyl, and optionally substituted heteroaryl;

each $R^{11}$ is independently selected from H, halogen, and optionally substituted alkyl;

n is 0, 1, 2, 3, or 4; and p is 0, 1, or 2;

or a pharmaceutically acceptable salt or solvate thereof.

In some embodiments is a compound of Formula (I), or a pharmaceutically acceptable salt or solvate thereof, wherein X, Y, and Z are each $=C(R^{11})—$. In some embodiments of Formula (I), or pharmaceutically acceptable salt or solvate thereof, wherein X and Y are each $=C(H)—$; and Z is $=C(CH)—$, $=C(CH_3)—$, or $=C(Cl)—$. In some embodiments is a compound of Formula (I), or a pharmaceutically acceptable salt or solvate thereof, wherein X, Y, and Z are each $=C(H)—$. In some embodiments is a compound of Formula (I), or a pharmaceutically acceptable salt or solvate thereof, wherein X is $=N—$, Y is $=C(R^{11})—$, and Z is $=C(R^{11})—$. In some embodiments is a compound of Formula (I), or a pharmaceutically acceptable salt or solvate thereof, wherein X is $=N—$, Y is $=C(H)—$, and Z is $=C(H)—$. In some embodiments is a compound of Formula (I), or a pharmaceutically acceptable salt or solvate thereof, wherein X is $=C(R^{11})—$, Y is $=N—$, and Z is $=C(R^{11})—$. In some embodiments is a compound of Formula (I), or a pharmaceutically acceptable salt or solvate thereof, wherein X is $=C(H)—$, Y is $=N—$, and Z is $=C(H)—$. In some embodiments is a compound of Formula (I), or a pharmaceutically acceptable salt or solvate thereof, wherein X is $=C(R^{11})—$, Y is $=C(R^{11})—$, and Z is $=N—$. In some embodiments is a compound of Formula (I), or a pharmaceutically acceptable salt or solvate thereof, wherein X is $=C(H)—$, Y is $=C(H)—$, and Z is $=N—$.

In some embodiments is a compound of Formula (I), or a pharmaceutically acceptable salt or solvate thereof, wherein $R^1$ and $R^2$ are independently selected from H and $C_{1-6}$alkyl. In some embodiments is a compound of Formula (I), or a pharmaceutically acceptable salt or solvate thereof, wherein $R^1$ and $R^2$ are each H. In some embodiments is a compound of Formula (I), or a pharmaceutically acceptable salt or solvate thereof, wherein $R^1$ and $R^2$ are each $C_{1-6}$alkyl. In some embodiments is a compound of Formula (I), or a pharmaceutically acceptable salt or solvate thereof, wherein $R^1$ and $R^2$ are each —$CH_3$. In some embodiments is a compound of Formula (I), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (I), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (I), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (I), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (I), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (I), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (I), or a pharmaceutically acceptable salt or solvate thereof, wherein $R^3$ is —N(H)C(O)$OR^5$. In some embodiments is a compound of Formula (I), or a pharmaceutically acceptable salt or solvate thereof, wherein $R^3$ is —N(H)C(O)$OR^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (I), or a pharmaceutically acceptable salt or solvate thereof, wherein $R^3$ is —N(H)C(O)$OR^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (I), or a pharmaceutically acceptable salt or solvate thereof, wherein $R^3$ is —N(H)C(O)$OR^5$ and $R^5$ is $C_{1-6}$alkyl. In some embodiments is a compound of Formula (I), or a pharmaceutically acceptable salt or solvate thereof, wherein $R^3$ is —N(H)C(O)$OR^5$ and $R^5$ is —$CH_3$. In some embodiments is a compound of Formula (I), or a pharmaceutically acceptable salt or solvate thereof, wherein $R^3$ is —N(H)C(O)$OR^5$ and $R^5$ is —$C_{1-6}$alkyl-OH. In some embodiments is a compound of Formula (I), or a pharmaceutically acceptable salt or solvate thereof, wherein $R^3$ is —N(H)C(O)$OR^5$ and $R^5$ is —$C_{1-6}$alkyl-O—$C_{1-6}$alkyl. In some embodiments is a compound of Formula (I), or a pharmaceutically acceptable salt or solvate thereof, wherein $R^3$ is —N(H)C(O)$OR^5$ and $R^5$ is —$C_{1-6}$alkyl-$C_{2-9}$heterocycloalkyl. In some embodiments is a compound of Formula (I), or a pharmaceutically acceptable salt or solvate thereof, wherein $R^3$ is —N(H)C(O)$OR^5$ and $R^5$ is —$C_{1-6}$alkyl-phenyl. In some embodiments is a compound of Formula (I), or a pharmaceutically acceptable salt or solvate thereof, wherein $R^3$ is —N(H)C(O)$OR^5$ and $R^5$ is —$CH_2$-phenyl. In some embodiments is a compound of Formula (I), or a pharmaceutically acceptable salt or solvate thereof, wherein $R^3$ is —OC(O)$NR^6R^7$. In some embodiments is a compound of Formula (I), or a pharmaceutically acceptable salt or solvate thereof, wherein $R^3$ is —OC(O)$NR^6R^7$ and $R^3$ is —N(H)C(O)$NR^6R^7$. In some embodiments is a compound of Formula (I), or a pharmaceutically acceptable salt or solvate thereof, wherein $R^3$ is —OC(O)$NR^6R^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (I), or a pharmaceutically acceptable salt or solvate thereof, wherein $R^3$ is —OC(O)$NR^6R^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (I), or a pharmaceutically acceptable salt or solvate thereof, wherein $R^3$ is —OC(O)$NR^6R^7$ and $R^6$ and $R^7$ are independently selected from $C_{1-6}$alkyl. In some embodiments is a compound of Formula (I), or a pharmaceutically acceptable salt or solvate thereof, wherein $R^3$ is —OC(O)$NR^6R^7$ and $R^6$ and $R^7$ are each —$CH_3$. In some embodiments is a compound of Formula (I), or a pharmaceutically acceptable salt or solvate thereof, wherein $R^3$ is —N(H)C(O)$R^8$. In some embodiments is a compound of Formula (I), or a pharmaceutically acceptable salt or solvate thereof, wherein $R^3$ is —N(H)C(O)$R^8$ and $R^8$ is —$C_{1-6}$alkyl-OH. In some embodiments is a compound of Formula (I), or a pharmaceutically acceptable salt or solvate thereof, wherein $R^3$ is —N(H)C(O)$R^8$ and $R^8$ is —$C_{1-6}$alkyl-O—$C_{1-6}$alkyl. In some embodiments is a compound of Formula (I), or a pharmaceutically acceptable salt or solvate thereof, wherein $R^3$ is —N(H)C(O)$R^8$ and $R^8$ is phenyl optionally substituted with one or two groups independently selected from halogen and $C_{1-6}$alkyl. In some embodiments is a compound of Formula (I), or a pharmaceutically acceptable salt or solvate thereof, wherein $R^3$ is —N(H)C(O)$R^8$ and $R^8$ is $C_{2-9}$heteroaryl optionally substituted with one or two groups independently selected from halogen and $C_{1-6}$alkyl.

In some embodiments is a compound of Formula (I), or pharmaceutically acceptable salt or solvate thereof, wherein $R^3$ is selected from —N(H)C(O)$OR^5$ and —OC(O)$NR^6R^7$. In some embodiments is a compound of Formula (I), or pharmaceutically acceptable salt or solvate thereof, wherein $R^3$ is selected from —N(H)C(O)$OR^5$ and —OC(O)$NR^6R^7$; $R^5$ is $C_{1-6}$alkyl; and $R^6$ and $R^7$ are independently selected from H and $C_{1-6}$alkyl. In some embodiments is a compound of Formula (I), or pharmaceutically acceptable salt or solvate thereof, wherein $R^3$ is —N(H)C(O)$OR^5$; and $R^5$ is methyl. In some embodiments is a compound of Formula (I), or pharmaceutically acceptable salt or solvate thereof, wherein $R^3$ is —OC(O)$NR^6R^7$; and $R^6$ and $R^7$ are independently selected from H and $C_{1-6}$alkyl. In some embodiments is a compound of Formula (I), or pharmaceutically acceptable salt or solvate thereof, wherein $R^3$ is —OC(O)$NR^6R^7$; and $R^6$ and $R^7$ are $C_{1-6}$alkyl. In some embodiments is a compound of Formula (I), or pharmaceutically acceptable salt or solvate thereof, wherein $R^3$ is —OC(O)$NR^6R^7$; and $R^6$ and $R^7$ are methyl.

In some embodiments is a compound of Formula (I), or a pharmaceutically acceptable salt or solvate thereof, wherein n is 0, 1, 2, or 3. In some embodiments is a compound of Formula (I), or a pharmaceutically acceptable salt or solvate thereof, wherein n is 0. In some embodiments is a compound of Formula (I), or a pharmaceutically acceptable salt or solvate thereof, wherein n is 1, 2, or 3. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein n is 3. In some embodiments is a compound of Formula (I), or a pharmaceutically acceptable salt or solvate thereof, wherein n is 4.

In some embodiments is a compound of Formula (I), or a pharmaceutically acceptable salt or solvate thereof, wherein each $R^4$ is independently selected from halogen, —$OR^9$, —$C(O)OR^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (I), or a pharmaceutically acceptable salt or solvate thereof, wherein each $R^4$ is independently selected from halogen, —$OR^9$, —$C(O)OR^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (I), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl.

In some embodiments is compound of Formula (I), or a pharmaceutically acceptable salt or solvate thereof, wherein

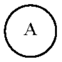

is selected from benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, and triazolopyrazinyl.

In some embodiments is a compound of Formula (I), or a pharmaceutically acceptable salt or solvate thereof, wherein

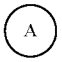

is selected from benzimidazolyl, imidazopyridinyl, purinyl, indoly, pyrrolopyridinyl, pyrrolopyrimidinyl, benzoxazolyl, and benzothiazolyl.

In some embodiments is a compound of Formula (I), or a pharmaceutically acceptable salt or solvate thereof, wherein

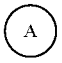

is selected from

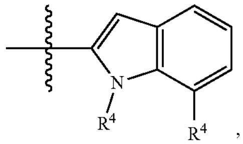
,
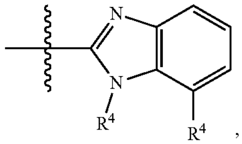
,
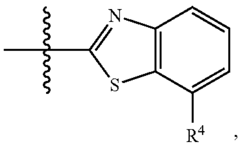
,
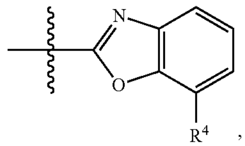
,
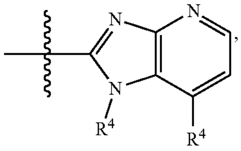
,
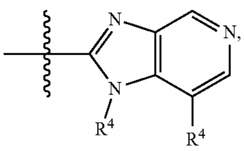
,
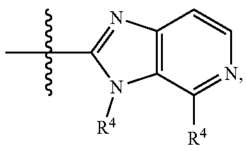
and
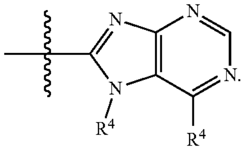
.

In some embodiments is a compound of Formula (I), or a pharmaceutically acceptable salt or solvate thereof, wherein

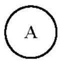

is selected from

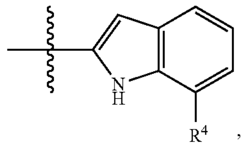
,
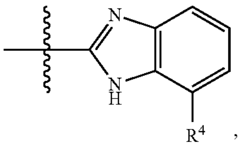
,
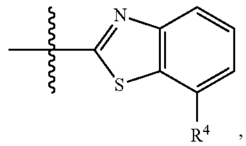
,
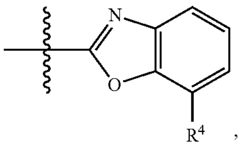
,
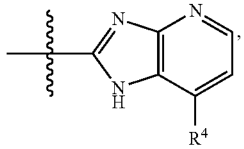
,
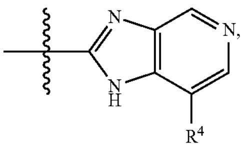
,
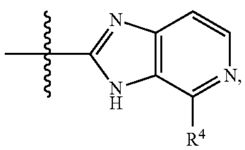
and
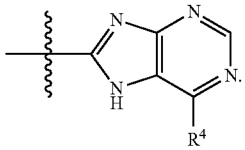
.

In some embodiments is a compound of Formula (I), or a pharmaceutically acceptable salt or solvate thereof, wherein

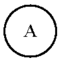 is 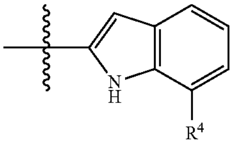.

In some embodiments is a compound of Formula (I), or a pharmaceutically acceptable salt or solvate thereof, wherein

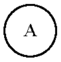 is 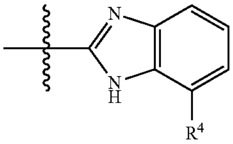.

In some embodiments is a compound of Formula (I), or a pharmaceutically acceptable salt or solvate thereof, wherein

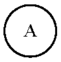 is 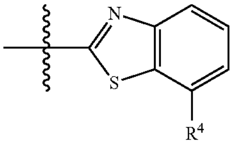.

In some embodiments is a compound of Formula (I), or a pharmaceutically acceptable salt or solvate thereof, wherein

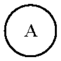 is 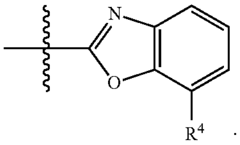.

In some embodiments is a compound of Formula (I), or a pharmaceutically acceptable salt or solvate thereof, wherein

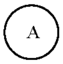 is 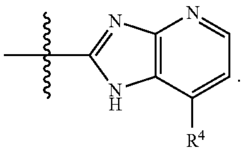

In some embodiments is a compound of Formula (I), or a pharmaceutically acceptable salt or solvate thereof, wherein

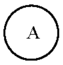 is 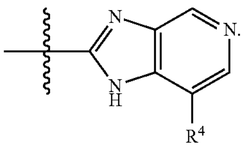

In some embodiments is a compound of Formula (I), or a pharmaceutically acceptable salt or solvate thereof, wherein

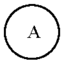 is 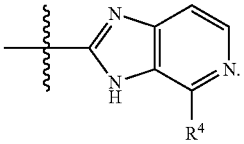

In some embodiments is a compound of Formula (I), or a pharmaceutically acceptable salt or solvate thereof, wherein

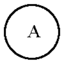 is 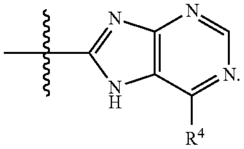

In some embodiments is a compound of Formula (I), or a pharmaceutically acceptable salt or solvate thereof, wherein $R^4$ is $C_{1-10}$alkyl. In some embodiments is a compound of Formula (I), or a pharmaceutically acceptable salt or solvate thereof, wherein $R^4$ is $C_{1-10}$haloalkyl. In some embodiments is a compound of Formula (I), or a pharmaceutically acceptable salt or solvate thereof, wherein $R^4$ is —$OR^9$. In some embodiments is a compound of Formula (I), or a pharmaceutically acceptable salt or solvate thereof, wherein $R^4$ is —$OR^9$ and $R^9$ is —$C_{1-6}$alkyl-phenyl optionally substituted with one or two halogens.

In some embodiments is a compound of Formula (I), or a pharmaceutically acceptable salt or solvate thereof, wherein

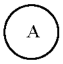

is selected from

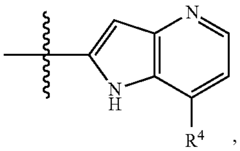, 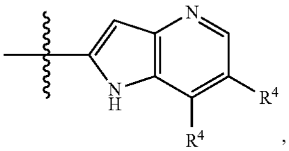, 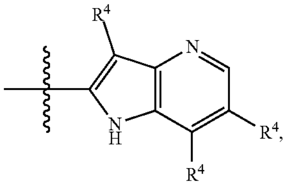 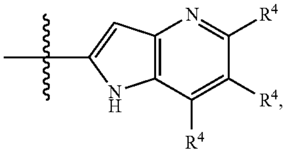 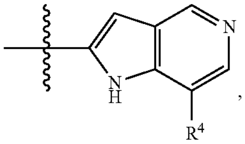, 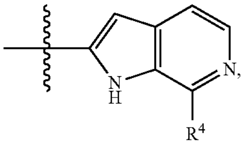 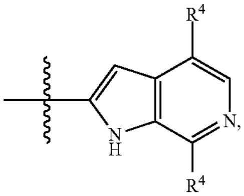

-continued

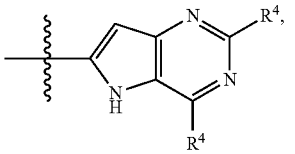

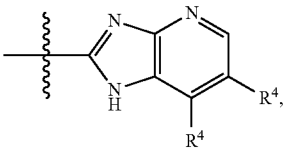

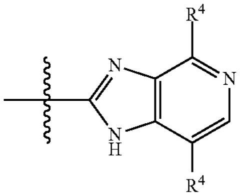
,

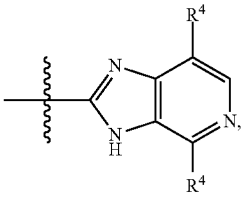
and

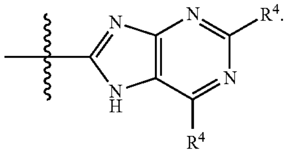

In some embodiments is a compound of Formula (I), or a pharmaceutically acceptable salt or solvate thereof, wherein

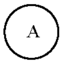 is 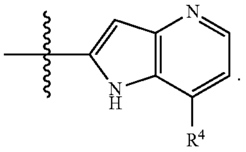

In some embodiments is a compound of Formula (I), or a pharmaceutically acceptable salt or solvate thereof, wherein

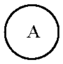 is 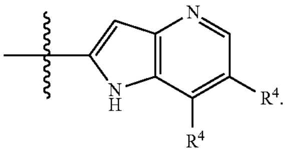

In some embodiments is a compound of Formula (I), or a pharmaceutically acceptable salt or solvate thereof, wherein

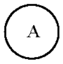 is 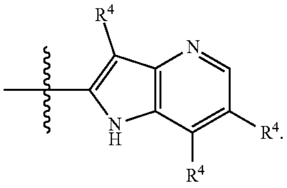

In some embodiments is a compound of Formula (I), or a pharmaceutically acceptable salt or solvate thereof, wherein

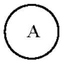 is 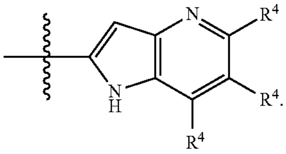

In some embodiments is a compound of Formula (I), or a pharmaceutically acceptable salt or solvate thereof, wherein

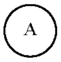 is 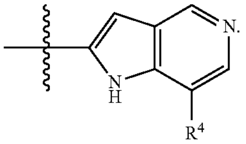

In some embodiments is a compound of Formula (I), or a pharmaceutically acceptable salt or solvate thereof, wherein

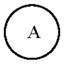 is 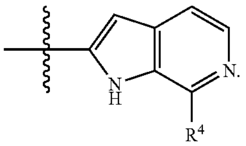

In some embodiments is a compound of Formula (I), or a pharmaceutically acceptable salt or solvate thereof, wherein

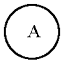 is 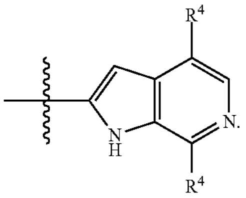

In some embodiments is a compound of Formula (I), or a pharmaceutically acceptable salt or solvate thereof, wherein

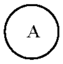 is 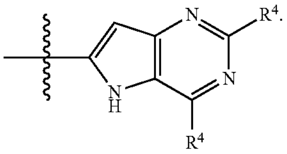

In some embodiments is a compound of Formula (I), or a pharmaceutically acceptable salt or solvate thereof, wherein

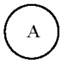 is 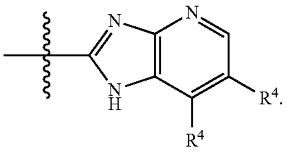

In some embodiments is a compound of Formula (I), or a pharmaceutically acceptable salt or solvate thereof, wherein

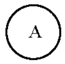 is 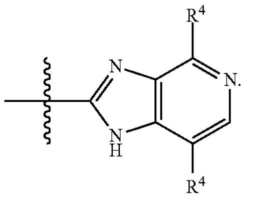

In some embodiments is a compound of Formula (I), or a pharmaceutically acceptable salt or solvate thereof, wherein

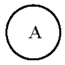 is 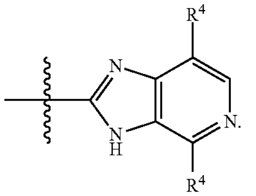

In some embodiments is a compound of Formula (I), or a pharmaceutically acceptable salt or solvate thereof, wherein

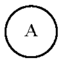 is 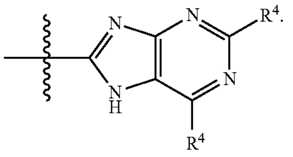

In some embodiments is a compound of Formula (I), or a pharmaceutically acceptable salt or solvate thereof, wherein

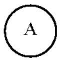

is selected from

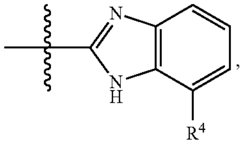,

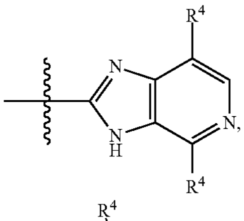 and

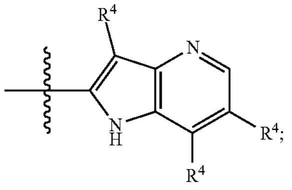

and each $R^4$ is independently selected from halogen and optionally substituted alkyl. In some embodiments is a compound of Formula (I), or a pharmaceutically acceptable salt or solvate thereof, wherein each $R^4$ is independently selected from chloro, fluoro, methyl, ethyl, butyl, and isobutyl. In some embodiments is a compound of Formula (I), or a pharmaceutically acceptable salt or solvate thereof, wherein each $R^4$ is independently selected from fluoro, methyl, and isobutyl.

In some embodiments is a compound of Formula (I), or a pharmaceutically acceptable salt or solvate thereof, wherein each $R^4$ is independently selected from halogen, —$OR^9$, —$N(R^{10})_2$, $C_{1-10}$alkyl, $C_{2-10}$alkenyl, $C_{1-10}$haloalkyl, and —$C_{1-6}$alkyl-$C_{3-12}$cycloalkyl. In some embodiments is a compound of Formula (I), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl. In some embodiments is a compound of Formula (I), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl and each $R^9$ is $C_{1-10}$alkyl. In some embodiments is a compound of Formula (I), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (I), or a pharmaceutically acceptable salt or solvate thereof, wherein each $R^4$ is independently selected from halogen and $C_{1-10}$alkyl.

In some embodiments is a compound of Formula (I), or a pharmaceutically acceptable salt or solvate thereof, wherein p is 0. In some embodiments is a compound of Formula (I), or a pharmaceutically acceptable salt or solvate thereof, wherein p is 1. In some embodiments is a compound of Formula (I), or a pharmaceutically acceptable salt or solvate thereof, wherein p is 2.

In another embodiment, this invention relates to compounds of Formula (I) wherein:

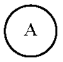

is a 9-membered bicyclic heteroaryl ring;

X, Y, and Z are =C($R^{11}$)—;

$R^1$ and $R^2$ are independently selected from H and $C_{1-6}$alkyl, $R^3$ is selected from —N(H)C(O)$OR^5$ and —OC(O)$NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^1$ is independently selected from H, halogen, and $C_{1-6}$alkyl;

n is 0, 1, 2, 3, or 4; and p is 0, 1, or 2;

or a pharmaceutically acceptable salt or solvate thereof.

In another embodiment, this invention relates to compounds of Formula (I) wherein:

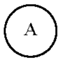

is benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, or triazolopyrazinyl;

X, Y, and Z are $=C(R^{11})-$;

$R^1$ and $R^2$ are independently selected from H and $C_{1-6}$alkyl, $R^3$ is selected from $-N(H)C(O)OR^5$ and $-OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^1$ is independently selected from H, halogen, and $C_{1-6}$alkyl;

n is 0, 1, 2, 3, or 4; and p is 0, 1, or 2;

or a pharmaceutically acceptable salt or solvate thereof.

In another embodiment, this invention relates to compounds of Formula (I) wherein:

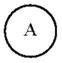

is benzimidazolyl, imidazopyridinyl, purinyl, indoly, pyrrolopyridinyl, pyrrolopyrimidinyl, benzoxazolyl, or benzothiazolyl;

X, Y, and Z are $=C(R^{11})-$;

$R^1$ and $R^2$ are independently selected from H and $C_{1-6}$alkyl, $R^3$ is selected from $-N(H)C(O)OR^5$ and $-OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^1$ is independently selected from H, halogen, and $C_{1-6}$alkyl;

n is 0, 1, 2, 3, or 4; and p is 0, 1, or 2;

or a pharmaceutically acceptable salt or solvate thereof.

In another embodiment, this invention relates to compounds of Formula (I) wherein:

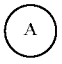

is benzimidazolyl, imidazopyridinyl, or pyrrolopyrimidinyl;

X, Y, and Z are $=C(R^{11})-$;

$R^1$ and $R^2$ are independently selected from H and $C_{1-6}$alkyl, $R^3$ is selected from $-N(H)C(O)OR^5$ and $-OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^1$ is independently selected from H, halogen, and $C_{1-6}$alkyl;

n is 0, 1, 2, 3, or 4; and p is 0, 1, or 2;

or a pharmaceutically acceptable salt or solvate thereof.

In some embodiments is a compound having the structure of Formula (II):

Formula (II)

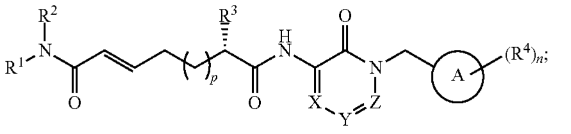

wherein:

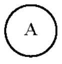

is a 9-membered bicyclic heteroaryl ring;

X, Y, and Z are selected from $=C(R^{11})-$ and $=N-$, wherein at least two of X, Y, and Z are $=C(R^{11})-$;

$R^1$ and $R^2$ are independently selected from H, $C_{1-6}$alkyl, and $-C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from $-N(H)C(O)OR^5$, $-OC(O)NR^6R^7$, $-N(H)C(O)NR^6R^7$, and $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, $-C_{1-6}$alkyl-$C_{3-12}$cycloalkyl, $-C_{2-6}$alkenyl-$C_{3-12}$cycloalkyl, phenyl, $-C_{1-6}$alkyl-phenyl, $-C_{2-6}$alkenyl-phenyl, $C_{2-9}$heterocycloalkyl, and $C_{2-9}$heteroaryl, wherein phenyl, $-C_{1-6}$alkyl-phenyl, $-C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, $-C_{1-6}$alkyl-OH, $-C_{1-6}$alkyl-O$-C_{1-6}$alkyl, $-C_{1-6}$alkyl-O$-C(O)C_{1-6}$alkyl, $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl, wherein $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, $-C_{1-6}$alkyl-OH, $-C_{1-6}$alkyl-O$-C_{1-6}$alkyl, and $-C_{1-6}$alkyl-N($C_{1-6}$alkyl$)_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{11}$ is independently selected from H, halogen, $C_{1-6}$alkyl, and $C_{1-6}$haloalkyl;

n is 0, 1, 2, 3, or 4; and p is 0, 1, or 2;

or a pharmaceutically acceptable salt or solvate thereof.

In some embodiments is a compound of Formula (II), or a pharmaceutically acceptable salt or solvate thereof, wherein X, Y, and Z are each =C($R^{11}$)—. In some embodiments of Formula (II), or pharmaceutically acceptable salt or solvate thereof, wherein X and Y are each =C(H)—; and Z is =C(CH)—, =C($CH_3$)—, or =C(Cl)—. In some embodiments is a compound of Formula (II), or a pharmaceutically acceptable salt or solvate thereof, wherein X, Y, and Z are each =C(H)—. In some embodiments is a compound of Formula (II), or a pharmaceutically acceptable salt or solvate thereof, wherein X and Y are each =C(H)—, and Z is each =C(Cl)—. In some embodiments is a compound of Formula (II), or a pharmaceutically acceptable salt or solvate thereof, wherein X and Y are each =C(H)—, and Z is each =C($CH_3$)—. In some embodiments is a compound of Formula (II), or a pharmaceutically acceptable salt or solvate thereof, wherein X is =N—, Y is =C($R^1$)—, and Z is =C($R^{11}$)—. In some embodiments is a compound of Formula (II), or a pharmaceutically acceptable salt or solvate thereof, wherein X is =N—, Y is =C(H)—, and Z is =C(H)—. In some embodiments is a compound of Formula (II), or a pharmaceutically acceptable salt or solvate thereof, wherein X is =C($R^{11}$)—, Y is =N—, and Z is =C($R^{11}$)—. In some embodiments is a compound of Formula (II), or a pharmaceutically acceptable salt or solvate thereof, wherein X is =C(H)—, Y is =N—, and Z is =C(H)—. In some embodiments is a compound of Formula (II), or a pharmaceutically acceptable salt or solvate thereof, wherein X is =C($R^{11}$)—, Y is =C($R^{11}$)—, and Z is =N—. In some embodiments is a compound of Formula (II), or a pharmaceutically acceptable salt or solvate thereof, wherein X is =C(H)—, Y is =C(H)—, and Z is =N—.

In some embodiments is a compound of Formula (II), or a pharmaceutically acceptable salt or solvate thereof, wherein $R^1$ and $R^2$ are independently selected from H and $C_{1-6}$alkyl. In some embodiments is a compound of Formula (II), or a pharmaceutically acceptable salt or solvate thereof, wherein $R^1$ and $R^2$ are each H. In some embodiments is a compound of Formula (II), or a pharmaceutically acceptable salt or solvate thereof, wherein $R^1$ and $R^2$ are each $C_{1-6}$alkyl. In some embodiments is a compound of Formula (II), or a pharmaceutically acceptable salt or solvate thereof, wherein $R^1$ and $R^2$ are each —$CH_3$. In some embodiments is a compound of Formula (II), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (II), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (II), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (II), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (II), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (II), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (II), or a pharmaceutically acceptable salt or solvate thereof, wherein $R^3$ is —N(H)C(O)O$R^5$. In some embodiments is a compound of Formula (II), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (II), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (II), or a pharmaceutically acceptable salt or solvate thereof, wherein $R^3$ is —N(H)C(O)O$R^5$ and $R^5$ is $C_{1-6}$alkyl. In some embodiments is a compound of Formula (II), or a pharmaceutically acceptable salt or solvate thereof, wherein $R^3$ is —N(H)C(O)O$R^5$ and $R^5$ is —$CH_3$. In some embodiments is a compound of Formula (II), or a pharmaceutically acceptable salt or solvate thereof, wherein $R^3$ is —N(H)C(O)O$R^5$ and $R^5$ is —$C_{1-6}$alkyl-OH. In some embodiments is a compound of Formula (II), or a pharmaceutically acceptable salt or solvate thereof, wherein $R^3$ is —N(H)C(O)O$R^5$ and $R^5$ is —$C_{1-6}$alkyl-O—$C_{1-6}$alkyl. In some embodiments is a compound of Formula (II), or a pharmaceutically acceptable salt or solvate thereof, wherein $R^3$ is —N(H)C(O)O$R^5$ and $R^5$ is —$C_{1-6}$alkyl-$C_{2-9}$heterocycloalkyl. In some embodiments is a compound of Formula (II), or a pharmaceutically acceptable salt or solvate thereof, wherein $R^3$ is —N(H)C(O)O$R^5$ and $R^5$ is —$C_{1-6}$alkyl-phenyl. In some embodiments is a compound of Formula (II), or a pharmaceutically acceptable salt or solvate thereof, wherein $R^3$ is —N(H)C(O)O$R^5$ and $R^5$ is —$CH_2$-phenyl. In some embodiments is a compound of Formula (II), or a pharmaceutically acceptable salt or solvate thereof, wherein $R^3$ is —OC(O)$NR^6R^7$. In some embodiments is a compound of Formula (II), or a pharmaceutically acceptable salt or solvate thereof, wherein $R^3$ is —OC(O)$NR^6R^7$ and $R^3$ is —N(H)C(O)$NR^6R^7$. In some embodiments is a compound of Formula (II), or a pharmaceutically acceptable salt or solvate thereof, wherein $R^3$ is —OC(O)$NR^6R^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (II), or a pharmaceutically acceptable salt or solvate thereof, wherein $R^3$ is —OC(O)$NR^6R^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (II), or a pharmaceutically acceptable salt or solvate thereof, wherein $R^3$ is —OC(O)$NR^6R^7$ and $R^6$ and $R^7$ are independently selected from $C_{1-6}$alkyl. In some embodiments is a compound of Formula (II), or a pharmaceutically acceptable salt or solvate thereof, wherein $R^3$ is —OC(O)$NR^6R^7$ and $R^6$ and $R^7$ are each —$CH_3$. In some embodiments is a compound of Formula (II), or a pharmaceutically acceptable salt or solvate thereof, wherein $R^3$ is —N(H)C(O)$R^8$. In some embodiments is a compound of Formula (II), or a pharmaceutically acceptable salt or solvate thereof, wherein $R^3$ is —N(H)C(O)$R^8$ and $R^8$ is —$C_{1-6}$alkyl-OH. In some embodiments is a compound of Formula (II), or a pharmaceutically acceptable salt or solvate thereof, wherein $R^3$ is —N(H)C(O)$R^8$ and $R^8$ is —$C_{1-6}$alkyl-O—$C_{1-6}$alkyl. In some embodiments is a compound of Formula (II), or a pharmaceutically acceptable salt or solvate thereof, wherein $R^3$ is —N(H)C(O)$R^8$ and $R^8$ is phenyl optionally substituted with one or two groups independently selected from halogen and $C_{1-6}$alkyl. In some embodiments is a compound of Formula (II), or a pharmaceutically acceptable salt or solvate thereof, wherein $R^3$ is —N(H)C(O)$R^8$ and $R^8$ is $C_{2-9}$heteroaryl optionally substituted with one or two groups independently selected from halogen and $C_{1-6}$alkyl.

In some embodiments is a compound of Formula (II), or pharmaceutically acceptable salt or solvate thereof, wherein $R^3$ is selected from —N(H)C(O)$OR^5$ and —OC(O)$NR^6R^7$. In some embodiments is a compound of Formula (II), or pharmaceutically acceptable salt or solvate thereof, wherein $R^3$ is selected from —N(H)C(O)$OR^5$ and —OC(O)$NR^6R^7$; $R^5$ is $C_{1-6}$alkyl; and $R^6$ and $R^7$ are independently selected from H and $C_{1-6}$alkyl. In some embodiments is a compound of Formula (II), or pharmaceutically acceptable salt or solvate thereof, wherein $R^3$ is —N(H)C(O)$OR^5$; and $R^5$ is methyl. In some embodiments is a compound of Formula (II), or pharmaceutically acceptable salt or solvate thereof, wherein $R^3$ is —OC(O)$NR^6R^7$; and $R^6$ and $R^7$ are independently selected from H and $C_{1-6}$alkyl. In some embodiments is a compound of Formula (II), or pharmaceutically acceptable salt or solvate thereof, wherein $R^3$ is —OC(O)$NR^6R^7$; and $R^6$ and $R^7$ are $C_{1-6}$alkyl. In some embodiments is a compound of Formula (II), or pharmaceutically acceptable salt or solvate thereof, wherein $R^3$ is —OC(O)$NR^6R^7$; and $R^6$ and $R^7$ are methyl.

In some embodiments is a compound of Formula (II), or a pharmaceutically acceptable salt or solvate thereof, wherein n is 0, 1, 2, or 3. In some embodiments is a compound of Formula (II), or a pharmaceutically acceptable salt or solvate thereof, wherein n is 0. In some embodiments is a compound of Formula (II), or a pharmaceutically acceptable salt or solvate thereof, wherein n is 1, 2, or 3. In some embodiments is a compound of Formula (II), or a pharmaceutically acceptable salt or solvate thereof, wherein n is 1. In some embodiments is a compound of Formula (II), or a pharmaceutically acceptable salt or solvate thereof, wherein n is 2. In some embodiments is a compound of Formula (II), or a pharmaceutically acceptable salt or solvate thereof, wherein n is 3. In some embodiments is a compound of Formula (II), or a pharmaceutically acceptable salt or solvate thereof, wherein n is 4.

In some embodiments is a compound of Formula (II), or a pharmaceutically acceptable salt or solvate thereof, wherein each $R^4$ is independently selected from halogen, —$OR^9$, —C(O)$OR^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (II), or a pharmaceutically acceptable salt or solvate thereof, wherein each $R^4$ is independently selected from halogen, —$OR^9$, —C(O)$OR^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (II), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl.

In some embodiments is compound of Formula (II), or a pharmaceutically acceptable salt or solvate thereof, wherein

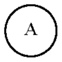

is selected from benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, and triazolopyrazinyl.

In some embodiments is a compound of Formula (I), or a pharmaceutically acceptable salt or solvate thereof, wherein

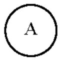

is selected from benzimidazolyl, imidazopyridinyl, purinyl, indoly, pyrrolopyridinyl, pyrrolopyrimidinyl, benzoxazolyl, and benzothiazolyl.

In some embodiments is a compound of Formula (II), or a pharmaceutically acceptable salt or solvate thereof, wherein

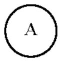

is selected from

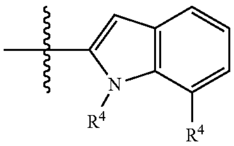, 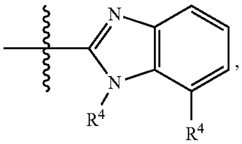,

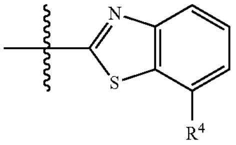, 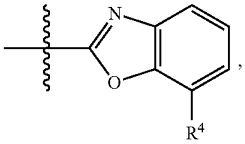,

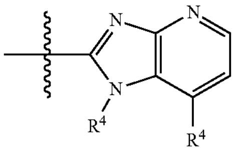, 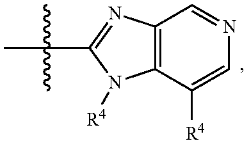,

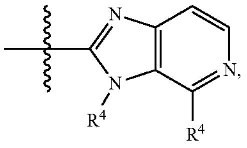, and 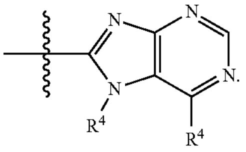.

In some embodiments is a compound of Formula (II), or a pharmaceutically acceptable salt or solvate thereof, wherein

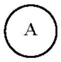

is selected from

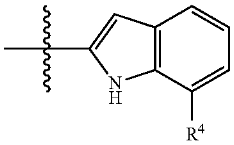, 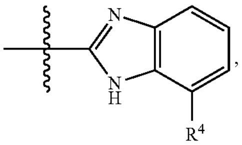,

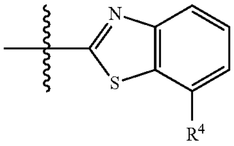, 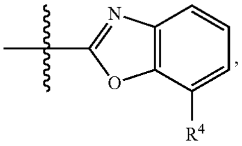,

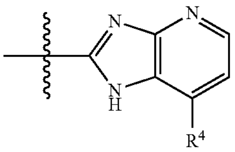, 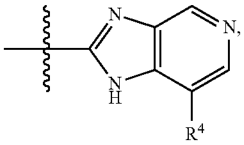,

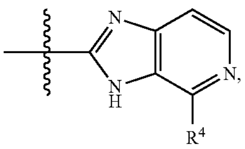, and 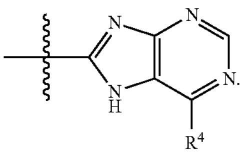.

In some embodiments is a compound of Formula (II), or a pharmaceutically acceptable salt or solvate thereof, wherein

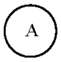 is 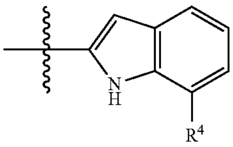.

In some embodiments is a compound of Formula (II), or a pharmaceutically acceptable salt or solvate thereof, wherein

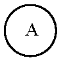 is 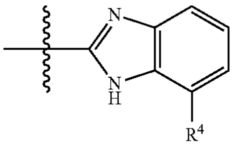.

In some embodiments is a compound of Formula (II), or a pharmaceutically acceptable salt or solvate thereof, wherein

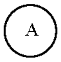 is 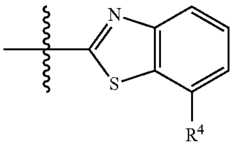.

In some embodiments is a compound of Formula (II), or a pharmaceutically acceptable salt or solvate thereof, wherein

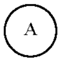 is 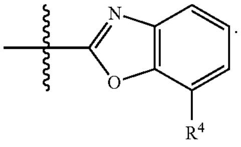.

In some embodiments is a compound of Formula (II), or a pharmaceutically acceptable salt or solvate thereof, wherein

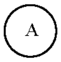 is 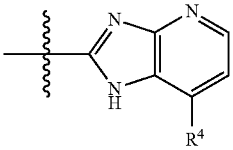.

In some embodiments is a compound of Formula (II), or a pharmaceutically acceptable salt or solvate thereof, wherein

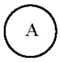 is 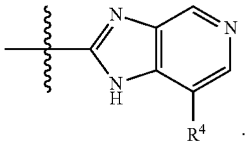.

In some embodiments is a compound of Formula (II), or a pharmaceutically acceptable salt or solvate thereof, wherein

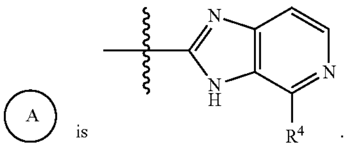

is

In some embodiments is a compound of Formula (II), or a pharmaceutically acceptable salt or solvate thereof, wherein

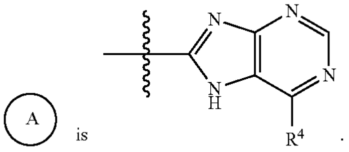

is

In some embodiments is a compound of Formula (II), or a pharmaceutically acceptable salt or solvate thereof, wherein $R^4$ is $C_{1-10}$alkyl. In some embodiments is a compound of Formula (II), or a pharmaceutically acceptable salt or solvate thereof, wherein $R^4$ is $C_{1-10}$haloalkyl. In some embodiments is a compound of Formula (II), or a pharmaceutically acceptable salt or solvate thereof, wherein $R^4$ is —$OR^9$. In some embodiments is a compound of Formula (II), or a pharmaceutically acceptable salt or solvate thereof, wherein $R^4$ is —$OR^9$ and $R^9$ is —$C_{1-6}$alkyl-phenyl optionally substituted with one or two halogens.

In some embodiments is a compound of Formula (II), or a pharmaceutically acceptable salt or solvate thereof, wherein

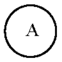

is selected from

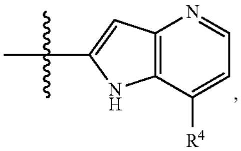

,

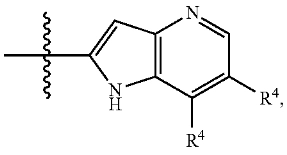

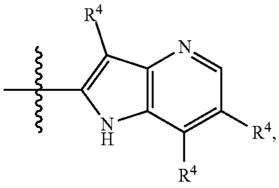

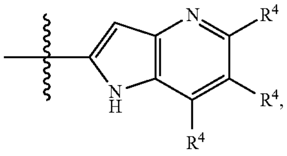

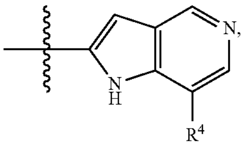

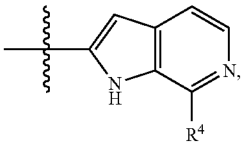

-continued

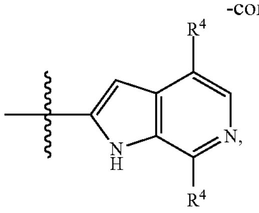

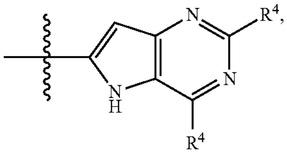

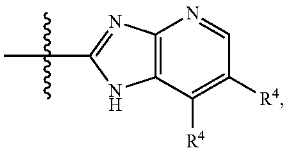

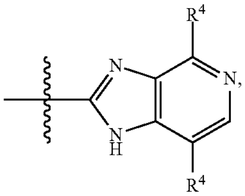

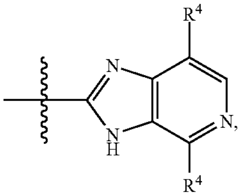

and

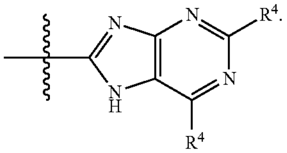

In some embodiments is a compound of Formula (II), or a pharmaceutically acceptable salt or solvate thereof, wherein

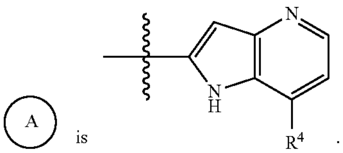

is

In some embodiments is a compound of Formula (II), or a pharmaceutically acceptable salt or solvate thereof, wherein

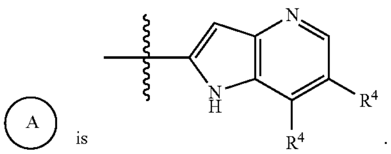

is

In some embodiments is a compound of Formula (II), or a pharmaceutically acceptable salt or solvate thereof, wherein

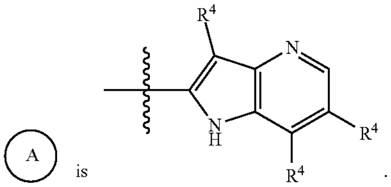

is

In some embodiments is a compound of Formula (II), or a pharmaceutically acceptable salt or solvate thereof, wherein

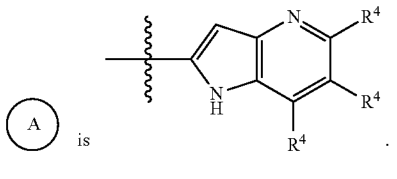

is .

In some embodiments is a compound of Formula (II), or a pharmaceutically acceptable salt or solvate thereof, wherein

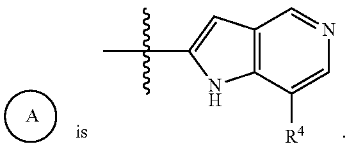

is .

In some embodiments is a compound of Formula (II), or a pharmaceutically acceptable salt or solvate thereof, wherein

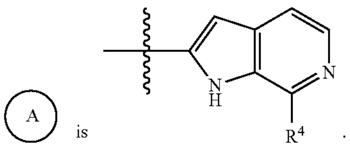

is .

In some embodiments is a compound of Formula (II), or a pharmaceutically acceptable salt or solvate thereof, wherein

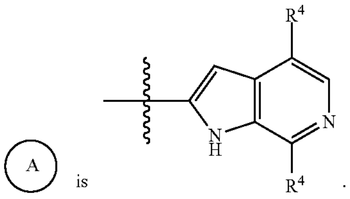

is .

In some embodiments is a compound of Formula (II), or a pharmaceutically acceptable salt or solvate thereof, wherein

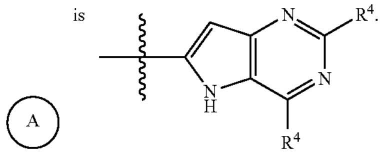

is

In some embodiments is a compound of Formula (II), or a pharmaceutically acceptable salt or solvate thereof, wherein

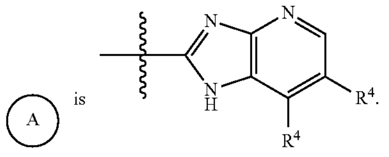

is

In some embodiments is a compound of Formula (II), or a pharmaceutically acceptable salt or solvate thereof, wherein

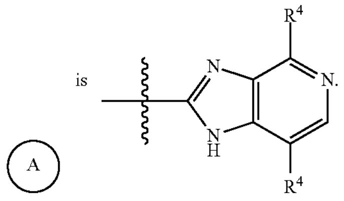

is

In some embodiments is a compound of Formula (II), or a pharmaceutically acceptable salt or solvate thereof, wherein

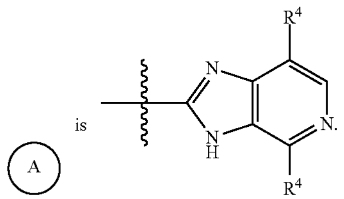

is

In some embodiments is a compound of Formula (II), or a pharmaceutically acceptable salt or solvate thereof, wherein

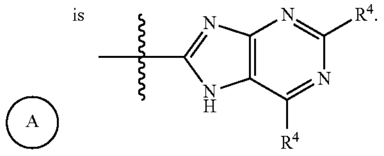

is

In some embodiments is a compound of Formula (II), or a pharmaceutically acceptable salt or solvate thereof, wherein

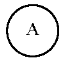

is selected from

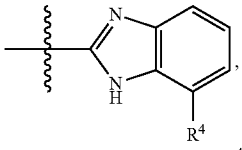,

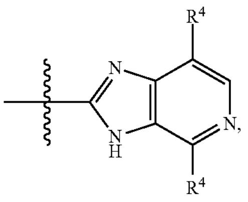, and

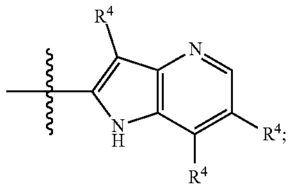

and each $R^4$ is independently selected from halogen and optionally substituted alkyl. In some embodiments is a compound of Formula (II), or a pharmaceutically acceptable salt or solvate thereof, wherein each $R^4$ is independently selected from chloro, fluoro, methyl, ethyl, butyl, and isobutyl. In some embodiments is a compound of Formula (II), or a pharmaceutically acceptable salt or solvate thereof, wherein each $R^4$ is independently selected from fluoro, methyl, and isobutyl.

In some embodiments is a compound of Formula (II), or a pharmaceutically acceptable salt or solvate thereof, wherein each $R^4$ is independently selected from halogen, —$OR^9$, —$N(R^{10})_2$, $C_{1-10}$alkyl, $C_{2-10}$alkenyl, $C_{1-10}$haloalkyl, and —$C_{1-6}$alkyl-$C_{3-12}$cycloalkyl. In some embodiments is a compound of Formula (II), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl. In some embodiments is a compound of Formula (II), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl and each $R^9$ is $C_{1-10}$alkyl. In some embodiments is a compound of Formula (II), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (II), or a pharmaceutically acceptable salt or solvate thereof, wherein each $R^4$ is independently selected from halogen and $C_{1-10}$alkyl.

In some embodiments is a compound of Formula (II), or a pharmaceutically acceptable salt or solvate thereof, wherein p is 0. In some embodiments is a compound of Formula (II), or a pharmaceutically acceptable salt or solvate thereof, wherein p is 1. In some embodiments is a compound of Formula (II), or a pharmaceutically acceptable salt or solvate thereof, wherein p is 2.

In another embodiment, this invention relates to compounds of Formula (II) wherein:

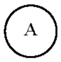

is a 9-membered bicyclic heteroaryl ring;

X, Y, and Z are =$C(R^{11})$—;

$R^1$ and $R^2$ are independently selected from H and $C_{1-6}$alkyl, $R^3$ is selected from —$N(H)C(O)OR^5$ and —$OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^{11}$ is independently selected from H, halogen, and $C_{1-6}$alkyl;

n is 0, 1, 2, 3, or 4; and p is 0, 1, or 2;

or a pharmaceutically acceptable salt or solvate thereof.

In another embodiment, this invention relates to compounds of Formula (II) wherein:

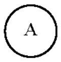

is benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, or triazolopyrazinyl;

X, Y, and Z are =$C(R^1)$ $R^1$ and $R^2$ are independently selected from H and $C_{1-6}$alkyl, $R^3$ is selected from —$N(H)C(O)OR^5$ and —$OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^{11}$ is independently selected from H, halogen, and $C_{1-6}$alkyl;

n is 0, 1, 2, 3, or 4; and p is 0, 1, or 2;

or a pharmaceutically acceptable salt or solvate thereof.

In another embodiment, this invention relates to compounds of Formula (II) wherein:

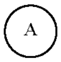

is benzimidazolyl, imidazopyridinyl, purinyl, indoly, pyrrolopyridinyl, pyrrolopyrimidinyl, benzoxazolyl, or benzothiazolyl X, Y, and Z are =$C(R^{11})$—;

$R^1$ and $R^2$ are independently selected from H and $C_{1-6}$alkyl, $R^3$ is selected from —$N(H)C(O)OR^5$ and —$OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^{11}$ is independently selected from H, halogen, and $C_{1-6}$alkyl;

n is 1, 2, or 3; and p is 1;

or a pharmaceutically acceptable salt or solvate thereof.

In another embodiment, this invention relates to compounds of Formula (II) wherein:

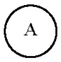

is benzimidazolyl, imidazopyridinyl, or pyrrolopyridinyl;

X, Y, and Z are =$C(R^1)$—;

$R^1$ and $R^2$ are independently selected from H and $C_{1-6}$alkyl, $R^3$ is selected from —$N(H)C(O)OR^5$ and —$OC(O)NR^6R^7$;

each $R^4$ is independently selected from halogen and $C_{1-10}$alkyl;

$R^5$ is $C_{1-6}$alkyl;

$R^6$ and $R^7$ are independently selected from H and $C_{1-6}$alkyl;

each $R^{11}$ is independently selected from H, halogen, and $C_{1-6}$alkyl;

n is 1, 2, or 3; and p is 1;

or a pharmaceutically acceptable salt or solvate thereof.

In another aspect are compounds having the structure of Formula (IIa):

Formula (IIa)

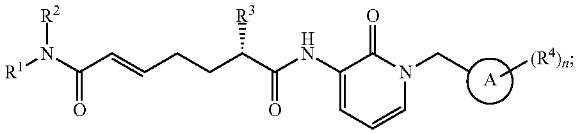

wherein:

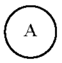

is a 9-membered bicyclic heteroaryl ring;

$R^1$ and $R^2$ are independently selected from H, $C_{1-6}$alkyl, and —$C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from —N(H)C(O)$OR^5$, —OC(O)$NR^6R^7$, —N(H)C(O)$NR^6R^7$, and —N(H)C(O)$R^8$;

each $R^4$ is independently selected from halogen, —CN, —$OR^9$, —$SR^9$, —$N(R^{10})_2$, —S(O)$R^9$, —$S(O)_2R^9$, —$NHS(O)_2R^9$, —$S(O)_2N(R^1)_2$, —C(O)$R^9$, —C(O)$OR^9$, —OC(O)$R^9$, —C(O)$N(R^{10})_2$, —OC(O)$N(R^{10})_2$, —$NR^{10}$C(O)$N(R^{10})_2$, —$NR^{10}$C(O)$R^9$, —$NR^{10}$C(O)$OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, —$C_{2-6}$alkenyl-$C_{3-12}$cycloalkyl, phenyl, —$C_{1-6}$alkyl-phenyl, —$C_{2-6}$alkenyl-phenyl, $C_{2-9}$heterocycloalkyl, and $C_{2-9}$heteroaryl, wherein phenyl, —$C_{1-6}$alkyl-phenyl, —$C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, —$C_{1-6}$alkyl-OH, —$C_{1-6}$alkyl-O—$C_{1-6}$alkyl, —$C_{1-6}$alkyl-O—C(O)$C_{1-6}$alkyl, $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl, wherein $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl$)_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl; and n is 0, 1, 2, 3, or 4;

or a pharmaceutically acceptable salt or solvate thereof.

In some embodiments is a compound of Formula (IIa), or a pharmaceutically acceptable salt or solvate thereof, wherein $R^1$ and $R^2$ are independently selected from H and $C_{1-6}$alkyl. In some embodiments is a compound of Formula (IIa), or a pharmaceutically acceptable salt or solvate thereof, wherein $R^1$ and $R^2$ are each H. In some embodiments is a compound of Formula (IIa), or a pharmaceutically acceptable salt or solvate thereof, wherein $R^1$ and $R^2$ are each $C_{1-6}$alkyl. In some embodiments is a compound of Formula (IIa), or a pharmaceutically acceptable salt or solvate thereof, wherein $R^1$ and $R^2$ are each —$CH_3$. In some embodiments is a compound of Formula (IIa), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (IIa), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (IIa), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (IIa), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (IIa), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (IIa), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (IIa), or a pharmaceutically acceptable salt or solvate thereof, wherein $R^3$ is —N(H)C(O)$OR^5$. In some embodiments is a compound of Formula (IIa), or a pharmaceutically acceptable salt or solvate thereof, wherein $R^3$ is —N(H)C(O)$OR^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (IIa), or a pharmaceutically acceptable salt or solvate thereof, wherein $R^3$ is —N(H)C(O)OR$^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (IIa), or a pharmaceutically acceptable salt or solvate thereof, wherein $R^3$ is —N(H)C(O)OR$^5$ and $R^5$ is $C_{1-6}$alkyl. In some embodiments is a compound of Formula (IIa), or a pharmaceutically acceptable salt or solvate thereof, wherein $R^3$ is —N(H)C(O)OR$^5$ and $R^5$ is —$CH_3$. In some embodiments is a compound of Formula (IIa), or a pharmaceutically acceptable salt or solvate thereof, wherein $R^3$ is —N(H)C(O)OR$^5$ and $R^5$ is —$C_{1-6}$alkyl-OH. In some embodiments is a compound of Formula (IIa), or a pharmaceutically acceptable salt or solvate thereof, wherein $R^3$ is —N(H)C(O)OR$^5$ and $R^5$ is —$C_{1-6}$alkyl-O—$C_{1-6}$alkyl. In some embodiments is a compound of Formula (IIa), or a pharmaceutically acceptable salt or solvate thereof, wherein $R^3$ is —N(H)C(O)OR$^5$ and $R^5$ is —$C_{1-6}$alkyl-$C_{2-9}$heterocycloalkyl. In some embodiments is a compound of Formula (IIa), or a pharmaceutically acceptable salt or solvate thereof, wherein $R^3$ is —N(H)C(O)OR$^5$ and $R^5$ is —$C_{1-6}$alkyl-phenyl. In some embodiments is a compound of Formula (IIa), or a pharmaceutically acceptable salt or solvate thereof, wherein $R^3$ is —N(H)C(O)OR$^5$ and $R^5$ is —$CH_2$-phenyl. In some embodiments is a compound of Formula (IIa), or a pharmaceutically acceptable salt or solvate thereof, wherein $R^3$ is —OC(O)NR$^6$R$^7$. In some embodiments is a compound of Formula (IIa), or a pharmaceutically acceptable salt or solvate thereof, wherein $R^3$ is —OC(O)NR$^6$R$^7$ and $R^3$ is —N(H)C(O)NR$^6$R$^7$. In some embodiments is a compound of Formula (IIa), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (IIa), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (IIa), or a pharmaceutically acceptable salt or solvate thereof, wherein $R^3$ is —OC(O)NR$^6$R$^7$ and $R^6$ and $R^7$ are independently selected from $C_{1-6}$alkyl. In some embodiments is a compound of Formula (IIa), or a pharmaceutically acceptable salt or solvate thereof, wherein $R^3$ is —OC(O)NR$^6$R$^7$ and $R^6$ and $R^7$ are each —$CH_3$. In some embodiments is a compound of Formula (IIa), or a pharmaceutically acceptable salt or solvate thereof, wherein $R^3$ is —N(H)C(O)R$^8$. In some embodiments is a compound of Formula (IIa), or a pharmaceutically acceptable salt or solvate thereof, wherein $R^3$ is —N(H)C(O)R$^8$ and $R^8$ is —$C_{1-6}$alkyl-OH. In some embodiments is a compound of Formula (IIa), or a pharmaceutically acceptable salt or solvate thereof, wherein $R^3$ is —N(H)C(O)R$^8$ and $R^8$ is —$C_{1-6}$alkyl-O—$C_{1-6}$alkyl. In some embodiments is a compound of Formula (IIa), or a pharmaceutically acceptable salt or solvate thereof, wherein $R^3$ is —N(H)C(O)R$^8$ and $R^8$ is phenyl optionally substituted with one or two groups independently selected from halogen and $C_{1-6}$alkyl. In some embodiments is a compound of Formula (IIa), or a pharmaceutically acceptable salt or solvate thereof, wherein $R^3$ is —N(H)C(O)R$^8$ and $R^8$ is $C_{2-9}$heteroaryl optionally substituted with one or two groups independently selected from halogen and $C_{1-6}$alkyl.

In some embodiments is a compound of Formula (IIa), or a pharmaceutically acceptable salt or solvate thereof, wherein n is 0, 1, 2, or 3. In some embodiments is a compound of Formula (IIa), or a pharmaceutically acceptable salt or solvate thereof, wherein n is 0. In some embodiments is a compound of Formula (IIa), or a pharmaceutically acceptable salt or solvate thereof, wherein n is 1, 2, or 3. In some embodiments is a compound of Formula (IIa), or a pharmaceutically acceptable salt or solvate thereof, wherein n is 1. In some embodiments is a compound of Formula (IIa), or a pharmaceutically acceptable salt or solvate thereof, wherein n is 2. In some embodiments is a compound of Formula (IIa), or a pharmaceutically acceptable salt or solvate thereof, wherein n is 3. In some embodiments is a compound of Formula (IIa), or a pharmaceutically acceptable salt or solvate thereof, wherein n is 4.

In some embodiments is a compound of Formula (IIa), or a pharmaceutically acceptable salt or solvate thereof, wherein each $R^4$ is independently selected from halogen, —OR$^9$, —C(O)OR$^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (IIa), or a pharmaceutically acceptable salt or solvate thereof, wherein each $R^4$ is independently selected from halogen, —OR$^9$, —C(O)OR$^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (IIa), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl.

In some embodiments is a compound of Formula (IIa), or a pharmaceutically acceptable salt or solvate thereof, wherein

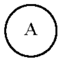

is selected from

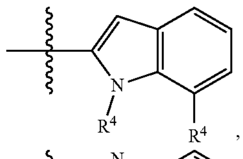,
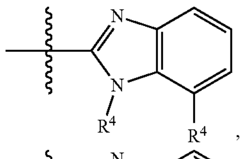,
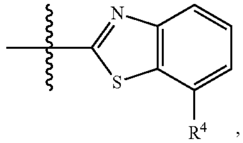,
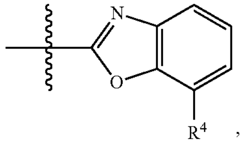,
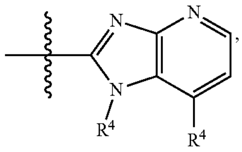,
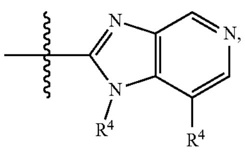

-continued

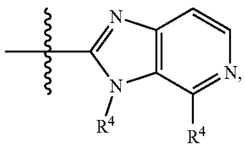 and 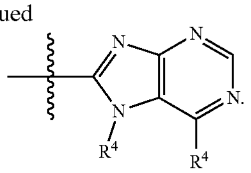

In some embodiments is a compound of Formula (IIa), or a pharmaceutically acceptable salt or solvate thereof, wherein

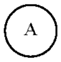

is selected from

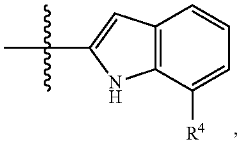, 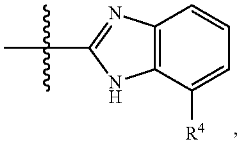,

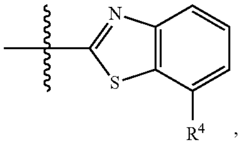, 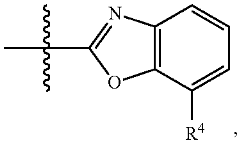,

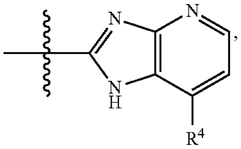, 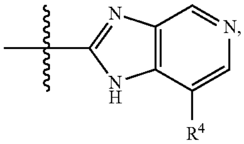

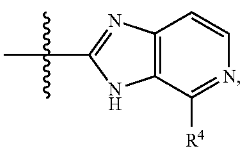 and 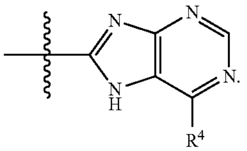

In some embodiments is a compound of Formula (IIa), or a pharmaceutically acceptable salt or solvate thereof, wherein

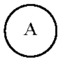 is 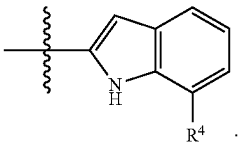.

In some embodiments is a compound of Formula (IIa), or a pharmaceutically acceptable salt or solvate thereof, wherein

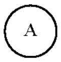 is 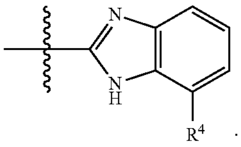.

In some embodiments is a compound of Formula (IIa), or a pharmaceutically acceptable salt or solvate thereof, wherein

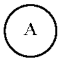 is 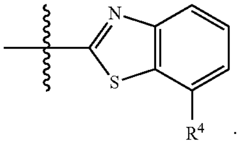.

In some embodiments is a compound of Formula (IIa), or a pharmaceutically acceptable salt or solvate thereof, wherein

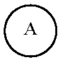 is 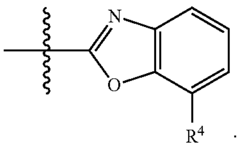.

In some embodiments is a compound of Formula (IIa), or a pharmaceutically acceptable salt or solvate thereof, wherein

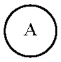 is 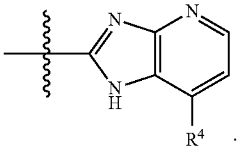.

In some embodiments is a compound of Formula (IIa), or a pharmaceutically acceptable salt or solvate thereof, wherein

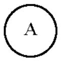 is 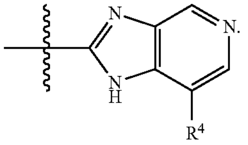

In some embodiments is a compound of Formula (IIa), or a pharmaceutically acceptable salt or solvate thereof, wherein

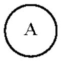 is 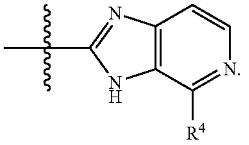

In some embodiments is a compound of Formula (IIa), or a pharmaceutically acceptable salt or solvate thereof, wherein

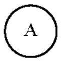 is 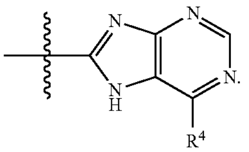

In some embodiments is a compound of Formula (IIa), or a pharmaceutically acceptable salt or solvate thereof, wherein $R^4$ is $C_{1-10}$alkyl. In some embodiments is a compound of Formula (IIa), or a pharmaceutically acceptable salt or solvate thereof, wherein $R^4$ is $C_{1-10}$haloalkyl. In some embodiments is a compound of Formula (IIa), or a pharmaceutically acceptable salt or solvate thereof, wherein $R^4$ is —$OR^9$. In some embodiments is a compound of Formula (IIa), or a pharmaceutically acceptable salt or solvate thereof, wherein $R^4$ is —$OR^9$ and $R^9$ is —$C_{1-6}$alkyl-phenyl optionally substituted with one or two halogens.

In some embodiments is a compound of Formula (IIa), or a pharmaceutically acceptable salt or solvate thereof, wherein

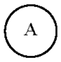

is selected from

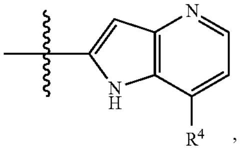 ,

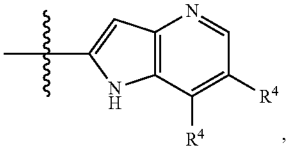 ,

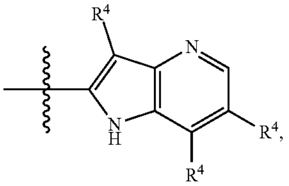

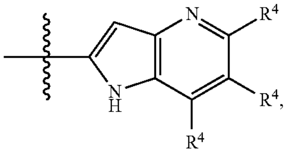

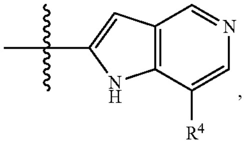 ,

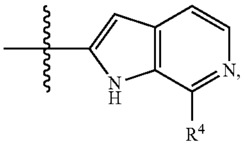

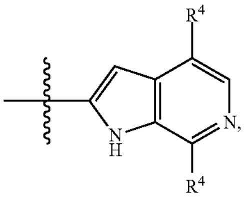

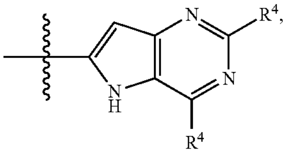

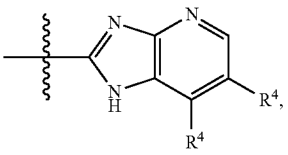

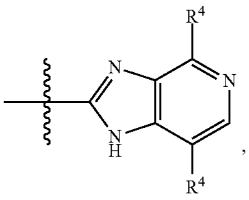 ,

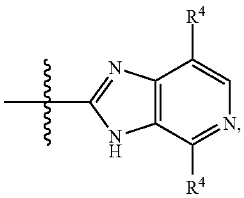 and

-continued

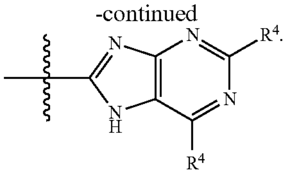

In some embodiments is a compound of Formula (IIa), or a pharmaceutically acceptable salt or solvate thereof, wherein

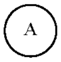 is 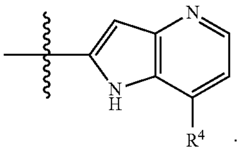 .

In some embodiments is a compound of Formula (IIa), or a pharmaceutically acceptable salt or solvate thereof, wherein

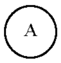 is 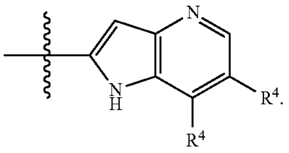

In some embodiments is a compound of Formula (IIa), or a pharmaceutically acceptable salt or solvate thereof, wherein

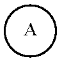 is 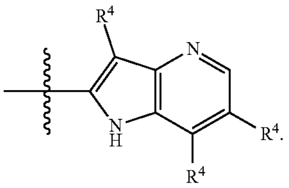

In some embodiments is a compound of Formula (IIa), or a pharmaceutically acceptable salt or solvate thereof, wherein

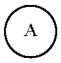 is 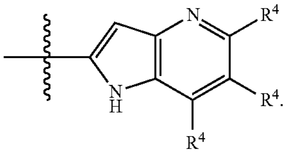

In some embodiments is a compound of Formula (IIa), or a pharmaceutically acceptable salt or solvate thereof, wherein

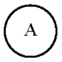 is 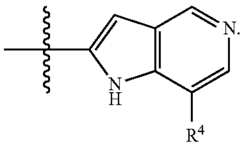

In some embodiments is a compound of Formula (IIa), or a pharmaceutically acceptable salt or solvate thereof, wherein is

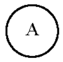
is
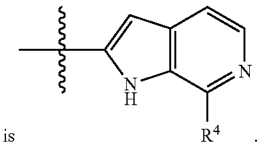
.

In some embodiments is a compound of Formula (IIa), or a pharmaceutically acceptable salt or solvate thereof, wherein

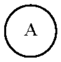
is
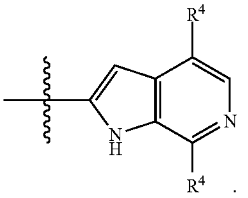
.

In some embodiments is a compound of Formula (IIa), or a pharmaceutically acceptable salt or solvate thereof, wherein

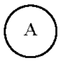
is
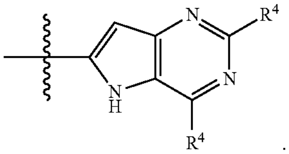
.

In some embodiments is a compound of Formula (IIa), or a pharmaceutically acceptable salt or solvate thereof, wherein

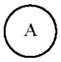
is
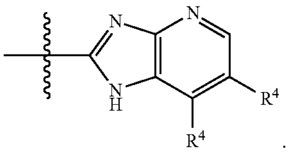
.

In some embodiments is a compound of Formula (IIa), or a pharmaceutically acceptable salt or solvate thereof, wherein

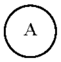
is
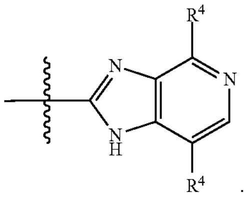
.

In some embodiments is a compound of Formula (IIa), or a pharmaceutically acceptable salt or solvate thereof, wherein

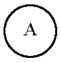
is
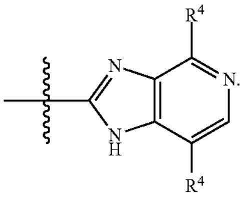

In some embodiments is a compound of Formula (IIa), or a pharmaceutically acceptable salt or solvate thereof, wherein

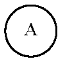
is
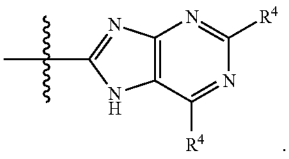
.

In some embodiments is a compound of Formula (IIa), or a pharmaceutically acceptable salt or solvate thereof, wherein each $R^4$ is independently selected from halogen, —$OR^9$, —$N(R^{10})_2$, $C_{1-10}$alkyl, $C_{2-10}$alkenyl, $C_{1-10}$haloalkyl, and —$C_{1-6}$alkyl-$C_{3-12}$cycloalkyl. In some embodiments is a compound of Formula (IIa), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl. In some embodiments is a compound of Formula (IIa), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl and each $R^9$ is $C_{1-10}$alkyl. In some embodiments is a compound of Formula (IIa), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (IIa), or a pharmaceutically acceptable salt or solvate thereof, wherein each $R^4$ is independently selected from halogen and $C_{1-10}$alkyl.

In another aspect are compounds having the structure of Formula (IIb):

Formula (IIb)

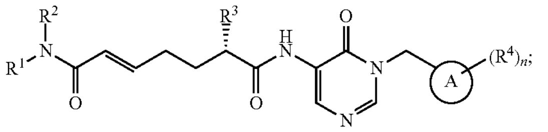

wherein:

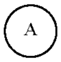

is a 9-membered bicyclic heteroaryl ring;

$R^1$ and $R^2$ are independently selected from H, $C_{1-6}$alkyl, and —$C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from —N(H)C(O)OR$^5$, —OC(O)NR$^6$R$^7$, —N(H)C(O)NR$^6$R$^7$, and —N(H)C(O)R$^8$;

each $R^4$ is independently selected from halogen, —CN, —OR$^9$, —SR$^9$, —N(R$^{10}$)$_2$, —S(O)R$^9$, —S(O)$_2$R$^9$, —NHS(O)$_2$R$^9$, —S(O)$_2$N(R$^1$)$_2$, —C(O)R$^9$, —C(O)OR$^9$, —OC(O)R$^9$, —C(O)N(R$^{10}$)$_2$, —OC(O)N(R$^{10}$)$_2$, —NR$^{10}$C(O)N(R$^{10}$)$_2$, —NR$^{10}$C(O)R$^9$, —NR$^1$C(O)OR$^9$, $C_{1-10}$alkyl, $C_{1-10}$alkyl-OH, $C_{1-10}$alkyl-OR$^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, —$C_{2-6}$alkenyl-$C_{3-12}$cycloalkyl, phenyl, —$C_{1-6}$alkyl-phenyl, —$C_{2-6}$alkenyl-phenyl, $C_{2-9}$heterocycloalkyl, and $C_{2-9}$heteroaryl, wherein phenyl, —$C_{1-6}$alkyl-phenyl, —$C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, —$C_{1-6}$alkyl-OH, —$C_{1-6}$alkyl-O—$C_{1-6}$alkyl, —$C_{1-6}$alkyl-O—C(O)$C_{1-6}$alkyl, $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl, wherein $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl; and n is 0, 1, 2, 3, or 4;

or a pharmaceutically acceptable salt or solvate thereof.

In some embodiments is a compound of Formula (IIb), or a pharmaceutically acceptable salt or solvate thereof, wherein $R^1$ and $R^2$ are independently selected from H and $C_{1-6}$alkyl. In some embodiments is a compound of Formula (IIb), or a pharmaceutically acceptable salt or solvate thereof, wherein $R^1$ and $R^2$ are each H. In some embodiments is a compound of Formula (IIb), or a pharmaceutically acceptable salt or solvate thereof, wherein $R^1$ and $R^2$ are each $C_{1-6}$alkyl. In some embodiments is a compound of Formula (IIb), or a pharmaceutically acceptable salt or solvate thereof, wherein $R^1$ and $R^2$ are each —$CH_3$. In some embodiments is a compound of Formula (IIb), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (IIb), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (IIb), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (IIb), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (IIb), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (IIb), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (IIb), or a pharmaceutically acceptable salt or solvate thereof, wherein $R^3$ is —N(H)C(O)OR$^5$. In some embodiments is a compound of Formula (IIb), or a pharmaceutically acceptable salt or solvate thereof, wherein $R^3$ is —N(H)C(O)OR$^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (IIb), or a pharmaceutically acceptable salt or solvate thereof, wherein $R^3$ is —N(H)C(O)OR$^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (IIb), or a pharmaceutically acceptable salt or solvate thereof, wherein $R^3$ is —N(H)C(O)OR$^5$ and $R^5$ is $C_{1-6}$alkyl. In some embodiments is a compound of Formula (IIb), or a pharmaceutically acceptable salt or solvate thereof, wherein $R^3$ is —N(H)C(O)OR$^5$ and $R^5$ is —$CH_3$. In some embodiments is a compound of Formula (IIb), or a pharmaceutically acceptable salt or solvate thereof, wherein $R^3$ is —N(H)C(O)OR$^5$ and $R^5$ is —$C_{1-6}$alkyl-OH. In some embodiments is a compound of Formula (IIb), or a pharmaceutically acceptable salt or solvate thereof, wherein $R^3$ is —N(H)C(O)OR$^5$ and $R^5$ is —$C_{1-6}$alkyl-O—$C_{1-6}$alkyl. In some embodiments is a compound of Formula (IIb), or a pharmaceutically acceptable salt or solvate thereof, wherein $R^3$ is —N(H)C(O)OR$^5$ and $R^5$ is —$C_{1-6}$alkyl-$C_{2-9}$heterocycloalkyl. In some embodiments is a compound of Formula (IIb), or a pharmaceutically acceptable salt or solvate thereof, wherein $R^3$ is —N(H)C(O)OR$^5$ and $R^5$ is —$C_{1-6}$alkyl-phenyl. In some embodiments is a compound of Formula (IIb), or a pharmaceutically acceptable salt or solvate thereof, wherein $R^3$ is —N(H)C(O)OR$^5$ and $R^5$ is —$CH_2$-phenyl. In some embodiments is a compound of Formula (IIb), or a pharmaceutically acceptable salt or solvate thereof, wherein $R^3$ is —OC(O)NR$^6$R$^7$. In some embodiments is a compound of Formula (IIb), or a pharmaceutically acceptable salt or solvate thereof, wherein $R^3$ is —OC(O)NR$^6$R$^7$ and $R^3$ is —N(H)C(O)NR$^6$R$^7$. In some embodiments is a compound of Formula (IIb), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (IIb), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (IIb), or a pharmaceutically acceptable salt or solvate thereof, wherein $R^3$ is —OC(O)NR$^6$R$^7$ and $R^6$ and $R^7$ are independently selected from $C_{1-6}$alkyl. In some embodiments is a compound of Formula (IIb), or a pharmaceutically acceptable salt or solvate thereof, wherein $R^3$ is —OC(O)NR$^6$R$^7$ and $R^6$ and $R^7$ are each —$CH_3$. In some embodiments is a compound of Formula (IIb), or a pharmaceutically acceptable salt or solvate thereof, wherein $R^3$ is —N(H)C(O)R$^8$. In some embodiments is a compound of Formula (IIb), or a pharmaceutically acceptable salt or solvate thereof, wherein $R^3$ is —N(H)C(O)R$^8$ and $R^8$ is —$C_{1-6}$alkyl-OH. In some embodiments is a compound of Formula (IIb), or a pharmaceutically acceptable salt or solvate thereof, wherein $R^3$ is —N(H)C(O)R$^8$ and $R^8$ is —$C_{1-6}$alkyl-O—$C_{1-6}$alkyl. In some embodiments is a compound of Formula (IIb), or a pharmaceutically acceptable salt or solvate thereof, wherein $R^3$ is —N(H)C(O)R$^8$ and $R^8$ is phenyl optionally substituted with one or two groups independently selected from halogen and $C_{1-6}$alkyl. In some embodiments is a compound of Formula (IIb), or a pharmaceutically acceptable salt or solvate thereof, wherein $R^3$ is —N(H)C(O)R$^8$ and $R^8$ is $C_{2-9}$heteroaryl optionally substituted with one or two groups independently selected from halogen and $C_{1-6}$alkyl.

In some embodiments is a compound of Formula (IIb), or a pharmaceutically acceptable salt or solvate thereof, wherein n is 0, 1, 2, or 3. In some embodiments is a compound of Formula (IIb), or a pharmaceutically acceptable salt or solvate thereof, wherein n is 0. In some embodiments is a compound of Formula (IIb), or a pharmaceutically acceptable salt or solvate thereof, wherein n is 1, 2, or 3. In some embodiments is a compound of Formula (IIb), or a pharmaceutically acceptable salt or solvate thereof, wherein n is 1. In some embodiments is a compound of Formula (IIb), or a pharmaceutically acceptable salt or solvate thereof, wherein n is 2. In some embodiments is a compound of Formula (IIb), or a pharmaceutically acceptable salt or solvate thereof, wherein n is 3. In some embodiments is a compound of Formula (IIb), or a pharmaceutically acceptable salt or solvate thereof, wherein n is 4.

In some embodiments is a compound of Formula (IIb), or a pharmaceutically acceptable salt or solvate thereof, wherein each $R^4$ is independently selected from halogen, —OR$^9$, —C(O)OR$^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (IIb), or a pharmaceutically acceptable salt or solvate thereof, wherein each $R^4$ is independently selected from halogen, —OR$^9$, —C(O)OR$^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (IIb), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl. In some embodiments is a compound of Formula (IIb), or a pharmaceutically acceptable salt or solvate thereof, wherein

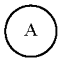

is selected from

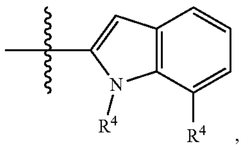

,

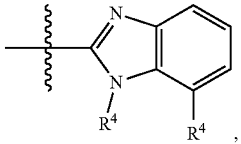

,

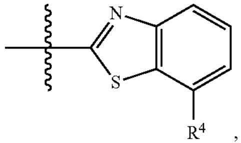

,

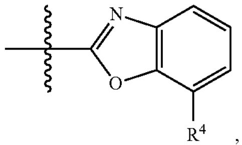

,

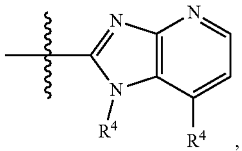

,

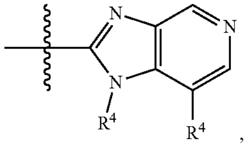

,

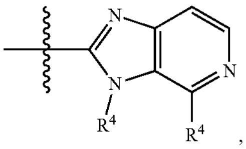

, and

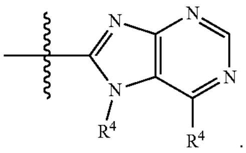

.

In some embodiments is a compound of Formula (IIb), or a pharmaceutically acceptable salt or solvate thereof, wherein

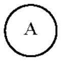

is selected from

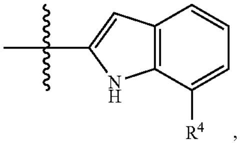

,

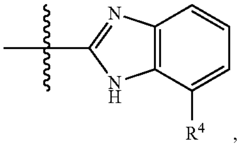

,

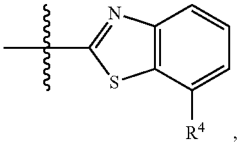

,

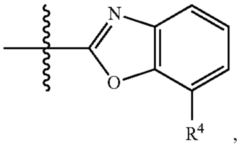

,

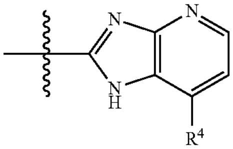

,

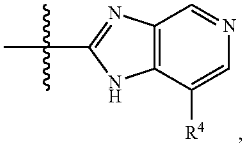

,

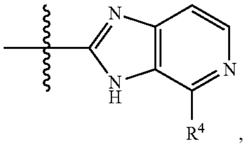

, and

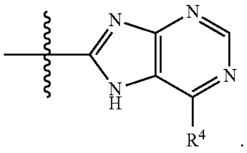

.

In some solvate thereof, wherein

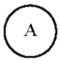 is 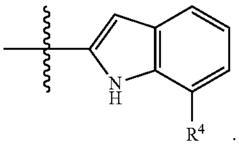 .

In some embodiments is a compound of Formula (IIb), or a pharmaceutically acceptable salt or solvate thereof, wherein

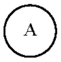 is 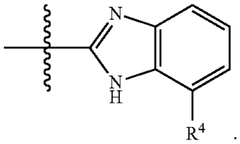 .

In some embodiments is a compound of Formula (IIb), or a pharmaceutically acceptable salt or solvate thereof, wherein

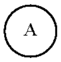 is 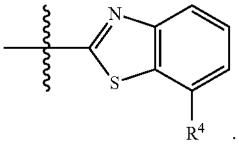 .

In some embodiments is a compound of Formula (IIb), or a pharmaceutically acceptable salt or solvate thereof, wherein

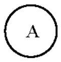 is 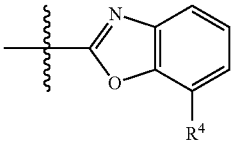 .

In some embodiments is a compound of Formula (IIb), or a pharmaceutically acceptable salt or solvate thereof, wherein

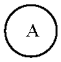 is 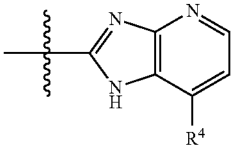 .

In some embodiments is a compound of Formula (IIb), or a pharmaceutically acceptable salt or solvate thereof, wherein

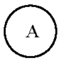 is 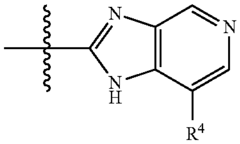 .

In some embodiments is a compound of Formula (IIb), or a pharmaceutically acceptable salt or solvate thereof, wherein

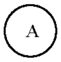 is 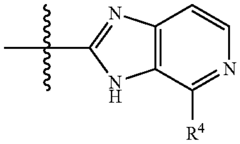 .

In some embodiments is a compound of Formula (IIb), or a pharmaceutically acceptable salt or solvate thereof, wherein

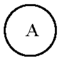 is 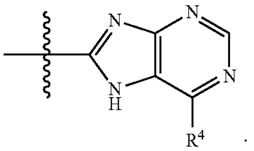

In some embodiments is a compound of Formula (IIb), or a pharmaceutically acceptable salt or solvate thereof, wherein $R^4$ is $C_{1-10}$alkyl. In some embodiments is a compound of Formula (IIb), or a pharmaceutically acceptable salt or solvate thereof, wherein $R^4$ is $C_{1-10}$haloalkyl. In some embodiments is a compound of Formula (IIb), or a pharmaceutically acceptable salt or solvate thereof, wherein $R^4$ is —$OR^9$. In some embodiments is a compound of Formula (IIb), or a pharmaceutically acceptable salt or solvate thereof, wherein $R^4$ is —$OR^9$ and $R^9$ is —$C_{1-6}$alkyl-phenyl optionally substituted with one or two halogens.

In some embodiments is a compound of Formula (IIb), or a pharmaceutically acceptable salt or solvate thereof, wherein

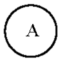

is selected from

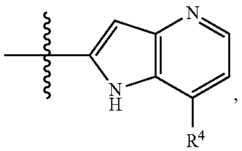
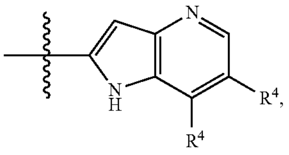
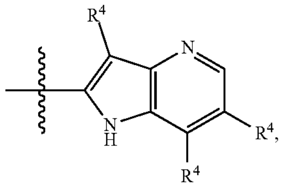
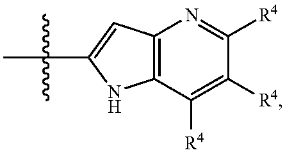
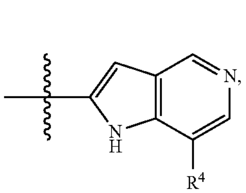
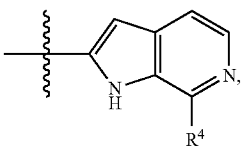
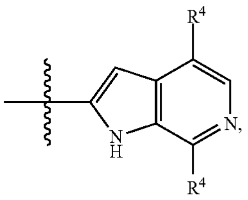
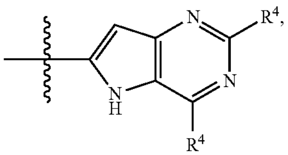

-continued

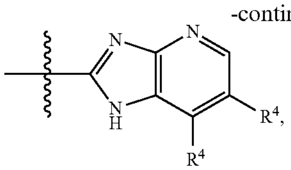
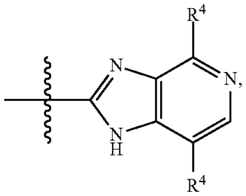
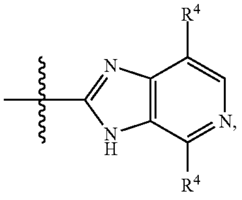
and
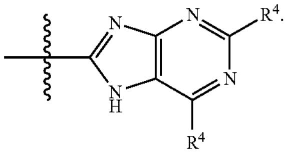

In some embodiments is a compound of Formula (IIb), or a pharmaceutically acceptable salt or solvate thereof, wherein

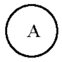 is 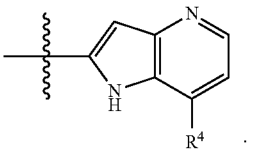

In some embodiments is a compound of Formula (IIb), or a pharmaceutically acceptable salt or solvate thereof, wherein

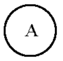 is 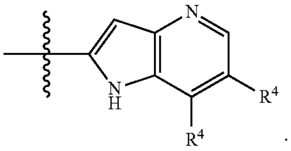

In some embodiments is a compound of Formula (IIb), or a pharmaceutically acceptable salt or solvate thereof, wherein

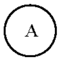 is 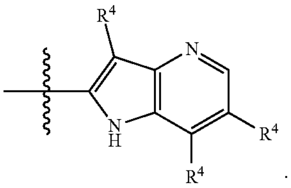

In some embodiments is a compound of Formula (IIb), or a pharmaceutically acceptable salt or solvate thereof, wherein

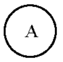 is 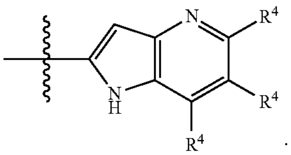

In some embodiments is a compound of Formula (IIb), or a pharmaceutically acceptable salt or solvate thereof, wherein

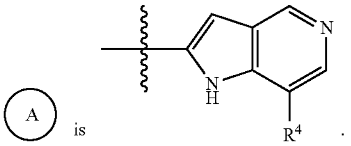

In some embodiments is a compound of Formula (IIb), or a pharmaceutically acceptable salt or solvate thereof, wherein

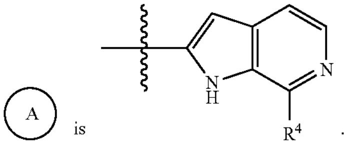

In some embodiments is a compound of Formula (IIb), or a pharmaceutically acceptable salt or solvate thereof, wherein

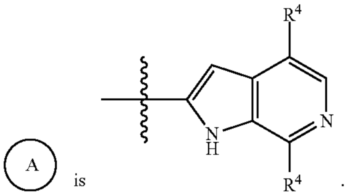

In some embodiments is a compound of Formula (IIb), or a pharmaceutically acceptable salt or solvate thereof, wherein

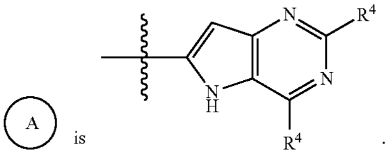

In some embodiments is a compound of Formula (IIb), or a pharmaceutically acceptable salt or solvate thereof, wherein

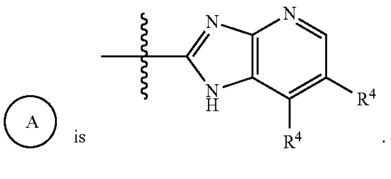

In some embodiments is a compound of Formula (IIb), or a pharmaceutically acceptable salt or solvate thereof, wherein

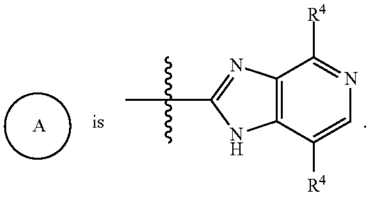

In some embodiments is a compound of Formula (IIb), or a pharmaceutically acceptable salt or solvate thereof, wherein

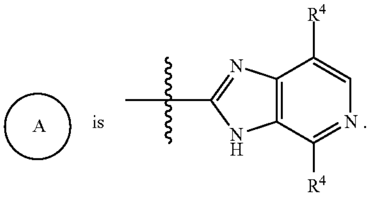

In some embodiments is a compound of Formula (IIb), or a pharmaceutically acceptable salt or solvate thereof, wherein

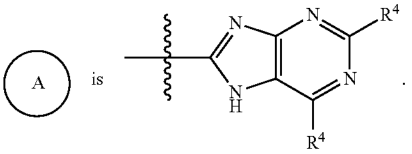

In some embodiments is a compound of Formula (IIb), or a pharmaceutically acceptable salt or solvate thereof, wherein each $R^4$ is independently selected from halogen, —$OR^9$, —$N(R^{10})_2$, $C_{1-10}$alkyl, $C_{2-10}$alkenyl, $C_{1-10}$haloalkyl, and —$C_{1-6}$alkyl-$C_{3-12}$cycloalkyl. In some embodiments is a compound of Formula (IIb), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl. In some embodiments is a compound of Formula (IIb), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl and each $R^9$ is $C_{1-10}$alkyl. In some embodiments is a compound of Formula (IIb), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (IIb), or a pharmaceutically acceptable salt or solvate thereof, wherein each $R^4$ is independently selected from halogen and $C_{1-10}$alkyl.

In another aspect are compounds having the structure of Formula (IIc):

Formula (IIc)

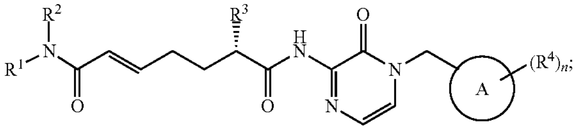

wherein:

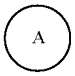

is a 9-membered bicyclic heteroaryl ring;

$R^1$ and $R^2$ are independently selected from H, $C_{1-6}$alkyl, and —$C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from —N(H)C(O)O$R^5$, —OC(O)N$R^6R^7$, —N(H)C(O)N$R^6R^7$, and —N(H)C(O)$R^8$;

each $R^4$ is independently selected from halogen, —CN, —O$R^9$, —S$R^9$, —N($R^{10}$)$_2$, —S(O)$R^9$, —S(O)$_2R^9$, —NHS(O)$_2R^9$, —S(O)$_2$N($R^{10}$)$_2$, —C(O)$R^9$, —C(O)O$R^9$, —OC(O)$R^9$, —C(O)N($R^{10}$)$_2$, —OC(O)N($R^{10}$)$_2$, —N$R^{10}$C(O)N($R^{10}$)$_2$, —N$R^{10}$C(O)$R^9$, —N$R^{10}$C(O)O$R^9$, $C_{1-10}$alkyl, $C_{1-10}$alkyl-OH, $C_{1-10}$alkyl-O$R^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, —$C_{2-6}$alkenyl-$C_{3-12}$cycloalkyl, phenyl, —$C_{1-6}$alkyl-phenyl, —$C_{2-6}$alkenyl-phenyl, $C_{2-9}$heterocycloalkyl, and $C_{2-9}$heteroaryl, wherein phenyl, —$C_{1-6}$alkyl-phenyl, —$C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, —$C_{1-6}$alkyl-OH, —$C_{1-6}$alkyl-O—$C_{1-6}$alkyl, —$C_{1-6}$alkyl-O—C(O)$C_{1-6}$alkyl, $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl, wherein $C_{2-9}$heterocycloalkyl, —$C_{1-6}$alkyl-$C_{2-9}$heterocycloalkyl, phenyl, —$C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl; and n is 0, 1, 2, 3, or 4;

or a pharmaceutically acceptable salt or solvate thereof.

In some embodiments is a compound of Formula (IIc), or a pharmaceutically acceptable salt or solvate thereof, wherein $R^1$ and $R^2$ are independently selected from H and $C_{1-6}$alkyl. In some embodiments is a compound of Formula (IIc), or a pharmaceutically acceptable salt or solvate thereof, wherein $R^1$ and $R^2$ are each H. In some embodiments is a compound of Formula (IIc), or a pharmaceutically acceptable salt or solvate thereof, wherein $R^1$ and $R^2$ are each $C_{1-6}$alkyl. In some embodiments is a compound of Formula (IIc), or a pharmaceutically acceptable salt or solvate thereof, wherein $R^1$ and $R^2$ are each —$CH_3$. In some embodiments is a compound of Formula (IIc), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (IIc), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (IIc), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (IIc), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (IIc), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (IIc), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (IIc), or a pharmaceutically acceptable salt or solvate thereof, wherein $R^3$ is —N(H)C(O)O$R^5$. In some embodiments is a compound of Formula (IIc), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (IIc), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (IIc), or a pharmaceutically acceptable salt or solvate thereof, wherein $R^3$ is —N(H)C(O)O$R^5$ and $R^5$ is $C_{1-6}$alkyl. In some embodiments is a compound of Formula (IIc), or a pharmaceutically acceptable salt or solvate thereof, wherein $R^3$ is —N(H)C(O)O$R^5$ and $R^5$ is —$CH_3$. In some embodiments is a compound of Formula (IIc), or a pharmaceutically acceptable salt or solvate thereof, wherein $R^3$ is —N(H)C(O)O$R^5$ and $R^5$ is —$C_{1-6}$alkyl-OH. In some embodiments is a compound of Formula (IIc), or a pharmaceutically acceptable salt or solvate thereof, wherein $R^3$ is —N(H)C(O)O$R^5$ and $R^5$ is —$C_{1-6}$alkyl-O—$C_{1-6}$alkyl. In some embodiments is a compound of Formula (IIc), or a pharmaceutically acceptable salt or solvate thereof, wherein $R^3$ is —N(H)C(O)OR$^5$ and $R^5$ is —$C_{1-6}$alkyl-$C_{2-9}$heterocycloalkyl. In some embodiments is a compound of Formula (IIc), or a pharmaceutically acceptable salt or solvate thereof, wherein $R^3$ is —N(H)C(O)OR$^5$ and $R^5$ is —$C_{1-6}$alkyl-phenyl. In some embodiments is a compound of Formula (IIc), or a pharmaceutically acceptable salt or solvate thereof, wherein $R^3$ is —N(H)C(O)OR$^5$ and $R^5$ is —$CH_2$-phenyl. In some embodiments is a compound of Formula (IIc), or a pharmaceutically acceptable salt or solvate thereof, wherein $R^3$ is —OC(O)NR$^6$R$^7$. In some embodiments is a compound of Formula (IIc), or a pharmaceutically acceptable salt or solvate thereof, wherein $R^3$ is —OC(O)NR$^6$R$^7$ and $R^3$ is —N(H)C(O)NR$^6$R$^7$. In some embodiments is a compound of Formula (IIc), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (IIc), or a pharmaceutically acceptable salt or solvate thereof, wherein $R^3$ is —OC(O)NR$^6$R$^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (IIc), or a pharmaceutically acceptable salt or solvate thereof, wherein $R^3$ is —OC(O)NR$^6$R$^7$ and $R^6$ and $R^7$ are independently selected from $C_{1-6}$alkyl. In some embodiments is a compound of Formula (IIc), or a pharmaceutically acceptable salt or solvate thereof, wherein $R^3$ is —OC(O)NR$^6$R$^7$ and $R^6$ and $R^7$ are each —$CH_3$. In some embodiments is a compound of Formula (IIc), or a pharmaceutically acceptable salt or solvate thereof, wherein $R^3$ is —N(H)C(O)R$^8$. In some embodiments is a compound of Formula (IIc), or a pharmaceutically acceptable salt or solvate thereof, wherein $R^3$ is —N(H)C(O)R$^8$ and $R^8$ is —$C_{1-6}$alkyl-OH. In some embodiments is a compound of Formula (IIc), or a pharmaceutically acceptable salt or solvate thereof, wherein $R^3$ is —N(H)C(O)R$^8$ and $R^8$ is —$C_{1-6}$alkyl-O—$C_{1-6}$alkyl. In some embodiments is a compound of Formula (IIc), or a pharmaceutically acceptable salt or solvate thereof, wherein $R^3$ is —N(H)C(O)R$^8$ and $R^8$ is phenyl optionally substituted with one or two groups independently selected from halogen and $C_{1-6}$alkyl. In some embodiments is a compound of Formula (IIc), or a pharmaceutically acceptable salt or solvate thereof, wherein $R^3$ is —N(H)C(O)R$^8$ and $R^8$ is $C_{2-9}$heteroaryl optionally substituted with one or two groups independently selected from halogen and $C_{1-6}$alkyl.

In some embodiments is a compound of Formula (IIc), or a pharmaceutically acceptable salt or solvate thereof, wherein n is 0, 1, 2, or 3. In some embodiments is a compound of Formula (IIc), or a pharmaceutically acceptable salt or solvate thereof, wherein n is 0. In some embodiments is a compound of Formula (IIc), or a pharmaceutically acceptable salt or solvate thereof, wherein n is 1, 2, or 3. In some embodiments is a compound of Formula (IIc), or a pharmaceutically acceptable salt or solvate thereof, wherein n is 1. In some embodiments is a compound of Formula (IIc), or a pharmaceutically acceptable salt or solvate thereof, wherein n is 2. In some embodiments is a compound of Formula (IIc), or a pharmaceutically acceptable salt or solvate thereof, wherein n is 3. In some embodiments is a compound of Formula (IIc), or a pharmaceutically acceptable salt or solvate thereof, wherein n is 4.

In some embodiments is a compound of Formula (IIc), or a pharmaceutically acceptable salt or solvate thereof, wherein each $R^4$ is independently selected from halogen, —OR$^9$, —C(O)OR$^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (IIc), or a pharmaceutically acceptable salt or solvate thereof, wherein each $R^4$ is independently selected from halogen, —OR$^9$, —C(O)OR$^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (IIc), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl. In some embodiments is a compound of Formula (IIc), or a pharmaceutically acceptable salt solvate thereof, wherein

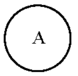

is selected from

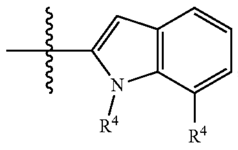,
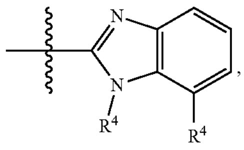,
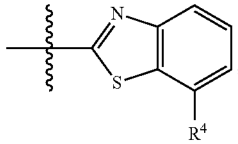,
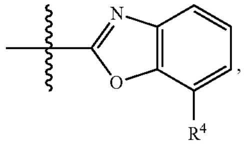,
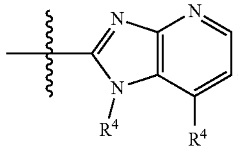,
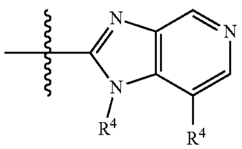,
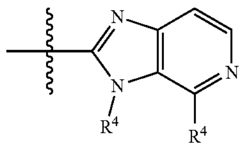, and
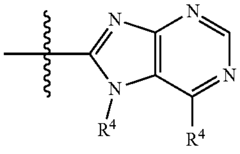.

In some embodiments is a compound of Formula (IIc), or a pharmaceutically acceptable salt or solvate thereof, wherein

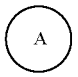 is 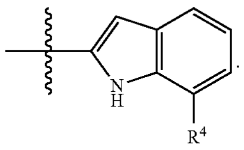.

is selected from

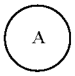

In some embodiments is a compound of Formula (IIc), or a pharmaceutically acceptable salt or solvate thereof, wherein

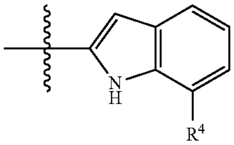, 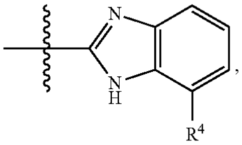, 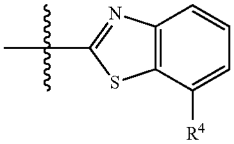, 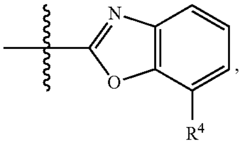, 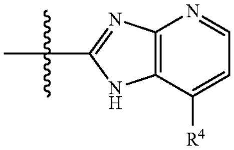, 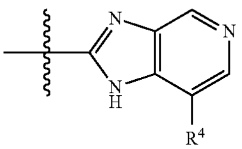, 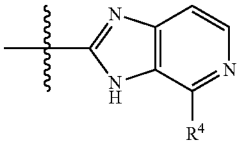, and 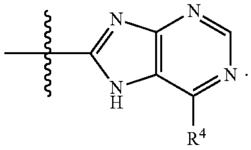.

In some embodiments is a compound of Formula (IIc), or a pharmaceutically acceptable salt or solvate thereof, wherein

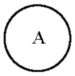 is 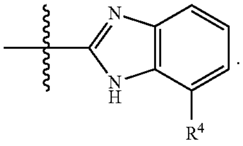

In some embodiments is a compound of Formula (IIc), or a pharmaceutically acceptable salt or solvate thereof, wherein

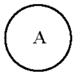 is 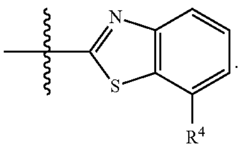

In some embodiments is a compound of Formula (IIc), or a pharmaceutically acceptable salt or solvate thereof, wherein

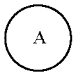 is 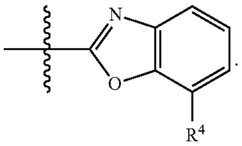

In some embodiments is a compound of Formula (IIc), or a pharmaceutically acceptable salt or solvate thereof, wherein

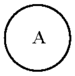 is 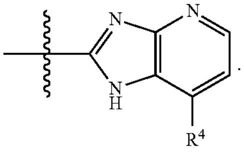

In some embodiments is a compound of Formula (IIc), or a pharmaceutically acceptable salt or solvate thereof, wherein

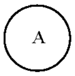 is 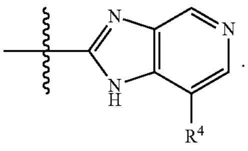

In some embodiments is a compound of Formula (IIc), or a pharmaceutically acceptable salt or solvate thereof, wherein

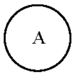 is 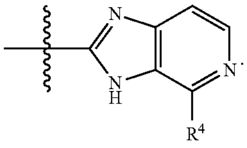

In some embodiments is a compound of Formula (IIc), or a pharmaceutically acceptable salt or solvate thereof, wherein

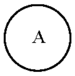 is 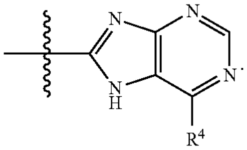

In some embodiments is a compound of Formula (IIc), or a pharmaceutically acceptable salt or solvate thereof, wherein $R^4$ is $C_{1-10}$alkyl. In some embodiments is a compound of Formula (IIc), or a pharmaceutically acceptable salt or solvate thereof, wherein $R^4$ is $C_{1-10}$haloalkyl. In some embodiments is a compound of Formula (IIc), or a pharmaceutically acceptable salt or solvate thereof, wherein $R^4$ is —$OR^9$. In some embodiments is a compound of Formula (IIc), or a pharmaceutically acceptable salt or solvate thereof, wherein $R^4$ is —$OR^9$ and $R^9$ is —$C_{1-6}$alkyl-phenyl optionally substituted with one or two halogens.

In some embodiments is a compound of Formula (IIc), or a pharmaceutically acceptable salt or solvate thereof, wherein

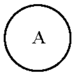

is selected from

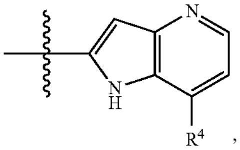,
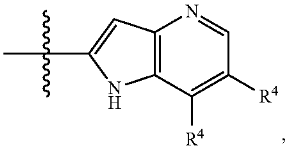,
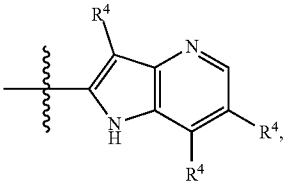
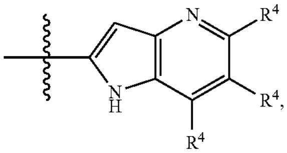
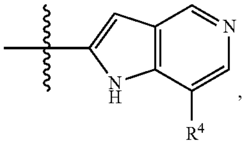,
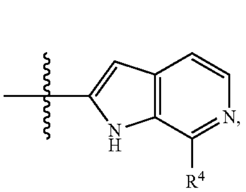
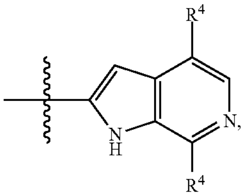
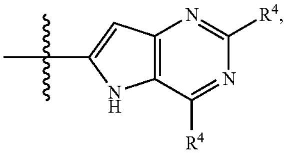
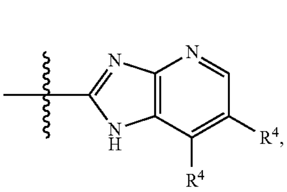
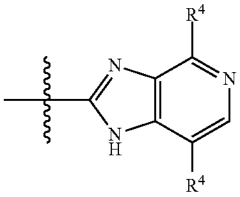,
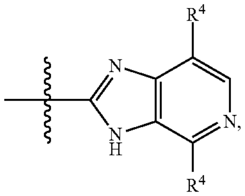 and
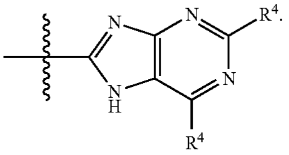

In some embodiments is a compound of Formula (IIc), or a pharmaceutically acceptable salt or solvate thereof, wherein

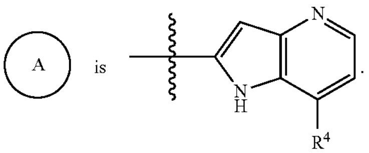

In some embodiments is a compound of Formula (IIc), or a pharmaceutically acceptable salt or solvate thereof, wherein

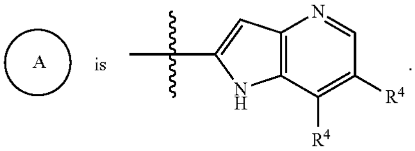

In some embodiments is a compound of Formula (IIc), or a pharmaceutically acceptable salt or solvate thereof, wherein

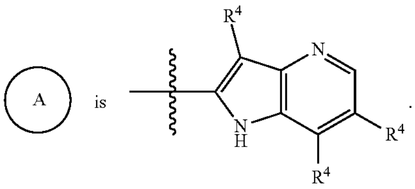

In some embodiments is a compound of Formula (IIc), or a pharmaceutically acceptable salt or solvate thereof, wherein

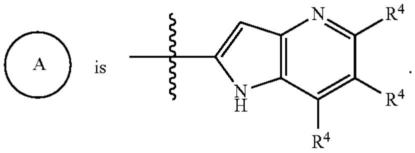

In some embodiments is a compound of Formula (IIc), or a pharmaceutically acceptable salt or solvate thereof, wherein

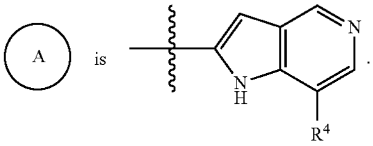

In some embodiments is a compound of Formula (IIc), or a pharmaceutically acceptable salt or solvate thereof, wherein

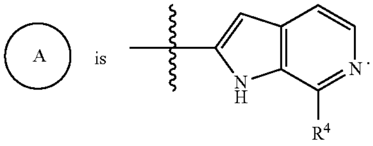

In some embodiments is a compound of Formula (IIc), or a pharmaceutically acceptable salt or solvate thereof, wherein

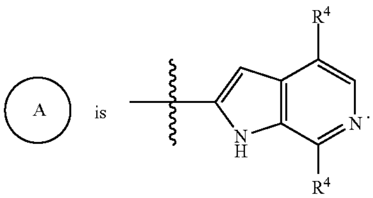

In some embodiments is a compound of Formula (IIc), or a pharmaceutically acceptable salt or solvate thereof, wherein

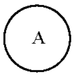 is 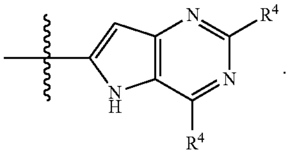.

In some embodiments is a compound of Formula (IIc), or a pharmaceutically acceptable salt or solvate thereof, wherein

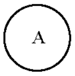 is 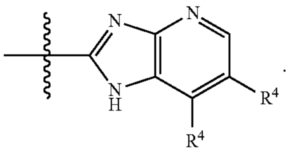.

In some embodiments is a compound of Formula (IIc), or a pharmaceutically acceptable salt or solvate thereof, wherein

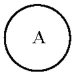 is 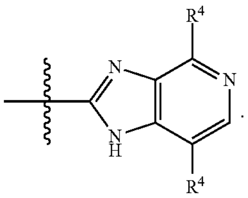.

In some embodiments is a compound of Formula (IIc), or a pharmaceutically acceptable salt or solvate thereof, wherein

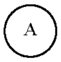 is 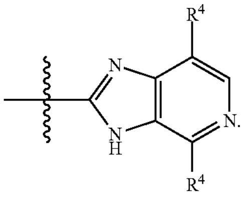.

In some embodiments is a compound of Formula (IIc), or a pharmaceutically acceptable salt or solvate thereof, wherein

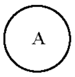 is 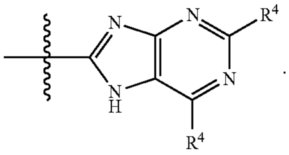.

In some embodiments is a compound of Formula (IIc), or a pharmaceutically acceptable salt or solvate thereof, wherein each $R^4$ is independently selected from halogen, $—OR^9$, $—N(R^{10})_2$, $C_{1-10}$alkyl, $C_{2-10}$alkenyl, $C_{1-10}$haloalkyl, and $—C_{1-6}$alkyl-$C_{3-12}$cycloalkyl. In some embodiments is a compound of Formula (IIc), or a pharmaceutically acceptable salt or solvate thereof, wherein each $R^4$ is independently selected from halogen, $—OR^9$, $—N(R^{10})_2$, $C_{1-10}$alkyl, and $C_{1-10}$haloalkyl. In some embodiments is a compound of Formula (IIc), or a pharmaceutically acceptable salt or solvate thereof, wherein each $R^4$ is independently selected from halogen, $—OR^9$, $—N(R^{10})_2$, $C_{1-10}$alkyl, and $C_{1-10}$haloalkyl and each $R^9$ is $C_{1-10}$alkyl. In some embodiments is a compound of Formula (IIc), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (IIc), or a pharmaceutically acceptable salt or solvate thereof, wherein each $R^4$ is independently selected from halogen and $C_{1-10}$alkyl.

In another aspect are compounds having the structure of Formula (IId):

Formula (IId)

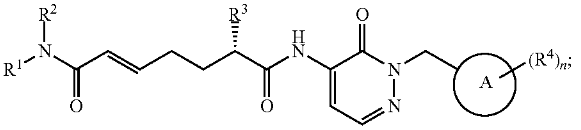

wherein:

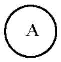

is a 9-membered bicyclic heteroaryl ring;

$R^1$ and $R^2$ are independently selected from H, $C_{1-6}$alkyl, and $—C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from $—N(H)C(O)OR^5$, $—OC(O)NR^6R^7$, $—N(H)C(O)NR^6R^7$, and $—N(H)C(O)R^8$;

each $R^4$ is independently selected from halogen, —CN, $—OR^9$, $—SR^9$, $—N(R^{10})_2$, $—S(O)R^9$, $—S(O)_2R^9$, $—NHS(O)_2R^9$, $—S(O)_2N(R^1)_2$, $—C(O)R^9$, $—C(O)OR^9$, $—OC(O)R^9$, $—C(O)N(R^{10})_2$, $—OC(O)N(R^{10})_2$, $—NR^{10}C(O)N(R^{10})_2$, $—NR^{10}C(O)R^9$, $—NR^1C(O)OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, $—C_{1-6}$alkyl-$C_{3-12}$cycloalkyl, $—C_{2-6}$alkenyl-$C_{3-12}$cycloalkyl, phenyl, $—C_{1-6}$alkyl-phenyl, $—C_{2-6}$alkenyl-phenyl, $C_{2-9}$heterocycloalkyl, and $C_{2-9}$heteroaryl, wherein phenyl, $—C_{1-6}$alkyl-phenyl, $—C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, $—C_{1-6}$alkyl-OH, $—C_{1-6}$alkyl-O—$C_{1-6}$alkyl, $—C_{1-6}$alkyl-O—C(O)$C_{1-6}$alkyl, $C_{2-9}$heterocycloalkyl, $—C_{1-6}$alkyl-$C_{2-9}$heterocycloalkyl, phenyl, $—C_{1-6}$alkyl-phenyl, and $C_{2-9}$heteroaryl, wherein $C_{2-9}$heterocycloalkyl, $—C_{1-6}$alkyl-$C_{2-9}$heterocycloalkyl, phenyl, $—C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, $—C_{1-6}$alkyl-OH, $—C_{1-6}$alkyl-O—$C_{1-6}$alkyl, and $—C_{1-6}$alkyl-N($C_{1-6}$alkyl$)_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, —$C_{1-6}$alkyl-OH, —$C_{1-6}$alkyl-O—$C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl; and n is 0, 1, 2, 3, or 4;

or a pharmaceutically acceptable salt or solvate thereof.

In some embodiments is a compound of Formula (IId), or a pharmaceutically acceptable salt or solvate thereof, wherein $R^1$ and $R^2$ are independently selected from H and $C_{1-6}$alkyl. In some embodiments is a compound of Formula (IId), or a pharmaceutically acceptable salt or solvate thereof, wherein $R^1$ and $R^2$ are each H. In some embodiments is a compound of Formula (IId), or a pharmaceutically acceptable salt or solvate thereof, wherein $R^1$ and $R^2$ are each $C_{1-6}$alkyl. In some embodiments is a compound of Formula (IId), or a pharmaceutically acceptable salt or solvate thereof, wherein $R^1$ and $R^2$ are each —$CH_3$. In some embodiments is a compound of Formula (IId), or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl. In some embodiments is a compound of Formula (IId), or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring. In some embodiments is a compound of Formula (IId), or a pharmaceutically acceptable salt or solvate thereof, wherein $R^1$ and $R^2$, together with the nitrogen to which they are attached, form an unsubstituted 3-membered heterocycloalkyl ring. In some embodiments is a compound of Formula (IId), or a pharmaceutically acceptable salt or solvate thereof, wherein $R^1$ and $R^2$, together with the nitrogen to which they are attached, form an unsubstituted 4-membered heterocycloalkyl ring. In some embodiments is a compound of Formula (IId), or a pharmaceutically acceptable salt or solvate thereof, wherein $R^1$ and $R^2$, together with the nitrogen to which they are attached, form an unsubstituted 5-membered heterocycloalkyl ring. In some embodiments is a compound of Formula (IId), or a pharmaceutically acceptable salt or solvate thereof, wherein $R^1$ and $R^2$, together with the nitrogen to which they are attached, form an unsubstituted 6-membered heterocycloalkyl ring.

In some embodiments is a compound of Formula (IId), or a pharmaceutically acceptable salt or solvate thereof, wherein $R^3$ is —N(H)C(O)O$R^5$. In some embodiments is a compound of Formula (IId), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl. In some embodiments is a compound of Formula (IId), or a pharmaceutically acceptable salt or solvate thereof, wherein $R^3$ is —N(H)C(O)O$R^5$ and $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl. In some embodiments is a compound of Formula (IId), or a pharmaceutically acceptable salt or solvate thereof, wherein $R^3$ is —N(H)C(O)O$R^5$ and $R^5$ is $C_{1-6}$alkyl. In some embodiments is a compound of Formula (IId), or a pharmaceutically acceptable salt or solvate thereof, wherein $R^3$ is —N(H)C(O)O$R^5$ and $R^5$ is —$CH_3$. In some embodiments is a compound of Formula (IId), or a pharmaceutically acceptable salt or solvate thereof, wherein $R^3$ is —N(H)C(O)O$R^5$ and $R^5$ is —$C_{1-6}$alkyl-OH. In some embodiments is a compound of Formula (IId), or a pharmaceutically acceptable salt or solvate thereof, wherein $R^3$ is —N(H)C(O)O$R^5$ and $R^5$ is —$C_{1-6}$alkyl-O—$C_{1-6}$alkyl. In some embodiments is a compound of Formula (IId), or a pharmaceutically acceptable salt or solvate thereof, wherein $R^3$ is —N(H)C(O)O$R^5$ and $R^5$ is —$C_{1-6}$alkyl-$C_{2-9}$heterocycloalkyl. In some embodiments is a compound of Formula (IId), or a pharmaceutically acceptable salt or solvate thereof, wherein $R^3$ is —N(H)C(O)O$R^5$ and $R^5$ is —$C_{1-6}$alkyl-phenyl. In some embodiments is a compound of Formula (IId), or a pharmaceutically acceptable salt or solvate thereof, wherein $R^3$ is —N(H)C(O)O$R^5$ and $R^5$ is —$CH_2$-phenyl. In some embodiments is a compound of Formula (IId), or a pharmaceutically acceptable salt or solvate thereof, wherein $R^3$ is —OC(O)N$R^6R^7$. In some embodiments is a compound of Formula (IId), or a pharmaceutically acceptable salt or solvate thereof, wherein $R^3$ is —OC(O)N$R^6R^7$ and $R^3$ is —N(H)C(O)N$R^6R^7$. In some embodiments is a compound of Formula (IId), or a pharmaceutically acceptable salt or solvate thereof, wherein $R^3$ is —OC(O)N$R^6R^7$ and $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$. In some embodiments is a compound of Formula (IId), or a pharmaceutically acceptable salt or solvate thereof, wherein $R^3$ is —OC(O)N$R^6R^7$ and $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$. In some embodiments is a compound of Formula (IId), or a pharmaceutically acceptable salt or solvate thereof, wherein $R^3$ is —OC(O)N$R^6R^7$ and $R^6$ and $R^7$ are independently selected from $C_{1-6}$alkyl. In some embodiments is a compound of Formula (IId), or a pharmaceutically acceptable salt or solvate thereof, wherein $R^3$ is —OC(O)N$R^6R^7$ and $R^6$ and $R^7$ are each —$CH_3$. In some embodiments is a compound of Formula (IId), or a pharmaceutically acceptable salt or solvate thereof, wherein $R^3$ is —N(H)C(O)$R^8$. In some embodiments is a compound of Formula (IId), or a pharmaceutically acceptable salt or solvate thereof, wherein $R^3$ is —N(H)C(O)$R^8$ and $R^8$ is —$C_{1-6}$alkyl-OH. In some embodiments is a compound of Formula (IId), or a pharmaceutically acceptable salt or solvate thereof, wherein $R^3$ is —N(H)C(O)$R^8$ and $R^8$ is —$C_{1-6}$alkyl-O—$C_{1-6}$alkyl. In some embodiments is a compound of Formula (IId), or a pharmaceutically acceptable salt or solvate thereof, wherein $R^3$ is —N(H)C(O)$R^8$ and $R^8$ is phenyl optionally substituted with one or two groups independently selected from halogen and $C_{1-6}$alkyl. In some embodiments is a compound of Formula (IId), or a pharmaceutically acceptable salt or solvate thereof, wherein $R^3$ is —N(H)C(O)$R^8$ and $R^8$ is $C_{2-9}$heteroaryl optionally substituted with one or two groups independently selected from halogen and $C_{1-6}$alkyl.

In some embodiments is a compound of Formula (IId), or a pharmaceutically acceptable salt or solvate thereof, wherein n is 0, 1, 2, or 3. In some embodiments is a compound of Formula (IId), or a pharmaceutically acceptable salt or solvate thereof, wherein n is 0. In some embodiments is a compound of Formula (IId), or a pharmaceutically acceptable salt or solvate thereof, wherein n is 1, 2, or 3. In some embodiments is a compound of Formula (IId), or a pharmaceutically acceptable salt or solvate thereof, wherein n is 1. In some embodiments is a compound of Formula (IId), or a pharmaceutically acceptable salt or solvate thereof, wherein n is 2. In some embodiments is a compound of Formula (IId), or a pharmaceutically acceptable salt or solvate thereof, wherein n is 3. In some embodiments is a compound of Formula (IId), or a pharmaceutically acceptable salt or solvate thereof, wherein n is 4.

In some embodiments is a compound of Formula (IId), or a pharmaceutically acceptable salt or solvate thereof, wherein each $R^4$ is independently selected from halogen, —$OR^9$, —C(O)$OR^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl. In some embodiments is a compound of Formula (IId), or a pharmaceutically acceptable salt or solvate thereof, wherein each $R^4$ is independently selected from halogen, —$OR^9$, —C(O)$OR^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens. In some embodiments is a compound of Formula (IId), or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl. In some embodiments is a compound of Formula (IId), or a pharmaceutically acceptable salt or solvate thereof, wherein

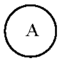

is selected from

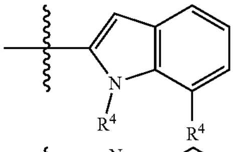 ,
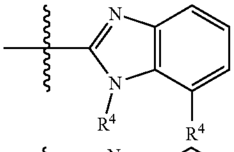 ,
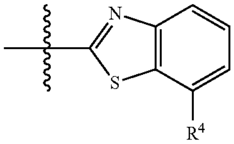 ,
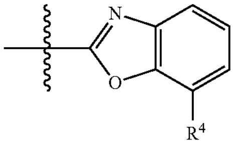 ,

-continued

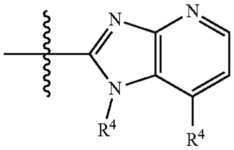 ,
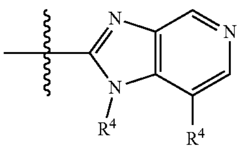 ,
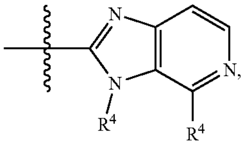 and
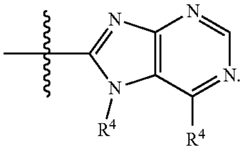

In some embodiments is a compound of Formula (IId), or a pharmaceutically acceptable salt or solvate thereof, wherein

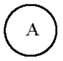

is selected from

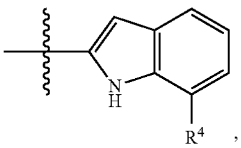 ,
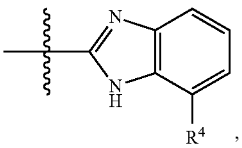 ,
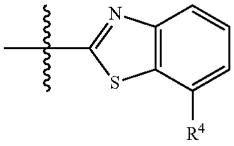 ,
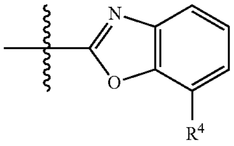 ,
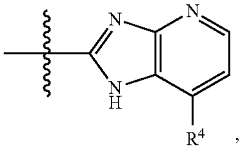 ,
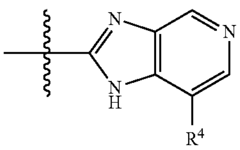 ,
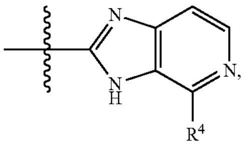 and
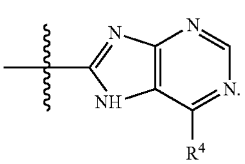

In some embodiments is a compound of Formula (IId), or a pharmaceutically acceptable salt or solvate thereof, wherein

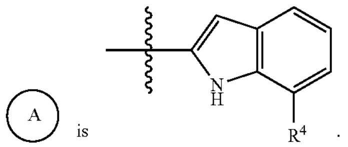

In some embodiments is a compound of Formula (IId), or a pharmaceutically acceptable salt or solvate thereof, wherein

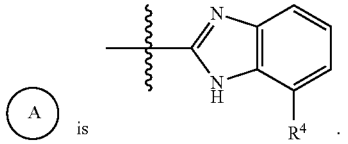

In some embodiments is a compound of Formula (IId), or a pharmaceutically acceptable salt or solvate thereof, wherein

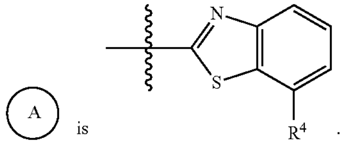

In some embodiments is a compound of Formula (IId), or a pharmaceutically acceptable salt or solvate thereof, wherein

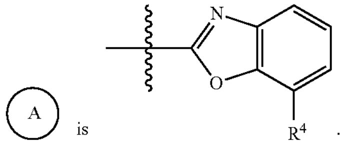

In some embodiments is a compound of Formula (IId), or a pharmaceutically acceptable salt or solvate thereof, wherein

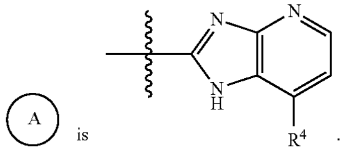

In some embodiments is a compound of Formula (IId), or a pharmaceutically acceptable salt or solvate thereof, wherein

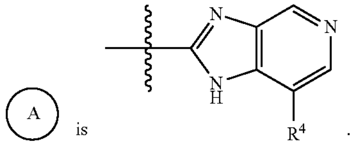

In some embodiments is a compound of Formula (IId), or a pharmaceutically acceptable salt or solvate thereof, wherein

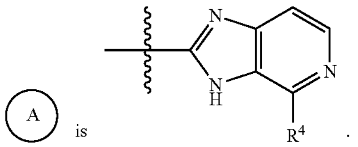

In some embodiments is a compound of Formula (IId), or a pharmaceutically acceptable salt or solvate thereof, wherein

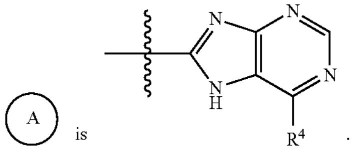

In some embodiments is a compound of Formula (IId), or a pharmaceutically acceptable salt or solvate thereof, wherein $R^4$ is $C_{1-10}$alkyl. In some embodiments is a compound of Formula (IId), or a pharmaceutically acceptable salt or solvate thereof, wherein $R^4$ is $C_{1-10}$haloalkyl. In some embodiments is a compound of Formula (IId), or a pharmaceutically acceptable salt or solvate thereof, wherein $R^4$ is —$OR^9$. In some embodiments is a compound of Formula (IId), or a pharmaceutically acceptable salt or solvate thereof, wherein $R^4$ is —$OR^9$ and $R^9$ is —$C_{1-6}$alkyl-phenyl optionally substituted with one or two halogens.

In another aspect are compounds having the structure of Formula (IIe):

Formula (IIe)

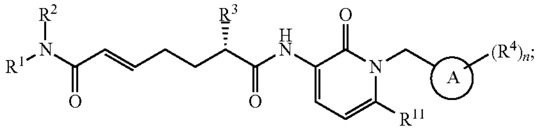

wherein:

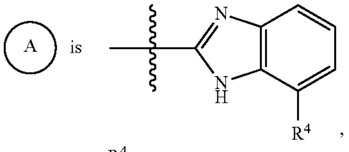

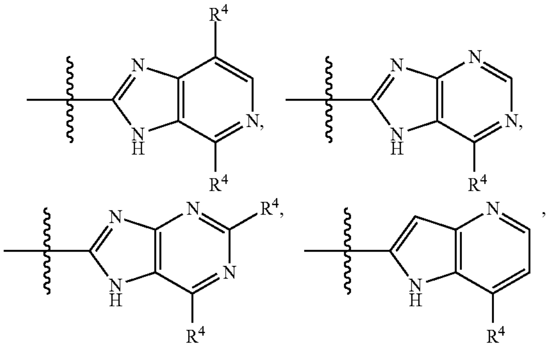

-continued

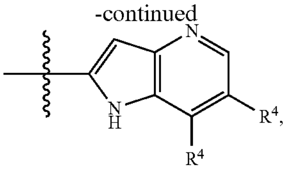

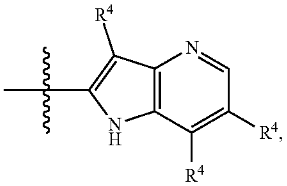

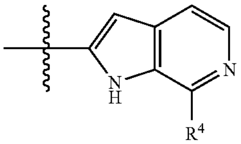

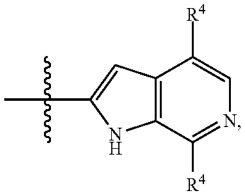

and

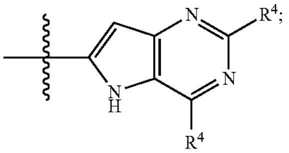

$R^1$ and $R^2$ are independently selected from $C_{1-6}$alkyl;

$R^3$ is selected from —N(H)C(O)OR$^5$ and —OC(O)NR$^6$R$^7$;

each $R^4$ is independently selected from halogen, —OR$^9$, —N(R$^{10}$)$_2$, $C_{1-10}$alkyl, $C_{2-10}$alkenyl, $C_{2-10}$alkynyl, $C_{1-10}$haloalkyl, $C_{3-12}$cycloalkyl, and —$C_{1-6}$alkyl-$C_{3-12}$cycloalkyl;

$R^5$ is $C_{1-6}$alkyl;

$R^6$ and $R^7$ are independently selected from $C_{1-6}$alkyl;

each $R^9$ is independently selected from $C_{1-10}$alkyl, $C_{1-10}$haloalkyl, and —$C_{1-6}$alkyl-phenyl;

each $R^{10}$ is independently selected from H and $C_{1-10}$alkyl; and $R^{11}$ is selected from H, halogen, $C_{1-6}$alkyl, and $C_{1-6}$haloalkyl;

or a pharmaceutically acceptable salt or solvate thereof.

In some embodiments is a compound of Formula (IIe), or a pharmaceutically acceptable salt or solvate thereof, wherein $R^1$ and $R^2$ are each —$CH_3$.

In some embodiments is a compound of Formula (IIe), or a pharmaceutically acceptable salt or solvate thereof, wherein $R^3$ is —N(H)C(O)OR$^5$. In some embodiments is a compound of Formula (IIe), or a pharmaceutically acceptable salt or solvate thereof, wherein $R^3$ is —N(H)C(O)OR$^5$ and $R^5$ is —$CH_3$. In some embodiments is a compound of Formula (IIe), or a pharmaceutically acceptable salt or solvate thereof, wherein $R^3$ is —OC(O)NR$^6$R$^7$. In some embodiments is a compound of Formula (IIe), or a pharmaceutically acceptable salt or solvate thereof, wherein $R^3$ is —OC(O)NR$^6$R$^7$ and $R^6$ and $R^7$ are each —$CH_3$.

In some embodiments is a compound of Formula (IIe), or a pharmaceutically acceptable salt or solvate thereof, wherein

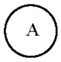 is 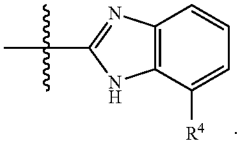

In some embodiments is a compound of Formula (IIe), or a pharmaceutically acceptable salt or solvate thereof, wherein

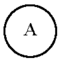 is 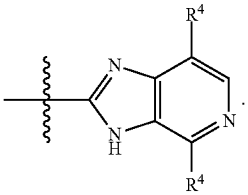

In some embodiments is a compound of Formula (IIe), or a pharmaceutically acceptable salt or solvate thereof, wherein

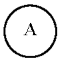 is 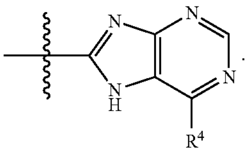

In some embodiments is a compound of Formula (IIe), or a pharmaceutically acceptable salt or solvate thereof, wherein

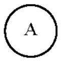 is 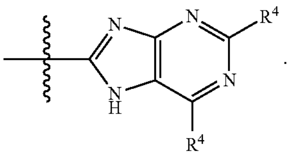

In some embodiments is a compound of Formula (IIe), or a pharmaceutically acceptable salt or solvate thereof, wherein

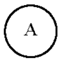 is 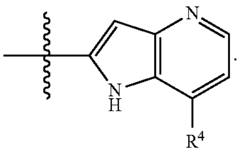

In some embodiments is a compound of Formula (IIe), or a pharmaceutically acceptable salt or solvate thereof, wherein

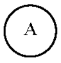 is 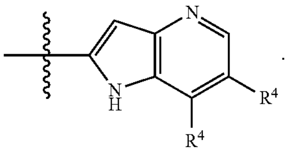

In some embodiments is a compound of Formula (IIe), or a pharmaceutically acceptable salt or solvate thereof, wherein

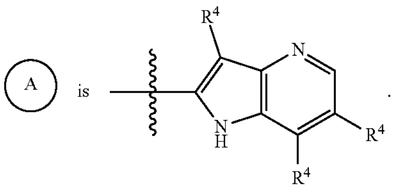

In some embodiments is a compound of Formula (IIe), or a pharmaceutically acceptable salt or solvate thereof, wherein

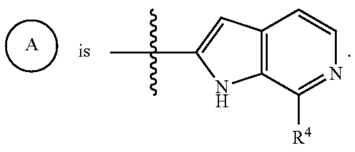

In some embodiments is a compound of Formula (IIe), or a pharmaceutically acceptable salt or solvate thereof, wherein

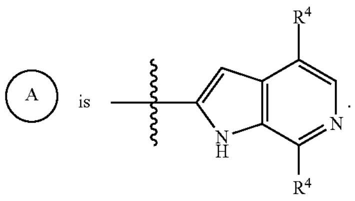

In some embodiments is a compound of Formula (IIe), or a pharmaceutically acceptable salt or solvate thereof, wherein

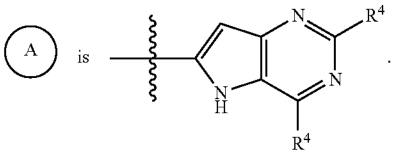

In some embodiments is a compound of Formula (IIe), or a pharmaceutically acceptable salt or solvate thereof, wherein each $R^4$ is independently selected from halogen, —$OR^9$, —$N(R^{10})_2$, $C_{1-10}$alkyl, $C_{2-10}$alkenyl, $C_{1-10}$haloalkyl, and —$C_{1-6}$alkyl-$C_{3-12}$cycloalkyl. In some embodiments is a compound of Formula (IIe), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl. In some embodiments is a compound of Formula (IIe), or a pharmaceutically acceptable salt or solvate thereof, wherein each $R^4$ is independently selected from halogen, —$OR^9$, —$N(R^{10})_2$, $C_{1-10}$alkyl, and $C_{1-10}$haloalkyl and each $R^9$ is $C_{1-10}$alkyl. In some embodiments is a compound of Formula (IIe), or a pharmaceutically acceptable salt or solvate thereof, wherein each $R^4$ is independently selected from halogen, $C_{1-10}$alkyl, and $C_{1-10}$haloalkyl. In some embodiments is a compound of Formula (IIe), or a pharmaceutically acceptable salt or solvate thereof, wherein each $R^4$ is independently selected from halogen and $C_{1-10}$alkyl.

Described herein is a compound of Formula (IIe), or a pharmaceutically acceptable salt or solvate thereof, wherein:

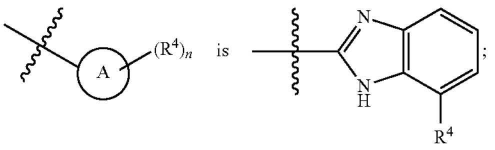

$R^1$ and $R^2$ are independently selected from $C_{1-6}$alkyl;

$R^3$ is selected from —N(H)C(O)$OR^5$ and —OC(O)$NR^6R^7$;

$R^4$ is $C_{1-10}$alkyl;

$R^5$ is $C_{1-6}$alkyl;

$R^6$ and $R^7$ are independently selected from $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

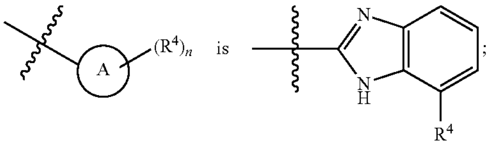

$R^1$ and $R^2$ are independently selected from $C_{1-6}$alkyl;

$R^3$ is —N(H)C(O)$OR^5$;

$R^4$ is $C_{1-10}$alkyl;

$R^5$ is $C_{1-6}$alkyl; and $R^{11}$ is H.

Described herein is a compound of Formula (IIe), or a pharmaceutically acceptable salt or solvate thereof, wherein:

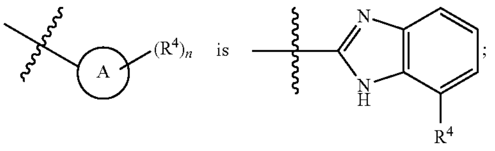

$R^1$ and $R^2$ are independently selected from $C_{1-6}$alkyl;

$R^3$ is —N(H)C(O)$OR^5$;

$R^4$ is $C_{1-10}$alkyl;

$R^5$ is $C_{1-6}$alkyl; and $R^{11}$ is halogen.

Described herein is a compound of Formula (IIe), or a pharmaceutically acceptable salt or solvate thereof, wherein:

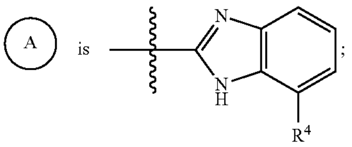

$R^1$ and $R^2$ are independently selected from $C_{1-6}$alkyl;

$R^3$ is —N(H)C(O)$OR^5$;

$R^4$ is $C_{1-10}$alkyl;

$R^5$ is $C_{1-6}$alkyl; and $R^{11}$ is $C_{1-6}$alkyl.

Described herein is a compound of Formula (IIe), or a pharmaceutically acceptable salt or solvate thereof, wherein:

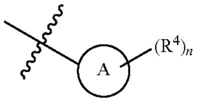 is 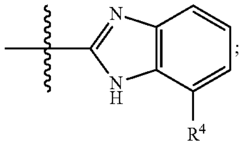

$R^1$ and $R^2$ are independently selected from $C_{1-6}$alkyl;

$R^3$ is —OC(O)$NR^6R^7$;

$R^4$ is $C_{1-10}$alkyl;

$R^6$ and $R^7$ are independently selected from $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

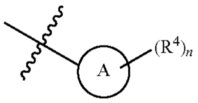 is 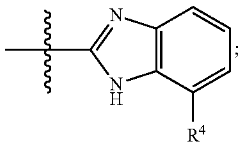

$R^1$ and $R^2$ are independently selected from $C_{1-6}$alkyl;

$R^3$ is —OC(O)$NR^6R^7$;

$R^4$ is $C_{1-10}$alkyl;

$R^6$ and $R^7$ are independently selected from $C_{1-6}$alkyl; and $R^{11}$ is H.

Described herein is a compound of Formula (IIe), or a pharmaceutically acceptable salt or solvate thereof, wherein:

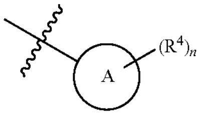 is 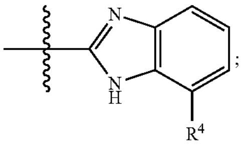

$R^1$ and $R^2$ are independently selected from $C_{1-6}$alkyl;

$R^3$ is —OC(O)$NR^6R^7$;

$R^4$ is $C_{1-10}$alkyl;

$R^6$ and $R^7$ are independently selected from $C_{1-6}$alkyl; and $R^{11}$ is halogen.

Described herein is a compound of Formula (IIe), or a pharmaceutically acceptable salt or solvate thereof, wherein:

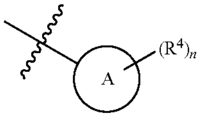 is 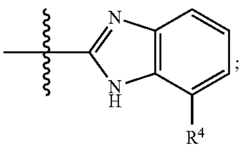

$R^1$ and $R^2$ are independently selected from $C_{1-6}$alkyl;

$R^3$ is —OC(O)$NR^6R^7$;

$R^4$ is $C_{1-10}$alkyl;

$R^6$ and $R^7$ are independently selected from $C_{1-6}$alkyl; and $R^{11}$ is $C_{1-6}$alkyl.

Described herein is a compound of Formula (IIe), or a pharmaceutically acceptable salt or solvate thereof, wherein:

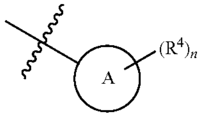 is 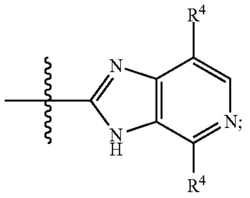

$R^1$ and $R^2$ are independently selected from $C_{1-6}$alkyl;

$R^3$ is selected from —N(H)C(O)$OR^5$ and —OC(O)$NR^6R^7$;

each $R^4$ is independently selected from halogen and $C_{1-10}$alkyl;

$R^5$ is $C_{1-6}$alkyl;

$R^6$ and $R^7$ are independently selected from $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

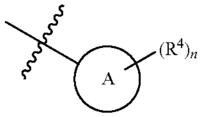 is 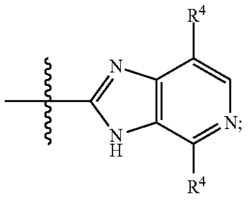

$R^1$ and $R^2$ are independently selected from $C_{1-6}$alkyl;

$R^3$ is —N(H)C(O)$OR^5$;

each $R^4$ is independently selected from halogen and $C_{1-10}$alkyl;

$R^5$ is $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

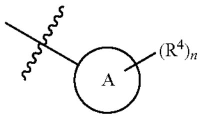 is 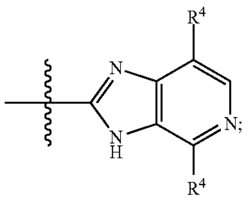

$R^1$ and $R^2$ are independently selected from $C_{1-6}$alkyl;

$R^3$ is —N(H)C(O)$OR^5$;

each $R^4$ is independently selected from halogen and $C_{1-10}$alkyl;

$R^5$ is $C_{1-6}$alkyl; and $R^{11}$ is H.

Described herein is a compound of Formula (IIe), or a pharmaceutically acceptable salt or solvate thereof, wherein:

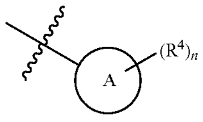 is 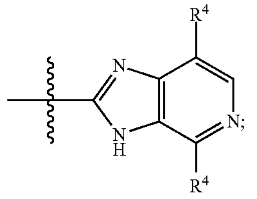

$R^1$ and $R^2$ are independently selected from $C_{1-6}$alkyl;

$R^3$ is —N(H)C(O)$OR^5$;

each $R^4$ is independently selected from halogen and $C_{1-10}$alkyl;

$R^5$ is $C_{1-6}$alkyl; and $R^{11}$ is halogen.

Described herein is a compound of Formula (IIe), or a pharmaceutically acceptable salt or solvate thereof, wherein:

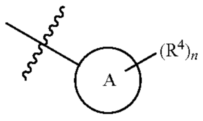 is 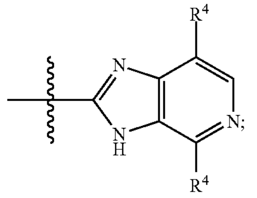

$R^1$ and $R^2$ are independently selected from $C_{1-6}$alkyl;

$R^3$ is —N(H)C(O)$OR^5$;

each $R^4$ is independently selected from halogen and $C_{1-10}$alkyl;

$R^5$ is $C_{1-6}$alkyl; and $R^{11}$ is $C_{1-6}$alkyl.

Described herein is a compound of Formula (IIe), or a pharmaceutically acceptable salt or solvate thereof, wherein:

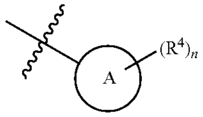 is 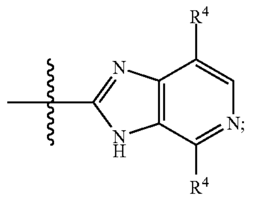

$R^1$ and $R^2$ are independently selected from $C_{1-6}$alkyl;

$R^3$ is —OC(O)$NR^6R^7$;

each $R^4$ is independently selected from halogen and $C_{1-10}$alkyl;

$R^6$ and $R^7$ are independently selected from $C_{1-6}$alkyl; and $R^{11}$ is H.

Described herein is a compound of Formula (IIe), or a pharmaceutically acceptable salt or solvate thereof, wherein:

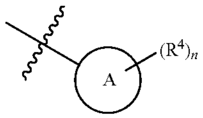 is 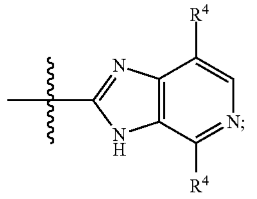

$R^1$ and $R^2$ are independently selected from $C_{1-6}$alkyl;

$R^3$ is —OC(O)$NR^6R^7$;

each $R^4$ is independently selected from halogen and $C_{1-10}$alkyl;

$R^6$ and $R^7$ are independently selected from $C_{1-6}$alkyl; and $R^{11}$ is halogen.

Described herein is a compound of Formula (IIe), or a pharmaceutically acceptable salt or solvate thereof, wherein:

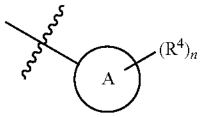 is 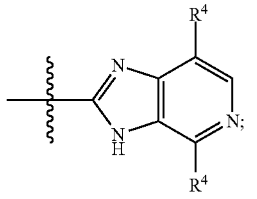

$R^1$ and $R^2$ are independently selected from $C_{1-6}$alkyl;

$R^3$ is —OC(O)$NR^6R^7$;

each $R^4$ is independently selected from halogen and $C_{1-10}$alkyl;

$R^6$ and $R^7$ are independently selected from $C_{1-6}$alkyl; and $R^{11}$ is halogen.

Described herein is a compound of Formula (IIe), or a pharmaceutically salt or solvate thereof, wherein:

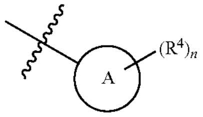 is 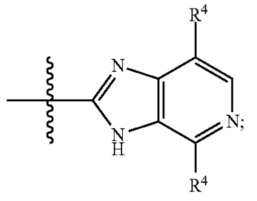

$R^1$ and $R^2$ are independently selected from $C_{1-6}$alkyl;

$R^3$ is —OC(O)$NR^6R^7$;

each $R^4$ is independently selected from halogen and $C_{1-10}$alkyl;

$R^6$ and $R^7$ are independently selected from $C_{1-6}$alkyl; and $R^{11}$ is $C_{1-6}$alkyl.

Described herein is a compound of Formula (IIe), or a pharmaceutically acceptable salt or solvate thereof, wherein:

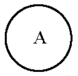 is 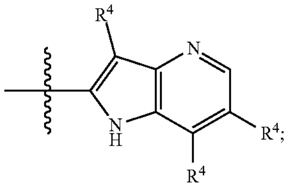

$R^1$ and $R^2$ are independently selected from $C_{1-6}$alkyl;

$R^3$ is selected from —N(H)C(O)$OR^5$ and —OC(O)$NR^6R^7$;

each $R^4$ is independently selected from halogen and $C_{1-10}$alkyl;

$R^5$ is $C_{1-6}$alkyl;

$R^6$ and $R^7$ are independently selected from $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

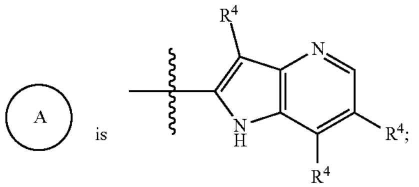

$R^1$ and $R^2$ are independently selected from $C_{1-6}$alkyl;

$R^3$ is —N(H)C(O)O$R^5$;

each $R^4$ is independently selected from halogen and $C_{1-10}$alkyl;

$R^5$ is $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

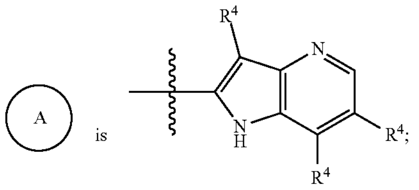

$R^1$ and $R^2$ are independently selected from $C_{1-6}$alkyl;

$R^3$ is —N(H)C(O)O$R^5$;

each $R^4$ is independently selected from halogen and $C_{1-10}$alkyl;

$R^5$ is $C_{1-6}$alkyl; and $R^{11}$ is H.

Described herein is a compound of Formula (IIe), or a pharmaceutically acceptable salt or solvate thereof, wherein:

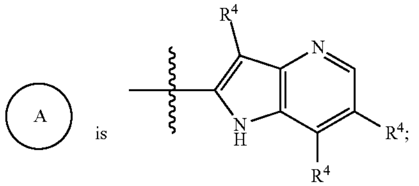

$R^1$ and $R^2$ are independently selected from $C_{1-6}$alkyl;

$R^3$ is —N(H)C(O)O$R^5$;

each $R^4$ is independently selected from halogen and $C_{1-10}$alkyl;

$R^5$ is $C_{1-6}$alkyl; and $R^{11}$ is halogen.

Described herein is a compound of Formula (IIe), or a pharmaceutically acceptable salt or solvate thereof, wherein:

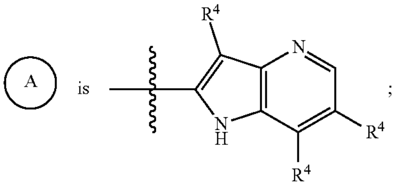

$R^1$ and $R^2$ are independently selected from $C_{1-6}$alkyl;

$R^3$ is —N(H)C(O)O$R^5$;

each $R^4$ is independently selected from halogen and $C_{1-10}$alkyl;

$R^5$ is $C_{1-6}$alkyl; and $R^{11}$ is $C_{1-6}$alkyl.

Described herein is a compound of Formula (IIe), or a pharmaceutically acceptable salt or solvate thereof, wherein:

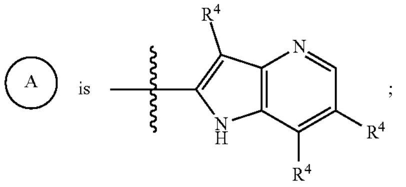

$R^1$ and $R^2$ are independently selected from $C_{1-6}$alkyl;

$R^3$ is —OC(O)N$R^6R^7$;

each $R^4$ is independently selected from halogen and $C_{1-10}$alkyl;

$R^6$ and $R^7$ are independently selected from $C_{1-6}$alkyl; and $R^{11}$ is selected from H, halogen, and $C_{1-6}$alkyl.

Described herein is a compound of Formula (IIe), or a pharmaceutically acceptable salt or solvate thereof, wherein:

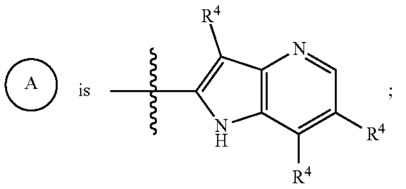

$R^1$ and $R^2$ are independently selected from $C_{1-6}$alkyl;

$R^3$ is —OC(O)N$R^6R^7$;

each $R^4$ is independently selected from halogen and $C_{1-10}$alkyl;

$R^6$ and $R^7$ are independently selected from $C_{1-6}$alkyl; and $R^{11}$ is H.

Described herein is a compound of Formula (IIe), or a pharmaceutically acceptable salt or solvate thereof, wherein:

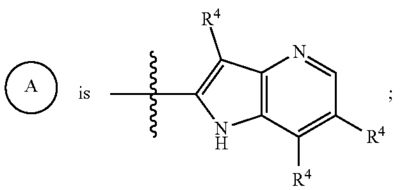

$R^1$ and $R^2$ are independently selected from $C_{1-6}$alkyl;

$R^3$ is —OC(O)N$R^6R^7$;

each $R^4$ is independently selected from halogen and $C_{1-10}$alkyl;

$R^6$ and $R^7$ are independently selected from $C_{1-6}$alkyl; and $R^{11}$ is halogen.

Described herein is a compound of Formula (IIe), or a pharmaceutically acceptable salt or solvate thereof, wherein:

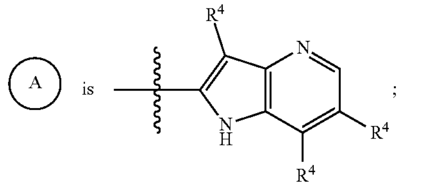

$R^1$ and $R^2$ are independently selected from $C_{1-6}$alkyl;

$R^3$ is —OC(O)NR$^6$R$^7$;

each $R^4$ is independently selected from halogen and $C_{1-10}$alkyl;

$R^6$ and $R^7$ are independently selected from $C_{1-6}$alkyl; and $R^{11}$ is $C_{1-6}$alkyl.

In some embodiments is a compound selected from: tert-butyl 2-[[3-[[(E,2S)-7-(dimethylamino)-2-(methoxycarbonylamino)-7-oxo-hept-5-enoyl]amino]-2-oxo-1-pyridyl]methyl]-4-isobutyl-benzimidazole-1-carboxylate; methyl N-[(E,1S)-6-(dimethylamino)-1-[[1-[(4-isobutyl-1H-benzimidazol-2-yl)methyl]-2-oxo-3-pyridyl]carbamoyl]-6-oxo-hex-4-enyl]carbamate; tert-butyl (S,E)-2-((3-(7-amino-2-(((benzyloxy)carbonyl)amino)-7-oxohept-5-enamido)-2-oxopyridin-1(2H)-yl)methyl)-4-isobutyl-1H-benzo[d]imidazole-1-carboxylate; benzyl (S,E)-(7-amino-1-((1-((4-isobutyl-1H-benzo[d]imidazol-2-yl)methyl)-2-oxo-1,2-dihydropyridin-3-yl)amino)-1,7-dioxohept-5-en-2-yl) carbamate; tert-butyl (S,E)-2-((3-(7-amino-2-((methoxycarbonyl)amino)-7-oxohept-5-enamido)-2-oxopyridin-1(2H)-yl)methyl)-4-isobutyl-1H-benzo[d]imidazole-1-carboxylate; methyl (S,E)-(7-amino-1-((1-((4-isobutyl-1H-benzo[d]imidazol-2-yl)methyl)-2-oxo-1,2-dihydropyridin-3-yl)amino)-1,7-dioxohept-5-en-2-yl) carbamate; tert-butyl (S,E)-2-((3-(2-(((benzyloxy)carbonyl)amino)-7-(dimethylamino)-7-oxohept-5-enamido)-2-oxopyridin-1(2H)-yl)methyl)-4-isobutyl-1H-benzo[d]imidazole-1-carboxylate; benzyl (S,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate; tert-butyl 2-((3-((2S,E)-7-amino-7-oxo-2-((((tetrahydrofuran-3-yl)oxy)carbonyl)amino)hept-5-enamido)-2-oxopyridin-1(2H)-yl)methyl)-4-isobutyl-1H-benzo[d]imidazole-1-carboxylate; (tetrahydrofuran-3-yl) methyl ((S,E)-7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate; tetrahydrofuran-3-yl ((S,E)-7-amino-1-((1-((4-isobutyl-1H-benzo[d]imidazol-2-yl)methyl)-2-oxo-1,2-dihydropyridin-3-yl)amino)-1,7-dioxohept-5-en-2-yl)carbamate; tert-butyl 2-((3-((2S,E)-7-amino-7-oxo-2-((((tetrahydrofuran-3-yl)methoxy)carbonyl)amino)hept-5-enamido)-2-oxopyridin-1(2H)-yl)methyl)-4-isobutyl-1H-benzo[d]imidazole-1-carboxylate; (tetrahydrofuran-3-yl)methyl ((S,E)-7-amino-1-((1-((4-isobutyl-1H-benzo[d]imidazol-2-yl)methyl)-2-oxo-1,2-dihydropyridin-3-yl)amino)-1,7-dioxohept-5-en-2-yl) carbamate; 2-hydroxyethyl (S,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl) carbamate; tert-butyl (S,E)-4-isobutyl-2-((3-(2-((methoxycarbonyl)amino)-7-(methylamino)-7-oxohept-5-enamido)-2-oxopyridin-1(2H)-yl)methyl)-1H-benzo[d]imidazole-1-carboxylate; methyl (S,E)-(1-((1-((4-isobutyl-1H-benzo[d]imidazol-2-yl)methyl)-2-oxo-1,2-dihydropyridin-3-yl)amino)-7-(methylamino)-1,7-dioxohept-5-en-2-yl)carbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-4-isobutyl-1H-benzo[d]imidazole-1-carboxylate; (S,E)-7-(dimethylamino)-1-((1-((7-isobutyl-1H-benzo[d]imidazol-2-yl)methyl)-2-oxo-1,2-dihydropyridin-3-yl)amino)-1,7-dioxohept-5-en-2-yl dimethylcarbamate; (S,E)-1-((1-((5,6-difluoro-7-isobutyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-4-isobutyl-1H-benzo[d]imidazole-1-carboxylate; methyl (S,E)-(1-((1-((5,6-difluoro-7-isobutyl-1H-benzo[d]imidazol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-isobutyl-1H-benzo[d]imidazole-1-carboxylate; (S,E)-7-(dimethylamino)-1-((1-((5-fluoro-7-isobutyl-1H-benzo[d]imidazol-2-yl)methyl)-2-oxo-1,2-dihydropyridin-3-yl)amino)-1,7-dioxohept-5-en-2-yl dimethylcarbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-6-fluoro-4-isobutyl-1H-benzo[d]imidazole-1-carboxylate; methyl (S,E)-(7-(dimethylamino)-1-((1-((6-fluoro-4-isobutyl-1H-benzo[d]imidazol-2-yl)methyl)-2-oxo-1,2-dihydropyridin-3-yl)amino)-1,7-dioxohept-5-en-2-yl)carbamate; (S,E)-6-(3,3-dimethylureido)-N7-(1-((5-fluoro-7-isobutyl-1H-benzo[d]imidazol-2-yl)methyl)-2-oxo-1,2-dihydropyridin-3-yl)-N1,N1-dimethylhept-2-enediamide; tert-butyl (S,E)-2-((3-(7-(dimethylamino)-2-(3,3-dimethylureido)-7-oxohept-5-enamido)-2-oxopyridin-1(2H)-yl)methyl)-6-fluoro-4-isobutyl-1H-benzo[d]imidazole-1-carboxylate; methyl (R,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate; tert-butyl (S,E)-2-((3-(7-(dimethylamino)-2-(3,3-dimethylureido)-7-oxohept-5-enamido)-2-oxopyridin-1(2H)-yl)methyl)-4-isobutyl-1H-benzo[d]imidazole-1-carboxylate; (S,E)-6-(3,3-dimethylureido)-N7-(1-((4-isobutyl-1H-benzo[d]imidazol-2-yl)methyl)-2-oxo-1,2-dihydropyridin-3-yl)-N1,N1-dimethylhept-2-enediamide; tert-butyl (S,E)-2-((3-(7-(dimethylamino)-2-(3-(2-methoxyethyl)-3-methylureido)-7-oxohept-5-enamido)-2-oxopyridin-1(2H)-yl)methyl)-6-fluoro-4-isobutyl-1H-benzo[d]imidazole-1-carboxylate; (S,E)-N7-(1-((5-fluoro-7-isobutyl-1H-benzo[d]imidazol-2-yl)methyl)-2-oxo-1,2-dihydropyridin-3-yl)-6-(3-(2-methoxyethyl)-3-methylureido)-N1,N1-dimethylhept-2-enediamide; tert-butyl (S,E)-2-((3-(7-(dimethylamino)-2-((methoxycarbonyl)amino)-7-oxohept-5-enamido)-2-oxopyridin-1(2H)-yl)methyl)-4-isobutyl-1H-imidazo[4,5-c]pyridine-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-7-isobutyl-3H-imidazo[4,5-b]pyridine-3-carboxylate; methyl (S,E)-(7-(dimethylamino)-1-((1-((7-isobutyl-3H-imidazo[4,5-b]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((4-isobutyl-1H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((6-isobutyl-2-methyl-9H-purin-8-yl)methyl)-2-oxo-1,2-dihydropyridin-3-yl)amino)-1,7-dioxohept-5-en-2-yl)carbamate; tert-butyl (S,E)-8-((3-(7-(dimethylamino)-2-((methoxycarbonyl)amino)-7-oxohept-5-enamido)-2-oxopyridin-1(2H)-yl)methyl)-6-isobutyl-2- methyl-9H-purine-9-carboxylate; methyl (S,E)-(1-((1-((6-(2-cyclopropylethyl)-9H-purin-8-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1,7-dioxo-1-((2-oxo-1-((6-pentyl-9H-purin-8-yl)methyl)-1,2-dihydropyridin-3-yl)amino)hept-5-en-2-yl)carbamate; methyl N-[(E,1S)-6-(dimethylamino)-1-[[1-[[6-(2-methylprop-1-enyl)-9H-purin-8-yl]methyl]-2-oxo-3-pyridyl]carbamoyl]-6-oxo-hex-4-enyl]carbamate; methyl (S,E)-(7-(dimethylamino)-1-((1-((6-isobutyl-9H-purin-8-yl)methyl)-2-oxo-1,2-dihydropyridin-3-yl)amino)-1,7-dioxohept-5-en-2-yl)carbamate; (S,E)-7-(dimethylamino)-1-((1-((6-(2-methylprop-1-en-1-yl)-9H-purin-8-yl)methyl)-2-oxo-1,2-dihydropyridin-3-yl)amino)-1,7-dioxohept-5-en-2-yl dimethylcarbamate; (S,E)-7-(dimethylamino)-1-((1-((6-isobutyl-9H-purin-8-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((7-(2-methylprop-1-en-1-yl)-3H-imidazo[4,5-b]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate; methyl (S,E)-(1-((1-((6-cyclohexyl-9H-purin-8-yl)methyl)-2-oxo-1,2-dihydropyridin-3-yl)amino)-7-(dimethylamino)-1,7-dioxohept-5-en-2-yl)carbamate; (S,E)-1-((1-((6-cyclohexyl-9H-purin-8-yl)methyl)-2-oxo-1,2-dihydropyridin-3-yl)amino)-7-(dimethylamino)-1,7-dioxohept-5-en-2-yl dimethylcarbamate; methyl (S,E)-(7-(dimethylamino)-1-((1-((7-fluoro-4-isobutyl-1H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((2-methyl-6-(2-methylprop-1-en-1-yl)-9H-purin-8-yl)methyl)-2-oxo-1,2-dihydropyridin-3-yl)amino)-1,7-dioxohept-5-en-2-yl)carbamate; methyl (S,E)-(7-(dimethylamino)-1-((1-((7-(2-methylprop-1-en-1-yl)-3H-imidazo[4,5-c]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((7-fluoro-4-isobutyl-1H-imidazo[4,5-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate; methyl ((S,E)-7-(dimethylamino)-1,7-dioxo-1-((2-oxo-1-((6-((E)-styryl)-9H-purin-8-yl)methyl)-1,2-dihydropyridin-3-yl)amino)hept-5-en-2-yl)carbamate; methyl (S,E)-(7-(dimethylamino)-1-((1-((7-isobutyl-3H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((4-isobutyl-6-methyl-1H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((6-methyl-4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1,7-dioxo-1-((2-oxo-1-((6-phenethyl-7H-purin-8-yl)methyl)-1,2-dihydropyridin-3-yl)amino)hept-5-en-2-yl)carbamate; (S,E)-7-(dimethylamino)-1,7-dioxo-1-((2-oxo-1-((6-phenethyl-9H-purin-8-yl)methyl)-1,2-dihydropyridin-3-yl)amino)hept-5-en-2-yl dimethylcarbamate; (S,E)-7-(dimethylamino)-1-((1-((7-(2-methylprop-1-en-1-yl)-3H-imidazo[4,5-c]pyridin-2-yl)methyl)-2-oxo-1,2-dihydropyridin-3-yl)amino)-1,7-dioxohept-5-en-2-yl dimethylcarbamate; (S,E)-7-(dimethylamino)-1-((1-((7-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate; methyl ((S,E)-1-((1-((6-((E)-2-cyclopropylvinyl)-9H-purin-8-yl)methyl)-2-oxo-1,2-dihydropyridin-3-yl)amino)-7-(dimethylamino)-1,7-dioxohept-5-en-2-yl)carbamate; tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-isobutyl-benzimidazole-1-carboxylate; methyl N-[(E,1S)-1-[[1-[(5,7-difluoro-4-isobutyl-1H-benzimidazol-2-yl)methyl]-2-oxo-3-pyridyl]carbamoyl]-6-(dimethylamino)-6-oxo-hex-4-enyl]carbamate; (S,E)-tert-butyl 2-((3-(2-((tert-butoxycarbonyl)amino)-7-(dimethylamino)-7-oxohept-5-enamido)-2-oxopyridin-1(2H)-yl)methyl)-4-isobutyl-1H-benzo[d]imidazole-1-carboxylate; (S,E)-N7-(1-((4-isobutyl-1H-benzo[d]imidazol-2-yl)methyl)-2-oxo-1,2-dihydropyridin-3-yl)-N1,N1-dimethyl-6-(oxazole-5-carboxamido)hept-2-enediamide; (S,E)-N7-(1-((4-isobutyl-1H-benzo[d]imidazol-2-yl)methyl)-2-oxo-1,2-dihydropyridin-3-yl)-N1,N1-dimethyl-6-(pyrimidine-2-carboxamido)hept-2-enediamide; (S,E)-6-(2-fluorobenzamido)-N7-(1-((4-isobutyl-1H-benzo[d]imidazol-2-yl)methyl)-2-oxo-1,2-dihydropyridin-3-yl)-N1,N1-dimethylhept-2-enediamide; (S,E)-N7-(1-((4-isobutyl-1H-benzo[d]imidazol-2-yl)methyl)-2-oxo-1,2-dihydropyridin-3-yl)-N1,N1-dimethyl-6-(oxazole-2-carboxamido)hept-2-enediamide; (S,E)-N7-(1-((4-isobutyl-1H-benzo[d]imidazol-2-yl)methyl)-2-oxo-1,2-dihydropyridin-3-yl)-N1,N1-dimethyl-6-(1-methyl-1H-imidazole-5-carboxamido)hept-2-enediamide; (S,E)-N7-(1-((4-isobutyl-1H-benzo[d]imidazol-2-yl)methyl)-2-oxo-1,2-dihydropyridin-3-yl)-N1,N1-dimethyl-6-(1-methyl-1H-imidazole-2-carboxamido)hept-2-enediamide; (S,E)-N7-(1-((4-isobutyl-1H-benzo[d]imidazol-2-yl)methyl)-2-oxo-1,2-dihydropyridin-3-yl)-N1,N1-dimethyl-6-(picolinamido)hept-2-enediamide; (S,E)-N7-(1-((4-isobutyl-1H-benzo[d]imidazol-2-yl)methyl)-2-oxo-1,2-dihydropyridin-3-yl)-6-(3-methoxypropanamido)-N1,N1-dimethylhept-2-enediamide; (S,E)-N7-(1-((7-isobutyl-1H-benzo[d]imidazol-2-yl)methyl)-2-oxo-1,2-dihydropyridin-3-yl)-6-(2-methoxy acetamido)-N1,N1-dimethylhept-2-enediamide; (6S,E)-N7-(1-((7-isobutyl-1H-benzo[d]imidazol-2-yl)methyl)-2-oxo-1,2-dihydropyridin-3-yl)-N1,N1-dimethyl-6-(tetrahydrofuran-2-carboxamido)hept-2-enediamide; (S,E)-tert-butyl 2-((3-(7-amino-2-(((2-methoxyethoxy)carbonyl)amino)-7-oxohept-5-enamido)-2-oxopyridin-1(2H)-yl)methyl)-1H-benzo[d]imidazole-1-carboxylate; (S,E)-2-methoxyethyl (1-((1-((1H-benzo[d]imidazol-2-yl)methyl)-2-oxo-1,2-dihydropyridin-3-yl)amino)-7-amino-1,7-dioxohept-5-en-2-yl)carbamate; methyl (S,E)-(1-((1-((1H-benzo[d]imidazol-2-yl)methyl)-2-oxo-1,2-dihydropyridin-3-yl)amino)-7-amino-1,7-dioxohept-5-en-2-yl)carbamate; methyl (S,E)-(1-((1-((1H-benzo[d]imidazol-2-yl)methyl)-2-oxo-1,2-dihydropyridin-3-yl)amino)-7-(dimethylamino)-1,7-dioxohept-5-en-2-yl)carbamate; benzyl (S,E)-(1-((1-((1H-benzo[d]imidazol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(2-((tert-butoxycarbonyl)amino)-7-(dimethylamino)-7-oxohept-5-enamido)-2-oxopyridin-1(2H)-yl)methyl)-1H-benzo[d]imidazole-1-carboxylate; tert-butyl (S,E)-2-((3-(2-((methoxycarbonyl)amino)-7-(methylamino)-7-oxohept-5-enamido)-2-oxopyridin-1(2H)-yl)methyl)-1H-benzo[d]imidazole-1-carboxylate; methyl (S,E)-(1-((1-((1H-benzo[d]imidazol-2-yl)methyl)-2-oxo-1,2-dihydropyridin-3-yl)amino)-7-(methylamino)-1,7-dioxohept-5-en-2-yl)carbamate; methyl (S,E)-(7-(dimethylamino)-1-((1-((5-fluoro-1H-benzo[d]imidazol-2-yl)methyl)-2-oxo-1,2-dihydropyridin-3-yl)amino)-1,7-dioxohept-5-en-2-yl)carbamate; (S,E)-1-((1-((5,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate; methyl (S,E)-(1-((1-((5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; (R,E)-7-(dimethylamino)-1-((1-((5-fluoro-TH-benzo[d]imidazol-2-yl)methyl)-2-oxo-1,2-dihydropyridin-3-yl)amino)-1,7-dioxohept-5-en-2-yl-3,3-$d_2$ dimethylcarbamate; (S,E)-7-(dimethylamino)-1-((1-((5-fluoro-TH-benzo[d]imidazol-2-yl)methyl)-2-oxo-1,2-dihydropyridin-3-yl)amino)-1,7-dioxohept-5-en-2-yl-3,3-$d_2$ dimethylcarbamate; (S,E)-2-hydroxyethyl(1-((1-((1H-benzo[d]imidazol-2-yl)methyl)-2-oxo-1,2-dihydropyridin-3-yl)amino)-7-amino-1,7-dioxohept-5-en-2-yl)carbamate; (S)-2-((((S,E)-1-((1-((1H-benzo[d]imidazol-2-yl)methyl)-2-oxo-1,2-dihydropyridin-3-yl)amino)-7-amino-1,7-dioxohept-5-en-2-yl)carbamoyl)oxy)ethyl2-((S)-2-amino-3-methylbutanamido)-3-methylbutanoate; (S,E)-N7-(1-((1H-benzo[d]imidazol-2-yl)methyl)-2-oxo-1,2-dihydropyridin-3-yl)-6-(2-hydroxyacetamido)-N1,N1-dimethylhept-2-enediamide; (E,6S)—N'-[1-(1H-benzimidazol-2-ylmethyl)-2-oxo-3-pyridyl]-6-(3-hydroxypropanoylamino)-N,N-dimethyl-hept-2-enediamide; (S,E)-N7-(1-((1H-benzo[d]imidazol-2-yl)methyl)-2-oxo-1,2-dihydropyridin-3-yl)-6-(4-hydroxybutanamido)-N1,N1-dimethylhept-2-enediamide; (S,E)-methyl(1-((1-((1H-benzo[d]imidazol-2-yl)methyl)-2-oxo-1,2-dihydropyridin-3-yl)amino)-7-((2-hydroxyethyl)amino)-1,7-dioxohept-5-en-2-yl)carbamate; (S,E)-methyl (7-(dimethylamino)-1-((1-((6-fluoro-4-neopentyl-TH-benzo[d]imidazol-2-yl)methyl)-2-oxo-1,2-dihydropyridin-3-yl)amino)-1,7-dioxohept-5-en-2-yl)carbamate; methyl (S,E)-(1-((1-((6-fluoro-4-neopentyl-TH-benzo[d]imidazol-2-yl)methyl)-2-oxo-1,2-dihydropyridin-3-yl)amino)-1,7-dioxo-7-(pyrrolidin-1-yl)hept-5-en-2-yl)carbamate; (S,E)-7-(dimethylamino)-1-((1-((5-fluoro-7-neopentyl-1H-benzo[d]imidazol-2-yl)methyl)-2-oxo-1,2-dihydropyridin-3-yl)amino)-1,7-dioxohept-5-en-2-yl dimethylcarbamate; 2-methoxyethyl (S,E)-(7-(dimethylamino)-1-((1-((6-fluoro-4-neopentyl-1H-benzo[d]imidazol-2-yl)methyl)-2-oxo-1,2-dihydropyridin-3-yl)amino)-1,7-dioxohept-5-en-2-yl)carbamate; (S,E)-7-(dimethylamino)-1-((1-((5-fluoro-7-neopentyl-1H-benzo[d]imidazol-2-yl)methyl)-2-oxo-1,2-dihydropyridin-3-yl)amino)-1,7-dioxohept-5-en-2-yl (2-methoxyethyl)(methyl)carbamate; (S,E)-1-((1-((5-fluoro-7-neopentyl-1H-benzo[d]imidazol-2-yl)methyl)-2-oxo-1,2-dihydropyridin-3-yl)amino)-1,7-dioxo-7-(pyrrolidin-1-yl)hept-5-en-2-yl dimethylcarbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-6-methoxy-4-neopentyl-1H-benzo[d]imidazole-1-carboxylate; (S,E)-7-(dimethylamino)-1-((1-((6-methoxy-4-neopentyl-1H-benzo[d]imidazol-2-yl)methyl)-2-oxo-1,2-dihydropyridin-3-yl)amino)-1,7-dioxohept-5-en-2-yl dimethylcarbamate; tert-butyl (S,E)-2-((3-(7-amino-2-((methoxycarbonyl)amino)-7-oxohept-5-enamido)-2-oxopyridin-1(2H)-yl)methyl)-4-neopentyl-1H-benzo[d]imidazole-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-4-neopentyl-1H-benzo[d]imidazole-1-carboxylate; methyl (S,E)-(7-amino-1-((1-((7-neopentyl-1H-benzo[d]imidazol-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-neopentyl-1H-benzo[d]imidazol-2-yl)methyl)-2-oxo-1,2-dihydropyridin-3-yl)amino)-1,7-dioxohept-5-en-2-yl)carbamate; tert-butyl (S,E)-2-((3-(7-(dimethylamino)-7-oxo-2-((((tetrahydro-2H-pyran-4-yl)methoxy)carbonyl)amino)hept-5-enamido)-2-oxopyridin-1(2H)-yl)methyl)-4-neopentyl-1H-benzo[d]imidazole-1-carboxylate; (tetrahydro-2H-pyran-4-yl)methyl (S,E)-(7-(dimethylamino)-1-((1-((7-neopentyl-1H-benzo[d]imidazol-2-yl)methyl)-2-oxo-1,2-dihydropyridin-3-yl)amino)-1,7-dioxohept-5-en-2-yl)carbamate; tetrahydrofuran-3-yl ((S,E)-7-(dimethylamino)-1-((1-((4-neopentyl-1H-benzo[d]imidazol-2-yl)methyl)-2-oxo-1,2-dihydropyridin-3-yl)amino)-1,7-dioxohept-5-en-2-yl)carbamate; tert-butyl 2-((3-((2S,E)-7-amino-7-oxo-2-((((tetrahydrofuran-3-yl)oxy)carbonyl)amino)hept-5-enamido)-2-oxopyridin-1(2H)-yl)methyl)-4-neopentyl-1H-benzo[d]imidazole-1-carboxylate; tetrahydrofuran-3-yl ((S,E)-7-amino-1-((1-((4-neopentyl-1H-benzo[d]imidazol-2-yl)methyl)-2-oxo-1,2-dihydropyridin-3-yl)amino)-1,7-dioxohept-5-en-2-yl)carbamate; tert-butyl (S,E)-2-((3-(7-amino-7-oxo-2-((((tetrahydro-2H-pyran-4-yl)methoxy)carbonyl)amino)hept-5-enamido)-2-oxopyridin-1(2H)-yl)methyl)-4-neopentyl-1H-benzo[d]imidazole-1-carboxylate; (tetrahydro-2H-pyran-4-yl)methyl (S,E)-(7-amino-1-((1-((4-neopentyl-1H-benzo[d]imidazol-2-yl)methyl)-2-oxo-1,2-dihydropyridin-3-yl)amino)-1,7-dioxohept-5-en-2-yl)carbamate; (S,E)-7-(dimethylamino)-1-((1-((7-fluoro-4-neopentyl-1H-benzo[d]imidazol-2-yl)methyl)-2-oxo-1,2-dihydropyridin-3-yl)amino)-1,7-dioxohept-5-en-2-yl dimethylcarbamate; tert-butyl (S,E)-2-((3-(7-(dimethylamino)-2-((methoxycarbonyl)amino)-7-oxohept-5-enamido)-2-oxopyridin-1(2H)-yl)methyl)-5,7-difluoro-4-neopentyl-1H-benzo[d]imidazole-1-carboxylate; methyl (S,E)-(1-((1-((5,7-difluoro-4-neopentyl-1H-benzo[d]imidazol-2-yl)methyl)-2-oxo-1,2-dihydropyridin-3-yl)amino)-7-(dimethylamino)-1,7-dioxohept-5-en-2-yl)carbamate; [(E,1S)-6-(dimethylamino)-1-[[1-[[4-(2,2-dimethylpropyl)-6-fluoro-1-methyl-benzimidazol-2-yl]methyl]-2-oxo-3-pyridyl]carbamoyl]-6-oxo-hex-4-enyl] N,N-dimethylcarbamate; 2-methoxyethyl (S,E)-(7-(dimethylamino)-1-((1-((6-fluoro-1-methyl-4-neopentyl-1H-benzo[d]imidazol-2-yl)methyl)-2-oxo-1,2-dihydropyridin-3-yl)amino)-1,7-dioxohept-5-en-2-yl)carbamate; tert-butyl 2-[[5-[[(E,2S)-7-(dimethylamino)-2-(dimethylcarbamoyloxy)-7-oxo-hept-5-enoyl]amino]-6-oxo-pyridazin-1-yl]methyl]-4-(2,2-dimethylpropyl)-6-fluoro-benzimidazole-1-carboxylate; [(E,1S)-6-(dimethylamino)-1-[[2-[[7-(2,2-dimethylpropyl)-5-fluoro-1H-benzimidazol-2-yl]methyl]-3-oxo-pyridazin-4-yl]carbamoyl]-6-oxo-hex-4-enyl]N,N-dimethylcarbamate TFA salt; tert-butyl (S,E)-2-((3-(7-(dimethylamino)-2-((dimethylcarbamoyl)oxy)-7-oxohept-5-enamido)-2-oxopyrazin-1(2H)-yl)methyl)-6-fluoro-4-neopentyl-1H-benzo[d]imidazole-1-carboxylate; (S,E)-7-(dimethylamino)-1-((1-((5-fluoro-7-neopentyl-1H-benzo[d]imidazol-2-yl)methyl)-6-oxo-1,6-dihydropyrimidin-5-yl)amino)-1,7-dioxohept-5-en-2-yl dimethylcarbamate; tert-butyl 2-[[3-[[(E,2S)-7-(dimethylamino)-2-(methoxycarbonylamino)-7-oxo-hept-5-enoyl]amino]-2-oxo-1-pyridyl]methyl]-6-fluoro-4-(3,3,3-trifluoropropyl)benzimidazole-1-carboxylate; methyl N-[(E,1S)-6-(dimethylamino)-1-[[1-[[5-fluoro-7-(3,3,3-trifluoropropyl)-1H-benzimidazol-2-yl]methyl]-2-oxo-3-pyridyl]carbamoyl]-6-oxo-hex-4-enyl]carbamate; methyl (S,E)-(7-amino-1,7-dioxo-1-((2-oxo-1-((4-(3,3,3-trifluoropropyl)-1H-benzo[d]imidazol-2-yl)methyl)-1,2-dihydropyridin-3-yl)amino)hept-5-en-2-yl)carbamate; methyl (S,E)-(7-(dimethylamino)-1,7-dioxo-1-((2-oxo-1-((4-(3,3,3-trifluoropropyl)-1H-benzo[d]imidazol-2-yl)methyl)-1,2-dihydropyridin-3-yl)amino)hept-5-en-2-yl)carbamate; (S,E)-7-(dimethylamino)-1-((1-((5-fluoro-7-(3,3,3-trifluoropropyl)-1H-benzo[d]imidazol-2-yl)methyl)-2-oxo-1,2-dihydropyridin-3-yl)amino)-1,7-dioxohept-5-en-2-yl dimethylcarbamate; tert-butyl (S,E)-6-fluoro-2-((3-(2-((methoxycarbonyl)amino)-7-oxo-7-(pyrrolidin-1-yl)hept-5-enamido)-2-oxopyridin-1(2H)-yl)methyl)-4-(3,3,3-trifluoropropyl)-1H-benzo[d]imidazole-1-carboxylate; methyl (S,E)-(1-((1-((6-fluoro-4-(3,3,3-trifluoropropyl)-1H-benzo[d]imidazol-2-yl)methyl)-2-oxo-1,2-dihydropyridin-3-yl)amino)-1,7-dioxo-7-(pyrrolidin-1-yl)hept-5-en-2-yl)carbamate; tert-butyl (S,E)-2-((3-(2-((dimethylcarbamoyl)oxy)-7-(methylamino)-7-oxohept-5-enamido)-2-oxopyridin-1(2H)-yl)methyl)-5-fluoro-7-(3,3,3-trifluoropropyl)-1H-benzo[d]imidazole-1-carboxylate; (S,E)-1-((1-((5-fluoro-7-(3,3,3-trifluoropropyl)-1H-benzo[d]imidazol-2-yl)methyl)-2-oxo-1,2-dihydropyridin-3-yl)amino)-7-(methylamino)-1,7-dioxohept-5-en-2-yl dimethylcarbamate; methyl (S,E)-(1-((1-((4,6-difluoro-7-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-5,7-difluoro-4-(3,3,3-trifluoropropyl)-1H-benzo[d]imidazole-1-carboxylate; (S,E)-1-((1-((4,6-difluoro-7-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-(3,3,3-trifluoropropyl)-1H-benzo[d]imidazole-1-carboxylate; methyl (S,E)-(1-((1-((5,6-difluoro-4-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; [(E,1S)-6-(dimethylamino)-1-[[1-[[6-fluoro-1-methyl-4-(3,3,3-trifluoropropyl)benzimidazol-2-yl]methyl]-2-oxo-3-pyridyl]carbamoyl]-6-oxo-hex-4-enyl] N,N-dimethylcarbamate; 2-methoxyethyl (S,E)-(7-(dimethylamino)-1-((1-((6-fluoro-1-methyl-4-(3,3,3-trifluoropropyl)-1H-benzo[d]imidazol-2-yl)methyl)-2-oxo-1,2-dihydropyridin-3-yl)amino)-1,7-dioxohept-5-en-2-yl)carbamate; tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-6-fluoro-4-(3,3,3-trifluoropropyl)benzimidazole-1-carboxylate; methyl N-[(E,1S)-6-(dimethylamino)-1-[[1-[[5-fluoro-7-(3,3,3-trifluoropropyl)-1H-benzimidazol-2-yl]methyl]-6-oxo-pyrimidin-5-yl]carbamoyl]-6-oxo-hex-4-enyl]carbamate; methyl (S,E)-(1-((1-((5-fluoro-7-(3,3,3-trifluoropropyl)-1H-benzo[d]imidazol-2-yl)methyl)-6-oxo-1,6-dihydropyrimidin-5-yl)amino)-7-(methylamino)-1,7-dioxohept-5-en-2-yl)carbamate; tert-butyl (S,E)-6-fluoro-2-((5-(2-((methoxycarbonyl)amino)-7-(methylamino)-7-oxohept-5-enamido)-6-oxopyrimidin-1(6H)-yl)methyl)-4-(3,3,3-trifluoropropyl)-1H-benzo[d]imidazole-1-carboxylate; tert-butyl 4-(cyclopropylmethyl)-2-[[3-[[(E,2S)-7-(dimethylamino)-2-methoxycarbonylamino)-7-oxo-hept-5-enoyl]amino]-2-oxo-1-pyridyl]methyl]-6-fluoro-benzimidazole-1-carboxylate; methyl N-[(E,1S)-1-[[1-[[4-(cyclopropylmethyl)-6-fluoro-1H-benzimidazol-2-yl]methyl]-2-oxo-3-pyridyl]carbamoyl]-6-(dimethylamino)-6-oxo-hex-4-enyl]carbamate; tert-butyl (S,E)-4-(cyclopropylmethyl)-2-((3-(7-(dimethylamino)-2-((methoxycarbonyl)amino)-7-oxohept-5-enamido)-2-oxopyridin-1(2H)-yl)methyl)-1H-benzo[d]imidazole-1-carboxylate; methyl (S,E)-(1-((1-((4-(cyclopropylmethyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-amino-2-((methoxycarbonyl)amino)-7-oxohept-5-enamido)-2-oxopyridin-1(2H)-yl)methyl)-4-(cyclopropylmethyl)-1H-benzo[d]imidazole-1-carboxylate; methyl (S,E)-(7-amino-1-((1-((4-(cyclopropylmethyl)-1H-benzo[d]imidazol-2-yl)methyl)-2-oxo-1,2-dihydropyridin-3-yl)amino)-1,7-dioxohept-5-en-2-yl)carbamate; (S,E)-methyl (1-((1-((4-(2,4-difluorophenoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-(dimethylamino)-2-((methoxycarbonyl)amino)-7-oxohept-5-enamido)-2-oxopyridin-1(2H)-yl)methyl)-4-phenoxy-TH-benzo[d]imidazole-1-carboxylate; methyl (S,E)-(7-(dimethylamino)-1,7-dioxo-1-((2-oxo-1-((7-phenoxy-TH-benzo[d]imidazol-2-yl)methyl)-1,2-dihydropyridin-3-yl)amino)hept-5-en-2-yl)carbamate; methyl (S,E)-(7-amino-1,7-dioxo-1-((2-oxo-1-((4-phenoxy-TH-benzo[d]imidazol-2-yl)methyl)-1,2-dihydropyridin-3-yl)amino)hept-5-en-2-yl)carbamate; methyl (S,E)-(1-((1-((6-(2,4-difluorophenoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-methyl(1-((1-((7-((2,4-difluorobenzyl)oxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; benzyl (S,E)-(7-amino-1-((1-((4-isopropoxy-TH-benzo[d]imidazol-2-yl)methyl)-2-oxo-1,2-dihydropyridin-3-yl)amino)-1,7-dioxohept-5-en-2-yl)carbamate; methyl (S,E)-(1-((1-((7-(benzyloxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; benzyl (S,E)-(7-(dimethylamino)-1-((1-((7-isobutoxy-1-methyl-TH-benzo[d]imidazol-2-yl)methyl)-2-oxo-1,2-dihydropyridin-3-yl)amino)-1,7-dioxohept-5-en-2-yl)carbamate; methyl (S,E)-(7-amino-1-((1-((7-isobutoxy-1H-benzo[d]imidazol-2-yl)methyl)-2-oxo-1,2-dihydropyridin-3-yl)amino)-1,7-dioxohept-5-en-2-yl)carbamate; methyl (S,E)-(7-amino-1-((1-((7-(benzyloxy)-1H-benzo[d]imidazol-2-yl)methyl)-2-oxo-1,2-dihydropyridin-3-yl)amino)-1,7-dioxohept-5-en-2-yl)carbamate; methyl (S,E)-(7-amino-1-((1-((4-isopropoxy-1H-benzo[d]imidazol-2-yl)methyl)-2-oxo-1,2-dihydropyridin-3-yl)amino)-1,7-dioxohept-5-en-2-yl)carbamate; methyl (S,E)-(7-amino-1-((1-((7-(cyclopropylmethoxy)-1H-benzo[d]imidazol-2-yl)methyl)-2-oxo-1,2-dihydropyridin-3-yl)amino)-1,7-dioxohept-5-en-2-yl)carbamate; methyl (S,E)-(1-((1-((6-((2,4-difluorobenzyl)oxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((4-(2,2-difluoroethoxy)-6-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(7-amino-1-((1-((4-(2,2-difluoroethoxy)-6-fluoro-1H-benzo[d]imidazol-2-yl)methyl)-2-oxo-1,2-dihydropyridin-3-yl)amino)-1,7-dioxohept-5-en-2-yl)carbamate; methyl (S,E)-(7-(dimethylamino)-1-((1-((6-fluoro-4-(2,2,2-trifluoroethoxy)-1H-benzo[d]imidazol-2-yl)methyl)-2-oxo-1,2-dihydropyridin-3-yl)amino)-1,7-dioxohept-5-en-2-yl)carbamate; methyl (S,E)-(7-amino-1-((1-((6-fluoro-4-(2, 2,2-trifluoroethoxy)-1H-benzo[d]imidazol-2-yl)methyl)-2-oxo-1,2-dihydropyridin-3-yl)amino)-1,7-dioxohept-5-en-2-yl)carbamate; methyl (S,E)-(1-((1-((7-((2,4-difluorobenzyl)oxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((4-((2,4-difluorobenzyl)oxy)-6-fluoro-1H-benzo[d]imidazol-2-yl)methyl)-2-oxo-1,2-dihydropyridin-3-yl)amino)-7-(methylamino)-1,7-dioxohept-5-en-2-yl)carbamate; methyl (S,E)-(7-amino-1-((1-((7-((2,4-difluorobenzyl)oxy)-5-fluoro-1H-benzo[d]imidazol-2-yl)methyl)-2-oxo-1,2-dihydropyridin-3-yl)amino)-1,7-dioxohept-5-en-2-yl)carbamate; 2-methoxyethyl (S,E)-(1-((1-((7-((2,4-difluorobenzyl)oxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-1-((1-((7-((2,4-difluorobenzyl)oxy)-5-fluoro-TH-benzo[d]imidazol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((7-((2,4-difluorobenzyl)oxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl (2-methoxyethyl)(methyl)carbamate; methyl (S,E)-(1-((1-((7-(cyclopropylmethoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-methyl (7-(dimethyl-amino)-1-((1-((5-fluoro-7-(1,1,2,2-tetrafluoroethoxy)-1H-benzo[d]imidazol-2-yl)methyl)-2-oxo-1,2-dihydropyridin-3-yl)amino)-1,7-dioxohept-5-en-2-yl)carbamate; (S,E)-N7-(1-((7-(2,4-difluorophenoxy)-1H-benzo[d]imidazol-2-yl)methyl)-2-oxo-1,2-dihydropyridin-3-yl)-N1,N1-dimethyl-6-(oxazole-2-carboxamido)hept-2-enediamide; (S,E)-N7-(1-((7-(2,4-difluorophenoxy)-1H-benzo[d]imidazol-2-yl)methyl)-2-oxo-1,2-dihydropyridin-3-yl)-6-(2-methoxyacetamido)-N1,N1-dimethylhept-2-enediamide; (S,E)-N7-(1-((7-(2,4-difluorophenoxy)-1H-benzo[d]imidazol-2-yl)methyl)-2-oxo-1,2-dihydropyridin-3-yl)-N1,N1-dimethyl-6-(1-methyl-1H-imidazole-5-carboxamido)hept-2-enediamide; (S,E)-N7-(1-((4-((2,4-difluorobenzyl)oxy)-1H-benzo[d]imidazol-2-yl)methyl)-2-oxo-1,2-dihydropyridin-3-yl)-N1,N1-dimethyl-6-(oxazole-2-carboxamido)hept-2-enediamide; (S,E)-N7-(1-((7-((2,4-difluorobenzyl)oxy)-1H-benzo[d]imidazol-2-yl)methyl)-2-oxo-1,2-dihydropyridin-3-yl)-6-(2-methoxyacetamido)-N1,N1-dimethylhept-2-enediamide; (S,E)-N7-(1-((4-((2,4-difluorobenzyl)oxy)-1H-benzo[d]imidazol-2-yl)methyl)-2-oxo-1,2-dihydropyridin-3-yl)-N1,N1-dimethyl-6-(1-methyl-1H-imidazole-2-carboxamido)hept-2-enediamide; (S,E)-N7-(1-((7-((2,4-difluorobenzyl)oxy)-1H-benzo[d]imidazol-2-yl)methyl)-2-oxo-1,2-dihydropyridin-3-yl)-6-(4,4-difluorocyclohexane-1-carboxamido)-N1,N1-dimethylhept-2-enediamide; (S,E)-N7-(1-((7-((2,4-difluorobenzyl)oxy)-5-fluoro-1H-benzo[d]imidazol-2-yl)methyl)-2-oxo-1,2-dihydropyridin-3-yl)-6-(2-methoxyacetamido)hept-2-enediamide; (S,E)-N7-(1-((7-((2,4-difluorobenzyl)oxy)-5-fluoro-1H-benzo[d]imidazol-2-yl)methyl)-2-oxo-1,2-dihydropyridin-3-yl)-6-(5-fluoropicolinamido)hept-2-enediamide; (S,E)-N7-(1-((4-((2,4-difluorobenzyl)oxy)-6-fluoro-1H-benzo[d]imidazol-2-yl)methyl)-2-oxo-1,2-dihydropyridin-3-yl)-6-(2-methoxyacetamido)-N1,N1-dimethylhept-2-enediamide; (S,E)-N7-(1-((4-((2,4-difluorobenzyl)oxy)-6-fluoro-1H-benzo[d]imidazol-2-yl)methyl)-2-oxo-1,2-dihydropyridin-3-yl)-6-(5-fluoropicolinamido)-N1,N1-dimethylhept-2-enediamide; methyl N-[(E,1S)-1-[[1-[[4-[(2,4-difluorophenoxy) methyl]-1H-benzimidazol-2-yl]methyl]-2-oxo-3-pyridyl]carbamoyl]-6-(dimethylamino)-6-oxo-hex-4-enyl]carbamate; methyl (S,E)-(7-(dimethylamino)-1-((1-((4-(isopropoxymethyl)-1H-benzo[d]imidazol-2-yl)methyl)-2-oxo-1,2-dihydropyridin-3-yl)amino)-1,7-dioxohept-5-en-2-yl)carbamate; (S,E)-tert-butyl 2-((3-(7-(dimethylamino)-2-((methoxycarbonyl)amino)-7-oxohept-5-enamido)-2-oxopyridin-1(2H)-yl)methyl)-4-(3,3,3-trifluoro-2-(trifluoromethyl)propyl)-1H-benzo[d]imidazole-1-carboxylate; (S,E)-methyl(7-(dimethylamino)-1,7-dioxo-1-((2-oxo-1-((4-(3,3,3-trifluoro-2-(trifluoromethyl)propyl)-1H-benzo[d]imidazol-2-yl)methyl)-1,2-dihydropyridin-3-yl)amino)hept-5-en-2-yl)carbamate; methyl (S,E)-(7-amino-1,7-dioxo-1-((2-oxo-1-((4-(3,3,3-trifluoro-2-(trifluoromethyl)propyl)-1H-benzo[d]imidazol-2-yl)methyl)-1,2-dihydropyridin-3-yl)amino)hept-5-en-2-yl)carbamate; methyl ((2S,E)-7-(dimethylamino)-1-((1-((4-(1-hydroxy-2-methylpropyl)-1H-benzo [d]imidazol-2-yl)methyl)-2-oxo-1,2-dihydropyridin-3-yl)amino)-1,7-dioxohept-5-en-2-yl)carbamate; methyl ((2S,E)-7-amino-1-((1-((4-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-(dimethylamino)-1-((1-((7-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-(dimethylamino)-1-((1-((7-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-(dimethylamino)-1-((1-((7-(1-fluoro-2-methylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-amino-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate; tert-butyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate; (6S,E)-N7-(1-((7-(1-hydroxy-2,2-dimethylpropyl)-1H-benzo[d]imidazol-2-yl)methyl)-2-oxo-1,2-dihydropyridin-3-yl)-N1,N1-dimethyl-6-(oxazole-2-carboxamido)hept-2-enediamide; (S,E)-methyl (7-(dimethylamino)-1,7-dioxo-1-((2-oxo-1-((7-pivaloyl-1H-benzo[d]imidazol-2-yl)methyl)-1,2-dihydropyridin-3-yl)amino)hept-5-en-2-yl)carbamate; methyl ((2S,E)-7-(dimethylamino)-1-((1-((7-(1-fluoro-2,2-dimethylpropyl)-1H-benzo[d]imidazol-2-yl)methyl)-2-oxo-1,2-dihydropyridin-3-yl)amino)-1,7-dioxohept-5-en-2-yl)carbamate; methyl ((2S,E)-7-amino-1-((1-((4-(1-fluoro-2,2-dimethylpropyl)-1H-benzo[d]imidazol-2-yl)methyl)-2-oxo-1,2-dihydropyridin-3-yl)amino)-1,7-dioxohept-5-en-2-yl)carbamate; (S,E)-methyl(1-((1-((4-(1,1-difluoro-2-hydroxy-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-methyl (1-((1-((4-(1,1-difluoro-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(7-amino-1-((1-((4-(1,1-difluoro-2-methylpropyl)-1H-benzo[d]imidazol-2-yl)methyl)-2-oxo-1,2-dihydropyridin-3-yl)amino)-1,7-dioxohept-5-en-2-yl)carbamate; methyl (S,E)-(1-((1-((4-(1,1-difluoro-2-methylallyl)-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(7-amino-1-((1-((4-(1,1-difluoro- 2-methylallyl)-1H-benzo[d]imidazol-2-yl)methyl)-2-oxo-1,2-dihydropyridin-3-yl)amino)-1,7-dioxohept-5-en-2-yl)carbamate; (S,E)-methyl (1-((1-((7-(tert-butoxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(7-amino-1-((1-((7-(tert-butoxy)-5-fluoro-1H-benzo[d]imidazol-2-yl)methyl)-2-oxo-1,2-dihydropyridin-3-yl)amino)-1,7-dioxohept-5-en-2-yl)carbamate; [(E,1S)-6-(dimethylamino)-1-[[1-[(5-fluoro-1-methyl-benzimidazol-2-yl)methyl]-2-oxo-3-pyridyl]carbamoyl]-6-oxo-hex-4-enyl] N,N-dimethylcarbamate; methyl N-[(E,1S)-6-(dimethylamino)-1-[[1-[(5-fluoro-1-methyl-benzimidazol-2-yl) methyl]-6-oxo-pyrimidin-5-yl]carbamoyl]-6-oxo-hex-4-enyl]carbamate; (S,E)-1-((1-((5,6-difluoro-1-isopentyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((1-(cyclopropylmethyl)-5-fluoro-1H-benzo[d]imidazol-2-yl) methyl)-2-oxo-1,2-dihydropyridin-3-yl)amino)-7-(dimethylamino)-1,7-dioxohept-5-en-2-yl dimethylcarbamate; (S,E)-7-(dimethylamino)-1-((1-((5-fluoro-1-neopentyl-1H-benzo[d]imidazol-2-yl)methyl)-2-oxo-1,2-dihydropyridin-3-yl)amino)-1,7-dioxohept-5-en-2-yl dimethylcarbamate; (S,E)-7-(dimethylamino)-1-((1-((1-ethyl-5-fluoro-1H-benzo[d]imidazol-2-yl)methyl)-2-oxo-1,2-dihydropyridin-3-yl)amino)-1,7-dioxohept-5-en-2-yl dimethylcarbamate; (S,E)-7-(dimethylamino)-1-((1-((5-fluoro-1-isobutyl-1H-benzo[d]imidazol-2-yl)methyl)-2-oxo-1,2-dihydropyridin-3-yl)amino)-1,7-dioxohept-5-en-2-yl dimethylcarbamate; (S,E)-7-(dimethylamino)-1-((1-((5-fluoro-1-(3,3,3-trifluoropropyl)-1H-benzo[d]imidazol-2-yl) methyl)-2-oxo-1,2-dihydropyridin-3-yl)amino)-1,7-dioxohept-5-en-2-yl dimethylcarbamate; (S,E)-1-((1-((1-(2-cyclopropylethyl)-5,6-difluoro-1H-benzo[d]imidazol-2-yl) methyl)-2-oxo-1,2-dihydropyridin-3-yl)amino)-7-(dimethylamino)-1,7-dioxohept-5-en-2-yl dimethylcarbamate; methyl (S,E)-(1-((1-((1-(2-cyclopropylethyl)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-1-((1-((1-(2-((difluoro-l3-methyl)-l2-fluoraneyl)ethyl)-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl dimethylcarbamate; (S,E)-1-((1-((1-benzyl-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl dimethylcarbamate; (S,E)-1-((1-((1-(2,4-difluorobenzyl)-5-fluoro-1H-benzo[d]imidazol-2-yl) methyl)-6-oxo-1,6-dihydropyrimidin-5-yl)amino)-7-(dimethylamino)-1,7-dioxohept-5-en-2-yl dimethylcarbamate; methyl (S,E)-(1-((1-((1-(2,4-difluorobenzyl)-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl)carbamate; (S,E)-7-(dimethylamino)-1-((1-((5-fluoro-1-neopentyl-1H-benzo[d] imidazol-2-yl)methyl)-6-oxo-1,6-dihydropyrimidin-5-yl) amino)-1,7-dioxohept-5-en-2-yl dimethylcarbamate; methyl (S,E)-(1-((1-((5,6-difluoro-1-(2-isopropoxyethyl)-1H-benzo [d]imidazol-2-yl)methyl)-2-oxo-1,2-dihydropyridin-3-yl) amino)-7-(dimethylamino)-1,7-dioxohept-5-en-2-yl)carbamate; methyl (S,E)-(7-(dimethylamino)-1-((1-((5-fluoro-1-(4-fluorobenzyl)-1H-benzo[d]imidazol-2-yl)methyl)-6-oxo-1,6-dihydropyrimidin-5-yl)amino)-1,7-dioxohept-5-en-2-yl)carbamate; methyl (S,E)-(1-((1-((1-(cyclopropylmethyl)-5-fluoro-1H-benzo[d]imidazol-2-yl) methyl)-6-oxo-1,6-dihydropyrimidin-5-yl)amino)-7-(dimethylamino)-1,7-dioxohept-5-en-2-yl)carbamate; methyl (S,E)-(7-(dimethylamino)-1-((1-((5-fluoro-1-isobutyl-1H-benzo[d]imidazol-2-yl)methyl)-6-oxo-1,6-dihydropyrimidin-5-yl)amino)-1,7-dioxohept-5-en-2-yl)carbamate; (S,E)-7-(dimethylamino)-1-((1-((1-ethyl-5-fluoro-1H-benzo[d]imidazol-2-yl)methyl)-6-oxo-1,6-dihydropyrimidin-5-yl)amino)-1,7-dioxohept-5-en-2-yl dimethylcarbamate; (S,E)-7-(dimethylamino)-1-((1-((5-fluoro-1-methyl-1H-benzo[d]imidazol-2-yl)methyl)-6-oxo-1,6-dihydropyrimidin-5-yl)amino)-1,7-dioxohept-5-en-2-yl dimethylcarbamate; ethyl 2-[[3-[[(E,2S)-7-(dimethylamino)-2-(dimethylcarbamoyloxy)-7-oxo-hept-5-enoyl] amino]-2-oxo-1-pyridyl]methyl]-5-fluoro-benzimidazole-1-carboxylate; cyclopropylmethyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-benzimidazole-1-carboxylate; methyl (S,E)-2-((3-(7-(dimethylamino)-2-((dimethylcarbamoyl)oxy)-7-oxohept-5-enamido)-2-oxopyridin-1(2H)-yl)methyl)-5-fluoro-1H-benzo[d]imidazole-1-carboxylate; ethyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-1H-benzo[d]imidazole-1-carboxylate; cyclopropylmethyl (S,E)-2-((3-(7-(dimethylamino)-2-((methoxycarbonyl) amino)-7-oxohept-5-enamido)-2-oxopyridin-1(2H)-yl) methyl)-5,6-difluoro-1H-benzo[d]imidazole-1-carboxylate; ethyl (S,E)-2-((3-(7-(dimethylamino)-2-((methoxycarbonyl) amino)-7-oxohept-5-enamido)-2-oxopyridin-1(2H)-yl) methyl)-5,6-difluoro-1H-benzo[d]imidazole-1-carboxylate; cyclopropylmethyl (S,E)-2-((3-(7-(dimethylamino)-2-((methoxycarbonyl)amino)-7-oxohept-5-enamido)-2-oxopyridin-1(2H)-yl)methyl)-5-fluoro-TH-benzo[d]imidazole-1-carboxylate; ethyl (S,E)-2-((3-(7-(dimethylamino)-2-((methoxycarbonyl)amino)-7-oxohept-5-enamido)-2-oxopyridin-1(2H)-yl)methyl)-5-fluoro-TH-benzo[d] imidazole-1-carboxylate; methyl 2-[[5-[[(E,2S)-7-(dimethylamino)-2-(methoxy carbonylamino)-7-oxo-hept-5-enoyl]amino]-6-oxo-pyrimidin-1-yl]methyl]-5-fluoro-benzimidazole-1-carboxylate; [(E,1S)-1-[[1-[(1-benzyl-6-fluoro-benzimidazol-2-yl)methyl]-2-oxo-3-pyridyl] carbamoyl]-6-(dimethylamino)-6-oxo-hex-4-enyl] N,N-dimethylcarbamate; [(E,1S)-1-[[1-[(1-benzyl-5-fluoro-benzimidazol-2-yl)methyl]-2-oxo-3-pyridyl]carbamoyl]-6-(dimethylamino)-6-oxo-hex-4-enyl] N,N-dimethylcarbamate; (S,E)-1-((1-((1-(2,4-difluorobenzyl)-5-fluoro-TH-benzo[d]imidazol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((1-(2,4-difluorobenzyl)-6-fluoro-1H-benzo[d]imidazol-2-yl) methyl)-2-oxo-1,2-dihydropyridin-3-yl)amino)-7-(dimethylamino)-1,7-dioxohept-5-en-2-yl dimethylcarbamate; (S,E)-7-(dimethylamino)-1-((1-((5-fluoro-1-(4-fluorobenzyl)-1H-benzo[d]imidazol-2-yl) methyl)-2-oxo-1,2-dihydropyridin-3-yl)amino)-1,7-dioxohept-5-en-2-yl dimethylcarbamate; (S,E)-7-(dimethylamino)-1-((1-((6-fluoro-1-(4-fluorobenzyl)-1H-benzo[d]imidazol-2-yl)methyl)-2-oxo-1,2-dihydropyridin-3-yl)amino)-1,7-dioxohept-5-en-2-yl dimethylcarbamate; (S,E)-methyl (7-(dimethylamino)-1-((1-((5-fluoro-1H-indol-2-yl)methyl)-2-oxo-1,2-dihydropyridin-3-yl)amino)-1,7-dioxohept-5-en-2-yl)carbamate; tert-butyl (S,E)-5-fluoro-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate; tert-butyl (S,E)-5-fluoro-2-((3-(2-(((2-hydroxyethoxy)carbonyl)amino)-7-oxo-7-(pyrrolidin-1-yl)hept-5-enamido)-2-oxopyridin-1(2H)-yl)methyl)-1H-indole-1-carboxylate; 2-hydroxyethyl (S,E)-(1-((1-((5- fluoro-1H-indol-2-yl)methyl)-2-oxo-1,2-dihydropyridin-3-yl)amino)-1,7-dioxo-7-(pyrrolidin-1-yl)hept-5-en-2-yl)carbamate; methyl (S,E)-(7-amino-1-((1-((5-fluoro-1H-indol-2-yl)methyl)-2-oxo-1,2-dihydropyridin-3-yl)amino)-1,7-dioxohept-5-en-2-yl)carbamate; methyl (S,E)-(1-((1-((5-fluoro-1H-indol-2-yl)methyl)-2-oxo-1,2-dihydropyridin-3-yl)amino)-1,7-dioxo-7-(pyrrolidin-1-yl)hept-5-en-2-yl) carbamate; (S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl dimethylcarbamate; (S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl (2-methoxyethyl)(methyl)carbamate; (S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl pyrrolidine-1-carboxylate; tert-butyl (S,E)-2-((3-(7-amino-2-((dimethylcarbamoyl)oxy)-7-oxohept-5-enamido)-2-oxopyridin-1(2H)-yl)methyl)-5-fluoro-1H-indole-1-carboxylate; (S,E)-7-amino-1-((1-((5-fluoro-1H-indol-2-yl) methyl)-2-oxo-1,2-dihydropyridin-3-yl)amino)-1,7-dioxohept-5-en-2-yl dimethylcarbamate; tert-butyl (S,E)-2-((3-(2-((bis(2-methoxyethyl)carbamoyl)oxy)-7-(dimethylamino)-7-oxohept-5-enamido)-2-oxopyridin-1 (2H)-yl)methyl)-5-fluoro-1H-indole-1-carboxylate; (S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl bis(2-methoxyethyl)carbamate; benzyl (S,E)-2-((3-(7-(dimethylamino)-2-((dimethylcarbamoyl)oxy)-7-oxohept-5-enamido)-2-oxopyridin-1(2H)-yl)methyl)-5-fluoro-TH-indole-1-carboxylate; (E)-7-(dimethylamino)-1-((1-((5-fluoro-TH-indol-2-yl)methyl)-2-oxo-1,2-dihydropyridin-3-yl)amino)-1,7-dioxohept-5-en-2-yl-3,3-$d_2$ dimethylcarbamate; tert-butyl (E)-2-((3-(7-(dimethylamino)-2-((dimethylcarbamoyl)oxy)-7-oxohept-5-enamido-3,3-$d_2$)-2-oxopyridin-1(2H)-yl)methyl)-5-fluoro-1H-indole-1-carboxylate; tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-5-fluoro-indole-1-carboxylate; [(E,1S)-6-(dimethylamino)-1-[[4-[(5-fluoro-1H-indol-2-yl) methyl]-3-oxo-pyrazin-2-yl]carbamoyl]-6-oxo-hex-4-enyl] N,N-dimethylcarbamate; (S,E)-7-(dimethylamino)-1-((1-((5-fluoro-1H-indol-2-yl)methyl)-6-oxo-1,6-dihydropyrimidin-5-yl)amino)-1,7-dioxohept-5-en-2-yl dimethylcarbamate; (S,E)-tert-butyl 2-((3-(7-(dimethylamino)-2-((methoxycarbonyl)amino)-7-oxohept-5-enamido)-2-oxopyridin-1(2H)-yl)methyl)-4-isobutyl-TH-indole-1-carboxylate; (S,E)-methyl (7-(dimethylamino)-1-((1-((4-isobutyl-1H-indol-2-yl)methyl)-2-oxo-1,2-dihydropyridin-3-yl)amino)-1,7-dioxohept-5-en-2-yl) carbamate; tert-butyl (S,E)-2-((3-(7-amino-2-((methoxycarbonyl)amino)-7-oxohept-5-enamido)-2-oxopyridin-1(2H)-yl)methyl)-4-isobutyl-TH-indole-1-carboxylate; methyl (S,E)-(7-amino-1-((1-((4-isobutyl-1H-indol-2-yl)methyl)-2-oxo-1,2-dihydropyridin-3-yl)amino)-1,7-dioxohept-5-en-2-yl)carbamate; tert-butyl (S,E)-2-((3-(7-amino-2-((methoxycarbonyl)amino)-7-oxohept-5-enamido)-2-oxopyridin-1(2H)-yl)methyl)-7-isobutyl-1H-indole-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-7-isobutyl-1H-indole-1-carboxylate; methyl (S,E)-(7-amino-1-((1-((7-isobutyl-1H-indol-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-isobutyl-1H-indol-2-yl) methyl)-2-oxo-1,2-dihydropyridin-3-yl)amino)-1,7-dioxohept-5-en-2-yl)carbamate; (S,E)-7-(dimethylamino)-1-((1-((7-isobutyl-TH-indol-2-yl)methyl)-2-oxo-1,2-dihydropyridin-3-yl)amino)-1,7-dioxohept-5-en-2-yl dimethylcarbamate; tert-butyl (S,E)-2-((3-(7-(dimethylamino)-2-((methylcarbamoyl)oxy)-7-oxohept-5-enamido)-2-oxopyridin-1(2H)-yl)methyl)-7-isobutyl-1H-indole-1-carboxylate; (S,E)-7-(dimethylamino)-1-((1-((7-isobutyl-1H-indol-2-yl)methyl)-2-oxo-1,2-dihydropyridin-3-yl)amino)-1,7-dioxohept-5-en-2-yl methylcarbamate; (S,E)-1-((1-((7-isobutyl-TH-indol-2-yl)methyl)-2-oxo-1,2-dihydropyridin-3-yl)amino)-7-(methylamino)-1,7-dioxohept-5-en-2-yl dimethylcarbamate; tert-butyl (S,E)-2-((3-(7-(dimethylamino)-7-oxo-2-((pyrrolidine-1-carbonyl)oxy)hept-5-enamido)-2-oxopyridin-1(2H)-yl)methyl)-7-isobutyl-TH-indole-1-carboxylate; (S,E)-7-(dimethylamino)-1-((1-((7-isobutyl-1H-indol-2-yl)methyl)-2-oxo-1,2-dihydropyridin-3-yl)amino)-1,7-dioxohept-5-en-2-yl pyrrolidine-1-carboxylate; tert-butyl (S,E)-7-isobutyl-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate; methyl (S,E)-(1-((1-((7-isobutyl-1H-indol-2-yl)methyl)-2-oxo-1,2-dihydropyridin-3-yl)amino)-1,7-dioxo-7-(pyrrolidin-1-yl)hept-5-en-2-yl)carbamate; (E)-7-(dimethylamino)-1-((1-((7-isobutyl-1H-indol-2-yl)methyl)-2-oxo-1,2-dihydropyridin-3-yl)amino)-1,7-dioxohept-5-en-2-yl-3,3-$d_2$ dimethylcarbamate; tert-butyl (E)-2-((3-(7-(dimethylamino)-2-((dimethylcarbamoyl)oxy)-7-oxohept-5-enamido-3,3-$d_2$)-2-oxopyridin-1(2H)-yl)methyl)-7-isobutyl-1H-indole-1-carboxylate; (S,E)-2-(((7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamoyl)oxy)ethyl acetate; (S,E)-tert-butyl 2-((3-(7-(dimethylamino)-2-(((2-hydroxyethoxy)carbonyl)amino)-7-oxohept-5-enamido)-2-oxopyridin-1(2H)-yl)methyl)-7-isobutyl-1H-indole-1-carboxylate; (S,E)-2-hydroxyethyl (7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamate; tert-butyl (S,E)-2-((3-(2-(((2-hydroxyethoxy)carbonyl)amino)-7-oxo-7-(pyrrolidin-1-yl) hept-5-enamido)-2-oxopyridin-1(2H)-yl)methyl)-7-isobutyl-1H-indole-1-carboxylate; 2-hydroxyethyl (S,E)-(1-((1-((7-isobutyl-1H-indol-2-yl)methyl)-2-oxo-1,2-dihydropyridin-3-yl)amino)-1,7-dioxo-7-(pyrrolidin-1-yl) hept-5-en-2-yl)carbamate; (S,E)-N7-(1-((7-((2,4-difluorobenzyl)oxy)-1H-indol-2-yl)methyl)-2-oxo-1,2-dihydropyridin-3-yl)-6-(4,4-difluorocyclohexanecarboxamido)-N1,N1-dimethylhept-2-enediamide; tert-butyl (S,E)-(1-((1-((7-((2,4-difluorobenzyl)oxy)-1H-indol-2-yl)methyl)-2-oxo-1,2-dihydropyridin-3-yl)amino)-7-(dimethylamino)-1,7-dioxohept-5-en-2-yl)carbamate; (S,E)-N7-(1-((7-((2,4-difluorobenzyl)oxy)-1H-indol-2-yl)methyl)-2-oxo-1,2-dihydropyridin-3-yl)-N1,N1-dimethyl-6-(oxazole-2-carboxamido)hept-2-enediamide; (S,E)-N7-(1-((7-((2,4-difluorobenzyl)oxy)-1H-indol-2-yl)methyl)-2-oxo-1,2-dihydropyridin-3-yl)-6-(2-methoxyacetamido)-N1,N1-dimethylhept-2-enediamide; (S,E)-N7-(1-((7-((2,4-difluorobenzyl)oxy)-1H-indol-2-yl)methyl)-2-oxo-1,2-dihydropyridin-3-yl)-N1,N1-dimethyl-6-(3,3,3-trifluoropropanamido)hept-2-enediamide; (S,E)-N7-(1-((7-((2,4-difluorobenzyl)oxy)-1H-indol-2-yl)methyl)-2-oxo-1,2-dihydropyridin-3-yl)-6-(2-fluorobenzamido)-N1,N1-dimethylhept-2-enediamide; methyl (S,E)-(1-((1-((7-((2,4-difluorobenzyl)oxy)-1H-indol-2-yl)methyl)-2-oxo-1,2-dihydropyridin-3-yl)amino)-7-(dimethylamino)-1,7-dioxohept-5-en-2-yl)carbamate; tert-butyl (S,E)-7-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-1H-indole-1-carboxylate;

tert-butyl (S,E)-2-((3-(7-amino-2-((tert-butoxycarbonyl)amino)-7-oxohept-5-enamido)-2-oxopyridin-1(2H)-yl)methyl)-7-((2,4-difluorobenzyl)oxy)-1H-indole-1-carboxylate; tert-butyl (S,E)-2-((3-(7-amino-2-((methoxycarbonyl)amino)-7-oxohept-5-enamido)-2-oxopyridin-1(2H)-yl)methyl)-7-((2,4-difluorobenzyl)oxy)-1H-indole-1-carboxylate; (S,E)-N7-(1-((7-((2,4-difluorobenzyl)oxy)-1H-indol-2-yl)methyl)-2-oxo-1,2-dihydropyridin-3-yl)-6-(2-fluorobenzamido)hept-2-enediamide; methyl (S,E)-(7-amino-1-((1-((7-(2,2-difluoroethoxy)-1H-indol-2-yl)methyl)-2-oxo-1,2-dihydropyridin-3-yl)amino)-1,7-dioxohept-5-en-2-yl)carbamate; methyl (S,E)-(1-((1-((7-(2,2-difluoroethoxy)-1H-indol-2-yl)methyl)-2-oxo-1,2-dihydropyridin-3-yl)amino)-7-(dimethylamino)-1,7-dioxohept-5-en-2-yl)carbamate; tert-butyl (S,E)-7-(2,2-difluoroethoxy)-2-((3-(7-(dimethylamino)-2-((methoxycarbonyl)amino)-7-oxohept-5-enamido)-2-oxopyridin-1(2H)-yl)methyl)-1H-indole-1-carboxylate; methyl (S,E)-(7-amino-1-((1-((7-((2,4-difluorobenzyl)oxy)-1H-indol-2-yl)methyl)-2-oxo-1,2-dihydropyridin-3-yl)amino)-1,7-dioxohept-5-en-2-yl)carbamate; (S,E)-N7-(1-((7-((2,4-difluorobenzyl)oxy)-1H-indol-2-yl)methyl)-2-oxo-1,2-dihydropyridin-3-yl)-6-(2-methoxyacetamido)hept-2-enediamide; (S,E)-tert-butyl 7-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate; (S,E)-methyl (1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-amino-2-((methoxycarbonyl)amino)-7-oxohept-5-enamido)-2-oxopyridin-1(2H)-yl)methyl)-7-((2,4-difluorobenzyl)oxy)-5-fluoro-1H-indole-1-carboxylate; methyl (S,E)-(7-amino-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl)carbamate; tert-butyl (S,E)-7-(2,2-difluoroethoxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate; methyl (S,E)-(1-((1-((7-(2,2-difluoroethoxy)-5-fluoro-1H-indol-2-yl)methyl)-2-oxo-1,2-dihydropyridin-3-yl)amino)-7-(dimethylamino)-1,7-dioxohept-5-en-2-yl)carbamate; tert-butyl (S,E)-2-((3-(7-amino-2-((methoxycarbonyl)amino)-7-oxohept-5-enamido)-2-oxopyridin-1(2H)-yl)methyl)-7-(2,2-difluoroethoxy)-5-fluoro-1H-indole-1-carboxylate; methyl (S,E)-(7-amino-1-((1-((7-(2,2-difluoroethoxy)-5-fluoro-1H-indol-2-yl)methyl)-2-oxo-1,2-dihydropyridin-3-yl)amino)-1,7-dioxohept-5-en-2-yl)carbamate; tert-butyl (S,E)-7-((2,4-difluorobenzyl)oxy)-5-fluoro-2-((3-(2-((methoxycarbonyl)amino)-7-(methylamino)-7-oxohept-5-enamido)-2-oxopyridin-1(2H)-yl)methyl)-1H-indole-1-carboxylate; methyl (S,E)-(1-((1-((7-((2,4-difluorobenzyl)oxy)-5-fluoro-1H-indol-2-yl)methyl)-2-oxo-1,2-dihydropyridin-3-yl)amino)-7-(methylamino)-1,7-dioxohept-5-en-2-yl)carbamate; tert-butyl (S,E)-7-((2,4-difluorobenzyl)oxy)-2-((3-(7-(dimethylamino)-2-(((2-methoxyethoxy)carbonyl)amino)-7-oxohept-5-enamido)-2-oxopyridin-1(2H)-yl)methyl)-5-fluoro-1H-indole-1-carboxylate; tert-butyl (S,E)-7-((2,4-difluorobenzyl)oxy)-5-fluoro-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate; methyl (S,E)-(1-((1-((7-((2,4-difluorobenzyl)oxy)-5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate; tert-butyl (S,E)-2-((3-(7-(dimethylamino)-2-((methoxycarbonyl)amino)-7-oxohept-5-enamido)-2-oxopyridin-1(2H)-yl)methyl)-5-fluoro-7-isobutyl-1H-indole-1-carboxylate; methyl (S,E)-(7-(dimethylamino)-1-((1-((5-fluoro-7-isobutyl-1H-indol-2-yl)methyl)-2-oxo-1,2-dihydropyridin-3-yl)amino)-1,7-dioxohept-5-en-2-yl)carbamate; 2-hydroxyethyl (S,E)-(1-((1-((7-((2,4-difluorobenzyl)oxy)-5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate; (S,E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate; tert-butyl (S,E)-7-((2,4-difluorobenzyl)oxy)-2-((3-(7-(dimethylamino)-2-(((2-methoxyethyl)(methyl)carbamoyl)oxy)-7-oxohept-5-enamido)-2-oxopyridin-1(2H)-yl)methyl)-5-fluoro-1H-indole-1-carboxylate; (S,E)-1-((1-((7-((2,4-difluorobenzyl)oxy)-5-fluoro-TH-indol-2-yl)methyl)-2-oxo-1,2-dihydropyridin-3-yl)amino)-7-(dimethylamino)-1,7-dioxohept-5-en-2-yl (2-methoxyethyl)(methyl)carbamate; tert-butyl (S,E)-7-((2,4-difluorobenzyl)oxy)-2-((3-(7-(dimethylamino)-7-oxo-2-((pyrrolidine-1-carbonyl)oxy)hept-5-enamido)-2-oxopyridin-1(2H)-yl)methyl)-5-fluoro-1H-indole-1-carboxylate; (S,E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl pyrrolidine-1-carboxylate; 2-methoxyethyl (S,E)-(1-((1-((7-((2,4-difluorobenzyl)oxy)-5-fluoro-TH-indol-2-yl)methyl)-2-oxo-1,2-dihydropyridin-3-yl)amino)-7-(dimethylamino)-1,7-dioxohept-5-en-2-yl)carbamate; tert-butyl (S,E)-7-((2,4-difluorobenzyl)oxy)-2-((3-(2-((dimethylcarbamoyl)oxy)-7-oxo-7-(pyrrolidin-1-yl)hept-5-enamido)-2-oxopyridin-1(2H)-yl)methyl)-5-fluoro-1H-indole-1-carboxylate; (S,E)-1-((1-((7-((2,4-difluorobenzyl)oxy)-5-fluoro-TH-indol-2-yl)methyl)-2-oxo-1,2-dihydropyridin-3-yl)amino)-1,7-dioxo-7-(pyrrolidin-1-yl)hept-5-en-2-yl dimethylcarbamate; (S,E)-7-amino-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl dimethylcarbamate; methyl (S,E)-(1-((1-((5-fluoro-7-isobutyl-1H-indol-2-yl)methyl)-2-oxo-1,2-dihydropyridin-3-yl)amino)-1,7-dioxo-7-(pyrrolidin-1-yl)hept-5-en-2-yl)carbamate; tert-butyl (S,E)-5-fluoro-7-isobutyl-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate; methyl (S,E)-(7-(bis(methyl-$d_3$)amino)-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl)carbamate; tert-butyl (S,E)-2-((3-(7-(bis(methyl-$d_3$)amino)-2-((methoxycarbonyl)amino)-7-oxohept-5-enamido)-2-oxopyridin-1(2H)-yl)methyl)-7-((2,4-difluorobenzyl)oxy)-5-fluoro-1H-indole-1-carboxylate; tert-butyl (E)-7-((2,4-difluorobenzyl)oxy)-2-((3-(7-(dimethylamino)-2-((dimethylcarbamoyl)oxy)-7-oxohept-5-enamido-3,3-$d_2$)-2-oxopyridin-1(2H)-yl)methyl)-5-fluoro-1H-indole-1-carboxylate; (E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl-3,3-$d_2$ dimethylcarbamate; tert-butyl (E)-2-((3-(7-(dimethylamino)-2-((dimethylcarbamoyl)oxy)-7-oxohept-5-enamido-3,3-$d_2$)-2-oxopyridin-1(2H)-yl)methyl)-5-fluoro-7-isobutyl-1H-indole-1-carboxylate; (E)-7-(dimethylamino)-1-((1-((5-fluoro-7-isobutyl-1H-indol-2-yl)methyl)-2-oxo-1,2-dihydropyridin-3-yl)amino)-1,7-dioxohept-5-en-2-yl-3,3-$d_2$ dimethylcarbamate; [(E,1S)-6-(dimethylamino)-1-[[1-[[5-fluoro-7-(3,3,3-trifluoropropyl)-1H-indol-2-yl]methyl]-2-oxo-3-pyridyl]carbamoyl]-6-oxo-hex-4-enyl] N,N-dimethylcarbamate; tert-butyl (S,E)-5-fluoro-2-((3-(2-

((methoxycarbonyl)amino)-7-oxo-7-(pyrrolidin-1-yl)hept-5-enamido)-2-oxopyridin-1(2H)-yl)methyl)-7-(3,3,3-trifluoropropyl)-1H-indole-1-carboxylate; methyl (S,E)-(1-((1-((5-fluoro-7-(3,3,3-trifluoropropyl)-1H-indol-2-yl) methyl)-2-oxo-1,2-dihydropyridin-3-yl)amino)-1,7-dioxo-7-(pyrrolidin-1-yl)hept-5-en-2-yl)carbamate; methyl (S,E)-(7-(dimethylamino)-1-((1-((5-fluoro-7-(3,3,3-trifluoropropyl)-1H-indol-2-yl)methyl)-2-oxo-1,2-dihydropyridin-3-yl)amino)-1,7-dioxohept-5-en-2-yl) carbamate; tert-butyl (S,E)-2-((3-(7-(dimethylamino)-2-((methoxycarbonyl)amino)-7-oxohept-5-enamido)-2-oxopyridin-1(2H)-yl)methyl)-5-fluoro-7-(3,3,3-trifluoropropyl)-1H-indole-1-carboxylate; (S,E)-7-(dimethylamino)-1-((1-((5-fluoro-7-(trifluoromethyl)-1H-indol-2-yl)methyl)-2-oxo-1,2-dihydropyridin-3-yl)amino)-1,7-dioxohept-5-en-2-yl dimethylcarbamate; tert-butyl (S,E)-2-((3-(7-(dimethylamino)-2-((dimethylcarbamoyl) oxy)-7-oxohept-5-enamido)-2-oxopyridin-1(2H)-yl) methyl)-5-fluoro-7-(trifluoromethyl)-1H-indole-1-carboxylate; tert-butyl (S,E)-2-((3-(2-((dimethylcarbamoyl)oxy)-7-(methylamino)-7-oxohept-5-enamido)-2-oxopyridin-1(2H)-yl)methyl)-5-fluoro-7-(3,3,3-trifluoropropyl)-1H-indole-1-carboxylate; (S,E)-1-((1-((5-fluoro-7-(3,3,3-trifluoropropyl)-1H-indol-2-yl)methyl)-2-oxo-1,2-dihydropyridin-3-yl)amino)-7-(methylamino)-1,7-dioxohept-5-en-2-yl dimethylcarbamate; tert-butyl 2-[[3-[[(E,2S)-7-(dimethylamino)-7-oxo-2-(pyrrolidine-1-carbonyloxy)hept-5-enoyl]amino]-2-oxo-1-pyridyl] methyl]-7-(2,2-dimethylpropyl)-5-fluoro-indole-1-carboxylate; [(E,1S)-6-(dimethylamino)-1-[[1-[[7-(2,2-dimethylpropyl)-5-fluoro-1H-indol-2-yl]methyl]-2-oxo-3-pyridyl]carbamoyl]-6-oxo-hex-4-enyl] pyrrolidine-1-carboxylate; 2-methoxyethyl (S,E)-(7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl) carbamate; (S,E)-7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl dimethylcarbamate; methyl (S,E)-(1-((1-((5-fluoro-7-neopentyl-TH-indol-2-yl)methyl)-2-oxo-1,2-dihydropyridin-3-yl)amino)-1,7-dioxo-7-(pyrrolidin-1-yl)hept-5-en-2-yl)carbamate; (S,E)-7-(dimethylamino)-1-((1-((5-fluoro-7-neopentyl-TH-indol-2-yl)methyl)-2-oxo-1,2-dihydropyridin-3-yl)amino)-1,7-dioxohept-5-en-2-yl (2-methoxyethyl)(methyl)carbamate; (S,E)-1-((1-((5-fluoro-7-neopentyl-1H-indol-2-yl)methyl)-2-oxo-1,2-dihydropyridin-3-yl)amino)-1,7-dioxo-7-(pyrrolidin-1-yl)hept-5-en-2-yl pyrrolidine-1-carboxylate; methyl (S,E)-(7-(dimethylamino)-1-((1-((5-fluoro-7-neopentyl-TH-indol-2-yl)methyl)-2-oxo-1,2-dihydropyridin-3-yl)amino)-1,7-dioxohept-5-en-2-yl)carbamate; tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-7-(2,2-dimethylpropyl)-5-fluoro-indole-1-carboxylate; [(E,1S)-6-(dimethylamino)-1-[[4-[[7-(2,2-dimethylpropyl)-5-fluoro-TH-indol-2-yl]methyl]-3-oxo-pyrazin-2-yl]carbamoyl]-6-oxo-hex-4-enyl] N,N-dimethylcarbamate; tert-butyl (S,E)-2-((5-(7-(dimethylamino)-2-((dimethylcarbamoyl)oxy)-7-oxohept-5-enamido)-6-oxopyrimidin-1(6H)-yl)methyl)-5-fluoro-7-neopentyl-1H-indole-1-carboxylate; (S,E)-7-(dimethylamino)-1-((1-((5-fluoro-7-neopentyl-1H-indol-2-yl)methyl)-6-oxo-1,6-dihydropyrimidin-5-yl)amino)-1,7-dioxohept-5-en-2-yl dimethylcarbamate; tert-butyl (S,E)-2-((3-(7-(dimethylamino)-2-((dimethylcarbamoyl)oxy)-7-oxohept-5-enamido)-2-oxopyrazin-1(2H)-yl)methyl)-5-fluoro-7-(3,3,3-trifluoropropyl)-1H-indole-1-carboxylate; tert-butyl (S,E)-2-((5-(7-(dimethylamino)-2-((dimethylcarbamoyl)oxy)-7-oxohept-5-enamido)-6-oxopyrimidin-1(6H)-yl)methyl)-5-fluoro-7-(3,3,3-trifluoropropyl)-1H-indole-1-carboxylate; (S,E)-7-(dimethylamino)-1-((1-((5-fluoro-7-(3,3,3-trifluoropropyl)-1H-indol-2-yl)methyl)-6-oxo-1,6-dihydropyrimidin-5-yl)amino)-1,7-dioxohept-5-en-2-yl dimethylcarbamate; tert-butyl (S,E)-2-((5-(2-((dimethylcarbamoyl)oxy)-7-(methylamino)-7-oxohept-5-enamido)-6-oxopyrimidin-1(6H)-yl)methyl)-5-fluoro-7-(3,3,3-trifluoropropyl)-1H-indole-1-carboxylate; (S,E)-1-((1-((5-fluoro-7-(3,3,3-trifluoropropyl)-1H-indol-2-yl)methyl)-6-oxo-1,6-dihydropyrimidin-5-yl)amino)-7-(methylamino)-1,7-dioxohept-5-en-2-yl dimethylcarbamate; [(E,1S)-6-(dimethylamino)-1-[[1-[(5-fluoro-1-isobutyl-indol-2-yl) methyl]-6-oxo-pyrimidin-5-yl]carbamoyl]-6-oxo-hex-4-enyl]N,N-dimethylcarbamate; (S,E)-1-((1-((1-benzyl-5-fluoro-1H-indol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((1-(cyclopropylmethyl)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate; (S,E)-7-(dimethylamino)-1-((1-((5-fluoro-1-methyl-1H-indol-2-yl)methyl)-2-oxo-1,2-dihydropyridin-3-yl)amino)-1,7-dioxohept-5-en-2-yl dimethylcarbamate; (S,E)-7-(dimethylamino)-1-((1-((5-fluoro-1-(4-fluorobenzyl)-1H-indol-2-yl)methyl)-2-oxo-1,2-dihydropyridin-3-yl) amino)-1,7-dioxohept-5-en-2-yl dimethylcarbamate; (S,E)-7-(dimethylamino)-1-((1-((1-ethyl-5-fluoro-1H-indol-2-yl) methyl)-2-oxo-1,2-dihydropyridin-3-yl)amino)-1,7-dioxohept-5-en-2-yl dimethylcarbamate; (S,E)-1-((1-((1-(2,4-difluorobenzyl)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate; methyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-indole-1-carboxylate; 2,4-difluorobenzyl (S,E)-2-((3-(7-(dimethylamino)-2-((dimethylcarbamoyl)oxy)-7-oxohept-5-enamido)-2-oxopyridin-1(2H)-yl)methyl)-5-fluoro-1H-indole-1-carboxylate; [(E,1S)-6-(dimethylamino)-1-[[4-[(5-fluoro-1-isobutyl-indol-2-yl)methyl]-3-oxo-pyrazin-2-yl] carbamoyl]-6-oxo-hex-4-enyl] N,Ndimethylcarbamate; (S,E)-7-(dimethylamino)-1-((4-((1-ethyl-5-fluoro-1H-indol-2-yl)methyl)-3-oxo-3,4-dihydropyrazin-2-yl)amino)-1,7-dioxohept-5-en-2-yl dimethylcarbamate; (S,E)-1-((4-((1-benzyl-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate; (S,E)-1-((4-((1-(cyclopropylmethyl)-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate; (S,E)-7-(dimethylamino)-1-((4-((5-fluoro-1-(4-fluorobenzyl)-1H-indol-2-yl)methyl)-3-oxo-3,4-dihydropyrazin-2-yl)amino)-1,7-dioxohept-5-en-2-yl dimethylcarbamate; (S,E)-7-(dimethylamino)-1-((1-((5-fluoro-1-isobutyl-1H-indol-2-yl) methyl)-6-oxo-1,6-dihydropyrimidin-5-yl)amino)-1,7-dioxohept-5-en-2-yl dimethylcarbamate; (S,E)-1-((4-((1-(2,4-difluorobenzyl)-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate; [(E,1S)-6-(dimethylamino)-1-[[1-[(5-fluoro-1-methyl-indol-2-yl) methyl]-2-oxo-3-pyridyl]carbamoyl]-6-oxo-hex-4-enyl]N-[2-[tert-butoxycarbonyl(methyl)amino]ethyl]-N-methyl-carbamate; [(E,1S)-6-(dimethylamino)-1-[[1-[(5-fluoro-1-methyl-indol-2-yl)methyl]-2-oxo-3-pyridyl]carbamoyl]-6-oxo-hex-4-enyl]N-2-(dimethylamino)ethyl]-N-methyl-carbamate; (S,E)-tert-butyl 7-((3-(7-amino-2-((methoxycarbonyl)amino)-7-oxohept-5-enamido)-2-oxopyridin-1(2H)-yl)methyl)-1H-indole-1-carboxylate;

(S,E)-methyl (7-(dimethylamino)-1-((1-((7-isobutylbenzo[d]oxazol-2-yl)methyl)-2-oxo-1,2-dihydropyridin-3-yl)amino)-1,7-dioxohept-5-en-2-yl)carbamate; methyl (S,E)-(7-amino-1-((1-((7-isobutylbenzo[d]oxazol-2-yl)methyl)-2-oxo-1,2-dihydropyridin-3-yl)amino)-1,7-dioxohept-5-en-2-yl)carbamate; methyl (S,E)-(7-(dimethylamino)-1-((1-((4-isobutylbenzo[d]oxazol-2-yl)methyl)-2-oxo-1,2-dihydropyridin-3-yl)amino)-1,7-dioxohept-5-en-2-yl)carbamate; methyl (S,E)-(7-amino-1-((1-((4-isobutylbenzo[d]oxazol-2-yl)methyl)-2-oxo-1,2-dihydropyridin-3-yl)amino)-1,7-dioxohept-5-en-2-yl)carbamate; 2-hydroxyethyl (S,E)-(7-(dimethylamino)-1-((1-((7-isobutylbenzo[d]oxazol-2-yl)methyl)-2-oxo-1,2-dihydropyridin-3-yl)amino)-1,7-dioxohept-5-en-2-yl)carbamate; (S,E)-methyl (7-(dimethylamino)-1-((1-((7-isobutylbenzo[d]thiazol-2-yl)methyl)-2-oxo-1,2-dihydropyridin-3-yl)amino)-1,7-dioxohept-5-en-2-yl)carbamate; methyl (S,E)-(7-amino-1-((1-((7-isobutylbenzo[d]thiazol-2-yl)methyl)-2-oxo-1,2-dihydropyridin-3-yl)amino)-1,7-dioxohept-5-en-2-yl)carbamate; 2-hydroxyethyl (S,E)-(7-(dimethylamino)-1-((1-((7-isobutylbenzo[d]thiazol-2-yl)methyl)-2-oxo-1,2-dihydropyridin-3-yl)amino)-1,7-dioxohept-5-en-2-yl)carbamate; (S,E)-tert-butyl (1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate; (S,E)-N7-(1-((7-((2,4-difluorobenzyl)oxy)benzo [d]thiazol-2-yl)methyl)-2-oxo-1,2-dihydropyridin-3-yl)-N1,N1-dimethyl-6-(oxazole-2-carboxamido)hept-2-enediamide; (S,E)-N7-(1-((7-((2,4-difluorobenzyl)oxy)benzo[d]thiazol-2-yl)methyl)-2-oxo-1,2-dihydropyridin-3-yl)-6-(4,4-difluorocyclohexane-1-carboxamido)-N1,N1-dimethylhept-2-enediamide; (S,E)-N7-(1-((7-((2,4-difluorobenzyl)oxy)benzo[d]thiazol-2-yl)methyl)-2-oxo-1,2-dihydropyridin-3-yl)-6-(2-fluorobenzamido)-N1,N1-dimethylhept-2-enediamide; methyl (S,E)-(7-amino-1-((1-((7-((2,4-difluorobenzyl)oxy)benzo[d]thiazol-2-yl)methyl)-2-oxo-1,2-dihydropyridin-3-yl)amino)-1,7-dioxohept-5-en-2-yl)carbamate; methyl (S,E)-(1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate; (S,E)-N7-(1-((7-((2,4-difluorobenzyl)oxy)benzo[d]thiazol-2-yl)methyl)-2-oxo-1,2-dihydropyridin-3-yl)-6-(2-methoxyacetamido)-N1,N1-dimethylhept-2-enediamide; methyl (S,E)-(7-amino-1-((1-((7-(2,2-difluoroethoxy)benzo[d]thiazol-2-yl)methyl)-2-oxo-1,2-dihydropyridin-3-yl)amino)-1,7-dioxohept-5-en-2-yl)carbamate; methyl (S,E)-(1-((1-((7-(2,2-difluoroethoxy)benzo[d]thiazol-2-yl)methyl)-2-oxo-1,2-dihydropyridin-3-yl)amino)-7-(dimethylamino)-1,7-dioxohept-5-en-2-yl)carbamate; methyl (S,E)-(7-amino-1,7-dioxo-1-((2-oxo-1-((7-(1,1,2,2-tetrafluoroethoxy)benzo[d]thiazol-2-yl)methyl)-1,2-dihydropyridin-3-yl)amino)hept-5-en-2-yl)carbamate; methyl (S,E)-(7-(dimethylamino)-1,7-dioxo-1-((2-oxo-1-((7-(1,1,2,2-tetrafluoroethoxy)benzo[d]thiazol-2-yl)methyl)-1,2-dihydropyridin-3-yl)amino)hept-5-en-2-yl)carbamate; methyl (S,E)-(7-(dimethylamino)-1,7-dioxo-1-((2-oxo-1-((7-(2,2,2-trifluoroethoxy)benzo[d]thiazol-2-yl)methyl)-1,2-dihydropyridin-3-yl)amino)hept-5-en-2-yl)carbamate; methyl (S,E)-(7-amino-1,7-dioxo-1-((2-oxo-1-((7-(2,2,2-trifluoroethoxy)benzo[d]thiazol-2-yl)methyl)-1,2-dihydropyridin-3-yl)amino)hept-5-en-2-yl)carbamate; tert-butyl (S,E)-(7-amino-1-((1-((7-((2,4-difluorobenzyl)oxy)benzo[d]thiazol-2-yl)methyl)-2-oxo-1,2-dihydropyridin-3-yl)amino)-1,7-dioxohept-5-en-2-yl)carbamate; (S,E)-N7-(1-((7-((2,4-difluorobenzyl)oxy)benzo[d]thiazol-2-yl)methyl)-2-oxo-1,2-dihydropyridin-3-yl)-6-(2-methoxyacetamido)hept-2-enediamide; (S,E)-N7-(1-((7-((2,4-difluorobenzyl)oxy)benzo[d]thiazol-2-yl)methyl)-2-oxo-1,2-dihydropyridin-3-yl)-6-(2-fluorobenzamido)hept-2-enediamide; (S,E)-methyl (7-(dimethylamino)-1-((1-((5-fluorobenzo[d]thiazol-2-yl)methyl)-2-oxo-1,2-dihydropyridin-3-yl)amino)-1,7-dioxohept-5-en-2-yl)carbamate; methyl (S,E)-(7-amino-1-((1-((5-fluorobenzo[d]thiazol-2-yl)methyl)-2-oxo-1,2-dihydropyridin-3-yl)amino)-1,7-dioxohept-5-en-2-yl)carbamate; methyl (S,E)-(1-((1-((5-fluorobenzo[d]thiazol-2-yl)methyl)-2-oxo-1,2-dihydropyridin-3-yl)amino)-1,7-dioxo-7-(pyrrolidin-1-yl)hept-5-en-2-yl)carbamate; methyl (S,E)-methyl (1-((1-((7-((2,4-difluorophenoxy)methyl)benzo[d]thiazol-2-yl)methyl)-2-oxo-1,2-dihydropyridin-3-yl)amino)-7-(dimethylamino)-1,7-dioxohept-5-en-2-yl)carbamate; (S,E)-2-hydroxyethyl (1-((1-(benzo[d]thiazol-2-ylmethyl)-2-oxo-1,2-dihydropyridin-3-yl)amino)-7-(dimethylamino)-1,7-dioxohept-5-en-2-yl)carbamate; tert-butyl (S,E)-2-((3-(7-(dimethylamino)-2-(((2-hydroxyethoxy)carbonyl)amino)-7-oxohept-5-enamido)-2-oxopyridin-1(2H)-yl)methyl)-1H-indole-1-carboxylate; 2-hydroxyethyl (S,E)-(7-amino-1-((1-(benzo[d]oxazol-2-ylmethyl)-2-oxo-1,2-dihydropyridin-3-yl)amino)-1,7-dioxohept-5-en-2-yl)carbamate; 2-hydroxyethyl (S,E)-(7-amino-1-((1-(benzo[d]thiazol-2-ylmethyl)-2-oxo-1,2-dihydropyridin-3-yl)amino)-1,7-dioxohept-5-en-2-yl)carbamate; 2-hydroxyethyl (S,E)-(1-((1-((1H-indol-2-yl)methyl)-2-oxo-1,2-dihydropyridin-3-yl)amino)-7-amino-1,7-dioxohept-5-en-2-yl)carbamate; tert-butyl (S,E)-2-((3-(7-amino-2-(((2-hydroxyethoxy)carbonyl)amino)-7-oxohept-5-enamido)-2-oxopyridin-1(2H)-yl)methyl)-1H-indole-1-carboxylate; (S,E)-methyl (7-amino-1-((1-((7-((2,4-difluorobenzyl)oxy)-5-fluorobenzo[d]thiazol-2-yl)methyl)-2-oxo-1,2-dihydropyridin-3-yl)amino)-1,7-dioxohept-5-en-2-yl)carbamate; tert-butyl (S,E)-2-((3-(7-(dimethylamino)-2-(((2-hydroxyethoxy)carbonyl)amino)-7-oxohept-5-enamido)-2-oxopyridin-1(2H)-yl)methyl)-1H-indole-1-carboxylate; methyl (S,E)-(1-((1-((7-((2,4-difluorobenzyl)oxy)-5-fluorobenzo[d]thiazol-2-yl)methyl)-2-oxo-1,2-dihydropyridin-3-yl)amino)-7-(methylamino)-1,7-dioxohept-5-en-2-yl)carbamate; methyl N-[(E)-1-[[[1-[(5,7-difluoro-4-isobutyl-1H-benzimidazol-2-yl)methyl]-2-oxo-3-pyridyl]amino]methyl]-6-(dimethylamino)-6-oxo-hex-4-enyl]carbamate; methyl N-[(E,1S)-1-[[1-[[4-(2,4-difluorophenoxy)-5,6-difluoro-1H-benzimidazol-2-yl]methyl]-2-oxo-3-pyridyl]carbamoyl]-6-(dimethylamino)-6-oxo-hex-4-enyl]carbamate; methyl (S,E)-(1-((1-((5,6-difluoro-7-isopropoxy-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((7-(benzyloxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((7-((2,4-difluorobenzyl)oxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((5,6-difluoro-7-phenoxy-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-1-((1-((5,6-difluoro-7-isopropoxy-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((4-(2,4-difluorophenoxy)-5,6-difluoro-TH-benzo[d]imidazol-2-yl)methyl)-2-oxo-1,2-dihydropyridin-3-yl)amino)-7-(dimethylamino)-1,7-dioxohept-5-en-2-yl dimethylcarbamate; (S,E)-1-((1-((4-((2,4-difluorobenzyl)oxy)-5,6-difluoro-TH-benzo[d]imidazol-2-yl)methyl)-2- oxo-1,2-dihydropyridin-3-yl)amino)-7-(dimethylamino)-1,7-dioxohept-5-en-2-yl dimethylcarbamate; tert-butyl 4-(2,4-difluorophenoxy)-2-[[3-[[(E,2S)-7-(dimethylamino)-2-(methoxycarbonylamino)-7-oxo-hept-5-enoyl]amino]-2-oxo-1-pyridyl]methyl]-5,6-difluoro-benzimidazole-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-isopropoxy-1H-benzo[d]imidazole-1-carboxylate; tert-butyl (S,E)-4-(benzyloxy)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate; tert-butyl (S,E)-4-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-5,6-difluoro-TH-benzo[d]imidazole-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-phenoxy-1H-benzo[d]imidazole-1-carboxylate; tert-butyl (S,E)-4-((2,4-difluorobenzyl)oxy)-2-((3-(7-(dimethyl-amino)-2-((dimethylcarbamoyl)oxy)-7-oxohept-5-enamido)-2-oxopyridin-1(2H)-yl)methyl)-5,6-difluoro-TH-benzo[d]imidazole-1-carboxylate; tert-butyl 2-[[3-[[(E,2S)-7-(dimethylamino)-2-(methoxycarbonylamino)-7-oxo-hept-5-enoyl]amino]-2-oxo-1-pyridyl]methyl]-4-(2,2-dimethylpropyl)-5,6-difluoro-benzimidazole-1-carboxylate; methyl N-[(E,1S)-6-(dimethylamino)-1-[[1-[[4-(2,2-dimethylpropyl)-5,6-difluoro-1H-benzimidazol-2-yl]methyl]-2-oxo-3-pyridyl]carbamoyl]-6-oxo-hex-4-enyl]carbamate; tert-butyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-4-neopentyl-1H-benzo[d]imidazole-1-carboxylate; (S,E)-1-((1-((5,6-difluoro-4-neopentyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-phenoxy-benzimidazole-1-carboxylate; tert-butyl (S,E)-4-(2,4-difluorophenoxy)-2-((3-(7-(dimethylamino)-2-((methoxycarbonyl)amino)-7-oxohept-5-enamido)-2-oxopyridin-1(2H)-yl)methyl)-5,7-difluoro-TH-benzo[d]imidazole-1-carboxylate; methyl N-[(E,1S)-1-[[1-[(5,7-difluoro-4-phenoxy-1H-benzimidazol-2-yl)methyl]-2-oxo-3-pyridyl]carbamoyl]-6-(dimethylamino)-6-oxo-hex-4-enyl]carbamate; tert-butyl (S,E)-4-(benzyloxy)-2-((3-(7-(dimethylamino)-2-((methoxycarbonyl)amino)-7-oxohept-5-enamido)-2-oxopyridin-1(2H)-yl)methyl)-5,7-difluoro-1H-benzo[d]imidazole-1-carboxylate; tert-butyl (S,E)-2-((3-(7-(dimethylamino)-2-((methoxycarbonyl)amino)-7-oxohept-5-enamido)-2-oxopyridin-1(2H)-yl)methyl)-5,7-difluoro-4-isopropoxy-1H-benzo[d]imidazole-1-carboxylate; methyl (S,E)-(1-((1-((4-(2,4-difluorophenoxy)-5,7-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((4-(benzyloxy)-5,7-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate; methyl (S,E)-(1-((1-((4-((2,4-difluorobenzyl)oxy)-5,7-difluoro-TH-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-1-((1-((7-((2,4-difluorobenzyl)oxy)-4,6-difluoro-TH-benzo[d]imidazol-2-yl)methyl)-2-oxo-1,2-dihydropyridin-3-yl)amino)-7-(dimethylamino)-1,7-dioxohept-5-en-2-yl dimethylcarbamate; methyl N-[(E,1S)-6-(dimethylamino)-6-oxo-1-[[2-oxo-1-[(6-phenoxy-9H-purin-8-yl)methyl]-3-pyridyl]carbamoyl]hex-4-enyl]carbamate; tert-butyl (S,E)-6-(2,4-difluorophenoxy)-8-((3-(7-(dimethylamino)-2-((methoxycarbonyl)amino)-7-oxohept-5-enamido)-2-oxopyridin-1(2H)-yl)methyl)-9H-purine-9-carboxylate; methyl (S,E)-(1-((1-((6-(2,4-difluorophenoxy)-9H-purin-8-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1-((1-((6-isopropoxy-9H-purin-8-yl)methyl)-2-oxo-1,2-dihydropyridin-3-yl)amino)-1,7-dioxohept-5-en-2-yl)carbamate; methyl (S,E)-(7-(dimethylamino)-1-((1-((6-isobutoxy-9H-purin-8-yl)methyl)-2-oxo-1,2-dihydropyridin-3-yl)amino)-1,7-dioxohept-5-en-2-yl)carbamate; methyl N-[(E,1S)-1-[[1-[(6-benzyloxy-9H-purin-8-yl)methyl]-2-oxo-3-pyridyl]carbamoyl]-6-(dimethylamino)-6-oxo-hex-4-enyl]carbamate; methyl (S,E)-(1-((1-((6-((2,4-difluorobenzyl)oxy)-9H-purin-8-yl)methyl)-2-oxo-1,2-dihydropyridin-3-yl)amino)-7-(dimethylamino)-1,7-dioxohept-5-en-2-yl)carbamate; (S,E)-1-((1-((6-((2,4-difluorobenzyl)oxy)-9H-purin-8-yl)methyl)-2-oxo-1,2-dihydropyridin-3-yl)amino)-7-(dimethylamino)-1,7-dioxohept-5-en-2-yl dimethylcarbamate; methyl N-[(E,1S)-1-[[1-[(6-benzyl-9H-purin-8-yl)methyl]-2-oxo-3-pyridyl]carbamoyl]-6-(dimethylamino)-6-oxo-hex-4-enyl]carbamate; methyl (S,E)-(7-(dimethylamino)-1,7-dioxo-1-((2-oxo-1-((6-(3,3,3-trifluoropropyl)-9H-purin-8-yl)methyl)-1,2-dihydropyridin-3-yl)amino)hept-5-en-2-yl)carbamate; methyl (S,E)-(1-((1-((6-(cyclopropylmethyl)-9H-purin-8-yl)methyl)-2-oxo-1,2-dihydropyridin-3-yl)amino)-7-(dimethylamino)-1,7-dioxohept-5-en-2-yl)carbamate; methyl ((2S,E)-7-(dimethylamino)-1,7-dioxo-1-((2-oxo-1-((9-(tetrahydro-2H-pyran-2-yl)-6-(3,3,3-trifluoropropyl)-9H-purin-8-yl)methyl)-1,2-dihydropyridin-3-yl)amino)hept-5-en-2-yl)carbamate; (2S,E)-7-(dimethylamino)-1,7-dioxo-1-((2-oxo-1-((9-(tetrahydro-2H-pyran-2-yl)-6-(3,3,3-trifluoropropyl)-9H-purin-8-yl)methyl)-1,2-dihydropyridin-3-yl)amino)hept-5-en-2-yl dimethylcarbamate; (S,E)-7-(dimethylamino)-1,7-dioxo-1-((2-oxo-1-((6-(3,3,3-trifluoropropyl)-9H-purin-8-yl)methyl)-1,2-dihydropyridin-3-yl)amino)hept-5-en-2-yl dimethylcarbamate; methyl N-[(E,1S)-6-(dimethylamino)-1-[[1-[[6-(2,2-dimethylpropyl)-9H-purin-8-yl]methyl]-2-oxo-3-pyridyl]carbamoyl]-6-oxo-hex-4-enyl]carbamate; (S,E)-7-(dimethylamino)-1-((1-((6-neopentyl-9H-purin-8-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-isopentyl-9H-purin-8-yl)methyl)-2-oxo-1,2-dihydropyridin-3-yl)amino)-1,7-dioxohept-5-en-2-yl)carbamate; methyl (S,E)-(1-((1-((6-(2-cyclohexylethyl)-7H-purin-8-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1-((1-((6-(3,3-dimethylbutyl)-9H-purin-8-yl)methyl)-2-oxo-1,2-dihydropyridin-3-yl)amino)-1,7-dioxohept-5-en-2-yl)carbamate; (S,E)-7-(dimethylamino)-1-((1-((6-(3,3-dimethylbutyl)-9H-purin-8-yl)methyl)-2-oxo-1,2-dihydropyridin-3-yl)amino)-1,7-dioxohept-5-en-2-yl dimethylcarbamate; (2S,E)-7-(dimethylamino)-1-((1-((6-(3,3-dimethylbutyl)-9-(tetrahydro-2H-pyran-2-yl)-9H-purin-8-yl)methyl)-2-oxo-1,2-dihydropyridin-3-yl)amino)-1,7-dioxohept-5-en-2-yl dimethylcarbamate; methyl ((2S,E)-7-(dimethylamino)-1-((1-((6-(3,3-dimethylbutyl)-9-(tetrahydro-2H-pyran-2-yl)-9H-purin-8-yl)methyl)-2-oxo-1,2-dihydropyridin-3-yl)amino)-1,7-dioxohept-5-en-2-yl)carbamate; (2S,E)-7-(dimethylamino)-1-((1-((6-isopentyl-9-(tetrahydro-2H- pyran-2-yl)-9H-purin-8-yl)methyl)-2-oxo-1,2-dihydropyridin-3-yl)amino)-1,7-dioxohept-5-en-2-yl dimethylcarbamate; (S,E)-7-(dimethylamino)-1-((1-((6-isopentyl-9H-purin-8-yl)methyl)-2-oxo-1,2-dihydropyridin-3-yl)amino)-1,7-dioxohept-5-en-2-yl dimethylcarbamate; methyl N-[(E,1S)-6-(dimethylamino)-1-[[1-[(4-isobutyl-5H-pyrrolo[3,2-d]pyrimidin-6-yl)methyl]-2-oxo-3-pyridyl]carbamoyl]-6-oxo-hex-4-enyl]carbamate; (S,E)-7-(dimethylamino)-1-((1-((4-isobutyl-5H-pyrrolo[3,2-d]pyrimidin-6-yl)methyl)-2-oxo-1,2-dihydropyridin-3-yl)amino)-1,7-dioxohept-5-en-2-yl dimethylcarbamate; methyl (S,E)-(7-(dimethylamino)-1,7-dioxo-1-((2-oxo-1-((4-(3,3,3-trifluoropropyl)-5H-pyrrolo[3,2-d]pyrimidin-6-yl)methyl)-1,2-dihydropyridin-3-yl)amino)hept-5-en-2-yl)carbamate; (S,E)-7-(dimethylamino)-1,7-dioxo-1-((2-oxo-1-((4-(3,3,3-trifluoropropyl)-5H-pyrrolo[3,2-d]pyrimidin-6-yl)methyl)-1,2-dihydropyridin-3-yl)amino)hept-5-en-2-yl dimethylcarbamate; methyl ((2S,E)-7-(dimethylamino)-1-((1-((2-methyl-6-neopentyl-9-(tetrahydro-2H-pyran-2-yl)-9H-purin-8-yl)methyl)-2-oxo-1,2-dihydropyridin-3-yl)amino)-1,7-dioxohept-5-en-2-yl)carbamate; methyl (S,E)-(7-(dimethylamino)-1-((1-((2-methyl-6-neopentyl-9H-purin-8-yl)methyl)-2-oxo-1,2-dihydropyridin-3-yl)amino)-1,7-dioxohept-5-en-2-yl)carbamate; (S,E)-7-(dimethylamino)-1-((1-((2-methyl-6-neopentyl-9H-purin-8-yl)methyl)-2-oxo-1,2-dihydropyridin-3-yl)amino)-1,7-dioxohept-5-en-2-yl dimethylcarbamate; methyl (S,E)-(1-((1-((6-(cyclohexylmethyl)-9H-purin-8-yl)methyl)-2-oxo-1,2-dihydropyridin-3-yl)amino)-7-(dimethylamino)-1,7-dioxohept-5-en-2-yl)carbamate; (S,E)-1-((1-((6-(cyclohexylmethyl)-9H-purin-8-yl)methyl)-2-oxo-1,2-dihydropyridin-3-yl)amino)-7-(dimethylamino)-1,7-dioxohept-5-en-2-yl dimethylcarbamate; methyl (S,E)-(7-(dimethylamino)-1-((1-((4-isobutyl-2-methyl-5H-pyrrolo[3,2-d]pyrimidin-6-yl)methyl)-2-oxo-1,2-dihydropyridin-3-yl)amino)-1,7-dioxohept-5-en-2-yl)carbamate; (S,E)-7-(dimethylamino)-1-((1-((4-isobutyl-2-methyl-5H-pyrrolo[3,2-d]pyrimidin-6-yl)methyl)-2-oxo-1,2-dihydropyridin-3-yl)amino)-1,7-dioxohept-5-en-2-yl dimethylcarbamate; (S,E)-7-(dimethylamino)-1,7-dioxo-1-((2-oxo-1-((6-(3,3,3-trifluoro-2-(trifluoromethyl)propyl)-9H-purin-8-yl)methyl)-1,2-dihydropyridin-3-yl)amino)hept-5-en-2-yl dimethylcarbamate; 2-methoxyethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate; (S,E)-7-(dimethylamino)-1-((1-((6-fluoro-7-isobutyl-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-isobutyl-1H-pyrrolo[3,2-b]pyridin-2-yl)methyl)-2-oxo-1,2-dihydropyridin-3-yl)amino)-1,7-dioxohept-5-en-2-yl)carbamate; (S,E)-6-(3,3-dimethylureido)-N7-(1-((6-fluoro-7-isobutyl-1H-pyrrolo[3,2-b]pyridin-2-yl)methyl)-2-oxo-1,2-dihydropyridin-3-yl)-N1,N1-dimethylhept-2-enediamide; methyl N-[(E,1S)-6-(dimethylamino)-1-[[1-[(6-fluoro-7-isobutyl-1H-pyrrolo[3,2-b]pyridin-2-yl)methyl]-6-methyl-2-oxo-3-pyridyl]carbamoyl]-6-oxo-hex-4-enyl]carbamate; (S,E)-7-(dimethylamino)-1-((1-((6-fluoro-7-isobutyl-1H-pyrrolo[3,2-b]pyridin-2-yl)methyl)-6-methyl-2-oxo-1,2-dihydropyridin-3-yl)amino)-1,7-dioxohept-5-en-2-yl dimethylcarbamate; methyl (S,E)-(1-((6-chloro-1-((6-fluoro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate; (S,E)-1-((6-chloro-1-((6-fluoro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((1-((7-(cyclobutylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate; (S,E)-1-((1-((7-(cyclobutylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(7-(dimethylamino)-1-((1-((6-fluoro-7-isopropoxy-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((6-fluoro-7-isopropoxy-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-isobutoxy-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((6-fluoro-7-isobutoxy-TH-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(1-((1-((7-(benzyloxy)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate; (S,E)-1-((1-((7-(benzyloxy)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate; methyl N-[(E,1S)-1-[[1-[(6-chloro-7-isobutyl-1H-pyrrolo[3,2-b]pyridin-2-yl)methyl]-2-oxo-3-pyridyl]carbamoyl]-6-(dimethylamino)-6-oxo-hex-4-enyl]carbamate; (S,E)-1-((1-((6-chloro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((1-((7-(cyclopropylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1-((1-((7-isobutyl-6-(trifluoromethyl)-1H-pyrrolo[3,2-b]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-isobutyl-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((7-isobutyl-1H-pyrrolo[3,2-b]pyridin-2-yl)methyl)-2-oxo-1,2-dihydropyridin-3-yl)amino)-1,7-dioxohept-5-en-2-yl dimethylcarbamate; (S,E)-7-(dimethylamino)-1-((1-((7-isobutyl-1H-pyrrolo[3,2-c]pyridin-2-yl)methyl)-2-oxo-1,2-dihydropyridin-3-yl)amino)-1,7-dioxohept-5-en-2-yl dimethylcarbamate; methyl (E)-(7-(dimethylamino)-1-((1-((7-isobutyl-1H-pyrrolo[3,2-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-(2-methylprop-1-en-1-yl)-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((7-(2-methylprop-1-en-1-yl)-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((7-(2-methylprop-1-en-1-yl)-6-(trifluoromethyl)-1H-pyrrolo[3,2-b]pyridin-2-yl)methyl)-2-oxo-1,2-dihydropyridin-3-yl)amino)-1,7-dioxohept-5-en-2-yl)carbamate; methyl N-[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl]carbamate; (S,E)-7-(dimethylamino)-1-((1-((6-fluoro-7-isobutyl-3-methyl-1H-pyrrolo[3,2-b]pyridin-2-yl)methyl)-

2-oxo-1,2-dihydropyridin-3-yl)amino)-1,7-dioxohept-5-en-2-yl dimethylcarbamate; (S,E)-7-(dimethylamino)-1-((1-((6-fluoro-7-isobutyl-3-methyl-1H-pyrrolo[3,2-b]pyridin-2-yl)methyl)-6-methyl-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-isobutyl-3-methyl-1H-pyrrolo[3,2-b]pyridin-2-yl)methyl)-6-methyl-2-oxo-1,2-dihydropyridin-3-yl)amino)-1,7-dioxohept-5-en-2-yl)carbamate; methyl (S,E)-(7-(dimethylamino)-1-((1-((6-fluoro-7-isobutyl-5-methyl-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((6-fluoro-7-isobutyl-5-methyl-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl dimethylcarbamate; (S,E)-7-(dimethylamino)-1-((1-((4-fluoro-7-isobutyl-1H-pyrrolo[2,3-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((4-fluoro-7-isobutyl-1H-pyrrolo[2,3-c]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((4-fluoro-7-isobutyl-1H-pyrrolo[2,3-c]pyridin-2-yl)methyl)-6-methyl-2-oxo-1,2-dihydropyridin-3-yl)amino)-1,7-dioxohept-5-en-2-yl dimethylcarbamate; methyl (S,E)-(7-(dimethylamino)-1-((1-((4-fluoro-7-isobutyl-1H-pyrrolo[2,3-c]pyridin-2-yl)methyl)-6-methyl-2-oxo-1,2-dihydropyridin-3-yl)amino)-1,7-dioxohept-5-en-2-yl)carbamate; (S,E)-1-((6-chloro-1-((4-fluoro-7-isobutyl-TH-pyrrolo[2,3-c]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((6-chloro-1-((4-fluoro-7-isobutyl-TH-pyrrolo[2,3-c]pyridin-2-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1-((1-((4-fluoro-7-(2-methylprop-1-en-1-yl)-1H-pyrrolo[2,3-c]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((4-fluoro-7-(2-methylprop-1-en-1-yl)-1H-pyrrolo[2,3-c]pyridin-2-yl)methyl)-2-oxo-1,2-dihydropyridin-3-yl)amino)-1,7-dioxohept-5-en-2-yl dimethylcarbamate; methyl N-[(E,1S)-6-(dimethylamino)-1-[[1-[(7-isobutyl-1H-pyrrolo[2,3-c]pyridin-2-yl)methyl]-2-oxo-3-pyridyl]carbamoyl]-6-oxo-hex-4-enyl]carbamate; (S,E)-7-(dimethylamino)-1-((1-((7-isobutyl-TH-pyrrolo[2,3-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-(dimethylamino)-2-methyl-9H-purin-8-yl)methyl)-2-oxo-1,2-dihydropyridin-3-yl)amino)-1,7-dioxohept-5-en-2-yl)carbamate; methyl N-[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl]carbamate; (S,E)-7-(dimethylamino)-1-((1-((7-isobutyl-1H-benzo[d]imidazol-2-yl)methyl)-6-methyl-2-oxo-1,2-dihydropyridin-3-yl)amino)-1,7-dioxohept-5-en-2-yl dimethylcarbamate; methyl (S,E)-(1-((6-chloro-1-((4-isobutyl-1H-benzo[d]imidazol-2-yl)methyl)-2-oxo-1,2-dihydropyridin-3-yl)amino)-7-(dimethylamino)-1,7-dioxohept-5-en-2-yl)carbamate; (S,E)-1-((6-chloro-1-((7-isobutyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate; methyl-N-[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl]carbamate; (S,E)-7-(dimethylamino)-1-((1-((7-fluoro-4-isobutyl-1H-imidazo[4,5-c]pyridin-2-yl)methyl)-6-methyl-2-oxo-1,2-dihydropyridin-3-yl)amino)-1,7-dioxohept-5-en-2-yl dimethylcarbamate; methyl (S,E)-(1-((1-((7-fluoro-4-isobutyl-3H-imidazo[4,5-c]pyridin-2-yl)methyl)-6-methyl-2-oxo-1,2-dihydropyridin-3-yl)amino)-6-(methylsulfonyl)-1-oxohex-5-en-2-yl)carbamate; methyl N-[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]carbamate; [(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl] N,N-dimethylcarbamate; (S,E)-7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl)carbamate; (S,E)-7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate; methyl (S,E)-(1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-1-((1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((1-((4-(cyclopropylmethyl)-7-fluoro-3H-imidazo[4,5-c]pyridin-2-yl)methyl)-6-methyl-2-oxo-1,2-dihydropyridin-3-yl)amino)-7-(dimethylamino)-1,7-dioxohept-5-en-2-yl)carbamate; (S,E)-1-((1-((4-(cyclopropylmethyl)-7-fluoro-3H-imidazo[4,5-c]pyridin-2-yl)methyl)-6-methyl-2-oxo-1,2-dihydropyridin-3-yl)amino)-7-(dimethylamino)-1,7-dioxohept-5-en-2-yl dimethylcarbamate; methyl (S,E)-(1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; methyl N-[(E,1S)-6-(dimethylamino)-1-[[1-[(7-fluoro-4-isobutyl-3H-imidazo[4,5-c]pyridin-2-yl)methyl]-5-methyl-2-oxo-3-pyridyl]carbamoyl]-6-oxo-hex-4-enyl]carbamate; (S,E)-7-(dimethylamino)-1-((1-((7-fluoro-4-isobutyl-3H-imidazo[4,5-c]pyridin-2-yl)methyl)-5-methyl-2-oxo-1,2-dihydropyridin-3-yl)amino)-1,7-dioxohept-5-en-2-yl dimethylcarbamate; methyl (S,E)-(1-((5-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-1-((5-chloro-1-((7-fluoro-4-isobutyl-3H- imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(7-(dimethylamino)-1-((5-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate; (S,E)-7-(dimethylamino)-1-((5-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-isobutyl-3H-imidazo[4,5-c]pyridin-2-yl)methyl)-6-isobutyl-2-oxo-1,2-dihydropyridin-3-yl)amino)-1,7-dioxohept-5-en-2-yl)carbamate; (S,E)-7-(dimethylamino)-1-((1-((7-fluoro-4-isobutyl-3H-imidazo[4,5-c]pyridin-2-yl)methyl)-6-isobutyl-2-oxo-1,2-dihydropyridin-3-yl)amino)-1,7-dioxohept-5-en-2-yl dimethylcarbamate; (S,E)-7-(dimethylamino)-1-((1-((7-fluoro-4-isobutyl-3H-imidazo[4,5-c]pyridin-2-yl)methyl)-6-isopropyl-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-isobutyl-3H-imidazo[4,5-c]pyridin-2-yl)methyl)-6-isopropyl-2-oxo-1,2-dihydropyridin-3-yl)amino)-1,7-dioxohept-5-en-2-yl)carbamate; (S,E)-7-(dimethylamino)-1-((6-ethyl-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((6-ethyl-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-fluoro-4-isobutyl-3H-imidazo[4,5-c]pyridin-2-yl)methyl)-2-oxo-6-propyl-1,2-dihydropyridin-3-yl)amino)-1,7-dioxohept-5-en-2-yl)carbamate; (S,E)-7-(dimethylamino)-1-((1-((7-fluoro-4-isobutyl-3H-imidazo[4,5-c]pyridin-2-yl)methyl)-2-oxo-6-propyl-1,2-dihydropyridin-3-yl)amino)-1,7-dioxohept-5-en-2-yl dimethylcarbamate; (S,E)-7-(dimethylamino)-1-((1-((7-fluoro-4-isobutyl-3H-imidazo[4,5-c]pyridin-2-yl)methyl)-5,6-dimethyl-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-isobutyl-3H-imidazo[4,5-c]pyridin-2-yl)methyl)-5,6-dimethyl-2-oxo-1,2-dihydropyridin-3-yl)amino)-1,7-dioxohept-5-en-2-yl)carbamate; methyl (S,E)-(7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-1,7-dioxohept-5-en-2-yl)carbamate; (S,E)-7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-1,7-dioxohept-5-en-2-yl dimethylcarbamate; methyl (S,E)-(7-(dimethylamino)-1-((1-((7-fluoro-4-isobutyl-3H-imidazo[4,5-c]pyridin-2-yl)methyl)-6-(methoxymethyl)-2-oxo-1,2-dihydropyridin-3-yl)amino)-1,7-dioxohept-5-en-2-yl)carbamate; (S,E)-7-(dimethylamino)-1-((1-((7-fluoro-4-isobutyl-3H-imidazo[4,5-c]pyridin-2-yl)methyl)-6-(hydroxymethyl)-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-isobutyl-3H-imidazo[4,5-c]pyridin-2-yl)methyl)-6-(hydroxymethyl)-2-oxo-1,2-dihydropyridin-3-yl)amino)-1,7-dioxohept-5-en-2-yl)carbamate; methyl (S,E)-(7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate; (S,E)-7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((5-fluoro-1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl)carbamate; (S,E)-7-(dimethylamino)-1-((5-fluoro-1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-isobutyl-3H-imidazo[4,5-b]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((6-fluoro-7-isobutyl-1H-imidazo[4,5-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((1-((6-fluoro-7-isobutyl-3H-imidazo[4,5-b]pyridin-2-yl)methyl)-6-methyl-2-oxo-1,2-dihydropyridin-3-yl)amino)-1,7-dioxohept-5-en-2-yl)carbamate; (S,E)-7-(dimethylamino)-1-((1-((6-fluoro-7-isobutyl-1H-imidazo[4,5-b]pyridin-2-yl)methyl)-6-methyl-2-oxo-1,2-dihydropyridin-3-yl)amino)-1,7-dioxohept-5-en-2-yl dimethylcarbamate; (S,E)-1-((6-chloro-1-((6-fluoro-7-isobutyl-3H-imidazo[4,5-b]pyridin-2-yl)methyl)-2-oxo-1,2-dihydropyridin-3-yl)amino)-7-(dimethylamino)-1,7-dioxohept-5-en-2-yl dimethylcarbamate; methyl (S,E)-(1-((6-chloro-1-((6-fluoro-7-isobutyl-1H-imidazo[4,5-b]pyridin-2-yl)methyl)-2-oxo-1,2-dihydropyridin-3-yl)amino)-7-(dimethylamino)-1,7-dioxohept-5-en-2-yl)carbamate; [(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]N-[2-(dimethylamino)ethyl]-N-methyl-carbamate; 2-(dimethylamino)ethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate; methyl (S,E)-(1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; (S,E)-7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl dimethylcarbamate; (S,E)-7-(dimethylamino)-1-((1-((6-fluoro-7-isobutyl-3-methyl-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate; (S,E)-7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate; methyl (S,E)-(7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl)carbamate; methyl (S,E)-(7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl)carbamate; methyl (S,E)-(1-((6-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; methyl (S,E)-(7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-

1,7-dioxohept-5-en-2-yl)carbamate; (S,E)-1-((6-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate; (S,E)-7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl dimethylcarbamate; methyl (S,E)-(1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate; (S,E)-7-(dimethylamino)-1-((1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate; and methyl (S,E)-(7-(dimethylamino)-1-((1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl)carbamate; [(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl] N,N-dimethylcarbamate; [(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl] N,N-dimethylcarbamate; and [(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl] N,N-dimethylcarbamate; or a pharmaceutically acceptable salt or solvate thereof.

In some embodiments is a compound selected from:

methyl N-[(E,1S)-6-(dimethylamino)-1-[[1-[(4-isobutyl-1H-benzimidazol-2-yl)methyl]-2-oxo-3-pyridyl]carbamoyl]-6-oxo-hex-4-enyl]carbamate;

methyl N-[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl]carbamate;

[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl] N,N-dimethylcarbamate;

methyl N-[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]carbamate;

[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl] N,N-dimethylcarbamate;

methyl-N-[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl]carbamate;

[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl] N,N-dimethylcarbamate;

methyl N-[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl]carbamate; or

[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl] N,N-dimethylcarbamate;

or a pharmaceutically acceptable salt thereof.

Any combination of the groups described above for the various variables is contemplated herein.

Throughout the specification, groups and substituents thereof can be chosen to provide stable moieties and compounds.

In some embodiments, the compound disclosed herein is a compound of any one of the compounds described herein, or a pharmaceutically acceptable salt or solvate thereof.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2;

"Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

Solvates

In some embodiments, the compounds described herein exist as solvates. In some embodiments, are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Further described herein are methods of treating diseases by administering such prodrugs. Also described herein are methods of treating diseases by administering such prodrugs as pharmaceutical compositions.

In some embodiments, prodrugs include compounds wherein an amino acid residue, or a polypeptide chain of two or more (e.g., two, three, or four) amino acid residues is covalently joined through an amide or ester bond to a free amino, hydroxy or carboxylic acid group of compounds described herein. The amino acid residues include, but are not limited to, the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters, and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to, the following groups and combinations of groups:

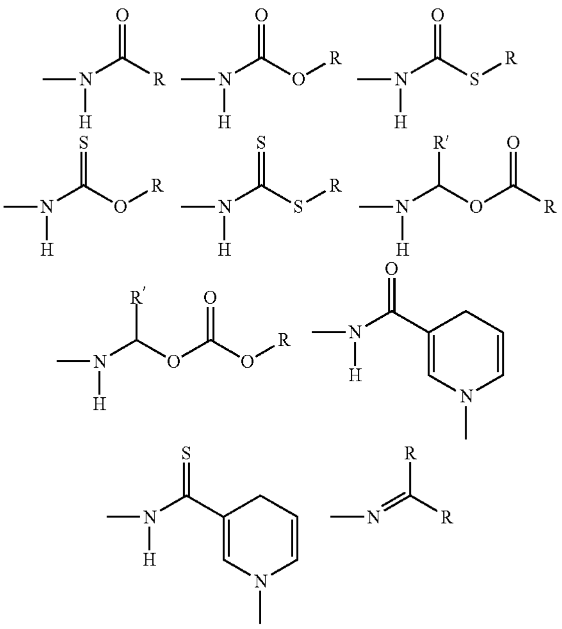

-continued

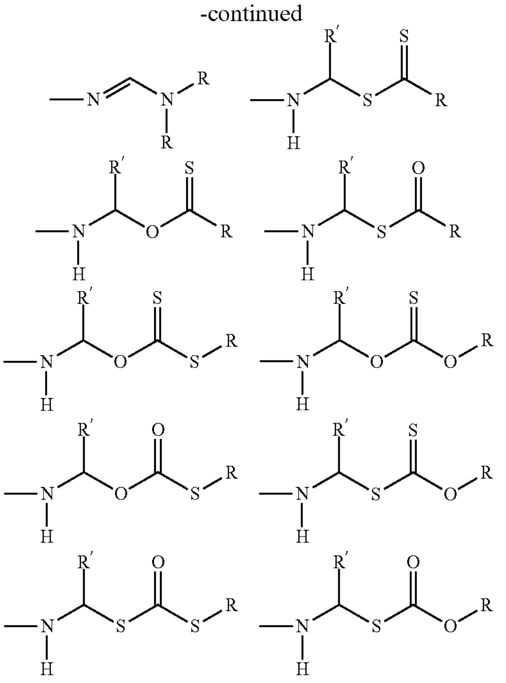

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions and Methods of Administration

In certain embodiments, the compound of Formula (I), (II), (IIa), (IIb), (IIc), (IId), or (IIe) as described herein is administered as a pure chemical. In some embodiments, the compound of Formula (I), (II), (IIa), (IIb), (IIc), (IId), or (IIe) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Accordingly, provided herein is a pharmaceutical composition comprising at least one compound of Formula (I), (II), (IIa), (IIb), (IIc), (IId), or (IIe) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (IIa), or a pharmaceutically acceptable salt thereof.

One embodiment provides a pharmaceutical composition comprising a pharmaceutically acceptable excipient and a compound of Formula (IIb), or a pharmaceutically acceptable salt thereof.

One embodiment provides a pharmaceutical composition comprising a pharmaceutically acceptable excipient and a compound of Formula (IIc), or a pharmaceutically acceptable salt thereof.

One embodiment provides a pharmaceutical composition comprising a pharmaceutically acceptable excipient and a compound of Formula (IId), or a pharmaceutically acceptable salt thereof.

One embodiment provides a pharmaceutical composition comprising a pharmaceutically acceptable excipient and a compound of Formula (IIe), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (IIa), or a pharmaceutically acceptable salt thereof. Another embodiment provides a pharmaceutical composition consisting essentially of a pharmaceutically acceptable excipient and a compound of Formula (IIb), or a pharmaceutically acceptable salt thereof. Another embodiment provides a pharmaceutical composition consisting essentially of a pharmaceutically acceptable excipient and a compound of Formula (IIc), or a pharmaceutically acceptable salt thereof. Another embodiment provides a pharmaceutical composition consisting essentially of a pharmaceutically acceptable excipient and a compound of Formula (IId), or a pharmaceutically acceptable salt thereof. Another embodiment provides a pharmaceutical composition consisting essentially of a pharmaceutically acceptable excipient and a compound of Formula (IIe), or a pharmaceutically acceptable salt thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Generally, an agent, such as a compound of Formula (I), (II), (IIa), (IIb), (IIc), (IId), or (IIe), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

Oral doses typically range from about 1.0 mg to about 1000 mg, one to four times, or more, per day.

Methods

Abnormal levels of TG2 and/or activity have been observed in many disease states including, but not limited to celiac sprue, neurodegenerative diseases (Alzheimer, Parkinson, Huntington disease), fibrosis, cataract, and cancer metastasis. Disclosed herein are methods of inhibiting the activity of TG2. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (II), (IIa), (IIb), (IIc), (IId), or (IIe), or a pharmaceutically acceptable salt or solvate thereof. The ability of compounds described herein to inhibit TG2 is evaluated by procedures known in the art and/or described herein.

In celiac sprue, inflammation is triggered by disease-specific T cells that reside in the small intestine and recognize toxic gluten peptides from the diet. This recognition process is facilitated by modification of gluten peptides by TG2. As such, enteric inhibition of TG2 is a target for non-dietary therapy of celiac sprue.

In some embodiments is a method of treating an enteric inflammatory disorder in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating an enteric inflammatory disorder in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof, wherein the enteric inflammatory disorder is selected from celiac disease, irritable bowel syndrome, Crohn's disease, and dermatitis herpetiformis.

In some embodiments is a method of treating celiac disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating irritable bowel syndrome in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating Crohn's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating dermatitis herpetiformis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating fibrosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating kidney fibrosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating idiopathic pulmonary fibrosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating cystic fibrosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating liver fibrosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating reperfusion injury/ischemia in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating myocardial ischemia in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating lung ischemia in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating retinal ischemia-reperfusion in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating reperfusion injury to the brain in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating cutaneous inflammation in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating an inflammatory skin condition in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating dermatitis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating a neurodegenerative disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating Huntington's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating Alzheimer's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating Parkinson's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating Sjogren's Syndrome in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating systemic lupus erythematosus in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating diabetic nephropathy in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating cardiovascular disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating atherosclerosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating hypertension in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating cardiac hypertrophy in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating cancer in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating melanoma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating glioblastoma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating meningioma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating pancreatic cancer in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating renal cell carcinoma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating breast cancer in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating pancreatitis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating multiple sclerosis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating an ocular disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating macular degeneration in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating cataracts in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating glaucoma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating uveitis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating choroidal neovascularization in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating corneal neovascularization in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating retinal inflammation in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating irritable bowel disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating Crohn's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating ulcerative colitis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating amyotrophic lateral sclerosis (ALS) in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating Charcot's disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof. In some embodiments is a method of treating motor neuron disease in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating scleroderma in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating muscular dystrophy in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating inflammatory uveitis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating chronic allograft injury in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of treating preclampsia in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of sepsis in a patient in need thereof, comprising administering to the patient a therapeutically effective amount of a compound of Formula (I), (II), (IIa), (IIb), (IIc), (IId), or (IIe) described herein, or a pharmaceutically acceptable salt or solvate thereof.

In some embodiments is a method of reducing transglutaminase 2 (TG2) activation in an individual comprising administering to the individual a compound of Formula (I), (II), (IIa), (IIb), (IIc), (IId), or (IIe) described herein, or a pharmaceutically acceptable salt or solvate thereof, in a dose effective to provide for a reduction in TG2 activity.

In certain embodiments, a disclosed compound utilized by one or more of the foregoing methods is one of the generic, subgeneric, or specific compounds described herein, such as a compound of Formula (I), (II), (IIa), (IIb), (IIc), (IId), or (IIe).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants, and vehicles. Parenteral administration includes subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by TG2 inhibition.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

The invention includes the following items:

Item 1. A compound having the structure of Formula (I):

Formula (I)

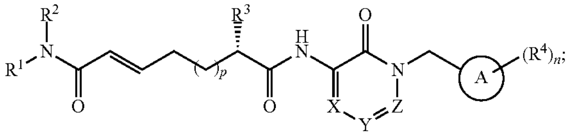

wherein:

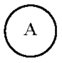

is a 9-membered bicyclic heteroaryl ring;

X, Y, and Z are selected from $=C(R^{11})-$ and $=N-$, wherein at least two of X, Y, and Z are $=C(R^{11})-$;

$R^1$ and $R^2$ are independently selected from H and optionally substituted alkyl; or $R^1$ and $R^2$, together with the nitrogen to which they are attached, form an optionally substituted 3-, 4-, 5- or 6-membered heterocycloalkyl ring;

$R^3$ is $-N(H)C(O)OR^5$, $-OC(O)NR^6R^7$, $-N(H)C(O)NR^6R^7$, or $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, optionally substituted alkyl, optionally substituted alkenyl, optionally substituted alkynyl, optionally substituted cycloalkyl, optionally substituted phenyl, and optionally substituted heteroaryl;

$R^5$ is selected from optionally substituted alkyl, optionally substituted heterocycloalkyl, optionally substituted phenyl, and optionally substituted heteroaryl;

$R^6$ and $R^7$ are independently selected from H and optionally substituted alkyl; or $R^6$ and $R^7$, together with the nitrogen to which they are attached, form an optionally substituted 5- or 6-membered heterocycloalkyl ring;

$R^8$ is selected from optionally substituted alkyl, optionally substituted cycloalkyl, optionally substituted phenyl, optionally substituted heterocycloalkyl, and optionally substituted heteroaryl;

each $R^9$ is independently selected from optionally substituted alkyl, optionally substituted cycloalkyl, optionally substituted phenyl, and optionally substituted heteroaryl;

each $R^{10}$ is independently selected from H, optionally substituted alkyl, optionally substituted cycloalkyl, optionally substituted phenyl, and optionally substituted heteroaryl;

each $R^{11}$ is independently selected from H, halogen, and optionally substituted alkyl;

n is 0, 1, 2, 3, or 4; and p is 0, 1, or 2;

or a pharmaceutically acceptable salt or solvate thereof.

Item 2. A compound having the structure of Formula (II):

Formula (II)

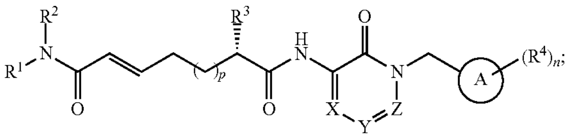

wherein:

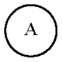

is a 9-membered bicyclic heteroaryl ring;

X, Y, and Z are selected from $=C(R^{11})-$ and $=N-$, wherein at least two of X, Y, and Z are $=C(R^{11})-$;

$R^1$ and $R^2$ are independently selected from H, $C_{1-6}$alkyl, and $-C_{1-6}$alkyl-OH; or $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl;

$R^3$ is selected from $-N(H)C(O)OR^5$, $-OC(O)NR^6R^7$, $-N(H)C(O)NR^6R^7$, and $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^1)_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, $-C_{1-6}$alkyl-$C_{3-12}$cycloalkyl, $-C_{2-6}$alkenyl-$C_{3-12}$cycloalkyl, phenyl, $-C_{1-6}$alkyl-phenyl, $-C_{2-6}$alkenyl-phenyl, $C_{2-9}$heterocycloalkyl, and $C_{2-9}$heteroaryl, wherein phenyl, $-C_{1-6}$alkyl-phenyl, $-C_{2-6}$alkenyl-phenyl, $C_{2-9}$heterocycloalkyl, and $C_{2-9}$heteroaryl are optionally substituted with one, two, or three groups independently selected from halogen and $C_{1-6}$alkyl;

$R^5$ is selected from $C_{1-6}$alkyl, $-C_{1-6}$alkyl-OH, $-C_{1-6}$alkyl-O$-C_{1-6}$alkyl, $-C_{1-6}$alkyl-O$-$C(O)$C_{1-6}$alkyl, $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl, wherein $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl are optionally substituted with one or two groups independently selected from halogen and $C_{1-6}$alkyl;

$R^6$ and $R^7$ are independently selected from H, $C_{1-6}$alkyl, $-C_{1-6}$alkyl-OH, $-C_{1-6}$alkyl-O$-C_{1-6}$alkyl, and $-C_{1-6}$alkyl-N($C_{1-6}$alkyl$)_2$; or $R^6$ and $R^7$, together with the nitrogen to which they are attached, form a 5- or 6-membered heterocycloalkyl ring optionally substituted with one or two groups independently selected from halogen and $C_{1-6}$alkyl;

$R^8$ is selected from $C_{1-6}$alkyl, $C_{1-6}$haloalkyl, $-C_{1-6}$alkyl-OH, $-C_{1-6}$alkyl-O$-C_{1-6}$alkyl, $C_{3-6}$cycloalkyl, phenyl, $C_{2-9}$heterocycloalkyl, and $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen and $C_{1-6}$alkyl;

each $R^9$ is independently selected from $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{10}$ is independently selected from H, $C_{1-10}$alkyl, $C_{1-10}$haloalkyl, $C_{3-12}$cycloalkyl, —$C_{1-6}$alkyl-$C_{3-12}$cycloalkyl, phenyl, —$C_{1-6}$alkyl-phenyl, and $C_{2-9}$heteroaryl, wherein phenyl, —$C_{1-6}$alkyl-phenyl, and $C_{2-9}$heteroaryl are optionally substituted with one or two groups independently selected from halogen and $C_{1-6}$alkyl;

each $R^{11}$ is independently selected from H, halogen, $C_{1-6}$alkyl, and $C_{1-6}$haloalkyl;

n is 0, 1, 2, 3, or 4; and p is 0, 1, or 2;

or a pharmaceutically acceptable salt or solvate thereof.

Item 3. The compound of item 1 or item 2, or a pharmaceutically acceptable salt or solvate thereof, wherein $R^1$ and $R^2$ are independently selected from H and $C_{1-6}$alkyl.

Item 4. The compound of item 3, or a pharmaceutically acceptable salt or solvate thereof, wherein $R^1$ and $R^2$ are each H.

Item 5. The compound of item 3, or a pharmaceutically acceptable salt or solvate thereof, wherein $R^1$ and $R^2$ are each $C_{1-6}$alkyl.

Item 6. The compound of item 5, or a pharmaceutically acceptable salt or solvate thereof, wherein $R^1$ and $R^2$ are each —$CH_3$.

Item 7. The compound of item 1 or item 2, or a pharmaceutically acceptable salt or solvate thereof, wherein $R^1$ and $R^2$, together with the nitrogen to which they are attached, form a 3-, 4-, 5- or 6-membered heterocycloalkyl ring optionally substituted with one or two groups independently selected from halogen and $C_{1-6}$alkyl.

Item 8. The compound of item 1 or item 2, or a pharmaceutically acceptable salt or solvate thereof, wherein $R^1$ and $R^2$, together with the nitrogen to which they are attached, form an unsubstituted 3-, 4-, 5- or 6-membered heterocycloalkyl ring.

Item 9. The compound of any one of items 1 to 8, or a pharmaceutically acceptable salt or solvate thereof, wherein $R^3$ is —N(H)C(O)$OR^5$.

Item 10. The compound of any one of items 1 to 9, or a pharmaceutically acceptable salt or solvate thereof, wherein $R^5$ is selected from $C_{1-6}$alkyl, —$C_{1-6}$alkyl-OH, $C_{1-6}$alkyl-O—$C_{1-6}$alkyl, $C_{1-6}$alkyl-O—C(O)$C_{1-6}$alkyl, $C_{2-9}$heterocycloalkyl, —$C_{1-6}$alkyl-$C_{2-9}$heterocycloalkyl, —$C_{1-6}$alkyl-phenyl, and $C_{2-9}$heteroaryl.

Item 11. The compound of any one of items 1 to 10, or a pharmaceutically acceptable salt or solvate thereof, wherein $R^5$ is selected from $C_{1-6}$alkyl, —$C_{1-6}$alkyl-OH, —$C_{1-6}$alkyl-O—$C_{1-6}$alkyl, —$C_{1-6}$alkyl-$C_{2-9}$heterocycloalkyl, and —$C_{1-6}$alkyl-phenyl.

Item 12. The compound of item 11, or a pharmaceutically acceptable salt or solvate thereof, wherein $R^5$ is $C_{1-6}$alkyl.

Item 13. The compound of item 12, or a pharmaceutically acceptable salt or solvate thereof, wherein $R^5$ is —$CH_3$.

Item 14. The compound of item 11, or a pharmaceutically acceptable salt or solvate thereof, wherein $R^5$ is —$C_{1-6}$alkyl-OH.

Item 15. The compound of item 11, or a pharmaceutically acceptable salt or solvate thereof, wherein $R^5$ is —$C_{1-6}$alkyl-O—$C_{1-6}$alkyl.

Item 16. The compound of item 11, or a pharmaceutically acceptable salt or solvate thereof, wherein $R^5$ is —$C_{1-6}$alkyl-$C_{2-9}$heterocycloalkyl.

Item 17. The compound of item 11, or a pharmaceutically acceptable salt or solvate thereof, wherein $R^5$ is —$C_{1-6}$alkyl-phenyl.

Item 18. The compound of item 17, or a pharmaceutically acceptable salt or solvate thereof, wherein $R^5$ is —$CH_2$-phenyl.

Item 19. The compound of any one of items 1 to 8, or a pharmaceutically acceptable salt or solvate thereof, wherein $R^3$ is —OC(O)$NR^6R^7$.

Item 20. The compound of any one of items 1 to 8, or a pharmaceutically acceptable salt or solvate thereof, wherein $R^3$ is —N(H)C(O)$NR^6R^7$.

Item 21. The compound of item 19 or item 20, or a pharmaceutically acceptable salt or solvate thereof, wherein $R^6$ and $R^7$ are independently selected from H, $C_{1-6}$alkyl, —$C_{1-6}$alkyl-OH, —$C_{1-6}$alkyl-O—$C_{1-6}$alkyl, and —$C_{1-6}$alkyl-N($C_{1-6}$alkyl)$_2$.

Item 22. The compound of item 21, or a pharmaceutically acceptable salt or solvate thereof, wherein $R^6$ and $R^7$ are independently selected from H, $C_{1-6}$alkyl, —$C_{1-6}$alkyl-O—$C_{1-6}$alkyl, and —$C_{1-6}$alkyl-N($C_{1-6}$alkyl)$_2$.

Item 23. The compound of item 22, or a pharmaceutically acceptable salt or solvate thereof, wherein $R^6$ and $R^7$ are independently selected from $C_{1-6}$alkyl.

Item 24. The compound of item 23, or a pharmaceutically acceptable salt or solvate thereof, wherein $R^6$ and $R^7$ are each —$CH_3$.

Item 25. The compound of any one of items 1 to 8, or a pharmaceutically acceptable salt or solvate thereof, wherein $R^3$ is —N(H)C(O)$R^8$.

Item 26. The compound of item 25, or a pharmaceutically acceptable salt or solvate thereof, wherein $R^8$ is —$C_{1-6}$alkyl-OH.

Item 27. The compound of item 25, or a pharmaceutically acceptable salt or solvate thereof, wherein $R^8$ is —$C_{1-6}$alkyl-O—$C_{1-6}$alkyl.

Item 28. The compound of item 25, or a pharmaceutically acceptable salt or solvate thereof, wherein $R^8$ is phenyl optionally substituted with one or two groups independently selected from halogen and $C_{1-6}$alkyl.

Item 29. The compound of item 25, or a pharmaceutically acceptable salt or solvate thereof, wherein $R^8$ is $C_{2-9}$heteroaryl optionally substituted with one or two groups independently selected from halogen and $C_{1-6}$alkyl.

Item 30. The compound of any one of items 1 to 29, or a pharmaceutically acceptable salt or solvate thereof, wherein each $R^4$ is independently selected from halogen, —$OR^9$, —C(O)$OR^9$, —C(O)—$C_{1-10}$alkyl, $C_{1-10}$alkyl, $C_{1-10}$alkyl-OH, $C_{2-10}$alkenyl, $C_{1-10}$haloalkyl, $C_{1-10}$haloalkyl-OH, $C_{2-10}$haloalkenyl, $C_{3-12}$cycloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one, two, or three groups independently selected from halogen and $C_{1-6}$alkyl.

Item 31. The compound of any one of items 1 to 29, or a pharmaceutically acceptable salt or solvate thereof, wherein each $R^4$ is independently selected from halogen, —$OR^9$, —C(O)$OR^9$, $C_{1-10}$alkyl, $C_{1-10}$alkyl-OH, $C_{1-10}$haloalkyl, —$C_{1-6}$alkyl-$C_{3-12}$cycloalkyl, and —$C_{1-6}$alkyl-phenyl, wherein —$C_{1-6}$alkyl-phenyl is optionally substituted with one or two halogens.

Item 32. The compound of any one of items 1 to 31, or a pharmaceutically acceptable salt or solvate thereof, wherein each $R^4$ is independently selected from halogen, —$OR^9$, —$C(O)OR^9$, $C_{1-10}$alkyl, $C_{1-10}$haloalkyl, and —$C_{1-6}$alkyl-phenyl, wherein —$C_{1-6}$alkyl-phenyl is optionally substituted with one or two halogens.

Item 33. The compound of any one of items 1 to 32, or a pharmaceutically acceptable salt or solvate thereof, wherein each $R^9$ is independently selected from $C_{1-10}$alkyl, $C_{1-10}$haloalkyl, —$C_{1-6}$alkyl-$C_{3-12}$cycloalkyl, phenyl, and —$C_{1-6}$alkyl-phenyl, wherein phenyl and —$C_{1-6}$alkyl-phenyl are optionally substituted with one or two groups independently selected from halogen and $C_{1-6}$alkyl.

Item 34. The compound of any one of items 1 to 33, or a pharmaceutically acceptable salt or solvate thereof, wherein

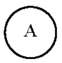

is selected from

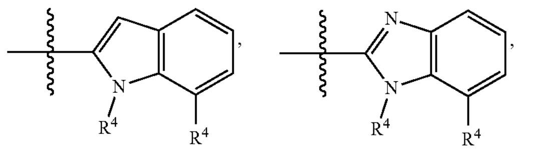

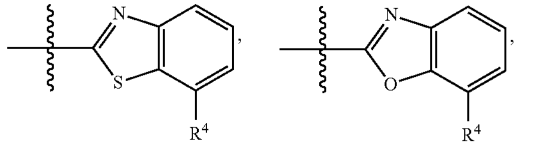

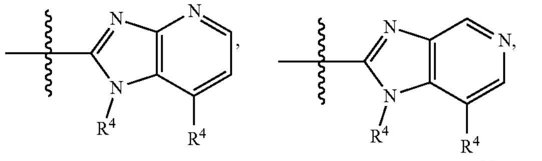

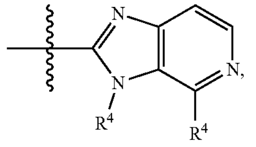

and

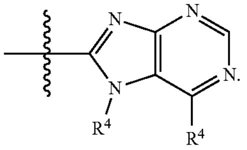

Item 35. The compound of any one of items 1 to 34, or a pharmaceutically acceptable salt or solvate thereof, wherein

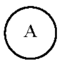

is selected from

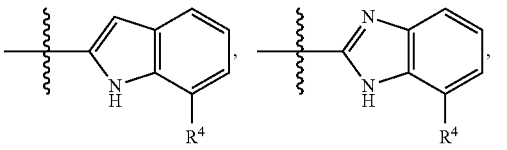

-continued

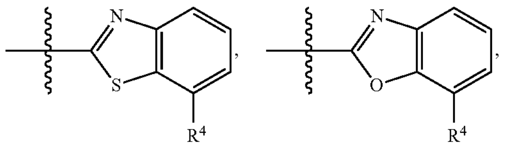

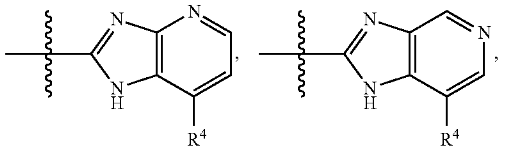

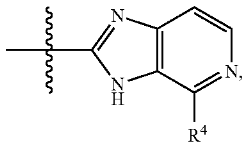

and

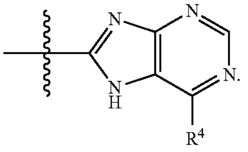

Item 36. The compound of item 35, or a pharmaceutically acceptable salt or solvate thereof, wherein

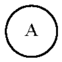

is

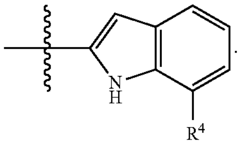

Item 37. The compound of item 35, or a pharmaceutically acceptable salt or solvate thereof, wherein

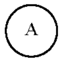

is

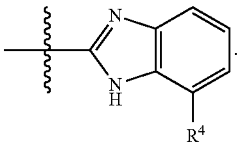

Item 38. The compound of item 35, or a pharmaceutically acceptable salt or solvate thereof, wherein

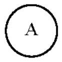

is

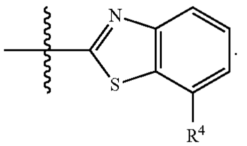

Item 39. The compound of item 35, or a pharmaceutically acceptable salt or solvate thereof, wherein

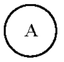

is

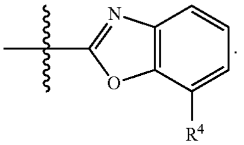

Item 40. The compound of item 35, or a pharmaceutically acceptable salt or solvate thereof, wherein

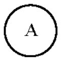 is 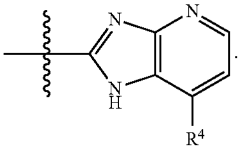

Item 41. The compound of item 36, or a pharmaceutically acceptable salt or solvate thereof, wherein

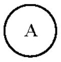 is 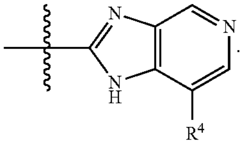

Item 42. The compound of item 35, or a pharmaceutically acceptable salt or solvate thereof, wherein

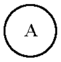 is 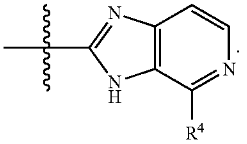

Item 43. The compound of item 35, or a pharmaceutically acceptable salt or solvate thereof, wherein

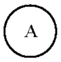 is 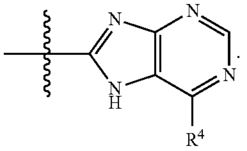

Item 44. The compound of any one of items 35 to 43, or a pharmaceutically acceptable salt or solvate thereof, wherein $R^4$ is $C_{1-10}$alkyl.

Item 45. The compound of any one of items 35 to 43, or a pharmaceutically acceptable salt or solvate thereof, wherein $R^4$ is $C_{1-10}$haloalkyl.

Item 46. The compound of any one of items 35 to 43, or a pharmaceutically acceptable salt or solvate thereof, wherein $R^4$ is —$OR^9$.

Item 47. The compound of item 46, or a pharmaceutically acceptable salt or solvate thereof, wherein $R^9$ is —$C_{1-6}$alkyl-phenyl optionally substituted with one or two halogens.

Item 48. The compound of any one of items 1 to 33, or a pharmaceutically acceptable salt or solvate thereof, wherein

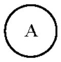

is selected from

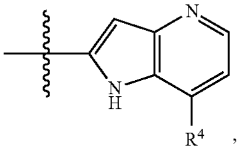 , 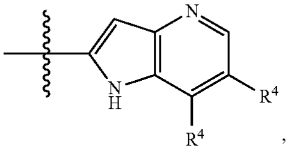 ,

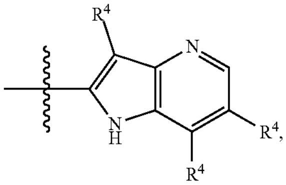

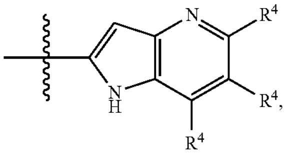 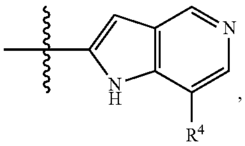 ,

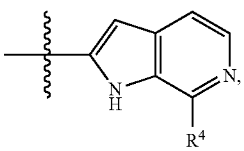 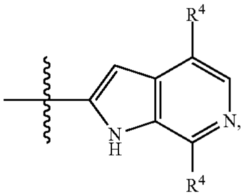

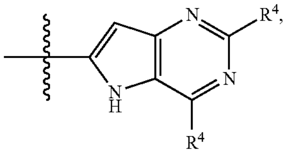

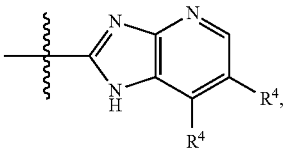 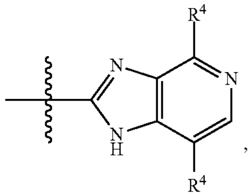 ,

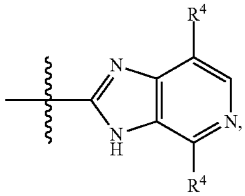 and

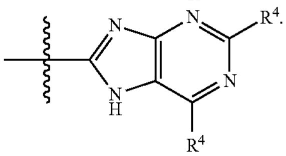

Item 49. The compound of item 48, or a pharmaceutically acceptable salt or solvate thereof, wherein

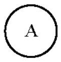 is 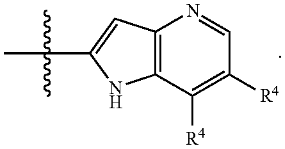

Item 50. The compound of item 48, or a pharmaceutically acceptable salt or solvate thereof, wherein

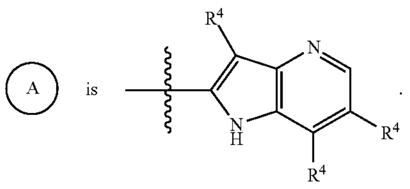

Item 51. The compound of item 48, or a pharmaceutically acceptable salt or solvate thereof, wherein

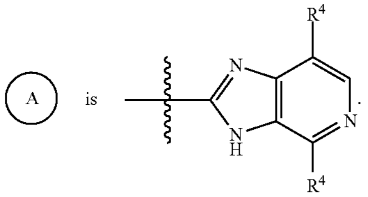

Item 52. The compound of any one of items 48 to 51, or a pharmaceutically acceptable salt or solvate thereof, wherein each $R^4$ is independently selected from halogen and $C_{1-10}$alkyl.

Item 53. The compound of any one of items 1 to 52, or a pharmaceutically acceptable salt or solvate thereof, wherein p is 0.

Item 54. The compound of any one of items 1 to 52, or a pharmaceutically acceptable salt or solvate thereof, wherein p is 1.

Item 55. The compound of any one of items 1 to 52, or a pharmaceutically acceptable salt or solvate thereof, wherein p is 2.

Item 56. The compound of any one of items 1 to 55, or a pharmaceutically acceptable salt or solvate thereof, wherein X, Y, and Z are each $=C(R^{11})-$.

Item 57. The compound of any one of items 1 to 55, or a pharmaceutically acceptable salt or solvate thereof, wherein X is $=N-$, Y is $=C(R^{11})-$, and Z is $=C(R^{11})-$.

Item 58. The compound of any one of items 1 to 55, or a pharmaceutically acceptable salt or solvate thereof, wherein X is $=C(R^{11})-$, Y is $=C(R^{11})-$, and Z is $=N-$.

Item 59. The compound of any one of items 1 to 55, or a pharmaceutically acceptable salt or solvate thereof, wherein X is $=C(R^{11})-$, Y is $=N-$, and Z is $=C(R^{11})-$.

Item 60. The compound of any one of items 1 to 59, or a pharmaceutically acceptable salt or solvate thereof, wherein each $R^{11}$ is H.

Item 61. The compound of any one of items 1 to 55, or a pharmaceutically acceptable salt or solvate thereof, wherein X is $=C(H)-$, Y is $=C(H)-$, and Z is $=C(Cl)-$.

Item 62. The compound of any one of items 1 to 55, or a pharmaceutically acceptable salt or solvate thereof, wherein X is $=C(H)-$, Y is $=C(H)-$, and Z is $=C(CH_3)-$.

Item 63. A pharmaceutical composition comprising a compound of any one of items 1 to 62, or a pharmaceutically acceptable salt or solvate thereof, and at least one pharmaceutically acceptable excipient.

Item 64. A method of treating celiac disease in a patient in need thereof, comprising administering to the patient a therapeutically effective amount of a compound of any one of items 1 to 62, or a pharmaceutically acceptable salt or solvate thereof.

Item 65. A method of treating a neurodegenerative disease in a patient in need thereof, comprising administering to the patient a therapeutically effective amount of a compound of any one of items 1 to 62, or a pharmaceutically acceptable salt or solvate thereof.

Item 66. The method of item 65, wherein the neurodegenerative disease is selected from Parkinson's disease, Huntington's disease, and Alzheimer's disease.

Item 67. A method of treating an ocular disease in a patient in need thereof, comprising administering to the patient a therapeutically effective amount of a compound of any one of items 1 to 62, or a pharmaceutically acceptable salt or solvate thereof.

Item 68. The method of item 67, wherein the ocular disease is selected from macular degeneration, glaucoma, cataracts, and uveitis.

Item 69. A method of treating cancer in a patient in need thereof, comprising administering to the patient a therapeutically effective amount of a compound of any one of items 1 to 62, or a pharmaceutically acceptable salt or solvate thereof.

Item 70. The method of item 69, wherein the cancer is selected from melanoma, glioblastoma, meningioma, pancreatic cancer, renal cell carcinoma, and breast cancer.

Item 71. A method of treating fibrosis in a patient in need thereof, comprising administering to the patient a therapeutically effective amount of a compound of any one of items 1 to 62, or a pharmaceutically acceptable salt or solvate thereof.

Item 72. A method of treating kidney fibrosis in a patient in need thereof, comprising administering to the patient a therapeutically effective amount of a compound of any one of items 1 to 62, or a pharmaceutically acceptable salt or solvate thereof.

Item 73. A method of treating idiopathic pulmonary fibrosis in a patient in need thereof, comprising administering to the patient a therapeutically effective amount of a compound of any one of items 1 to 62, or a pharmaceutically acceptable salt or solvate thereof.

Item 74. A method of treating liver fibrosis in a patient in need thereof, comprising administering to the patient a therapeutically effective amount of a compound of any one of items 1 to 62, or a pharmaceutically acceptable salt or solvate thereof.

Item 75. A method of reducing transglutaminase 2 (TG2) activation in an individual comprising administering to the individual a compound of any one of items 1 to 62, or a pharmaceutically acceptable salt or solvate thereof, in a dose effective to provide for a reduction in TG2 activity.

Item 76. A compound of any one of items 1 to 62, or a pharmaceutically acceptable salt or solvate thereof, for use in treating celiac disease.

Item 77. A compound of any one of items 1 to 62, or a pharmaceutically acceptable salt or solvate thereof, for use in treating a neurodegenerative disease.

Item 78. The compound for use of item 77, wherein the neurodegenerative disease is selected from Parkinson's disease, Huntington's disease, and Alzheimer's disease.

Item 79. A compound of any one of items 1 to 62, or a pharmaceutically acceptable salt or solvate thereof, for use in treating an ocular disease.

Item 80. The compound for use of item 79, wherein the ocular disease is selected from macular degeneration, glaucoma, cataracts, and uveitis.

Item 81. A compound of any one of items 1 to 62, or a pharmaceutically acceptable salt or solvate thereof, for use in treating cancer.

Item 82. The compound for use of item 81, wherein the cancer is selected from melanoma, glioblastoma, meningioma, pancreatic cancer, renal cell carcinoma, and breast cancer.

Item 83. A compound of any one of items 1 to 62, or a pharmaceutically acceptable salt or solvate thereof, for use in treating fibrosis.

Item 84. A compound of any one of items 1 to 62, or a pharmaceutically acceptable salt or solvate thereof, for use in treating kidney fibrosis.

Item 85. A compound of any one of items 1 to 62, or a pharmaceutically acceptable salt or solvate thereof, for use in treating idiopathic pulmonary fibrosis.

Item 86. A compound of any one of items 1 to 62, or a pharmaceutically acceptable salt or solvate thereof, for use in treating liver fibrosis.

Item 87. A compound of any one of items 1 to 62, or a pharmaceutically acceptable salt or solvate thereof, for use in reducing transglutaminase 2 (TG2) activation.

EXAMPLES

Abbreviations

DMF: N,N-dimethylformamide
EtOAc: ethyl acetate
DCM: dichloromethane
MeOH: methanol
Py: pyridine
DMSO: dimethyl sulfoxide
THF: tetrahydrofuran
IPA: isopropyl
IPAm: isopropamide
TFA: trifluoroacetic acid
CAN: acetonitrile
TEA: N,N-dimethylformamide triethylamine
Me: methyl
Boc: t-butoxycarbonyl
DMP: Dess-Martin periodinane
PMB: p-methoxybenzyl
Ph: phenyl
Bn: benzyl
TBDPS: t-butyldiphenylsilyl
TBS: t-butyldimethylsilyl
SEM: 2-(trimethylsilyl)ethoxymethyl
DIBALH: diisobutylaluminum hydride
PTSA: p-toluenesulfonic acid
TBAF: tetrabutylammonium fluoride
HATU: 0-(7-azabenzotriazol-1-yl)-N,N,N',N'-tetramethyluronium hexafluorophosphate
EDCl: 1-ethyl-3-(3-dimethylaminopropyl)carbodiimide hydrochloride
CDI: N,N-Carbonyldiimidazole
$Pd_2(dba)_3$: tris(dibenzylideneacetone)dipalladium(0) CAS: 51364-51-3
$Pd(dppf)Cl_2$: [1,1'-bis(diphenylphosphino)ferrocene]dichloropalladium(II)
t-BuXphos: 2-di-tert-butylphosphino-2',4',6'-triisopropylbiphenyl
MsCl: mesyl (methanesulfonyl) chloride
$POCl_3$: phosphorus oxychloride
t-BuOK: potassium tert-butoxide
DMAP: N,N-4-dimethylaminopyridine
DIPEA/DIEA: diisopropylethylamine
$T_3P$: propylphosphonic anhydride
HPLC: high pressure liquid chromatography
LCMS: liquid chromatography and mass spectrometry SFC: supercritical fluid chromatography
MS: mass spectrometry
m/z: mass to charge ratio
eq: equivalent Synthesis of the Intermediate Carbamate Acid (I-9)

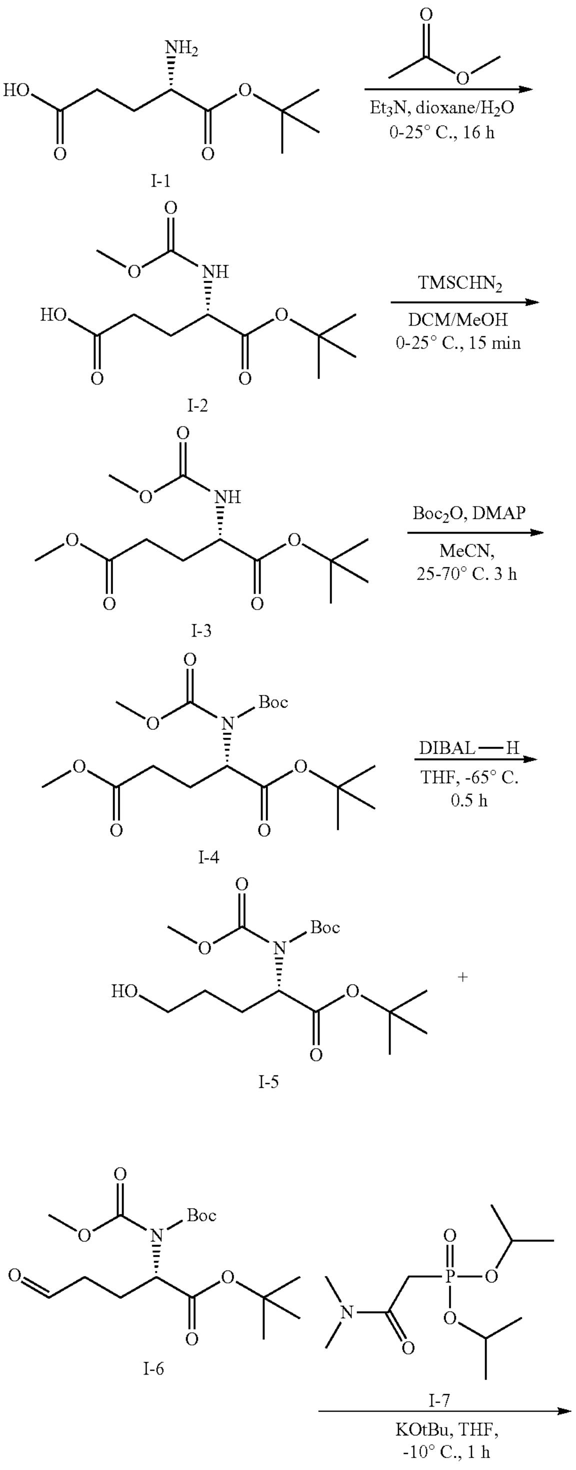

I-1

I-2

I-3

I-4

I-5

I-6

I-7

-continued

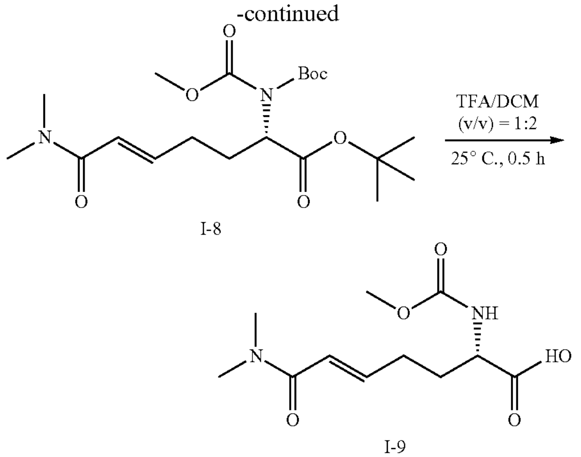

I-8

I-9

To a solution of (4S)-4-amino-5-tert-butoxy-5-oxo-pentanoic acid (100 g, 492 mmol) and TEA (99.6 g, 984 mmol, 137 mL) in dioxane (500 mL) and $H_2O$ (500 mL) was added methyl carbonochloridate (55.8 g, 590 mmol, 45.7 mL) at 0° C. The mixture was stirred at 25° C. for 16 h. Sat. $Na_2CO_3$ (aq) was added to adjust pH~9. Then washed with ethyl acetate (500 mL×2). HCl (6 N) was then added to adjust pH~3, and the mixture was extracted with ethyl acetate (500 mL×2). The combined organic layers were washed with brine (500 mL×1), dried over $Na_2SO_4$ and concentrated to afford a yellow oil. The crude product (4S)-5-tert-butoxy-4-(methoxycarbonylamino)-5-oxo-pentanoic acid (I-2) (320 g) was used in the next step without further purification as a light yellow oil.

To a solution of (4S)-5-tert-butoxy-4-(methoxycarbonylamino)-5-oxo-pentanoic acid (150 g, 574 mmol) in DCM (750 mL) and MeOH (750 mL) was added diazomethyl (trimethyl)silane (2 M, 344 mL) at 0° C. The mixture was stirred at 25° C. for 15 min. The mixture was filtered and concentrated under reduced pressure to give O1-tert-butyl O5-methyl (2S)-2-(methoxycarbonylamino)pentanedioate (I-3) (250 g) as a yellow oil. $^1$H NMR (400 MHz, $CDCl_3$) δ 5.30-5.28 (m, 1H), 4.27-4.24 (m, 1H), 3.68 (s, 6H), 2.46-2.29 (m, 2H), 2.25-2.12 (m, 1H), 2.02-1.85 (m, 1H), 1.46 (s, 9H).

To a solution of O1-tert-butyl O5-methyl (2S)-2-(methoxycarbonylamino) pentanedioate (125 g, 454 mmol) in MeCN (1300 mL) was added DMAP (55.5 g, 454 mmol) and $Boc_2O$ (248 g, 1.14 mol, 261 mL) at 25° C. The mixture was stirred at 70° C. for 3 h. The mixture was concentrated under reduced pressure to give crude product. The crude product was purified by column chromatography to give O1-tert-butyl O5-methyl (2S)-2-[tert-butoxycarbonyl (methoxycarbonyl)amino] pentanedioate (I-4) (264 g, 77% yield) as a yellow oil. $^1$H NMR (400 MHz, $CDCl_3$) δ 4.87 (dd, J=9.2, 4.4 Hz, 1H), 3.81 (s, 3H), 3.67 (s, 3H), 2.50-2.31 (m, 3H), 2.23-2.12 (m, 1H), 1.50 (s, 9H), 1.44 (s, 9H).

To a solution of O1-tert-butyl O5-methyl (2S)-2-[tert-butoxycarbonyl (methoxycarbonyl)amino]pentanedioate (100 g, 266 mmol) in THF (1 L) was added DIBAL-H (1 M, 532.7 mL) at −65° C. The mixture was stirred at −65° C. for 30 min. The reaction mixture was quenched with saturated $NH_4Cl$ solution (500 mL) at 0° C. The resulting suspension was extracted with EtOAc (1000 mL×2). The combined organic layers were washed with brine (500 mL) dried over anhydrous $Na_2SO_4$. Filtered and concentrated under reduced pressure to give oil. The oil was purified by column chromatography to afford tert-butyl (2S)-2-[tert-butoxycarbonyl (methoxycarbonyl)amino]-5-hydroxy-pentanoate (I-5) (37 g, 20% yield) as a yellow oil and tert-butyl (2S)-2-[tert-butoxycarbonyl (methoxycarbonyl)amino]-5-oxo-pentanoate (I-6) (107 g, 58% yield) as a colorless oil. $^1$H NMR (400 MHz, $CDCl_3$) δ 9.77-9.73 (m, 1H), 4.81 (dd, J=5.2, 9.4 Hz, 1H), 4.13-4.06 (m, 1H), 4.10 (q, J=7.1 Hz, 1H), 3.81-3.79 (m, 3H), 3.70-3.62 (m, 2H), 2.50-2.41 (m, 2H), 2.29 (br dd, J=5.6, 13.6 Hz, 1H), 2.21-2.06 (m, 1H), 1.49 (s, 9H), 1.43 (s, 9H), 1.24 (t, J=7.2 Hz, 2H), 0.23-0.15 (m, 1H).

To a solution of 2-diisopropoxyphosphoryl-N,N-dimethyl-acetamide (I-7) (20.7 g, 82.5 mmol) in THF (200 mL) was added t-BuOK (7.41 g, 66.0 mmol) at −10° C. The mixture was stirred for 0.5 hr. Then tert-butyl (2S)-2-[tert-butoxycarbonyl (methoxycarbonyl)amino]-5-oxo-pentanoate (I-6) (19 g, 55.0 mmol) was added at −10° C. and the resulting reaction mixture was stirred for additional 0.5 hr. The reaction mixture was quenched with saturated $NH_4Cl$ solution (500 mL) at 0° C. The resulting suspension was extracted with EtOAc (500 mL×2). The combined organic layers were washed with brine (250 mL), dried over anhydrous $Na_2SO_4$, filtered and concentrated under reduced pressure to give an oil. The oil was purified by column chromatography to afford tert-butyl (E,2S)-2-[tert-butoxycarbonyl(methoxycarbonyl)amino]-7-(dimethylamino)-7-oxo-hept-5-enoate (I-8) (44 g, 55% yield) as a yellow oil. $^1$H NMR (400 MHz, $CDCl_3$) δ 6.87-6.76 (m, 1H), 6.25 (d, J=14.9 Hz, 1H), 4.84-4.77 (m, 1H), 3.80 (s, 3H), 3.05 (s, 3H), 2.97 (s, 3H), 2.29-2.18 (m, 3H), 2.07-1.97 (m, 1H), 1.48 (s, 9H), 1.42 (s, 9H).

To a solution of tert-butyl (E,2S)-2-[tert-butoxycarbonyl (methoxycarbonyl)amino]-7-(dimethylamino)-7-oxo-hept-5-enoate (20.5 g, 49.5 mmol) in TFA (40 mL) and DCM (100 mL) at 25° C. The mixture was stirred for 30 min. The mixture was concentrated under reduced pressure to give crude product. The crude product (E,2S)-7-(dimethylamino)-2-(methoxycarbonylamino)-7-oxo-hept-5-enoic acid (I-9) (48 g) was used in the next step without further purification as a yellow oil.

Synthesis of i-Pr Phosphate (I-7)

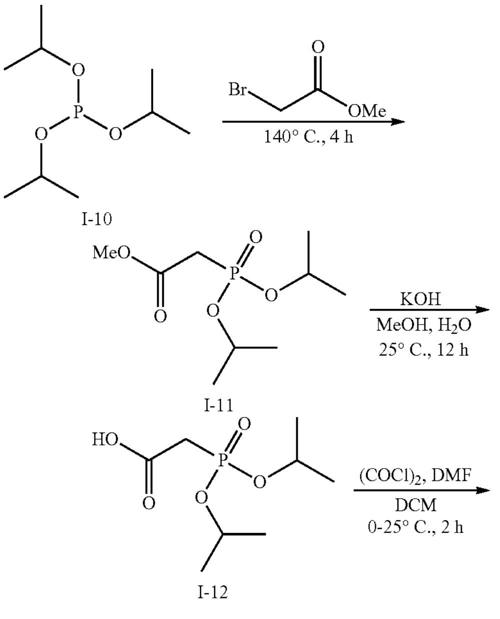

I-10

I-11

I-12

-continued

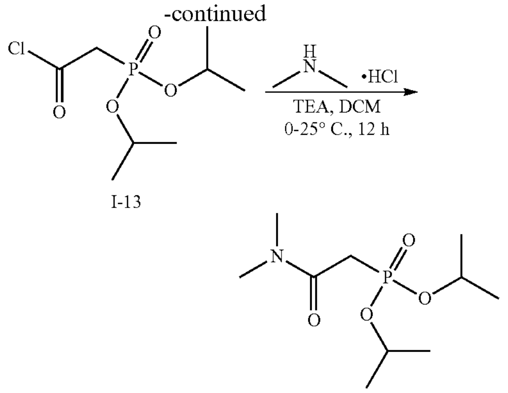

I-13

I-7

Triisopropyl phosphite (44.5 g, 213.70 mmol, 49.17 mL) and methyl 2-bromoacetate (35.96 g, 235.07 mmol, 22.20 mL) were charged into a reactor and the reaction was stirred at 140° C. for 4 h. The mixture was concentrated to afford methyl 2-diisopropoxyphosphorylacetate (I-11) (220 g) as a colorless oil which was used in the next step without further purification.

To a solution of methyl 2-diisopropoxyphosphorylacetate (55 g, 230.88 mmol) in MeOH (280 mL) and $H_2O$ (280 mL) was added KOH (25.91 g, 461.76 mmol) at 25° C. The reaction mixture was stirred at 25° C. for 12 hours. The reaction mixture was concentrated under reduced pressure to remove MeOH, then the residue was washed with EtOAc (100 mL*2), separated the water phase which was adjusted pH~1 by HCl (12 N) and extracted with EtOAc (150 mL×3), the combined organic layers were washed with brine (100 mL×2), dried over anhydrous $Na_2SO_4$, and then concentrated under reduced pressure to give 2-diisopropoxyphosph-orylacetic acid (I-12) (150 g) as a light yellow oil. $^1$H NMR (400 MHz, $CDCl_3$) δ 7.50 (br s, 2H), 4.78 (quind, J=6.2, 7.7 Hz, 2H), 3.02-2.84 (m, 2H), 1.33 (d, J=6.2 Hz, 12H).

A solution of 2-diisopropoxyphosphorylacetic acid (25 g, 111.51 mmol, 1 eq) in DCM (250 mL), then oxalyl dichloride (28.31 g, 223.02 mmol, 19.52 mL) and DMF (815.09 mg, 11.15 mmol, 857.98 uL) was added under $N_2$ at 0° C. The mixture was stirred at 25° C. for 2 h. The reaction mixture was concentrated to give the crude product 2-diisopropoxyphosphorylacetyl chloride (I-13) (104 g) as a red liquid which was used in the next step without further purification.

A mixture of N-methylmethanamine HCl (13.11 g, 160.73 mmol, 14.73 mL) and TEA (32.53 g, 321.47 mmol, 44.74 mL) in DCM (120 mL) was stirred at 0° C. for 0.5 hour, and then 2-diisopropoxyphosphorylacetyl chloride (26 g, 107.16 mmol, 1 eq) was added under $N_2$. The mixture was stirred at 25° C. for 10 hours under $N_2$ atmosphere. The reaction mixture was quenched by addition sat. $NH_4Cl$ solution 200 mL, and the organic phase was washed with sat. $NH_4Cl$ solution (100 mL*5), brine (100 mL*2), dried over $Na_2SO_4$, filtered and concentrated under reduced pressure to give 2-diisopropoxyphosphoryl-N,N-dimethyl-acetamide (I-7) (100 g) as a red oil. $^1$H NMR (400 MHz, $CDCl_3$) δ7.25 (s, 1H), 4.80-4.67 (m, 2H), 3.11 (s, 1H), 3.13-3.07 (m, 1H), 3.15-3.07 (m, 1H), 3.02 (s, 1H), 3.04-3.00 (m, 1H), 2.98-2.96 (m, 1H), 2.95 (d, J=1.3 Hz, 1H), 2.99-2.93 (m, 1H), 1.39-1.21 (m, 12H).

The following intermediate acids were prepared according to the previous procedures described for the synthesis of I-9 using the appropriate reagents.

| Compound | Structure | Characterization Data |
|---|---|---|
| I-14 | 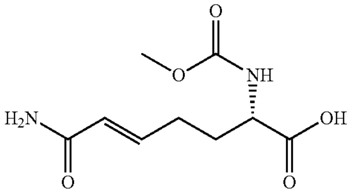 [SMILES: COC(=O)N[C@@H](CC/C=C/C(N)=O)C(=O)O] | MS m/z 231.2 (M + 1)$^+$ |
| I-15 | 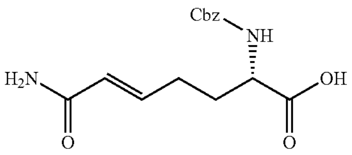 [SMILES: NC(=O)/C=C/CC[C@H](NC(=O)OCc1ccccc1)C(=O)O] | MS m/z 307.1 (M + 1)$^+$ |
| I-16 | 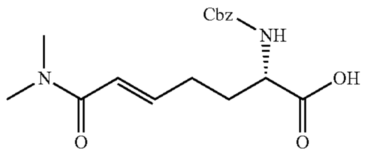 [SMILES: CN(C)C(=O)/C=C/CC[C@H](NC(=O)OCc1ccccc1)C(=O)O] | MS m/z 335.1 (M + 1)$^+$ |

-continued
| Compound | Structure | Characterization Data |
|---|---|---|
| I-17 | 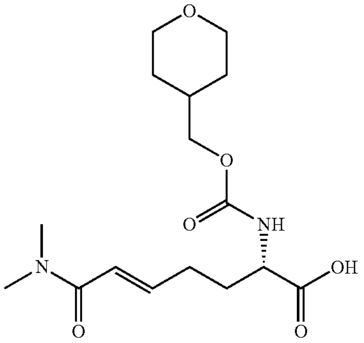 [SMILES: CN(C)C(=O)/C=C/CC[C@H](NC(=O)OCC1CCOCC1)C(=O)O] | $^{1}H$ NMR (400 MHz, $CDCl_3$) δ 6.78-6.66 (m, 1H), 6.28 (d, J = 15.2 Hz, 1H), 5.79 (d, J = 7.2 Hz, 1H), 4.21-4.13 (m, 1H), 3.97 (dd, J = 11.2, 3.2 Hz, 2H), 3.90 (d, J = 6.4 Hz, 2H), 3.43-3.31 (m, 3H), 3.07 (s, 3H), 2.98 (s, 3H), 2.35-2.22 (m, 2H), 2.10-1.96 (m, 1H), 1.93-1.78 (m, 2H), 1.64-1.53 (m, 2H), 1.42-1.27 (m, 2H). |
| I-18 | 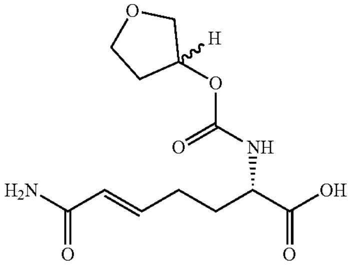 [SMILES: NC(=O)/C=C/CC[C@H](NC(=O)OC1CCOC1)C(=O)O] | MS m/z 287.2 $(M + 1)^+$ |
| I-19 | 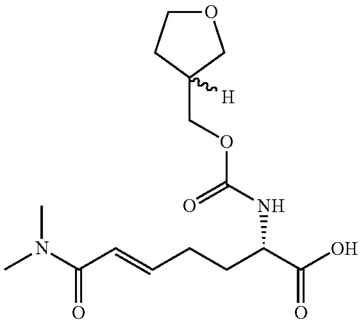 [SMILES: CN(C)C(=O)/C=C/CC[C@H](NC(=O)OCC1CCOC1)C(=O)O] | 1H NMR (400 MHz, DMSO-$d_6$) δ 7.58-7.48 (m, 1H), 6.66-6.55 (m, 1H), 6.40 (d, J = 15.2 Hz, 1H), 3.92-3.86 (m, 3H), 3.74-3.68 (m, 2H), 3.65-3.58 (m, 1H), 3.47-3.39 (m, 1H), 3.02 (s, 3H), 2.88-2.82 (m, 3H), 2.48-2.43 (m, 1H), 2.29-2.18 (m, 2H), 1.98-1.89 (m, 1H), 1.86-1.78 (m, 1H), 1.77-1.68 (m, 1H), 1.58-1.54 (m, 1H). |
| I-20 | 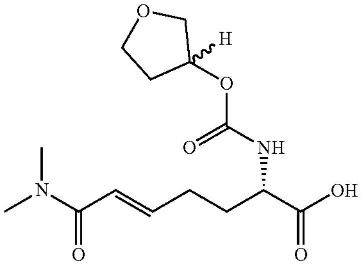 [SMILES: CN(C)C(=O)/C=C/CC[C@H](NC(=O)OC1CCOC1)C(=O)O] | MS m/z 314.2 $(M + 1)^+$ |
| I-21 | 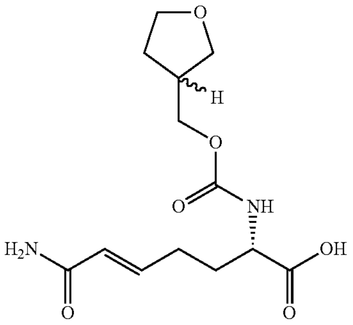 [SMILES: NC(=O)/C=C/CC[C@H](NC(=O)OCC1CCOC1)C(=O)O] | 1H NMR (400 MHz, DMSO-$d_6$) δ 7.58-7.48 (m, 1H), 6.66-6.55 (m, 1H), 6.40 (d, J = 15.2 Hz, 1H), 3.92-3.86 (m, 3H), 3.74-3.68 (m, 2H), 3.65-3.58 (m, 1H), 3.47-3.39 (m, 1H), 3.02 (s, 3H), 2.88-2.82 (m, 3H), 2.48-2.43 (m, 1H), 2.29-2.18 (m, 2H), 1.98-1.89 (m, 1H), 1.86-1.78 (m, 1H), 1.77-1.68 (m, 1H), 1.58-1.54 (m, 1H). |

-continued
| Compound | Structure | Characterization Data |
|---|---|---|
| I-22 | 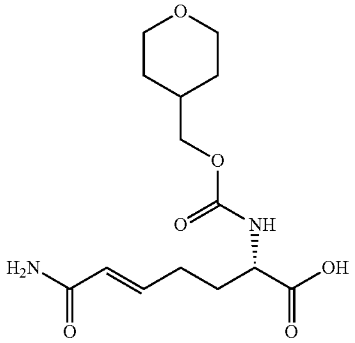 [SMILES: NC(=O)/C=C/CC[C@H](NC(=O)OCC1CCOCC1)C(=O)O] | LCMS m/z 315.2 $(M + H)^+$ |
| I-23 | 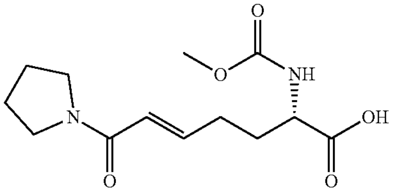 [SMILES: COC(=O)N[C@@H](CC/C=C/C(=O)N1CCCC1)C(=O)O] | LCMS m/z 285.0 $(M + H)^+$ |
| I-24 | 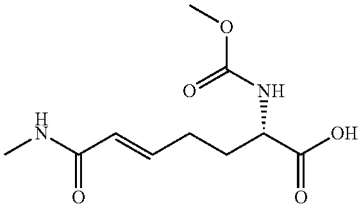 [SMILES: CNC(=O)/C=C/CC[C@H](NC(=O)OC)C(=O)O] | LCMS m/z 245.1 $(M + 1)^+$ |
| I-25 | 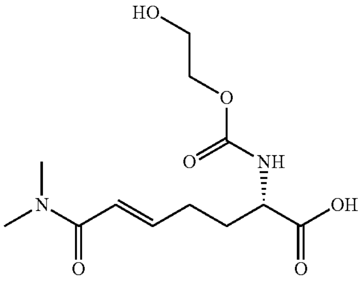 [SMILES: CN(C)C(=O)/C=C/CC[C@H](NC(=O)OCCO)C(=O)O] | 1H NMR (400 MHz, DMSO-$d_6$) δ 7.50 (d, J = 8.0 Hz, 1H), 6.65-6.53 (m, 1H), 6.40 (d, J = 15.2 Hz, 1H), 4.02-3.85 (m, 3H), 3.54 (t, J = 4.8 Hz, 2H), 3.01 (s, 3H), 2.84 (s, 3H), 2.29-2.15 (m, 2H), 1.87-1.64 (m, 2H). |
| I-26 | 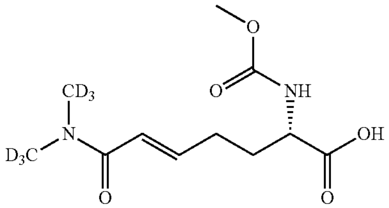 [SMILES: [2H]C([2H])([2H])N(C(=O)/C=C/CC[C@H](NC(=O)OC)C(=O)O)C([2H])([2H])[2H]] | LCMS m/z 265.2 $(M + H)^+$ |
| I-532 | 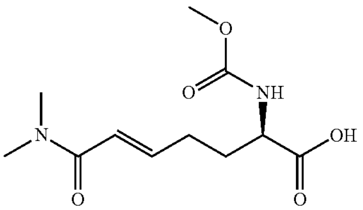 [SMILES: COC(=O)N[C@H](CC/C=C/C(=O)N(C)C)C(=O)O] | LCMS m/z 259.2 $(M + H)^+$ |

Synthesis of Intermediate Reverse Carbamate Acids (I-37)

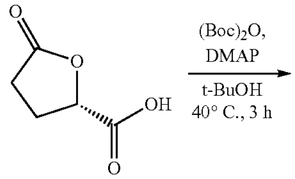

I-27

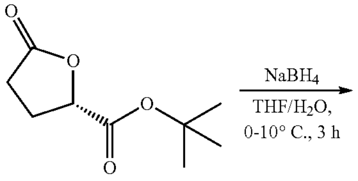

I-28

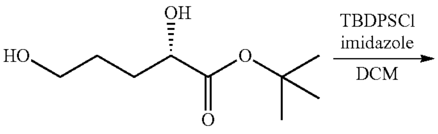

I-29

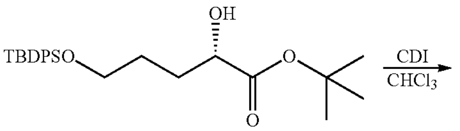

I-30

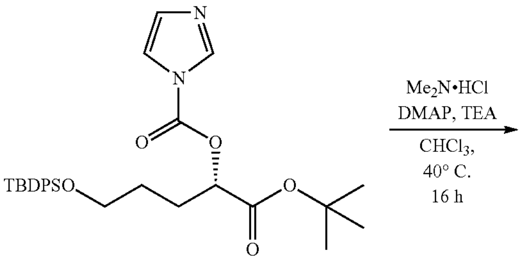

I-31

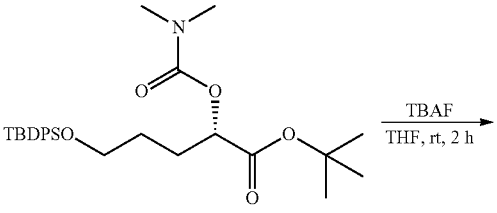

I-32

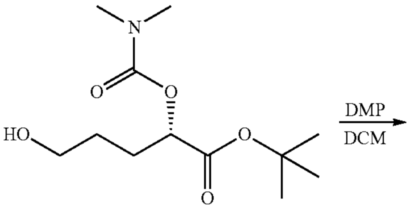

I-33

-continued

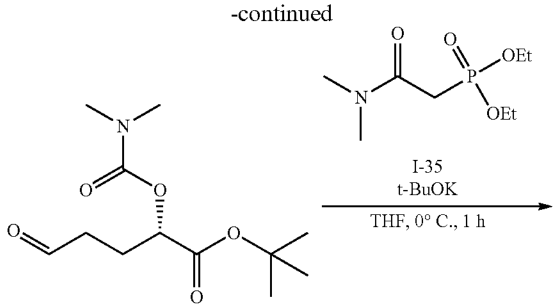

I-34

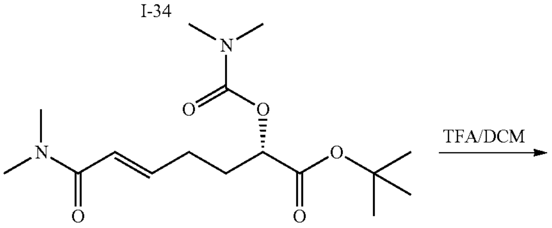

I-36

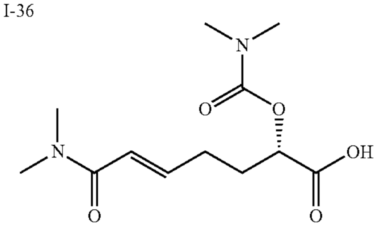

I-37

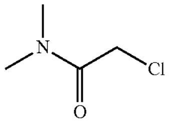

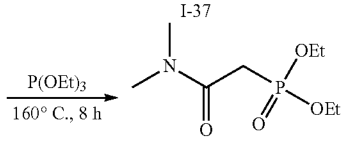

I-35A I-35

To a mixture of (S)-5-oxotetrahydrofuran-2-carboxylic acid (5 g, 38.4 mmol) and DMAP (2.35 g, 19.2 mmol) in t-BuOH (50 mL) was added $Boc_2O$ (10.1 g, 46.1 mmol, 10.6 mL). The mixture was stirred at 40° C. for 3 h. The mixture was diluted with water (100 mL) and extracted with ethyl acetate (100 mL×3). The combined organic layers were washed with brine (200 mL), dried over anhydrous $Na_2SO_4$, filtered and concentrated in vacuum to give a residue. The residue was purified by silica gel chromatography to afford (S)-tert-butyl 5-oxotetrahydrofuran-2-carboxylate (I-28) (3.9 g) as a white solid. $^1H$ NMR (400 MHz, $CDCl_3$) δ 4.87-4.78 (m, 1H), 2.70-2.43 (m, 3H), 2.35-2.19 (m, 1H), 1.50 (s, 9H).

To a mixture of (S)-tert-butyl 5-oxotetrahydrofuran-2-carboxylate (10.1 g, 54.2 mmol) in THF (60 mL) was added a solution of $NaBH_4$ (8.21 g, 217 mmol) in ice $H_2O$ (30 mL). $NaBH_4$ (4.1 g, 108 mmol) was added to the above solution in small portions at 0° C. The mixture was stirred at 10° C. for 3 h. The mixture was quenched with saturated $NH_4Cl$ (100 mL) and extracted with ethyl acetate (100 mL×3). The combined organic layers were dried over anhydrous $Na_2SO_4$, filtered and concentrated in vacuum to give a residue. The residue was purified by silica gel chromatography to afford (S)-tert-butyl 2,5-dihydroxypentanoate (I-29) (4.8 g) as a colorless oil. $^1H$ NMR (400 MHz, $CDCl_3$) δ 4.17-4.03 (m, 1H), 3.75-3.60 (m, 2H), 2.02-1.85 (m, 1H), 1.78-1.61 (m, 3H), 1.57-1.44 (m, 9H).

To a mixture of (S)-tert-butyl 2,5-dihydroxypentanoate (4.8 g, 25.2 mmol) in DCM (40 mL) were added TBDPS-Cl (8.32 g, 30.3 mmol, 7.78 mL) and imidazole (5.15 g, 75.7 mmol). The mixture was stirred at 10° C. for 1 h under $N_2$ atmosphere. The mixture was diluted with water (100 mL) and extracted with DCM (100 mL×3). The combined organic layers were washed with brine (250 mL), dried over anhydrous $Na_2SO_4$, filtered and concentrated in vacuum to give a residue. The residue was purified by silica gel chromatography to afford (S)-tert-butyl 5-((tert-butyldiphenylsilyl)oxy)-2-hydroxypentanoate (I-30) (8.8 g) as a colorless oil. $^1$H NMR (400 MHz, $CDCl_3$) δ 7.71-7.63 (m, 4H), 7.47-7.35 (m, 6H), 4.15-4.04 (m, 1H), 3.75-3.64 (m, 2H), 2.91 (s, 1H), 1.80-1.61 (m, 1H), 1.80-1.55 (m, 3H), 1.50 (s, 9H), 1.06 (s, 9H).

To a mixture of (S)-tert-butyl 5-((tert-butyldiphenylsilyl)oxy)-2-hydroxypentanoate (0.8 g, 1.87 mmol) in $CHCl_3$ (10 mL) was added CDI (333 mg, 2.05 mmol). The mixture was stirred at 15° C. for 2 h. The mixture was concentrated in vacuum to afford (S)-1-(tert-butoxy)-5-((tert-butyldiphenylsilyl)oxy)-1-oxopentan-2-yl 1H-imidazole-1-carboxylate (I-31) (976 mg) as a colorless oil.

To a mixture of (S)-1-(tert-butoxy)-5-((tert-butyldiphenylsilyl)oxy)-1-oxopentan-2-yl 1H-imidazole-1-carboxylate (976 mg, 1.87 mmol) and N-methylmethanamine hydrochloride (167 mg, 2.05 mmol) in $CHCl_3$ (20 mL) were added DMAP (228 mg, 1.87 mmol) and TEA (378 mg, 3.73 mmol, 0.520 mL). The mixture was stirred at 40° C. for 16 h. The reaction mixture was diluted with water (20 mL) and extracted with DCM (15 mL×2). The combined organic layers were washed with brine (30 mL), dried over anhydrous $Na_2SO_4$, filtered and concentrated in vacuum. The residue was purified by silica gel chromatography to afford (S)-tert-butyl 5-((tert-butyldiphenylsilyl)oxy)-2-((dimethylcarbamoyl)oxy)pentanoate (I-32) (800 mg) as a colorless oil. $^1$H NMR (400 MHz, $CDCl_3$) δ 7.70-7.61 (m, 4H), 7.48-7.33 (m, 6H), 4.95-4.75 (m, 1H), 3.78-3.62 (m, 2H), 2.93 (s, 6H), 2.04-1.82 (m, 2H), 1.75-1.61 (m, 2H), 1.47 (s, 9H), 1.06 (s, 9H).

To a mixture of (S)-tert-butyl 5-((tert-butyldiphenylsilyl)oxy)-2-((dimethylcarbamoyl) oxy)pentanoate (0.8 g, 1.6 mmol) in THF (10 mL) was added TBAF (1 M, 1.6 mL). The mixture was stirred at 15° C. for 2 h. The mixture was concentrated in vacuum to give a residue. The residue was purified by silica gel chromatography to afford (S)-tert-butyl 2-((dimethylcarbamoyl)oxy)-5-hydroxypentanoate (I-33) (0.36 g) as a colorless oil. $^1$H NMR (400 MHz, $CDCl_3$) δ 4.94-4.84 (m, 1H), 3.70 (t, J=6.4 Hz, 2H), 3.03-2.87 (m, 6H), 2.00-1.82 (m, 2H), 1.76-1.66 (m, 2H), 1.47 (s, 9H).

To a mixture of (S)-tert-butyl 2-((dimethylcarbamoyl)oxy)-5-hydroxypentanoate (0.31 g, 1.19 mmol) in DCM (20 mL) was added DMP (755 mg, 1.78 mmol, 0.551 mL) at 0° C. The mixture was stirred at 15° C. for 0.5 h. The mixture was concentrated in vacuum to give a residue. The residue was purified by silica gel chromatography to afford (S)-tert-butyl 2-((dimethylcarbamoyl)oxy)-5-oxopentanoate (I-34) (0.3 g) as a white solid. $^1$H NMR (400 MHz, $CDCl_3$) δ9.83-9.76 (m, 1H), 4.96-4.82 (m, 1H), 3.00-2.83 (m, 6H), 2.67-2.49 (m, 2H), 2.28-2.11 (m, 2H), 1.48 (s, 9H).

To a mixture of diethyl (2-(dimethylamino)-2-oxoethyl) phosphonate (I-35) (310 mg, 1.39 mmol) in THF (10 mL) was added t-BuOK (156 mg, 1.39 mmol) at 0° C. The mixture was stirred at 0° C. for 0.5 h. (S)-tert-butyl 2-((dimethylcarbamoyl)oxy)-5-oxopentanoate (I-34) (0.3 g, 1.16 mmol) in THF (5 mL) was added to the above solution. The mixture was stirred at 0° C. for 0.5 h. The resulting solution was diluted with water (10 mL) and extracted with ethyl acetate (20 mL×2). The combined organic layers were washed with brine (30 mL), dried over anhydrous $Na_2SO_4$, filtered and concentrated in vacuum to give a residue. The residue was purified by silica gel chromatography to afford (S,E)-tert-butyl 7-(dimethylamino)-2-((dimethylcarbamoyl)oxy)-7-oxohept-5-enoate (I-36) (0.3 g, 78% yield) as a colorless oil.

To a mixture of (S,E)-tert-butyl 7-(dimethylamino)-2-((dimethylcarbamoyl)oxy)-7-oxohept-5-enoate (0.3 g, 0.904 mmol) in DCM (1 mL) was added TFA (3.08 g, 27 mmol, 2 mL) at 0° C. The mixture was stirred at 15° C. for 3.5 h. The mixture was concentrated in vacuum and lyophilized to afford (S,E)-7-(dimethylamino)-2-((dimethylcarbamoyl)oxy)-7-oxohept-5-enoic acid (I-37) (250 mg) as a pink oil.

A mixture of 2-chloro-N,N-dimethylacetamide (5.0 g, 41.1 mmol) and triethyl phosphite (6.83 g, 41.1 mmol) was degassed and purged with $N_2$ for 3 times. The mixture was stirred at 160° C. for 8 h under $N_2$ atmosphere. The mixture was concentrated and purified by column chromatography to provide diethyl (2-(dimethylamino)-2-oxoethyl)phosphonate (I-35) (4.5 g) as a yellow oil. LCMS m/z 224.3 $(M+1)^+$. $^1$H NMR (400 MHz, $CDCl_3$) δ 4.20-4.12 (m, 4H), 3.11 (s, 3H), 3.07-3.01 (d, J=22 Hz, 2H), 2.97 (s, 3H), 1.35-1.31 (t, J=7.2 Hz, 6H).

The following intermediate reverse carbamate acids were prepared according to the previous procedures described for the synthesis of I-37 using the appropriate reagents.

| Compound | Structure | Characterization Data |
|---|---|---|
| I-38 | 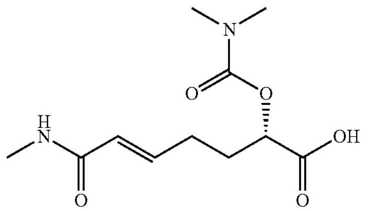 [SMILES: CNC(=O)/C=C/CC[C@H](OC(=O)N(C)C)C(=O)O] | $^1$H NMR (400 MHz, $CDCl_3$) δ 6.83 (m, 1H), 5.79 (m, 1H), 5.45 (s, 1H), 4.87 (dd, J = 7.1, 5.3 Hz, 1H), 2.95 (d, J = 16.9 Hz, 6H), 2.88 (d, J = 4.9 Hz, 3H), 2.36-2.27 (m, 2H), 2.01-1.93 (m, 2H), 1.47 (s, 9H). |
| I-39 | 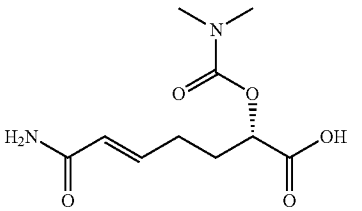 [SMILES: CN(C)C(=O)O[C@@H](CC/C=C/C(N)=O)C(=O)O] | $^1$H NMR (400 MHz, $CDCl_3$) δ 6.96-6.75 (m, 1H), 6.28 (d, J = 15.2 Hz, 1H), 5.28-5.27 (m, 1H), 5.01 (m, 1H), 3.97-3.47 (m, 3H), 3.46-3.35 (m, 3H), 3.21-3.17 (m, 1H), 3.12-2.96 (m, 9H), 2.46-2.30 (m, 2H), 2.17-1.99 (m, 2H). |

-continued
| Compound | Structure | Characterization Data |
|---|---|---|
| I-40 | 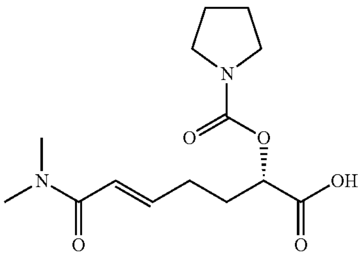 [SMILES: CN(C)C(=O)/C=C/CC[C@H](OC(=O)N1CCCC1)C(=O)O] | $^{1}H$ NMR (400 MHz, $CDCl_3$) δ 6.90-6.83 (m, 1H), 6.28 (d, J = 15.0 Hz, 1H), 5.04-5.01 (m, 1H), 3.50-3.40 (m, 4H), 3.12-3.06 (m, 6H), 2.43-2.38 (m, 2H), 2.08-1.91 (m, 6H). |
| I-41 | 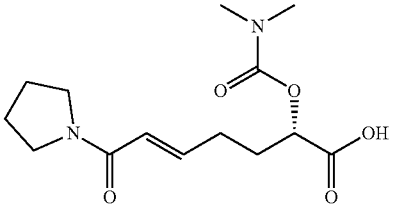 [SMILES: CN(C)C(=O)O[C@@H](CC/C=C/C(=O)N1CCCC1)C(=O)O] | $^{1}H$ NMR (400 MHz, $CDCl_3$) δ 7.00-6.87 (m, 1H), 6.20-6.11 (m, 1H), 5.06-4.94 (m, 1H), 3.58-3.55 (m, 4H), 2.99-2.94 (m, 6H), 2.42-2.40 (m, 2H), 2.09-1.90 (m, 6H). |
| I-42 | 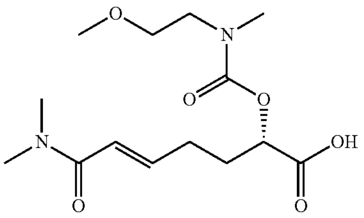 [SMILES: COCCN(C)C(=O)O[C@@H](CC/C=C/C(=O)N(C)C)C(=O)O] | $^{1}H$ NMR (400 MHz, $CDCl_3$) δ 6.96-6.75 (m, 1H), 6.28 (d, J = 15.2 Hz, 1H), 5.28-5.27 (m, 1H), 5.01 (m, 1H), 3.97-3.47 (m, 3H), 3.46-3.35 (m, 3H), 3.21-3.17 (m, 1H), 3.12-2.96 (m, 9H), 2.46-2.30 (m, 2H), 2.17-1.99 (m, 2H). |
| I-43 | 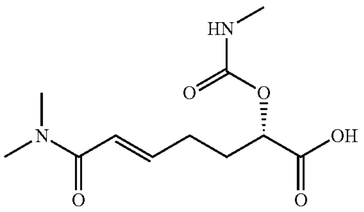 [SMILES: CNC(=O)O[C@@H](CC/C=C/C(=O)N(C)C)C(=O)O] | $^{1}H$ NMR (400 MHz, $CDCl_3$) δ 9.28 (s, 1H), 6.89-6.70 (m, 1H), 6.24 (d, J = 15.2 Hz, 1H), 5.27-5.15 (m, 1H), 5.05-5.02 (m, 1H), 3.07 (s, 3H), 3.01 (s, 3H), 2.78 (d, J = 4.8 Hz, 2H), 2.40-2.27 (m, 2H), 2.10-1.88 (m, 2H). |
| I-44 | 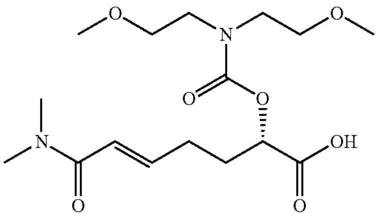 | LCMS m/z 361.2 $(M + H)^+$ |
| I-45 | 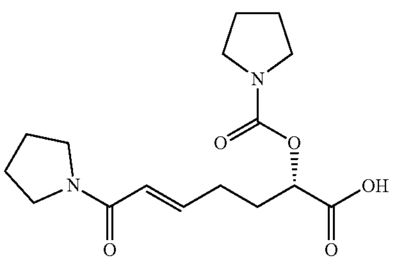 [SMILES: O=C(O)[C@H](CC/C=C/C(=O)N1CCCC1)OC(=O)N1CCCC1] | LCMS m/z 325.2 $(M + H)^+$ |

Synthesis of Deuterated Reverse Carbamate Acid (I-54)

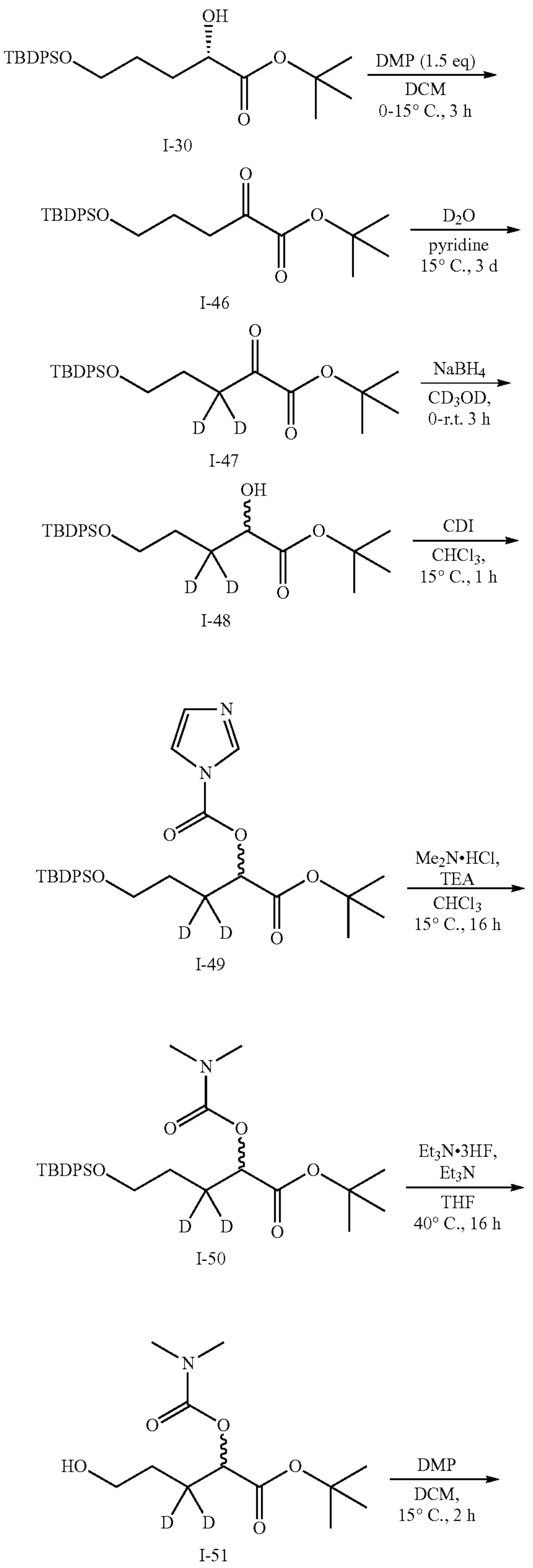

I-30

I-46

I-47

I-48

I-49

I-50

I-51

-continued

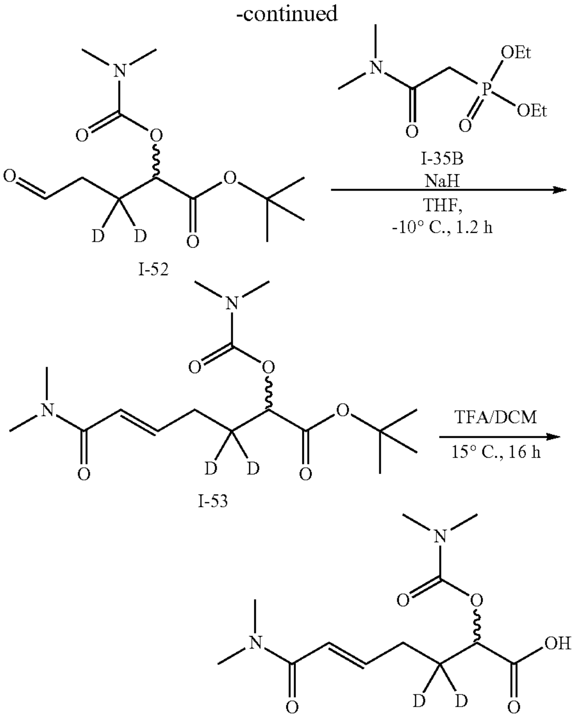

I-52

I-53

I-54

To a solution of (S)-tert-butyl 5-((tert-butyldiphenylsilyl)oxy)-2-hydroxypentanoate (20 g, 46.7 mmol) in DCM (200 mL) was added DMP (27.8 g, 65.3 mmol) in portions at 0° C. After stirring at 15° C. for 18 h, the mixture was poured into $H_2O$ (300 mL). The aqueous phase was extracted with EtOAc (200 mL×2). The combined organic layers (DCM and EtOAc) were dried over $Na_2SO_4$, filtered and concentrated to give a residue. The residue was purified by column chromatography to give tert-butyl 5-((tert-butyldiphenylsilyl)oxy)-2-oxopentanoate (I-46) (14 g) as a light yellow oil. LCMS m/z 449.2 $(M+23)^+$.

To a solution of tert-butyl 5-[tert-butyl(diphenyl)silyl]oxy-2-oxo-pentanoate (15.5 g, 26.9 mmol) in pyridine (32.0 mL) was added $D_2O$ (10.8 g, 538 mmol). The mixture was stirred at 15° C. for 24 h. The reaction was concentrated to give a residue. The residue was dissolved in pyridine (32.0 mL) and added $D_2O$ (10.8 g, 538 mmol). The mixture was stirred at 15° C. for 72 h. The reaction was concentrated to give a residue second time and the residue was dissolved in pyridine (32.0 mL) and added $D_2O$ (10.8 g, 538 mmol). The reaction was stirred at 15° C. for another 24 h. The reaction was concentrated to give tert-butyl 5-[tert-butyl(diphenyl)silyl]oxy-3,3-dideuterio-2-oxo-pentanoate (I-47) (16 g) as a light yellow oil. LCMS m/z 451.2 $(M+23)^+$.

To a solution of tert-butyl 5-[tert-butyl(diphenyl)silyl]oxy-3,3-dideuterio-2-oxo-pentanoate (10 g, 23.3 mmol) in $CD_3OD$ (30 mL) was added $NaBH_4$ (265 mg, 7.00 mmol) at 0° C. After stirring at 0° C. for 0.25 h, the mixture was quenched by $H_2O$ (100 mL) and adjusted pH=7 by HCl (1 M). The resultant was extracted with EtOAc (100 mL×3). The combined organic layers were dried over $Na_2SO_4$, filtered and concentrated to give a residue. The residue was purified by column chromatography to give tert-butyl 5-[tert-butyl(diphenyl)silyl]oxy-3,3-dideuterio-2-hydroxy-pentanoate (I-48) (7.5 g) as a white solid. $^1H$ NMR (400 MHz, $CDCl_3$) δ 7.71-7.64 (m, 4H), 7.46-7.35 (m, 6H), 4.09

(s, 1H), 3.70 (t, J=6.0 Hz, 2H), 2.90 (br s, 1H), 1.77-1.61 (m, 2H), 1.50 (s, 9H), 1.06 (s, 9H).

To a solution of tert-butyl 5-[tert-butyl(diphenyl)silyl]oxy-3,3-dideuterio-2-hydroxy-pentanoate (7 g, 16.3 mmol) in trichloromethane (120 mL) was added di(imidazol-1-yl) methanone (3.16 g, 19.5 mmol). The mixture was stirred at 15° C. for 1 hr. The desired compound (I-49) [1-tert-butoxycarbonyl-4-[tert-butyl(diphenyl)silyl]oxy-2,2-dideuterio-butyl]imidazole-1-carboxylate was obtained as a colorless solution in $CHCl_3$ (120 mL) which was used in the next step without further purification. LCMS m/z 524.3 $(M+23)^+$.

To a solution of [1-tert-butoxycarbonyl-4-[tert-butyl(diphenyl)silyl]oxy-2,2-dideuterio-butyl]imidazole-1-carboxylate (8.5 g, 16.2 mmol) in $CHCl_3$ (120 mL) were added N-methylmethanamine HCl (2.10 g, 25.9 mmol) and TEA (3.28 g, 22.4 mmol) at 0° C. After stirred at 15° C. for 88 h, the mixture was poured into $H_2O$ (100 mL). The resultant was separated. The aqueous phase was extracted with EtOAc (50 mL×2). The combined organic layers (EtOAc and DCM) were dried over $Na_2SO_4$, filtered and concentrated to give tert-butyl 5-[tert-butyl(diphenyl)silyl]oxy-3,3-dideuterio-2-(dimethylcarbamoyloxy)pentanoate (I-50) (8.3 g, 11.6 mmol) as a light yellow oil. LCMS m/z 524.3 $(M+23)^+$.

To a solution of tert-butyl 5-[tert-butyl(diphenyl)silyl]oxy-3,3-dideuterio-2-(dimethylcarbamoyloxy)pentanoate (8.3 g, 11.6 mmol) in THF (100 mL) was added N,N-diethylethanamine trihydrofluoride (3.73 g, 23.2 mmol) and TEA (2.93 g, 29.0 mmol). After stirring at 15° C. for 16 h, the mixture was poured into $H_2O$ (200 mL). The resultant mixture was extracted with EtOAc (100 mL×2). The combined organic layers were concentrated to give a residue. The residue was purified by column chromatography to give tert-butyl 3,3-dideuterio-2-(dimethylcarbamoyloxy)-5-hydroxy-pentanoate (I-51) (3.5 g) as a light yellow oil. $^1H$ NMR (400 MHz, $CDCl_3$) δ 4.88 (s, 1H), 3.69 (t, J=6.4 Hz, 2H), 2.97 (s, 3H), 2.93 (s, 3H), 1.69 (t, J=6.4 Hz, 2H), 1.47 (s, 9H).

To a solution of tert-butyl 3,3-dideuterio-2-(dimethylcarbamoyloxy)-5-hydroxy-pentanoate (3.5 g, 13.3 mmol) in DCM (50 mL) was added DMP (8.46 g, 19.9 mmol) at 0° C. After stirred at 15° C. for 2 h, the mixture was diluted with EtOAc (100 mL) and then poured into $H_2O$ (100 mL). A white solid formed and the mixture was filtered. The filtrate was separated and concentrated the organic layer to give a residue. The residue was purified by column chromatography to give tert-butyl 3,3-dideuterio-2-(dimethylcarbamoyloxy)-5-oxo-pentanoate (I-52) (2.7 g) as a light yellow oil. $^1H$ NMR (400 MHz, $CDCl_3$) δ 9.80 (t, J=1.2 Hz, 1H), 4.89 (s, 1H), 2.95 (s, 3H), 2.93 (s, 3H), 2.51-2.64 (m, 2H), 1.47 (s, 9H).

To a solution of diethyl (2-(dimethylamino)-2-oxoethyl) phosphonate (I-35) (2.77 g, 12.4 mmol) in THF (20 mL) was added NaH (496 mg, 12.4 mmol, 60% purity) at −10° C., The mixture was stirred for 10 min. Then the solution of tert-butyl 3,3-dideuterio-2-(dimethylcarbamoyloxy)-5-oxo-pentanoate (I-52) (2.7 g, 10.3 mmol) in THF (10 mL) was add dropwise to the reaction at −10° C. After stirred at −10° C. for 1 h, the mixture was poured into $H_2O$ (100 mL). The resultant was extracted with EtOAc (50 mL×3). The combined organic layers were dried over $Na_2SO_4$, filtered and concentrated to give tert-butyl (E)-3,3-dideuterio-7-(dimethylamino)-2-(dimethylcarbamoyloxy)-7-oxo-hept-5-enoate (I-53) (3.0 g, 8.72 mmol) as a light yellow oil. LCMS m/z 331.1 $(M+1)^+$.

To a solution of tert-butyl (E)-3,3-dideuterio-7-(dimethylamino)-2-(dimethyl carbamoyloxy)-7-oxo-hept-5-enoate (3 g, 8.72 mmol) in DCM (10 mL) was added TFA (20 mL). After stirred at 15° C. for 16 h, the mixture was concentrated to give a residue at 30° C. to give a residue. The residue was purified by prep-HPLC to afford (E)-3,3-dideuterio-7-(dimethylamino)-2-(dimethyl carbamoyloxy)-7-oxo-hept-5-enoic acid (I-54) (1.7 g, 5.39 mmol) as a white solid. LCMS m/z 275.1 $(M+1)^+$.

Synthesis of Intermediate (I-63)

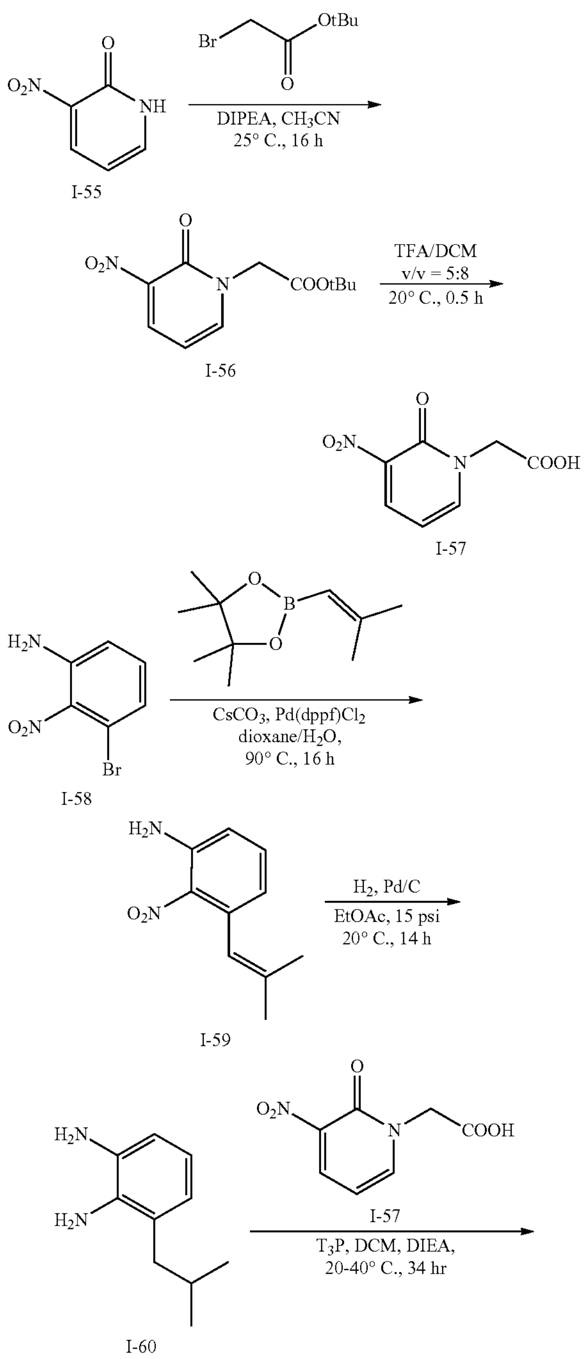

-continued

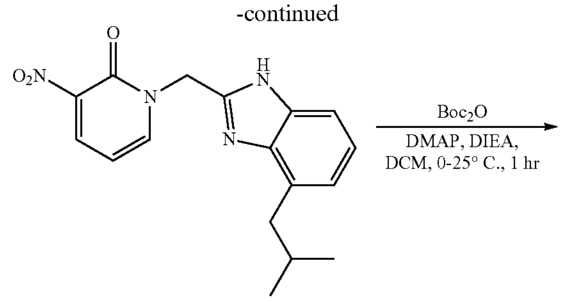

I-61

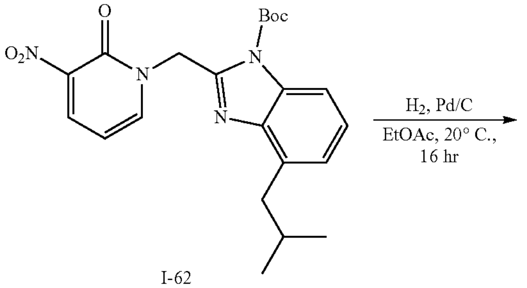

I-62

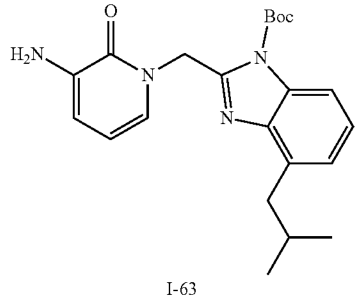

I-63

To a solution of 3-nitro-1H-pyridin-2-one (50.00 g, 356.90 mmol, 1 eq) in $CH_3CN$ (600 mL) was added tert-butyl 2-bromoacetate (83.54 g, 428.28 mmol, 63.29 mL, 1.2 eq) and DIEA (92.25 g, 713.79 mmol, 124.33 mL, 2 eq) at 25° C. The reaction mixture was stirred at 25° C. for 16 h. The mixture was concentrated in vacuum to remove most of $CH_3CN$, diluted with water (1500 mL), extracted with EtOAc (1500 mL*2). The combined organic layers were washed with brine (1500 mL*2), dried over $Na_2SO_4$, filtered and concentrated in vacuum to give tert-butyl 2-(3-nitro-2-oxo-1-pyridyl)acetate (I-56) (230 g) as a red solid.

To a mixture of tert-butyl 2-(3-nitro-2-oxo-1-pyridyl) acetate (110 g, 432.66 mmol, 1 eq) in $CF_3COOH$ (250 mL) and DCM (400 mL) was stirred at 20° C. for 0.5 hours. The mixture was concentrated under reduce pressure. The residue was washed with ethyl acetate (200 mL*3) and 2-(3-nitro-2-oxo-1-pyridyl)acetic acid (I-57) (160 g) was obtained as a green solid. $^1H$ NMR (400 MHz, DMSO-$d_6$) δ 8.48 (dd, J=8.0 Hz, 1.6 Hz, 1H), 8.20 (dd, J=7.2 Hz, 2.0 Hz, 2H), 6.50 (t, J=6.8 Hz, 1H), 4.79 (s, 2H).

To a solution of 3-bromo-2-nitro-aniline (44 g, 202.75 mmol, 1 eq) and 4,4,5,5-tetramethyl-2-(2-methylprop-1-enyl)-1,3,2-dioxaborolane (40.60 g, 223.02 mmol, 1.1 eq) in dioxane (450 mL)/$H_2O$ (45 mL) was added Pd(dppf)$Cl_2$ (2.97 g, 4.05 mmol, 0.02 eq) and $Cs_2CO_3$ (132.12 g, 405.49 mmol, 2 eq) at 25° C. The mixture was stirred at 90° C. for 16 h. The mixture was concentrated in vacuum to remove most of the dioxane and water, then diluted with water (450 mL)/EtOAc (350 mL) and filtered. The filtrate was separated and the aqueous phase was extracted with EtOAc (300 mL×2). The combined organic layer was washed with brine (500 mL), dried over $Na_2SO_4$ and concentrated in vacuum to give the product. The residue was purified by column chromatography to afford 3-(2-methylprop-1-enyl)-2-nitro-aniline (I-59) (45 g) as a brown liquid. $^1H$ NMR (400 MHz, $CDCl_3$) δ 1.60 (s, 3H) 1.80 (s, 3H) 5.03 (br. s, 2H) 6.25 (s, 1H) 6.47 (d, J=7.21 Hz, 1H) 6.61 (d, J=8.43 Hz, 1H) 7.12 (t, J=8.02 Hz, 1H).

To a solution of 3-(2-methylprop-1-enyl)-2-nitro-aniline (38 g, 197.70 mmol) and $Et_3N$ (6.14 g, 60.67 mmol, 8.44 mL) in MeOH (300 mL) was added Pd/C (10 g). The suspension was degassed under vacuum and purged with $H_2$ several times. The mixture was stirred under $H_2$ (15 psi) at 20° C. for 14 hours. The mixture was filtered and the filtrate was concentrated to give 3-isobutylbenzene-1,2-diamine (I-60) (30 g) as a red oil. $^1H$ NMR (400 MHz, DMSO-$d_6$) δ 0.87 (d, J=6.60 Hz, 6H) 1.85 (dquin, J=13.46, 6.75, 6.75, 6.75, 6.75 Hz, 1H) 2.29 (d, J=7.09 Hz, 2H) 4.09 (s, 2H) 4.37 (s, 2H) 6.22-6.27 (m, 1H) 6.32 (t, J=7.52 Hz, 1H) 6.40 (dd, J=7.58, 1.47 Hz, 1H).

To a mixture of 3-isobutylbenzene-1,2-diamine (30 g, 182.65 mmol, 1 eq), 2-(3-nitro-2-oxo-1-pyridyl)acetic acid (38.00 g, 191.78 mmol, 1.05 eq), and DIPEA (47.21 g, 365.30 mmol, 63.63 mL, 2 eq) in DCM (300 mL) was added $T_3P$ (127.86 g, 200.92 mmol, 119.49 mL, 50% purity, 1.1 eq) at 20° C. for 16 h. The mixture was stirred at 40° C. for 18 h. The mixture was cooled to 20° C. and concentrated in vacuum. The residue was poured into water (300 mL). The aqueous phase was extracted with ethyl acetate (300 mL*2). The combined organic phase was washed with brine (250 mL*2), dried with anhydrous $Na_2SO_4$, filtered and concentrated in vacuum. The crude product was purified by column chromatography on silica gel to give 1-[(4-isobutyl-1H-benzimidazol-2-yl)methyl]-3-nitro-pyridin-2-one (I-61) (23.9 g, 40% yield) as a yellow solid. $^1H$ NMR (400 MHz, DMSO-$d_6$) δ 8.47 (dd, J=8.0 Hz, 2.0 Hz, 1H), 8.36 (dd, J=6.4 Hz, 2.0 Hz, 1H), 7.31 (d, J=8.0 Hz, 1H), 7.06 (t, J=8.0 Hz, 1H), 6.93 (d, J=6.8 Hz, 1H), 6.54 (t, J=6.8 Hz, 1H), 2.69 (d, J=7.2 Hz, 2H), 2.02-1.96 (m, 1H), 0.85 (d, J=6.8 Hz, 6H).

To a solution of 1-[(4-isobutyl-1H-benzimidazol-2-yl) methyl]-3-nitro-pyridin-2-one (5 g, 15.32 mmol, 1 eq) and $Boc_2O$ (4.01 g, 18.39 mmol, 4.22 mL, 1.2 eq) in DCM (50 mL) was added DIEA (2.97 g, 22.98 mmol, 4.00 mL, 1.5 eq) and DMAP (93.59 mg, 766.05 umol, 0.05 eq) at 0° C., then the reaction was stirred at 25° C. for 1 h. The organic phase was concentrated in vacuum to give a residue. The residue was purified by column chromatography to afford tert-butyl 4-isobutyl-2-[(3-nitro-2-oxo-1-pyridyl)methyl]benzimidazole-1-carboxylate (I-62) (23.4 g, 90% yield) as a brown solid. $^1H$ NMR (400 MHz, DMSO-$d_6$) δ 8.54 (dd, J=7.67, 1.97 Hz, 1H) 8.29 (dd, J=6.80, 1.97 Hz, 1H) 7.76 (d, J=7.89 Hz, 1H) 7.29 (t, J=7.89 Hz, 1H) 7.09 (d, J=7.45 Hz, 1H) 6.55 (dd, J=7.45, 6.58 Hz, 1H) 5.72 (s, 2H) 2.62 (d, J=6.58 Hz, 2H) 1.87 (dquin, J=13.43, 6.62, 6.62, 6.62, 6.62 Hz, 1H) 1.70 (s, 9H) 0.72 (d, J=6.58 Hz, 6H).

To a solution of tert-butyl 4-isobutyl-2-[(3-nitro-2-oxo-1-pyridyl)methyl]benzimidazole-1-carboxylate (25.1 g, 58.86 mmol, 1 eq) in EtOAc (300 mL) was added Pd/C (8 g, 58.86 mmol, 10% purity) under $N_2$. The suspension was degassed under vacuum and purged with $H_2$ several times. The mixture was stirred under $H_2$ (15 psi) at 25° C. for 1 hour and then filtered and concentrated under reduced pressure to give tert-butyl 2-[(3-amino-2-oxo-1-pyridyl)methyl]-4-isobutyl-benzimidazole-1-carboxylate (23.9 g) as a brown oil. $^1H$ NMR (I-63) (400 MHz, DMSO-$d_6$) δ 7.71-7.79 (m, 1H) 7.21-7.32 (m, 1H) 7.09 (d, J=7.02 Hz, 1H) 6.94 (dd, J=6.80, 1.53 Hz, 1H) 6.50 (dd, J=7.24, 1.53 Hz, 1H) 6.08 (t, J=6.80

Hz, 1H) 5.55 (s, 2H) 5.05 (s, 2H) 2.65 (d, J=7.02 Hz, 2H) 1.87-2.00 (m, 1H) 1.63-1.72 (m, 9H) 0.76 (d, J=6.58 Hz, 6H).
The following intermediates were prepared according to the procedures described for the synthesis of I-63 using the appropriate reagents.
| Compound | Structure | LCMS Data |
| --- | --- | --- |
| I-64 | 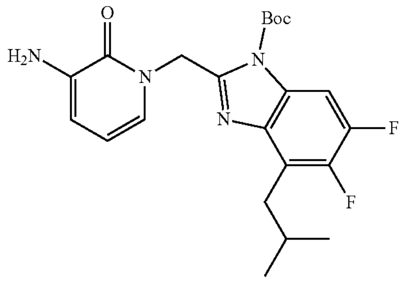 [SMILES: CC(C)Cc1c(F)c(F)cc2c1nc(Cn1cccc(N)c1=O)n2C(=O)OC(C)(C)C] | LCMS m/z 433.2 (M + H)$^+$ |
| I-67 | 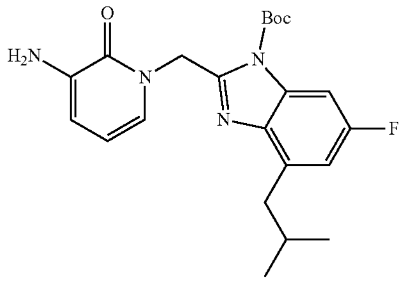 [SMILES: CC(C)Cc1cc(F)cc2c1nc(Cn1cccc(N)c1=O)n2C(=O)OC(C)(C)C] | LCMS m/z 415.2 (M + H)$^+$ |
| I-583 | 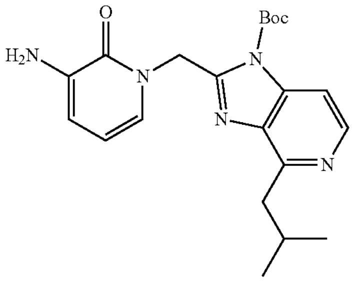 [SMILES: CC(C)Cc1nccc2c1nc(Cn1cccc(N)c1=O)n2C(=O)OC(C)(C)C] | LCMS m/z 398.2 (M + H)$^+$ |
| I-584 | 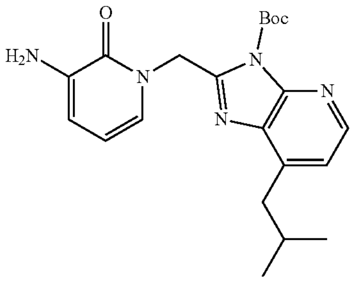 [SMILES: CC(C)Cc1ccnc2c1nc(Cn1cccc(N)c1=O)n2C(=O)OC(C)(C)C] | LCMS m/z 398.2 (M + H)$^+$ |
| I-591 | 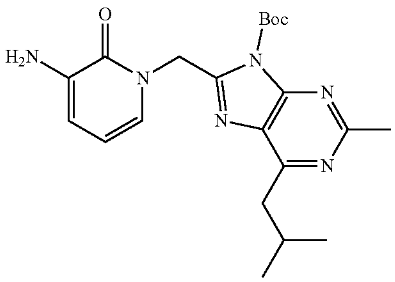 [SMILES: Cc1nc(CC(C)C)c2nc(Cn3cccc(N)c3=O)n(C(=O)OC(C)(C)C)c2n1] | LCMS m/z 413.2 (M + H)$^+$ |

-continued
| Compound | Structure | LCMS Data |
|---|---|---|
| I-605 | 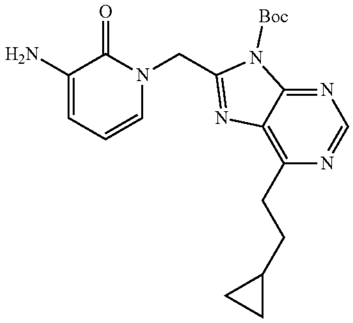 [SMILES: CC(C)(C)OC(=O)n1c(Cn2cccc(N)c2=O)nc2c(CCC3CC3)ncnc21] | LCMS m/z 411.2 $(M + H)^+$ |
| I-606 | 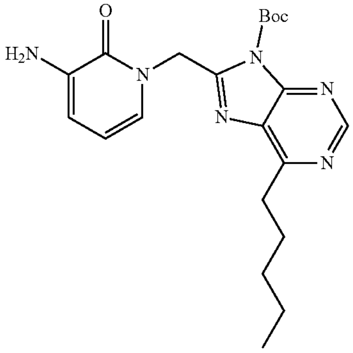 [SMILES: CCCCCc1ncnc2c1nc(Cn1cccc(N)c1=O)n2C(=O)OC(C)(C)C] | LCMS m/z 413.2 $(M + H)^+$ |
Synthesis of 3-amino-1-[[6-(2-methylprop-1-enyl)-9H-purin-8-yl]methyl]pyridin-2-one (I-65)
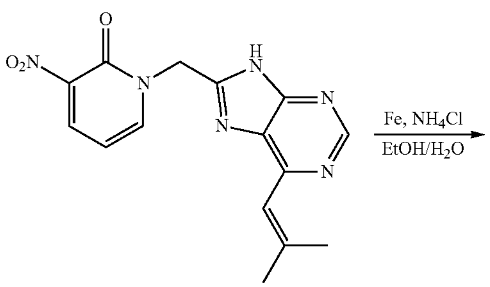
I-65A
-continued
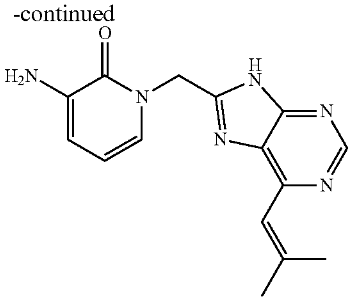
I-65
A mixture of 1-[[6-(2-methylprop-1-enyl)-9H-purin-8-yl]methyl]-3-nitro-pyridin-2-one (100 mg, 306.46 umol) in $H_2O$ (0.5 mL) and EtOH (2.5 mL) then was added Fe (85.57 mg, 1.53 mmol), $NH_4Cl$ (163.93 mg, 3.06 mmol, 107.14 uL)

at 15° C., and then the mixture was stirred at 80° C. for 1 hr. The mixture was filtered and filtrate was concentrated under reduced pressure to give a solid. The residue was diluted with water 10 mL and extracted with EtOAc 16 mL (8 mL×2). The combined organic layers were washed with brine 8 mL, dried over anhydrous $Na_2SO_4$, filtered and concentrated under reduced pressure to give 3-amino-1-[[6-(2-methylprop-1-enyl)-9H-purin-8-yl]methyl]pyridin-2-one (I-65) (100 mg) as a brown solid. LCMS m/z 297.2 $(M+H)^+$.

The following intermediates were prepared according to the procedures described for the synthesis of I-65 using the appropriate reagents.

| Compound | Structure | LCMS Data |
| --- | --- | --- |
| I-66 | 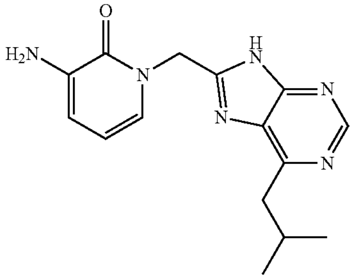 [SMILES: CC(C)Cc1ncnc2[nH]c(Cn3cccc(N)c3=O)nc12] | LCMS m/z 299.2 $(M + H)^+$ |
| I-585 | 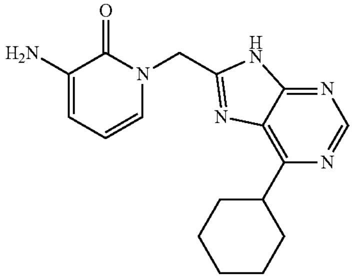 [SMILES: Nc1cccn(Cc2nc3c(C4CCCCC4)ncnc3[nH]2)c1=O] | LCMS m/z 325.2 $(M + H)^+$ |
| I-586 | 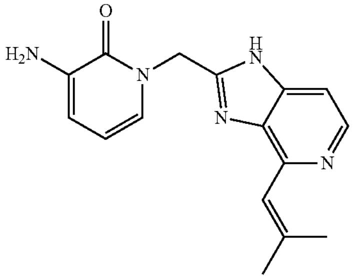 [SMILES: CC(C)=Cc1nccc2[nH]c(Cn3cccc(N)c3=O)nc12] | LCMS m/z 296.2 $(M + H)^+$ |
| I-587 | 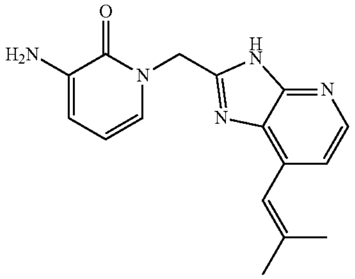 [SMILES: CC(C)=Cc1ccnc2[nH]c(Cn3cccc(N)c3=O)nc12] | LCMS m/z 296.2 $(M + H)^+$ |
| I-588 | 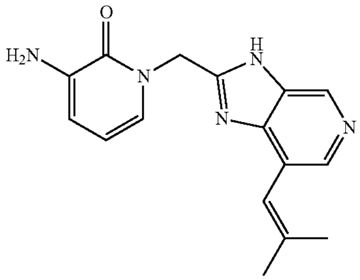 [SMILES: CC(C)=Cc1cncc2[nH]c(Cn3cccc(N)c3=O)nc12] | LCMS m/z 296.2 $(M + H)^+$ |

-continued
| Compound | Structure | LCMS Data |
|---|---|---|
| I-589 | 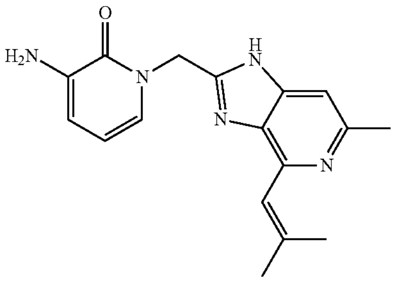 [SMILES: CC(C)=Cc1nc(C)cc2[nH]c(Cn3cccc(N)c3=O)nc12] | LCMS m/z 311.2 (M + H)+ |
| I-590 | 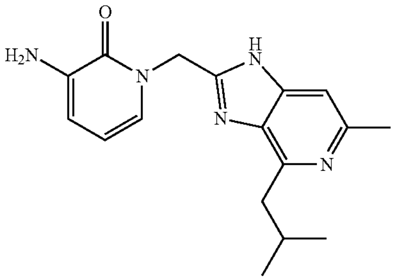 [SMILES: Cc1cc2[nH]c(Cn3cccc(N)c3=O)nc2c(CC(C)C)n1] | LCMS m/z 313.2 (M + H)+ |
| I-592 | 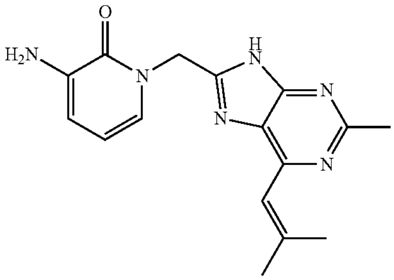 [SMILES: CC(C)=Cc1nc(C)nc2[nH]c(Cn3cccc(N)c3=O)nc12] | LCMS m/z 311.2 (M + H)+ |
| I-593 | 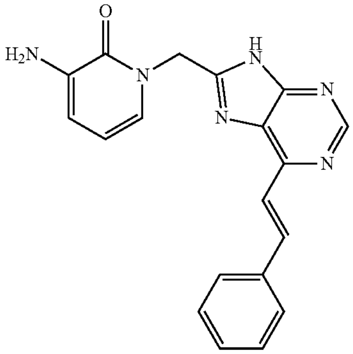 [SMILES: Nc1cccn(Cc2nc3c(/C=C/c4ccccc4)ncnc3[nH]2)c1=O] | LCMS m/z 345.2 (M + H)+ |
| I-594 | 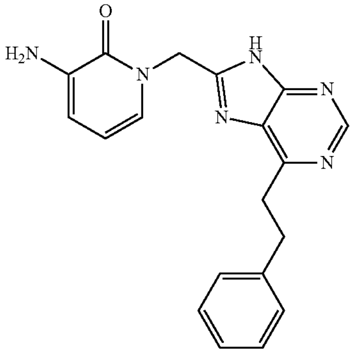 [SMILES: Nc1cccn(Cc2nc3c(CCc4ccccc4)ncnc3[nH]2)c1=O] | LCMS m/z 347.2 (M + H)+ |

-continued
| Compound | Structure | LCMS Data |
|---|---|---|
| I-607 | 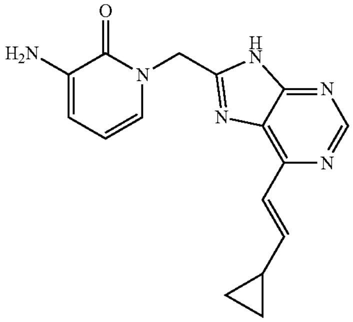 [SMILES: Nc1cccn(Cc2nc3c(/C=C/C4CC4)ncnc3[nH]2)c1=O] | LCMS m/z 309.2 $(M + H)^+$ |
Example 1
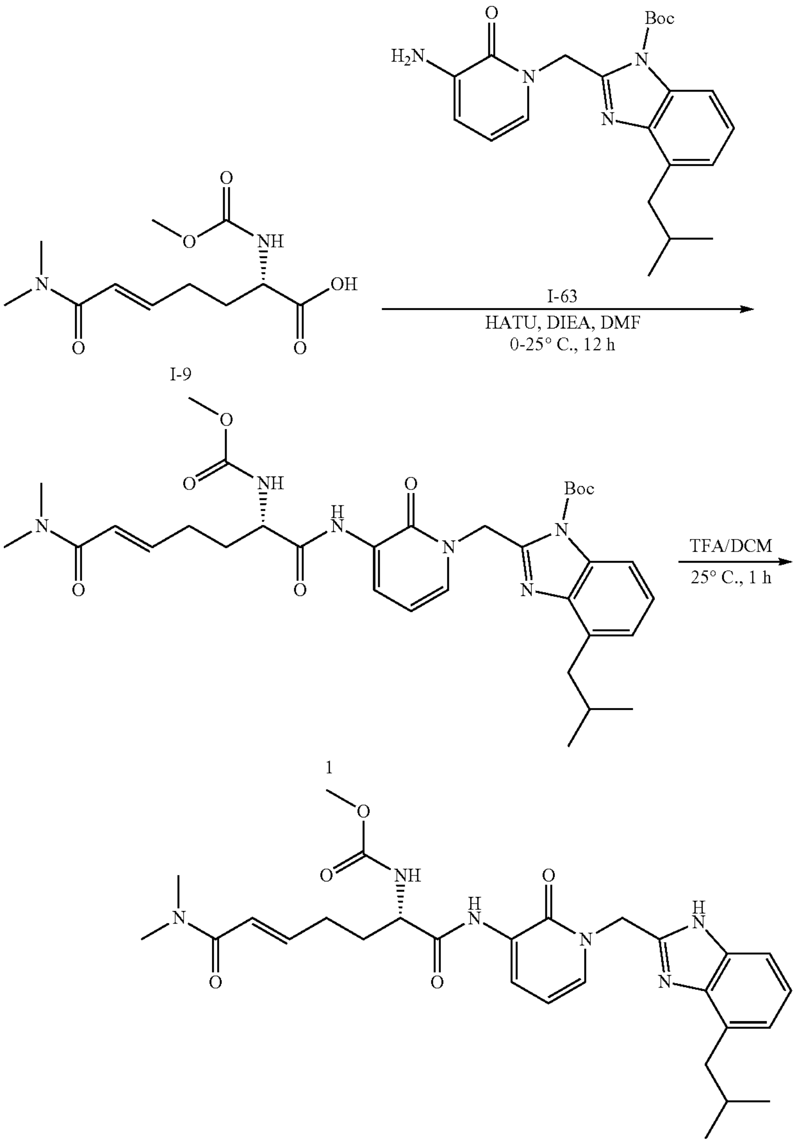
I-9
1
2

The mixture of tert-butyl 2-[(3-amino-2-oxo-1-pyridyl) methyl]-4-isobutyl-benzimidazole-1-carboxylate (I-63) (11.6 g, 29.26 mmol), (E,2S)-7-(dimethylamino)-2-(methoxycarbonylamino)-7-oxo-hept-5-enoic acid (I-9) (23 g, 89.05 mmol) and DIEA (30.25 g, 234.06 mmol, 40.77 mL) in DMF (80 mL) was cooled to 0° C., then HATU (18.91 g, 49.74 mmol, 1.7 eq) in DMF (40 mL) was added dropwise to the mixture at 0° C. Then the reaction mixture was stirred at 25° C. for 12 hours. The reaction mixture was poured into ice sat. aq. $NH_4Cl$ (1000 mL), and extracted with ethyl acetate (200 mL*3). The combined organic phase was washed with brine (500 mL*2), dried with anhydrous $Na_2SO_4$, filtered and concentrated in vacuum. The residue was purified by column chromatography to give tert-butyl 2-[[3-[[(E,2S)-7-(dimethylamino)-2-(methoxycarbonylamino)-7-oxo-hept-5-enoyl]amino]-2-oxo-1-pyridyl] methyl]-4-isobutyl-benzimidazole-1-carboxylate (Compound 1) (25 g, 39.26 mmol, 67% yield) as a light green foam. LCMS m/z 637.3 $(M+1)^+$.

To the mixture of tert-butyl 2-[[3-[[(E,2S)-7-(dimethylamino)-2-(methoxycarbonylamino)-7-oxo-hept-5-enoyl] amino]-2-oxo-1-pyridyl]methyl]-4-isobutyl-benzimidazole-1-carboxylate (Compound 1) (12.5 g, 19.63 mmol) in DCM (100 mL) was added TFA (30.80 g, 270.12 mmol, 20.00 mL, 13.76 eq) in one portion at 25° C. Then the reaction mixture was stirred at 25° C. for 1 hour. Two batches in parallel of the reaction were set up. The two parallel reaction mixtures were combined and the reaction mixture was dried by flowing $N_2$, then added ice sat. aq. $NaHCO_3$ adjust the pH to ~8. Then extracted with ethyl acetate (100 mL*3). The combined organic phase was washed with brine (200 mL*1), dried with anhydrous $Na_2SO_4$, filtered and concentrated in vacuum to give a light green solid. The residue was added ethyl acetate (100 mL), some solid was not dissolved, and the mixture was stirred at 60° C. for 0.5 hour. The mixture was filtered to give methyl N-[(E,1S)-6-(dimethylamino)-1-[[1-[(4-isobutyl-1H-benzimidazol-2-yl)methyl]-2-oxo-3-pyridyl]carbamoyl]-6-oxo-hex-4-enyl]carbamate (Compound 2) (12.1 g, 57% yield) as an off-white solid. LCMS m/z 537.3 $(M+1)^+$. $^1H$ NMR (400 MHz, DMSO-$d_6$) δ 12.17-12.60 (m, 1H) 9.27 (br d, J=11.62 Hz, 1H) 8.26 (br d, J=7.09 Hz, 1H) 7.68-7.81 (m, 1H) 7.74 (br s, 1H) 7.56 (br t, J=5.93 Hz, 1H) 7.21-7.39 (m, 1H) 7.05 (dt, J=11.92, 7.61 Hz, 1H) 6.87-6.97 (m, 1H) 6.53-6.68 (m, 1H) 6.29-6.43 (m, 2H) 5.41 (s, 2H) 4.18 (brs, 1H) 3.55 (brs, 3H) 2.98 (s, 3H) 2.83 (s, 3H) 2.65-2.78 (m, 2H) 2.19-2.31 (m, 2H) 1.94-2.17 (m, 1H) 1.65-1.94 (m, 2H) 0.88 (br dd, J=18.95, 6.48 Hz, 6H).

The following compounds were prepared according to the procedures described in Example 1 using the appropriate intermediates.

| Compound | Structure | Characterization Data |
| --- | --- | --- |
| 3 | 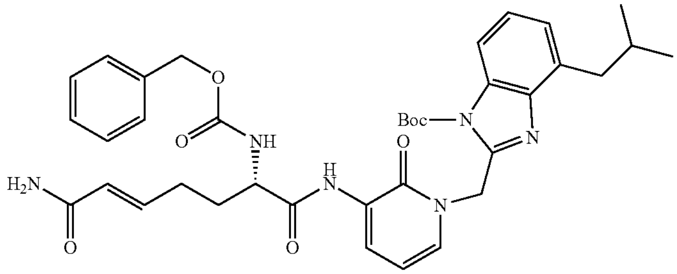 [SMILES: CC(C)Cc1cccc2c1nc(Cn1cccc(NC(=O)[C@H](CC/C=C/C(N)=O)NC(=O)OCc3ccccc3)c1=O)n2C(=O)OC(C)(C)C] | LCMS m/z 685.3 $(M + 1)^+$ |
| 4 | 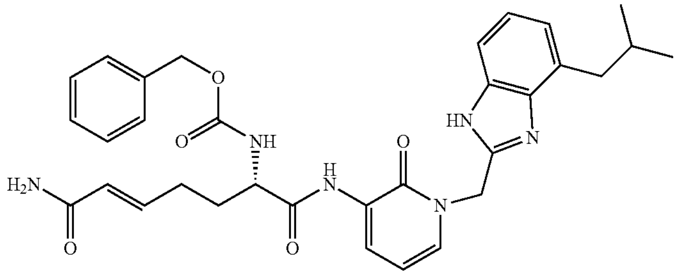 [SMILES: CC(C)Cc1cccc2[nH]c(Cn3cccc(NC(=O)[C@H](CC/C=C/C(N)=O)NC(=O)OCc4ccccc4)c3=O)nc12] | LCMS m/z 585.3 $(M + 1)^+$. |
| 5 | 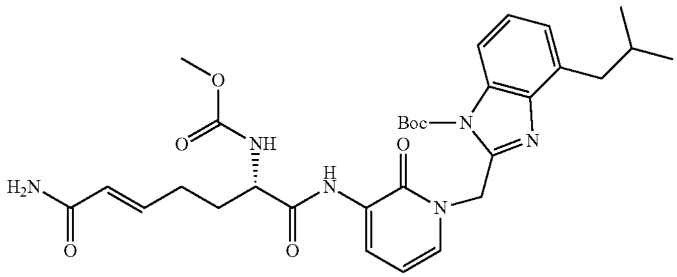 [SMILES: COC(=O)N[C@@H](CC/C=C/C(N)=O)C(=O)Nc1cccn(Cc2nc3c(CC(C)C)cccc3n2C(=O)OC(C)(C)C)c1=O] | LCMS m/z 609.3 $(M + 1)^+$ |

-continued
| Compound | Structure | Characterization Data |
|---|---|---|
| 6 | 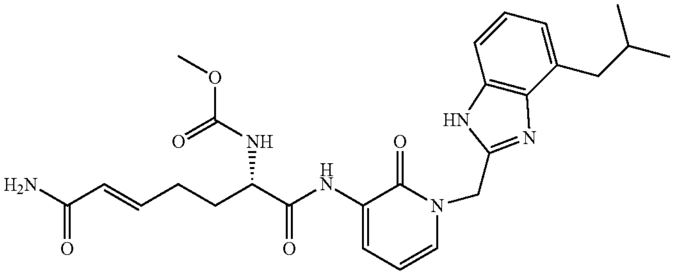 [SMILES: COC(=O)N[C@@H](CC/C=C/C(N)=O)C(=O)Nc1cccn(Cc2nc3c(CC(C)C)cccc3[nH]2)c1=O] | LCMS m/z 509.3 $(M + 1)^+$ |
| 7 | 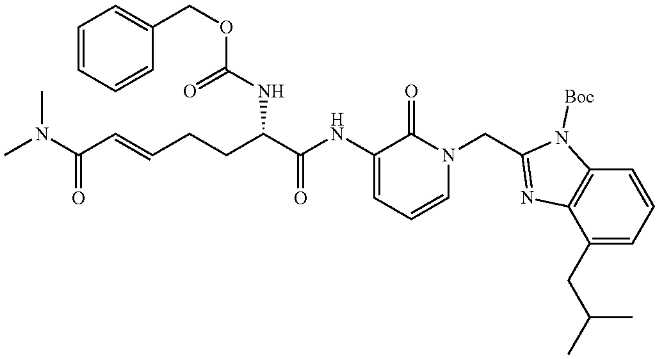 [SMILES: CC(C)Cc1cccc2c1nc(Cn1cccc(NC(=O)[C@H](CC/C=C/C(=O)N(C)C)NC(=O)OCc3ccccc3)c1=O)n2C(=O)OC(C)(C)C] | LCMS m/z 713.3 $(M + 1)^+$ |
| 8 | 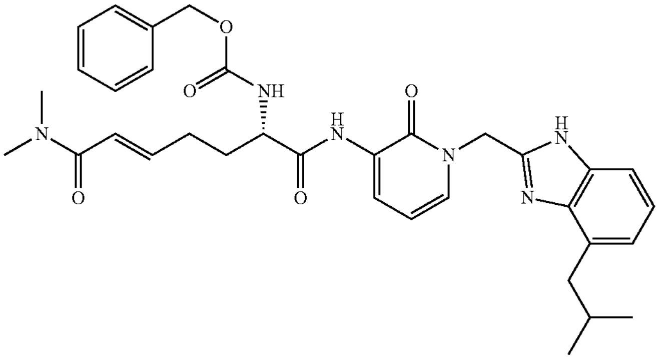 [SMILES: CC(C)Cc1cccc2[nH]c(Cn3cccc(NC(=O)[C@H](CC/C=C/C(=O)N(C)C)NC(=O)OCc4ccccc4)c3=O)nc12] | LCMS m/z 613.3 $(M + 1)^+$ |
| 9 | 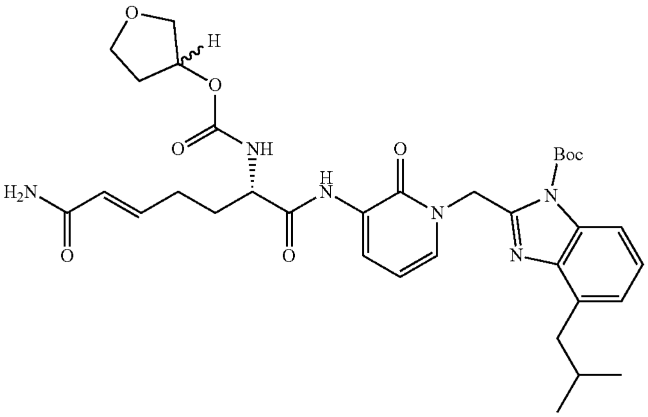 [SMILES: CC(C)Cc1cccc2c1nc(Cn1cccc(NC(=O)[C@H](CC/C=C/C(N)=O)NC(=O)OC3CCOC3)c1=O)n2C(=O)OC(C)(C)C] | $^1H$ NMR (400 MHz, DMSO-$d_6$) δ 9.25 (s, 1H), 8.28 (d, J = 7.2 Hz, 1H), 7.83 (t, J = 6.8 Hz, 1H), 7.75 (d, J = 8.0 Hz, 1H), 7.51-7.46 (m, 1H), 7.35-7.25 (m, 2H), 7.09 (d, J = 7.2 Hz, 1H), 6.88 (s, 1H), 6.62-6.52 (m, 1H), 6.34 (t, J = 7.2 Hz, 1H), 5.83 (d, J = 15.6 Hz, 1H), 5.63 (s, 2H), 5.15-5.02 (m, 1H), 4.22-4.13 (m, 1H), 3.80-3.60 (m, 4H), 2.64-2.59 (m, 2H), 2.25-2.10 (m, 2H), 2.10-1.98 (m, 1H), 1.93-1.78 (m, 3H), 1.69 (s, 10H), 0.72 (d, J = 6.7 Hz, 6H) |

-continued
| Compound | Structure | Characterization Data |
|---|---|---|
| 10 | 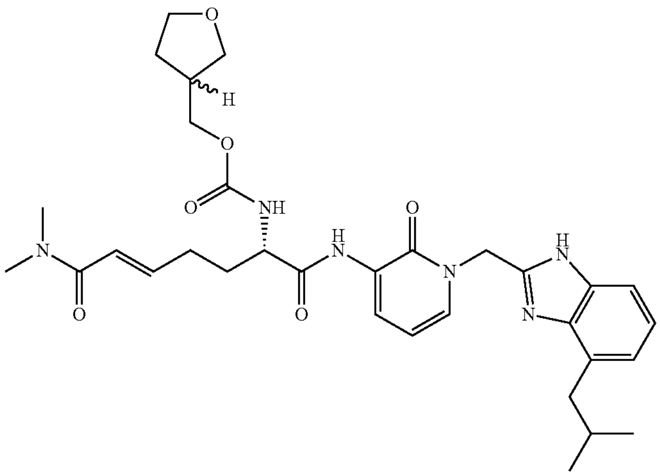 [SMILES: CC(C)Cc1cccc2[nH]c(Cn3cccc(NC(=O)[C@H](CC/C=C/C(=O)N(C)C)NC(=O)OCC4CCOC4)c3=O)nc12] | LCMS m/z 607.5 $(M+1)^+$ |
| 11 | 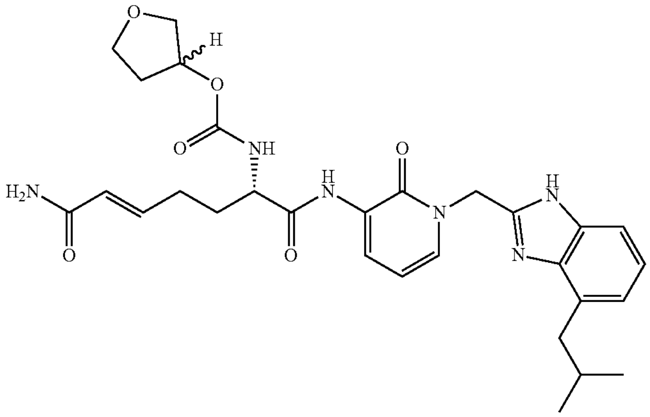 [SMILES: CC(C)Cc1cccc2[nH]c(Cn3cccc(NC(=O)[C@H](CC/C=C/C(N)=O)NC(=O)OC4CCOC4)c3=O)nc12] | LCMS m/z 565.3 $(M+1)^+$ |
| 12 | 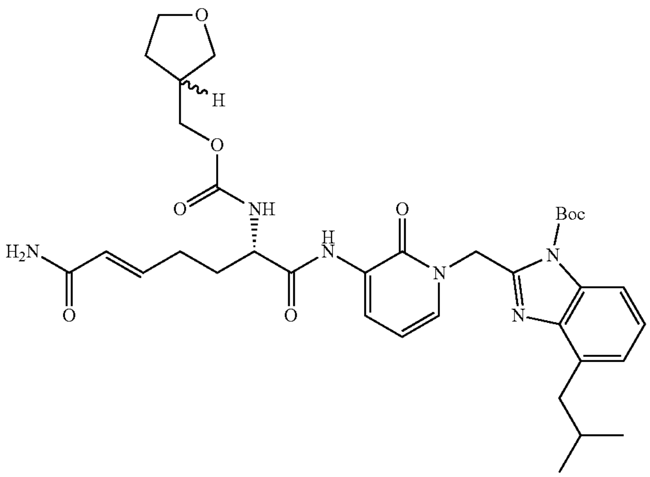 [SMILES: CC(C)Cc1cccc2c1nc(Cn1cccc(NC(=O)[C@H](CC/C=C/C(N)=O)NC(=O)OCC3CCOC3)c1=O)n2C(=O)OC(C)(C)C] | LCMS m/z 679.4 $(M+1)^+$ |

-continued
| Compound | Structure | Characterization Data |
|---|---|---|
| 13 | 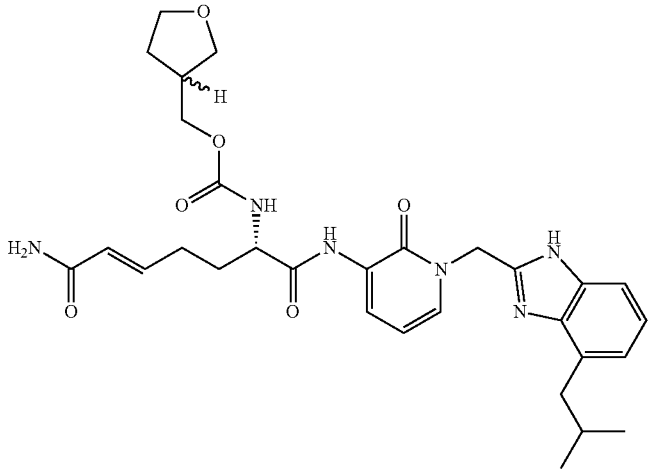 [SMILES: CC(C)Cc1cccc2[nH]c(Cn3cccc(NC(=O)[C@H](CC/C=C/C(N)=O)NC(=O)OCC4CCOC4)c3=O)nc12] | LCMS m/z 579.4 $(M+1)^+$ |
| 14 | 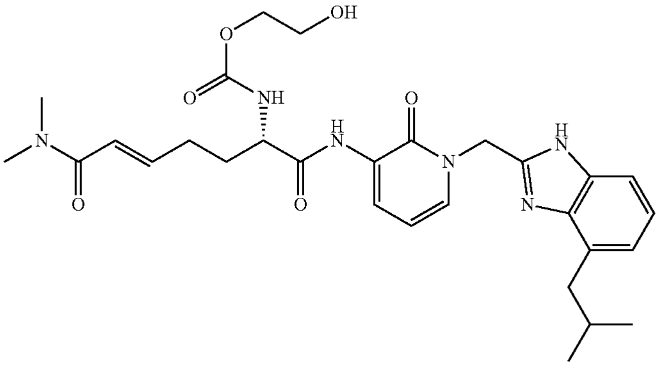 [SMILES: CC(C)Cc1cccc2[nH]c(Cn3cccc(NC(=O)[C@H](CC/C=C/C(=O)N(C)C)NC(=O)OCCO)c3=O)nc12] | LCMS m/z 567.1 $(M+1)^+$ |
| 15 | 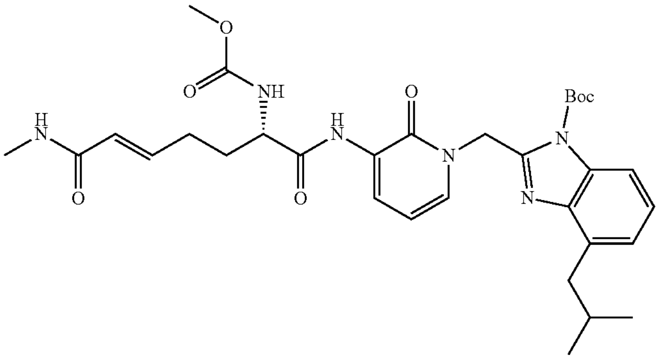 [SMILES: CNC(=O)/C=C/CC[C@H](NC(=O)OC)C(=O)Nc1cccn(Cc2nc3c(CC(C)C)cccc3n2C(=O)OC(C)(C)C)c1=O] | LCMS m/z 623.2 $(M+1)^+$ |
| 16 | 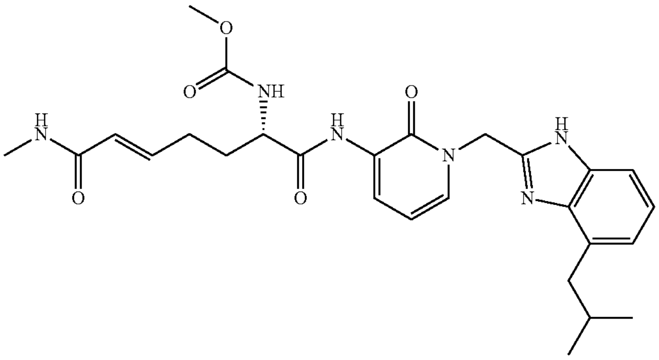 [SMILES: CNC(=O)/C=C/CC[C@H](NC(=O)OC)C(=O)Nc1cccn(Cc2nc3c(CC(C)C)cccc3[nH]2)c1=O] | LCMS m/z 523.3 $(M+1)^+$ |

-continued
| Compound | Structure | Characterization Data |
| --- | --- | --- |
| 17 | 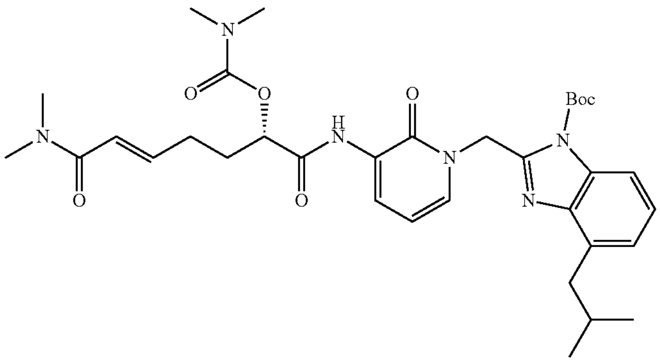 [SMILES: CC(C)Cc1cccc2c1nc(Cn1cccc(NC(=O)[C@H](CC/C=C/C(=O)N(C)C)OC(=O)N(C)C)c1=O)n2C(=O)OC(C)(C)C] | LCMS m/z 651.4 $(M + 1)^+$ |
| 18 | 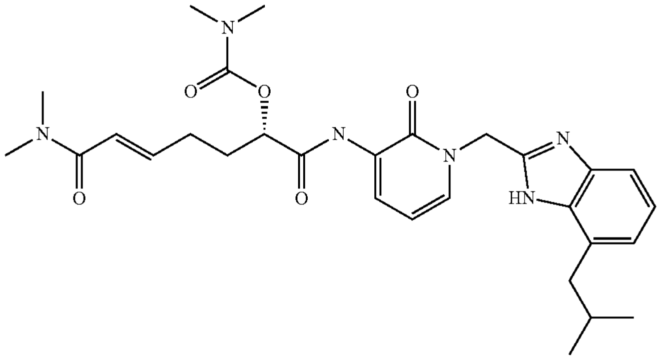 [SMILES: CC(C)Cc1cccc2nc(Cn3cccc(NC(=O)[C@H](CC/C=C/C(=O)N(C)C)OC(=O)N(C)C)c3=O)[nH]c12] | LCMS m/z 551.2 $(M + 1)^+$ |
| 19 | 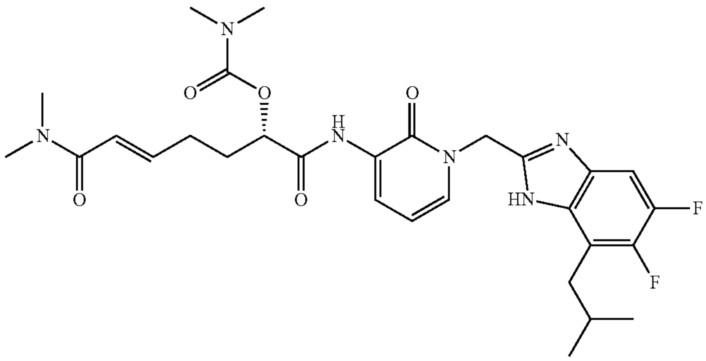 [SMILES: CC(C)Cc1c(F)c(F)cc2nc(Cn3cccc(NC(=O)[C@H](CC/C=C/C(=O)N(C)C)OC(=O)N(C)C)c3=O)[nH]c12] | LCMS m/z 587.3 $(M + 1)^+$ |
| 20 | 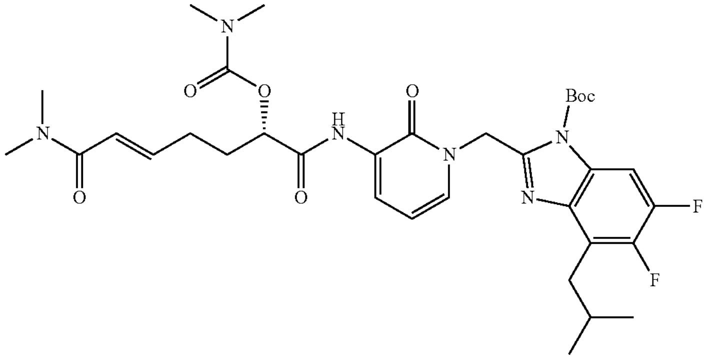 [SMILES: CC(C)Cc1c(F)c(F)cc2c1nc(Cn1cccc(NC(=O)[C@H](CC/C=C/C(=O)N(C)C)OC(=O)N(C)C)c1=O)n2C(=O)OC(C)(C)C] | LCMS m/z 687.4 $(M + 1)^+$ |

-continued
| Compound | Structure | Characterization Data |
| --- | --- | --- |
| 21 | 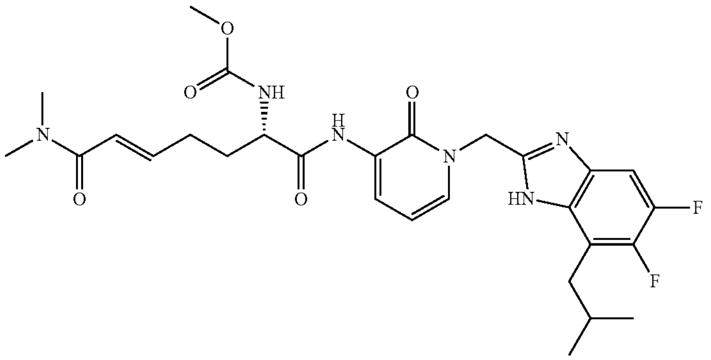 [SMILES: COC(=O)N[C@@H](CC/C=C/C(=O)N(C)C)C(=O)Nc1cccn(Cc2nc3cc(F)c(F)c(CC(C)C)c3[nH]2)c1=O] | LCMS m/z 573.3 $(M + 1)^+$ |
| 22 | 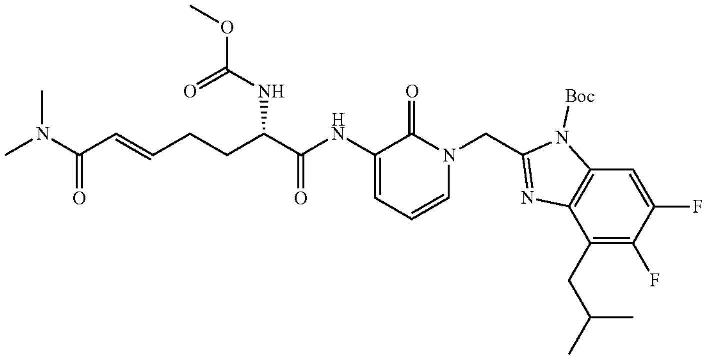 [SMILES: COC(=O)N[C@@H](CC/C=C/C(=O)N(C)C)C(=O)Nc1cccn(Cc2nc3c(CC(C)C)c(F)c(F)cc3n2C(=O)OC(C)(C)C)c1=O] | LCMS m/z 673.5 $(M + 1)^+$ |
| 23 | 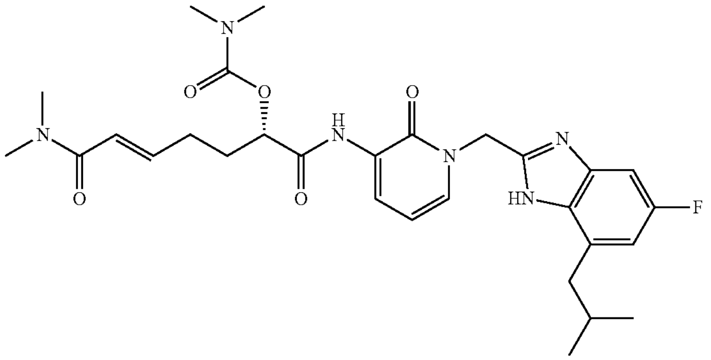 [SMILES: CC(C)Cc1cc(F)cc2nc(Cn3cccc(NC(=O)[C@H](CC/C=C/C(=O)N(C)C)OC(=O)N(C)C)c3=O)[nH]c12] | LCMS m/z 569.4 $(M + 1)^+$ |
| 24 | 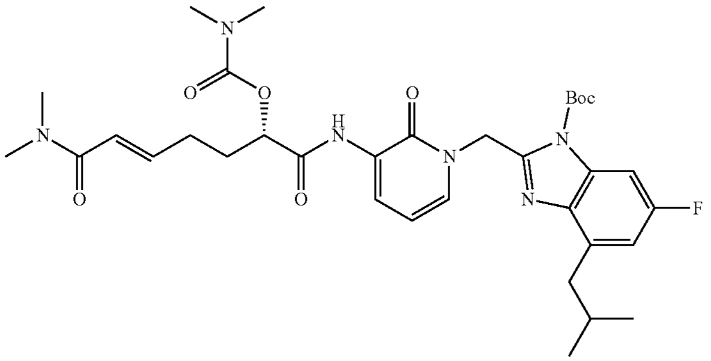 [SMILES: CC(C)Cc1cc(F)cc2c1nc(Cn1cccc(NC(=O)[C@H](CC/C=C/C(=O)N(C)C)OC(=O)N(C)C)c1=O)n2C(=O)OC(C)(C)C] | LCMS m/z 669.4 $(M + 1)^+$ |

-continued
| Compound | Structure | Characterization Data |
| --- | --- | --- |
| 25 | 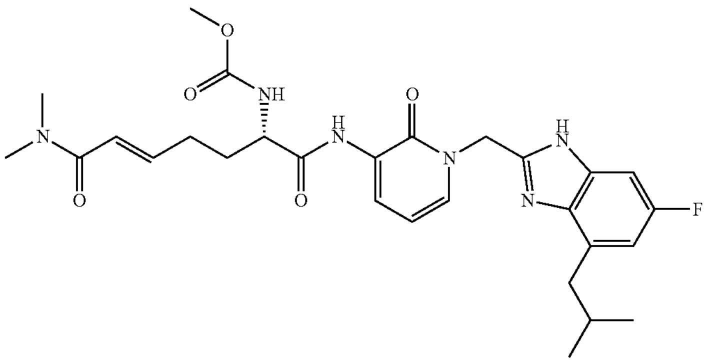 [SMILES: COC(=O)N[C@@H](CC/C=C/C(=O)N(C)C)C(=O)Nc1cccn(Cc2nc3c(CC(C)C)cc(F)cc3[nH]2)c1=O] | LCMS m/z 555.2 $(M + 1)^+$ |
| 26 | 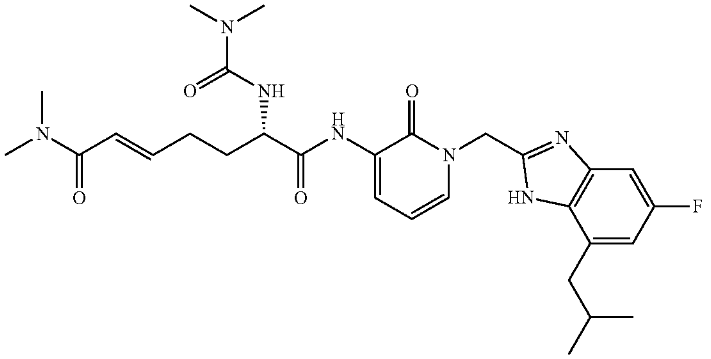 [SMILES: CC(C)Cc1cc(F)cc2nc(Cn3cccc(NC(=O)[C@H](CC/C=C/C(=O)N(C)C)NC(=O)N(C)C)c3=O)[nH]c12] | LCMS m/z 568.3 $(M + 1)^+$ |
| 414 | 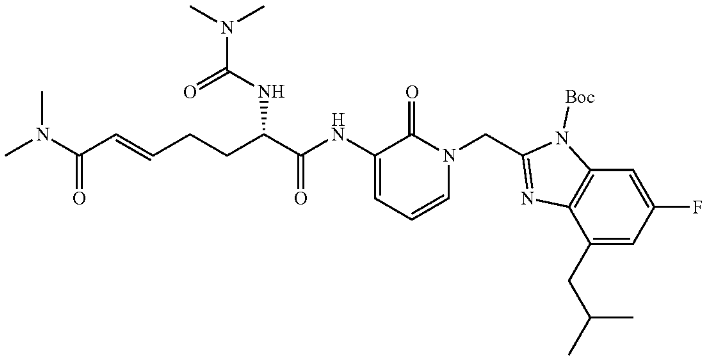 [SMILES: CC(C)Cc1cc(F)cc2c1nc(Cn1cccc(NC(=O)[C@H](CC/C=C/C(=O)N(C)C)NC(=O)N(C)C)c1=O)n2C(=O)OC(C)(C)C] | LCMS m/z 668.3 $(M + 1)^+$ |
| 396 | 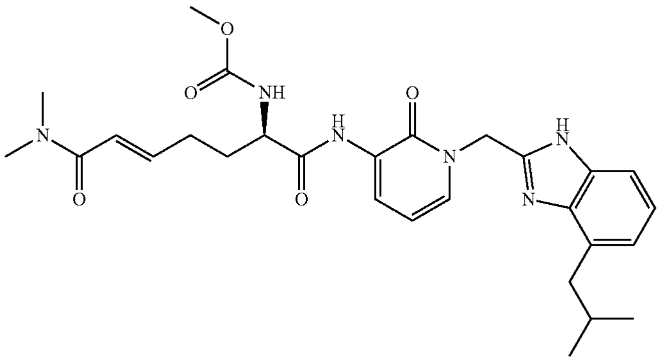 [SMILES: COC(=O)N[C@H](CC/C=C/C(=O)N(C)C)C(=O)Nc1cccn(Cc2nc3c(CC(C)C)cccc3[nH]2)c1=O] | LCMS m/z 537.1 $(M + 1)^+$ |

-continued
| Compound | Structure | Characterization Data |
|---|---|---|
| 398 | 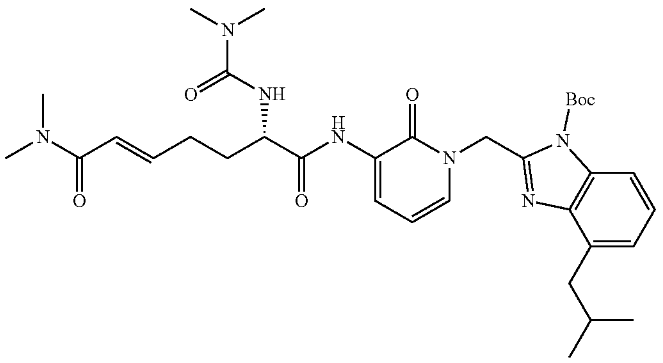 [SMILES: CC(C)Cc1cccc2c1nc(Cn1cccc(NC(=O)[C@H](CC/C=C/C(=O)N(C)C)NC(=O)N(C)C)c1=O)n2C(=O)OC(C)(C)C] | LCMS m/z 650.4 $(M + 1)^+$ |
| 399 | 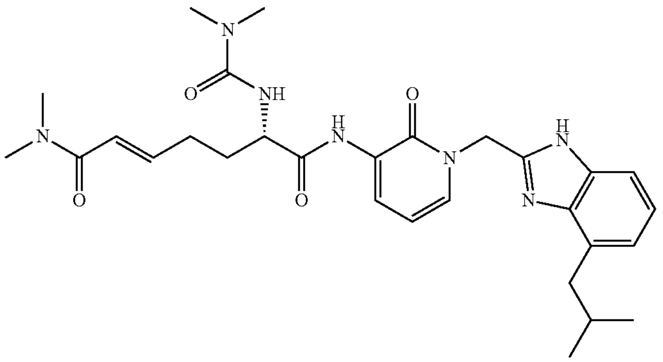 [SMILES: CC(C)Cc1cccc2[nH]c(Cn3cccc(NC(=O)[C@H](CC/C=C/C(=O)N(C)C)NC(=O)N(C)C)c3=O)nc12] | LCMS m/z 550.3 $(M + 1)^+$ |
| 401 | 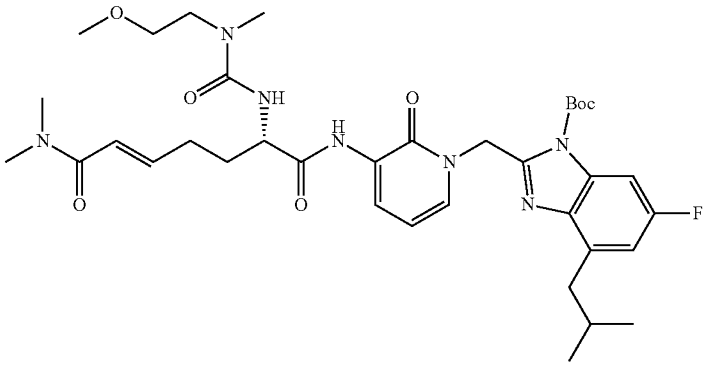 [SMILES: COCCN(C)C(=O)N[C@@H](CC/C=C/C(=O)N(C)C)C(=O)Nc1cccn(Cc2nc3c(CC(C)C)cc(F)cc3n2C(=O)OC(C)(C)C)c1=O] | LCMS m/z 694.4 $(M + 1)^+$ |
| 402 | 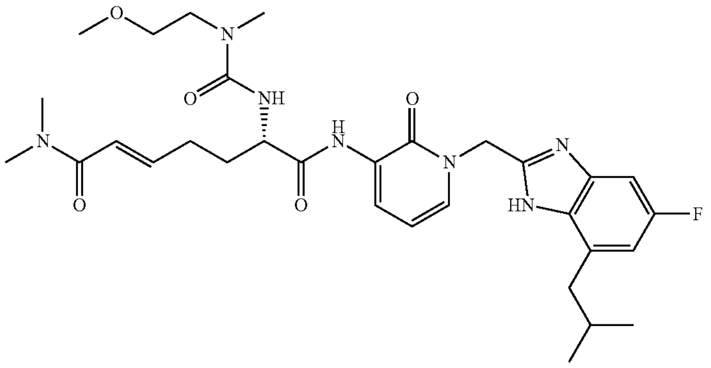 [SMILES: COCCN(C)C(=O)N[C@@H](CC/C=C/C(=O)N(C)C)C(=O)Nc1cccn(Cc2nc3cc(F)cc(CC(C)C)c3[nH]2)c1=O] | LCMS m/z 594.3 $(M + 1)^+$ |

-continued
| Compound | Structure | Characterization Data |
| --- | --- | --- |
| 419 | 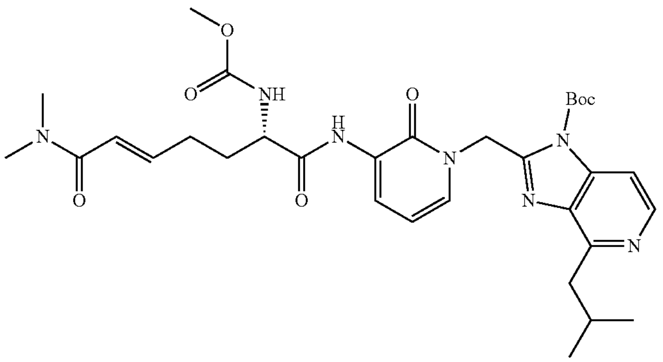 [SMILES: COC(=O)N[C@@H](CC/C=C/C(=O)N(C)C)C(=O)Nc1cccn(Cc2nc3c(CC(C)C)nccc3n2C(=O)OC(C)(C)C)c1=O] | LCMS m/z 638.3 $(M + 1)^+$ |
| 421 | 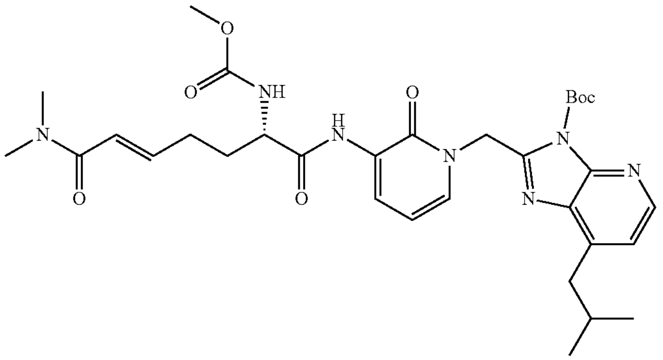 [SMILES: COC(=O)N[C@@H](CC/C=C/C(=O)N(C)C)C(=O)Nc1cccn(Cc2nc3c(CC(C)C)ccnc3n2C(=O)OC(C)(C)C)c1=O] | LCMS m/z 638.3 $(M + 1)^+$ |
| 424 | 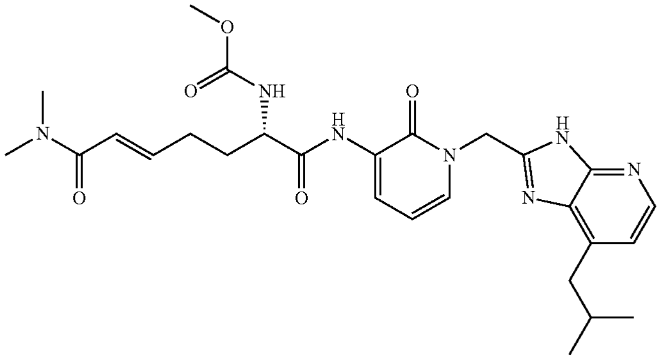 [SMILES: COC(=O)N[C@@H](CC/C=C/C(=O)N(C)C)C(=O)Nc1cccn(Cc2nc3c(CC(C)C)ccnc3[nH]2)c1=O] | LCMS m/z 538.3 $(M + 1)^+$ |
| 431 | 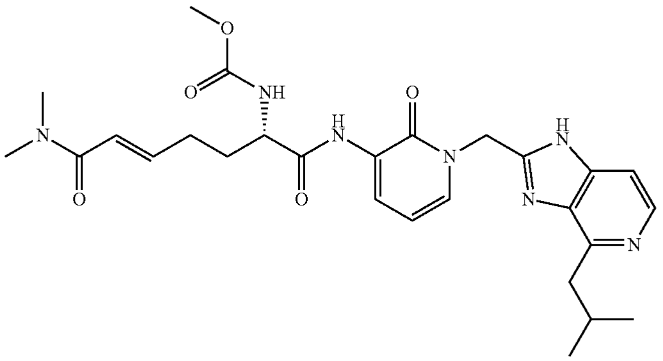 [SMILES: COC(=O)N[C@@H](CC/C=C/C(=O)N(C)C)C(=O)Nc1cccn(Cc2nc3c(CC(C)C)nccc3[nH]2)c1=O] | LCMS m/z 538.3 $(M + 1)^+$ |

-continued
| Compound | Structure | Characterization Data |
| --- | --- | --- |
| 442 | 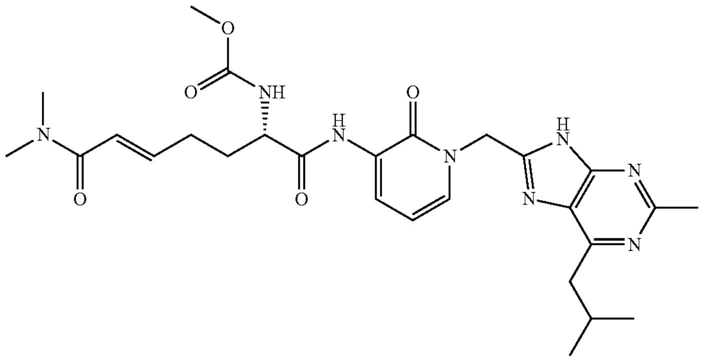 | LCMS m/z 553.2 (M + 1)$^+$ |
| 443 | 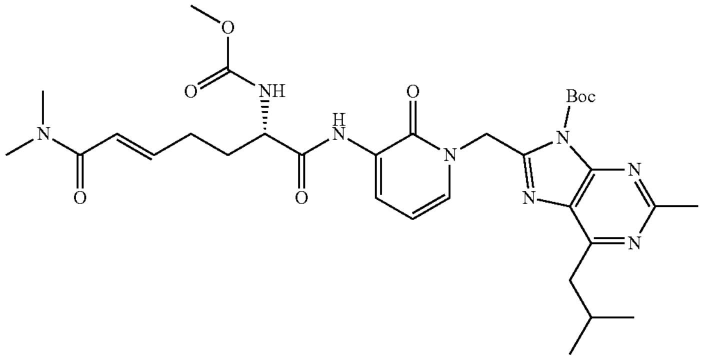 | LCMS m/z 653.3 (M + 1)$^+$ |
| 446 | 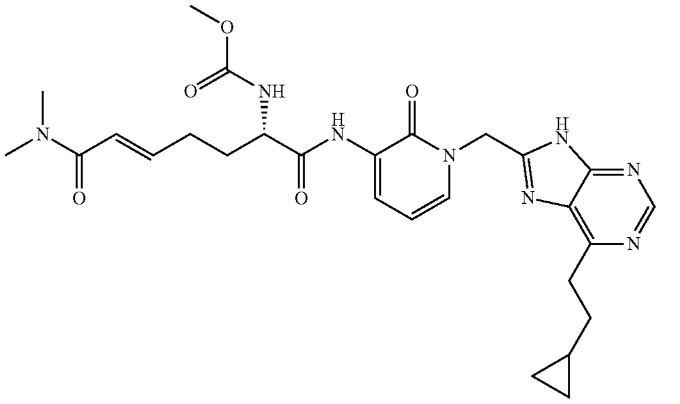 [SMILES: COC(=O)N[C@@H](CC/C=C/C(=O)N(C)C)C(=O)Nc1cccn(Cc2nc3c(CCC4CC4)ncnc3[nH]2)c1=O] | LCMS m/z 551.2 (M + 1)$^+$ |
| 447 | 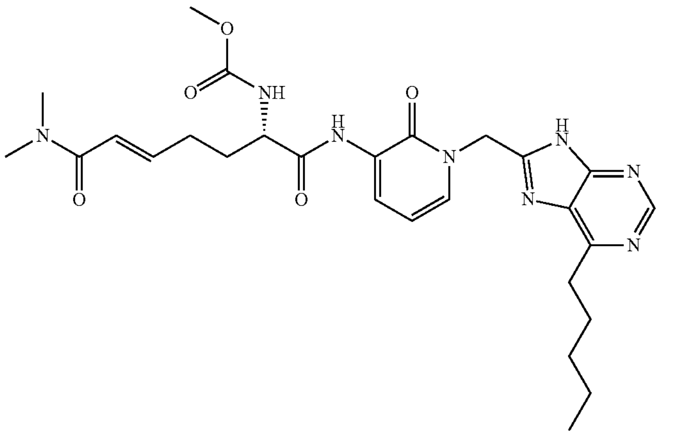 [SMILES: CCCCCc1ncnc2[nH]c(Cn3cccc(NC(=O)[C@H](CC/C=C/C(=O)N(C)C)NC(=O)OC)c3=O)nc12] | LCMS m/z 553.2 (M + 1)$^+$ |

Example 2

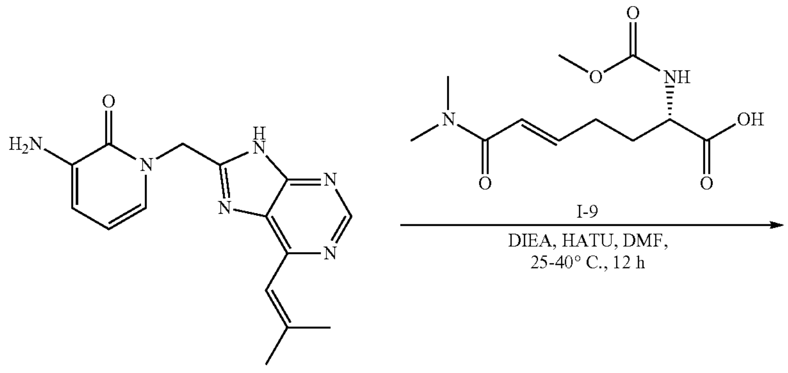

I-65

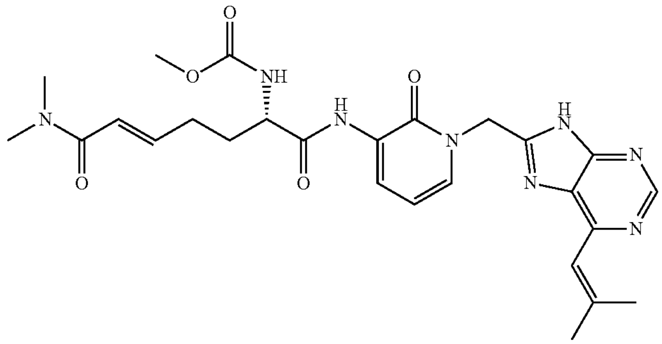

27

To a mixture of 3-amino-1-[[6-(2-methylprop-1-enyl)-9H-purin-8-yl]methyl]pyridine-2-one (220 mg, 742.42 umol) and (E,2S)-7-(dimethylamino)-2-(methoxycarbonylamino)-7-oxo-hept-5-enoic acid (153.40 mg, 593.94 umol) in DMF (2.5 mL) was added HATU (508.13 mg, 1.34 mmol), DIEA (143.93 mg, 1.11 mmol) at 25° C. The mixture was stirred at 40° C. for 12 h. The mixture was filtered and concentrated. The residue was purified by prep-HPLC to give methyl N-[(E,1S)-6-(dimethylamino)-1-[[1-[[6-(2-methylprop-1-enyl)-9H-purin-8-yl]methyl]-2-oxo-3-pyridyl]carbamoyl]-6-oxo-hex-4-enyl]carbamate (Compound 27) (91.8 mg, 21% yield) as a brown solid. LCMS m/z 537.2 $(M+1)^+$. $^1H$ NMR (400 MHz, DMSO-$d_6$) δ 13.43 (br s, 1H) 9.27 (s, 1H) 8.76 (s, 1H) 8.27 (dd, J=7.46, 1.59 Hz, 1H) 7.72 (br d, J=7.95 Hz, 1H) 7.56-7.64 (m, 1H) 6.73 (br s, 1H) 6.54-6.65 (m, 1H) 6.32-6.43 (m, 2H) 5.44 (s, 2H) 4.14-4.21 (m, 1H) 3.54 (s, 3H) 2.99 (s, 3H) 2.78-2.87 (m, 3H) 2.34 (d, J=0.73 Hz, 3H) 2.17-2.27 (m, 2H) 2.02 (s, 3H) 1.68-1.92 (m, 1H) 1.66-1.94 (m, 1H).

The following compounds were prepared according to the procedures described in Example 2 using the appropriate intermediates.

| Compound | Structure | LCMS Data |
|---|---|---|
| 28 | 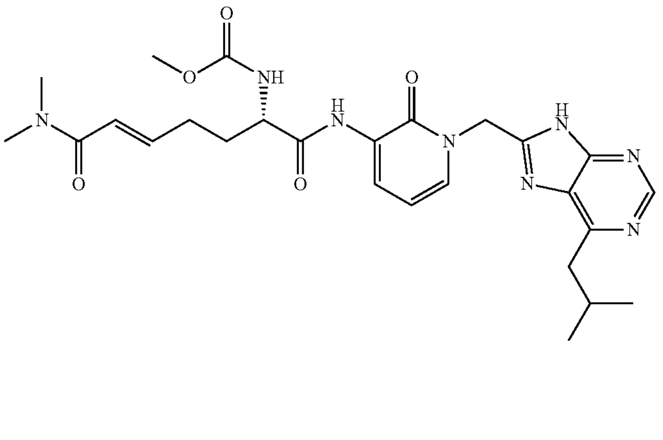 [SMILES: COC(=O)N[C@@H](CC/C=C/C(=O)N(C)C)C(=O)Nc1cccn(Cc2nc3c(CC(C)C)ncnc3[nH]2)c1=O] | LCMS m/z 539.3 $(M + 1)^+$ |

-continued
| Compound | Structure | LCMS Data |
|---|---|---|
| 422 | 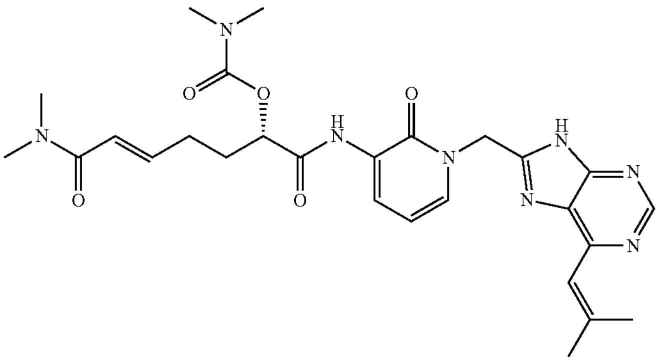 [SMILES: CC(C)=Cc1ncnc2[nH]c(Cn3cccc(NC(=O)[C@H](CC/C=C/C(=O)N(C)C)OC(=O)N(C)C)c3=O)nc12] | LCMS m/z 551.3 (M + 1)$^+$ |
| 423 | 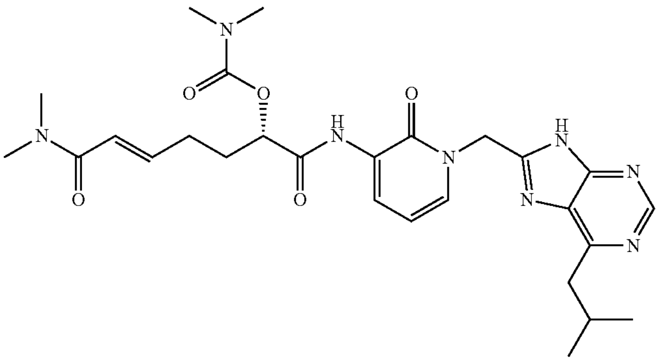 [SMILES: CC(C)Cc1ncnc2[nH]c(Cn3cccc(NC(=O)[C@H](CC/C=C/C(=O)N(C)C)OC(=O)N(C)C)c3=O)nc12] | LCMS m/z 553.3 (M + 1)$^+$ |
| 425 | 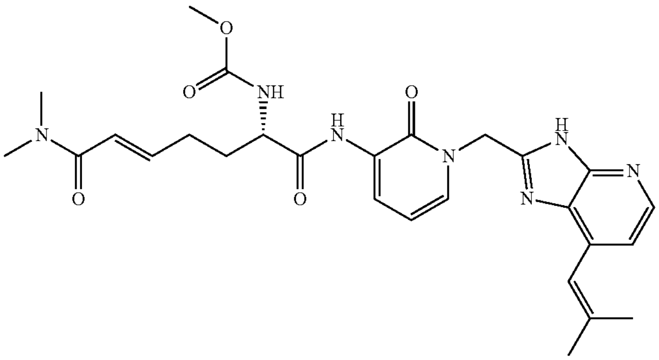 [SMILES: COC(=O)N[C@@H](CC/C=C/C(=O)N(C)C)C(=O)Nc1cccn(Cc2nc3c(C=C(C)C)ccnc3[nH]2)c1=O] | LCMS m/z 536.3 (M + 1)$^+$ |
| 426 | 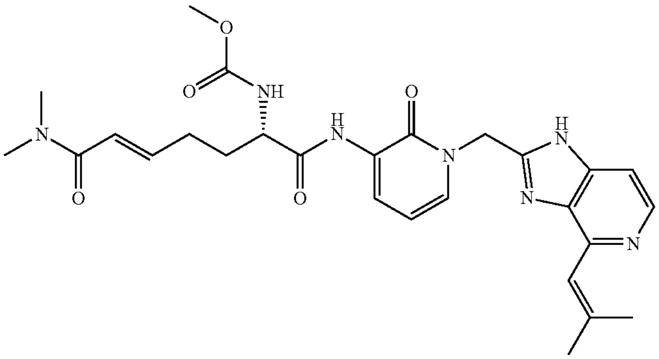 [SMILES: COC(=O)N[C@@H](CC/C=C/C(=O)N(C)C)C(=O)Nc1cccn(Cc2nc3c(C=C(C)C)nccc3[nH]2)c1=O] | LCMS m/z 536.3 (M + 1)$^+$ |

-continued
| Compound | Structure | LCMS Data |
|---|---|---|
| 427 | 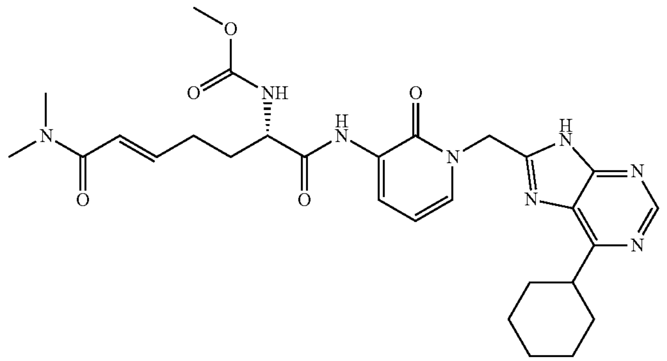 [SMILES: COC(=O)N[C@@H](CC/C=C/C(=O)N(C)C)C(=O)Nc1cccn(Cc2nc3c(C4CCCCC4)ncnc3[nH]2)c1=O] | LCMS m/z 565.3 $(M + 1)^+$ |
| 428 | 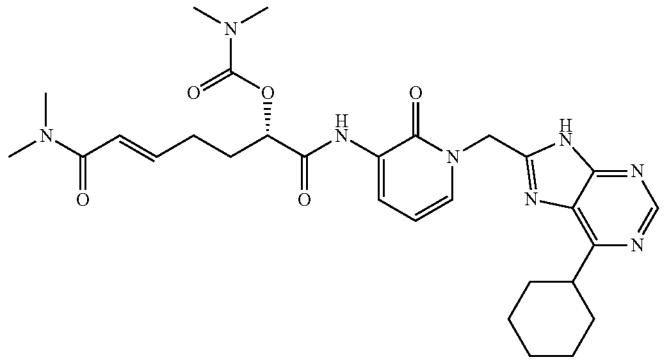 [SMILES: CN(C)C(=O)/C=C/CC[C@H](OC(=O)N(C)C)C(=O)Nc1cccn(Cc2nc3c(C4CCCCC4)ncnc3[nH]2)c1=O] | LCMS m/z 579.3 $(M + 1)^+$ |
| 441 | 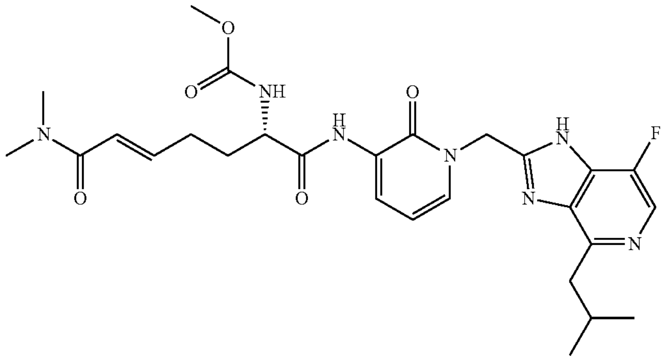 [SMILES: COC(=O)N[C@@H](CC/C=C/C(=O)N(C)C)C(=O)Nc1cccn(Cc2nc3c(CC(C)C)ncc(F)c3[nH]2)c1=O] | LCMS m/z 556.3 $(M + 1)^+$ |
| 448 | 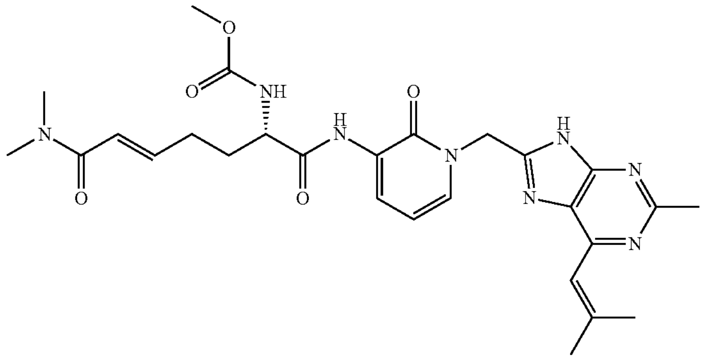 | LCMS m/z 551.2 $(M + 1)^+$ |

-continued
| Compound | Structure | LCMS Data |
| --- | --- | --- |
| 450 | 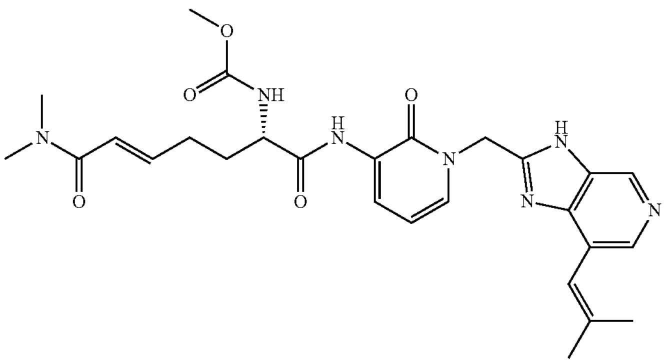 [SMILES: COC(=O)N[C@@H](CC/C=C/C(=O)N(C)C)C(=O)Nc1cccn(Cc2nc3c(C=C(C)C)cncc3[nH]2)c1=O] | LCMS m/z 536.3 (M + 1)+ |
| 451 | 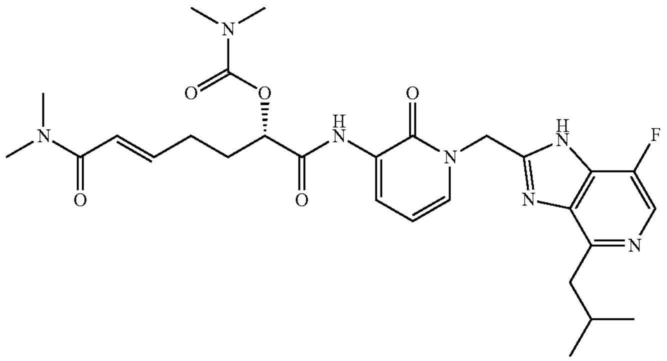 [SMILES: CC(C)Cc1ncc(F)c2[nH]c(Cn3cccc(NC(=O)[C@H](CC/C=C/C(=O)N(C)C)OC(=O)N(C)C)c3=O)nc12] | LCMS m/z 570.3 (M + 1)+ |
| 455 | 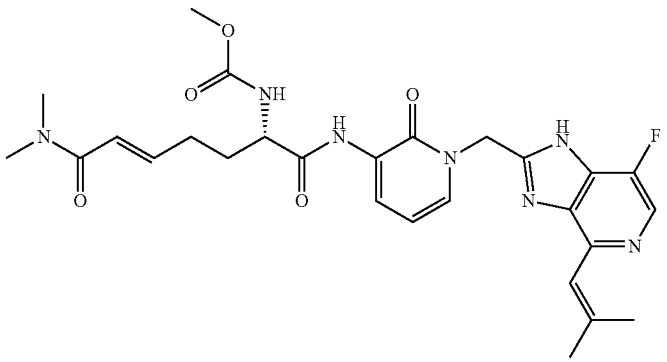 [SMILES: COC(=O)N[C@@H](CC/C=C/C(=O)N(C)C)C(=O)Nc1cccn(Cc2nc3c(C=C(C)C)ncc(F)c3[nH]2)c1=O] | LCMS m/z 554.2 (M + 1)+ |
| 457 | 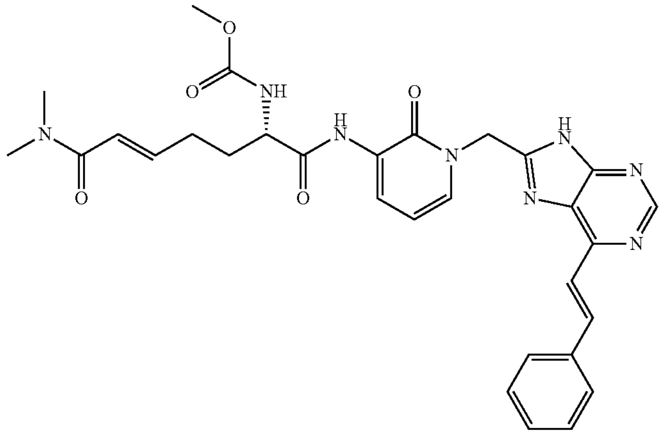 [SMILES: COC(=O)N[C@@H](CC/C=C/C(=O)N(C)C)C(=O)Nc1cccn(Cc2nc3c(/C=C/c4ccccc4)ncnc3[nH]2)c1=O] | LCMS m/z 585.2 (M + 1)+ |

-continued
| Compound | Structure | LCMS Data |
| --- | --- | --- |
| 460 | 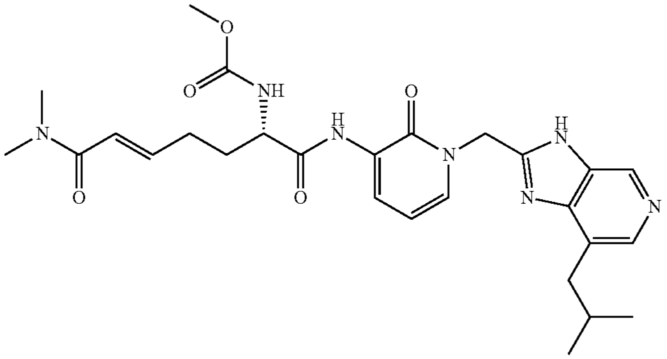 [SMILES: COC(=O)N[C@@H](CC/C=C/C(=O)N(C)C)C(=O)Nc1cccn(Cc2nc3c(CC(C)C)cncc3[nH]2)c1=O] | LCMS m/z 536.3 (M + 1)+ |
| 463 | 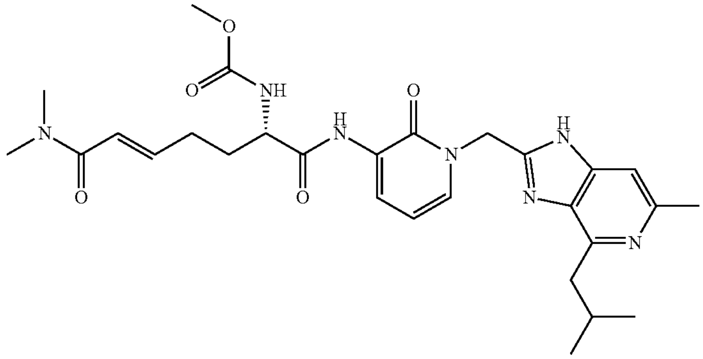 | LCMS m/z 552.3 (M + 1)+ |
| 464 | 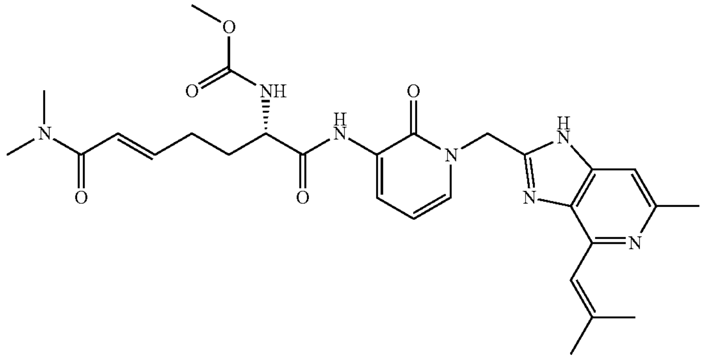 | LCMS m/z 550.2 (M + 1)+ |
| 479 | 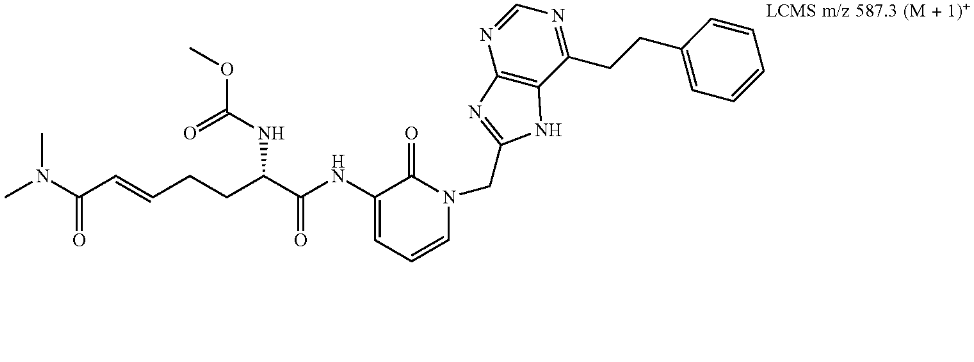 | LCMS m/z 587.3 (M + 1)+ |

-continued
| Compound | Structure | LCMS Data |
|---|---|---|
| 480 | 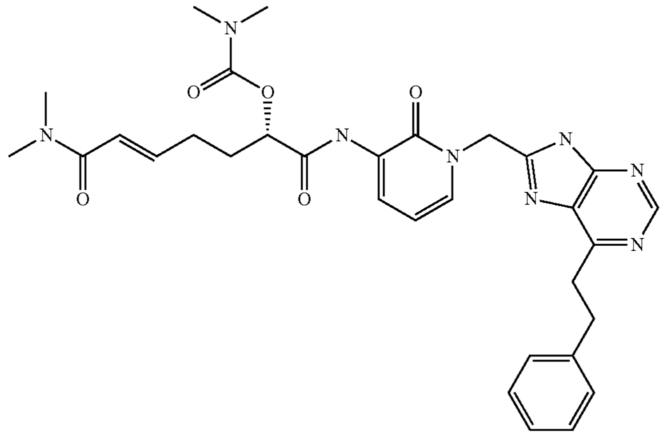 [SMILES: CN(C)C(=O)/C=C/CC[C@H](OC(=O)N(C)C)C(=O)Nc1cccn(Cc2nc3c(CCc4ccccc4)ncnc3[nH]2)c1=O] | LCMS m/z 601.3 (M + 1)$^+$ |
| 487 | 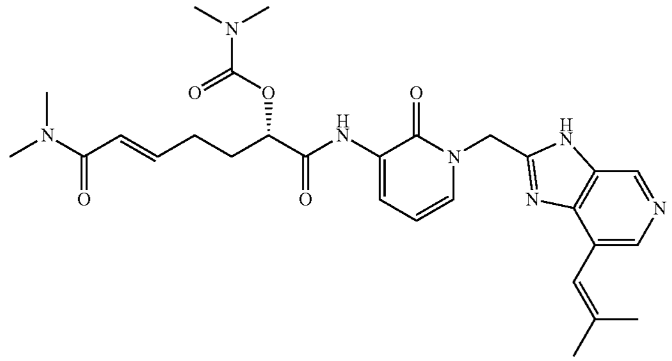 [SMILES: CC(C)=Cc1cncc2[nH]c(Cn3cccc(NC(=O)[C@H](CC/C=C/C(=O)N(C)C)OC(=O)N(C)C)c3=O)nc12] | LCMS m/z 550.3 (M + 1)$^+$ |
| 489 | 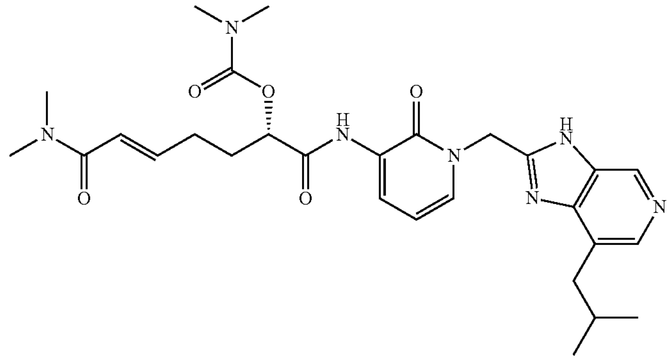 [SMILES: CC(C)Cc1cncc2[nH]c(Cn3cccc(NC(=O)[C@H](CC/C=C/C(=O)N(C)C)OC(=O)N(C)C)c3=O)nc12] | LCMS m/z 552.3 (M + 1)$^+$ |
| 444 | 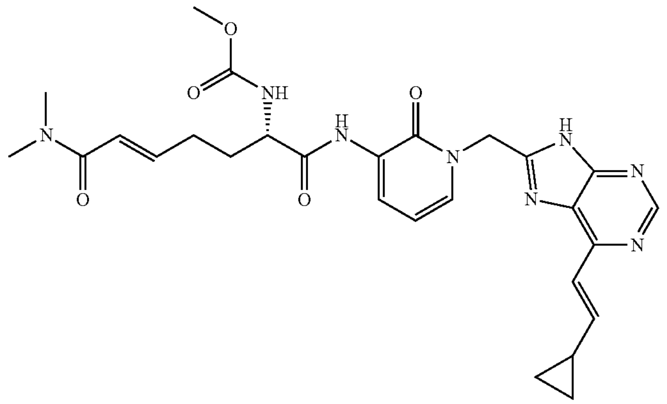 [SMILES: COC(=O)N[C@@H](CC/C=C/C(=O)N(C)C)C(=O)Nc1cccn(Cc2nc3c(/C=C/C4CC4)ncnc3[nH]2)c1=O] | LCMS m/z 549.3 (M + 1)$^+$ |

The Synthesis of Intermediate I-79

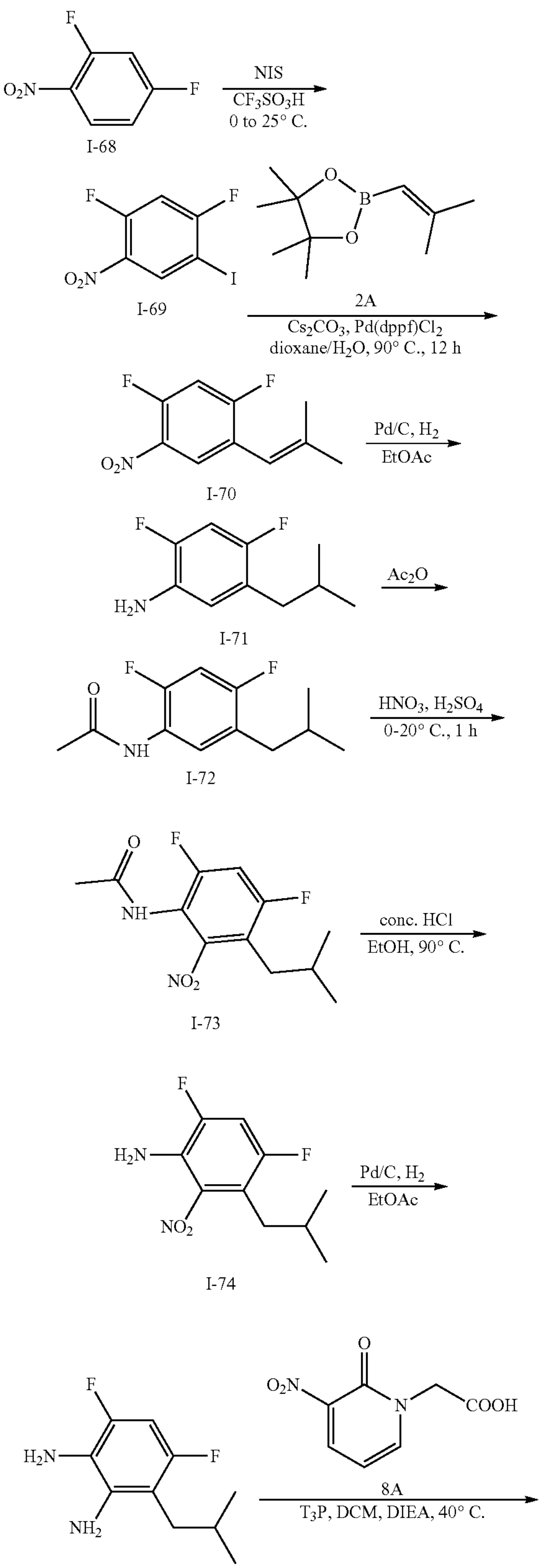

I-68

I-69

I-70

I-71

I-72

I-73

I-74

I-75

-continued

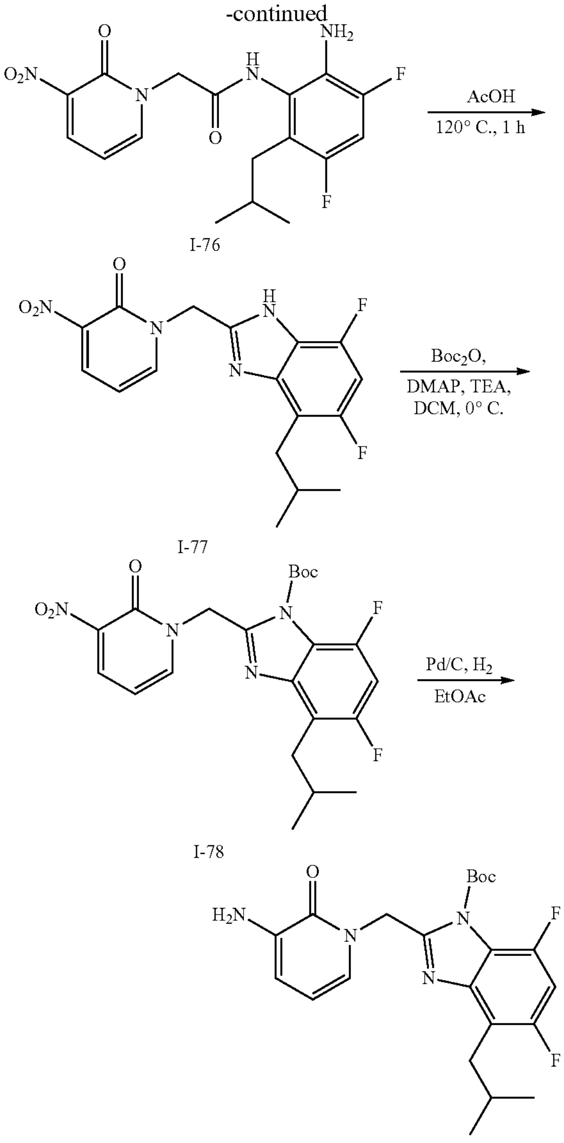

I-76

I-77

I-78

I-79

NIS (56.89 g, 252.86 mmol) was added in small portions to a well-stirred solution of 2,4-difluoro-1-nitro-benzene (35.6 g, 223.77 mmol, 24.55 mL) in $CF_3SO_3H$ (177.99 g, 1.19 mol, 104.70 mL) at 0° C., then the reaction mixture was warmed to 25° C. and stirred for 12 hours. The mixture was quenched with ice-cold water (400 mL) and extracted with EtOAc (100 mL×3). The combined organic layers were washed with sat. $Na_2SO_3$ aq. (200 mL×2) and brine (100 mL), then dried over $Na_2SO_4$, filtered and concentrated under reduced pressure to give an oil. The residue was purified by column chromatography to give 1,5-difluoro-2-iodo-4-nitro-benzene (I-69) (70 g) as a yellow oil.

A mixture of 1,5-difluoro-2-iodo-4-nitro-benzene (8 g, 28.07 mmol), 4,4,5,5-tetramethyl-2-(2-methylprop-1-enyl)-1,3,2-dioxaborolane (5.62 g, 30.88 mmol), $Pd(dppf)Cl_2$ (2.05 g, 2.81 mmol), $Cs_2CO_3$ (18.29 g, 56.14 mmol) in dioxane (100 mL) and $H_2O$ (10 mL) was degassed and purged with $N_2$ for 3 times, and then the mixture was stirred at 90° C. for 12 hours under $N_2$ atmosphere. The reaction mixture was filtered and the filtrate was concentrated to give the residue. The residue was purified by column chromatography to give 1,5-difluoro-2-(2-methylprop-1-enyl)-4-nitro-benzene (I-70) (3.3 g, 55% yield) as a yellow oil.

A mixture of 1,5-difluoro-2-(2-methylprop-1-enyl)-4-nitro-benzene (3.3 g, 15.48 mmol), Pd/C (0.5 g, 10% purity) in EtOAc (100 mL) was degassed and purged with $H_2$ for 3 times, and then the mixture was stirred at 40° C. for 12 hours under $H_2$ atmosphere (15 psi). The reaction mixture was filtered and the filtrate was concentrated under reduced pressure to give 2,4-difluoro-5-isobutyl-aniline (I-71) (2.7 g) as a yellow oil. LCMS m/z 186.1 $(M+1)^+$.

A mixture of 2,4-difluoro-5-isobutyl-aniline (2.7 g, 14.58 mmol) in $Ac_2O$ (30 mL) was stirred at 20° C. for 0.5 hr. The reaction mixture was poured into ice water 40 mL to quenched $Ac_2O$, then some solid separate out, the mixture was filtered and the filter cake was concentrated under reduced pressure to give N-(2,4-difluoro-5-isobutyl-phenyl)acetamide (I-72) (2.4 g, 72% yield) as a white solid. LCMS m/z 228.2 $(M+1)^+$.

A mixture of N-(2,4-difluoro-5-isobutyl-phenyl)acetamide (1.2 g, 5.28 mmol) in $H_2SO_4$ (12 mL) was added a mixture of $HNO_3$ (998.18 mg, 15.84 mmol, 712.99 Ul) in $H_2SO_4$ (1 mL) dropwise at 0° C., and then the mixture was stirred at 20° C. for 1 hr. The reaction mixture was poured into ice water 50 mL and then extracted with EtOAc 40 mL (20 mL×2). The combined organic phase was washed with brine 30 mL, dried over anhydrous $Na_2SO_4$, filtered and the filtrate was concentrated under reduced pressure to give N-(4,6-difluoro-3-isobutyl-2-nitro-phenyl)acetamide (I-73) (3 g) as an orange oil.

A mixture of N-(4,6-difluoro-3-isobutyl-2-nitro-phenyl)acetamide (3 g, 11.02 mmol) in HCl (20 mL, 12M) and EtOH (10 mL) was stirred at 90° C. for 12 hours. The reaction mixture was poured into ice water 50 mL and then extracted with EtOAc (20 mL×2). The combined organic layers were washed with sat. $NaHCO_3$ (30 mL×2), dried over $Na_2SO_4$, filtered and the filtrate was concentrated to give the residue. The residue was purified by column chromatography) to give 4,6-difluoro-3-isobutyl-2-nitro-aniline (I-74) (0.83 g, 33% yield) as an orange oil. LCMS m/z 231.2 $(M+1)^+$ A mixture of 4,6-difluoro-3-isobutyl-2-nitro-aniline (1.36 g, 5.91 mmol), Pd/C (0.5 g) in EtOAc (30 mL) was degassed and purged with $H_2$ for 3 times, and then the mixture was stirred at 30° C. for 5 hours under $H_2$ atmosphere (15 psi). The reaction mixture was filtered and the filtrate was concentrated under reduced pressure to give 4,6-difluoro-3-isobutyl-benzene-1,2-diamine (I-75) (1.2 g) as a brown oil.

A mixture of 4,6-difluoro-3-isobutyl-benzene-1,2-diamine (1.2 g, 5.99 mmol), 2-(3-nitro-2-oxo-1-pyridyl)acetic acid (1.19 g, 5.99 mmol), DIEA (1.55 g, 11.99 mmol, 2.09 mL), $T_3P$ (5.72 g, 8.99 mmol, 5.35 mL) in DCM (15 mL) was stirred at 40° C. for 12 hours. The reaction mixture was diluted with sat. $NH_4Cl$ (40 mL) and extracted with DCM (30 mL×2). The combined organic layers were concentrated under reduced pressure to give N-(2-amino-3,5-difluoro-6-isobutyl-phenyl)-2-(3-nitro-2-oxo-1-pyridyl)acetamide (I-76) (2.8 g) as a brown solid.

A mixture of N-(2-amino-3,5-difluoro-6-isobutyl-phenyl)-2-(3-nitro-2-oxo-1-pyridyl)acetamide (2.8 g, 7.36 mmol) in AcOH (30 mL) was stirred at 120° C. for 1 hr. The reaction mixture was concentrated under reduced pressure to give the residue and the residue was diluted with sat. $NaHCO_3$ (50 mL) and then extracted with EtOAc (20 mL×10). The combined organic layers were concentrated under reduced pressure to give the residue. The residue was diluted with the mixture of EtOAc (4 mL) and PE (40 mL) and stirred at 20° C. for 15 mins. The mixture was filtered to give 1-[(5,7-difluoro-4-isobutyl-1H-benzimidazol-2-yl)methyl]-3-nitro-pyridin-2-one (I-77) (1.8 g) as a brown solid.

A mixture of 1-[(5,7-difluoro-4-isobutyl-1H-benzimidazol-2-yl)methyl]-3-nitro-pyridin-2-one (1.75 g, 4.83 mmol), $Boc_2O$ (1.37 g, 6.28 mmol, 1.44 mL) in DCM (20 mL) was added DMAP (59.01 mg, 482.98 umol) and TEA (733.10 mg, 7.24 mmol, 1.01 mL) at 0° C. and then the mixture was stirred at 0° C. for 1 hr. The reaction mixture was quenched by addition sat. $NH_4Cl$ solution (40 mL) at 0° C., then extracted with DCM (20 mL×10). The combined organic layers were concentrated under reduced pressure to give a residue. The residue was purified by column chromatography to give tert-butyl5,7-difluoro-4-isobutyl-2-[(3-nitro-2-oxo-1-pyridyl)methyl]benzimidazole-1-carboxylate (I-78) (0.88 g, 39% yield) as a brown solid.

A mixture of tert-butyl 5,7-difluoro-4-isobutyl-2-[(3-nitro-2-oxo-1-pyridyl)methyl]benzimidazole-1-carboxylate (0.15 g, 324.36 umol), Pd/C (0.2 g) in EtOAc (25 mL) was degassed and purged with $H_2$ for 3 times, and then the mixture was stirred at 20° C. for 0.5 hr under $H_2$ atmosphere (15 psi). The reaction mixture was filtered and the filtrate was concentrated under reduced pressure to give tert-butyl 2-[(3-amino-2-oxo-1-pyridyl)methyl]-5,7-difluoro-4-isobutyl-benzimidazole-1-carboxylate (I-79) (0.15 g) as a brown oil. LCMS m/z 433.2 $(M+1)^+$.

Example 3

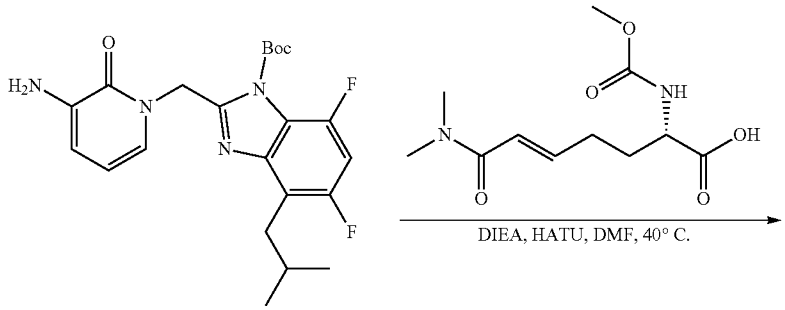

I-79

-continued

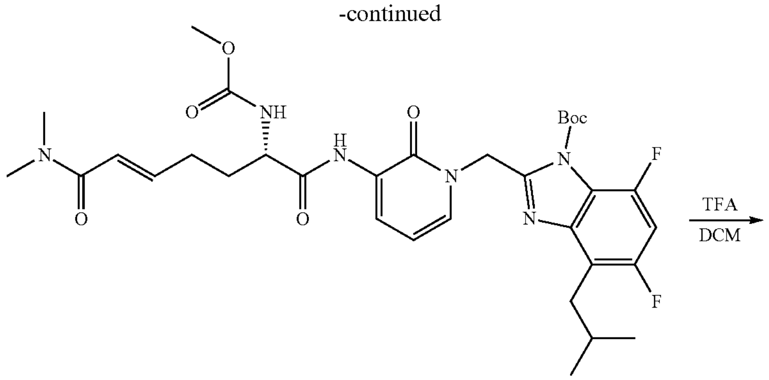

29

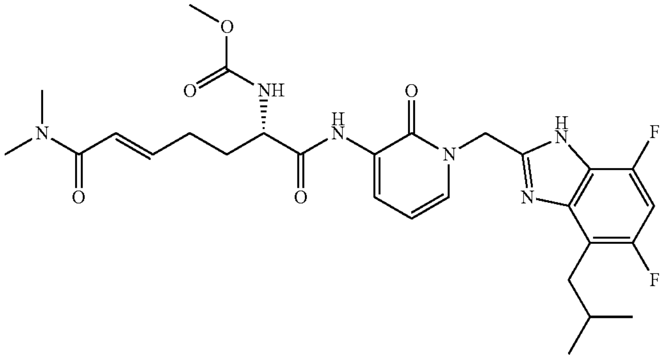

30

A mixture of (E,2S)-7-(dimethylamino)-2-(methoxycarbonylamino)-7-oxo-hept-5-enoic acid (125.41 mg, 485.59 umol), tert-butyl 2-[(3-amino-2-oxo-1-pyridyl)methyl]-5,7-difluoro-4-isobutyl-benzimidazole-1-carboxylate (0.14 g, 323.73 umol), DIEA (83.68 mg, 647.45 umol) in DMF (2 mL) was added HATU (184.64 mg, 485.59 umol) at 40° C., and then the mixture was stirred at 40° C. for 12 hours. The reaction mixture was poured into water (20 mL) and extracted with EtOAc (8 mL×3). The combined organic layers were washed with brine (20 mL) and concentrated under reduced pressure to give a residue. The residue was purified by prep-TLC to give tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-isobutyl-benzimidazole-1-carboxylate (Compound 29) 0.1 g, 45% yield) as a brown gum. LCMS m/z 673.3 $(M+1)^+$. $^1H$ NMR (400 MHz, DMSO-$d_6$) δ 9.28 (s, 1H) 8.34 (dd, J=7.40, 1.65 Hz, 1H) 7.79 (br d, J=7.70 Hz, 1H) 7.56 (dd, J=6.85, 1.71 Hz, 1H) 7.29 (t, J=11.13 Hz, 1H) 6.60-6.73 (m, 1H) 6.37-6.48 (m, 2H) 5.65 (s, 2H) 4.17-4.28 (m, 1H) 3.59 (s, 3H) 3.05 (s, 3H) 2.90 (s, 3H) 2.63 (br d, J=6.85 Hz, 2H) 2.22-2.35 (m, 2H) 1.83-1.98 (m, 2H) 1.66-1.81 (m, 10H) 0.77 (d, J=6.60 Hz, 6H).

A mixture of tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-isobutyl-benzimidazole-1-carboxylate (Compound 29) (0.1 g, 144.19 umol) in TFA (0.5 mL) and DCM (2 mL) was stirred at 20° C. for 1 hr. The reaction mixture was poured into sat. $NaHCO_3$ aq. 10 mL, then extracted with DCM (8 mL×2), the combined organic layers were washed with brine 10 mL, then dried over anhydrous $Na_2SO_4$, filtered and concentrated under reduced pressure to give methyl N-[(E,1S)-1-[[1-[(5,7-difluoro-4-isobutyl-1H-benzimidazol-2-yl)methyl]-2-oxo-3-pyridyl]carbamoyl]-6-(dimethylamino)-6-oxo-hex-4-enyl]carbamate (Compound 30) (77.9 mg, 92% yield) as a brown solid. LCMS m/z 573.3 $(M+1)^+$. $^1H$ NMR (400 MHz, DMSO-$d_6$) δ 13.00 (br s, 1H) 9.26 (s, 1H) 8.21-8.31 (m, 1H) 7.72 (br d, J=7.34 Hz, 1H) 7.51-7.62 (m, 1H) 6.95 (t, J=10.76 Hz, 1H) 6.55-6.65 (m, 1H) 6.32-6.42 (m, 2H) 5.40 (s, 2H) 4.11-4.23 (m, 1H) 3.54 (s, 3H) 2.98 (s, 3H) 2.83 (s, 3H) 2.69 (br d, J=7.34 Hz, 2H) 2.17-2.30 (m, 2H) 1.82-1.98 (m, 2H) 1.64-1.78 (m, 1H) 0.82-0.92 (m, 6H).

The Synthesis of Intermediates I-86 and I-87

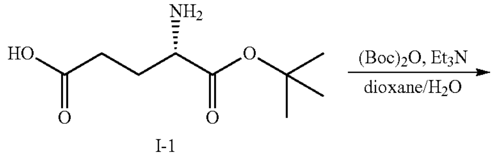

I-1

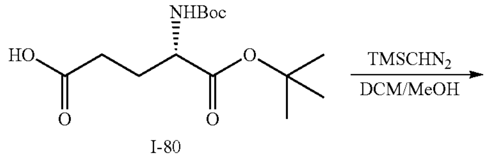

I-80

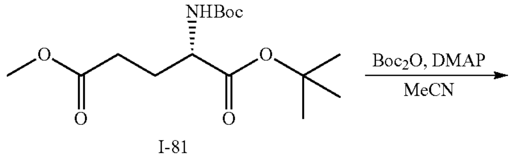

I-81

-continued

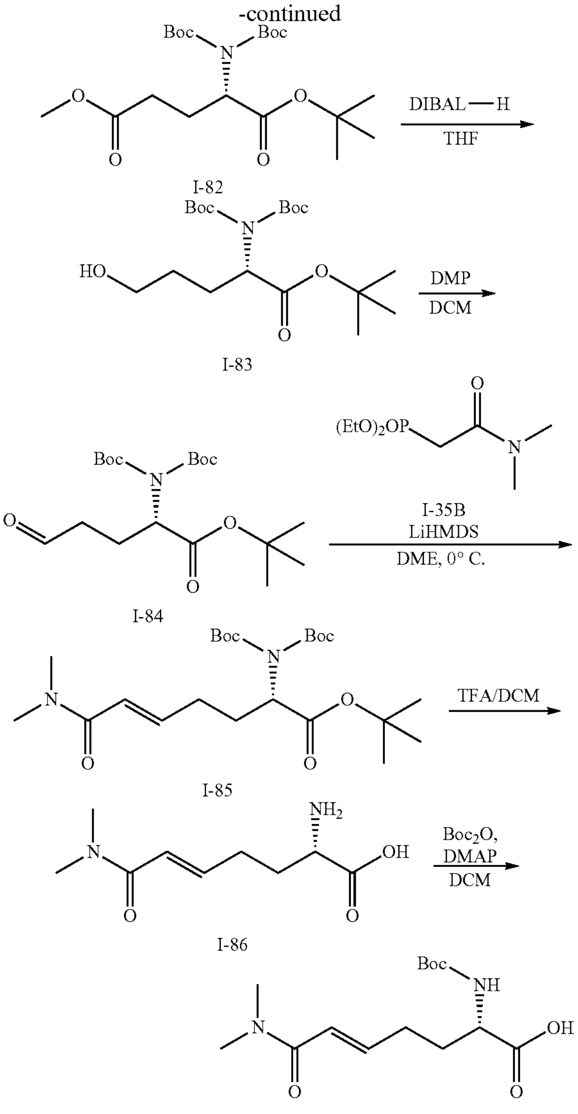

I-82

I-83

I-84

I-85

I-86

I-87

To a mixture of (4S)-4-amino-5-tert-butoxy-5-oxo-pentanoic acid (50 g, 246 mmol) in dioxane (150 mL) and $H_2O$ (150 mL) were added $Et_3N$ (49.7 g, 492 mmol) and $Boc_2O$ (59.1 g, 270 mmol). The mixture was stirred at 25° C. for 16 h. The mixture was diluted with NaOH solution (2 M, 800 mL) and EtOAc (200 mL). The resulting solution was extracted with NaOH solution (2 M, 200 mL). HCl (aq., 6M) was added to the resulting aqueous layer above to adjust Ph-5. The resultant solution was extracted with EtOAc (500 mL×2). The combined organic layers were washed with brine (300 mL), dried over anhydrous $Na_2SO_4$ and concentrated in vacuum to afford (S)-5-(tert-butoxy)-4-((tert-butoxycarbonyl)amino)-5-oxopentanoic acid (I-80) (55 g, 73% yield) as an orange oil. $^1$H NMR (400 MHz, $CDCl_3$) δ 5.16 (d, J=7.3 Hz, 1H), 4.29-4.15 (m, J=5.0 Hz, 1H), 2.53-2.33 (m, 2H), 2.21-2.11 (m, 1H), 1.99-1.84 (m, 1H), 1.50-1.39 (m, 18H).

To a solution of (S)-5-(tert-butoxy)-4-((tert-butoxycarbonyl)amino)-5-oxopentanoic acid (27.5 g, 90.6 mmol) in DCM (200 mL) and MeOH (200 mL) was added $TMSCHN_2$ (2 M, 90.6 mL) under ice-bath until no gas released and the solution turned yellow. The mixture was stirred at 25° C. for 30 min. The reaction mixture was concentrated in vacuum to afford (S)-1-tert-butyl 5-methyl 2-((tert-butoxycarbonyl)amino)pentanedioate (I-81) (46 g, 80% yield, 2 batches) as a yellow oil.

To a mixture of (S)-1-tert-butyl 5-methyl 2-((tert-butoxycarbonyl)amino) pentanedioate (28 g, 88.2 mmol) and DMAP (5.39 g, 44.1 mmol) in MeCN (400 mL) was added $Boc_2O$ (20 g, 88.1 mmol) at 25° C. To the reaction mixture was added $Boc_2O$ (40 g, 176 mmol) at 80° C. The mixture was stirred at 80° C. for 1.5 h until the color turned black. The resulting solution was concentrated in vacuum to give a residue. The residue was purified by column chromatography to afford (S)-1-tert-butyl 5-methyl 2-(bis(tert-butoxycarbonyl)amino)pentanedioate (I-82) (53 g, 72% yield) as a yellow oil. $^1$H NMR (400 MHz, $CDCl_3$) δ 4.81-4.72 (m, 1H), 3.65 (s, 3H), 2.43-2.34 (m, 3H), 2.19-2.10 (m, 1H), 1.49 (s, 18H), 1.43 (s, 9H).

To a solution of (S)-1-tert-butyl 5-methyl 2-(bis(tert-butoxycarbonyl)amino) pentanedioate (26.5 g, 63.4 mmol) in dry THF (300 mL) in a stand-up flask was added DIBAL-H (95.2 mL, 1M) at −65° C. The mixture was stirred at −65° C. for 30 min. The reaction mixture was quenched with saturated $NH_4Cl$ solution (100 mL) at 0° C., diluted with potassium sodium tartrate solution (100 mL), and stirred for 1 h. The mixture was extracted with EtOAc (200 mL×3). The combined organic layers were washed with brine (200 mL), dried over anhydrous $Na_2SO_4$, filtered and concentrated in vacuum to give a residue. The residue was purified by column chromatography to afford (S)-tert-butyl 2-(bis(tert-butoxycarbonyl)amino)-5-oxopentanoate (I-84) (7.5 g, 15% yield) as a yellow oil and (S)-tert-butyl 2-(bis (tert-butoxycarbonyl) amino)-5-hydroxypentanoate (I-83) (33 g, 66% yield) as a yellow oil. $^1$H NMR (400 MHz, $CDCl_3$) δ 4.70 (dd, J=5.4, 9.2 Hz, 1H), 3.62 (br. S., 2H), 2.20-2.06 (m, 1H), 1.93-1.80 (m, 2H), 1.63-1.54 (m, 2H), 1.47 (s, 18H), 1.41 (s, 9H).

To a solution of (S)-tert-butyl 2-(bis(tert-butoxycarbonyl) amino)-5-hydroxypentanoate (I-83) (18.7 g, 48.1 mmol) in DCM (200 mL) was added Dess-Martin reagent (26.4 g, 62.4 mmol) under ice-bath. The mixture was stirred at 25° C. for 30 min. The reaction mixture was concentrated in vacuum to give a residue. The residue was purified by column chromatography to afford (S)-tert-butyl 2-(bis(tert-butoxycarbonyl)amino)-5-oxopentanoate (I-84) (13.5 g, 72% yield) as a yellow oil. $^1$H NMR (400 MHz, $CDCl_3$) δ 9.75 (s, 1H), 4.72 (dd, J=5.1, 9.4 Hz, 1H), 2.64-2.36 (m, 3H), 2.19-2.07 (m, 1H), 1.49 (s, 18H), 1.44 (s, 9H).

To a solution of 2-diethoxyphosphoryl-N,N-dimethyl-acetamide (633 mg, 2.84 mmol) in DME (10 mL) was added LiHMDS (1 M, 2.84 mL) at 0° C. The mixture was stirred at ° C. for 0.5 h. Then tert-butyl (2S)-2-[bis(tert-butoxycarbonyl)amino]-5-oxo-pentanoate (1 g, 2.58 mmol) in DME (5 mL) was added, the mixture was stirred at 0° C. for 1 h. The mixture was added $H_2O$ (50 mL), and extracted with EtOAc (30 mL×3). The combined organic layers were washed with brine (30 mL×3), dried over anhydrous $Na_2SO_4$, filtered and concentrated under reduced pressure to give a residue. The residue was purified by column chromatography to give (E,2S)-2-[bis(tert-butoxycarbonyl)amino]-7-(dimethylamino)-7-oxo-hept-5-enoate (I-85) (1.1 g) as a yellow oil. $^1$H NMR (400 MHz, $CDCl_3$) δ 6.93-6.78 (m, 1H), 6.27 (d, J=15.2 Hz, 1H), 4.80-4.64 (m, 1H), 3.09-2.94 (m, 6H), 2.30-2.16 (m, 3H), 2.03-1.95 (m, 1H), 1.49 (s, 18H), 1.43 (s, 9H).

To a solution of tert-butyl (E,2S)-2-[bis(tert-butoxycarbonyl)amino]-7-(dimethylamino)-7-oxo-hept-5-enoate (1.1 g, 2.41 mmol) in DCM (2.5 mL) was added TFA (5.39 g, 47.28 mmol, 3.50 mL) at 0° C. The mixture was stirred at 25° C. for 4 h. The reaction was concentrated in vacuum to give (S,E)-2-amino-7-(dimethylamino)-7-oxohept-5-enoic acid (I-86) (482 mg) as a yellow oil.

Step 8: Synthesis of (S,E)-2-((tert-butoxycarbonyl) amino)-7-(dimethylamino)-7-oxohept-5-enoic acid (I-87)

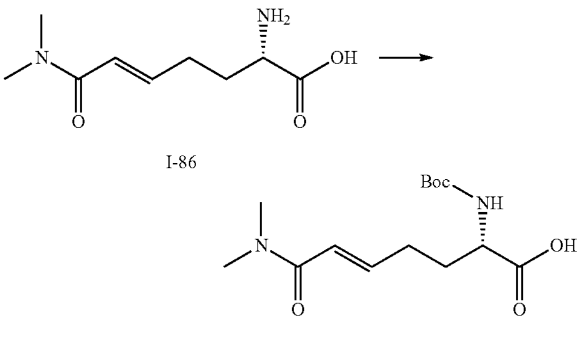

I-86

I-87

To a solution of (S,E)-2-amino-7-(dimethylamino)-7-oxo-hept-5-enoic acid (920 mg, 4.59 mmol) in DCM (10 mL) were added $(Boc)_2O$ (2 g, 9.18 mmol) and DIPEA (2.97 g, 23 mmol) at 0° C. The mixture was stirred at 25° C. for 16 h. The mixture was diluted with saturated $NaHCO_3$ (60 mL), washed with DCM (30 mL). The aqueous phase was adjusted to Ph-2 with HCl (1M) and extracted with DCM (30 mL×3). The organic layers were dried over anhydrous $Na_2SO_4$ and concentrated in vacuum to give (S,E)-2-((tert-butoxycarbonyl)amino)-7-(dimethylamino)-7-oxohept-5-enoic acid (I-87) (1.5 g) as a yellow oil. $^1H$ NMR (400 MHz, $CDCl_3$) δ 6.85-6.71 (m, 1H), 6.27 (d, J=15.2 Hz, 1H), 5.22 (d, J=7.6 Hz, 1H), 4.40-4.21 (m, 1H), 3.09-2.99 (m, 6H), 2.37-2.17 (m, 2H), 2.06-1.91 (m, 1H), 1.81-1.67 (m, 1H), 1.43 (s, 9H).

The following intermediates were prepared according to the procedures described in I-87 using the appropriate intermediates.

| Compound | Structure | Characterization Data |
|---|---|---|
| I-88 | 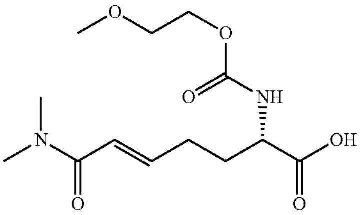 [SMILES: COCCOC(=O)N[C@@H](CC/C=C/C(=O)N(C)C)C(=O)O] | $^1H$ NMR (400 MHz, $CDCl_3$) δ 6.96-6.75 (m, 1H), 6.28 (d, J = 15.2 Hz, 1H), 5.28-5.27 (m, 1H), 5.01 (m, 1H), 3.97-3.47 (m, 3H), 3.46-3.35 (m, 3H), 3.21-3.17 (m, 1H), 3.12-2.96 (m, 9H), 2.46-2.30 (m, 2H), 2.17-1.99 (m, 2H) |
| I-89 | 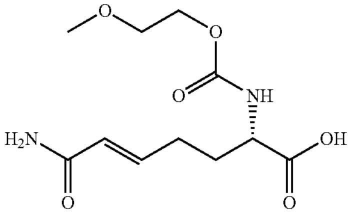 [SMILES: COCCOC(=O)N[C@@H](CC/C=C/C(N)=O)C(=O)O] | LCMS m/z 275.3 $(M + 1)^+$ |
| I-527 | 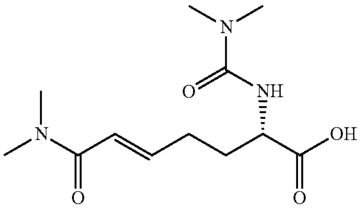 [SMILES: CN(C)C(=O)/C=C/CC[C@H](NC(=O)N(C)C)C(=O)O] | LCMS m/z 272.2 $(M + 1)^+$ |
| I-528 | 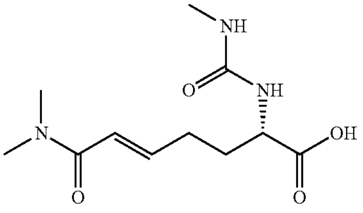 [SMILES: CNC(=O)N[C@@H](CC/C=C/C(=O)N(C)C)C(=O)O] | LCMS m/z 258.2 $(M + 1)^+$ |

-continued
| Compound | Structure | Characterization Data |
| --- | --- | --- |
| I-530 | 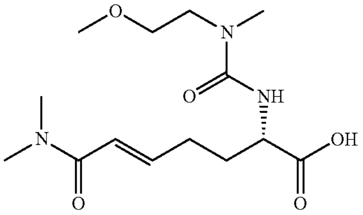 [SMILES: COCCN(C)C(=O)N[C@@H](CC/C=C/C(=O)N(C)C)C(=O)O] | $^1$H NMR (400 MHz, $CDCl_3$) δ 6.74-6.88 (m, 1 H) 6.29 (d, J = 15.16 Hz, 1 H) 5.90-6.13 (m, 1 H) 4.36 (q, J = 6.32 Hz, 1 H) 3.08 (s, 3 H) 2.99-3.04 (m, 3 H) 2.96 (s, 3 H) 2.89 (s, 7 H) 2.25-2.42 (m, 2 H) 2.00-2.17 (m, 1 H) 1.77-1.91 (m, 1 H) |
Example 4
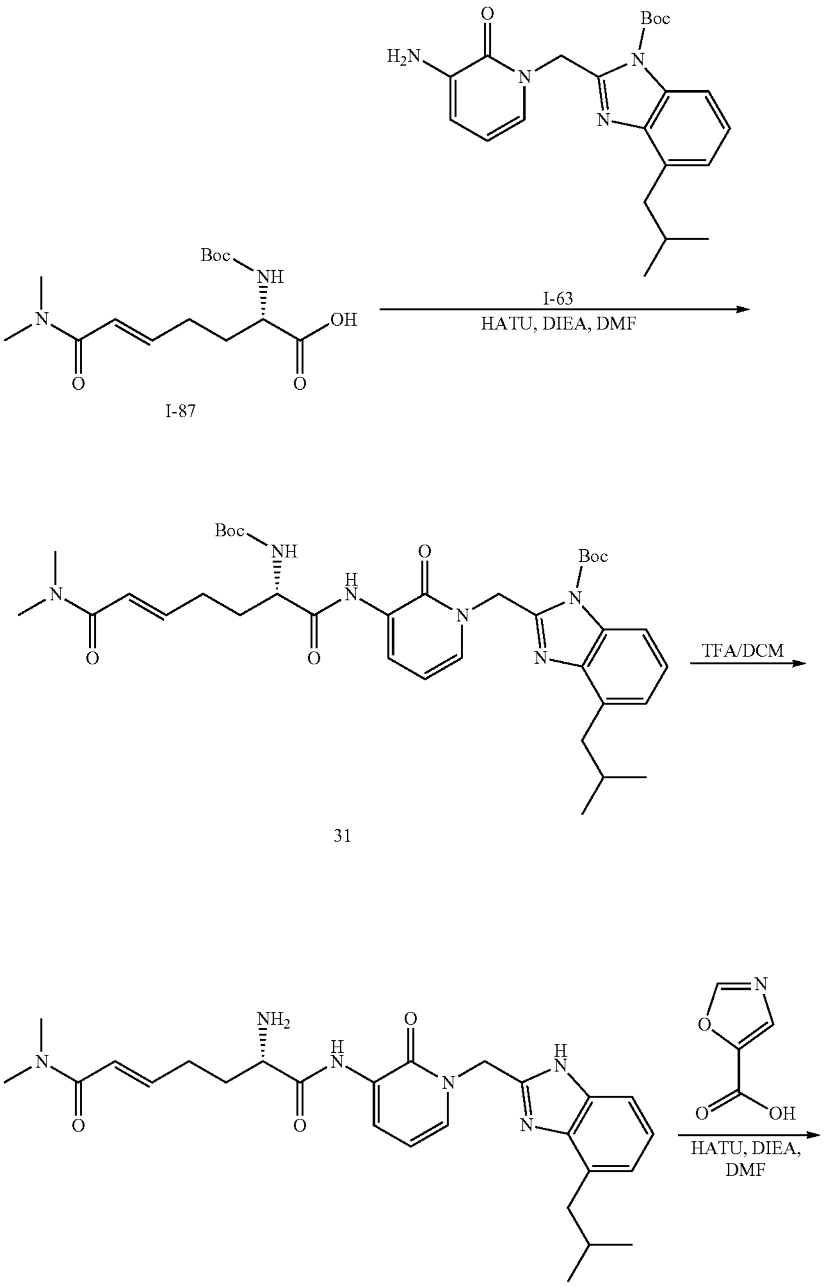
I-87
31
I-90

-continued

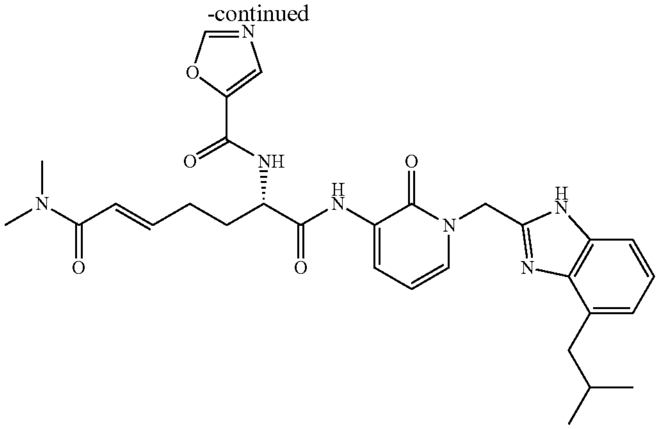

32

To a solution of (S,E)-2-((tert-butoxycarbonyl)amino)-7-(dimethylamino)-7-oxohept-5-enoic acid (485 mg, 1.61 mmol) and tert-butyl 2-((3-amino-2-oxopyridin-1(2H)-yl) methyl)-4-isobutyl-1H-benzo[d]imidazole-1-carboxylate (320 mg, 0.807 mmol) in DMF (3 mL) were added HATU (614 mg, 1.61 mmol) and DIPEA (313 mg, 2.42 mmol) at 0° C. The mixture was stirred at 25° C. for 2 h. The reaction mixture was diluted with $H_2O$ (50 mL) and extracted with EtOAc (30 mL×3). The combined organic layers were washed with brine (30 mL×3), dried over anhydrous $Na_2SO_4$, filtered and concentrated under reduced pressure to give a residue. The residue was purified by column chromatography and prep-HPLC to give (S,E)-tert-butyl 2-((3-(2-((tert-butoxycarbonyl)amino)-7-(dimethylamino)-7-oxohept-5-enamido)-2-oxopyridin-1(2H)-yl)methyl)-4-isobutyl-1H-benzo[d]imidazole-1-carboxylate (Compound 31) (475 mg, 83% yield) as a yellow oil. LCMS m/z 679.5 $(M+1)^+$.

To a solution of (S,E)-tert-butyl 2-((3-(2-((tert-butoxycarbonyl)amino)-7-(dimethylamino)-7-oxohept-5-enamido)-2-oxopyridin-1(2H)-yl)methyl)-4-isobutyl-1H-benzo[d]imidazole-1-carboxylate (1.7 g, 2.50 mmol) in DCM (6 mL) was added TFA (4.62 g, 40.5 mmol, 3.00 mL) at 0° C. The mixture was stirred at 25° C. for 2 h. The reaction mixture was concentrated in vacuum to give (S,E)-6-amino-N7-(1-((4-isobutyl-1H-benzo[d]imidazol-2-yl)methyl) 2-oxo-1,2-dihydropyridin-3-yl)-N1,N1-dimethylhept-2-enediamide (I-90) (1.48 g, crude, TFA) as a yellow oil. LCMS m/z 479.2 $(M+1)^+$.

To a solution of (S,E)-6-amino-N7-(1-((4-isobutyl-1H-benzo[d]imidazol-2-yl)methyl)-2-oxo-1,2-dihydropyridin-3-yl)-N1,N1-dimethylhept-2-enediamide (200 mg, 0.337 mmol, TFA) and oxazole-5-carboxylic acid (57.2 mg, 0.506 mmol) in DMF (2 mL) were added HATU (257 mg, 0.675 mmol) and DIPEA (131 mg, 1.01 mmol) at 0° C. The mixture was stirred at 25° C. for 16 h. The reaction mixture was purified by prep-HPLC to give (S,E)-N7-(1-((4-isobutyl-1H-benzo[d]imidazol-2-yl)methyl)-2-oxo-1,2-dihydropyridin-3-yl)-N1,N1-dimethyl-6-(oxazole-5-carboxamido)hept-2-enediamide (Compound 32) (78.5 mg, 39% yield) as a white solid. LCMS m/z 574.3 $(M+1)^+$. $^1H$ NMR (400 MHz, DMSO-$d_6$) δ 12.71 (s, 1H), 9.39 (s, 1H), 9.00 (d, J=7.6 Hz, 1H), 8.59 (s, 1H), 8.25 (dd, J=7.6, 2.0 Hz, 1H), 7.87 (s, 1H), 7.57 (dd, J=6.8, 1.6 Hz, 1H), 7.32 (d, J=7.6 Hz, 1H), 7.08 (t, J=7.6 Hz, 1H), 6.95 (d, J=7.2 Hz, 1H), 6.69-6.56 (m, 1H), 6.41-6.31 (m, 2H), 5.50-5.34 (m, 2H), 4.71-4.58 (m, 1H), 2.95 (s, 3H), 2.81 (s, 3H), 2.76-2.69 (m, 2H), 2.36-2.19 (m, 2H), 2.08-1.77 (m, 3H), 0.88 (d, J=6.4 Hz, 6H).

The following compounds were prepared according to the procedures described in Example 4 using the appropriate intermediates.

| Compound | Structure | LCMS Data |
|---|---|---|
| 33 | 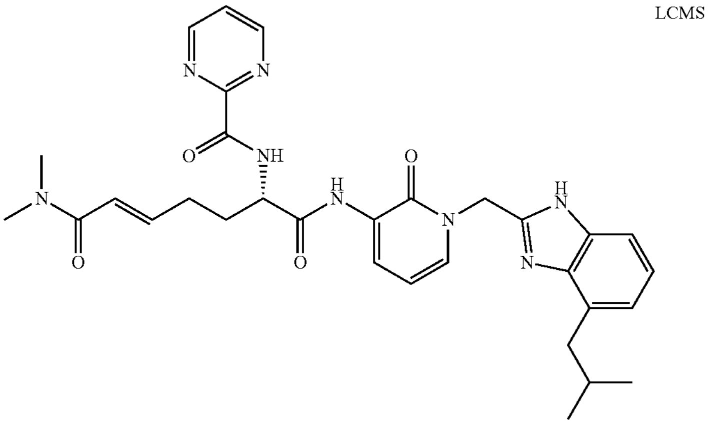 | LCMS m/z 585.4 $(M + 1)^+$ |

-continued
| Compound | Structure | LCMS Data |
| --- | --- | --- |
| 34 | 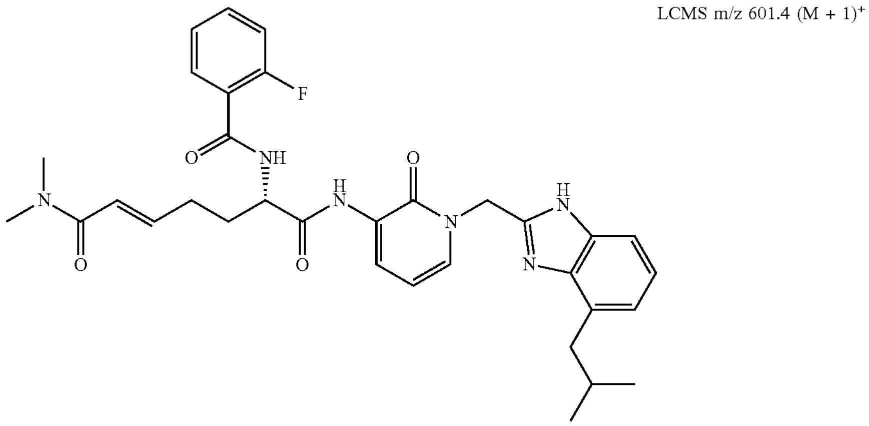 | LCMS m/z 601.4 $(M + 1)^+$ |
| 35 | 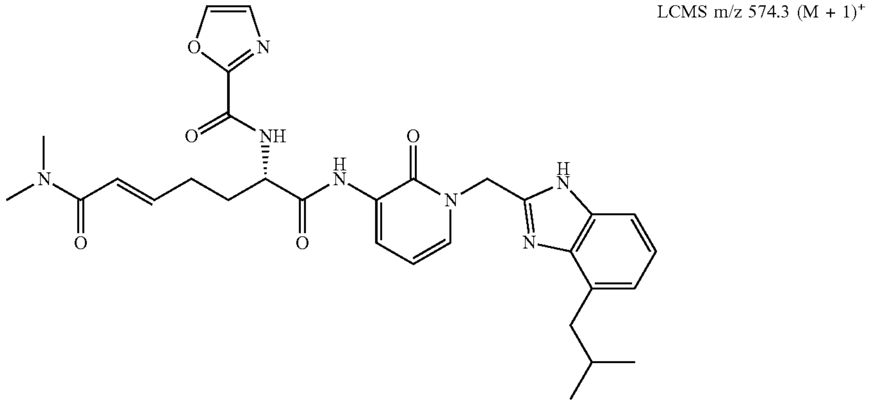 | LCMS m/z 574.3 $(M + 1)^+$ |
| 36 | 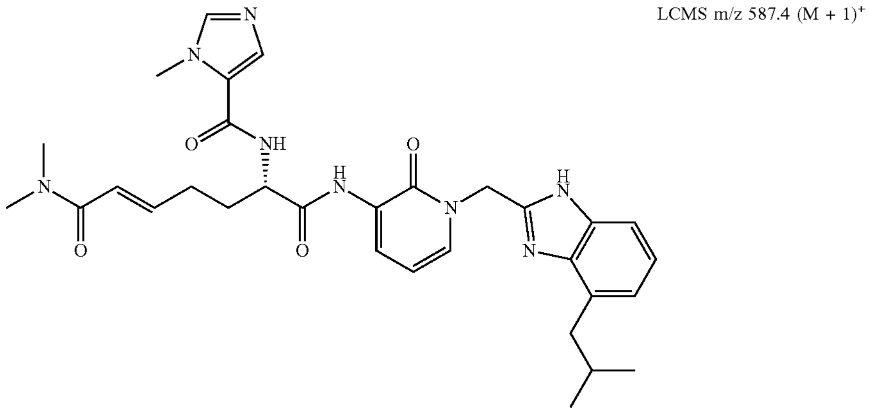 | LCMS m/z 587.4 $(M + 1)^+$ |

-continued
| Compound | Structure | LCMS Data |
|---|---|---|
| 37 | 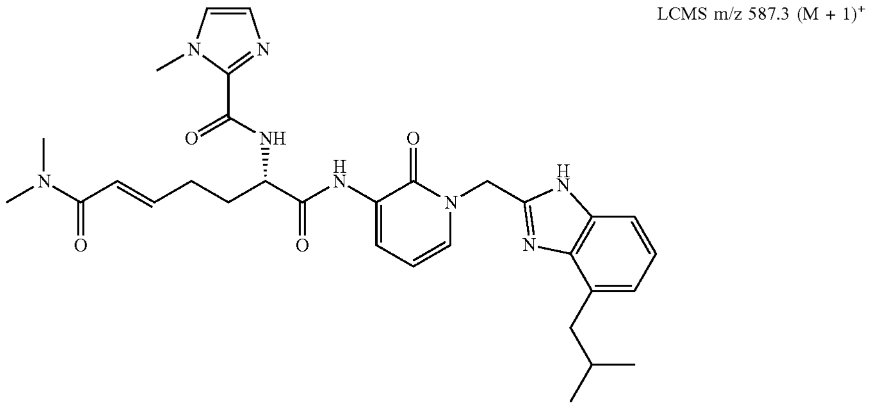 | LCMS m/z 587.3 $(M + 1)^+$ |
| 38 | 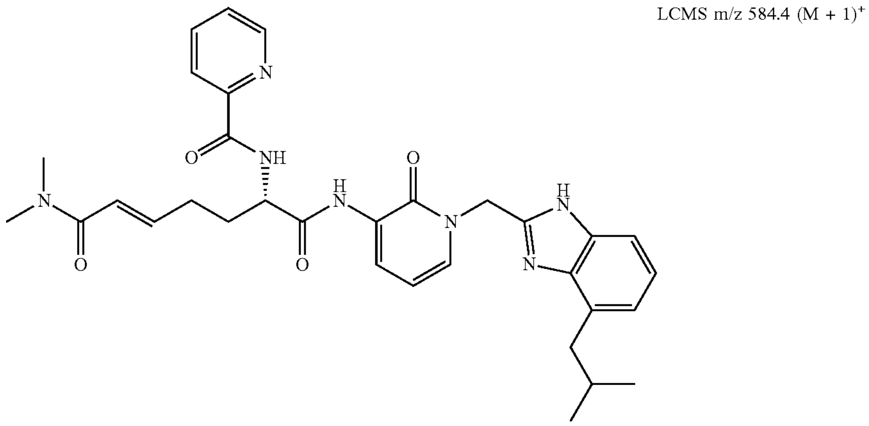 | LCMS m/z 584.4 $(M + 1)^+$ |
| 39 | 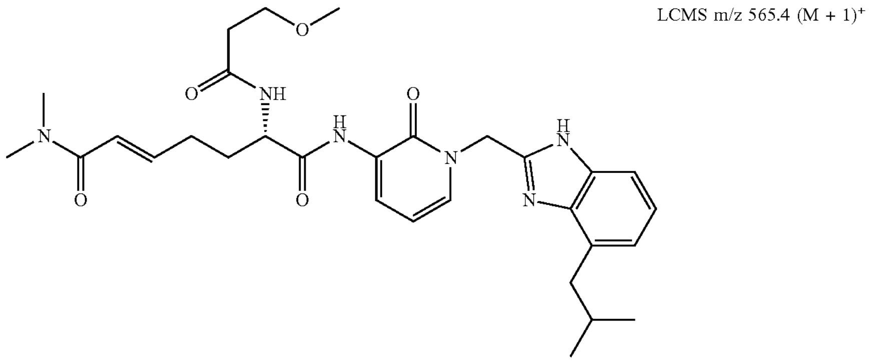 | LCMS m/z 565.4 $(M + 1)^+$ |
| 40 | 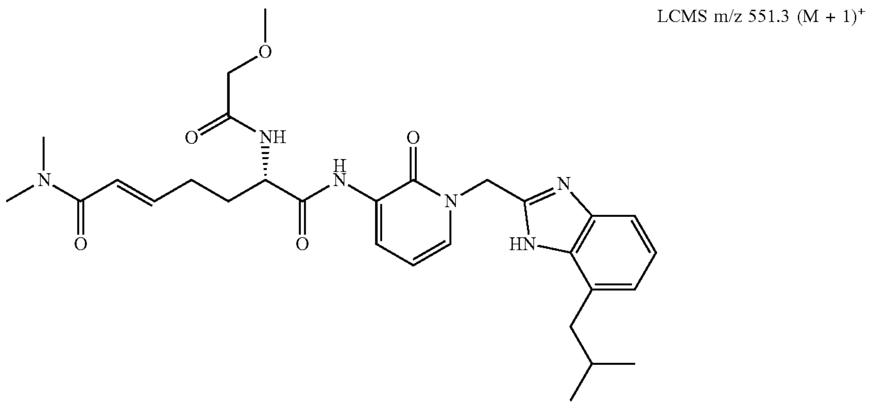 | LCMS m/z 551.3 $(M + 1)^+$ |

-continued

| Compound | Structure | LCMS Data |
| --- | --- | --- |
| 41 | 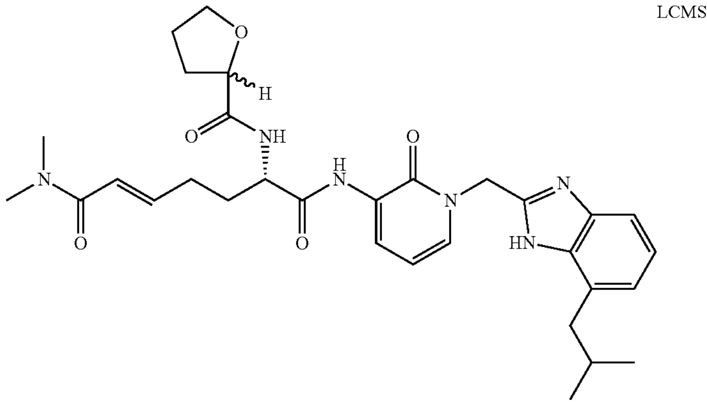 | LCMS m/z 577.3 $(M + 1)^+$ |

The Synthesis of Intermediate I-95

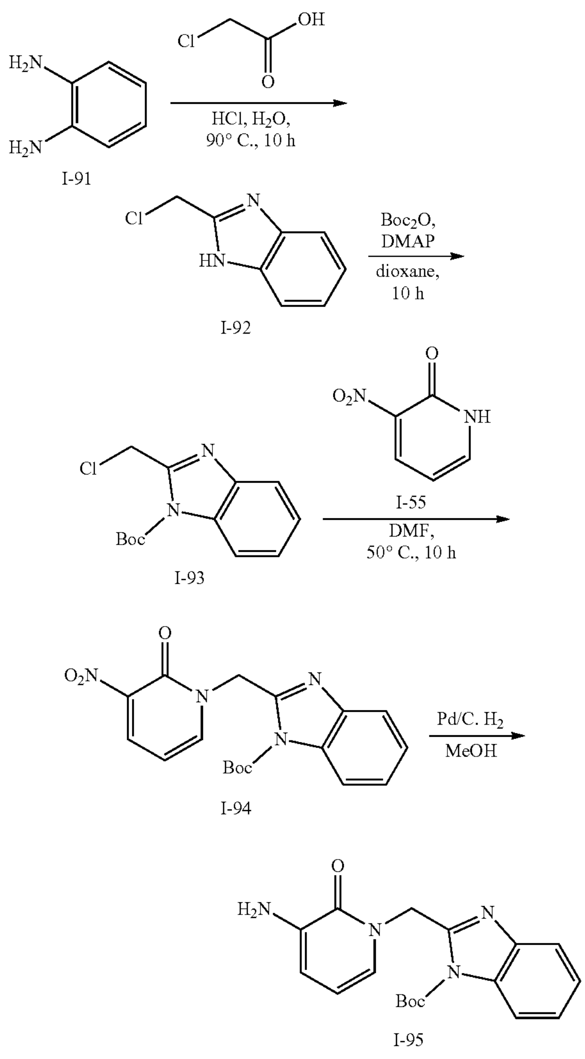

2-chloroacetic acid (1.3 g, 13.8 mmol) and benzene-1,2-diamine (1.0 g, 9.3 mmol) were dissolved in HCl (5 mL)/$H_2O$ (15 mL). The mixture was stirred at 100° C. for 10 h. Ammonium hydroxide (25%-28%) was added to adjust pH~8. The resulting suspension was filtered. The solid residue was washed with water (50 mL) and then it was dried under the reduced pressure to give 2-(chloromethyl)-1H-benzimidazole (I-92) (800 mg, 4.8 mmol) as a yellow solid. $^1$H NMR (400 MHz, DMSO-$d_6$) δ 7.58-7.51 (m, 2H), 7.25-7.19 (m, 2H), 4.92 (s, 2H).

2-(chloromethyl)-1H-benzimidazole (500 mg, 3.0 mmol) was dissolved in dioxane (10 mL). $Boc_2O$ (720 mg, 3.3 mmol) and DMAP (366 mg, 3.0 mmol) were added to the reaction mixture. The mixture was stirred at 20° C. for 10 h. The resulting solution was concentrated and purified by column chromatography to give tert-butyl 2-(chloromethyl) benzimidazole-1-carboxylate (I-93) (690 mg) as a light yellow oil.

3-nitro-1H-pyridin-2-one (341 mg, 2.4 mmol) and TEA (493 mg, 4.9 mmol) were added to a solution of tert-butyl 2-(chloromethyl)benzimidazole-1-carboxylate (650 mg, 2.4 mmol) in DMF (3 mL). The mixture was stirred at 50° C. for 10 h. The resulting solution was diluted with ethyl acetate (30 mL) and washed with water (50 mL) and brine (50 mL). The organic phase was dried over anhydrous $Na_2SO_4$, filtered and concentrated under reduced pressure to give tert-butyl 2-((3-nitro-2-oxopyridin-1(2H)-yl)methyl)-1H-benzo[d]imidazole-1-carboxylate (I-94) (850 mg) as a brown solid. LCMS m/z 271.0 $(M+1)^+$.

To a solution of tert-butyl 2-((3-nitro-2-oxopyridin-1(2H)-yl)methyl)-1H-benzo[d]imidazole-1-carboxylate (400 mg) in MeOH (30 mL) was added Pd/C (50 mg) (10% wet). The mixture was stirred at 20° C. under $H_2$ atmosphere (15 psi) for 1 hr. After filtration, the filtrate was concentrated to give tert-butyl 2-((3-amino-2-oxopyridin-1(2H)-yl)methyl)-1H-benzo[d]imidazole-1-carboxylate (I-95) (350 mg) as a yellow solid.

Example 5

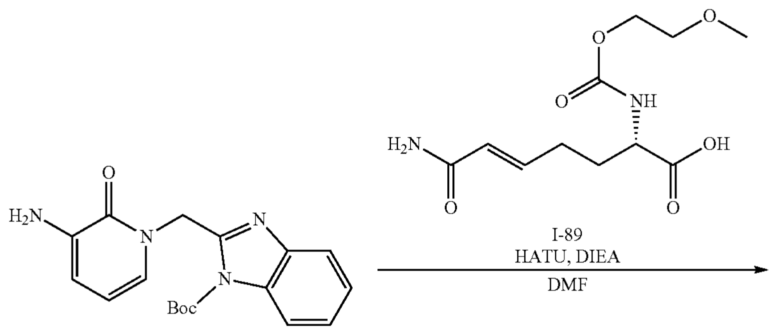

I-95

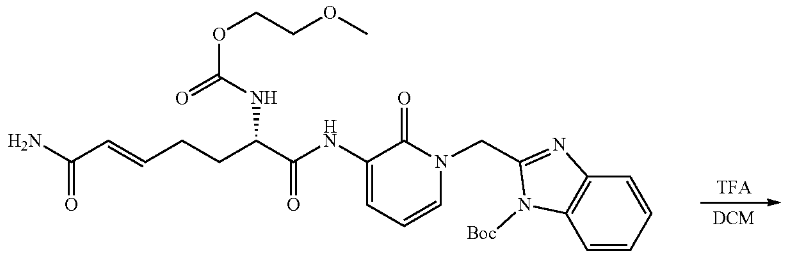

42

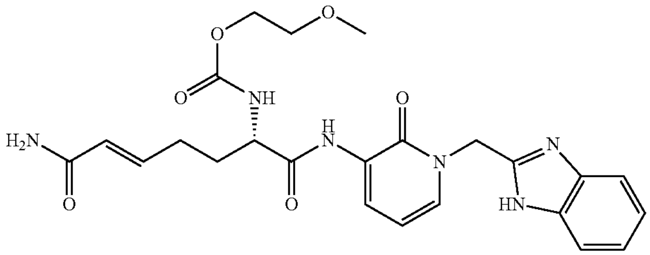

43

To a solution of (S,E)-7-amino-2-(((2-methoxyethoxy) carbonyl)amino)-7-oxohept-5-enoic acid (0.17 g, 620 μmol) and tert-butyl 2-((3-amino-2-oxopyridin-1(2H)-yl) methyl)-1H-benzo[d]imidazole-1-carboxylate (211 mg, 620 μmol) in DCM (2 mL) were added HATU (354 mg, 930 μmol) and DIPEA (240 mg, 1.86 mmol). The mixture was stirred at 30° C. for 12 hours. It was diluted with EtOAc (30 mL), washed with brine (30 mL×2). The organic phase was concentrated in vacuum. The residue was purified by prep-TLC and prep-SFC to give desired product (S,E)-tert-butyl 2-((3-(7-amino-2-(((2-methoxyethoxy)carbonyl)amino)-7-oxohept-5-enamido)-2-oxopyridin-1(2H)-yl)methyl)-1H-benzo[d] imidazole-1-carboxylate (Compound 42) (0.1 g, 26% yield) as a yellow solid. LCMS m/z 597.1 $(M+1)^+$.

To a solution of (S,E)-tert-butyl 2-((3-(7-amino-2-(((2-methoxyethoxy)carbonyl) amino)-7-oxohept-5-enamido)-2-oxopyridin-1(2H)-yl)methyl)-1H-benzo[d]imidazole-1-carboxylate (0.08 g, 134 μmol) in DCM (2 mL) was added TFA (924 mg, 8.10 mmol) at 0° C. The mixture was stirred at 10° C. for 3 hours and concentrated in vacuum. The residue was purified by prep-HPLC to give desired product (S,E)-2-methoxyethyl (1-((1-((1H-benzo[d]imidazol-2-yl)methyl)-2-oxo-1,2-dihydropyridin-3-yl)amino)-7-amino-1,7-dioxohept-5-en-2-yl)carbamate (Compound 43) (0.05 g, 67% yield) as a white solid. LCMS m/z 497.1 $(M+1)^+$. $^1H$ NMR (400 MHz, DMSO-$d_6$) δ13.10-11.80 (m, 1H), 9.28 (s, 1H), 8.28-8.23 (m, 1H), 7.84 (d, J=8.0 Hz, 1H), 7.57 (dd, J=7.2, 1.6 Hz, 1H), 7.55-7.45 (m, 2H), 7.34 (s, 1H), 7.18-7.11 (m, 2H), 6.90 (s, 1H), 6.62-6.50 (m, 1H), 6.36 (t, J=7.2 Hz, 1H), 5.83 (d, J=15.6 Hz, 1H), 5.40 (s, 2H), 4.21-4.14 (m, 1H), 4.11-4.01 (m, 2H), 3.54-3.44 (m, 2H), 3.21 (s, 3H), 2.26-2.09 (m, 2H), 1.89-1.78 (m, 1H), 1.74-1.62 (m, 1H).

The following compounds were prepared according to the procedures described in Example 6 using the appropriate intermediates.

| Compound | Structure | LCMS Data |
|---|---|---|
| 44 | 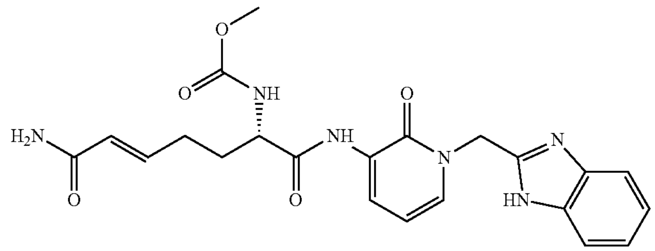 [SMILES: COC(=O)N[C@@H](CC/C=C/C(N)=O)C(=O)Nc1cccn(Cc2nc3ccccc3[nH]2)c1=O] | LCMS m/z 453.2 $(M + 1)^+$ |
| 45 | 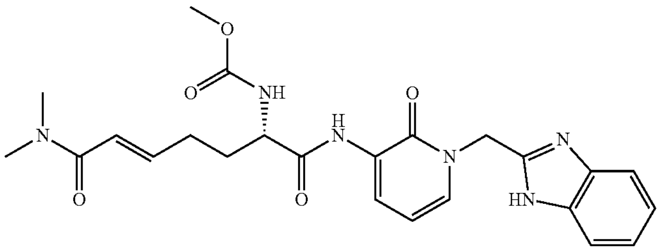 [SMILES: COC(=O)N[C@@H](CC/C=C/C(=O)N(C)C)C(=O)Nc1cccn(Cc2nc3ccccc3[nH]2)c1=O] | LCMS m/z 481.3 $(M + 1)^+$ |
| 46 | 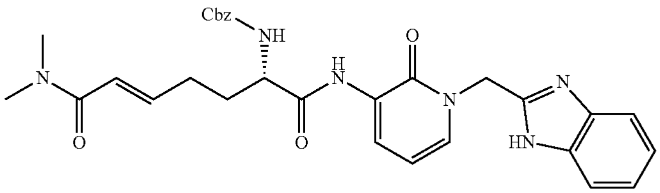 [SMILES: CN(C)C(=O)/C=C/CC[C@H](NC(=O)OCc1ccccc1)C(=O)Nc1cccn(Cc2nc3ccccc3[nH]2)c1=O] | LCMS m/z 557.4 $(M + 1)^+$ |
| 47 | 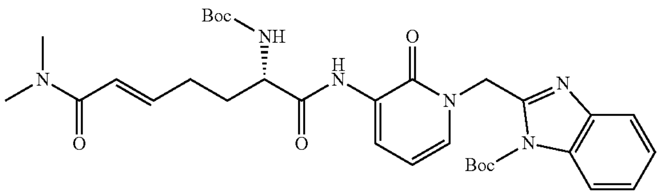 [SMILES: CN(C)C(=O)/C=C/CC[C@H](NC(=O)OC(C)(C)C)C(=O)Nc1cccn(Cc2nc3ccccc3n2C(=O)OC(C)(C)C)c1=O] | LCMS m/z 623.2 $(M + 1)^+$ |
| 48 | 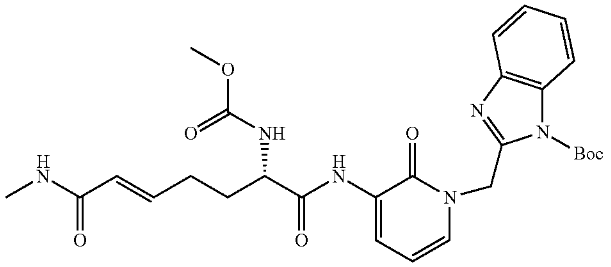 [SMILES: CNC(=O)/C=C/CC[C@H](NC(=O)OC)C(=O)Nc1cccn(Cc2nc3ccccc3n2C(=O)OC(C)(C)C)c1=O] | LCMS m/z 567.2 $(M + 1)^+$ |
| 49 | 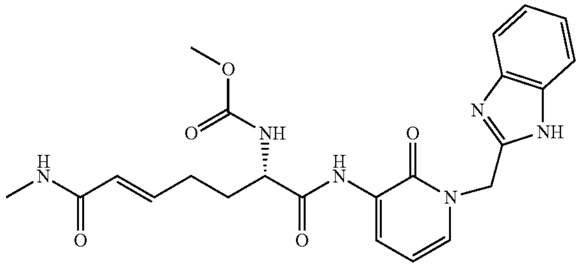 [SMILES: CNC(=O)/C=C/CC[C@H](NC(=O)OC)C(=O)Nc1cccn(Cc2nc3ccccc3[nH]2)c1=O] | LCMS m/z 467.1 $(M + 1)^+$ |

-continued
| Compound | Structure | LCMS Data |
| --- | --- | --- |
| 50 | 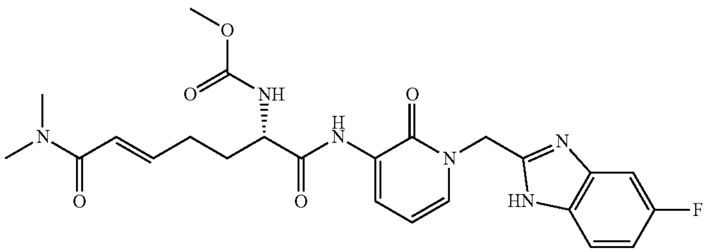 [SMILES: COC(=O)N[C@@H](CC/C=C/C(=O)N(C)C)C(=O)Nc1cccn(Cc2nc3cc(F)ccc3[nH]2)c1=O] | LCMS m/z 499.1 $(M + 1)^+$ |
| 51 | 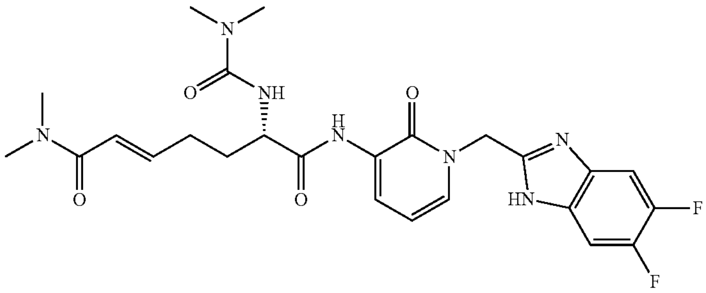 [SMILES: CN(C)C(=O)/C=C/CC[C@H](NC(=O)N(C)C)C(=O)Nc1cccn(Cc2nc3cc(F)c(F)cc3[nH]2)c1=O] | LCMS m/z 531.0 $(M + 1)^+$ |
| 52 | 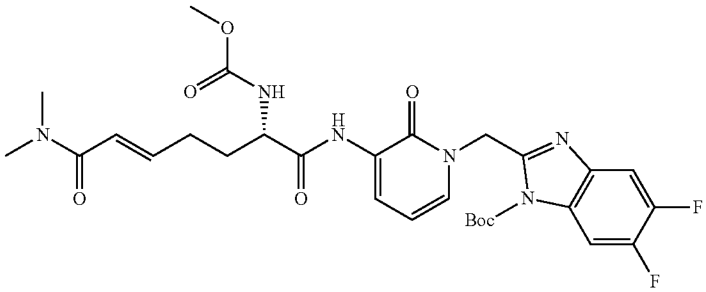 [SMILES: COC(=O)N[C@@H](CC/C=C/C(=O)N(C)C)C(=O)Nc1cccn(Cc2nc3cc(F)c(F)cc3n2C(=O)OC(C)(C)C)c1=O] | LCMS m/z 617.3 $(M + 1)^+$ |
| 53 | 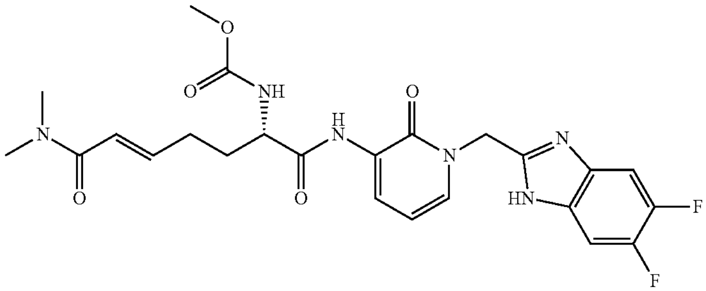 [SMILES: COC(=O)N[C@@H](CC/C=C/C(=O)N(C)C)C(=O)Nc1cccn(Cc2nc3cc(F)c(F)cc3[nH]2)c1=O] | LCMS m/z 517.0 $(M + 1)^+$ |
| 54 | 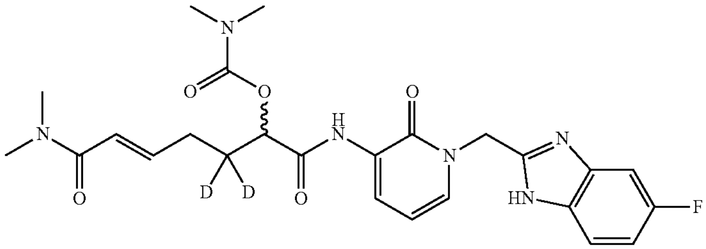 | LCMS m/z 515.2 $(M + 1)^+$ |

-continued
| Compound | Structure | LCMS Data |
|---|---|---|
| 55 | 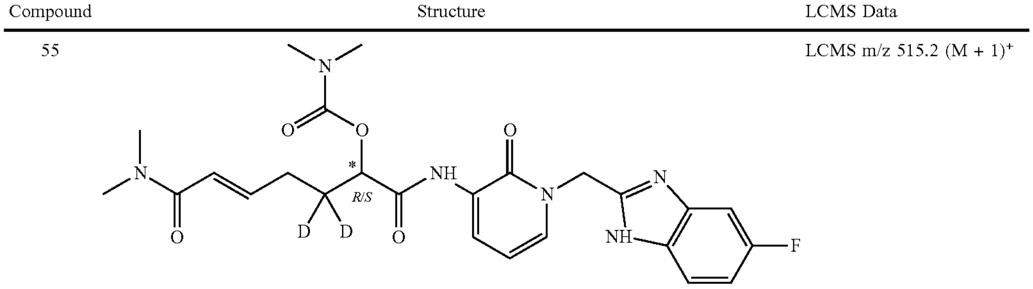 | LCMS m/z 515.2 $(M + 1)^+$ |
The Synthesis of Intermediates I-106 and I-111
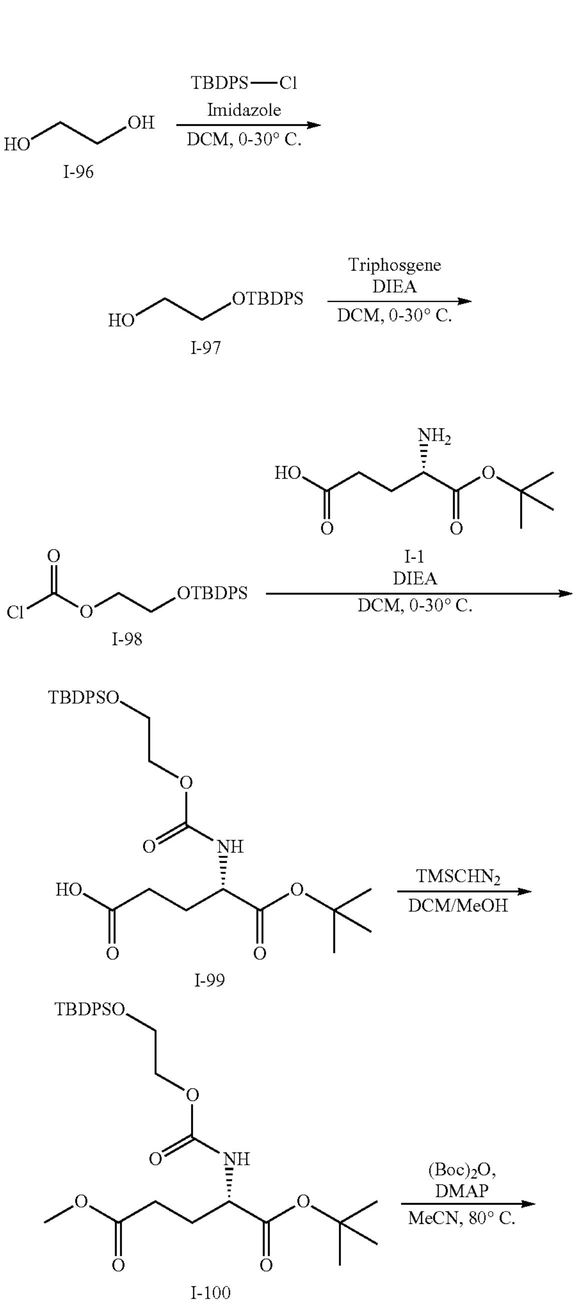
-continued
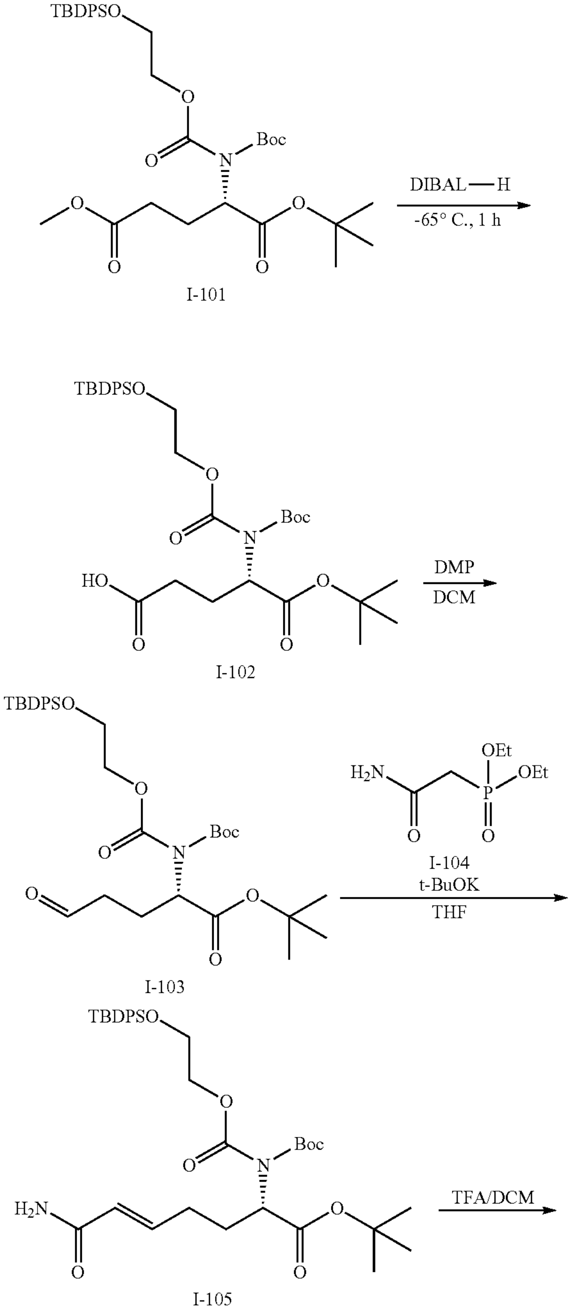

-continued

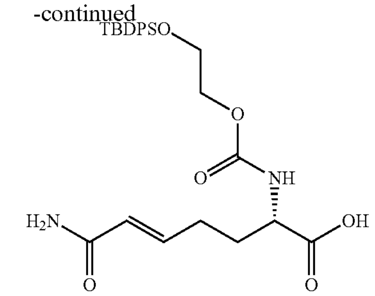

I-106

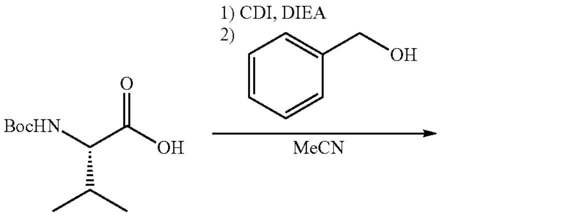

I-107

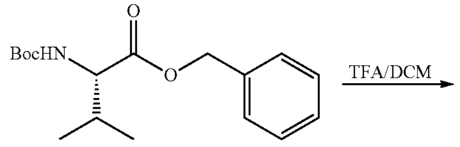

I-108

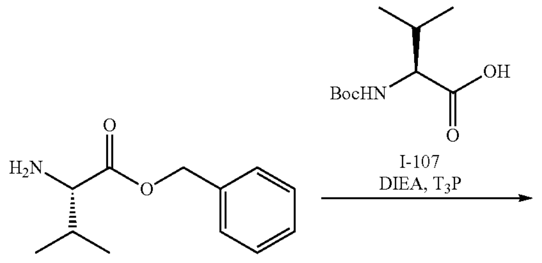

I-109

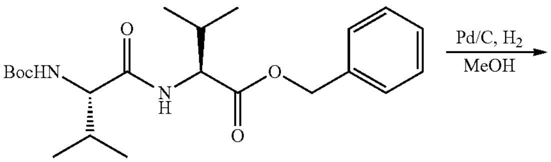

I-110

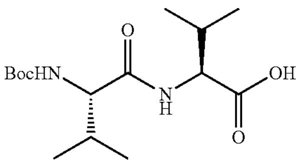

I-111

To a solution of ethylene glycol (100 g, 1.61 mol) and imidazole (219 g, 3.22 mol) in DCM (2 L) was added dropwise TBDPSCl (354 g, 1.29 mol) at 0° C. The mixture was stirred at 30° C. for 2 h under $N_2$ atmosphere. The mixture was poured into $H_2O$ (1 L) and extracted with DCM (1 L×2). The combined organic layers were dried over anhydrous $Na_2SO_4$, filtered and concentrated to give a residue. The residue was purified by column chromatography to give 2-((tert-butyldiphenylsilyl)oxy)ethanol (I-97) (117 g, 389 mmol) as a light yellow oil. $^1$H NMR (400 MHz, $CDCl_3$) δ 7.73-7.68 (m, 4H), 7.49-7.39 (m, 6H), 3.82-3.77 (m, 2H), 3.74-3.68 (m, 2H), 1.10 (s, 9H).

To a solution of 2-((tert-butyldiphenylsilyl)oxy)ethanol (117 g, 389 mmol) and DIEA (69.8 mL) in dry DCM (1000 mL) was added triphosgene (57.8 g, 195 mmol) in portions at 0° C. The mixture was stirred at 30° C. for 1 hr. 2-((tert-butyldiphenylsilyl)oxy)ethyl carbonochloridate (I-98) as a colorless solution in DCM (1000 mL) was used in the next step without further treatment.

To a mixture of (S)-4-amino-5-(tert-butoxy)-5-oxopentanoic acid (87.1 g, 428 mmol) and DIEA (23.3 mL) in dry DCM (500 mL) was added dropwise a solution of 2-((tert-butyldiphenylsilyl)oxy)ethyl carbonochloridate (~389 mmol) in DCM (1000 mL) at 0° C. over 1 hr. The reaction mixture was stirred at 30° C. for 2 h under $N_2$ atmosphere. The mixture was poured into ice water (1 L). The resultant was adjusted pH~3 by HCl (1M), and extracted with EtOAc (1 L×3). The combined organic layers were dried over anhydrous $Na_2SO_4$, filtered and concentrated to give a residue. The residue was purified by column chromatography to afford (S)-10-(tert-butoxycarbonyl)-2,2-dimethyl-8-oxo-3,3-diphenyl-4,7-dioxa-9-aza-3-silatridecan-13-oic acid (I-99) (110 g, 162 mmol) as a yellow oil. LCMS m/z 552.1 $(M+23)^+$.

To a solution of (S)-10-(tert-butoxycarbonyl)-2,2-dimethyl-8-oxo-3,3-diphenyl-4,7-dioxa-9-aza-3-silatridecan-13-oic acid (110 g, 162 mmol) in DCM (500 mL)/MeOH (500 mL) was added $TMSCHN_2$ (2 M, 243 mL) at 0° C. over 0.5 hr. The mixture was stirred at 30° C. for 1 hr. The reaction mixture was concentrated to give (S)-1-tert-butyl 5-methyl 2-(((2-((tert-butyldiphenylsilyl)oxy)ethoxy)carbonyl)amino) pentanedioate (I-100) (100 g) as alight yellow oil. LCMS m/z 566.4 $(M+23)^+$.

To a solution of (S)-1-tert-butyl 5-methyl 2-(((2-((tert-butyldiphenylsilyl)oxy)ethoxy) carbonyl)amino)pentanedioate (100 g, 184 mmol) and DMAP (112 g, 920 mmol) in MeCN (1 L) was added dropwise $(Boc)_2O$ (169 mL, 736 mmol) at 80° C. over 0.5 hr. The mixture was stirred at 80° C. for 16 h. The resulting solution was concentrated, diluted with EtOAc (1 L) and then poured into $H_2O$ (1 L). The resultant was extracted with EtOAc (1 L×2). The combined organic layers were dried over anhydrous $Na_2SO_4$, filtered and concentrated to give a residue. The residue was purified by column chromatography to afford (2S)—O1-tert-butyl-O5-methyl-2-[tert-butoxycarbonyl-[2-[tert-butyl(diphenyl)silyl]oxyethoxycarbonyl]amino]pentanedioate (I-101) (51 g, 53.9 mmol) as a light yellow oil. LCMS m/z 666.3 $(M+23)^+$.

To a solution of (2S)—O1-tert-butyl-O5-methyl-2-[tert-butoxycarbonyl-[2-[tert-butyl (diphenyl)silyl]oxyethoxycarbonyl]amino]pentanedioate (41 g, 63.7 mmol) in THF (500 mL) was added dropwise DIBAL-H (1 M, 382 mL) at −65° C. over 0.5 hr. The mixture was stirred at −65° C. for 1 hr under $N_2$ atmosphere. The reaction was quenched with EtOAc (500 mL) at −65° C. The mixture was poured into saturated potassium sodium tartrate (1 L) at 0° C. and stirred at the same temperature for 1 hr. The resulting solution was extracted with EtOAc (1 L×2). The combined organic layers were dried over anhydrous $Na_2SO_4$, filtered and concentrated to give a residue. The residue was purified by column chromatography to afford (2S)-tert-butyl-2-[tert-butoxy carbonyl-[2-[tert-butyl(diphenyl)silyl]oxyethoxycarbonyl] amino]-5-hydroxy-pentanoate (I-102) (15 g, 14.6 mmol) as a light yellow oil. LCMS m/z 638.1 $(M+23)^+$.

To a solution of (2S)-tert-butyl-2-[tert-butoxycarbonyl-[2-[tert-butyl(diphenyl)silyl]oxyethoxycarbonyl]amino]-5-hydroxy-pentanoate (15 g, 14.6 mmol) in dry DCM (200 mL) was added DMP (12.4 g, 29.2 mmol) at 0° C. The mixture was stirred at 30° C. for 2 h. The resulting suspension was filtered through a pad of celite. The filtrate was concentrated to give a residue. The residue was purified by column chromatography to afford (2S)-tert-butyl-2-[tert-butoxycarbonyl-[2-[tert-butyl(diphenyl)silyl] oxyethoxy-carbonyl]amino]-5-oxo-pentanoate (I-103) (9.7 g, 10.8 mmol) as a light yellow oil. LCMS m/z 636.3 $(M+23)^+$.

To a solution of diethyl (2-amino-2-oxoethyl)phosphonate (I-104) (4.77 g, 24.4 mmol) in THF (250 mL) was added t-BuOK (2.74 g, 24.4 mmol) at −10° C. The reaction mixture was stirred at −10° C. for 0.5 hr. Then a solution of (2S)-tert-butyl-2-[tert-butoxycarbonyl-[2-[tert-butyl(diphenyl)silyl]oxyethoxycarbonyl]amino]-5-oxo-pentanoate (I-103) (15 g, 12.2 mmol) in THF (50 mL) was added dropwise to the reaction mixture at −10° C. over 1 hr. The resultant was stirred at −10° C. for another 1 hr. The mixture was poured into $H_2O$ (500 mL) and extracted with EtOAc (500 mL×3). The combined organic layers were dried over anhydrous $Na_2SO_4$, filtered and concentrated to give a residue. The residue was purified by column chromatography to afford (E,2S)-tert-butyl-7-amino-2-[tert-butoxycarbonyl-[2-[tert-butyl(diphenyl)silyl] oxyethoxycarbonyl] amino]-7-oxo-hept-5-enoate (I-105) (5.60 g, 8.55 mmol) as a light yellow oil. LCMS m/z 677.4 $(M+23)^+$.

To a solution of (E,2S)-tert-butyl-7-amino-2-[tert-butoxycarbonyl-[2-[tert-butyl (diphenyl)silyl]oxyethoxycarbonyl] amino]-7-oxo-hept-5-enoate (9.6 g, 14.7 mmol) in DCM (120 mL) was added TFA (405 mmol, 30 mL). The mixture was stirred at 25° C. for 2 h. The mixture was diluted with EtOAc (100 mL) and adjusted pH~3 with saturated $NaHCO_3$. The resultant was extracted with EtOAc (300 mL×2). The combined organic layers were dried over anhydrous $Na_2SO_4$, filtered and concentrated to give a residue. The residue was purified by column chromatography to give (S,E)-10-(5-amino-5-oxopent-3-en-1-yl)-2,2-dimethyl-8-oxo-3,3-diphenyl-4,7-dioxa-9-aza-3-silaundecan-11-oic acid (I-106) (1.6 g, 2.95 mmol) as a light yellow oil. LCMS m/z 499.2 $(M+1)^+$.

To a solution of (S)-2-((tert-butoxycarbonyl)amino)-3-methylbutanoic acid (I-107) (3 g, 13.8 mmol) in MeCN (5 mL) were added CDI (4.48 g, 27.6 mmol) and DIEA (5.35 g, 41.4 mmol, 7.23 mL) at 0° C. The mixture was stirred at 25° C. for 1 hr. Then phenylmethanol (2.24 g, 20.7 mmol, 2.15 mL) was added into the reaction above. The mixture was stirred at 25° C. for another 2 h. The resulting solution was concentrated to give a residue. The residue was diluted with EtOAc (300 mL) and washed with $H_2O$ (200 mL). The organic phase was concentrated and purified by column chromatography to afford (S)-benzyl 2-((tert-butoxycarbonyl)amino)-3-methylbutanoate (I-108) (3.8 g, 12.2 mmol) as a light yellow oil. LCMS m/z 330.1 $(M+23)^+$.

To a solution of benzyl (S)-benzyl 2-((tert-butoxycarbonyl)amino)-3-methylbutanoate (3.8 g, 12.4 mmol) in DCM (30 mL) was added TFA (15 mL). The mixture was stirred at 25° C. for 1 hr. The reaction mixture was concentrated to give a residue. The residue was diluted with $H_2O$ (100 mL) and adjusted pH~8 by saturated $NaHCO_3$. The resultant was extracted with EtOAc (100 mL×3). The combined organic layers were dried over anhydrous $Na_2SO_4$, filtered and concentrated to give (S)-benzyl 2-amino-3-methylbutanoate (I-109) (3.00 g) as a light yellow oil. LCMS m/z 208.1 $(M+1)^+$.

To a solution of (S)-2-((tert-butoxycarbonyl)amino)-3-methylbutanoic acid (3.77 g, 17.4 mmol) in MeCN (50 mL) were added $T_3P$ (18.4 g, 29.0 mmol, 17.2 mL) and DIEA (5.61 g, 43.4 mmol, 7.58 mL) at 0° C. The mixture was stirred at 25° C. for 0.5 hr. Then (S)-benzyl 2-amino-3-methylbutanoate (3 g, 14.5 mmol) was added into the reaction mixture and stirred at 25° C. for another another 18 h. The reaction was concentrated, extracted with EtOAc (100 mL) and washed with water (100 mL). The organic phase was concentrated and purified by column chromatography to afford (S)-benzyl2-((S)-2-((tert-butoxycarbonyl) amino)-3-methyl butanamido)-3-methylbutanoate (I-110) (1.5 g, 3.65 mmol) as a light yellow oil. LCMS m/z 407.2 $(M+1)^+$.

To a solution of benzyl (S)-benzyl 2-((S)-2-((tert-butoxycarbonyl)amino)-3-methyl butanamido)-3-methylbutanoate (1.50 g, 3.69 mmol) in MeOH (30 mL) was added $Pd(OH)_2$ (518 mg). The mixture was stirred at 25° C. for 16 h under $H_2$ (15 psi). The resulting suspension was filtered through a pad of celite. The filtrate was concentrated to give (S)-2-((S)-2-((tert-butoxycarbonyl)amino)-3-methylbutanamido)-3-methylbutanoic acid (I-111) (1.00 g, 3.16 mmol) as a white solid. $^1H$ NMR (400 MHz, DMSO-$d_6$) δ37.77 (d, J=8.4 Hz, 1H), 6.78 (d, J=9.2 Hz, 1H), 4.14 (dd, J=8.0, 5.6 Hz, 1H), 3.85 (dd, J=8.8, 7.2 Hz, 1H), 2.11-2.00 (m, 1H), 1.99-1.88 (m, 1H), 1.38 (s, 9H), 0.95-0.78 (m, 12H).

Example 6

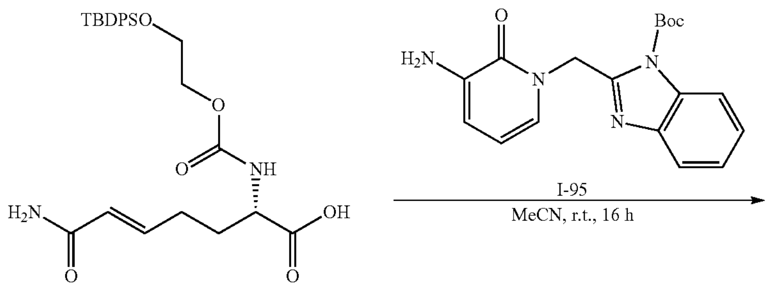

I-106

-continued

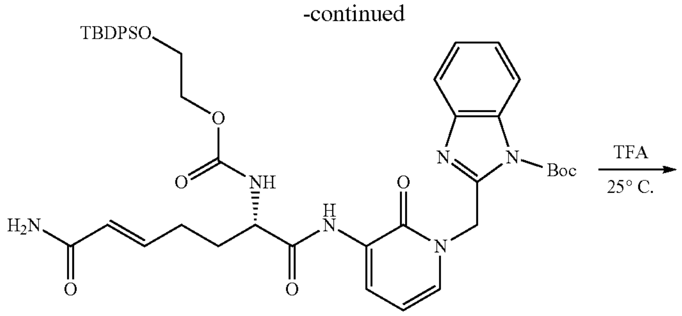

I-112

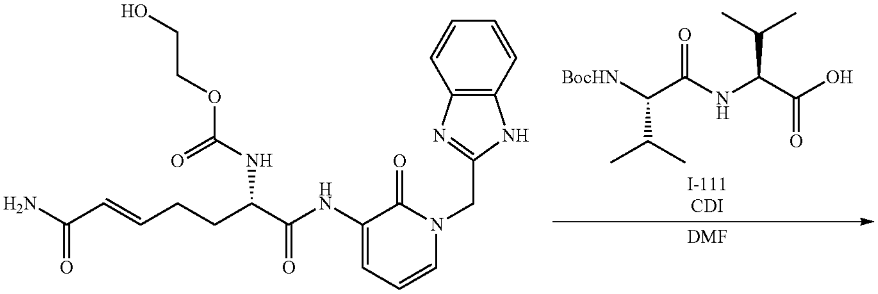

57

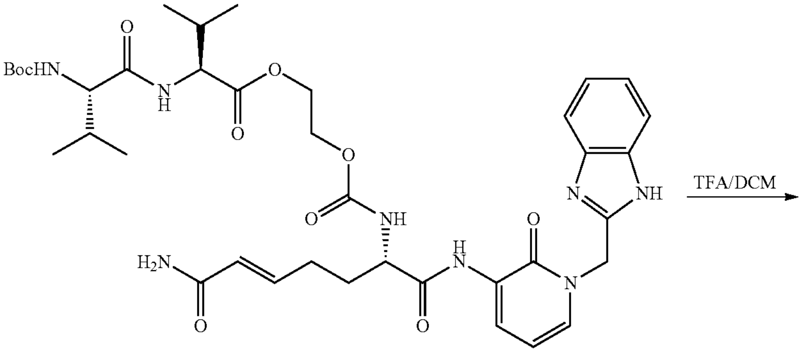

I-113

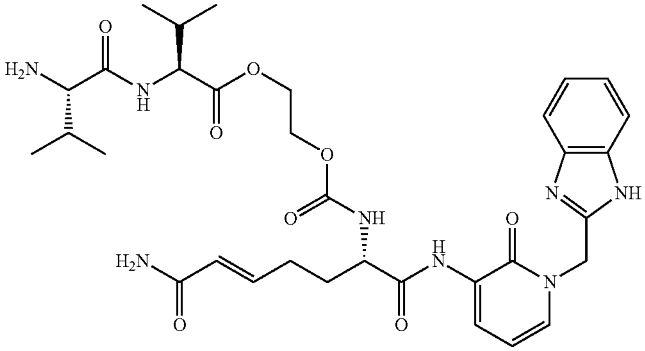

58

To a solution of (S,E)-10-(5-amino-5-oxopent-3-en-1-yl)-2,2-dimethyl-8-oxo-3,3-diphenyl-4,7-dioxa-9-aza-3-silaundecan-11-oic acid (600 mg, 1.03 mmol) and tert-butyl2-((3-amino-2-oxopyridin-1(2H)-yl)methyl)-1H-benzo[d]imidazole-1-carboxylate (423 mg, 1.24 mmol) in MeCN (1 mL) were added HATU (787 mg, 2.07 mmol) and DIEA (401 mg, 3.10 mmol) at 0° C. The mixture was stirred at 25° C. for 18 h. The resulting solution was poured into $H_2O$ (100 mL) and extracted with EtOAc (100 mL×2). The combined organic layers were dried over anhydrous $Na_2SO_4$, filtered and concentrated to give a residue. The residue was purified by column chromatography to afford (S,E)-tert-butyl2-((3-(10-(5-amino-5-oxopent-3-en-1-yl)-2,2-dimethyl-8-oxo-3,3-diphenyl-4,7-dioxa-9-aza-3-silaundecanamido)-2-oxopyridin-1(2H)-yl)methyl)-1H-benzo[d]imidazole-1-carboxylate (I-112) (1 g) as a brown solid. LCMS m/z 821.1 $(M+1)^+$.

(S,E)-tert-butyl2-((3-(10-(5-amino-5-oxopent-3-en-1-yl)-2,2-dimethyl-8-oxo-3,3-diphenyl-4,7-dioxa-9-aza-3-silaundecanamido)-2-oxopyridin-1(2H)-yl)methyl)-1H-benzo[d]imidazole-1-carboxylate (900 mg, 1.10 mmol) was added into TFA (18 mL). The mixture was stirred at 25° C. for 2 h. The mixture was concentrated to give a residue. The residue was diluted with $H_2O$ (10 mL) and adjusted pH~8 by saturated $NaHCO_3$. The resultant was lyophilized to give a residue which was purified by prep-HPLC to give (S,E)-2-hydroxyethyl(1-((1-((1H-benzo[d]imidazol-2-yl)methyl)-2-oxo-1,2-dihydropyridin-3-yl)amino)-7-amino-1,7-dioxo-hept-5-en-2-yl)carbamate (Compound 57) (250 mg) as a white solid. LCMS m/z 483.2 $(M+1)^+$.

To a solution of (S)-2-((S)-2-((tert-butoxycarbonyl)amino)-3-methylbutanamido)-3-methylbutanoic acid (I-111) (197 mg, 622 μmol) in DMF (2 mL) were added CDI (101 mg, 622 μmol) and DMAP (75.9 mg, 622 μmol). The mixture was stirred at 10° C. for 1 hr. Then (S,E)-2-hydroxyethyl(1-((1-((1H-benzo[d]imidazol-2-yl)methyl)-2-oxo-1,2-dihydropyridin-3-yl)amino)-7-amino-1,7-dioxo-hept-5-en-2-yl)carbamate (Compound 57) (150 mg, 311 μmol) was added into the reaction mixture above and the resultant was stirred at 60° C. for 72 h. The reaction mixture was poured into $H_2O$ (20 mL) and extracted with EtOAc (20 mL×3). The combined organic layers were concentrated to give a residue. The residue was purified by prep-TLC to give (S)-2-((((S,E)-1-((1-((1H-benzo[d]imidazol-2-yl)methyl)-2-oxo-1,2-dihydropyridin-3-yl)amino)-7-amino-1,7-dioxo-hept-5-en-2-yl)carbamoyl)oxy)ethyl 2-((S)-2-((tert-butoxycarbonyl)amino)-3-methylbutanamido)-3-methylbutanoate (I-113) (50 mg) as a white solid. LCMS m/z 781.4 $(M+1)^+$.

To a solution of (S)-2-((((S,E)-1-((1-((1H-benzo[d]imidazol-2-yl)methyl)-2-oxo-1,2-dihydropyridin-3-yl)amino)-7-amino-1,7-dioxohept-5-en-2-yl)carbamoyl)oxy) ethyl2-((S)-2-((tert-butoxycarbonyl)amino)-3-methylbutanamido)-3-methylbutanoate (80 mg, 102 μmol) in DCM (3 mL) was added TFA (4.62 g, 40.5 mmol, 3 mL). The reaction mixture was stirred at 15° C. for 1 hr. The resulting solution was concentrated to give a residue and purified by prep-HPLC to afford (S)-2-((((S,E)-1-((1-((1H-benzo[d]imidazol-2-yl)methyl)-2-oxo-1,2-dihydropyridin-3-yl)amino)-7-amino-1,7-dioxohept-5-en-2-yl)carbamoyl)oxy)ethyl 2-((S)-2-amino-3-methylbutanamido)-3-methylbutanoate (Compound 58) (33.8 mg) as a white solid. LCMS m/z 681.3 $(M+1)^+$. $^1H$ NMR (400 MHz, DMSO-$d_6$) δ 9.29 (s, 1H), 8.31-8.22 (m, 2H), 8.16 (d, J=8.8 Hz, 1H), 7.84 (d, J=7.6 Hz, 1H), 7.56 (dd, J=7.2, 2.0 Hz, 1H), 7.49 (dd, J=5.6, 3.2 Hz, 2H), 7.32 (br s, 1H), 7.17-7.09 (m, 2H), 6.87 (br s, 1H), 6.63-6.52 (m, 1H), 6.35 (t, J=7.2 Hz, 1H), 5.83 (d, J=15.6 Hz, 1H), 5.40 (s, 2H), 4.33-4.09 (m, 6H), 3.19-3.13 (m, 1H), 2.23-2.10 (m, 2H), 2.10-1.99 (m, 1H), 1.94-1.76 (m, 2H), 1.75-1.61 (m, 1H), 0.73-0.93 (m, 12H).

Example 7

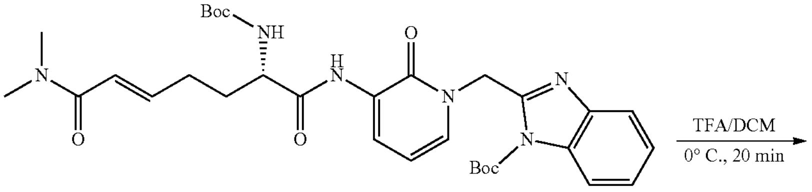

47

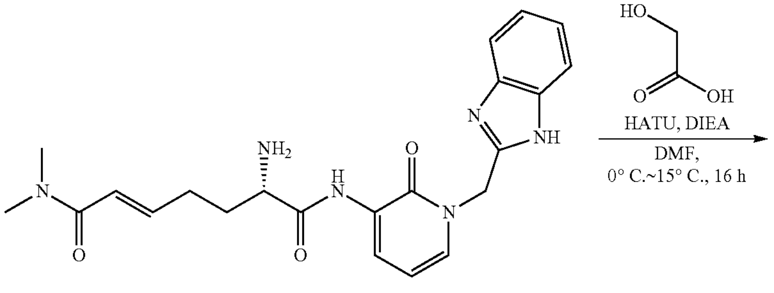

I-114

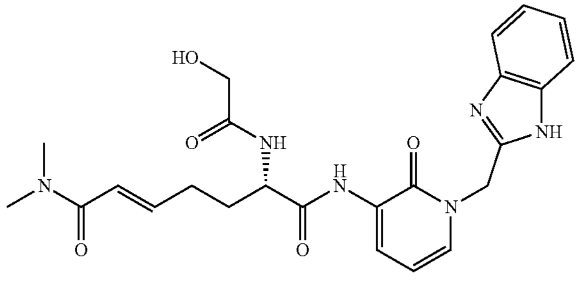

59

To a mixture of tert-butyl 2-[[3-[[(E,2S)-2-(tert-butoxycarbonylamino)-7-(dimethylamino)-7-oxo-hept-5-enoyl]amino]-2-oxo-1-pyridyl]methyl]benzimidazole-1-carboxylate (0.3 g, 482 μmol) in DCM (3 mL) was added TFA (1.54 g, 13.5 mmol, 1 mL) at 0° C. The mixture was stirred at 0° C. for 20 min. The mixture was concentrated under room temperature to give (E,6S)-6-amino-N'-[1-(1H-benzimidazol-2-ylmethyl)-2-oxo-3-pyridyl]-N,N-dimethyl-hept-2-enediamide (I-114) (0.25 g, TFA salt) as a light brown oil. LCMS m/z 423.3 $(M+1)^+$.

To a mixture of 2-hydroxyacetic acid (32.4 mg, 426 μmol, 25.9 μL) and (E,6S)-6-amino-N'-[1-(1H-benzimidazol-2-ylmethyl)-2-oxo-3-pyridyl]-N,N-dimethyl-hept-2-enediamide (0.12 g, 284 μmol) in DMF (2 mL) were added HATU (162 mg, 426 μmol) and DIEA (73.4 mg, 568 μmol, 99.0 μL) at 0° C. The mixture was stirred at 15° C. for 16 h. The reaction mixture was (combined with a smaller scale) diluted with EtOAc (20 mL), washed with water (10 mL), and brine (10 mL). The organic phase was dried over anhydrous $Na_2SO_4$ and concentrated to give a residue. The residue was purified by prep-HPLC to give (S,E)-N7-(1-((1H-benzo[d]imidazol-2-yl)methyl)-2-oxo-1,2-dihydropyridin-3-yl)-6-(2-hydroxyacetamido)-N1,N1-dimethylhept-2-enediamide (Compound 59) (28 mg, 20% yield) as a white solid. LCMS m/z 481.1 $(M+1)^+$. $^1$H NMR (400 MHz, DMSO-$d_6$) δ9.40 (s, 1H), 8.29 (d, J=7.2 Hz, 1H), 8.11 (d, J=8.2 Hz, 1H), 7.73-7.68 (m, 2H), 7.62 (d, J=5.8 Hz, 1H), 7.45 (s, 2H), 6.63-6.54 (m, 1H), 6.44 (t, J=6.8 Hz, 1H), 6.37-6.34 (m, 1H), 6.39-6.31 (m, 1H), 5.58 (s, 2H), 4.53 (m, 1H), 3.96-3.80 (m, 2H), 2.98 (s, 3H), 2.83 (s, 3H), 2.19 (m, 2H), 1.92-1.79 (m, 2H), 1.25 (t, J=5.9 Hz, 1H).

Example 8

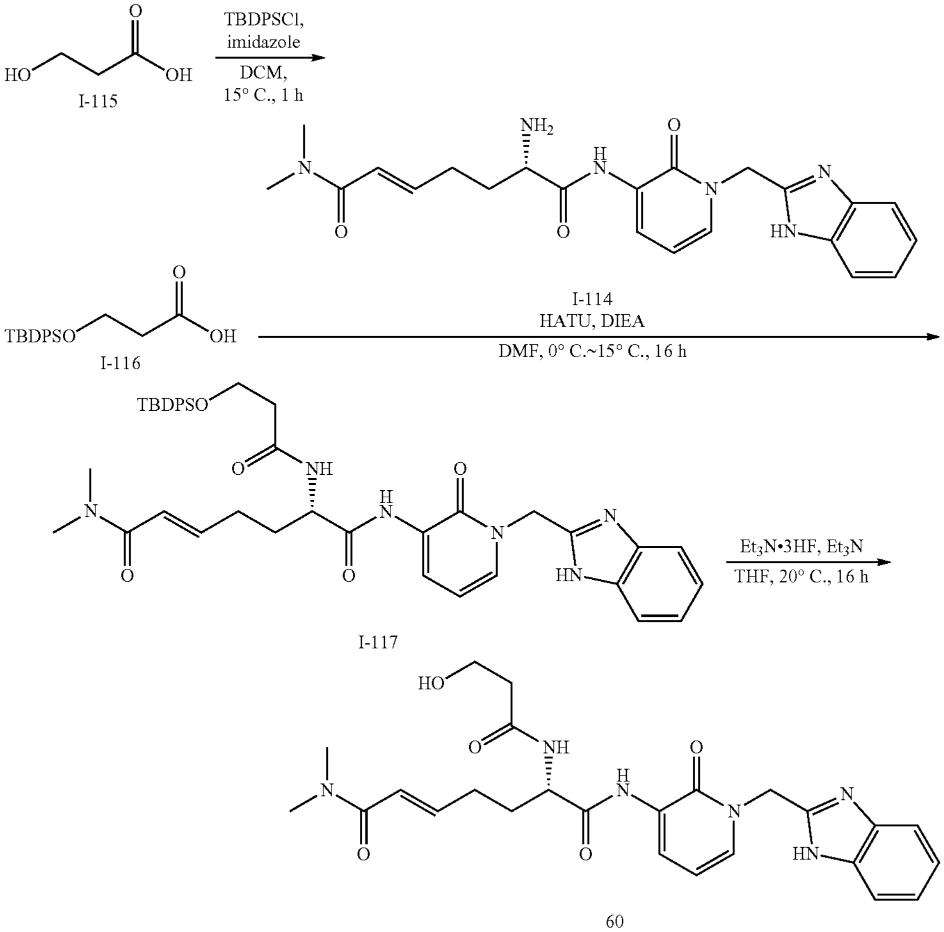

I-115 I-114 I-116 I-117 60

To a mixture of 3-hydroxypropanoic acid (1 g, 11.1 mmol) and TBDPSCl (3.66 g, 13.32 mmol, 3 mL) in DCM (30 mL) was added imidazole (1.51 g, 22.2 mmol). The mixture was stirred at 15° C. for 1 hr. The mixture was washed with brine (15 mL×2), dried over anhydrous $Na_2SO_4$ and concentrated to give a residue. The residue was purified by column chromatography to give 3-[tert-butyl(diphenyl)silyl]oxypropanoic acid (I-116) (1.5 g) as a white solid. $^1$H NMR (400 MHz, $CDCl_3$) δ 7.72-7.65 (m, 4H), 7.46-7.37 (m, 6H), 4.00-3.92 (m, 2H), 2.62 (t, J=6.2 Hz, 2H), 1.13-1.04 (m, 9H).

To a solution of (E,6S)-6-amino-N'-[1-(1H-benzimidazol-2-ylmethyl)-2-oxo-3-pyridyl]-N,N-dimethyl-hept-2-enediamide (0.15 g, 279.59 μmol, TFA salt) and 3-[tert-butyl(diphenyl)silyl]oxypropanoic acid (184 mg, 559 μmol) in DMF (3 mL) were added HATU (127.57 mg, 336 μmol) and DIEA (72.3 mg, 559 μmol, 97.4 μL) at 0° C. The mixture was stirred at 15° C. for 16 h. The mixture was diluted with water (10 mL) and extracted with EtOAc (30 mL×2). The combined organic layers were washed with brine (20 mL×3), dried over anhydrous $Na_2SO_4$ and concentrated to give a residue. The residue was purified by prep-TLC to give (E,6S)—N'-[1-(1H-benzimidazol-2-ylmethyl)-2-oxo-3-pyridyl]-6-[3-[tert-butyl(diphenyl)silyl]oxypropanoylamino]-N,N-dimethyl-hept-2-enediamide (I-117) (0.07 g) as a white solid.

To a mixture of (E,6S)—N'-[1-(1H-benzimidazol-2-ylmethyl)-2-oxo-3-pyridyl]-6-[3-[tert-butyl(diphenyl)silyl]oxypropanoylamino]-N,N-dimethyl-hept-2-enediamide (0.07 g, 95.5 μmol) in THF (5 mL) were added $Et_3N \cdot 3HF$ (92.3 mg, 573 μmol) and $Et_3N$ (29.0 mg, 287 μmol, 39 μL) at 0° C. The mixture was stirred at 15° C. for 16 h. The reaction mixture was (combined with a smaller scale) concentrated to give a residue. The residue was purified by prep-HPLC to give (E,6S)—N'-[1-(1H-benzimidazol-2-ylmethyl)-2-oxo-3-pyridyl]-6-(3-hydroxypropanoylamino)-N,N-dimethyl-hept-2-enediamide (Compound 60) (13.5 mg, 28% yield) as a white solid. LCMS m/z 495.2 $(M+1)^+$. $^1H$ NMR (400 MHz, DMSO-$d_6$) δ12.47 (s, 1H), 9.23 (s, 1H), 8.34 (d, J=7.6 Hz, 1H), 8.24 (d, J=6.1 Hz, 1H), 7.57 (d, J=5.6 Hz, 1H), 7.49 (s, 2H), 7.15 (s, 2H), 6.65-6.55 (m, 1H), 6.41-6.32 (m, 2H), 5.39 (s, 2H), 4.60 (s, 1H), 4.45-4.34 (m, 1H), 3.62 (t, J=6.5 Hz, 2H), 2.98 (s, 3H), 2.83 (s, 3H), 2.40-2.15 (m, 4H), 1.97-1.84 (m, 1H), 1.79-1.64 (m, 1H).

The following intermediate was prepared according to the procedures described for the Example 8 using the appropriate reagents.

-continued

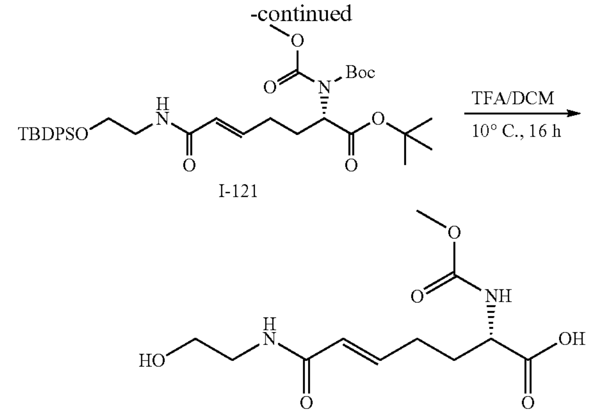

I-121

I-122

To a solution of methyl 2-(diethoxyphosphoryl)acetate (5.00 g, 23.8 mmol) in MeOH (10 mL) was added 2-aminoethanol (2.91 g, 47.6 mmol). The mixture was stirred at 70° C. for 16 h. The resulting solution was concentrated to give a residue. The residue was purified by column chromatography to give diethyl (2-((2-hydroxyethyl)amino)-2-oxoethyl)phosphonate (I-119) (4.2 g) as a yellow oil. LCMS

| Compound | Structure | LCMS Data |
| --- | --- | --- |
| 61 | 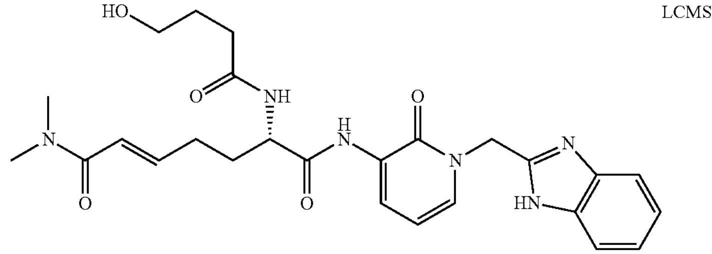 | LCMS m/z 509.2 $(M + 1)^+$ |

The Synthesis of Intermediate I-122

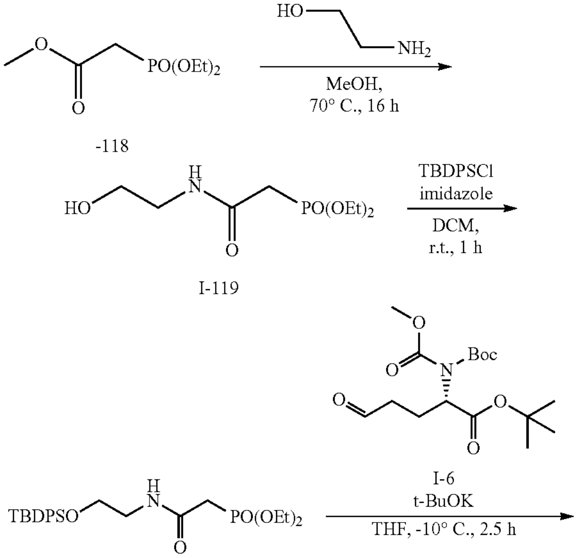

-118

I-119

I-6

I-120 m/z 240.1 $(M+1)^+$. $^1H$ NMR (400 MHz, $CDCl_3$) δ 7.22 (br. s, 1H), 4.19-4.12 (m, 4H), 3.71-3.70 (m, 3H), 3.44-3.41 (m, 2H), 2.89 (d, J=20.8 Hz, 2H), 1.36-1.33 (m, 6H).

To a mixture of diethyl (2-((2-hydroxyethyl)amino)-2-oxoethyl)phosphonate (2.7 g, 11.3 mmol) and imidazole (1.54 g, 22.6 mmol) in DCM (30 mL) was added TBDPSCl (3.72 g, 13.5 mmol). After stirring at 15° C. for 1 h, the mixture was diluted with water (30 mL) and extracted with DCM (30 mL×2). The combined organic layers were washed with brine (50 mL), dried over anhydrous $Na_2SO_4$, filtered and concentrated in vacuum to give a residue. The residue was purified by silica gel chromatography to afford diethyl (2-((2-((tert-butyldiphenylsilyl) oxy)ethyl)amino)-2-oxoethyl) phosphonate (I-120) (4.2 g) as a yellow oil. $^1H$ NMR (400 MHz, $CDCl_3$) δ 7.79-7.58 (m, 4H), 7.57-7.34 (m, 6H), 6.89 (s, 1H), 4.28-4.04 (m, 4H), 3.85-3.64 (m, 2H), 3.56-3.34 (m 2H), 2.92-2.72 (m, 2H), 1.33 (t, J=6.8 Hz, 6H), 1.08 (s, 9H).

To a solution of diethyl(2-((2-((tert-butyldiphenylsilyl) oxy)ethyl)amino)-2-oxoethyl) phosphonate (3.1 g, 6.49 mmol) in THF (45 mL) was added t-BuOK (874 mg, 7.79 mmol) at −10° C. The reaction mixture was stirred at the same temperature for 0.5 h. A solution of (S)tert-butyl-2-[tert-butoxycarbonyl(methoxycarbonyl)amino]-5-oxo-pentanoate (2.24 g, 6.49 mmol) in THF (15 mL) was added dropwise into the reaction mixture above. After stirring at −10° C. for 2 h under $N_2$ atmosphere, the mixture was poured into $H_2O$ (100 mL). The resultant was extracted with EtOAc (100 mL×2). The combined organic layers were dried over anhydrous $Na_2SO_4$, filtered and concentrated to give a residue. The residue was purified by column chromatography to give (S,E)-2-[tert-butoxycarbonyl(methoxycarbonyl)amino]-7-[2-[tert-butyl(diphenyl)silyl]oxyethylamino]-7-oxo-hept-5-enoate (I-121) (1.7 g) as a colorless oil. LCMS m/z 569.3 $(M-99)^+$. $^1H$ NMR (400 MHz, $CDCl_3$) δ 7.69-7.61 (m, 4H), 7.47-7.35 (m, 6H), 6.82-6.72 (m, 1H), 5.79-5.69 (m, 2H), 5.11-5.01 (m, 1H), 4.87-4.79 (m, 1H), 4.28-4.17 (m, 1H), 3.75-3.85 (m, 3H), 3.47 (q, J=5.44 Hz, 2H), 2.31-2.16 (m, 2H), 2.02-1.86 (m, 1H), 1.80-1.67 (m, 1H), 1.41-1.55 (m, 18H), 1.08 (s, 9H).

To a solution of tert-butyl (S,E)-2-[tert-butoxycarbonyl (methoxycarbonyl)amino]-7-[2-[tert-butyl(diphenyl)silyl] oxyethylamino]-7-oxo-hept-5-enoate (1.7 g, 2.39 mmol) in DCM (10 mL) was added TFA (18.8 mL, 254 mmol). After stirring at 10° C. for 16 h, the mixture was concentrated to give a residue at 10° C. The residue was purified by reverse-flash and prep-HPLC in sequence to give (S,E)-7-((2-hydroxyethyl)amino)-2-((methoxycarbonyl)amino)-7-oxohept-5-enoic acid (I-122) (130 mg) as a light yellow oil. LCMS m/z 275.0 $(M+1)^+$.

Example 9

To a solution of (S,E)-7-((2-hydroxyethyl)amino)-2-((methoxycarbonyl)amino)-7-oxohept-5-enoic acid (130 mg, 469 μmol) and tert-butyl 2-((3-amino-2-oxopyridin-1 (2H)-yl)methyl)-1H-benzo[d]imidazole-1-carboxylate (176 mg, 516 μmol) in MeCN (3 mL)/DMF (1 mL) were added HATU (357 mg, 938 μmol) and DIEA (182 mg, 1.41 mmol) at 0° C. After stirring at 30° C. for 40 h, the mixture was poured into $H_2O$ (50 mL) and the resultant was extracted with EtOAc (50 mL×4). The combined organic layers were dried over anhydrous $Na_2SO_4$, filtered and concentrated to give a residue. The residue was purified by column chromatography and prep-TLC to give (S,E)-tert-butyl 2-((3-(7-((2-hydroxyethyl)amino)-2-((methoxy-carbonyl) amino)-7-oxohept-5-enamido)-2-oxopyridin-1(2H)-yl)methyl)-1H-benzo[d]imidazole-1-carboxylate (I-123) (50 mg) as alight yellow solid. LCMS m/z 597.3 $(M+1)^+$.

To a solution of (S,E)-tert-butyl 2-((3-(7-((2-hydroxyethyl)amino)-2-((methoxycarbonyl)amino)-7-oxohept-5-enamido)-2-oxopyridin-1(2H)-yl)methyl)-1H-benzo[d]imidazole-1-carboxylate (38 mg, 45.9 μmol) in DCM (3 mL) was added $ZnBr_2$ (51.6 mg, 229 μmol). After stirring at 30° C. for 16 h, the mixture was concentrated to give a residue. The residue was purified by prep-HPLC to give (S,E)-methyl(1-((1-((1H-benzo[d]imidazol-2-yl)methyl)-2-oxo-1,2-dihydropyridin-3-yl)amino)-7-((2-hydroxyethyl)amino)-1,7-dioxohept-5-en-2-yl)carbamate (Compound 62) (10.3 mg) as a white solid. LCMS m/z 497.2 $(M+1)^+$. $^1H$ NMR (400 MHz, DMSO-$d_6$) δ12.51 (br s, 1H), 9.28 (s, 1H), 8.25

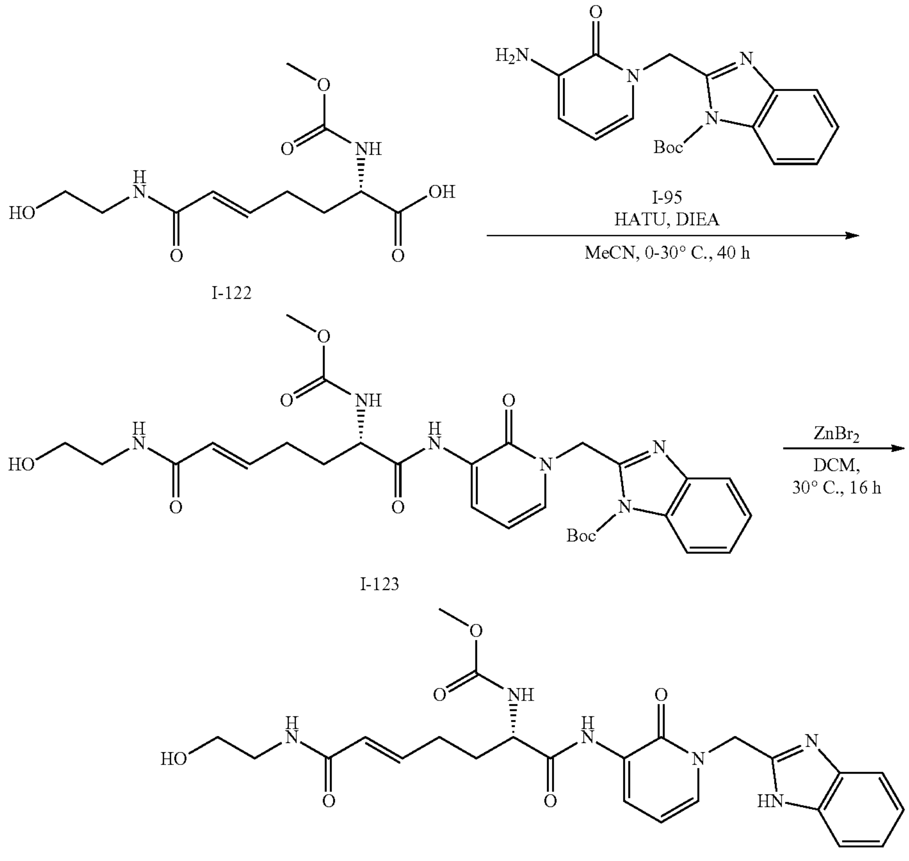

62

(dd, J=7.2, 1.6 Hz, 1H), 7.94 (t, J=5.6 Hz, 1H), 7.75 (d, J=7.6 Hz, 1H), 7.57 (dd, J=7.2, 1.6 Hz, 1H), 7.49 (s, 2H), 7.18-7.10 (m, 2H), 6.62-6.51 (m, 1H), 6.36 (t, J=7.2 Hz, 1H), 5.88 (d, J=15.6 Hz, 1H), 5.40 (s, 2H), 4.69 (br. s, 1H), 4.22-4.12 (m, 1H), 3.54 (s, 3H), 3.15 (q, J=6.0 Hz, 2H), 2.24-2.10 (m, 2H), 1.90-1.78 (m, 1H), 1.73-1.62 (m, 1H).
Synthesis of tert-butyl 2-((3-amino-2-oxopyridin-1(2H)-yl)methyl)-6-fluoro-4-neopentyl-1H-benzo[d]imidazole-1-carboxylate
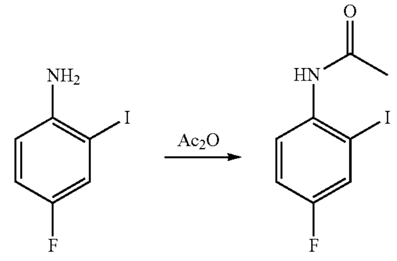
I-124 I-125
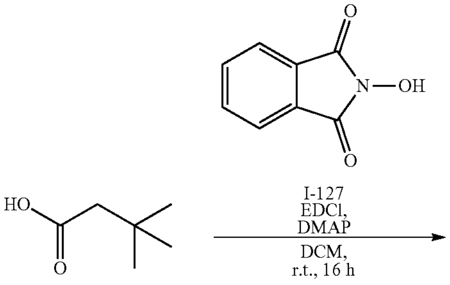
I-126
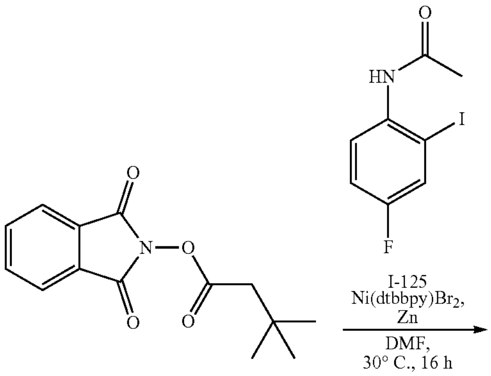
I-128
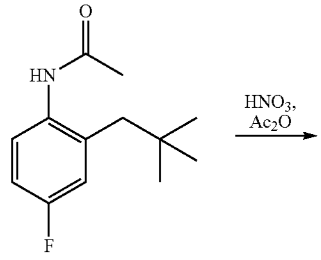
I-129
-continued
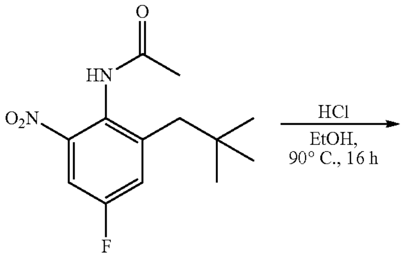
I-130
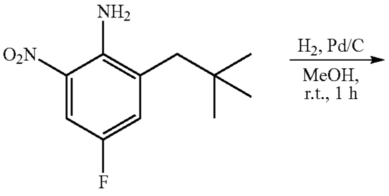
I-131
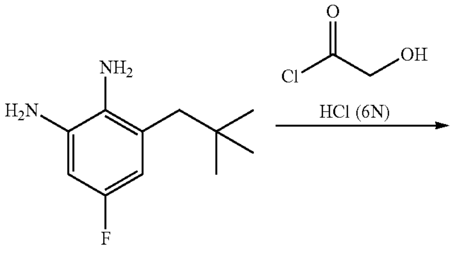
I-132
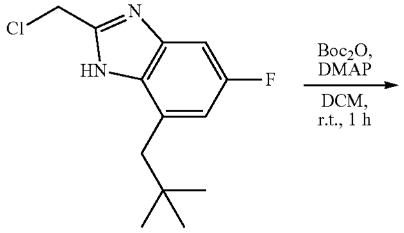
I-133
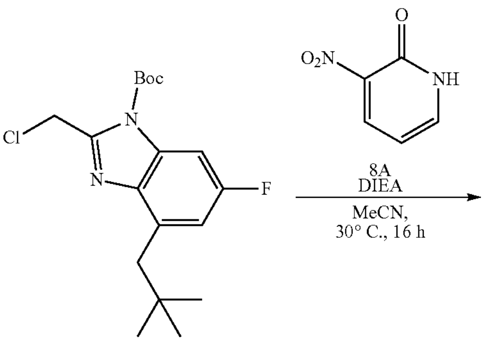
I-134

-continued

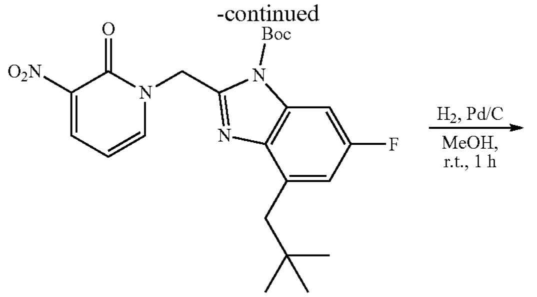

I-135

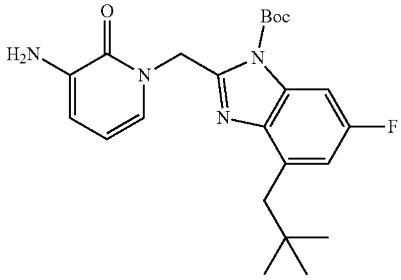

I-136

A mixture of 4-fluoro-2-iodo-aniline (10 g, 42.2 mmol) in $Ac_2O$ (50 mL) was stirred at 15° C. for 1 h. The mixture was diluted with water (100 mL) and extracted with ethyl acetate (50 mL×2). The combined organic layers were washed with brine (100 mL), dried over anhydrous $Na_2SO_4$, filtered and concentrated in vacuum to give a residue. The residue was purified by silica gel chromatography to give N-(4-fluoro-2-iodophenyl)acetamide (I-125) (12 g) as a yellow oil. $^1H$ NMR (400 MHz, $CDCl_3$) δ 8.12-8.08 (m, 1H), 7.50 (dd, J=7.6, 1.6 Hz, 1H), 7.29 (s, 1H), 7.13-7.02 (m, 1H), 2.23 (s, 3H).

To a solution of 3,3-dimethylbutanoic acid (3 g, 25.8 mmol) in DCM (20 mL) were added 2-hydroxyisoindoline-1,3-dione (4.21 g, 25.8 mmol), DMAP (631 mg, 5.17 mmol) and EDCI (5.45 g, 28.4 mmol). The mixture was stirred at 15° C. for 16 h. The reaction solution was concentrated, diluted with water (40 mL) and extracted with ethyl acetate (40 mL×2). The combined organic layers were washed with brine (80 mL), dried over anhydrous $Na_2SO_4$, filtered and concentrated in vacuum to give a residue. The residue was purified by column chromatography to give 1,3-dioxoisoindolin-2-yl 3,3-dimethylbutanoate (I-128) (5.3 g) as a white solid. $^1H$ NMR (400 MHz, $CDCl_3$) δ7.94-7.87 (m, 2H), 7.84-7.77 (m, 2H), 2.55 (s, 2H), 1.24-1.13 (m, 9H).

To a suspension of 1,3-dioxoisoindolin-2-yl 3,3-dimethylbutanoate (7.02 g, 26.9 mmol), N-(4-fluoro-2-iodophenyl) acetamide (5 g, 17.9 mmol) and Zn (2.34 g, 35.8 mmol) in DMA (17 mL) was added a solution of (dtbbpy)$NiBr_2$ (610 mg, 1.25 mmol) in DMA (3 mL). The mixture was stirred at 30° C. for 16 h. The reaction mixture was diluted with $H_2O$ (50 mL) and EtOAc (50 mL). The resulting suspension was filtered and the filtrate was collected. The filtrate was extracted with ethyl acetate (30 mL×2). The combined organic layers were washed with brine (30 mL×2), dried over anhydrous $Na_2SO_4$, filtered and concentrated in vacuum to give a residue. The residue was purified by column chromatography to give N-(4-fluoro-2-neopentylphenyl)acetamide (I-129) (4.25 g) as a white solid.

To a mixture of N-(4-fluoro-2-neopentylphenyl)acetamide (1 g, 4.48 mmol) in $Ac_2O$ (2 mL) was added a mixed solution of $HNO_3$ (941 mg) and $Ac_2O$ (914 mg, 8.96 mmol) at 0° C. The mixture was stirred at 15° C. for 7 h. The resulting solution was diluted with water (50 mL) and extracted with ethyl acetate (30 mL×2). The combined organic layers were washed with saturated $NaHCO_3$ (50 mL), dried over anhydrous $Na_2SO_4$, filtered and concentrated in vacuum to give a residue. The residue was purified by column chromatography to give N-(4-fluoro-2-neopentyl-6-nitrophenyl)acetamide (I-130) (440 mg) as a yellow solid.

To a solution of N-(4-fluoro-2-neopentyl-6-nitrophenyl) acetamide (440 mg, 1.64 mmol) in EtOH (3 mL) was added HCl (12M, 6 mL). The mixture was stirred at 90° C. for 16 h. The pH of the mixture was adjusted to 7 by adding NaOH solution (1M) at 0° C. The resulting solution was extracted with ethyl acetate (30 mL×3). The combined organic layers were washed with brine (50 mL), dried over anhydrous $Na_2SO_4$, filtered and concentrated in vacuum to give a residue. The residue was purified by column chromatography to give 4-fluoro-2-neopentyl-6-nitroaniline (I-131) (400 mg) as a yellow solid. $^1H$ NMR (400 MHz, $CDCl_3$) δ7.77 (dd, J=8.8, 3.2 Hz, 1H), 7.04 (dd, J=8.4, 3.2 Hz, 1H), 6.19 (s, 2H), 2.50 (s, 2H), 1.00 (m, 9H).

To a solution of 4-fluoro-2-neopentyl-6-nitroaniline (400 mg, 1.77 mmol) in MeOH (50 mL) was added wet Pd/C (300 mg). The suspension was degassed under vacuum and purged with $H_2$ for 3 times. The mixture was stirred under $H_2$ (15 psi) at 15° C. for 1 h. The resulting suspension was filtered and the filtrate was concentrated in vacuum to give 5-fluoro-3-neopentylbenzene-1,2-diamine (I-132) (200 mg) as a yellow solid. LCMS m/z 197.1 $(M+1)^+$.

A mixture of 5-fluoro-3-neopentylbenzene-1,2-diamine (200 mg, 1.02 mmol) and 2-chloroacetic acid (193 mg, 2.04 mmol) in HCl (6 M, 5 mL) was stirred at 100° C. for 16 h. The mixture was adjusted to pH~9 with $NH_3$—$H_2O$ and extracted with EtOAc (50 mL×3). The combined organic layers were washed with brine (50 mL×2), dried over anhydrous $Na_2SO_4$, filtered and the filtrate was concentrated in vacuum to give 2-(chloromethyl)-5-fluoro-7-neopentyl-1H-benzo[d]imidazole (I-133) (260 mg) as a yellow oil. LCMS m/z 355.1 $(M+1)^+$.

To a solution of 2-(chloromethyl)-5-fluoro-7-neopentyl-1H-benzo[d]imidazole (260 mg, 1.02 mmol) in DCM (10 mL) were added $(Boc)_2O$ (245 mg, 1.12 mmol) and DMAP (137 mg, 1.12 mmol). The mixture was stirred at 15° C. for 1 hour. The resulting solution was concentrated in vacuum to give a residue. The residue was purified by column chromatography to give tert-butyl 2-(chloromethyl)-6-fluoro-4-neopentyl-1H-benzo[d]imidazole-1-carboxylate (I-134) (140 mg) as a yellow oil. LCMS m/z 355.1 $(M+1)^+$.

To a solution of tert-butyl 2-(chloromethyl)-6-fluoro-4-neopentyl-1H-benzo[d]imidazole-1-carboxylate (140 mg, 0.395 mmol) and 3-nitro-1H-pyridin-2-one (82.9 mg, 0.592 mmol) in $CH_3CN$ (5 mL) was added DIPEA (102 mg, 0.790 mmol). The mixture was stirred at 25° C. for 16 h. The reaction mixture was concentrated in vacuum to give a residue. The residue was diluted with $H_2O$ (50 mL), and extracted with EtOAc (20 mL×3). The combined organic layers were washed with brine (30 mL), dried over anhydrous $Na_2SO_4$, filtered and concentrated under reduced pressure to give a residue. The residue was purified by prep-TLC to give tert-butyl 6-fluoro-4-neopentyl-2-((3-nitro-2-oxopyridin-1(2H)-yl)methyl)-1H-benzo[d]imidazole-1-carboxylate (I-135) (100 mg). LCMS m/z 459.3 $(M+1)^+$.

To a solution of tert-butyl 6-fluoro-4-neopentyl-2-((3-nitro-2-oxopyridin-1(2H)-yl)methyl)-1H-benzo[d]imidazole-1-carboxylate (100 mg, 0.218 mmol) in MeOH (5 mL)

was added wet Pd/C (50 mg). The suspension was degassed under vacuum and purged with $H_2$ for 3 times. The mixture was stirred under $H_2$ (15 psi) at 15° C. for 0.5 h. The resulting suspension was filtered and concentrated in vacuum to give tert-butyl 2-((3-amino-2-oxopyridin-1(2H)-yl)methyl)-6-fluoro-4-neopentyl-1H-benzo[d]imidazole-1-carboxylate (I-136) (90 mg) as a yellow solid. LCMS m/z 429.1 $(M+1)^+$.

The following intermediates were prepared according to the procedures described in I-136 using the appropriate regents.

| Compound | Structure | LCMS Data |
|---|---|---|
| I-137 | 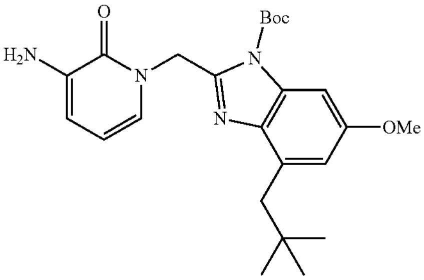 [SMILES: COc1cc(CC(C)(C)C)c2nc(Cn3cccc(N)c3=O)n(C(=O)OC(C)(C)C)c2c1] | LCMS m/z 441..2 $(M + 1)^+$ |
| I-138 | 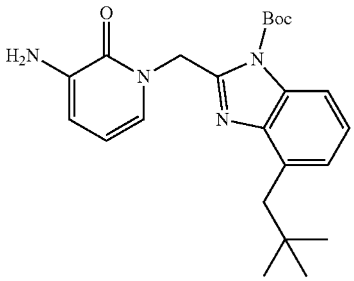 [SMILES: CC(C)(C)Cc1cccc2c1nc(Cn1cccc(N)c1=O)n2C(=O)OC(C)(C)C] | LCMS m/z 411..2 $(M + 1)^+$ |
| I-139 | 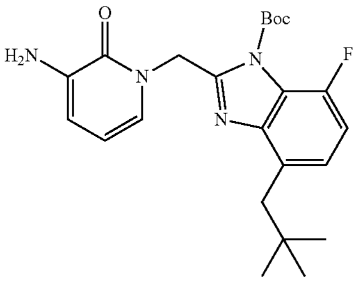 [SMILES: CC(C)(C)Cc1ccc(F)c2c1nc(Cn1cccc(N)c1=O)n2C(=O)OC(C)(C)C] | LCMS m/z 429..2 $(M + 1)^+$ |
| I-531 | 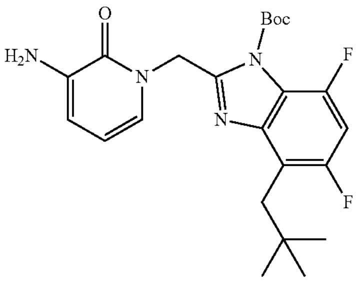 [SMILES: CC(C)(C)Cc1c(F)cc(F)c2c1nc(Cn1cccc(N)c1=O)n2C(=O)OC(C)(C)C] | LCMS m/z 447.2 $(M + 1)^+$ |

Example 10

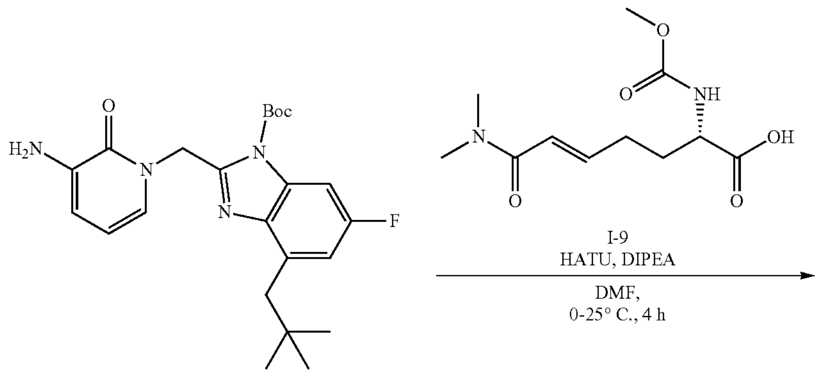

I-136

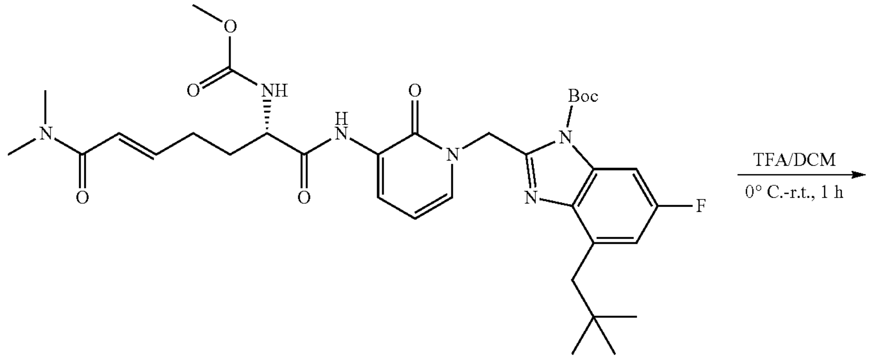

I-140

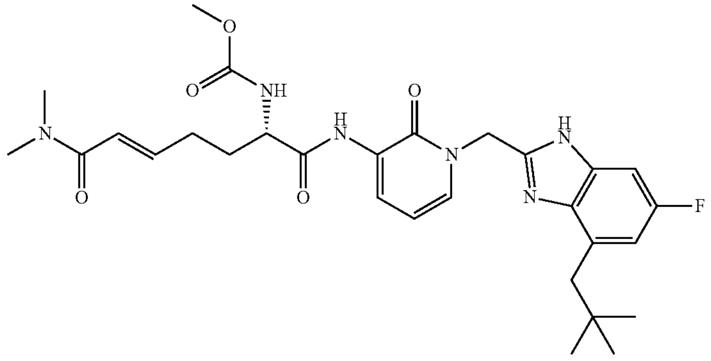

63

To a solution of (S,E)-7-(dimethylamino)-2-((methoxycarbonyl)amino)-7-oxohept-5-enoic acid (81.4 mg, 0.315 mmol) and tert-butyl 2-((3-amino-2-oxopyridin-1(2H)-yl)methyl)-6-fluoro-4-neopentyl-1H-benzo[d]imidazole-1-carboxylate (90 mg, 0.210 mmol) in DMF (2 mL) were added HATU (160 mg, 0.420 mmol) and DIEA (81.4 mg, 0.630 mmol) at 0° C. The mixture was stirred at 30° C. for 4 h. The reaction mixture was diluted with $H_2O$ (50 mL), and extracted with EtOAc (30 mL×3). The combined organic layers were washed with brine (30 mL×3), dried over anhydrous $Na_2SO_4$, filtered and concentrated under reduced pressure to give a residue. The residue was purified by prep-TLC to give (S,E)-tert-butyl 2-((3-(7-(dimethylamino)-2-((methoxycarbonyl)amino)-7-oxohept-5-enamido)-2-oxopyridin-1(2H)-yl)methyl)-6-fluoro-4-neopentyl-1H-benzo[d]imidazole-1-carboxylate (I-140) (130 mg) as a yellow oil. LCMS m/z 569.2 $(M+1)^+$.

To a solution of (S,E)-tert-butyl 2-((3-(7-(dimethylamino)-2-((methoxycarbonyl) amino)-7-oxohept-5-enamido)-2-oxopyridin-1(2H)-yl)methyl)-6-fluoro-4-neopentyl-1H-benzo[d]imidazole-1-carboxylate (130 mg, 0.194 mmol) in DCM (4 mL) was added TFA (3.08 g, 27 mmol, 2 mL) at 0° C. The mixture was stirred at 15° C. for 1 h. The reaction mixture was concentrated in vacuum to give a residue. The residue was purified by prep-HPLC to give (S,E)-methyl (7-(dimethylamino)-1-((1-((6-fluoro-4-neopentyl-1H-benzo[d]imidazol-2-yl)methyl)-2-oxo-1,2-dihydropyridin-3-yl)amino)-1,7-dioxohept-5-en-2-yl)carbamate (Compound 63) (47.2 mg, 36% yield) as a white solid. LCMS m/z 569.2 $(M+1)^+$. $^1H$ NMR (400 MHz, DMSO-$d_6$) δ9.26 (s, 1H), 8.25 (dd, J=7.2, 1.6 Hz, 1H), 7.73 (d, J=7.6, 1H), 7.55 (dd, J=7.2, 1.6 Hz, 1H), 7.16 (dd, J=9.2, 2.0 Hz, 1H), 6.80 (dd, J=10.6, 2.0 Hz, 1H), 6.66-6.53 (m, 1H), 6.42-6.30 (m, 2H), 5.40 (s, 1H), 4.24-4.09 (m, 1H), 3.54 (s, 3H), 2.98 (s, 3H), 2.83 (s, 3H), 2.78 (s, 2H), 2.29-2.14 (m, 2H), 1.93-1.64 (m, 2H), 0.91 (s, 9H).

The following compounds were prepared according to the procedures described in Example 10 using the appropriate intermediates.
| Compound | Structure | LCMS Data |
| --- | --- | --- |
| 64 | 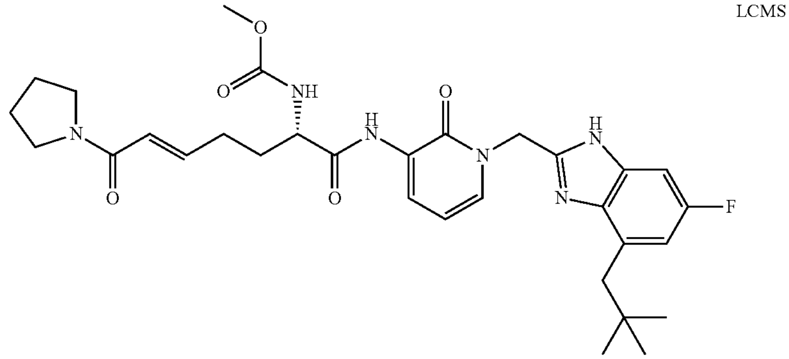 | LCMS m/z 595.2 (M + 1)$^+$ |
| 65 | 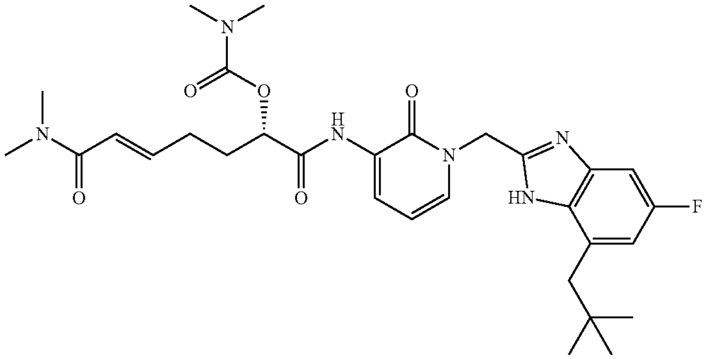 [SMILES: CN(C)C(=O)/C=C/CC[C@H](OC(=O)N(C)C)C(=O)Nc1cccn(Cc2nc3cc(F)cc(CC(C)(C)C)c3[nH]2)c1=O] | LCMS m/z 583.3 (M + 1)$^+$ |
| 66 | 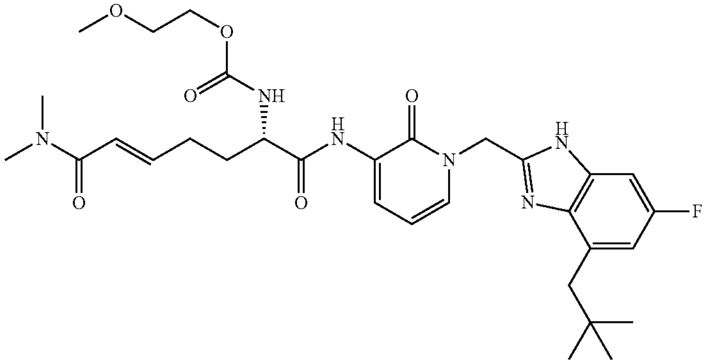 [SMILES: COCCOC(=O)N[C@@H](CC/C=C/C(=O)N(C)C)C(=O)Nc1cccn(Cc2nc3c(CC(C)(C)C)cc(F)cc3[nH]2)c1=O] | LCMS m/z 613.2 (M + 1)$^+$ |
| 67 | 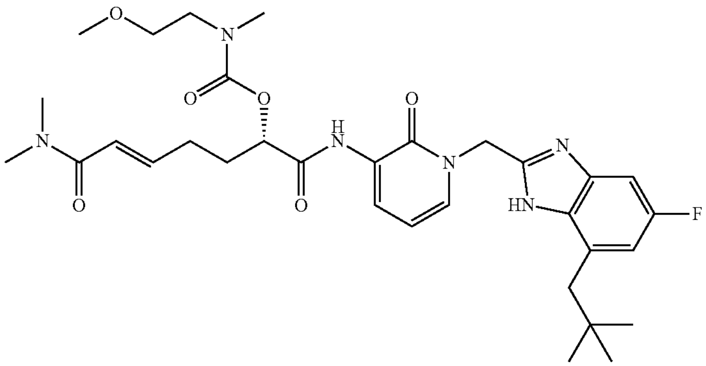 [SMILES: COCCN(C)C(=O)O[C@@H](CC/C=C/C(=O)N(C)C)C(=O)Nc1cccn(Cc2nc3cc(F)cc(CC(C)(C)C)c3[nH]2)c1=O] | LCMS m/z 627.3 (M + 1)$^+$ |

-continued
| Compound | Structure | LCMS Data |
| --- | --- | --- |
| 68 | 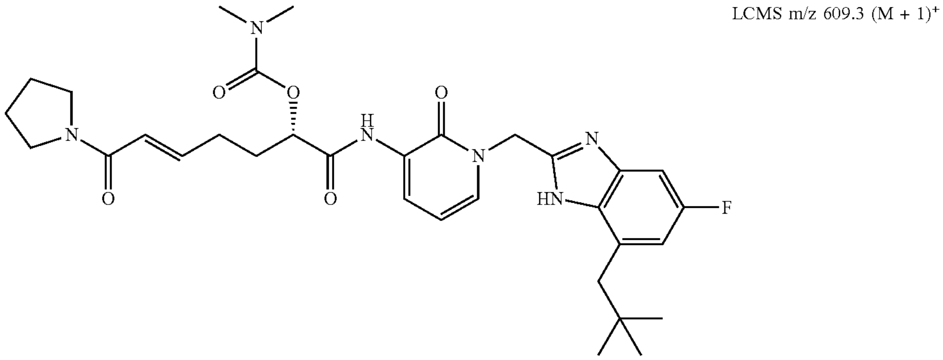 | LCMS m/z 609.3 $(M + 1)^+$ |
| 69 | 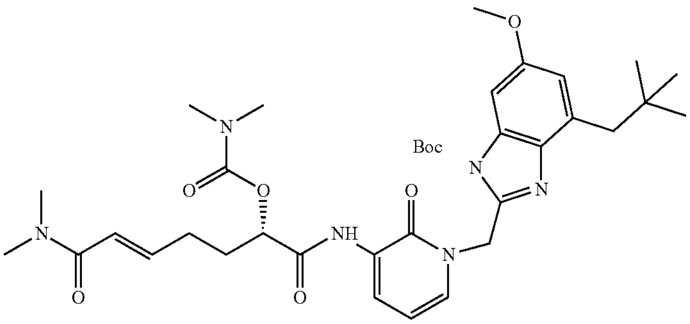 | LCMS m/z 695.3 $(M + 1)^+$ |
| 70 | 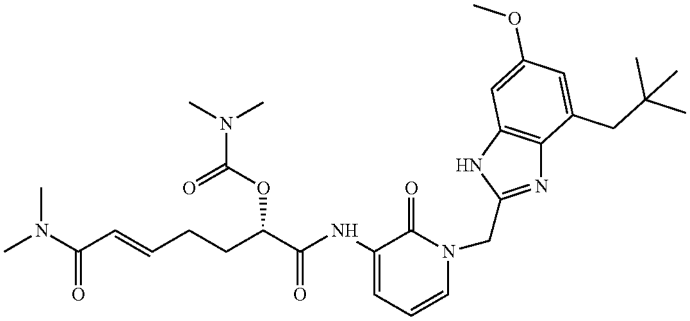 [SMILES: COc1cc(CC(C)(C)C)c2nc(Cn3cccc(NC(=O)[C@H](CC/C=C/C(=O)N(C)C)OC(=O)N(C)C)c3=O)[nH]c2c1] | LCMS m/z 595.4 $(M + 1)^+$ |
| 71 | 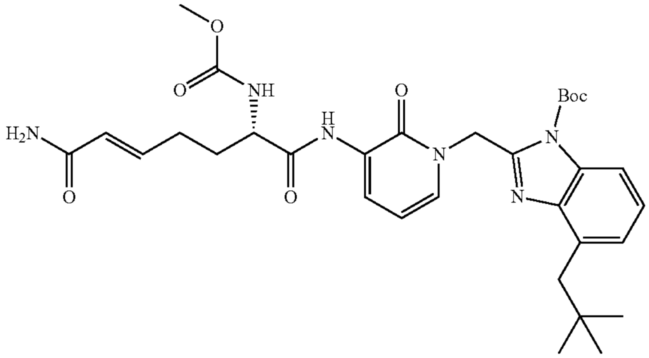 [SMILES: COC(=O)N[C@@H](CC/C=C/C(N)=O)C(=O)Nc1cccn(Cc2nc3c(CC(C)(C)C)cccc3n2C(=O)OC(C)(C)C)c1=O] | LCMS m/z 623.4 $(M + 1)^+$ |

-continued
| Compound | Structure | LCMS Data |
| --- | --- | --- |
| 72 | 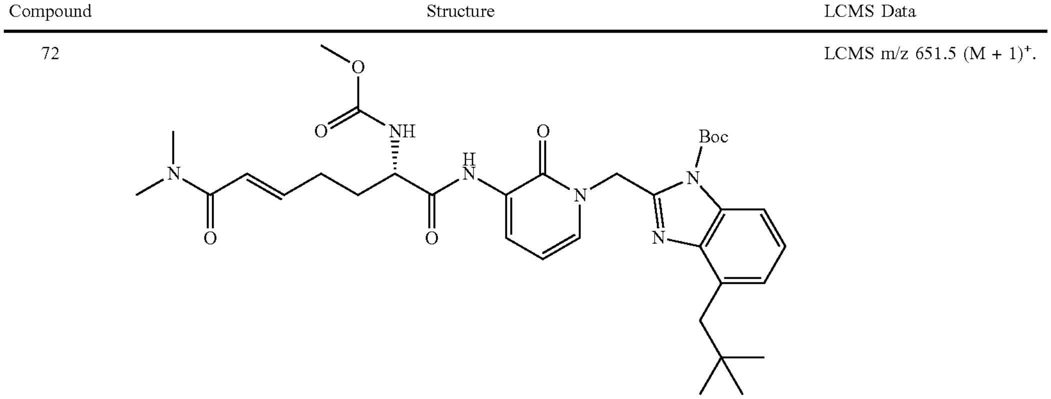 | LCMS m/z 651.5 (M + 1)$^+$. |
| 73 | 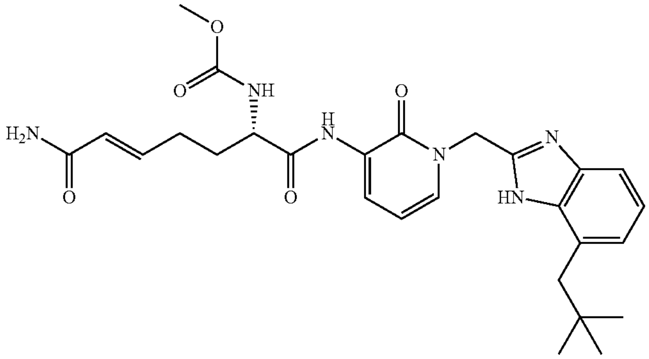 [SMILES: COC(=O)N[C@@H](CC/C=C/C(N)=O)C(=O)Nc1cccn(Cc2nc3cccc(CC(C)(C)C)c3[nH]2)c1=O] | LCMS m/z 523.3 (M + 1)$^+$ |
| 74 | 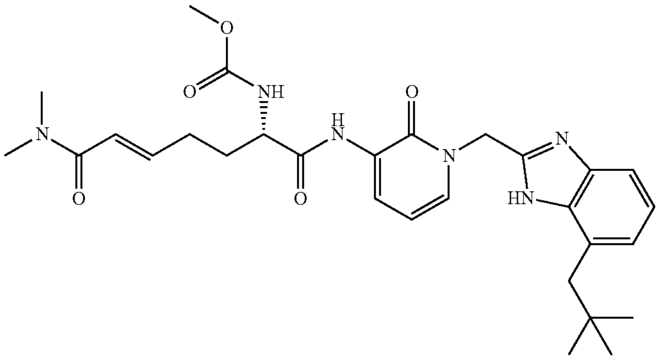 [SMILES: COC(=O)N[C@@H](CC/C=C/C(=O)N(C)C)C(=O)Nc1cccn(Cc2nc3cccc(CC(C)(C)C)c3[nH]2)c1=O] | LCMS m/z 551.3 (M + 1)$^+$. |
| 75 | 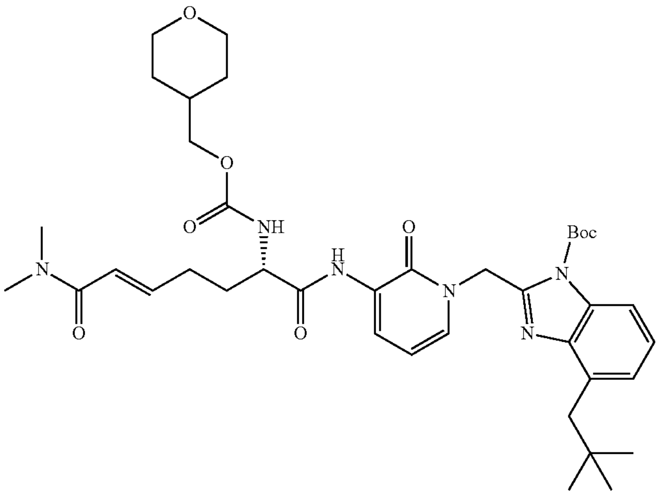 [SMILES: CN(C)C(=O)/C=C/CC[C@H](NC(=O)OCC1CCOCC1)C(=O)Nc1cccn(Cc2nc3c(CC(C)(C)C)cccc3n2C(=O)OC(C)(C)C)c1=O] | LCMS m/z 735.4 (M + 1)$^+$ |

-continued
| Compound | Structure | LCMS Data |
| --- | --- | --- |
| 76 | 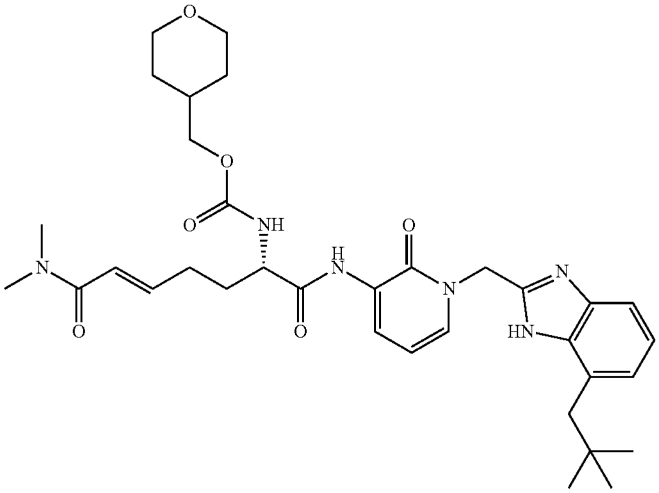 [SMILES: CN(C)C(=O)/C=C/CC[C@H](NC(=O)OCC1CCOCC1)C(=O)Nc1cccn(Cc2nc3cccc(CC(C)(C)C)c3[nH]2)c1=O] | LCMS m/z 635.5 (M + 1)$^+$ |
| 77 | 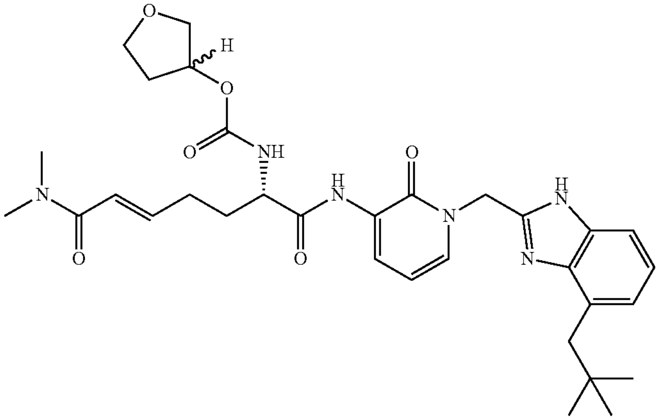 [SMILES: CN(C)C(=O)/C=C/CC[C@H](NC(=O)OC1CCOC1)C(=O)Nc1cccn(Cc2nc3c(CC(C)(C)C)cccc3[nH]2)c1=O] | LCMS m/z 607.4 (M + 1)$^+$ |
| 78 | 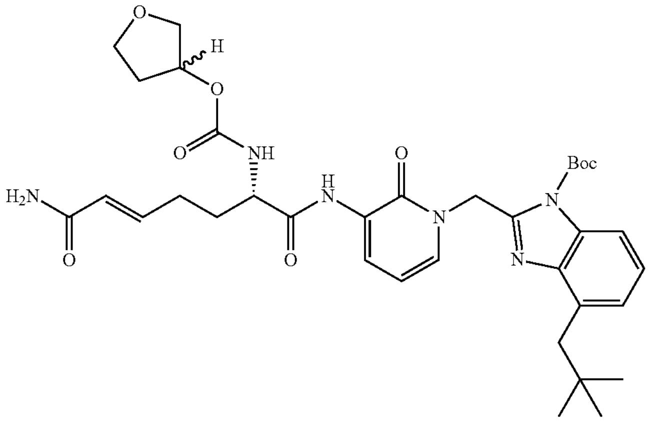 [SMILES: CC(C)(C)Cc1cccc2c1nc(Cn1cccc(NC(=O)[C@H](CC/C=C/C(N)=O)NC(=O)OC3CCOC3)c1=O)n2C(=O)OC(C)(C)C] | LCMS m/z 679.4 (M + 1)$^+$ |

-continued
| Compound | Structure | LCMS Data |
| --- | --- | --- |
| 79 | 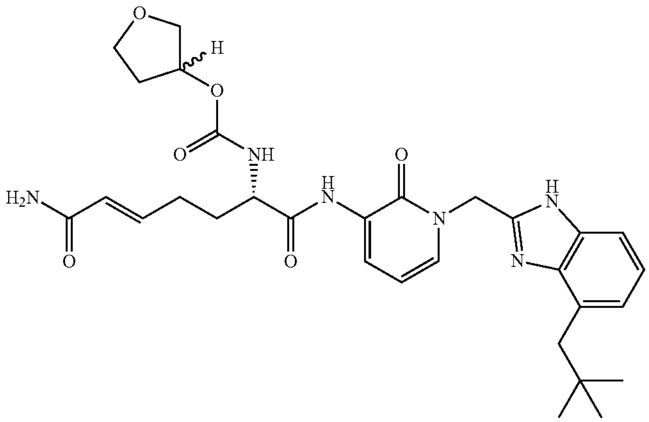 [SMILES: CC(C)(C)Cc1cccc2[nH]c(Cn3cccc(NC(=O)[C@H](CC/C=C/C(N)=O)NC(=O)OC4CCOC4)c3=O)nc12] | LCMS m/z 579.3 $(M + 1)^+$ |
| 80 | 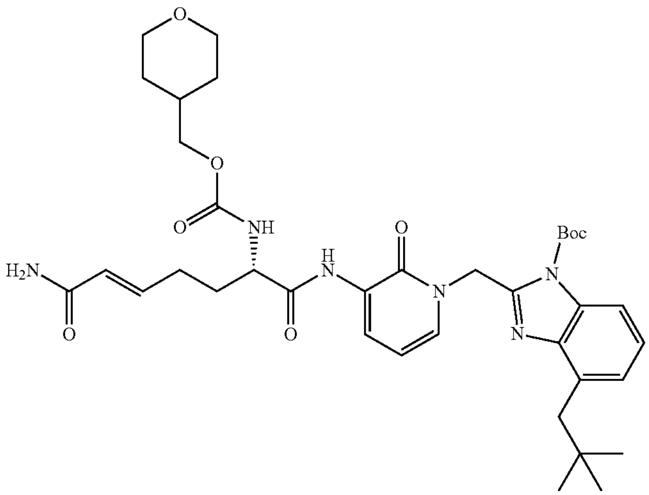 [SMILES: CC(C)(C)Cc1cccc2c1nc(Cn1cccc(NC(=O)[C@H](CC/C=C/C(N)=O)NC(=O)OCC3CCOCC3)c1=O)n2C(=O)OC(C)(C)C] | LCMS m/z 707.5 $(M + 1)^+$ |
| 81 | 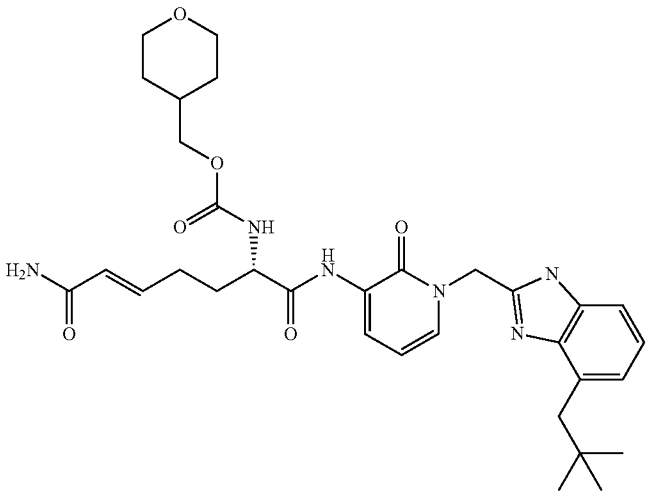 [SMILES: CC(C)(C)Cc1cccc2[nH]c(Cn3cccc(NC(=O)[C@H](CC/C=C/C(N)=O)NC(=O)OCC4CCOCC4)c3=O)nc12] | LCMS m/z 607.4 $(M + 1)^+$ |

-continued
| Compound | Structure | LCMS Data |
| --- | --- | --- |
| 161 | 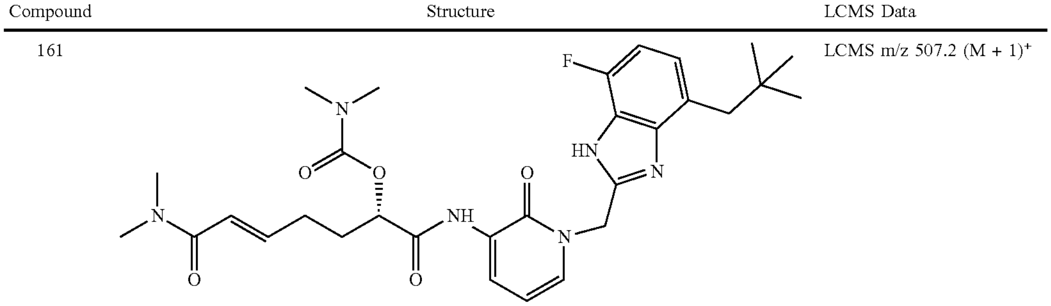 | LCMS m/z 507.2 (M + 1)+ |
| 403 | 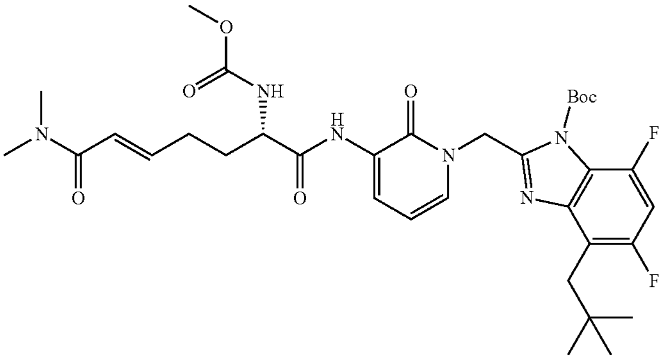 [SMILES: COC(=O)N[C@@H](CC/C=C/C(=O)N(C)C)C(=O)Nc1cccn(Cc2nc3c(CC(C)(C)C)c(F)cc(F)c3n2C(=O)OC(C)(C)C)c1=O] | LCMS m/z 687.4 (M + 1)+ |
| 404 | 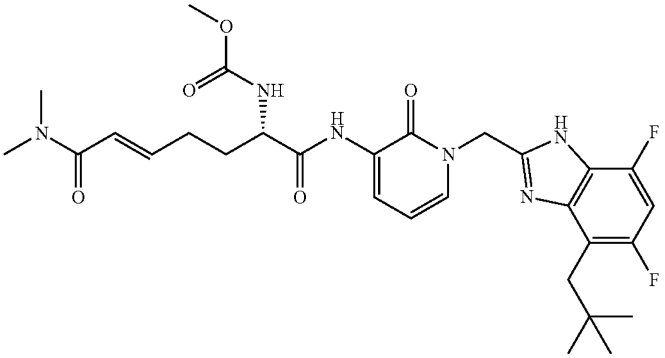 [SMILES: COC(=O)N[C@@H](CC/C=C/C(=O)N(C)C)C(=O)Nc1cccn(Cc2nc3c(CC(C)(C)C)c(F)cc(F)c3[nH]2)c1=O] | LCMS m/z 587.3 (M + 1)+ |
Example 11
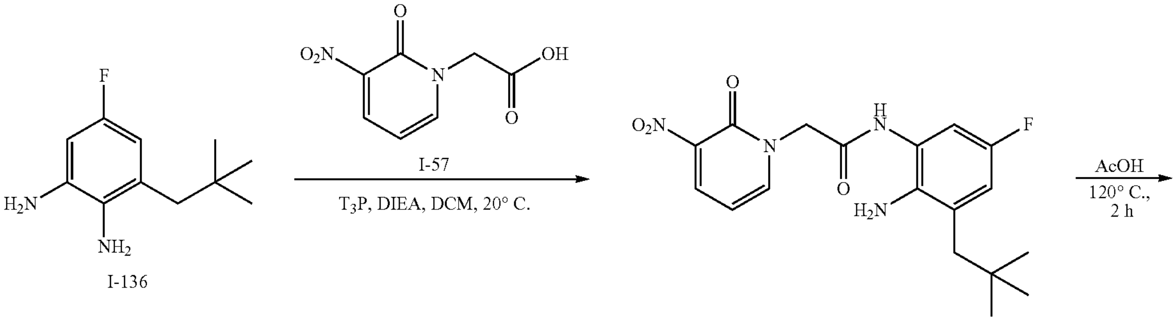
I-136
I-141

-continued

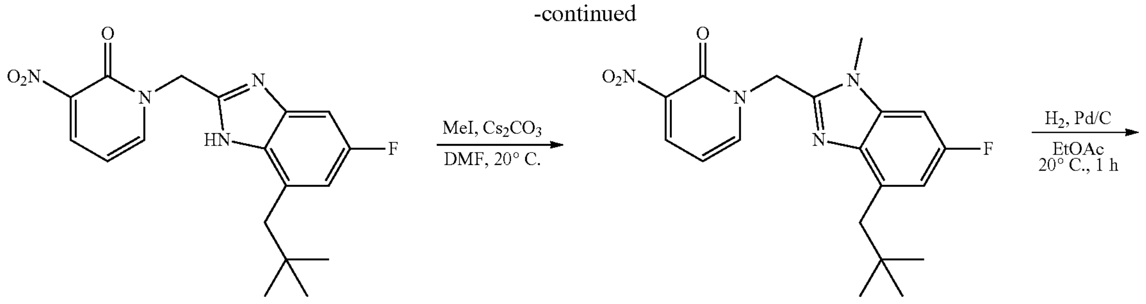

I-142 I-143

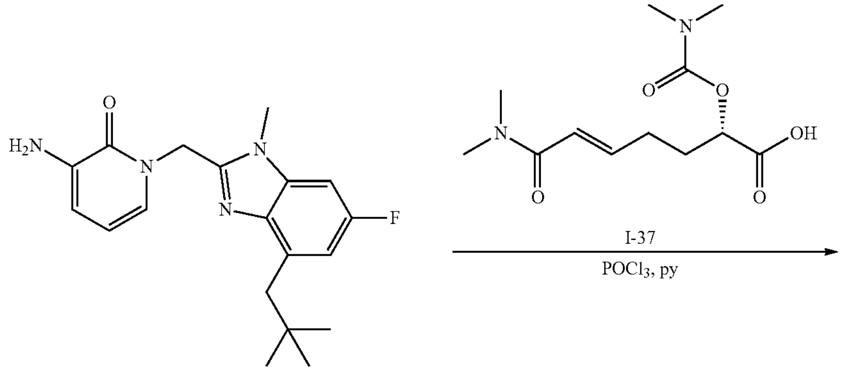

I-144

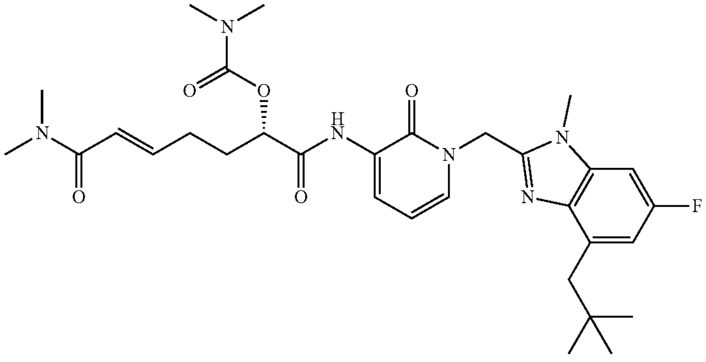

82

To a solution of 2-(3-nitro-2-oxo-1-pyridyl)acetic acid (77.23 mg, 389.78 μmol), 3-(2,2-dimethylpropyl)-5-fluoro-benzene-1,2-diamine (85 mg, 433.09 μmol) and DIEA (111.95 mg, 866.18 μmol) in DCM (2 mL) was added $T_3P$ (413.40 mg) at 20° C. and the reaction was stirred for 12 h at this temperature. The reaction mixture was concentrated. The residue was diluted with sat. $NH_4Cl$ (10 mL) and extracted with EtOAc (5 mL×3). The combined organic layers were washed with brine (10 mL×2), dried over $Na_2SO_4$, filtered and the filtrate was concentrated to give N-[2-amino-3-(2,2-dimethylpropyl)-5-fluoro-phenyl]-2-(3-nitro-2-oxo-1-pyridyl)acetamide (I-141) (140 mg) as a brown gum.

A solution of N-[2-amino-3-(2,2-dimethylpropyl)-5-fluoro-phenyl]-2-(3-nitro-2-oxo-1-pyridyl)acetamide (140 mg, 371.96 μmol) in AcOH (2 mL) was stirred for 2 h at 120° C. The reaction mixture was concentrated and the residue was diluted with sat. $NaHCO_3$ (5 mL) and then extracted with EtOAc (5 mL×3). The combined organic layers were dried over $Na_2SO_4$, filtered and the residue was concentrated. The residue was diluted into EtOAc (2 mL) and filtered. The cake was 1-[[4-(2,2-dimethylpropyl)-6-fluoro-1H-benzimidazol-2-yl]methyl]-3-nitro-pyridin-2-one (I-142) (94 mg, 262.30 μmol, 70.52% yield) as a white solid.

To a solution of 1-[[4-(2,2-dimethylpropyl)-6-fluoro-1H-benzimidazol-2-yl]methyl]-3-nitro-pyridin-2-one (84 mg, 234.40 μmol) and $Cs_2CO_3$ (152.74 mg, 468.79 μmol) in DMF (2 mL) was added MeI (66.54 mg, 468.79 μmol) at 0° C. and the reaction was stirred for 1 h at 20° C. The reaction mixture was diluted with sat. $NH_4Cl$ (10 mL) and extracted with EtOAc (10 mL×3). The combined organic layers were washed with brine (20 mL×2), dried over $Na_2SO_4$, filtered and the filtrate was concentrated. The residue was purified by prep-TLC to afford 1-[[4-(2,2-dimethylpropyl)-6-fluoro-1-methyl-benzimidazol-2-yl]methyl]-3-nitro-pyridin-2-one (I-143) (40 mg, 46% yield) as an orange solid. $^1H$ NMR (400 MHz, $CDCl_3$) δ 8.26 (dd, J=2.1, 7.6 Hz, 1H), 8.13 (dd, J=2.1, 6.7 Hz, 1H), 6.85-6.71 (m, 2H), 6.28 (dd, J=6.8, 7.6 Hz, 1H), 5.47 (s, 2H), 3.82 (s, 3H), 2.84 (s, 2H), 0.87 (s, 9H).

A solution of 1-[[4-(2,2-dimethylpropyl)-6-fluoro-1-methyl-benzimidazol-2-yl]methyl]-3-nitro-pyridin-2-one (65 mg, 174.55 umol, 1 eq.) in EtOAc (10 mL) was hydrogenated over Pd/C (10 mg) (50% wet) under $H_2$ atmosphere (about 15 psi) at 25° C. for 15 min. The mixture was filtered and filtrate was concentrated to dryness to give 3-amino-1-[[4-(2,2-dimethylpropyl)-6-fluoro-1-methyl-benzimidazol-2-yl] methyl]pyridin-2-one (I-144) (60 mg) was got as a brown gum, which was used directly.

To a mixture of (E,2S)-7-(dimethylamino)-2-(dimethylcarbamoyloxy)-7-oxo-hept-5-enoic acid (65 mg, 238.71 umol, 1.49 eq) and 3-amino-1-[[4-(2,2-dimethylpropyl)-6-fluoro-1-methyl-benzimidazol-2-yl]methyl]pyridin-2-one (55 mg, 160.63 umol, 1 eq) in pyridine (2 mL) was added $POCl_3$ (30 mg, 195.66 umol, 18.18 uL, 1.22 eq) at −30° C. The mixture was stirred at that temperature for 30 min. Desired MS was observed on LCMS. The mixture was quenched with $H_2O$ (10 mL) and extracted with EtOAc/MeOH (10:1, 5 mL×3). The combined organic layers were washed with brine (10 mL), dried over $Na_2SO_4$, filtered and concentrated. The residue was purified by prep-HPLC to give [(E,1S)-6-(dimethylamino)-1-[[1-[[4-(2,2-dimethylpropyl)-6-fluoro-1-methyl-benzimidazol-2-yl]methyl]-2-oxo-3-pyridyl]carbamoyl]-6-oxo-hex-4-enyl] N,N-dimethylcarbamate (Compound 82) (15.2 mg, 15% yield) as an off-white solid. LCMS m/z 597.3 $(M+1)^+$. $^1H$ NMR (400 MHz, DMSO-$d_6$) δ 9.32 (s, 1H), 8.21 (dd, J=1.5, 7.3 Hz, 1H), 7.51 (dd, J=1.5, 6.8 Hz, 1H), 7.28 (dd, J=2.3, 9.2 Hz, 1H), 6.78 (dd, J=2.2, 10.8 Hz, 1H), 6.69-6.57 (m, 1H), 6.41-6.30 (m, 2H), 5.45 (s, 2H), 5.08 (dd, J=4.6, 7.5 Hz, 1H), 3.83 (s, 3H), 2.99-2.92 (m, 6H), 2.85-2.78 (m, 6H), 2.31-2.20 (m, 2H), 1.98-1.86 (m, 2H), 0.83 (s, 10H).

The following compound was prepared according to the procedures described in Example 11 using the appropriate intermediates.

-continued

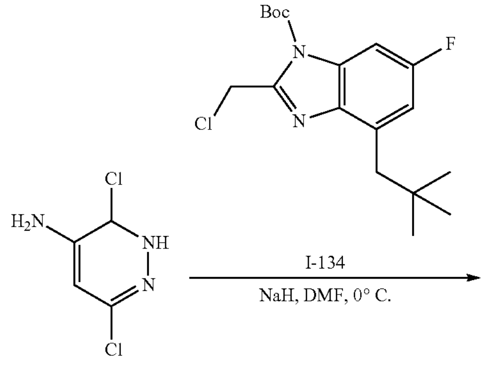

I-146

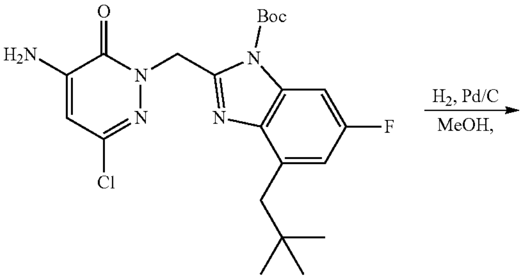

I-147

| Compound | Structure | LCMS Data |
|---|---|---|
| 83 | 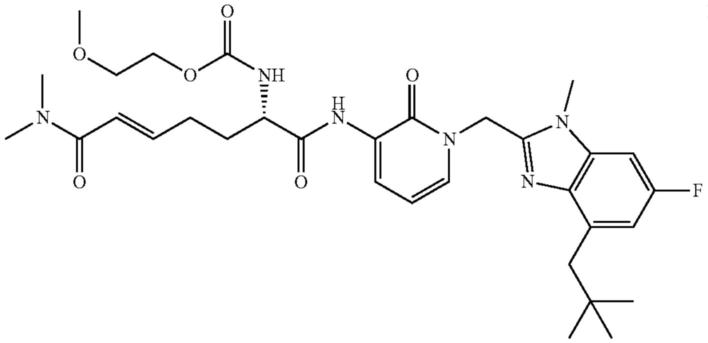 [SMILES: COCCOC(=O)N[C@@H](CC/C=C/C(=O)N(C)C)C(=O)Nc1cccn(Cc2nc3c(CC(C)(C)C)cc(F)cc3n2C)c1=O] | LCMS m/z 627.4 $(M + 1)^+$ |

The Synthesis of Intermediate I-148

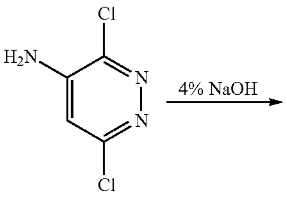

I-145

-continued

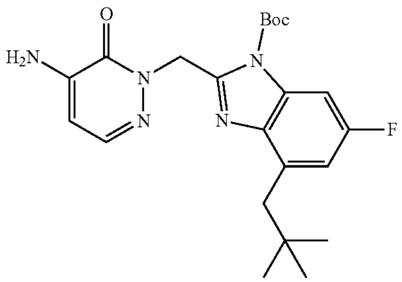

I-148

A mixture of 3,6-dichloropyridazin-4-amine (6 g, 36.59 mmol, 1 eq) in NaOH aq. (100 mL, 4% aq.) was stirred at 100° C. for 24 h. The reaction mixture was quenched by addition HCl 1N until pH~5~6, and then extracted with EtOAc (30 mL×3). The combined organic layers were washed with brine (150 mL×1), dried over $Na_2SO_4$, filtered and concentrated under reduced pressure to give 5-amino-3-chloro-1H-pyridazin-6-one (I-145) (4.1 g) as a brown solid which was used to do next step without purification.

To a solution of 5-amino-3-chloro-1H-pyridazin-6-one (98.44 mg, 676.35 umol, 1.2 eq) in DMF (3 mL) was added NaH (33.81 mg, 845.44 umol, 60% purity, 1.5 eq) at −10° C., then tert-butyl 2-(chloromethyl)-4-(2,2-dimethylpropyl)-6-fluoro-benzimidazole-1-carboxylate (200.00 mg, 563.63 umol, 1 eq) was added at −10° C. The mixture was stirred at 25° C. for 1 hr. The reaction mixture was quenched by addition sat. $NH_4Cl$ (3 mL) and extracted with EtOAc (2 mL×3). The combined organic layers were washed with brine sat. (5 mL×1), dried over $Na_2SO_4$, filtered and concentrated under reduced pressure to give a residue. The residue was purified by prep-TLC to give tert-butyl 2-[(5-amino-3-chloro-6-oxo-pyridazin-1-yl)methyl]-4-(2,2-dimethylpropyl)-6-fluoro-benzimidazole-1-carboxylate (I-147) (0.11 g) as a yellow oil.

To a solution of tert-butyl 2-[(5-amino-3-chloro-6-oxo-pyridazin-1-yl)methyl]-4-(2,2-dimethylpropyl)-6-fluoro-benzimidazole-1-carboxylate (I-147) (110.00 mg, 237.10 umol, 1 eq) in EtOAc (5 mL) was added Pd/C (0.1 g, 237.10 umol, 10% purity) under $N_2$. The suspension was degassed under vacuum and purged with $H_2$ several times. The mixture was stirred under $H_2$ (15 psi) at 25° C. for 1 hour. LCMS showed I-147 remained, so the mixture was stirred for another 3 h under $H_2$ 15 psi at 25° C. The reaction mixture was filtered and the filter was concentrated to give tert-butyl 2-[(5-amino-6-oxo-pyridazin-1-yl)methyl]-4-(2,2-dimethylpropyl)-6-fluoro-benzimidazole-1-carboxylate (I-148) (100 mg) as a yellow oil which was used in the next step without purification.

Example 12

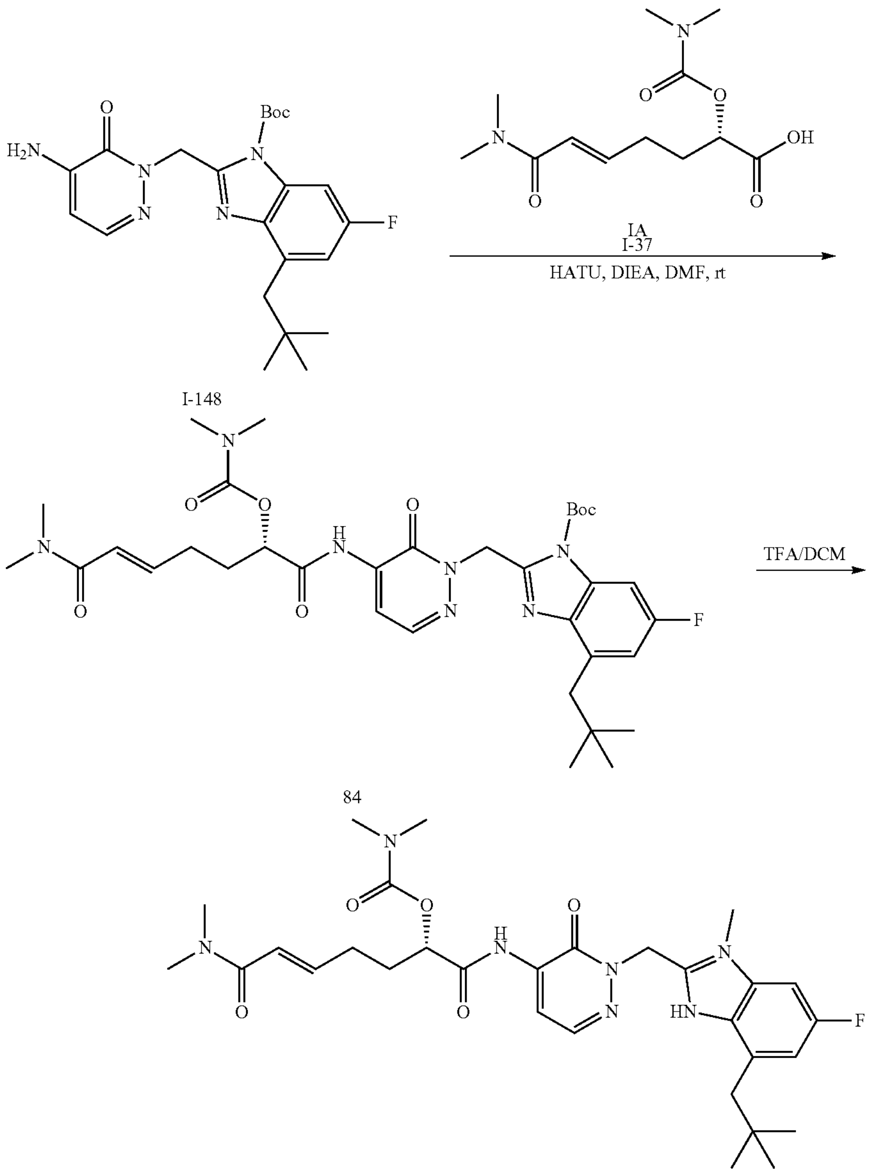

I-148

84

85

To a solution of tert-butyl 2-[(5-amino-6-oxo-pyridazin-1-yl)methyl]-4-(2,2-dimethylpropyl)-6-fluoro-benzimidazole-1-carboxylate (90 mg, 209.55 umol, 1 eq) and (E,2S)-7-(dimethylamino)-2-(dimethylcarbamoyloxy)-7-oxo-hept-5-enoic acid (57.06 mg, 209.55 umol, 1 eq) in py (3 mL) was added $POCl_3$ (64.26 mg, 419.10 umol, 38.95 uL, 2 eq) at −30° C. The mixture was stirred at −30° C. for 0.5 hr. The mixture was quenched with 1N HCl 0.5 mL, and concentrated to give a residue. The residue was purified by prep-TLC to give tert-butyl 2-[[5-[[(E,2S)-7-(dimethylamino)-2-(dimethylcarbamoyloxy)-7-oxo-hept-5-enoyl]amino]-6-oxo-pyridazin-1-yl]methyl]-4-(2,2-dimethylpropyl)-6-fluoro-benzimidazole-1-carboxylate (Compound 84) (52 mg, 36% yield) as a white solid.

A mixture of tert-butyl 2-[[5-[[(E,2S)-7-(dimethylamino)-2-(dimethylcarbamoyloxy)-7-oxo-hept-5-enoyl]amino]-6-oxo-pyridazin-1-yl]methyl]-4-(2,2-dimethylpropyl)-6-fluoro-benzimidazole-1-carboxylate (48.00 mg, 70.20 umol, 1 eq), TFA (320.17 mg, 2.81 mmol, 207.90 uL, 40 eq) in DCM (1 mL) was degassed and purged with $N_2$ for 3 times, and then the mixture was stirred at 25° C. for 1 hr under $N_2$ atmosphere. The mixture was concentrated to give [(E,1S)-6-(dimethylamino)-1-[[2-[[7-(2,2-dimethylpropyl)-5-fluoro-1H-benzimidazol-2-yl]methyl]-3-oxo-pyridazin-4-yl]carbamoyl]-6-oxo-hex-4-enyl]N,N-dimethylcarbamate TFA salt (Compound 85) (29.3 mg, 59% yield) as a light green solid. $^1H$ NMR (400 MHz, DMSO-$d_6$) δ 0.89 (s, 8H) 1.82-2.00 (m, 2H) 2.23-2.34 (m, 2H) 2.51 (br s, 2H) 2.80 (br d, J=11.03 Hz, 7H) 2.85-3.00 (m, 6H) 5.16 (dd, J=8.38, 4.19 Hz, 1H) 5.61 (s, 2H) 6.38 (d, J=15.21 Hz, 1H) 6.59-6.68 (m, 1H) 6.91 (brd, J=10.36 Hz, 1H) 7.25 (br d, J=7.28 Hz, 1H) 7.93 (d, J=4.63 Hz, 1H) 8.02 (d, J=4.85 Hz, 1H) 10.12 (s, 1H).

The following compounds were prepared according to the procedures described in Example 12 using the appropriate intermediates.

The Synthesis of Intermediate I-157

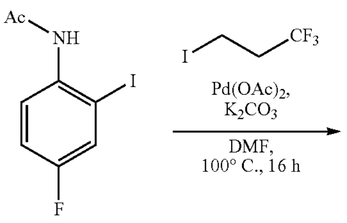

I-125

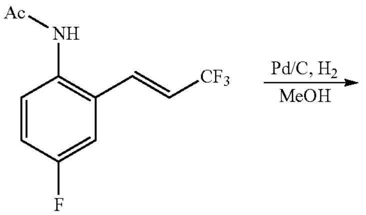

I-149

| Compound | Structure | LCMS Data |
|---|---|---|
| 86 | 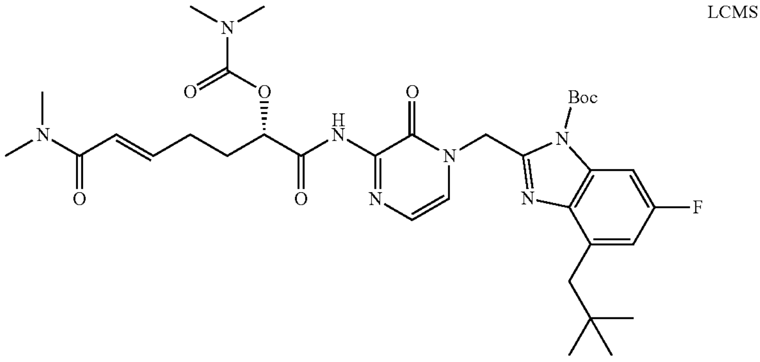 | LCMS m/z 584.3 (M + 1)$^+$ |
| 87 | 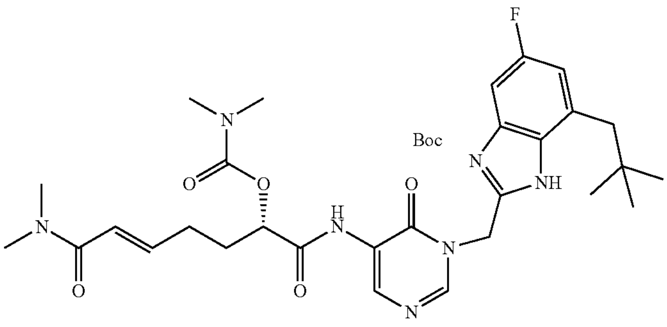 [SMILES: CN(C)C(=O)/C=C/CC[C@H](OC(=O)N(C)C)C(=O)Nc1cncn(Cc2nc3cc(F)cc(CC(C)(C)C)c3[nH]2)c1=O ; "Boc"] | LCMS m/z 584.3 (M + 1)$^+$ |

-continued

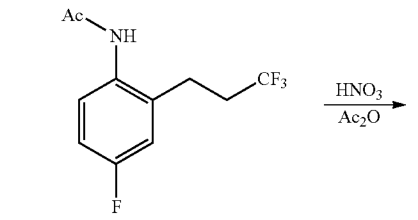

I-150

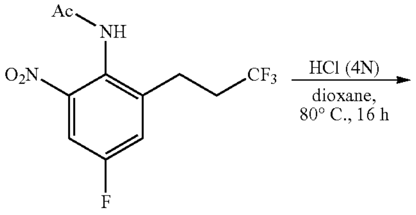

I-151

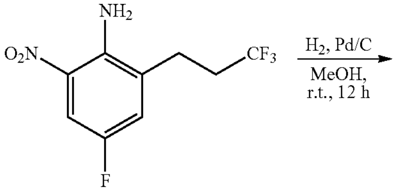

I-152

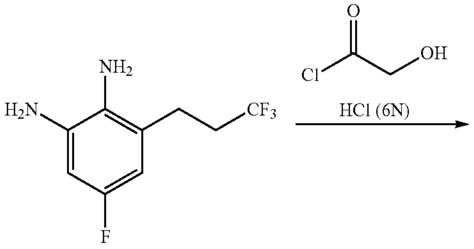

I-153

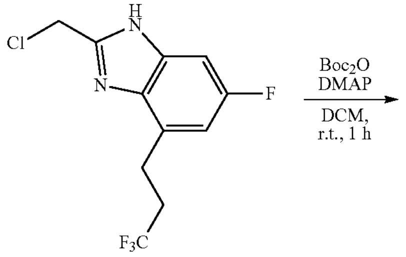

I-154

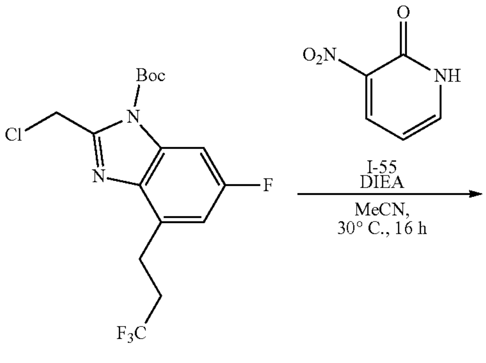

I-155

-continued

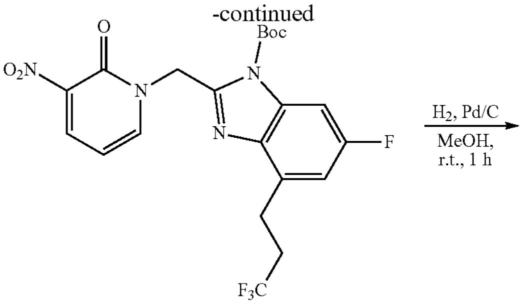

I-156

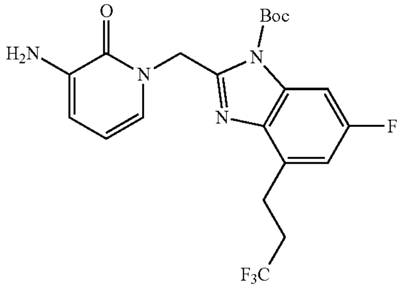

I-157

To a solution of N-(4-fluoro-2-iodo-phenyl)acetamide (20.0 g, 71.7 mmol) in DMF (20 mL) were added $Pd(OAc)_2$ (322 mg, 1.43 mmol), $K_2CO_3$ (34.7 g, 251 mmol) and 1,1,1-trifluoro-3-iodopropane (48.2 g, 215 mmol, 25.2 mL). The mixture was stirred at 110° C. for 36 hr under $N_2$ atmosphere. The mixture was diluted with water (200 mL). The resultant mixture was extracted with EtOAc (200 mL×2). The combined organic layers were washed with brine (100×2 mL), dried over anhydrous $Na_2SO_4$ and concentrated to give a residue. The residue was triturated with (Petroleum ether/EtOAc=20/1, 100 mL) to give N-[4-fluoro-2-[(E)-3,3,3-trifluoroprop-1-enyl] phenyl]acetamide (I-149) (13.5 g, 57% yield) as a light yellow solid. $^1$H NMR (400 MHz, $CDCl_3$) δ7.53 (dd, J=8.8, 5.3 Hz, 1H), 7.24-7.16 (m, 2H), 7.14-7.07 (m, 2H), 6.16 (m, 1H), 2.23 (s, 3H).

To a solution of N-[4-fluoro-2-[(E)-3,3,3-trifluoroprop-1-enyl]phenyl]acetamide (13.5 g, 41.0 mmol) in MeOH (80 mL) was added wet Pd/C (0.1 g, 10% purity). The mixture was stirred at 15° C. for 12 hr under $H_2$ (15 psi) atmosphere. The resulting suspension was filtered and the filtrate was concentrated to give a residue. The residue was purified by chromatography on silica gel to give N-[4-fluoro-2-(3,3,3-trifluoropropyl)phenyl]acetamide (I-150) (12 g) as a light yellow solid.

To a solution of N-[4-fluoro-2-(3,3,3-trifluoropropyl)phenyl]acetamide (5.5 g, 22.1 mmol) in $Ac_2O$ (15 mL) was added $HNO_3$ (4.28 g, 44.1 mmol, 3.06 mL, 65% purity) dropwise at 0° C. The mixture was stirred at 0° C. for 15 min. The mixture was stirred at 12° C. for 6 h. The mixture was diluted with water (40 mL) and extracted with EtOAc (40 mL×2). The combined organic layers were washed with saturated $NaHCO_3$ (40 mL×2) and brine (60 mL) in turn, dried over anhydrous $Na_2SO_4$ and concentrated to give a residue. The residue was purified by chromatography on silica gel to give N-[4-fluoro-2-nitro-6-(3,3,3-trifluoropropyl)phenyl]acetamide (I-151) (3.4 g, 47% yield) as a yellow solid. $^1$H NMR (400 MHz, $CDCl_3$) δ8.02 (s, 1H), 7.66 (dd, J=7.5, 2.9 Hz, 1H), 7.29 (dd, J=8.3, 2.9 Hz, 1H), 2.97-2.88 (m, 2H), 2.54-2.41 (m, 2H), 2.25 (s, 3H).

To a solution of N-[4-fluoro-2-nitro-6-(3,3,3-trifluoropropyl)phenyl]acetamide (2.90 g, 8.87 mmol) in $H_2O$ (20 mL)/dioxane (20 mL) was added conc. HCl (18.4 g, 171 mmol, 18.0 mL). The mixture was stirred at 80° C. for 14 h under $N_2$ atmosphere. The mixture was diluted with water (60 mL). The resultant mixture was extracted with EtOAc (60 mL×2). The combined organic layers were washed with brine (60 mL×2) and saturated $NaHCO_3$ (60 mL×2) in turn, dried over anhydrous $Na_2SO_4$ and concentrated to give 4-fluoro-2-nitro-6-(3,3,3-trifluoropropyl)aniline (I-152) (2.5 g) as a brown solid. The residue was used in the next step without further purification. $^1$H NMR (400 MHz, $CDCl_3$) δ7.83 (dd, J=8.8, 2.9 Hz, 1H), 7.13 (dd, J=8.1, 2.9 Hz, 1H), 6.23-5.90 (m, 2H), 2.91-2.78 (m, 2H), 2.56-2.38 (m, 2H).

To a solution of 4-fluoro-2-nitro-6-(3,3,3-trifluoropropyl) aniline (2.50 g, 9.91 mmol) in MeOH (25 mL) was added Pd/C (0.2 g, 10% purity). The mixture was stirred at 15° C. for 12 hr under $H_2$ (15 psi) atmosphere. The resulting suspension was filtered and the filtrate was concentrated to give 5-fluoro-3-(3,3,3-trifluoropropyl) benzene-1,2-diamine (I-153) (2.2 g) as a brown oil. The residue was used in the next step without purification. $^1$H NMR (400 MHz, $CDCl_3$) δ 6.51-6.23 (m, 2H), 3.24 (br. s., 4H), 2.82-2.68 (m, 2H), 2.50-2.26 (m, 2H).

A mixture of 5-fluoro-3-(3,3,3-trifluoropropyl)benzene-1, 2-diamine (1.20 g, 5.40 mmol) and 2-chloroacetic acid (612 mg, 6.48 mmol, 729 μL) in HCl (6 M, 12 mL) was stirred at 100° C. for 6 hr. The mixture was quenched with $NH_3$—$H_2O$ (40 mL). The resulting solution was extracted with EtOAc (50 mL×2). The combined organic layers were washed with brine (50 mL), dried over anhydrous $Na_2SO_4$ and concentrated to give 2-(chloromethyl)-6-fluoro-4-(3,3,3-trifluoro propyl)-1H-benzimidazole (I-154) (1.5 g, 79% yield) as a brown solid. The residue was used in the next step without purification. LCMS m/z 281.0 $(M+1)^+$.

To a solution of 2-(chloromethyl)-6-fluoro-4-(3,3,3-trifluoropropyl)-1H-benzimidazole (1.50 g, 4.28 mmol) and DMAP (522 mg, 4.28 mmol) in DCM (20 mL) was added $Boc_2O$ (933 mg, 4.28 mmol, 982 μL) in portions. The mixture was stirred at 15° C. for 1 hr. The resulting solution was concentrated to give a residue. The residue was purified by chromatography on silica to give tert-butyl 2-(chloromethyl)-6-fluoro-4-(3,3,3-trifluoropropyl)benzimidazole-1-carboxylate (I-155) (1.2 g, 63% yield) as alight yellow oil. $^1$H NMR (400 MHz, $CDCl_3$) δ 7.61 (dd, J=9.2, 2.3 Hz, 1H), 6.95 (dd, J=9.9, 1.9 Hz, 1H), 5.04 (s, 2H), 3.30-3.22 (m, 2H), 2.69-2.54 (m, 2H), 1.74 (s, 9H).

To a solution of tert-butyl 2-(chloromethyl)-6-fluoro-4-(3,3,3-trifluoropropyl)benzimidazole-1-carboxylate (1.20 g, 2.68 mmol) and 3-nitropyridin-2(1H)-one (450 mg, 3.21 mmol) in MeCN (10 mL) was added DIEA (692 mg, 5.36 mmol, 933 μL). The mixture was stirred at 30° C. for 14 hr. The resulting solution was concentrated to give a residue. The residue was triturated with ($H_2O$/ethyl acetate=5/1, 24 mL) to give tert-butyl 6-fluoro-2-[(3-nitro-2-oxo-1-pyridyl)methyl]-4-(3,3,3-trifluoropropyl)benzimidazole-1-carboxylate (I-156) (0.7 g, 51% yield) as a light purple solid. $^1$H NMR (400 MHz, DMSO-$d_6$) δ 8.54 (dd, J=7.7, 2.1 Hz, 1H), 8.28 (dd, J=6.7, 2.0 Hz, 1H), 7.53 (dd, J=9.3, 2.4 Hz, 1H), 7.22 (dd, J=10.4, 2.4 Hz, 1H), 6.58-6.54 (m, 1H), 5.72 (s, 2H), 3.04-2.94 (m, 2H), 2.65-2.54 (m, 2H), 1.70 (s, 9H).

To a solution of tert-butyl 6-fluoro-2-[(3-nitro-2-oxo-1-pyridyl)methyl]-4-(3,3,3-trifluoropropyl)benzimidazole-1-carboxylate (0.7 g, 1.37 mmol) in ethyl acetate (20 mL) was added wet Pd/C (70 mg, 10% purity). The mixture was stirred at 15° C. for 1 hr under $H_2$ (15 psi) atmosphere. The mixture was filtered and the filtrate was concentrated to give tert-butyl 2-[(3-amino-2-oxo-1-pyridyl)methyl]-6-fluoro-4-(3,3,3-trifluoropropyl) benzimidazole-1-carboxylate (I-157) (0.65 g, 99% yield) as a light brown solid. LCMS m/z 455.3 $(M+1)^+$. $^1$H NMR (400 MHz, $CDCl_3$) δ 7.50 (dd, J=9.2, 2.4 Hz, 1H), 6.87 (dd, J=9.9, 2.4 Hz, 1H), 6.76 (dd, J=6.8, 1.6 Hz, 1H), 6.62 (dd, J=7.2, 1.6 Hz, 1H), 6.14 (t, J=7.0 Hz, 1H), 5.59 (s, 2H), 4.20 (s, 2H), 3.14-3.01 (m, 2H), 2.56-2.41 (m, 2H), 1.72 (s, 9H).

The following intermediates were prepared according to the procedures described for the synthesis of I-157 using the appropriate reagents.

| Compound | Structure | LCMS Data |
|---|---|---|
| I-158 | 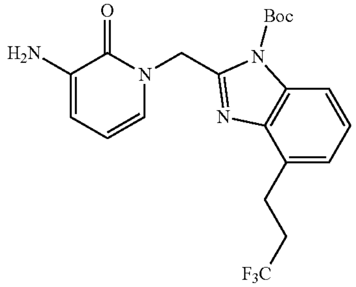 [SMILES: CC(C)(C)OC(=O)n1c(Cn2cccc(N)c2=O)nc2c(CCC(F)(F)F)cccc21] | LCMS m/z 337.1 $(M - 100 + 1)^+$ |
| I-159 | 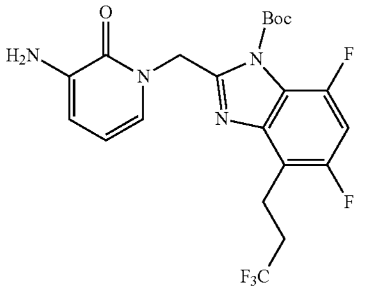 [SMILES: CC(C)(C)OC(=O)n1c(Cn2cccc(N)c2=O)nc2c(CCC(F)(F)F)c(F)cc(F)c21] | LCMS m/z 373.1 $(M - 100 + 1)^+$ |

-continued
| Compound | Structure | LCMS Data |
|---|---|---|
| I-529 | 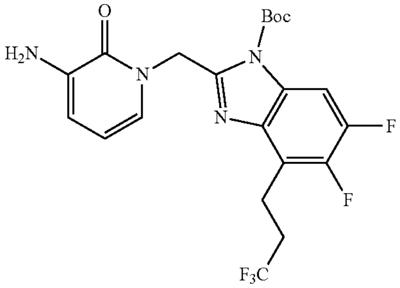 [SMILES: CC(C)(C)OC(=O)n1c(Cn2cccc(N)c2=O)nc2c(CCC(F)(F)F)c(F)c(F)cc21] | LCMS m/z 373.1 (M − 100 + 1)$^+$ |
Example 13
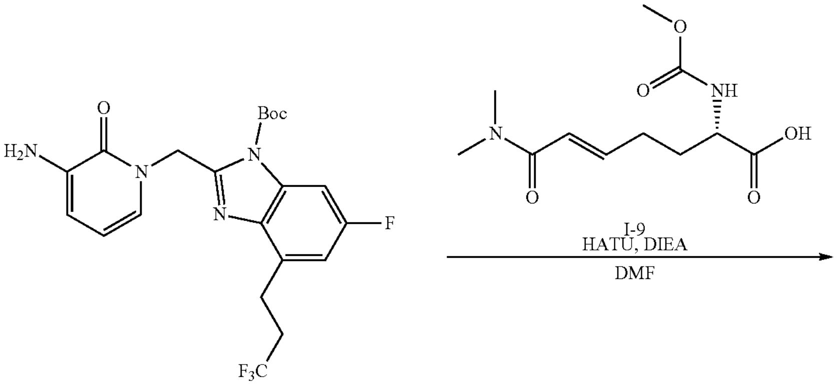
I-157
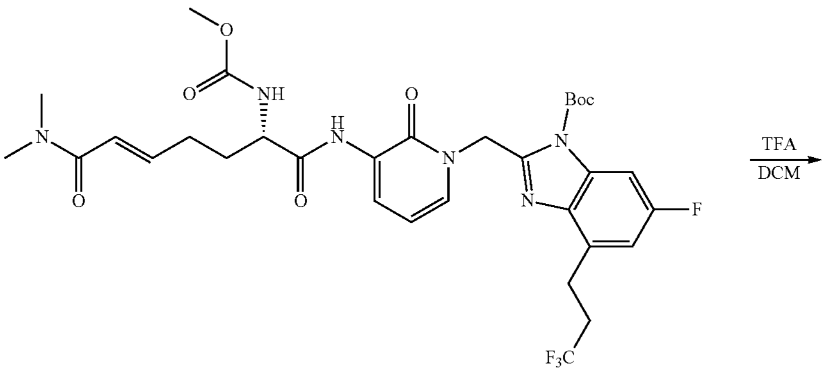
88

-continued

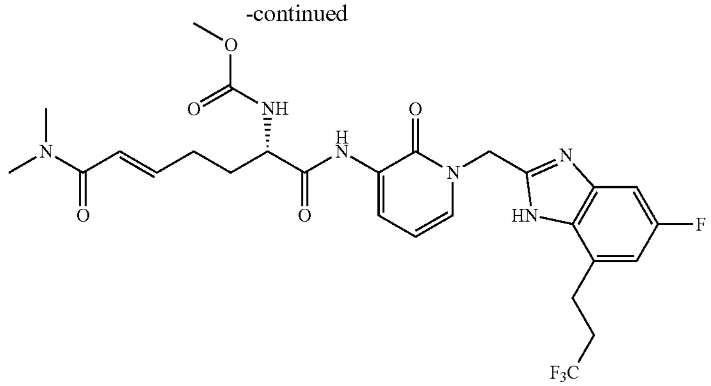

89

To a solution of tert-butyl 2-[(3-amino-2-oxo-1-pyridyl) methyl]-6-fluoro-4-(3,3,3-trifluoropropyl)benzimidazole-1-carboxylate (30 mg, 62.7 μmol) and (E,2S)-7-(dimethyl-amino)-2-(methoxycarbonylamino)-7-oxo-hept-5-enoic acid (19.4 mg, 75.3 μmol) in DMF (1 mL) were added HATU (28.6 mg, 75.3 μmol), DIEA (16.2 mg, 125 μmol, 21.9 μL) in turn. The mixture was stirred at 30° C. for 16 hr. The mixture was diluted with water (40 mL). The resultant mixture was extracted with EtOAc (30 mL×2). The combined organic layers were washed with brine (60×3 mL), dried over anhydrous $Na_2SO_4$ and concentrated to give a residue. The residue was purified by chromatography on silica gel to give tert-butyl 2-[[3-[[(E,2S)-7-(dimethyl-amino)-2-(methoxycarbonylamino)-7-oxo-hept-5-enoyl] amino]-2-oxo-1-pyridyl]methyl]-6-fluoro-4-(3,3,3-trifluoropropyl)benzimidazole-1-carboxylate (Compound 88) (24.9 mg, 57% yield) as a white solid. LCMS m/z 695.2 $(M+1)^+$. $^1H$ NMR (400 MHz, DMSO-$d_6$) δ8.43 (s, 1H), 7.45 (d, J=7.0 Hz, 1H), 7.00-6.85 (m, 1H), 6.90 (d, J=7.7 Hz, 1H), 6.74-6.61 (m, 2H), 6.37 (d, J=8.9 Hz, 1H), 5.84-5.69 (m, 1H), 5.58-5.46 (m, 2H), 4.81 (s, 2H), 3.34 (br. s., 1H), 2.70 (s, 3H), 2.21-2.09 (m, 5H), 2.00 (s, 3H), 1.85-1.71 (m, 2H), 1.45-1.31 (m, 2H), 1.03 (d, J=5.3 Hz, 2H), 0.88-0.83 (m, 1H), 0.86 (s, 7H), 0.88-0.81 (m, 1H).

To a solution of tert-butyl 2-[[3-[[(E,2S)-7-(dimethyl-amino)-2-(methoxycarbonylamino)-7-oxo-hept-5-enoyl] amino]-2-oxo-1-pyridyl]methyl]-6-fluoro-4-(3,3,3-trifluoropropyl)benzimidazole-1-carboxylate (0.120 g, 173 μmol) in DCM (6 mL) was added TFA (3.08 g, 27.0 mmol, 2 mL) at 0° C. The mixture was stirred at 10° C. for 1 hr. The mixture was concentrated to give a residue. The residue was purified by prep-HPLC and prep-SFC to give methyl N-[(E, 1S)-6-(dimethylamino)-1-[[1-[[5-fluoro-7-(3,3,3-trifluoro-propyl)-1H-benzimidazol-2-yl] methyl]-2-oxo-3-pyridyl] carbamoyl]-6-oxo-hex-4-enyl]carbamate (Compound 89) (41.2 mg, 67% yield) as a white solid. LCMS m/z 595.2 $(M+1)^+$. $^1H$ NMR (400 MHz, DMSO-$d_6$) δ9.27 (s, 1H), 8.25 (dd, J=7.4, 1.6 Hz, 1H), 7.74 (d, J=7.8 Hz, 1H), 7.57 (dd, J=6.9, 1.6 Hz, 1H), 7.15 (s, 1H), 7.00 (d, J=8.9 Hz, 1H), 6.68-6.53 (m, 1H), 6.43-6.29 (m, 2H), 5.40 (s, 2H), 4.28-4.07 (m, 1H), 3.54 (s, 3H), 3.16-3.06 (m, 2H), 2.98 (s, 3H), 2.83 (s, 3H), 2.77-2.63 (m, 2H), 2.30-2.16 (m, 2H), 1.94-1.65 (m, 2H).

The following compounds were prepared according to the procedures described for the synthesis of Example 13 using the appropriate intermediates.

| Compound | Structure | LCMS Data |
|---|---|---|
| 90 | 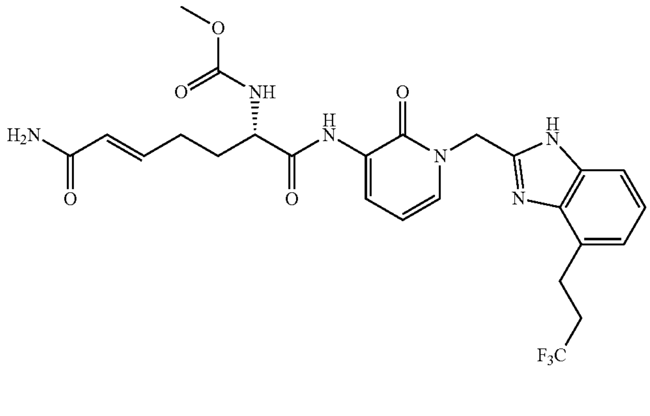 [SMILES: COC(=O)N[C@@H](CC/C=C/C(N)=O)C(=O)Nc1cccn(Cc2nc3c(CCC(F)(F)F)cccc3[nH]2)c1=O] | LCMS m/z 549.3 $(M + 1)^+$. |

-continued
| Compound | Structure | LCMS Data |
| --- | --- | --- |
| 91 | 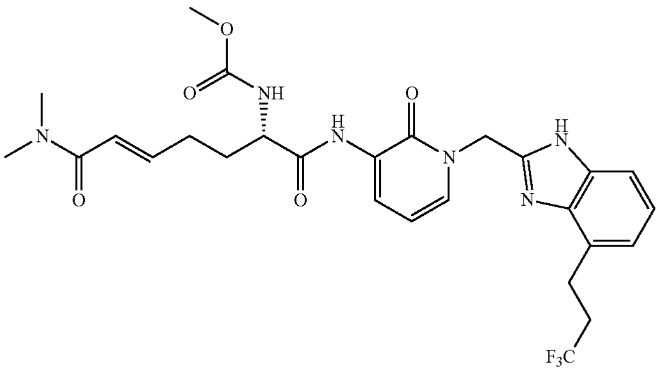 [SMILES: COC(=O)N[C@@H](CC/C=C/C(=O)N(C)C)C(=O)Nc1cccn(Cc2nc3c(CCC(F)(F)F)cccc3[nH]2)c1=O] | LCMS m/z 577.4 (M + 1)$^+$. |
| 92 | 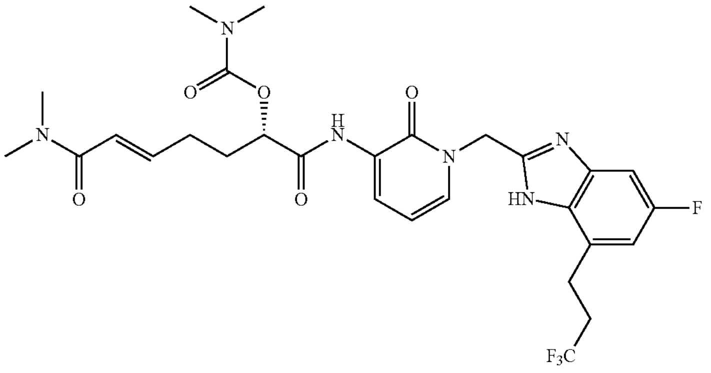 [SMILES: CN(C)C(=O)/C=C/CC[C@H](OC(=O)N(C)C)C(=O)Nc1cccn(Cc2nc3cc(F)cc(CCC(F)(F)F)c3[nH]2)c1=O] | LCMS m/z 609.2 (M + 1)$^+$ |
| 93 | 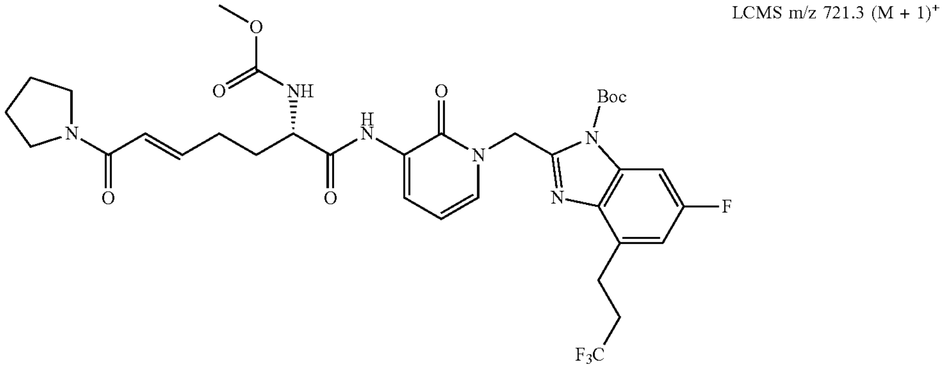 | LCMS m/z 721.3 (M + 1)$^+$ |
| 94 | 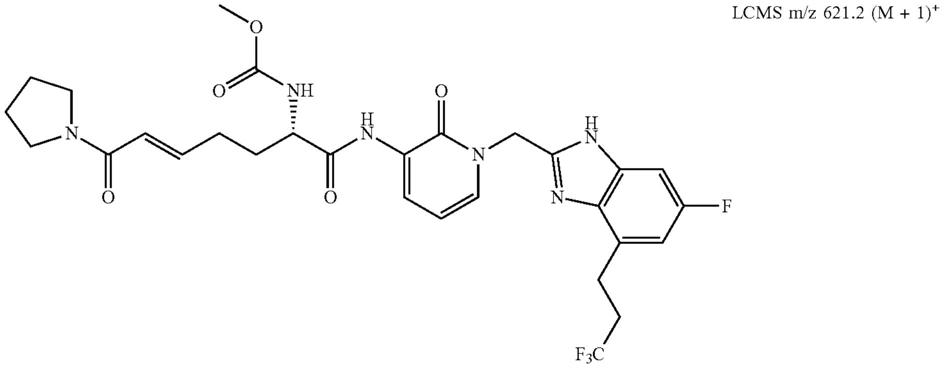 | LCMS m/z 621.2 (M + 1)$^+$ |

-continued
| Compound | Structure | LCMS Data |
|---|---|---|
| 95 | 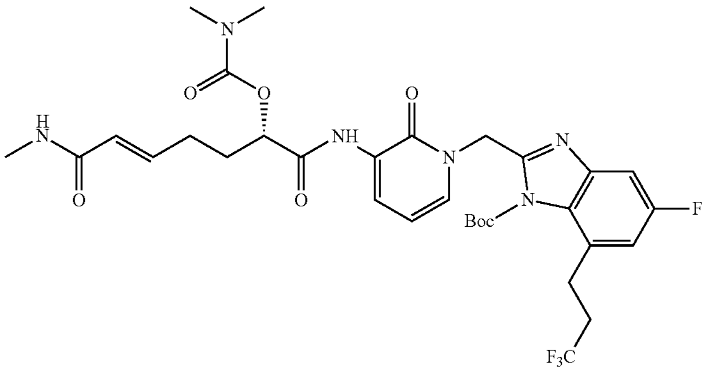 [SMILES: CNC(=O)/C=C/CC[C@H](OC(=O)N(C)C)C(=O)Nc1cccn(Cc2nc3cc(F)cc(CCC(F)(F)F)c3n2C(=O)OC(C)(C)C)c1=O] | LCMS m/z 595.2 (M + 1 − 100)$^+$ |
| 96 | 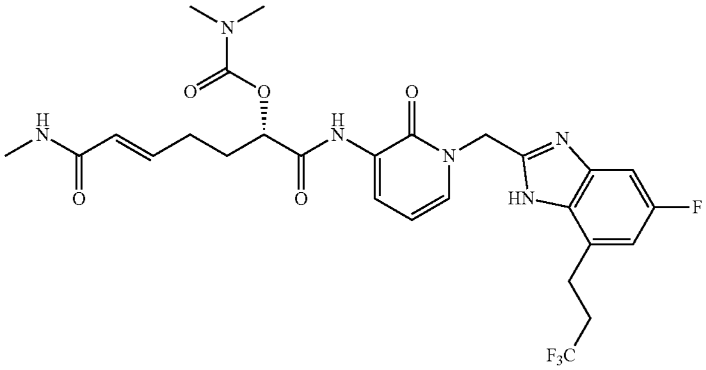 | LCMS m/z 595.2 (M + 1)$^+$ |
| 97 | 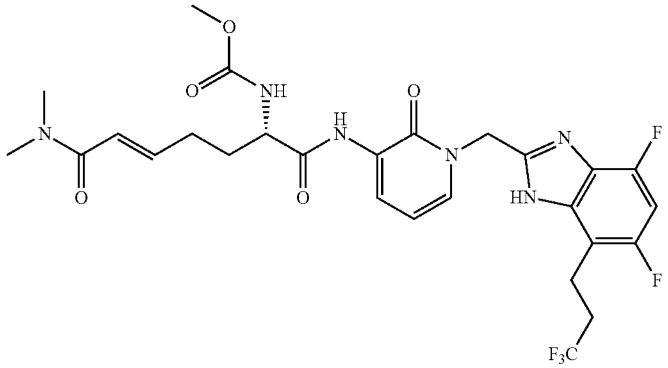 [SMILES: COC(=O)N[C@@H](CC/C=C/C(=O)N(C)C)C(=O)Nc1cccn(Cc2nc3c(F)cc(F)c(CCC(F)(F)F)c3[nH]2)c1=O] | LCMS m/z 612.2 (M + 1)$^+$ |
| 98 | 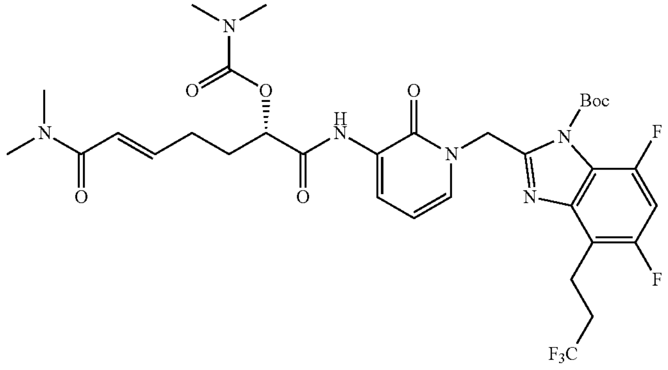 [SMILES: CN(C)C(=O)/C=C/CC[C@H](OC(=O)N(C)C)C(=O)Nc1cccn(Cc2nc3c(CCC(F)(F)F)c(F)cc(F)c3n2C(=O)OC(C)(C)C)c1=O] | LCMS m/z 727.3 (M + 1)$^+$ |

-continued
| Compound | Structure | LCMS Data |
|---|---|---|
| 99 | 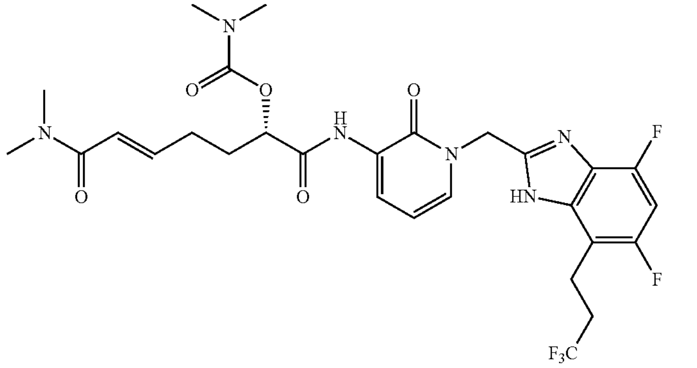 [SMILES: CN(C)C(=O)/C=C/CC[C@H](OC(=O)N(C)C)C(=O)Nc1cccn(Cc2nc3c(F)cc(F)c(CCC(F)(F)F)c3[nH]2)c1=O] | LCMS m/z 627.3 $(M+1)^+$ |
| 405 | 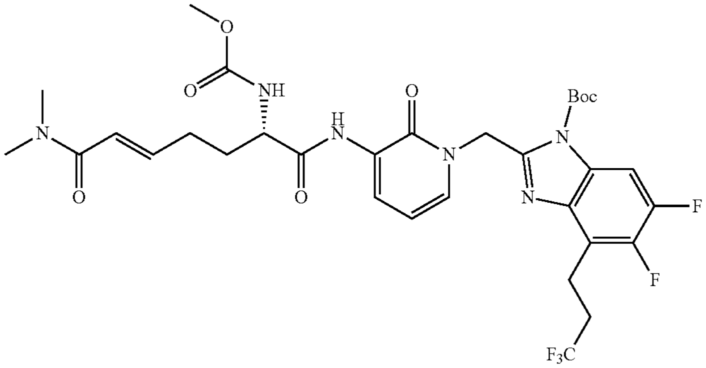 [SMILES: COC(=O)N[C@@H](CC/C=C/C(=O)N(C)C)C(=O)Nc1cccn(Cc2nc3c(CCC(F)(F)F)c(F)c(F)cc3n2C(=O)OC(C)(C)C)c1=O] | LCMS m/z 713.3 $(M+1)^+$ |
| 406 | 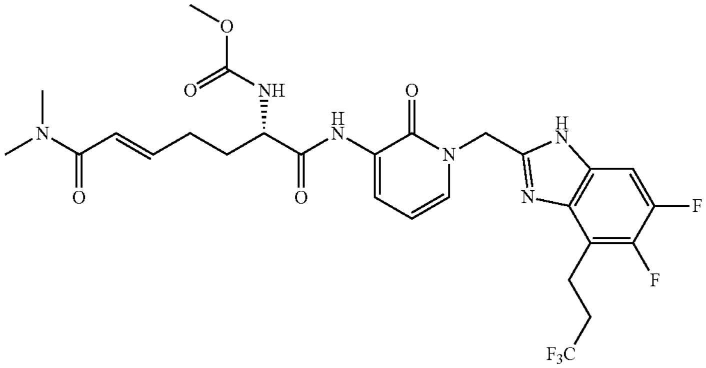 [SMILES: COC(=O)N[C@@H](CC/C=C/C(=O)N(C)C)C(=O)Nc1cccn(Cc2nc3c(CCC(F)(F)F)c(F)c(F)cc3[nH]2)c1=O] | LCMS m/z 613.3 $(M+1)^+$ |
The Synthesis of Intermediate I-164
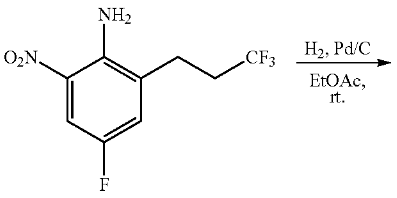
I-152
-continued
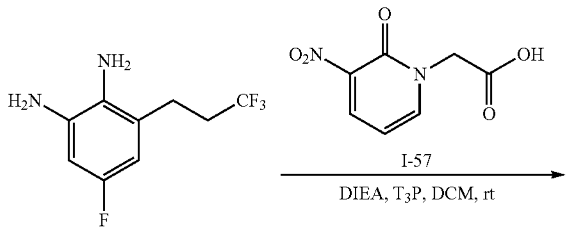
I-160

-continued

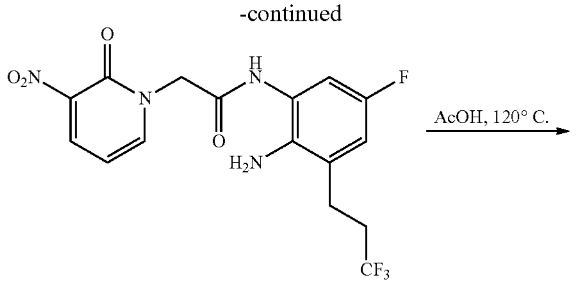

I-161

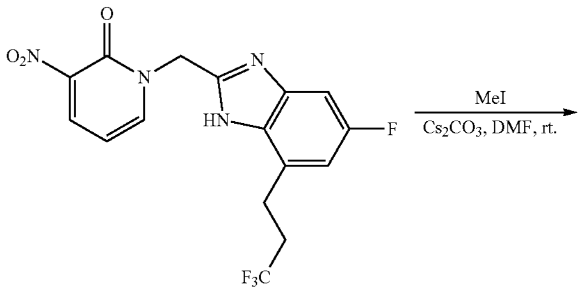

I-162

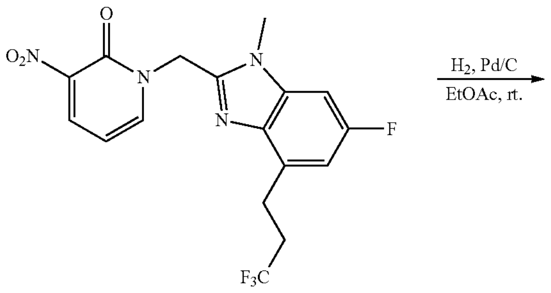

I-163

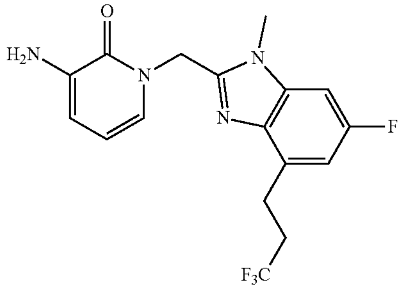

I-164

To a solution of 4-fluoro-2-nitro-6-(3,3,3-trifluoropropyl) aniline (1.5 g, 5.95 mmol) in EtOAc (40 mL) was added Pd/C (0.5 g, 10% purity) under $N_2$. The suspension was degassed under vacuum and purged with $H_2$ several times. The mixture was stirred under $H_2$ (15 psi) at 25° C. for 1 hour. The reaction mixture was filtered and the filtrate was concentrated in vacuum to give 5-fluoro-3-(3,3,3-trifluoro-propyl)benzene-1,2-diamine (I-160) (1.35 g) as a yellow oil.

The mixture of 5-fluoro-3-(3,3,3-trifluoropropyl)benzene-1,2-diamine (0.45 g, 2.03 mmol), 2-(3-nitro-2-oxo-1-pyridyl)acetic acid (300.97 mg, 1.52 mmol) and DIEA (523.53 mg, 4.05 mmol) in DCM (5 mL) was added $T_3P$ (1.93 g, 3.04 mmol, 50% purity) at 30° C. The reaction mixture was stirred at 30° C. for 12 hours. The reaction mixture was added $H_2O$ (10 mL), and then extracted with DCM (5 mL*2). The combined organic phase was dried with anhydrous $Na_2SO_4$, filtered and concentrated in vacuum to give N-[2-amino-5-fluoro-3-(3,3,3-trifluoropropyl)phenyl]-2-(3-nitro-2-oxo-1-pyridyl)acetamide (I-161) (0.67 g) as a brown solid.

The reaction mixture of N-[2-amino-5-fluoro-3-(3,3,3-trifluoropropyl)phenyl]-2-(3-nitro-2-oxo-1-pyridyl)acetamide (0.67 g, 1.67 mmol) in AcOH (6 mL) was stirred at 120° C. for 11 hours. The reaction mixture was concentrated in vacuum to give a brown solid. The residue was washed by petroleum ether (20 mL) to give 1-[[5-fluoro-7-(3,3,3-trifluoropropyl)-1H-benzimidazol-2-yl]methyl]-3-nitro-pyridin-2-one (I-162) (0.6 g) as a brown solid.

The mixture of 1-[[5-fluoro-7-(3,3,3-trifluoropropyl)-1H-benzimidazol-2-yl]methyl]-3-nitro-pyridin-2-one (200 mg, 520.45 umol) and $Cs_2CO_3$ (339.14 mg, 1.04 mmol) in DMF (3 mL) was added MeI (147.74 mg, 1.04 mmol) at 0° C. The reaction mixture was stirred at 25° C. for 1 hour. The reaction mixture was quenched by adding saturated $NH_4Cl$ (20 mL), and extracted with ethyl acetate (5 mL*3). The combined organic phase was washed with brine (20 mL*1), dried with anhydrous $Na_2SO_4$, filtered and concentrated in vacuum. The residue was purified by column chromatography to give 1-[[6-fluoro-1-methyl-4-(3,3,3-trifluoropropyl) benzimidazol-2-yl]methyl]-3-nitro-pyridin-2-one (I-163) (0.15 g, 56% yield) as a light yellow solid.

To a solution of 1-[[6-fluoro-1-methyl-4-(3,3,3-trifluoro-propyl)benzimidazol-2-yl]methyl]-3-nitro-pyridin-2-one (0.15 g, 376.59 umol) in EtOAc (10 mL) was added Pd/C (0.2 g, 10% purity) under $N_2$. The suspension was degassed under vacuum and purged with $H_2$ several times. The mixture was stirred under $H_2$ (15 psi) at 25° C. for 1 hr. The reaction mixture was filtered and the filtrate was concentrated in vacuum to give 3-amino-1-[[6-fluoro-1-methyl-4-(3,3,3-trifluoropropyl)benzimidazol-2-yl]methyl]pyridin-2-one (I-164) (150 mg) as a brown solid. LCMS m/z 369.3 $(M+1)^+$.

Example 14

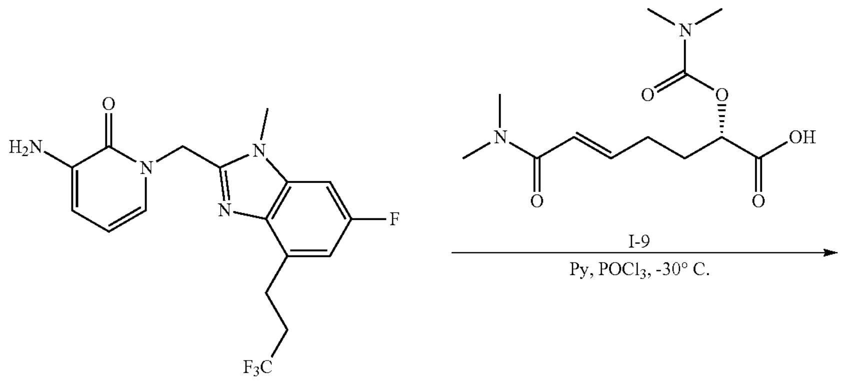

I-164

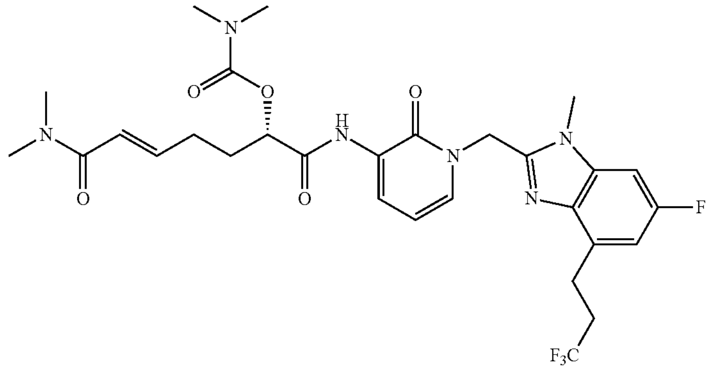

100

The mixture of 3-amino-1-[[6-fluoro-1-methyl-4-(3,3,3-trifluoropropyl)benzimidazol-2-yl]methyl]pyridin-2-one (65 mg, 176.47 umol) and (E,2S)-7-(dimethylamino)-2-(dimethylcarbamoyloxy)-7-oxo-hept-5-enoic acid (52.86 mg, 194.12 umol) in Py (2 mL) was cooled to −30° C., then $POCl_3$ (54.12 mg, 352.95 umol) was added dropwise at −30° C. The reaction mixture was stirred at −30° C. for 0.5 hour. TLC showed the reaction was reacted mostly. The reaction mixture was quenched by adding saturated $NaHCO_3$ (10 mL), and extracted with ethyl acetate (5 mL*2). The combined organic phase was washed with brine (10 mL*1), dried with anhydrous $Na_2SO_4$, filtered and concentrated in vacuum. The residue was purified by prep-TLC to give [(E,1S)-6-(dimethylamino)-1-[[1-[[6-fluoro-1-methyl-4-(3,3,3-trifluoropropyl)benzimidazol-2-yl]methyl]-2-oxo-3-pyridyl]carbamoyl]-6-oxo-hex-4-enyl] N,N-dimethylcarbamate (Compound 100) (23.6 mg, 20% yield) as a brown gum. LCMS m/z 623.4 $(M+1)^+$. $^1H$ NMR (400 MHz, DMSO-$d_6$) δ 9.33 (d, J=16.75 Hz, 1H) 8.22 (dd, J=7.34, 1.71 Hz, 1H) 7.57 (d, J=6.36 Hz, 1H) 7.36 (dd, J=9.17, 2.20 Hz, 1H) 7.01 (dd, J=10.70, 2.14 Hz, 1H) 6.58-6.69 (m, 1H) 6.31-6.43 (m, 2H) 5.46 (s, 2H) 5.05-5.12 (m, 1H) 3.87 (s, 3H) 3.05-3.13 (m, 2H) 3.01 (br d, J=6.48 Hz, 1H) 2.91-2.98 (m, 4H) 2.78-2.86 (m, 6H) 2.65-2.73 (m, 3H) 2.21-2.35 (m, 2H) 1.82-2.02 (m, 2H).

The following compound was prepared according to the procedures described for the synthesis of Example 14 by using the appropriate intermediates.

| Compound | Structure | LCMS Data |
| --- | --- | --- |
| 101 | 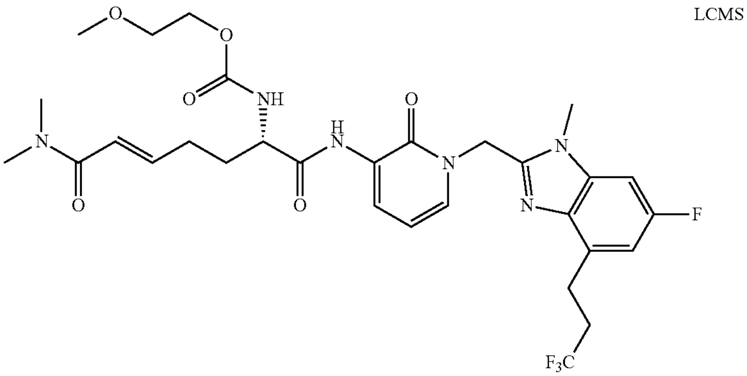 | LCMS m/z 653.3 $(M + 1)^+$ |

Example 15
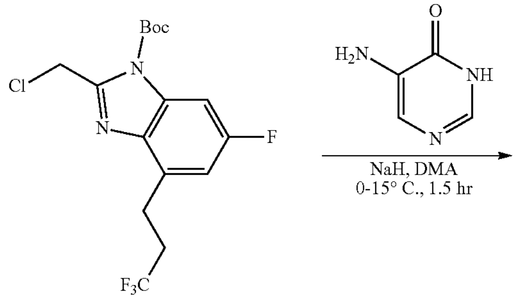
I-155
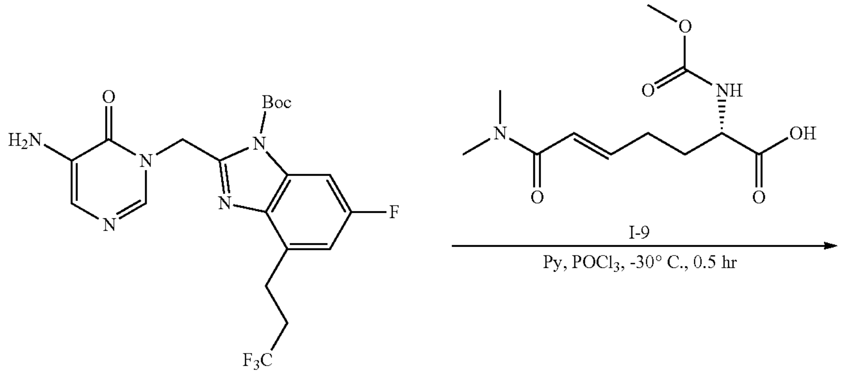
I-165
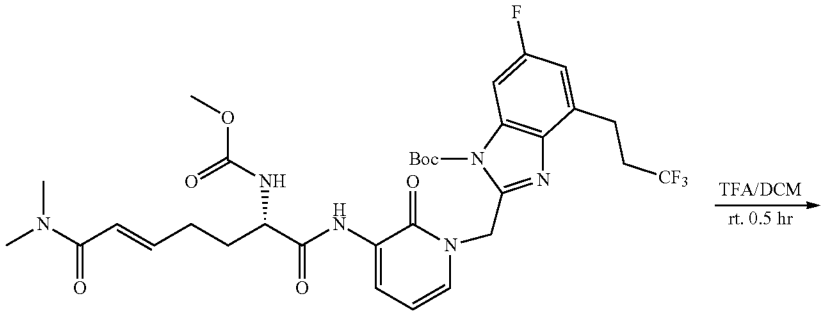
102
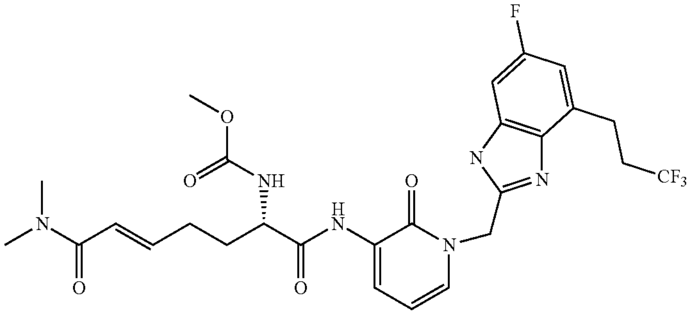
103

Step 1: Synthesis of tert-butyl 2-[(5-amino-6-oxo-pyrimidin-1-yl)methyl]-6-fluoro-4-(3,3, 3-trifluoro-propyl)benzimidazole-1-carboxylate (I-165)

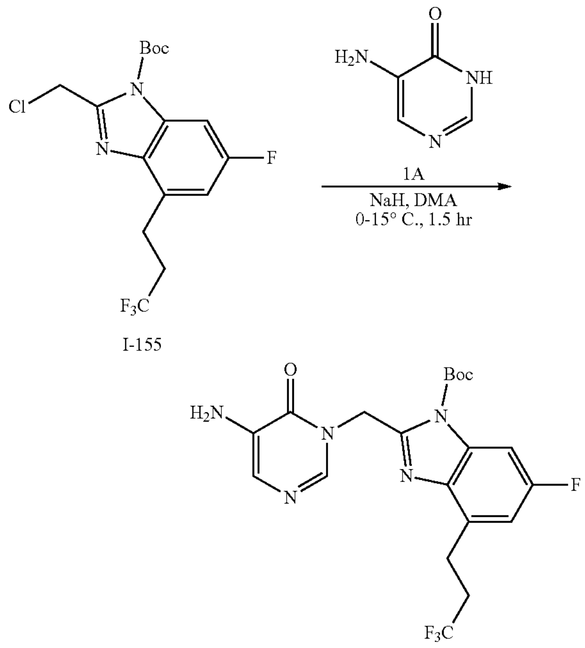

I-155

I-165

The mixture of 5-amino-1H-pyrimidin-6-one (87.54 mg, 787.89 umol) in DMA (3 mL) was cooled to 0° C., then NaH (52.53 mg, 1.31 mmol, 60% purity) was added. The mixture was stirred at 0° C. for 30 mins. Then tert-butyl 2-(chloromethyl)-6-fluoro-4-(3,3,3-trifluoropropyl)benzimidazole-1-carboxylate (250 mg, 656.57 umol) was added. The reaction mixture was stirred at 25° C. for 1 hour. The reaction mixture was quenched by adding $H_2O$ (20 mL), and extracted with ethyl acetate (10 mL*3). The combined organic phase was dried with anhydrous $Na_2SO_4$, filtered and concentrated in vacuum. The residue purified by prep-TLC to give tert-butyl 2-[(5-amino-6-oxo-pyrimidin-1-yl)methyl]-6-fluoro-4-(3,3,3-trifluoropropyl)benzimidazole-1-carboxylate (~165) (70 mg, 20% yield) as a light yellow solid. LCMS m/z 456.3 $(M+1)^+$.

The mixture of tert-butyl 2-[(5-amino-6-oxo-pyrimidin-1-yl)methyl]-6-fluoro-4-(3,3,3-trifluoropropyl)benzimidazole-1-carboxylate (55.00 mg, 120.77 umol) and (E,2S)-7-(dimethylamino)-2-(methoxycarbonylamino)-7-oxo-hept-5-enoic acid (37.43 mg, 144.93 umol) in Py (1 mL) was cooled to −30° C., then $POCl_3$ (55.55 mg, 362.31 umol, 33.67 uL) was added dropwise at −30° C. The reaction mixture was stirred at −30° C. for 0.5 hour. The reaction mixture was quenched by adding saturated $NaHCO_3$ (20 mL), and extracted with ethyl acetate (5 mL*3). The combined organic phase was washed with HCl (1N) (10 mL*1) and brine (10 mL*1), dried with anhydrous $Na_2SO_4$, filtered and concentrated in vacuum. The residue was purified by prep-TLC to give tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-6-fluoro-4-(3,3,3-trifluoropropyl)benzimidazole-1-carboxylate (Compound 102) (30.0 mg, 33% yield) as a white solid. LCMS m/z 696.2 $(M+1)^+$.

The mixture of tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-6-fluoro-4-(3,3,3-trifluoropropyl)benzimidazole-1-carboxylate (27.0 mg, 36.30 umol) in DCM (0.6 mL) was added TFA (308.00 mg, 2.70 mmol, 0.2 mL) at 20° C. Then the reaction was stirred at 20° C. for 0.5 hour. The reaction mixture was dried by flowing $N_2$. Cold sat. aq. $NaHCO_3$ was added to adjust the pH of the mixture ~8. The mixture was extracted with ethyl acetate (5 mL*3). The combined organic phase was dried with anhydrous $Na_2SO_4$, filtered and concentrated in vacuum to give methyl N-[(E,1S)-6-(dimethylamino)-1-[[1-[[5-fluoro-7-(3,3-trifluoropropyl)-1H-benzimidazol-2-yl]methyl]-6-oxo-pyrimidin-5-yl]carbamoyl]-6-oxo-hex-4-enyl]carbamate (Compound 103) (19.5 mg, 88% yield) as alight yellow solid. LCMS m/z 596.2 $(M+1)^+$.

The following compounds were prepared according to the procedures described for the synthesis of Example 15 by using the appropriate intermediates.

| Compound | Structure | LCMS Data |
| --- | --- | --- |
| 400 | 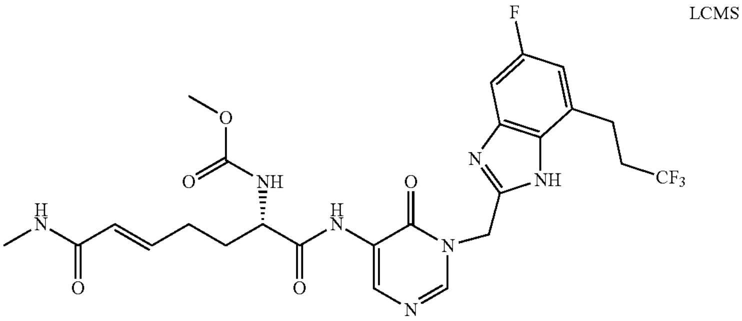 | LCMS m/z 582.0 $(M + 1)^+$ |

-continued
| Compound | Structure | LCMS Data |
|---|---|---|
| 397 | 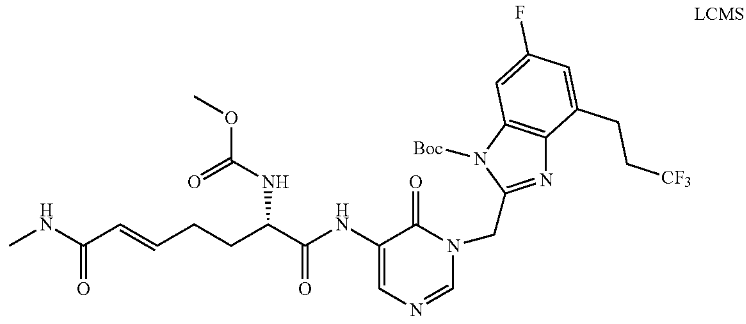 | LCMS m/z 682.2 $(M - 100 + 1)^+$ |
The Synthesis of Intermediate I-174
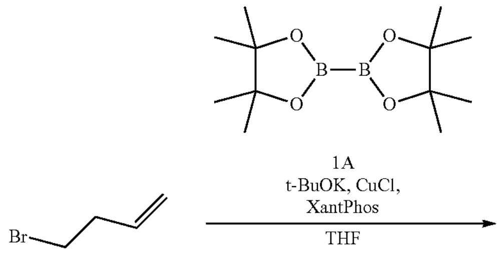
I-166
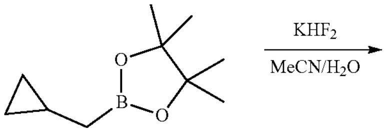
I-167
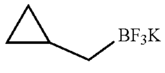
I-168
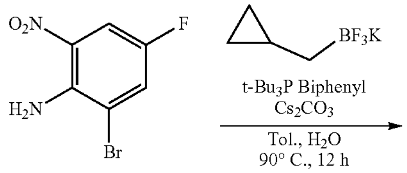
I-169
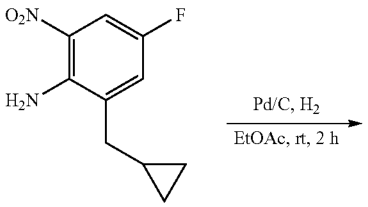
I-170
-continued
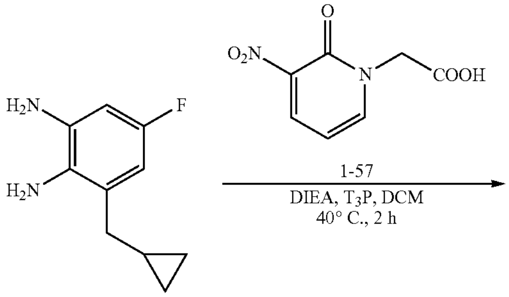
I-171
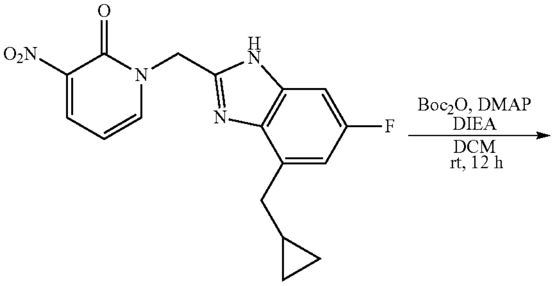
I-172
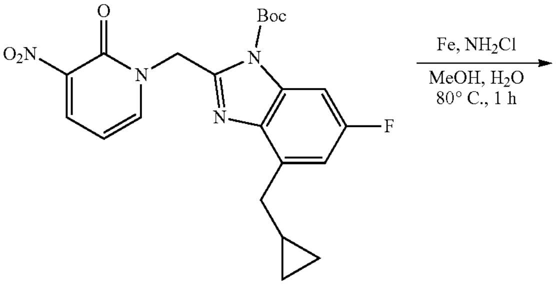
I-173

-continued

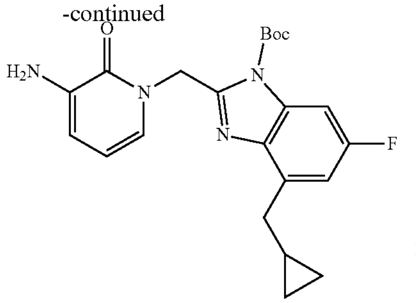

I-174

To a solution of 4-bromobut-1-ene (50 g, 370 mmol) and 4,4,5,5-tetramethyl-2-(4,4,5,5-tetramethyl-1,3,2-dioxaborolan-2-yl)-1,3,2-dioxaborolane (106 g, 418.5 mmol) in THF (500 mL) were added CuCl (1.83 g, 18.52 mmol) and Xantphos (10.72 g, 18.5 mmol). t-BuOK (49.9 g, 444.4 mmol) was added to the mixture at 0-30° C. The mixture was stirred at 30° C. for 12 h. The resulting suspension was filtered and the filtrate was concentrated to give a residue. The residue was purified by column chromatography to give 2-(cyclopropylmethyl)-4,4,5,5-tetramethyl-1,3,2-dioxaborolane (I-167) (70.0 g) as a colorless oil.

To a solution of 2-(cyclopropylmethyl)-4,4,5,5-tetramethyl-1,3,2-dioxaborolane (120 g, 659 mmol) in MeCN (600 mL) and $H_2O$ (200 mL) was added $KHF_2$ (103 g, 1.32 mol). The mixture was stirred at 30° C. for 12 h. The mixture was filtered and the filtrate was concentrated to about 300 mL. The mixture was stirred at 30° C. for 30 min and then filtered to afford a white solid, washed with MeCN (30 mL×2) to give cyclopropylmethyl(trifluoro)boron;potassium hydride (I-168) (26 g, 24% yield) as a white solid. $^1H$ NMR (400 MHz, DMSO-$d_6$+$D_2O$) δ 0.5-0.49 (m, 1H), 0.17-0.14 (m, 2H), 0.05-0.04 (m, 2H), 0.22-0.21 (m, 2H).

To a solution of 2-bromo-4-fluoro-6-nitro-aniline (5 g, 21.28 mmol) and cyclopropylmethyl(trifluoro)boron;potassium hydride (8.62 g, 53.19 mmol) in Tol. (50 mL) and $H_2O$ (5 mL) was added [2-(2-aminophenyl)phenyl]-chloro-palladium;tritert-butylphosphane (545.09 mg, 1.06 mmol) and $Cs_2CO_3$ (13.86 g, 42.55 mmol) under $N_2$ atmosphere. The mixture was stirred at 90° C. for 12 hr. The reaction mixture was filtered and the filtrate was concentrated. The residue was purified by column chromatography to give 2-(cyclopropylmethyl)-4-fluoro-6-nitro-aniline (I-170) (1.6 g, 33% yield) as a yellow solid.

To a solution of 2-(cyclopropylmethyl)-4-fluoro-6-nitro-aniline (1 g, 4.76 mmol) in EtOAc (10 mL) was added Pd/C (10%, 100 mg) under $N_2$. The suspension was degassed under vacuum and purged with $H_2$ several times. The mixture was stirred under $H_2$ (15 psi) at 25° C. for 2 hr. The reaction mixture was filtered and the filtrate was concentrated to give 3-(cyclopropylmethyl)-5-fluoro-benzene-1,2-diamine (I-171) (890 mg) as a brown oil which was used in the next step without further purification.

To a solution of 3-(cyclopropylmethyl)-5-fluoro-benzene-1,2-diamine (890 mg, 4.94 mmol) and 2-(3-nitro-2-oxo-1-pyridyl)acetic acid (1.17 g, 5.93 mmol) in DCM (10 mL) was added $T_3P$ (4.09 g, 6.42 mmol, 3.82 mL, 50% purity) and DIEA (1.28 g, 9.88 mmol, 1.72 mL). The mixture was stirred at 40° C. for 2 hr and concentrated to give 1-[[4-(cyclopropylmethyl)-6-fluoro-1H-benzimidazol-2-yl]methyl]-3-nitro-pyridin-2-one (I-172) (1.6 g) as a purple oil which was used in the next step without further purification.

To a solution of 1-[[4-(cyclopropylmethyl)-6-fluoro-1H-benzimidazol-2-yl]methyl]-3-nitro-pyridin-2-one (1.6 g, 4.67 mmol) in DCM (15 mL) was added $Boc_2O$ (1.33 g, 6.08 mmol, 1.40 mL) and DIEA (1.21 g, 9.35 mmol, 1.63 mL) and DMAP (28.55 mg, 233.70 umol). The mixture was stirred at 25° C. for 12 hr. The reaction mixture was concentrated under reduced pressure to remove solvent. The residue was purified by column chromatography to give tert-butyl 4-(cyclopropylmethyl)-6-fluoro-2-[(3-nitro-2-oxo-1-pyridyl)methyl]benzimidazole-1-carboxylate (I-173) (400 mg, 19% yield) as a yellow solid.

To a solution of tert-butyl 4-(cyclopropylmethyl)-6-fluoro-2-[(3-nitro-2-oxo-1-pyridyl) methyl]benzimidazole-1-carboxylate (370 mg, 836.27 umol) in MeOH (5 mL) and $H_2O$ (1 mL) was added Fe (233.51 mg, 4.18 mmol) and $NH_4Cl$ (447.33 mg, 8.36 mmol, 292.38 uL). The mixture was stirred at 80° C. for 1 hr. The reaction mixture was filtered and the filtrate was concentrated. The residue was purified by column chromatography to give tert-butyl 2-[(3-amino-2-oxo-1-pyridyl)methyl]-4-(cyclopropylmethyl)-6-fluoro-benzimidazole-1-carboxylate (I-174) (80 mg, 23% yield) as a green oil. LCMS m/z 312.9 $(M-100+1)^+$.

The following aniline was prepared according to the procedures described for the synthesis of I-174 using the appropriate reagents.

| Compound | Structure | LCMS Data |
|---|---|---|
| I-175 | 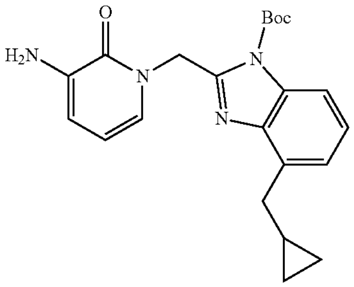 [SMILES: CC(C)(C)OC(=O)n1c(Cn2cccc(N)c2=O)nc2c(CC3CC3)cccc21] | LCMS m/z 395.1 $(M+H)^+$ |

Example 16

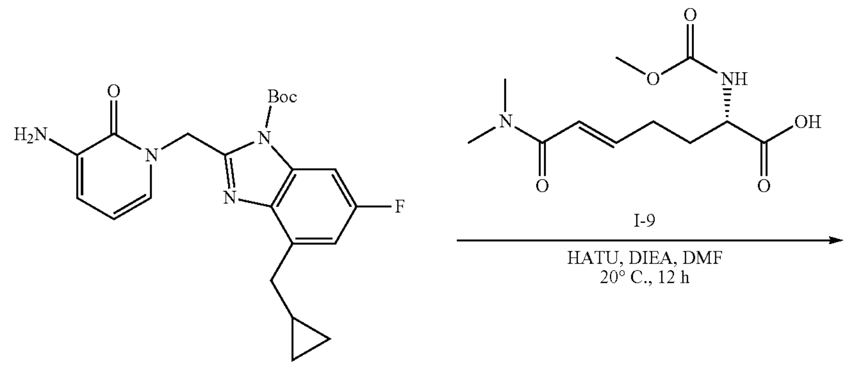

I-174

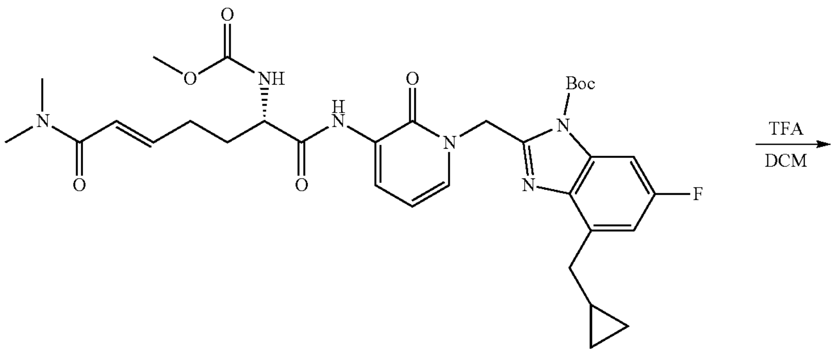

104

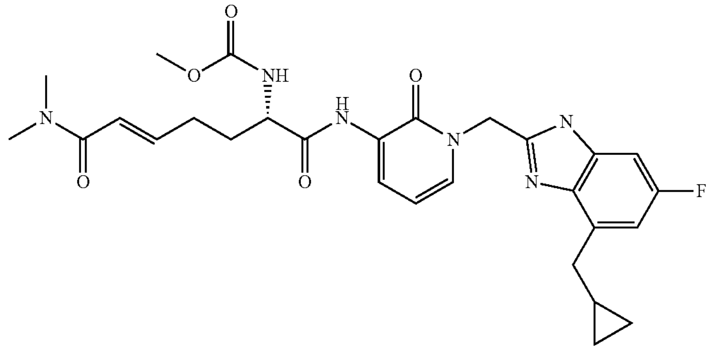

105

To a solution of tert-butyl 2-[(3-amino-2-oxo-1-pyridyl) methyl]-4-(cyclopropylmethyl)-6-fluoro-benzimidazole-1-carboxylate (70 mg, 169.71 umol) and (E,2S)-7-(dimethyl-amino)-2-(methoxycarbonylamino)-7-oxo-hept-5-enoic acid (48.22 mg, 186.69 umol) in DMF (1 mL) was added HATU (96.80 mg, 254.57 umol) and DIEA (43.87 mg, 339.43 umol, 59.12 uL). The mixture was stirred at 20° C. for 12 hr. The residue was poured into saturated ammonium chloride solution (5 mL), and extracted with ethyl acetate (3 mL*3). The combined organic phase was washed with saturated brine (5 mL*2), dried with anhydrous $Na_2SO_4$, filtered and concentrated in vacuum. The residue was purified by prep-HPLC to give tert-butyl 4-(cyclopropylmethyl)-2-[[3-[[(E,2S)-7-(dimethylamino)-2-methoxycarbonylamino)-7-oxo-hept-5-enoyl]amino]-2-oxo-1-pyridyl] methyl]-6-fluoro-benzimidazole-1-carboxylate (Compound 104) (87.3 mg, 60% yield) as a white solid. LCMS m/z 653.3 $(M+1)^+$. $^1H$ NMR (400 MHz, DMSO-$d_6$) δ 9.26 (s, 1H) 8.28 (dd, J=7.45, 1.32 Hz, 1H) 7.74 (br d, J=7.89 Hz, 1H) 7.45-7.51 (m, 2H) 7.14 (dd, J=10.52, 2.63 Hz, 1H) 6.55-6.65 (m, 1H) 6.31-6.40 (m, 2H) 5.62 (s, 2H) 4.12-4.21 (m, 1H) 3.53 (s, 3H) 2.98 (s, 3H) 2.83 (s, 3H) 2.63 (d, J=7.02 Hz, 2H) 2.16-2.30 (m, 2H) 1.86 (br d, J=7.89 Hz, 1H) 1.69 (s, 9H) 0.89 (br t, J=7.24 Hz, 1H) 0.29-0.36 (m, 2H) 0.09-0.16 (m, 2H).

To a solution of tert-butyl 4-(cyclopropylmethyl)-2-[[3-[[(E,2S)-7-(dimethylamino)-2-(methoxycarbonylamino)-7-oxo-hept-5-enoyl]amino]-2-oxo-1-pyridyl]methyl]-6-fluoro-benzimidazole-1-carboxylate (80 mg, 102.87 umol) in DCM (2 mL) was added TFA (646.27 mg, 5.67 mmol, 419.66 uL). The mixture was stirred at 20° C. for 2 hr. The reaction mixture was concentrated under reduced pressure to remove solution. And then the residue was added saturated $NaHCO_3$ solution 5 mL and extracted with ethyl acetate (5 mL*3). The combined organic phase was washed with saturated brine (5 mL*2), dried with anhydrous $Na_2SO_4$, filtered and concentrated in vacuum. The residue was purified by prep-HPLC to give methyl N-[(E,1S)-1-[[1-[[4-

(cyclopropylmethyl)-6-fluoro-1H-benzimidazol-2-yl]methyl]-2-oxo-3-pyridyl]carbamoyl]-6-(dimethylamino)-6-oxo-hex-4-enyl]carbamate (Compound 105) (30.7 mg, 53% yield) as a white solid. LCMS m/z 553.3 $(M+1)^+$. $^1H$ NMR (400 MHz, DMSO-$d_6$) δ 12.37-12.78 (m, 1H) 9.27 (br d, J=7.89 Hz, 1H) 8.25 (d, J=7.45 Hz, 1H) 7.75 (br s, 1H) 7.57 (d, J=5.26 Hz, 1H) 7.04-7.20 (m, 1H) 6.96 (br dd, J=16.22, 10.96 Hz, 1H) 6.56-6.65 (m, 1H) 6.31-6.42 (m, 2H) 5.38 (brs, 2H) 4.17 (brs, 1H) 3.54 (brs, 3H) 2.99 (s, 3H) 2.84 (s, 3H) 2.73-2.80 (m, 2H) 2.15-2.30 (m, 2H) 1.87 (brs, 1H) 1.72 (br s, 1H) 1.11 (br s, 1H) 0.40-0.53 (m, 2H) 0.24 (br d, J=11.40 Hz, 2H).

The following compounds were prepared according to the procedures described for the synthesis of Example 16 using the appropriate intermediates.

| Compound | Structure | LCMS Data |
| --- | --- | --- |
| 106 | 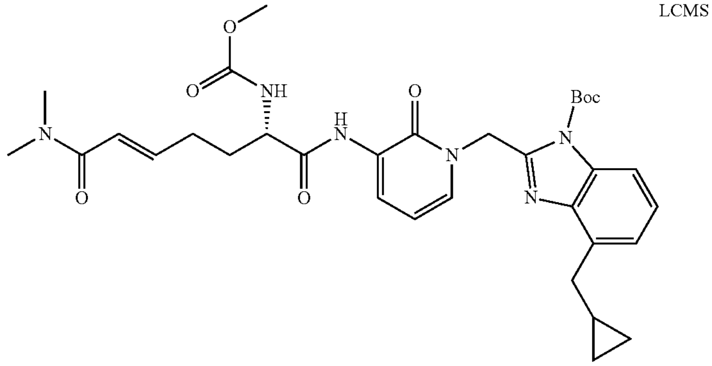 | LCMS m/z 635.4 $(M + 1)^+$ |
| 107 | 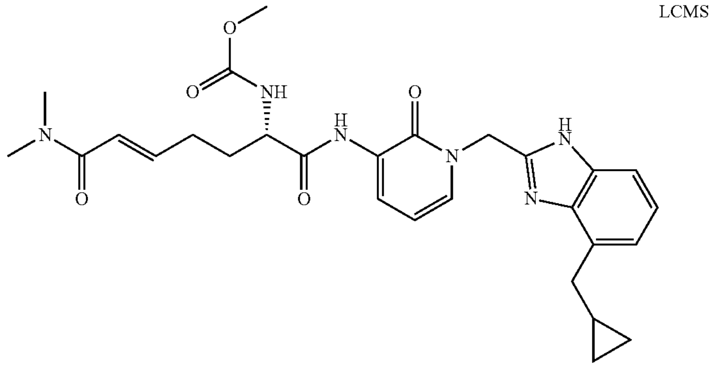 | LCMS m/z 535.4 $(M + 1)^+$ |
| 108 | 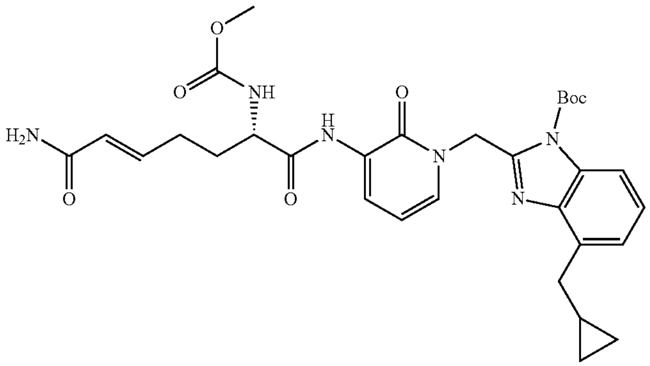 [SMILES: COC(=O)N[C@@H](CC/C=C/C(N)=O)C(=O)Nc1cccn(Cc2nc3c(CC4CC4)cccc3n2C(=O)OC(C)(C)C)c1=O] | LCMS m/z 607.4 $(M + H)^+$ |

-continued
| Compound | Structure | LCMS Data |
|---|---|---|
| 109 | 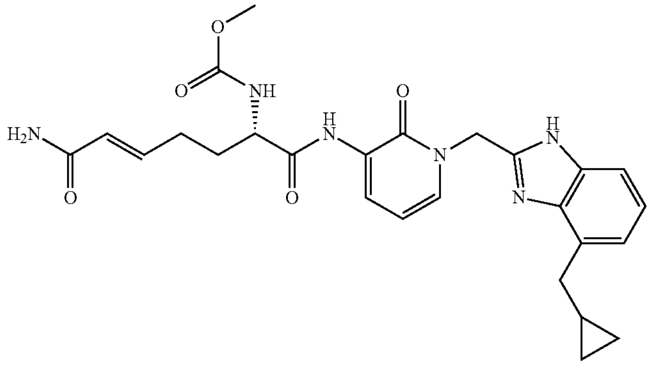 [SMILES: COC(=O)N[C@@H](CC/C=C/C(N)=O)C(=O)Nc1cccn(Cc2nc3c(CC4CC4)cccc3[nH]2)c1=O] | LCMS m/z 507.3 $(M + H)^+$ |
The Synthesis of Intermediate I-184
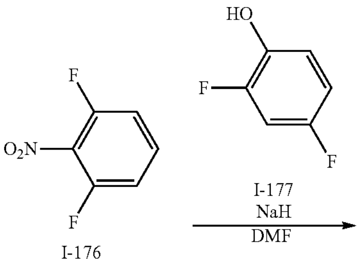
I-176
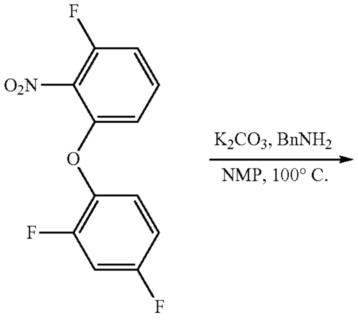
I-178
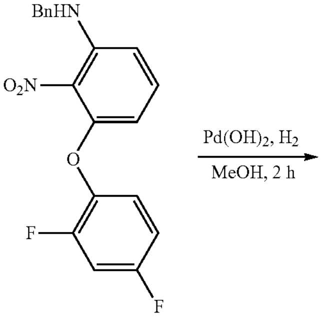
I-179
-continued
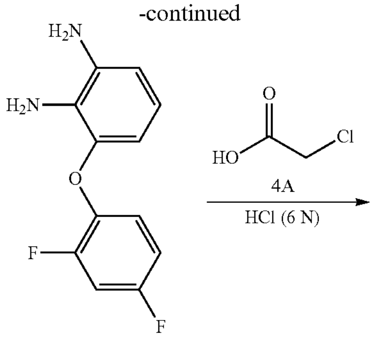
I-180
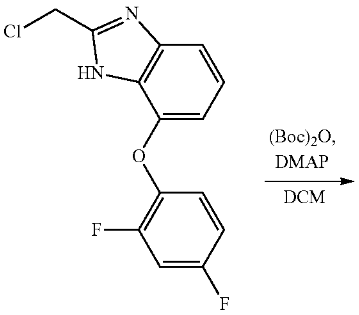
I-181
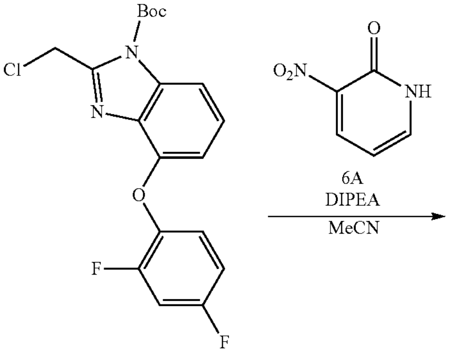
I-182

-continued

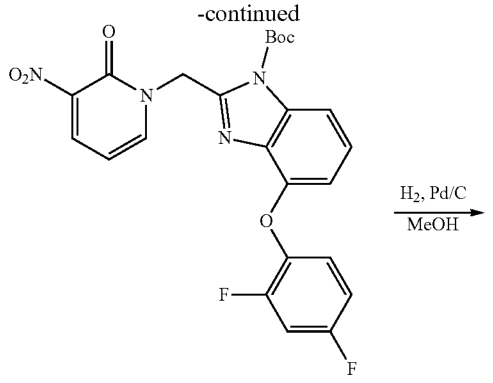

I-183

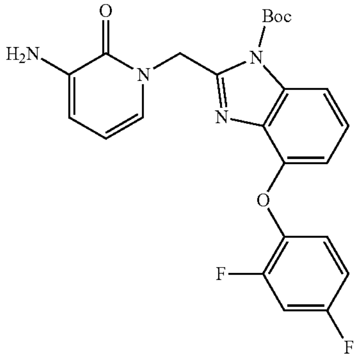

I-184

To a solution of 2,4-difluorophenol (5.00 g, 38.4 mmol) in DMF (50 mL) was added NaH (1.84 g, 46.1 mmol, 60% purity) at 0° C. The mixture was stirred at 25° C. for 1 h. Then 1,3-difluoro-2-nitrobenzene (6.11 g, 38.4 mmol) in DMF (10 mL) was added to the reaction mixture. The mixture was stirred at 25° C. for 16 h. The resulting solution was diluted with water (100 mL), and extracted with ethyl acetate (50 mL×3). The combined organic layers were washed with brine (50 mL×3), dried over anhydrous $Na_2SO_4$, filtered and concentrated to give a residue. The residue was purified by column chromatography to give 1-(2,4-difluorophenoxy)-3-fluoro-2-nitrobenzene (I-178) (9.40 g) as a yellow oil.

To a solution of 1-(2,4-difluorophenoxy)-3-fluoro-2-nitrobenzene (9.40 g, 34.9 mmol) and phenylmethanamine (4.12 g, 38.4 mmol) in NMP (20 mL) was added $K_2CO_3$ (9.65 g, 69.8 mmol). The mixture was stirred at 100° C. for 16 hours. The mixture was diluted with water (150 mL) and then extracted with ethyl acetate (50 mL×3). The combined organic layers were washed with brine (50 mL×3), dried over anhydrous $Na_2SO_4$, filtered and concentrated to give a residue. The residue was purified by column chromatography to give N-benzyl-3-(2,4-difluorophenoxy)-2-nitroaniline (I-179) (10.0 g) as a red oil.

To a solution of N-benzyl-3-(2,4-difluorophenoxy)-2-nitroaniline (5.00 g, 14.0 mmol) in MeOH (100 mL) was added $Pd(OH)_2$ (2.00 g, 2.14 mmol, 15% purity). The mixture was stirred under $H_2$ (15 psi) at 25° C. for 2 h. The resulting suspension was filtered and the filtrate was concentrated under reduced pressure to give a residue. The residue was purified by column chromatography to give 3-(2,4-difluorophenoxy)benzene-1,2-diamine (I-180) (2.50 g, 70% yield) as a red oil. LCMS m/z 237.0 $(M+1)^+$.

To a solution of 3-(2,4-difluorophenoxy)benzene-1,2-diamine (5.00 g, 21.2 mmol) in $H_2O$ (20 mL) and HCl (20 mL) was added 2-chloroacetic acid (4.00 g, 42.3 mmol) at 25° C. The mixture was stirred at 90° C. for 16 h. The pH of the mixture was adjusted to 7 by adding saturated ammonium hydroxide at 0° C. The resulting suspension was extracted with ethyl acetate (100 mL×3). The combined organic layers were washed with brine (100 mL), dried over anhydrous $Na_2SO_4$, filtered and concentrated in vacuum to give 2-(chloromethyl)-7-(2,4-difluorophenoxy)-1H-benzo[d]imidazole (I-181) (6.35 g) as a brown solid.

To a solution of 2-(chloromethyl)-7-(2,4-difluorophenoxy)-1H-benzo[d]imidazole (6.35 g, 21.6 mmol) in DCM (30 mL) were added $Boc_2O$ (5.17 g, 23.7 mmol) and DMAP (2.90 g, 23.7 mmol). The mixture was stirred at 25° C. for 1 hour. The mixture was added $H_2O$ (100 mL) and extracted with Ethyl acetate (100 mL×3). The combined organic layers dried over $Na_2SO_4$, filtered and concentrated under reduced pressure. The residue was purified by column chromatography to give tert-butyl 2-(chloromethyl)-4-(2,4-difluorophenoxy)-1H-benzo [d]imidazole-1-carboxylate (I-182) (2.0 g, 21% yield) as a yellow solid. LCMS m/z 338.9 $(M+1)^+$.

To a solution of 3-nitropyridin-2(1H)-one (427 mg, 3.04 mmol) and tert-butyl 2-(chloromethyl)-4-(2,4-difluorophenoxy)-1H-benzo[d]imidazole-1-carboxylate (800 mg, 2.03 mmol) in MeCN (15 mL) was added DIPEA (787 mg, 6.09 mmol). The mixture was stirred at 25° C. for 16 hours. The reaction mixture (combined with two batches) was concentrated under reduced pressure to give a residue. The residue was purified by column chromatography to give tert-butyl 4-(2,4-difluorophenoxy)-2-((3-nitro-2-oxopyridin-1(2H)-yl)methyl)-1H-benzo[d]imidazole-1-carboxylate (I-183) (1.15 g, 56% yield) as a yellow solid. LCMS m/z 399.0 $(M+1)^+$.

To a solution of tert-butyl 4-(2,4-difluorophenoxy)-2-((3-nitro-2-oxopyridin-1(2H)-yl) methyl)-1H-benzo[d]imidazole-1-carboxylate (1.15 g, 2.31 mmol) in MeOH (100 mL) was added Pd/C (200 mg, 10% purity). The mixture was stirred at 20° C. for 0.5 hour under $H_2$ (15 psi) atmosphere. The reaction mixture was filtered and the filtrate was concentrated under reduced pressure to give tert-butyl 2-((3-amino-2-oxopyridin-1(2H)-yl)methyl)-4-(2,4-difluorophenoxy)-1H-benzo[d]imidazole-1-carboxylate (I-184) (900 mg, 77% yield) as a brown solid. LCMS m/z 469.0 $(M+1)^+$.

The following intermediate was prepared according to the procedures described in I-184 using the appropriate reagents.

| Compound | Structure | LCMS Data |
|---|---|---|
| I-185 | 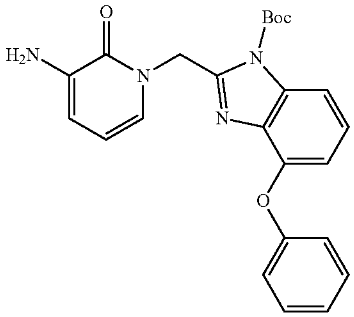 [SMILES: CC(C)(C)OC(=O)n1c(Cn2cccc(N)c2=O)nc2c(Oc3ccccc3)cccc21] | LCMS m/z 433.3 $(M + 1)^+$ |
Example 17
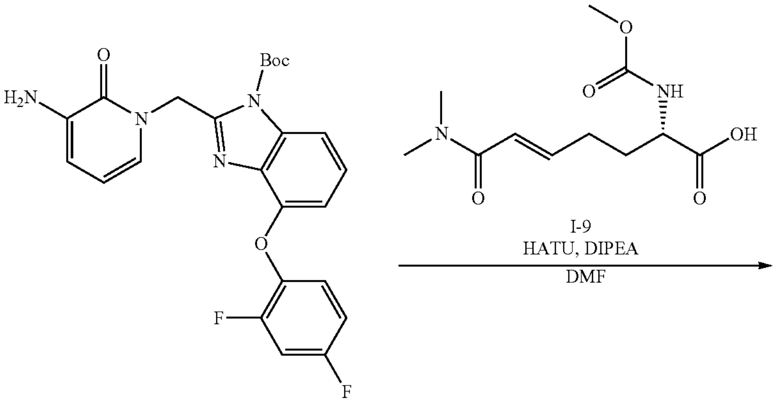
I-184
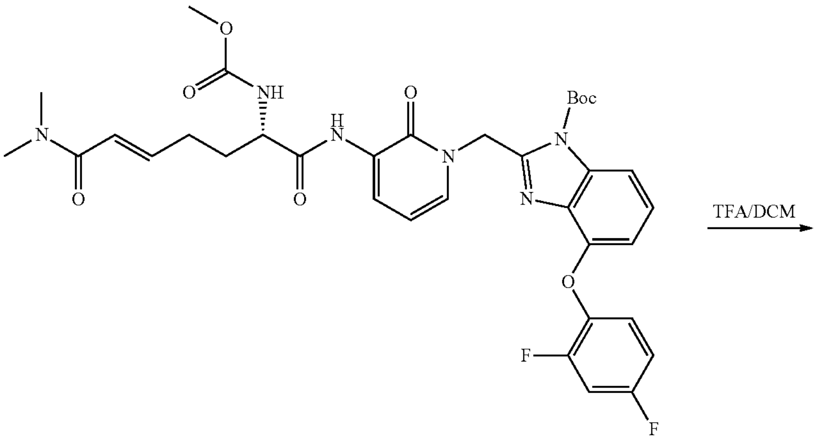
I-186

-continued

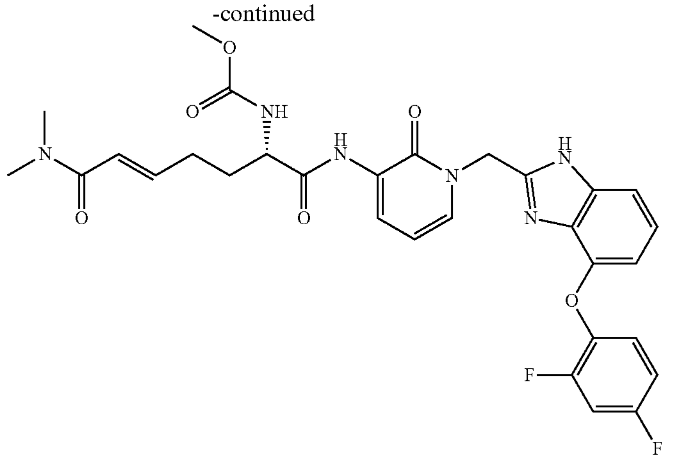

110

To a solution of (S,E)-7-(dimethylamino)-2-((methoxycarbonyl)amino)-7-oxohept-5-enoic acid (185 mg, 718 umol) and tert-butyl 2-((3-amino-2-oxopyridin-1(2H)-yl) methyl)-4-(2,4-difluorophenoxy)-1H-benzo[d]imidazole-1-carboxylate (100 mg, 213 umol) in DMF (3 mL) were added HATU (218 mg, 574 umol) and DIPEA (186 mg, 1.44 mmol) at 0° C. The solution was stirred at 25° C. for 16 hours. The resulting solution was concentrated under reduced pressure to give a residue. The residue was purified by prep-TLC to give (S,E)-tert-butyl4-(2,4-difluorophenoxy)-2-((3-(7-(dimethylamino)-2-((methoxycarbonyl) amino)-7-oxohept-5-enamido)-2-oxopyridin-1(2H)-yl) methyl)-1H-benzo[d]imidazole-1-carboxylate (I-186) (100 mg, 29% yield) as a white solid. LCMS m/z 709.1 $(M+1)^+$.

To a solution of (S,E)-tert-butyl4-(2,4-difluorophenoxy)-2-((3-(7-(dimethylamino)-2-((methoxycarbonyl)amino)-7-oxohept-5-enamido)-2-oxopyridin-1(2H)-yl)methyl)-1H-benzo[d]imidazole-1-carboxylate (95 mg, 134 umol) in DCM (6 mL) was added TFA (2 mL) at 0° C. The mixture was stirred at 20° C. for 2 hours. The reaction mixture was concentrated under reduced pressure to give a residue. The residue was purified by prep-HPLC to give (S,E)-methyl (1-((1-((4-(2,4-difluorophenoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate (Compound 110) (68.4 mg, 83% yield) as a white solid. LCMS m/z 609.2 $(M+1)^+$. $^1H$ NMR (400 MHz, DMSO-$d_6$) δ9.27 (s, 1H), 8.26 (dd, J=7.6, 1.6 Hz, 1H), 7.75 (d, J=7.6 Hz, 1H), 7.58 (dd, J=6.8, 1.6 Hz, 1H), 7.52-7.43 (m, 1H), 7.29-7.16 (m, 2H), 7.08 (t, J=8.0 Hz, 2H), 6.65-6.57 (m, 1H), 6.51 (d, J=7.8 Hz, 1H), 6.41-6.34 (m, 2H), 5.40 (s, 2H), 4.21-4.14 (m, 1H), 3.55 (s, 3H), 2.99 (s, 3H), 2.84 (s, 3H), 2.28-2.19 (m, 2H), 1.95-1.85 (m, 1H), 1.78-1.69 (m, 1H).

The following compounds were prepared according to the procedures described in Example 17 using the appropriate intermediates.

| Compound | Structure | LCMS Data |
| --- | --- | --- |
| 111 | 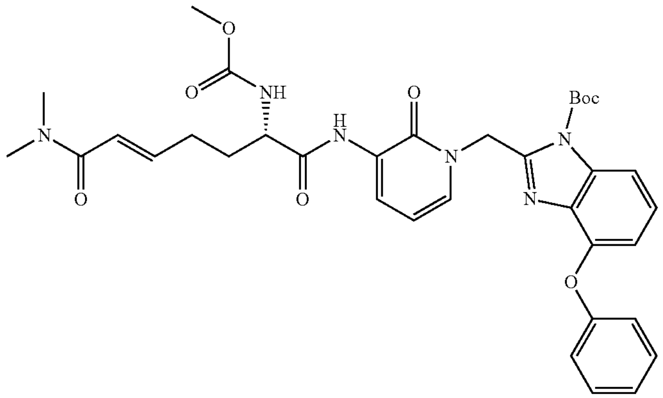 [SMILES: COC(=O)N[C@@H](CC/C=C/C(=O)N(C)C)C(=O)Nc1cccn(Cc2nc3c(Oc4ccccc4)cccc3n2C(=O)OC(C)(C)C)c1=O] | LCMS m/z 673.1 $(M + 1)^+$ |

-continued
| Compound | Structure | LCMS Data |
|---|---|---|
| 112 | 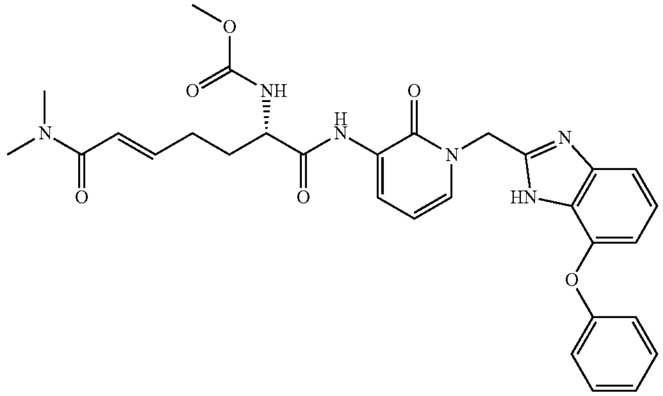 [SMILES: COC(=O)N[C@@H](CC/C=C/C(=O)N(C)C)C(=O)Nc1cccn(Cc2nc3cccc(Oc4ccccc4)c3[nH]2)c1=O] | LCMS m/z 573.1 (M + 1)+ |
| 113 | 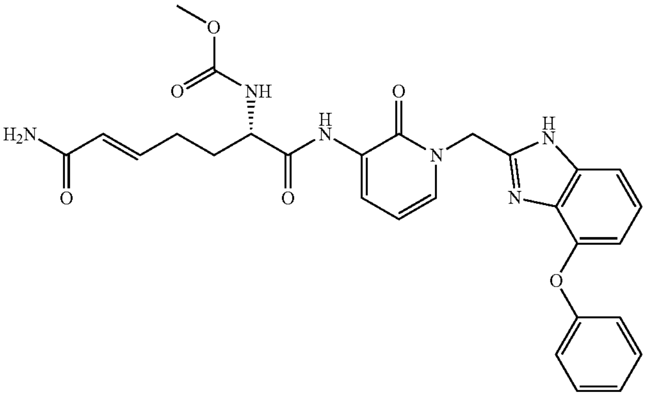 [SMILES: COC(=O)N[C@@H](CC/C=C/C(N)=O)C(=O)Nc1cccn(Cc2nc3c(Oc4ccccc4)cccc3[nH]2)c1=O] | LCMS m/z 545.1 (M + 1)+ |
| 114 | 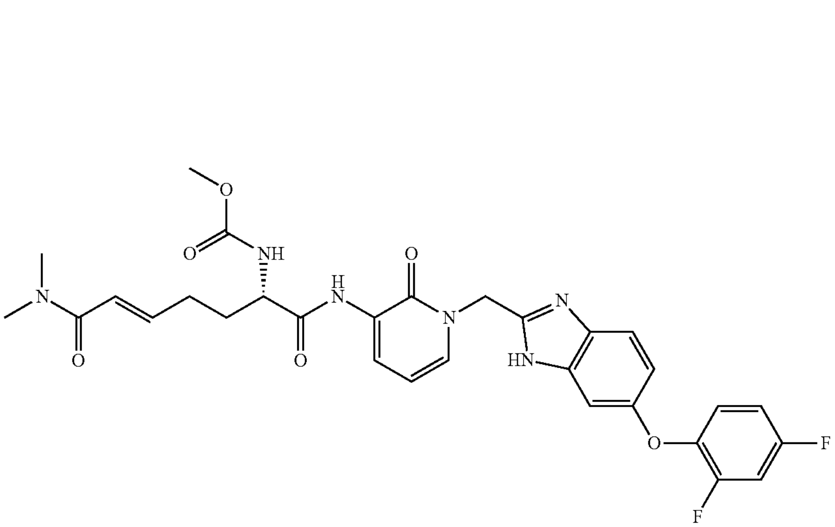 [SMILES: COC(=O)N[C@@H](CC/C=C/C(=O)N(C)C)C(=O)Nc1cccn(Cc2nc3ccc(Oc4ccc(F)cc4F)cc3[nH]2)c1=O] | LCMS m/z: 609.2 (M + 1)+ |

The Synthesis of Intermediate I-195
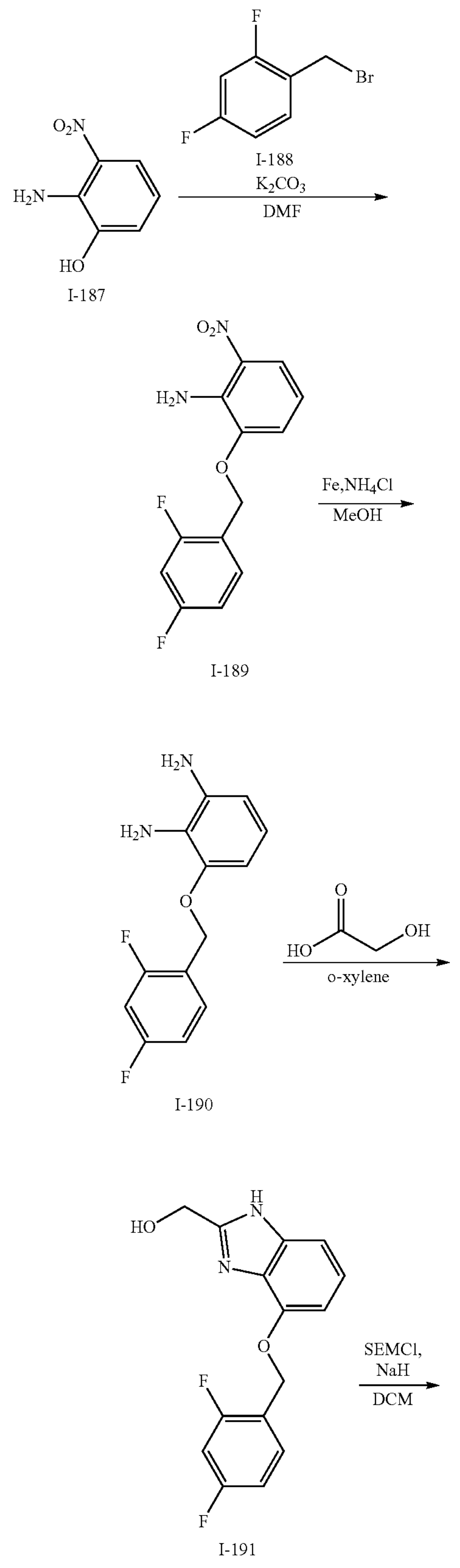
-continued
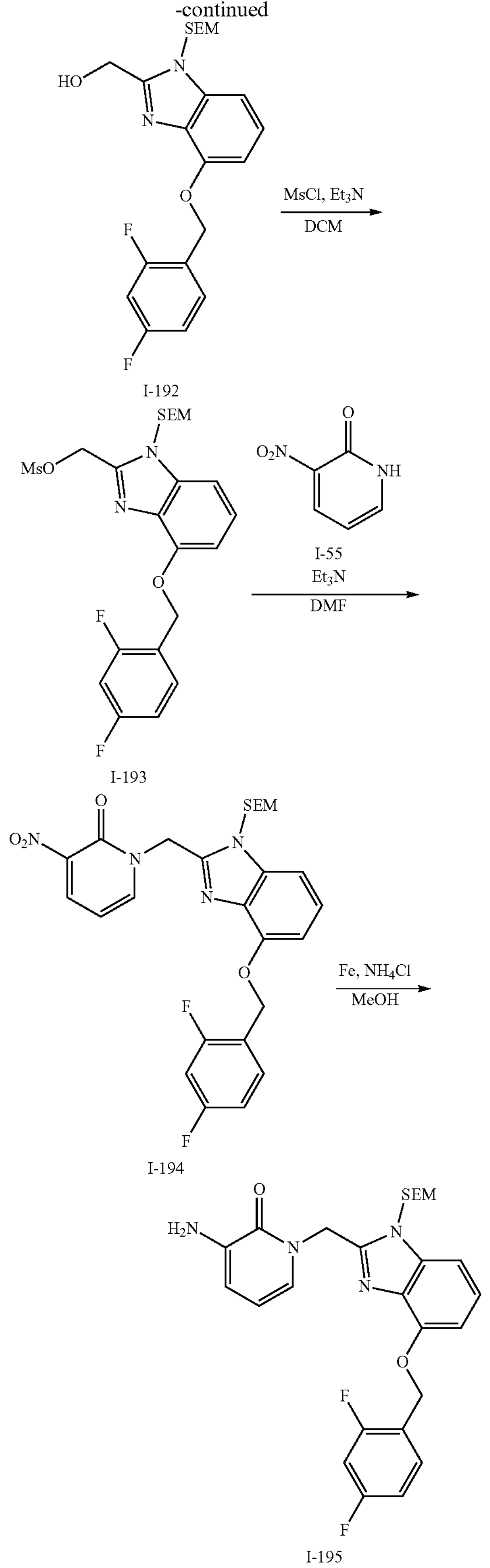

To a solution of 2-amino-3-nitrophenol (5.00 g, 32.4 mmol) and $K_2CO_3$ (4.04 g, 29.2 mmol) in DMF (40 mL) was added 1-(bromomethyl)-2, 4-difluorobenzene (6.72 g, 32.4 mmol). The mixture was stirred at 23° C. for 2 h. The mixture was poured into water (100 mL) and extracted with ethyl acetate (50 mL×4). The combined organic layers were washed with brine (200 mL), dried over anhydrous $Na_2SO_4$, filtered and concentrated in vacuum to give a residue. The residue was purified by column chromatography to afford 2-((2,4-difluorobenzyl)oxy)-6-nitroaniline (I-189) (9.00 g) as a white solid. LCMS m/z 281.0 $(M+1)^+$.

To a solution of 2-((2,4-difluorobenzyl)oxy)-6-nitroaniline (7.00 g, 25.0 mmol) in MeOH (70 mL) and $H_2O$ (7 mL) were added Fe (6.98 g, 125 mmol) and $NH_4Cl$ (13.4 g, 250 mmol, 8.73 mL). The mixture was stirred at 85° C. for 2 h. The resulting suspension was filtered and the filtrate was concentrated in vacuum to give a residue. The residue was diluted with water (50 mL) and extracted with ethyl acetate (50 mL×3). The combined organic layers were washed with brine (150 mL), dried over anhydrous $Na_2SO_4$, filtered and concentrated in vacuum to give a residue. The residue was purified by column chromatography to afford 3-((2,4-difluorobenzyl)oxy)benzene-1,2-diamine (I-190) (5.60 g) as a black oil.

To a solution of 3-((2,4-difluorobenzyl)oxy)benzene-1,2-diamine (5.60 g, 22.4 mmol) in o-xylene (50 mL) was added 2-hydroxyacetic acid (1.70 g, 22.4 mmol, 1.36 mL). The reaction mixture was stirred at 150° C. for 7 hr. The resulting solution was poured into ice-water (50 mL) and extracted with ethyl acetate (50 mL×3). The combined organic layers were washed with brine (150 mL), dried over anhydrous $Na_2SO_4$, filtered and concentrated in vacuum to give a residue. The residue was purified by column chromatography to afford (7-((2,4-difluorobenzyl)oxy)-1H-benzo[d]imidazol-2-yl) methanol (I-191) (5.70 g, 18.7 mmol, 83% yield) as a brown solid. LCMS m/z 291.0 $(M+1)^+$. $^1H$ NMR (400 MHz, $CDCl_3$) δ 7.50-7.52 (m, 1H), 7.19-7.23 (m, 2H), 6.80-6.90 (m, 3H), 5.47 (d, J=3.6 Hz, 1H), 5.27-5.32 (m, 2H), 4.27 (s, 1H).

To a solution of (7-((2,4-difluorobenzyl)oxy)-1H-benzo[d]imidazol-2-yl)methanol (5.70 g, 19.6 mmol) in THF (60 mL) was added NaH (1.18 g, 29.5 mmol) at 0° C. The mixture was stirred at the same temperature for 30 min, and then SEM-Cl (2.95 g, 17.7 mmol, 3.14 mL) was added to the reaction mixture above. The resulting suspension was stirred at 23° C. for 2 hr. The reaction mixture was poured into water (80 mL) and extracted with ethyl acetate (100 mL×3). The combined organic layers were washed with brine (300 mL), dried over anhydrous $Na_2SO_4$, filtered and concentrated in vacuum to give a residue. The residue was purified by column chromatography to afford (4-((2,4-difluorobenzyl)oxy)-1-((2-(trimethylsilyl)ethoxy)methyl)-1H-benzo[d]imidazol-2-yl)methanol (I-192) (6.00 g) as a brown oil. $^1H$ NMR (400 MHz, $CDCl_3$) δ57.75-7.55 (m, 1H), 7.48 (dd, J=8.4, 3.2 Hz, 1H), 7.31-7.25 (m, 1H), 7.07-6.91 (m, 3H), 5.89 (s, 1H), 5.67 (s, 1H), 5.49-5.40 (m, 1H), 5.32 (s, 1H), 5.08-5.00 (m, 2H), 3.67-3.54 (m, 2H), 1.02-0.83 (m, 2H), 0.05-0.03 (m, 3H), 0.00 (s, 6H).

To a solution of (4-((2,4-difluorobenzyl)oxy)-1-((2-(trimethylsilyl)ethoxy)methyl)-1H-benzo[d]imidazol-2-yl) methanol (6.00 g, 14.3 mmol) in DCM (50 mL) were added $Et_3N$ (2.89 g, 28.5 mmol, 3.96 mL) and MsCl (1.63 g, 14.3 mmol, 1.10 mL) at 0° C. The mixture was stirred at 0-23° C. for 1 h. The resulting solution was poured into water (50 mL) and extracted with ethyl acetate (50 mL×3). The combined organic layers were washed with brine (150 mL), dried over anhydrous $Na_2SO_4$, filtered and concentrated in vacuum to give (4-((2,4-difluorobenzyl)oxy)-1-((2-(trimethylsilyl)ethoxy)methyl)-1H-benzo[d]imidazol-2-yl)methyl methanesulfonate (I-193) (6.60 g) as a brown oil.

To a solution of (4-((2,4-difluorobenzyl)oxy)-1-((2-(trimethylsilyl)ethoxy) methyl)-1H-benzo[d]imidazol-2-yl) methyl methanesulfonate (6.60 g, 14.2 mmol) in DMF (50 mL) were added $Et_3N$ (2.88 g, 28.5 mmol, 3.95 mL) and 3-nitropyridin-2(1H)-one (2.00 g, 14.24 mmol). The mixture was stirred at 23° C. for 16 h. The resulting solution was poured into water (100 mL) and extracted with ethyl acetate (100 mL×3). The combined organic layers were washed with brine (300 mL), dried over anhydrous $Na_2SO_4$, filtered and concentrated in vacuum to give a residue. The residue was purified by column chromatography to afford 1-((4-((2,4-difluorobenzyl)oxy)-1-((2-(trimethylsilyl)ethoxy) methyl)-1H-benzo[d]imidazol-2-yl)methyl)-3-nitropyridin-2(1H)-one (I-194) (5.00 g) as a brown oil.

To a solution of 1-((4-((2,4-difluorobenzyl)oxy)-1-((2-(trimethylsilyl)ethoxy) methyl)-1H-benzo[d]imidazol-2-yl) methyl)-3-nitropyridin-2(1H)-one (5.00 g, 9.21 mmol) in MeOH (50 mL) and $H_2O$ (5 mL) were added Fe (2.57 g, 46.1 mmol) and $NH_4Cl$ (4.93 g, 92.1 mmol, 3.22 mL). The mixture was stirred at 85° C. for 1 h. The resulting suspension was filtered and the filtrate was concentrated in vacuum to give a residue. The residue was poured into water (100 mL) and extracted with ethylacetate (100 mL×3). The combined organic layers were washed with brine (300 mL), dried over anhydrous $Na_2SO_4$, filtered and concentrated in vacuum. The residue was purified by column chromatography to afford 3-amino-1-((4-((2,4-difluorobenzyl)oxy)-1-((2-(trimethylsilyl) ethoxy) methyl)-1H-benzo[d]imidazol-2-yl)methyl)pyridin-2(1H)-one (~195) (4.00 g) as a brown oil. LCMS m/z 513.1 $(M+1)^+$.

The following intermediates were prepared according to the procedures described in I-195 using the appropriate regents.

| Compound | Structure | LCMS Data |
|---|---|---|
| I-196 | 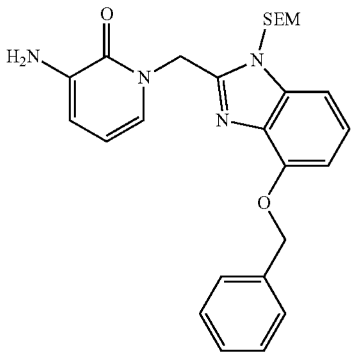 [SMILES: C[Si](C)(C)CCOCn1c(Cn2cccc(N)c2=O)nc2c(OCc3ccccc3)cccc21] | LCMS m/z 477.3 (M + 1)$^+$ |

-continued
| Compound | Structure | LCMS Data |
|---|---|---|
| I-197 | 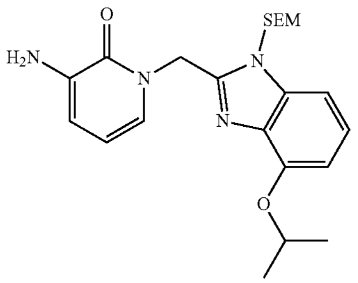 [SMILES: CC(C)Oc1cccc2c1nc(Cn1cccc(N)c1=O)n2COCC[Si](C)(C)C] | LCMS m/z 429.3 $(M+1)^+$ |
| I-198 | 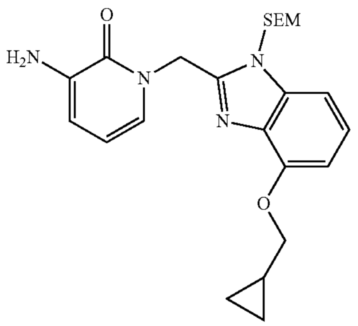 [SMILES: C[Si](C)(C)CCOCn1c(Cn2cccc(N)c2=O)nc2c(OCC3CC3)cccc21] | LCMS m/z 441.3 $(M+1)^+$ |
| I-199 | 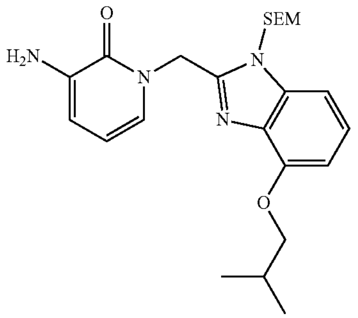 [SMILES: CC(C)COc1cccc2c1nc(Cn1cccc(N)c1=O)n2COCC[Si](C)(C)C] | LCMS m/z 443.3 $(M+1)^+$ |
| I-200 | 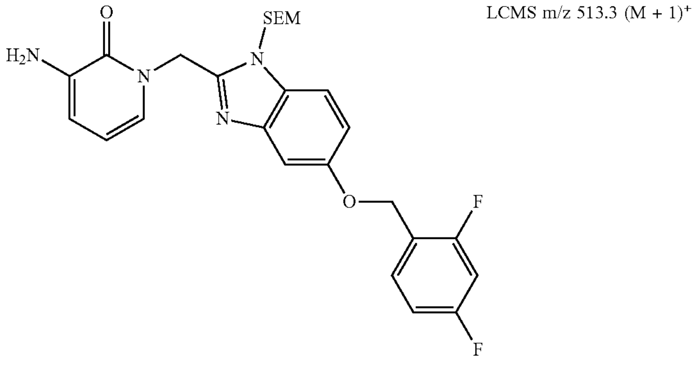 | LCMS m/z 513.3 $(M+1)^+$ |

-continued
| Compound | Structure | LCMS Data |
| --- | --- | --- |
| I-201 | 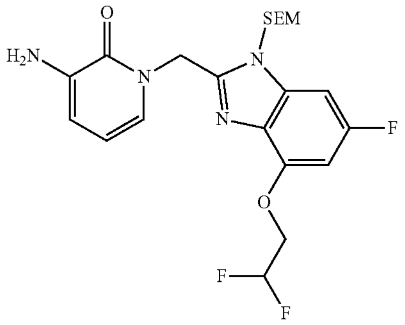 [SMILES: C[Si](C)(C)CCOCn1c(Cn2cccc(N)c2=O)nc2c(OCC(F)F)cc(F)cc21] | LCMS m/z 469.0 $(M + 1)^+$ |
| I-202 | 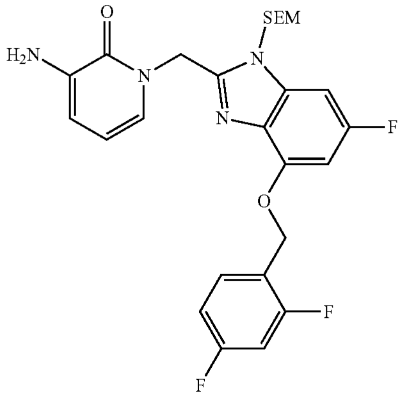 [SMILES: C[Si](C)(C)CCOCn1c(Cn2cccc(N)c2=O)nc2c(OCc3ccc(F)cc3F)cc(F)cc21] | LCMS m/z 531.2 $(M + 1)^+$ |
| I-203 | 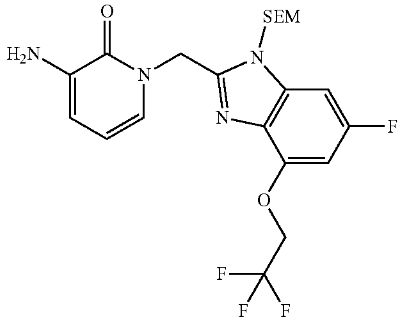 [SMILES: C[Si](C)(C)CCOCn1c(Cn2cccc(N)c2=O)nc2c(OCC(F)(F)F)cc(F)cc21] | LCMS m/z 487.3 $(M + 1)^+$ |
| I-204 | 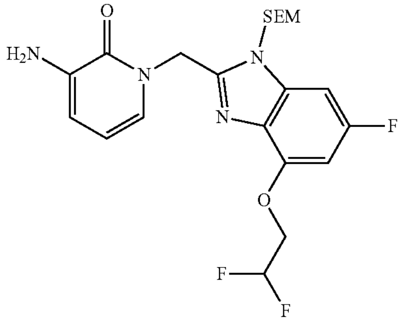 [SMILES: C[Si](C)(C)CCOCn1c(Cn2cccc(N)c2=O)nc2c(OCC(F)F)cc(F)cc21] | LCMS m/z 469.3 $(M + 1)^+$ |

Example 18

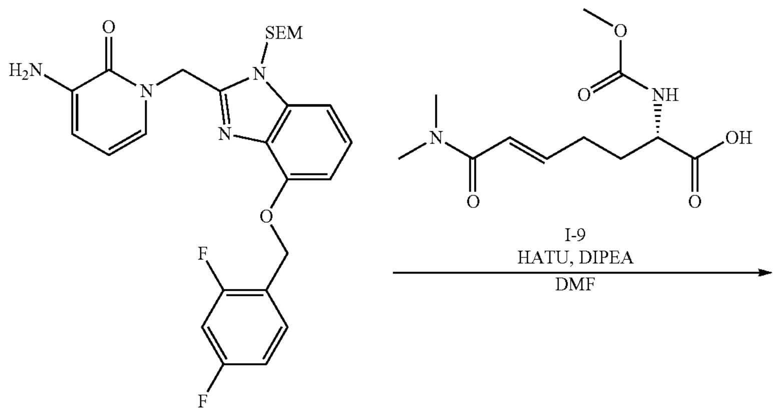

I-195

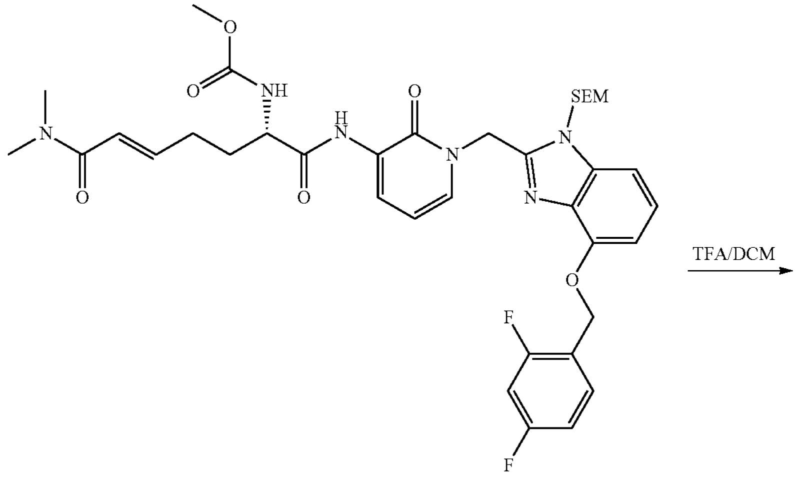

I-205

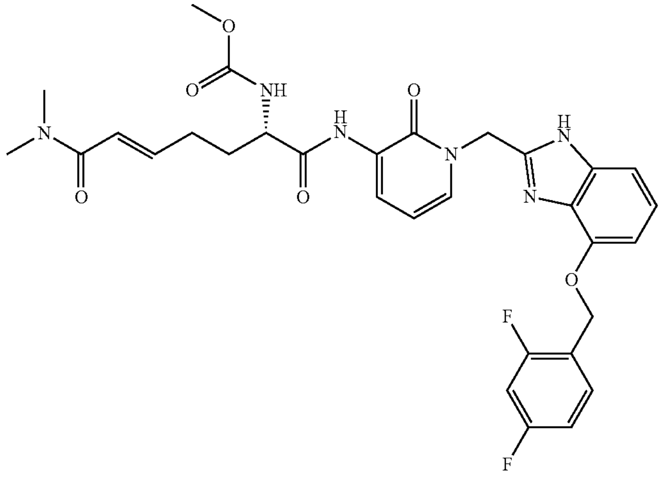

115

To a mixture of 3-amino-1-((2,4-difluorobenzyl)oxy)-1-((2-(trimethylsilyl)ethoxy) methyl)-1H-benzo[d]imidazol-2-yl)methyl)pyridin-2(1H)-one (200 mg, 0.390 mmol), (S,E)-7-(dimethylamino)-2-((methoxycarbonyl)amino)-7-oxohept-5-enoic acid (151 mg, 0.585 mmol) and HATU (223 mg, 0.585 mmol) in DMF (3 mL) was added DIPEA (151 mg, 1.17 mmol, 0.2 mL) at 0° C. The mixture was stirred at 0-20° C. for 16 h. The mixture was poured into ice-water (30 mL) and extracted with ethyl acetate (30 mL×3). The combined organic layers were washed with brine (100 mL), dried over anhydrous $Na_2SO_4$, filtered and concentrated in vacuum to give a residue. The residue was purified by prep-TLC to afford (S,E)-methyl (1-((1-((4-((2, 4-difluorobenzyl)oxy)-1-((2-(trimethylsilyl)ethoxy) methyl)-1H-benzo[d]imidazol-2-yl)methyl)-2-oxo-1,2-dihydropyridin-3-yl)amino)-7-(dimethylamino)-1,7- dioxohept-5-en-2-yl)carbamate (I-205) (280 mg) as a brown oil. LCMS m/z 753.4 $(M+1)^+$.

To a mixture of (S,E)-methyl (1-((1(4-((2,4-difluorobenzyl)oxy)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl)carbamate (280 mg, 0.372 mmol) in DCM (1 mL) was added TFA (2.31 g, 20.3 mmol, 1.5 mL) at 0° C. The mixture was stirred at 0-20° C. for 6 h. The reaction mixture was concentrated under reduced pressure to give a residue. The residue was purified by prep-HPLC to afford methyl(S,E)-methyl(1-((1-((7-((2,4-difluorobenzyl)oxy)-1H-benzo[d]imidazol-2-yl)methyl)-2-oxo-1,2-dihydropyridin-3-yl)amino)-7-(dimethylamino)-1,7-dioxohept-5-en-2-yl)carbamate (Compound 115) (61.1 mg, 26% yield) as a white solid. LCMS m/z 623.3 $(M+1)^+$. $^1H$ NMR (400 MHz, DMSO-$d_6$) δ 9.25 (s, 1H), 8.27 (d, J=7.2 Hz, 1H), 7.72 (d, J=7.6 Hz, 1H), 7.60-7.50 (m, 3H), 7.46-7.32 (m, 4H), 7.28-7.17 (m, 2H), 6.99 (d, J=8.0 Hz, 1H), 6.89 (s, 1H), 6.52-6.63 (m, 1H), 6.39 (t, J=7.2 Hz, 1H), 5.84 (d, J=15.6 Hz, 1H), 5.48 (s, 2H), 5.32 (s, 2H), 4.47-3.95 (m, 1H), 3.62-3.59 (m, 3H), 2.29-2.08 (m, 3H), 1.90-1.76 (m, 1H), 1.73-1.62 (m, 1H).

The following compounds were prepared according to the procedures described in Example 18 using the appropriate intermediates.

| Compound | Structure | LCMS Data |
|---|---|---|
| 116 | 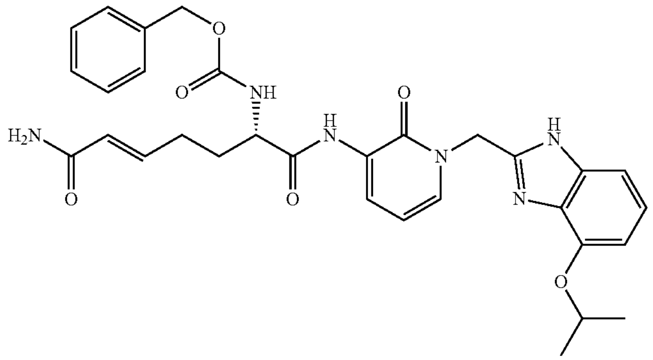 [SMILES: CC(C)Oc1cccc2[nH]c(Cn3cccc(NC(=O)[C@H](CC/C=C/C(N)=O)NC(=O)OCc4ccccc4)c3=O)nc12] | LCMS m/z 587.4 $(M + 1)^+$ |
| 117 | 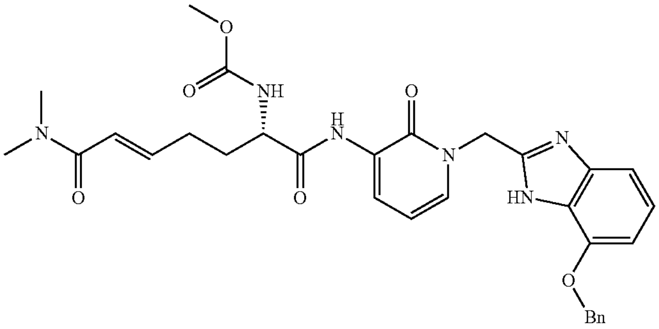 [SMILES: COC(=O)N[C@@H](CC/C=C/C(=O)N(C)C)C(=O)Nc1cccn(Cc2nc3cccc(OCc4ccccc4)c3[nH]2)c1=O] | LCMS m/z 587.3 $(M + 1)^+$ |
| 118 | 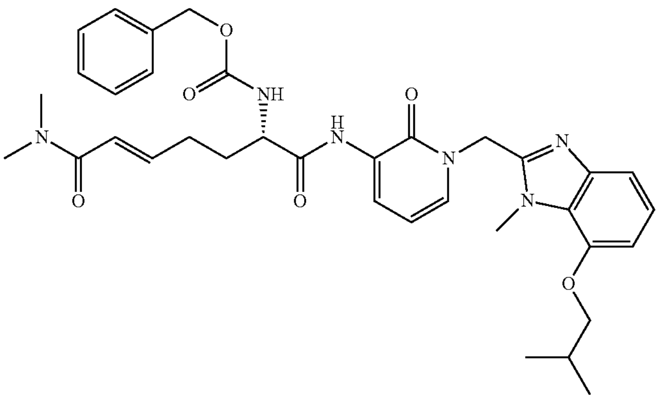 [SMILES: CC(C)COc1cccc2nc(Cn3cccc(NC(=O)[C@H](CC/C=C/C(=O)N(C)C)NC(=O)OCc4ccccc4)c3=O)n(C)c12] | LCMS m/z 643.4 $(M + 1)^+$ |

-continued
| Compound | Structure | LCMS Data |
| --- | --- | --- |
| 119 | 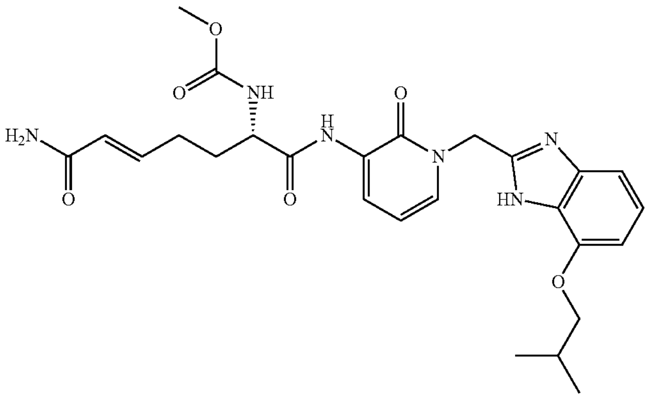 [SMILES: COC(=O)N[C@@H](CC/C=C/C(N)=O)C(=O)Nc1cccn(Cc2nc3cccc(OCC(C)C)c3[nH]2)c1=O] | LCMS m/z 525.3 (M + 1)+ |
| 120 | 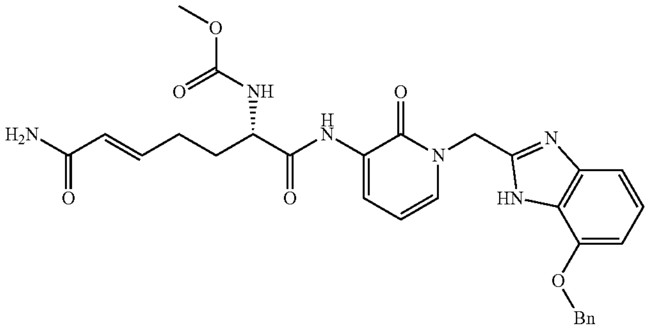 [SMILES: COC(=O)N[C@@H](CC/C=C/C(N)=O)C(=O)Nc1cccn(Cc2nc3cccc(OCc4ccccc4)c3[nH]2)c1=O] | LCMS m/z 559.3 (M + 1)+ |
| 121 | 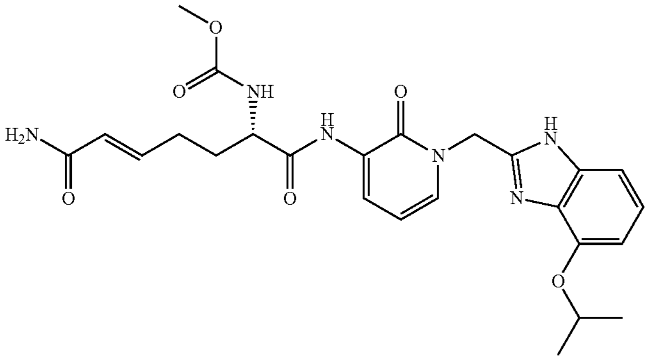 [SMILES: COC(=O)N[C@@H](CC/C=C/C(N)=O)C(=O)Nc1cccn(Cc2nc3c(OC(C)C)cccc3[nH]2)c1=O] | LCMS m/z 511.2 (M + H)+ |
| 122 | 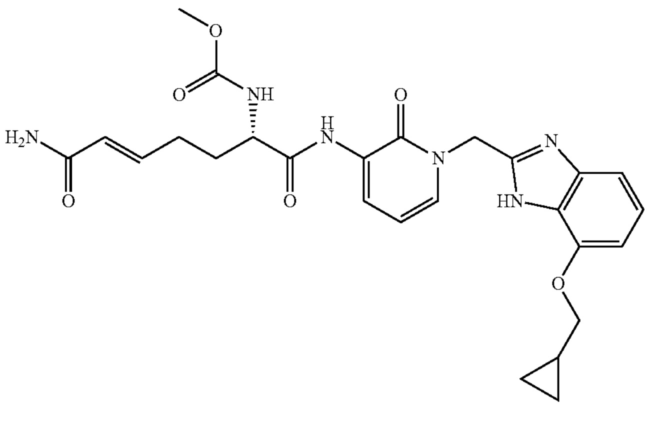 | LCMS m/z 707.5 (M + 1)+ |

-continued
| Compound | Structure | LCMS Data |
| --- | --- | --- |
| 123 | 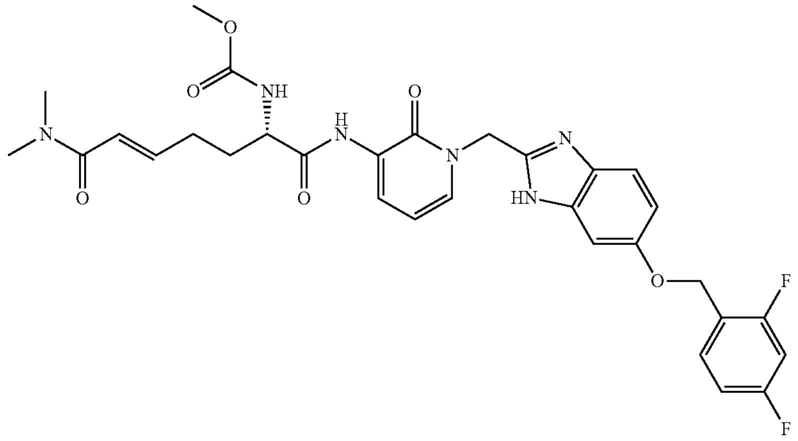 [SMILES: COC(=O)N[C@@H](CC/C=C/C(=O)N(C)C)C(=O)Nc1cccn(Cc2nc3ccc(OCc4ccc(F)cc4F)cc3[nH]2)c1=O] | LCMS m/z 623.3 $(M + 1)^+$ |
| 124 | 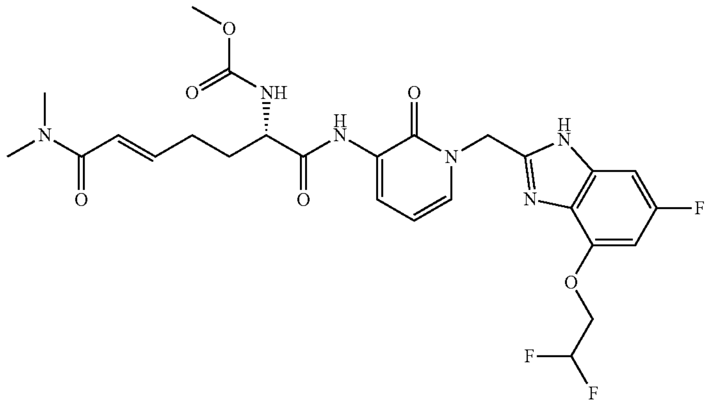 [SMILES: COC(=O)N[C@@H](CC/C=C/C(=O)N(C)C)C(=O)Nc1cccn(Cc2nc3c(OCC(F)F)cc(F)cc3[nH]2)c1=O] | LCMS m/z 579.1 $(M + 1)^+$ |
| 125 | 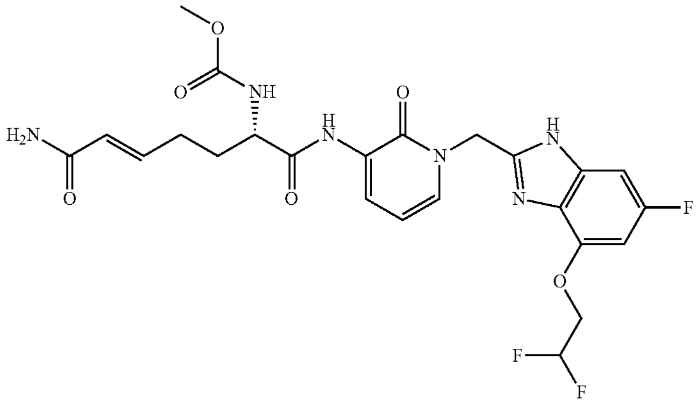 [SMILES: COC(=O)N[C@@H](CC/C=C/C(N)=O)C(=O)Nc1cccn(Cc2nc3c(OCC(F)F)cc(F)cc3[nH]2)c1=O] | LCMS m/z 551.1 $(M + 1)^+$ |

-continued
| Compound | Structure | LCMS Data |
|---|---|---|
| 126 | 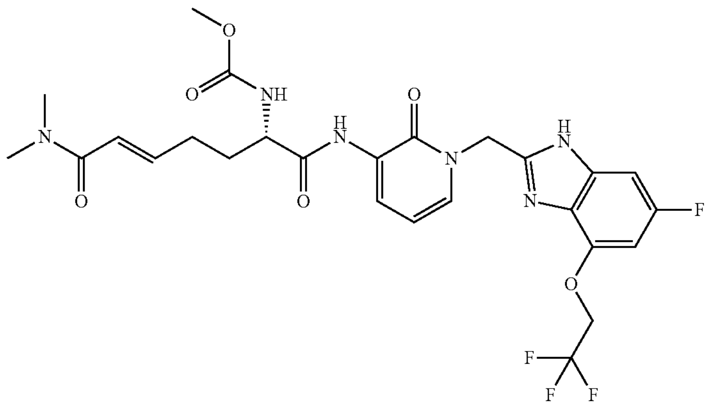 [SMILES: COC(=O)N[C@@H](CC/C=C/C(=O)N(C)C)C(=O)Nc1cccn(Cc2nc3c(OCC(F)(F)F)cc(F)cc3[nH]2)c1=O] | LCMS m/z 597.0 $(M+1)^+$ |
| 127 | 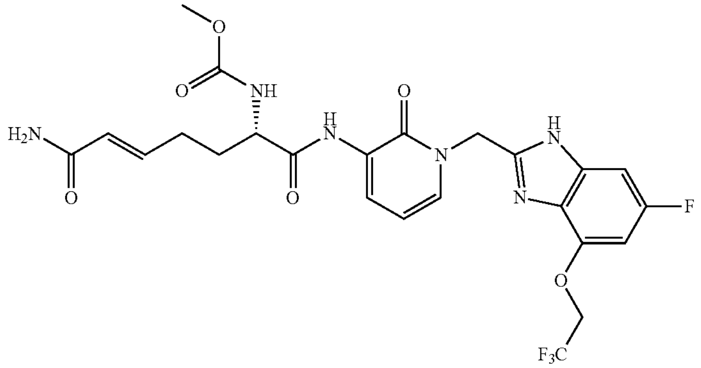 [SMILES: COC(=O)N[C@@H](CC/C=C/C(N)=O)C(=O)Nc1cccn(Cc2nc3c(OCC(F)(F)F)cc(F)cc3[nH]2)c1=O] | LCMS m/z 569.0 $(M+1)^+$ |
| 128 | 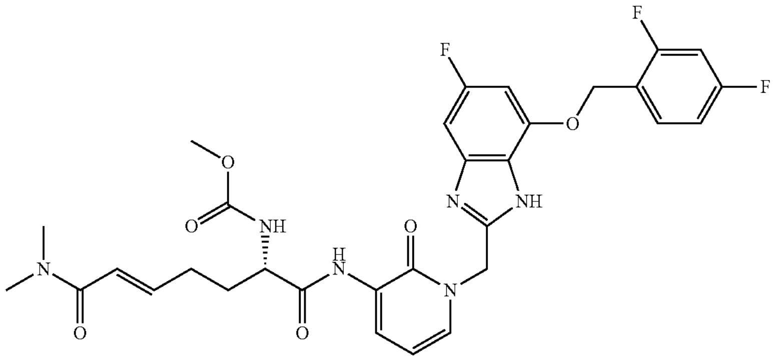 [SMILES: COC(=O)N[C@@H](CC/C=C/C(=O)N(C)C)C(=O)Nc1cccn(Cc2nc3cc(F)cc(OCc4ccc(F)cc4F)c3[nH]2)c1=O] | LCMS m/z 641.2 $(M+1)^+$ |
| 129 | 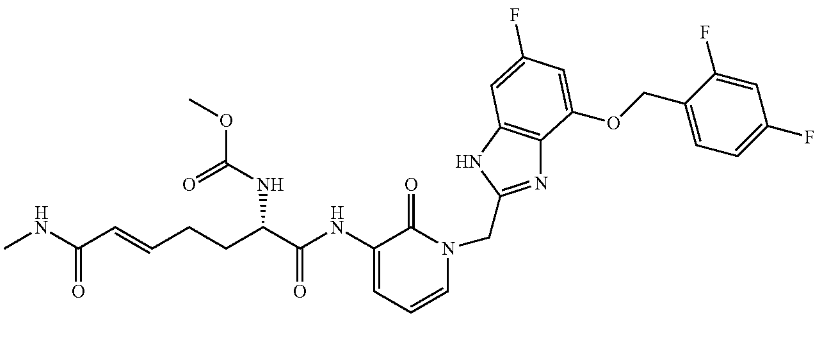 [SMILES: CNC(=O)/C=C/CC[C@H](NC(=O)OC)C(=O)Nc1cccn(Cc2nc3c(OCc4ccc(F)cc4F)cc(F)cc3[nH]2)c1=O] | LCMS m/z 627.2 $(M+1)^+$ |

-continued
| Compound | Structure | LCMS Data |
| --- | --- | --- |
| 130 | 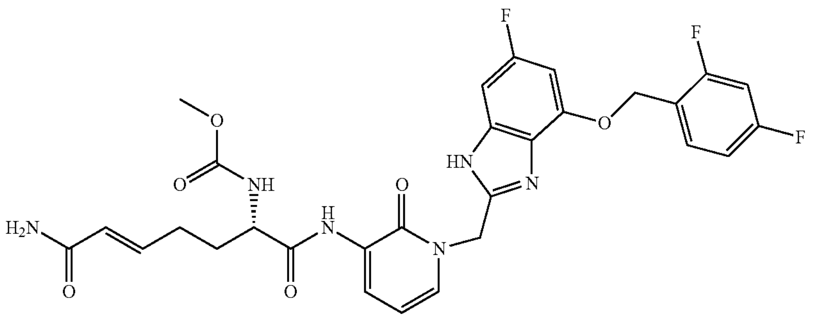 [SMILES: COC(=O)N[C@@H](CC/C=C/C(N)=O)C(=O)Nc1cccn(Cc2nc3c(OCc4ccc(F)cc4F)cc(F)cc3[nH]2)c1=O] | LCMS m/z 613.1 (M + 1)+ |
| 131 | 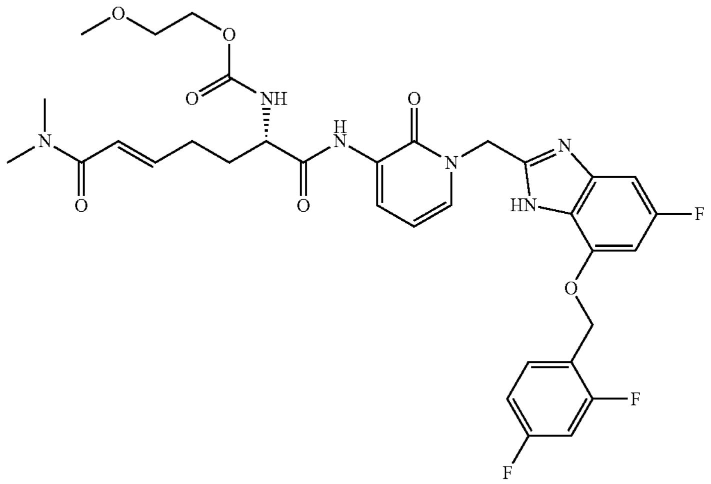 [SMILES: COCCOC(=O)N[C@@H](CC/C=C/C(=O)N(C)C)C(=O)Nc1cccn(Cc2nc3cc(F)cc(OCc4ccc(F)cc4F)c3[nH]2)c1=O] | LCMS m/z 685.2 (M + 1)+ |
| 132 | 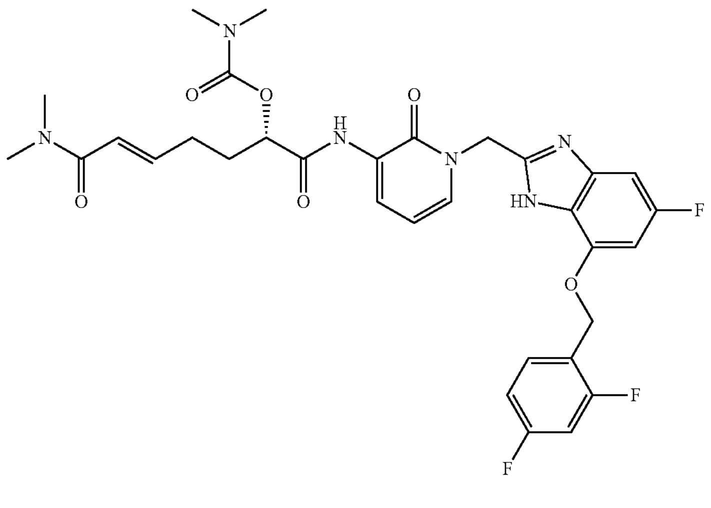 [SMILES: CN(C)C(=O)/C=C/CC[C@H](OC(=O)N(C)C)C(=O)Nc1cccn(Cc2nc3cc(F)cc(OCc4ccc(F)cc4F)c3[nH]2)c1=O] | LCMS m/z 655.2 (M + 1)+ |

-continued
| Compound | Structure | LCMS Data |
|---|---|---|
| 133 | 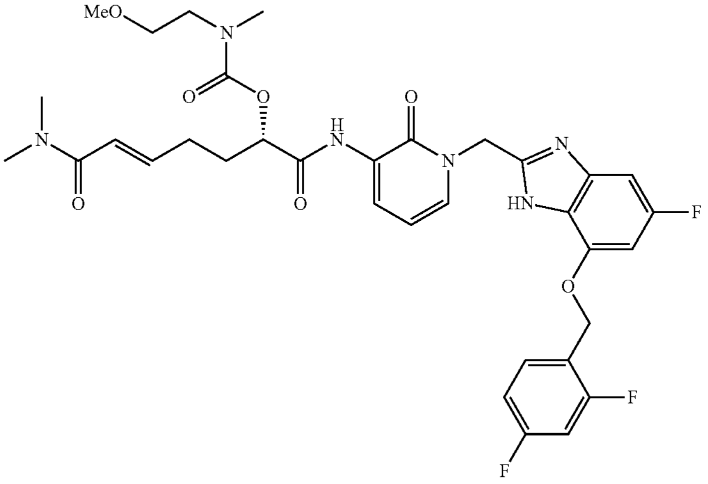 [SMILES: COCCN(C)C(=O)O[C@@H](CC/C=C/C(=O)N(C)C)C(=O)Nc1cccn(Cc2nc3cc(F)cc(OCc4ccc(F)cc4F)c3[nH]2)c1=O] | LCMS m/z 699.3 $(M + 1)^+$ |
| 259 | 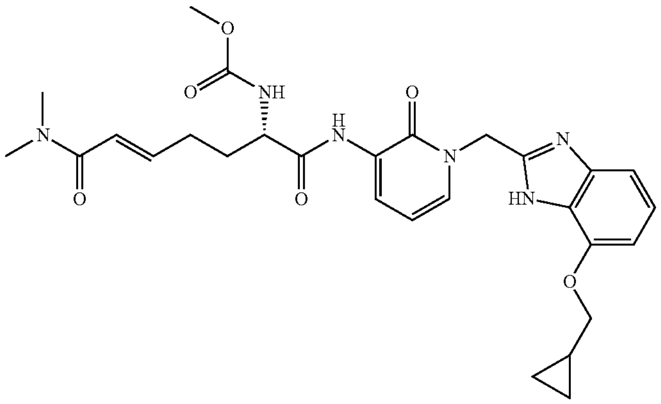 [SMILES: COC(=O)N[C@@H](CC/C=C/C(=O)N(C)C)C(=O)Nc1cccn(Cc2nc3cccc(OCC4CC4)c3[nH]2)c1=O] | LCMS m/z 551.3 $(M + 1)^+$. |
The Synthesis of Intermediate I-218
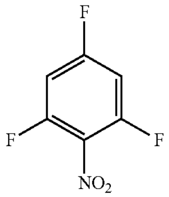
I-206
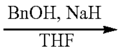
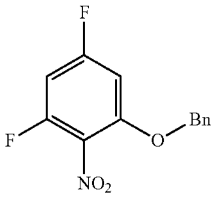
I-207
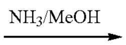
-continued
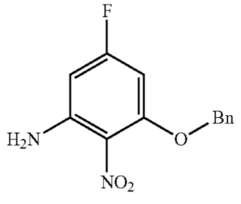
I-208
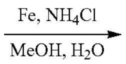
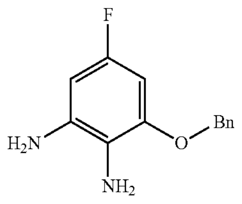
I-209
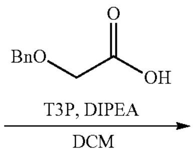

-continued

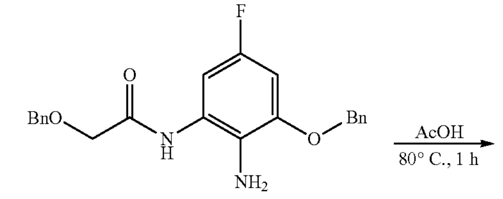

I-210

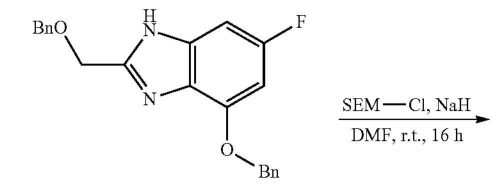

I-211

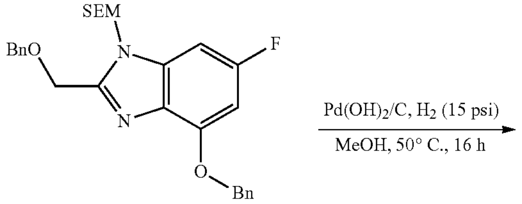

I-212

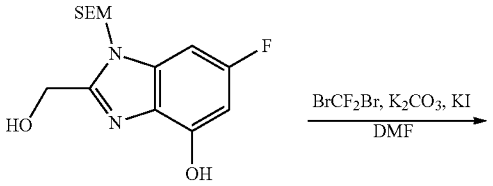

I-213

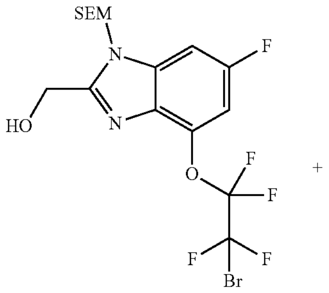

I-214

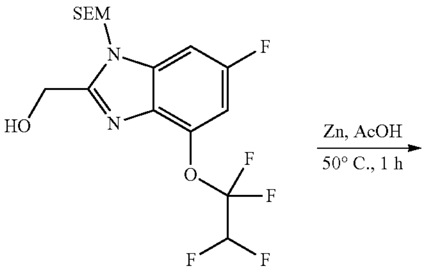

I-215

-continued

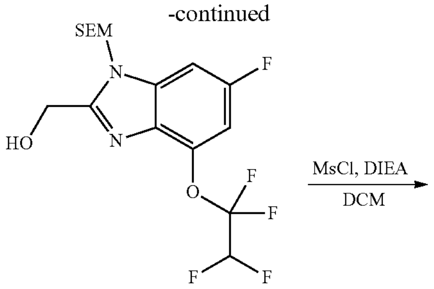

I-215

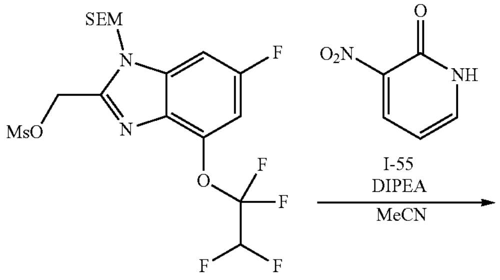

I-216

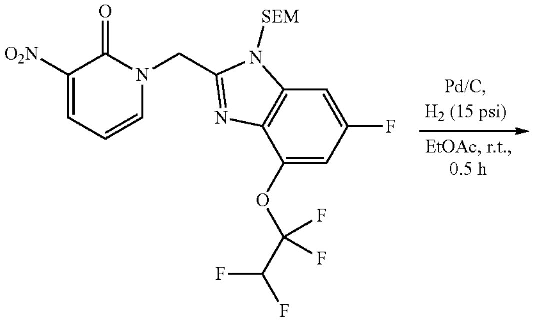

I-217

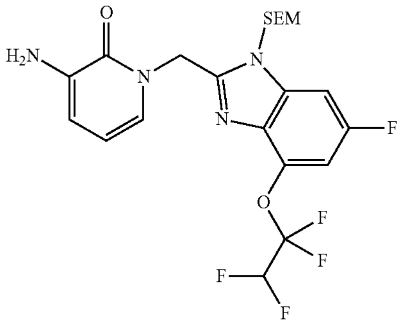

I-218

To a solution of BnOH (24.4 g, 226 mmol) in THF (500 mL) was added NaH (10.8 g, 271 mmol, 60% purity) at 0° C. The mixture was stirred at 15° C. for 0.5 hr. 1,3,5-trifluoro-2-nitrobenzene (40 g, 225 mmol) was then added to the reaction mixture above at 0° C. The mixture was stirred at 15° C. for 16 hr. The resulting solution was quenched with ice-water (800 mL) at 0° C. and extracted with EtOAc (1000 mL×3). The combined organic layers were washed with brine (800 mL×2), dried over $Na_2SO_4$, filtered and concentrated under reduced pressure to give a residue. The residue was purified by column chromatography to afford 1-(benzyloxy)-3,5-difluoro-2-nitrobenzene (I-207) (21.2 g) as alight yellow solid. $^1$H NMR (400 MHz, $CDCl_3$) δ 7.47-7.34 (m, 5H), 6.65-6.55 (m, 2H), 5.20 (s, 2H).

A solution of 1-(benzyloxy)-3,5-difluoro-2-nitrobenzene (5.6 g×3, 21.1 mmol) in $NH_3$-MeOH (5 M, 21.1 mL) was stirred at 60° C. for 16 hr in Stuffy tank. The reaction mixture was concentrated under reduced pressure to give a residue. The residue was purified by column chromatography to afford 3-(benzyloxy)-5-fluoro-2-nitroaniline (I-208) (15.5 g) as a light yellow solid. $^1H$ NMR (400 MHz, DMSO-$d_6$) δ 7.45-7.32 (m, 5H), 6.47 (s, 2H), 6.36 (dd, J=10.8, 2.4 Hz, 1H), 6.25 (dd, J=11.2, 2.4 Hz, 1H), 5.17 (s, 2H).

To a solution of 3-(benzyloxy)-5-fluoro-2-nitroaniline (15.5 g, 59.1 mmol) and Fe (16.5 g, 295 mmol) in MeOH (300 mL) and $H_2O$ (60 mL) was added $NH_4Cl$ (31.6 g, 591 mmol). The mixture was stirred at 60° C. for 3 hr. The resulting suspension was filtered and the filtrate was concentrated under reduced pressure to give a residue. The residue was diluted with water (200 mL) and extracted with EtOAc (200 mL×3). The combined organic layers were washed with brine (200 mL×2), dried over anhydrous $Na_2SO_4$, filtered and concentrated under reduced pressure to give 3-(benzyloxy)-5-fluorobenzene-1,2-diamine (I-209) (14 g) which was used in the next step without further purification.

To a solution of 3-(benzyloxy)-5-fluorobenzene-1,2-diamine (10.0 g, 60.3 mmol), DIPEA (15.6 g, 121 mmol) and $T_3P$ (57.5 g, 90.4 mmol) in DCM (200 mL) was added 3-benzyloxy-5-fluoro-benzene-1,2-diamine (14 g, 60.3 mmol) at 0° C. The mixture was stirred at 15° C. for 16 hr. The resulting solution was diluted with water (300 mL) and extracted with DCM (300 mL×3). The combined organic layers were washed with citric acid (5%, 300 mL×2), washed with water (300 mL×2), dried over anhydrous $Na_2SO_4$, filtered and concentrated under reduced pressure to give N-(2-amino-3-(benzyloxy)-5-fluorophenyl)-2-(benzyloxy)acetamide (I-210) (20 g), which was used in the next step without further purification. LCMS m/z 381.0 $(M+1)^+$.

A solution of N-(2-amino-3-benzyloxy-5-fluoro-phenyl)-2-benzyloxy-acetamide (20 g, 21.03 mmol) in AcOH (200 mL) was stirred at 85° C. for 1 hr. The reaction mixture was concentrated under reduced pressure to give a residue. The residue was diluted with water (300 mL) and extracted with EtOAc (200 mL×3). The combined organic layers were washed with saturated $Na_2CO_3$ (200 mL×3), brine (200 mL×2), dried over anhydrous $Na_2SO_4$, filtered and concentrated under reduced pressure to give a residue. The residue was purified by column chromatography to afford 4-(benzyloxy)-2-((benzyloxy)methyl)-6-fluoro-1H-benzo[d]imidazole (I-211) (5.1 g, 11.26 mmol) as a red oil. LCMS m/z 363.2 $(M+1)^+$.

To a solution of 4-(benzyloxy)-2-((benzyloxy)methyl)-6-fluoro-1H-benzo[d]-imidazole (10 g, 27.6 mmol) in THF (100 mL) was added NaH (1.32 g, 33.11 mmol, 60% purity) at 0° C. The mixture was stirred at 15° C. for 0.5 hr. SEM-Cl (5.52 g, 33.1 mmol) was added to the reaction mixture above at 0° C. The resulting solution was stirred at 15° C. for 1 hr. The reaction mixture was quenched with ice-water (200 mL) at 0° C., and extracted with EtOAc (200 mL×3). The combined organic layers were washed with brine (200 mL×2), dried over anhydrous $Na_2SO_4$, filtered and concentrated under reduced pressure to give a residue. The residue was purified by column chromatography to afford 4-(benzyloxy)-2-((benzyloxy)methyl)-6-fluoro-1-((2-(trimethylsilyl)ethoxy)methyl)-1H-benzo[d]imidazole (I-212) (7 g, 46% yield) as a yellow oil. LCMS m/z 493.1 $(M+1)^+$.

To a solution of 4-(benzyloxy)-2-((benzyloxy)methyl)-6-fluoro-1-((2-(trimethylsilyl)-ethoxy)methyl)-1H-benzo[d]imidazole (6.6 g, 13.4 mmol) in MeOH (60 mL) were added $Pd(OH)_2/C$ (1.52 g, 1.63 mmol) and Pd/C (1.5 g, 13.40 mmol, 15% purity). The mixture was stirred at 50° C. for 30 hr under $H_2$ (45 psi) atmosphere. The reaction mixture was filtered and concentrated under reduced pressure to give 6-fluoro-2-(hydroxymethyl)-1-((2-(trimethylsilyl)ethoxy)methyl)-1H-benzo[d] imidazol-4-ol (I-213) (3.5 g) as a light yellow oil. LCMS m/z 313.1 $(M+1)^+$.

To a solution of 6-fluoro-2-(hydroxymethyl)-1-((2-(trimethylsilyl)ethoxy)methyl)-1H-benzo[d]imidazol-4-ol (1.2 g, 3.84 mmol) and 1,2-dibromo-1,1,2,2-tetrafluoro-ethane (1.50 g, 5.76 mmol) in DMF (10 mL) were added $K_2CO_3$ (1.06 g, 7.68 mmol) and KI (63.7 mg, 0.384 mmol). The mixture was stirred at 90° C. for 16 hr. $Cs_2CO_3$ (1.25 g, 3.84 mmol) was then added to the reaction mixture above. The mixture was stirred at 90° C. for another 6 hr. The resulting solution was diluted with water (20 mL) and extracted with EtOAc (30 mL×3). The combined organic layers were washed with brine (50 mL×3), dried over anhydrous $Na_2SO_4$, filtered and concentrated under reduced pressure to give a residue. The residue was purified by column chromatography to afford (4-(2-bromo-1,1,2,2-tetrafluoroethoxy)-6-fluoro-1-((2-(trimethyl-silyl)ethoxy)methyl)-1H-benzo[d]imidazol-2-yl)methanol (I-214) (500 mg, 24% yield) as a yellow oil. LCMS m/z 493.0 $(M+1)^+$.

To a solution of (4-(2-bromo-1,1,2,2-tetrafluoroethoxy)-6-fluoro-1-((2-(trimethyl-silyl)ethoxy)methyl)-1H-benzo[d] imidazol-2-yl)methanol (510 mg, 1.04 mmol) in AcOH (5 mL) was added Zn (339 mg, 5.19 mmol). The mixture was stirred at 50° C. for 1 hr. The resulting solution was diluted with water (20 mL) and extracted with EtOAc (30 mL×3). The combined organic layers were washed with saturated $NaHCO_3$ (30 mL×3), brine (30 mL×2) and dried over anhydrous $Na_2SO_4$, filtered and concentrated under reduced pressure to give (6-fluoro-4-(1,1,2,2-tetrafluoroethoxy)-1-((2-(trimethylsilyl)-ethoxy)methyl)-1H-benzo[d]imidazol-2-yl)methyl methanesulfonate (I-215) (0.41 g) as a brown oil. $^1H$ NMR (400 MHz, DMSO-$d_6$) δ 7.67-6.75 (m, 3H), 5.82-5.74 (m, 1H), 5.73-5.61 (m, 2H), 4.75 (s, 2H), 3.56-3.46 (m, 2H), 0.85-0.72 (m, 2H), −0.06-−0.16 (m, 9H).

To a solution of (6-fluoro-4-(1,1,2,2-tetrafluoroethoxy)-1-((2-(trimethylsilyl)ethoxy)-methyl)-1H-benzo[d]imidazol-2-yl)methanol (0.41 g, 0.994 mmol) and DIPEA (256 mg, 1.99 mmol) in DCM (10 mL) was added MsCl (170 mg, 1.49 mmol) at 0° C. The mixture was stirred at 15° C. for 1 hr. The resulting solution was diluted with water (30 mL) and extracted with DCM (30 mL×3). The combined organic layers were washed with water (30 mL×2), dried over anhydrous $Na_2SO_4$, filtered and concentrated under reduced pressure at 15° C. to give (6-fluoro-4-(1,1,2,2-tetrafluoroethoxy)-1-((2-(trimethylsilyl)-ethoxy)methyl)-1H-benzo[d] imidazol-2-yl)methyl methanesulfonate (I-216) (550 mg), which was used in the next step without further purification. LCMS m/z 513.0 $(M+1)^+$.

To a solution of (6-fluoro-4-(1,1,2,2-tetrafluoroethoxy)-1-((2-(trimethylsilyl)-ethoxy)methyl)-1H-benzo[d]imidazol-2-yl)methyl methanesulfonate (550 mg, 1.12 mmol) and 3-nitro-1H-pyridin-2-one (157 mg, 1.12 mmol) in MeCN (10 mL) was added DIPEA (289 mg, 2.24 mmol) at 0° C. The mixture was stirred at 30° C. for 16 hr. The reaction mixture was diluted with water (30 mL) and extracted with EtOAc (40 mL×3). The combined organic layers were washed with brine (30 mL×2), dried over anhydrous $Na_2SO_4$, filtered and concentrated under reduced pressure to give a residue. The residue was purified by column chromatography to afford 1-((6-fluoro-4-(1,1,2,2-tetrafluoroethoxy)-1-((2-(trimethylsilyl)ethoxy)methyl)-1H-benzo[d]imidazol-2-yl)methyl)-3-nitropyridin-2(1H)-one (I-217) (0.29 g) as alight yellow oil. LCMS m/z 535.0 $(M+1)^+$.

To a solution of 1-((6-fluoro-4-(1,1,2,2-tetrafluoroethoxy)-1-((2-(trimethylsilyl)-ethoxy)methyl)-1H-benzo[d]imidazol-2-yl)methyl)-3-nitropyridin-2(1H)-one (290 mg, 0.542 mmol) in EtOAc (8 mL) was added Pd/C (150 mg, 15% purity). The mixture was stirred at 15° C. for 0.5 hr under $H_2$ (15 psi). The reaction mixture was filtered and concentrated under reduced pressure to give 3-amino-1-((6-fluoro-4-(1,1,2,2-tetrafluoroethoxy)-1-((2-(trimethylsilyl)ethoxy) methyl)-1H-benzo[d]imidazol-2-yl)methyl)pyridin-2(1H)-one (I-218) (250 mg) as a light yellow oil. LCMS m/z 505.1 $(M+1)^+$.

Example 19 and DIPEA (76.9 mg, 0.594 mmol) in DMF (2 mL) was added HATU (128 mg, 0.336 mmol) at 0° C. The mixture was stirred at 30° C. for 16 hr. The reaction mixture was diluted with water (20 mL) and extracted with EtOAc (20 mL×3). The combined organic layers were washed with brine (20 mL×2), dried over anhydrous $Na_2SO_4$, filtered and concentrated under reduced pressure to give a residue. The residue was purified by prep-TLC to afford (S,E)-methyl (7-(dimethylamino)-1-((1-((6-fluoro-4-(1,1,2,2-tetrafluoroethoxy)-1-((2-(trimethylsilyl)ethoxy)methyl)-1H-benzo[d]imidazol-2-yl)methyl)-2-oxo-1,2-dihydropyridin-3-yl)amino)-1,7-dioxohept-5-en-2-yl)carbamate (I-219) (75 mg, 0.096 mmol, 48% yield) as a colorless oil. LCMS m/z 745.3 $(M+1)^+$.

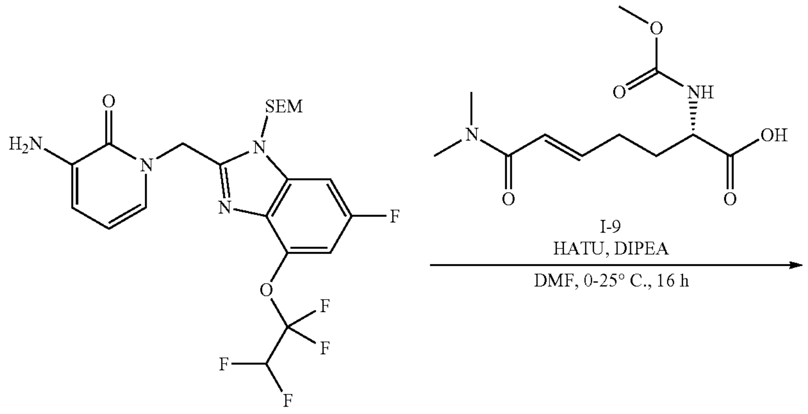

I-218

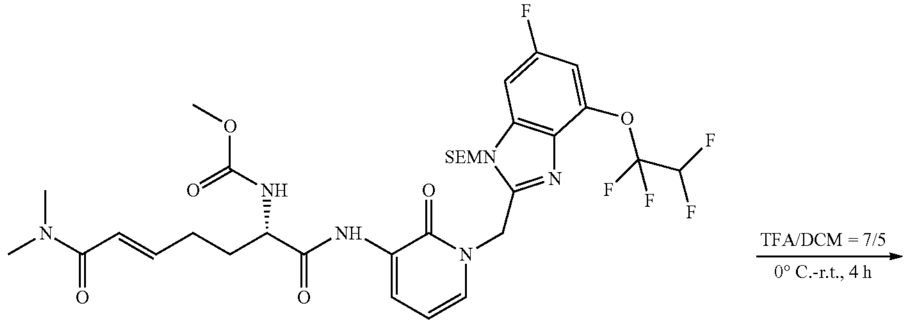

I-219

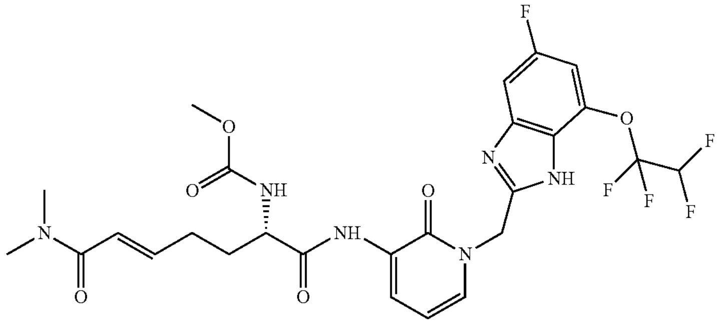

134

To a solution of 3-amino-1-((6-fluoro-4-(1,1,2,2-tetrafluoroethoxy)-1-((2-(trimethyl-silyl)ethoxy)methyl)-1H-benzo[d]imidazol-2-yl)methyl)pyridin-2(1H)-one (100 mg, 0.198 mmol), (E,2S)-7-(dimethylamino)-2-(methoxycarbonylamino)-7-oxo-hept-5-enoic acid (76.8 mg, 0.297 mmol)

To a solution of (S,E)-methyl (7-(dimethylamino)-1-((1-((6-fluoro-4-(1,1,2,2-tetrafluoroethoxy)-1-((2-(trimethylsilyl)ethoxy)methyl)-1H-benzo[d]imidazol-2-yl)methyl)-2-oxo-1,2-dihydropyridin-3-yl)amino)-1,7-dioxohept-5-en-2-yl)carbamate (75 mg, 0.0956 mmol) in DCM (1 mL) was added TFA (1.4 mL) at 0° C. The mixture was stirred at 15° C. for 6 hr. The reaction mixture was concentrated under reduced pressure to give a residue at 30° C. The residue was purified by prep-HPLC to afford (S,E)-methyl (7-(dimethylamino)-1-((1-((5-fluoro-7-(1,1,2,2-tetrafluoroethoxy)-1H-benzo[d]imidazol-2-yl)methyl)-2-oxo-1,2-dihydropyridin-3-yl)amino)-1,7-dioxohept-5-en-2-yl)carbamate (Compound 134) (28.7 mg, 48% yield) as a white solid. LCMS m/z 615.2 $(M+1)^+$. $^1H$ NMR (400 MHz, DMSO-$d_6$) 9.27 (s, 1H), 8.26 (dd, J=7.6, 1.6 Hz, 1H), 7.73 (d, J=8.0 Hz, 1H), 7.58 (dd, J=6.8, 2.0 Hz, 1H), 7.36 (dd, J=8.8, 2.0 Hz, 1H), 7.06 (d, J=9.2 Hz, 1H), 7.03-6.74 (m, 1H), 6.67-6.55 (m, 1H), 6.42-6.33 (m, 2H), 5.41 (s, 2H), 4.20-4.13 (m, 1H), 3.54 (s, 3H), 2.98 (s, 3H), 2.83 (s, 3H), 2.26-2.21 (m, 2H), 1.90-1.86 (m, 1H), 1.82-1.73 (m, 1H).

Example 20

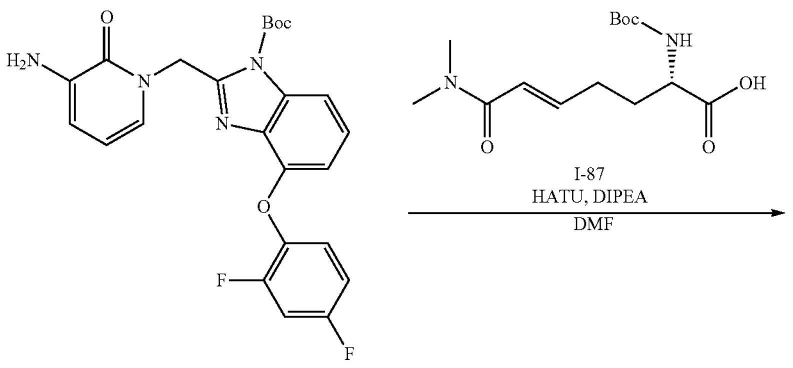

I-184

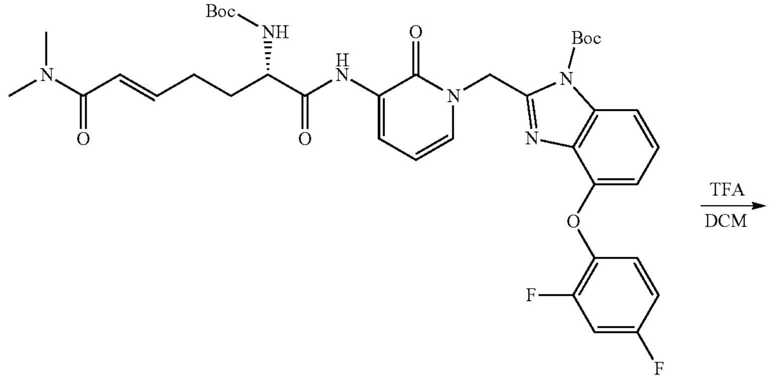

I-220

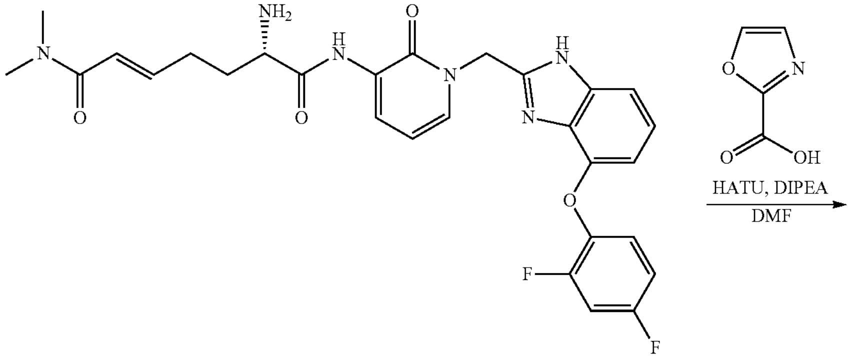

I-221

-continued

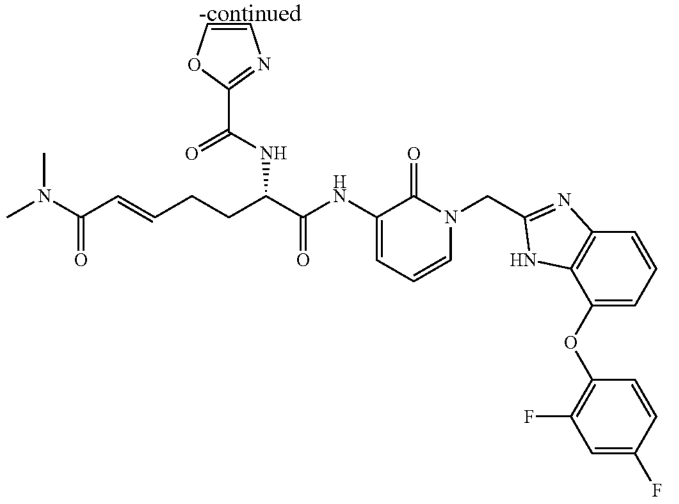

135

To a solution of tert-butyl 2-((3-amino-2-oxopyridin-1(2H)-yl)methyl)-4-(2,4-difluorophenoxy)-1H-benzo[d]imidazole-1-carboxylate (200 mg, 427 μmol) and (S,E)-2-((tert-butoxycarbonyl)amino)-7-(dimethylamino)-7-oxohept-5-enoic acid (256 mg, 854 μmol) in DMF (3 mL) were added HATU (195 mg, 512 μmol) and DIPEA (166 mg, 1.28 mmol) at 0° C. The reaction mixture was stirred at 25° C. for 16 hours. The resulting solution was concentrated under reduced pressure to give a residue. The residue was purified by prep-TLC to give (S,E)-tert-butyl 2-((3-(2-((tert-butoxycarbonyl)amino)-7-(dimethylamino)-7-oxohept-5-enamido)-2-oxopyridin-1(2H)-yl)methyl)-4-(2,4-difluorophenoxy)-1H-benzo[d]imidazole-1-carboxylate (I-220) (190 mg, 53% yield) as a brown solid. LCMS m/z 751.1 $(M+1)^+$.

To a solution of (S,E)-tert-butyl 2-((3-(2-((tert-butoxycarbonyl)amino)-7-(dimethylamino)-7-oxohept-5-enamido)-2-oxopyridin-1(2H)-yl)methyl)-4-(2,4-difluorophenoxy)-1H-benzo[d]imidazole-1-carboxylate (190 mg, 253 μmol) in DCM (6 mL) was added TFA (2 mL) at 0° C. The mixture was stirred at 20° C. for 2 hours. The resulting solution was concentrated to give (S,E)-6-amino-N7-(1-((4-(2,4-difluorophenoxy)-1H-benzo[d]imidazol-2-yl)methyl)-2-oxo-1,2-dihydropyridin-3-yl)-N1,N1-dimethylhept-2-enediamide (I-221) (140 mg) as a gray oil which was used into next step reaction without further purification. LCMS m/z 551.3 $(M+1)^+$.

To a solution of (S,E)-6-amino-N7-(1-((4-(2,4-difluorophenoxy)-1H-benzo[d]imidazol-2-yl)methyl)-2-oxo-1,2-dihydropyridin-3-yl)-N1,N1-dimethylhept-2-enediamide (140 mg, 254 μmol) and oxazole-2-carboxylic acid (51.9 mg, 381 μmol) in DMF (3 mL) were added HATU (116 mg, 305 μmol) and DIPEA (98.6 mg, 763 μmol) at 0° C. The reaction mixture was stirred at 25° C. for 16 hours. The resulting solution was concentrated under reduced pressure to give a residue. The residue was purified by prep-HPLC to give (S,E)-N7-(1-((7-(2,4-difluorophenoxy)-1H-benzo[d]imidazol-2-yl)methyl)-2-oxo-1,2-dihydropyridin-3-yl)-N1,N1-dimethyl-6-(oxazole-2-carboxamido)hept-2-enediamide (Compound 135) (118 mg, 71% yield) as a white solid. LCMS m/z 646.2 $(M+1)^+$. $^1H$ NMR (400 MHz, DMSO-$d_6$) δ 9.43 (s, 1H), 9.30 (d, J=8.0 Hz, 1H), 8.35 (s, 1H), 8.25 (dd, J=7.2, 1.6 Hz, 1H), 7.57 (dd, J=6.8, 1.2 Hz, 1H), 7.52-7.40 (m, 2H), 7.28-7.15 (m, 2H), 7.07 (t, J=8.0 Hz, 2H), 6.66-6.56 (m, 1H), 6.50 (d, J=7.2 Hz, 1H), 6.40-6.33 (m, 2H), 5.38 (s, 2H), 4.68-4.60 (m, 1H), 2.96 (s, 3H), 2.82 (s, 3H), 2.30-2.20 (m, 2H), 2.04-1.95 (m, 2H).

The following compounds were prepared according to the procedures described in Example 20 using the appropriate intermediates.

| Compound | Structure | LCMS Data |
|---|---|---|
| 136 | 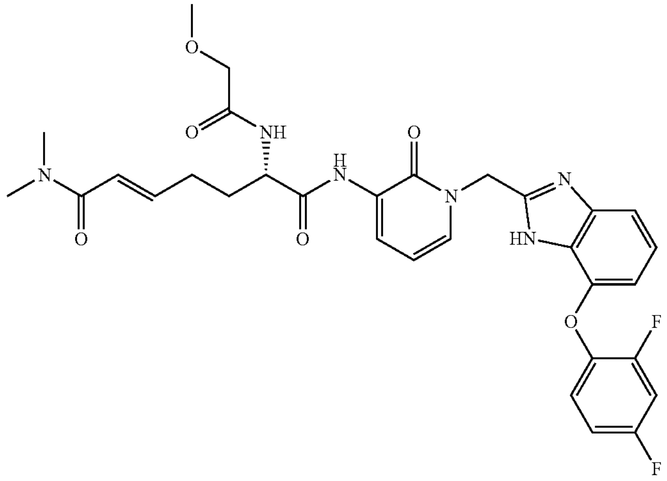 [SMILES: COCC(=O)N[C@@H](CC/C=C/C(=O)N(C)C)C(=O)Nc1cccn(Cc2nc3cccc(Oc4ccc(F)cc4F)c3[nH]2)c1=O] | LCMS m/z 623.2 (M + 1)$^+$ |
| 137 | 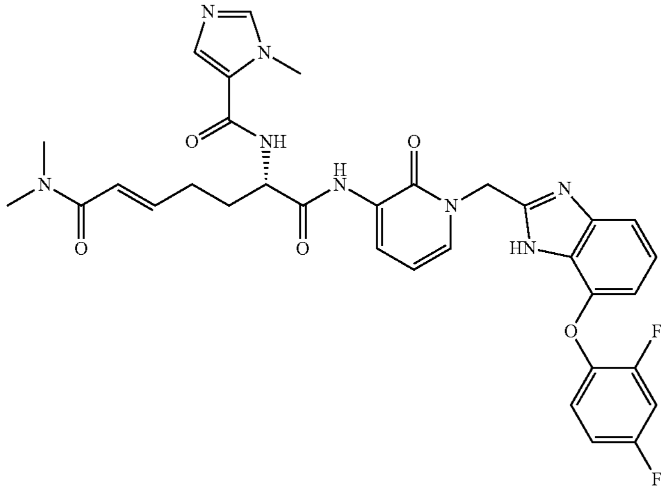 [SMILES: CN(C)C(=O)/C=C/CC[C@H](NC(=O)c1cncn1C)C(=O)Nc1cccn(Cc2nc3cccc(Oc4ccc(F)cc4F)c3[nH]2)c1=O] | LCMS m/z 659.2 (M + 1)$^+$ |
| 138 | 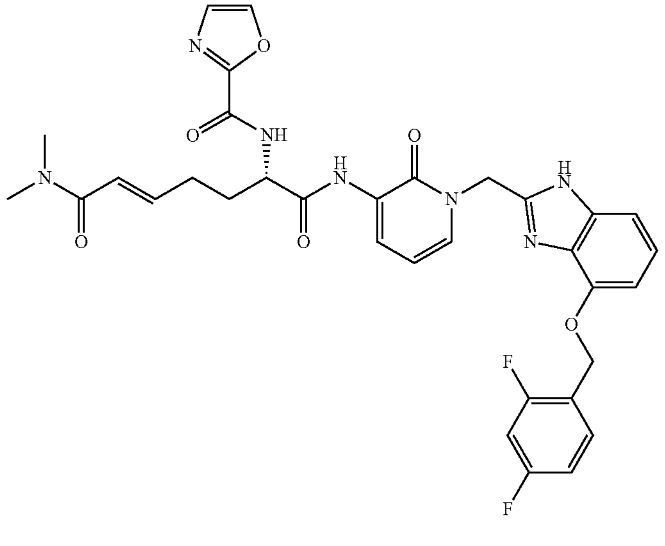 [SMILES: CN(C)C(=O)/C=C/CC[C@H](NC(=O)c1ncco1)C(=O)Nc1cccn(Cc2nc3c(OCc4ccc(F)cc4F)cccc3[nH]2)c1=O] | LCMS m/z 660.2 (M + 1)$^+$ |

-continued
| Compound | Structure | LCMS Data |
|---|---|---|
| 139 | 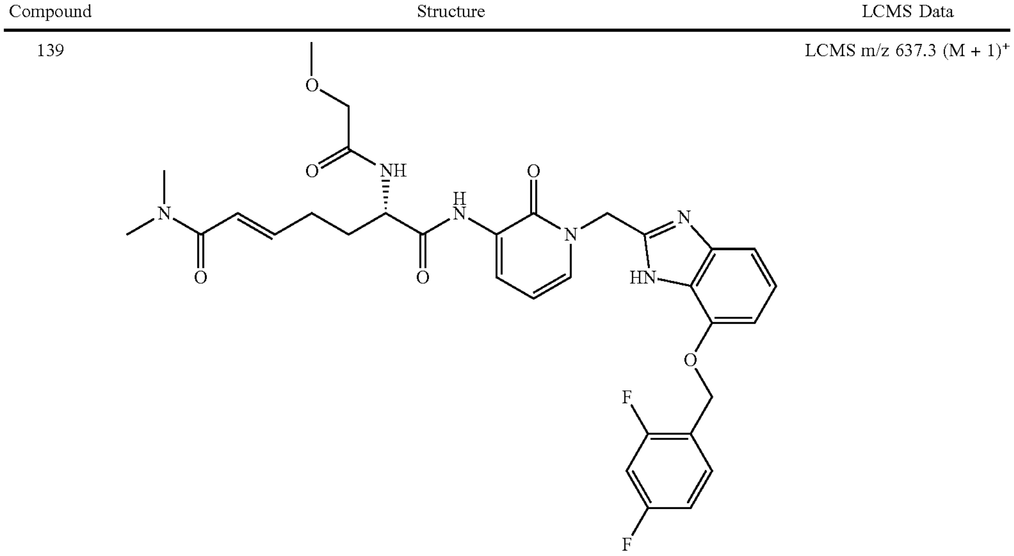 | LCMS m/z 637.3 $(M + 1)^+$ |
| 140 | 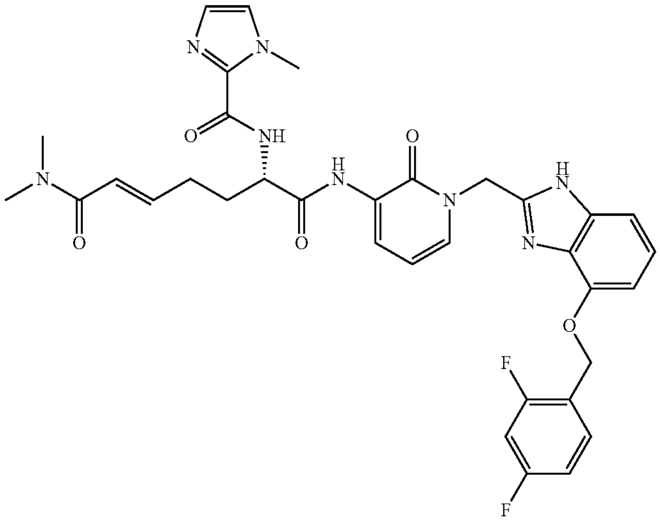 [SMILES: CN(C)C(=O)/C=C/CC[C@H](NC(=O)c1nccn1C)C(=O)Nc1cccn(Cc2nc3c(OCc4ccc(F)cc4F)cccc3[nH]2)c1=O] | LCMS m/z 673.2 $(M + 1)^+$ |
| 141 | 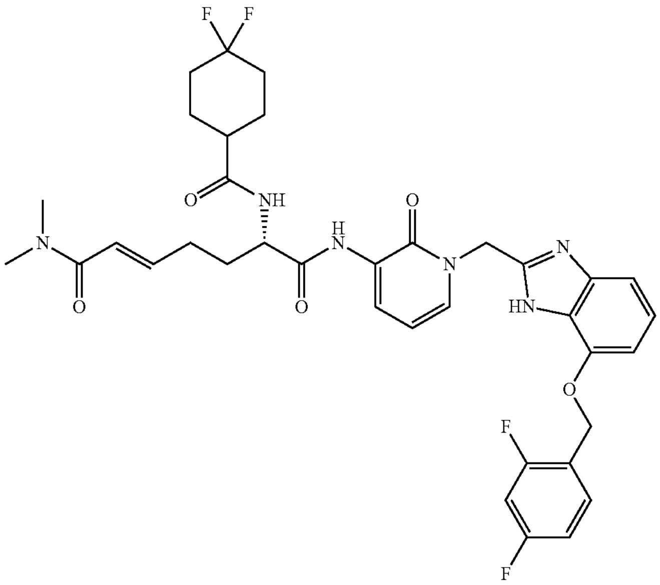 [SMILES: CN(C)C(=O)/C=C/CC[C@H](NC(=O)C1CCC(F)(F)CC1)C(=O)Nc1cccn(Cc2nc3cccc(OCc4ccc(F)cc4F)c3[nH]2)c1=O] | LCMS m/z 711.2 $(M + 1)^+$ |

-continued
| Compound | Structure | LCMS Data |
| --- | --- | --- |
| 142 | 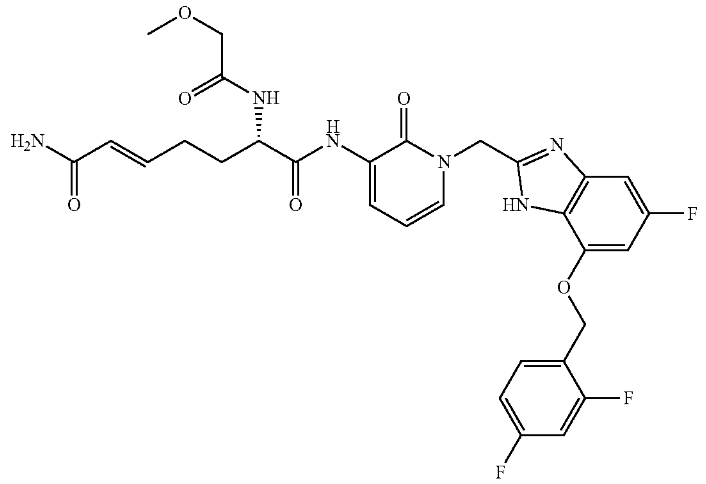 [SMILES: COCC(=O)N[C@@H](CC/C=C/C(N)=O)C(=O)Nc1cccn(Cc2nc3cc(F)cc(OCc4ccc(F)cc4F)c3[nH]2)c1=O] | LCMS m/z 627.1 $(M + 1)^+$ |
| 143 | 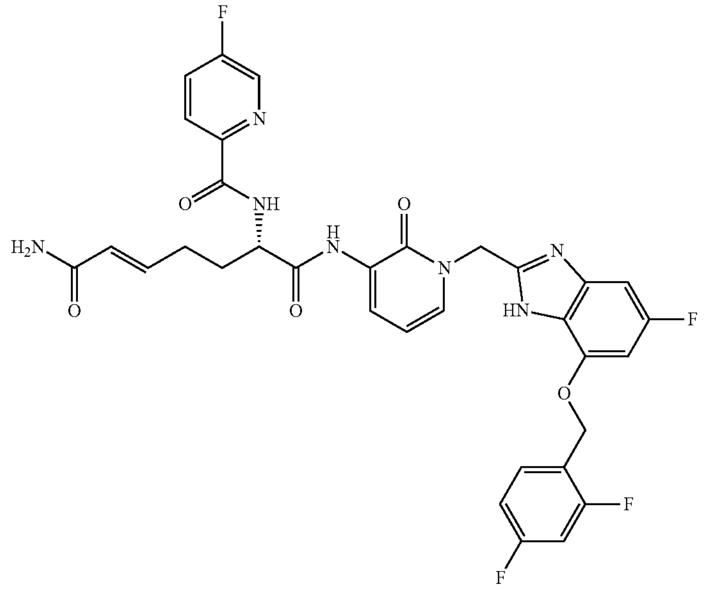 [SMILES: NC(=O)/C=C/CC[C@H](NC(=O)c1ccc(F)cn1)C(=O)Nc1cccn(Cc2nc3cc(F)cc(OCc4ccc(F)cc4F)c3[nH]2)c1=O] | LCMS m/z 678.1 $(M + 1)^+$ |
| 144 | 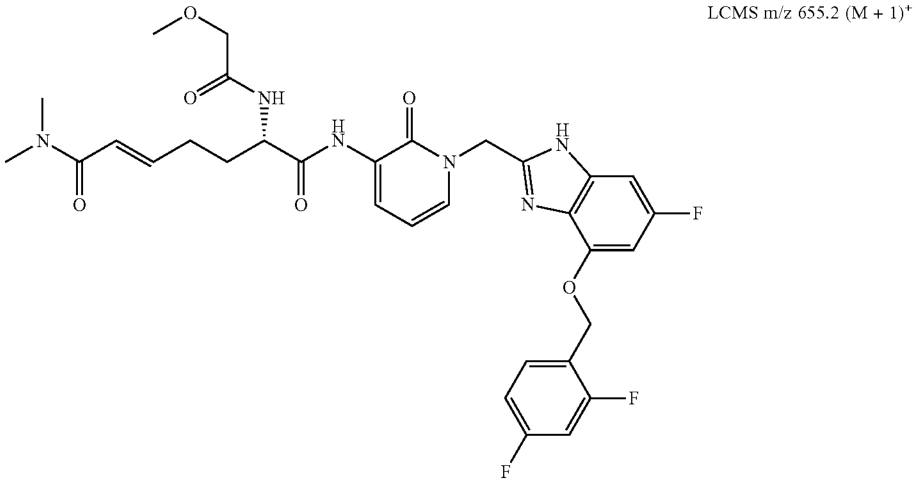 | LCMS m/z 655.2 $(M + 1)^+$ |

-continued
| Compound | Structure | LCMS Data |
| --- | --- | --- |
| 145 | 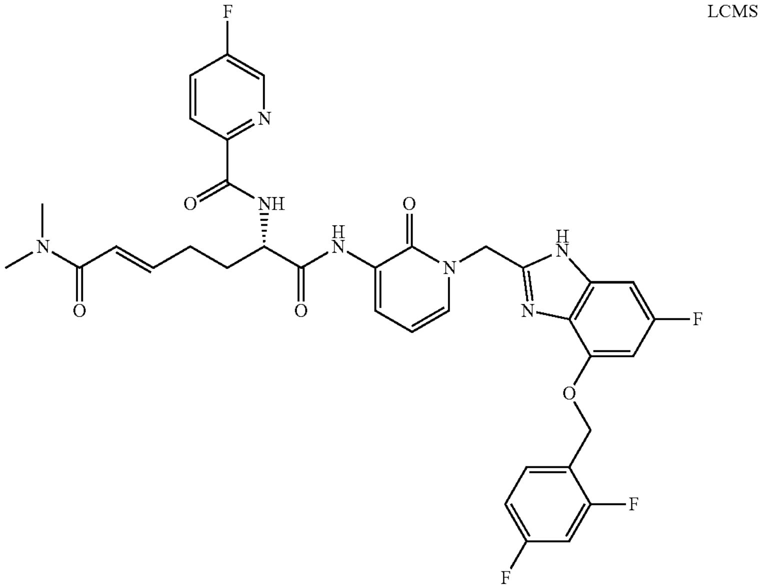 | LCMS m/z 706.2 $(M + 1)^+$ |
The Synthesis of Intermediate I-233
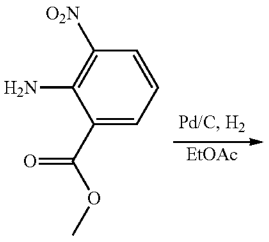
I-222
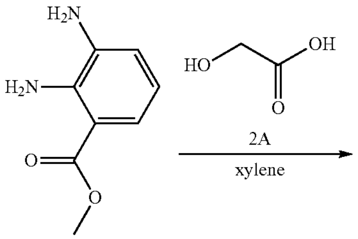
I-223
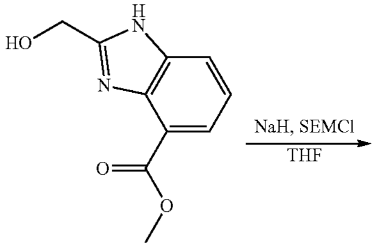
I-224
-continued
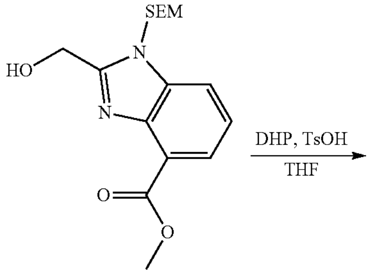
I-225
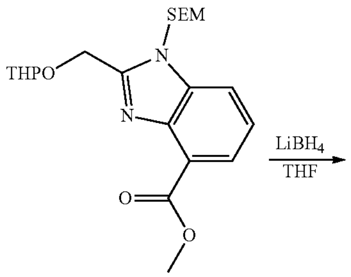
I-226
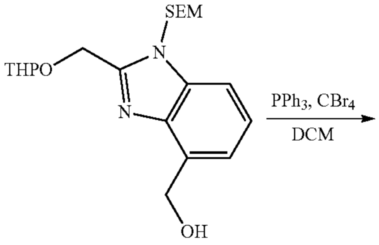
I-227

-continued

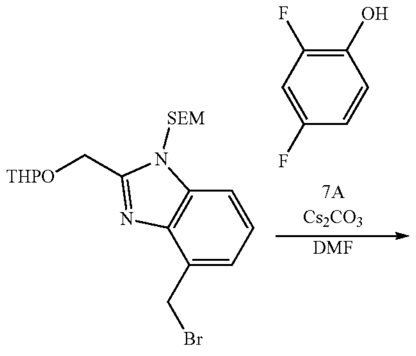

I-228

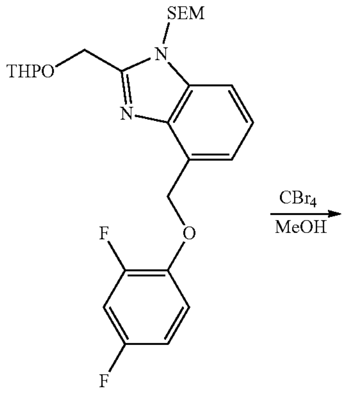

I-229

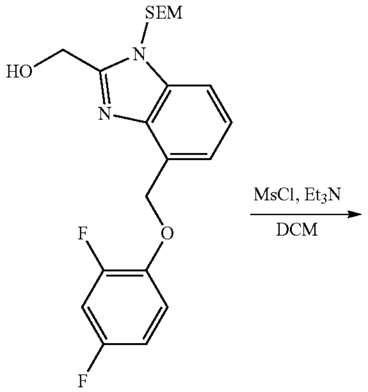

I-230

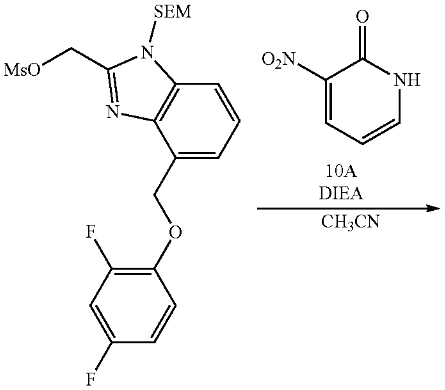

I-231

-continued

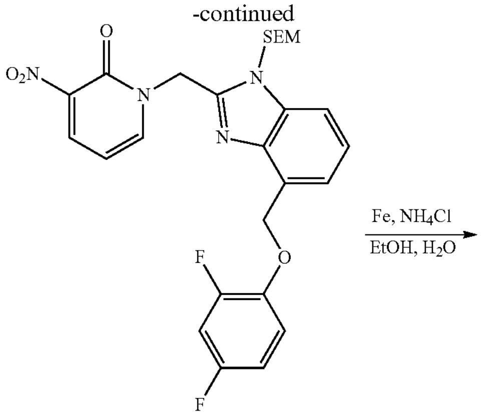

I-232

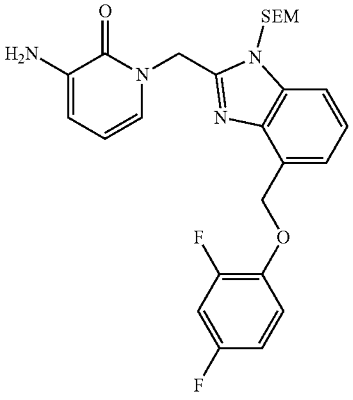

I-233

To a solution of methyl 2-amino-3-nitro-benzoate (45.0 g, 255 mmol) in ethyl acetate (250 mL) was added Pd/C (5 g, 10% purity) under $N_2$ atmosphere. The suspension was degassed under vacuum and purged with $H_2$ 3 times. The mixture was stirred under $H_2$ (50 psi) atmosphere at 25° C. for 18 h. The reaction mixture was filtered and the filtrate was concentrated to give a crude product. The crude product was purified by MPLC to give methyl 2,3-diaminobenzoate (I-223) (36.9 g) as a yellow solid.

To a mixture of methyl 2,3-diaminobenzoate (5.0 g, 30.1 mmol) in o-xylene (20 mL) was added 2-hydroxyacetic acid (3.43 g, 45.1 mmol) in one portion at 25° C. under $N_2$ atmosphere. The mixture was heated to 130° C. and stirred for 6 h. The mixture was cooled to 25° C. and concentrated in reduced pressure to give a residue. The residue was poured into water (20 mL) and extracted with ethyl acetate (30 mL×3). The combined organic layers were washed with brine (30 mL), dried over anhydrous $Na_2SO_4$, filtered and concentrated in vacuum to give a residue. The residue was purified by column chromatography (Dichloromethane/Methanol=40/1, 20/1) to afford methyl 2-(hydroxymethyl)-1H-benzo [d]imidazole-4-carboxylate (I-224) (3.0 g, 11.6 mmol, 39% yield) as a yellow solid. $^1H$ NMR (400 MHz, DMSO-$d_6$) δ512.08 (s, 1H), 7.88 (d, J=7.6 Hz, 1H), 7.81 (d, J=7.6 Hz, 1H), 4.73 (s, 2H), 3.98 (s, 3H).

To a mixture of methyl 2-(hydroxymethyl)-1H-benzimidazole-4-carboxylate (3.0 g, 11.6 mmol) in THF (20 mL) was added NaH (559 mg, 14.0 mmol, 60% purity) in portions at 0° C. under $N_2$ atmosphere. The mixture was stirred at 0° C. for 0.5 h. SEM-Cl (1.94 g, 11.6 mmol) was added to the mixture at 0° C. The mixture was heated to 25° C. and stirred at the same temperature for 2.5 h. The mixture was poured into water (50 mL) and extracted with ethyl acetate (50 mL×3). The combined organic layers were washed with brine (50 mL), dried over anhydrous $Na_2SO_4$ and concentrated in vacuum to afford methyl 2-(hydroxymethyl)-1-(2-trimethylsilylethoxymethyl) benzimidazole-4-carboxylate (I-225) (2.30 g) as a yellow solid.

To a mixture of methyl 2-(hydroxymethyl)-1-(2-trimethylsilylethoxymethyl) benzimidazole-4-carboxylate (550 mg, 1.63 mmol) and DHP (274 mg, 3.26 mmol) in THF (15 mL) was added TsOH (56.1 mg, 326 μmol) in one portion at 25° C. under $N_2$ atmosphere. The mixture was heated to 70° C. and stirred for 2 h. The mixture was cooled to 25° C. and poured into water (50 mL). The resulting solution was extracted with ethyl acetate (50 mL×3). The combined organic layers were washed with brine (50 mL), dried over anhydrous $Na_2SO_4$, filtered and concentrated in vacuum to afford 2-(((tetrahydro-2H-pyran-2-yl)oxy)methyl)-1-((2-(trimethylsilyl)ethoxy)methyl)-1H-benzo[d]imidazole-4-carboxylate (I-226) (560 mg).

To a mixture of methyl 2-(((tetrahydro-2H-pyran-2-yl)oxy)methyl)-1-((2-(trimethylsilyl)ethoxy)methyl)-1H-benzo[d]imidazole-4-carboxylate (560 mg, 1.33 mmol) in THF (150 mL) was added $LiBH_4$ (58.5 mg, 2.66 mmol) in one portion at 0° C. under $N_2$ atmosphere. The mixture was heated to 25° C. and stirred for 2 h. The mixture was poured into water (50 mL). The resulting solution was extracted with ethyl acetate (50 mL×3). The combined organic layers were washed with brine (70 mL), dried over anhydrous $Na_2SO_4$, filtered and concentrated in vacuum to afford (2-(((tetrahydro-2H-pyran-2-yl)oxy)methyl)-1-((2-(trimethylsilyl)ethoxy) methyl)-1H-benzo[d]imidazol-4-yl)methanol (I-227) (500 mg) as a yellow oil.

To a mixture of [2-(tetrahydropyran-2-yloxymethyl)-1-(2-trimethylsilylethoxymethyl) benzimidazol-4-yl]methanol (500 mg, 1.27 mmol) and $CBr_4$ (548 mg, 1.65 mmol) in DCM (10 mL) was added $PPh_3$ (433 mg, 1.65 mmol) in one portion at 0° C. under $N_2$ atmosphere. The mixture was heated to 25° C. and stirred for 2 h. The mixture was poured into water (30 mL). The resulting solution was extracted with DCM (40 mL×3). The combined organic layers were washed with brine (30 mL), dried over anhydrous $Na_2SO_4$, filtered and concentrated in vacuum to give a residue. The residue was purified by column chromatography to afford 2-[[4-(bromomethyl)-2-(tetrahydropyran-2-yloxymethyl) benzimidazol-1-yl]methoxy]ethyl-trimethyl-silane (I-228) (240 mg) as a yellow solid. $^1H$ NMR (400 MHz, $CDCl_3$) δ 7.51 (d, J=8.0 Hz, 1H), 7.40 (d, J=8.0 Hz, 1H), 7.35-7.31 (m, 1H), 5.76-5.73 (m, 2H), 5.35 (s, 1H), 5.14 (s, 2H), 4.94 (s, 1H), 4.83 (s, 1H), 4.18-4.16 (m, 1H), 3.97-3.58 (m, 3H), 1.85-1.78 (m, 2H), 1.67-1.60 (m, 6H), 1.31-1.26 (m, 1H), 1.67-1.60 (m, 6H), 0.97-0.93 (m, 2H), 0.02 (s, 9H).

To a mixture of 2-[[4-(bromomethyl)-2-(tetrahydropyran-2-yloxymethyl) benzimidazol-1-yl]methoxy]ethyl-trimethyl-silane (240 mg, 527 μmol) and 2,4-difluorophenol (82.3 mg, 632 μmol) in DMF (2 mL) was added $Cs_2CO_3$ (258 mg, 790 μmol) in one portion at 25° C. under $N_2$ atmosphere. The mixture was heated to 70° C. and stirred for 1 h. The mixture was cooled to 25° C. and poured into water (30 mL). The resulting solution was extracted with ethyl acetate (30 mL×3). The combined organic layers were washed with brine (50 mL), dried over anhydrous $Na_2SO_4$, filtered and concentrated in vacuum to afford 2-[[4-[(2,4-difluorophenoxy) methyl]-2-(tetrahydropyran-2-yloxymethyl)benzimidazol-1-yl]methoxy]ethyl-trimethyl-silane (I-229) (300 mg, 482 μmol, 91% yield) as a yellow oil.

To a mixture of 2-[[4-[(2,4-difluorophenoxy)methyl]-2-(tetrahydropyran-2-yloxymethyl)benzimidazol-1-yl] methoxy]ethyl-trimethyl-silane (240 mg, 385 μmol) in MeOH (3 mL) was added $CBr_4$ (383 mg, 1.16 mmol) in one portion at 25° C. under $N_2$ atmosphere. The mixture was heated to 70° C. and stirred for 3 h. The mixture was cooled to 25° C. and poured into saturated $NaHCO_3$ aqueous solution (20 mL). The resulting solution was extracted with ethyl acetate (30 mL×3). The combined organic phase was washed with brine (50 mL), dried over anhydrous $Na_2SO_4$, filtered and concentrated in vacuum to give a residue. The residue was purified by prep-TLC to afford [4-[(2,4-difluorophenoxy)methyl]-1-(2-trimethylsilylethoxymethyl)benzimidazol-2-yl]methanol (I-230) (170 mg) as a yellow oil. $^1H$ NMR (400 MHz, DMSO-$d_6$) δ 7.47-7.43 (m, 2H), 7.36-7.32 (m, 1H), 7.06-7.05 (m, 1H), 6.87-6.86 (m, 1H), 6.73-6.72 (m, 1H), 5.60 (s, 2H), 5.59 (s, 2H), 4.98 (s, 2H), 3.69-3.55 (m, 2H), 0.94-0.90 (m, 2H), −0.03 (s, 9H).

To a mixture of [4-[(2,4-difluorophenoxy)methyl]-1-(2-trimethylsilylethoxymethyl) benzimidazol-2-yl]methanol (170 mg, 404 μmol) and $Et_3N$ (61.4 mg, 606 μmol) in DCM (10 mL) was added MsCl (60.2 mg, 526 μmol) in one portion at 0° C. under $N_2$ atmosphere. The mixture was heated to 25° C. and stirred for 1 h. The mixture was poured into water (30 mL). The resulting solution was extracted with ethyl acetate (30 mL×3). The combined organic phase was washed with brine (30 mL), dried over anhydrous $Na_2SO_4$, filtered and concentrated in vacuum to afford [4-[(2,4-difluorophenoxy)methyl]-1-(2-trimethylsilylethoxymethyl)benzimidazol-2-yl]methyl methanesulfonate (I-231) (200 mg) as a yellow oil.

To a mixture of [4-[(2,4-difluorophenoxy)methyl]-1-(2-trimethylsilylethoxymethyl) benzimidazol-2-yl]methyl methanesulfonate (200 mg, 401 μmol) and 3-nitropyridin-2(1H)-one (84.3 mg, 602 μmol) in $CH_3CN$ (10 mL) was added DIPEA (104 mg, 802 μmol) in one portion at 25° C. under $N_2$ atmosphere. The mixture was stirred at 25° C. for 18 h. The mixture was poured into water (30 mL). The resulting solution was extracted with ethyl acetate (30 mL×3). The combined organic phase was washed with brine (30 mL), dried over anhydrous $Na_2SO_4$, filtered and concentrated in vacuum to afford 1-[[4-[(2,4-difluorophenoxy) methyl]-1-(2-trimethylsilylethoxymethyl)benzimidazol-2-yl]methyl]-3-nitro-pyridin-2-one (I-232) (210 mg) as a yellow oil. LCMS m/z 543.2 $(M+1)^+$.

To a mixture of 1-[[4-[(2,4-difluorophenoxy)methyl]-1-(2-trimethylsilylethoxymethyl) benzimidazol-2-yl]methyl]-3-nitro-pyridin-2-one (210 mg, 387 μmol) in EtOH (5 mL) and $H_2O$ (5 mL) were added Fe (64.9 mg, 1.16 mmol) and $NH_4Cl$ (104 mg, 1.94 mmol) in one portion at 25° C. under $N_2$ atmosphere. The mixture was heated to 70° C. and stirred for 1 h. The mixture was cooled to 25° C. and filtered. The filtrate was extracted with ethyl acetate (30 mL×3). The combined organic layers were washed with brine (50 mL), dried over anhydrous $Na_2SO_4$, filtered and concentrated in vacuum to give a residue. The residue was purified by prep-TLC to afford 3-amino-1-[[4-[(2,4-difluorophenoxy) methyl]-1-(2-trimethylsilylethoxymethyl)benzimidazol-2-yl]methyl]pyridin-2-one (I-233) (140 mg) as a yellow oil. LCMS m/z 513 $(M+1)^+$.

The following intermediate was prepared according to the procedures described in I-233 using the appropriate regents.

| Compound | Structure | LCMS Data |
|---|---|---|
| I-234 | 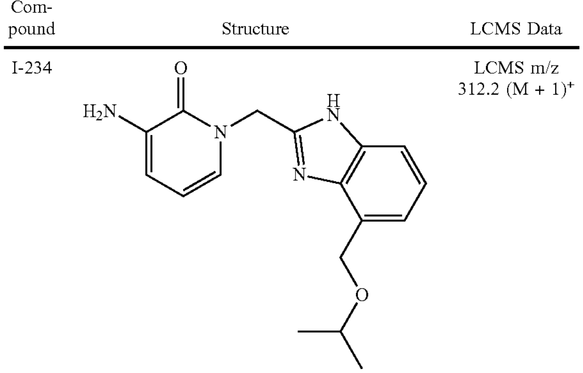 | LCMS m/z 312.2 (M + 1)$^+$ |
Example 21
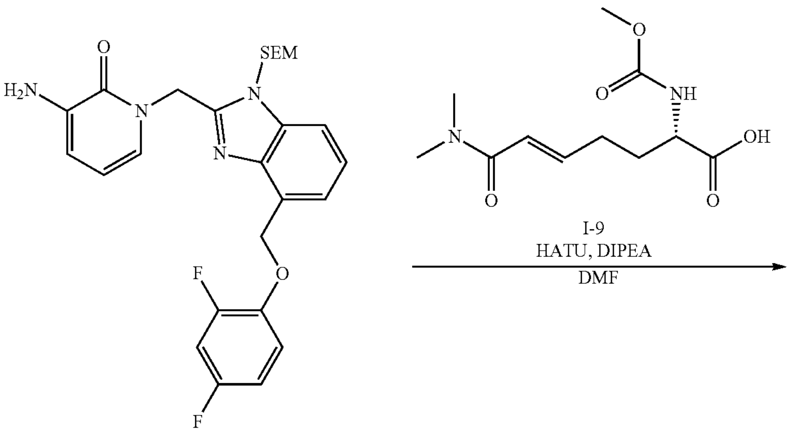
I-233
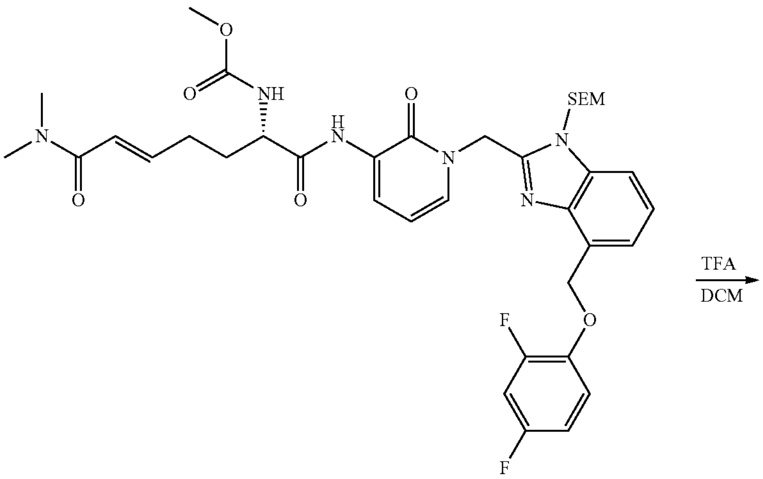
I-235

-continued

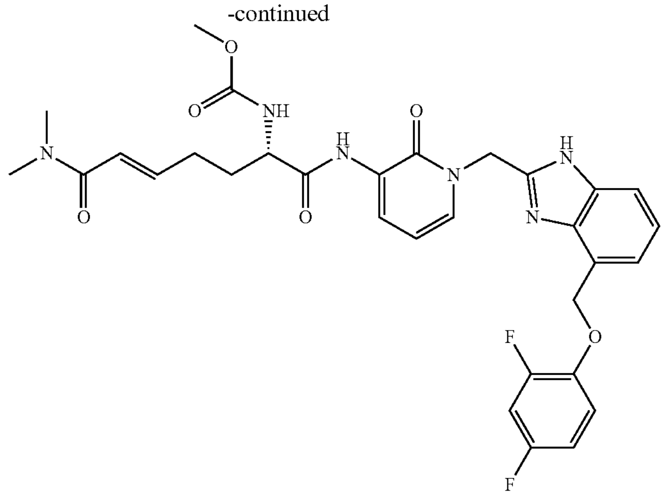

146

To a mixture of 3-amino-1-[[4-[(2,4-difluorophenoxy) methyl]-1-(2-trimethylsilylethoxymethyl)benzimidazol-2-yl]methyl]pyridin-2-one (140 mg, 273 μmol) and (E,2S)-7-(dimethylamino)-2-(methoxycarbonylamino)-7-oxo-hept-5-enoic acid (141 mg, 546 μmol) in DMF (2 mL) were added HATU (156 mg, 410 μmol) and DIPEA (70.6 mg, 546 μmol) in one portion at 25° C. under $N_2$ atmosphere. The mixture was stirred at 25° C. for 18 h. The resulting solution was poured into water (20 mL) and extracted with ethyl acetate (20 mL×3). The combined organic layers were washed with brine (20 mL), dried over anhydrous $Na_2SO_4$, filtered and concentrated in vacuum to give a residue. The residue was purified by prep-TLC to afford methyl N-[(E,1S)-1-[[1-[[4-[(2,4-difluorophenoxy)methyl]-1-(2-trimethylsilylethoxymethyl) benzimidazol-2-yl]methyl]-2-oxo-3-pyridyl]carbamoyl]-6-(dimethylamino)-6-oxo-hex-4-enyl]carbamate (I-235) (130 mg) as a white solid. LCMS m/z 753.3 $(M+1)^+$.

To a mixture of methyl N-[(E,1S)-1-[[1-[[4-[(2,4-difluorophenoxy)methyl]-1-(2-trimethylsilylethoxymethyl)benzimidazol-2-yl]methyl]-2-oxo-3-pyridyl]carbamoyl]-6-(dimethylamino)-6-oxo-hex-4-enyl]carbamate (110 mg, 146 μmol) in DCM (1 mL) was added TFA (1 mL) in one portion at 25° C. under $N_2$ atmosphere. The mixture was stirred at 25° C. for 6 h. The mixture was poured into saturated $NaHCO_3$ aqueous solution (15 mL). The resulting solution was extracted with ethyl acetate (30 mL×3). The combined organic layers were washed with brine (30 mL), dried over anhydrous $Na_2SO_4$, filtered and concentrated in vacuum to give a residue. The residue was purified by HPLC to afford methyl N-[(E,1S)-1-[[1-[[4-[(2,4-difluorophenoxy) methyl]-1H-benzimidazol-2-yl]methyl]-2-oxo-3-pyridyl]carbamoyl]-6-(dimethylamino)-6-oxo-hex-4-enyl]carbamate (Compound 146) (62.2 mg, 68% yield) as a white solid. LCMS m/z 623.2 $(M+1)^+$. $^1$H NMR (400 MHz, DMSO-$d_6$) (9.28 (s, 1H), 8.29 (d, J=7.8 Hz, 1H), 7.62 (d, J=6.8 Hz, 1H), 7.61-7.59 (m, 2H), 7.39-7.31 (m, 4H), 7.32-7.31 (m, 1H), 6.62-6.58 (m, 1H), 6.43-6.35 (m, 2H), 5.52 (s, 2H), 5.43 (s, 2H), 4.21-4.14 (m, 1H), 3.54 (s, 3H), 2.98 (s, 3H), 2.83 (s, 3H), 2.77-2.73 (m, 2H), 2.23-2.21 (m, 2H), 1.88-1.86 (m, 1H), 1.73-1.71 (m, 1H).

The following compound was prepared according to the procedures described in Example 21 using the appropriate intermediates.

| Compound | Structure | LCMS Data |
|---|---|---|
| 147 | 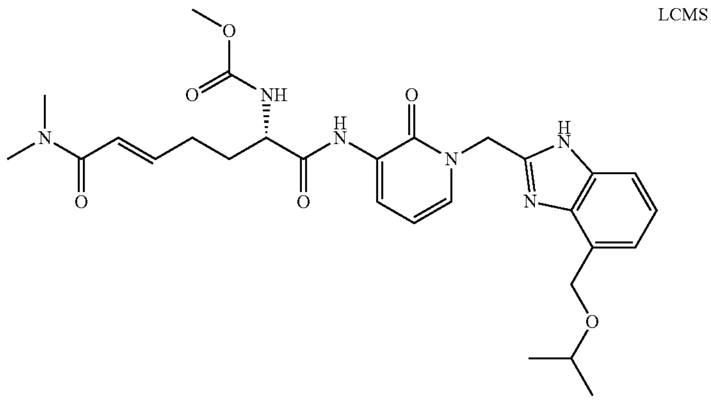 | LCMS m/z 533.2 $(M + 1)^+$ |

The Synthesis of Intermediate I-246
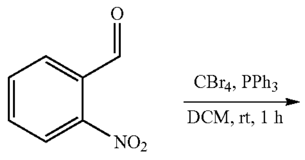
I-236
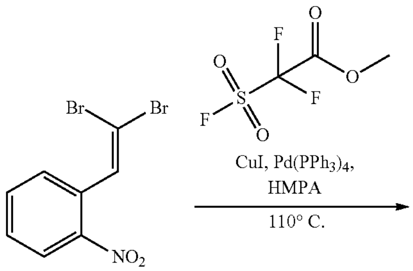
I-237
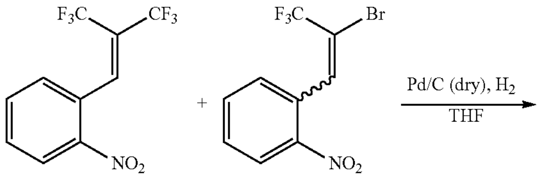
I-238 I-238A
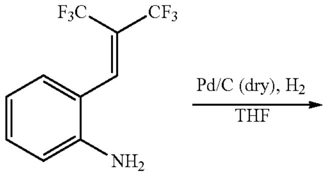
I-239
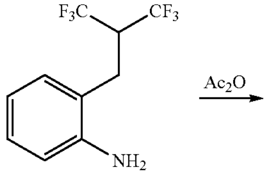
I-240
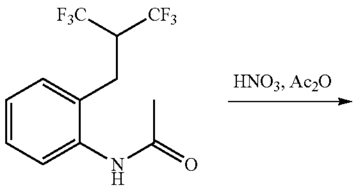
I-241
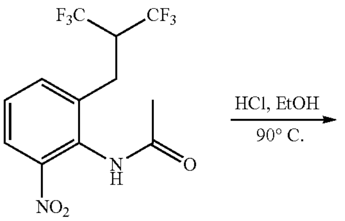
I-242
-continued
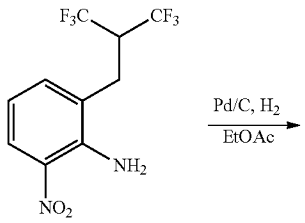
I-243
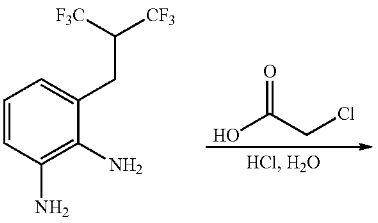
I-244
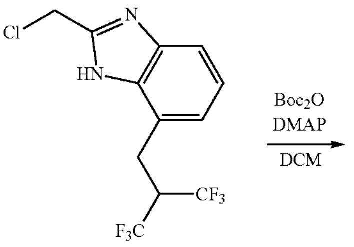
I-245
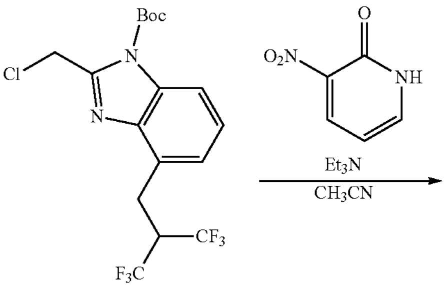
I-246
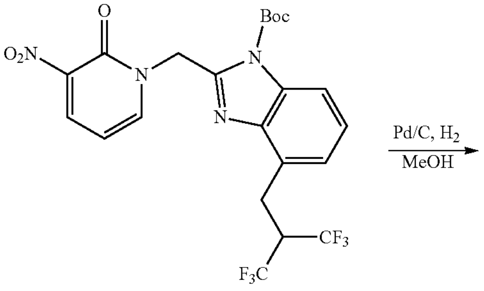
I-247

-continued

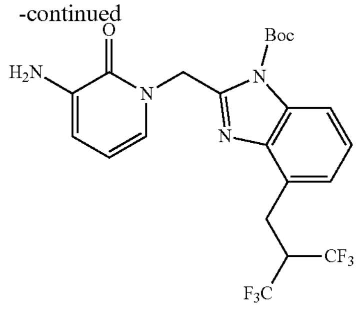

I-248

To a mixture of 2-nitrobenzaldehyde (17 g, 112 mmol) in DCM (1 L) were added $CBr_4$ (149 g, 450 mmol) and $PPh_3$ (236 g, 900 mmol) at 0° C. under $N_2$. The mixture was stirred at 20° C. for 0.5 h. The mixture was filtered, and the filtrate was concentrated in vacuo. The residue was purified by silica gel chromatography to 1-(2,2-dibromovinyl)-2-nitrobenzene (I-237) (46 g) as a yellow oil. $^1$H NMR (400 MHz, $CDCl_3$) δ 8.16-8.10 (m, 1H), 7.79 (s, 1H), 7.72-7.49 (m, 3H).

To a mixture of 1-(2,2-dibromovinyl)-2-nitrobenzene (23 g, 74.9 mmol), CuI (4.28 g, 22.5 mmol), $Pd(PPh_3)_4$ (4.33 g, 3.75 mmol) and HMPA (40.8 g, 228 mmol, 40 mL) in DMF (200 mL) was added methyl 2,2-difluoro-2-(fluorosulfonyl) acetate (72 g, 375 mmol, 47.7 mL) under $N_2$ atmosphere. The mixture was stirred at 110° C. for 60 h. The mixture was concentrated in vacuo and diluted with water (400 mL). The aqueous phase was extracted with ethyl acetate (400 mL×2). The combined organic layers were washed with brine (500 mL×3), dried over anhydrous $Na_2SO_4$, filtered and concentrated in vacuum. The residue was purified by silica gel chromatography to afford the mixture of 1-nitro-2-(3,3,3-trifluoro-2-(trifluoromethyl)prop-1-en-1-yl)benzene (I-238) and 1-(2-bromo-3,3,3-trifluoroprop-1-en-1-yl)-2-nitrobenzene (I-238A) (20 g) as a yellow oil.

To a mixture of 1-nitro-2-(3,3,3-trifluoro-2-(trifluoromethyl)prop-1-en-1-yl)benzene and 1-(2-bromo-3,3,3-trifluoroprop-1-en-1-yl)-2-nitrobenzene (5 g) in THF (80 mL) was added Pd/C (2.5 g) under $N_2$ atmosphere. The suspension was degassed under vacuum and purged with $H_2$ three times. The mixture was stirred under $H_2$ (15 psi) at 20° C. for 12 hours. The mixture was filtered, and the filtrate was concentrated in vacuum to give a residue. The residue was purified by silica gel chromatography to afford 2-(3,3,3-trifluoro-2-(trifluoromethyl)prop-1-en-1-yl)aniline (I-239) (2.5 g) as a yellow oil.

To a solution of 2-(3,3,3-trifluoro-2-(trifluoromethyl) prop-1-en-1-yl)aniline (2.5 g, 9.8 mmol) in THF (40 mL) was added Pd/C (2 g) under $N_2$. The suspension was degassed under vacuum and purged with $H_2$ three times. The mixture was stirred under $H_2$ (45 psi) atmosphere at 45° C. for 16 hours. The resulting suspension was filtered, and the filtrate was concentrated under vacuum to give a residue. The residue was purified by prep-HPLC to afford 2-(3,3,3-trifluoro-2-(trifluoromethyl) propyl)aniline (I-240) (700 mg) as a yellow oil. $^1$H NMR (400 MHz, $CDCl_3$) δ 7.16-7.11 (m, 1H), 7.11-7.06 (m, 1H), 6.82-6.76 (m, 1H), 6.75-6.71 (m, 1H), 3.59-3.43 (m, 1H), 3.05-3.00 (m, 2H).

A mixture of 2-(3,3,3-trifluoro-2-(trifluoromethyl)propyl) aniline (2.6 g, 10.1 mmol) in $Ac_2O$ (5 mL) was stirred at 25° C. for 1 h. The mixture was diluted with water (40 mL) and extracted with ethyl acetate (40 mL×2). The combined organic layers were washed with brine (80 mL), dried over anhydrous $Na_2SO_4$, filtered and concentrated in vacuum to give a residue. The residue was purified by silica gel chromatography to afford N-(2-(3,3,3-trifluoro-2-(trifluoromethyl)propyl)phenyl)acetamide (I-241) (2.6 g) as a white solid.

To a mixture of N-(2-(3,3,3-trifluoro-2-(trifluoromethyl) propyl)phenyl)acetamide (2.6 g, 8.69 mmol) in $Ac_2O$ (9 mL) was added a solution of $HNO_3$ (1.83 g, 17.4 mmol, 1.30 mL, 60% purity) in $Ac_2O$ (1 mL) at 0° C. The mixture was stirred at 0° C. for 3 h. The mixture was diluted with water (30 mL) and extracted with ethyl acetate (30 mL×2). The combined organic layers were washed with saturated $NaHCO_3$ (50 mL), dried over anhydrous $Na_2SO_4$, filtered and concentrated in vacuum. The residue was purified by silica gel chromatography to afford N-(2-nitro-6-(3,3,3-trifluoro-2-(trifluoromethyl)propyl) phenyl)acetamide (I-242) (1.1 g) as a yellow solid. $^1$H NMR (300 MHz, $CDCl_3$) δ 8.37 (s, 1H), 8.00 (dd, J=10.8, 2.0 Hz, 1H), 7.65-7.55 (m, 1H), 7.48-7.37 (m, 1H), 3.45-3.21 (m, 3H), 2.25 (s, 3H).

To a mixture of N-(2-nitro-6-(3,3,3-trifluoro-2-(trifluoromethyl)propyl) phenyl) acetamide (1.1 g, 3.2 mmol) in EtOH (5 mL) was added HCl (4.38 g, 120 mmol, 10 mL). The mixture was stirred at 90° C. for 12 h. The pH of the mixture was adjusted to 7 by adding NaOH solution (1M) at 0° C. The resulting solution was extracted with ethyl acetate (30 mL×3). The combined organic layers were washed with brine (70 mL), dried over anhydrous $Na_2SO_4$, filtered and concentrated in vacuum. The residue was purified by silica gel chromatography to afford 2-nitro-6-(3,3,3-trifluoro-2-(trifluoromethyl)propyl) aniline (I-243) (900 mg) as a yellow oil. $^1$H NMR (400 MHz, $CDCl_3$) δ 8.16 (dd, J=8.8, 1.2 Hz, 1H), 7.41-734 (m, 1H), 6.76 (dd, J=8.6, 7.4 Hz, 1H), 6.11 (s, 2H), 3.43-3.29 (m, 1H), 3.16-3.08 (m, 2H).

To a mixture of 2-nitro-6-(3,3,3-trifluoro-2-(trifluoromethyl)propyl)aniline (900 mg, 2.98 mmol) in EtOAc (50 mL) was added Pd/C (400 mg, 10% purity) under $H_2$ (15 psi). The mixture was stirred at 25° C. for 1.5 h. The mixture was filtered, and the filtrate was concentrated in vacuum to afford 3-(3,3,3-trifluoro-2-(trifluoromethyl) propyl) benzene-1,2-diamine (I-244) (800 mg) as a yellow oil. $^1$H NMR (400 MHz, $CDCl_3$) δ 6.75-6.65 (m, 3H), 3.43 (s, 2H), 3.40-3.36 (m, 1H), 3.08-3.00 (m, 2H).

To a mixture of 3-(3,3,3-trifluoro-2-(trifluoromethyl)propyl)benzene-1,2-diamine (800 mg, 2.94 mmol) in HCl (18 mL) and $H_2O$ (36 mL) was added 2-chloroacetic acid (555 mg, 5.88 mmol, 0.661 mL) at 0° C. under $N_2$ atmosphere. The mixture was stirred at 90° C. for 12 h. The pH of the mixture was adjusted to 7 by adding ammonium hydroxide at 0° C. The resulting solution was extracted with ethyl acetate (20 mL×2). The combined organic layers were washed with brine (30 mL), dried over anhydrous $Na_2SO_4$, filtered and concentrated in vacuum to afford 2-(chloromethyl)-7-(3,3,3-trifluoro-2-(trifluoromethyl)propyl)-1H-benzo[d]imidazole (I-245) (900 mg) as a yellow oil.

To a mixture of 2-(chloromethyl)-7-(3,3,3-trifluoro-2-(trifluoromethyl)propyl)-1H-benzo[d]imidazole (900 mg, 2.72 mmol) in DCM (10 mL) were added DMAP (366 mg, 2.99 mmol) and $Boc_2O$ (653 mg, 2.99 mmol, 0.688 mL). The mixture was stirred at 25° C. for 1 h. The mixture was diluted with water (30 mL) and extracted with DCM (30 mL×2). The combined organic layers were washed with brine (50 mL), dried over anhydrous $Na_2SO_4$, filtered and concentrated in vacuum to give a residue. The residue was purified by silica gel chromatography to afford tert-butyl 2-(chloromethyl)-4-(3,3,3-trifluoro-2-(trifluoromethyl)propyl)-1H-benzo[d]imidazole-1-carboxylate (I-246) (800 mg, 62% yield) as a white solid. LCMS m/z 431.0 $(M+1)^+$.

To a mixture of tert-butyl 2-(chloromethyl)-4-(3,3,3-trifluoro-2-(trifluoromethyl) propyl)-1H-benzo[d]imidazole-1-carboxylate (350 mg, 0.748 mmol) and 3-nitro-1H-pyridin-2-one (157 mg, 1.12 mmol) in $CH_3CN$ (10 mL) was added $Et_3N$ (151 mg, 1.49 mmol, 0.207 mL). The mixture was stirred at 25° C. for 12 h. The mixture was diluted with water (20 mL) and extracted with ethyl acetate (20 mL×2). The combined organic layers were washed with brine (30 mL), dried over anhydrous $Na_2SO_4$, filtered and concentrated in vacuum. The residue was purified by prep-TLC to afford tert-butyl 2-((3-nitro-2-oxopyridin-1(2H)-yl)methyl)-4-(3,3,3-trifluoro-2-(trifluoromethyl)propyl)-1H-benzo[d]imidazole-1-carboxylate (I-247) (230 mg) as a yellow solid.

To a mixture of tert-butyl 2-((3-nitro-2-oxopyridin-1(2H)-yl)methyl)-4-(3,3,3-trifluoro-2-(trifluoromethyl)propyl)-1H-benzo[d]imidazole-1-carboxylate (230 mg, 0.43 mmol) in MeOH (5 mL) was added Pd/C (200 mg, 10% purity). The mixture was stirred at 25° C. under $H_2$ (15 psi) for 0.5 h. The mixture was filtered, and the filtrate was concentrated in vacuum to afford tert-butyl 2-((3-amino-2-oxopyridin-1(2H)-yl)methyl)-4-(3,3,3-trifluoro-2-(trifluoromethyl)propyl)-1H-benzo[d]imidazole-1-carboxylate (I-248) (190 mg) as a colorless oil. LCMS m/z 505.3 $(M+1)^+$.

Example 22

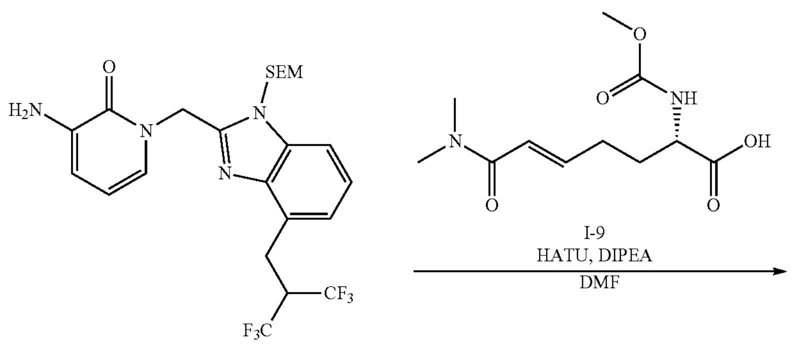

I-248

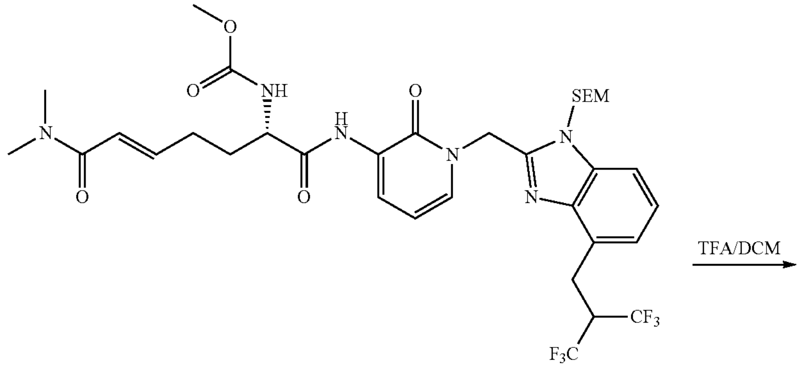

148

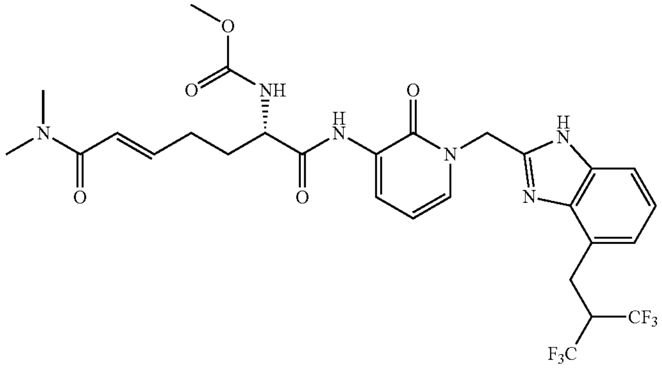

149

To a mixture of tert-butyl 2-((3-amino-2-oxopyridin-1(2H)-yl)methyl)-4-(3,3,3-trifluoro-2-(trifluoromethyl)propyl)-1H-benzo[d]imidazole-1-carboxylate (50 mg, 0.0991 mmol) and (S,E)-7-(dimethylamino)-2-((methoxycarbonyl)amino)-7-oxohept-5-enoic acid (38.4 mg, 0.149 mmol) in DMF (1 mL) were added HATU (67.8 mg, 0.178 mmol) and DIEA (38.4 mg, 0.297 mmol, 0.0519 mL) at 0° C. The mixture was stirred at 25° C. for 16 h. The mixture was diluted with water (20 mL) and extracted with ethyl acetate (20 mL×3). The combined organic layers were washed with brine (50 mL×3), dried over anhydrous $Na_2SO_4$, filtered and concentrated in vacuum to give a residue. The residue was purified by prep-TLC to afford (S,E)-tert-butyl 2-((3-(7-(dimethylamino)-2-((methoxycarbonyl)amino)-7-oxohept-5-enamido)-2-oxopyridin-1(2H)-yl)methyl)-4-(3,3,3-trifluoro-2-(trifluoromethyl)propyl)-1H-benzo[d]imidazole-1-carboxylate (Compound 148) (5.4 mg, 7% yield) as a white solid. LCMS m/z 745.1 $(M+1)^+$.

To a mixture of (S,E)-tert-butyl 2-((3-(7-(dimethylamino)-2-((methoxycarbonyl) amino)-7-oxohept-5-enamido)-2-oxopyridin-1(2H)-yl)methyl)-4-(3,3,3-trifluoro-2-(trifluoromethyl)propyl)-1H-benzo[d]imidazole-1-carboxylate (150 mg, 0.201 mmol) in DCM (3 mL) was added TFA (1.54 g, 13.5 mmol, 1 mL) at 0° C. The mixture was stirred at 25° C. for 1 h The mixture was concentrated in vacuo and purified by prep-HPLC to afford (S,E)-methyl (7-(dimethylamino)-1,7-dioxo-1-((2-oxo-1-((4-(3,3,3-trifluoro-2-(trifluoromethyl)propyl)-1H-benzo[d]imidazol-2-yl)methyl)-1,2-dihydropyridin-3-yl)amino)hept-5-en-2-yl) carbamate (Compound 149) (78.4 mg, 59% yield) as a white solid. LCMS m/z 645.1 $(M+1)^+$. $^1H$ NMR (400 MHz, DMSO-$d_6$) δ 9.28 (s, 1H), 8.28 (dd, J=7.6, 1.6 Hz, 1H), 7.77-7.69 (m, 1H), 7.60 (dd, J=6.8, 1.6 Hz, 1H), 7.5-7.44 (m, 1H), 7.33-7.22 (m, 2H), 6.65-6.54 (m, 1H), 6.43-6.32 (m, 2H), 5.51 (s, 2H), 4.75-4.62 (m, 1H), 4.22-4.12 (m, 1H), 3.53 (s, 3H), 3.48 (d, J=7.0 Hz, 2H), 2.98 (s, 3H), 2.83 (s, 3H), 2.28-2.15 (m, 2H), 1.92-1.80 (m, 1H), 1.78-1.62 (m, 1H).

The following compound was prepared according to the procedures described in Example 22 using the appropriate intermediates.

-continued

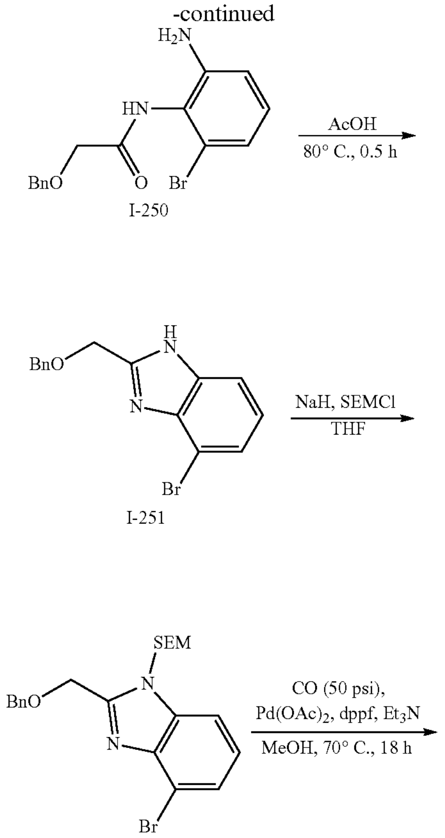

I-250

I-251

I-252

| Compound | Structure | LCMS Data |
|---|---|---|
| 150 | 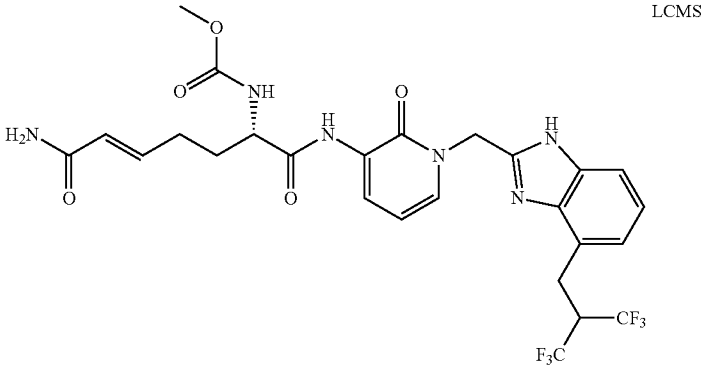 | LCMS m/z 617.1 $(M + 1)^+$ |

The Synthesis of Intermediate I-261

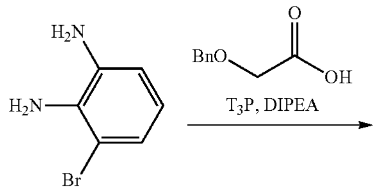

I-249

-continued

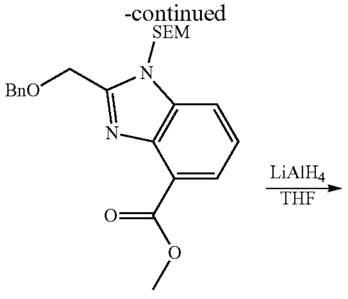

I-253

-continued

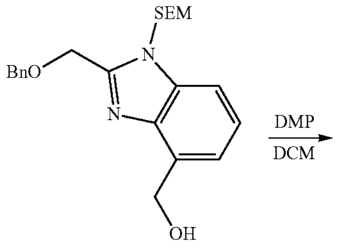

I-254

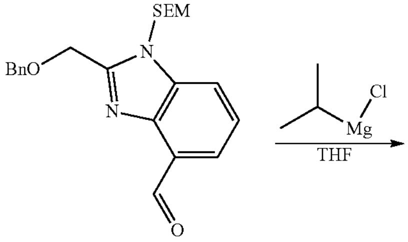

I-255

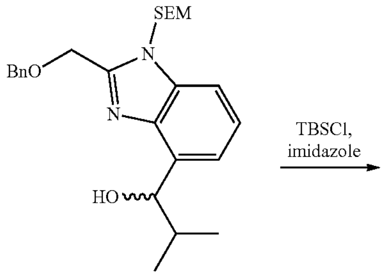

I-256

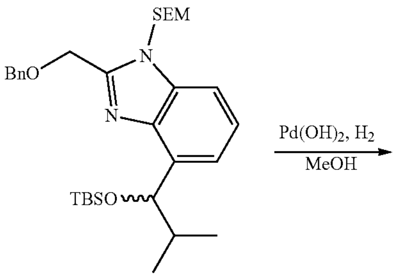

I-257

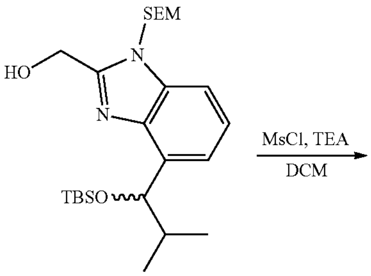

I-258

-continued

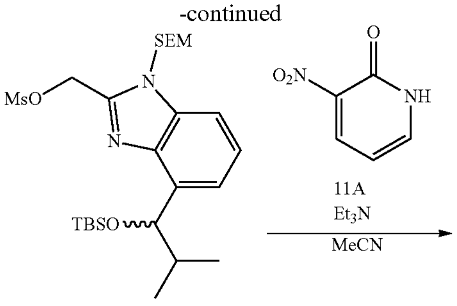

I-259

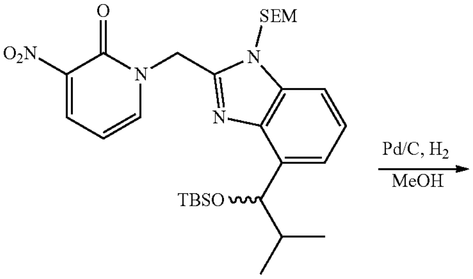

I-260

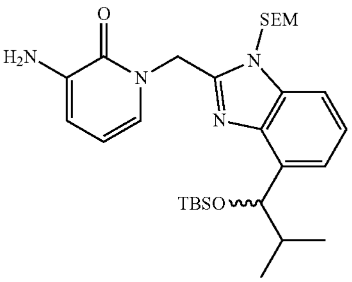

I-261

To a mixture of 3-bromobenzene-1,2-diamine (20.0 g, 107 mmol) and 2-(benzyloxy)acetic acid (26.8 g, 161 mmol) in DCM (30 mL) were added $T_3P$ (102 g, 160 mmol, 50% purity) and DIPEA (27.6 g, 214 mmol) in one portion at 25° C. under $N_2$ atmosphere. The mixture was stirred at 25° C. for 18 h. The reaction mixture was poured into $H_2O$ (300 mL). The resulting solution was extracted with DCM (200 mL×2). The combined organic layers were washed with brine (200 mL×2), dried over anhydrous $Na_2SO_4$, filtered and concentrated in vacuum to give a residue. The residue was purified by column chromatography to afford N-(2-amino-6-bromophenyl)-2-(benzyloxy)acetamide (I-250) (26.0 g, 73% yield) as a yellow oil.

A solution of N-(2-amino-6-bromophenyl)-2-(benzyloxy)acetamide (26.0 g, 77.6 mmol) in AcOH (8 mL) was stirred at 25° C. under $N_2$ atmosphere. The mixture was heated to 80° C. and stirred for 0.5 h. The resulting solution was cooled to 25° C. and poured into saturated $NaHCO_3$ aqueous solution (100 mL). The resulting solution was extracted with ethyl acetate (300 mL×3). The combined organic layers were washed with brine (400 mL), dried over anhydrous $Na_2SO_4$, filtered and concentrated in vacuum to afford 2-((benzyloxy)methyl)-4-bromo-1H-benzo[d]imidazole (I-251) (19.0 g) as a yellow oil.

To a mixture of 2-((benzyloxy)methyl)-4-bromo-1H-benzo[d]imidazole (19.0 g) in THF (20 mL) was added NaH (2.16 g, 89.9 mmol, 60% purity) in portions at 25° C. under $N_2$ atmosphere. The mixture was stirred at 25° C. for 0.5 h.

SEM-Cl (12.0 g, 71.9 mmol) was added to the mixture above. The resulting solution was stirred at 25° C. for 2 h. The reaction mixture was poured into $H_2O$ (300 mL). The resulting solution was extracted with ethyl acetate (300 mL×3). The combined organic layers were washed with brine (200 mL×2), dried over anhydrous $Na_2SO_4$, filtered and concentrated in vacuum to give a residue. The residue was purified by column chromatography to afford 2-((benzyloxy)methyl)-4-bromo-1-((2-(trimethylsilyl)ethoxy)methyl)-1H-benzo[d] imidazole (I-252) (26.0 g, 97% yield) as a yellow oil.

To a solution of 2-((benzyloxy)methyl)-4-bromo-1-((2-(trimethylsilyl)ethoxy)methyl)-1H-benzo[d]imidazole (10.0 g, 22.4 mmol) in MeOH (30 mL) were added $Et_3N$ (4.52 g, 44.7 mmol), $Pd(OAc)_2$ (1.0 g, 4.47 mmol) and DPPF (2.48 g, 4.47 mmol) under $N_2$ atmosphere. The suspension was degassed under vacuum and purged with CO 3 times. The mixture was stirred under CO (50 psi) at 80° C. for 18 h. The mixture was cooled to 0° C. and concentrated in reduced pressure to give a residue. The residue was poured into $H_2O$ (20 mL). The resulting solution was extracted with ethyl acetate (30 mL×2). The combined organic layers were washed with brine (40 mL), dried over anhydrous $Na_2SO_4$, filtered and concentrated in vacuum to give a residue. The residue was purified by column chromatography to afford methyl 2-((benzyloxy)methyl)-1-((2-(trimethylsilyl)ethoxy)methyl)-1H-benzo[d]imidazole-4-carboxylate (I-253) (4.30 g, 10.1 mmol, 45% yield) as a yellow oil.

To a mixture of methyl 2-((benzyloxy)methyl)-1-((2-(trimethylsilyl)ethoxy) methyl)-1H-benzo[d]imidazole-4-carboxylate (3.30 g, 7.74 mmol) in THF (20 mL) was added $LiAlH_4$ (352 mg, 9.28 mmol) in portions at 25° C. under $N_2$ atmosphere. The mixture was stirred at 25° C. for 1.5 h. The resulting solution was poured into water (50 mL) and extracted with ethyl acetate (50 mL×2). The combined organic layers were washed with brine (50 mL), dried over anhydrous $Na_2SO_4$, filtered and concentrated in vacuum to give a residue. The residue was purified by column chromatography to afford 2-((benzyloxy)methyl)-1-((2-(trimethylsilyl)ethoxy)methyl)-1H-benzo[d]imidazol-4-yl)methanol (I-254) (1.20 g, 3.01 mmol, 39% yield) as a yellow oil. LCMS m/z 399.1 $(M+1)^+$.

To a mixture of 2-((benzyloxy)methyl)-1-((2-(trimethylsilyl)ethoxy)methyl)-1H-benzo[d]imidazol-4-yl)methanol (1.20 g, 3.01 mmol) in DCM (10 mL) was added DMP (1.91 g, 4.51 mmol) in one portion at 25° C. under $N_2$ atmosphere. The mixture was stirred at 25° C. for 2 h. The resulting suspension was filtered and the filtrate was concentrated in reduced pressure to give a residue. The residue was purified by column chromatography to afford 2-((benzyloxy) methyl)-1-((2-(trimethylsilyl)ethoxy)methyl)-1H-benzo[d] imidazole-4-carbaldehyde (I-255) (860 mg, 2.05 mmol, 68% yield) as a yellow oil. LCMS m/z 397.1 $(M+1)^+$.

To a mixture of isopropyl magnesium chloride-lithium chloride complex (1.3 M, 8.04 mL) in THF (3 mL) was added 2-((benzyloxy)methyl)-1-((2-(trimethylsilyl) ethoxy) methyl)-1H-benzo[d]imidazole-4-carbaldehyde (830 mg, 2.09 mmol) in one portion at −20° C. under $N_2$ atmosphere. The mixture was warmed to 25° C. and stirred for 0.5 h. The mixture was poured into water (30 mL). The resulting solution was extracted with ethyl acetate (30 mL×3). The combined organic layers were washed with brine (50 mL), dried over anhydrous $Na_2SO_4$, filtered and concentrated in vacuum to afford 1-(2-((benzyloxy)methyl)-1-((2-(trimethylsilyl)ethoxy)methyl)-1H-benzo[d]imidazol-4-yl)-2-methylpropan-1-ol (I-256) (730 mg) as a yellow oil. LCMS m/z 441.1 $(M+1)^+$.

To a mixture of 1-(2-((benzyloxy)methyl)-1-((2-(trimethylsilyl)ethoxy)methyl)-1H-benzo[d]imidazol-4-yl)-2-methylpropan-1-ol (570 mg, 1.29 mmol) and TBSCl (390 mg, 2.59 mmol) in DMF (2 mL) was added imidazole (264 mg, 3.88 mmol) in one portion at 25° C. under $N_2$ atmosphere. The mixture was heated to 80° C. and stirred for 4 h. The mixture was cooled to 25° C. and poured into water (30 mL). The resulting solution was extracted with ethyl acetate (50 mL×2). The combined organic layers were washed with brine (50 mL), dried over anhydrous $Na_2SO_4$, filtered and concentrated in vacuum to afford 2-((benzyloxy)methyl)-4-(1-((tert-butyldimethylsilyl)oxy)-2-methylpropyl)-1-((2-(trimethylsilyl)ethoxy)methyl)-1H-benzo[d]imidazole (I-257) (680 mg, 92% yield) as a yellow oil. LCMS m/z 555.2 $(M+1)^+$.

To a solution of 2-((benzyloxy)methyl)-4-(1-((tert-butyldimethylsilyl)oxy)-2-methylpropyl)-1-((2-(trimethylsilyl)ethoxy)methyl)-1H-benzo[d]imidazole (176 mg, 317 μmol) in MeOH (15 mL) was added $Pd(OH)_2/C$ (15% purity) under $N_2$ atmosphere. The suspension was degassed under vacuum and purged with $H_2$ 3 times. The mixture was stirred under $H_2$ (15 psi) at 25° C. for 18 h. The reaction mixture was filtered and the filtrate was concentrated to give (4-(1-((tert-butyldimethylsilyl)oxy)-2-methylpropyl)-1-((2-(trimethylsilyl)ethoxy)methyl)-1H-benzo[d]imidazol-2-yl) methanol (I-258) (120 mg, 81% yield) as a white solid. LCMS m/z 465.1 $(M+1)^+$.

To a mixture of (4-(1-((tert-butyldimethylsilyl)oxy)-2-methylpropyl)-1-((2-(trimethylsilyl)ethoxy)methyl)-1H-benzo[d]imidazol-2-yl)methanol (400 mg, 861 μmol) and MsCl (148 mg, 1.29 mmol) in DCM (10 mL) was added $Et_3N$ (174 mg, 1.72 mmol) in one portion at 25° C. under $N_2$ atmosphere. The mixture was stirred at 25° C. for 2 h. The mixture was poured into water (20 mL) and extracted with ethyl acetate (30 mL×2). The combined organic layers were washed with brine (30 mL), dried over anhydrous $Na_2SO_4$, filtered and concentrated in vacuum to afford (4-(1-((tert-butyldimethylsilyl)oxy)-2-methylpropyl)-1-((2-(trimethylsilyl)ethoxy)methyl)-1H-benzo[d]imidazol-2-yl)methylmethanesulfonate (I-259) (467 mg) as a yellow oil.

To a mixture of (4-(1-((tert-butyldimethylsilyl)oxy)-2-methylpropyl)-1-((2-(trimethylsilyl)ethoxy)methyl)-1H-benzo[d]imidazol-2-yl)methylmethanesulfonate (467 mg, 860 μmol) and 3-nitropyridin-2(1H)-one (181 mg, 1.29 mmol) in $CH_3CN$ (3 mL) was added $Et_3N$ (174 mg, 1.72 mmol) in one portion at 25° C. under $N_2$ atmosphere. The mixture was stirred at 25° C. for 18 h. The resulting solution was poured into water (20 mL) and extracted with ethyl acetate (30 mL×2). The combined organic layers were washed with brine (30 mL), dried over anhydrous $Na_2SO_4$, filtered and concentrated in vacuum to give a residue. The residue was purified by column chromatography to afford 1-((4-(1-((tert-butyldimethylsilyl)oxy)-2-methylpropyl)-1-((2-(trimethylsilyl)ethoxy)methyl)-1H-benzo[d]imidazol-2-yl)methyl)-3-nitropyridin-2(1H)-one (I-260) (460 mg, 91% yield) as a yellow oil. LCMS m/z 587.1 $(M+1)^+$.

To a solution of 1-((4-(1-((tert-butyldimethylsilyl)oxy)-2-methylpropyl)-1-((2-(trimethylsilyl)ethoxy)methyl)-1H-benzo[d]imidazol-2-yl)methyl)-3-nitropyridin-2(1H)-one (460 mg, 784 μmol) in EtOAc (5 mL) was added Pd/C (10.0 mg, 15% purity) under $N_2$ atmosphere. The suspension was degassed under vacuum and purged with $H_2$ 3 times. The mixture was stirred under $H_2$ (15 psi) at 25° C. for 1 h. The reaction mixture was filtered and the filtrate was concentrated to give a residue. The residue was purified by column chromatography to give 3-amino-1-((4-(1-((tert-butyldimethylsilyl)oxy)-2-methylpropyl)-1-((2-(trimethylsilyl)

ethoxy)methyl)-1H-benzo[d]imidazol-2-yl)methyl)pyridin-2(1H)-one (I-261) (420 mg, 96% yield) as a yellow oil. LCMS m/z 557.2 $(M+1)^+$.

Example 23 prep-TLC (ethyl acetate) to afford methyl ((2S,E)-1-((1-((4-(1-((tert-butyldimethylsilyl)oxy)-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl)carbamate

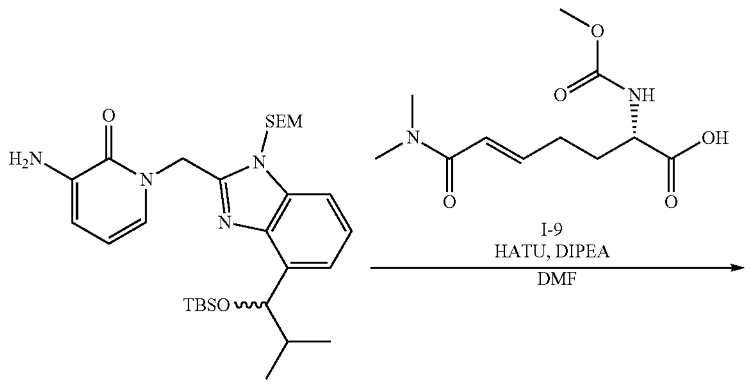

I-261

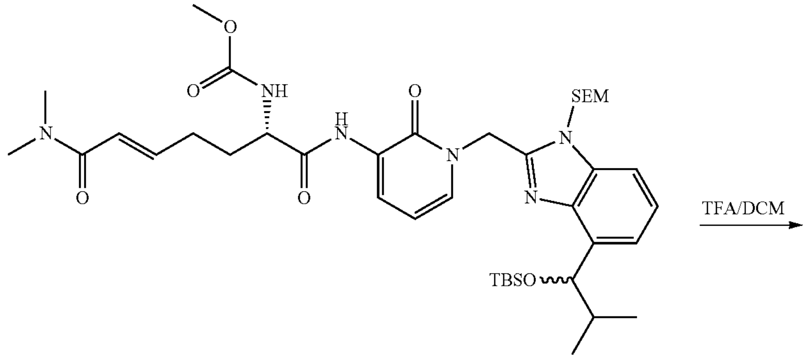

I-262

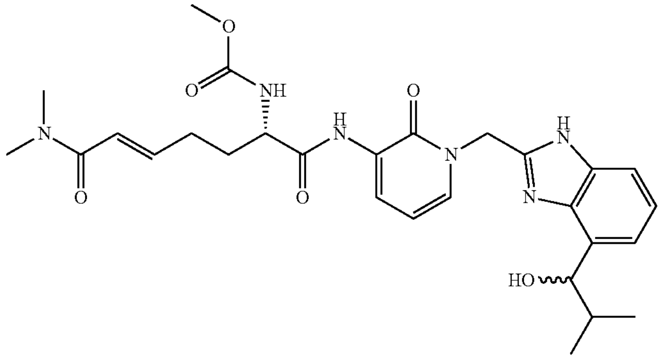

151

To a mixture of 3-amino-1-((4-(1-((tert-butyldimethylsilyl)oxy)-2-methylpropyl)-1-((2-(trimethylsilyl)ethoxy)methyl)-1H-benzo[d]imidazol-2-yl)methyl)pyridin-2(1H)-one (100 mg, 180 μmol) and (E)-7-(dimethylamino)-2-(methoxycarbonylamino)-7-oxo-hept-5-enoic acid (92.8 mg, 359 μmol) in DMF (1 mL) were added DIPEA (46.4 mg, 359 μmol) and HATU (102 mg, 269 μmol) in one portion at 25° C. under $N_2$ atmosphere. The mixture was stirred at 25° C. for 18 h. The resulting solution was poured into water (20 mL) and extracted with ethyl acetate (30 mL×2). The combined organic layers were washed with brine (30 mL), dried over anhydrous $Na_2SO_4$, filtered and concentrated in vacuum to give a residue. The residue was purified by (I-262) (99.0 mg, 118 μmol, 66% yield) as a yellow oil. LCMS m/z 797.2 $(M+1)^+$.

To a mixture of methyl ((2S,E)-1-((1-((4-(1-((tert-butyldimethylsilyl)oxy)-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-7-oxohept-5-en-2-yl)carbamate (163 mg, 204 μmol) in DCM (3 mL) was added TFA (1 mL) in one portion at 25° C. The mixture was stirred at 25° C. for 8 h. The resulting solution was concentrated in reduced pressure to give a residue. The residue was purified by HPLC (TFA) to afford methyl ((2S,E)-7-(dimethylamino)-1-((1-((4-(1-hydroxy-2-methylpropyl)-1H-benzo [d]imidazol-2-yl)methyl)-2-oxo-1,2-dihydropyridin-3-yl)amino)-1,7-dioxohept-5-en-2-yl)carbamate (Compound 151) (43.2 mg, 38% yield) as a yellow solid. LCMS m/z 553.3 $(M+1)^+$. $^1H$ NMR (400 MHz, DMSO-$d_6$) δ 9.27 (s, 1H), 8.30 (d, J=7.6 Hz, 1H), 7.69 (d, J=7.6 Hz, 1H), 7.61 (d, J=6.8 Hz, 1H), 7.53 (d, J=7.2 Hz, 1H), 7.38-7.33 (m, 2H), 6.57-6.46 (m, 1H), 6.44-6.42 (m, 1H), 6.38-6.34 (m, 1H), 5.61 (s, 2H), 4.73-4.72 (m, 1H), 4.19-4.17 (m, 1H), 3.53 (s, 3H), 2.98-2.91 (m, 3H), 2.91-2.83 (m, 3H), 2.26-2.24 (m, 2H), 2.02-2.01 (m, 1H), 1.99-1.84 (m, 1H), 1.84-1.71 (m, 1H), 0.93-0.91 (m, 3H), 0.80-0.79 (m, 3H).

The following compounds were prepared according to the procedures described in Example 23 using the appropriate intermediates.

| Compound | Structure | LCMS Data |
| --- | --- | --- |
| 152 | 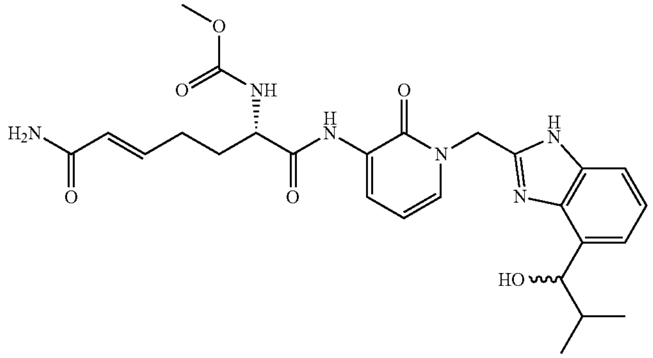 [SMILES: COC(=O)N[C@@H](CC/C=C/C(N)=O)C(=O)Nc1cccn(Cc2nc3c(C(O)C(C)C)cccc3[nH]2)c1=O] | LCMS m/z 525.1 (M + 1)$^+$ |
| 153 | 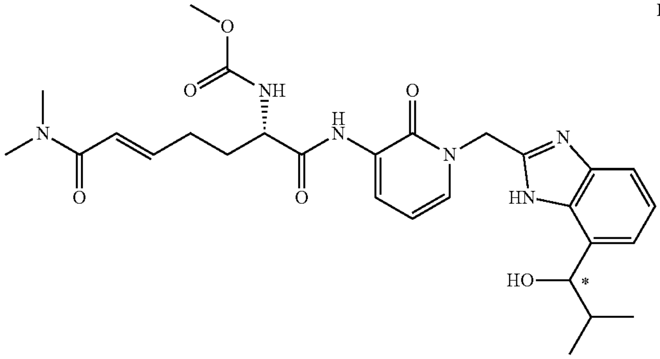 | LCMS m/z 553.3 (M + 1)$^+$ |
| 154 | 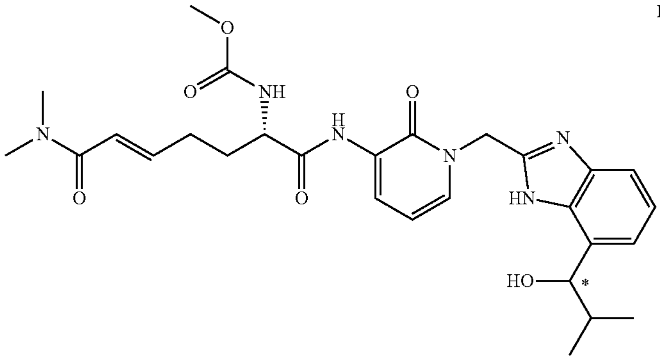 | LCMS m/z 553.3 (M + 1)$^+$ |

Example 24

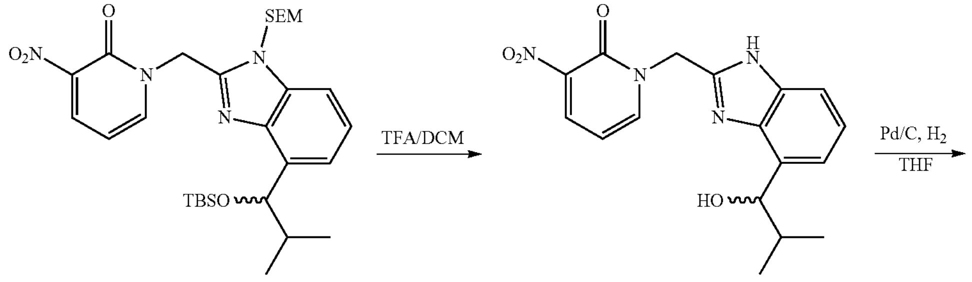

I-260 I-263

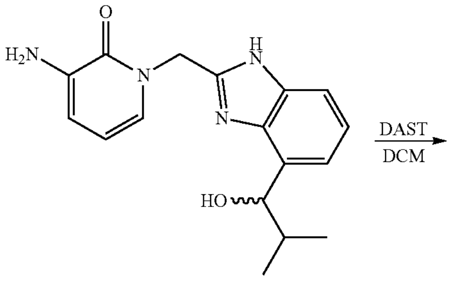

I-264

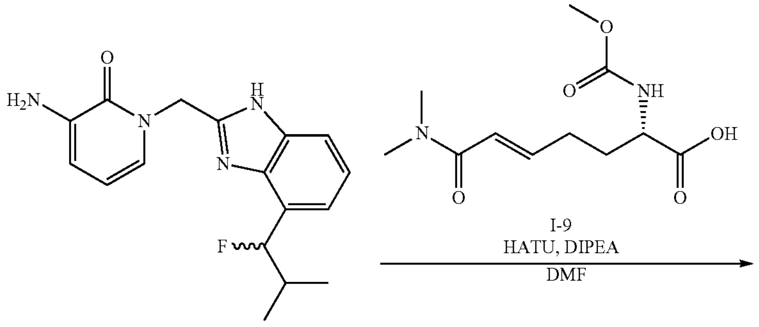

I-265

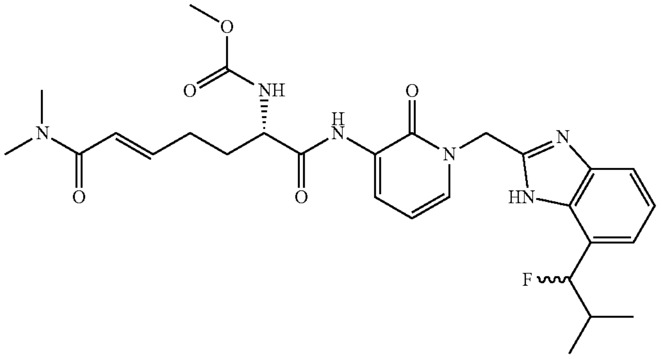 [SMILES: COC(=O)N[C@@H](CC/C=C/C(=O)N(C)C)C(=O)Nc1cccn(Cc2nc3cccc(C(O)C(C)C)c3[nH]2)c1=O]

155

To a mixture of 1-((4-(1-((tert-butyldimethylsilyl)oxy)-2-methylpropyl)-1-((2-(trimethylsilyl)ethoxy)methyl)-1H-benzo[d]imidazol-2-yl)methyl)-3-nitropyridin-2(1H)-one (1.20 g, 2.04 mmol) in DCM (3 mL) was added TFA (3 mL) in one portion at 25° C. under $N_2$ atmosphere. The mixture was stirred at 25° C. for 18 h. The mixture was concentrated in reduced pressure to give a residue. The residue was poured into saturated $NaHCO_3$ aqueous solution (20 mL). The resulting solution was extracted with DCM (30 mL×2). The combined organic layers were washed with brine (30 mL), dried over anhydrous $Na_2SO_4$, filtered and concentrated in vacuum to give a residue. The residue was purified by column chromatography to afford 1-((4-(1-hydroxy-2-methylpropyl)-1H-benzo[d]imidazol-2-yl)methyl)-3-nitropyridin-2(1H)-one (I-263) (400 mg, 45% yield) as a yellow solid. LCMS m/z 343 $(M+1)^+$.

To a solution of 1-((4-(1-hydroxy-2-methylpropyl)-1H-benzo[d]imidazol-2-yl)methyl)-3-nitropyridin-2(1H)-one (400 mg, 923 μmol) in THF (20 mL) was added Pd/C (40.0 mg, 10% purity) under $N_2$ atmosphere. The suspension was degassed under vacuum and purged with $H_2$ 3 times. The mixture was stirred under $H_2$ (15 psi) at 25° C. for 2 h. The resulting suspension was filtered and the filtrate was concentrated to give a residue. The residue was purified by prep-TLC (ethyl acetate) to give 3-amino-1-((4-(1-hydroxy-2-methylpropyl)-1H-benzo[d]imidazol-2-yl)methyl)pyridin-2(1H)-one (I-264) (220 mg, 72% yield) as a yellow solid. LCMS m/z 313 $(M+1)^+$.

To a mixture of 3-amino-1-((4-(1-hydroxy-2-methylpropyl)-1H-benzo[d]imidazol-2-yl)methyl)pyridin-2(1H)-one (160 mg, 512 μmol) in DCM (3 mL) was added DAST (107 mg, 666 μmol) in one portion at 0° C. under $N_2$ atmosphere. The mixture was warmed to 25° C. and stirred 1 h. The mixture was poured into water (20 mL). The resulting solution was extracted with DCM (30 mL×2). The combined organic layers were washed with brine (30 mL), dried over anhydrous $Na_2SO_4$, filtered and concentrated in vacuum to give a residue. The residue was purified by prep-TLC to afford 3-amino-1-((4-(1-fluoro-2-methylpropyl)-1H-benzo[d]imidazol-2-yl)methyl)pyridin-2(1H)-one (I-265) (86.0 mg, 50% yield) as a yellow oil. LCMS m/z 315 $(M+1)^+$.

To a mixture of 3-amino-1-((4-(1-fluoro-2-methylpropyl)-1H-benzo[d]imidazol-2-yl)methyl)pyridin-2(1H)-one (86.0 mg, 274 μmol) and (S,E)-7-(dimethylamino)-2-((methoxycarbonyl)amino)-7-oxohept-5-enoic acid (141 mg, 547 μmol) in DMF (500 μL) were added HATU (156 mg, 410 μmol) and DIPEA (70.7 mg, 547 μmol) in one portion at 25° C. under $N_2$ atmosphere. The mixture was stirred at 25° C. for 18 h. The mixture was poured into water (20 mL). The resulting solution was extracted with ethyl acetate (20 mL×2). The combined organic layers were washed with brine (20 mL), dried over anhydrous $Na_2SO_4$, filtered and concentrated in vacuum to give a residue. The residue was purified by HPLC (TFA) to afford methyl ((2S,E)-7-(dimethylamino)-1-((1-((7-(1-fluoro-2-methylpropyl)-1H-benzo[d]imidazol-2-yl)methyl)-2-oxo-1,2-dihydropyridin-3-yl)amino)-1,7-dioxohept-5-en-2-yl)carbamate (Compound 155) (67.1 mg, 41% yield) as a white solid. LCMS m/z 555.3 $(M+1)^+$. $^1$H NMR (400 MHz, DMSO-$d_6$) δ9.27 (s, 1H), 8.28 (d, J=7.6 Hz, 1H), 7.70 (d, J=7.6 Hz, 1H), 7.59-7.55 (m, 2H), 7.32-7.27 (m, 2H), 6.61-6.57 (m, 1H), 6.42-6.34 (m, 2H), 5.71 (dd, $J_1$=46.8 Hz, $J_2$=6.8 Hz, 1H), 5.51 (s, 2H), 4.18-4.17 (m, 1H), 3.54 (s, 3H), 2.98 (s, 3H), 2.91 (s, 3H), 2.33-2.21 (m, 3H), 1.86-1.76 (m, 1H), 1.72-1.70 (m, 1H), 1.03-1.01 (m, 3H), 0.83-0.81 (m, 3H).

The synthesis of intermediate I-271:

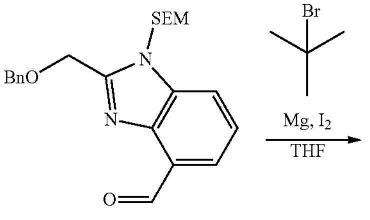

I-255

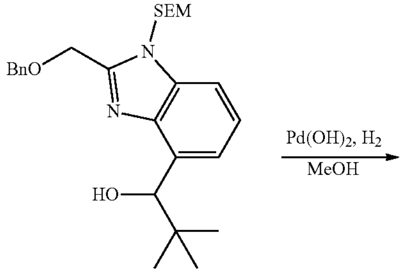

I-266

-continued

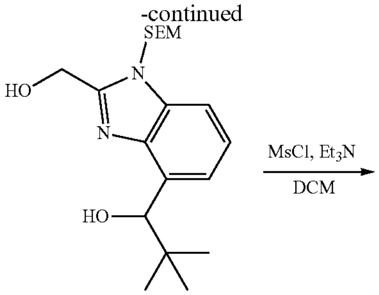

I-267

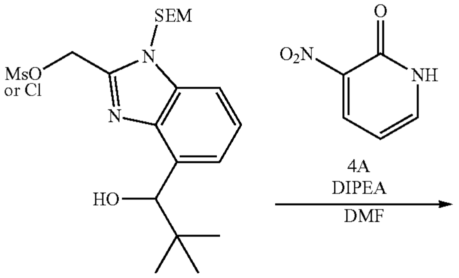

I-268

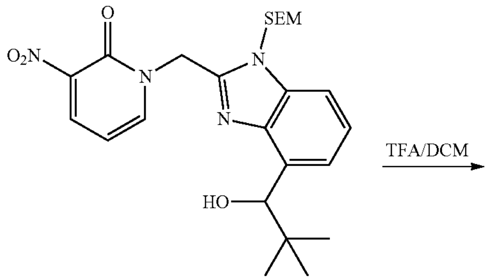

I-269

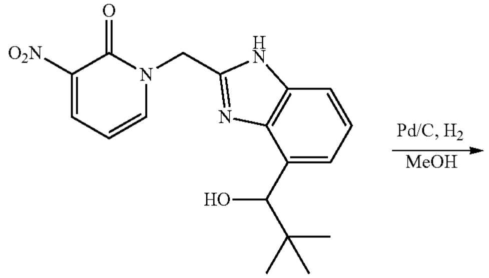

I-270

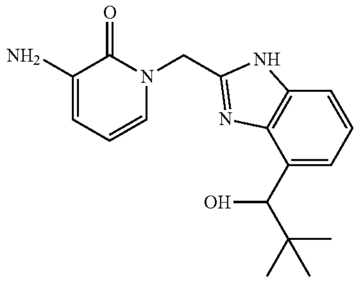

I-271

To a mixture of Mg (4.1 g, 168 mmol) in THF (151 mL) was added 12 (2.8 g, 11.2 mmol). The mixture was heated to 70° C. To the reaction mixture above was added slowly 2-bromo-2-methylpropane (15.3 g, 111.9 mmol) over 0.5 hr. It was stirred at 70° C. for 0.5 hr. To a solution of 2-(benzyloxymethyl)-3-(2-trimethylsilylethoxymethyl) benzimidazole-4-carbaldehyde (6.0 g, 15.1 mmol) in THF (20 mL)

was added bromo(tert-butyl)magnesium (1M, 15 mL, from above) at 0° C. The mixture was stirred at 0-30° C. for 1 hr. The reaction mixture was quenched with saturated $NH_4Cl$ (100 mL) at 0° C. and extracted with ethyl acetate (100 mL×3). The combined organic layers were dried over anhydrous $Na_2SO_4$, filtered and concentrated under reduced pressure to give a residue. The residue was purified by column chromatography to give 1-(2-((benzyloxy)methyl)-1-((2-(trimethylsilyl)ethoxy)methyl)-1H-benzo[d]imidazol-4-yl)-2,2-dimethylpropan-1-ol (I-266) (3.0 g) as a yellow oil.

To a solution of 1-(2-((benzyloxy)methyl)-1-((2-(trimethylsilyl)ethoxy)methyl)-1H-benzo[d]imidazol-4-yl)-2,2-dimethylpropan-1-ol (3.0 g, 6.6 mmol) in MeOH (20 mL) was added $Pd(OH)_2/C$ (3.0 g, 10% wet) under $N_2$ atmosphere. The suspension was degassed under vacuum and purged with $H_2$ three times. It was stirred under $H_2$ (50 psi) at 30° C. for 20 hours. The reaction mixture was filtered and the filtrate was concentrated to give the residue. The residue was purified by column chromatography to give 1-(2-(hydroxymethyl)-1-((2-(trimethylsilyl)ethoxy)methyl)-1H-benzo[d]imidazol-4-yl)-2,2-dimethylpropan-1-ol (1.00 g) as a yellow oil and recovered 1-(2-((benzyloxy)methyl)-1-((2-(trimethylsilyl)ethoxy)methyl)-1H-benzo[d]imidazol-4-yl)-2,2-dimethylpropan-1-ol (I-267) (3.4 g) as a yellow oil.

To a mixture of 1-(2-(hydroxymethyl)-1-((2-(trimethylsilyl)ethoxy)methyl)-1H-benzo[d]imidazol-4-yl)-2,2-dimethylpropan-1-ol (1.0 g, 2.7 mmol) in DCM (60 mL) were added MsCl (314 mg, 2.7 mmol) and TEA (555 mg, 5.5 mmol) in one portion at 0° C. under $N_2$ atmosphere. The mixture was stirred at 0-30° C. for 2 hours, The reaction mixture was poured into water (100 mL). The aqueous phase was extracted with ethyl acetate (80 mL×2). The combined organic layers were dried over anhydrous $Na_2SO_4$, filtered and concentrated in vacuum to afford (4-(1-hydroxy-2,2-dimethylpropyl)-1-((2-(trimethylsilyl)ethoxy)methyl)-1H-benzo[d]imidazol-2-yl)methyl methanesulfonate (I-268) (1.2 g) as a yellow oil.

To a mixture of (4-(1-hydroxy-2,2-dimethylpropyl)-1-((2-(trimethylsilyl)ethoxy) methyl)-1H-benzo[d]imidazol-2-yl) methyl methanesulfonate (1.2 g, 2.7 mmol) and 3-nitro-1H-pyridin-2-one (569 mg, 4.1 mmol) in MeCN (50 mL) was added DIPEA (700 mg, 5.4 mmol) in one portion at 20° C. The mixture was stirred at 20° C. for 10 hr. The reaction mixture was quenched with addition water (80 mL) and extracted with ethyl acetate (80 mL×2). The combined organic layers were dried over anhydrous $Na_2SO_4$, filtered and concentrated under reduced pressure to give a residue. The residue was purified by prep-HPLC to give 1-((4-(1-hydroxy-2,2-dimethylpropyl)-1-((2-(trimethylsilyl)ethoxy) methyl)-1H-benzo[d]imidazol-2-yl)methyl)-3-nitropyridin-2(1H)-one (I-269) (500 mg, 1.0 mmol) as a yellow oil. $^1H$ NMR (400 MHz, $CDCl_3$) δ 8.40 (d, J=7.8 Hz, 2H), 7.51-7.37 (m, 2H), 7.29-7.25 (m, 1H), 6.45 (t, J=7.2 Hz, 1H), 6.05-5.88 (m, 2H), 5.81-5.64 (m, 2H), 4.81 (s, 1H), 3.64-3.58 (m, 3H), 0.93 (s, 9H), 0.01 (s, 9H).

To a solution of 1-((4-(1-hydroxy-2,2-dimethylpropyl)-1-((2-(trimethylsilyl)ethoxy) methyl)-1H-benzo[d]imidazol-2-yl)methyl)-3-nitropyridin-2(1H)-one (400 mg, 822 μmol) in DCM (2 mL) was added TFA (3 mL). The mixture was stirred at 0-30° C. for 3 h. The solvent was removed to give 1-((4-(1-hydroxy-2,2-dimethylpropyl)-1H-benzo[d] imidazol-2-yl)methyl)-3-nitropyridin-2(1H)-one (I-270) (220 mg) as a yellow oil.

To a solution of 1-((4-(1-hydroxy-2,2-dimethylpropyl)-1H-benzo[d]imidazol-2-yl)methyl)-3-nitropyridin-2(1H)-one (220 mg, 617 μmol) in MeOH (10 mL) was added Pd/C (30 mg, 10% purity) under $N_2$ atmosphere. The suspension was degassed under vacuum and purged with $H_2$ three times. The mixture was stirred under $H_2$ (15 psi) at 20° C. for 1 hour. The resulting suspension was filtered and the filtrate was concentrated to give 3-amino-1-((4-(1-hydroxy-2,2-dimethylpropyl)-1H-benzo[d] imidazol-2-yl)methyl)pyridine-2(1H)-one (I-271) (200 mg) as a yellow oil. LCMS m/z 327.1 $(M+1)^+$.

Example 25

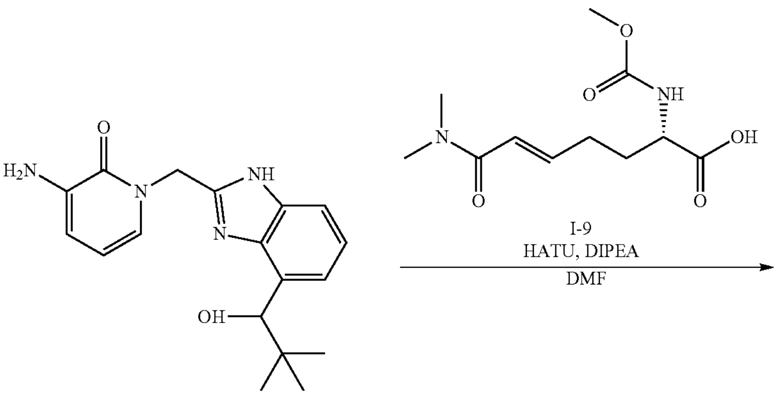

I-271

-continued

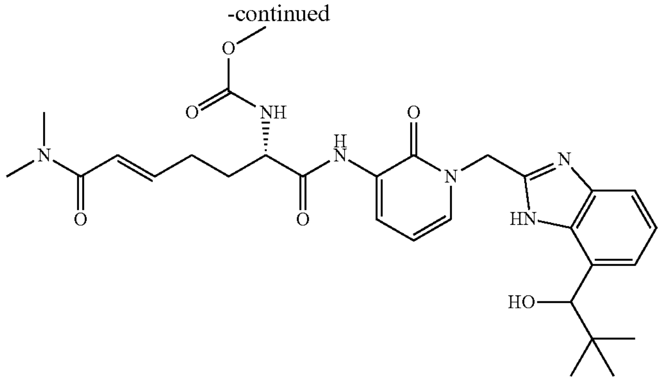

156

To a solution of (S,E)-7-(dimethylamino)-2-((methoxycarbonyl)amino)-7-oxohept-5-enoic acid (205 mg, 796 μmol) and 3-amino-1-[[4-(1-hydroxy-2,2-dimethyl-propyl)-1H-benzimidazol-2-yl]methyl]pyridin-2-one (200 mg, 612 μmol) in DMF (3.0 mL) were added HATU (280 mg, 735 μmol) and DIPEA (237 mg, 1.8 mmol). The mixture was stirred at 0-20° C. for 10 h. After filtration, the filtrate was purified by prep-HPLC twice to give methyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate (Compound 156) (20 mg, 33 μmol) as a white solid. LCMS m/z 658.4 $(M+1)^+$. $^1$H NMR (400 MHz, DMSO-$d_6$) δ9.25 (s, 1H), 8.30-8.25 (m, 1H), 7.75-7.65 (m, 1H), 7.61-7.55 (m, 1H), 7.51-7.46 (m, 1H), 7.36-7.29 (m, 1H), 7.26-7.23 (m, 1H), 6.63-6.54 (m, 1H), 6.43 (t, J=7.2 Hz, 1H), 6.36 (d, J=15.2 Hz, 1H), 5.63-5.51 (m, 2H), 4.69 (s, 1H), 4.23-4.11 (m, 1H), 3.53 (s, 3H), 2.97 (s, 3H), 2.82 (s, 3H), 2.26-2.14 (m, 2H), 1.91-1.80 (m, 1H), 1.75-1.63 (m, 1H), 0.88 (s, 9H).

The following compounds were prepared according to the procedures described in Example 25 using the appropriate intermediates.

| Compound | Structure | LCMS Data |
| --- | --- | --- |
| 157 | 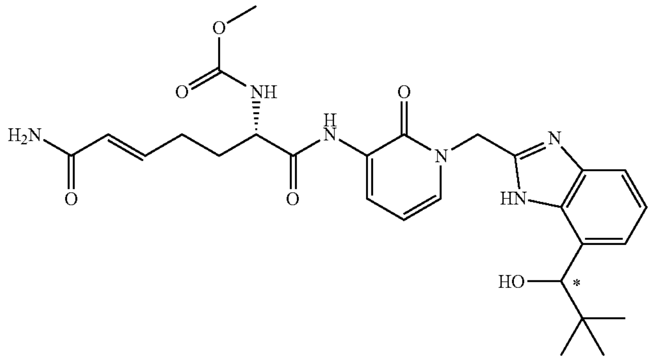 [SMILES: COC(=O)N[C@@H](CC/C=C/C(N)=O)C(=O)Nc1cccn(Cc2nc3cccc(C(O)C(C)(C)C)c3[nH]2)c1=O] | LCMS m/z 539.2 $(M + 1)^+$ |
| 158 | 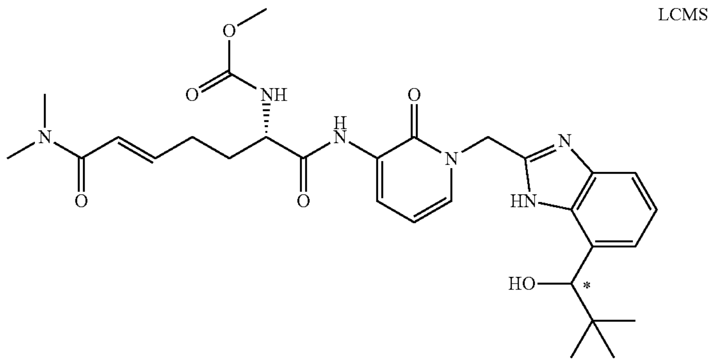 | LCMS m/z 567.2 $(M + 1)^+$ |

-continued
| Compound | Structure | LCMS Data |
| --- | --- | --- |
| 159 | 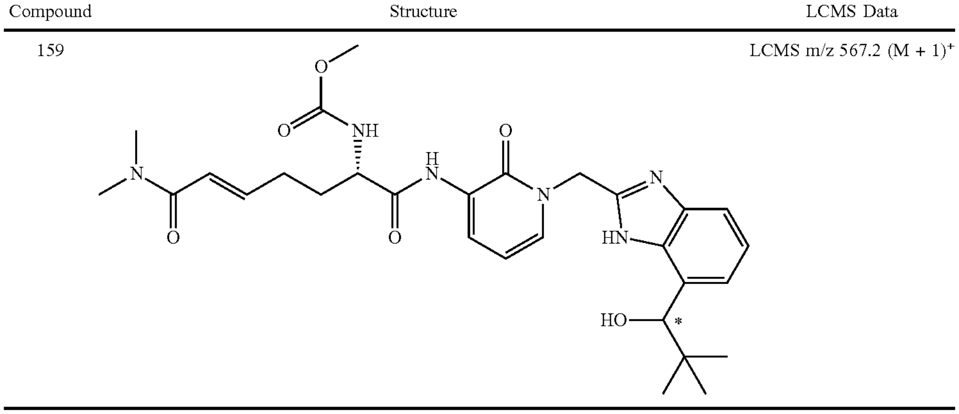 | LCMS m/z 567.2 $(M + 1)^+$ |
Example 26
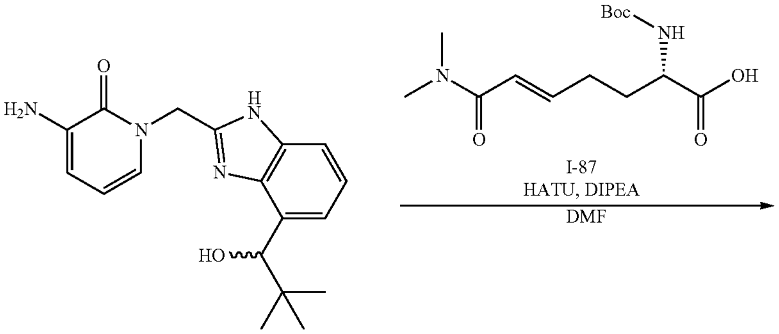
I-271
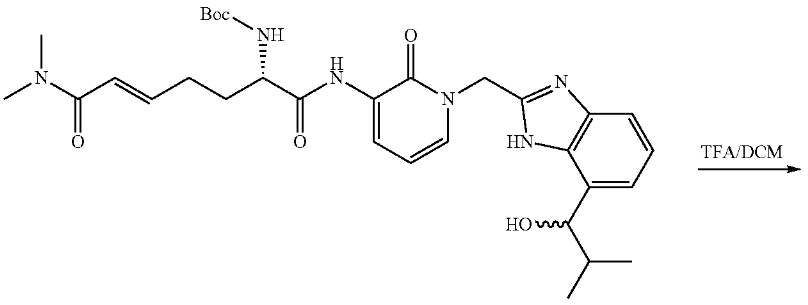
160
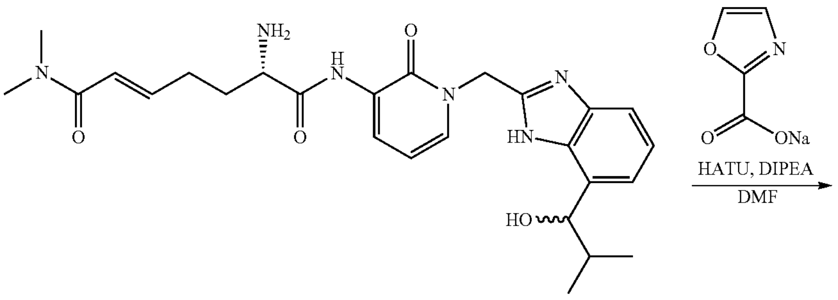
I-272

-continued

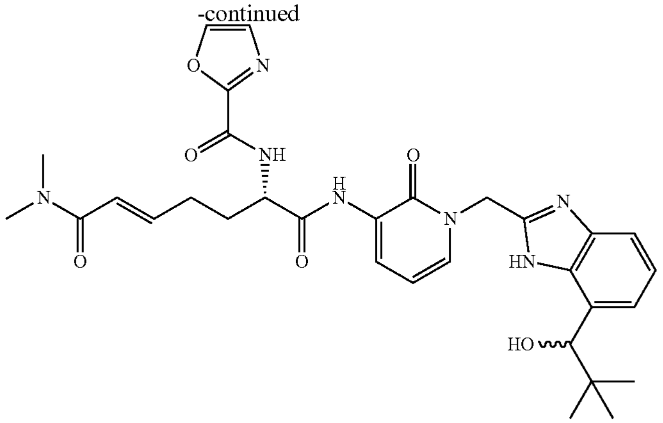

162

To a solution of (E,2S)-2-(tert-butoxycarbonylamino)-7-(dimethylamino)-7-oxo-hept-5-enoic acid (69 mg, 229 μmol) and 3-amino-1-[[4-(1-hydroxy-2,2-dimethyl-propyl)-1H-benzimidazol-2-yl]methyl]pyridin-2-one (50 mg, 153 μmol) in DMF (3 mL) were added HATU (87 mg, 229 μmol) and DIPEA (59 mg, 459 μmol). The mixture was stirred at 0-20° C. for 10 h. After filtration, the filtrate was purified by prep-HPLC to give tert-butyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate (Compound 160) (23.9 mg, 38 μmol) as a white solid. LCMS m/z 609.3 $(M+1)^+$. $^1H$ NMR (400 MHz, DMSO-$d_6$) δ 9.21 (s, 1H), 8.25 (dd, J=7.6, 1.6 Hz, 1H), 7.57-7.51 (m, 1H), 7.49-7.44 (m, 1H), 7.43-7.33 (m, 1H), 7.15-7.01 (m, 2H), 6.63-6.51 (m, 1H), 6.41-6.33 (m, 2H), 5.58-5.36 (m, 3H), 4.65-4.56 (m, 1H), 4.11-4.01 (m, 1H), 2.97 (s, 3H), 2.82 (s, 3H), 2.27-2.15 (m, 2H), 1.91-1.81 (m, 1H), 1.74-1.61 (m, 1H), 1.35 (s, 9H), 0.88 (s, 9H).

To a solution of tert-butyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate (60 mg, 98 μmol) in DCM (1 mL) was added TFA (0.75 mL) at 0° C. The mixture was stirred at 20° C. for 2 h. The reaction mixture was concentrated to give (6S,E)-6-amino-N7-(1-((7-(1-hydroxy-2,2-dimethylpropyl)-1H-benzo[d]imidazol-2-yl)methyl)-2-oxo-1,2-dihydropyridin-3-yl)-N1,N1-dimethylhept-2-enediamide (I-272) (50 mg) as a yellow oil.

To a solution of (6S,E)-6-amino-N7-(1-((7-(1-hydroxy-2,2-dimethylpropyl)-1H-benzo[d]imidazol-2-yl)methyl)-2-oxo-1,2-dihydropyridin-3-yl)-N1,N1-dimethylhept-2-enediamide (50 mg, 98 μmol) and sodium oxazole-2-carboxylate (20 mg, 147 μmol) in DMF (3 mL) were added HATU (56 mg, 147 μmol) and DIPEA (38 mg, 294 μmol). The mixture was stirred at 0-20° C. for 10 h. After filtration, the filtrate was purified by prep-HPLC to give (6S,E)-N7-(1-((7-(1-hydroxy-2,2-dimethylpropyl)-1H-benzo[d]imidazol-2-yl)methyl)-2-oxo-1,2-dihydropyridin-3-yl)-N1,N1-dimethyl-6-(oxazole-2-carboxamido)hept-2-enediamide (Compound 162) (25 mg, 41 μmol) as a white solid. LCMS m/z 604.3 $(M+1)^+$. $^1H$ NMR (400 MHz, DMSO-$d_6$) δ9.45-9.41 (m, 1H), 9.35-9.26 (m, 1H), 8.35 (s, 1H), 8.26-8.21 (m, 1H), 7.56-7.52 (m, 1H), 7.49 (s, 1H), 7.40-7.28 (m, 1H), 7.13-7.02 (m, 2H), 6.66-6.56 (m, 1H), 6.40-6.30 (m, 2H), 5.54-5.35 (m, 3H), 4.66-4.56 (m, 2H), 2.97 (s, 3H), 2.82 (s, 3H), 2.31-2.21 (m, 2H), 2.05-1.95 (m, 2H), 0.95-0.77 (m, 9H).

Example 27

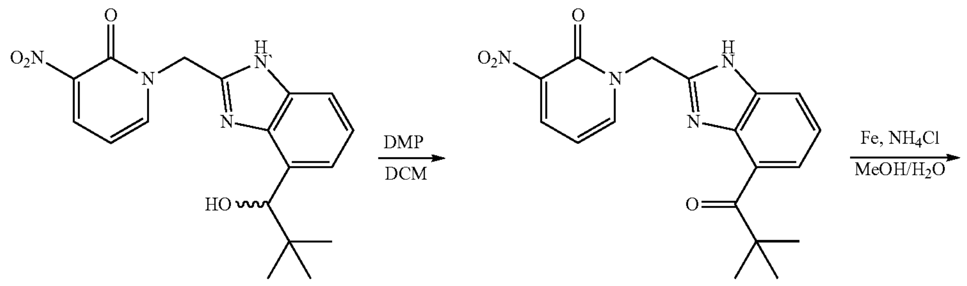

I-270 I-273

-continued

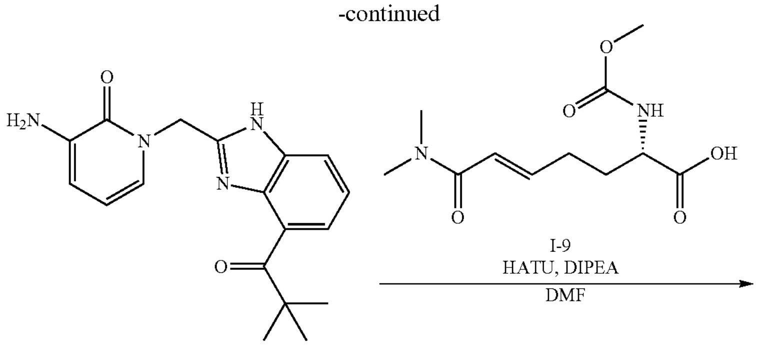

I-274

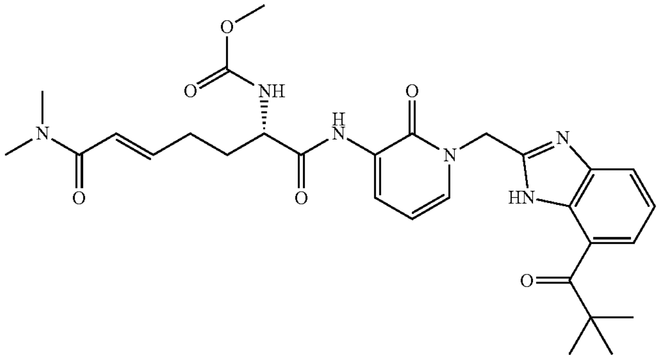 [SMILES: COC(=O)N[C@@H](CC/C=C/C(=O)N(C)C)C(=O)Nc1cccn(Cc2nc3cccc(C(O)C(C)(C)C)c3[nH]2)c1=O]

163

To a solution of 1-[[4-(1-hydroxy-2,2-dimethyl-propyl)-1H-benzimidazol-2-yl]methyl]-3-nitro-pyridin-2-one (300 mg, 841 μmol) in DCM (3 mL) was added DMP (535 mg, 1.3 mmol). The mixture was stirred at 20° C. for 1 hr. The reaction mixture was concentrated and purified by column chromatography to give 3-nitro-1-((4-pivaloyl-1H-benzo[d]imidazol-2-yl)methyl)pyridin-2(1H)-one (I-273) (200 mg, 496 μmol) as a yellow solid.

To a solution of 3-nitro-1-((4-pivaloyl-1H-benzo[d]imidazol-2-yl)methyl)pyridin-2(1H)-one (200 mg, 564 μmol) in MeOH (30 mL) were added Fe (157 mg, 2.8 mmol) and $NH_4Cl$ (301 mg, 5.6 mmol). The mixture was stirred at 80° C. for 3 hr. The reaction mixture was filtered and the filtrate was diluted with water (50 mL), extracted with ethyl acetate (50 mL×2). The combined organic layers were dried over anhydrous $Na_2SO_4$, filtered and concentrated under reduced pressure to give a residue. The residue was purified by prep-TLC to give 3-amino-1-[[4-(2,2-dimethylpropanoyl)-1H-benzimidazol-2-yl]methyl] pyridin-2-one (I-274) (150 mg) as a yellow solid. LCMS m/z 325.1 $(M+1)^+$.

To a solution of (E,2S)-7-(dimethylamino)-2-(methoxycarbonylamino)-7-oxo-hept-5-enoic acid (114 mg, 443 μmol) and 3-amino-1-[[4-(2,2-dimethylpropanoyl)-1H-benzimidazol-2-yl]methyl]pyridin-2-one (120 mg, 369 μmol) in DMF (3 mL) were added HATU (211 mg, 555 μmol) and DIPEA (143 mg, 1.1 mmol). The mixture was stirred at 0-20° C. for 10 h. After filtration, the filtrate was purified by prep-HPLC to give (S,E)-methyl (7-(dimethylamino)-1,7-dioxo-1-((2-oxo-1-((7-pivaloyl-1H-benzo[d]imidazol-2-yl)methyl)-1,2-dihydropyridin-3-yl)amino)hept-5-en-2-yl)carbamate (Compound 163) (182 mg, 306 μmol) as a white solid. LCMS m/z 565.3 $(M+1)^+$. $^1H$ NMR (400 MHz, DMSO-$d_6$) δ 9.28 (s, 1H), 8.27 (dd, J=7.6, 1.6 Hz, 1H), 7.98-7.90 (m, 1H), 7.77 (d, J=8.0 Hz, 1H), 7.75-7.66 (m, 1H), 7.59 (dd, J=6.8, 1.6 Hz, 1H), 7.36 (t, J=7.6 Hz, 1H), 6.64-6.54 (m, 1H), 6.43-6.34 (m, 2H), 5.62 (s, 2H), 4.21-4.10 (m, 1H), 3.52 (s, 3H), 2.97 (s, 3H), 2.82 (s, 3H), 2.30-2.15 (m, 2H), 1.95-1.85 (m, 1H), 1.76-1.63 (m, 1H), 1.37 (s, 9H).

Example 28

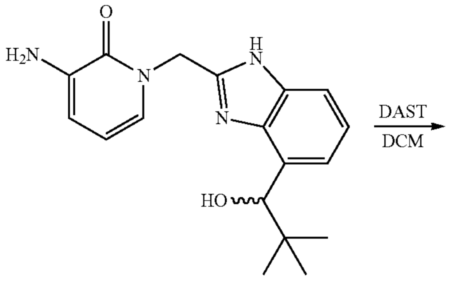

I-271

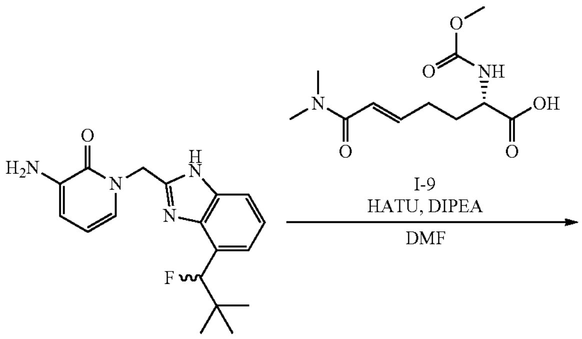

I-275

-continued

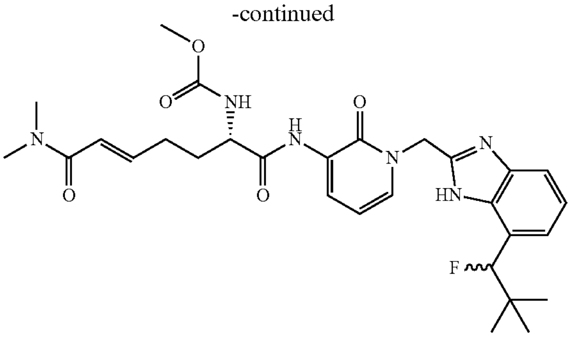

164

To a mixture of 3-amino-1-[[4-(1-hydroxy-2,2-dimethyl-propyl)-1H-benzimidazol-2-yl]methyl]pyridin-2-one (300 mg, 919 μmol) in DCM (3 mL) was added BAST (305 mg, 1.4 mmol) in one portion at 0° C. under $N_2$ atmosphere. The mixture was stirred at 30° C. for 1 hr. The reaction mixture was quenched with water (50 mL) at 0° C., and extracted with ethyl acetate (50 mL×2). The combined organic layers were dried over anhydrous $Na_2SO_4$. After filtration, the filtrate was concentrated under reduced pressure to give a residue which was purified by prep-TLC to give 3-amino-1-((4-(1-fluoro-2,2-dimethylpropyl)-1H-benzo[d]imidazol-2-yl)methyl)pyridin-2(1H)-one (I-275) (60 mg) as a yellow oil. LCMS m/z 329.1 $(M+1)^+$.

To a solution of (E,2S)-7-(dimethylamino)-2-(methoxy-carbonylamino)-7-oxo-hept-5-enoic acid (66 mg, 255 μmol) and 3-amino-1-((4-(1-fluoro-2,2-dimethylpropyl)-1H-benzo[d]imidazol-2-yl)methyl)pyridin-2(1H)-one (70 mg, 213 μmol) in DMF (3 mL) were added HATU (121 mg, 319 μmol) and DIPEA (82 mg, 639 μmol). The mixture was stirred at 0-20° C. for 10 h. After filtration, the filtrate was purified by prep-HPLC to give methyl ((2S,E)-7-(dimethyl-amino)-1-((1-((7-(1-fluoro-2,2-dimethylpropyl)-1H-benzo[d]imidazol-2-yl)methyl)-2-oxo-1,2-dihydropyridin-3-yl)amino)-1,7-dioxohept-5-en-2-yl)carbamate (Compound 164) (33.1 mg, 55 μmol) as a white solid. LCMS m/z 569.3 $(M+1)^+$. $^1$H NMR (400 MHz, DMSO-$d_6$) δ 9.27 (s, 1H), 8.26 (d, J=7.2 Hz, 1H), 7.76-7.73 (m, 1H), 7.56 (dd, J=7.2, 1.6 Hz, 1H), 7.51-7.46 (m, 1H), 7.25-7.19 (m, 1H), 7.15-7.11 (m, 1H), 6.65-6.56 (m, 1H), 6.41-6.34 (m, 2H), 5.85-5.68 (m, 1H), 5.51-5.45 (m, 2H), 4.25-4.15 (m, 1H), 3.54 (s, 3H), 2.98 (s, 3H), 2.83 (s, 3H), 2.27-2.16 (m, 2H), 1.95-1.84 (m, 1H), 1.77-1.64 (m, 1H), 0.95 (s, 9H).

The following compound was prepared according to the procedures described in Example 28 using the appropriate intermediates.

| Compound | Structure | LCMS Data |
| --- | --- | --- |
| 165 | 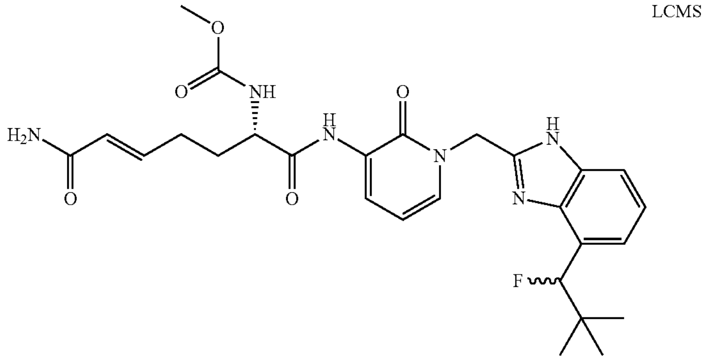 | LCMS m/z 541.2 (M + 1)$^+$ |

The Synthesis of Intermediate I-284

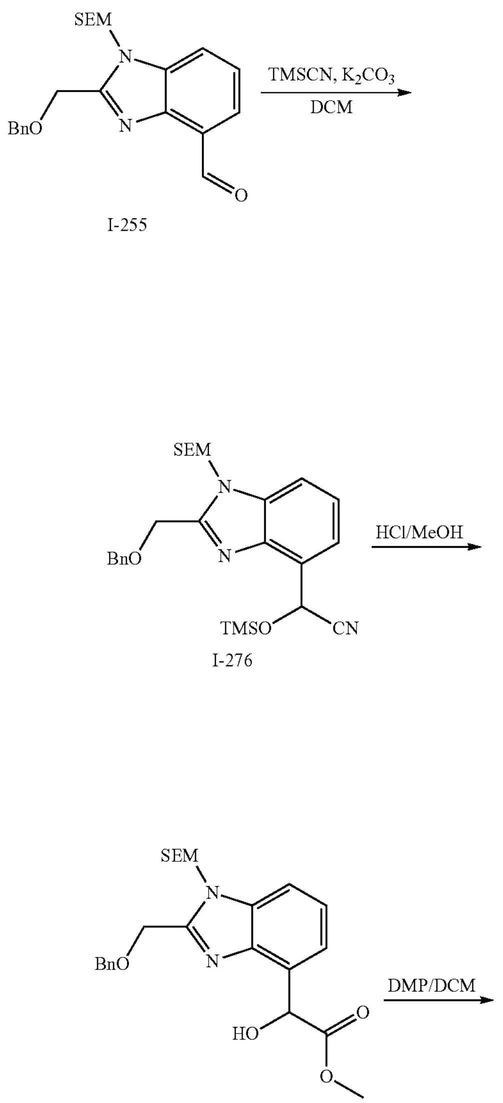

I-255

I-276

I-277

-continued

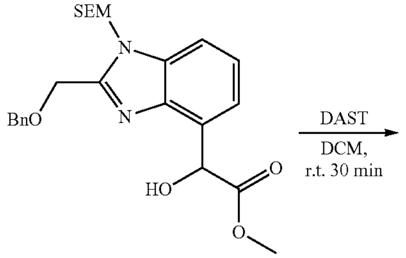

I-278

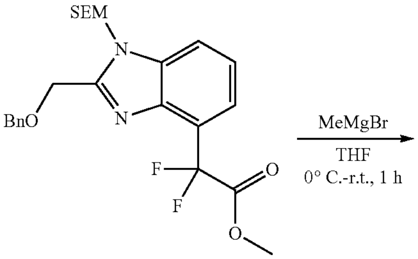

I-279

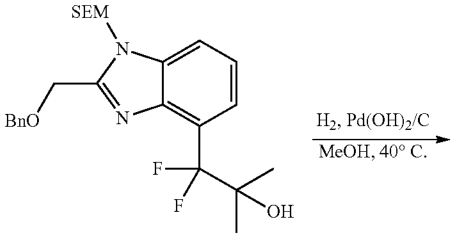

I-280

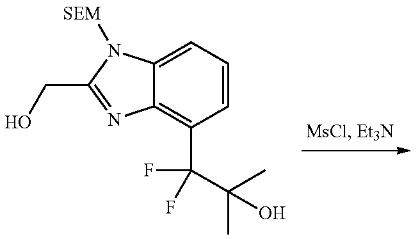

I-281

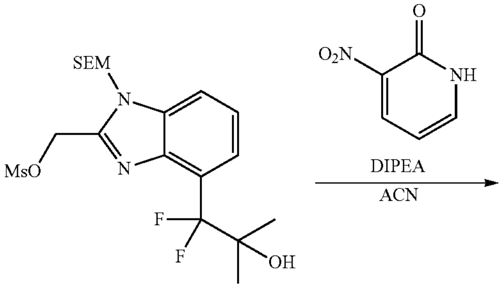

I-282

-continued

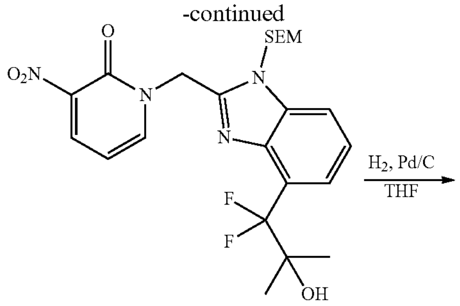

I-283

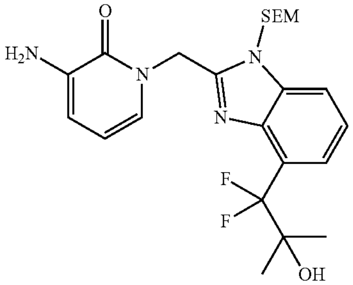

I-284

To a mixture of 2-(benzyloxymethyl)-1-(2-trimethylsilylethoxymethyl) benzimidazole-4-carbaldehyde (10 g, 25.2 mmol) and TMSCN (3.75 g, 37.8 mmol) in DCM (50 mL) was added $K_2CO_3$ (1.74 g, 12.61 mmol). The reaction mixture was stirred at 20° C. for 1.5 hr. The resulting solution was quenched with water (100 mL), and extracted with DCM (200 mL×2). The combined organic layers were dried over anhydrous $Na_2SO_4$, filtered and concentrated to give 2-(2-((benzyloxy)methyl)-1-((2-(trimethylsilyl)ethoxy)methyl)-1H-benzo[d]imidazol-4-yl)-2-((trimethylsilyl)oxy)acetonitrile (I-276) (12 g) as a yellow oil.

To a solution of 2-(2-((benzyloxy)methyl)-1-((2-(trimethylsilyl)ethoxy)methyl)-1H-benzo[d]imidazol-4-yl)-2-((trimethylsilyl)oxy)acetonitrile (12 g, 24.2 mmol) in MeOH (50 mL) was added HCl/MeOH (50 mL) at 0° C. The reaction mixture was stirred at 25° C. for 2 hr. The resulting solution was diluted with water (50 mL), adjusted pH~8 with ice saturated $NaHCO_3$, extracted with EtOAc (200 mL×2). The combined organic layers were dried over anhydrous $Na_2SO_4$, filtered and concentrated to give 2-(2-((benzyloxy)methyl)-1-((2-(trimethylsilyl)ethoxy)methyl)-1H-benzo[d]imidazol-4-yl)-2-hydroxyacetate (I-277) (11 g) as a yellow solid.

To a mixture of methyl 2-[2-(benzyloxymethyl)-1-(2-trimethylsilylethoxymethyl)benzimidazol-4-yl]-2-hydroxyacetate (11 g, 24.1 mmol) in DCM (100 mL) was added DMP (20.4 g, 48.2 mmol). The reaction mixture was stirred at 25° C. for 1 hr. The resulting solution was concentrated and purified by silica gel chromatography to give methyl 2-(2-((benzyloxy)methyl)-1-((2-(trimethylsilyl)ethoxy)methyl)-1H-benzo[d]imidazol-4-yl)-2-oxoacetate (I-278) (10 g) as a yellow oil. LCMS m/z 455.3 $(M+1)^+$. $^1H$ NMR (400 MHz, $CDCl_3$) δ8.04 (d, J=6.8 Hz, 1H), 7.87 (d, J=7.2 Hz, 1H), 7.51 (t, J=7.6 Hz, 1H), 7.43-7.34 (m, 5H), 5.73 (s, 2H), 4.96 (s, 2H), 4.67 (s, 3H), 4.09 (s, 3H), 2.55 (t, J=8.0 Hz, 2H), 0.93 (t, J=8.0 Hz, 2H), 0.00 (s, 9H).

To a solution of methyl 2-[2-(benzyloxymethyl)-1-(2-trimethylsilylethoxymethyl) benzimidazol-4-yl]-2-oxo-acetate (10 g, 22 mmol) in DCE (20 mL) was added DAST (17.7 g, 110 mmol, 14.5 mL) at 0° C. The reaction mixture was stirred at 20° C. for 1.5 hr. The reaction mixture was quenched with ice saturated $NaHCO_3$ (100 mL) and extracted with DCM (150 mL×2). The combined organic layers were dried over anhydrous $Na_2SO_4$, filtered and concentrated to give methyl 2-(2-((benzyloxy) methyl)-1-((2-(trimethylsilyl)ethoxy)methyl)-1H-benzo [d]imidazol-4-yl)-2,2-difluoroacetate (I-279) (10 g) as a yellow oil. LCMS m/z 477.3 $(M+1)^+$.

To a solution of methyl 2-[2-(benzyloxymethyl)-1-(2-trimethylsilylethoxymethyl) benzimidazol-4-yl]-2,2-difluoro-acetate (8 g, 16.8 mmol) in THF (10 mL) was added MeMgBr (3 M, 33.6 mL) at 0° C. The reaction mixture was stirred at 20° C. for 1 hr. The resulting solution was quenched with ice saturated $NH_4Cl$ (150 mL), extracted with EtOAc (200 mL×2). The combined organic layers were dried over anhydrous $Na_2SO_4$, filtered and concentrated to give a residue. The residue was purified by silica gel chromatography to give 1-(2-((benzyloxy)methyl)-1-((2-(trimethylsilyl)ethoxy)methyl)-1H-benzo[d]imidazol-4-yl)-1,1-difluoro-2-methylpropan-2-ol (I-280) (5 g) as a yellow oil.

To a mixture of 1-[2-(benzyloxymethyl)-1-(2-trimethylsilylethoxymethyl) benzimidazol-4-yl]-1,1-difluoro-2-methyl-propan-2-ol (2.50 g, 5.25 mmol) in MeOH (10 mL) was added $Pd(OH)_2/C$ (1.50 g). The reaction mixture was stirred at 40° C. for 16 hr under $H_2$ (15 psi). The reaction mixture was filtered and concentrated to give 1,1-difluoro-1-(2-(hydroxymethyl)-1-((2-(trimethylsilyl)ethoxy)methyl)-1H-benzo[d] imidazol-4-yl)-2-methylpropan-2-ol (I-281) (4 g) as a yellow oil. LCMS m/z 387.2 $(M+1)^+$.

To a solution of methyl 2,2-difluoro-2-[2-(hydroxymethyl)-1-(2-trimethylsilylethoxymethyl)benzimidazol-4-yl] acetate (4 g, 10.4 mmol) and MsCl (3.81 g, 33.3 mmol, 2.57 mL) in DCM (100 mL) was added DIPEA (4.01 g, 31.01 mmol, 5.42 mL) at 0° C. The reaction mixture was stirred at 20° C. for 2 hr. The resulting solution was quenched with saturated $NaHCO_3$ (80 mL), and extracted with DCM (100 mL×2). The combined organic layers were dried over anhydrous $Na_2SO_4$, filtered and concentrated to give (4-(1,1-difluoro-2-hydroxy-2-methylpropyl)-1-((2-(trimethylsilyl) ethoxy)methyl)-1H-benzo[d]imidazol-2-yl)methyl methanesulfonate (I-282) (4.50 g) as a yellow oil. LCMS m/z 465.0 $(M+1)^+$.

To a solution of 3-nitro-1H-pyridin-2-one (2.72 g, 19.4 mmol) and [4-(1,1-difluoro-2-hydroxy-2-methyl-propyl)-1-(2-trimethylsilylethoxymethyl)benzimidazol-2-yl]methyl methanesulfonate (4.5 g, 9.69 mmol) in MeCN (50 mL) was added DIPEA (3.76 g, 29.1 mmol, 5.08 mL). The reaction mixture was stirred at 20° C. for 5 hr. The resulting solution was diluted with EtOAc (150 mL) and washed with saturated $NH_4Cl$ (70 mL×2). The organic phase was dried over anhydrous $Na_2SO_4$, filtered and concentrated to give a residue. The residue was purified by prep-TLC to give 1-((4-(1,1-difluoro-2-hydroxy-2-methylpropyl)-1-((2-(trimethylsilyl)ethoxy)methyl)-1H-benzo[d]imidazol-2-yl) methyl)-3-nitropyridin-2(1H)-one (I-283) (4 g) as a yellow oil. LCMS m/z 509.1 $(M+1)^+$. $^1H$ NMR (400 MHz, DMSO-$d_6$) δ 8.40 (dd, J=7.6, 2.0 Hz, 1H), 8.13 (dd, J=6.8, 1.2 Hz, 1H), 7.65-7.62 (m, 2H), 7.48 (t, J=8.0 Hz, 1H), 6.49 (t, J=7.6 Hz, 1H), 6.40 (s, 1H), 5.88 (s, 2H), 5.58 (s, 2H), 3.63 (t, J=8.4 Hz, 1H), 1.31 (s, 6H), 0.92 (t, J=8.4 Hz, 1H), 0.00 (s, 9H).

To a mixture of 1-[[4-(1,1-difluoro-2-hydroxy-2-methyl-propyl)-1-(2-trimethylsilylethoxymethyl)benzimidazol-2-yl]methyl]-3-nitro-pyridin-2-one (1.80 g, 3.54 mmol) in THF (20 mL) was added Pd/C (500 mg, 10% purity). The reaction mixture was stirred at 20° C. for 1 hr under $H_2$ (15 psi). The resulting suspension was filtered and the filtrate was concentrated to give 3-amino-1-((4-(1,1-difluoro-2-hydroxy-2-methylpropyl)-1-((2-(trimethylsilyl)ethoxy) methyl)-1H-benzo[d]imidazol-2-yl)methyl)pyridin-2(1H)-one (I-284) (1.60 g) as a yellow oil. LCMS m/z 479.1 $(M+1)^+$. $^1H$ NMR (400 MHz, DMSO-$d_6$) δ 7.68-7.66 (m, 2H), 7.47 (t, J=7.6 Hz, 1H), 7.10-7.08 (m, 1H), 6.57-6.55 (m, 1H), 6.19 (t, J=6.8 Hz, 1H), 5.87 (s, 2H), 5.36 (s, 2H), 4.26 (s, 2H), 3.54 (t, J=8.0 Hz, 1H), 1.35 (s, 6H), 0.93 (t, J=8.4 Hz, 1H), 0.00 (s, 9H).

Example 29

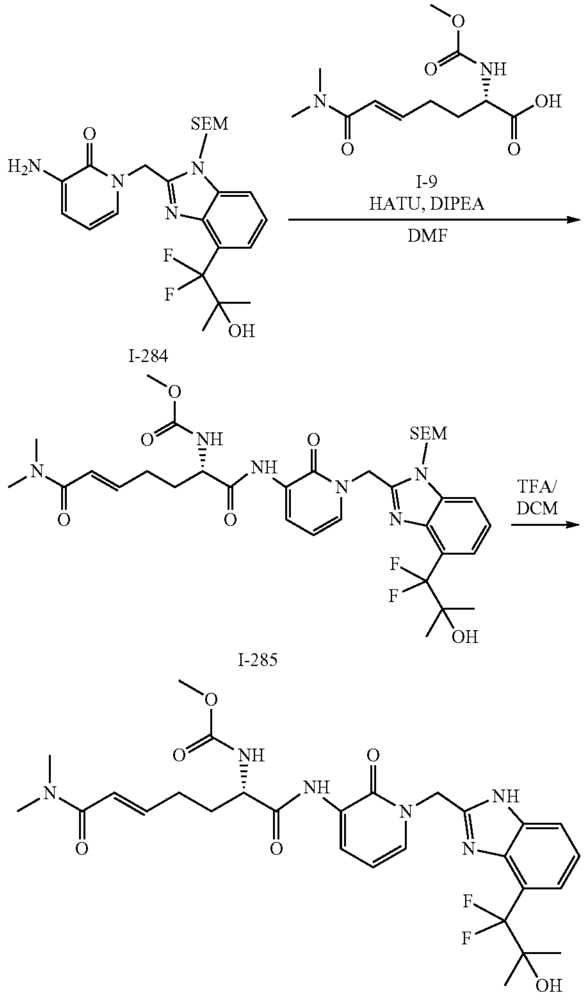

I-9

I-284

I-285

166

To a mixture of 1-[[4-(1,1-difluoro-2-hydroxy-2-methyl-propyl)-1-(2-trimethylsilylethoxymethyl)benzimidazol-2-yl]methyl]-3-nitro-pyridin-2-one (200 mg, 0.393 mmol), (S,E)-7-(dimethylamino)-2-((methoxycarbonyl)amino)-7-oxohept-5-enoic acid (183 mg, 0.708 mmol) and HATU (449 mg, 1.18 mmol) in DMF (10 mL) was added DIPEA (254 mg, 1.97 mmol, 0.343 mL). The reaction mixture was stirred at 20° C. for 16 hr. The reaction mixture was diluted with EtOAc (40 mL), washed with brine (30 mL×3). The organic phase was dried over anhydrous $Na_2SO_4$, filtered and concentrated to give a residue. The residue was purified by prep-TLC to give (S,E)-methyl (1-((1-((4-(1,1-difluoro- 2-hydroxy-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl)carbamate (I-285) (200 mg) as a yellow solid. LCMS m/z 723.6 $(M+1)^+$.

To a solution of (S,E)-methyl (1-((1-((4-(1,1-difluoro-2-hydroxy-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl)carbamate (180 mg, 0.25 mmol) in DCM (5 mL) was added TFA (5 mL). The reaction mixture was stirred at 20° C. for 3 hr. The resulting solution was adjusted pH~8 with saturated $NaHCO_3$, and extracted with DCM (30 mL×2). The combined organic layers were dried over anhydrous $Na_2SO_4$, filtered and concentrated to give a residue. The residue was purified by prep-HPLC to give (S,E)-methyl(1-((1-((4-(1,1-difluoro-2-hydroxy-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate (Compound 166) (82.8 mg, 56% yield) as a white solid. LCMS m/z 589.2 $(M+1)^+$. $^1H$ NMR (400 MHz, DMSO-$d_6$) δ12.20 (br s, 1H), 9.25 (s, 1H), 8.26 (dd, J=7.2, 1.6 Hz, 1H), 7.75-7.73 (m, 1H), 7.63-7.56 (m, 2H), 7.26-7.20 (m, 2H), 6.64-6.56 (m, 1H), 6.39-6.33 (m, 2H), 5.44-5.35 (m, 3H), 4.19-4.14 (m, 1H), 3.54 (s, 3H), 2.98 (s, 3H), 2.79 (s, 3H), 2.27-2.19 (m, 2H), 1.89-1.85 (m, 1H), 1.74-1.69 (m, 1H), 1.25 (s, 6H).

Synthesis of Intermediate I-289

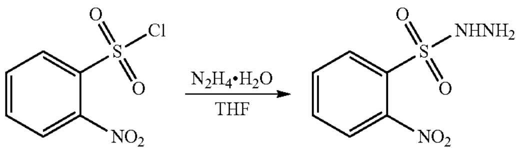

I-286 I-287

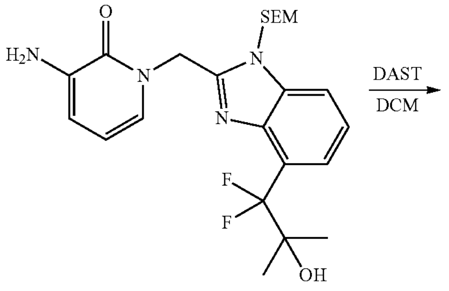

I-284

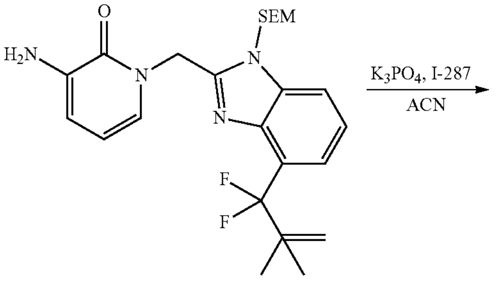

I-288

-continued

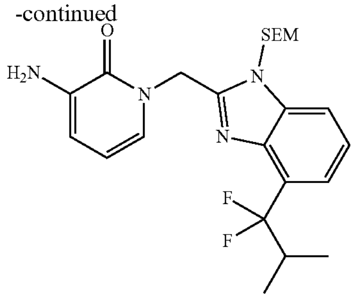

I-289

To a mixture of 2-nitrobenzenesulfonyl chloride (5 g, 22.6 mmol) in THF (60 mL) was added $N_2H_4 \cdot H_2O$ (2.82 g, 56.4 mmol, 2.74 mL) dropwise at −30° C. The reaction mixture was stirred at −30° C. for 1 hr under $N_2$ atmosphere, diluted with EtOAc (100 mL), washed with ice brine (50 mL×2). The organic phase was poured into petroleum ether (400 mL) and filtered. The filter cake was washed with Petroleum ether (100 mL), the resulting solid residue was dried under vacuum to give 2-nitrobenzenesulfonohydrazide (I-287) (5.30 g) as a yellow solid. $^1H$ NMR (400 MHz, $CDCl_3$) δ8.24-8.21 (m, 1H), 7.92-7.90 (m, 1H), 7.84-7.81 (m, 2H), 6.57 (s, 1H).

To a solution of 3-amino-1-[[4-(1,1-difluoro-2-hydroxy-2-methyl-propyl)-1-(2-trimethylsilylethoxymethyl)benzimidazol-2-yl]methyl]pyridin-2-one (1.80 g, 3.76 mmol) in DCM (20 mL) was added DAST (1.82 g, 11.3 mmol, 1.49 mL) at −70° C. The reaction solution was stirred at −70° C. for 0.5 hr and 0° C. for another 0.5 hr under $N_2$ atmosphere. The reaction mixture was quenched with saturated $NaHCO_3$ (30 mL), extracted with DCM (50 mL×2). The organic phase was dried over anhydrous $Na_2SO_4$, filtered and concentrated to give a residue. The residue was purified by silica gel chromatography to give 3-amino-1-[[4-(1,1-difluoro-2-methyl-allyl)-1-(2-trimethylsilylethoxymethyl)benzimidazol-2-yl]methyl]pyridin-2-one (I-288) (1.10 g) as a yellow oil. LCMS m/z 461.3 $(M+1)^+$.

To a mixture of 2-nitrobenzenesulfonohydrazide (660 mg, 3.04 mmol) and $K_3PO_4$ (323 mg, 1.52 mmol) in MeCN (10 mL) was added 2-nitrobenzenesulfonohydrazide (660 mg, 3.04 mmol). The reaction mixture was stirred at 28° C. for 16 hr. Then another batch of 2-nitrobenzenesulfonohydrazide (377 mg, 1.74 mmol) and $K_3PO_4$ (184 mg, 0.868 mmol) was added. The reaction mixture was stirred at 28° C. for another 3 hr. The resulting solution was diluted with brine (30 mL) and extracted with EtOAc (40 mL×2). The combined organic layers were dried over anhydrous $Na_2SO_4$, filtered and concentrated to give a residue. The residue was purified by prep-TLC to give 3-amino-1-((4-(1,1-difluoro-2-methylpropyl)-1-((2-(trimethylsilyl)ethoxy)methyl)-1H-benzo[d]imidazol-2-yl)methyl)pyridin-2(1H)-one (I-289) (200 mg) as a yellow oil. LCMS m/z 455.3 $(M+1)^+$.

Example 30

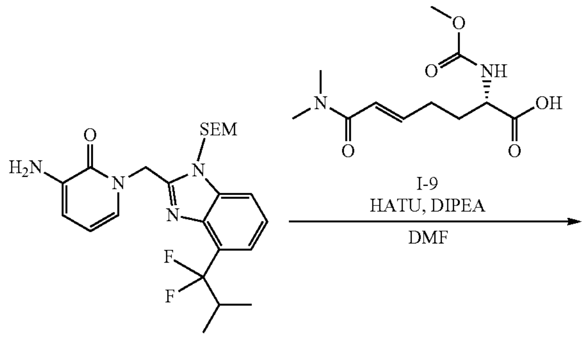

I-289

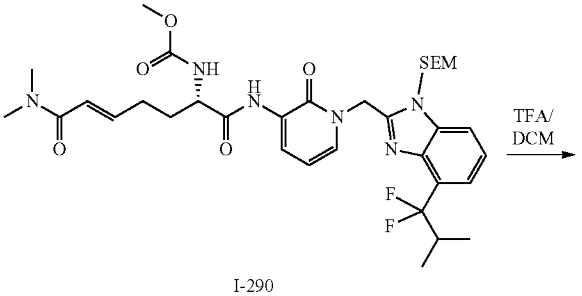

I-290

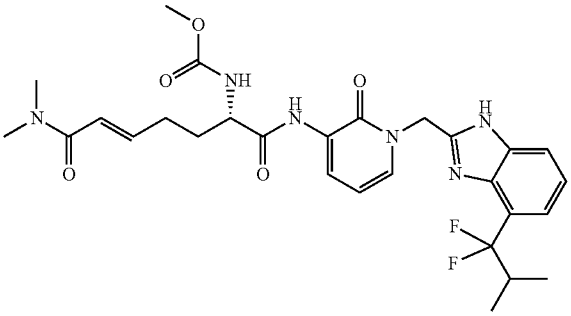

167

To a mixture of 3-amino-1-[[4-(1,1-difluoro-2-methyl-propyl)-1-(2-trimethylsilylethoxymethyl)benzimidazol-2-yl]methyl]pyridin-2-one (200 mg, 0.432 mmol), (S, E)-7-(dimethylamino)-2-(methoxycarbonylamino)-7-oxo-hept-5-enoic acid (201 mg, 0.778 mmol) and HATU (493 mg, 1.30 mmol) in DMF (10 mL) was added DIPEA (279 mg, 2.16 mmol). The reaction mixture was stirred at 20° C. for 16 h. The reaction mixture was diluted with EtOAc (40 mL) and washed with brine (30 mL×3). The organic phase was dried over anhydrous $Na_2SO_4$, filtered and concentrated to give a residue. The residue was purified by prep-TLC to give (S,E)-methyl (1-((1-((4-(1,1-difluoro-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl)carbamate (I-290) (200 mg) as a yellow solid. LCMS m/z 703.6 $(M+1)^+$.

To a solution of (S,E)-methyl (1-((1-((4-(1,1-difluoro-2-methylpropyl)-1-((2-(trimethylsilyl)ethoxy)methyl)-1H-benzo[d]imidazol-2-yl)methyl)-2-oxo-1,2-dihydropyridin-3-yl)amino)-7-(dimethylamino)-1,7-dioxohept-5-en-2-yl) carbamate (200 mg, 0.285 mmol) in DCM (3 mL) was added TFA (3 mL). The reaction mixture was stirred at 20° C. for 3 hr. The reaction mixture was adjusted pH~8 with saturated $NaHCO_3$. The resulting solution was extracted with DCM (100 mL×2). The combined organic layers were dried over anhydrous $Na_2SO_4$, filtered and concentrated to give a residue. The residue was purified by prep-HPLC to give (S,E)-methyl (1-((1-((4-(1,1-difluoro-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl) carbamate (Compound 167) (64.30 mg, 39% yield) as a yellow solid. LCMS m/z 573.2 $(M+1)^+$. $^1H$ NMR (400 MHz, DMSO-$d_6$) δ 12.57 (br. s, 1H), 9.26 (s, 1H), 8.28-8.26 (m, 1H), 7.75-7.57 (m, 3H), 7.31-7.24 (m, 2H), 6.64-6.56 (m, 1H), 6.39-6.35 (m, 2H), 5.44 (s, 2H), 4.19-4.15 (m, 1H), 3.55 (s, 3H), 2.99 (s, 3H), 2.84 (s, 3H), 2.61-2.53 (m, 1H), 2.27-2.22 (m, 2H), 1.89-1.85 (m, 1H), 1.75-1.70 (m, 1H), 1.06-0.86 (m, 6H). LCMS $[M+1]^+$=573.2.

The following compounds were prepared according to the procedures described in Example 30 using the appropriate intermediates.

| Compound | Structure | LCMS Data |
| --- | --- | --- |
| 168 | 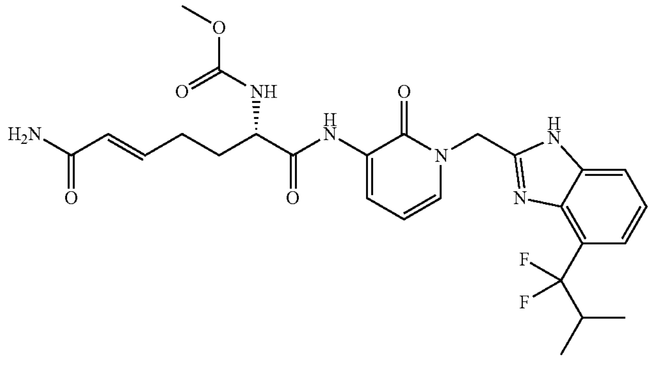 [SMILES: COC(=O)N[C@@H](CC/C=C/C(N)=O)C(=O)Nc1cccn(Cc2nc3c(C(F)(F)C(C)C)cccc3[nH]2)c1=O] | LCMS m/z 545.2 $(M + 1)^+$ |

-continued
| Compound | Structure | LCMS Data |
| --- | --- | --- |
| 169 | 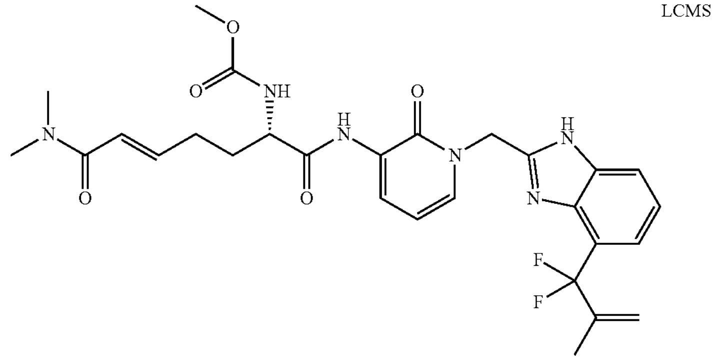 | LCMS m/z 571.2 $(M + 1)^+$ |
| 170 | 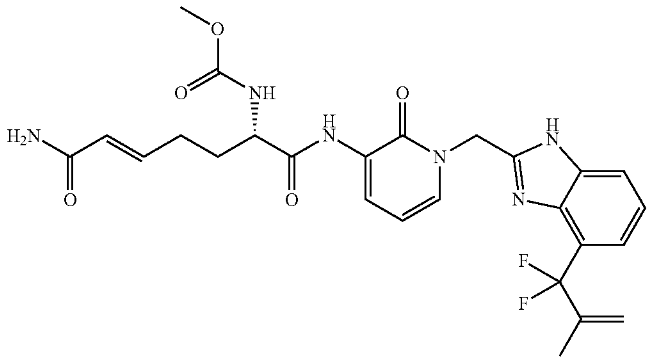 [SMILES: C=C(C)C(F)(F)c1cccc2[nH]c(Cn3cccc(NC(=O)[C@H](CC/C=C/C(N)=O)NC(=O)OC)c3=O)nc12] | LCMS m/z 543.2 $(M + 1)^+$ |
Synthesis of Intermediate I-300
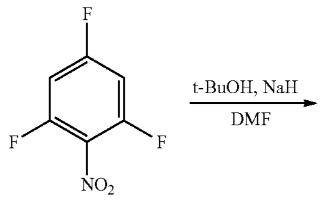
I-206
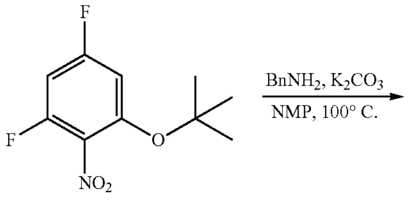
I-291
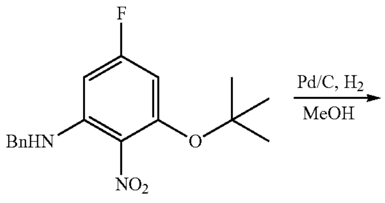
I-292
-continued
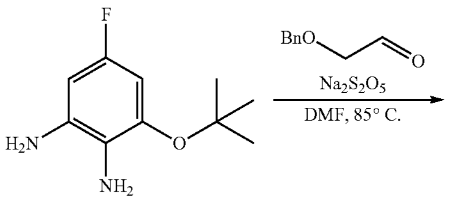
I-293
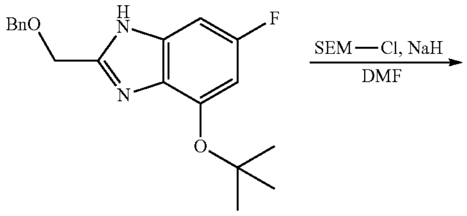
I-294
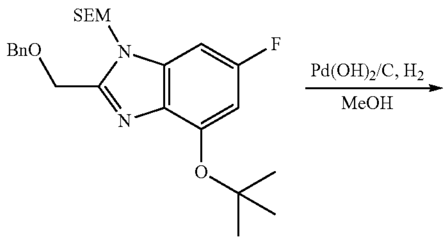
I-295

-continued

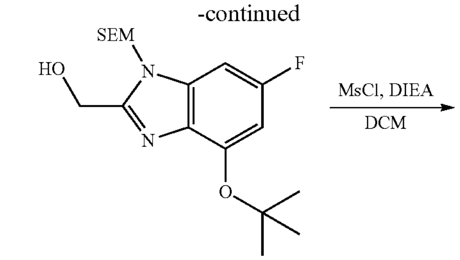

I-296

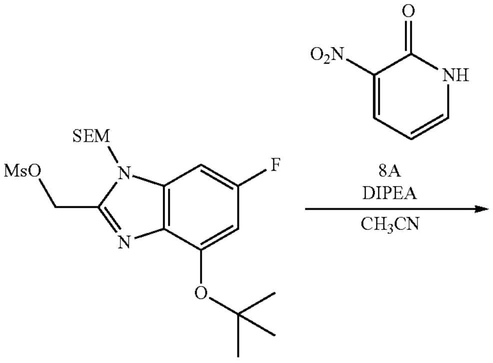

I-297

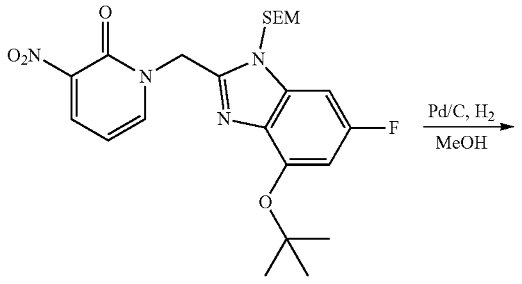

I-298

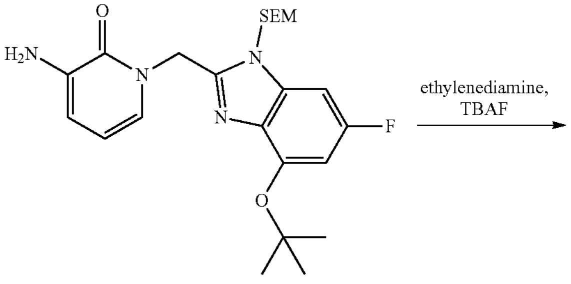

I-299

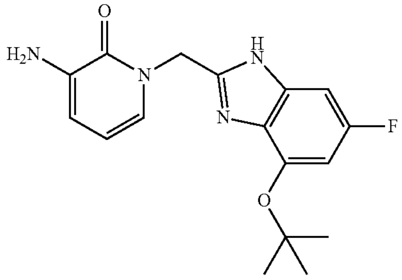

I-300

To a solution of 1,3,5-trifluoro-2-nitrobenzene (10.0 g, 56.5 mmol) in toluene (120 mL) was added tert-butoxypotassium (7.0 g, 62.1 mmol) at 0° C. The mixture was stirred at 25° C. for 2 h. The mixture was poured into saturated $NH_4Cl$ (20 mL) and extracted with ethyl acetate (100 mL×2). The combined organic layers were washed with brine (50 mL), dried over anhydrous $Na_2SO_4$, filtered off and concentrated to give a residue. The residue was purified by column chromatography to give 1-(tert-butoxy)-3,5-difluoro-2-nitrobenzene (I-291) (8.0 g) as a yellow oil. $^1H$ NMR (400 MHz, DMSO-$d_6$) δ 6.75-6.72 (m, 1H), 6.65-6.64 (m, 1H), 1.47 (s, 9H).

To a solution of 1-(tert-butoxy)-3,5-difluoro-2-nitrobenzene (8.0 g, 34.6 mmol) and phenylmethanamine (3.89 g, 36.3 mmol) in NMP (80 mL) was added $K_2CO_3$ (9.56 g, 69.2 mmol). The mixture was stirred at 100° C. for 16 h. The mixture was poured into water (200 mL) and extracted with EtOAc (100 mL×2). The combined organic layers were washed with brine (50 mL×4), dried over anhydrous $Na_2SO_4$, filtered and concentrated to give a residue. The residue was purified by column chromatography to give N-benzyl-3-(tert-butoxy)-5-fluoro-2-nitroaniline (I-292) (5.5 g) as a brown solid. $^1H$ NMR (400 MHz, DMSO-$d_6$) δ 7.40-7.32 (m, 2H), 6.40 (s, 1H), 6.21-6.18 (m, 1H), 6.14-6.11 (m, 1H), 4.37 (d, J=5.6 Hz, 1H), 1.45 (s, 9H).

To a solution of N-benzyl-3-(tert-butoxy)-5-fluoro-2-nitroaniline (5.50 g, 17.3 mmol) in MeOH (50 mL) was added Pd/C (10%, 1 g) under $N_2$ atmosphere. The suspension was degassed and purged with $H_2$ for 3 times. The mixture was stirred under $H_2$ (15 psi) atmosphere at 25° C. for 1 h. The mixture was filtered off and the filtrate was concentrated to give 3-(tert-butoxy)-5-fluorobenzene-1,2-diamine (I-293) (3.5 g) as a brown oil.

To a solution of 3-(tert-butoxy)-5-fluorobenzene-1,2-diamine (3.0 g, 15.1 mmol) in DMF (35 mL) were added $Na_2S_2O_5$ (5.75 g, 30.3 mmol) and 2-benzyloxyacetaldehyde (4.55 g, 30.3 mmol). The mixture was stirred at 85° C. for 12 h. The mixture was poured to water (100 mL) and extracted with EtOAc (50 mL×2). The combined organic layers were washed with brine (30 mL×4), dried over anhydrous $Na_2SO_4$ and concentrated to give a residue. The residue was purified by column chromatography to give 2-((benzyloxy)methyl)-4-(tert-butoxy)-6-fluoro-1H-benzo[d] imidazole (I-294) (2.6 g) as a brown solid. LCMS m/z 329.0 $(M+1)^+$.

To a solution of 2-((benzyloxy)methyl)-4-(tert-butoxy)-6-fluoro-1H-benzo[d]imidazole (1.3 g, 3.96 mmol) in DMF (20 mL) was added NaH (237 mg, 5.94 mmol, 60% purity). After stirring at 25° C. for 0.5 h, SEM-Cl (726 mg, 4.35 mmol) was added into the above mixture at 0° C. The mixture was stirred at 25° C. for 12 h. The resulting solution was poured into water (100 mL) and extracted with EtOAc (80 mL×2). The combined organic layers were washed with brine (30 mL×4), dried over anhydrous $Na_2SO_4$ and concentrated to give a residue. The residue was purified by column chromatography to give 2-((benzyloxy)methyl)-4-(tert-butoxy)-6-fluoro-1-((2-(trimethylsilyl)ethoxy)methyl)-1H-benzo[d]imidazole (I-295) (2.7 g, 5.89 mmol, 74% yield) as a yellow oil. LCMS m/z 459.1 $(M+1)^+$.

To a solution of 2-((benzyloxy)methyl)-4-(tert-butoxy)-6-fluoro-1-((2-(trimethylsilyl) ethoxy)methyl)-1H-benzo[d] imidazole (2.7 g, 5.89 mmol) in MeOH (30 mL) was added $Pd(OH)_2/C$ (10%, 2 g) under $N_2$ atmosphere. The suspension was degassed and purged with $H_2$ for 3 times. The mixture was stirred under $H_2$ (45 psi) at 25° C. for 12 h. The mixture was filtered off and the filtrate was concentrated to give a residue. The residue was purified by column chromatography to give (4-(tert-butoxy)-6-fluoro-1-((2-(trimethylsilyl)

ethoxy) methyl)-1H-benzo[d] imidazol-2-yl)methanol (I-296) (1.5 g, 68% yield) as a yellow oil. LCMS m/z 369.1 $(M+1)^+$.

To a solution of (4-(tert-butoxy)-6-fluoro-1-((2-(trimethylsilyl)ethoxy)methyl)-1H-benzo[d]imidazol-2-yl)methanol (1.5 g, 4.07 mmol) in DCM (20 mL) were added DIPEA (1.58 g, 12.2 mmol) and MsCl (699 mg, 6.11 mmol) at 0° C. The mixture was stirred at 25° C. for 1 h. The resulting solution was diluted with DCM (50 mL) and washed with brine (30 mL). The organic layer was dried over anhydrous $Na_2SO_4$ and concentrated to give (4-(tert-butoxy)-6-fluoro-1-((2-(trimethylsilyl)ethoxy)methyl)-1H-benzo[d] imidazol-2-yl)methyl methanesulfonate (I-297) (1.9 g) as a yellow oil.

To a solution of (4-(tert-butoxy)-6-fluoro-1-((2-(trimethylsilyl)ethoxy)methyl)-1H-benzo[d]imidazol-2-yl)methyl methanesulfonate (1.9 g, 4.25 mmol) and 3-nitropyridin-2(1H)-one (893 mg, 6.38 mmol) in $CH_3CN$ (2 mL) was added DIPEA (1.65 g, 12.8 mmol). The mixture was stirred at 30° C. for 16 h. The mixture was concentrated to give a residue. The residue was purified by column chromatography to give 1-((4-(tert-butoxy)-6-fluoro-1-((2-(trimethylsilyl)ethoxy) methyl)-1H-benzo[d]imidazol-2-yl)methyl)-3-nitropyridin-2(1H)-one (I-298) (1.5 g, 67% yield) as a yellow oil. LCMS m/z 491.3 $(M+1)^+$.

To a solution of 1-((4-(tert-butoxy)-6-fluoro-1-((2-(trimethylsilyl)ethoxy)methyl)-1H-benzo[d]imidazol-2-yl) methyl)-3-nitropyridin-2(1H)-one (1.5 g, 3.06 mmol) in MeOH (20 mL) was added Pd/C (10%, 200 mg) under $N_2$ atmosphere. The suspension was degassed and purged with $H_2$ for 3 times. The mixture was stirred under $H_2$ (15 psi) atmosphere at 20° C. for 1 h. The mixture was filtered off and the filtrate was concentrated to give 3-amino-1-((4-(tert-butoxy)-6-fluoro-1-((2-(trimethylsilyl)ethoxy) methyl)-1H-benzo[d]imidazol-2-yl)methyl)pyridin-2(1H)-one (I-299) (1.2 g) as a yellow oil. LCMS m/z 461.1 $(M+1)^+$.

To a solution of 3-amino-1-((4-(tert-butoxy)-6-fluoro-1-((2-(trimethylsilyl)ethoxy) methyl)-1H-benzo[d]imidazol-2-yl)methyl)pyridin-2(1H)-one (1.2 g, 2.61 mmol) in TBAF (1 M, 10 mL) was added ethane-1,2-diamine (470 mg, 7.82 mmol). The mixture was stirred at 80° C. for 4 h. The reaction mixture was concentrated to give a residue. The residue was purified by column chromatography to give 3-amino-1-((4-(tert-butoxy)-6-fluoro-1H-benzo[d]imidazol-2-yl)methyl)pyridin-2(1H)-one (I-300) (220 mg, 24% yield) as a brown oil. LCMS m/z 331.1 $(M+1)^+$.

Example 31

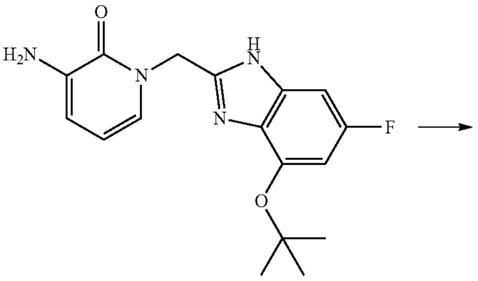

I-300

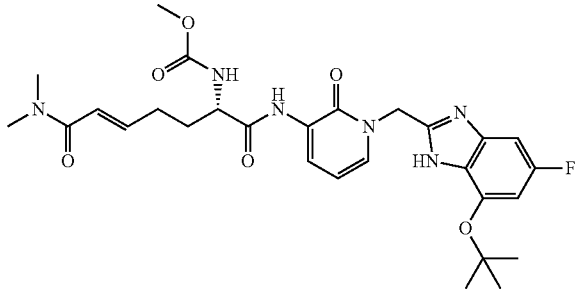

171

To a solution of 3-amino-1-((4-(tert-butoxy)-6-fluoro-1H-benzo[d]imidazol-2-yl) methyl)pyridin-2(1H)-one (60 mg, 182 μmol) and (S,E)-7-(dimethylamino)-2-((methoxycarbonyl)amino)-7-oxohept-5-enoic acid (70 mg, 272 μmol) in DMF (1 mL) were added HATU (117 mg, 309 μmol) and DIEA (117 mg, 908 μmol) at 0° C. The mixture was stirred at 30° C. for 12 h. The mixture was poured into water (10 mL) and extracted with EtOAc (15 mL×2). The organic layers were washed with brine (10 mL×3), dried over anhydrous $Na_2SO_4$, filtered and concentrated to give a residue. The residue was purified by prep-HPLC to give (S,E)-methyl (1-((1-((7-(tert-butoxy)-5-fluoro-1H-benzo[d] imidazol-2-yl)methyl)-2-oxo-1,2-dihydropyridin-3-yl) amino)-7-(dimethylamino)-1,7-dioxohept-5-en-2-yl)carbamate (Compound 171) (19 mg, 18% yield) as a yellow solid. LCMS m/z 571.3 $(M+1)^+$. $^1H$ NMR (400 MHz, DMSO-$d_6$) δ9.26-9.25 (m, 1H), 8.25-8.24 (m, 1H), 7.73-7.72 (m, 1H), 7.56-7.53 (m, 1H), 7.05 (dd, J=9.2, 2.0 Hz, 1H), 6.94 (dd, J=8.4, 2.0 Hz, 1H), 6.74-6.56 (m, 2H), 6.39-6.33 (m, 2H), 5.38-5.35 (m, 1H), 4.17-4.16 (m, 1H), 3.54 (s, 3H), 2.98 (m, 3H), 2.83 (s, 3H), 2.24-2.21 (m, 2H), 1.41-1.35 (m, 9H).

The following compound was prepared according to the procedures described in Example 31 using the appropriate intermediates.

| Compound | Structure | LCMS Data |
| --- | --- | --- |
| 172 | 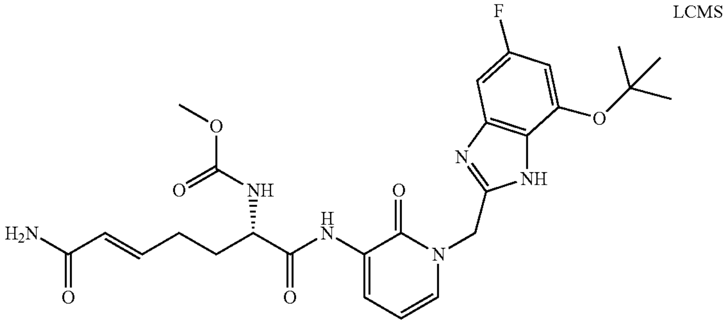 | LCMS m/z 543.2 (M + 1)$^+$ |

The Synthesis of Intermediate I-306

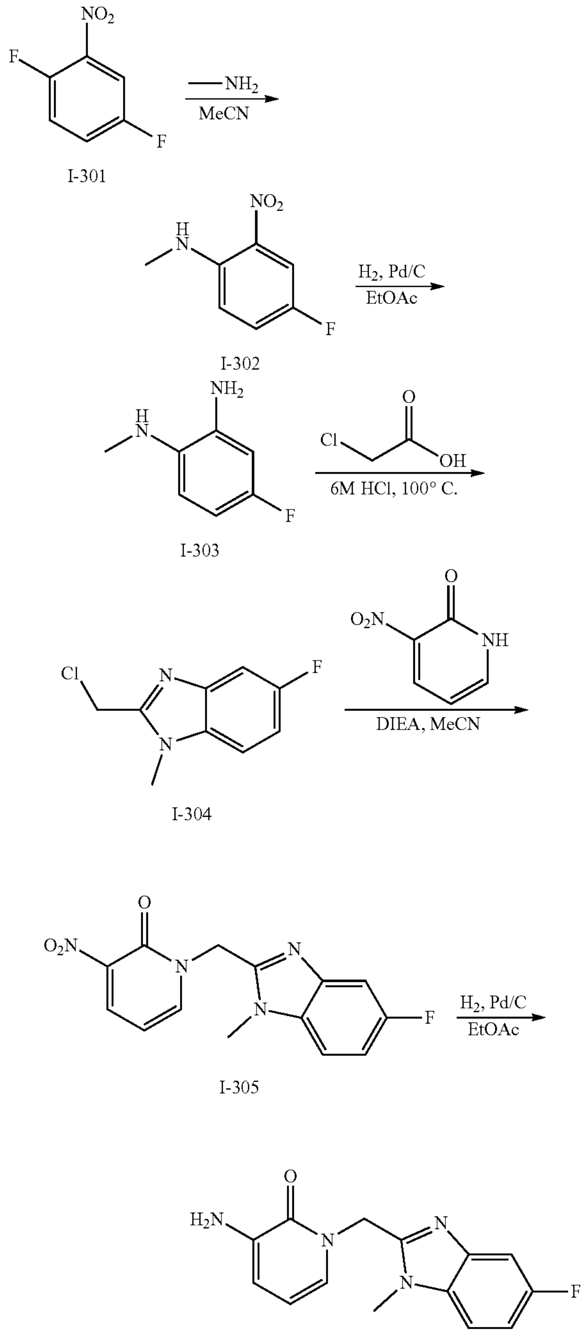

I-301

I-302

I-303

I-304

I-305

I-306

To a mixture of 1,4-difluoro-2-nitro-benzene (0.5 g, 3.14 mmol, 340.14 uL, 1 eq) and methanamine (2 M, 6.29 mL, 4 eq) in $CH_3CN$ (10 mL) at 25° C. The mixture was stirred at 25° C. for 2 hours. The reaction mixture was concentrated to give 4-fluoro-N-methyl-2-nitro-aniline (I-302) (1.33 g) as an orange solid which was used directly.

To a solution of 4-fluoro-N-methyl-2-nitro-aniline (1.28 g, 7.52 mmol, 1 eq) in EA (10 mL) was added Pd/C (1 g, 10% purity). The suspension was degassed under vacuum and purged with $H_2$ several times. The mixture was stirred under $H_2$ (15 psi) at 25° C. for 30 min. The reaction mixture was filtered and concentrated under reduced pressure to give 4-fluoro-N1-methyl-benzene-1, 2-diamine (I-303) (750 mg) as a brown oil which was used directly.

To a mixture of 4-fluoro-N1-methyl-benzene-1,2-diamine (700 mg, 4.99 mmol, 1 eq) and 2-chloroacetic acid (707.93 mg, 7.49 mmol, 842.77 uL, 1.5 eq) in HCl (5.5 mL) (6M) and $H_2O$ (5.5 mL) in one portion at 25° C. The mixture was stirred at 100° C. for 12 hours. The reaction mixture was quenched by addition water 30 mL and extracted with EtOAc 30 mL (15 mL×2). The combined organic layers were washed with sat. $NaHCO_3$ (100 mL), The combined organic layers were washed with brine 30 mL (15 mL×2), then dried over anhydrous $Na_2SO_4$, filtered and concentrated under reduced pressure to give 2-(chloromethyl)-5-fluoro-1-methyl-benzimidazole (I-304) (1 g) as a yellow solid. $^1H$ NMR (400 MHz, $CDCl_3$) δ 7.42 (dd, J=2.3, 9.2 Hz, 1H), 7.32-7.27 (m, 1H), 7.10 (dt, J=2.3, 9.1 Hz, 1H), 4.83 (s, 2H), 3.87 (s, 3H).

To a solution of 3-nitro-1H-pyridin-2-one (193.97 mg, 1.38 mmol, 1.1 eq) in MeCN (5 mL) was added DIEA (325.34 mg, 2.52 mmol, 438.47 uL, 2 eq) at 0° C. 2-(chloromethyl)-5-fluoro-1-methyl-benzimidazole (250 mg, 1.26 mmol, 1 eq) in MeCN (5 mL) was then dropped in the solution at 0° C. The mixture was stirred at 0° C. for 30 min, then heated to 25° C. and stirred for 12 hour. The reaction mixture was quenched by addition water (10 mL) at 25° C., and then diluted with ethyl acetate (10 mL) and extracted with ethyl acetate (10 mL×2). The combined organic layers were washed with brine (5 mL×2), dried over anhydrous $Na_2SO_4$, filtered and concentrated under reduced pressure to give a residue. The residue was purified by prep-TLC to give 1-[(5-fluoro-1-methyl-benzimidazol-2-yl)methyl]-3-nitro-pyridin-2-one (I-305) (187 mg) as a yellow solid which was used directly. $^1H$ NMR (400 MHz, $CDCl_3$) δ 8.30 (dd, J=2.1, 7.6 Hz, 1H), 8.14 (dd, J=2.1, 6.7 Hz, 1H), 7.31 (dd, J=2.3, 9.2 Hz, 1H), 7.23 (dd, J=4.5, 8.9 Hz, 1H), 7.19 (s, 2H), 7.03 (dt, J=2.4, 9.2 Hz, 1H), 6.35 (t, J=7.3 Hz, 1H), 5.42 (s, 2H), 3.94 (s, 3H), 1.53 (br s, 9H).

To a solution of 1-[(5-fluoro-1-methyl-benzimidazol-2-yl)methyl]-3-nitro-pyridin-2-one (167 mg, 552.50 umol, 1 eq) in EA (5 mL) was added Pd/C (0.3 g, 10% purity). The suspension was degassed under vacuum and purged with $H_2$ several times. The mixture was stirred under H2 (15 psi) at 25° C. for 15 min. The reaction mixture was filtered and concentrated under reduced pressure to give 3-amino-1-[(5-fluoro-1-methyl-benzimidazol-2-yl)methyl]pyridin-2-one (I-306) (120 mg) as a yellow oil, which was used directly.

The following intermediates were prepared according to the procedures described in I-306 using the appropriate reagents.

| Compound | Structure | LCMS Data |
|---|---|---|
| I-307 | 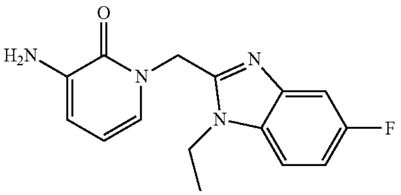 [SMILES: CCn1c(Cn2cccc(N)c2=O)nc2cc(F)ccc21] | LCMS m/z 287.1 (M + 1)$^+$. |
| I-308 | 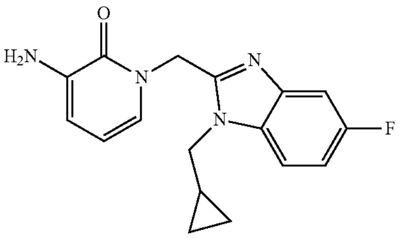 [SMILES: Nc1cccn(Cc2nc3cc(F)ccc3n2CC2CC2)c1=O] | LCMS m/z 313.4 (M + 1)$^+$. |
| I-309 | 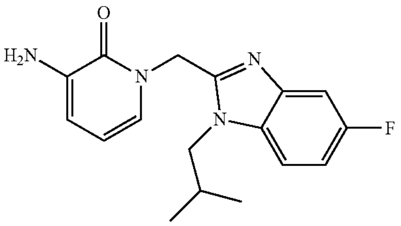 [SMILES: CC(C)Cn1c(Cn2cccc(N)c2=O)nc2cc(F)ccc21] | LCMS m/z 315.4 (M + 1)$^+$. |
| I-310 | 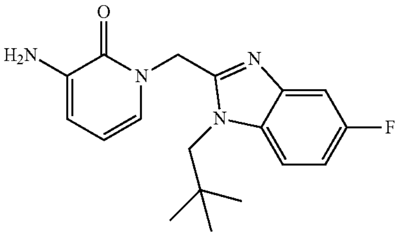 [SMILES: CC(C)(C)Cn1c(Cn2cccc(N)c2=O)nc2cc(F)ccc21] | LCMS m/z 329.3 (M + 1)$^+$. |
| I-311 | 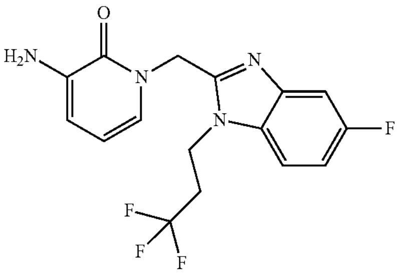 [SMILES: Nc1cccn(Cc2nc3cc(F)ccc3n2CCC(F)(F)F)c1=O] | LCMS m/z 355.2 (M + 1)$^+$. |
| I-312 | 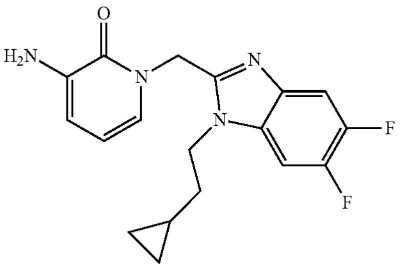 [SMILES: Nc1cccn(Cc2nc3cc(F)c(F)cc3n2CCC2CC2)c1=O] | LCMS m/z 345.2 (M + 1)$^+$. |

-continued

| Compound | Structure | LCMS Data |
| --- | --- | --- |
| I-313 | 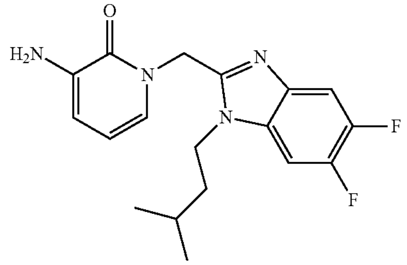 [SMILES: CC(C)CCn1c(Cn2cccc(N)c2=O)nc2cc(F)c(F)cc21] | LCMS m/z 347.2 (M + 1)$^+$. |
| I-526 | 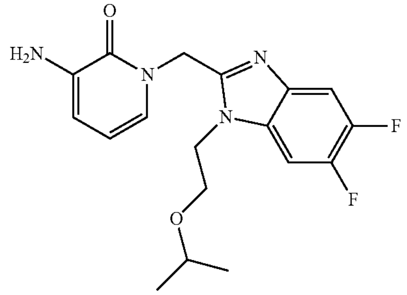 [SMILES: CC(C)OCCn1c(Cn2cccc(N)c2=O)nc2cc(F)c(F)cc21] | LCMS m/z 363.2 (M + 1)$^+$. |

The Synthesis of Intermediate I-314

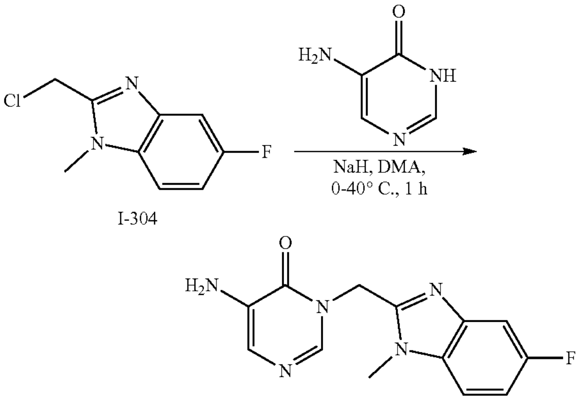

I-304

I-314

A mixture of 5-amino-1H-pyrimidin-6-one (234.93 mg, 2.11 mmol) in DMA (4 mL), then was added NaH (176.19 mg, 4.41 mmol, 60% purity) at 0° C. and the mixture was stirred at 25° C. for 15 min. Then was added 2-(chloromethyl)-5-fluoro-1-methyl-benzimidazole (350 mg, 1.76 mmol) at 0° C. and the mixture was stirred at 40° C. for 45 min. The reaction mixture was diluted with sat. $NH_4Cl$ solution (10 mL) and extracted with EtOAc (15 mL×2). The combined organic phase were washed with brine (15 mL), dried over anhydrous $Na_2SO_4$, filtered and concentrated under reduced pressure The residue was diluted with EtOAc 3 mL and filtered to give 5-amino-3-[(5-fluoro-1-methyl-benzimidazol-2-yl)methyl]pyrimidin-4-one (I-314) (320 mg) as a gray solid.

The following intermediates were prepared according to the procedures described in I-314 using the appropriate reagents.

| Compound | Structure | LCMS Data |
| --- | --- | --- |
| I-315 | 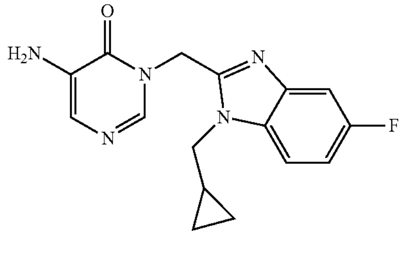 [SMILES: Nc1cncn(Cc2nc3cc(F)ccc3n2CC2CC2)c1=O] | LCMS m/z 314.2 (M + 1)$^+$. |

-continued
| Compound | Structure | LCMS Data |
| --- | --- | --- |
| I-316 | 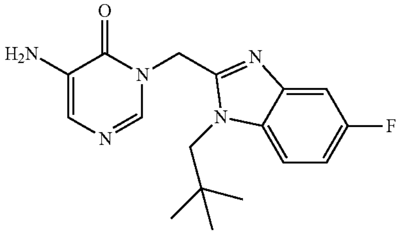 [SMILES: CC(C)(C)Cn1c(Cn2cncc(N)c2=O)nc2cc(F)ccc21] | LCMS m/z 330.2 (M + 1)+. |
| I-317 | 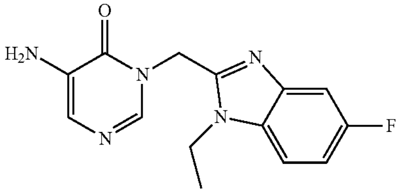 [SMILES: CCn1c(Cn2cncc(N)c2=O)nc2cc(F)ccc21] | LCMS m/z 288.2 (M + 1)+. |
| I-318 | 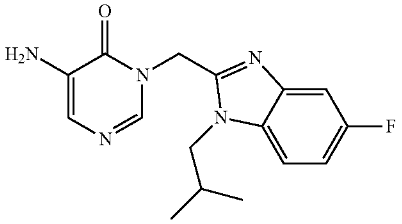 [SMILES: CC(C)Cn1c(Cn2cncc(N)c2=O)nc2cc(F)ccc21] | LCMS m/z 316.1 (M + 1)+. |
| I-319 | 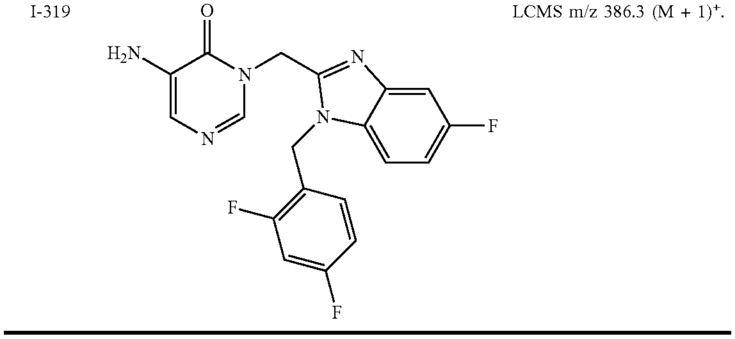 | LCMS m/z 386.3 (M + 1)+. |
Example 32
Method 1:
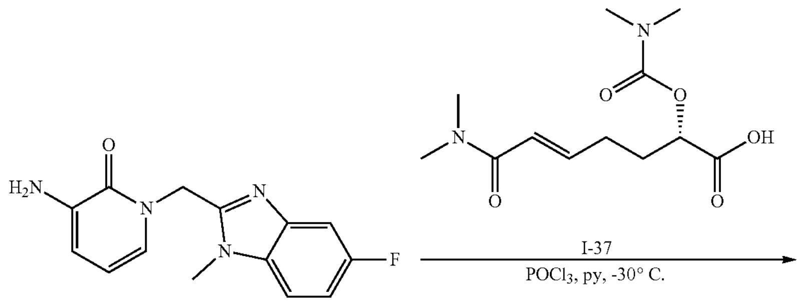
I-306

-continued

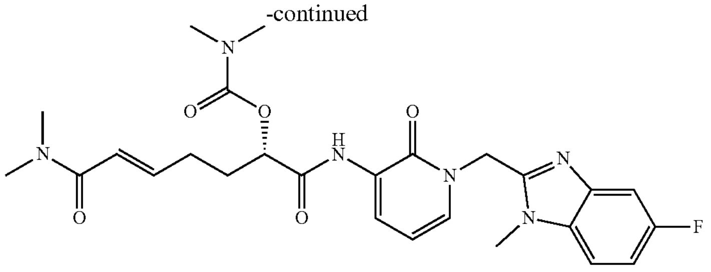

173

To a mixture of (E,2S)-7-(dimethylamino)-2-(dimethylcarbamoyloxy)-7-oxo-hept-5-enoic acid (180.01 mg, 661.10 umol, 1.5 eq) and 3-amino-1-[(5-fluoro-1-methyl-benzimidazol-2-yl)methyl]pyridin-2-one (120 mg, 440.73 umol, 1 eq) in pyridine (1 mL) was added $POCl_3$ (135.15 mg, 881.46 umol, 81.91 uL, 2 eq) in one portion at −30° C. The mixture was stirred at −30° C. for 15 min. The reaction mixture was quenched by water 5 mL at 0° C., and then diluted with water 10 mL and extracted with EtOAc (10 mL×3). The combined organic layers were washed with brine (5 mL×2), dried over $Na_2SO_4$, filtered and concentrated under reduced pressure to give a residue. The residue was purified by prep-TLC and prep-HPLC to give [(E,1S)-6-(dimethylamino)-1-[[1-[(5-fluoro-1-methyl-benzimidazol-2-yl)methyl]-2-oxo-3-pyridyl]carbamoyl]-6-oxo-hex-4-enyl] N,N-dimethylcarbamate (Compound 173) (11.8 mg, 5% yield) as a white solid. LCMS m/z 527.2 $(M+1)^+$.

Method 2:

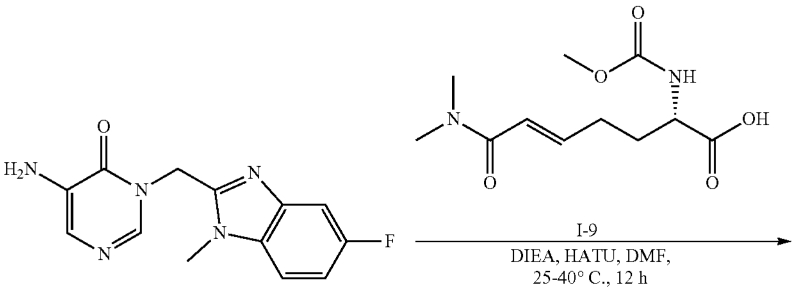

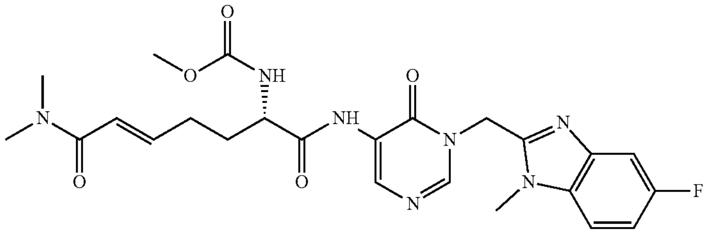

174

To a mixture of (E,2S)-7-(dimethylamino)-2-(methoxycarbonylamino)-7-oxo-hept-5-enoic acid (129.01 mg, 499.51 umol), 5-amino-3-[(5-fluoro-1-methyl-benzimidazol-2-yl)methyl]pyrimidin-4-one (130 mg, 475.73 umol) in DMF (2 mL) was added HATU (325.60 mg, 856.31 umol) and DIEA (92.22 mg, 713.59 umol, 124.29 uL) at 25° C. The mixture was stirred at 40° C. for 12 hr. The reaction mixture was diluted with sat. $NH_4Cl$ aq. (10 mL) and extracted with EtOAc (6 mL×2). The combined organic phase was washed with brine (10 mL), dried over anhydrous $Na_2SO_4$, filtered and concentrated. The residue was purified by prep-HPLC to give methyl N-[(E,1S)-6-(dimethylamino)-1-[[1-[(5-fluoro-1-methyl-benzimidazol-2-yl) methyl]-6-oxo-pyrimidin-5-yl]carbamoyl]-6-oxo-hex-4-enyl]carbamate (Compound 174) (37.9 mg, 15% yield) as a white solid. LCMS m/z 514.2 $(M+1)^+$. $^1H$ NMR (400 MHz, DMSO-$d_6$) δ 9.43 (s, 1H) 8.76 (s, 1H) 8.42 (s, 1H) 7.63 (br d, J=7.58 Hz, 1H) 7.53 (dd, J=8.93, 4.65 Hz, 1H) 7.43 (dd, J=9.66, 2.32 Hz, 1H) 7.28-7.35 (m, 2H) 7.15-7.22 (m, 2H) 7.10 (td, J=9.26, 2.26 Hz, 1H) 6.57-6.67 (m, 1H) 6.37 (d, J=15.04 Hz, 1H) 5.65 (s, 2H) 5.53 (s, 2H) 4.29 (br d, J=3.67 Hz, 1H) 3.54 (s, 3H) 2.99 (s, 3H) 2.84 (s, 3H) 2.20-2.29 (m, 2H) 1.66-1.89 (m, 2H).

The following compounds were prepared according to the procedures described for method 1 of Example 32 by using the appropriate intermediates.

| Compound | Structure | LCMS Data |
| --- | --- | --- |
| 175 | 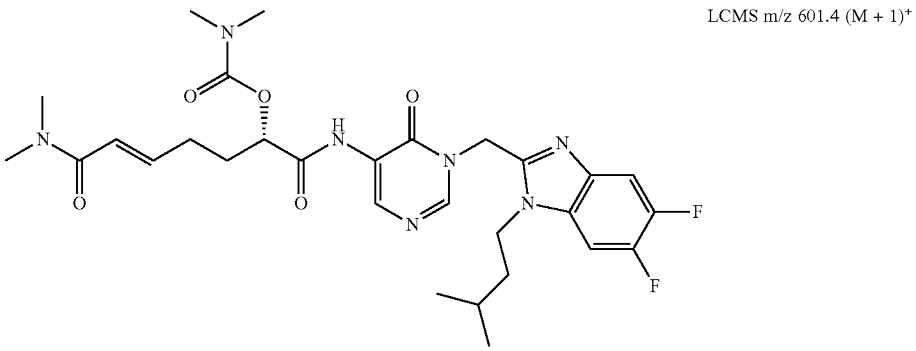 | LCMS m/z 601.4 (M + 1)+ |
| 176 | 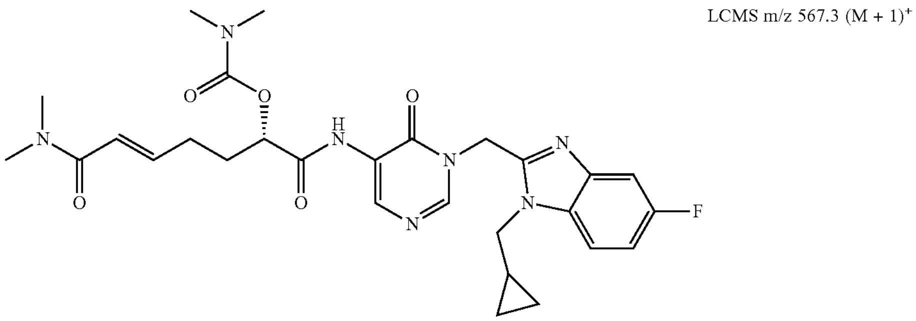 | LCMS m/z 567.3 (M + 1)+ |
| 177 | 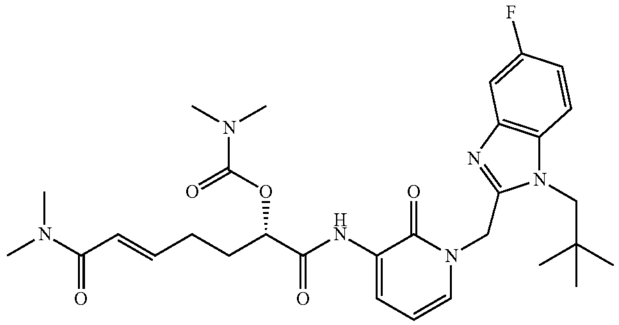 [SMILES: CN(C)C(=O)/C=C/CC[C@H](OC(=O)N(C)C)C(=O)Nc1cccn(Cc2nc3cc(F)ccc3n2CC(C)(C)C)c1=O] | LCMS m/z 583.4 (M + 1)+ |
| 178 | 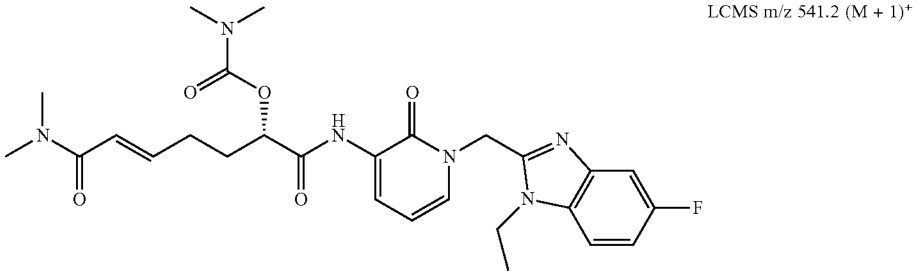 | LCMS m/z 541.2 (M + 1)+ |
| 179 | 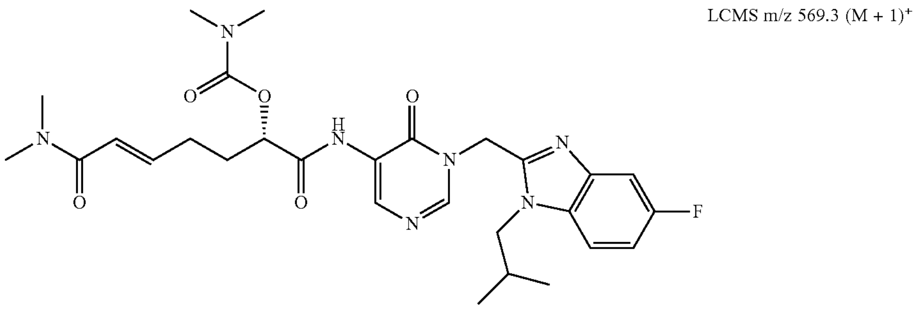 | LCMS m/z 569.3 (M + 1)+ |

-continued
| Compound | Structure | LCMS Data |
| --- | --- | --- |
| 180 | 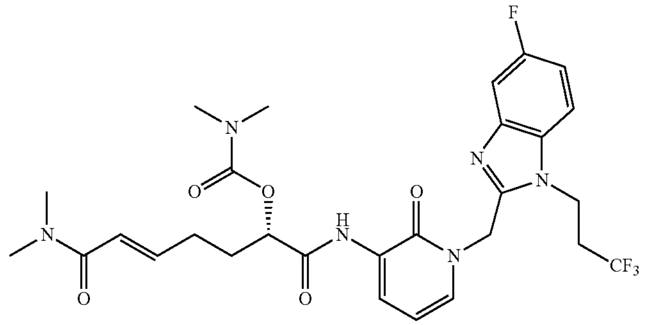 [SMILES: CN(C)C(=O)/C=C/CC[C@H](OC(=O)N(C)C)C(=O)Nc1cccn(Cc2nc3cc(F)ccc3n2CCC(F)(F)F)c1=O] | LCMS m/z 609.2 (M + 1)$^+$ |
| 181 | 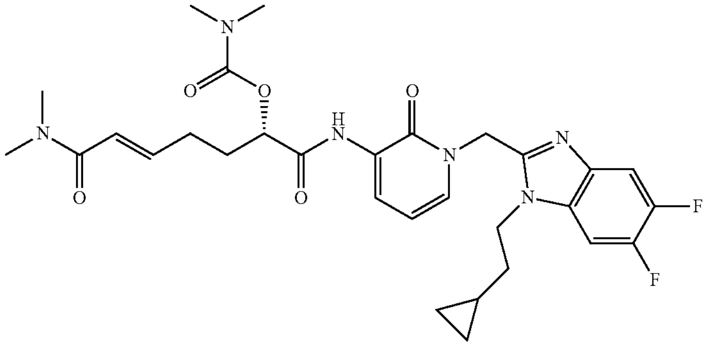 [SMILES: CN(C)C(=O)/C=C/CC[C@H](OC(=O)N(C)C)C(=O)Nc1cccn(Cc2nc3cc(F)c(F)cc3n2CCC2CC2)c1=O] | LCMS m/z 599.4 (M + 1)$^+$ |
| 182 | 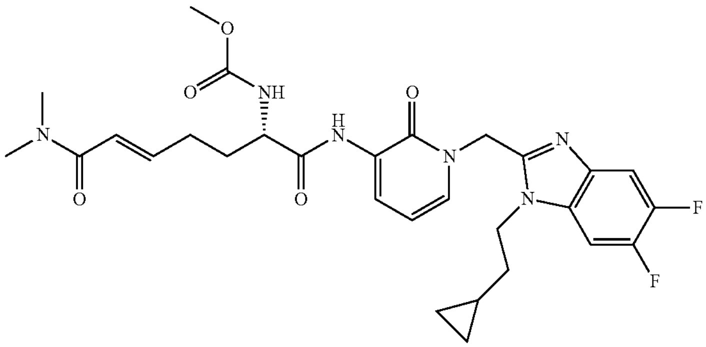 [SMILES: COC(=O)N[C@@H](CC/C=C/C(=O)N(C)C)C(=O)Nc1cccn(Cc2nc3cc(F)c(F)cc3n2CCC2CC2)c1=O] | LCMS m/z 585.4 (M + 1)$^+$ |
| 183 | 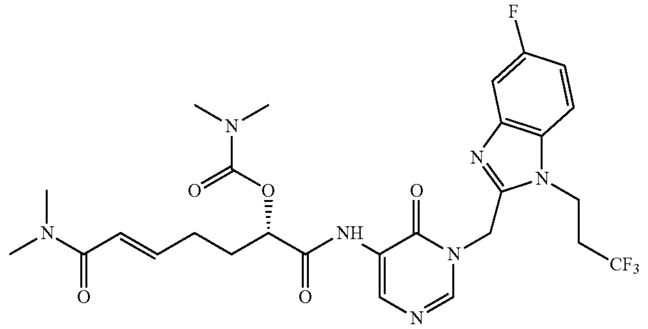 [SMILES: CN(C)C(=O)/C=C/CC[C@H](OC(=O)N(C)C)C(=O)Nc1cncn(Cc2nc3cc(F)ccc3n2CCC(F)(F)F)c1=O] | LCMS m/z 610.2 (M + 1)$^+$ |

-continued
| Compound | Structure | LCMS Data |
| --- | --- | --- |
| 184 | 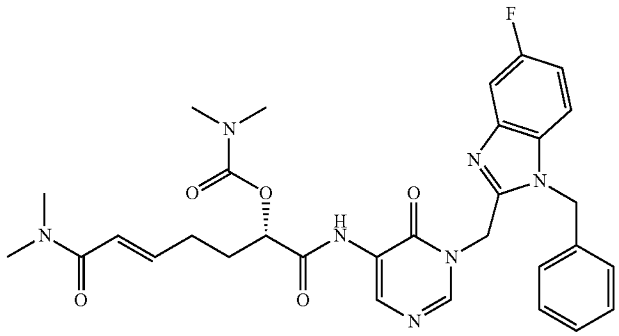 [SMILES: CN(C)C(=O)/C=C/CC[C@H](OC(=O)N(C)C)C(=O)Nc1cncn(Cc2nc3cc(F)ccc3n2Cc2ccccc2)c1=O] | LCMS m/z 604.2 (M + 1)+ |
| 185 | 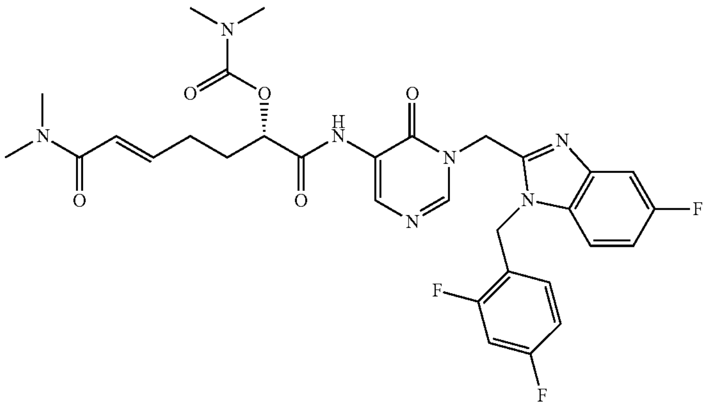 [SMILES: CN(C)C(=O)/C=C/CC[C@H](OC(=O)N(C)C)C(=O)Nc1cncn(Cc2nc3cc(F)ccc3n2Cc2ccc(F)cc2F)c1=O] | LCMS m/z 640.1 (M + 1)+ |
| 186 | 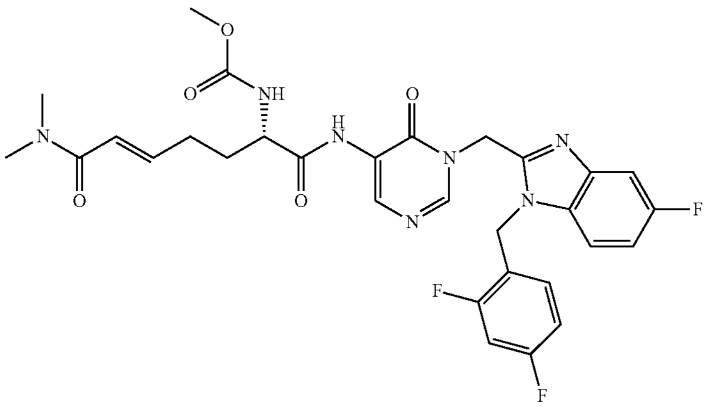 [SMILES: COC(=O)N[C@@H](CC/C=C/C(=O)N(C)C)C(=O)Nc1cncn(Cc2nc3cc(F)ccc3n2Cc2ccc(F)cc2F)c1=O] | LCMS m/z 626.3 (M + 1)+ |
| 187 | 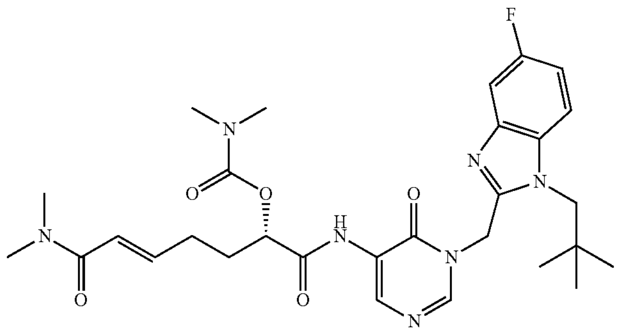 [SMILES: CN(C)C(=O)/C=C/CC[C@H](OC(=O)N(C)C)C(=O)Nc1cncn(Cc2nc3cc(F)ccc3n2CC(C)(C)C)c1=O] | LCMS m/z 584.3 (M + 1)+ |

-continued
| Compound | Structure | LCMS Data |
| --- | --- | --- |
| 393 | 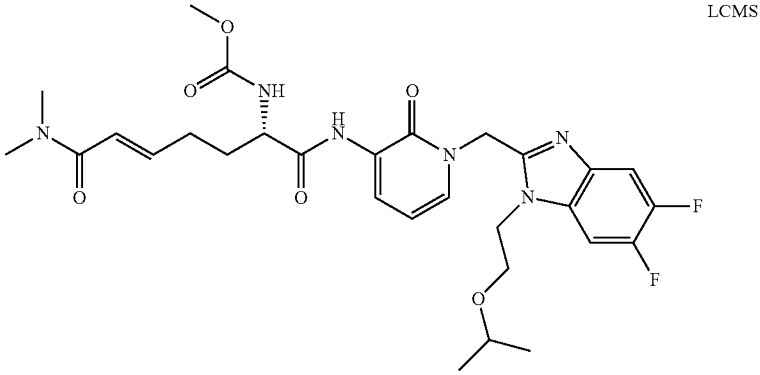 | LCMS m/z 603.2 (M + 1)$^+$ |
The following targets were prepared according to the procedures described for the method 2 of Example 3 by using the appropriate intermediates.
| Compound | Structure | LCMS Data |
| --- | --- | --- |
| 188 | 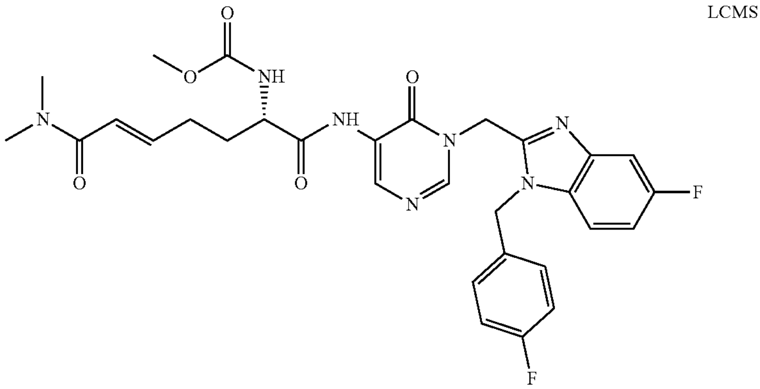 | LCMS m/z 608.1 (M + 1)$^+$ |
| 189 | 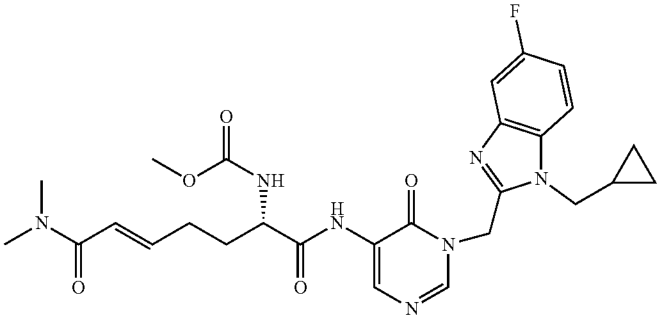 [SMILES: COC(=O)N[C@@H](CC/C=C/C(=O)N(C)C)C(=O)Nc1cncn(Cc2nc3cc(F)ccc3n2CC2CC2)c1=O] | LCMS m/z 554.3 (M + 1)$^+$ |
| 190 | 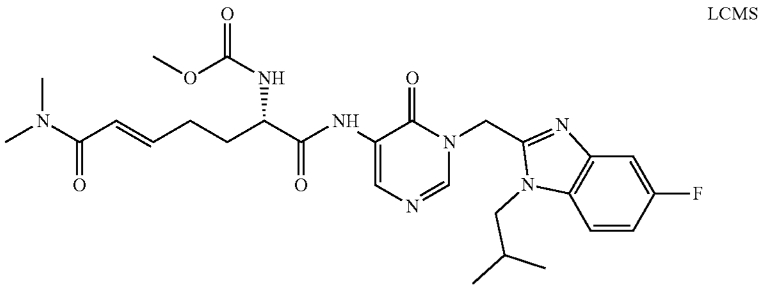 | LCMS m/z 556.4 (M + 1)$^+$ |

-continued
| Compound | Structure | LCMS Data |
| --- | --- | --- |
| 191 | 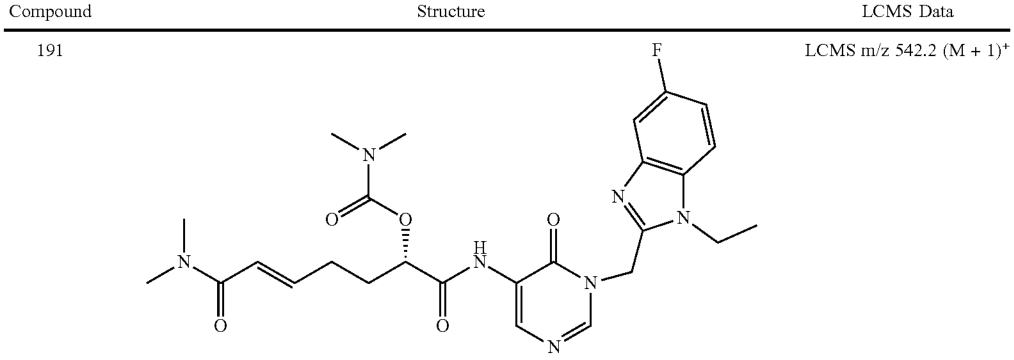 | LCMS m/z 542.2 $(M + 1)^+$ |
| 192 | 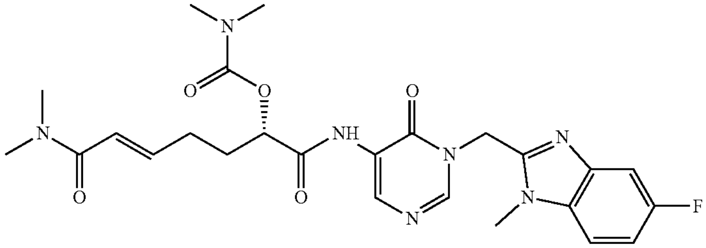 [SMILES: CN(C)C(=O)/C=C/CC[C@H](OC(=O)N(C)C)C(=O)Nc1cncn(Cc2nc3cc(F)ccc3n2C)c1=O] | LCMS m/z 528.4 $(M + 1)^+$ |
Example 33
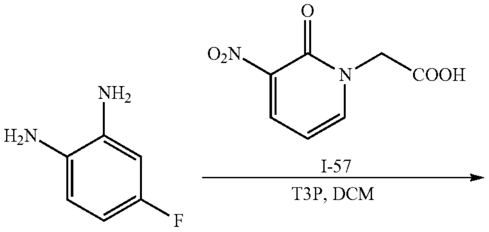
I-320
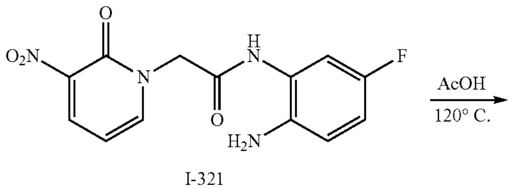
I-321
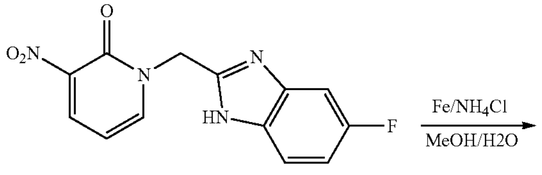
I-322

-continued

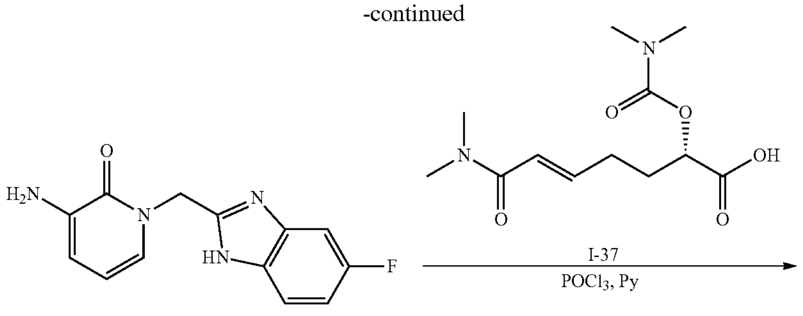

I-323

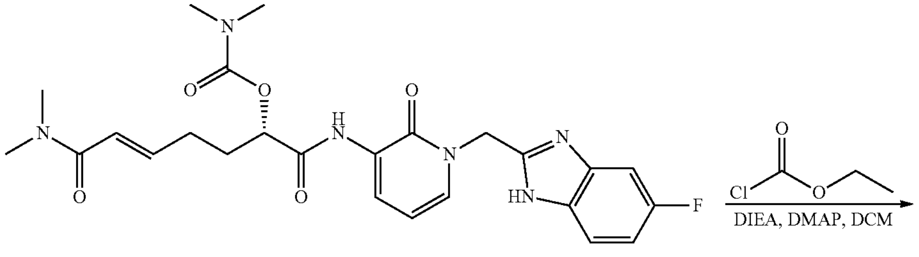

I-324

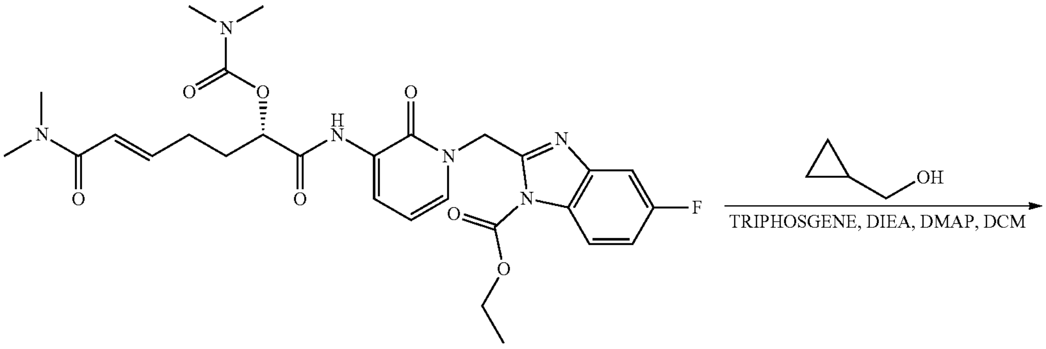

193

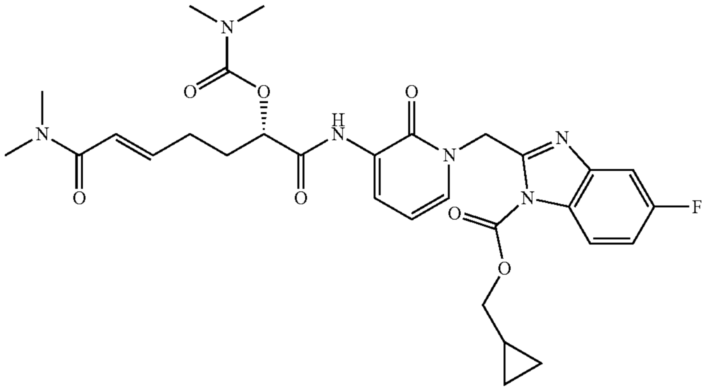

194

To a mixture of 4-fluorobenzene-1,2-diamine (5 g, 39.64 mmol, 1 eq), DIPEA (10.25 g, 79.28 mmol, 13.81 mL, 2 eq) and 2-(3-nitro-2-oxo-1-pyridyl)acetic acid (7.85 g, 39.64 mmol, 1 eq) in DCM (50 mL) was added $T_3P$ (37.84 g, 59.46 mmol, 35.36 mL, 50% purity, 1.5 eq) dropwise at 25° C. under $N_2$. The mixture was stirred at 25° C. for 16 hr. The reaction mixture was filtered. The cake was washed by $H_2O$ and the cake was concentrated under reduced pressure to give N-(2-amino-5-fluoro-phenyl)-2-(3-nitro-2-oxo-1-pyridyl)acetamide (I-321) (12.9 g) as a purple solid. LCMS m/z 307.0 $(M+1)^+$.

A mixture of N-(2-amino-5-fluoro-phenyl)-2-(3-nitro-2-oxo-1-pyridyl)acetamide (12.9 g, 42.12 mmol, 1 eq) in AcOH (160 mL) was heated to 120° C. and stirred for 3 hours. The reaction mixture was cooled to 25° C. The mixture was filtered and the cake concentrated under reduced pressure to give 1-[(5-fluoro-1H-benzimidazol-2- yl)methyl]-3-nitro-pyridin-2-one (I-322) (8.18 g) as a white solid. LCMS m/z 289.1 $(M+1)^+$.

A mixture of 1-[(5-fluoro-1H-benzimidazol-2-yl)methyl]-3-nitro-pyridin-2-one (1 g, 3.47 mmol, 1 eq), Fe (968.83 mg, 17.35 mmol, 5 eq) and $NH_4Cl$ (1.86 g, 34.69 mmol, 1.21 mL, 10 eq) in MeOH (15 mL) and $H_2O$ (3 mL) was heated to 80° C. and stirred for 1 hr. The reaction mixture was filtered, and then diluted with $H_2O$ 10 mL, and extracted with EtOAc 200 mL (50 mL×4). The combined organic layers were washed with brine 150 mL, dried over $Na_2SO_4$, filtered and concentrated under reduced pressure to give 3-amino-1-[(5-fluoro-1H-benzimidazol-2-yl)methyl]pyridin-2-one (I-323) (0.735 g) as a brown solid. LCMS m/z 259.3 $(M+1)^+$.

To a mixture of 3-amino-1-[(5-fluoro-1H-benzimidazol-2-yl)methyl]pyridin-2-one (0.355 g, 1.37 mmol, 1 eq) and (E,2S)-7-(dimethylamino)-2-(dimethylcarbamoyloxy)-7-oxo-hept-5-enoic acid (411.74 mg, 1.51 mmol, 1.1 eq) in Py (6 mL) was added $POCl_3$ (210.77 mg, 1.37 mmol, 127.74 uL, 1 eq) dropwise at −30° C. under $N_2$. The mixture was stirred at −30° C. for 10 mins. The reaction mixture was quenched by addition $H_2O$ 0.5 mL. The reaction mixture was concentrated and purified by prep-TLC to give [(E,1S)-6-(dimethylamino)-1-[[1-[(5-fluoro-1H-benzimidazol-2-yl)methyl]-2-oxo-3-pyridyl]carbamoyl]-6-oxo-hex-4-enyl]N,N-dimethylcarbamate (I-324) (270 mg, 38% yield) as a yellow solid.

To a mixture of [(E,1S)-6-(dimethylamino)-1-[[1-[(5-fluoro-1H-benzimidazol-2-yl) methyl]-2-oxo-3-pyridyl]carbamoyl]-6-oxo-hex-4-enyl] N,N-dimethylcarbamate (0.09 g, 175.60 umol, 1 eq), DIEA (34.04 mg, 263.40 umol, 45.88 uL, 1.5 eq), and ethyl carbonochloridate (22.87 mg, 210.72 umol, 20.06 uL, 1.2 eq) in DCM (2 mL) was added DMAP (214.53 ug, 1.76 umol, 0.01 eq) in one portion at 0° C. under $N_2$. The mixture was stirred at 30° C. for 1 hour. The reaction mixture was concentrated and purified by prep-HPLC (neutral condition) to give ethyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-benzimidazole-1-carboxylate (Compound 193) (6.4 mg, 5% yield) as a light yellow solid. $^1H$ NMR (400 MHz, DMSO-$d_6$) δ 9.35-9.26 (m, 1H), 8.32-8.22 (m, 1H), 7.78-7.63 (m, 1H), 7.61-7.48 (m, 2H), 7.35-7.17 (m, 1H), 6.71-6.59 (m, 1H), 6.45-6.34 (m, 2H), 5.67 (br s, 2H), 5.10 (br s, 1H), 4.64-4.50 (m, 2H), 2.97 (br d, J=16.8 Hz, 6H), 2.83 (br d, J=10.1 Hz, 6H), 2.30 (br d, J=6.7 Hz, 2H), 1.96 (br d, J=6.7 Hz, 2H), 1.48 (br t, J=7.0 Hz, 3H). LCMS m/z 585.3 $(M+1)^+$.

To a mixture of cyclopropylmethanol (20.10 mg, 278.73 umol, 22.04 uL, 1 eq) and DIPEA (180.11 mg, 1.39 mmol, 242.74 uL, 5 eq) in DCM (2 mL) was added triphosgene (41.36 mg, 139.36 umol, 0.5 eq) in one portion at 0° C. under $N_2$. The mixture was stirred at 0° C. for 30 mins. Then DMAP (3.41 mg, 27.87 umol, 0.1 eq) and [(E,1S)-6-(dimethylamino)-1-[[1-[(5-fluoro-1H-benzimidazol-2-yl) methyl]-2-oxo-3-pyridyl]carbamoyl]-6-oxo-hex-4-enyl] N,N-dimethylcarbamate (0.1 g, 195.11 umol, 0.7 eq) were added into the mixture at 0° C. The reaction mixture was stirred at 0° C. for 30 mins. The reaction mixture was quenched by addition $H_2O$ (5 mL) at 0° C., and then extracted with EtOAc (15 mL×3). The combined organic layers were washed with brine (30 mL), dried over $Na_2SO_4$, filtered and concentrated under reduced pressure to give a residue. The residue was purified by prep-TLC to give cyclopropylmethyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-benzimidazole-1-carboxylate (Compound 194) (16.1 mg, 5% yield) as a white solid. LCMS m/z 611.4 $(M+1)^+$. $^1H$ NMR (400 MHz, DMSO-$d_6$) δ 9.45-9.31 (m, 1H), 8.34 (dd, J=1.5, 7.4 Hz, 1H), 8.11-7.94 (m, 1H), 7.87-7.69 (m, 1H), 7.63-7.54 (m, 1H), 7.41-7.23 (m, 1H), 6.78-6.65 (m, 1H), 6.54-6.38 (m, 2H), 5.79-5.68 (m, 2H), 5.16 (dd, J=4.8, 7.3 Hz, 1H), 4.45 (br d, J=7.6 Hz, 2H), 3.06-3.00 (m, 6H), 2.88 (br d, J=10.8 Hz, 6H), 2.79-2.66 (m, 1H), 2.42-2.33 (m, 2H), 1.46 (dt, J=4.5, 7.8 Hz, 1H), 0.81-0.67 (m, 2H), 0.62-0.45 (m, 2H).

The following compounds were prepared according to the procedures described in Example 33 using the appropriate intermediates.

| Compound | Structure | LCMS Data |
|---|---|---|
| 195 | 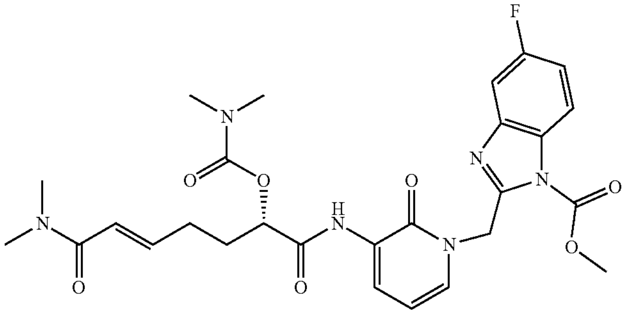 [SMILES: COC(=O)n1c(Cn2cccc(NC(=O)[C@H](CC/C=C/C(=O)N(C)C)OC(=O)N(C)C)c2=O)nc2cc(F)ccc21] | LCMS m/z 571.2 $(M + 1)^+$ |
| 196 | 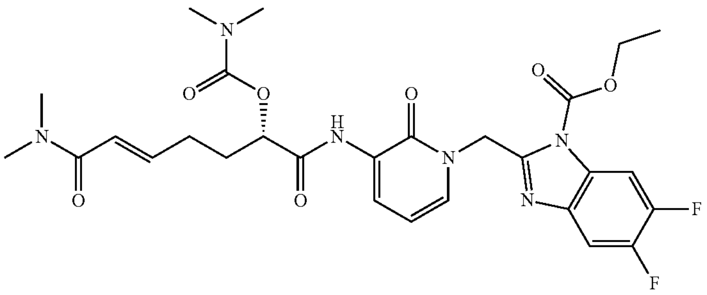 [SMILES: CCOC(=O)n1c(Cn2cccc(NC(=O)[C@H](CC/C=C/C(=O)N(C)C)OC(=O)N(C)C)c2=O)nc2cc(F)c(F)cc21] | LCMS m/z 603.3 $(M + 1)^+$ |

-continued
| Compound | Structure | LCMS Data |
| --- | --- | --- |
| 197 | 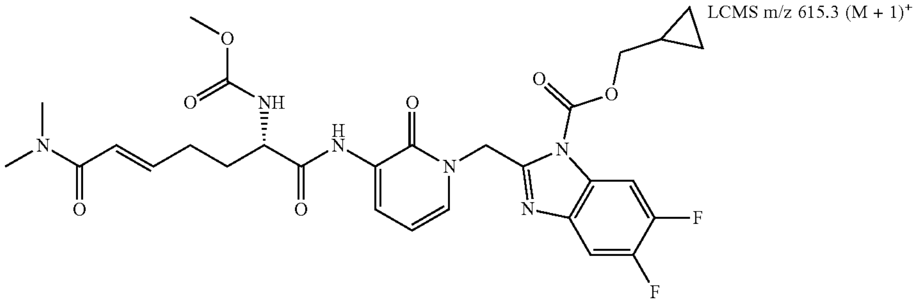 | LCMS m/z 615.3 $(M + 1)^+$ |
| 198 | 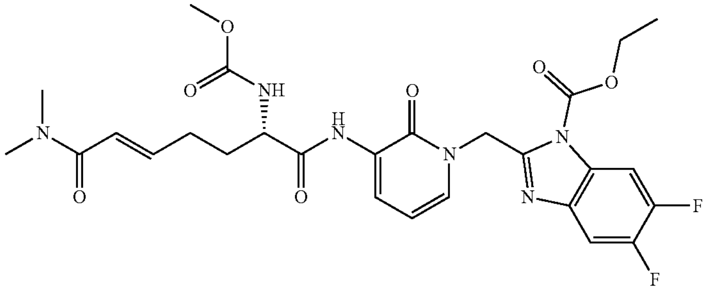 [SMILES: CCOC(=O)n1c(Cn2cccc(NC(=O)[C@H](CC/C=C/C(=O)N(C)C)NC(=O)OC)c2=O)nc2cc(F)c(F)cc21] | LCMS m/z 589.4 $(M + 1)^+$ |
| 199 | 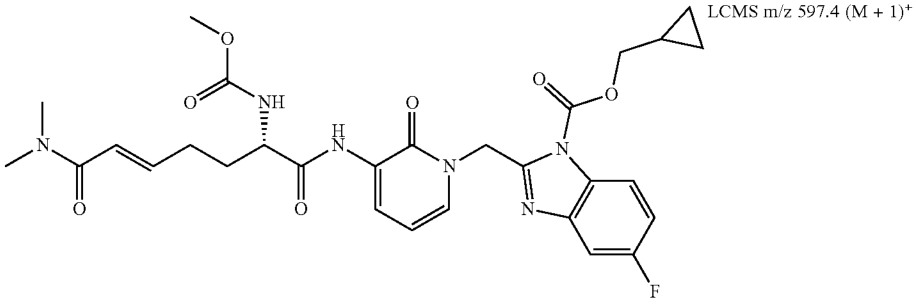 | LCMS m/z 597.4 $(M + 1)^+$ |
| 200 | 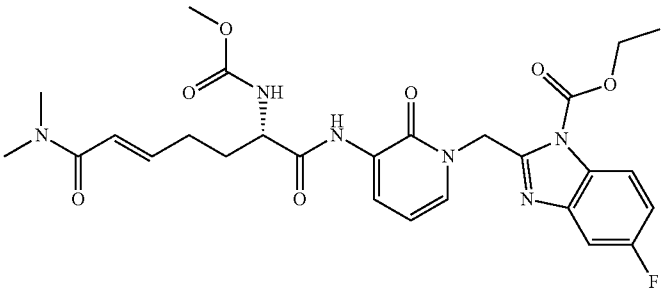 [SMILES: CCOC(=O)n1c(Cn2cccc(NC(=O)[C@H](CC/C=C/C(=O)N(C)C)NC(=O)OC)c2=O)nc2cc(F)ccc21] | LCMS m/z 571.2 $(M + 1)^+$ |
Example 34
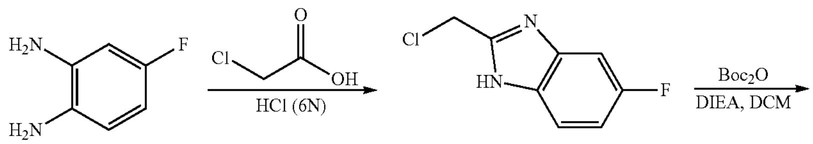
I-320 I-325

-continued

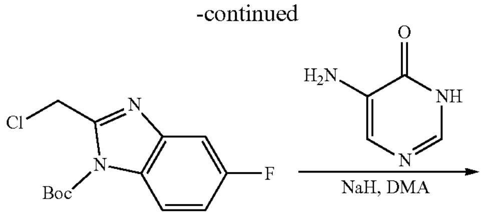

I-326

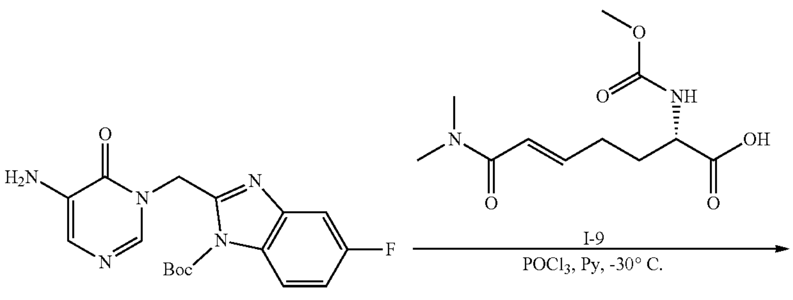

I-327

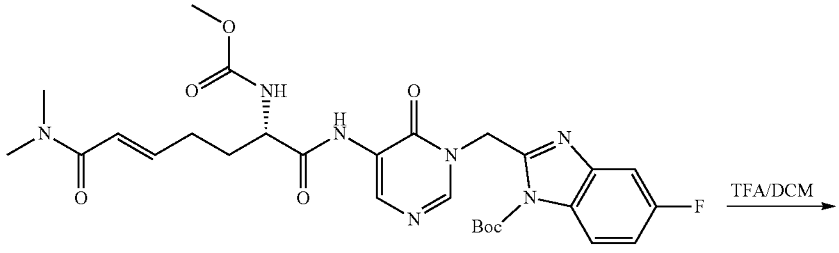

I-328

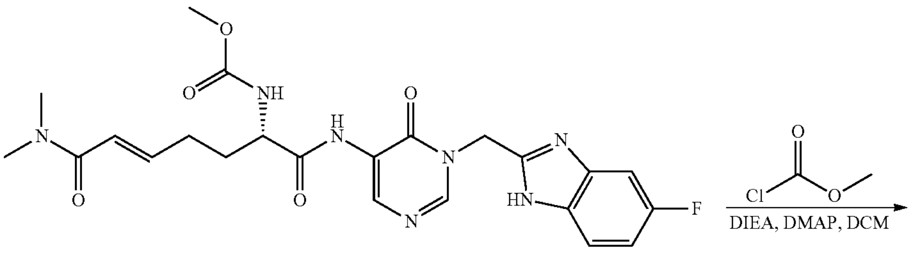

I-329

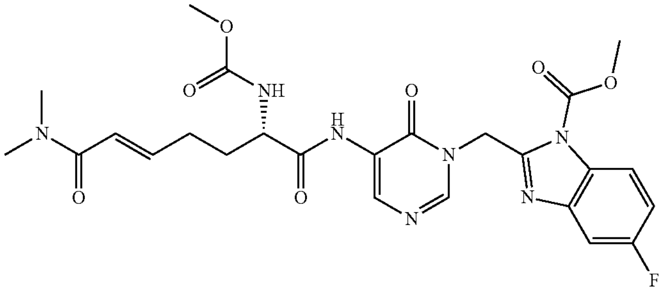

201

A mixture of 4-fluorobenzene-1,2-diamine (1 g, 7.93 mmol, 1 eq) and 2-chloroacetic acid (1.12 g, 11.89 mmol, 1.34 mL, 1.5 eq) in HCl (15 mL) (6N) was heated to 100° C. and stirred for 6 hours. The reaction mixture was quenched by addition sat. aq $NaHCO_3$ to pH=7. The mixture was filtered and concentrated under reduced pressure to give 2-(chloromethyl)-5-fluoro-1H-benzimidazole (I-325) (1.46 g) as a brown solid.

To a mixture of 2-(chloromethyl)-5-fluoro-1H-benzimidazole (0.5 g, 2.71 mmol, 1 eq), DIPEA (420.07 mg, 3.25 mmol, 566.13 uL, 1.2 eq) and $Boc_2O$ (591.14 mg, 2.71 mmol, 622.25 uL, 1 eq) in DCM (5 mL) was added DMAP (3.31 mg, 27.09 umol, 0.01 eq) in one portion at 0° C. under $N_2$. The mixture was stirred at 15° C. for 30 mins. The reaction mixture was addition $H_2O$ (5 mL), and then extracted with DCM (20 mL×2). The combined organic layers were washed with brine (30 mL), dried over $Na_2SO_4$, filtered, concentrated and purified by column chromatography to give tert-butyl 2-(chloromethyl)-5-fluoro-benzimidazole-1-carboxylate (I-326) (466 mg, 53% yield) as a yellow oil. LCMS m/z 229.2 (M+1−tert-butyl).

To a mixture of 5-amino-1H-pyrimidin-6-one (218.21 mg, 1.96 mmol, 1.2 eq) in DMA (1 mL) was added NaH (130.94 mg, 3.27 mmol, 60% purity, 2 eq) in portion at 0° C. under $N_2$. The mixture was stirred at 0° C. for 30 min, then tert-butyl 2-(chloromethyl)-5-fluoro-benzimidazole-1-carboxylate (466 mg, 1.64 mmol, 1 eq) in DMA (1 mL) was dropwise at 0° C. The mixture was stirred at 15° C. for 1.5 hours. The reaction mixture was added $H_2O$ (10 mL), and then diluted with EtOAc (10 mL) and extracted with EtOAc (20 mL×3). The combined organic layers were washed with brine (20 mL×2), dried over $Na_2SO_4$, filtered, concentrated and purified by column chromatography to give tert-butyl 2-[(5-amino-6-oxo-pyrimidin-1-yl)methyl]-5-fluoro-benzimidazole-1-carboxylate (I-327) (342 mg, 58% yield) as a yellow solid. LCMS m/z 360.0 $(M+1)^+$.

To a mixture of tert-butyl 2-[(5-amino-6-oxo-pyrimidin-1-yl)methyl]-5-fluoro-benzimidazole-1-carboxylate (237 mg, 659.52 umol, 1 eq) and (E,2S)-7-(dimethylamino)-2-(methoxycarbonylamino)-7-oxo-hept-5-enoic acid (170.33 mg, 659.52 umol, 1 eq) in Py (1 mL) was added $POCl_3$ (101.12 mg, 659.52 umol, 61.29 uL, 1 eq) dropwise at −30° C. under $N_2$. The mixture was stirred at −30° C. for 10 mins. The reaction mixture was quenched by addition $H_2O$ (0.5 mL), and then concentrated and purified by column chromatography and prep-TLC to give tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-5-fluoro-benzimidazole-1-carboxylate (I-328) (100 mg, 25% yield) as a yellow solid. LCMS m/z 600.2 $(M+1)^+$.

A mixture of tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-5-fluoro-benzimidazole-1-carboxylate (85 mg, 141.76 umol, 1 eq) in TFA (0.4 mL) and DCM (1.5 mL) was heated to 25° C. and stirred for 30 mins. The reaction mixture was quenched by addition sat. $NaHCO_3$ until pH=7, and then diluted with EtOAc (8 mL) and extracted with EtOAc (20 mL×2). The combined organic layers were washed with brine (30 mL), dried over $Na_2SO_4$, filtered, concentrated and purified by prep-TLC to give N-[(E,1S)-6-(dimethylamino)-1[1-[(5-fluoro-1H-benzimidazol-2-yl)methyl]-6-oxo-pyrimidin-5-yl]carbamoyl]-6-oxo-hex-4-enyl]carbamate (I-329) (65 mg, 92% yield) as a white solid.

To a mixture of methyl N-[(E,1S)-6-(dimethylamino)-1-[[1-[(5-fluoro-1H-benzimidazol-2-yl)methyl]-6-oxo-pyrimidin-5-yl]carbamoyl]-6-oxo-hex-4-enyl]carbamate (60 mg, 120.12 umol, 1 eq), DIPEA (23.29 mg, 180.18 umol, 31.38 uL, 1.5 eq) and methyl carbonochloridate (13.62 mg, 144.15 umol, 11.17 uL, 1.2 eq) in DCM (0.5 mL) was added DMAP (146.75 ug, 1.20 umol, 0.01 eq) in one portion at 0° C. under $N_2$. The mixture was stirred at 15° C. for 30 mins. The reaction mixture was quenched by addition $H_2O$ 5 mL, and then diluted with EtOAc 5 mL and extracted with EtOAc 20 mL (5 mL×4). The combined organic layers were washed with brine 15 mL, dried over $Na_2SO_4$, filtered, concentrated and purified by prep-TLC to give methyl 2-[[5-[[(E,2S)-7-(dimethylamino)-2-(methoxycarbonylamino)-7-oxo-hept-5-enoyl]amino]-6-oxo-pyrimidin-1-yl]methyl]-5-fluoro-benzimidazole-1-carboxylate (Compound 201) (8.3 mg, 12% yield) as a white solid. SFC showed it was a mixture about 39:61. LCMS m/z 558.2 $(M+1)^+$. $^1H$ NMR (400 MHz, DMSO-$d_6$) δ 9.45 (s, 1H), 8.78 (s, 1H), 8.31 (d, J=1.8 Hz, 1H), 7.95 (dd, J=4.9, 9.0 Hz, 1H), 7.75 (dd, J=2.5, 9.4 Hz, 1H), 7.70-7.66 (m, 1H), 7.64 (br d, J=9.5 Hz, 1H), 7.55 (dd, J=2.4, 9.0 Hz, 1H), 7.29-7.16 (m, 1H), 6.69-6.54 (m, 1H), 6.36 (d, J=15.0 Hz, 1H), 5.66 (d, J=4.0 Hz, 2H), 4.33-4.21 (m, 1H), 4.11 (d, J=1.1 Hz, 3H), 3.52 (s, 3H), 2.98 (s, 3H), 2.82 (s, 3H), 2.28-2.16 (m, 2H), 1.88-1.65 (m, 2H).

The Synthesis of Intermediate I-331

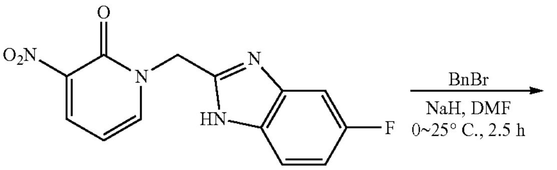

I-322

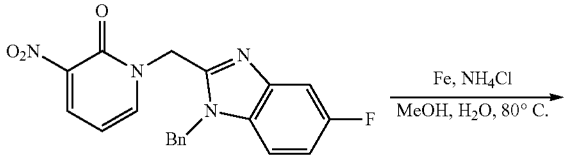

I-330

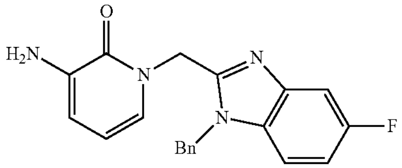

I-331 (mixture)

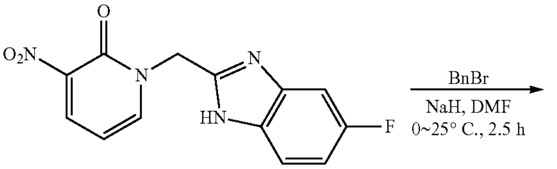

I-322

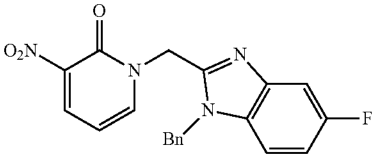

I-330

To a mixture of 1-[(5-fluoro-1H-benzimidazol-2-yl)methyl]-3-nitro-pyridin-2-one (0.2 g, 693.88 umol, 1 eq) in DMF (5 mL) was added NaH (33.30 mg, 832.66 umol, 60% purity, 1.2 eq) in one portion at 0° C. under $N_2$. The mixture was stirred at 0° C. for 30 min, then bromomethylbenzene (130.55 mg, 763.27 umol, 90.66 uL, 1.1 eq) was added at 0° C. The mixture was warmed to 25° C. and stirred for 2 hours. The reaction mixture was quenched by addition sat. aq. $NH_4Cl$ (15 mL) at 0° C., and then extracted with EtOAc (30 mL×5). The combined organic layers were washed with brine (50 mL×1), dried over $Na_2SO_4$, filtered and concentrated under reduced pressure to give a residue. The residue was purified by prep-TLC to give 1-[(1-benzyl-5-fluoro-benzimidazol-2-yl)methyl]-3-nitro-pyridin-2-one (I-330) (0.135 g, 41% yield) as a yellow solid. LCMS m/z 379.1 $(M+1)^+$.

A mixture of 1-[(1-benzyl-5-fluoro-benzimidazol-2-yl)methyl]-3-nitro-pyridin-2-one (0.115 g, 303.95 umol, 1 eq), Fe (84.88 mg, 1.52 mmol, 5 eq) and $NH_4Cl$ (162.58 mg, 3.04 mmol, 106.26 uL, 10 eq) in MeOH (5 mL) and $H_2O$ (1 mL) was heated to 80° C. and stirred for 1 hour. The reaction mixture was added $H_2O$ (10 mL), and then diluted with EtOAc (10 mL) and extracted with EtOAc (10 mL×3). The combined organic layers were washed with brine 20 mL, dried over $Na_2SO_4$, filtered and concentrated under reduced pressure to give 3-amino-1-[(1-benzyl-5-fluoro-benzimidazol-2-yl)methyl]pyridin-2-one (I-331) (0.12 g) as a yellow solid. LCMS m/z 349.0 $(M+1)^+$.

The following intermediates were prepared according to the procedures described in I-331 using the appropriate reagents.

| Compound | Structure | LCMS Data |
| --- | --- | --- |
| I-332 (mixture) | 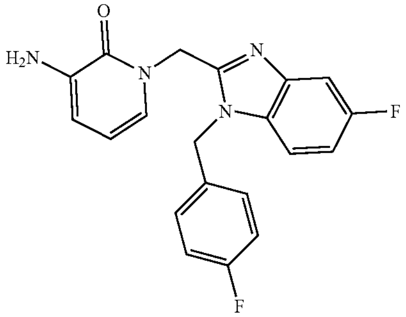 [SMILES: Nc1cccn(Cc2nc3cc(F)ccc3n2Cc2ccc(F)cc2)c1=O] | LCMS m/z 367.4 $(M + 1)^+$. |
| I-333 (mixture) | 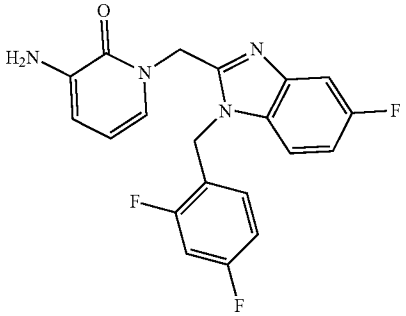 [SMILES: Nc1cccn(Cc2nc3cc(F)ccc3n2Cc2ccc(F)cc2F)c1=O] | LCMS m/z 385.2 $(M + 1)^+$. |

Example 35

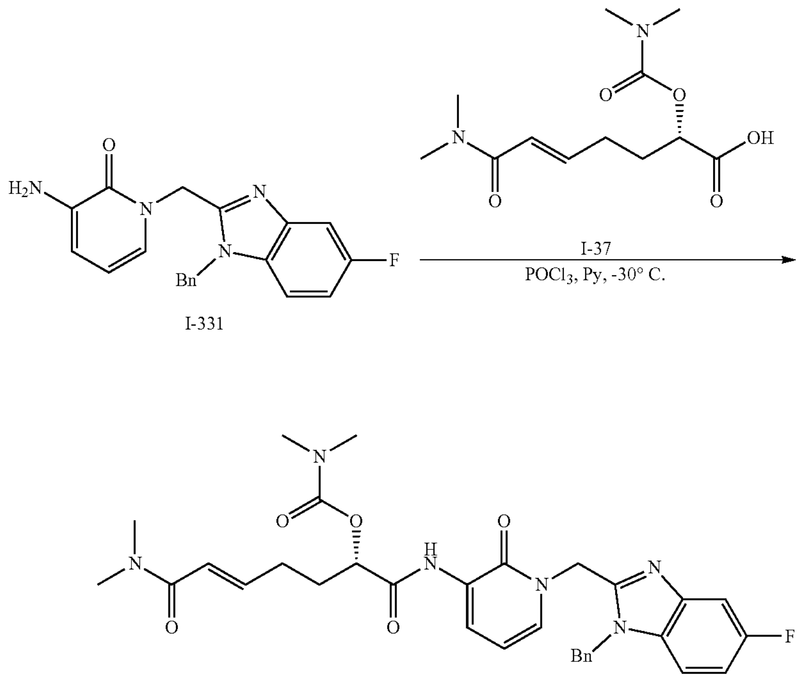

I-331

I-37

202(mixture)

-continued

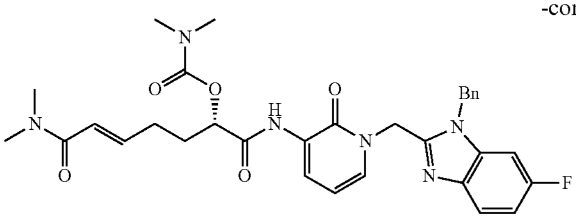

203

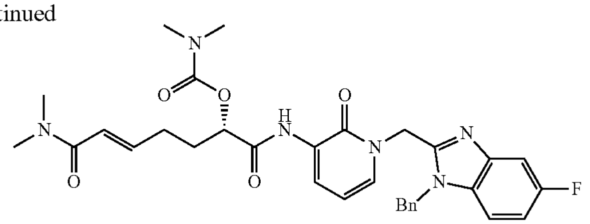

204 separation by SFC

To a mixture of 3-amino-1-[(1-benzyl-5-fluoro-benzimidazol-2-yl)methyl]pyridin-2-one (0.070 g, 200.93 umol, 1.1 eq) and (E,2S)-7-(dimethylamino)-2-(dimethylcarbamoyloxy)-7-oxo-hept-5-enoic acid (49.74 mg, 182.67 umol, 1 eq) in Py (3 mL) was added $POCl_3$ (28.01 mg, 182.67 umol, 16.98 uL, 1 eq) in one portion at −30° C. under $N_2$. The mixture was stirred at −30° C. for 40 mins. The reaction mixture was quenched by addition $H_2O$ (1 mL), and then filtered and concentrated and purified by prep-TLC to give 32.2 mg of Compound 202 as a white solid. 26 mg of Compound 202 was further separated by SFC to give [(E,1S)-1-[[1-[(1-benzyl-6-fluoro-benzimidazol-2-yl)methyl]-2-oxo-3-pyridyl]carbamoyl]-6-(dimethylamino)-6-oxo-hex-4-enyl] N,N-dimethylcarbamate (5.4 mg) and [(E,1S)-1-[[1-[(1-benzyl-5-fluoro-benzimidazol-2-yl)methyl]-2-oxo-3-pyridyl]carbamoyl]-6-(dimethylamino)-6-oxo-hex-4-enyl] N,N-dimethylcarbamate (5.6 mg) as a white solid. LCMS m/z 603.3 $(M+1)^+$.

Compound 202: $^1$H NMR (400 MHz, DMSO-$d_6$ δ 9.27 (s, 1H), 8.15 (dd, J=1.8, 7.5 Hz, 1H), 7.57 (dd, J=4.8, 8.8 Hz, 1H), 7.50 (dd, J=1.8, 6.6 Hz, 1H), 7.38 (dd, J=2.6, 9.2 Hz, 1H), 7.32-7.21 (m, 3H), 7.16 (d, J=6.6 Hz, 2H), 7.01 (dt, J=2.4, 9.3 Hz, 1H), 6.67-6.57 (m, 1H), 6.41-6.26 (m, 2H), 5.60 (s, 2H), 5.46 (s, 2H), 5.05 (dd, J=4.6, 7.7 Hz, 1H), 2.99-2.85 (m, 6H), 2.84-2.73 (m, 6H), 2.31-2.21 (m, 2H), 1.99-1.87 (m, 2H).

Compound 203: $^1$H NMR (400 MHz, DMSO-$d_6$) δ 9.28 (s, 1H), 8.17 (dd, J=1.8, 7.5 Hz, 1H), 7.53 (dd, J=1.8, 7.0 Hz, 1H), 7.46 (dd, J=4.6, 9.0 Hz, 1H), 7.39 (dd, J=2.4, 9.9 Hz, 1H), 7.32-7.22 (m, 3H), 7.17 (d, J=7.0 Hz, 2H), 7.05 (dt, J=2.4, 9.3 Hz, 1H), 6.68-6.54 (m, 1H), 6.43-6.25 (m, 2H), 5.62 (s, 2H), 5.48 (s, 2H), 5.05 (dd, J=4.8, 7.5 Hz, 1H), 2.99-2.86 (m, 6H), 2.85-2.74 (m, 6H), 2.34-2.19 (m, 2H), 1.96-1.87 (m, 2H).

Compound 204: $^1$H NMR (400 MHz, DMSO-$d_6$) δ 9.30 (d, J=2.2 Hz, 1H), 8.17 (ddd, J=1.8, 4.4, 7.5 Hz, 1H), 7.63-7.45 (m, 2H), 7.40 (td, J=2.7, 9.5 Hz, 1H), 7.34-7.23 (m, 3H), 7.21-7.15 (m, 2H), 7.04 (dtd, J=2.2, 9.4, 16.8 Hz, 1H), 6.68-6.58 (m, 1H), 6.42-6.29 (m, 2H), 5.62 (d, J=9.6 Hz, 2H), 5.48 (d, J=9.2 Hz, 2H), 5.06 (dd, J=4.6, 7.7 Hz, 1H), 2.98-2.91 (m, 6H), 2.82-2.78 (m, 6H), 2.33-2.23 (m, 2H), 1.96-1.86 (m, 2H).

The following compounds were prepared according to the procedures described in Example 35 using the appropriate intermediates.

| Compound | Structure | LCMS Data |
| --- | --- | --- |
| 205 | 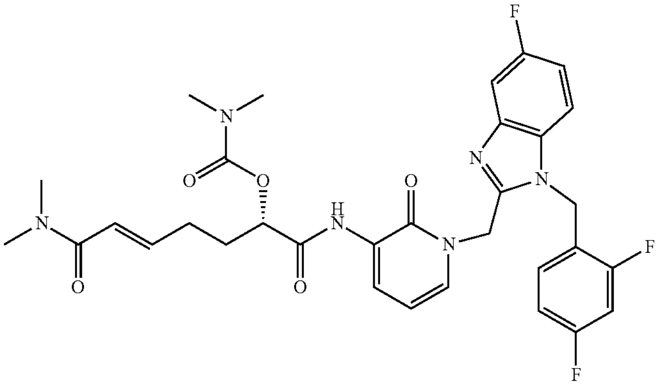 [SMILES: CN(C)C(=O)/C=C/CC[C@H](OC(=O)N(C)C)C(=O)Nc1cccn(Cc2nc3cc(F)ccc3n2Cc2ccc(F)cc2F)c1=O] | LCMS m/z 639.2 $(M + 1)^+$ |

-continued
| Compound | Structure | LCMS Data |
|---|---|---|
| 206 | 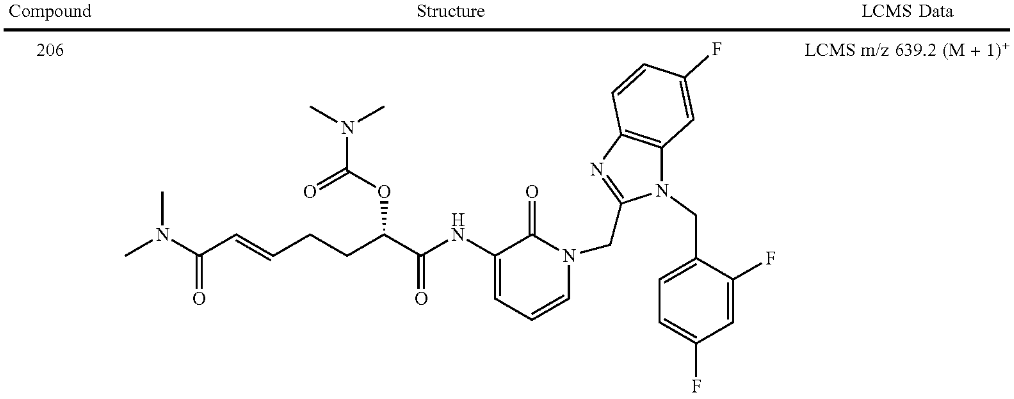 | LCMS m/z 639.2 $(M + 1)^+$ |
| 207 | 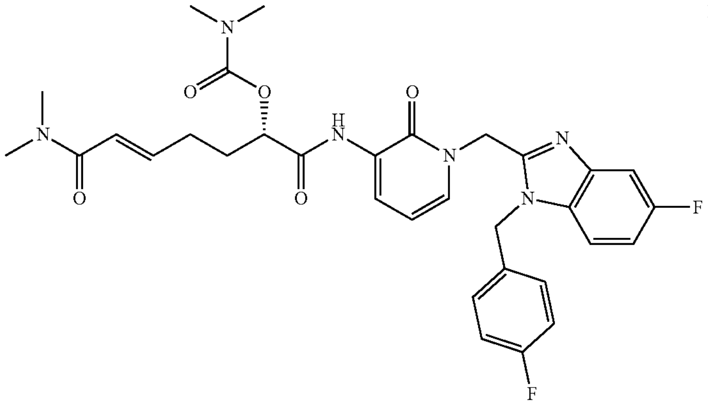 [SMILES: CN(C)C(=O)/C=C/CC[C@H](OC(=O)N(C)C)C(=O)Nc1cccn(Cc2nc3cc(F)ccc3n2Cc2ccc(F)cc2)c1=O] | LCMS m/z 621.3 $(M + 1)^+$ |
| 208 | 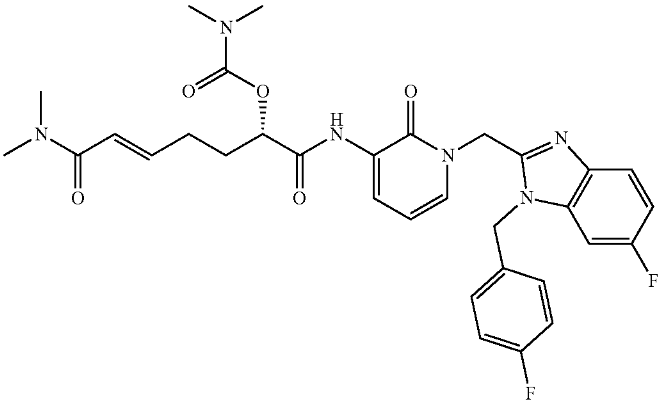 [SMILES: CN(C)C(=O)/C=C/CC[C@H](OC(=O)N(C)C)C(=O)Nc1cccn(Cc2nc3ccc(F)cc3n2Cc2ccc(F)cc2)c1=O] | LCMS m/z 621.3 $(M + 1)^+$ |
The Synthesis of Intermediate I-339
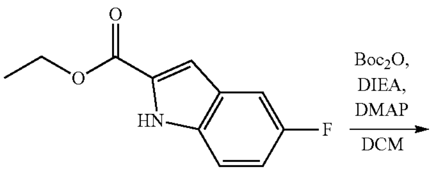
I-334
-continued
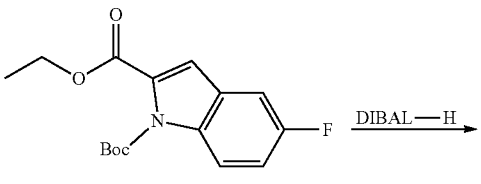
I-335

-continued

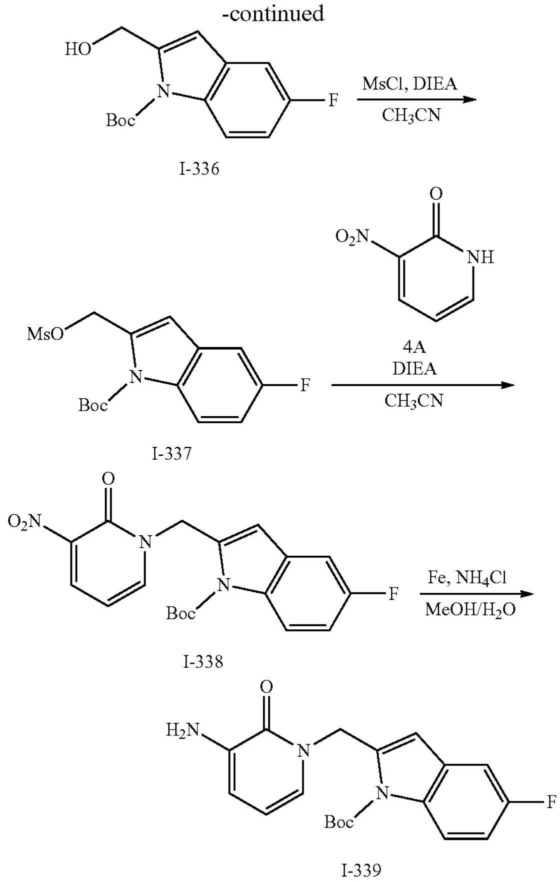

To a solution of ethyl 5-fluoro-1H-indole-2-carboxylate (5 g, 24.1 mmol) in DCM (20 mL) were added $Boc_2O$ (7.90 g, 36.2 mmol), DMAP (2.95 g, 24.1 mmol) and DIEA (7.80 g, 60.3 mmol) at 10° C. The mixture was stirred at 10° C. for 2 hours. The reaction mixture was concentrated in vacuum to give a residue. The residue was purified by silica gel chromatography to give desired product 1-tert-butyl 2-ethyl 5-fluoro-1H-indole-1,2-dicarboxylate (I-335) (6 g) as a yellow oil.

To a solution of 1-tert-butyl 2-ethyl 5-fluoro-1H-indole-1,2-dicarboxylate (6 g, 19.5 mmol) in toluene (50 mL) was added DIBAL-H (1M, 48.8 mL) at −70° C. The mixture was stirred at −70° C. for 1 hour. The resulting solution was concentrated in vacuum to give a residue. The residue was purified by silica gel chromatography to give tert-butyl 5-fluoro-2-(hydroxymethyl)-1H-indole-1-carboxylate (I-336) (4 g) as a yellow oil.

To a solution of tert-butyl 5-fluoro-2-(hydroxymethyl)-1H-indole-1-carboxylate (4 g, 15.1 mmol) in DCM (50 mL) were added DIPEA (5.85 g, 45.2 mmol) and MsCl (2.07 g, 18.1 mmol) at 0° C. The mixture was stirred at 10° C. for 1.5 hours. The mixture was concentrated in vacuum to give tert-butyl 5-fluoro-2-(((methylsulfonyl)oxy)methyl)-1H-indole-1-carboxylate (I-337) (5.18 g) as a yellow oil.

To a solution of tert-butyl 5-fluoro-2-(((methylsulfonyl)oxy)methyl)-1H-indole-1-carboxylate (5.18 g, 15.1 mmol) and 3-nitro-1H-pyridin-2-one (4.23 g, 30.2 mmol) in $CH_3CN$ (50 mL) was added DIPEA (5.85 g, 45.3 mmol). The mixture was stirred at 30° C. for 12 hours. The mixture was concentrated in vacuum to give a residue. The residue was purified by silica gel chromatography to give tert-butyl 5-fluoro-2-((3-nitro-2-oxopyridin-1(2H)-yl)methyl)-1H-indole-1-carboxylate (I-338) (2 g) as a yellow solid.

To a solution of tert-butyl 5-fluoro-2-((3-nitro-2-oxopyridin-1(2H)-yl)methyl)-1H-indole-1-carboxylate (0.2 g, 516 μmol) in MeOH (5 mL) and $H_2O$ (1 mL) were added Fe (144 mg, 2.58 mmol) and $NH_4Cl$ (221 mg, 4.13 mmol). The mixture was stirred at 80° C. for 5 hours. The resulting suspension was filtered and the filtrate was concentrated in vacuum to give tert-butyl 2-((3-amino-2-oxopyridin-1(2H)-yl)methyl)-5-fluoro-1H-indole-1-carboxylate (I-339) (0.1 g) as a green oil.

Example 36

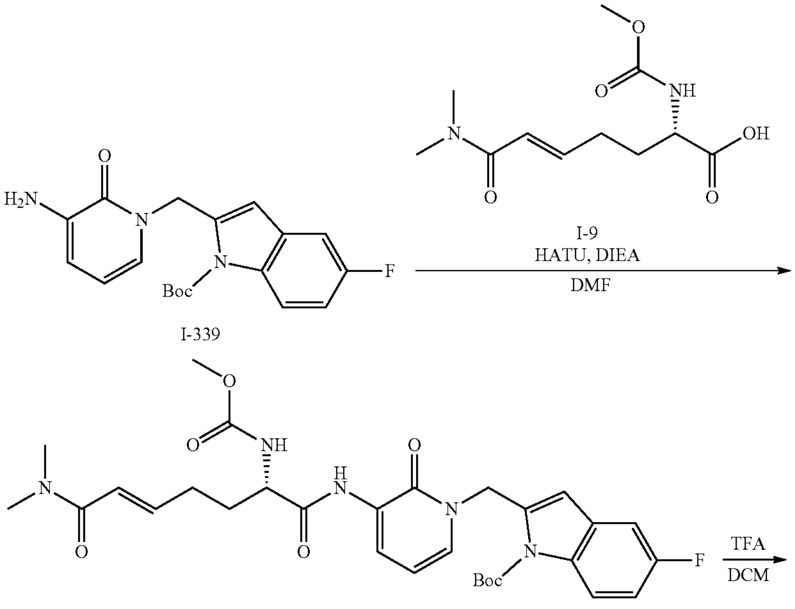

I-340

-continued

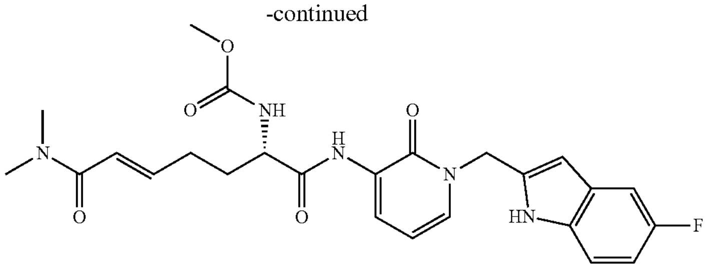

209

To a solution of (S,E)-7-(dimethylamino)-2-((methoxycarbonyl)amino)-7-oxohept-5-enoic acid (108 mg, 420 μmol) and tert-butyl 2-((3-amino-2-oxopyridin-1(2H)-yl)methyl)-5-fluoro-1H-indole-1-carboxylate (0.1 g, 280 μmol) in DCM (3 mL) were added HATU (213 mg, 560 μmol) and DIEA (108 mg, 839 μmol) at 0° C. The mixture was stirred at 30° C. for 12 hours. The reaction mixture was concentrated to give a residue. The residue was purified by prep-HPLC to give (S,E)-tert-butyl 2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate (I-340) (0.08 g) as a white solid.

To a solution of (S,E)-tert-butyl 2-((3-(7-(dimethylamino)-2-((methoxycarbonyl) amino)-7-oxohept-5-enamido)-2-oxopyridin-1(2H)-yl)methyl)-5-fluoro-1H-indole-1-carboxylate (0.08 g, 134 μmol) in DCM (5 mL) was added TFA (1.54 g, 1 mL) at 0° C. The mixture was stirred at 10° C. for 1 hour. The mixture was concentrated in vacuum to give a residue. The residue was purified by prep-HPLC to give (S,E)-methyl (7-(dimethylamino)-1-((1-((5-fluoro-1H-indol-2-yl)methyl)-2-oxo-1,2-dihydropyridin-3-yl)amino)-1,7-dioxohept-5-en-2-yl)carbamate (Compound 209) (57 mg, 85% yield) as a white solid. LCMS m/z 498.1 $(M+1)^+$. $^1H$ NMR (400 MHz, DMSO-$d_6$) δ11.21 (s, 1H), 9.31 (s, 1H), 8.22 (dd, J=7.2, 1.6 Hz, 1H), 7.78 (d, J=7.6 Hz, 1H), 7.51 (dd, J=6.8, 2.0 Hz, 1H), 7.34 (dd, J=8.8, 4.4 Hz, 1H), 7.23 (dd, J=9.6, 2.4 Hz, 1H), 6.95-6.83 (m, 1H), 6.66-6.56 (m, 1H), 6.42-6.28 (m, 3H), 5.29 (s, 2H), 4.24-4.13 (m, 1H), 3.56 (s, 3H), 2.99 (s, 3H), 2.84 (s, 3H), 2.30-2.17 (m, 2H), 1.98-1.80 (m, 1H), 1.78-1.66 (m, 1H).

The following compounds were prepared according to the procedures described in Example 36 using the appropriate intermediates.

| Compound | Structure | LCMS Data |
| --- | --- | --- |
| 210 | 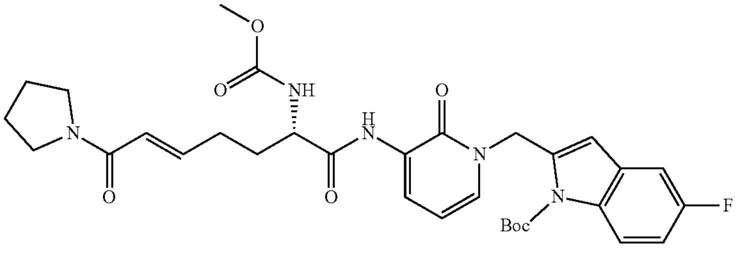 [SMILES: COC(=O)N[C@@H](CC/C=C/C(=O)N1CCCC1)C(=O)Nc1cccn(Cc2cc3cc(F)ccc3n2C(=O)OC(C)(C)C)c1=O] | LCMS m/z 624.2 $(M + 1)^+$ |
| 211 | 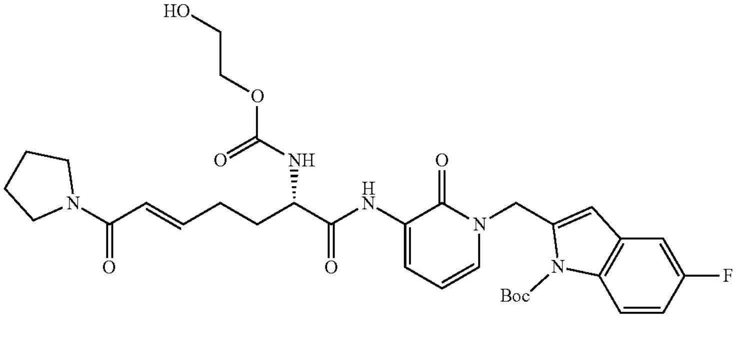 [SMILES: CC(C)(C)OC(=O)n1c(Cn2cccc(NC(=O)[C@H](CC/C=C/C(=O)N3CCCC3)NC(=O)OCCO)c2=O)cc2cc(F)ccc21] | LCMS m/z 654.3 $(M + 1)^+$ |

-continued
| Compound | Structure | LCMS Data |
|---|---|---|
| 212 | 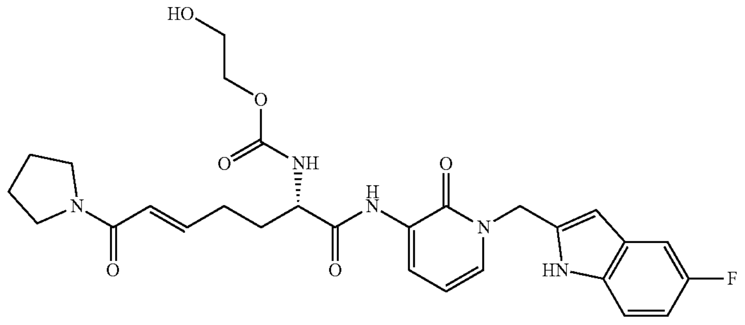 [SMILES: O=C(N[C@@H](CC/C=C/C(=O)N1CCCC1)C(=O)Nc1cccn(Cc2cc3cc(F)ccc3[nH]2)c1=O)OCCO] | LCMS m/z 554.2 (M + 1)$^+$ |
| 213 | 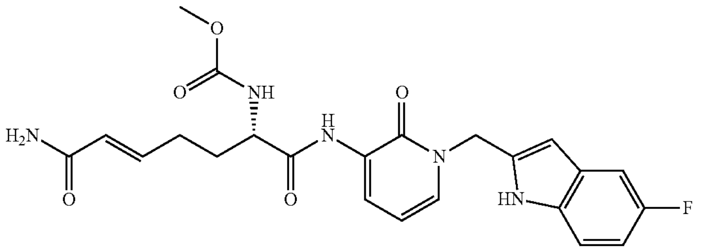 [SMILES: COC(=O)N[C@@H](CC/C=C/C(N)=O)C(=O)Nc1cccn(Cc2cc3cc(F)ccc3[nH]2)c1=O] | LCMS m/z 470.1 (M + 1)$^+$ |
| 214 | 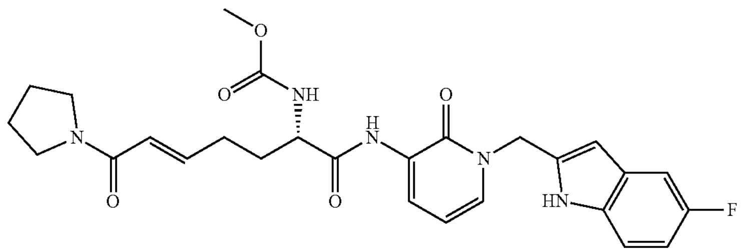 [SMILES: COC(=O)N[C@@H](CC/C=C/C(=O)N1CCCC1)C(=O)Nc1cccn(Cc2cc3cc(F)ccc3[nH]2)c1=O] | LCMS m/z 524.2 (M + 1)$^+$ |
| 215 | 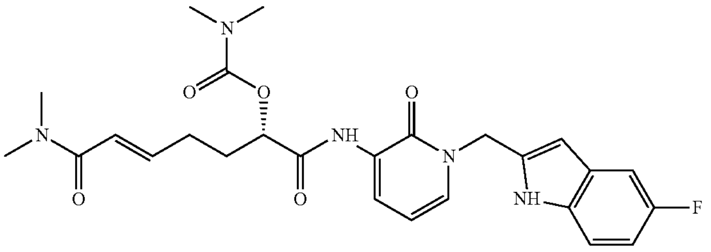 [SMILES: CN(C)C(=O)/C=C/CC[C@H](OC(=O)N(C)C)C(=O)Nc1cccn(Cc2cc3cc(F)ccc3[nH]2)c1=O] | LCMS m/z 512.3 (M + 1)$^+$ |
| 216 | 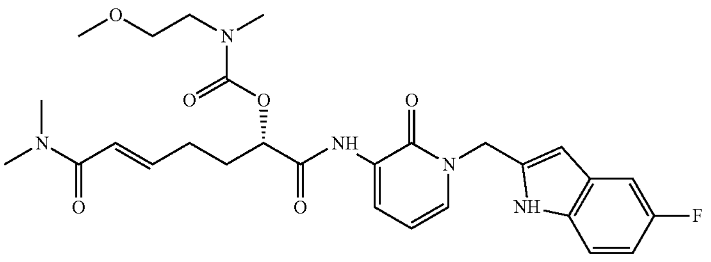 [SMILES: COCCN(C)C(=O)O[C@@H](CC/C=C/C(=O)N(C)C)C(=O)Nc1cccn(Cc2cc3cc(F)ccc3[nH]2)c1=O] | LCMS m/z 556.3 (M + 1)$^+$ |

-continued
| Compound | Structure | LCMS Data |
|---|---|---|
| 217 | 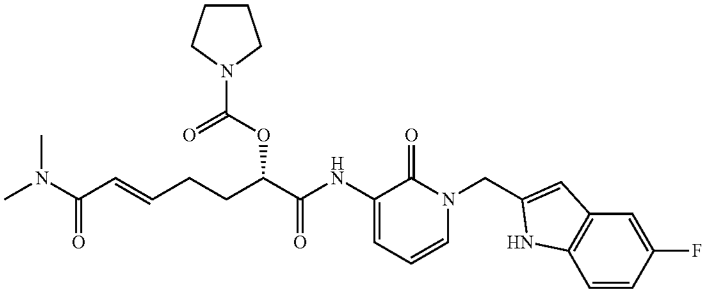 [SMILES: CN(C)C(=O)/C=C/CC[C@H](OC(=O)N1CCCC1)C(=O)Nc1cccn(Cc2cc3cc(F)ccc3[nH]2)c1=O] | LCMS m/z 538.3 (M + 1)$^+$. |
| 218 | 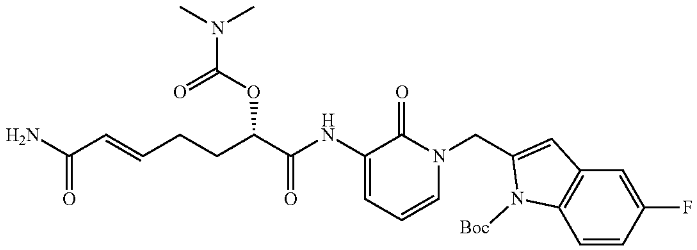 [SMILES: CN(C)C(=O)O[C@@H](CC/C=C/C(N)=O)C(=O)Nc1cccn(Cc2cc3cc(F)ccc3n2C(=O)OC(C)(C)C)c1=O] | LCMS m/z 584.2 (M + 1)$^+$ |
| 219 | 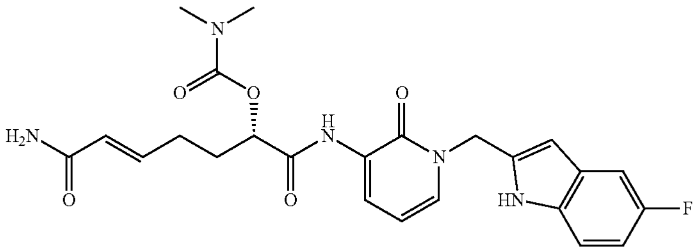 [SMILES: CN(C)C(=O)O[C@@H](CC/C=C/C(N)=O)C(=O)Nc1cccn(Cc2cc3cc(F)ccc3[nH]2)c1=O] | LCMS m/z 484.1 (M + 1)$^+$ |
| 220 | 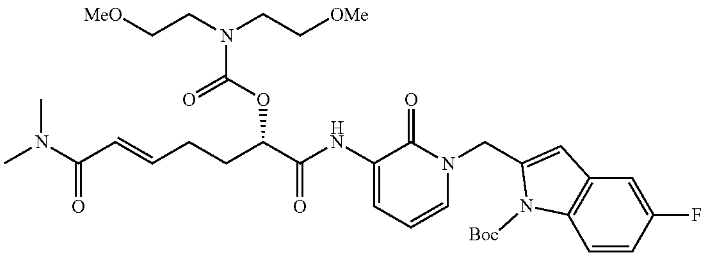 [SMILES: COCCN(CCOC)C(=O)O[C@@H](CC/C=C/C(=O)N(C)C)C(=O)Nc1cccn(Cc2cc3cc(F)ccc3n2C(=O)OC(C)(C)C)c1=O] | LCMS m/z 700.1 (M + 1)$^+$ |
| 221 | 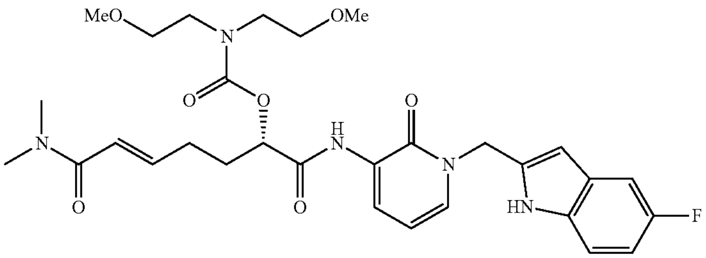 [SMILES: COCCN(CCOC)C(=O)O[C@@H](CC/C=C/C(=O)N(C)C)C(=O)Nc1cccn(Cc2cc3cc(F)ccc3[nH]2)c1=O] | LCMS m/z 600.2 (M + 1)$^+$ |
| 222 | 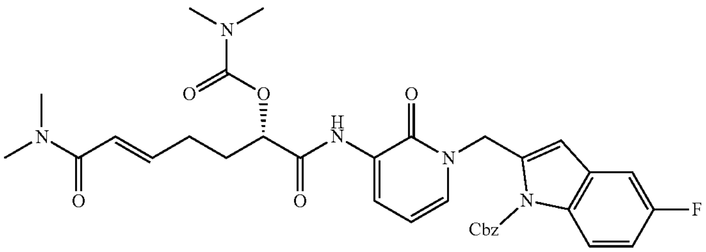 [SMILES: CN(C)C(=O)/C=C/CC[C@H](OC(=O)N(C)C)C(=O)Nc1cccn(Cc2cc3cc(F)ccc3n2C(=O)OCc2ccccc2)c1=O] | LCMS m/z 646.3 (M + 1)$^+$ |

-continued

| Compound | Structure | LCMS Data |
|---|---|---|
| 223 | 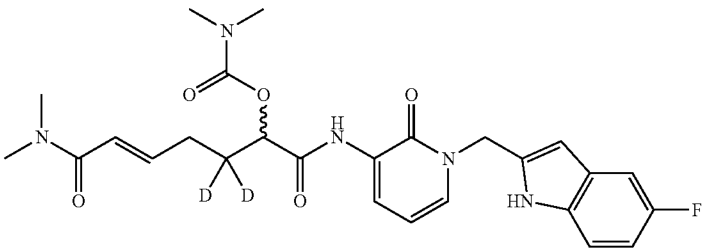 | LCMS m/z 514.2 (M + 1)$^+$ |
| 224 | 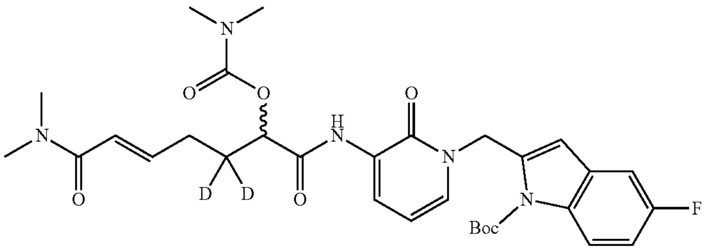 [SMILES: [2H]C([2H])(C/C=C/C(=O)N(C)C)C(OC(=O)N(C)C)C(=O)Nc1cccn(Cc2cc3cc(F)ccc3n2C(=O)OC(C)(C)C)c1=O] | LCMS m/z 614.2 (M + 1)$^+$ |
| 225 | 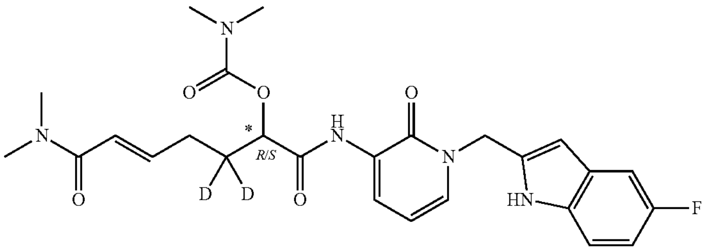 [SMILES: [2H]C([2H])(C/C=C/C(=O)N(C)C)C(OC(=O)N(C)C)C(=O)Nc1cccn(Cc2cc3cc(F)ccc3[nH]2)c1=O] | LCMS m/z 515.2 (M + 1)$^+$ |
| 226 | 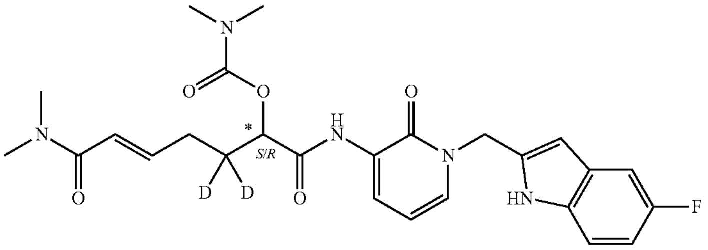 [SMILES: [2H]C([2H])(C/C=C/C(=O)N(C)C)C(OC(=O)N(C)C)C(=O)Nc1cccn(Cc2cc3cc(F)ccc3[nH]2)c1=O] | LCMS m/z 515.2 (M + 1)$^+$ |

The Synthesis of Intermediate I-341

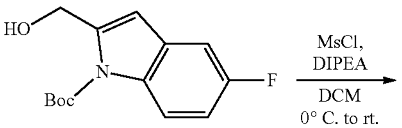

I-336

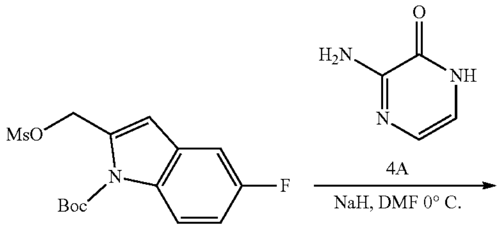

I-337

-continued

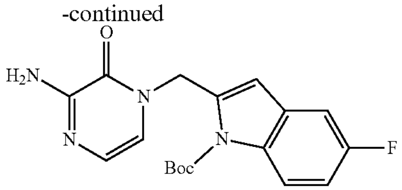

I-341

To a solution of tert-butyl 5-fluoro-2-(hydroxymethyl) indole-1-carboxylate (500 mg, 1.88 mmol, 1 eq) in DCM (5 mL) was added DIPEA (608.99 mg, 4.71 mmol, 820.75 uL, 2.5 eq) and MsCl (259.09 mg, 2.26 mmol, 175.06 uL, 1.20 eq) dropwise at 0° C. The mixture was stirred at 15° C. for 0.5 hr. The mixture was poured into a saturated solution of $NH_4Cl$ (20 mL), the mixture was extracted with DCM 50 mL (25 mL*2). The organic phase was washed with brine 50 mL (25 mL*2), dried over anhydrous $Na_2SO_4$, filtered and concentrated in vacuum to give a crude tert-butyl 5-fluoro- 2-(methylsulfonyloxymethyl)indole-1-carboxylate (I-337) (647 mg) as an orange oil which was used in the next step directly.

Solution one: To a solution of 3-aminopyrazin-2-ol (209.35 mg, 1.88 mmol, 1 eq) in DMF (5 mL) was added NaH (82.90 mg, 2.07 mmol, 60% purity, 1.1 eq) at 0° C., then the reaction was stirred at 0° C. for 15 mins then a solution of tert-butyl 5-fluoro-2-(methylsulfonyloxymethyl) indole-1-carboxylate (647 mg, 1.88 mmol, 1 eq) in DMF (10 mL) was dropwised into it, the reaction was stirred at 20° C. for 12 hr. The reaction was diluted with water (50 mL). The mixture was extracted with ethyl acetate (50 mL*2). The organic phase was washed with brine (50 mL*2), dried over anhydrous $Na_2SO_4$, filtered and concentrated in vacuum to give a residue. The residue was purified by column chromatography to give tert-butyl 2-[(3-amino-2-oxo-pyrazin-1-yl)methyl]-5-fluoro-indole-1-carboxylate (I-341) (350 mg, 52% yield) as a yellow solid. $^1H$ NMR (400 MHz, $CDCl_3$) δ 1.67 (s, 9H) 5.42 (s, 2H) 5.48 (s, 2H) 6.25 (s, 1H) 6.58 (d, J=4.63 Hz, 1H) 6.83 (d, J=4.63 Hz, 1H) 7.01 (td, J=9.15, 2.65 Hz, 1H) 7.11 (dd, J=8.60, 2.43 Hz, 1H) 8.03 (dd, J=9.04, 4.63 Hz, 1H).

The following aniline was prepared according to the procedures described for the synthesis of I-341 using the appropriate reagents.

| Compound | Structure | LCMS Data |
|---|---|---|
| I-342 | 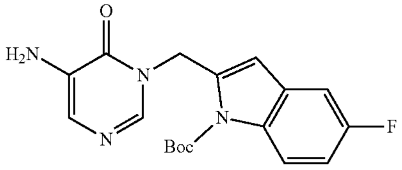 [SMILES: CC(C)(C)OC(=O)n1c(Cn2cncc(N)c2=O)cc2cc(F)ccc21] | LCMS m/z 259.2 (M − 100 + 1)$^+$ |

Example 37

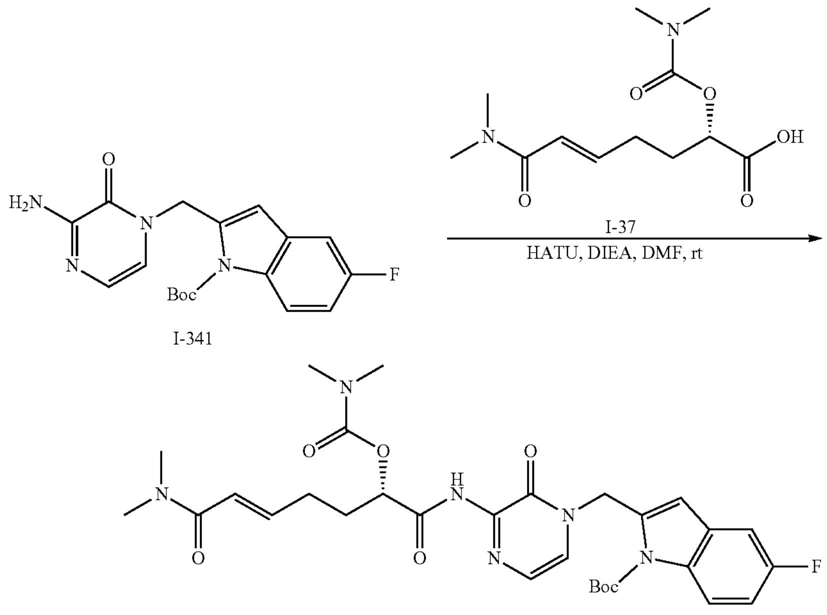

227

To a mixture of (E,2S)-7-(dimethylamino)-2-(dimethylcarbamoyloxy)-7-oxo-hept-5-enoic acid (66.86 mg, 245.56 umol, 1.1 eq) and tert-butyl 2-[(3-amino-2-oxo-pyrazin-1-yl)methyl]-5-fluoro-indole-1-carboxylate (80 mg, 223.24 umol, 1 eq) in DMF (2 mL) was added HATU (101.86 mg, 267.88 umol, 1.2 eq) and DIEA (34.62 mg, 267.88 umol, 46.66 uL, 1.2 eq) at 0° C. The reaction was stirred at 20° C. for 12 hr. The reaction mixture was poured into water (5 mL) and then extracted with EtOAc (10 mL×2). The combined organic layers were washed with brine (10 mL×2), dried over $Na_2SO_4$, filtered and concentrated under reduced pressure to give tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-5-fluoro-indole-1-carboxylate (Compound 227) (50 mg) as a brown oil. $^1H$ NMR (400 MHz, DMSO-$d_6$) δ 1.65 (s, 9H) 1.87-2.07 (m, 2H) 2.34 (q, J=7.21 Hz, 2H) 2.79-2.89 (m, 6H) 2.93-3.06 (m, 5H) 5.16-5.26 (m, 1H) 5.45 (s, 2H) 6.24 (s, 1H) 6.43 (d, J=15.04 Hz, 1H) 6.64-6.74 (m, 1H) 7.11-7.22 (m, 2H) 7.34 (dd, J=8.93, 2.57 Hz, 1H) 7.43 (d, J=4.40 Hz, 1H) 8.06 (dd, J=9.17, 4.65 Hz, 1H) 9.98 (s, 1H).

To a solution of tert-butyl 2-[[3-[[(E,2S)-7-(dimethylamino)-2-(dimethylcarbamoyloxy)-7-oxo-hept-5-enoyl] amino]-2-oxo-pyrazin-1-yl]methyl]-5-fluoro-indole-1-carboxylate (50 mg, 81.61 umol, 1 eq) in DCM (1 mL) was added TFA (50 mg, 438.51 umol, 32.47 uL, 5.37 eq) at 20° C. The reaction was stirred at 20° C. for 0.5 hr. The reaction was concentrated in vacuum to give an oil which was purified by prep-TLC to give [(E,1S)-6-(dimethylamino)-1-[[4-[(5-fluoro-1H-indol-2-yl)methyl]-3-oxo-pyrazin-2-yl] carbamoyl]-6-oxo-hex-4-enyl]N,N-dimethylcarbamate (Compound 228) (13.6 mg, 32% yield) as a brown gum. $^1H$ NMR (400 MHz, DMSO-$d_6$) δ 1.85-2.05 (m, 2H) 2.34 (s, 2H) 2.68 (s, 1H) 2.80-2.90 (m, 6H) 2.91-3.04 (m, 6H) 5.19 (d, J=4.89 Hz, 1H) 5.26 (s, 2H) 6.34-6.50 (m, 1H) 6.37-6.41 (m, 1H) 6.44 (s, 1H) 6.62-6.73 (m, 1H) 6.92 (td, J=9.20, 2.51 Hz, 1H) 7.11 (d, J=4.52 Hz, 1H) 7.25 (dd, J=9.96, 2.38 Hz, 1H) 7.34 (dd, J=8.86, 4.59 Hz, 1H) 7.42 (d, J=4.52 Hz, 1H) 9.93 (s, 1H) 11.25 (s, 1H).

The following compound was prepared according to the procedures described for the synthesis of Example 37 using the appropriate reagents.

| Compound | Structure | LCMS Data |
| --- | --- | --- |
| 229 | 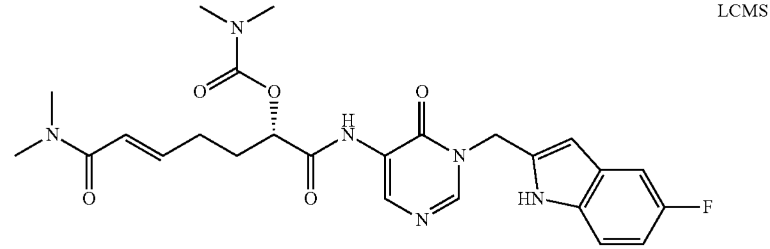 | LCMS m/z 513.2 (M + 1)$^+$ |

Synthesis of the I-350

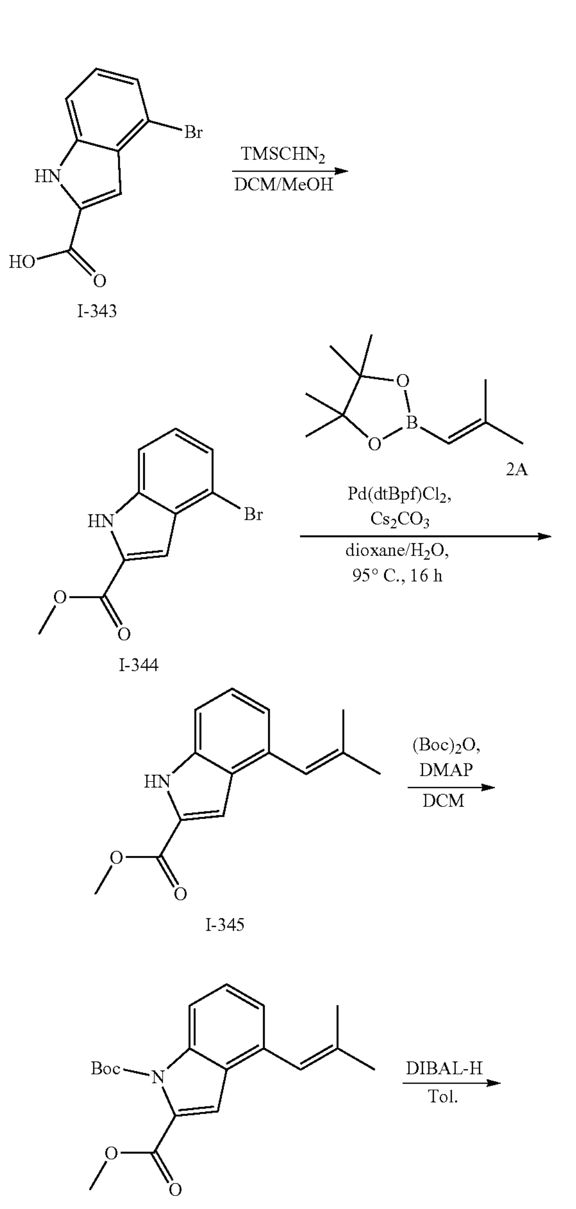

-continued

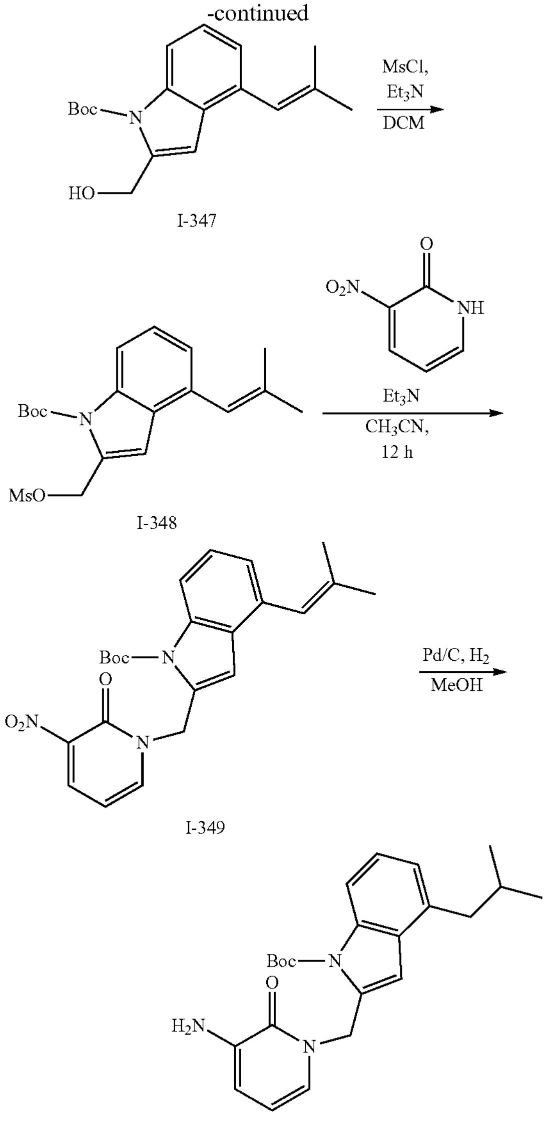

To a mixture of 4-bromo-1H-indole-2-carboxylic acid (5 g, 20.8 mmol) in MeOH (20 mL) and DCM (60 mL) was added TMSCHN$_2$ (2 M, 20.8 mL) at 0° C. The mixture was stirred at 20° C. for 20 min. The mixture was concentrated in vacuo to afford methyl 4-bromo-1H-indole-2-carboxylate (I-344) (5.3 g) as a white solid. $^1$H NMR (400 MHz, $CDCl_3$) δ 9.10 (s, 1H), 7.41-7.32 (m, 2H), 7.27-7.30 (m, 1H), 7.22-7.15 (m, 1H), 3.98 (s, 3H).

To a mixture of methyl 4-bromo-1H-indole-2-carboxylate (5.3 g, 20.9 mmol) and 4,4,5,5-tetramethyl-2-(2-methyl-prop-1-en-1-yl)-1,3,2-dioxaborolane (5.7 g, 31.3 mmol) in dioxane (100 mL) and $H_2O$ (10 mL) were added [1,1'-bis (di-tert-butylphosphino)ferrocene]dichloropalladium(II) (2.04 g, 3.13 mmol) and $Cs_2CO_3$ (13.6 g, 41.7 mmol) under $N_2$ atmosphere. The mixture was stirred at 95° C. for 16 h. The mixture was concentrated in vacuum and purified by silica gel chromatography to afford methyl 4-(2-methylprop-1-en-1-yl)-1H-indole-2-carboxylate (I-345) (3.8 g) as a brown oil.

To a mixture of methyl 4-(2-methylprop-1-en-1-yl)-1H-indole-2-carboxylate (3.3 g, 14.4 mmol) in DCM (10 mL) were added $Boc_2O$ (4.71 g, 21.6 mmol, 4.96 mL), TEA (2.91 g, 28.8 mmol, 3.99 mL) and DMAP (176 mg, 1.44 mmol). The mixture was stirred at 20° C. for 1 h. The resulting solution was concentrated in vacuum and purified by silica gel chromatography to afford 1-tert-butyl 2-methyl 4-(2-methylprop-1-en-1-yl)-1H-indole-1,2-dicarboxylate (I-346) (4.4 g) as a yellow oil. $^1$H NMR (400 MHz, $CDCl_3$) δ 7.97-7.91 (m, 1H), 7.41-7.35 (m, 1H), 7.16-7.11 (m, 2H), 6.47 (s, 1H), 3.92 (s, 3H), 1.99-1.95 (m, 3H), 1.83-1.78 (m, 3H), 1.63 (s, 9H).

To a solution of 1-tert-butyl 2-methyl 4-(2-methylprop-1-en-1-yl)-1H-indole-1,2-dicarboxylate (3.9 g, 11.8 mmol) in toluene (60 mL) was added DIBAL-H (1 M, 29.6 mL) at −78° C. The mixture was stirred at −78° C. for 1 h. The reaction mixture was quenched with saturated potassium sodium tartrate (60 mL). The resulting solution was extracted with ethyl acetate (60 mL×3). The combined organic layers were washed with brine (100 mL), dried over anhydrous $Na_2SO_4$, filtered and concentrated in vacuum. The residue was purified by silica gel chromatography to afford tert-butyl 2-(hydroxymethyl)-4-(2-methylprop-1-en-1-yl)-1H-indole-1-carboxylate (1.3 g, 4.31 mmol, 36.4% yield) as a yellow oil and tert-butyl 2-(hydroxymethyl)-4-(2-methylprop-1-en-1-yl)-1H-indole-1-carboxylate (I-347) (1.6 g) as a yellow oil. $^1$H NMR (400 MHz, $CDCl_3$) δ 7.89-7.83 (m, 1H), 7.29-7.22 (m, 1H), 7.13-7.07 (m, 1H), 6.6 (s, 1H), 6.46 (s, 1H), 4.84-4.79 (m, 2H), 3.74 (t, J=7.4 Hz, 1H), 1.99-1.95 (m, 3H), 1.82-1.78 (m, 3H), 1.73 (s, 9H).

To a mixture of tert-butyl 2-(hydroxymethyl)-4-(2-methylprop-1-en-1-yl)-1H-indole-1-carboxylate (2.1 g, 6.97 mmol) and $Et_3N$ (2.12 g, 21.0 mmol, 2.9 mL) in DCM (40 mL) was added MsCl (1.6 g, 13.9 mmol, 1.08 mL) at 0° C. under $N_2$ atmosphere. The mixture was stirred at 20° C. for 2 h. The resulting solution was diluted with water (40 mL) and extracted with DCM (30 mL×3). The combined organic layers were washed with brine (80 mL), dried over anhydrous $Na_2SO_4$, filtered and concentrated in vacuum to afford tert-butyl 4-(2-methylprop-1-en-1-yl)-2-(((methylsulfonyl)oxy)methyl)-1H-indole-1-carboxylate (I-348) (2.6 g) as a yellow oil.

To a mixture of tert-butyl 4-(2-methylprop-1-en-1-yl)-2-(((methylsulfonyl)oxy) methyl)-1H-indole-1-carboxylate (2.6 g, 6.85 mmol) and 3-nitropyridin-2(1H)-one (960 mg, 6.85 mmol) in $CH_3CN$ (50 mL) was added $Et_3N$ (1.39 g, 13.7 mmol, 1.90 mL). The mixture was stirred at 20° C. for 12 h. The resulting solution was diluted with water (30 mL) and extracted with ethyl acetate (30 mL×3). The combined organic layers were washed with brine (80 mL), dried over anhydrous $Na_2SO_4$, filtered and concentrated in vacuum. The residue was purified by silica gel chromatography to afford tert-butyl 4-(2-methylprop-1-en-1-yl)-2-((3-nitro-2-oxopyridin-1(2H)-yl)methyl)-1H-indole-1-carboxylate (I-349) (1.4 g) as a yellow oil. $^1$H NMR (400 MHz, $CDCl_3$) δ 8.37 (dd, J=7.8, 2.0 Hz, 1H), 7.97-7.91 (m, 1H), 7.78 (dd, J=6.8, 2.0 Hz, 1H), 7.31 (t, J=8.0 Hz, 1H), 7.15-7.11 (m, 1H), 6.69 (s, 1H), 6.44 (s, 1H), 6.28 (dd, J=7.6, 6.8 Hz, 1H), 5.60 (s, 2H), 1.97 (d, J=1.0 Hz, 3H), 1.80 (d, J=1.0 Hz, 3H), 1.64 (s, 9H).

To a solution of tert-butyl 4-(2-methylprop-1-en-1-yl)-2-((3-nitro-2-oxopyridin-1(2H)-yl)methyl)-1H-indole-1-carboxylate (300 mg, 0.708 mmol) in MeOH (15 mL) was added Pd/C (30 mg, 10% purity) under $N_2$. The suspension was degassed under vacuum and purged with $H_2$ three times. The mixture was stirred under $H_2$ (15 psi) at 20° C. for 2 h. The mixture was filtered, the filter was concentrated in vacuum to afford tert-butyl 2-((3-amino-2-oxopyridin-1 (2H)-yl)methyl)-4-isobutyl-1H-indole-1-carboxylate (I-350) (260 mg, 0.657 mmol, 92.8% yield) as a white solid. LCMS m/z 396.1 $(M+1)^+$.

The following intermediate was prepared according to the procedures described for the synthesis of I-350 using the appropriate reagent.

| Compound | Structure | LCMS Data |
|---|---|---|
| I-351 | 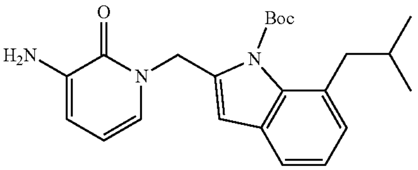 [SMILES: CC(C)Cc1cccc2cc(Cn3cccc(N)c3=O)n(C(=O)OC(C)(C)C)c12] | LCMS m/z 396.1 $(M + H)^+$ |

Example 38

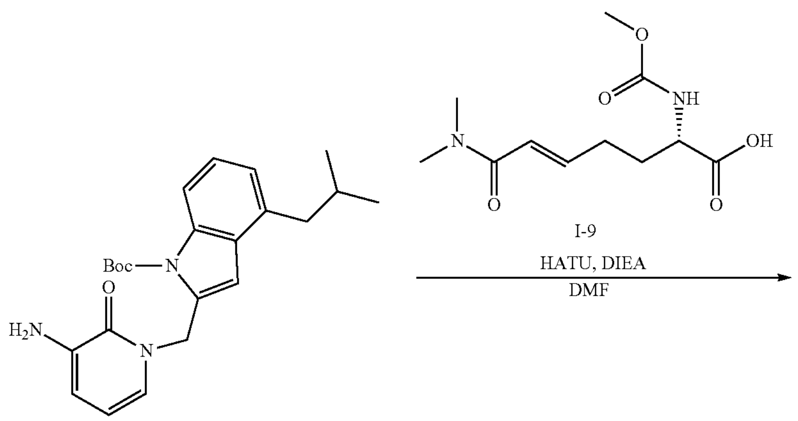

I-350

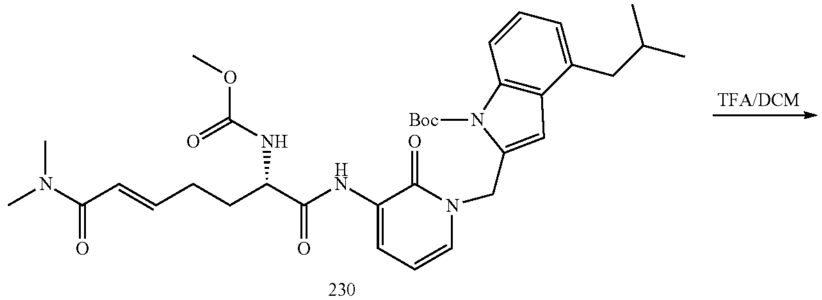

230

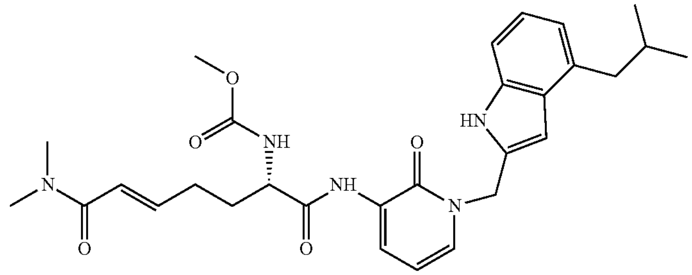

231

To a solution of tert-butyl 2-((3-amino-2-oxopyridin-1(2H)-yl)methyl)-4-isobutyl-1H-indole-1-carboxylate (130 mg, 0.329 mmol) and (S,E)-7-(dimethylamino)-2-((methoxycarbonyl)amino)-7-oxohept-5-enoic acid (127 mg, 0.493 mmol) in DMF (3 mL) were added HATU (225 mg, 0.592 mmol) and DIEA (170 mg, 1.31 mmol, 0.23 mL) at 0° C. The mixture was stirred at 20° C. for 12 h. Water (30 mL) was added to the mixture. The resulting solution was extracted with ethyl acetate (30 mL×2). The combined organic layers were washed with brine (50 mL×3), dried over anhydrous $Na_2SO_4$, filtered and concentrated in vacuum. The residue was purified by prep-HPLC to give (S,E)-tert-butyl 2-((3-(7-(dimethylamino)-2-((methoxycarbonyl)amino)-7-oxohept-5-enamido)-2-oxopyridin-1(2H)-yl)methyl)-4-isobutyl-1H-indole-1-carboxylate (90 mg, 39% yield) as a gray oil, and (S,E)-tert-butyl 2-((3-(7-(dimethylamino)-2-((methoxycarbonyl)amino)-7-oxohept-5-enamido)-2-oxopyridin-1(2H)-yl)methyl)-4-isobutyl-1H-indole-1-carboxylate (Compound 230) (27.4 mg, 13% yield) as a white solid. LCMS m/z 636.3 $(M+1)^+$.

To a mixture of (S,E)-tert-butyl 2-((3-(7-(dimethylamino)-2-((methoxycarbonyl) amino)-7-oxohept-5-enamido)-2-oxopyridin-1(2H)-yl)methyl)-4-isobutyl-1H-indole-1-carboxylate (90 mg, 0.142 mmol) in DCM (4 mL) was added TFA (1.54 g, 13.5 mmol, 1 mL) at 0° C. The mixture was stirred at 20° C. for 1 h. The mixture was concentrated in vacuum and purified by prep-HPLC to afford (S,E)-methyl (7-(dimethylamino)-1-((1-((4-isobutyl-1H-indol-2-yl)methyl)-2-oxo-1,2-dihydropyridin-3-yl)amino)-1,7-dioxohept-5-en-2-yl)carbamate (Compound 231) (31.9 mg, 40% yield) as a yellow solid. LCMS m/z 536.3 $(M+1)^+$. $^1H$ NMR (400 MHz, DMSO-$d_6$) δ 11.0 (s, 1H), 9.30 (s, 1H), 8.21 (dd, J=7.4, 1.6 Hz, 1H), 7.81-7.69 (m, 1H), 7.49 (dd, J=6.8, 1.6 Hz, 1H), 7.21-7.15 (m, 1H), 6.98 (t, J=7.6 Hz, 1H), 6.79-6.70 (m, 1H), 6.67-6.56 (m, 1H), 6.42-6.35 (m, 2H), 6.31 (t, 7.2 Hz, 1H), 5.29 (s, 2H), 4.23-4.14 (m, 1H), 3.57 (s, 3H), 2.99 (s, 3H), 2.84 (s, 3H), 2.66-2.58 (m, 2H), 2.28-2.19 (m, 2H), 2.02-1.85 (m, 2H), 1.80-1.67 (m, 1H), 0.87 (d, J=6.6 Hz, 6H).

The following compounds were prepared according to the procedures described in Example 38 using the appropriate intermediates.

| Compound | Structure | LCMS Data |
| --- | --- | --- |
| 232 | 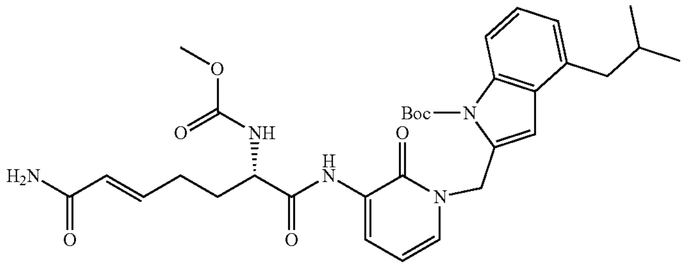 [SMILES: COC(=O)N[C@@H](CC/C=C/C(N)=O)C(=O)Nc1cccn(Cc2cc3c(CC(C)C)cccc3n2C(=O)OC(C)(C)C)c1=O] | LCMS m/z 608.4 $(M + 1)^+$ |
| 233 | 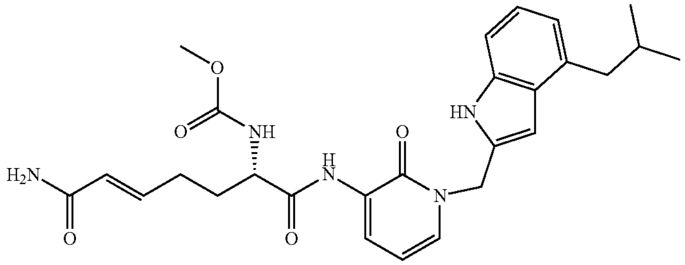 [SMILES: COC(=O)N[C@@H](CC/C=C/C(N)=O)C(=O)Nc1cccn(Cc2cc3c(CC(C)C)cccc3[nH]2)c1=O] | LCMS m/z 508.2 $(M + 1)^+$ |
| 234 | 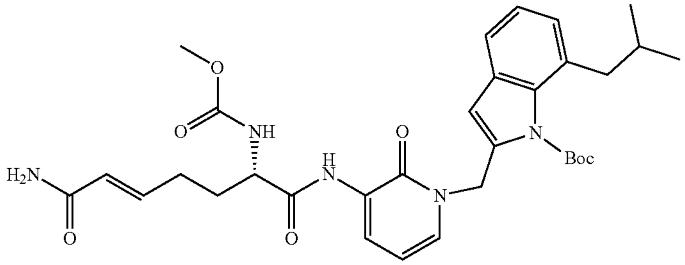 [SMILES: COC(=O)N[C@@H](CC/C=C/C(N)=O)C(=O)Nc1cccn(Cc2cc3cccc(CC(C)C)c3n2C(=O)OC(C)(C)C)c1=O] | LCMS m/z 608.3 $(M + 1)^+$ |
| 235 | 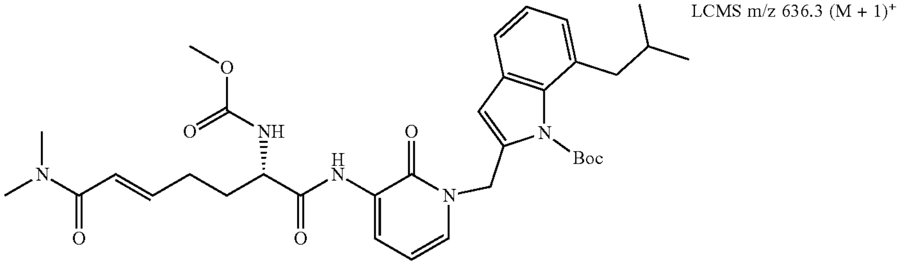 | LCMS m/z 636.3 $(M + 1)^+$ |
| 236 | 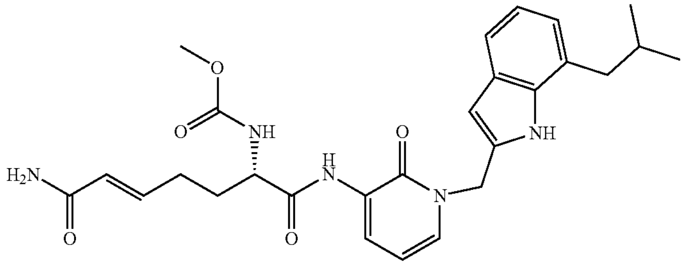 [SMILES: COC(=O)N[C@@H](CC/C=C/C(N)=O)C(=O)Nc1cccn(Cc2cc3cccc(CC(C)C)c3[nH]2)c1=O] | LCMS m/z 508.2 $(M + 1)^+$ |

-continued
| Compound | Structure | LCMS Data |
| --- | --- | --- |
| 237 | 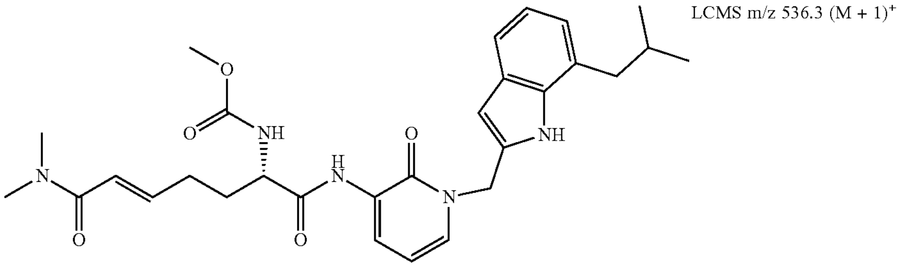 | LCMS m/z 536.3 (M + 1)+ |
| 238 | 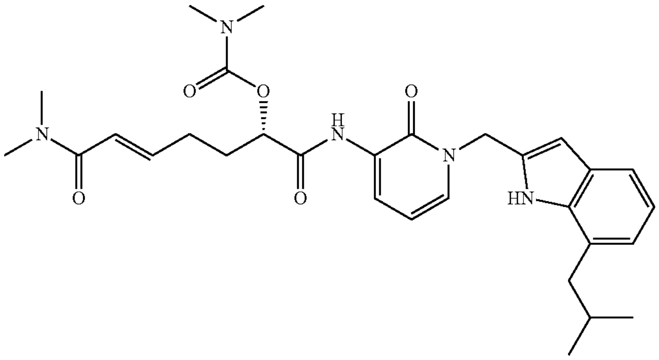 [SMILES: CC(C)Cc1cccc2cc(Cn3cccc(NC(=O)[C@H](CC/C=C/C(=O)N(C)C)OC(=O)N(C)C)c3=O)[nH]c12] | LCMS m/z 550.3 (M + 1)+ |
| 239 | 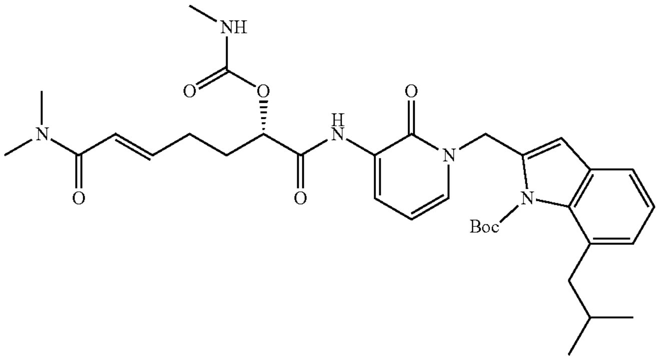 [SMILES: CNC(=O)O[C@@H](CC/C=C/C(=O)N(C)C)C(=O)Nc1cccn(Cc2cc3cccc(CC(C)C)c3n2C(=O)OC(C)(C)C)c1=O] | LCMS m/z 636.1 (M + 1)+ |
| 240 | 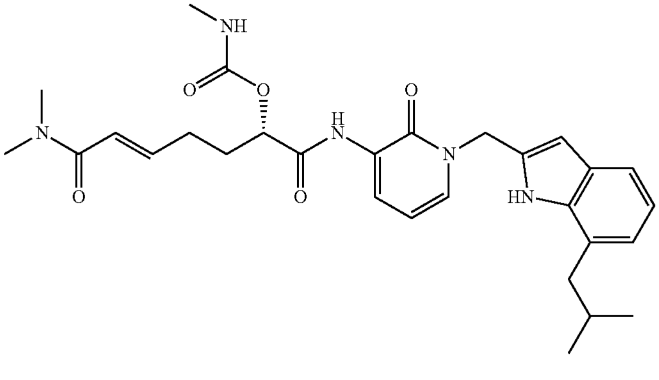 [SMILES: CNC(=O)O[C@@H](CC/C=C/C(=O)N(C)C)C(=O)Nc1cccn(Cc2cc3cccc(CC(C)C)c3[nH]2)c1=O] | LCMS m/z 536.2 (M + 1)+ |

-continued
| Compound | Structure | LCMS Data |
| --- | --- | --- |
| 241 | 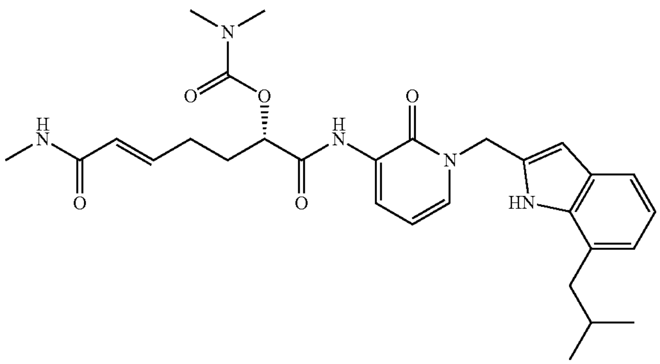 [SMILES: CNC(=O)/C=C/CC[C@H](OC(=O)N(C)C)C(=O)Nc1cccn(Cc2cc3cccc(CC(C)C)c3[nH]2)c1=O] | LCMS m/z 536.2 (M + 1)$^+$ |
| 242 | 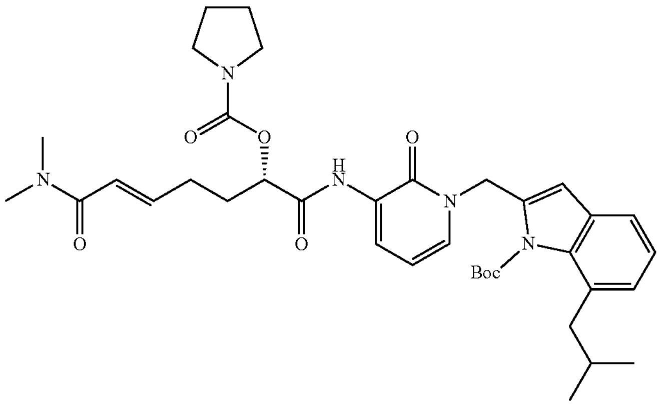 [SMILES: CC(C)Cc1cccc2cc(Cn3cccc(NC(=O)[C@H](CC/C=C/C(=O)N(C)C)OC(=O)N4CCCC4)c3=O)n(C(=O)OC(C)(C)C)c12] | LCMS m/z 676.4 (M + 1)$^+$ |
| 243 | 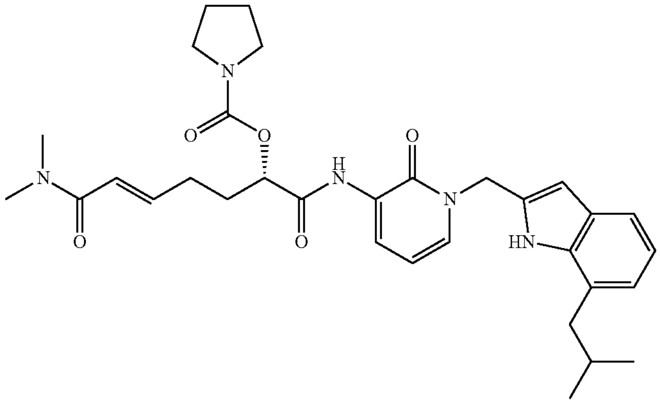 [SMILES: CC(C)Cc1cccc2cc(Cn3cccc(NC(=O)[C@H](CC/C=C/C(=O)N(C)C)OC(=O)N4CCCC4)c3=O)[nH]c12] | LCMS m/z 576.3 (M + 1)$^+$ |
| 244 | 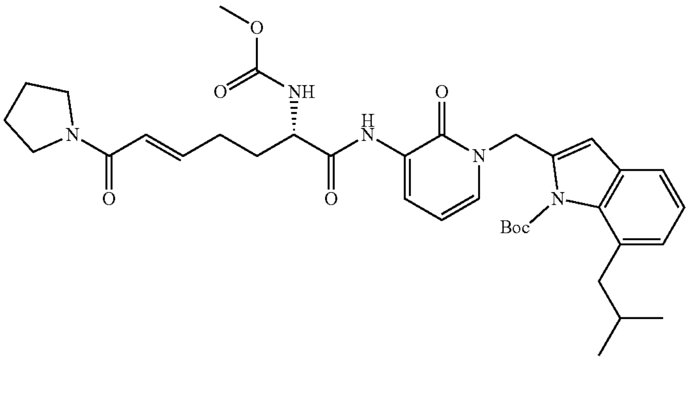 [SMILES: COC(=O)N[C@@H](CC/C=C/C(=O)N1CCCC1)C(=O)Nc1cccn(Cc2cc3cccc(CC(C)C)c3n2C(=O)OC(C)(C)C)c1=O] | LCMS m/z 662.3 (M + 1)$^+$ |

-continued
| Compound | Structure | LCMS Data |
| --- | --- | --- |
| 245 | 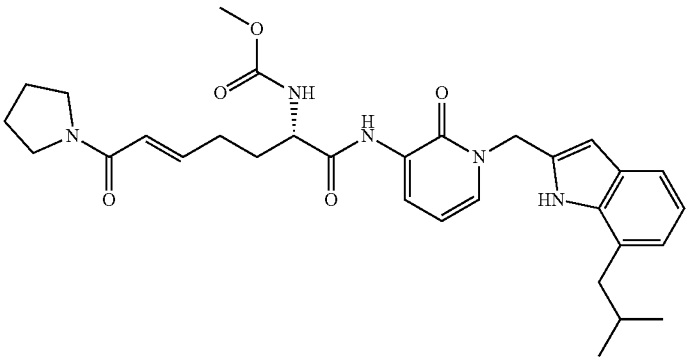 [SMILES: COC(=O)N[C@@H](CC/C=C/C(=O)N1CCCC1)C(=O)Nc1cccn(Cc2cc3cccc(CC(C)C)c3[nH]2)c1=O] | LCMS m/z 562.4 $(M + 1)^+$ |
| 246 | 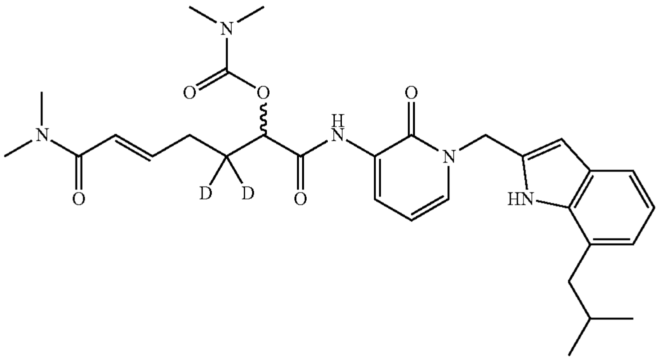 [SMILES: [2H]C([2H])(C/C=C/C(=O)N(C)C)C(OC(=O)N(C)C)C(=O)Nc1cccn(Cc2cc3cccc(CC(C)C)c3[nH]2)c1=O] | LCMS m/z 552.3 $(M + 1)^+$ |
| 247 | 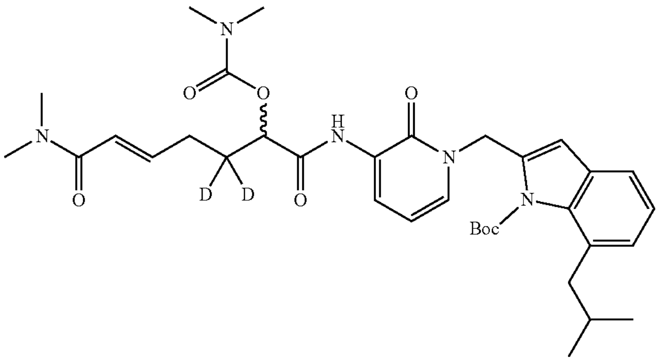 [SMILES: [2H]C([2H])(C/C=C/C(=O)N(C)C)C(OC(=O)N(C)C)C(=O)Nc1cccn(Cc2cc3cccc(CC(C)C)c3n2C(=O)OC(C)(C)C)c1=O] | LCMS m/z 652.3 $(M + 1)^+$ |
| 248 | 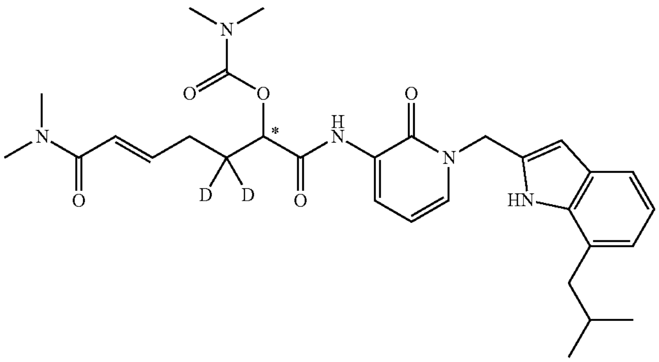 [SMILES: [2H]C([2H])(C/C=C/C(=O)N(C)C)C(OC(=O)N(C)C)C(=O)Nc1cccn(Cc2cc3cccc(CC(C)C)c3[nH]2)c1=O] | LCMS m/z 552.2 $(M + 1)^+$ |

-continued
| Compound | Structure | LCMS Data |
| --- | --- | --- |
| 249 | 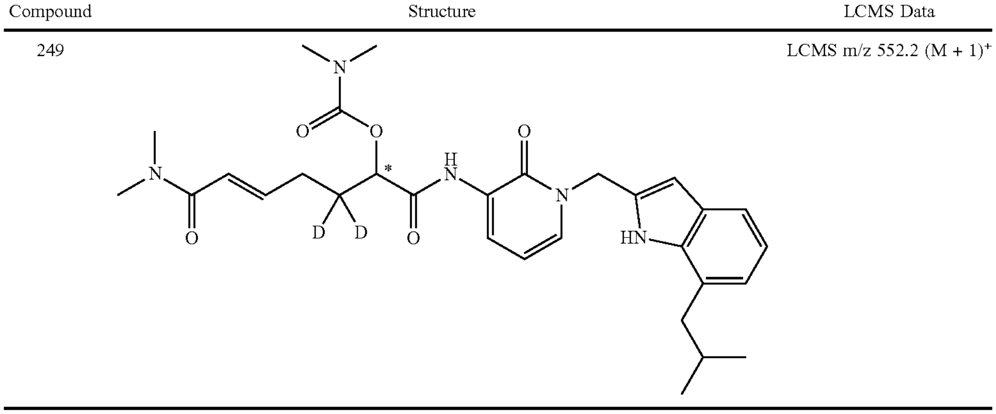 | LCMS m/z 552.2 (M + 1)$^+$ |
Example 39
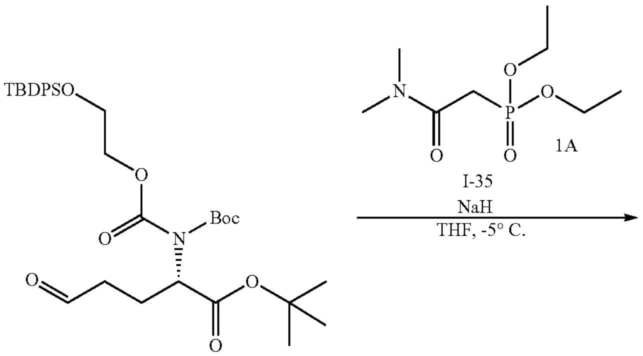
I-103
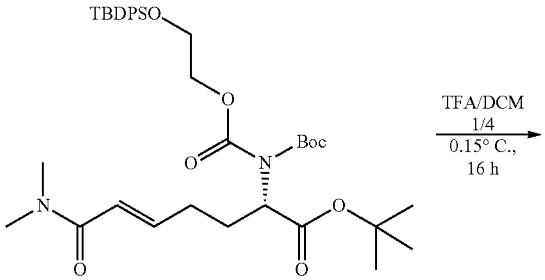
I-352
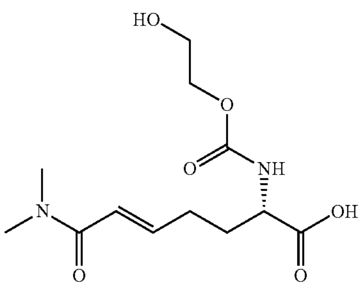
+
I-353

-continued
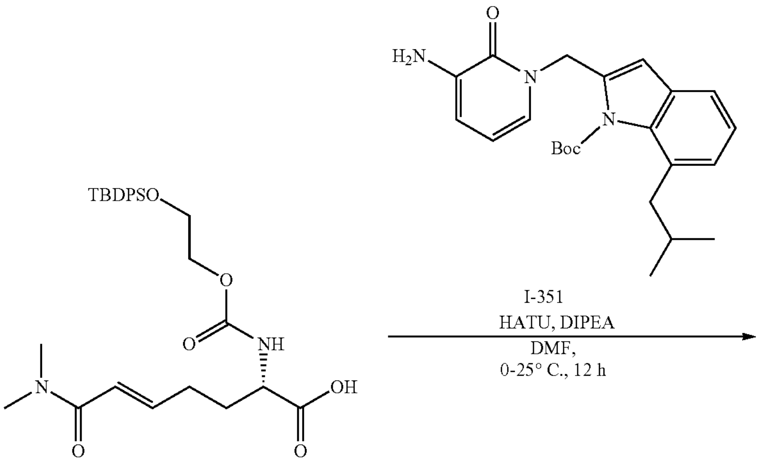
I-354
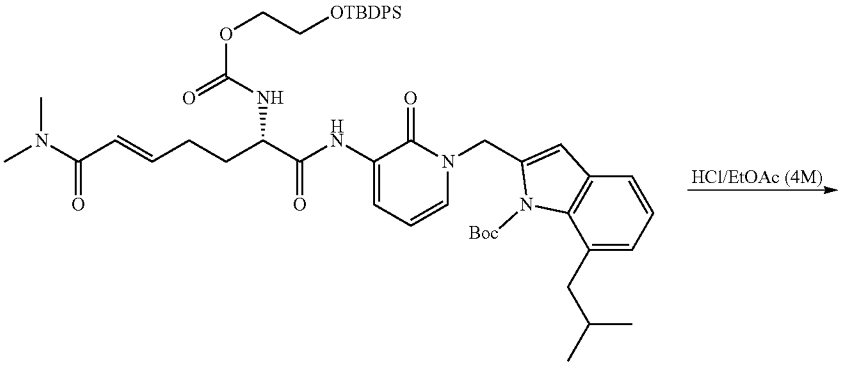
I-355
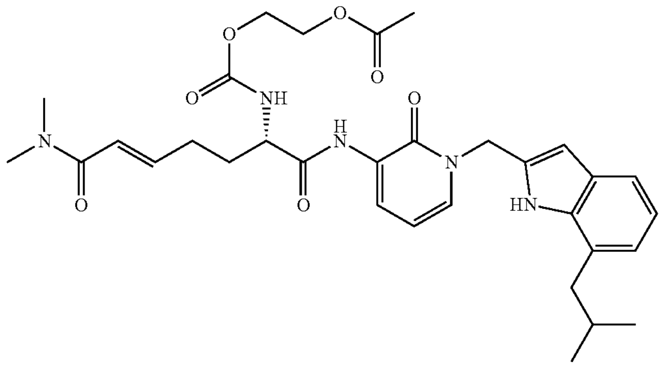
250
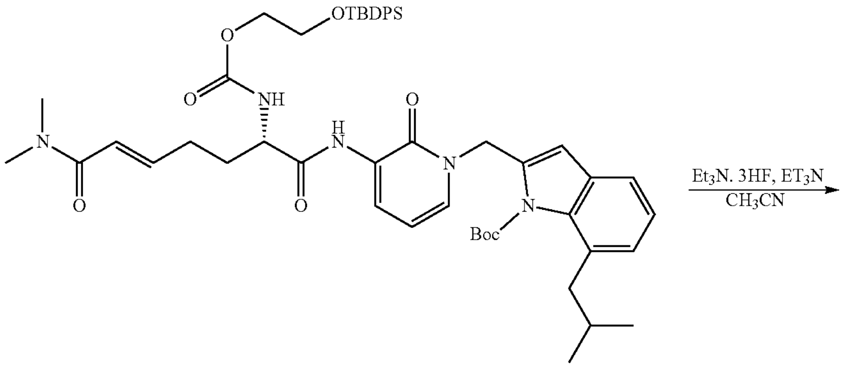
I-355

-continued

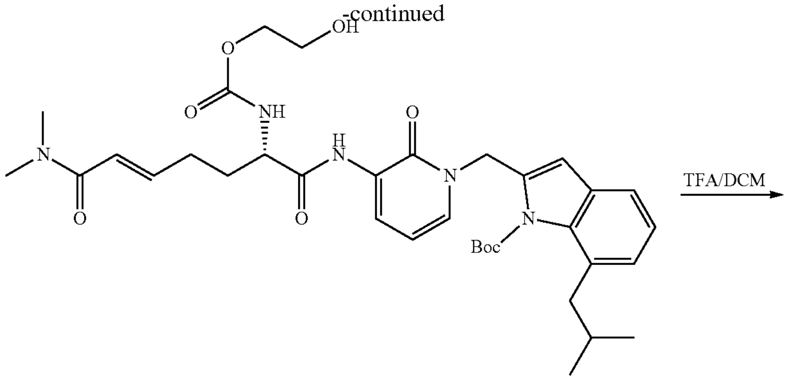

251

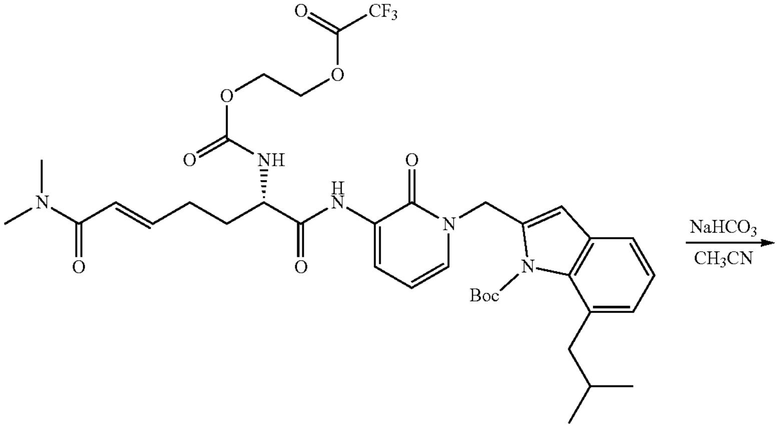

I-356

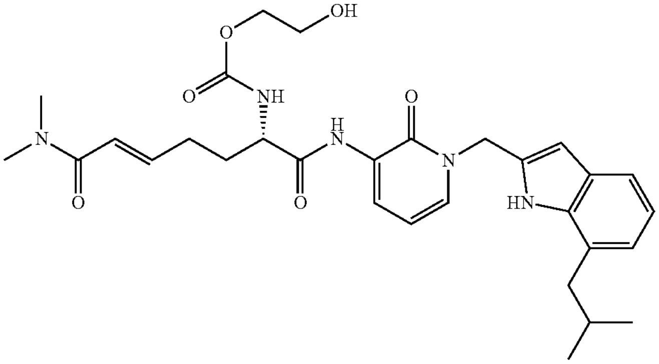

252

To a stirring solution of diethyl (2-(dimethylamino)-2-oxoethyl)phosphonate (2.18 g, 9.77 mmol) in THF (50 mL) was added NaH (391 mg, 9.77 mmol) at −5° C. The resulting suspension was stirred at 20° C. for 0.5 h. A solution of tert-butyl(2S)-2-[tert-butoxycarbonyl-[2-[tert-butyl(diphenyl)silyl]oxyethoxycarbonyl]amino]-5-oxo-pentanoate (5 g, 8.15 mmol) in THF (20 mL) was then added dropwise at −5° C. over 0.5 h. The reaction mixture (combined with the other four batches) was poured into saturated $NH_4Cl$ solution (200 mL) and extracted with EtOAc (200 mL×2). The combined organic layers were washed with brine (500 mL) and dried over anhydrous $Na_2SO_4$, filtered and concentrated in vacuum to give a residue. The residue was purified by silica gel chromatography to give tert-butyl(E,2S)-2-[tert-butoxycarbonyl-[2-[tert-butyl(diphenyl)silyl]oxyethoxycarbonyl]amino]-7-(dimethylamino)-7-oxo-hept-5-enoate (I-352) (6.3 g, 23% yield) as a colorless oil. $^1$H NMR (400 MHz, $CDCl_3$) δ7.69-7.64 (m, 4H), 7.45-7.36 (m, 6H), 6.88-6.79 (m, 1H), 6.24 (d, J=14.8 Hz, 1H), 4.86-4.78 (m, 1H), 4.39-4.21 (m, 2H), 3.88 (t, J=5.2 Hz, 2H), 3.49 (s, 3H), 3.02 (s, 3H), 2.99 (s, 3H), 2.30-2.19 (m, 3H), 2.14-1.97 (m, 1H), 1.49 (s, 9H), 1.43 (s, 9H), 1.05 (s, 9H).

To a solution of tert-butyl (E,2S)-2-[tert-butoxycarbonyl-[2-[tert-butyl(diphenyl)silyl] oxyethoxycarbonyl]amino]-7-(dimethylamino)-7-oxo-hept-5-enoate (5 g, 7.32 mmol) in DCM (10 mL) was added TFA (20 mL) at 0° C. The mixture was stirred at 20° C. for 4 h. The reaction mixture was concentrated under reduced pressure at 20° C. to give a residue. The residue was purified by prep-HPLC to give (S,E)-7-(dimethylamino)-2-(((2-hydroxyethoxy)carbonyl) amino)-7-oxohept-5-enoic acid (I-353) (1.36 g, 62% yield) as a colorless oil and (S,E)-10-(5-(dimethylamino)-5-oxopent-3-en-1-yl)-2,2-dimethyl-8-oxo-3,3-diphenyl-4,7-dioxa-9-aza-3-silaundecan-11-oic acid (I-354) (150 mg) as a white solid. LCMS m/z 527.1 $(M+1)^+$. Intermediate I-353: $^1$H NMR (400 MHz, DMSO-$d_6$) δ7.50 (d, J=8.0 Hz, 1H), 6.65-6.53 (m, 1H), 6.40 (d, J=15.2 Hz, 1H), 4.02-3.85 (m, 3H), 3.54 (t, J=4.8 Hz, 2H), 3.01 (s, 3H), 2.84 (s, 3H), 2.29-2.15 (m, 2H), 1.87-1.64 (m, 2H). Intermediate I-354: $^1$H NMR (400 MHz, DMSO-$d_6$) δ7.65-7.61 (m, 4H), 7.48-7.42 (m, 6H), 6.65-6.54 (m, 1H), 6.35 (d, J=15.2 Hz, 1H), 4.21-4.11 (m, 1H), 4.08-4.00 (m, 1H), 3.93-3.86 (m, 1H), 3.78 (t, J=4.8 Hz, 2H), 2.97 (s, 3H), 2.84 (s, 3H), 2.26-2.17 (m, 2H), 1.89-1.78 (m, 1H), 1.78-1.66 (m, 1H), 0.99 (s, 9H).

To a solution of tert-butyl 2-((3-amino-2-oxopyridin-1(2H)-yl)methyl)-7-isobutyl-1H-indole-1-carboxylate (80 mg, 202 μmol) and (S,E)-10-(5-(dimethylamino)-5-oxopent-3-en-1-yl)-2,2-dimethyl-8-oxo-3,3-diphenyl-4,7-dioxa-9-aza-3-silaundecan-11-oic acid (160 mg, 303 μmol) in DMF (1 mL) were added HATU (162 mg, 425 μmol) and DIPEA (78 mg, 607 μmol) at 0° C. The mixture was stirred at 20° C. for 12 h. The mixture (together with another 20 mg batch) was diluted with EtOAc (40 mL) and washed with brine (15 mL×3). The organic phase was dried over anhydrous $Na_2SO_4$ and concentrated to give a residue. The residue was purified by prep-HPLC to give (S,E)-tert-butyl 2-((3-(10-(5-(dimethylamino)-5-oxopent-3-en-1-yl)-2,2-dimethyl-8-oxo-3,3-diphenyl-4,7-dioxa-9-aza-3-silaundecanamido)-2-oxopyridin-1 (2H)-yl)methyl)-7-isobutyl-1H-indole-1-carboxylate (I-355) (90 mg, 49% yield) as a yellow solid. LCMS m/z 904.5 $(M+1)^+$.

To a solution of (S,E)-tert-butyl 2-((3-(10-(5-(dimethylamino)-5-oxopent-3-en-1-yl)-2,2-dimethyl-8-oxo-3,3-diphenyl-4,7-dioxa-9-aza-3-silaundecanamido)-2-oxopyridin-1(2H)-yl)methyl)-7-isobutyl-1H-indole-1-carboxylate (70 mg, 77 μmol) in DCM (0.5 mL) was added HCl/EtOAc (4 M, 0.7 mL). The mixture was stirred at 20° C. for 13 h. The mixture was concentrated to give a residue. The residue was purified by prep-HPLC to give (S,E)-2-(((7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamoyl)oxy)ethyl acetate (Compound 250) (19.4 mg, 40% yield) as a white solid. LCMS m/z 608.3 $(M+1)^+$.

To a solution of (S,E)-tert-butyl 2-((3-(10-(5-(dimethylamino)-5-oxopent-3-en-1-yl)-2,2-dimethyl-8-oxo-3,3-diphenyl-4,7-dioxa-9-aza-3-silaundecanamido)-2-oxopyridin-1(2H)-yl)methyl)-7-isobutyl-1H-indole-1-carboxylate (50 mg, 51 μmol) in THF (1 mL) were added $Et_3N{\cdot}3HF$ (49 mg, 305 μmol) and $Et_3N$ (15 mg, 153 μmol). The mixture was stirred at 25° C. for 12 h. The mixture was concentrated to give a residue. The residue was purified by prep-HPLC to give (S,E)-tert-butyl 2-((3-(7-(dimethylamino)-2-(((2-hydroxyethoxy)carbonyl)amino)-7-oxohept-5-enamido)-2-oxopyridin-1(2H)-yl)methyl)-7-isobutyl-1H-indole-1-carboxylate (Compound 251) (10 mg, 29% yield) as a white solid. LCMS m/z 666.3 $(M+1)^+$. $^1$H NMR (400 MHz, DMSO-$d_6$) δ 9.32 (s, 1H), 8.31 (dd, J=7.2, 1.6 Hz, 1H), 7.78 (d, J=7.6 Hz, 1H), 7.48 (dd, J=6.8, 1.6 Hz, 1H), 7.36 (d, J=6.8 Hz, 1H), 7.13-7.10 (m, 1H), 7.04-7.03 (m, 1H), 6.65-6.58 (m, 1H), 6.41-6.37 (m, 2H), 5.98 (s, 1H), 5.38 (s, 2H), 4.19-4.03 (m, 1H), 4.03-3.92 (m, 2H), 3.55-3.46 (m, 3H), 3.00 (s, 3H), 2.84-2.81 (m, 5H), 2.30-2.19 (m, 2H), 1.90-1.67 (m, 3H), 1.62 (s, 9H), 0.74 (s, 3H), 0.72 (s, 3H).

To a solution of (S,E)-tert-butyl 2-((3-(7-(dimethylamino)-2-(((2-hydroxyethoxy) carbonyl)amino)-7-oxohept-5-enamido)-2-oxopyridin-1(2H)-yl)methyl)-7-isobutyl-1H-indole-1-carboxylate (85.9 mg, 129 μmol) in DCM (5 mL) was added TFA (1 mL). The mixture was stirred at 15° C. for 1 h. The mixture was concentrated to give (S,E)-2-(((7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamoyl)oxy)ethyl2,2,2-trifluoroacetate (I-356) (90 mg) as a yellow oil.

To a solution of (S,E)-2-(((7-(dimethylamino)-1-((1-((7-isobutyl-1H-indol-2-yl) methyl)-2-oxo-1,2-dihydropyridin-3-yl)amino)-1,7-dioxohept-5-en-2-yl)carbamoyl) oxy)ethyl 2,2,2-trifluoroacetate (90 mg, 136 μmol) in $CH_3CN$ (3 mL) was added $NaHCO_3$ (57 mg, 680 μmol). The mixture was stirred at 20° C. for 12 h. The mixture was filtered off and the filtrate was concentrated to give a residue. The residue was purified by prep-HPLC to give (S,E)-2-hydroxyethyl (7-(dimethylamino)-1-((1-((7-isobutyl-1H-indol-2-yl) methyl)-2-oxo-1,2-dihydropyridin-3-yl)amino)-1,7-dioxohept-5-en-2-yl)carbamate (Compound 252) (22.3 mg, 29% yield) as a white solid. LCMS m/z 566.3 $(M+1)^+$. $^1$H NMR (400 MHz, DMSO-$d_6$) δ 11.02 (s, 1H), 9.32 (s, 1H), 8.26-8.22 (m, 1H), 7.79 (d, J=7.6 Hz, 1H), 7.49-7.46 (m, 1H), 7.28 (d, J=7.6 Hz, 1H), 6.91-6.83 (m, 2H), 6.65-6.58 (m, 1H), 6.40-6.30 (m, 2H), 6.21 (s, 1H), 5.30 (s, 2H), 4.77 (b.r., 1H), 4.22-4.16 (m, 1H), 4.04-3.95 (m, 2H), 3.56 (s, 2H), 2.99 (s, 3H), 2.83 (s, 3H), 2.68-2.67 (m, 2H), 2.30-2.21 (m, 1H), 2.01-1.71 (m, 3H), 0.91 (s, 3H), 0.89 (s, 3H).

The following compounds were prepared according to the procedures described in Example 39 using the appropriate intermediates.

| Compound | Structure | LCMS Data |
|---|---|---|
| 253 | 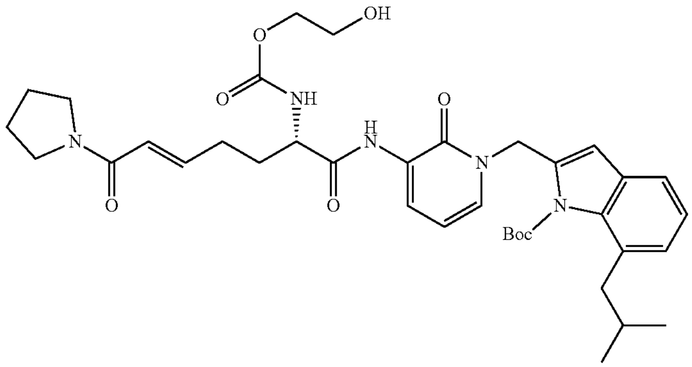 [SMILES: CC(C)Cc1cccc2cc(Cn3cccc(NC(=O)[C@H](CC/C=C/C(=O)N4CCCC4)NC(=O)OCCO)c3=O)n(C(=O)OC(C)(C)C)c12] | LCMS m/z 692.3 (M + 1)$^+$ |

-continued
| Compound | Structure | LCMS Data |
| --- | --- | --- |
| 254 | 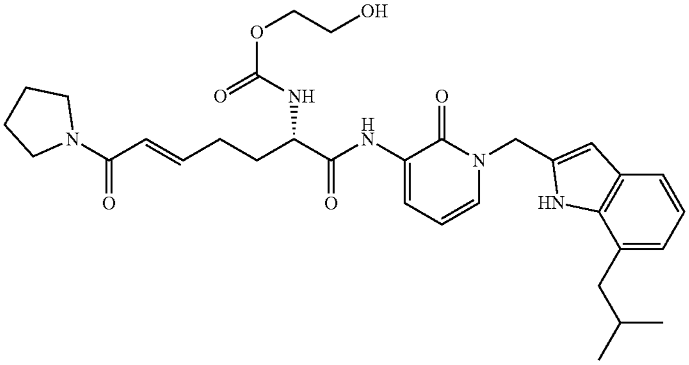 [SMILES: CC(C)Cc1cccc2cc(Cn3cccc(NC(=O)[C@H](CC/C=C/C(=O)N4CCCC4)NC(=O)OCCO)c3=O)[nH]c12] | LCMS m/z 592.3 (M + 1)+ |
Synthesis of Intermediate I-365
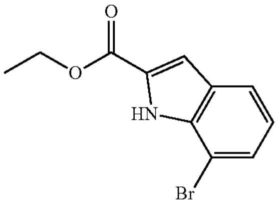
I-357
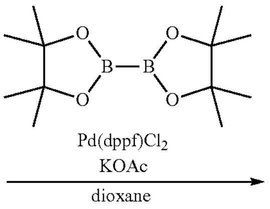
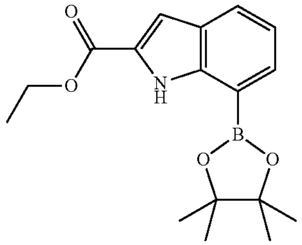
I-358
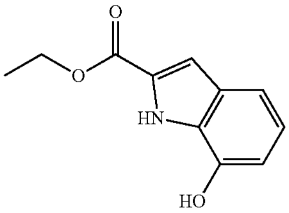
I-359
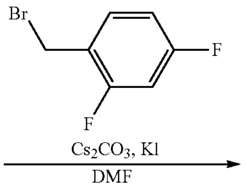
-continued
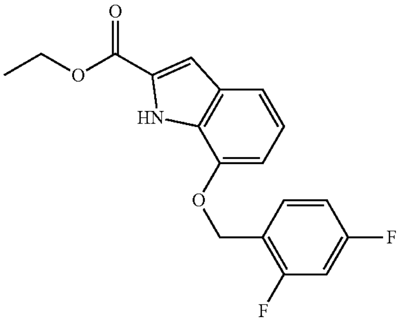
I-360
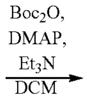
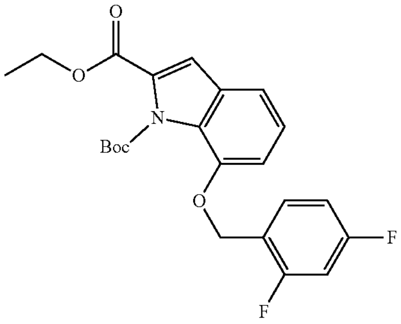
I-361
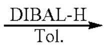
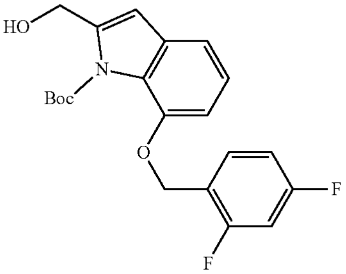
I-362
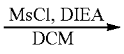

-continued

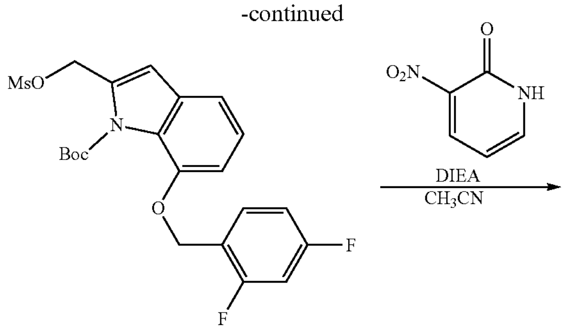

I-363

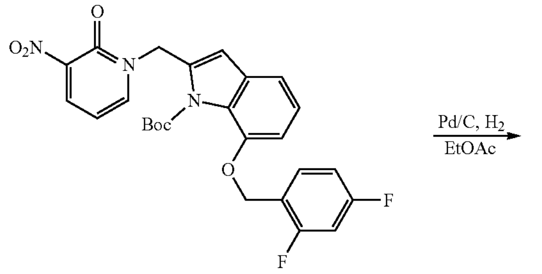

I-364

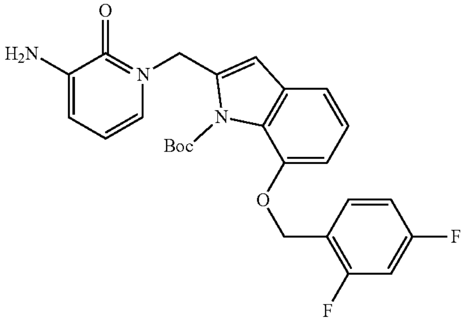

I-365

To a mixture of ethyl 7-bromo-1H-indole-2-carboxylate (7 g, 26.1 mmol) and 4,4,4',4',5,5,5',5'-octamethyl-2,2'-bi(1,3,2-dioxaborolane) (9.95 g, 39.2 mmol) in dioxane (70 mL) were added KOAc (5.12 g, 52.2 mmol) and Pd(dppf)$Cl_2$ (1.91 g, 2.61 mmol). The mixture was stirred at 90° C. for 2 h under $N_2$ atmosphere. The mixture was diluted with water (100 mL) and extracted with ethyl acetate (100 mL×2). The combined organic layers were washed with brine (300 mL), dried over anhydrous $Na_2SO_4$, filtered and concentrated in vacuum. The residue was purified by silica gel chromatography to afford ethyl 7-(4,4,5,5-tetramethyl-1,3,2-dioxaborolan-2-yl)-1H-indole-2-carboxylate (I-358) (10.4 g) as a yellow oil.

To a mixture of 7-(4,4,5,5-tetramethyl-1,3,2-dioxaborolan-2-yl)-1H-indole-2-carboxylate (11 g, 34.9 mmol) in THF (100 mL) was added $H_2O_2$ (39.6 g, 349 mmol, 33.5 mL, 30% purity) at 0° C. The mixture was stirred at 15° C. for 12 h. The reaction mixture was quenched with saturated $Na_2SO_3$ (200 mL), and extracted with ethyl acetate (200 mL×2). The combined organic layers were washed with brine (300 mL), dried over anhydrous $Na_2SO_4$, filtered and concentrated to give a residue. The residue was purified by silica gel chromatography to afford ethyl 7-hydroxy-1H-indole-2-carboxylate (I-359) (6.5 g) as a yellow solid.

To a mixture ethyl 7-hydroxy-1H-indole-2-carboxylate (5.5 g, 26.8 mmol) and 1-(bromomethyl)-2,4-difluoro-benzene (3.33 g, 16.1 mmol) in DMF (40 mL) were added $Cs_2CO_3$ (17.5 g, 53.6 mmol) and KI (4.45 g, 26.8 mmol). The mixture was stirred at 20° C. for 1 h. The resulting solution was diluted with water (30 mL) and extracted with ethyl acetate (30 mL×2). The combined organic layers were washed with brine (50 mL×3), dried over anhydrous $Na_2SO_4$, filtered and concentrated in vacuum to give a residue. The residue was purified by silica gel chromatography to afford ethyl 7-((2,4-difluorobenzyl)oxy)-1H-indole-2-carboxylate (I-360) (3 g) as a yellow solid. $^1H$ NMR (400 MHz, $CDCl_3$) δ 9.04 (s, 1H), 7.56-7.47 (m, 1H), 7.36-7.29 (m, 1H), 7.24-7.19 (m, 1H), 7.07 (t, J=8.0 Hz, 1H), 6.99-6.86 (m, 2H), 6.85-6.77 (m, 1H), 5.24 (s, 2H), 4.46-4.37 (m, 2H), 1.47-1.38 (m, 3H).

To a mixture of ethyl 7-((2,4-difluorobenzyl)oxy)-1H-indole-2-carboxylate (1.9 g, 5.73 mmol) in DCM (20 mL) were added $Boc_2O$ (1.88 g, 8.6 mmol, 1.98 mL), TEA (1.16 g, 11.5 mmol, 1.59 mL) and DMAP (70.1 mg, 0.573 mmol). The mixture was stirred at 20° C. for 1 h. The resulting solution was concentrated in vacuum to give a residue. The residue was purified by silica gel chromatography to afford 1-tert-butyl 2-ethyl 7-((2,4-difluorobenzyl)oxy)-1H-indole-1,2-dicarboxylate (I-361) (1.7 g) as a white solid. $^1H$ NMR (400 MHz, $CDCl_3$) δ 7.58-7.49 (m, 1H), 7.27-7.24 (m, 1H), 7.20 (s, 1H), 7.07 (t, J=7.6 Hz, 1H), 6.92-6.79 (m, 3H), 5.27 (s, 2H), 4.43-4.34 (m, 2H), 1.50 (s, 9H), 1.40 (t, J=7.2 Hz, 3H).

To a mixture of 1-tert-butyl 2-ethyl 7-((2,4-difluorobenzyl)oxy)-1H-indole-1,2-dicarboxylate (1.7 g, 3.94 mmol) in toluene (15 mL) was added DIBAL-H (1 M, 9.85 mL) at −78° C. The mixture was stirred at −20° C. for 1 h under $N_2$ atmosphere. The mixture was quenched with sodium potassium tartrate tetrahydrate solution (40 mL) and stirred for 1 h. The resulting solution was extracted with ethyl acetate (30 mL×2). The combined organic layers were washed with brine (50 mL), dried over anhydrous $Na_2SO_4$, filtered and concentrated in vacuum. The residue was purified by silica gel chromatography to afford tert-butyl 7-((2,4-difluorobenzyl)oxy)-2-(hydroxymethyl)-1H-indole-1-carboxylate (I-362) (950 mg) as a yellow oil. $^1H$ NMR (400 MHz, $CDCl_3$) δ 7.54-7.44 (m, 1H), 7.20-7.12 (m, 2H), 6.95-6.81 (m, 3H), 6.52 (s, 1H), 5.22 (s, 2H), 4.72 (s, 2H), 3.34 (s, 1H), 1.45 (s, 9H).

To a mixture of tert-butyl 7-((2,4-difluorobenzyl)oxy)-2-(hydroxymethyl)-1H-indole-1-carboxylate (950 mg, 2.44 mmol) and DIEA (631 mg, 4.88 mmol, 0.852 mL) in DCM (15 mL) was added MsCl (419 mg, 3.66 mmol, 0.283 mL) at 0° C. The mixture was stirred at 20° C. for 1 h. The resulting solution was quenched with water (30 mL) and extracted with DCM (30 mL×2). The combined organic layers were washed with brine (50 mL), dried over anhydrous $Na_2SO_4$, filtered and concentrated in vacuum to afford tert-butyl 7-((2,4-difluorobenzyl)oxy)-2-(((methylsulfonyl)oxy) methyl)-1H-indole-1-carboxylate (I-363) (1.14 g) as a red oil.

To a mixture of tert-butyl 7-((2,4-difluorobenzyl)oxy)-2-(((methylsulfonyl)oxy) methyl)-1H-indole-1-carboxylate (1.14 g, 2.44 mmol) and 3-nitropyridin-2(1H)-one (512 mg, 3.66 mmol) in $CH_3CN$ (10 mL) was added DIEA (631 mg, 4.88 mmol, 0.852 mL). The mixture was stirred at 30° C. for 12 h. The mixture was diluted with water (30 mL) and extracted with ethyl acetate (30 mL×2). The combined organic layers were washed with brine (50 mL), dried over anhydrous $Na_2SO_4$, filtered and concentrated in vacuum. The residue was purified by silica gel chromatography to afford tert-butyl 7-((2,4-difluorobenzyl) oxy)-2-((3-nitro-2-oxopyridin-1(2H)-yl)methyl)-1H-indole-1-carboxylate (I-364) (750 mg) as a yellow oil. $^1$H NMR (400 MHz, $CDCl_3$) δ 8.35 (dd, J=7.6, 2.00 Hz, 1H), 7.81 (dd, J=6.8, 2.4 Hz, 1H), 7.57-7.46 (m, 1H), 7.24-7.17 (m, 2H), 6.95-6.80 (m, 3H), 6.74 (s, 1H), 6.31-6.24 (m, 1H), 5.42 (s, 2H), 5.22 (s, 2H), 1.36 (s, 9H).

To a mixture of tert-butyl 7-((2,4-difluorobenzyl)oxy)-2-((3-nitro-2-oxopyridin-1(2H)-yl)methyl)-1H-indole-1-carboxylate (750 mg, 1.47 mmol) in EtOAc (5 mL) was added Pd/C (300 mg, 10% purity). The mixture was stirred at 15° C. for 30 min under $H_2$ (15 psi) atmosphere. The mixture was filtered, the filtrate was concentrated in vacuum to afford tert-butyl 2-((3-amino-2-oxopyridin-1(2H)-yl) methyl)-7-((2,4-difluorobenzyl) oxy)-1H-indole-1-carboxylate (I-365) (600 mg) as a yellow solid. LCMS m/z 482.2 $(M+1)^+$.

The following intermediate was prepared according to the procedures described for the synthesis of I-365 using the appropriate reagents.

| Compound | Structure | LCMS Data |
|---|---|---|
| I-366 | 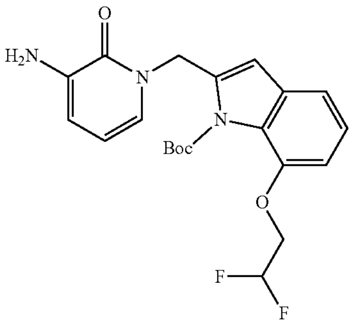 [SMILES: CC(C)(C)OC(=O)n1c(Cn2cccc(N)c2=O)cc2cccc(OCC(F)F)c21] | LCMS m/z 420.1 $(M+1)^+$ |

Example 40

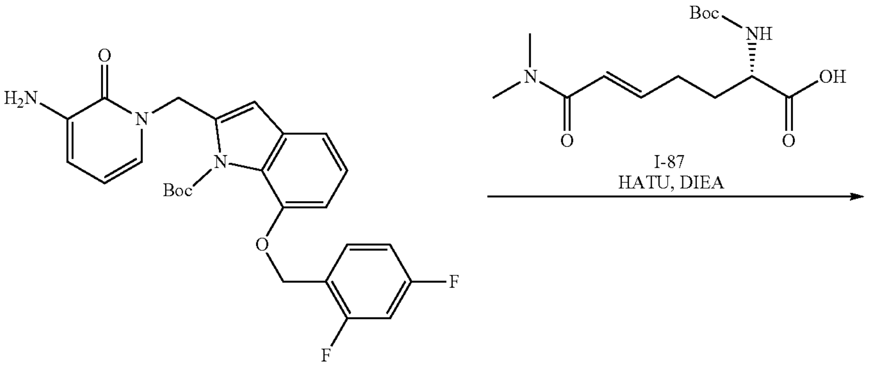

I-365

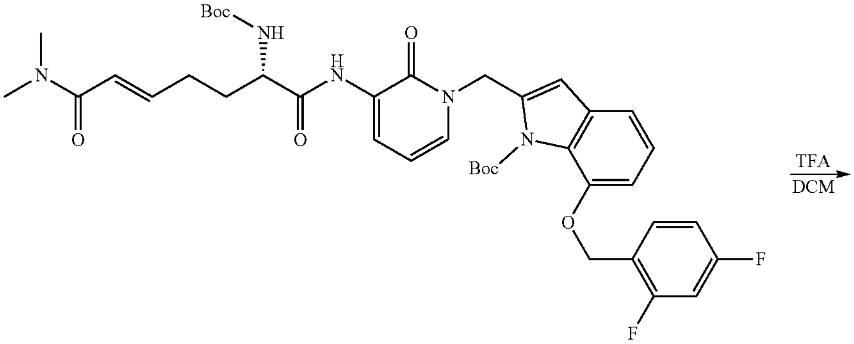

I-367

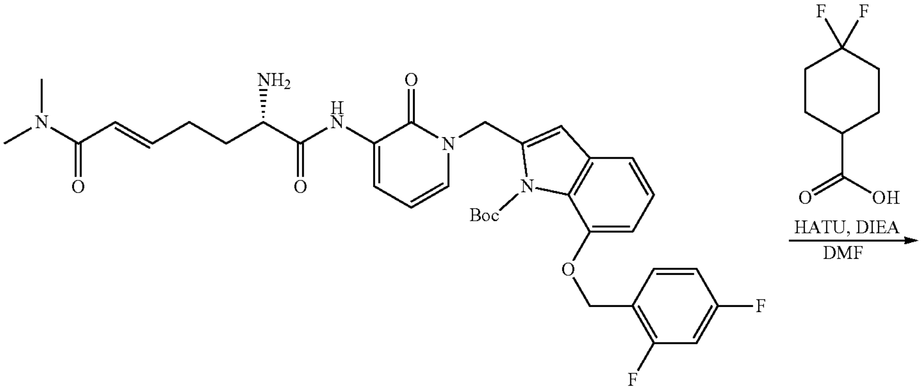

I-368

-continued

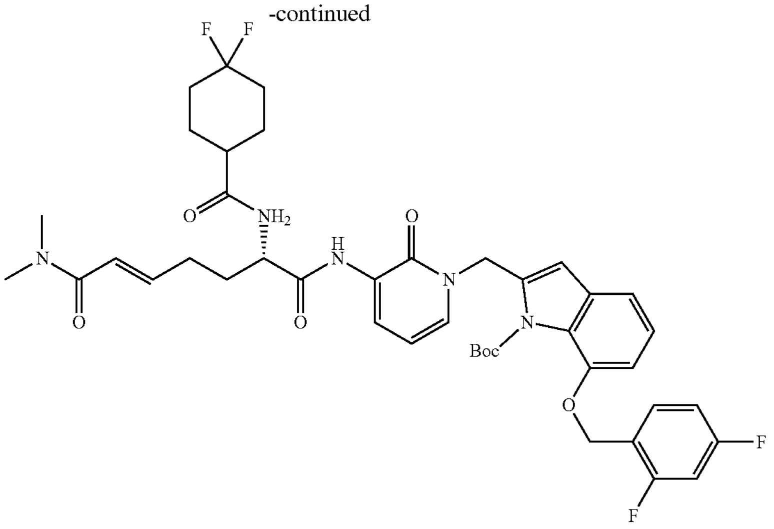

255

To a mixture of tert-butyl 2-((3-amino-2-oxopyridin-1(2H)-yl)methyl)-7-((2,4-difluorobenzyl)oxy)-1H-indole-1-carboxylate (600 mg, 1.25 mmol) and (S,E)-2-((tert-butoxycarbonyl)amino)-7-(dimethylamino)-7-oxohept-5-enoic acid (751 mg, 2.5 mmol) in DMF (5 mL) were added HATU (1.14 g, 3 mmol) and DIEA (646 mg, 5 mmol, 0.873 mL) at 0° C. The mixture was stirred at 15° C. for 12 h. The resulting solution was diluted with water (30 mL) and extracted with ethyl acetate (30 mL×2). The combined organic layers were washed with brine (50 mL×3), dried over anhydrous $Na_2SO_4$, filtered and concentrated in vacuum to give a residue. The residue was purified by silica gel chromatography to afford (S,E)-tert-butyl 2-((3-(2-((tert-butoxycarbonyl)amino)-7-(dimethylamino)-7-oxohept-5-enamido)-2-oxopyridin-1(2H)-yl)methyl)-7-((2,4-difluorobenzyl)oxy)-1H-indole-1-carboxylate (I-367) (600 mg) as a yellow solid. LCMS m/z 764.4 $(M+1)^+$.

To a mixture of (S,E)-tert-butyl 2-((3-(2-((tert-butoxycarbonyl)amino)-7-(dimethylamino)-7-oxohept-5-enamido)-2-oxopyridin-1(2H)-yl)methyl)-7-((2,4-difluorobenzyl)oxy)-1H-indole-1-carboxylate (200 mg, 0.262 mmol) in DCM (3 mL) was added TFA (1.54 g, 13.5 mmol, 1 mL) at 0° C. The mixture was stirred at 15° C. for 1.5 h. The resulting solution was concentrated in vacuum to afford (S,E)-6-amino-N7-(1-((7-((2,4-difluorobenzyl)oxy)-1H-indol-2-yl)methyl)-2-oxo-1,2-dihydropyridin-3-yl)-N1,N1-dimethylhept-2-enediamide (I-368) (177 mg, crude, TFA) as a green oil and used directly in the next step without further purification. LCMS m/z 564.3 $(M+1)^+$.

To a mixture of ((S,E)-6-amino-N7-(1-((7-((2,4-difluorobenzyl)oxy)-1H-indol-2-yl)methyl)-2-oxo-1,2-dihydropyridin-3-yl)-N1,N1-dimethylhept-2-enediamide (177 mg, 0.261 mmol, TFA) and 4,4-difluorocyclohexanecarboxylic acid (85.8 mg, 0.522 mmol) in DMF (2 mL) were added HATU (238 mg, 0.627 mmol) and DIEA (203 mg, 1.57 mmol, 0.274 mL) at 0° C. The mixture was stirred at 15° C. for 12 h. The reaction mixture was purified by prep-HPLC to afford (S,E)-N7-(1-((7-((2,4-difluorobenzyl)oxy)-1H-indol-2-yl)methyl)-2-oxo-1,2-dihydropyridin-3-yl)-6-(4,4-difluorocyclohexanecarboxamido)-N1,N1-dimethylhept-2-enediamide (Compound 255) (84 mg, 45% yield) as a white solid. LCMS m/z 710.2 $(M+1)^+$. $^1H$ NMR (400 MHz, DMSO-$d_6$) δ 11.2 (s, 1H), 9.25 (s, 1H), 8.43 (d, J=7.6 Hz, 1H), 8.19 (dd, J=7.2, 1.8 Hz, 1H), 7.81-7.71 (m, 1H), 7.48 (dd, J=7.2, 2.0 Hz, 1H), 7.39-7.29 (m, 1H), 7.21-7.13 (m, 1H), 7.07 (d, J=7.6 Hz, 1H), 6.90 (t, J=8.0 Hz, 1H), 6.78 (d, J=7.6 Hz, 1H), 6.68-6.56 (m, 1H), 6.37 (d, J=15.1 Hz, 1H), 6.29 (t, J=7.2 Hz, 1H), 6.23 (d, J=2.0 Hz, 1H), 5.30-5.19 (m, 4H), 4.45-4.30 (m, 1H), 2.99 (s, 3H), 2.84 (s, 3H), 2.46-2.36 (m, 1H), 2.30-2.16 (m, 2H), 2.12-2.00 (m, 2H), 1.98-1.70 (m, 6H), 1.70-1.56 (m, 2H).

The following compounds were prepared according to the procedures described in Example 40 using the appropriate intermediates

| Compound | Structure | LCMS Data |
| --- | --- | --- |
| 256 | 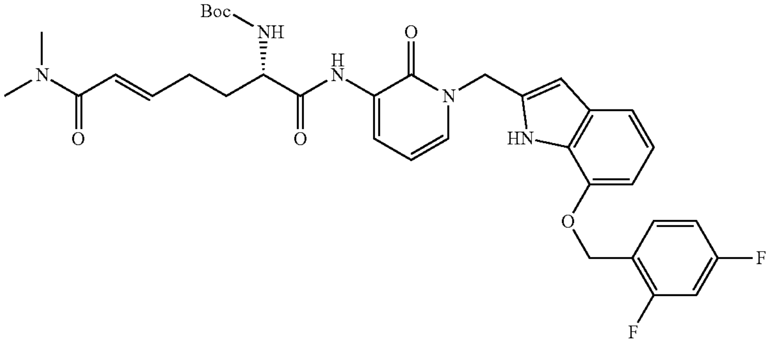 [SMILES: CN(C)C(=O)/C=C/CC[C@H](NC(=O)OC(C)(C)C)C(=O)Nc1cccn(Cc2cc3cccc(OCc4ccc(F)cc4F)c3[nH]2)c1=O] | LCMS m/z 664.2 $(M + 1)^+$ |

-continued
| Compound | Structure | LCMS Data |
| --- | --- | --- |
| 257 | 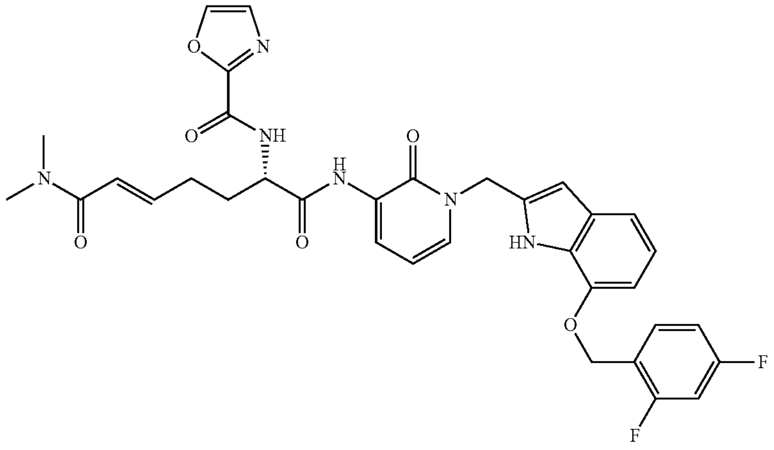 [SMILES: CN(C)C(=O)/C=C/CC[C@H](NC(=O)c1ncco1)C(=O)Nc1cccn(Cc2cc3cccc(OCc4ccc(F)cc4F)c3[nH]2)c1=O] | LCMS m/z 659.2 (M + 1)+ |
| 258 | 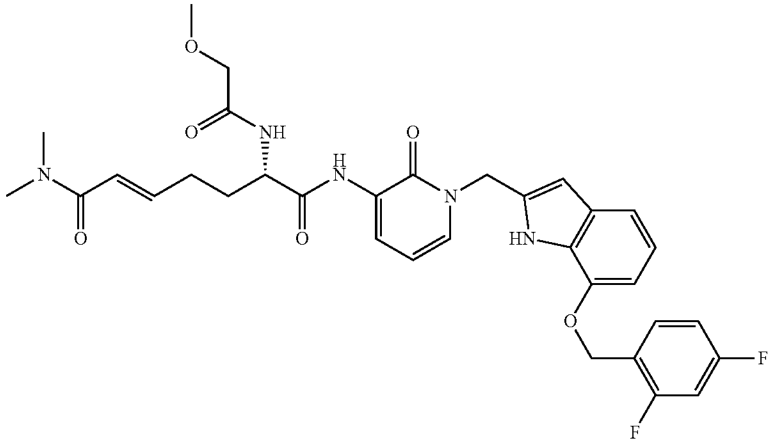 [SMILES: COCC(=O)N[C@@H](CC/C=C/C(=O)N(C)C)C(=O)Nc1cccn(Cc2cc3cccc(OCc4ccc(F)cc4F)c3[nH]2)c1=O] | LCMS m/z 636.2 (M + 1)+ |
| 260 | 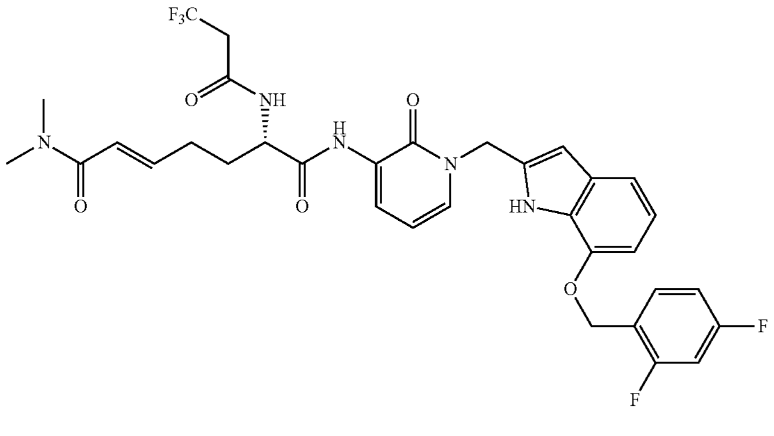 [SMILES: CN(C)C(=O)/C=C/CC[C@H](NC(=O)CC(F)(F)F)C(=O)Nc1cccn(Cc2cc3cccc(OCc4ccc(F)cc4F)c3[nH]2)c1=O] | LCMS m/z 674.1 (M + 1)+ |

-continued
| Compound | Structure | LCMS Data |
| --- | --- | --- |
| 261 | 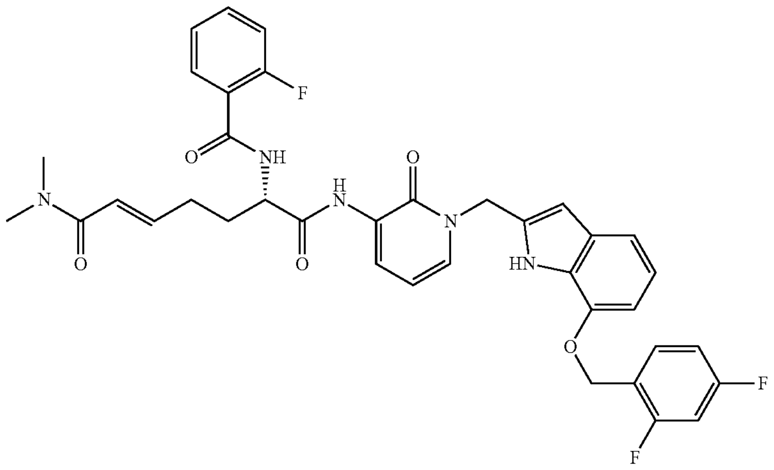 [SMILES: CN(C)C(=O)/C=C/CC[C@H](NC(=O)c1ccccc1F)C(=O)Nc1cccn(Cc2cc3cccc(OCc4ccc(F)cc4F)c3[nH]2)c1=O] | LCMS m/z 686.1 (M + 1)+ |
| 262 | 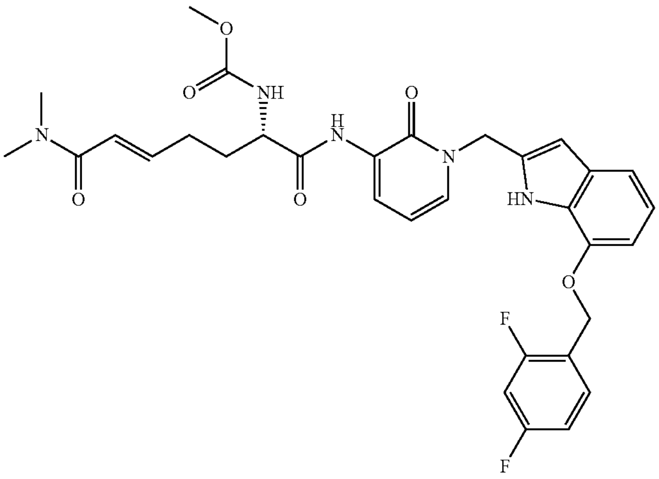 [SMILES: COC(=O)N[C@@H](CC/C=C/C(=O)N(C)C)C(=O)Nc1cccn(Cc2cc3cccc(OCc4ccc(F)cc4F)c3[nH]2)c1=O] | LCMS m/z 622.2 (M + 1)+ |
| 263 | 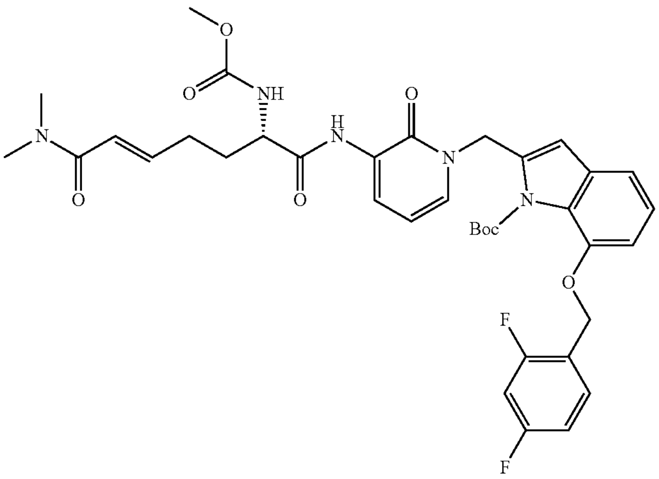 [SMILES: COC(=O)N[C@@H](CC/C=C/C(=O)N(C)C)C(=O)Nc1cccn(Cc2cc3cccc(OCc4ccc(F)cc4F)c3n2C(=O)OC(C)(C)C)c1=O] | LCMS m/z 722.3 (M + 1)+ |

-continued
| Compound | Structure | LCMS Data |
| --- | --- | --- |
| 264 | 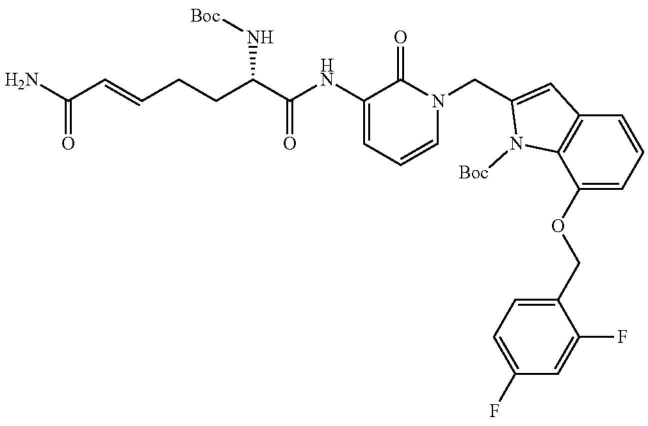 [SMILES: CC(C)(C)OC(=O)N[C@@H](CC/C=C/C(N)=O)C(=O)Nc1cccn(Cc2cc3cccc(OCc4ccc(F)cc4F)c3n2C(=O)OC(C)(C)C)c1=O] | LCMS m/z 758.2 (M + 23)+ |
| 265 | 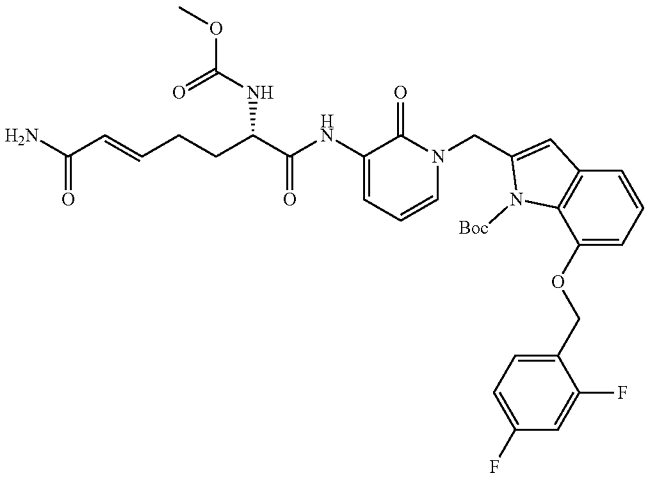 [SMILES: COC(=O)N[C@@H](CC/C=C/C(N)=O)C(=O)Nc1cccn(Cc2cc3cccc(OCc4ccc(F)cc4F)c3n2C(=O)OC(C)(C)C)c1=O] | LCMS m/z 694.3 (M + 1)+ |
| 266 | 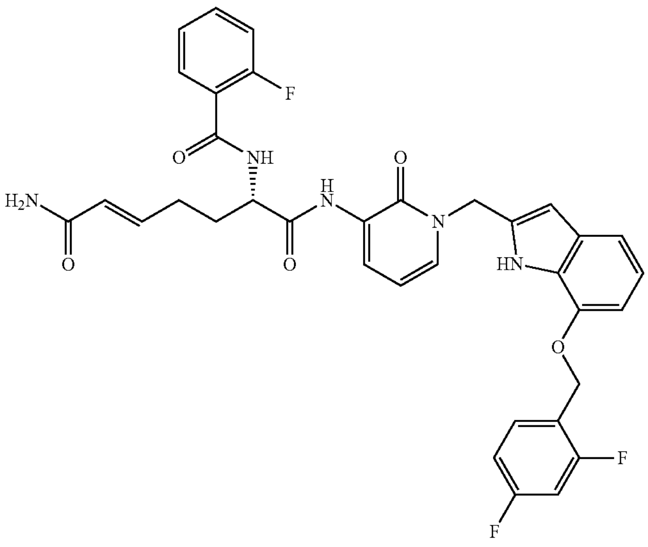 [SMILES: NC(=O)/C=C/CC[C@H](NC(=O)c1ccccc1F)C(=O)Nc1cccn(Cc2cc3cccc(OCc4ccc(F)cc4F)c3[nH]2)c1=O] | LCMS m/z 658.2 (M + 1)+ |

-continued
| Compound | Structure | LCMS Data |
| --- | --- | --- |
| 267 | 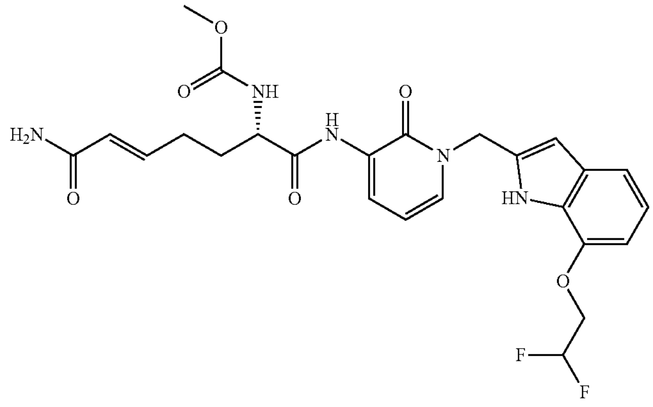 [SMILES: COC(=O)N[C@@H](CC/C=C/C(N)=O)C(=O)Nc1cccn(Cc2cc3cccc(OCC(F)F)c3[nH]2)c1=O] | LCMS m/z 532.2 (M + 1)$^+$ |
| 268 | 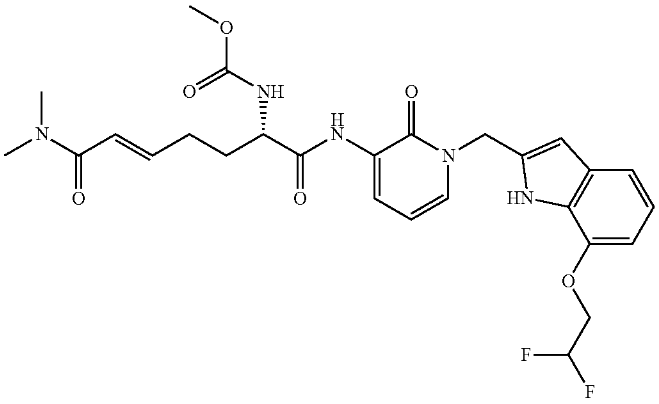 [SMILES: COC(=O)N[C@@H](CC/C=C/C(=O)N(C)C)C(=O)Nc1cccn(Cc2cc3cccc(OCC(F)F)c3[nH]2)c1=O] | LCMS m/z 560.3 (M + 1)$^+$ |
| 269 | 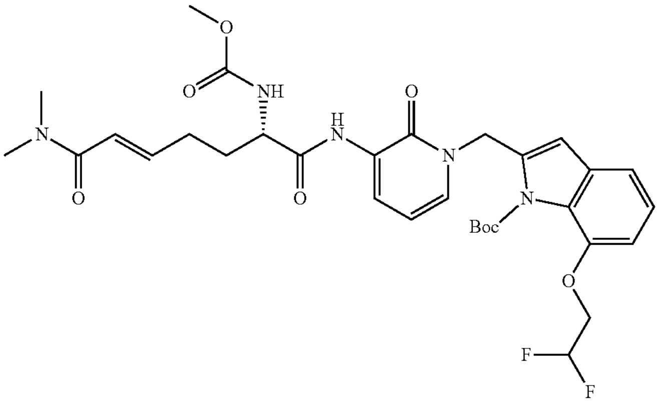 [SMILES: COC(=O)N[C@@H](CC/C=C/C(=O)N(C)C)C(=O)Nc1cccn(Cc2cc3cccc(OCC(F)F)c3n2C(=O)OC(C)(C)C)c1=O] | LCMS m/z 660.3 (M + 1)$^+$ |

-continued
| Compound | Structure | LCMS Data |
|---|---|---|
| 270 | 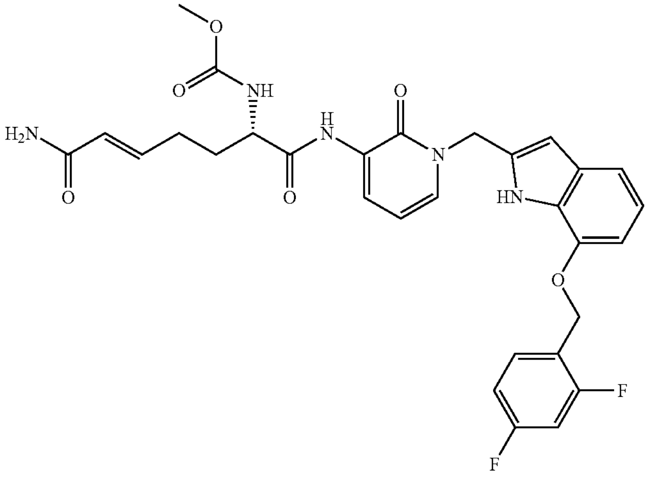 [SMILES: COC(=O)N[C@@H](CC/C=C/C(N)=O)C(=O)Nc1cccn(Cc2cc3cccc(OCc4ccc(F)cc4F)c3[nH]2)c1=O] | LCMS m/z 594.2 $(M+1)^+$ |
| 271 | 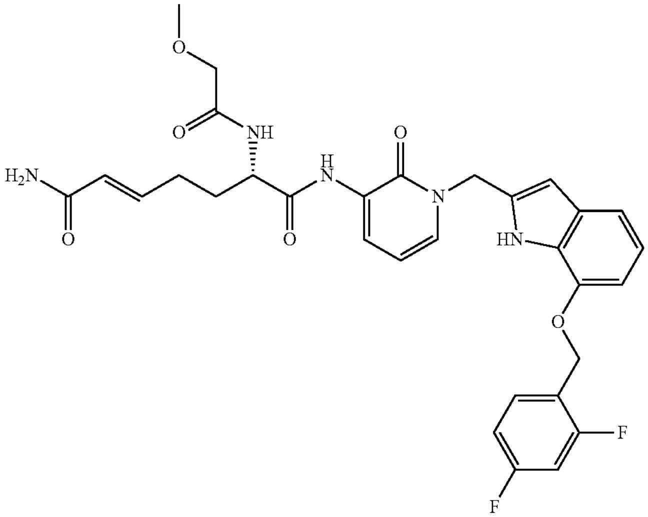 [SMILES: COCC(=O)N[C@@H](CC/C=C/C(N)=O)C(=O)Nc1cccn(Cc2cc3cccc(OCc4ccc(F)cc4F)c3[nH]2)c1=O] | LCMS m/z 608.0 $(M+1)^+$ |
The Synthesis of the I-380
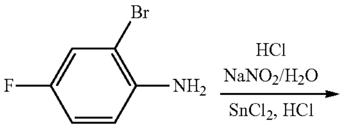
I-369
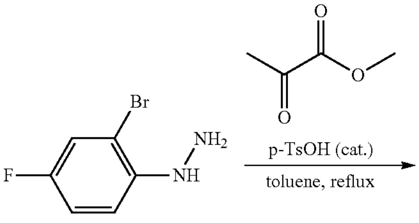
I-370
-continued
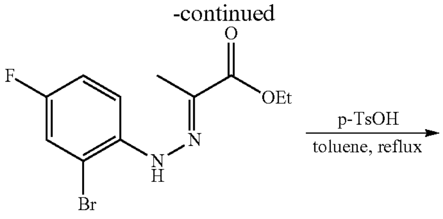
I-371
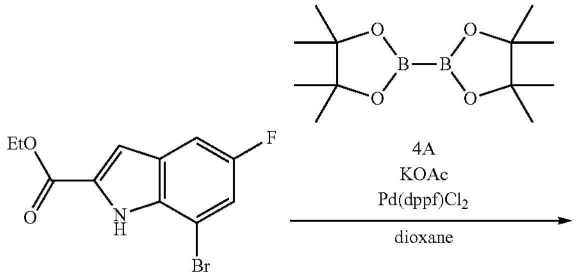
I-372

-continued

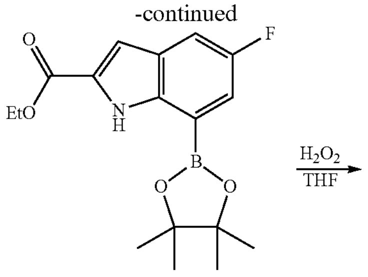

I-373

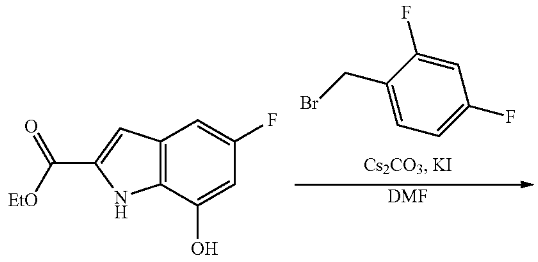

I-374

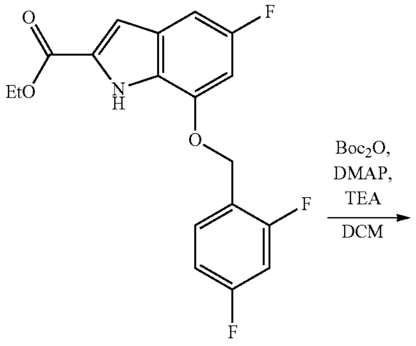

I-375

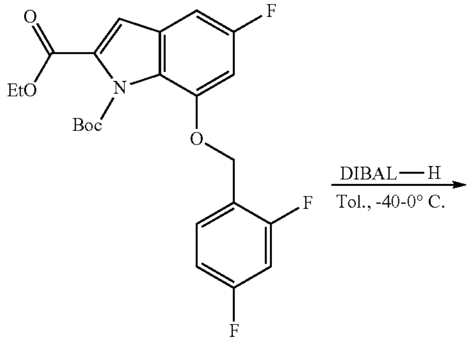

I-376

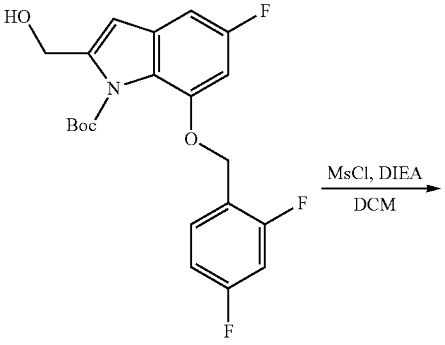

I-377

-continued

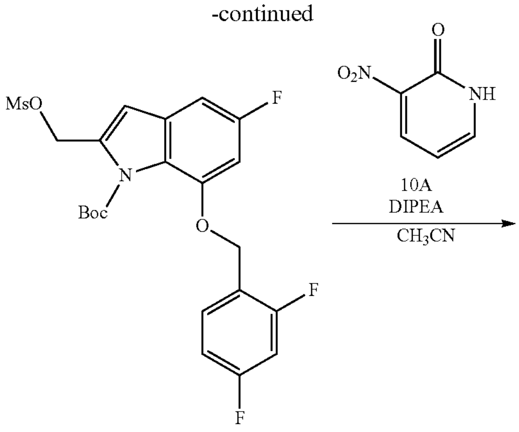

I-378

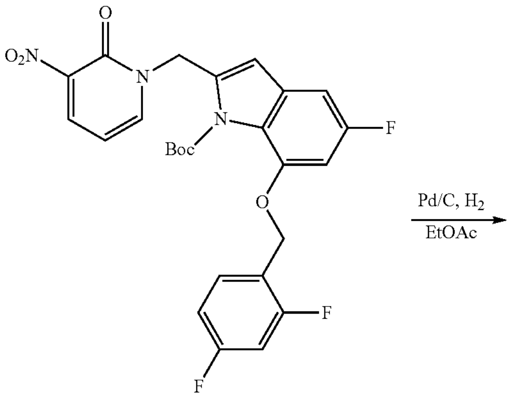

I-379

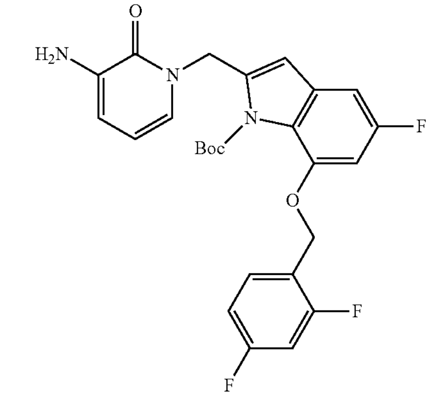

I-380

To a solution of 2-bromo-4-fluoro-aniline (10.0 g, 52.6 mmol) in HCl (30 mL) was added a solution of $NaNO_2$ (4.36 g, 63.2 mmol, 3.43 mL) in $H_2O$ (10 mL) at −5° C. The mixture was stirred at −5° C. for 1 h. Then a solution of $SnCl_2{\cdot}2H_2O$ (14.8 g, 65.8 mmol, 5.48 mL) in HCl (30 mL) was added dropwise at −5° C. The mixture was stirred at −5° C. for 2 h. The resulting suspension was filtered and the solid residue was washed with DCM (200 mL×3) and dried under reduced pressure to give (2-bromo-4-fluorophenyl)hydrazine (I-370) (12.0 g, 92% yield, HCl salt) as a white solid. $^1H$ NMR (400 MHz, DMSO-$d_6$) δ10.44 (s, 3H), 7.86 (s, 1H), 7.56 (dd, J=8.4, 2.8 Hz, 1H), 7.33-7.25 (m, 1H), 7.22-7.14 (m, 1H).

To a solution of (2-bromo-4-fluorophenyl)hydrazine (32.0 g, 133 mmol, HCl salt) and ethyl 2-oxopropanoate (15.4 g, 133 mmol, 14.7 mL) in toluene (500 mL) was added p-TsOH (228 mg, 1.33 mmol). The mixture was heated to reflux for 2 h and remove water by Dean-Stark trap. The reaction mixture was concentrated under reduced pressure to give a residue. The residue was purified by column chromatography to give (E)-ethyl 2-(2-(2-bromo-4-fluorophenyl) hydrazono)propanoate (I-371) (23.0 g) as a yellow solid. LCMS m/z 302.9 $(M+1)^+$.

To a solution of (E)-ethyl 2-(2-(2-bromo-4-fluorophenyl) hydrazono)propanoate (23.0 g, 75.9 mmol) in toluene (120 mL) was added p-TsOH (14.0 g, 81.3 mmol). The mixture was stirred at 110° C. for 16 h and remove water by Dean-Stark trap. The reaction mixture was concentrated under reduced pressure to give a residue. The residue was purified by column chromatography to give ethyl 7-bromo-5-fluoro-1H-indole-2-carboxylate (I-372) (13.0 g, 59% yield) as a yellow solid. LCMS m/z 285.9 $(M+1)^+$.

To a solution of ethyl 7-bromo-5-fluoro-1H-indole-2-carboxylate (13.0 g, 45.4 mmol) and 4,4,4',4',5,5,5',5'-octamethyl-2,2'-bi(1,3,2-dioxaborolane) (17.3 g, 68.2 mmol) in dioxane (100 mL) were added Pd(dppf)$Cl_2$ (4.99 g, 6.82 mmol) and KOAc (8.92 g, 90.9 mmol). The mixture was stirred at 90° C. for 2 hours. The mixture was diluted with water (100 mL) and extracted with ethyl acetate (200 mL×2). The combined organic layers were washed with brine (300 mL×3), dried over anhydrous $Na_2SO_4$, filtered and concentrated in vacuum to give a residue. The residue was purified by column chromatography to give ethyl 5-fluoro-7-(4,4,5,5-tetramethyl-1,3,2-dioxaborolan-2-yl)-1H-indole-2-carboxylate (I-373) (16.8 g) as a yellow solid. LCMS m/z 334.0 $(M+1)^+$.

To a solution of ethyl 5-fluoro-7-(4,4,5,5-tetramethyl-1,3,2-dioxaborolan-2-yl)-1H-indole-2-carboxylate (16.8 g, 50.4 mmol) in THF (20 mL) was added $H_2O_2$ (57.2 g, 504 mmol, 48.5 mL, 30% purity) at 0° C. The mixture was stirred at 20° C. for 16 h. The reaction solution was quenched with saturated $Na_2SO_3$ (200 mL), and extracted with ethyl acetate (200 mL×3). The combined organic layers were washed with brine (300 mL), dried over anhydrous $Na_2SO_4$, filtered and concentrated to give a residue. The residue was purified by silica gel chromatography to give ethyl 5-fluoro-7-hydroxy-1H-indole-2-carboxylate (I-374) (10 g, 83% yield) as a white solid. LCMS m/z 224.0 $(M+1)^+$.

To a solution of ethyl 5-fluoro-7-hydroxy-1H-indole-2-carboxylate (5.00 g, 22.4 mmol) and 1-(bromomethyl)-2,4-difluorobenzene (3.25 g, 15.7 mmol) in DMF (50 mL) were added KI (372 mg, 2.24 mmol) and $Cs_2CO_3$ (14.6 g, 44.8 mmol). The mixture was stirred at 20° C. for 2 hours. The reaction mixture (with another batch) was filtered and the filtrate was concentrated under reduced pressure to give a residue. The residue was purified by column chromatography to give ethyl 7-((2,4-difluorobenzyl)oxy)-5-fluoro-1H-indole-2-carboxylate (I-375) (3.00 g) as a yellow solid. $^1$H NMR (400 MHz, $CDCl_3$) δ 9.02 (s, 1H), 7.55-7.44 (m, 1H), 7.15 (d, J=2.4 Hz, 1H), 7.01-6.86 (m, 3H), 6.64 (dd, J=10.8, 2.0 Hz, 1H), 5.21 (s, 2H), 4.45-4.35 (m, 2H), 1.41 (t, J=7.2 Hz, 3H).

To a solution of ethyl 7-((2,4-difluorobenzyl)oxy)-5-fluoro-1H-indole-2-carboxylate (3.00 g, 8.59 mmol) in DCM (20 mL) were added $Boc_2O$ (2.81 g, 12.9 mmol, 2.96 mL), DMAP (105 mg, 859 μmol) and TEA (1.74 g, 17.2 mmol, 2.38 mL). The mixture was stirred at 20° C. for 16 hours. The mixture was diluted with $H_2O$ (100 mL) and extracted with ethyl acetate (100 mL×3). The combined organic layers were dried over anhydrous $Na_2SO_4$, filtered and concentrated under reduced pressure to give a residue. The residue was purified by column chromatography to give 1-tert-butyl 2-ethyl 7-((2,4-difluorobenzyl)oxy)-5-fluoro-1H-indole-1,2-dicarboxylate (I-376) (3.30 g, 80% yield) as a yellow solid. LCMS m/z 472.0 $(M+23)^+$.

To a solution of 1-tert-butyl 2-ethyl 7-((2,4-difluorobenzyl)oxy)-5-fluoro-1H-indole-1,2-dicarboxylate (2.00 g, 4.45 mmol) in toluene (20 mL) was added DIBAL-H (1 M, 13.4 mL) at −40° C. The mixture was stirred at 0° C. for 1 h. The reaction mixture was quenched with saturated $NH_4Cl$ solution (50 mL) at 0° C., and diluted with saturated potassium sodium tartrate solution (100 mL). The mixture was stirred for 2 h. The resulting solution was extracted with EtOAc (100 mL×3). The combined organic layers were washed with brine (200 mL), dried over anhydrous $Na_2SO_4$, filtered and concentrated in vacuum to give a residue. The residue was purified by column chromatography to give tert-butyl 7-((2,4-difluorobenzyl)oxy)-5-fluoro-2-(hydroxymethyl)-1H-indole-1-carboxylate (I-377) (1.00 g, 48% yield) as a white solid. LCMS m/z 430.0 $(M+1)^+$.

To a solution of tert-butyl 7-((2,4-difluorobenzyl)oxy)-5-fluoro-2-(hydroxymethyl)-1H-indole-1-carboxylate (1.30 g, 3.19 mmol) in DCM (20 mL) were added MsCl (5.0 g, 43.6 mmol, 3.38 mL) and DIPEA (825 mg, 6.38 mmol, 1.11 mL) at 0° C. The mixture was stirred at 20° C. for 1 h. The reaction mixture was diluted with ethyl acetate (100 mL) and washed with brine (100 mL). The organic phase was dried over anhydrous $Na_2SO_4$, filtered and concentrated under reduced pressure to give tert-butyl 7-((2,4-difluorobenzyl)oxy)-5-fluoro-2-(((methylsulfonyl)oxy)methyl)-1H-indole-1-carboxylate (I-378) (1.60 g) as a brown oil.

To a solution of tert-butyl 7-((2,4-difluorobenzyl)oxy)-5-fluoro-2-(((methylsulfonyl) oxy)methyl)-1H-indole-1-carboxylate (1.60 g, 3.30 mmol) and 3-nitropyridin-2(1H)-one (693 mg, 4.94 mmol) in MeCN (20 mL) was added DIPEA (1.28 g, 9.89 mmol, 1.73 mL). The mixture was stirred at 30° C. for 16 hours. The reaction mixture (with another batch) was filtered and the filter cake was washed with ethyl acetate (20 mL), dried under vacuum to give tert-butyl 7-((2,4-difluorobenzyl)oxy)-5-fluoro-2-((3-nitro-2-oxopyridin-1(2H)-yl)methyl)-1H-indole-1-carboxylate (I-379) (750 mg) as a yellow solid. $^1$H NMR (400 MHz, $CDCl_3$) δ 8.36 (dd, J=7.6, 2.0 Hz, 1H), 7.84 (dd, J=6.8, 2.0 Hz, 1H), 7.54-7.45 (m, 1H), 6.94-6.83 (m, 3H), 6.73-6.65 (m, 2H), 6.30 (dd, J=7.6, 6.8 Hz, 1H), 5.41 (s, 2H), 5.18 (s, 2H), 1.35 (s, 9H).

To a solution of tert-butyl 7-((2,4-difluorobenzyl)oxy)-5-fluoro-2-((3-nitro-2-oxopyridin-1(2H)-yl)methyl)-1H-indole-1-carboxylate (650 mg, 1.23 mmol) in EtOAc (5 mL) was added Pd/C (200 mg, 10% purity). The mixture was stirred at 20° C. for 0.5 hour under $H_2$ (15 psi) atmosphere. The reaction mixture (with another batch) was filtered and the filtrate was concentrated under reduced pressure to give tert-butyl 2-((3-amino-2-oxopyridin-1(2H)-yl)methyl)-7-((2,4-difluorobenzyl)oxy)-5-fluoro-1H-indole-1-carboxylate (I-380) (700 mg) as a brown solid.

The following intermediate was prepared according to the procedures described for the synthesis of I-380 using the appropriate reagents.

| Compound | Structure | LCMS Data |
|---|---|---|
| I-381 | 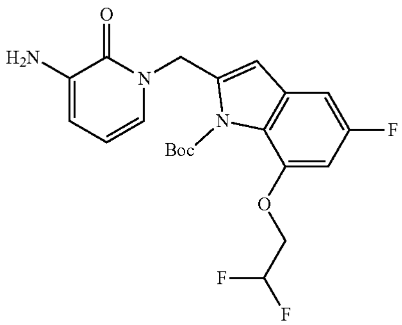 [SMILES: CC(C)(C)OC(=O)n1c(Cn2cccc(N)c2=O)cc2cc(F)cc(OCC(F)F)c21] | LCMS m/z 460.0 (M + 23)+ |

The Synthesis of Intermediate I-388

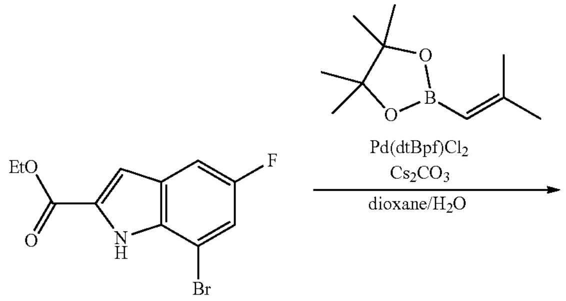

I-372

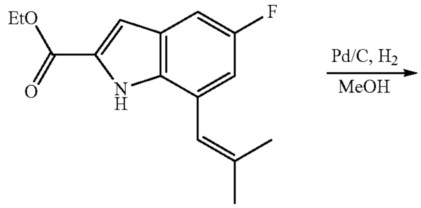

I-382

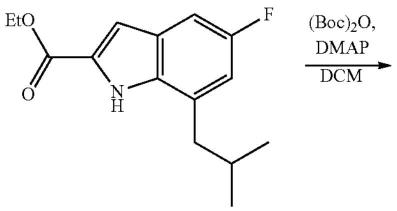

I-383

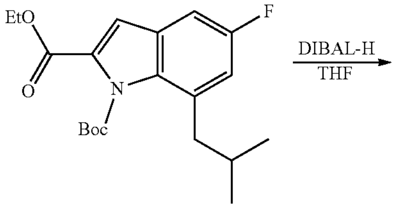

I-384

-continued

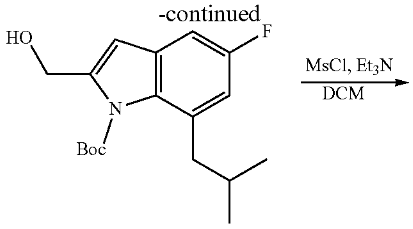

I-385

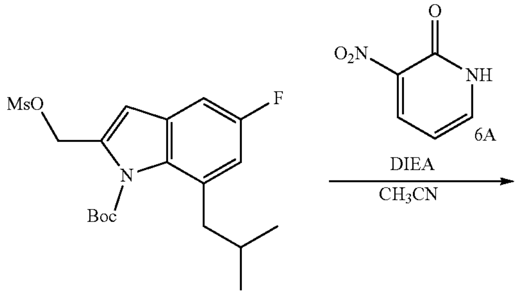

I-386

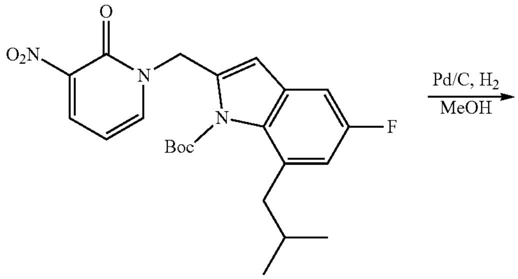

I-387

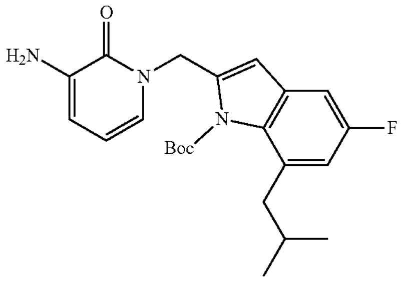

I-388

To a mixture of ethyl 7-bromo-5-fluoro-1H-indole-2-carboxylate (700 mg, 2.03 mmol) and 4,4,5,5-tetramethyl-2-(2-methylprop-1-enyl)-1,3,2-dioxaborolane (555 mg, 3.05 mmol) in dioxane (15 mL) and $H_2O$ (1 mL) were added $Cs_2CO_3$ (1.32 g, 4.06 mmol) and ditert-butyl(cyclopentyl) phosphane;dichloropalladium;iron (132 mg, 203 μmol) in one portion at 25° C. under $N_2$ atmosphere. The mixture was heated to 90° C. and stirred for 18 hours. The mixture was cooled to 25° C. The reaction mixture was poured into water (30 mL). The resulting solution was extracted with ethyl acetate (40 mL×3). The combined organic layers were washed with brine (50 mL), dried over anhydrous $Na_2SO_4$, filtered and concentrated in vacuum to give a residue. The residue was purified by column chromatography to afford ethyl 5-fluoro-7-(2-methylprop-1-enyl)-1H-indole-2-carboxylate (I-382) (0.45 g, 85% yield) as a yellow oil. $^1H$ NMR (400 MHz, $CDCl_3$) δ 8.76 (s, 1H), 7.21 (d, J=8.0 Hz, 1H), 6.96 (d, J=8.0 Hz, 1H), 6.37 (s, 1H), 4.46-4.41 (m, 2H), 2.03 (s, 3H), 1.59 (s, 3H), 1.44-1.42 (m, 3H).

To a solution of ethyl 5-fluoro-7-(2-methylprop-1-enyl)-1H-indole-2-carboxylate (0.42 g, 1.61 mmol) in MeOH (10 mL) was added Pd/C (0.05 g, 10% purity) under $N_2$ atmosphere. The suspension was degassed under vacuum and purged with $H_2$ 3 times. The mixture was stirred under $H_2$ (15 psi) at 25° C. for 2 hours. The reaction mixture was filtered and the filtrate was concentrated to give ethyl 5-fluoro-7-isobutyl-1H-indole-2-carboxylate (I-383) (0.4 g) as a yellow oil.

To a mixture of ethyl 5-fluoro-7-isobutyl-1H-indole-2-carboxylate (0.4 g, 1.52 mmol) and $Boc_2O$ (431 mg, 1.97 mmol) in DCM (10 mL) was added DMAP (92.8 mg, 760 μmol) in one portion at 25° C. under $N_2$ atmosphere. The mixture was stirred at 25° C. for 18 hours. The mixture was concentrated under reduced pressure to give a residue. The residue was purified by prep-TLC to afford 1-tert-butyl 2-ethyl 5-fluoro-7-isobutyl-1H-indole-1,2-dicarboxylate (I-384) (0.42 g, 76% yield) as a yellow oil. $^1H$ NMR (400 MHz, $CDCl_3$) δ 7.14 (s, 1H), 7.12 (d, J=8.0 Hz, 1H), 6.91 (d, J=8.0 Hz, 1H), 4.41-4.36 (m, 2H), 2.84-2.83 (m, 2H), 1.93-1.90 (m, 1H), 1.62 (s, 9H), 1.48-1.43 (m, 3H), 0.92-0.91 (m, 6H).

To a mixture of 1-tert-butyl 2-ethyl 5-fluoro-7-isobutyl-1H-indole-1,2-dicarboxylate (0.42 g, 1.16 mmol) in THF (10 mL) was added DIBAL-H (1M, 2.31 mL) in portions at −65° C. under $N_2$ atmosphere. The mixture was stirred at −65° C. for 1 hour. The mixture was poured into water (20 mL). The resulting solution was extracted with ethyl acetate (30 mL×3). The combined organic layers were washed with brine (40 mL), dried over anhydrous $Na_2SO_4$, filtered and concentrated in vacuum to afford tert-butyl 5-fluoro-2-(hydroxymethyl)-7-isobutyl-1H-indole-1-carboxylate (I-385) (90 mg, 24% yield) as a yellow oil. $^1H$ NMR (400 MHz, $CDCl_3$) δ57.05 (d, J=8.0 Hz, 1H), 6.85 (d, J=8.0 Hz, 1H), 6.53 (s, 1H), 4.78-4.77 (m, 2H), 2.85-2.83 (m, 2H), 1.89-1.86 (m, 1H), 1.70 (s, 9H), 0.83-0.82 (m, 6H).

To a mixture of tert-butyl 5-fluoro-2-(hydroxymethyl)-7-isobutyl-indole-1-carboxylate (80 mg, 249 μmol) and MsCl (42.8 mg, 373 μmol) in DCM (2 mL) was added DIPEA (64.3 mg, 498 μmol) in one portion at 25° C. under $N_2$ atmosphere. The mixture was stirred at 25° C. for 1 hour. The mixture was poured into water (20 mL). The resulting solution was extracted with ethyl acetate (20 mL×2). The combined organic layers were washed with brine (20 mL), dried over anhydrous $Na_2SO_4$, filtered and concentrated in vacuum to afford tert-butyl 5-fluoro-7-isobutyl-2-(methylsulfonyloxymethyl)indole-1-carboxylate (I-386) (100 mg) as a yellow oil.

To a mixture of tert-butyl 5-fluoro-7-isobutyl-2-(methylsulfonyloxymethyl)indole-1-carboxylate (100 mg, 250 μmol) and 3-nitropyridin-2(1H)-one (52.6 mg, 376 μmol) in $CH_3CN$ (3 mL) was added DIPEA (64.7 mg, 501 μmol) in one portion at 25° C. under $N_2$ atmosphere. The mixture was stirred at 25° C. for 18 hours. The mixture was poured into water (20 mL). The resulting solution was extracted with ethyl acetate (30 mL×3). The combined organic layers were washed with brine (20 mL), dried over anhydrous $Na_2SO_4$, filtered and concentrated in vacuum to give a residue. The residue was purified by prep-TLC to afford tert-butyl 5-fluoro-7-isobutyl-2-((3-nitro-2-oxopyridin-1(2H)-yl) methyl)-1H-indole-1-carboxylate (I-387) (80 mg, 72% yield) as a yellow oil. $^1H$ NMR (400 MHz, $CDCl_3$) δ 8.39-8.47 (m, 1H), 7.63-7.61 (m, 1H), 7.08-7.05 (m, 1H), 6.94-6.90 (m, 1H), 6.55 (s, 1H), 6.34-6.30 (m, 1H), 5.43 (s, 2H), 2.85-2.83 (m, 2H), 1.87-1.84 (m, 1H), 1.57 (s, 9H), 0.84-0.82 (m, 6H).

To a solution of tert-butyl 5-fluoro-7-isobutyl-2-((3-nitro-2-oxopyridin-1(2H)-yl) methyl)-1H-indole-1-carboxylate (170 mg, 383 μmol) in ethyl acetate (10 mL) was added Pd/C (30 mg, 10% purity) under $N_2$ atmosphere. The suspension was degassed under vacuum and purged with $H_2$ 3 times. The mixture was stirred under $H_2$ (15 psi) at 25° C. for 3 hours. The reaction mixture was filtered and the filtrate was concentrated to give tert-butyl 2-[(3-amino-2-oxo-1-pyridyl)methyl]-5-fluoro-7-isobutyl-indole-1-carboxylate (I-388) (160 mg) as a yellow oil.

Example 41

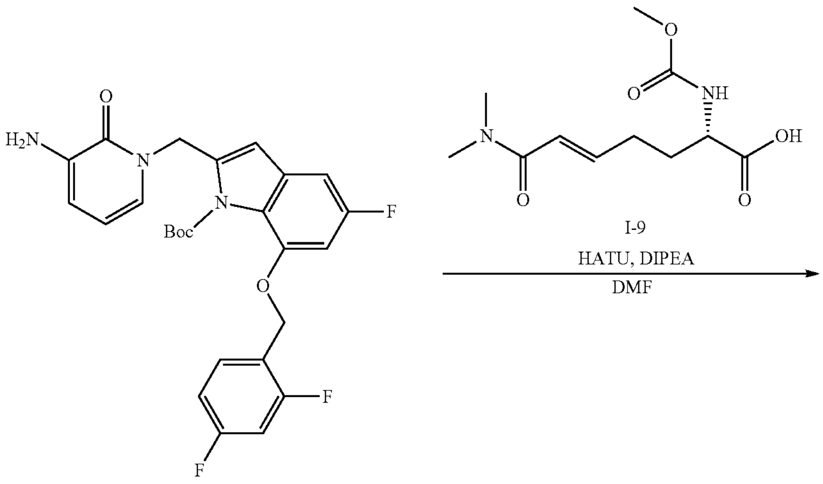

I-380
I-9

-continued

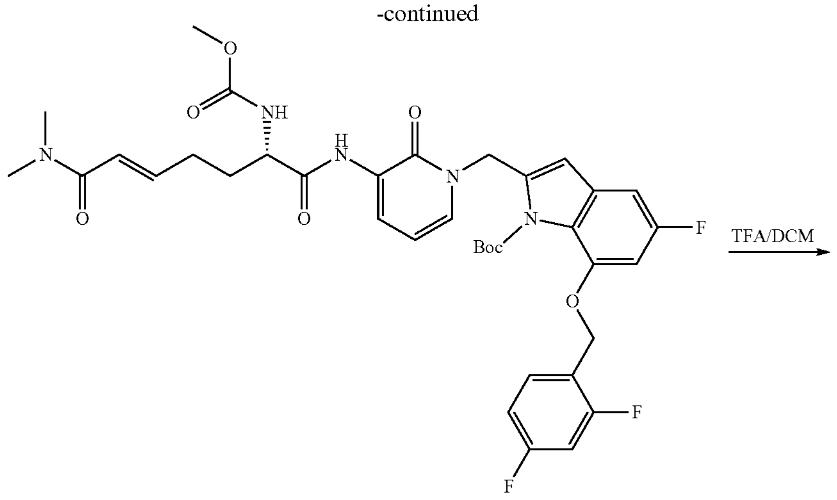

273

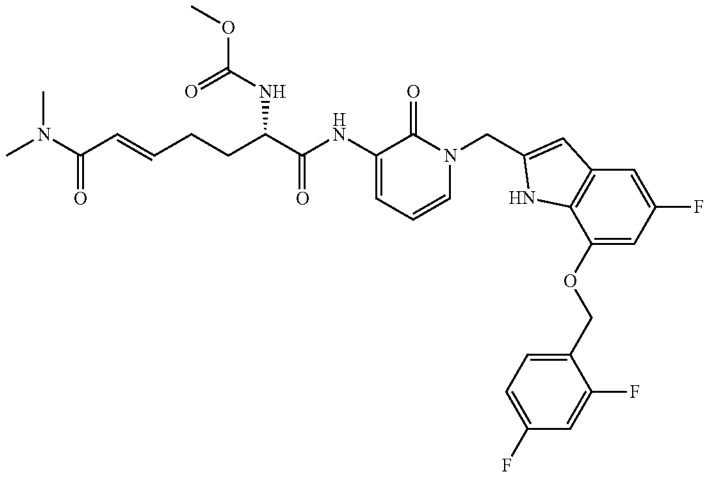

273

To a solution of tert-butyl 2-((3-amino-2-oxopyridin-1(2H)-yl)methyl)-7-((2,4-difluorobenzyl)oxy)-5-fluoro-1H-indole-1-carboxylate (200 mg, 400 μmol) and (S,E)-7-(dimethylamino)-2-((methoxycarbonyl)amino)-7-oxohept-5-enoic acid (155 mg, 601 μmol) in DMF (3 mL) were added HATU (183 mg, 481 μmol) and DIPEA (155 mg, 1.20 mmol, 210 μL) at 0° C. The solution was stirred at 30° C. for 16 h. The reaction mixture was concentrated under reduced pressure to give (S,E)-tert-butyl 7-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate (Compound 272) (230 mg) as a white solid. LCMS m/z 740.3 $(M+1)^+$.

To a solution of (S,E)-tert-butyl 7-(2,2-difluoroethoxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate (180 mg, 231 μmol) in DCM (3 mL) was added TFA (1 mL) at 0° C. The mixture was stirred at 20° C. for 1 hour. The reaction mixture was concentrated under reduced pressure to give a residue. The residue was purified by prep-HPLC to give (S,E)-methyl (1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl)carbamate (Compound 273) (73.8 mg, 47% yield) as a white solid. LCMS m/z 640.2 $(M+1)^+$. $^1$H NMR (400 MHz, DMSO-$d_6$) δ 11.32 (s, 1H), 9.32 (s, 1H), 8.21 (dd, J=7.4, 1.6 Hz, 1H), 7.81-7.72 (m, 2H), 7.49 (dd, J=6.8, 1.6 Hz, 1H), 7.40-7.32 (m, 1H), 7.22-7.15 (m, 1H), 6.86 (dd, J=9.6, 2.0 Hz, 1H), 6.77 (dd, J=11.2, 2.0 Hz, 1H), 6.66-6.56 (m, 1H), 6.38 (d, J=15.2 Hz, 1H), 6.30 (t, J=7.2 Hz, 1H), 6.23 (s, 1H), 5.30-5.18 (m, 4H), 4.25-4.13 (m, 1H), 3.56 (s, 3H), 2.99 (s, 3H), 2.83 (s, 3H), 2.30-2.17 (m, 2H), 1.95-1.80 (m, 1H), 1.78-1.65 (m, 1H).

The following compounds were prepared according to the procedures described in Example 41 using the appropriate intermediates.

| Compound | Structure | LCMS Data |
| --- | --- | --- |
| 274 | 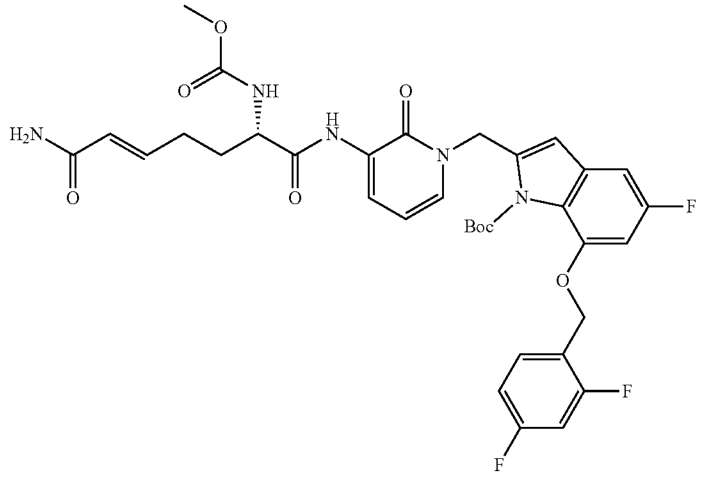 [SMILES: COC(=O)N[C@@H](CC/C=C/C(N)=O)C(=O)Nc1cccn(Cc2cc3cc(F)cc(OCc4ccc(F)cc4F)c3n2C(=O)OC(C)(C)C)c1=O] | LCMS m/z 734.2 (M + 23)+ |
| 275 | 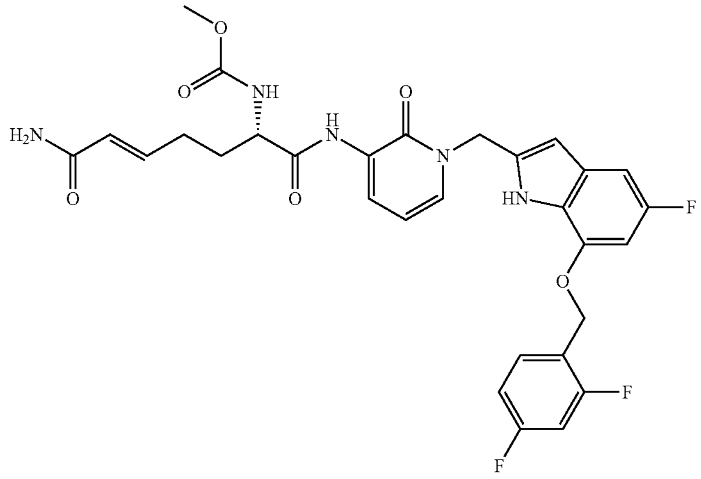 [SMILES: COC(=O)N[C@@H](CC/C=C/C(N)=O)C(=O)Nc1cccn(Cc2cc3cc(F)cc(OCc4ccc(F)cc4F)c3[nH]2)c1=O] | LCMS m/z 612.2 (M + 1)+ |
| 276 | 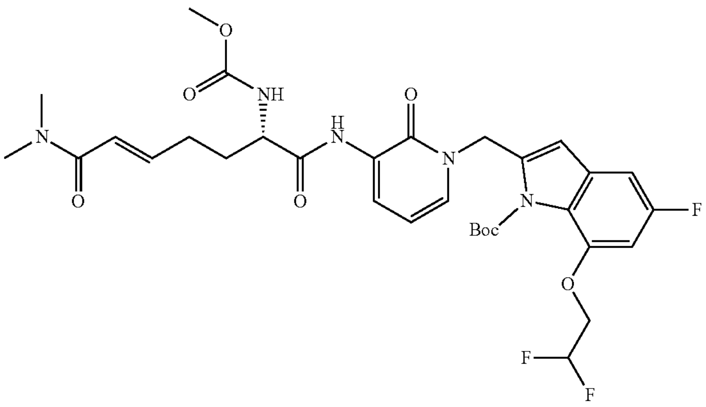 [SMILES: COC(=O)N[C@@H](CC/C=C/C(=O)N(C)C)C(=O)Nc1cccn(Cc2cc3cc(F)cc(OCC(F)F)c3n2C(=O)OC(C)(C)C)c1=O] | LCMS m/z 678.3 (M + 1)+ |

-continued
| Compound | Structure | LCMS Data |
|---|---|---|
| 277 | 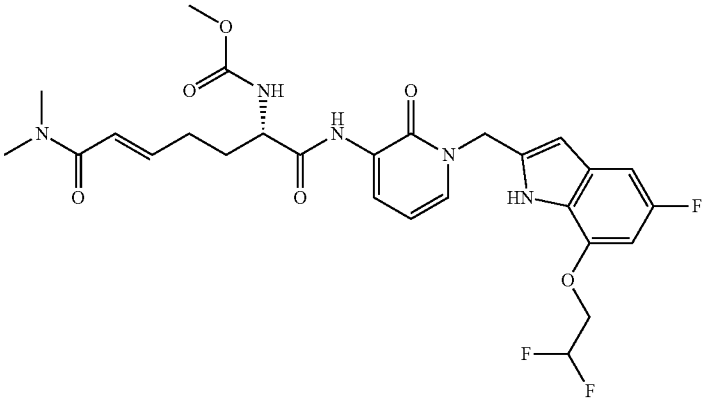 [SMILES: COC(=O)N[C@@H](CC/C=C/C(=O)N(C)C)C(=O)Nc1cccn(Cc2cc3cc(F)cc(OCC(F)F)c3[nH]2)c1=O] | LCMS m/z 578.2 $(M + 1)^+$ |
| 278 | 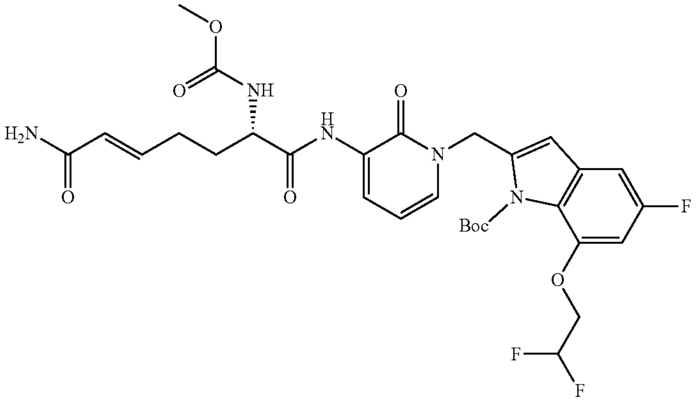 [SMILES: COC(=O)N[C@@H](CC/C=C/C(N)=O)C(=O)Nc1cccn(Cc2cc3cc(F)cc(OCC(F)F)c3n2C(=O)OC(C)(C)C)c1=O] | LCMS m/z 650.2 $(M + 1)^+$ |
| 279 | 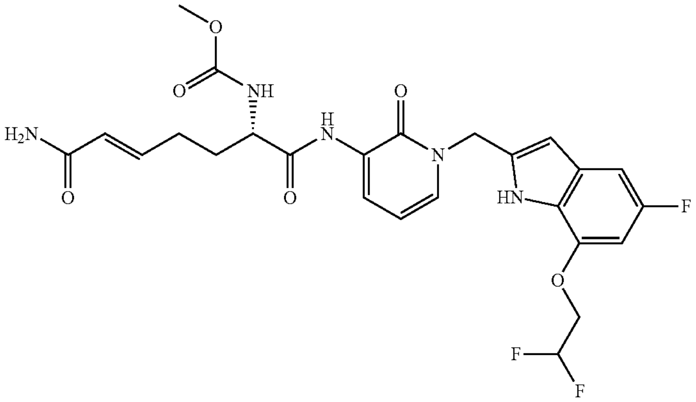 [SMILES: COC(=O)N[C@@H](CC/C=C/C(N)=O)C(=O)Nc1cccn(Cc2cc3cc(F)cc(OCC(F)F)c3[nH]2)c1=O] | LCMS m/z 550.1 $(M + 1)^+$ |

-continued
| Compound | Structure | LCMS Data |
| --- | --- | --- |
| 280 | 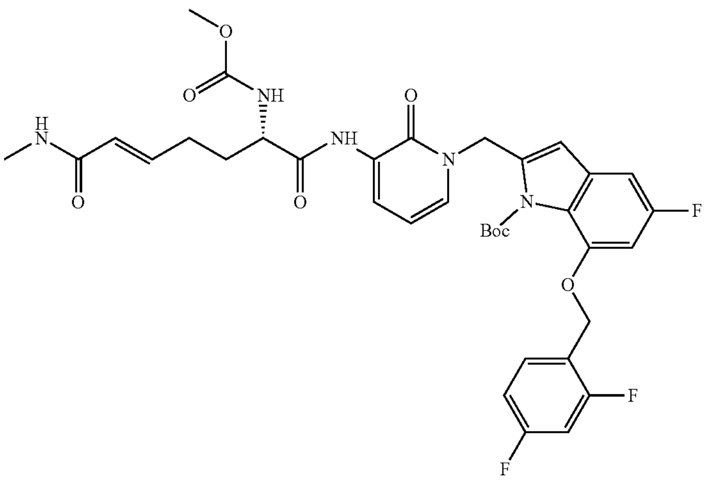 [SMILES: CNC(=O)/C=C/CC[C@H](NC(=O)OC)C(=O)Nc1cccn(Cc2cc3cc(F)cc(OCc4ccc(F)cc4F)c3n2C(=O)OC(C)(C)C)c1=O] | LCMS m/z 726.1 (M + 1)+. |
| 281 | 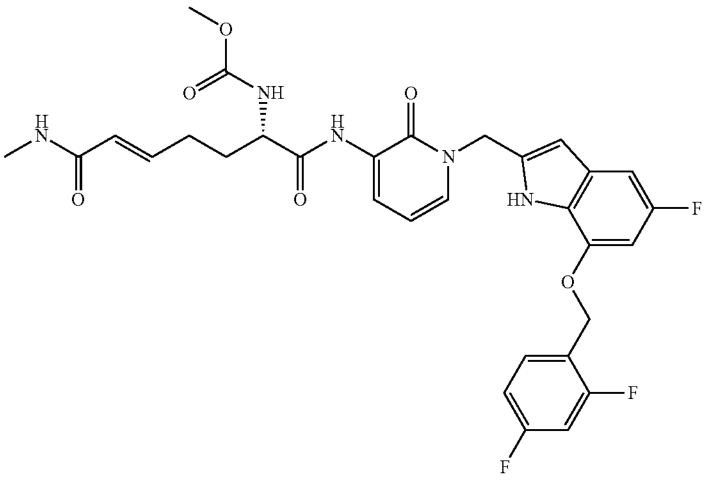 [SMILES: CNC(=O)/C=C/CC[C@H](NC(=O)OC)C(=O)Nc1cccn(Cc2cc3cc(F)cc(OCc4ccc(F)cc4F)c3[nH]2)c1=O] | LCMS m/z 626.2 (M + 1)+. |
| 282 | 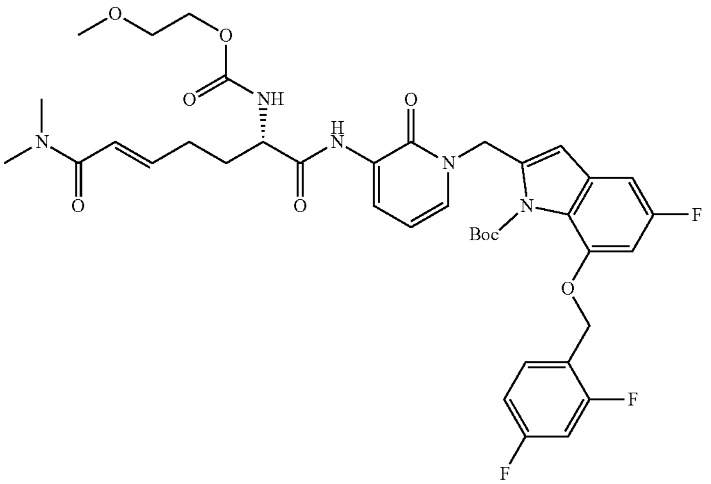 [SMILES: COCCOC(=O)N[C@@H](CC/C=C/C(=O)N(C)C)C(=O)Nc1cccn(Cc2cc3cc(F)cc(OCc4ccc(F)cc4F)c3n2C(=O)OC(C)(C)C)c1=O] | LCMS m/z 784.2 (M + 1)+ |

-continued
| Compound | Structure | LCMS Data |
| --- | --- | --- |
| 285 | 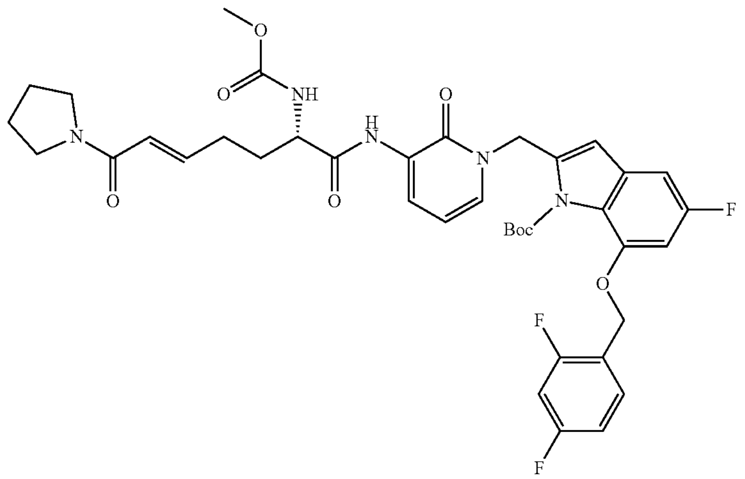 [SMILES: COC(=O)N[C@@H](CC/C=C/C(=O)N1CCCC1)C(=O)Nc1cccn(Cc2cc3cc(F)cc(OCc4ccc(F)cc4F)c3n2C(=O)OC(C)(C)C)c1=O] | LCMS m/z 766.1 (M + 1)$^+$ |
| 286 | 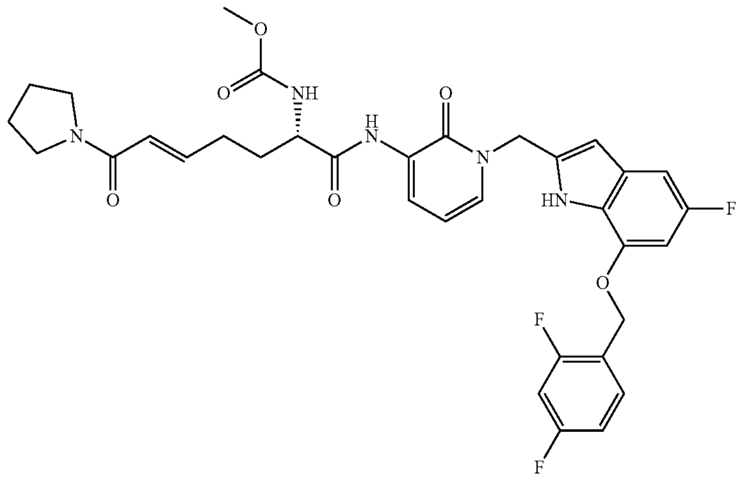 [SMILES: COC(=O)N[C@@H](CC/C=C/C(=O)N1CCCC1)C(=O)Nc1cccn(Cc2cc3cc(F)cc(OCc4ccc(F)cc4F)c3[nH]2)c1=O] | LCMS m/z 666.2 (M + 1)$^+$ |
| 287 | 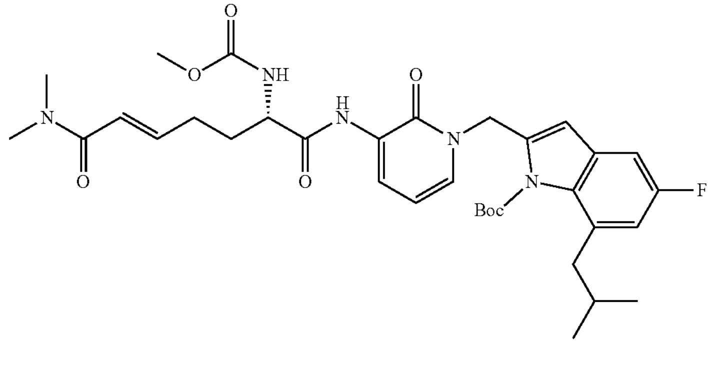 [SMILES: COC(=O)N[C@@H](CC/C=C/C(=O)N(C)C)C(=O)Nc1cccn(Cc2cc3cc(F)cc(CC(C)C)c3n2C(=O)OC(C)(C)C)c1=O] | LCMS m/z 654.3 (M + 1)$^+$ |

-continued
| Compound | Structure | LCMS Data |
|---|---|---|
| 288 | 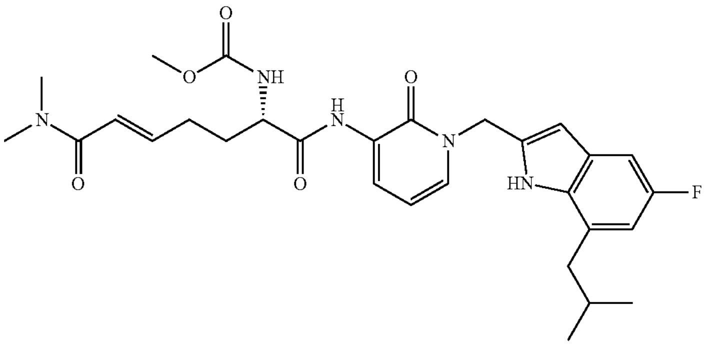 [SMILES: COC(=O)N[C@@H](CC/C=C/C(=O)N(C)C)C(=O)Nc1cccn(Cc2cc3cc(F)cc(CC(C)C)c3[nH]2)c1=O] | LCMS m/z 554.2 $(M + 1)^+$ |
| 289 | 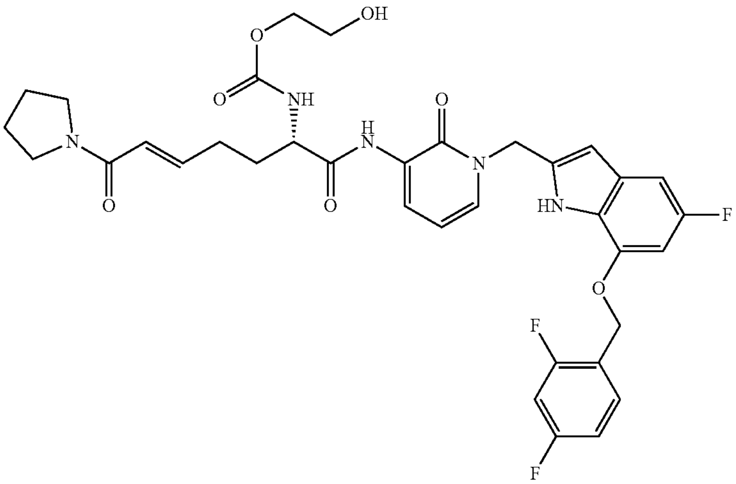 [SMILES: O=C(N[C@@H](CC/C=C/C(=O)N1CCCC1)C(=O)Nc1cccn(Cc2cc3cc(F)cc(OCc4ccc(F)cc4F)c3[nH]2)c1=O)OCCO] | LCMS m/z 696.2 $(M + 1)^+$ |
| 290 | 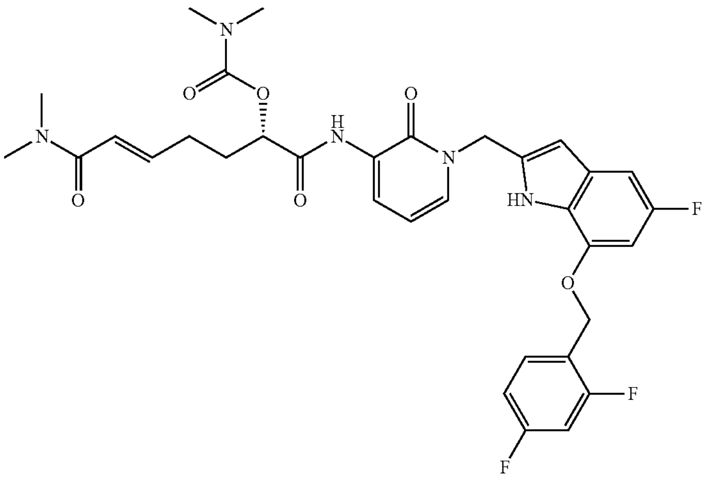 | LCMS m/z 654.1 $(M + 1)^+$ |

-continued
| Compound | Structure | LCMS Data |
| --- | --- | --- |
| 291 | 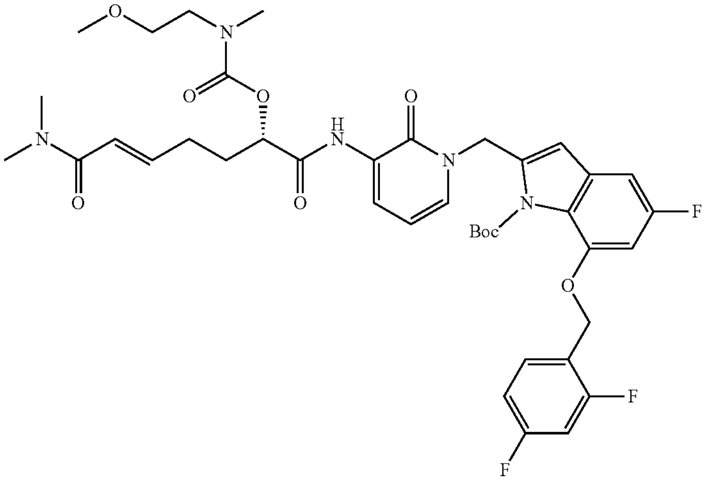 [SMILES: COCCN(C)C(=O)O[C@@H](CC/C=C/C(=O)N(C)C)C(=O)Nc1cccn(Cc2cc3cc(F)cc(OCc4ccc(F)cc4F)c3n2C(=O)OC(C)(C)C)c1=O] | LCMS m/z 798.4 (M + 1)$^+$ |
| 292 | 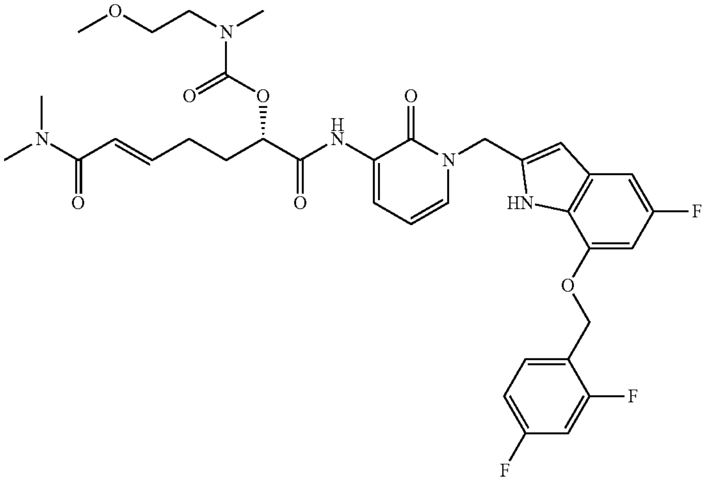 [SMILES: COCCN(C)C(=O)O[C@@H](CC/C=C/C(=O)N(C)C)C(=O)Nc1cccn(Cc2cc3cc(F)cc(OCc4ccc(F)cc4F)c3[nH]2)c1=O] | LCMS m/z 698.3 (M + 1)$^+$. |
| 293 | 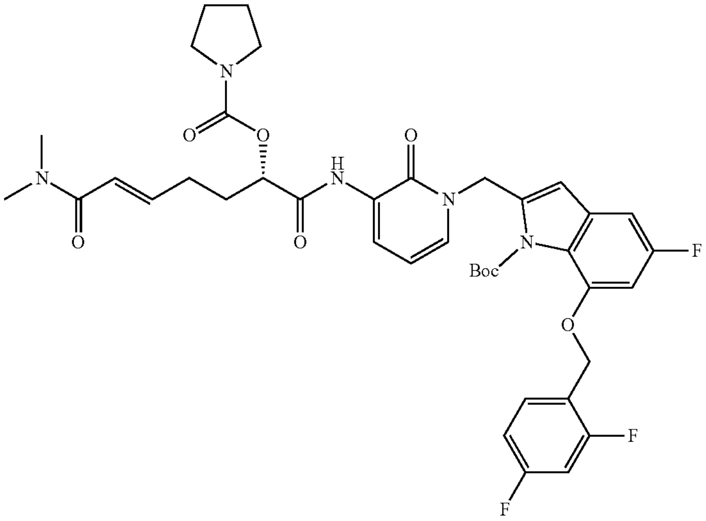 [SMILES: CN(C)C(=O)/C=C/CC[C@H](OC(=O)N1CCCC1)C(=O)Nc1cccn(Cc2cc3cc(F)cc(OCc4ccc(F)cc4F)c3n2C(=O)OC(C)(C)C)c1=O] | LCMS m/z 780.3 (M + 1)$^+$. |

-continued
| Compound | Structure | LCMS Data |
| --- | --- | --- |
| 294 | 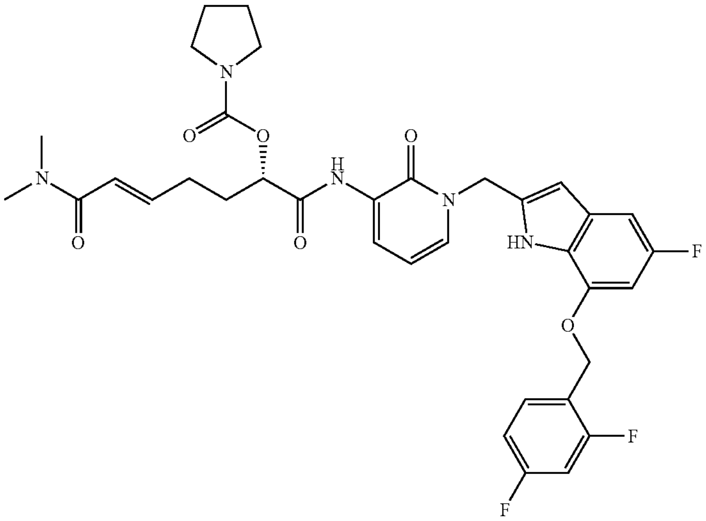 [SMILES: CN(C)C(=O)/C=C/CC[C@H](OC(=O)N1CCCC1)C(=O)Nc1cccn(Cc2cc3cc(F)cc(OCc4ccc(F)cc4F)c3[nH]2)c1=O] | LCMS m/z 680.2 $(M + 1)^+$. |
| 295 | 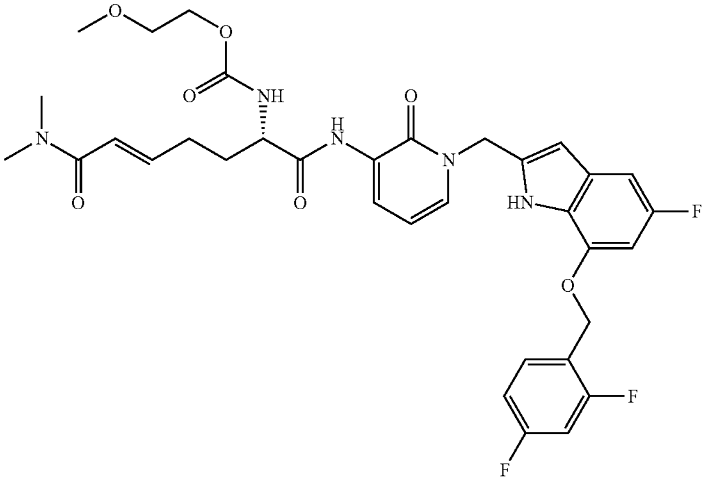 | LCMS m/z 684.3 $(M + 1)^+$. |
| 296 | 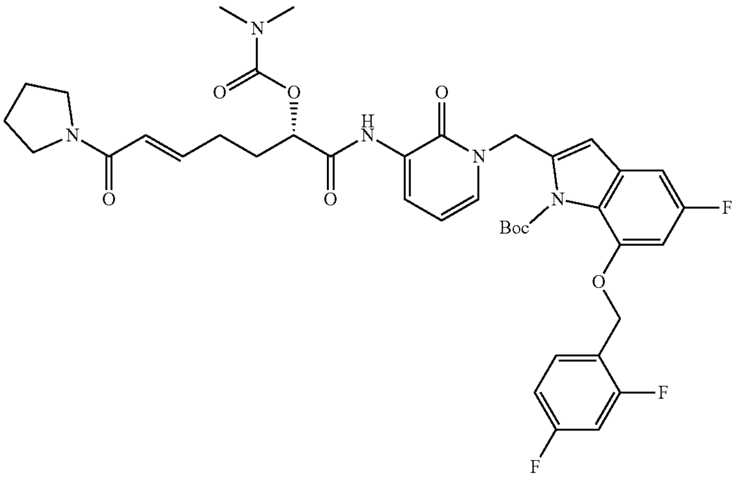 [SMILES: CN(C)C(=O)O[C@@H](CC/C=C/C(=O)N1CCCC1)C(=O)Nc1cccn(Cc2cc3cc(F)cc(OCc4ccc(F)cc4F)c3n2C(=O)OC(C)(C)C)c1=O] | LCMS m/z 780.3 $(M + 1)^+$. |

-continued
| Compound | Structure | LCMS Data |
| --- | --- | --- |
| 297 | 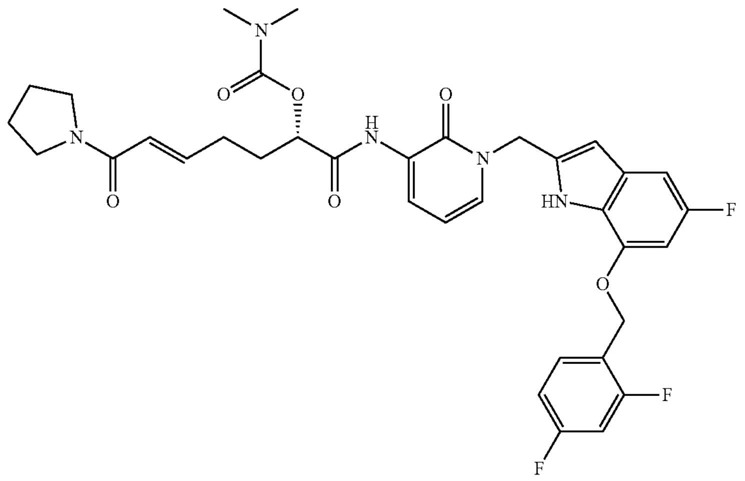 [SMILES: CN(C)C(=O)O[C@@H](CC/C=C/C(=O)N1CCCC1)C(=O)Nc1cccn(Cc2cc3cc(F)cc(OCc4ccc(F)cc4F)c3[nH]2)c1=O] | LCMS m/z 680.3 $(M + 1)^+$. |
| 298 | 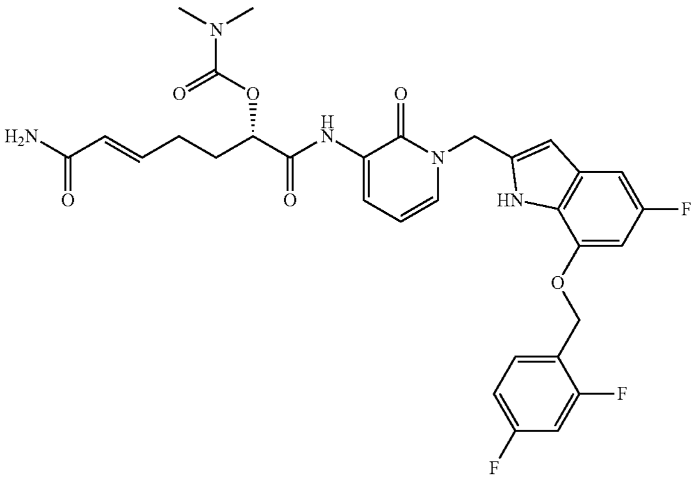 [SMILES: CN(C)C(=O)O[C@@H](CC/C=C/C(N)=O)C(=O)Nc1cccn(Cc2cc3cc(F)cc(OCc4ccc(F)cc4F)c3[nH]2)c1=O] | LCMS m/z 626.2 $(M + 1)^+$ |
| 299 | 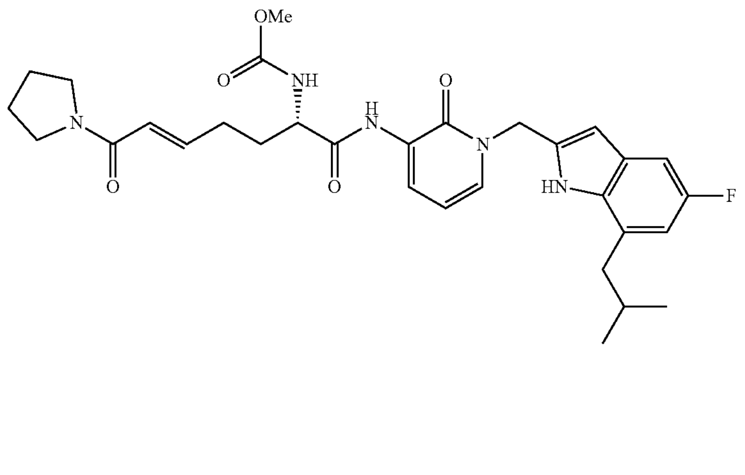 [SMILES: COC(=O)N[C@@H](CC/C=C/C(=O)N1CCCC1)C(=O)Nc1cccn(Cc2cc3cc(F)cc(CC(C)C)c3[nH]2)c1=O] | LCMS m/z 580.3 $(M + 1)^+$ |

-continued
| Compound | Structure | LCMS Data |
| --- | --- | --- |
| 300 | 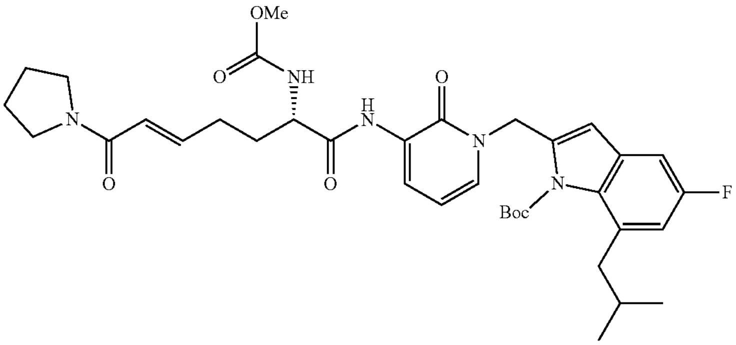 [SMILES: COC(=O)N[C@@H](CC/C=C/C(=O)N1CCCC1)C(=O)Nc1cccn(Cc2cc3cc(F)cc(CC(C)C)c3n2C(=O)OC(C)(C)C)c1=O] | LCMS m/z 680.3 $(M + 1)^+$ |
| 301 | 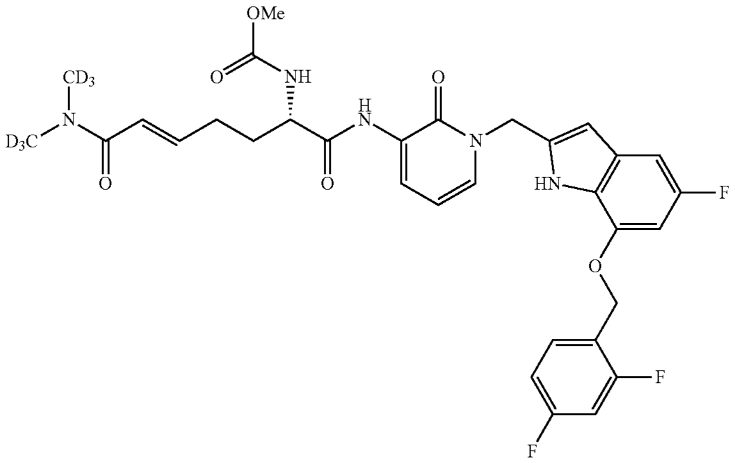 [SMILES: [2H]C([2H])([2H])N(C(=O)/C=C/CC[C@H](NC(=O)OC)C(=O)Nc1cccn(Cc2cc3cc(F)cc(OCc4ccc(F)cc4F)c3[nH]2)c1=O)C([2H])([2H])[2H]] | LCMS m/z 646.2 $(M + 1)^+$ |
| 302 | 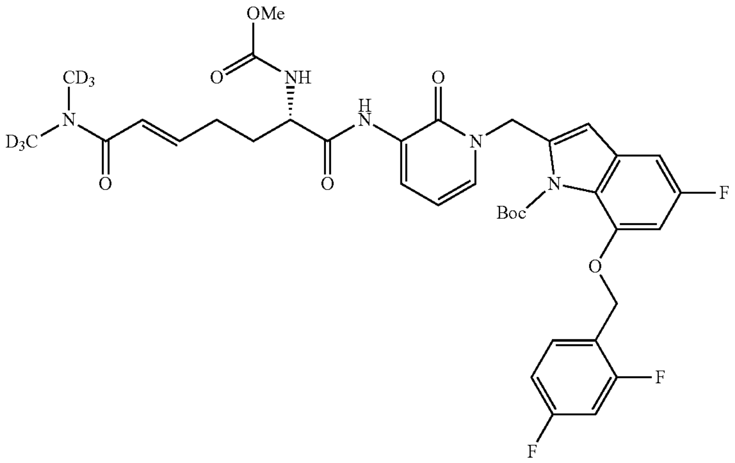 [SMILES: [2H]C([2H])([2H])N(C(=O)/C=C/CC[C@H](NC(=O)OC)C(=O)Nc1cccn(Cc2cc3cc(F)cc(OCc4ccc(F)cc4F)c3n2C(=O)OC(C)(C)C)c1=O)C([2H])([2H])[2H]] | LCMS m/z 746.2 $(M + 1)^+$ |

-continued
| Compound | Structure | LCMS Data |
| --- | --- | --- |
| 303 | 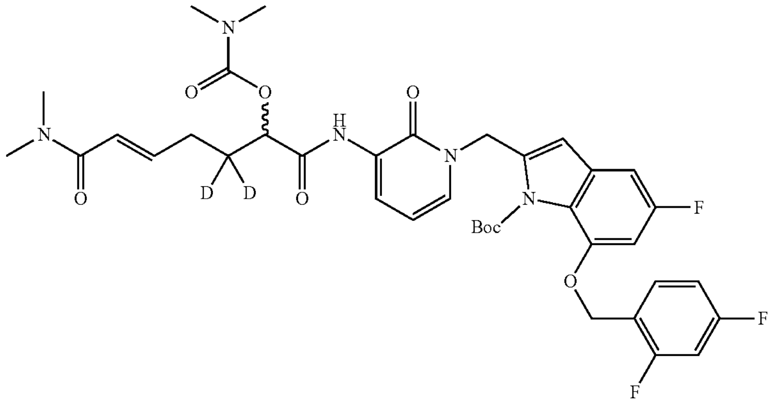 [SMILES: [2H]C([2H])(C/C=C/C(=O)N(C)C)C(OC(=O)N(C)C)C(=O)Nc1cccn(Cc2cc3cc(F)cc(OCc4ccc(F)cc4F)c3n2C(=O)OC(C)(C)C)c1=O] | LCMS m/z 756.3 (M + 1)+ |
| 304 | 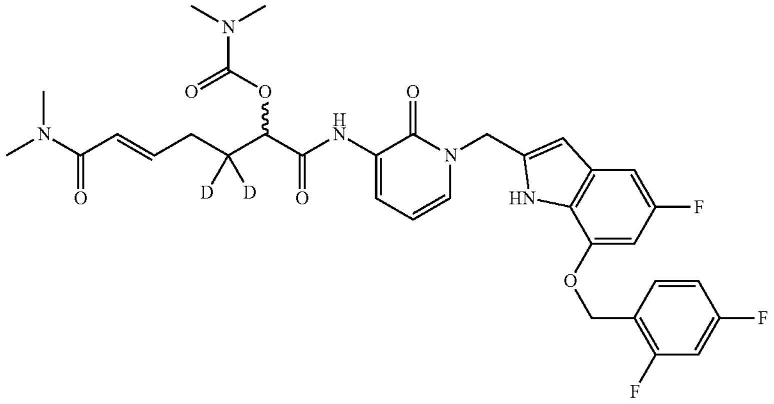 [SMILES: [2H]C([2H])(C/C=C/C(=O)N(C)C)C(OC(=O)N(C)C)C(=O)Nc1cccn(Cc2cc3cc(F)cc(OCc4ccc(F)cc4F)c3[nH]2)c1=O] | LCMS m/z 656.3 (M + 1)+ |
| 305 | 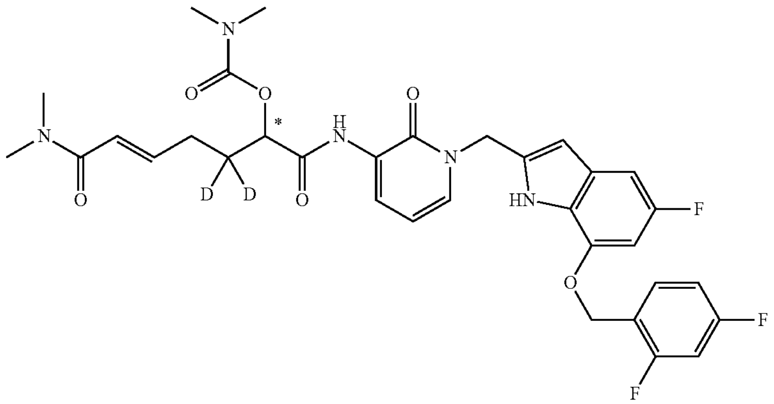 [SMILES: [2H]C([2H])(C/C=C/C(=O)N(C)C)C(OC(=O)N(C)C)C(=O)Nc1cccn(Cc2cc3cc(F)cc(OCc4ccc(F)cc4F)c3[nH]2)c1=O] | LCMS m/z 656.2 (M + 1)+ |
| 307 | 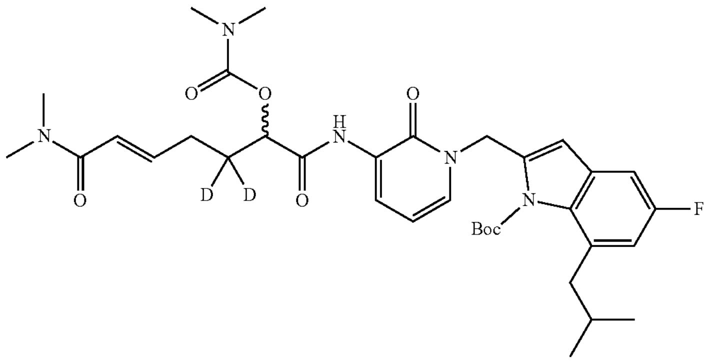 [SMILES: [2H]C([2H])(C/C=C/C(=O)N(C)C)C(OC(=O)N(C)C)C(=O)Nc1cccn(Cc2cc3cc(F)cc(CC(C)C)c3n2C(=O)OC(C)(C)C)c1=O] | LCMS m/z 670.5 (M + 1)+ |

-continued
| Compound | Structure | LCMS Data |
| --- | --- | --- |
| 308 | 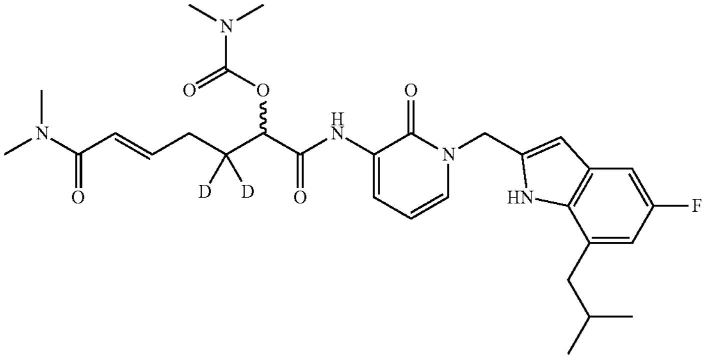 [SMILES: [2H]C([2H])(C/C=C/C(=O)N(C)C)C(OC(=O)N(C)C)C(=O)Nc1cccn(Cc2cc3cc(F)cc(CC(C)C)c3[nH]2)c1=O] | LCMS m/z 570.3 $(M + 1)^+$ |
The Synthesis of Intermediate I-396
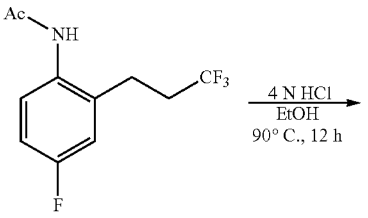
I-150
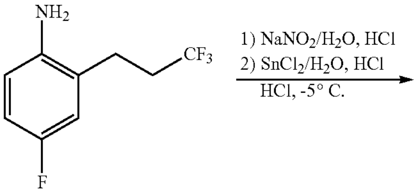
I-389
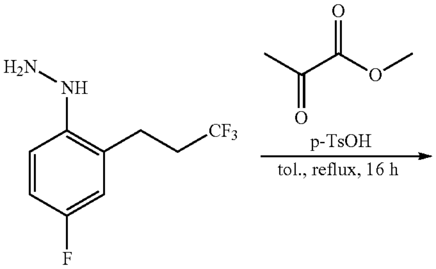
I-390
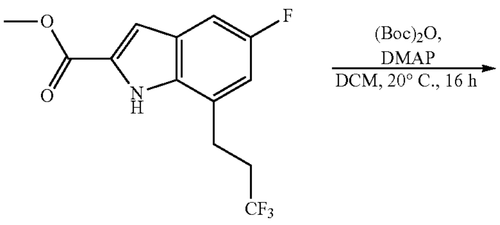
I-391
-continued
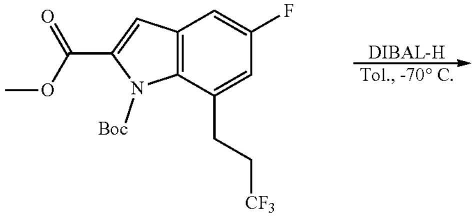
I-392
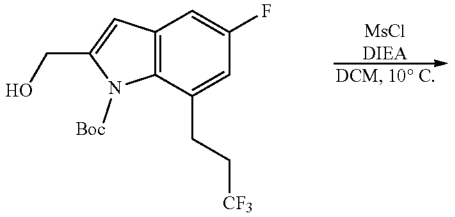
I-393
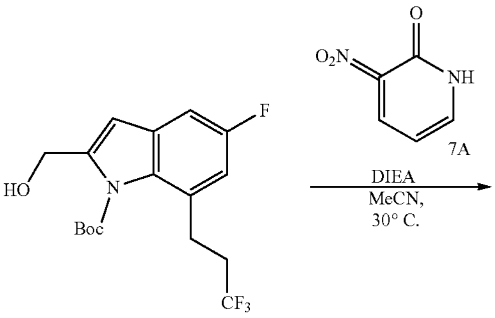
7A
I-394
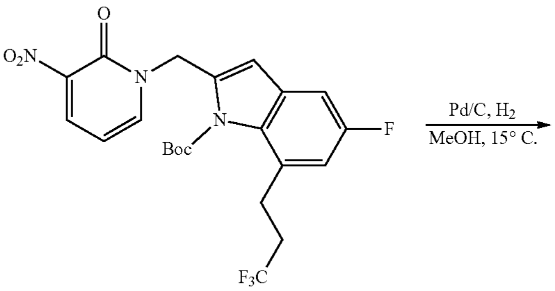
I-395

-continued

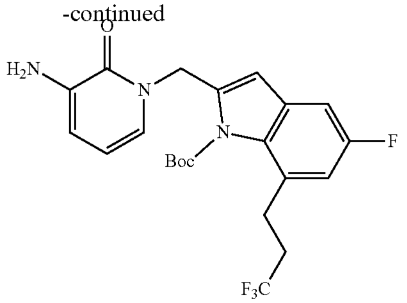

I-396

To a mixture of N-[4-fluoro-2-(3,3,3-trifluoropropyl)phenyl]acetamide (2 g, 8.03 mmol) in EtOH (15 mL) was added HCl (4 M, 15 mL). The mixture was stirred at 90° C. for 12 h. The resulting solution was concentrated, and NaOH (1M) solution was added to adjust pH~8. The mixture was extracted with EtOAc (15 mL×2). The combined organic layers were washed with brine (15 mL), dried over anhydrous $Na_2SO_4$ and concentrated to give a residue. The residue was purified by column chromatography to give 4-fluoro-2-(3,3,3-trifluoropropyl)aniline (I-389) (1.8 g) as a light brown oil. $^1$H NMR (400 MHz, $CDCl_3$) δ 6.86-6.73 (m, 2H), 6.65 (dd, J=5.0, 8.5 Hz, 1H), 3.63-3.30 (m, 2H), 2.77-2.67 (m, 2H), 2.50 (s, 1H), 2.50-2.32 (m, 1H).

To a solution of 4-fluoro-2-(3,3,3-trifluoropropyl)aniline (1.8 g, 8.69 mmol) in HCl (3 mL, 37%) was added a solution of $NaNO_2$ (719 mg, 10.4 mmol, 566 μL) in $H_2O$ (1 mL) dropwise in 10 min at −5° C. The mixture was stirred at −5° C. for 1 hr. A solution of $SnCl_2·2H_2O$ (2.45 g, 10.9 mmol, 904 μL) in HCl (3 mL, 37%) was added to the reaction mixture above dropwise at −5° C. in a period of 10 min. The reaction mixture was stirred at −5° C. for 2 h. The resulting suspension was filtered and the filter cake was collected and dried under vacuum to give [4-fluoro-2-(3,3,3-trifluoropropyl) phenyl]hydrazine (I-390) (1.8 g, crude, HCl) as a white solid.

To a mixture of methyl 2-oxopropanoate (852 mg, 8.35 mmol, 754 μL) in toluene (40 mL) was added PTSA (240 mg, 1.39 mmol). The mixture was stirred at 110° C. for 16 h. The mixture was concentrated to give a residue. The residue was diluted with EtOAc (30 mL) and washed with brine (15 mL). The organic phase was dried over anhydrous $Na_2SO_4$ and concentrated to give a residue. The residue was purified by column chromatography to give methyl 5-fluoro-7-(3,3,3-trifluoropropyl)-1H-indole-2-carboxylate (I-391) (0.3 g, 15% yield) as a light yellow solid. $^1$H NMR (400 MHz, $CDCl_3$) δ8.98 (s, 1H), 7.41-7.27 (m, 2H), 7.00 (d, J=8.4 Hz, 1H), 4.04 (s, 3H), 3.25-3.08 (m, 2H), 2.70-2.52 (m, 2H).

To a mixture of methyl 5-fluoro-7-(3,3,3-trifluoropropyl)-1H-indole-2-carboxylate (0.3 g, 1.02 mmol) and $(Boc)_2O$ (266 mg, 1.22 mmol, 280 μL) in DCM (30 mL) were added DMAP (24.8 mg, 203 μmol) and $Et_3N$ (206 mg, 2.03 mmol, 283 μL). The mixture was stirred at 20° C. for 16 h. The resulting solution was washed with $NH_4Cl$ (aq., 20 mL×2) and brine (15 mL). The organic phase was dried over anhydrous $Na_2SO_4$ and concentrated to give a residue. The residue was purified by column chromatography to give O1-tert-butyl O2-methyl 5-fluoro-7-(3,3,3-trifluoropropyl) indole-1,2-dicarboxylate (I-392) (0.3 g) as a white solid. $^1$H NMR (400 MHz, $CDCl_3$) δ 7.19 (dd, J=2.5, 7.9 Hz, 1H), 7.15 (s, 1H), 6.96 (dd, J=2.5, 9.9 Hz, 1H), 3.93 (s, 3H), 3.26-3.14 (m, 2H), 2.61-2.45 (m, 2H), 1.63 (s, 9H).

To a mixture of O1-tert-butyl O2-methyl 5-fluoro-7-(3,3,3-trifluoropropyl)indole-1,2-dicarboxylate (0.3 g, 771 μmol) in toluene (15 mL) was added DIBAL-H (1M, 2 mL) at −70° C. The mixture was stirred at −70° C. for 0.5 hr. The reaction mixture was quenched with $NH_4Cl$ (aq., 20 mL) and extracted with EtOAc (30 mL). The organic layer was dried over anhydrous $Na_2SO_4$ and concentrated to give a residue. The residue was purified by prep-TLC to give tert-butyl 5-fluoro-2-(hydroxymethyl)-7-(3,3,3-trifluoropropyl)indole-1-carboxylate (I-393) (0.22 g) as a white solid. $^1$H NMR (400 MHz, $CDCl_3$) δ57.08 (dd, J=2.4, 8.0 Hz, 1H), 6.86 (dd, J=2.5, 10.0 Hz, 1H), 6.54 (s, 1H), 4.78 (d, J=5.4 Hz, 2H), 3.19-3.08 (m, 2H), 2.60 (t, J=6.4 Hz, 1H), 2.52-2.36 (m, 2H), 1.68 (s, 9H).

To a mixture of tert-butyl 5-fluoro-2-(hydroxymethyl)-7-(3,3,3-trifluoropropyl) indole-1-carboxylate (0.22 g, 609 μmol) and MsCl (83.7 mg, 731 μmol, 56.6 μL) in DCM (10 mL) was added DIEA (157 mg, 1.22 mmol, 212 μL) at 0° C. The mixture was stirred at 15° C. for 0.5 hr. The resulting solution was diluted with DCM (20 mL) and washed with brine (15 mL). The organic phase was dried over anhydrous $Na_2SO_4$ and concentrated to give tert-butyl 2-(chloromethyl)-5-fluoro-7-(3,3,3-trifluoropropyl) indole-1-carboxylate (I-394) (0.25 g) as a light brown oil.

To a mixture of 3-nitro-1H-pyridin-2-one (138 mg, 987 μmol) and tert-butyl 2-(chloromethyl)-5-fluoro-7-(3,3,3-trifluoropropyl)indole-1-carboxylate (0.25 g, 658 μmol) in $CH_3CN$ (15 mL) was added DIEA (170 mg, 1.32 mmol, 229 μL). The mixture was stirred at 35° C. for 16 h. The mixture was diluted with EtOAc (30 mL), washed with water (15 mL) and brine (15 mL). The organic phase was dried over anhydrous $Na_2SO_4$ and concentrated to give a residue. The residue was purified by column chromatography to give tert-butyl 5-fluoro-2-[(3-nitro-2-oxo-1-pyridyl)methyl]-7-(3,3,3-trifluoropropyl)indole-1-carboxylate (I-395) (140 mg) as a yellow solid.

A mixture of tert-butyl 5-fluoro-2-[(3-nitro-2-oxo-1-pyridyl)methyl]-7-(3,3,3-trifluoropropyl)indole-1-carboxylate (0.115 g, 238 μmol) in MeOH (5 mL) was added Pd/C (0.01 g, 238 μmol, 10% purity). The mixture was stirred at 15° C. for 5 min under $H_2$ (15 psi) atmosphere. The reaction mixture was filtered and the filtrate was concentrated to give tert-butyl 2-[(3-amino-2-oxo-1-pyridyl)methyl]-5-fluoro-7-(3,3,3-trifluoropropyl)indole-1-carboxylate (I-396) (0.1 g) as a light yellow oil.

The following intermediate was prepared according to the procedures described in I-396 using the appropriate intermediates.

| Compound | Structure | LCMS Data |
|---|---|---|
| I-397 | 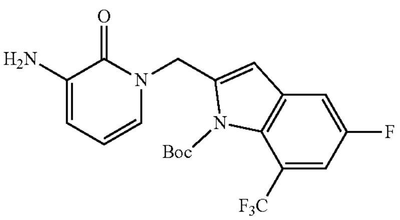 [SMILES: CC(C)(C)OC(=O)n1c(Cn2cccc(N)c2=O)cc2cc(F)cc(C(F)(F)F)c21] | LCMS m/z 426.1 $(M + 1)^+$ |

Example 42

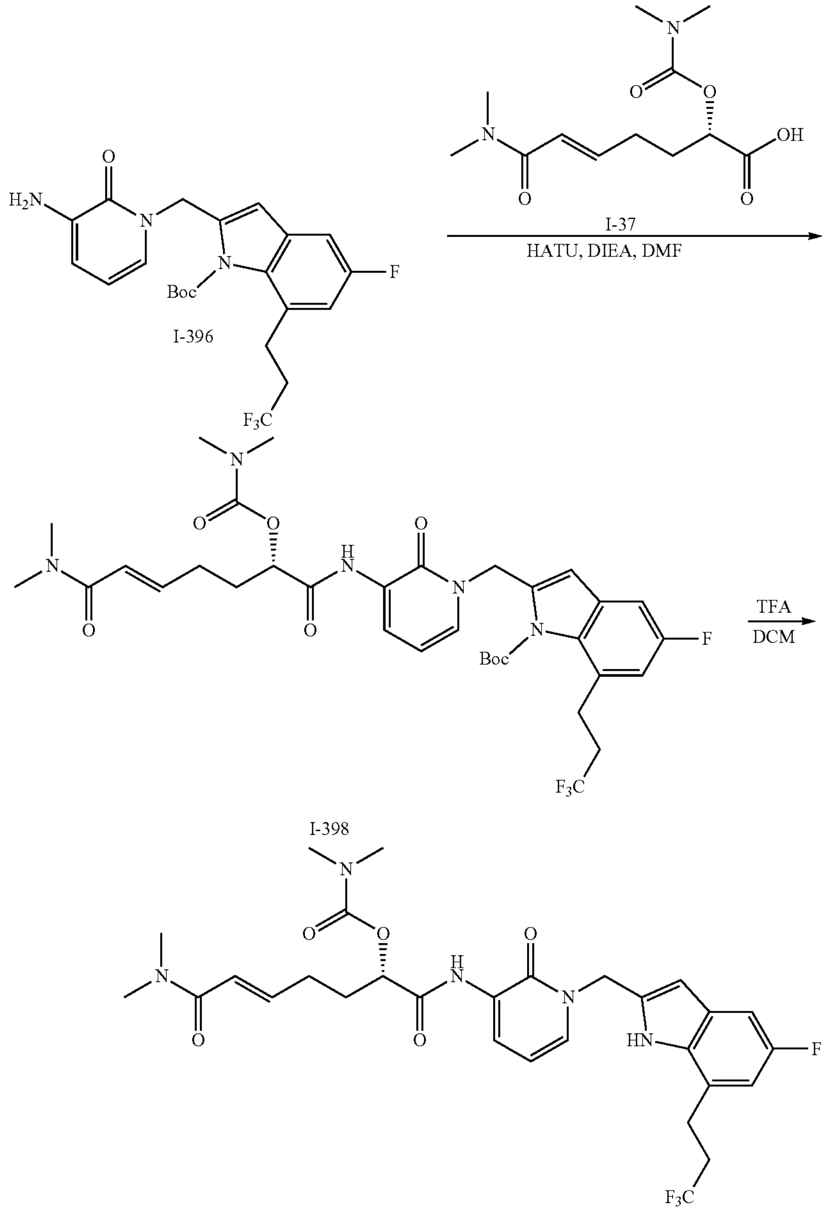

To a mixture of (E,2S)-7-(dimethylamino)-2-(dimethylcarbamoyloxy)-7-oxo-hept-5-enoic acid (0.08 g, 291 μmol) and tert-butyl 2-[(3-amino-2-oxo-1-pyridyl) methyl]-5-fluoro-7-(3,3,3-trifluoropropyl)indole-1-carboxylate (0.1 g, 221 μmol) in DMF (2 mL) were added HATU (101 mg, 265 μmol) and DIEA (57.0 mg, 441 μmol, 76.8 μL) at 0° C. The mixture was stirred at 30° C. for 12 h. The resulting solution was diluted with EtOAc (30 mL), washed with water (20 mL) and brine (20 mL). The organic layer was dried over anhydrous $Na_2SO_4$ and concentrated to give a residue. The residue was purified by prep-TLC to give tert-butyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-7-(3,3,3-trifluoropropyl)indole-1-carboxylate (I-398) (100 mg, 58% yield) as a light yellow solid.

To a mixture of tert-butyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-7-(3,3,3-trifluoropropyl)indole-1-carboxylate (0.09 g, 114 μmol) in DCM (2 mL) at 0° C. was added TFA (1.54 g, 13.5 mmol, 1 mL) dropwise. The mixture was stirred at 15° C. for 3 h. The reaction mixture was concentrated to give a residue. The residue was purified by prep-HPLC to give [(E,1S)-6-(dimethylamino)-1-[[1-[[5-fluoro-7-(3,3,3-trifluoropropyl)-1H-indol-2-yl]methyl]-2-oxo-3-pyridyl]carbamoyl]-6-oxo-hex-4-enyl] N,N-dimethylcarbamate (Compound 309) (25 mg, 36% yield) as a light yellow solid. LCMS m/z 608.2 $(M+1)^+$. $^1H$ NMR (400 MHz, DMSO-$d_6$) δ11.34 (s, 1H), 9.35 (s, 1H), 8.22 (d, J=6.6 Hz, 1H), 7.49 (d, J=6.0 Hz, 1H), 7.19-7.05 (m, 1H), 6.89 (d, J=10.4 Hz, 1H), 6.72-6.57 (m, 1H), 6.46-6.29 (m, 2H), 6.23 (s, 1H), 5.37-5.26 (m, 2H), 5.10 (dd, J=4.6, 7.3 Hz, 1H), 3.12-3.04 (m, 2H), 2.98 (s, 6H), 2.83 (s, 6H), 2.76-2.63 (m, 2H), 2.29 (q, J=6.8 Hz, 2H), 2.05-1.86 (m, 2H).

The following compounds were prepared according to the procedures described in Example 42 using the appropriate intermediates.
| Compound | Structure | LCMS Data |
|---|---|---|
| 310 | 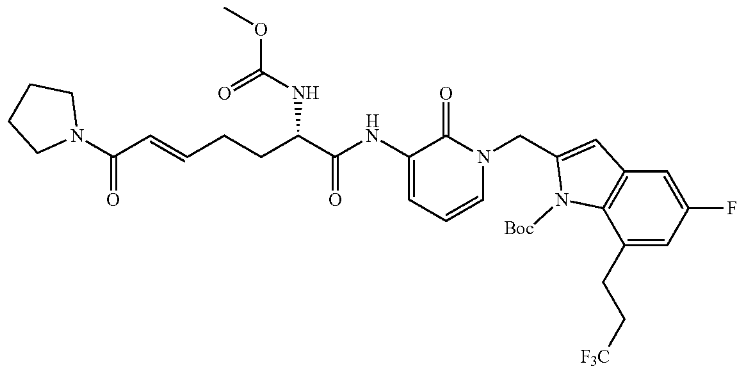 [SMILES: COC(=O)N[C@@H](CC/C=C/C(=O)N1CCCC1)C(=O)Nc1cccn(Cc2cc3cc(F)cc(CCC(F)(F)F)c3n2C(=O)OC(C)(C)C)c1=O] | LCMS m/z 720.4 (M + 1)$^+$ |
| 311 | 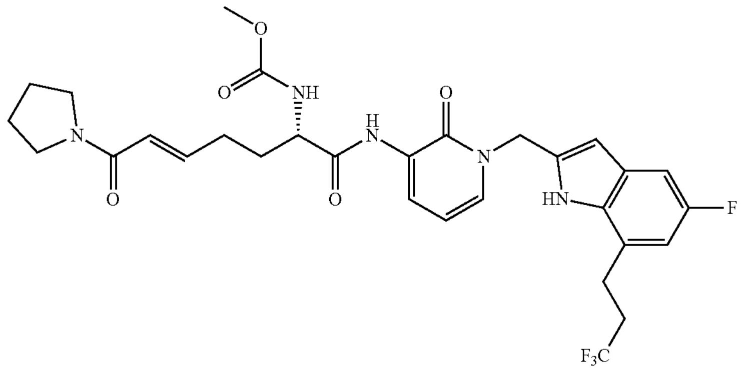 [SMILES: COC(=O)N[C@@H](CC/C=C/C(=O)N1CCCC1)C(=O)Nc1cccn(Cc2cc3cc(F)cc(CCC(F)(F)F)c3[nH]2)c1=O] | LCMS m/z 620.3 (M + 1)$^+$ |
| 312 | 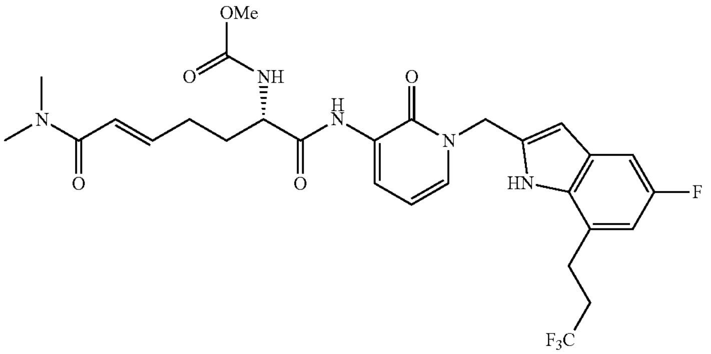 [SMILES: COC(=O)N[C@@H](CC/C=C/C(=O)N(C)C)C(=O)Nc1cccn(Cc2cc3cc(F)cc(CCC(F)(F)F)c3[nH]2)c1=O] | LCMS m/z 594.2 (M + 1)$^+$ |
| 313 | 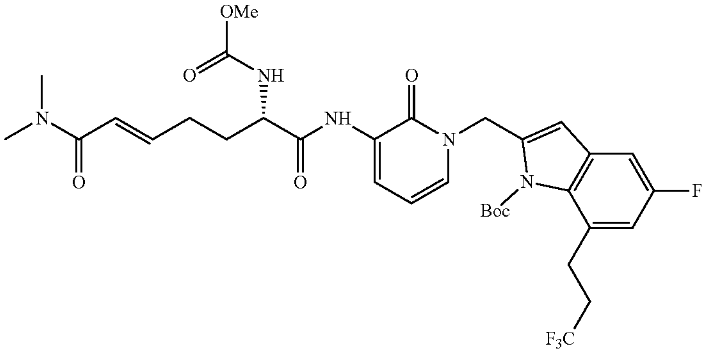 [SMILES: COC(=O)N[C@@H](CC/C=C/C(=O)N(C)C)C(=O)Nc1cccn(Cc2cc3cc(F)cc(CCC(F)(F)F)c3n2C(=O)OC(C)(C)C)c1=O] | LCMS m/z 694.2 (M + 1)$^+$ |

-continued
| Compound | Structure | LCMS Data |
| --- | --- | --- |
| 314 | 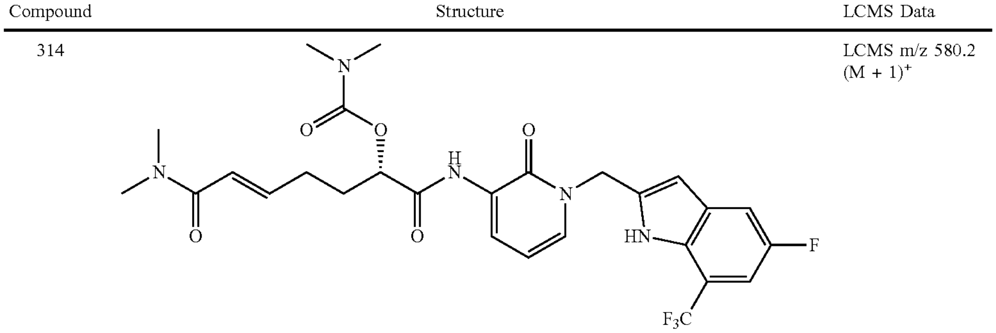 | LCMS m/z 580.2 $(M + 1)^+$ |
| 315 | 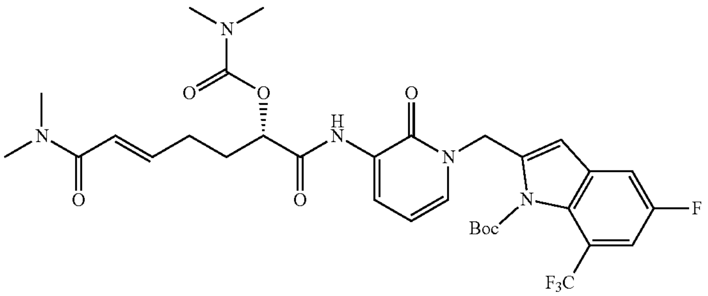 [SMILES: CN(C)C(=O)/C=C/CC[C@H](OC(=O)N(C)C)C(=O)Nc1cccn(Cc2cc3cc(F)cc(C(F)(F)F)c3n2C(=O)OC(C)(C)C)c1=O] | LCMS m/z 680.3 $(M + 1)^+$ |
| 316 | 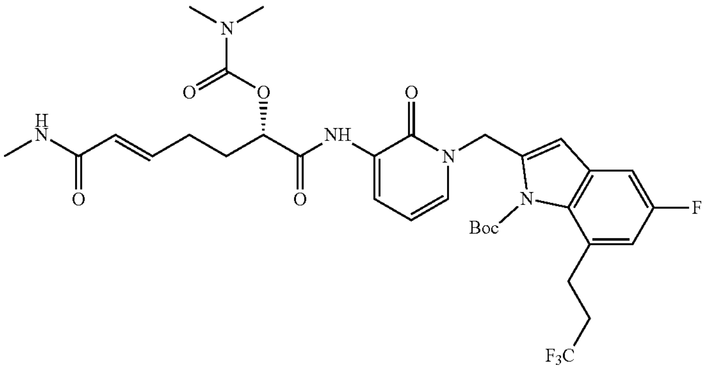 | LCMS m/z 694.2 $(M + 1)^+$ |
| 317 | 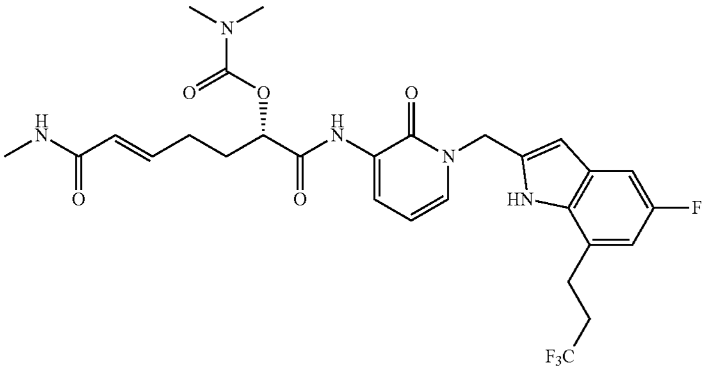 | LCMS m/z 594.2 $(M + 1)^+$ |

The Synthesis of Intermediate I-408
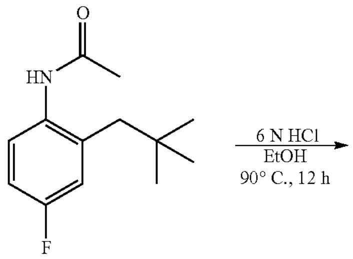
I-129
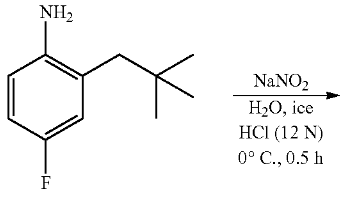
I-399
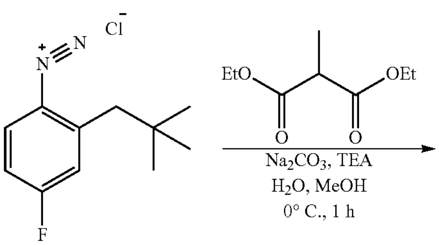
I-400
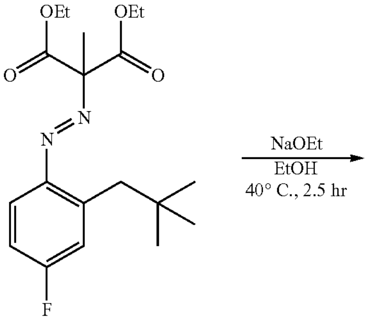
I-401
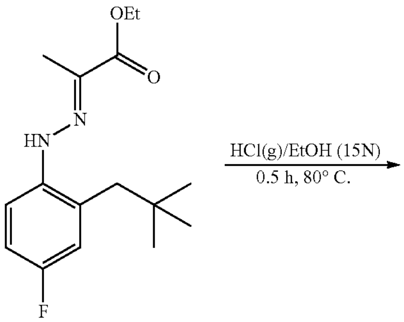
I-402
-continued
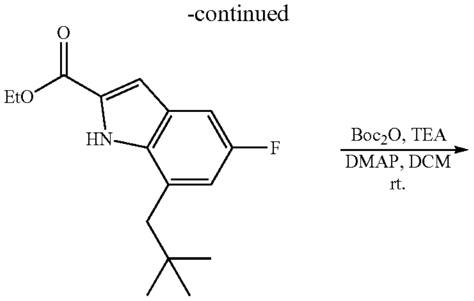
I-403
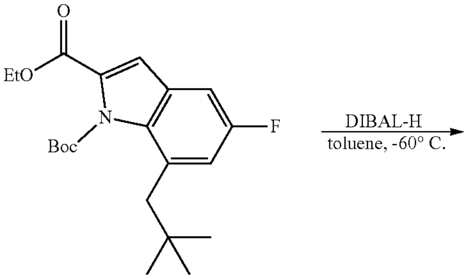
I-404
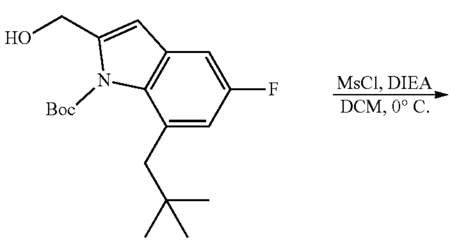
I-405
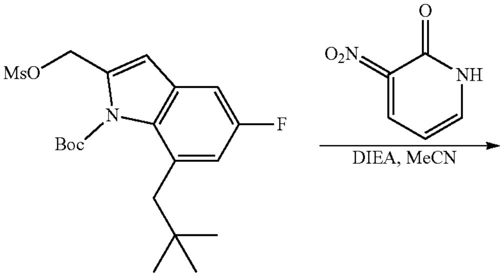
I-406
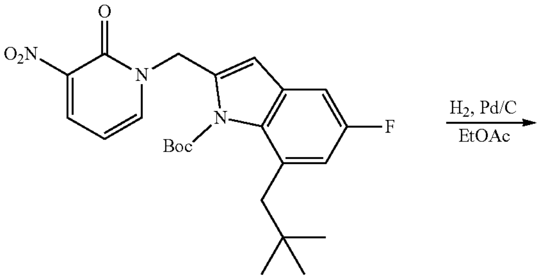
I-407

-continued

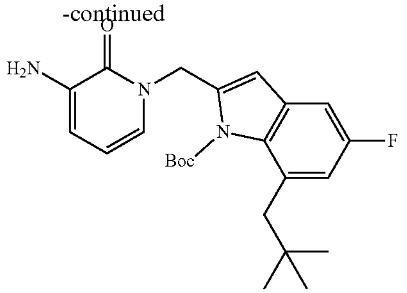

I-408

A mixture of N-[2-(2,2-dimethylpropyl)-4-fluoro-phenyl] acetamide (7 g, 31.35 mmol) in HCl (35 mL, 6N) and EtOH (35 mL) was degassed and purged with $N_2$ for 3 times, and then the mixture was stirred at 90° C. for 12 hours under $N_2$ atmosphere. The reaction mixture was concentrated under reduced pressure to remove the solvent to afford a yellow solid. The reaction mixture was partitioned between sat. $NaHCO_3$ (aq) (100 mL) and ethyl acetate (100 mL). The organic phase was separated, washed with brine (100 mL×1), dried over anhydrous $Na_2SO_4$, filtered and concentrated under reduced pressure to give an oil. The residue was purified by flash silica gel chromatography to give 2-(2,2-dimethylpropyl)-4-fluoro-aniline (I-399) (3.38 g, 59% yield) as an orange oil.

To a solution of 2-(2,2-dimethylpropyl)-4-fluoro-aniline (6.25 g, 34.48 mmol) in HCl (10.9 mL, 12N) and ice (50 mL) was added a solution of $NaNO_2$ (2.52 g, 36.55 mmol) in $H_2O$ (9.4 mL) at 0° C. The mixture was stirred at 0° C. for 0.5 hr. The crude product 4-fluoro-2-neopentylbenzene-diazonium (I-400) in solvent was used in the next step without further purification.

To a solution of compound 5A (6.01 g, 34.50 mmol, 5.89 mL), TEA (3.49 g, 34.50 mmol, 4.80 mL) and $Na_2CO_3$ (3.66 g, 34.50 mmol) in $H_2O$ (30 mL) and MeOH (60 mL) was added a solution of 4-fluoro-2-neopentylbenzenediazonium (7.89 g, 34.50 mmol) in a yellow solvent at 0° C. and then the mixture was stirred at 0° C. for 1 hr. The reaction mixture was diluted with water (50 mL) and extracted with TBME (50 mL×2). The combined organic phase was washed with brine (50 mL), dried over anhydrous $Na_2SO_4$, filtered and concentrated under reduced pressure to give an oil. The residue was purified by flash silica gel chromatography to give diethyl 2-[(E)-[2-(2,2-dimethylpropyl)-4-fluoro-phenyl]azo]-2-methyl-propanedioate (I-401) (8.5 g, 67% yield) as a brown oil.

A mixture of EtONa (1.58 g, 23.20 mmol) in EtOH (30 mL) was added a solution of diethyl 2-[(E)-[2-(2,2-dimethylpropyl)-4-fluoro-phenyl]azo]-2-methyl-propanedioate (8.5 g, 23.20 mmol) in EtOH (60 mL) at 40° C., and then the mixture was stirred at 40° C. for 2.5 hr. The reaction mixture was quenched by addition citric acid 100 mL at 0° C., and then concentrated. Then diluted with water (50 mL) and extracted with MTBE (100 mL×2). The combined organic layers were dried over anhydrous $Na_2SO_4$, filtered and concentrated under reduced pressure to give an oil. The residue was purified by flash silica gel chromatography to give ethyl (2E)-2-[[2-(2,2-dimethylpropyl)-4-fluoro-phenyl]hydrazono]propanoate (I-402) (5.5 g, 81% yield) as a yellow oil.

To a solution of ethyl (2E)-2-[[2-(2,2-dimethylpropyl)-4-fluoro-phenyl]hydrazono]propanoate (1 g, 3.40 mmol) in EtOH (1 mL) was added HCl (6.88 g, 67.94 mmol, 6.75 mL, 36% purity) at 80° C. The mixture was stirred at 80° C. for 30 mins. The reaction mixture was concentrated under reduced pressure to remove EtOH, then the residue was diluted with sat. $NaHCO_3$ solution (50 mL) and extracted with EtOAc (40 mL×2), the combined organic phase were dried over anhydrous $Na_2SO_4$, filtered and concentrated under reduced pressure to give an oil. The residue was purified by flash silica gel chromatography to give ethyl 7-(2,2-dimethylpropyl)-5-fluoro-1H-indole-2-carboxylate (I-403) (2.11 g, 45% yield) as a yellow solid.

To a solution of ethyl 7-(2,2-dimethylpropyl)-5-fluoro-1H-indole-2-carboxylate (2.11 g, 7.61 mmol) in DCM (25 mL) was added $Boc_2O$ (4.15 g, 19.02 mmol, 4.37 mL) and TEA (1.54 g, 15.22 mmol, 2.12 mL) and DMAP (278.84 mg, 2.28 mmol) at 0° C. The mixture was stirred at 25° C. for 12 hours. The reaction mixture was diluted with sat. $NH_4Cl$ solution (50 mL) and extracted with DCM (30 mL×2), the combined organic phase were dried over anhydrous $Na_2SO_4$, filtered and concentrated under reduced pressure to give an oil. The residue was purified by flash silica gel chromatography to give O1-tert-butyl O2-ethyl 7-(2,2-dimethylpropyl)-5-fluoro-indole-1,2-dicarboxylate (I-404) (2.3 g, 80% yield) as a yellow solid.

To a solution of O1-tert-butyl O2-ethyl 7-(2,2-dimethylpropyl)-5-fluoro-indole-1,2-dicarboxylate (1.02 g, 2.70 mmol) in toluene (8 mL) was added DIBAL-H (1 M, 5.40 mL) at −60° C. The mixture was stirred at −60° C. for 1 hr. The reaction mixture was quenched by addition to the solution of sat. $NH_4Cl$ solution (30 mL), then the mixture was filtered, the filter liquor was extracted with EtOAc 30 mL (15 mL×2), the combined organic phase were dried over anhydrous $Na_2SO_4$, filtered and concentrated under reduced pressure to give tert-butyl 7-(2,2-dimethylpropyl)-5-fluoro-2-(hydroxymethyl)indole-1-carboxylate (I-405) (830 mg, 92% yield) as a yellow oil.

To a solution of tert-butyl 7-(2,2-dimethylpropyl)-5-fluoro-2-(hydroxymethyl)indole-1-carboxylate (0.83 g, 2.47 mmol) in DCM (10 mL) was added DIEA (1.92 g, 14.85 mmol, 2.59 mL) and MsCl (1.42 g, 12.37 mmol, 957.65 uL) at 0° C. The mixture was stirred at 0° C. for 1 hr. The reaction mixture was diluted with sat. $NH_4Cl$ solution (20 mL) and extracted with DCM (8 mL×2). The combined organic phase were washed with brine (10 mL), dried over anhydrous $Na_2SO_4$, filtered and concentrated under reduced pressure to give tert-butyl 7-(2,2-dimethylpropyl)-5-fluoro-2-(methylsulfonyloxymethyl)indole-1-carboxylate (I-406) (1.02 g) as a yellow oil.

A mixture of compound 1A (298.15 mg, 2.13 mmol), DIEA (500.09 mg, 3.87 mmol, 673.98 uL) in ACN (8 mL) was added a solution of tert-butyl 7-(2,2-dimethylpropyl)-5-fluoro-2-(methylsulfonyloxymethyl)indole-1-carboxylate (0.8 g, 1.93 mmol) in ACN (2 mL) at 0° C., and then the mixture was stirred at 25° C. for 12 hours. The reaction mixture was diluted with sat. $NH_4Cl$ solution (20 mL), then extracted with EtOAc (8 mL×2), the combined organic phase were washed with brine (10 mL), then dried over anhydrous $Na_2SO_4$, filtered and concentrated under reduced pressure. The residue was purified by column chromatography to give tert-butyl 7-(2,2-dimethylpropyl)-5-fluoro-2-[(3-nitro-2-oxo-1-pyridyl)methyl]indole-1-carboxylate (I-407) (0.55 g, 62% yield) as a yellow gum.

A mixture of tert-butyl 7-(2,2-dimethylpropyl)-5-fluoro-2-[(3-nitro-2-oxo-1-pyridyl)methyl] indole-1-carboxylate (0.2 g, 437.16 umol), Pd/C (0.2 g, 10% purity) in EtOAc (20 mL) was degassed and purged with $H_2$ for 3 times, and then the mixture was stirred at 25° C. for 1 hr under $H_2$ atmosphere (15 psi). The reaction mixture was filtered and concentrated under reduced pressure to give tert-butyl 2-[(3-amino-2-oxo-1-pyridyl)methyl]-7-(2,2-dimethylpropyl)-5-fluoro-indole-1-carboxylate (I-408) as a light yellow gum.

Example 43

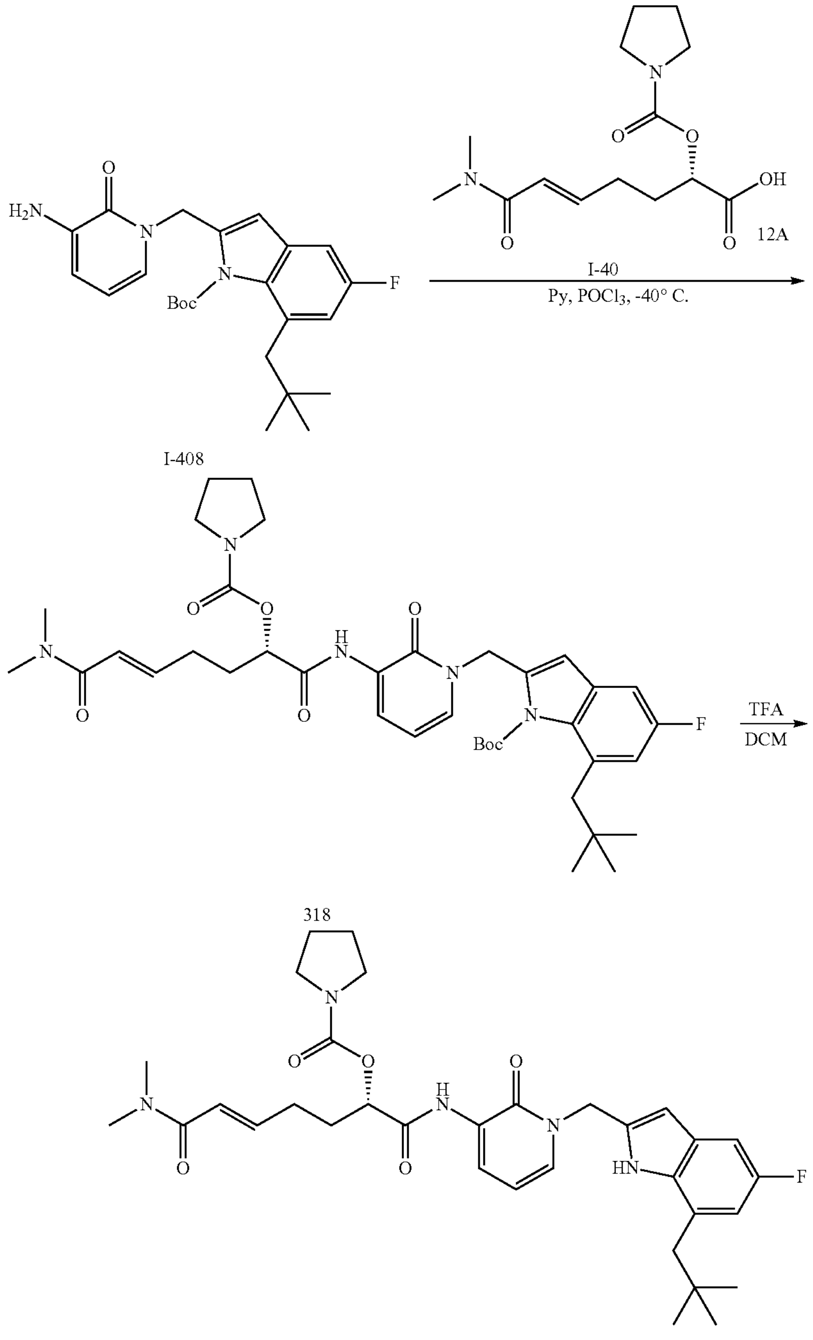

I-408

318

319

A mixture of tert-butyl 2-[(3-amino-2-oxo-1-pyridyl)methyl]-7-(2,2-dimethylpropyl)-5-fluoro-indole-1-carboxylate (0.11 g, 257.30 umol), (E,2S)-7-(dimethylamino)-7-oxo-2-(pyrrolidine-1-carbonyloxy)hept-5-enoic acid (61.41 mg, 205.84 umol) in pyridine (2 mL) was added $POCl_3$ (78.91 mg, 514.61 umol, 47.82 uL) at −40° C. and then the mixture was stirred at −40° C. for 15 min. The reaction mixture was quenched by added sat. $NaHCO_3$ solution (3 mL) and then extracted with EtOAc (5 mL×2). The combined organic layers were dried over anhydrous $Na_2SO_4$, filtered and concentrated under reduced pressure to give an oil. The residue was purified by prep-TLC to give tert-butyl 2-[[3-[[(E,2S)-7-(dimethylamino)-7-oxo-2-(pyrrolidine-1-carbonyloxy)hept-5-enoyl]amino]-2-oxo-1-pyridyl]methyl]-7-(2,2-dimethylpropyl)-5-fluoro-indole-1-carboxylate (Compound 318) (30 mg) as a light yellow solid which was used in the next step without further purification. LCMS m/z 708.3 $(M+1)^+$.

A mixture of tert-butyl 2-[[3-[[(E,2S)-7-(dimethylamino)-7-oxo-2-(pyrrolidine-1-carbonyloxy)hept-5-enoyl] amino]-2-oxo-1-pyridyl] methyl]-7-(2,2-dimethylpropyl)-5-fluoro-indole-1-carboxylate (30 mg, 42.38 umol) in TFA (0.5 mL) and DCM (2 mL) was stirred at 25° C. for 1 hr. The reaction mixture was poured into sat. $NaHCO_3$ solution (20 mL) and extracted with DCM (5 mL×2). The combined organic layers were dried over anhydrous $Na_2SO_4$, filtered and concentrated under reduced pressure to give [(E,1S)-6-

(dimethylamino)-1-[[1-[[7-(2,2-dimethylpropyl)-5-fluoro-1H-indol-2-yl]methyl]-2-oxo-3-pyridyl]carbamoyl]-6-oxo-hex-4-enyl] pyrrolidine-1-carboxylate (Compound 319) (14.2 mg, 51% yield) as a brown solid. LCMS m/z 612.3 $(M+1)^+$.

The following compounds were prepared according to the procedures described for the synthesis of Example 43 using the appropriate intermediates.

| Compound | Structure | LCMS Data |
| --- | --- | --- |
| 320 | 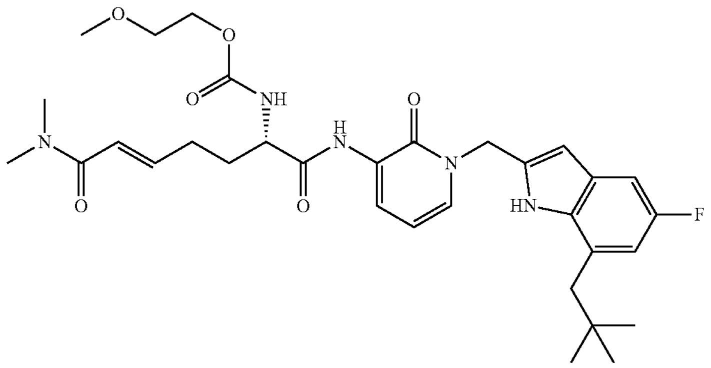 [SMILES: COCCOC(=O)N[C@@H](CC/C=C/C(=O)N(C)C)C(=O)Nc1cccn(Cc2cc3cc(F)cc(CC(C)(C)C)c3[nH]2)c1=O] | LCMS m/z 612.3 $(M + 1)^+$ |
| 321 | 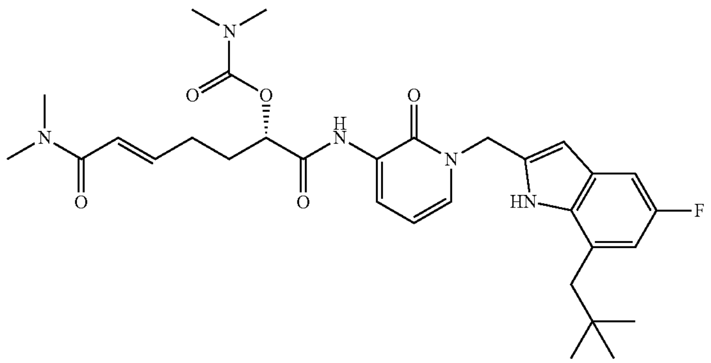 [SMILES: CN(C)C(=O)/C=C/CC[C@H](OC(=O)N(C)C)C(=O)Nc1cccn(Cc2cc3cc(F)cc(CC(C)(C)C)c3[nH]2)c1=O] | LCMS m/z 582.2 $(M + 1)^+$ |
| 322 | 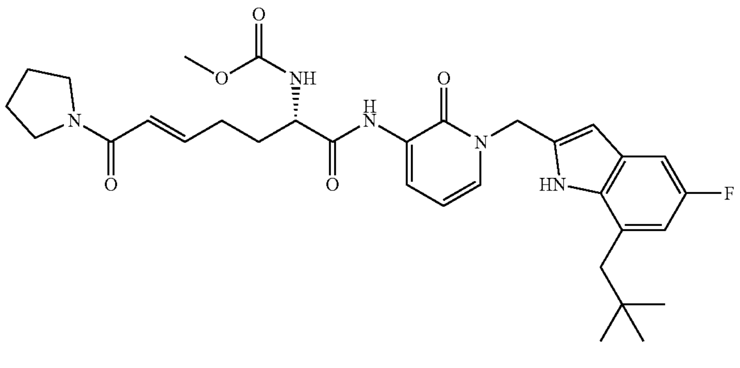 [SMILES: COC(=O)N[C@@H](CC/C=C/C(=O)N1CCCC1)C(=O)Nc1cccn(Cc2cc3cc(F)cc(CC(C)(C)C)c3[nH]2)c1=O] | LCMS m/z 594.3 $(M + 1)^+$ |

-continued
| Compound | Structure | LCMS Data |
| --- | --- | --- |
| 323 | 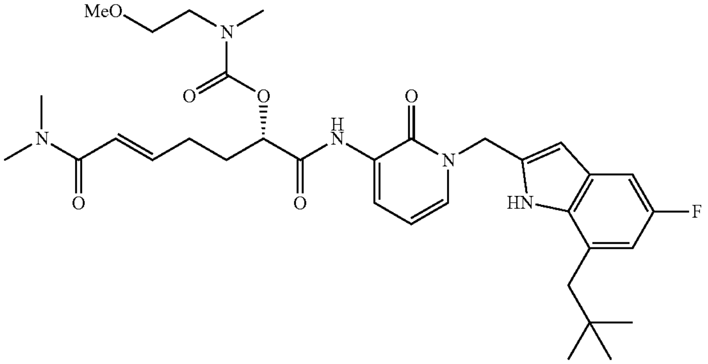 [SMILES: COCCN(C)C(=O)O[C@@H](CC/C=C/C(=O)N(C)C)C(=O)Nc1cccn(Cc2cc3cc(F)cc(CC(C)(C)C)c3[nH]2)c1=O] | LCMS m/z 626.3 (M + 1)$^+$ |
| 325 | 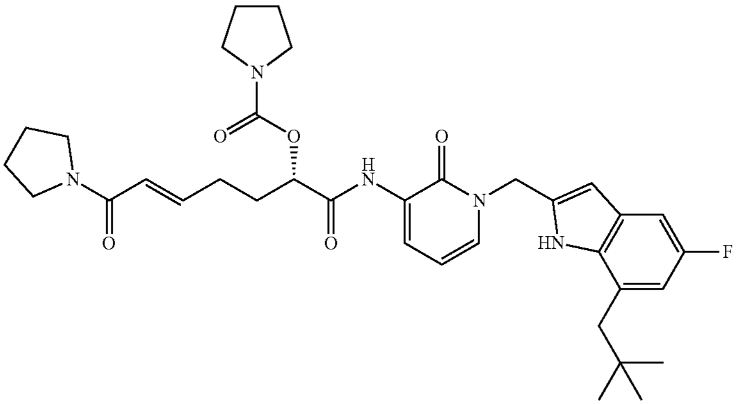 [SMILES: CC(C)(C)Cc1cc(F)cc2cc(Cn3cccc(NC(=O)[C@H](CC/C=C/C(=O)N4CCCC4)OC(=O)N4CCCC4)c3=O)[nH]c12] | LCMS m/z 634.3 (M + 1)$^+$ |
| 326 | 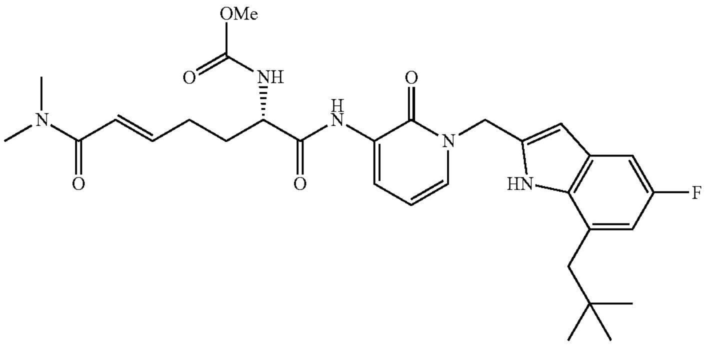 [SMILES: COC(=O)N[C@@H](CC/C=C/C(=O)N(C)C)C(=O)Nc1cccn(Cc2cc3cc(F)cc(CC(C)(C)C)c3[nH]2)c1=O] | LCMS m/z 568.3 (M + 1)$^+$ |
The Synthesis of Intermediate I-49
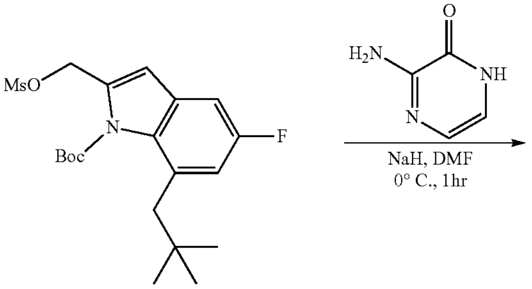
-continued
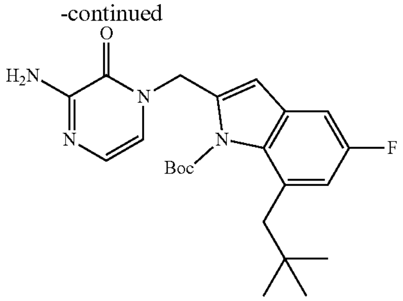
I-409
A mixture of compound 11A (64.48 mg, 580.41 umol) in DMF (1.5 mL) was added NaH (38.69 mg, 967.35 umol, 60% purity) at 0° C. The mixture was stirred at 0° C. for 0.5 hour. A solution of tert-butyl 7-(2,2-dimethylpropyl)-5-fluoro-2-(methylsulfonyloxymethyl)indole-1-carboxylate (0.2 g, 483.67 umol) in DMF (1.5 mL) was added followed by the addition of KI (40.15 mg, 241.84 umol). The mixture was stirred at 25° C. for 1.5 hr. The reaction mixture was quenched by addition to the solution of sat. $NH_4Cl$ solution (10 mL). The mixture was extracted with EtOAc (5 mL×2) and the combined organic phase was dried over anhydrous $Na_2SO_4$, filtered and concentrated under reduced pressure. The residue was purified by prep-TLC to give tert-butyl 2-[(3-amino-2-oxo-pyrazin-1-yl)methyl]-7-(2,2-dimethylpropyl)-5-fluoro-indole-1-carboxylate (I-409) (80 mg, 39% yield) as a yellow gum.

The following intermediates were prepared according to the procedures described in I-409 using the appropriate intermediate.

| Compound | Structure | LCMS Data |
|---|---|---|
| I-410 | 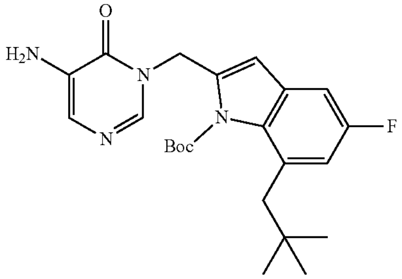 [SMILES: CC(C)(C)Cc1cc(F)cc2cc(Cn3cncc(N)c3=O)n(C(=O)OC(C)(C)C)c12] | LCMS m/z 429.1 (M + 1)+ |

-continued

| Compound | Structure | LCMS Data |
|---|---|---|
| I-410A | 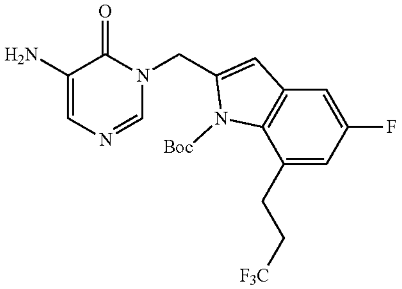 [SMILES: CC(C)(C)OC(=O)n1c(Cn2cncc(N)c2=O)cc2cc(F)cc(CCC(F)(F)F)c21] | LCMS m/z 455.1 (M + 1)+ |
| I-410B | 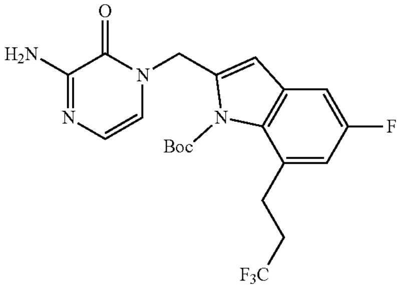 [SMILES: CC(C)(C)OC(=O)n1c(Cn2ccnc(N)c2=O)cc2cc(F)cc(CCC(F)(F)F)c21] | LCMS m/z 455.1 (M + 1)+ |

Example 44

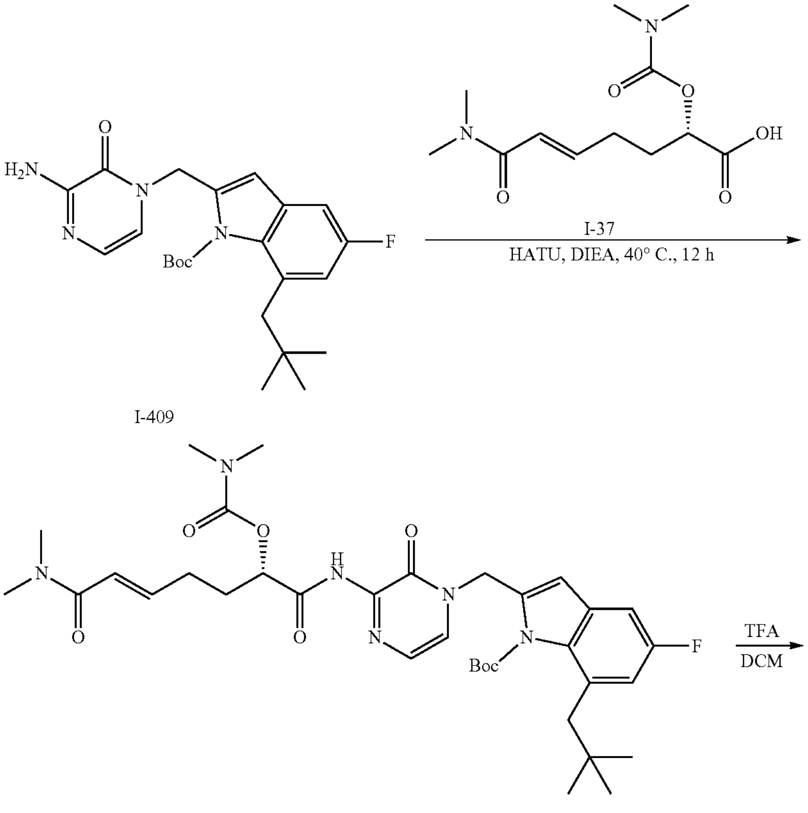

I-409

-continued

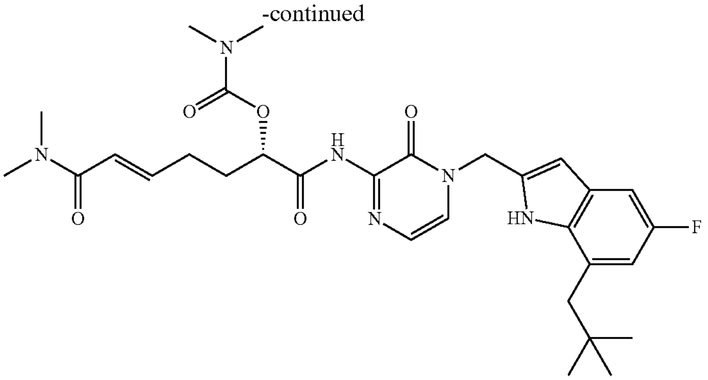

328

A mixture of (E,2S)-7-(dimethylamino)-2-(dimethylcarbamoyloxy)-7-oxo-hept-5-enoic acid (71.49 mg, 262.54 umol), tert-butyl 2-[(3-amino-2-oxo-pyrazin-1-yl)methyl]-7-(2,2-dimethylpropyl)-5-fluoro-indole-1-carboxylate (0.075 g, 175.03 umol), DIEA (45.24 mg, 350.06 umol, 60.97 uL) in DMA (2 mL) was added HATU (119.79 mg, 315.05 umol) at 25° C., and then the mixture was stirred at 40° C. for 12 hours. The reaction mixture was diluted with sat. $NH_4Cl$ solution (5 mL) and extracted with EtOAc (3 mL×2). The combined organic phase was washed with brine (5 mL), dried over anhydrous $Na_2SO_4$, filtered and concentrated under reduced pressure to give an oil. The residue was purified by prep-HPLC to give tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-7-(2,2-dimethylpropyl)-5-fluoro-indole-1-carboxylate (Compound 327) (89.0 mg, 63% yield) as a white solid. LCMS m/z 683.3 $(M+1)^+$.

A mixture of tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-7-(2,2-dimethylpropyl)-5-fluoro-indole-1-carboxylate (85 mg, 124.49 umol) in DCM (2.5 mL) was added TFA (0.5 mL) at 25° C., and then the mixture was stirred at 25° C. for 1 hr. The reaction mixture was poured into sat. $NH_4Cl$ solution 20 mL, then extracted with DCM (5 mL×2). The combined organic layers were dried over anhydrous $Na_2SO_4$, filtered and concentrated under reduced pressure to give the desired product. The residue was purified by prep-HPLC to give [(E,1S)-6-(dimethylamino)-1-[[4-[[7-(2,2-dimethylpropyl)-5-fluoro-1H-indol-2-yl]methyl]-3-oxo-pyrazin-2-yl]carbamoyl]-6-oxo-hex-4-enyl] N,N-dimethylcarbamate (Compound 328) (35.6 mg, 48% yield) as a white solid. LCMS m/z 583.3 $(M+1)^+$. $^1H$ NMR (400 MHz, DMSO-$d_6$) δ 11.07 (br s, 1H), 9.96 (br s, 1H), 7.35 (br d, J=4.16 Hz, 1H), 7.10 (br d, J=4.65 Hz, 2H), 6.62-6.74 (m, 2H), 6.42 (br d, J=14.43 Hz, 1H), 6.31 (s, 1H), 5.25 (br s, 2H), 5.19 (br s, 1H), 2.98 (br d, J=16.87 Hz, 6H), 2.84 (br d, J=10.76 Hz, 6H), 2.74 (br s, 2H), 2.33 (br s, 2H), 1.86-2.01 (m, 2H), 0.92 (br s, 9H).

The following compounds were prepared according to the procedures described for the synthesis of Example 44 using the appropriate intermediates.

| Compound | Structure | LCMS Data |
|---|---|---|
| 329 | 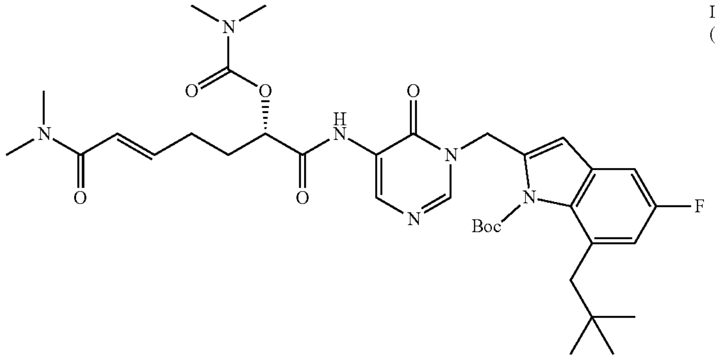 | LCMS m/z 683.5 $(M + 1)^+$ |

-continued
| Compound | Structure | LCMS Data |
| --- | --- | --- |
| 330 | 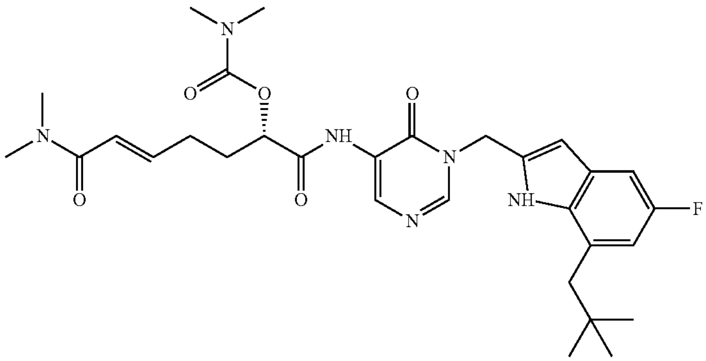 [SMILES: CN(C)C(=O)/C=C/CC[C@H](OC(=O)N(C)C)C(=O)Nc1cncn(Cc2cc3cc(F)cc(CC(C)(C)C)c3[nH]2)c1=O] | LCMS m/z 583.3 $(M + 1)^+$ |
| 331 | 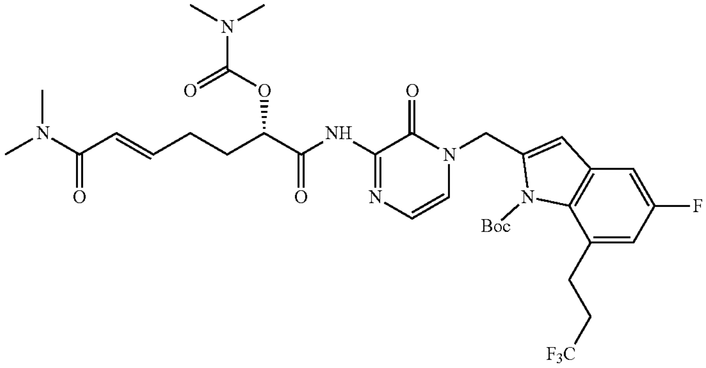 [SMILES: CN(C)C(=O)/C=C/CC[C@H](OC(=O)N(C)C)C(=O)Nc1nccn(Cc2cc3cc(F)cc(CCC(F)(F)F)c3n2C(=O)OC(C)(C)C)c1=O] | LCMS m/z 709.3 $(M + 1)^+$ |
| 332 | 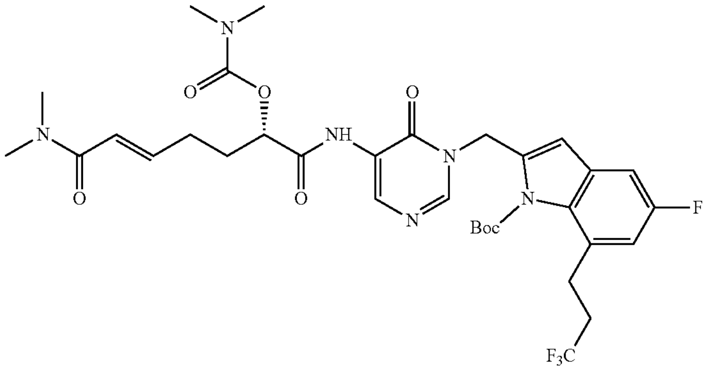 [SMILES: CN(C)C(=O)/C=C/CC[C@H](OC(=O)N(C)C)C(=O)Nc1cncn(Cc2cc3cc(F)cc(CCC(F)(F)F)c3n2C(=O)OC(C)(C)C)c1=O] | LCMS: $[M + 1]^+$ = 709.3 |
| 333 | 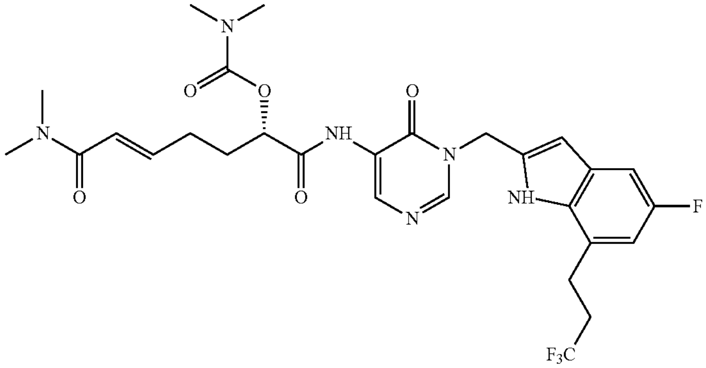 [SMILES: CN(C)C(=O)/C=C/CC[C@H](OC(=O)N(C)C)C(=O)Nc1cncn(Cc2cc3cc(F)cc(CCC(F)(F)F)c3[nH]2)c1=O] | LCMS: $[M + 1]^+$ = 609.0 |

-continued
| Compound | Structure | LCMS Data |
| --- | --- | --- |
| 334 | 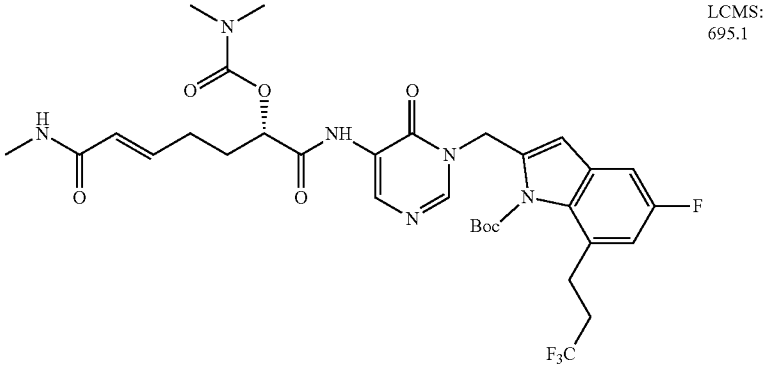 | LCMS: $[M + 1]^+$ = 695.1 |
| 358 | 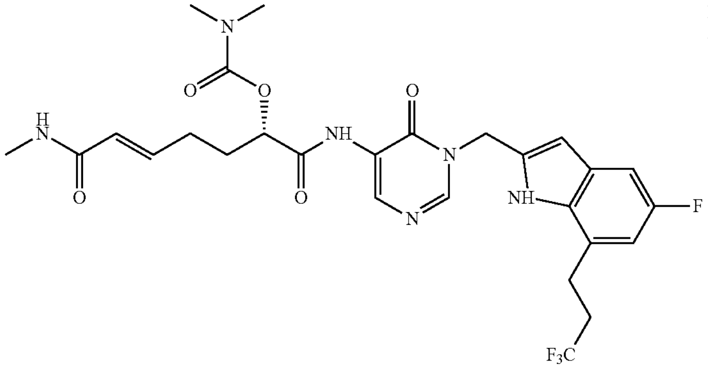 [SMILES: CNC(=O)/C=C/CC[C@H](OC(=O)N(C)C)C(=O)Nc1cncn(Cc2cc3cc(F)cc(CCC(F)(F)F)c3[nH]2)c1=O] | LCMS: $[M + 1]^+$ = 595.2 |
The Synthesis of Intermediate I-416
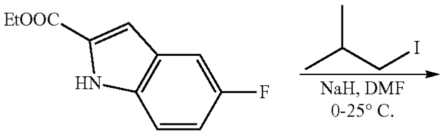
I-411
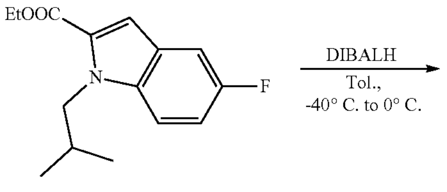
I-412
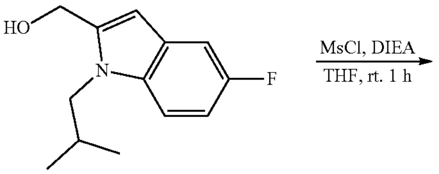
I-413
-continued
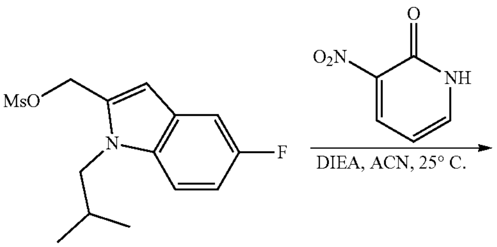
I-414
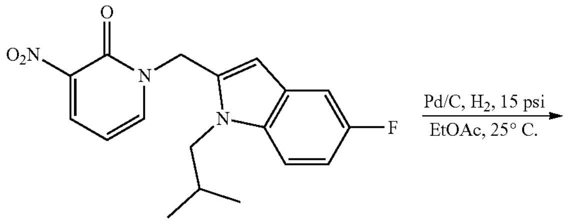
I-415

-continued

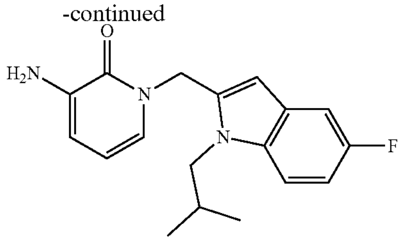

I-416

To a solution of ethyl 5-fluoro-1H-indole-2-carboxylate (2 g, 9.65 mmol) in DMF (20 mL) was added NaH (579.09 mg, 14.48 mmol, 60% purity) at 0° C. The mixture was stirred at 0° C. for 0.5 hr. 1-iodo-2-methyl-propane (3.55 g, 19.30 mmol, 2.22 mL) was added to the mixture, and the mixture was stirred at 0° C. for 1 hr. The reaction mixture was diluted with $NH_4Cl$ 40 mL and extracted with EtOAc (30 mL×3). The combined organic layers were washed with brine (30 mL×2), dried over anhydrous $Na_2SO_4$, filtered and concentrated in vacuum to give a residue. The residue was purified by column chromatography to afford ethyl 5-fluoro-1-isobutyl-indole-2-carboxylate (I-412) (1.1 g, 43% yield) as a light yellow oil.

To a solution of ethyl 5-fluoro-1-isobutyl-indole-2-carboxylate (2 g, 7.60 mmol) in toluene (25 mL) was added DIBALH (1 M, 15.19 mL) at −40° C. The mixture was stirred at −40° C. for 0.5 hr. The reaction mixture was quenched with saturated potassium sodium tartrate solution (100 mL). The mixture was stirred for 2 h. The resulting solution was extracted with EtOAc (100 mL×3). The combined organic layers were washed with brine (100 mL), dried over anhydrous $Na_2SO_4$, filtered and concentrated in vacuum to give a residue. The residue was purified by column chromatography to afford (5-fluoro-1-isobutyl-indol-2-yl)methanol (I-413) (1.5 g, 89% yield) as a brown gum. $^1H$ NMR (400 MHz, $CDCl_3$) δ 7.10-7.17 (m, 2H) 6.86 (td, J=9.14, 2.51 Hz, 1H) 6.34 (s, 1H) 4.66-4.77 (m, 2H) 3.92 (d, J=7.58 Hz, 2H) 2.08-2.27 (m, 1H) 0.84 (d, J=6.72 Hz, 6H).

To a solution of (5-fluoro-1-isobutyl-indol-2-yl)methanol (0.3 g, 1.36 mmol) in DCM (5 mL) was added DIEA (1.23 g, 9.49 mmol, 1.65 mL) and MsCl (776.55 mg, 6.78 mmol, 524.69 uL) at 0° C. The mixture was stirred at 0° C. for 1 hr. The reaction mixture was quenched by $NH_4Cl$ aq (5 mL) solution at 0° C., and then extracted with DCM (5 mL×3). The combined organic layers were washed with brine (5 mL), dried over anhydrous $Na_2SO_4$, filtered and concentrated in vacuum to give (5-fluoro-1-isobutyl-indol-2-yl)methyl methanesulfonate (I-414) (0.4 g) as a brown oil.

To a solution of 3-nitro-1H-pyridin-2-one (224.63 mg, 1.60 mmol) in ACN (5 mL) was added DIEA (414.46 mg, 3.21 mmol, 558.57 uL) and (5-fluoro-1-isobutyl-indol-2-yl)methyl methanesulfonate (0.32 g, 1.07 mmol) at 0° C. The mixture was stirred at 20° C. for 12 h. The reaction mixture was diluted with $NH_4Cl$ (50 mL) and extracted with DCM (50 mL×3). The combined organic layers were washed with brine (50 mL×2), dried over anhydrous $Na_2SO_4$, filtered and concentrated in vacuum to give a residue. The residue was purified by column chromatography to afford 1-[(5-fluoro-1-isobutyl-indol-2-yl)methyl]-3-nitro-pyridin-2-one (I-415) (0.12 g, 33% yield) as a brown gum. $^1H$ NMR (400 MHz, $CDCl_3$) δ 8.31 (dd, J=7.45, 2.19 Hz, 1H) 7.59 (dd, J=6.58, 1.75 Hz, 1H) 7.25 (brs, 1H) 7.23 (d, J=3.07 Hz, 1H) 7.00 (td, J=8.99, 2.63 Hz, 1H) 6.54 (s, 1H) 6.28 (t, J=7.24 Hz, 1H) 5.42 (s, 2H) 3.87 (d, J=7.89 Hz, 2H) 2.02-2.15 (m, 1H) 0.89 (d, J=6.58 Hz, 6H).

To a solution of 1-[(5-fluoro-1-isobutyl-indol-2-yl)methyl]-3-nitro-pyridin-2-one (0.12 g, 349.50 umol) in EtOAc (5 mL) was added Pd/C (0.1 g, 195.14 umol, 10% purity) under $N_2$. The suspension was degassed under vacuum and purged with $H_2$ several times. The mixture was stirred under $H_2$ (15 psi) at 25° C. for 1 hr. The reaction mixture was filtered and the filter was concentrated to give 3-amino-1-[(5-fluoro-1-isobutyl-indol-2-yl)methyl]pyridin-2-one (~416) (93 mg, 85% yield) as a colorless oil.

The following intermediate was prepared according to the procedures described in I-416 using the appropriate reagents.

| Compound | Structure | LCMS Data |
|---|---|---|
| I-417 | 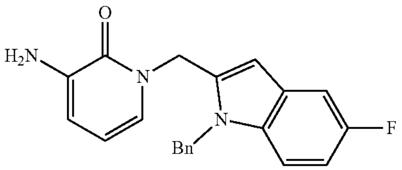 [SMILES: Nc1cccn(Cc2cc3cc(F)ccc3n2Cc2ccccc2)c1=O] | LCMS m/z 348.1 (M + 1)+ |
| I-418 | 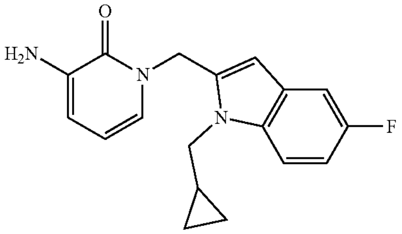 [SMILES: Nc1cccn(Cc2cc3cc(F)ccc3n2CC2CC2)c1=O] | LCMS m/z 312.2 (M + 1)+ |
| I-419 | 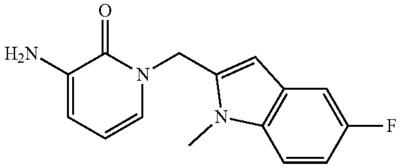 [SMILES: Cn1c(Cn2cccc(N)c2=O)cc2cc(F)ccc21] | LCMS m/z 272.2 (M + 1)+ |
| I-420 | 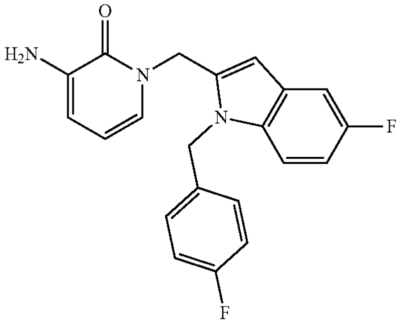 [SMILES: Nc1cccn(Cc2cc3cc(F)ccc3n2Cc2ccc(F)cc2)c1=O] | LCMS m/z 366.2 (M + 1)+ |
| I-421 | 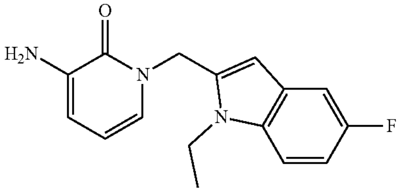 [SMILES: CCn1c(Cn2cccc(N)c2=O)cc2cc(F)ccc21] | LCMS m/z 286.2 (M + 1)+ |

-continued

| Compound | Structure | LCMS Data |
|---|---|---|
| I-422 | 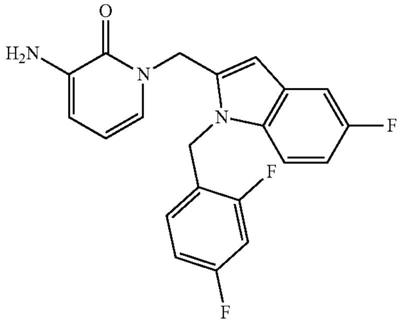 [SMILES: Nc1cccn(Cc2cc3cc(F)ccc3n2Cc2ccc(F)cc2F)c1=O] | LCMS m/z 384.2 $(M + 1)^+$ |

Example 45

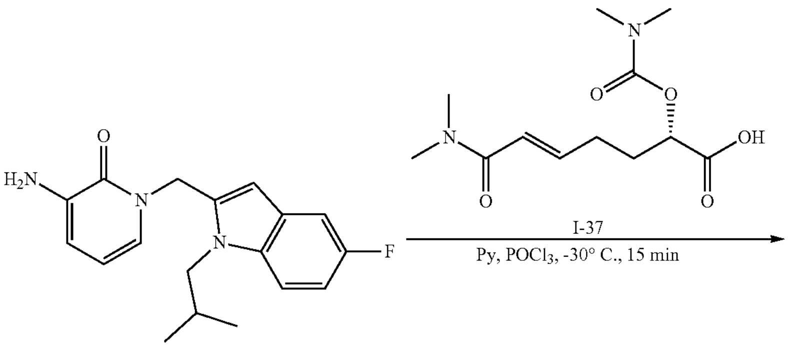

I-416

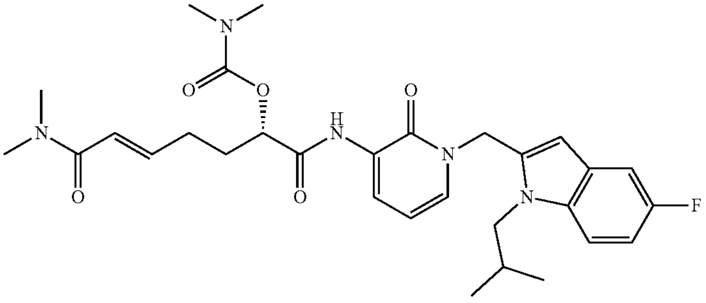

335

To a mixture of compound I-416 (85.5 mg, 272.84 umol) and compound I-37 (111.44 mg, 409.26 umol) in pyridine (2 mL) was added $POCl_3$ (83.67 mg, 545.68 umol, 50.71 uL) in one portion at −30° C. under $N_2$. The mixture was stirred at −30° C. for 15 mins. The reaction mixture was quenched by addition water 10 mL at −30° C., and then diluted with EtOAc 2 mL and extracted with EtOAc 20 mL (10 mL×2). The combined organic layers were washed with aq. HCl (1N) 10 mL and with brine (5 mL×2), dried over $Na_2SO_4$, filtered and concentrated under reduced pressure to give a residue. The residue was purified by prep-TLC and concentrated under lyophilization to give [(E,1S)-6-(dimethylamino)-1-[[1-[(5-fluoro-1-isobutyl-indol-2-yl) methyl]-6-oxo-pyrimidin-5-yl]carbamoyl]-6-oxo-hex-4-enyl]N,N-dimethylcarbamate (Compound 335) (38.2 mg, 24% yield) as a white solid. LCMS m/z 568.3 $(M+1)^+$. $^1$H NMR (400 MHz, DMSO-$d_6$) δ 9.48 (s, 1H), 8.30 (dd, J=1.8, 7.3 Hz, 1H), 7.58-7.49 (m, 2H), 7.31 (dd, J=2.4, 9.7 Hz, 1H), 7.02 (dt, J=2.5, 9.2 Hz, 1H), 6.77-6.66 (m, 1H), 6.53-6.37 (m, 2H), 6.29 (s, 1H), 5.47 (s, 2H), 5.17 (dd, J=4.6, 7.7 Hz, 1H), 4.12 (d, J=7.5 Hz, 2H), 3.08-3.00 (m, 6H), 2.93-2.84 (m, 6H), 2.42-2.30 (m, 2H), 2.10 (td, J=7.2, 14.2 Hz, 1H), 2.05-1.94 (m, 1H), 0.90 (dd, J=3.7, 6.6 Hz, 6H).

The following compounds were prepared according to the procedures described for the synthesis of Example 45 using the appropriate intermediates.

| Compound | Structure | LCMS Data |
|---|---|---|
| 336 | 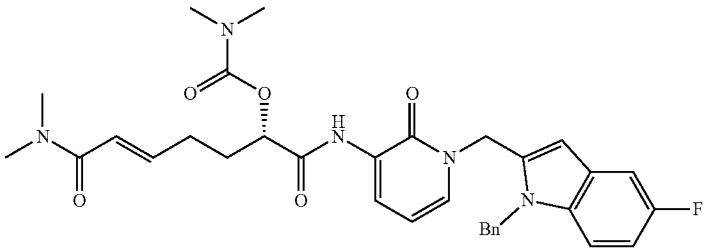 | LCMS m/z 602.4 $(M + 1)^+$ |
| 337 | 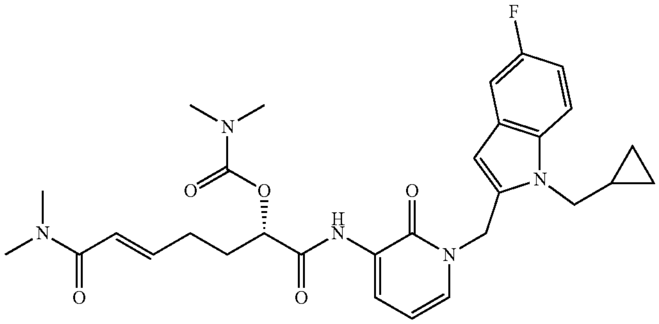 | LCMS m/z 566.2 $(M + 1)^+$ |
| 338 | 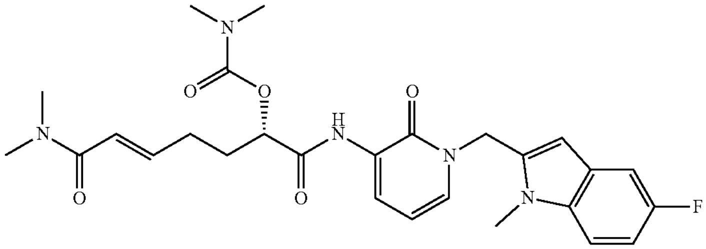 [SMILES: CN(C)C(=O)/C=C/CC[C@H](OC(=O)N(C)C)C(=O)Nc1cccn(Cc2cc3cc(F)ccc3n2C)c1=O] | LCMS m/z 526.2 $(M + 1)^+$ |
| 339 | 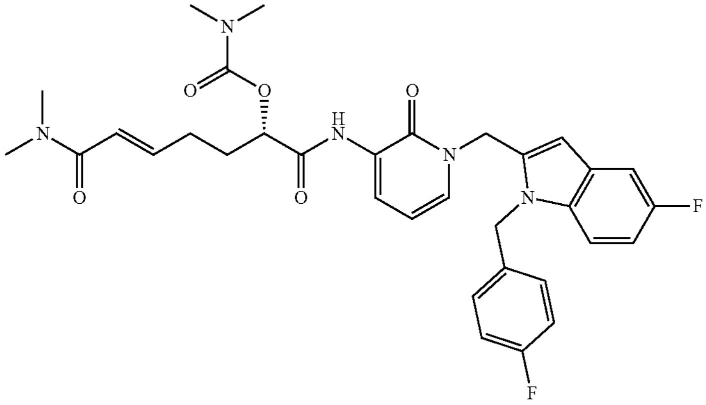 [SMILES: CN(C)C(=O)/C=C/CC[C@H](OC(=O)N(C)C)C(=O)Nc1cccn(Cc2cc3cc(F)ccc3n2Cc2ccc(F)cc2)c1=O] | LCMS m/z 620.3 $(M + 1)^+$ |
| 340 | 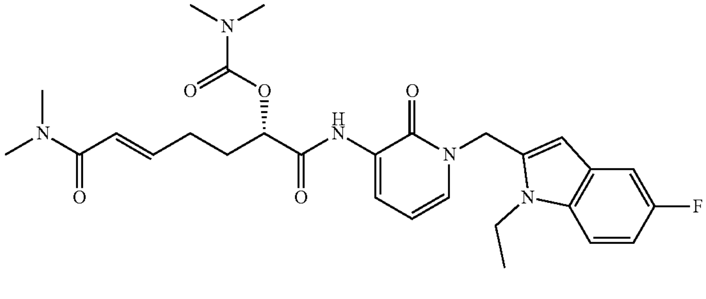 | LCMS m/z 540.2 $(M + 1)^+$ |

-continued

| Compound | Structure | LCMS Data |
|---|---|---|
| 341 | 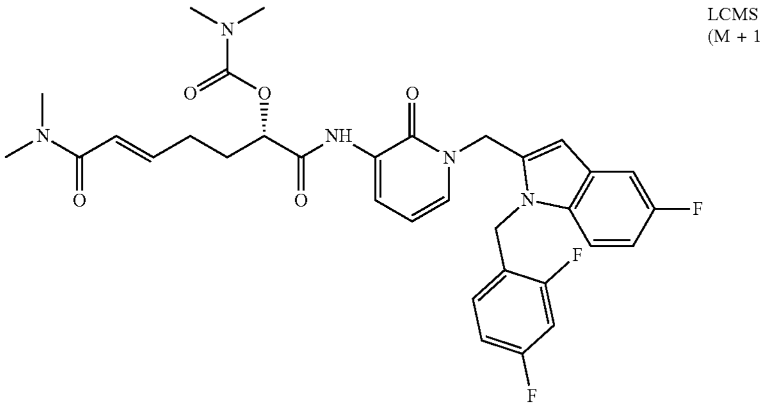 | LCMS m/z 638.2 $(M + 1)^+$ |

Example 46

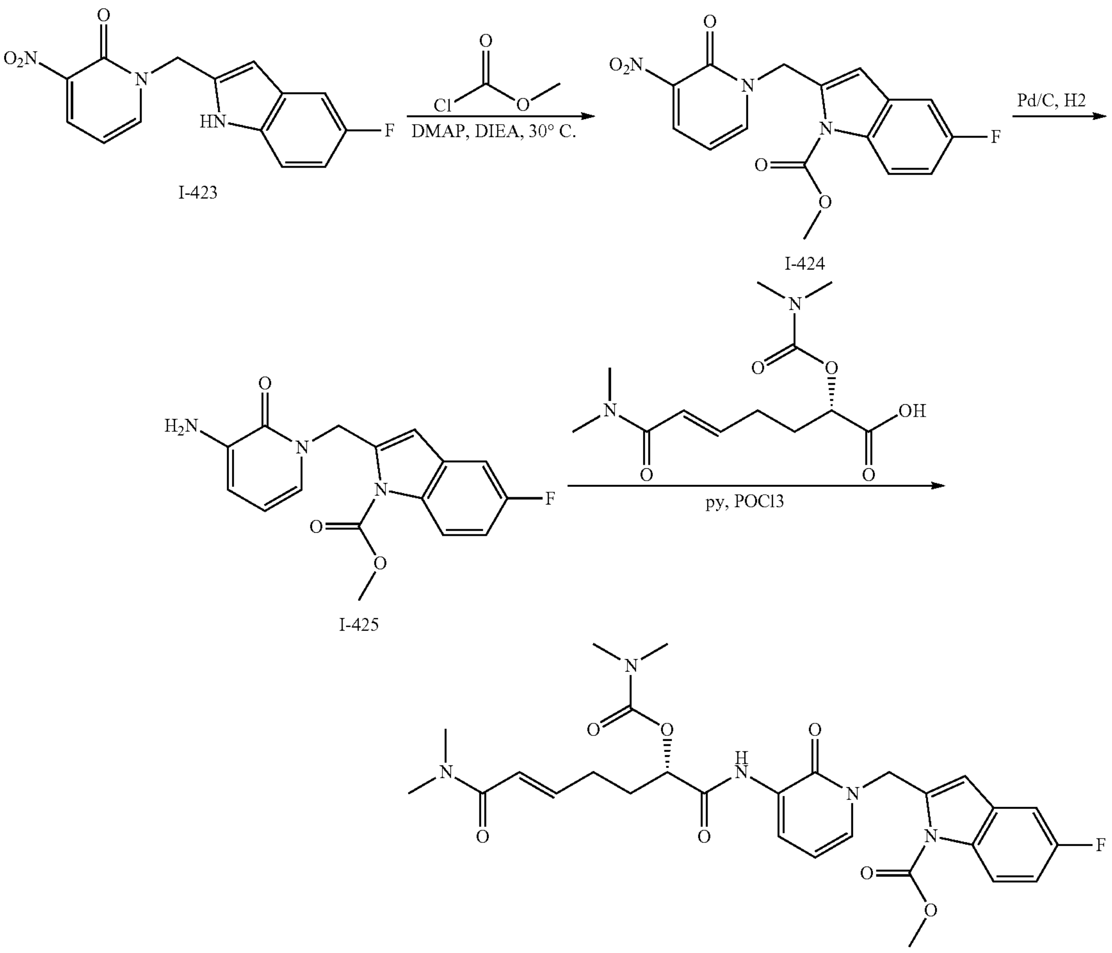

I-423

I-424

I-425

342

To a mixture of 1-[(5-fluoro-1H-indol-2-yl)methyl]-3-nitro-pyridin-2-one (199.31 mg, 693.88 umol, 1 eq) and DIEA (179.36 mg, 1.39 mmol, 241.72 uL, 2 eq) in DCM (2 mL) was added methyl carbonochloridate (98.35 mg, 1.04 mmol, 80.61 uL, 1.5 eq) and DMAP (8.48 mg, 69.39 umol, 0.1 eq) in portion at 0° C. under $N_2$. The mixture was warmed to 25° C. and stirred for 1.5 hours. The reaction mixture was added $H_2O$ (10 mL), and extracted with EtOAc (15 mL×3). The combined organic layers were washed with brine (20 me), dried over $Na_2SO_4$, filtered and concentrated under reduced pressure to give methyl 5-fluoro-2-[(3-nitro-2-oxo-1-pyridyl)methyl]indole-1-carboxylate (i-424) (0.17 g) as a light yellow solid.

To a solution of Pd/C (200 mg, 10% purity) in EtOAc (5 mL) was added methyl 5-fluoro-2-[(3-nitro-2-oxo-1-pyridyl)methyl]indole-1-carboxylate (150 mg, 434.43 umol, 1 eq) at 30° C., the reaction was stirred at 30° C. under $H_2$ (15 psi) for 15 min. The mixture was filtered and the filtrate was concentrated in vacuum to give methyl 2-[(3-amino-2-oxo-1-pyridyl)methyl]-5-fluoro-indole-1-carboxylate I-425) (150 mg) as yellow oil which was used directly in the next step.

To a solution of methyl 2-[(3-amino-2-oxo-1-pyridyl) methyl]-5-fluoro-indole-1-carboxylate (100 mg, 317.16 umol, 1 eq) and (E,2S)-7-(dimethylamino)-2-(dimethylcarbamoyloxy)-7-oxo-hept-5-enoic acid (103.63 mg, 380.59 umol, 1.2 eq) and DIEA (204.95 mg, 1.59 mmol, 276.21 uL, 5 eq) in DMF (3 mL) was added HATU (241.19 mg, 634.32 umol, 2 eq) at 30° C., the reaction was stirred at 30° C. for 12 h. The reaction mixture was poured into water 20 mL and extracted with EtOAc 40 mL (20 mL×2). The combined organic layers were washed with brine 20 mL (10 mL×2), dried over $Na_2SO_4$, filtered and concentrated under reduced pressure to give a oil. The oil was purified by prep-TLC to give an oil which was lyophilized to give methyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-indole-1-carboxylate (Compound 342) (33.3 mg, 17% yield) as a brown solid. $^1H$ NMR (400 MHz, DMSO-$d_6$) δ 1.84-2.02 (m, 2H) 2.22-2.33 (m, 2H) 2.75-2.84 (m, 6H) 2.87-3.02 (m, 6H) 4.01 (s, 3H) 5.09 (dd, J=7.61, 4.52 Hz, 1H) 5.50 (s, 2H) 6.03 (s, 1H) 6.32-6.44 (m, 2H) 6.57-6.69 (m, 1H) 7.12 (td, J=9.26, 2.65 Hz, 1H) 7.33 (dd, J=9.04, 2.65 Hz, 1H) 7.45 (dd, J=6.95, 1.87 Hz, 1H) 8.04 (dd, J=9.04, 4.63 Hz, 1H) 8.28 (dd, J=7.50, 1.76 Hz, 1H) 9.37 (s, 1H).

The following compound was prepared according to the procedures described for the synthesis of Example 46 using the appropriate intermediates The Synthesis of Intermediate I-426

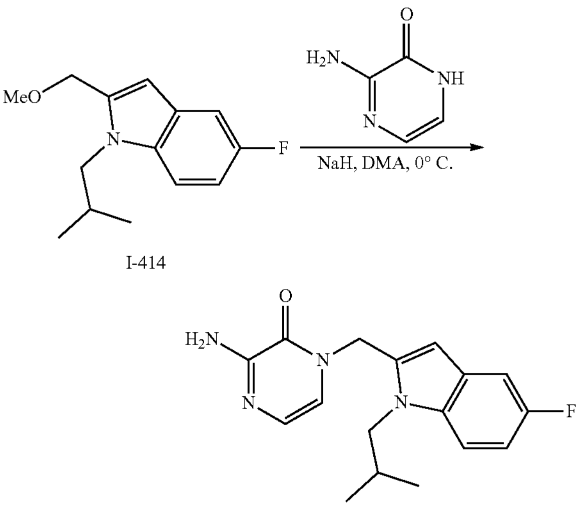

I-414

I-426

To a solution of 3-amino-1H-pyrazin-2-one (298.39 mg, 2.69 mmol) in DMA (10 mL) was added NaH (179.03 mg, 4.48 mmol, 60% purity) at 0° C. The mixture was stirred at 0° C. for 0.5 hr. (5-Fluoro-1-isobutyl-indol-2-yl)methyl methanesulfonate (0.67 g, 2.24 mmol) was added to the mixture, and the mixture was stirred at 0° C. for 1.5 hr. The reaction mixture was diluted with $NH_4Cl$ (5 mL) and extracted with EtOAc (5 mL×3). The combined organic layers were washed with brine (5 mL×2), dried over anhydrous $Na_2SO_4$, filtered and concentrated in vacuum to give a residue. The residue was purified by column chromatography to afford 3-amino-1-[(5-fluoro-1-isobutyl-indol-2-yl) methyl]pyrazin-2-one (I-426) (0.2 g) as a brown gum.

The following intermediates were prepared according to the procedures described in I-426 using the appropriate reagents.

| Compound | Structure | LCMS Data |
|---|---|---|
| 343 | 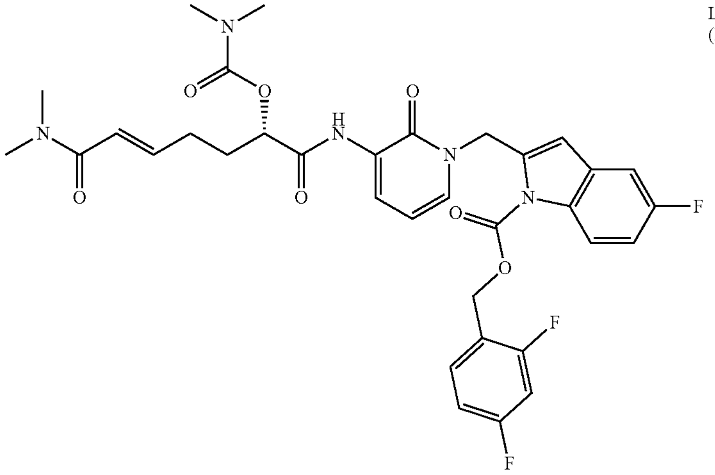 | LCMS m/z 682.2 $(M + 1)^+$ |

| Compound | Structure | LCMS Data |
|---|---|---|
| I-427 | 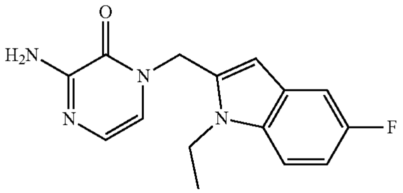 [SMILES: CCn1c(Cn2ccnc(N)c2=O)cc2cc(F)ccc21] | LCMS m/z 287.2 (M + 1)$^+$ |
| I-428 | 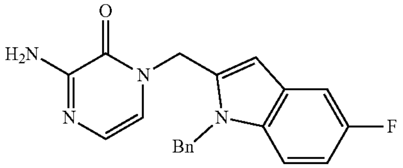 [SMILES: Nc1nccn(Cc2cc3cc(F)ccc3n2Cc2ccccc2)c1=O] | LCMS m/z 349.2 (M + 1)$^+$ |
| I-429 | 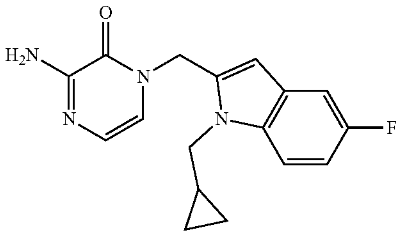 [SMILES: Nc1nccn(Cc2cc3cc(F)ccc3n2CC2CC2)c1=O] | LCMS m/z 313.2 (M + 1)$^+$ |
-continued
| Compound | Structure | LCMS Data |
|---|---|---|
| I-430 | 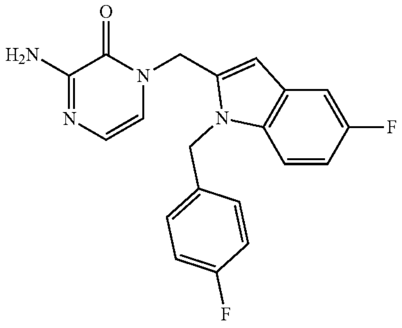 [SMILES: Nc1nccn(Cc2cc3cc(F)ccc3n2Cc2ccc(F)cc2)c1=O] | LCMS m/z 367.2 (M + 1)$^+$ |
| I-431 | 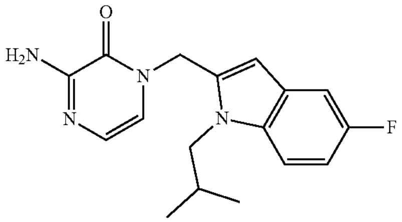 [SMILES: CC(C)Cn1c(Cn2ccnc(N)c2=O)cc2cc(F)ccc21] | LCMS m/z 315.2 (M + 1)$^+$ |
| I-432 | 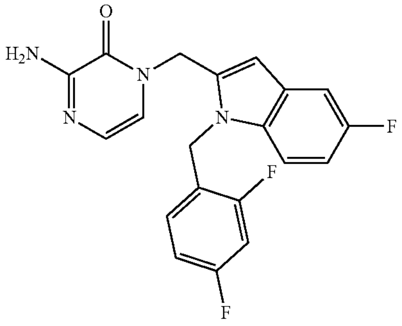 [SMILES: Nc1nccn(Cc2cc3cc(F)ccc3n2Cc2ccc(F)cc2F)c1=O] | LCMS m/z 385.2 (M + 1)$^+$ |
Example 47
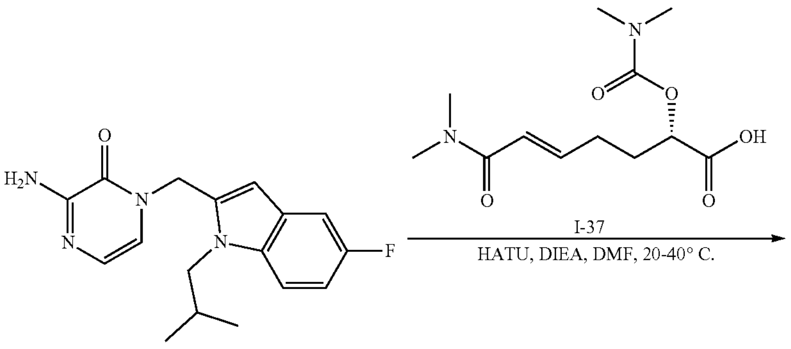
I-426

-continued

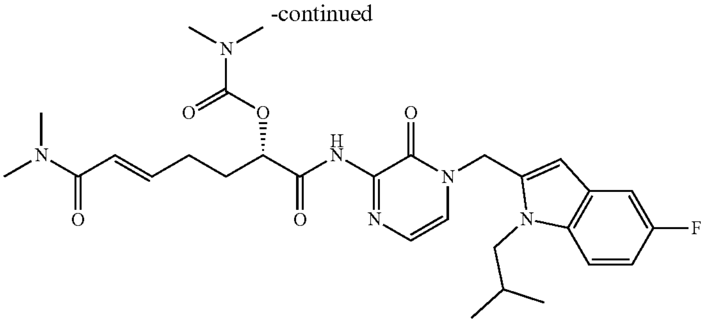

344

To a solution of 3-amino-1-[(5-fluoro-1-isobutyl-indol-2-yl)methyl]pyrazin-2-one (0.2 g, 636.22 umol) and (E,2S)-7-(dimethylamino)-2-(dimethylcarbamoyloxy)-7-oxo-hept-5-enoic acid (207.89 mg, 763.46 umol) in DMF (5 mL) was added DIEA (164.45 mg, 1.27 mmol, 221.63 uL) and HATU (435.44 mg, 1.15 mmol) at 20° C. The mixture was stirred at 40° C. for 12 h. The reaction mixture was diluted with water (20 mL) and extracted with EtOAc (20 mL×3). The combined organic layers were washed with brine (15 mL×2), dried over anhydrous $Na_2SO_4$, filtered and concentrated in vacuum to give a residue. The residue was purified by column chromatography and prep-HPLC to afford [(E, 1S)-6-(dimethylamino)-1-[[4-[(5-fluoro-1-isobutyl-indol-2-yl)methyl]-3-oxo-pyrazin-2-yl]carbamoyl]-6-oxo-hex-4-enyl] N,Ndimethylcarbamate (Compound 344) (19.9 mg, 5% yield) as a white solid. LCMS m/z 569.3 $(M+1)^+$. $^1H$ NMR (400 MHz, DMSO-$d_6$) δ 9.99 (s, 1H) 7.48 (dd, J=9.04, 4.41 Hz, 1H) 7.41 (d, J=4.63 Hz, 1H) 7.26 (br d, J=12.35 Hz, 1H) 7.12 (d, J=4.41 Hz, 1H) 6.93-7.00 (m, 1H) 6.66 (d, J=15.21 Hz, 1H) 6.41 (d, J=15.21 Hz, 1H) 6.35 (s, 1H) 5.34 (s, 2H) 5.18 (s, 1H) 4.03 (d, J=7.50 Hz, 2H) 2.92-3.01 (m, 6H) 2.79-2.85 (m, 6H) 2.32 (s, 2H) 1.83-2.09 (m, 2H) 0.83 (dd, J=6.39, 2.21 Hz, 6H).

The following compounds were prepared according to the procedures described for the synthesis of Example 47 using the appropriate intermediates.

| Compound | Structure | LCMS Data |
|---|---|---|
| 345 | 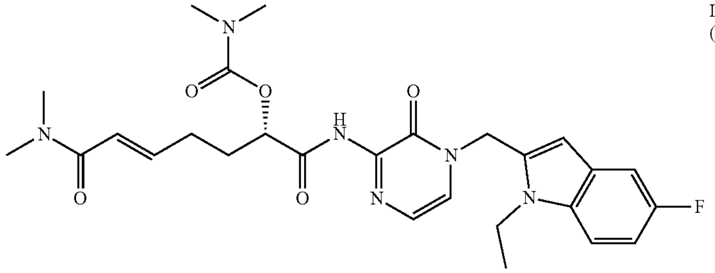 | LCMS m/z 541.2 $(M + 1)^+$ |
| 346 | 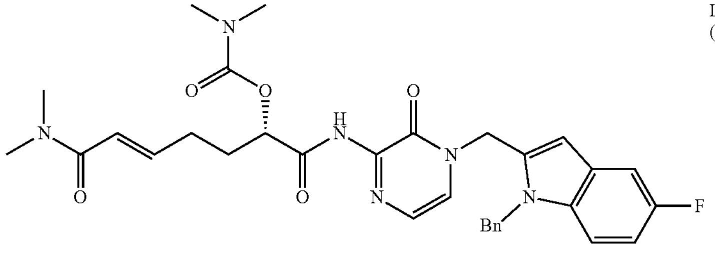 | LCMS m/z 603.4 $(M + 1)^+$ |
| 347 | 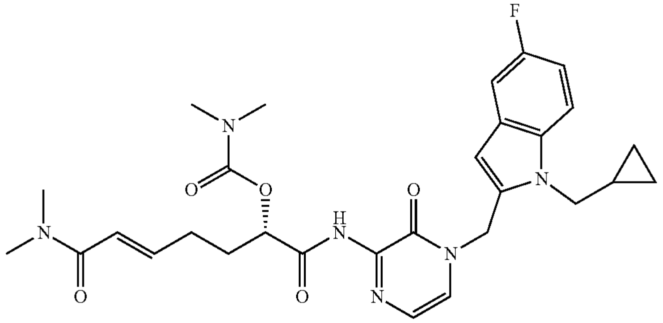 [SMILES: CN(C)C(=O)/C=C/CC[C@H](OC(=O)N(C)C)C(=O)Nc1nccn(Cc2cc3cc(F)ccc3n2CC2CC2)c1=O] | LCMS m/z 567.2 $(M + 1)^+$ |

-continued
| Compound | Structure | LCMS Data |
| --- | --- | --- |
| 348 | 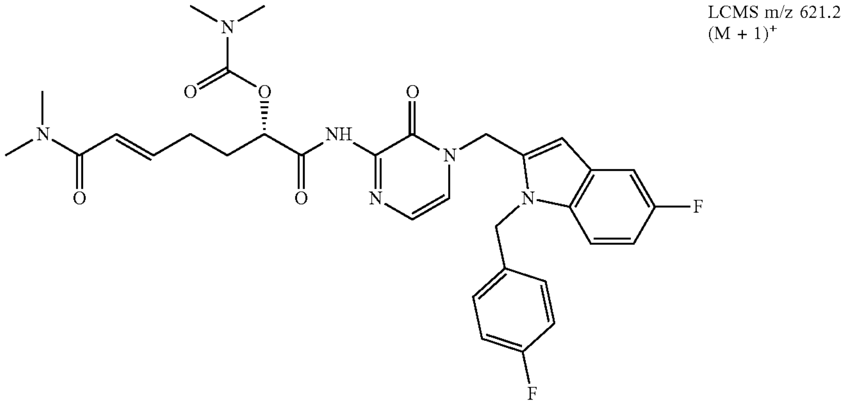 | LCMS m/z 621.2 (M + 1)$^+$ |
| 349 | 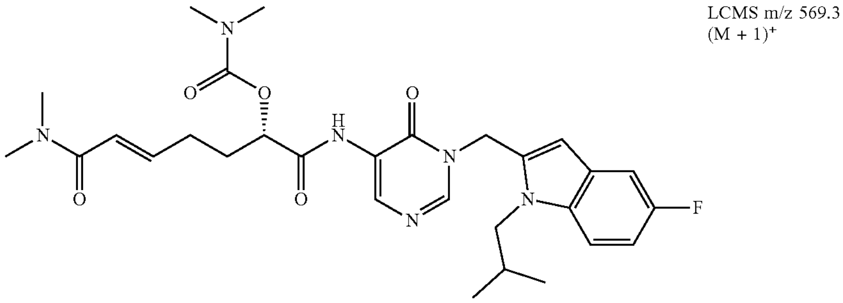 | LCMS m/z 569.3 (M + 1)$^+$ |
| 350 | 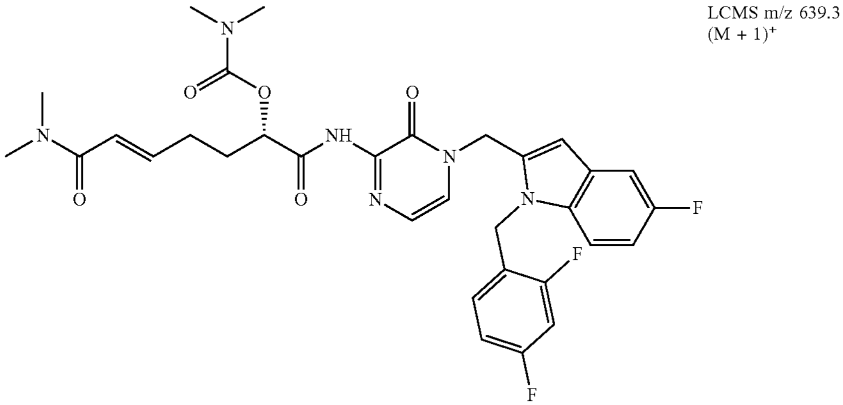 | LCMS m/z 639.3 (M + 1)$^+$ |
The Synthesis of Intermediate I-438
-continued
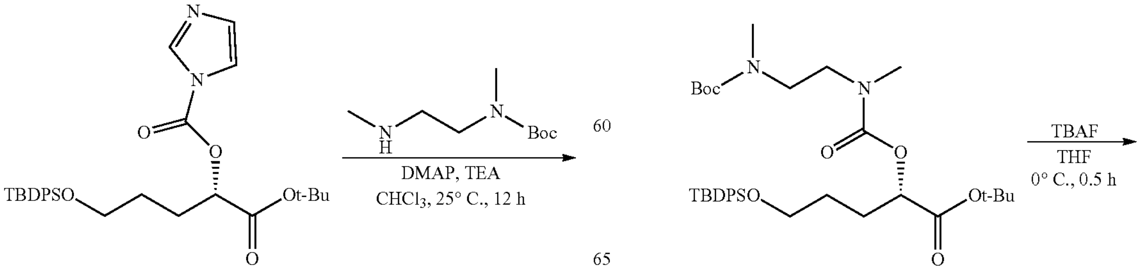
I-31
I-433

-continued

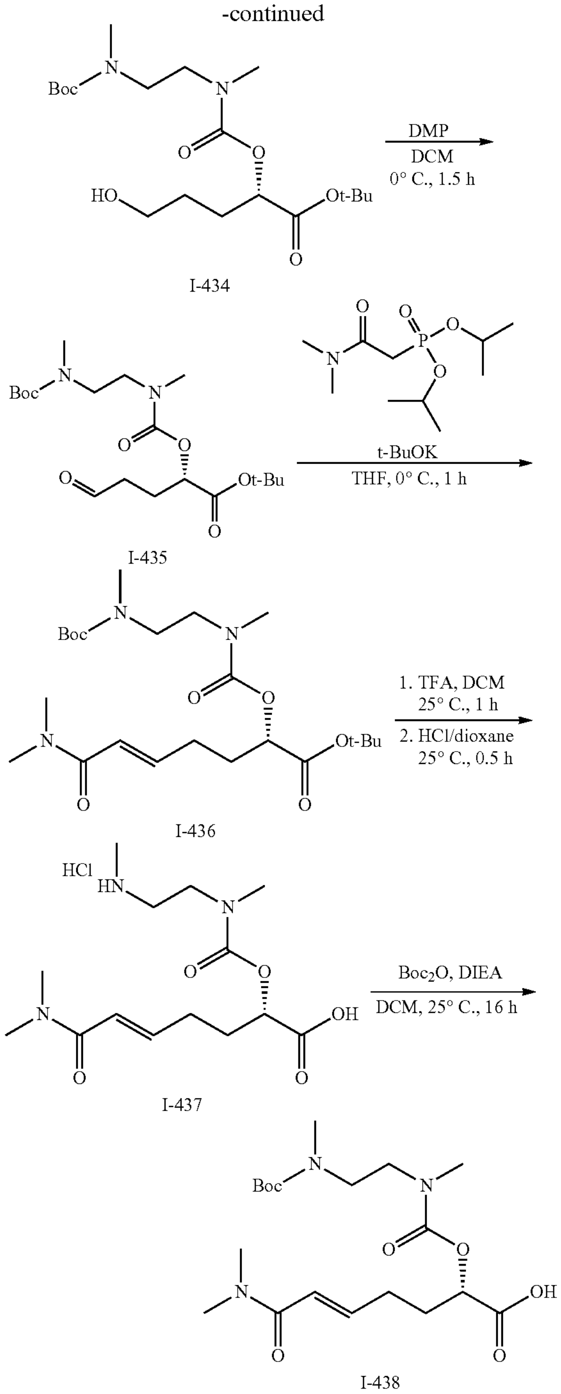

I-434

I-435

I-436

I-437

I-438

To a solution of [(1S)-1-tert-butoxycarbonyl-4-[tert-butyl(diphenyl)silyl]oxy-butyl]imidazole-1-carboxylate (6.05 g, 11.57 mmol) in $CHCl_3$ (100 mL) was added tert-butyl N-methyl-N-[2-(methylamino)ethyl]carbamate (2.61 g, 13.89 mmol, 72.52 uL), DMAP (282.81 mg, 2.31 mmol) and TEA (3.51 g, 34.72 mmol, 4.83 mL) at 25° C. The mixture was stirred at 25° C. for 12 h. Two batches in parallel of the reaction were set up. Two batches in parallel of the reaction mixture were combined and washed with a solution of saturated $NH_4Cl$ (80 mL), brine (80 mL) and separated, the organic layer was concentrated in vacuum to give a residue. The residue was purified by column chromatography to give tert-butyl(2S)-2-[2-[tert-butoxycarbonyl(methyl)amino]ethyl-methyl-carbamoyl]oxy-5-[tert-butyl(diphenyl)silyl]oxy-pentanoate (I-433) (8.2 g) as a colorless oil. LCMS m/z 665.4 $(M+23)^+$.

To a solution of tert-butyl(2S)-2-[2-[tert-butoxycarbonyl(methyl)amino]ethyl-methyl-carbamoyl]oxy-5-[tert-butyl(diphenyl)silyl]oxy-pentanoate (3.5 g, 5.44 mmol) in THF (22 mL) was added TBAF (1 M, 10.89 mL, 2 eq) at 25° C. The mixture was stirred at 25° C. for 0.5 h. The reaction mixture was concentrated in vacuum to remove most of THF, diluted with a solution of $NH_4Cl$ (40 mL) and extracted with EtOAc (30 mL×2). The combined organic layers were washed brine (40 mL×2), then dried over $Na_2SO_4$ and filtered and the filtrate was concentrated in vacuum to give a residue. The residue was purified by column chromatography to give tert-butyl(2S)-2-[2-[tert-butoxycarbonyl(methyl)amino]ethyl-methyl-carbamoyl]oxy-5-hydroxy-pentanoate (I-434) (3.4 g) as a colorless oil. $^1H$ NMR (400 MHz, $CDCl_3$) δ 4.75-5.03 (m, 1H), 3.68 (br s, 2H), 3.45-3.61 (m, 1H), 3.09-3.44 (m, 2H), 2.80-3.05 (m, 5H), 1.84-2.00 (m, 2H), 1.61-1.78 (m, 3H), 1.39-1.48 (m, 18H).

To a solution of tert-butyl (2S)-2-[2-[tert-butoxycarbonyl(methyl)amino]ethyl-methyl-carbamoyl]oxy-5-hydroxy-pentanoate (2.9 g, 7.17 mmol) in $CH_2Cl_2$ (25 mL) was added DMP (1.82 g, 4.30 mmol, 1.33 mL) at 0° C. The mixture was stirred at 0° C. for 0.5 h and additional DMP (1.82 g, 4.30 mmol, 1.33 mL) was added to the reaction mixture at 0° C. The mixture was stirred at 0° C. for 1 h. The reaction mixture was filtered and the filter cake was washed with $CH_2Cl_2$ (20 mL×3). The filtrate was washed with a mixture solution of $NaHCO_3$ (50 mL) and $Na_2SO_3$ (50 mL), separated and the organic layer was washed with brine (40 mL×2), dried over $Na_2SO_4$, filtered and the filtrate was concentrated in vacuum to give a residue. The residue was purified by column chromatography to give tert-butyl (2S)-2-[2-[tert-butoxycarbonyl(methyl)amino]ethyl-methyl-carbamoyl]oxy-5-oxo-pentanoate (I-435) (1.4 g, 49% yield) as a colorless oil.

To a solution of 2-diisopropoxyphosphoryl-N,N-dimethyl-acetamide (786.59 mg, 3.13 mmol) in THF (7 mL) was added t-BuOK (292.74 mg, 2.61 mmol) at 0° C. The mixture was stirred at 0° C. for 0.5 h. Then a solution of tert-butyl (2S)-2-[2-[tert-butoxycarbonyl(methyl)amino]ethyl-methyl-carbamoyl]oxy-5-oxo-pentanoate (0.7 g, 1.74 mmol, 1 eq) in THF (4 mL) was added to the above reactor at 0° C. The mixture was stirred at 0° C. for 0.5 h. Two batches in parallel of the reaction were set up. Two batches in parallel of the reaction mixture were combined and poured into a ice water solution of $NH_4Cl$ (60 mL), extracted with EtOAc (50 mL×3) and separated. The combined organic layers were washed brine (70 mL), dried over $Na_2SO_4$ and filtered. The filtrate was concentrated in vacuum to give a residue. The residue and the crude product of the preliminary experiment was purified by column chromatography to give tert-butyl (E,2S)-2-[2-[tert-butoxycarbonyl(methyl)amino]ethyl-methyl-carbamoyl]oxy-7-(dimethylamino)-7-oxo-hept-5-enoate (I-436) (1.4 g, 85% yield) as a colorless oil. $^1H$ NMR (400 MHz, $CDCl_3$) δ 6.77-6.91 (m, 1H), 6.29 (br dd, J=15.10, 6.79 Hz, 1H), 4.81-4.97 (m, 1H), 3.16-3.59 (m, 4H), 3.07 (s, 3H), 2.93-3.03 (m, 6H), 2.90 (br s, 3H), 2.33 (q, J=7.13 Hz, 2H), 1.91-2.02 (m, 2H), 1.40-1.51 (m, 18H).

To a solution of tert-butyl (E,2S)-2-[2-[tert-butoxycarbonyl(methyl)amino]ethyl-methyl-carbamoyl]oxy-7-(dimethylamino)-7-oxo-hept-5-enoate (1.5 g, 3.18 mmol) in DCM (8 mL) was added TFA (13.20 g, 115.77 mmol, 8.57 mL) at 25° C. The mixture was stirred at 25° C. for 1 h. The reaction mixture was concentrated in vacuum to give (E,2S)-7-

(dimethylamino)-2-[methyl-[2-(methylamino)ethyl]carbamoyl]oxy-7-oxo-hept-5-enoic acid (1.37 g, crude, TFA salt) as a light red oil. A mixture of tert-butyl (E,2S)-7-(dimethylamino)-2-[methyl-[2-(methylamino)ethyl]carbamoyl]oxy-7-oxo-hept-5-enoate (1.37 g, TFA) and HCl/dioxane (8 M, 150.55 mL) was stirred at 25° C. for 0.5 h. The reaction mixture was concentrated in vacuum to give tert-butyl (E,2S)-7-(dimethylamino)-2-[methyl-[2-(methylamino)ethyl]carbamoyl]oxy-7-oxo-hept-5-enoate (I-437) (1.15 g, HCl salt) as alight red oil. LCMS m/z 316.0 $(M+1)^+$.

To a solution of (E,2S)-7-(dimethylamino)-2-[methyl-[2-(methylamino)ethyl]carbamoyl]oxy-7-oxo-hept-5-enoic acid (1.15 g, 3.27 mmol, HCl) in $CH_2Cl_2$ (12 mL) was added $Boc_2O$ (1.43 g, 6.54 mmol, 1.50 mL) and DIEA (844.90 mg, 6.54 mmol, 1.14 mL) at 25° C. The mixture was stirred at 25° C. for 16 h. The reaction mixture was concentrated in vacuum, diluted with $K_2CO_3$ (2N, 25 mL) and extracted with EtOAc (30 mL). The water phase was adjusted pH=5 by HCl solution (1 N), then extracted by EtOAc (25 mL×3), washed with brine (40 mL×2), dried by $Na_2SO_4$, filtered and concentrated in vacuum to give (E,2S)-2-[2-[tert-butoxycarbonyl(methyl)amino]ethyl-methyl-carbamoyl]oxy-7-(dimethylamino)-7-oxo-hept-5-enoic acid (I-438) (1.17 g, 86% yield) as a light yellow oil. LCMS m/z 414.1 $(M-1)^+$.

Example 48

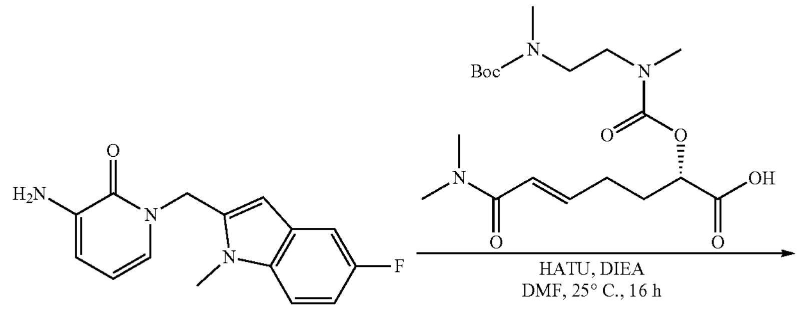

I-419

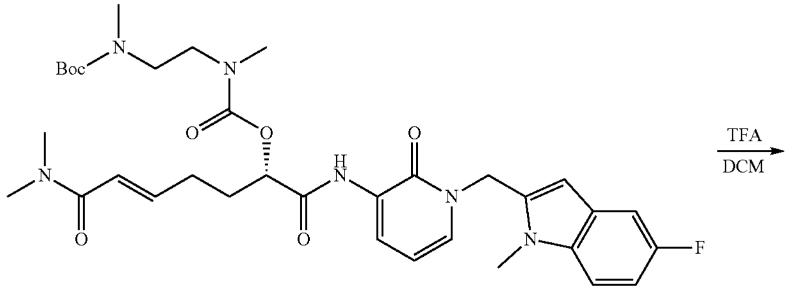

351

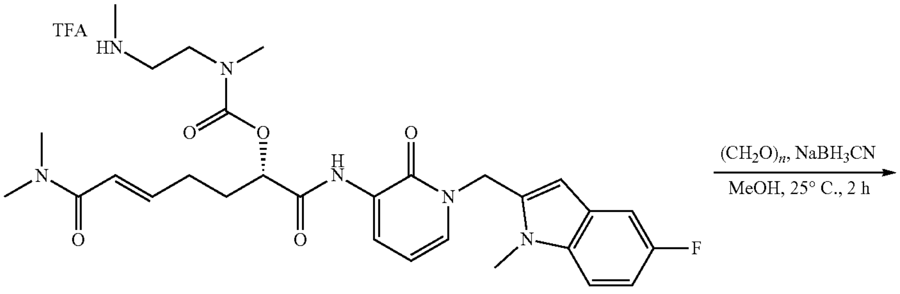

I-439

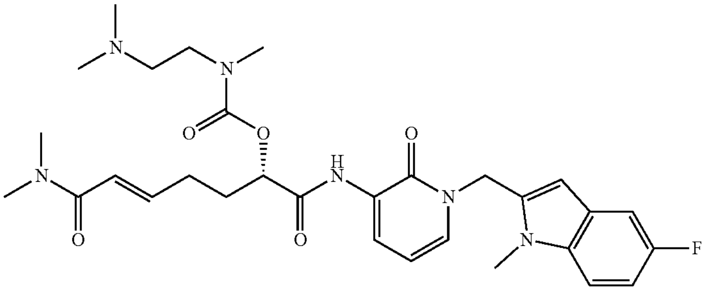

352

To a solution of 3-amino-1-[(5-fluoro-1-methyl-indol-2-yl)methyl]pyridin-2-one (110 mg, 405.47 umol) in DMF (4 mL) was added (E,2S)-2-[2-[tert-butoxycarbonyl (methyl) amino]ethyl-methyl-carbamoyl] oxy-7-(dimethylamino)-7-oxo-hept-5-enoic acid (336.93 mg, 810.94 umol), DIEA (262.02 mg, 2.03 mmol, 353.13 uL) and HATU (308.34 mg, 810.94 umol) at 25° C. The mixture was stirred at 25° C. for 16 h. The reaction mixture was diluted with a saturated solution of $NH_4Cl$ (25 mL) and extracted with EtOAc (15 mL×3). The combined organic layers were washed with brine (25 mL), dried over $Na_2SO_4$ and concentrated in vacuum to give a residue. The residue was purified by prep-TLC to give [(E,1S)-6-(dimethylamino)-1-[[1-[(5-fluoro-1-methyl-indol-2-yl)methyl]-2-oxo-3-pyridyl]carbamoyl]-6-oxo-hex-4-enyl]N-[2-[tert-butoxycarbonyl (methyl)amino]ethyl]-N-methyl-carbamate (Compound 351) (27 mg, 9% yield) as a gray solid. LCMS m/z 669.2 $(M+1)^+$.

To a solution of [(E,1S)-6-(dimethylamino)-1-[[1-[(5-fluoro-1-methyl-indol-2-yl) methyl]-2-oxo-3-pyridyl] carbamoyl]-6-oxo-hex-4-enyl]N-[2-[tert-butoxycarbonyl (methyl)amino]ethyl]-N-methyl-carbamate (30 mg, 44.86 umol) in DCM (2 mL) was added TFA (2.89 mg, 25.32 umol, 1.88 uL) at 25° C. The mixture was stirred at 25° C. for 1 h. The mixture was concentrated in vacuum to give [(E,1S)-6-(dimethylamino)-1-[[1-[(5-fluoro-1-methyl-indol-2-yl)methyl]-2-oxo-3-pyridyl]carbamoyl]-6-oxo-hex-4-enyl]N-methyl-N-[2-(methylamino)ethyl]carbamate (I-439) (35 mg, TFA salt) as a light brown oil.

To a solution of [(E,1S)-6-(dimethylamino)-1-[[1-[(5-fluoro-1-methyl-indol-2-yl) methyl]-2-oxo-3-pyridyl]carbamoyl]-6-oxo-hex-4-enyl]N-methyl-N-[2-(methylamino) ethyl]carbamate (35 mg, 51.27 umol, TFA) in MeOH (2 mL) was added TEA (5.19 mg, 51.27 umol, 7.14 uL) and paraformaldehyde (4 mg) at 25° C. The reaction mixture was stirred at 25° C. for 1 h. $NaBH_3CN$ (6.44 mg, 102.54 umol) was added to the reaction mixture. The mixture was stirred at 25° C. for 1 h. The reaction mixture was quenched by addition of $H_2O$ (5 mL) and concentrated in vacuum to remove most of the MeOH. Then the mixture was extracted with EtOAc (4 mL×3) and the combined organic layer was washed with brine (5 mL), dried over $Na_2SO_4$ and concentrated in vacuum to give a residue. The residue was purified by prep-HPLC to give [(E,1S)-6-(dimethylamino)-1-[[1-[(5-fluoro-1-methyl-indol-2-yl)methyl]-2-oxo-3-pyridyl]carbamoyl]-6-oxo-hex-4-enyl]N-2-(dimethylamino)ethyl]-N-methyl-carbamate (Compound 352) (6.6 mg, 21% yield) as a white solid. LCMS m/z 583.2 $(M+1)^+$. $^1H$ NMR (400 MHz, DMSO-$d_6$) δ 9.40 (br s, 1H), 8.13-8.26 (m, 2H), 7.45 (br d, J=3.53 Hz, 2H), 7.25 (br d, J=8.82 Hz, 1H), 6.93-7.03 (m, 1H), 6.60-6.70 (m, 1H), 6.31-6.44 (m, 2H), 6.27 (br d, J=7.72 Hz, 1H), 5.40 (br s, 2H), 5.11 (br s, 1H), 3.76 (s, 3H), 2.98 (br s, 4H), 2.83 (br s, 4H), 2.38 (br d, J=6.17 Hz, 1H), 2.25-2.34 (m, 2H), 2.18 (br d, J=16.32 Hz, 6H), 1.95 (br s, 2H).

Example 49

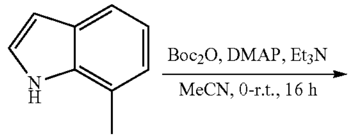

I-440

-continued

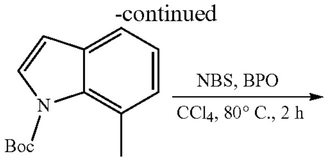

I-441

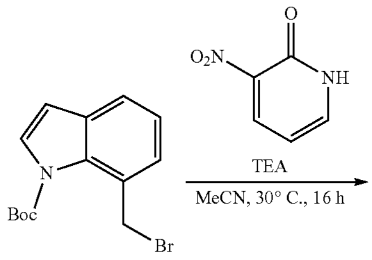

I-442

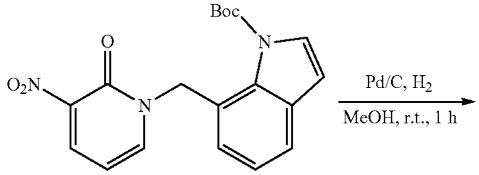

I-443

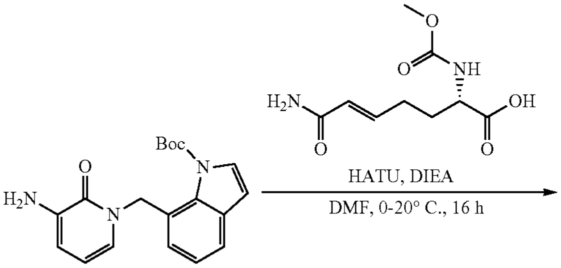

I-444

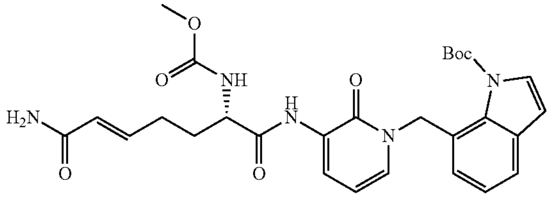

353

To a solution of 7-methyl-1H-indole (1.0 g, 7.62 mmol), DMAP (931 mg, 7.62 mmol) and $Et_3N$ (2.31 g, 22.9 mmol) in MeCN (20 mL) was added $Boc_2O$ (1.83 g, 8.38 mmol). The mixture was stirred at 20° C. for 16 h. The mixture was concentrated and the residue was diluted with EtOAc (100 mL). The resulting solution was washed with HCl (20 mL, 1M), $NaHCO_3$ (20 mL, 1M) and brine (20 mL). The organic phase was dried over anhydrous $Na_2SO_4$, filtered and concentrated in vacuum to give tert-butyl 7-methyl-1H-indole-1-carboxylate (I-441) (1.7 g) as a yellow oil. $^1H$ NMR (400 MHz, DMSO-$d_6$) δ 7.52 (d, J=3.6 Hz, 1H), 7.39 (d, J=7.4 Hz, 1H), 7.19-7.08 (m, 2H), 6.53 (d, J=3.6 Hz, 1H), 2.65 (s, 3H), 1.64 (s, 9H).

To a solution of tert-butyl 7-methyl-1H-indole-1-carboxylate (800 mg, 3.46 mmol) and BPO (83.8 mg, 0.346 mmol) in $CCl_4$ (10 mL) was added NBS (615 mg, 3.46 mmol). The mixture was stirred at 80° C. for 2 h under $N_2$ atmosphere. The mixture was concentrated and purified by silica gel chromatography to give tert-butyl 7-(bromomethyl)-1H-indole-1-carboxylate (I-442) (1.1 g) as a yellow oil. $^1$H NMR (400 MHz, $CDCl_3$) δ 7.60-7.52 (m, 2H), 7.31-7.27 (m, 1H), 7.23-7.17 (m, 1H), 6.59 (d, J=3.6 Hz, 1H), 5.25 (s, 2H), 1.68 (s, 9H).

To a solution of 3-nitropyridin-2(1H)-one (150 mg, 1.07 mmol) and tert-butyl 7-(bromomethyl)-1H-indole-1-carboxylate (332 mg, 1.07 mmol) in DMF (5 mL) was added K2CO3 (444 mg, 3.21 mmol). The mixture was stirred at 30° C. for 16 h. The mixture was diluted with EtOAc (100 mL) and washed with brine (30 mL×2). The organic phase was dried over anhydrous $Na_2SO_4$, filtered and concentrated in vacuum. The residue was purified by prep-TLC to give tert-butyl tert-butyl 7-((3-nitro-2-oxopyridin-1(2H)-yl)methyl)-1H-indole-1-carboxylate (I-443) (300 mg, 76% yield) as a yellow oil. $^1$H NMR (400 MHz, $CDCl_3$) δ 8.35 (dd, J=7.8, 2.0 Hz, 1H), 7.67 (dd, J=6.8, 2.0 Hz, 1H), 7.63-7.58 (m, 2H), 7.29 (d, J=7.8 Hz, 1H), 7.09 (d, J=7.4 Hz, 1H), 6.64 (d, J=3.8 Hz, 1H), 6.23 (dd, J=7.6, 6.8 Hz, 1H), 5.77 (s, 2H), 1.60 (s, 9H).

To a solution of tert-butyl 7-((3-nitro-2-oxopyridin-1(2H)-yl)methyl)-1H-indole-1-carboxylate (300 mg, 0.813 mmol) in MeOH (10 mL) was added wet Pd/C (100 mg, 10% purity) under $N_2$ atmosphere. The mixture was stirred at 20° C. for 0.25 h under $H_2$ (15 psi). The reaction mixture was filtered and the filter was concentrated to give tert-butyl 7-((3-amino-2-oxopyridin-1(2H)-yl)methyl)-1H-indole-1-carboxylate (I-444) (300 mg) as a yellow oil.

To a solution of (S,E)-7-amino-2-((methoxycarbonyl)amino)-7-oxohept-5-enoic acid (100 mg, 0.434 mmol) and tert-butyl 7-((3-amino-2-oxopyridin-1(2H)-yl)methyl)-1H-indole-1-carboxylate (147 mg, 0.434 mmol) in DMF (2 mL) were added HATU (248 mg, 652 mmol) and DIPEA (168 mg, 1.30 mmol) at 0° C. The mixture was stirred at 20° C. for 16 h. The resulting solution was concentrated and purified by prep-TLC and prep-HPLC to give (S,E)-tert-butyl 7-((3-(7-amino-2-((methoxycarbonyl)amino)-7-oxohept-5-enamido)-2-oxopyridin-1(2H)-yl)methyl)-1H-indole-1-carboxylate (Compound 353) (6.6 mg, 2% yield) as a white solid. LCMS m/z 552.2 $(M+1)^+$. $^1$H NMR (400 MHz, DMSO-$d_6$) δ 9.28 (s, 1H), 8.26 (d, J=7.2 Hz, 1H), 7.78-7.68 (m, 2H), 7.55 (d, J=7.6 Hz, 1H), 7.39 (d, J=6.4 Hz, 1H), 7.33 (br. s., 1H), 7.18 (t, J=7.6 Hz, 1H), 6.88 (br. s., 1H), 6.74 (d, J=3.6 Hz, 1H), 6.67 (d, J=7.2 Hz, 1H), 6.62-6.53 (m, 1H), 6.31 (t, J=7.2 Hz, 1H), 5.84 (d, J=15.6 Hz, 1H), 5.63-5.51 (m, 2H), 4.24-4.13 (m, 1H), 3.55 (s, 3H), 2.23-2.12 (m, 2H), 1.91-1.80 (m, 1H), 1.73-1.65 (m, 1H), 1.59 (s, 9H).

The Synthesis of Intermediate I-453

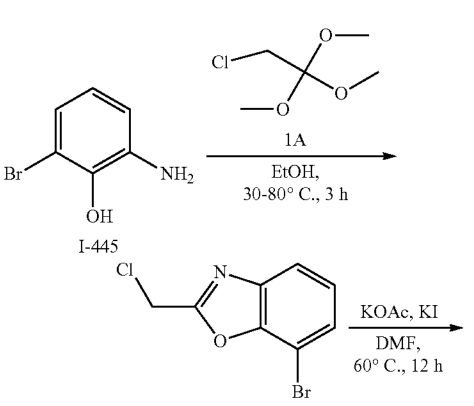

I-445

I-446

-continued

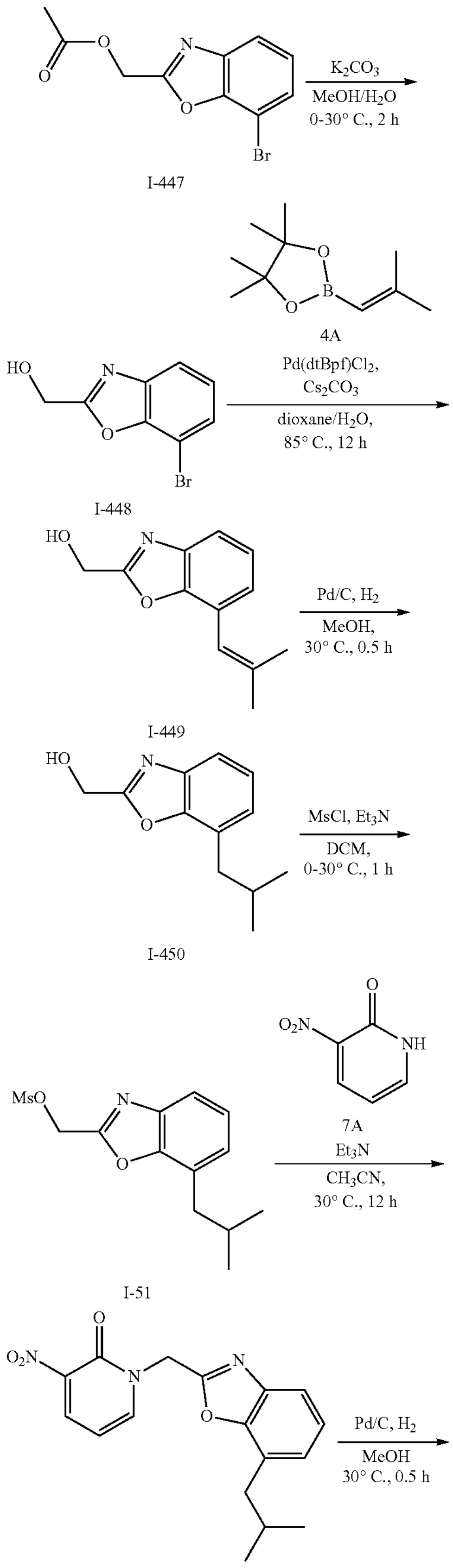

I-447

I-448

I-449

I-450

I-51

I-452

-continued

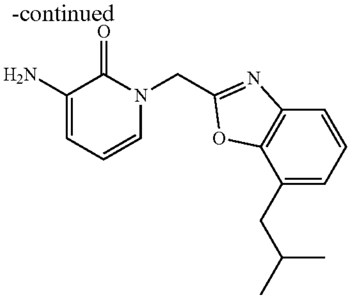

I-453

To a solution of 2-amino-6-bromo-phenol (5.00 g, 26.6 mmol) in EtOH (10 mL) was added dropwise 2-chloro-1,1,1-trimethoxyethane (4.32 g, 27.9 mmol) at 30° C. The mixture was stirred at 80° C. for 3 hr and concentrated to give a residue. The residue was purified by silica gel chromatography to give 7-bromo-2-(chloromethyl)benzo[d]oxazole (I-446) (6.10 g, 93% yield) as a yellow oil.

To a solution of 7-bromo-2-(chloromethyl)benzo[d]oxazole (3.50 g, 14.2 mmol) in DMF (20 mL) were added KOAc (2.09 g, 21.3 mmol) and KI (236 mg, 1.42 mmol). The mixture was stirred at 60° C. for 12 hours. The mixture was diluted with EtOAc (40 mL) and brine (50 mL). The organic layer was concentrated in vacuum to give (7-bromobenzo[d]oxazol-2-yl)methyl acetate (I-447) (3.70 g, 96% yield) as a yellow oil.

To a solution of (7-bromobenzo[d]oxazol-2-yl)methyl acetate (4.00 g, 14.8 mmol) in MeOH (36 mL) and $H_2O$ (4 mL) was added $K_2CO_3$ (4.91 g, 35.5 mmol) at 0° C. The mixture was stirred at 30° C. for 2 hours. The resulting suspension was filtered and the filtrate was concentrated to give (7-bromobenzo[d]oxazol-2-yl)methanol (I-448) (3.10 g, 92% yield) as a yellow solid. $^1H$ NMR (400 MHz, $CDCl_3$) δ7.66 (dd, J=8.0, 1.2 Hz, 1H), 7.50 (d, J=8.0 Hz, 1H), 7.24 (t, J=8.0 Hz, 1H), 4.98 (d, J=5.6 Hz, 2H), 3.60-3.50 (s, 1H).

To a solution of (7-bromobenzo[d]oxazol-2-yl)methanol (2.90 g, 12.7 mmol) and 4,4,5,5-tetramethyl-2-(2-methylprop-1-en-1-yl)-1,3,2-dioxaborolane (4.63 g, 25.4 mmol) in dioxane (40 mL) and $H_2O$ (8 mL) were added $Cs_2CO_3$ (7.46 g, 22.9 mmol) and ditert-butyl(cyclopentyl)phosphane;dichloropalladium;iron (829 mg, 1.27 mmol). The mixture was stirred at 85° C. for 12 hours and concentrated. The residue was purified by silica gel chromatography to give (7-(2-methylprop-1-en-1-yl)benzo[d]oxazol-2-yl)methanol (I-449) (3.00 g) as a red oil.

To a solution of (7-(2-methylprop-1-en-1-yl)benzo[d]oxazol-2-yl)methanol (1.00 g, 4.92 mmol) in MeOH (20 mL) was added Pd/C (400 mg, 10% purity) under $N_2$ atmosphere. The suspension was degassed under vacuum and purged with $H_2$ three times. The mixture was stirred under $H_2$ (15 psi) atmosphere at 30° C. for 30 min. The resulting suspension was filtered and the filtrate was concentrated to give (7-isobutylbenzo[d]oxazol-2-yl)methanol (I-450) (1.00 g) as a yellow oil. $^1H$ NMR (400 MHz, $CDCl_3$) δ57.58 (dd, J=7.6, 0.8 Hz, 1H), 7.31-7.28 (m, 1H), 7.15 (d, J=7.2 Hz, 1H), 4.96 (s, 2H), 3.27 (s, 1H), 2.78 (d, J=7.2 Hz, 2H), 2.16-2.06 (m, 1H), 0.97 (d, J=6.4 Hz, 6H).

To a solution of (7-isobutylbenzo[d]oxazol-2-yl)methanol (1.00 g, 4.87 mmol) in DCM (10 mL) were added $Et_3N$ (986 mg, 9.74 mmol) and MsCl (660 mg, 5.76 mmol) at 0° C. The mixture was stirred at 30° C. for 1 hour and concentrated to give (7-isobutylbenzo[d]oxazol-2-yl)methyl methanesulfonate (I-451) (900 mg, 65% yield) as a yellow oil.

To a solution of (7-isobutylbenzo[d]oxazol-2-yl)methyl methanesulfonate (900 mg, 3.18 mmol) and 3-nitropyridin-2(1H)-one (668 mg, 4.77 mmol) in $CH_3CN$ (10 mL) was added $Et_3N$ (644 mg, 6.36 mmol). The mixture was stirred at 30° C. for 12 hours and concentrated. The residue was purified by silica gel chromatography to give 1-((7-isobutylbenzo[d]oxazol-2-yl)methyl)-3-nitropyridin-2(1H)-one (I-452) (300 mg, 29% yield) as a yellow solid.

To a solution of 1-((7-isobutylbenzo[d]oxazol-2-yl)methyl)-3-nitropyridin-2(1H)-one (300 mg, 917 μmol) in MeOH (10 mL) was added Pd/C (100 mg, 10% purity) under $N_2$ atmosphere. The suspension was degassed under vacuum and purged with $H_2$ three times. The mixture was stirred under $H_2$ (15 psi) at 30° C. for 0.5 h. The resulting suspension was filtered and the filtrate was concentrated to give 3-amino-1-((7-isobutylbenzo[d]oxazol-2-yl)methyl)pyridin-2(1H)-one (I-453) (220 mg, 81% yield) as a yellow oil.

The following intermediate was prepared according to the procedures described for the synthesis of I-453 using the appropriate reagents.

| Compound | Structure | LCMS Data |
|---|---|---|
| I-454 | 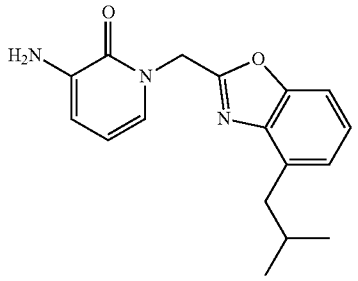 [SMILES: CC(C)Cc1cccc2oc(Cn3cccc(N)c3=O)nc12] | LCMS m/z 298.0 (M + 1)$^+$ |

Example 50

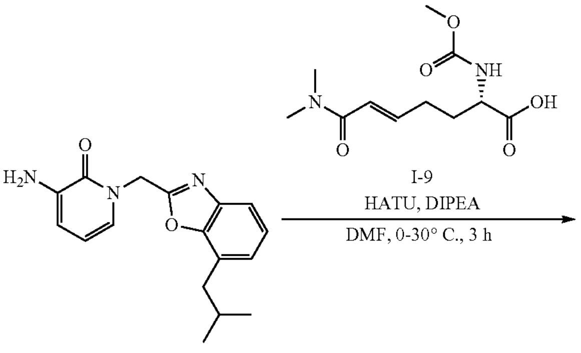

I-453

-continued

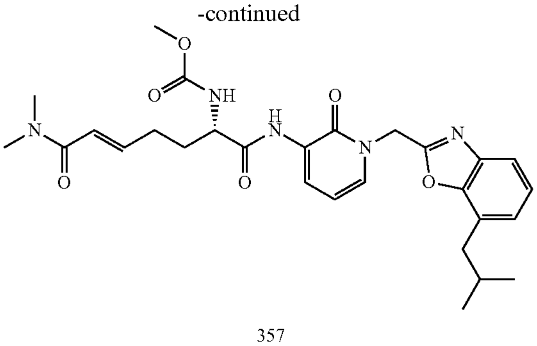

357

To a solution of 3-amino-1-((7-isobutylbenzo[d]oxazol-2-yl)methyl)pyridin-2(1H)-one (110 mg, 370 μmol) and (S,E)-7-(dimethylamino)-2-((methoxycarbonyl)amino)-7-oxohept-5-enoic acid (191 mg, 740 μmol) in DMF (3 mL) were added DIPEA (143 mg, 1.11 mmol) and HATU (352 mg, 925 μmol) at 0° C. The mixture was stirred at 30° C. for 3 h. The resulting solution was diluted with EtOAc (30 mL) and washed with brine (20 mL×2). The organic phase was concentrated in vacuum to give a residue. The residue was purified by prep-HPLC and prep-TLC to give (S,E)-methyl (7-(dimethylamino)-1-((1-((7-isobutylbenzo[d]oxazol-2-yl)methyl)-2-oxo-1,2-dihydropyridin-3-yl)amino)-1,7-dioxohept-5-en-2-yl)carbamate (Compound 357) (15.0 mg, 7% yield) as a white solid. LCMS m/z 538.1 $(M+1)^+$. $^1H$ NMR (400 MHz, DMSO-$d_6$) δ 9.28 (s, 1H), 8.28 (dd, J=7.2, 1.6 Hz, 1H), 7.71 (d, J=8.0 Hz, 1H), 7.61 (dd, J=6.8, 1.6 Hz, 1H), 7.51 (d, J=7.2 Hz, 1H), 7.27 (t, J=7.6 Hz, 1H), 7.18 (d, J=6.8 Hz, 1H), 6.64-6.55 (m, 1H), 6.43-6.33 (m, 2H), 5.51 (s, 2H), 4.23-4.13 (m, 1H), 3.53 (s, 3H), 2.98 (s, 3H), 2.83 (s, 3H), 2.70 (d, J=7.2 Hz, 2H), 2.30-2.14 (m, 2H), 2.08-1.94 (m, 1H), 1.92-1.80 (m, 1H), 1.77-1.64 (m, 1H), 0.87 (d, J=6.4 Hz, 6H).

The following compounds were prepared according to the procedures described in Example 50 using the appropriate intermediates.

| Compound | Structure | LCMS Data |
|---|---|---|
| 359 | 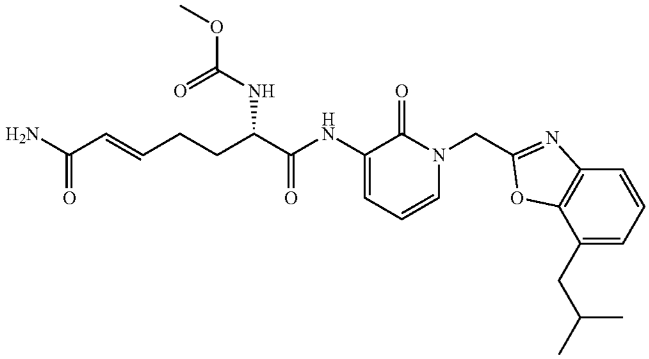 [SMILES: COC(=O)N[C@@H](CC/C=C/C(N)=O)C(=O)Nc1cccn(Cc2nc3cccc(CC(C)C)c3o2)c1=O] | LCMS m/z 510.0 $(M + 1)^+$ |
| 360 | 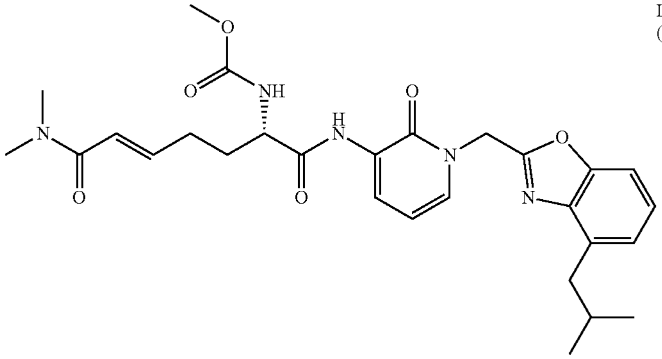 | LCMS m/z 538.2 $(M + 1)^+$ |
| 361 | 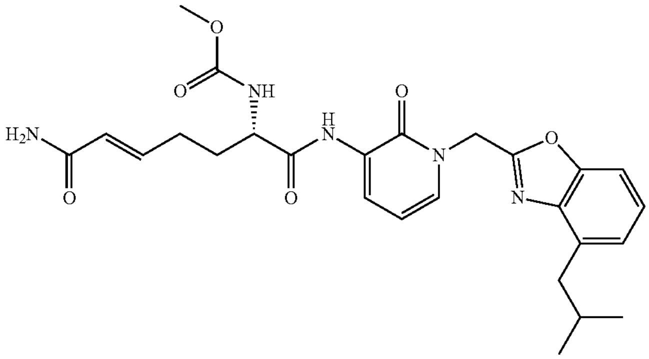 [SMILES: COC(=O)N[C@@H](CC/C=C/C(N)=O)C(=O)Nc1cccn(Cc2nc3c(CC(C)C)cccc3o2)c1=O] | LCMS m/z 510.2 $(M + 1)^+$ |

-continued
| Compound | Structure | LCMS Data |
| --- | --- | --- |
| 362 | 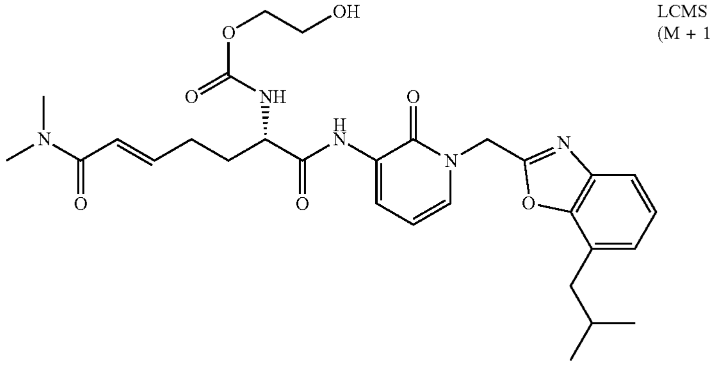 | LCMS m/z 568.1 $(M + 1)^+$ |
The Synthesis of Intermediate I-465
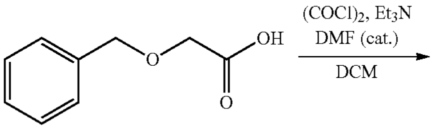
I-455
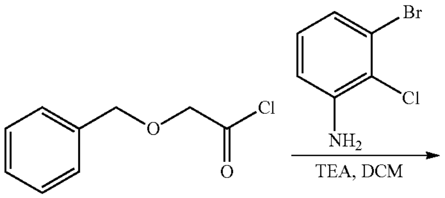
I-456
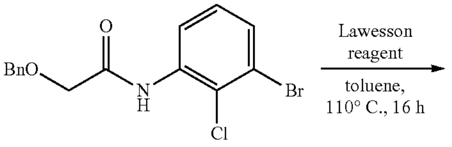
I-457
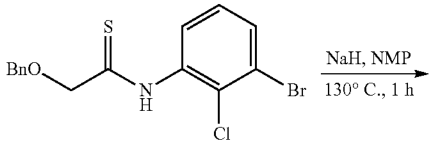
I-458
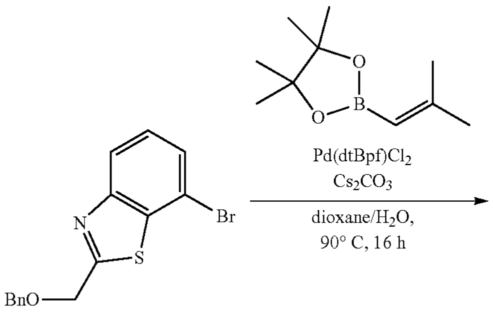
I-459
-continued
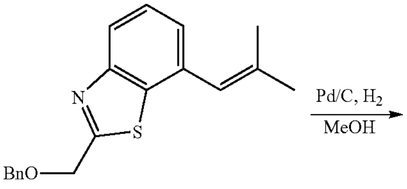
I-460
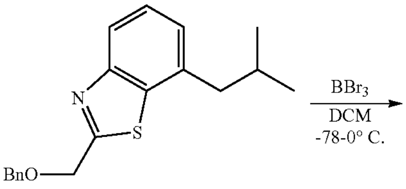
I-461
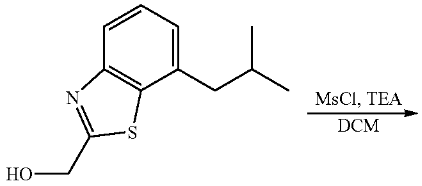
I-462
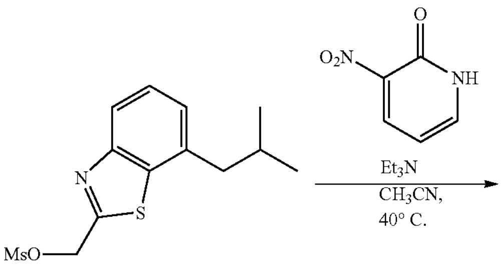
I-463

-continued

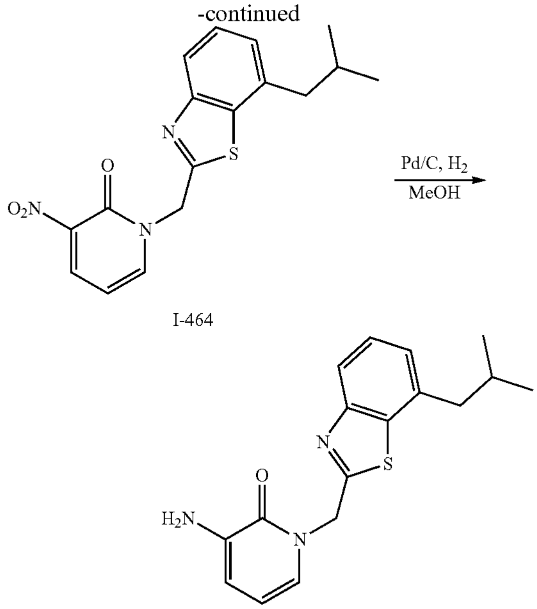

I-464

I-465

To a solution of 2-benzyloxyacetic acid (25.0 g, 150 mmol) and DMF (219 mg, 3.01 mmol) in DCM (250 mL) was added $(COCl)_2$ (28.64 g, 225 mmol) at 0° C. The mixture was stirred at 20° C. for 2 hr. The resulting solution was concentrated under reduced pressure at 20° C. to give 2-benzyloxyacetyl chloride (I-456) (60.0 g, crude, two batches) as a colorless oil which was used in the next step without further purification.

To a solution of 3-bromo-2-chloro-aniline (17.5 g, 84.7 mmol) and $Et_3N$ (17.1 g, 169 mmol) in DCM (50 mL) was added 2-(benzyloxy)acetyl chloride (29.6 g, 144 mmol) at 0° C. The mixture was stirred at 20° C. for 16 hr. The resulting solution was quenched with ice-water (100 mL) at 0° C., and extracted with DCM (300 mL×3). The combined organic layers were washed with citric acid solution (10%, 300 mL×2) and brine (300 mL×2). The organic phase was dried over anhydrous $Na_2SO_4$, filtered and concentrated under reduced pressure to afford 2-(benzyloxy)-N-(3-bromo-2-chlorophenyl)acetamide (I-457) (80.0 g, crude, two batches) which was used in the next step without further purification. LCMS m/z 353.9, 355.9 $(M+1)^+$.

To a solution of 2-(benzyloxy)-N-(3-bromo-2-chlorophenyl)acetamide (40.0 g, 112 mmol) in toluene (500 mL) was added 2,4-bis(4-methoxyphenyl)-2,4-dithioxo-1,3,2,4dithiadiphosphetane (41.0 g, 101 mmol). The mixture was stirred at 110° C. for 16 hr. The resulting suspension was filtered and concentrated under reduced pressure to give a residue. The residue was purified by column chromatography to afford 2-(benzyloxy)-N-(3-bromo-2-chlorophenyl)ethanethioamide (I-458) (52.0 g) as a green solid. LCMS m/z 371.8 $(M+1)^+$. $^1H$ NMR (400 MHz, $CDCl_3$) δ 10.48 (s, 1H), 8.91 (dd, J=8.0, 1.2 Hz, 1H), 7.55 (dd, J=8.0, 1.2 Hz, 1H), 7.42-7.34 (m, 5H), 7.23 (t, J=8.0 Hz, 1H), 4.74 (s, 2H), 4.52 (s, 2H).

To a solution of 2-(benzyloxy)-N-(3-bromo-2-chlorophenyl)ethanethioamide (42.0 g, 113 mmol) in NMP (400 mL) was added NaH (5.89 g, 147 mmol) at 20° C. The mixture was stirred at 130° C. for 1 hr. The resulting solution was diluted with water (800 mL) and extracted with EtOAc (800 mL×3). The combined organic layers were washed with brine (800 mL×4), dried over anhydrous $Na_2SO_4$, filtered and concentrated under reduced pressure to give a residue. The residue was purified by column chromatography to afford 2-((benzyloxy)methyl)-7-bromobenzo[d]thiazole (I-459) (26.0 g, 69% yield) as a brown oil. $^1H$ NMR (400 MHz, $CDCl_3$) δ 7.94 (d, J=8.0 Hz, 1H), 7.53 (d, J=8.0 Hz, 1H), 7.45-7.33 (m, 6H), 4.94 (s, 2H), 4.75 (s, 2H).

To a solution of 2-((benzyloxy)methyl)-7-bromobenzo[d]thiazole (6.80 g, 20.3 mmol), 4,4,5,5-tetramethyl-2-(2-methylprop-1-enyl)-1,3,2-dioxaborolane (9.26 g, 50.88 mmol) and $Cs_2CO_3$ (13.3 g, 40.7 mmol) in dioxane (100 mL)/$H_2O$ (10.0 mL) was added ditert-butyl(cyclopentyl)phosphane; dichloropalladium;iron (1.33 g, 2.03 mmol) under $N_2$ atmosphere. The mixture was stirred at 90° C. for 16 hr. The resulting solution was diluted with water (200 mL) and extracted with EtOAc (300 mL×3). The combined organic layers were washed with brine (300 mL×2), dried over anhydrous $Na_2SO_4$, filtered and concentrated under reduced pressure to give a residue. The residue was purified by column chromatography to afford 2-((benzyloxy)methyl)-7-(2-methylprop-1-en-1-yl)benzo[d]thiazole (I-460) (3.80 g, 60% yield) as a yellow oil. LCMS m/z 310.1 $(M+1)^+$.

To a solution of 2-((benzyloxy)methyl)-7-(2-methylprop-1-en-1-yl)benzo[d]thiazole (3.80 g, 12.3 mmol) in MeOH (40 mL) was added Pd/C (400 mg, 12.3 mmol). The mixture was stirred at 25° C. for 2 days under $H_2$ (15 psi) atmosphere. The reaction mixture was filtered and concentrated under reduced pressure to afford 2-((benzyloxy)-methyl)-7-isobutylbenzo[d]thiazole (I-461) (3.50 g, 91% yield) as a yellow oil. LCMS m/z 312.0 $(M+1)^+$.

To a solution of 2-((benzyloxy)methyl)-7-isobutylbenzo[d]thiazole (3.50 g, 11.24 mmol) in DCM (40 mL) was added $BBr_3$ (5.63 g, 22.48 mmol) at −78° C. The mixture was stirred at −78° C. for 1.5 h under $N_2$ atmosphere. The reaction mixture was quenched with water (20 mL) at −78° C., and extracted with EtOAc (30 mL×3). The combined organic layers were washed with saturated $NaHCO_3$ (30 mL×2), washed with brine (30 mL×2) and dried over anhydrous $Na_2SO_4$, filtered and concentrated under reduced pressure to give a residue. The residue was purified by column chromatography to afford (7-isobutylbenzo[d]thiazol-2-yl)-methanol (I-462) (2.00 g, 80% yield) as a yellow oil. $^1H$ NMR (400 MHz, $CDCl_3$) δ 7.85 (d, J=8.0 Hz, 1H), 7.42 (t, J=8.0 Hz, 1H), 7.17 (d, J=7.2 Hz, 1H), 5.08 (d, J=4.8 Hz, 2H), 3.18-3.12 (m, 1H), 2.74 (d, J=7.2 Hz, 2H), 2.17-2.08 (m, 1H), 0.96 (d, J=6.4 Hz, 6H).

To a solution of (7-isobutylbenzo[d]thiazol-2-yl)methanol (2.00 g, 9.04 mmol) and TEA (1.83 g, 18.08 mmol) in DCM (30.0 mL) was added MsCl (1.55 g, 13.56 mmol) at 0° C. The mixture was stirred at 25° C. for 1.5 hr. The reaction mixture was diluted with brine (20 mL) and extracted with DCM (30 mL×3). The combined organic layers were dried over anhydrous $Na_2SO_4$, filtered and concentrated under reduced pressure to give 3.00 g of (7-isobutylbenzo[d]thiazol-2-yl)methyl methanesulfonate (I-463) which was used in the next step without further purification.

To a solution of $Et_3N$ (1.83 g, 18.0 mmol) and 3-nitro-1H-pyridin-2-one (1.90 g, 13.5 mmol) in MeCN (40 mL) was added (7-isobutylbenzo[d]thiazol-2-yl)methyl methanesulfonate (3.00 g, 9.02 mmol) at 0° C. The mixture was stirred at 25° C. for 16 hr. The reaction mixture was diluted with water (60 mL) and extracted with EtOAc (80 mL×3). The combined organic layers were washed with brine (80 mL×2), dried over anhydrous $Na_2SO_4$, filtered and concentrated under reduced pressure to give a residue. The residue was purified prep-TLC to afford 1-((7-isobutylbenzo[d]thiazol-2-yl)methyl)-3-nitropyridin-2(1H)-one (I-464) (900 mg, 29% yield) as a yellow oil. LCMS m/z 305.1 $(M+1)^+$.

To a solution of 1-((7-isobutylbenzo[d]thiazol-2-yl)methyl)-3-nitropyridin-2(1H)-one (900 mg, 2.62 mmol) in MeOH (20 mL) was added Pd/C (100 mg, 2.62 mmol). The mixture was stirred at 25° C. for 0.5 hr under $H_2$ (15 psi). The reaction mixture was filtered and concentrated under reduced pressure to give a residue. The residue was purified by column chromatography to afford 3-amino-1-((7-isobutylbenzo[d]thiazol-2-yl)methyl)pyridin-2(1H)-one (I-465) (780 mg, 95% yield) as a yellow oil. LCMS m/z 314.0 $(M+1)^+$. $^1H$ NMR (400 MHz, $CDCl_3$) δ 7.87 (d, J=8.0 Hz, 1H), 7.42 (t, J=7.6 Hz, 1H), 7.16 (d, J=7.2 Hz, 1H), 6.96 (dd, J=6.8, 1.6 Hz, 1H), 6.56 (dd, J=7.2, 1.6 Hz, 1H), 6.13 (t, J=7.2 Hz, 1H), 5.55 (s, 2H), 4.32-4.26 (m, 2H), 2.69 (d, J=7.6 Hz, 2H), 2.13-2.06 (m, 1H), 0.92 (d, J=6.4 Hz, 6H).

Example 51

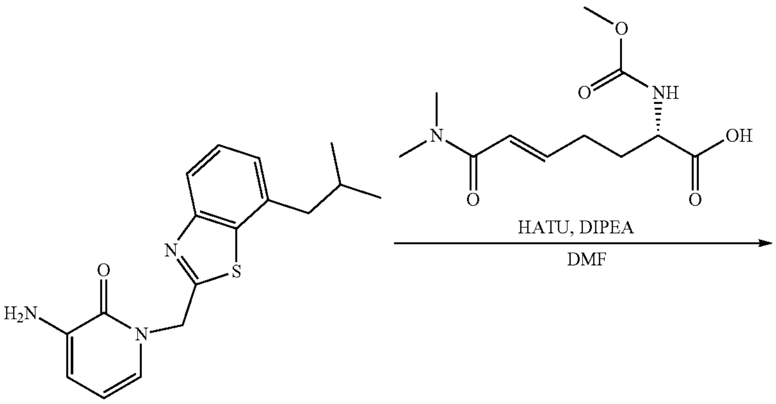

I-465

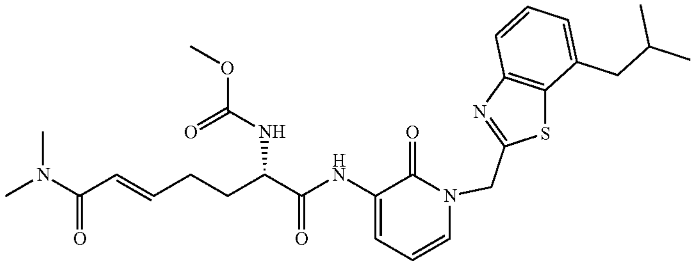

363

To a solution of (S,E)-7-(dimethylamino)-2-((methoxycarbonyl)amino)-7-oxohept-5-enoic acid (124 mg, 479 μmol) and 3-amino-1-((7-isobutylbenzo[d]thiazol-2-yl)methyl)pyridin-2(1H)-one (100 mg, 319 μmol) in DMF (3 mL) were added HATU (146 mg, 383 μmol) and DIPEA (124 mg, 957 μml, 167 μL) at 0° C. The solution was stirred at 25° C. for 16 h. The resulting solution was concentrated under reduced pressure to give a residue. The residue was purified by prep-HPLC to give (S,E)-methyl (7-(dimethylamino)-1-((1-((7-isobutylbenzo[d]thiazol-2-yl)methyl)-2-oxo-1,2-dihydropyridin-3-yl)amino)-1,7-dioxohept-5-en-2-yl)carbamate (Compound 363) (16.6 mg, 9% yield) as a white solid. LCMS m/z 554.4 $(M+1)^+$. $^1H$ NMR (400 MHz, DMSO-$d_6$) δ 9.34 (s, 1H), 8.28 (dd, J=7.4, 1.6 Hz, 1H), 7.83 (d, J=7.6 Hz, 1H), 7.72 (d, J=7.8 Hz, 1H), 7.64 (dd, J=6.8, 1.6 Hz, 1H), 7.45 (t, J=7.6 Hz, 1H), 7.25 (d, J=7.2 Hz, 1H), 6.66-6.56 (m, 1H), 6.42-6.34 (m, 2H), 5.67-5.55 (m, 2H), 4.26-4.16 (m, 1H), 3.55 (s, 3H), 2.98 (s, 3H), 2.83 (s, 3H), 2.67 (d, J=7.2 Hz, 2H), 2.30-2.16 (m, 2H), 2.06-1.96 (m, 1H), 1.92-1.80 (m, 1H), 1.79-1.63 (m, 1H), 0.87 (d, J=6.8 Hz, 6H).

The following compounds were s prepared according to the procedures described for the synthesis of Example 51 using the appropriate reagents.

| Compound | Structure | LCMS Data |
| --- | --- | --- |
| 364 | 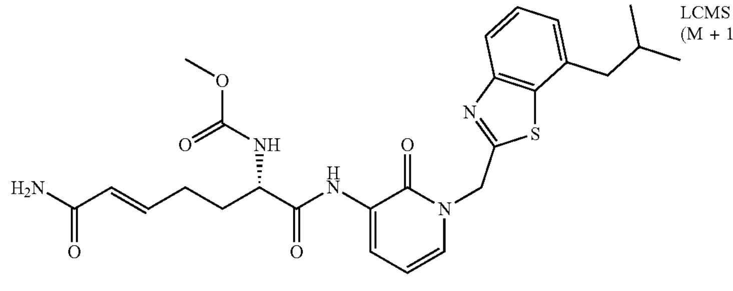 | LCMS m/z 526.4 $(M + 1)^+$ |
| 365 | 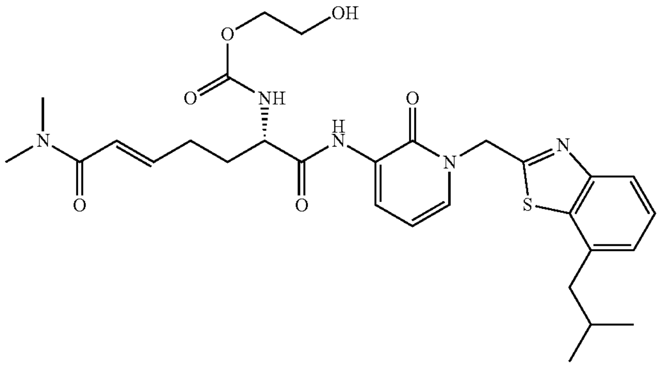 [SMILES: CC(C)Cc1cccc2nc(Cn3cccc(NC(=O)[C@H](CC/C=C/C(=O)N(C)C)NC(=O)OCCO)c3=O)sc12] | LCMS m/z 584.4 $(M + 1)^+$ |
The Synthesis of Intermediate I-472
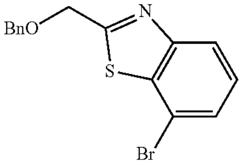
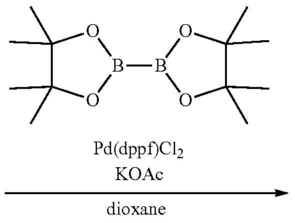
I-459
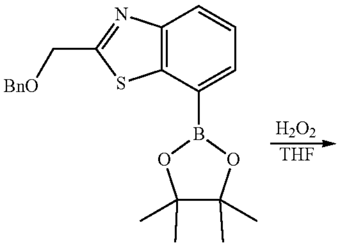
I-466
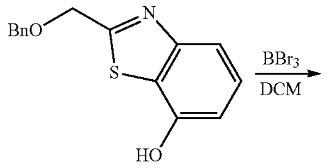
I-467
-continued
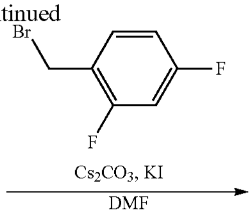
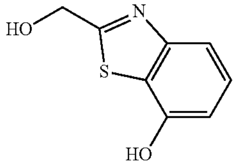
I-468
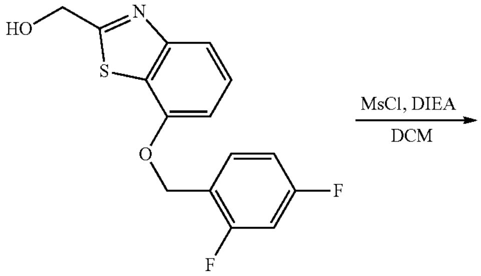
I-469
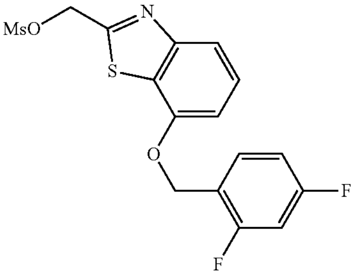
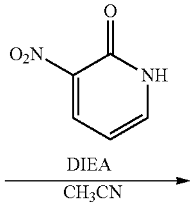
I-470

-continued

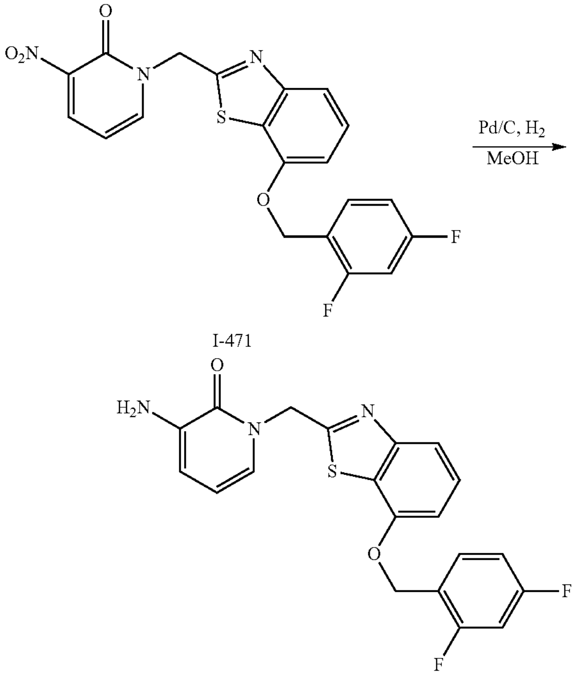

I-471

I-472

A mixture of 2-((benzyloxy)methyl)-7-bromobenzo[d]thiazole (3 g, 8.9 mmol), 4,4,4',4',5,5,5',5'-octamethyl-2,2'-bi(1,3,2-dioxaborolane) (3.4 g, 13.5 mmol), $Pd(dppf)Cl_2$ (656 mg, 897 μmol), KOAc (1.8 g, 17.9 mmol) in dioxane (20 mL) was degassed and purged with $N_2$ for 3 times. The mixture was stirred at 90° C. for 2 h under $N_2$ atmosphere. The resulting solution was concentrated in vacuum to give a residue. The residue was purified by column chromatography to give 2-((benzyloxy)methyl)-7-(4,4,5,5-tetramethyl-1,3,2-dioxaborolan-2-yl)benzo[d]thiazole (I-466) (3.1 g) as a yellow oil. LCMS m/z 382 $(M+1)^+$.

To a solution of 2-((benzyloxy)methyl)-7-(4,4,5,5-tetramethyl-1,3,2-dioxaborolan-2-yl)benzo[d]thiazole (3.1 g, 8.1 mmol) in THF (30 mL) was added $H_2O_2$ (9.2 g, 81.3 mmol, 7.8 mL, 30% purity) dropwise at 0° C. The mixture was stirred at 35° C. for 2 h. The reaction mixture was quenched with saturated $NaHSO_3$ (50 mL) and stirred at 35° C. for 30 min. The resulting solution was extracted with DCM (50 mL×3). The combined organic layers were washed with brine (50 mL), dried over anhydrous $Na_2SO_4$, filtered and concentrated in vacuum to give 2-((benzyloxy)methyl)benzo[d]thiazol-7-ol (I-467) (2.6 g) as a white solid. LCMS m/z 272.1 $(M+1)^+$.

To a solution of 2-((benzyloxy)methyl)benzo[d]thiazol-7-ol (2.1 g, 7.6 mmol) in DCM (20 mL) was added a solution of $BBr_3$ (2.8 g, 11.3 mmol) in DCM (5 mL) at −78° C. The mixture was stirred at −78° C. for 2 h. The resulting solution was quenched with water (20 mL) at −78° C. and extracted with EtOAc (50 mL×3). The combined organic layers were dried over anhydrous $Na_2SO_4$ and concentrated under reduced pressure to give a residue 1. The aqueous phase was concentrated in vacuum to give a residue 2. The residue 1 and the residue 2 were purified by column chromatography to give 2-(hydroxymethyl)benzo[d]thiazol-7-ol (I-468) (400 mg) as a yellow solid. LCMS m/z 182 $(M+1)^+$.

To a solution of 2-(hydroxymethyl)benzo[d]thiazol-7-ol (300 mg, 1.7 mmol) and 1-(bromomethyl)-2,4-difluorobenzene (446 mg, 2.2 mmol) in DMF (5 mL) were added $Cs_2CO_3$ (1.1 g, 3.3 mmol) and KI (275 mg, 1.7 mmol). The mixture was stirred at 30° C. for 12 h. The reaction mixture was diluted with water (10 mL) and extracted with EtOAc (10 mL×3). The combined organic layers were washed with brine (10 mL), dried over anhydrous $Na_2SO_4$, filtered and concentrated under reduced pressure to give a residue. The residue was purified by column chromatography to give (7-((2,4-difluorobenzyl)oxy)benzo[d]thiazol-2-yl)methanol (I-469) (600 mg) as a yellow oil. LCMS m/z 308 $(M+1)^+$.

To a solution of (7-((2,4-difluorobenzyl)oxy)benzo[d]thiazol-2-yl)methanol (400 mg, 1.3 mmol) in DCM (5 mL) were added DIPEA (336 mg, 2.6 mmol) and MsCl (194 mg, 1.69 mmol) at 0° C. The mixture was stirred at 30° C. for 1 h. The reaction mixture was quenched with water (10 mL) at 0° C., and extracted with DCM (10 mL×3). The combined organic layers were washed with brine (10 mL), dried over anhydrous $Na_2SO_4$, filtered and concentrated under reduced pressure to give (7-((2,4-difluorobenzyl)oxy)benzo[d]thiazol-2-yl)methyl methanesulfonate (I-470) (260 mg) as a brown oil. LCMS m/z 386 $(M+1)^+$.

To a solution of (7-((2,4-difluorobenzyl)oxy)benzo[d]thiazol-2-yl)methyl methanesulfonate (260 mg, 674 μmol) in $CH_3CN$ (4 mL) were added 3-nitropyridin-2(1H)-one (123 mg, 877 μmol) and DIPEA (174 mg, 1.4 mmol). The mixture was stirred at 30° C. for 12 h. The mixture was concentrated under reduced pressure to give a residue. The residue was purified by column chromatography to give 1-((7-((2,4-difluorobenzyl)oxy)benzo[d]thiazol-2-yl)methyl)-3-nitropyridin-2(1H)-one (I-471) (300 mg) as a yellow solid. LCMS m/z 430 $(M+1)^+$.

To a solution of 1-((7-((2,4-difluorobenzyl)oxy)benzo[d]thiazol-2-yl)methyl)-3-nitropyridin-2(1H)-one (300 mg, 698.6 μmol) in MeOH (10 mL) was added Pd/C (10%, 30 mg) under $N_2$ atmosphere. The suspension was degassed under vacuum and purged with $H_2$ three times. The mixture was stirred under $H_2$ (15 psi) at 30° C. for 20 min. The resulting suspension was filtered and the filtrate was concentrated to give 3-amino-1-((7-((2,4-difluorobenzyl)oxy)benzo[d]thiazol-2-yl)methyl)pyridin-2(1H)-one (I-472) (120 mg) as a yellow solid. LCMS m/z 400 $(M+1)^+$.

The following intermediates were prepared according to the procedures described for the synthesis of I-472 using the appropriate reagents.

-continued
| Compound | Structure | LCMS Data |
|---|---|---|
| I-473 | 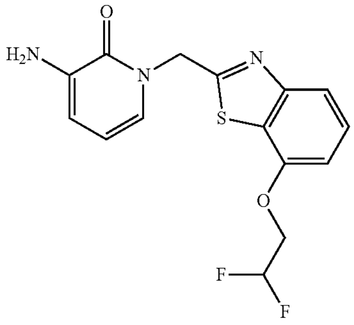 [SMILES: Nc1cccn(Cc2nc3cccc(OCC(F)F)c3s2)c1=O] | LCMS m/z 338.0 (M + 1)+ |
| I-474 | 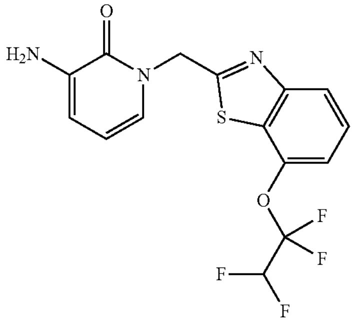 [SMILES: Nc1cccn(Cc2nc3cccc(OC(F)(F)C(F)F)c3s2)c1=O] | LCMS m/z 373.9 (M + 1)+ |
| I-475 | 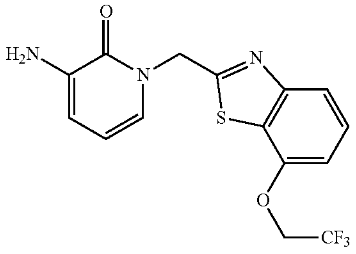 [SMILES: Nc1cccn(Cc2nc3cccc(OCC(F)(F)F)c3s2)c1=O] | LCMS m/z 356.1 (M + 1)+ |
| I-476 | 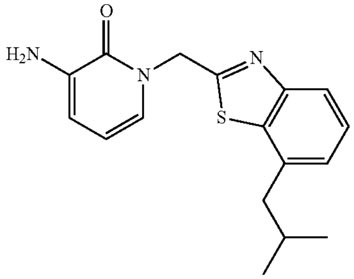 [SMILES: CC(C)Cc1cccc2nc(Cn3cccc(N)c3=O)sc12] | LCMS m/z 314.0 (M + 1)+ |
Example 52
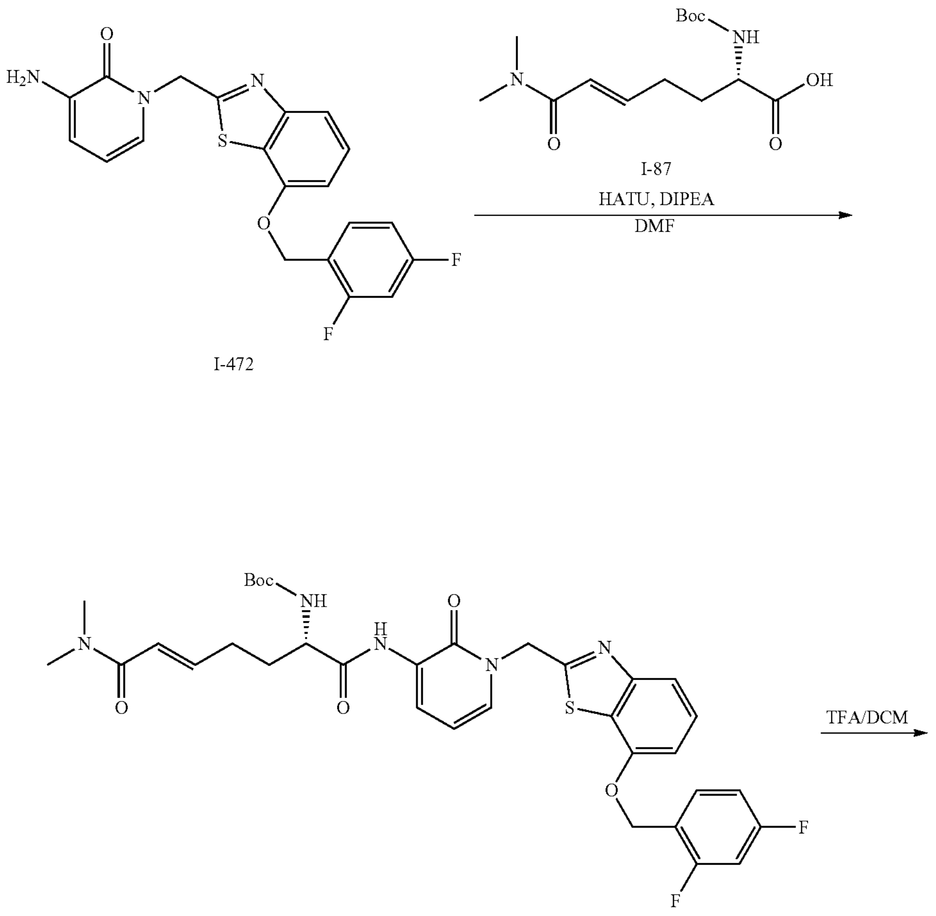

-continued

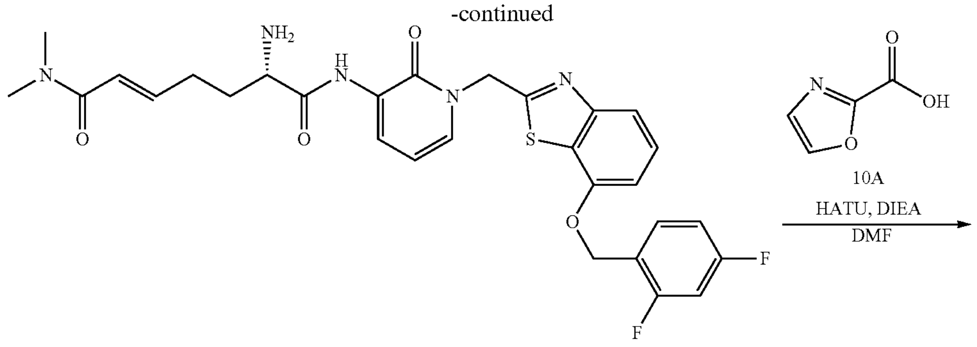

I-477

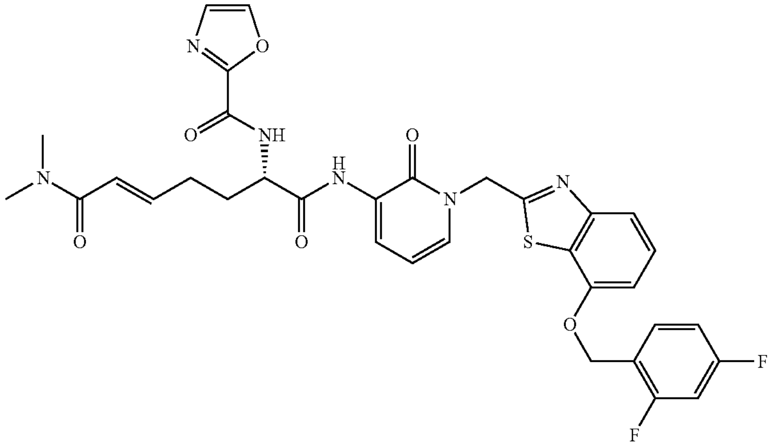

367

To a solution of 3-amino-1-((7-((2,4-difluorobenzyl)oxy benzo[d]thiazol-2-yl) methyl)pyridin-2(1H)-one (130 mg, 293 µmol) and (S,E)-2-((tert-butoxycarbonyl) amino)-7-(dimethylamino)-7-oxohept-5-enoic acid (176 mg, 586 µmol) in DMF (3 mL) were added HATU (223 mg, 586 µmol) and DIPEA (113 mg, 878 µmol) at 0° C. The mixture was stirred at 30° C. for 12 h. The mixture was diluted with water (15 mL) and extracted with EtOAc (10 mL×3). The combined organic layers were washed with brine (10 mL×3), dried over anhydrous $Na_2SO_4$, and concentrated in vacuum to give a residue. The residue was purified by prep-TLC and prep-HPLC to give (S,E)-tert-butyl (1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate (Compound 366) (18 mg) as a white solid. LCMS m/z 682.2 $(M+1)^+$.

To a solution of (S,E)-tert-butyl (1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate (73 mg, 107 µmol) in DCM (3 mL) was added TFA (1.5 g, 13.5 mmol, 1.00 mL) at 0° C. The mixture was stirred at 20° C. for 1 h. The mixture was concentrated in vacuum to give (S,E)-6-amino-N7-(1-((7-((2,4-difluorobenzyl) oxy)benzo[d]thiazol-2-yl)methyl)-2-oxo-1,2-dihydropyridin-3-yl)-N1,N1-dimethylhept-2-enediamide (I-477) (62 mg) as a brown oil. LCMS m/z 582.2 $(M+1)^+$.

To a solution of oxazole-2-carboxylic acid (18 mg, 160 µmol) in DMF (2 mL) were added HATU (81 mg, 213 µmol), DIPEA (41 mg, 320 µmol) and (S,E)-6-amino-N7-(1-((7-((2,4-difluorobenzyl)oxy)benzo[d]thiazol-2-yl) methyl)-2-oxo-1,2-dihydropyridin-3-yl)-N1,N1-dimethylhept-2-enediamide (62 mg, 106 µmol) at 0° C. The mixture was stirred at 30° C. for 2 h. The mixture was concentrated and the residue was purified by prep-HPLC to give (S,E)-N7-(1-((7-((2,4-difluorobenzyl)oxy)benzo[d]thiazol-2-yl) methyl)-2-oxo-1,2-dihydropyridin-3-yl)-N1,N1-dimethyl-6-(oxazole-2-carboxamido)hept-2-enediamide (Compound 367) (39 mg) as a light green solid. LCMS m/z 677.1 $(M+1)^+$. $^1H$ NMR (400 MHz, DMSO-$d_6$) 9.51 (s, 1H), 9.27 (d, J=8.0 Hz, 1H), 8.35 (s, 1H), 8.26 (d, J=6.8 Hz, 1H), 7.68-7.57 (m, 3H), 7.52-7.43 (m, 2H), 7.37-7.27 (m, 1H), 7.30-7.12 (m, 2H), 6.66-6.59 (m, 1H), 6.39-6.36 (m, 2H), 5.59 (s, 2H), 5.31 (s, 2H), 4.72-4.64 (m, 1H), 2.96 (s, 3H), 2.82 (s, 3H), 2.35-2.16 (m, 2H), 2.06-1.91 (m, 2H).

The following compounds were prepared according to the procedures described in Example 52 using the appropriate intermediates.

| Compound | Structure | LCMS Data |
| --- | --- | --- |
| 368 | 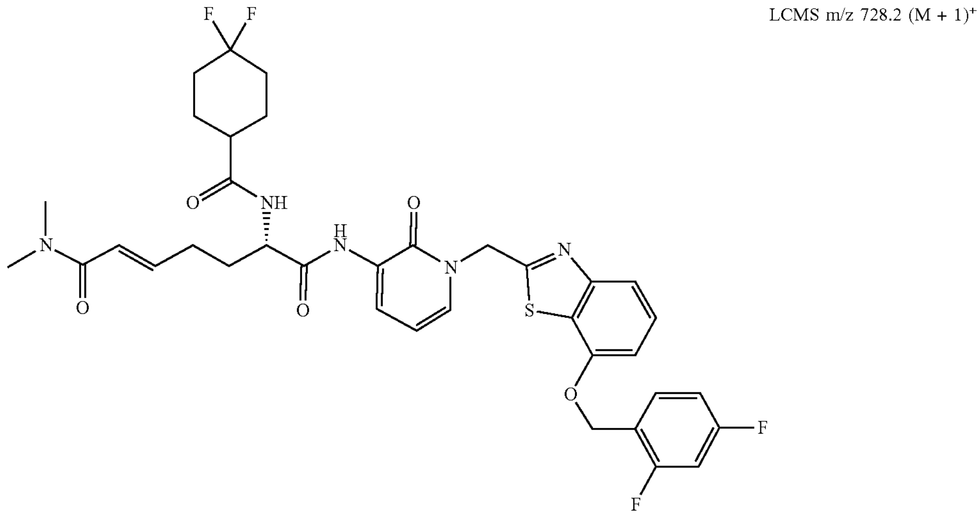 | LCMS m/z 728.2 $(M + 1)^+$ |
| 369 | 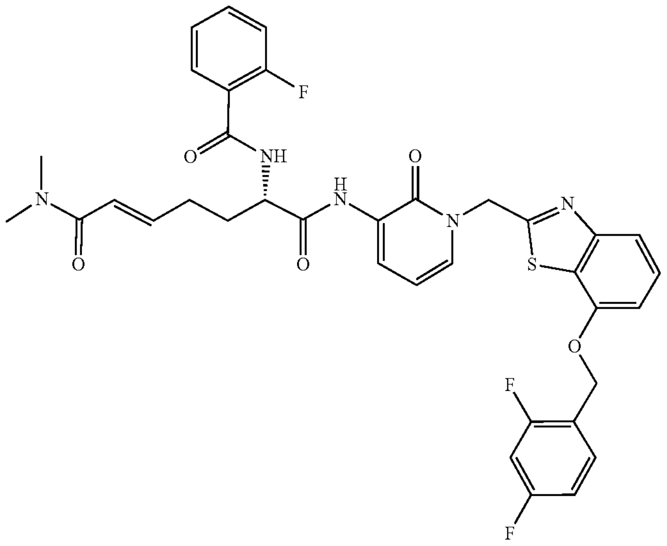 [SMILES: CN(C)C(=O)/C=C/CC[C@H](NC(=O)c1ccccc1F)C(=O)Nc1cccn(Cc2nc3cccc(OCc4ccc(F)cc4F)c3s2)c1=O] | LCMS m/z 704.2 $(M + 1)^+$ |
| 370 | 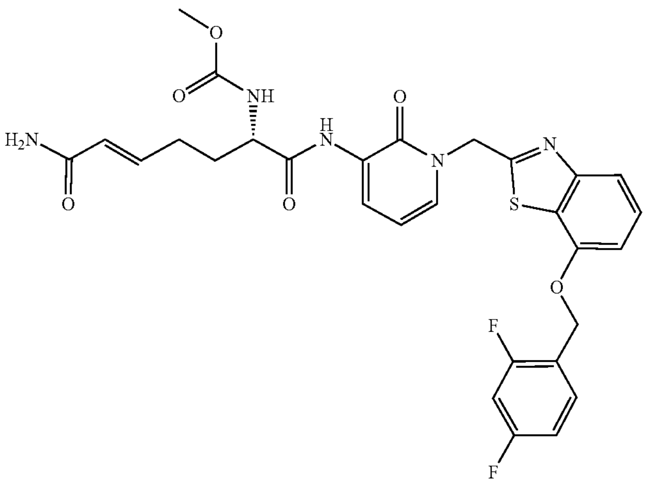 [SMILES: COC(=O)N[C@@H](CC/C=C/C(N)=O)C(=O)Nc1cccn(Cc2nc3cccc(OCc4ccc(F)cc4F)c3s2)c1=O] | LCMS m/z 612.2 $(M + 1)^+$ |

-continued
| Compound | Structure | LCMS Data |
| --- | --- | --- |
| 371 | 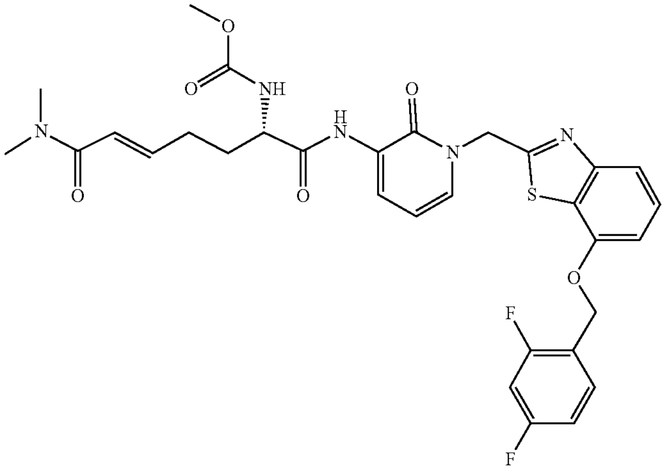 [SMILES: COC(=O)N[C@@H](CC/C=C/C(=O)N(C)C)C(=O)Nc1cccn(Cc2nc3cccc(OCc4ccc(F)cc4F)c3s2)c1=O] | LCMS m/z 640.2 $(M + 1)^+$ |
| 372 | 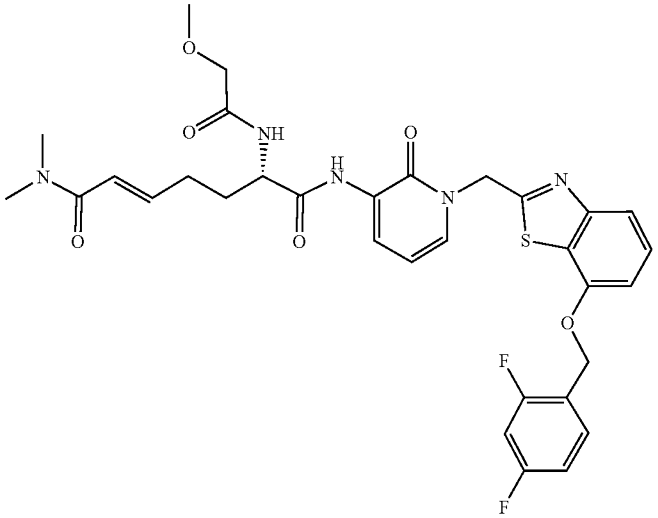 [SMILES: COCC(=O)N[C@@H](CC/C=C/C(=O)N(C)C)C(=O)Nc1cccn(Cc2nc3cccc(OCc4ccc(F)cc4F)c3s2)c1=O] | LCMS m/z 654.2 $(M + 1)^+$. |
| 373 | 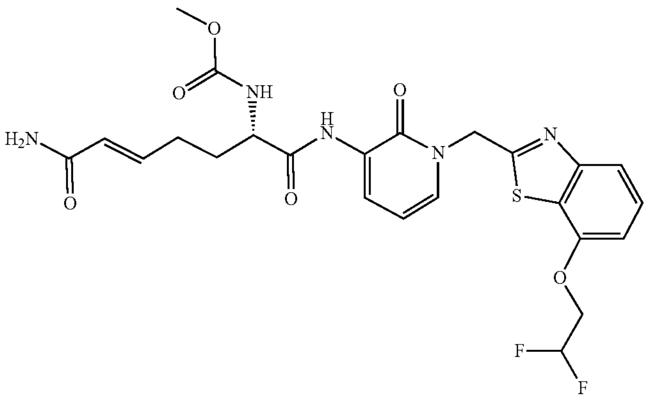 [SMILES: COC(=O)N[C@@H](CC/C=C/C(N)=O)C(=O)Nc1cccn(Cc2nc3cccc(OCC(F)F)c3s2)c1=O] | LCMS m/z 550.1 $(M + 1)^+$ |

-continued
| Compound | Structure | LCMS Data |
| --- | --- | --- |
| 374 | 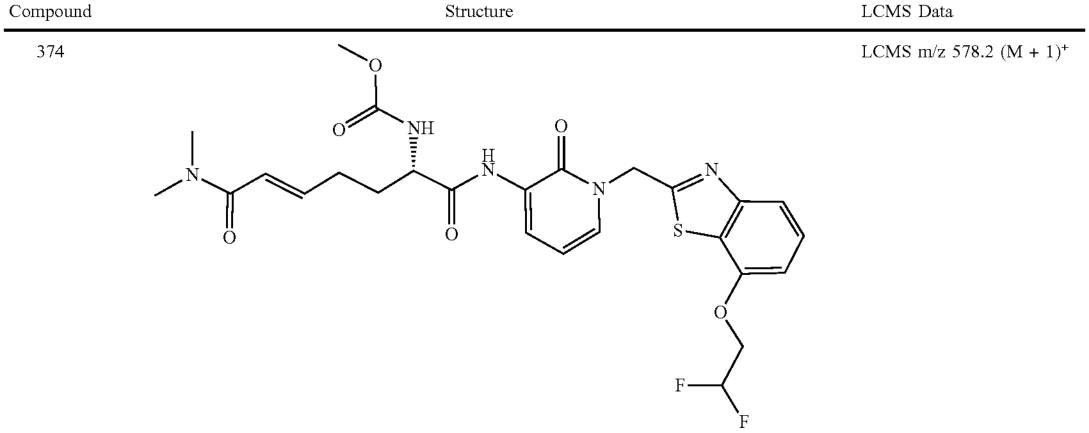 | LCMS m/z 578.2 $(M + 1)^+$ |
| 375 | 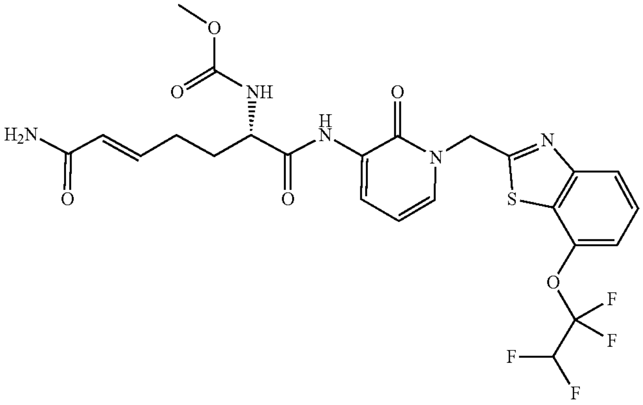 [SMILES: COC(=O)N[C@@H](CC/C=C/C(N)=O)C(=O)Nc1cccn(Cc2nc3cccc(OC(F)(F)C(F)F)c3s2)c1=O] | LCMS m/z 586.2 $(M + 1)^+$. |
| 376 | 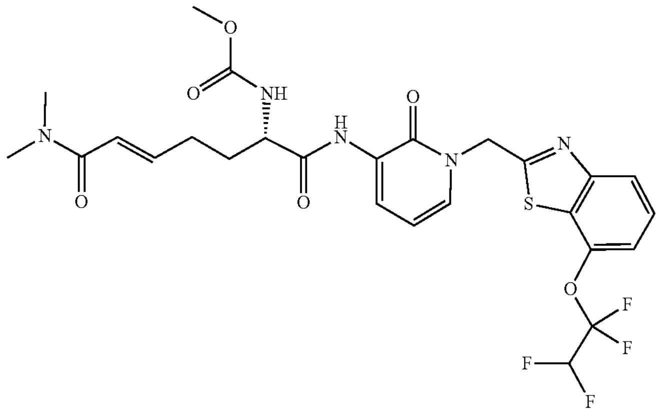 [SMILES: COC(=O)N[C@@H](CC/C=C/C(=O)N(C)C)C(=O)Nc1cccn(Cc2nc3cccc(OC(F)(F)C(F)F)c3s2)c1=O] | LCMS m/z 614.1 $(M + 1)^+$ |
| 377 | 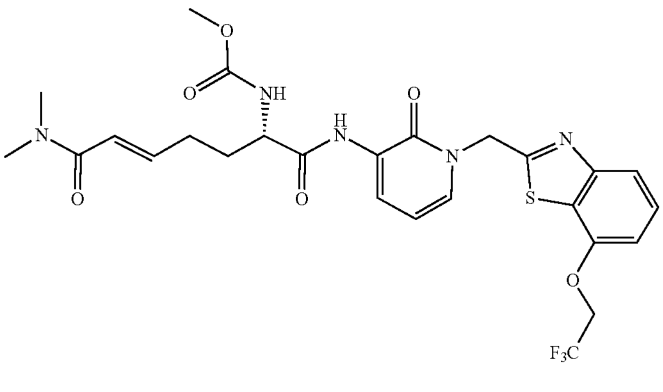 [SMILES: COC(=O)N[C@@H](CC/C=C/C(=O)N(C)C)C(=O)Nc1cccn(Cc2nc3cccc(OCC(F)(F)F)c3s2)c1=O] | LCMS m/z 596.2 $(M + 1)^+$. |

-continued
| Compound | Structure | LCMS Data |
|---|---|---|
| 378 | 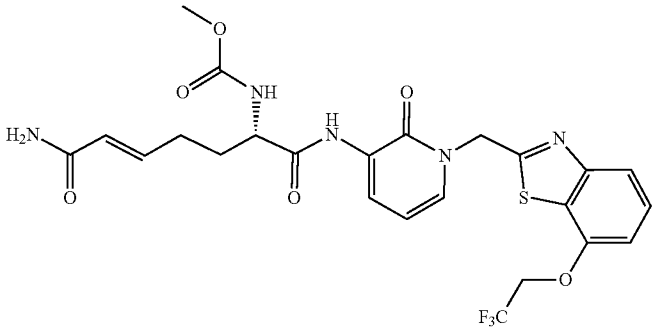 [SMILES: COC(=O)N[C@@H](CC/C=C/C(N)=O)C(=O)Nc1cccn(Cc2nc3cccc(OCC(F)(F)F)c3s2)c1=O] | LCMS m/z 568.1 (M + H)+ |
| 379 | 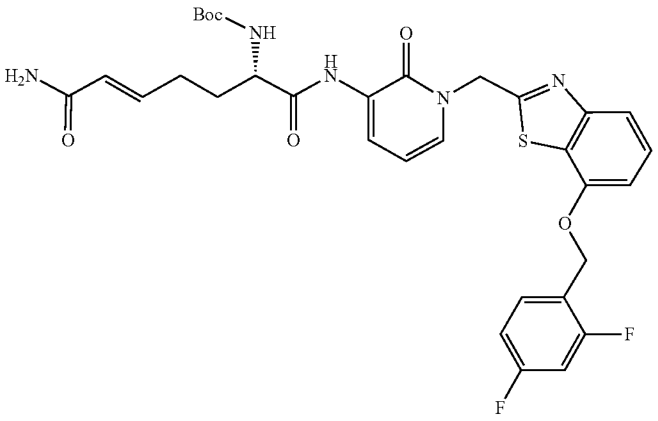 [SMILES: CC(C)(C)OC(=O)N[C@@H](CC/C=C/C(N)=O)C(=O)Nc1cccn(Cc2nc3cccc(OCc4ccc(F)cc4F)c3s2)c1=O] | LCMS m/z 654.2 (M + 1)+ |
| 380 | 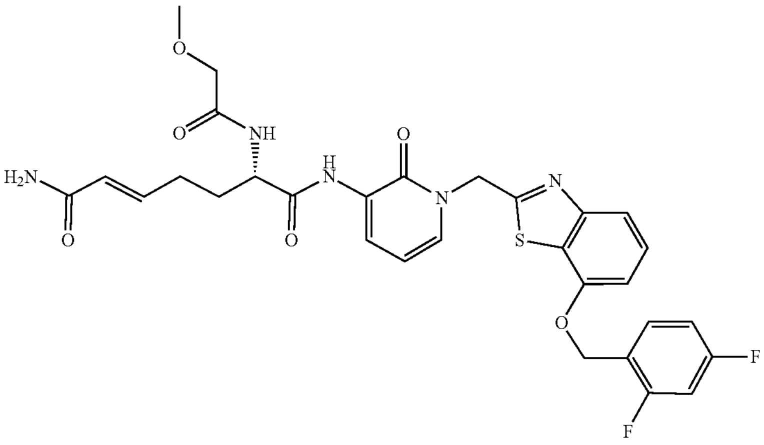 [SMILES: COCC(=O)N[C@@H](CC/C=C/C(N)=O)C(=O)Nc1cccn(Cc2nc3cccc(OCc4ccc(F)cc4F)c3s2)c1=O] | LCMS m/z 626.2 (M + 1)+ |

-continued
| Compound | Structure | LCMS Data |
| --- | --- | --- |
| 381 | 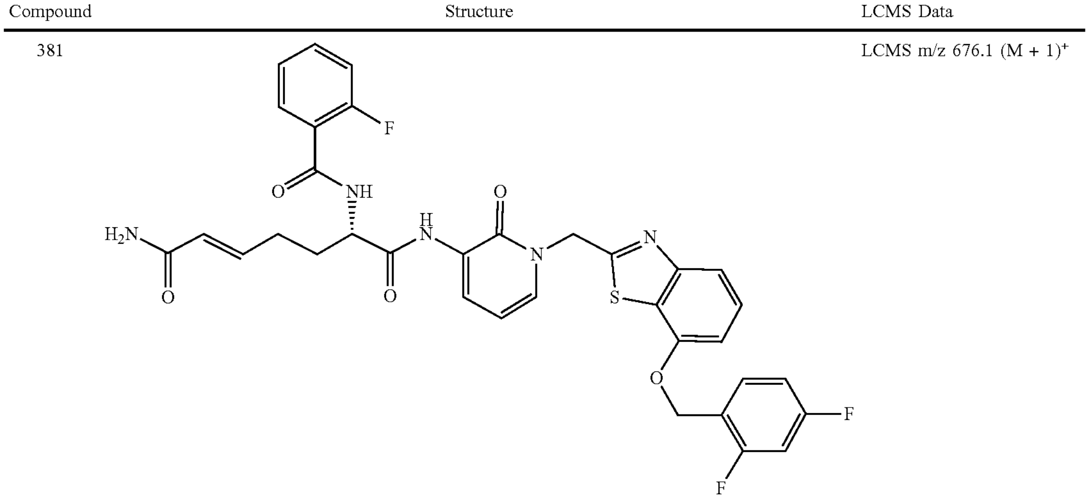 | LCMS m/z 676.1 (M + 1)$^+$ |
Example 53
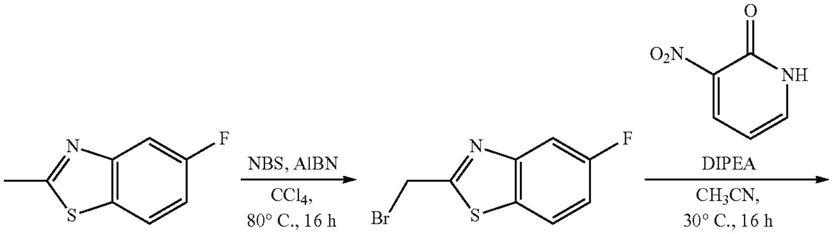
I-478 I-479
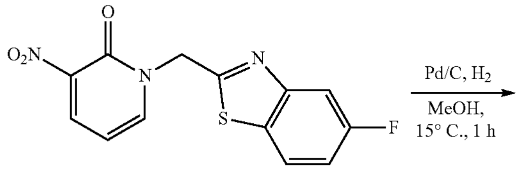
I-480
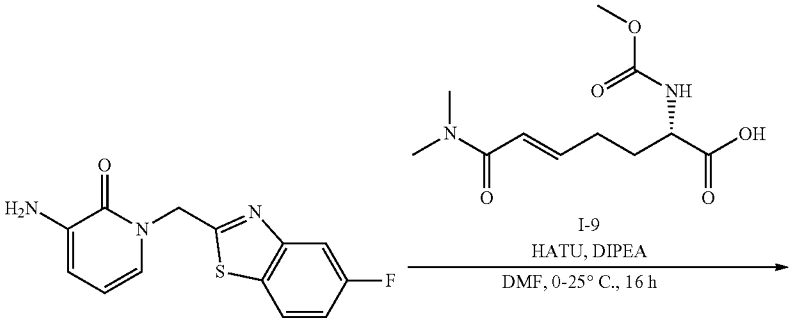
I-9
I-481

-continued

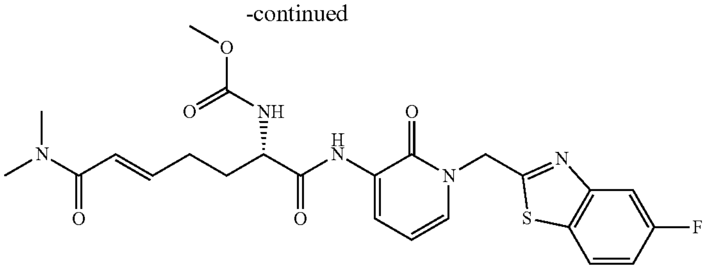

382

A mixture of 5-fluoro-2-methylbenzo[d]thiazole (1 g, 5.98 mmol), NBS (958 mg, 5.38 mmol), AIBN (250 mg, 1.52 mmol) in $CCl_4$ (25 mL) was degassed and purged with $N_2$ for 3 times, and then the mixture was stirred at 80° C. for 16 h under $N_2$ atmosphere. The reaction mixture was filtered and concentrated in vacuum. The residue was purified by column chromatography and prep-TLC to give 2-(bromomethyl)-5-fluorobenzo[d]thiazole (I-479) (0.24 g, 0.917 mmol, 15% yield) as a yellow solid. $^1H$ NMR (400 MHz, $CDCl_3$) δ 7.83-7.79 (m, 1H), 7.70 (dd, J=9.2, 2.0 Hz, 1H), 7.23-7.18 (m, 1H), 4.79 (s, 2H).

To a solution of 2-(bromomethyl)-5-fluorobenzo[d]thiazole (240 mg, 0.917 mmol) and 3-nitro-1H-pyridin-2-one (193 mg, 1.38 mmol) in $CH_3CN$ (5 mL) was added DIPEA (237 mg, 1.83 mmol). The mixture was stirred at 25° C. for 16 hours. The reaction was concentrated in vacuum to give a residue. The residue was purified by column chromatography to give 1-((5-fluorobenzo[d]thiazol-2-yl)methyl)-3-nitropyridin-2(1H)-one (I-480) (240 mg) as a yellow solid. $^1H$ NMR (400 MHz, $CDCl_3$) δ8.38 (dd, J=7.6, 2.0 Hz, 1H), 7.98 (dd, J=6.8, 1.6 Hz, 1H), 7.83-7.79 (m, 1H), 7.67 (dd, J=9.2, 2.4 Hz, 1H), 7.24-7.18 (m, 1H), 6.40 (t, J=7.2 Hz, 1H), 5.59 (s, 2H).

To a solution of 1-((5-fluorobenzo[d]thiazol-2-yl)methyl)-3-nitropyridin-2(1H)-one (240 mg, 0.786 mmol) in MeOH (50 mL) was added wet Pd/C (100 mg, 10% purity). The suspension was degassed under vacuum and purged with $H_2$ for 3 times. The mixture was stirred under $H_2$ (15 psi) at 15° C. for 0.5 h. The resulting suspension was filtered and the filtrate was concentrated in vacuum to give 3-amino-1-((5-fluorobenzo[d]thiazol-2-yl)methyl)pyridin-2(1H)-one (I-481) (160 mg) as a yellow solid. LCMS m/z 276.0 $(M+1)^+$.

To a solution of 3-amino-1-((5-fluorobenzo[d]thiazol-2-yl)methyl)pyridin-2(1H)-one (100 mg, 0.363 mmol) and (S,E)-7-(dimethylamino)-2-((methoxycarbonyl)amino)-7-oxohept-5-enoic acid (113 mg, 0.436 mmol) in DMF (5 mL) were added HATU (276 mg, 0.726 mmol) and DIPEA (141 mg, 1.09 mmol) at 0° C. The mixture was stirred at 25° C. for 16 h. The reaction mixture was concentrated in vacuum to give a residue. The residue was purified by prep-HPLC to give (S,E)-methyl(7-(dimethylamino)-1-((1-((5-fluorobenzo[d]thiazol-2-yl)methyl)-2-oxo-1,2-dihydropyridin-3-yl)amino)-1,7-dioxohept-5-en-2-yl)carbamate (Compound 382) (133.8 mg, 70% yield) as a yellow solid. LCMS m/z 516.1 $(M+1)^+$. $^1H$ NMR (400 MHz, DMSO-$d_6$) δ9.34 (s, 1H), 8.28 (dd, J=7.2, 1.2 Hz, 1H), 8.12 (dd, J=8.8, 5.2 Hz, 1H), 7.84 (dd, J=9.6, 2.4 Hz, 1H), 7.73 (d, J=7.6 Hz, 1H), 7.64 (dd, J=7.2, 2.0 Hz, 1H), 7.38-7.33 (m, 1H), 6.67-6.52 (m, 1H), 6.45-6.30 (m, 2H), 5.69-5.54 (m, 2H), 4.26-4.15 (m, 1H), 3.54 (s, 3H), 2.99 (s, 3H), 2.83 (s, 3H), 2.30-2.10 (m, 2H), 1.94-1.61 (m, 2H).

The following compounds were prepared according to the procedures described for Example 53 using the appropriate reagents.

| Compound | Structure | LCMS Data |
| --- | --- | --- |
| 383 | 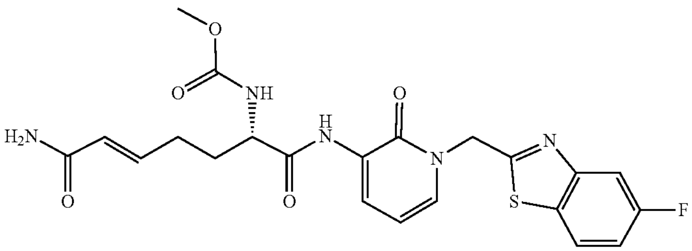 [SMILES: COC(=O)N[C@@H](CC/C=C/C(N)=O)C(=O)Nc1cccn(Cc2nc3cc(F)ccc3s2)c1=O] | LCMS m/z 488.1 $(M + 1)^+$ |
| 384 | 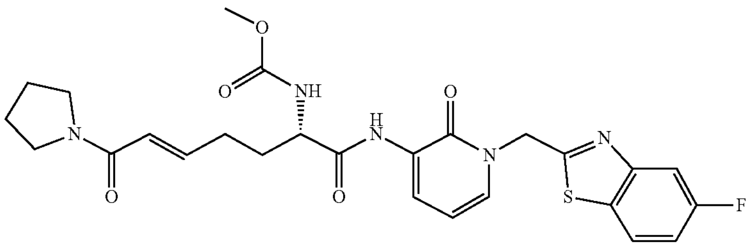 [SMILES: COC(=O)N[C@@H](CC/C=C/C(=O)N1CCCC1)C(=O)Nc1cccn(Cc2nc3cc(F)ccc3s2)c1=O] | LCMS m/z 542.1 $(M + 1)^+$ |

The Synthesis of Intermediate I-495
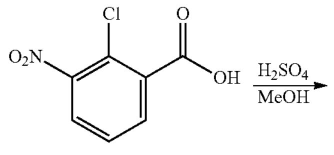
I-482
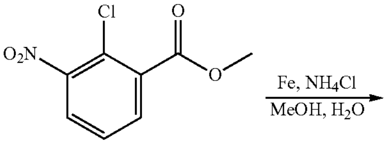
I-483
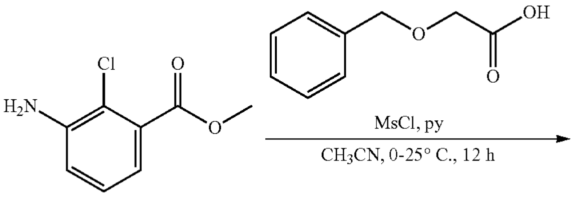
I-484
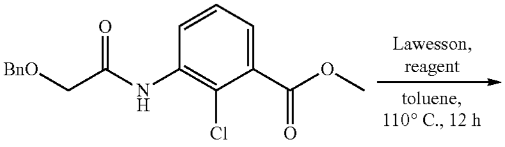
I-485
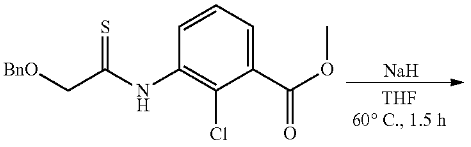
I-486
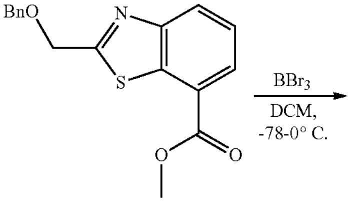
I-487
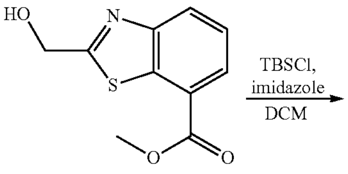
I-488
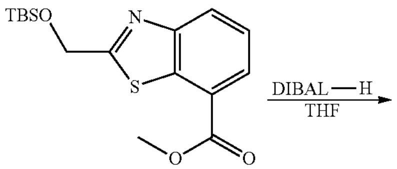
I-489
-continued
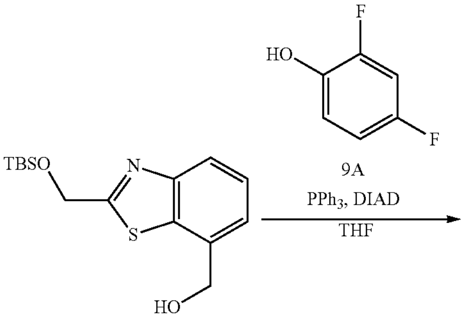
I-490
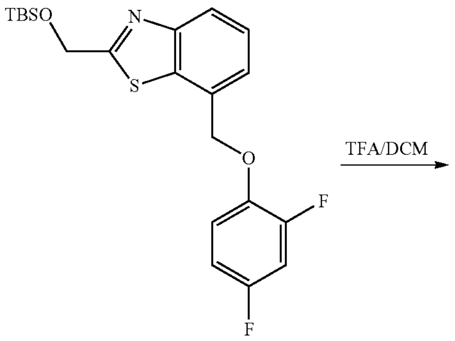
I-491
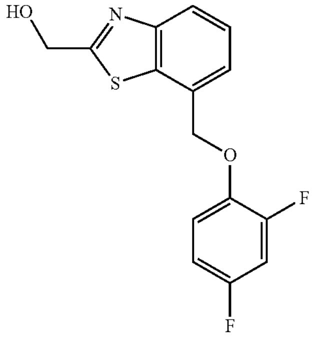
I-492
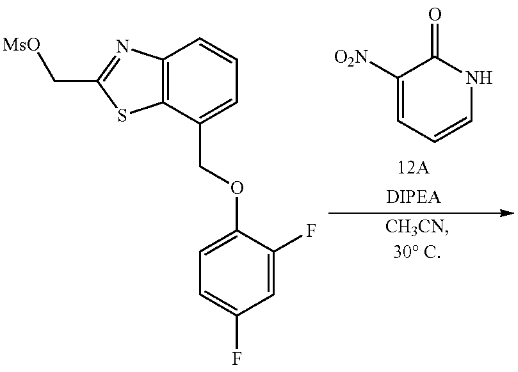
I-493

-continued

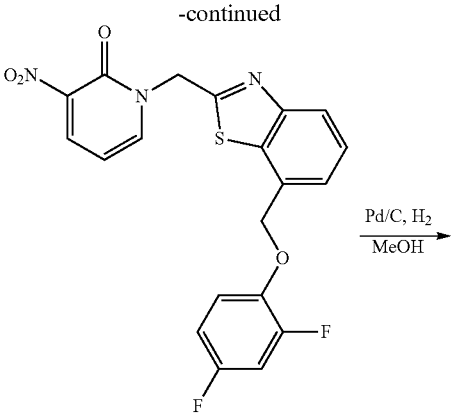

I-494

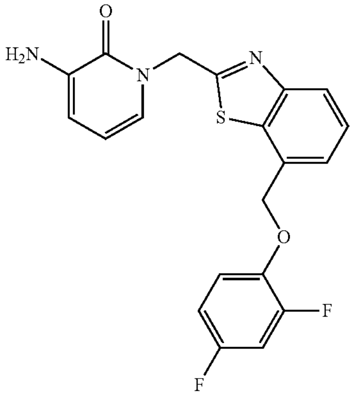

I-495

To a solution of 2-chloro-3-nitrobenzoic acid (25.0 g, 124 mmol) in MeOH (200 mL) was added $H_2SO_4$ (9.20 g, 93.8 mmol). The mixture was stirred at 60° C. for 12 hours. The reaction mixture was concentrated and diluted with EtOAc (100 mL), washed with saturated $NaHCO_3$ (150 mL). The organic phase was concentrated to give a residue. The residue was purified by MPLC to give methyl 2-chloro-3-nitrobenzoate (I-483) (25.0 g) as a white solid.

To a solution of methyl 2-chloro-3-nitrobenzoate (23.0 g, 107 mmol) in MeOH (100 mL) and $H_2O$ (20 mL) were added Fe (29.8 g, 533 mmol) and $NH_4Cl$ (45.7 g, 853 mmol). The mixture was stirred at 80° C. for 2 hours. The mixture was filtered out and the filtrate was concentrated to give a residue. The residue was purified by silica gel chromatography to give methyl 3-amino-2-chlorobenzoate (I-484) (19.0 g) as a yellow oil.

To a solution of 2-benzyloxyacetic acid (18.7 g, 113 mmol) and methyl 3-amino-2-chlorobenzoate (19.0 g, 102 mmol) in $CH_3CN$ (100 mL) were added pyridine (32.4 g, 409 mmol) and MsCl (18.4 g, 161 mmol). The mixture was stirred at 15° C. for 12 hours. The reaction mixture was concentrated to give a residue. The residue was purified by silica gel chromatography to give methyl 3-(2-(benzyloxy)acetamido)-2-chlorobenzoate (I-485) (30.0 g) as a yellow oil.

To a solution of methyl 3-(2-(benzyloxy)acetamido)-2-chlorobenzoate (2.00 g, 5.99 mmol) in toluene (20 mL) was added Lawesson's reagent (2.42 g, 5.99 mmol). The mixture was stirred at 110° C. for 12 hours. The mixture was concentrated in vacuum to give a residue. The residue was purified by silica gel chromatography to give methyl 3-(2-(benzyloxy)ethanethioamido)-2-chlorobenzoate (I-486) as a yellow solid.

To a solution of methyl 3-[(2-benzyloxyethanethioyl)amino]-2-chloro-benzoate (7.5 g, 21.4 mmol) in THF (30 mL) was added NaH (1.1 g, 27.5 mmol, 60% purity) at 0° C. The mixture was stirred at 60° C. for 1 hr. The reaction mixture was quenched with water (100 mL) and extracted with ethyl acetate (120 mL×2). The combined organic layers were dried over anhydrous $Na_2SO_4$, filtrated and concentrated to give a residue. The residue was purified by column chromatography to give methyl 2-((benzyloxy)methyl)benzo[d]thiazole-7-carboxylate (I-487) (2.5 g) as a yellow solid.

To a solution of methyl 2-((benzyloxy)methyl)benzo[d]thiazole-7-carboxylate (3.5 g, 11.1 mmol) in DCM (20 mL) was added $BBr_3$ (5.6 g, 22.3 mmol). The mixture was stirred at −70° C. for 1 hr. The reaction mixture was quenched with water (100 mL) followed by a saturated $NaHCO_3$ (80 mL). The mixture was extracted with ethyl acetate (100 mL×2). The combined organic layers were dried over anhydrous $Na_2SO_4$, filtrated and concentrated to give a residue. The residue was purified by column chromatography to give methyl 2-(hydroxymethyl)-1,3-benzothiazole-7-carboxylate (I-488) (2.0 g) as a yellow solid.

To a mixture of methyl 2-(hydroxymethyl)-1,3-benzothiazole-7-carboxylate (2.0 g, 8.9 mmol) in DCM (30 mL) were added imidazole (731 mg, 10.7 mmol) and TBS-Cl (1.6 g, 10.7 mmol). The mixture was stirred at 20° C. for 1 hr. The reaction mixture was quenched with water (100 mL) and extracted with DCM (100 mL×2). The combined organic layers were dried over anhydrous $Na_2SO_4$, filtered and concentrated under reduced pressure to give a residue. The residue was purified by column chromatography to afford methyl 2-(((tert-butyldimethylsilyl)oxy)methyl)benzo[d]thiazole-7-carboxylate (I-489) (2.4 g) as a yellow oil.

To a solution of methyl 2-(((tert-butyldimethylsilyl)oxy)methyl)benzo[d]thiazole-7-carboxylate (1.0 g, 2.9 mmol) in THF (3.0 mL) was added DIBAL-H (1 M, 5.9 mL) at −70° C. The mixture was stirred at 20° C. for 0.5 hr. The reaction mixture was quenched with saturated $NH_4Cl$ (80 mL) and sodium potassium tartrate tetrahydrate (80 mL). The mixture was stirred at 20° C. for 0.5 h. The reaction mixture was extracted with ethyl acetate (100 mL×2). The combined organic layers were dried over anhydrous $Na_2SO_4$, filtered and concentrated under reduced pressure to give a residue. The residue was purified by column chromatography to give (2-(((tert-butyldimethylsilyl)oxy)methyl)benzo[d]thiazol-7-yl)methanol (I-490) (500 mg) as a yellow oil.

To a solution of (2-(((tert-butyldimethylsilyl)oxy)methyl)benzo[d]thiazol-7-yl)methanol (400 mg, 1.3 mmol) and 2,4-difluorophenol (201 mg, 1.6 mmol) in THF (10 mL) was added $PPh_3$ (406 mg, 1.6 mmol) at 0° C. followed by DIAD (313 mg, 1.6 mmol). The mixture was stirred at 0-20° C. for 1 hr. The resulting solution was concentrated to give a residue. The residue was purified by column chromatography to give 2-(((tert-butyldimethylsilyl)oxy)methyl)-7-((2,4-difluorophenoxy)methyl)benzo[d]thiazole (I-491) (400 mg) as a yellow oil.

To a solution of 2-(((tert-butyldimethylsilyl)oxy)methyl)-7-((2,4-difluorophenoxy) methyl)benzo[d]thiazole (440 mg, 1.0 mmol) in DCM (2.0 mL) was added TFA (3.0 mL). The mixture was stirred at 20° C. for 10 h. The reaction mixture was concentrated to give (7-((2,4-difluorophenoxy)methyl)benzo[d]thiazol-2-yl)methanol (I-492) (319 mg) as a yellow oil. LCMS m/z 308.0 $(M+1)^+$.

To a mixture of (7-((2,4-difluorophenoxy)methyl)benzo[d]thiazol-2-yl)methanol (340 mg, 1.1 mmol) in DCM (10.0 mL) were added MsCl (253 mg, 2.2 mmol) and DIPEA (286 mg, 2.2 mmol) in one portion at 0° C. under $N_2$ atmosphere. The mixture was stirred at 0-30° C. for 2 hours. The reaction mixture was poured into water (100 mL). The resulting solution was extracted with ethyl acetate (80 mL×2). The combined organic layers were dried over anhydrous $Na_2SO_4$, filtered and concentrated in vacuum to afford (7-((2,4-difluorophenoxy)methyl)benzo[d]thiazol-2-yl) methyl methanesulfonate (I-493) (420 mg) as a yellow oil.

To a mixture of (7-((2,4-difluorophenoxy)methyl)benzo [d]thiazol-2-yl)methyl methanesulfonate (100 mg, 306 µmol) and 3-nitro-1H-pyridin-2-one (64 mg, 460 µmol) in DMF (1.0 mL) was added DIPEA (79 mg, 614 µmol) in one portion at 30° C. The mixture was stirred at 70° C. for 10 h. The reaction mixture was quenched with addition water (80 mL) and extracted with ethyl acetate (80 mL×2). The combined organic layers were dried over anhydrous $Na_2SO_4$, filtered and concentrated under reduced pressure to give a residue. The residue was purified by prep-TLC to give 1-((7-((2,4-difluorophenoxy)methyl) benzo[d]thiazol-2-yl) methyl)-3-nitropyridin-2(1H)-one (I-494) (120 mg, 271 µmol) as a yellow oil. LCMS m/z 430.0 $(M+1)^+$.

To a solution of 1-((7-((2,4-difluorophenoxy)methyl) benzo[d]thiazol-2-yl)methyl)-3-nitropyridin-2(1H)-one (80 mg, 186 µmol) in MeOH (10 mL) was added Pd/C (30 mg, 10% wet). The mixture was stirred at 20° C. for 1 hr under $H_2$ atmosphere (15 psi). After filtration, the filtrate was concentrated to give 3-amino-1-[[7-[(2,4-difluorophenoxy) methyl]-1,3-benzothiazol-2-yl] methyl]pyridin-2-one (I-495) (70 mg) as a yellow solid. LCMS m/z 400.0 $(M+1)^+$.

Example 54

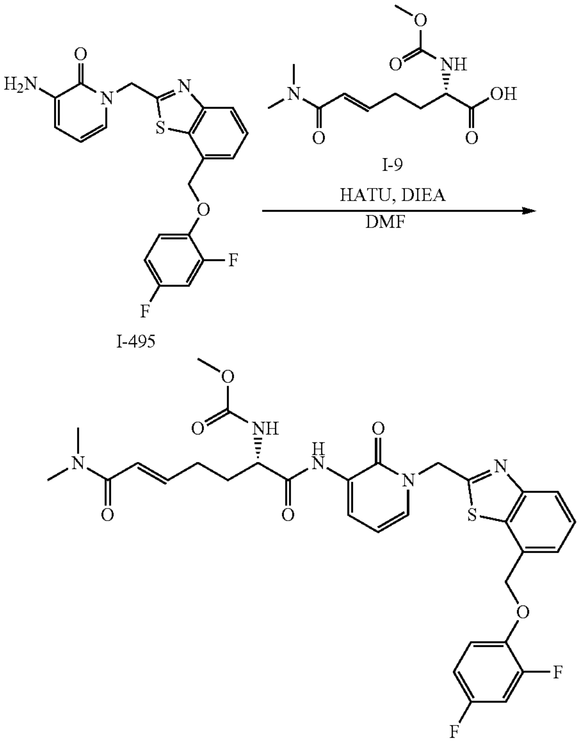

I-495
I-9
385

To a solution of 3-amino-1-((7-((2,4-difluorophenoxy) methyl)benzo[d]thiazol-2-yl)methyl)pyridin-2(1H)-one (70 mg, 175 µmol) and (S,E)-7-(dimethylamino)-2-((methoxy-carbonyl)amino)-7-oxohept-5-enoic acid (68 mg, 263 µmol) in DMF (1.0 mL) were added HATU (100 mg, 263 µmol) and DIPEA (68 mg, 525 µmol). The mixture was stirred at 0-20° C. for 10 h. The filtrate was purified by prep-HPLC to give methyl (S,E)-methyl (1-((1-((7-((2,4-difluorophenoxy) methyl)benzo[d]thiazol-2-yl)methyl)-2-oxo-1,2-dihydro-pyridin-3-yl)amino)-7-(dimethylamino)-1,7-dioxohept-5-en-2-yl)carbamate (Compound 385) (35 mg, 53 µmol) as a white solid. LCMS m/z 640.2 $(M+1)^+$. $^1H$ NMR (400 MHz, DMSO-$d_6$) δ9.34 (s, 1H), 8.28 (dd, J=7.2, 1.6 Hz, 1H), 7.98 (dd, J=6.8, 2.4 Hz, 1H), 7.76-7.71 (m, 1H), 7.65 (dd, J=7.2, 1.6 Hz, 1H), 7.59-7.51 (m, 2H), 7.35-7.25 (m, 2H), 7.04-6.96 (m, 1H), 6.69-6.56 (m, 1H), 6.43-6.31 (m, 2H), 5.70-5.57 (m, 2H), 5.43 (s, 2H), 4.26-4.15 (m, 1H), 3.54 (s, 3H), 2.98 (s, 3H), 2.83 (s, 3H), 2.30-2.16 (m, 2H), 1.91-1.83 (m, 1H), 1.76-1.65 (m, 1H).

The Synthesis of Intermediate I-500

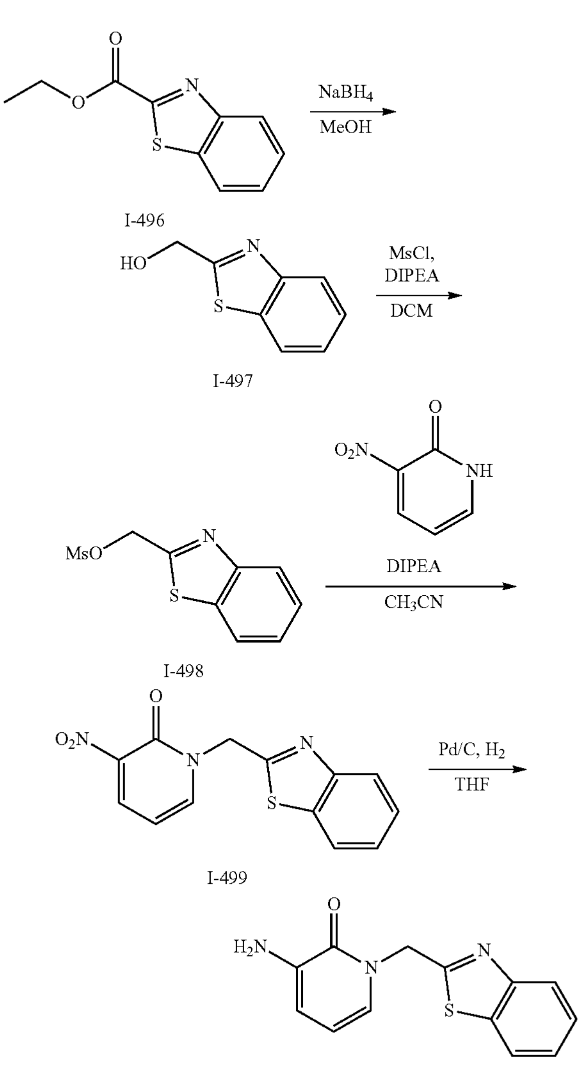

I-496
I-497
I-498
I-499
I-500

To a solution of ethyl benzo[d]thiazole-2-carboxylate (2.5 g, 12.1 mmol) in MeOH (10 mL) was added $NaBH_4$ (1.0 g, 26.5 mmol). The mixture was stirred at 25° C. for 2 h. The mixture was concentrated to give a residue. The pH of the residue was adjusted to 4-5 with HCl (1M) and the resultant was extracted with EtOAc (20 mL×2). The combined organic layers were washed with brine (20 mL) and concentrated to give a residue. The residue was purified by column chromatography to give benzo[d]thiazol-2-ylmethanol (I-497) (2.0 g) as a white solid. LCMS m/z 166.0 $(M+1)^+$.

To a solution of benzo[d]thiazol-2-ylmethanol (2.0 g, 12.1 mmol) in DCM (20 mL) was added DIPEA (3.91 g, 30.3 mmol) and MsCl (2.77 g, 24.2 mmol) at 0° C. The mixture was stirred at 20° C. for 12 h. The resulting solution was poured into water (30 mL) and extracted with DCM (30 mL×2). The combined organic layers were washed with brine (20 mL), dried over anhydrous $Na_2SO_4$, filtered and concentrated to give benzo[d]thiazol-2-ylmethyl methanesulfonate (I-498) (3.0 g) as a brown oil. LCMS m/z 244 $(M+1)^+$.

To a solution of benzo[d]thiazol-2-ylmethyl methanesulfonate (3.0 g, 12.3 mmol) and 3-nitropyridin-2(1H)-one (2.25 g, 16.0 mmol) in $CH_3CN$ (20 mL) was added DIPEA (4.78 g, 37.0 mmol). The mixture was stirred at 30° C. for 12 h. The mixture was concentrated to give a residue. The residue was purified by column chromatography to give 1-(benzo[d]thiazol-2-ylmethyl)-3-nitropyridin-2(1H)-one (I-499) (2.0 g) as a brown solid. LCMS m/z 287.9 $(M+1)^+$.

To a solution of 1-(benzo[d]thiazol-2-ylmethyl)-3-nitropyridin-2(1H)-one (2.0 g, 6.96 mmol) in MeOH (30 mL) was added Pd/C (10%, 300 mg) under $N_2$ atmosphere. The suspension was degassed and purged with $H_2$ for 3 times.

The mixture was stirred under $H_2$ (15 psi) atmosphere at 20° C. for 0.5 h. The resulting suspension was filtered off and the filtrate was concentrated to give a residue. The residue was purified by prep-HPLC to give 3-amino-1-(benzo[d]thiazol-2-ylmethyl)pyridin-2(1H)-one (I-500) (300 mg) as a brown solid. LCMS m/z 258.1 $(M+1)^+$.

The following intermediates were prepared according to the procedures described for the synthesis of I-500 using the appropriate reagents.

| Compound | Structure | LCMS Data |
|---|---|---|
| I-501 | 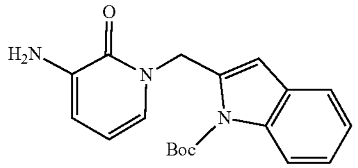 [SMILES: CC(C)(C)OC(=O)n1c(Cn2cccc(N)c2=O)cc2ccccc21] | LCMS m/z 340.1 $(M+1)^+$ |
| I-502 | 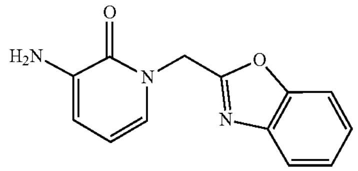 [SMILES: Nc1cccn(Cc2nc3ccccc3o2)c1=O] | LCMS m/z 242.1 $(M+1)^+$ |

Example 55

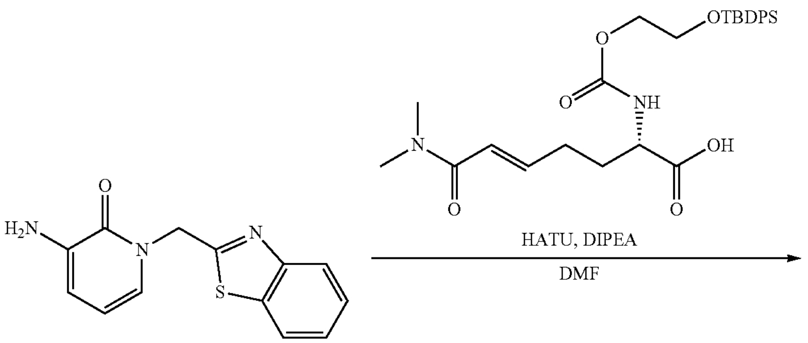

I-500

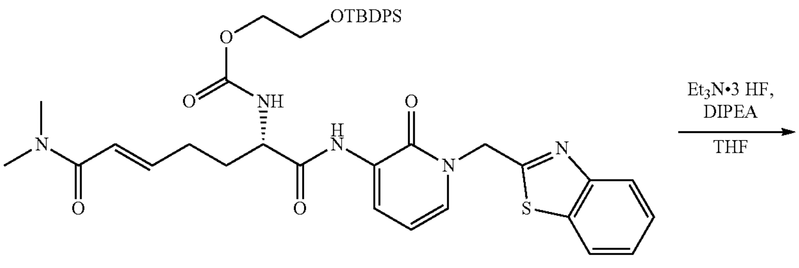

I-503

-continued

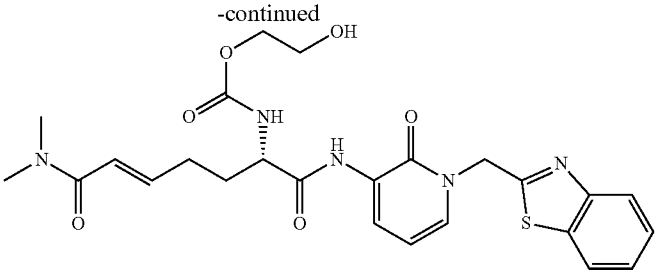

386

To a solution of 3-amino-1-(benzo[d]thiazol-2-ylmethyl) pyridin-2(1H)-one (65 mg, 253 μmol) and (S,E)-10-(5-(dimethylamino)-5-oxopent-3-en-1-yl)-2,2-dimethyl-8-oxo-3,3-diphenyl-4,7-dioxa-9-aza-3-silaundecan-11-oic acid (133 mg, 253 μmol) in DMF (0.5 mL) were added HATU (144 mg, 379 μmol) and DIPEA (97.9 mg, 759 μmol) at 0° C. The mixture was stirred at 20° C. for 12 h. The resulting solution was diluted with EtOAc (30 mL) and washed with brine (10 mL×4). The organic phase was concentrated to give a residue. The residue was purified by prep-TLC to give (S,E)-2-((tert-butyldiphenylsilyl)oxy) ethyl (1-((1-(benzo[d] thiazol-2-ylmethyl)-2-oxo-1,2-dihydropyridin-3-yl)amino)-7-(dimethylamino)-1,7-dioxohept-5-en-2-yl)carbamate (I-503) (90 mg) as a yellow solid. LCMS m/z 766.3 $(M+1)^+$.

To a solution of (S,E)-2-((tert-butyldiphenylsilyl)oxy) ethyl (1-((1-(benzo[d]thiazol-2-ylmethyl)-2-oxo-1,2-dihydropyridin-3-yl)amino)-7-(dimethylamino)-1,7-dioxohept-5-en-2-yl)carbamate (85 mg, 111 μmol) in THF (5 mL) were added $Et_3N{\cdot}3HF$ (107 mg, 666 μmol) and $Et_3N$ (28 mg, 277 μmol). The mixture was stirred at 25° C. for 2 h. The mixture (combined with another 5 mg batch) was concentrated to give a residue. The residue was purified by prep-HPLC to give (S,E)-2-hydroxyethyl (1-((1-(benzo[d]thiazol-2-ylmethyl)-2-oxo-1,2-dihydropyridin-3-yl)amino)-7-(dimethylamino)-1,7-dioxohept-5-en-2-yl)carbamate (Compound 386) (28.4 mg, 48% yield) as a white solid. LCMS m/z 528.0 $(M+1)^+$. $^1H$ NMR (400 MHz, DMSO-$d_6$) δ9.34 (s, 1H), 8.28 (dd, J=7.6, 1.6 Hz, 1H), 8.06 (d, J=7.6 Hz, 1H), 7.97 (d, J=8.0 Hz, 1H), 7.65 (d, J=7.6 Hz, 1H), 7.64 (dd, J=6.8, 1.6 Hz, 1H), 7.52-7.48 (m, 1H), 7.45-7.42 (m, 1H), 6.65-6.58 (m, 1H), 6.41-6.36 (m, 2H), 5.67-5.58 (m, 2H), 4.76-4.74 (m, 1H), 4.23-4.18 (m, 1H), 4.03-3.93 (m, 2H), 3.56-3.54 (m, 2H), 2.98 (s, 3H), 2.83 (m, 3H), 2.33-2.19 (m, 2H), 1.88-1.68 (m, 2H).

The following compounds were prepared according to the procedures described in Example 55 using the appropriate intermediates.

| Compound | Structure | LCMS Data |
|---|---|---|
| 387 | 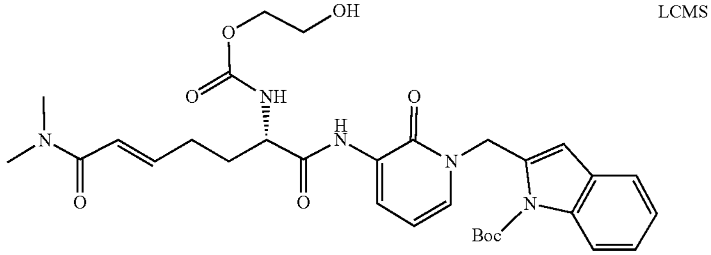 | LCMS m/z 610.1 $(M + 1)^+$ |
| 388 | 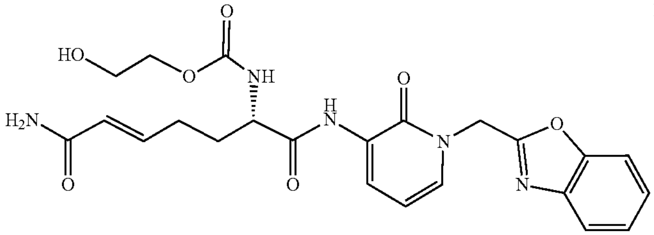 [SMILES: NC(=O)/C=C/CC[C@H](NC(=O)OCCO)C(=O)Nc1cccn(Cc2nc3ccccc3o2)c1=O] | LCMS m/z 484.1 $(M + 1)^+$ |
| 389 | 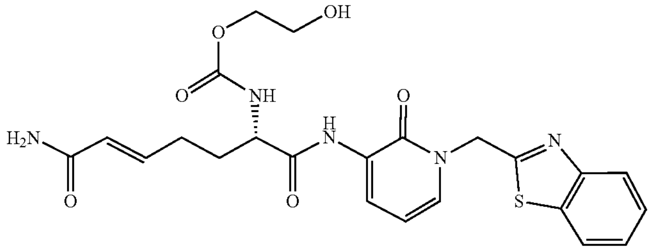 [SMILES: NC(=O)/C=C/CC[C@H](NC(=O)OCCO)C(=O)Nc1cccn(Cc2nc3ccccc3s2)c1=O] | LCMS m/z 500.1 $(M + 1)^+$ |

-continued
| Compound | Structure | LCMS Data |
|---|---|---|
| 390 | 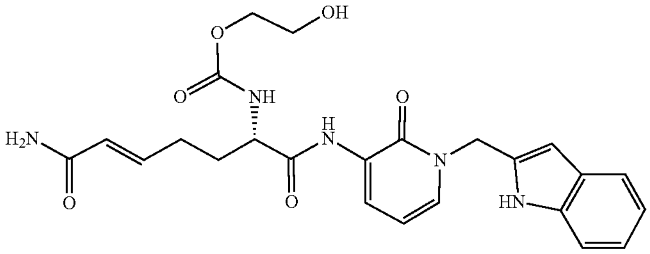 [SMILES: NC(=O)/C=C/CC[C@H](NC(=O)OCCO)C(=O)Nc1cccn(Cc2cc3ccccc3[nH]2)c1=O] | LCMS m/z 482.3 (M + 1)$^+$ |
| 391 | 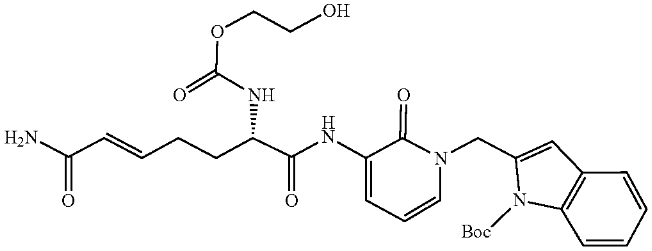 [SMILES: CC(C)(C)OC(=O)n1c(Cn2cccc(NC(=O)[C@H](CC/C=C/C(N)=O)NC(=O)OCCO)c2=O)cc2ccccc21] | LCMS m/z 582.3 (M + 1)$^+$ |
The Synthesis of Intermediate I-516
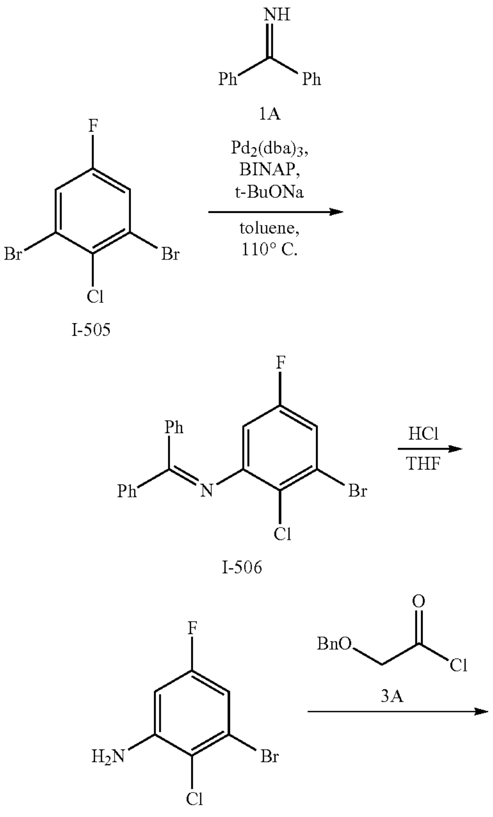
I-505
I-506
I-507
-continued
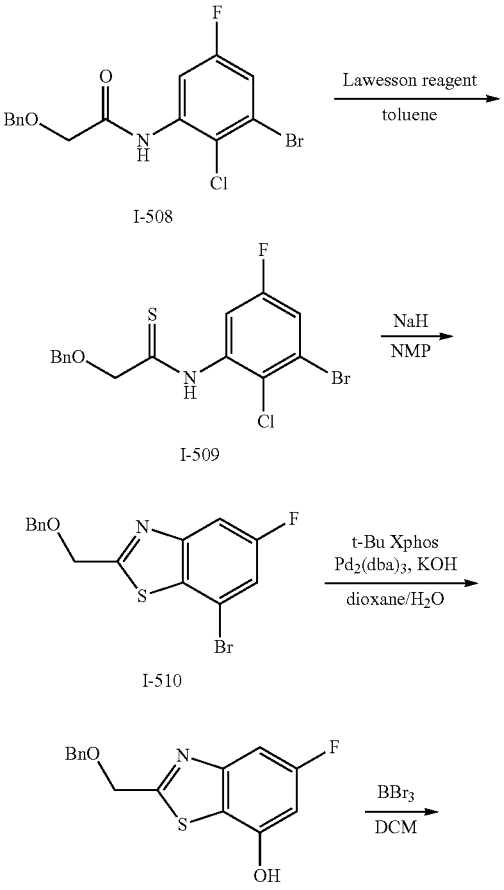
I-508
I-509
I-510
I-511

-continued

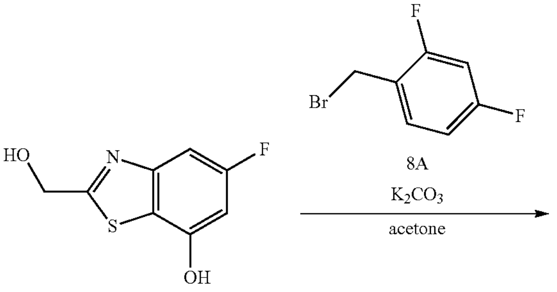

I-512

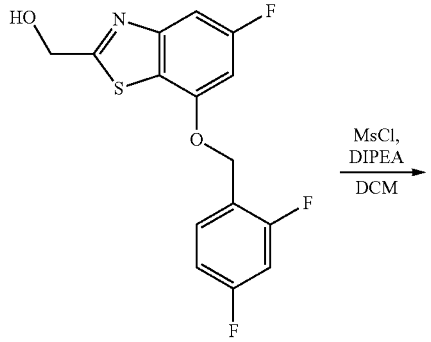

I-513

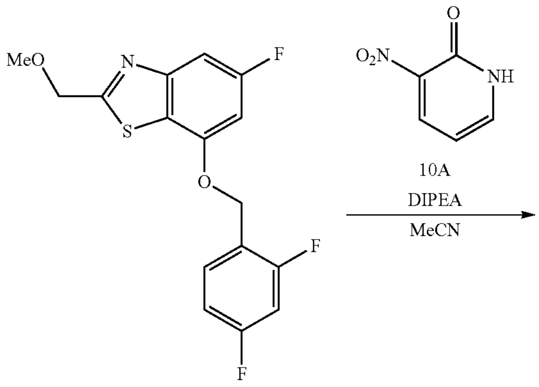

I-514

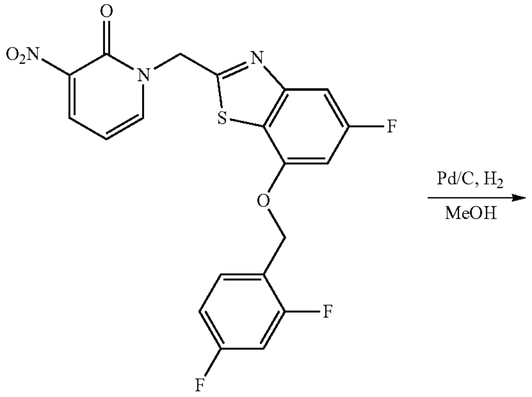

I-515

-continued

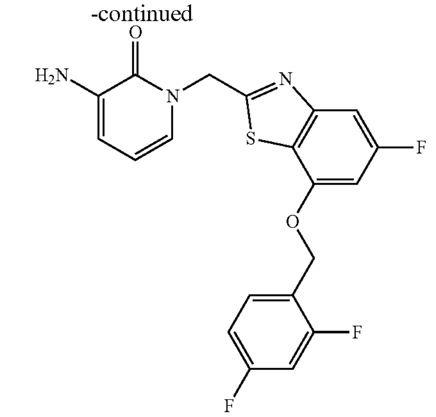

I-516

To a solution of 1,3-dibromo-2-chloro-5-fluoro-benzene (20 g, 69.4 mmol) and diphenylmethanimine (11.3 g, 62.4 mmol, 10.5 mL) in toluene (200 mL) were added t-BuONa (13 g, 135 mmol), $Pd_2(dba)_3$ (3.18 g, 3.47 mmol) and BINAP (3.46 g, 5.55 mmol). The mixture was stirred at 100° C. for 2 hours. The resulting suspension was filtered and the filtrate was concentrated to give a residue. The residue was purified by column chromatography to afford 3-bromo-2-chloro-N-(diphenylmethylene)-5-fluoroaniline (I-506) (10 g, 13.9 mmol) as a yellow solid. LCMS m/z 389.9 $(M+1)^+$.

To a solution of 3-bromo-2-chloro-N-(diphenylmethylene)-5-fluoroaniline (10 g, 13.9 mmol) in THF (100 mL) was added HCl (3 M, 20 mL). The mixture was stirred at 30° C. for 1 hour. Saturated $Na_2CO_3$ was added to adjust pH~8. The resulting solution was extracted with ethyl acetate (100 mL×2), washed with brine (100 mL), dried over anhydrous $Na_2SO_4$, filtered and concentrated to give a residue. The residue was purified by column chromatography to afford 3-bromo-2-chloro-5-fluoroaniline (I-507) (7.6 g) as a yellow oil.

To a solution of 2-benzyloxyacetic acid (2.9 g, 17.5 mmol, 2.5 mL), 3-bromo-2-chloro-5-fluoroaniline (7.60 g, 14.6 mmol) and pyridine (5.88 g, 74.3 mmol, 6 mL) in MeCN (50 mL) was added MsCl (2 g, 17.5 mmol, 1.35 mL) at 0-10° C. The mixture was stirred at 30° C. for 12 hours. The resulting solution was diluted with ethyl acetate (50 mL), washed with HCl (30 mL×2, 1M) and brine (50 mL). The organic layer was dried over anhydrous $Na_2SO_4$, filtered and concentrated to give a residue. The residue was purified by column chromatography to afford 2-(benzyloxy)-N-(3-bromo-2-chloro-5-fluorophenyl) acetamide (I-508) (4.5 g, 66.4% yield) as a colorless solid.

To a solution of 2-(benzyloxy)-N-(3-bromo-2-chloro-5-fluorophenyl)acetamide (1 g, 2.68 mmol) in Tol. (10 mL) was added Lawesson's reagent (976 mg, 2.41 mmol). The mixture was stirred at 110° C. for 12 hours. The resulting solution was concentrated in vacuum to give a residue. The residue was purified by silica gel chromatography to afford 2-(benzyloxy)-N-(3-bromo-2-chloro-5-fluorophenyl)ethanethioamide (I-509) (670 mg) as a yellow solid. $^1H$ NMR (400 MHz, $CDCl_3$) δ10.63 (br s, 1H), 9.10 (dd, J=10.8, 3.2 Hz, 1H), 7.44-7.34 (m, 5H), 7.31 (dd, J=7.2, 2.8 Hz, 1H), 4.73 (s, 2H), 4.50 (s, 2H).

To a mixture of 2-(benzyloxy)-N-(3-bromo-2-chloro-5-fluorophenyl)ethanethioamide (7.2 g, 18.5 mmol) in NMP (60 mL) was NaH (963 mg, 24.1 mmol, 60% purity). The mixture was stirred at 130° C. for 3 hours under $N_2$ atmosphere. The mixture was quenched with water (60 mL)

and extracted with ethyl acetate (50 mL×3). The combined organic layers were washed with brine (100 mL×3), dried over anhydrous $Na_2SO_4$, filtered and concentrated in vacuum. The residue was purified by silica gel chromatography to afford 2-((benzyoxy) methyl)-7-bromo-5-fluorobenzo[d]thiazole (I-510) (2.9 g) as a yellow solid. $^1H$ NMR (400 MHz, $CDCl_3$) δ 7.63 (dd, J=10.4, 2.4 Hz, 1H), 7.45-7.33 (m, 6H), 4.92 (s, 2H), 4.75 (s, 2H).

To a mixture of 2-((benzyloxy)methyl)-7-bromo-5-fluorobenzo[d]thiazole (2.3 g, 6.53 mmol) in dioxane (10 mL) and $H_2O$ (10 mL) were added ditert-butyl-[2-(2,4,6-triisopropylphenyl)phenyl]phosphane (111 mg, 0.261 mmol), $Pd_2(dba)_3$ (120 mg, 0.131 mmol) and KOH (1.1 g, 19.6 mmol). The mixture was stirred at 100° C. for 12 h under $N_2$ atmosphere. The mixture was diluted with HCl (5 mL, 2M) and $H_2O$ (15 mL) and extracted with ethyl acetate (20 mL×2). The combined organic layers were washed with brine (30 mL), dried over anhydrous $Na_2SO_4$, filtered and concentrated in vacuum. The residue was purified by silica gel chromatography to afford 2-((benzyloxy)methyl)-5-fluorobenzo[d]thiazol-7-ol (I-511) (730 mg) as a yellow solid. $^1H$ NMR (400 MHz, $CD_3OD$) δ 7.50-7.26 (m, 5H), 7.14 (dd, J=9.2, 2.0 Hz, 1H), 6.69-6.54 (m, 1H), 4.90 (s, 2H), 4.72 (s, 2H).

To a mixture of 2-((benzyloxy)methyl)-5-fluorobenzo[d]thiazol-7-ol (730 mg, 2.52 mmol) in DCM (10 mL) was added $BBr_3$ (2.21 g, 8.82 mmol, 0.850 mL) at −65° C. The mixture was stirred at −65° C. for 3 h under $N_2$ atmosphere. The mixture was quenched with saturated $NaHCO_3$ (20 mL) and stirred for 30 min. The mixture was washed with DCM (20 mL) and extracted with a solution of ethyl acetate and isopropanol (20 mL×2). The combined organic layers were dried over anhydrous $Na_2SO_4$, filtered and concentrated in vacuum to afford 5-fluoro-2-(hydroxymethyl) benzo[d]thiazol-7-ol (I-512) (380 mg) as a yellow solid. $^1H$ NMR (400 MHz, $CD_3OD$) δ 7.11 (dd, J=9.6, 2.4 Hz, 1H), 6.59 (dd, J=10.8, 2.4 Hz, 1H), 4.92 (s, 2H).

To a solution of 5-fluoro-2-(hydroxymethyl)benzo[d]thiazol-7-ol (356 mg, 1.72 mmol) in acetone (10 mL) was added $K_2CO_3$ (527 mg, 3.82 mmol). The mixture was stirred at 55° C. for 1 h under $N_2$ atmosphere. The mixture was diluted with water (30 mL) and extracted with ethyl acetate (20 mL×3). The combined organic layers were washed with brine (50 mL), dried over anhydrous $Na_2SO_4$, filtered and concentrated in vacuum to give a residue. The residue was purified by silica gel chromatography to afford (7-((2,4-difluorobenzyl)oxy)-5-fluorobenzo[d]thiazol-2-yl) methanol (I-513) (430 mg) as a white solid. $^1H$ NMR (400 MHz, $CD_3OD$) δ 7.65-7.52 (m, 1H), 7.27 (dd, J=9.2, 2.0 Hz, 1H), 7.11-6.90 (m, 3H), 5.32 (s, 2H), 4.92 (s, 2H).

To a mixture of (7-((2,4-difluorobenzyl)oxy)-5-fluorobenzo[d]thiazol-2-yl)methanol (430 mg, 1.32 mmol) and DIEA (341 mg, 2.64 mmol, 0.461 mL) in DCM (10 mL) was added MsCl (302 mg, 2.64 mmol, 0.204 mL) at 0° C. The mixture was stirred at 15° C. for 1 h. The mixture was diluted with water (20 mL) and extracted with DCM (20 mL×2). The combined organic layers were washed with brine (30 mL), dried over anhydrous $Na_2SO_4$, filtered and concentrated in vacuum to afford (7-((2,4-difluorobenzyl) oxy)-5-fluorobenzo[d]thiazol-2-yl) methyl methanesulfonate (I-514) (532 mg) as a yellow oil.

To a mixture of (7-((2,4-difluorobenzyl)oxy)-5-fluorobenzo[d]thiazol-2-yl)methyl methanesulfonate (532 mg, 1.32 mmol) and 3-nitropyridin-2(1H)-one (277 mg, 1.98 mmol) in $CH_3CN$ (10 mL) was added DIEA (341 mg, 2.64 mmol, 0.461 mL). The mixture was stirred at 30° C. for 12 h. The mixture was filtered, the filter cake was washed with ethyl acetate (10 mL×2) and concentrated in vacuum to afford 1-((7-((2,4-difluorobenzyl)oxy)-5-fluorobenzo[d]thiazol-2-yl)methyl)-3-nitropyridin-2(1H)-one (I-515) (320 mg) as a gray solid. $^1H$ NMR (400 MHz, DMSO-$d_6$) δ8.51 (dd, J=8.0, 2.0 Hz, 1H), 8.42 (dd, J=6.4, 2.0 Hz, 1H), 7.73-7.62 (m, 1H), 7.49 (dd, J=9.6, 2.0 Hz, 1H), 7.39-7.23 (m, 2H), 7.21-7.12 (m, 1H), 6.61-6.53 (m, 1H), 5.68 (s, 2H), 5.35 (s, 2H).

To a mixture of 1-((7-((2,4-difluorobenzyl)oxy)-5-fluorobenzo[d]thiazol-2-yl) methyl)-3-nitropyridin-2(1H)-one (320 mg, 0.715 mmol) in MeOH (10 mL) was added Pd/C (160 mg, 10% purity). The mixture was stirred at 30° C. for 1 h under $H_2$ atmosphere (15 psi). The resulting suspension was filtered, the filtrate was concentrated in vacuum to afford 3-amino-1-((7-((2,4-difluorobenzyl)oxy)-5-fluorobenzo[d]thiazol-2-yl)methyl)pyridin-2(1H)-one (I-516) (290 mg) as a white solid. $^1H$ NMR (400 MHz, DMSO-$d_6$) δ 7.70-7.59 (m, 1H), 7.48 (dd, J=9.6, 2.0 Hz, 1H), 7.37-7.28 (m, 1H), 7.27-7.20 (m, 1H), 7.19-7.11 (m, 1H), 7.09-7.03 (m, 1H), 6.52-6.45 (m, 1H), 6.13 (t, J=7.2 Hz, 1H), 5.49 (s, 2H), 5.33 (s, 2H), 5.22-5.12 (m, 1H).

Example 56

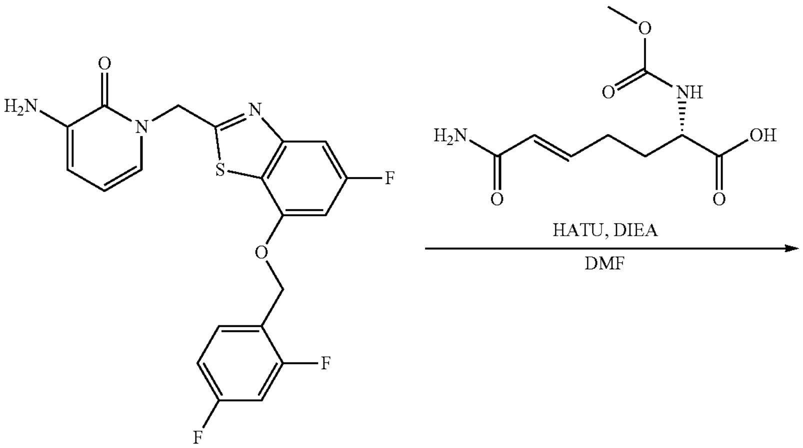

I-516

-continued

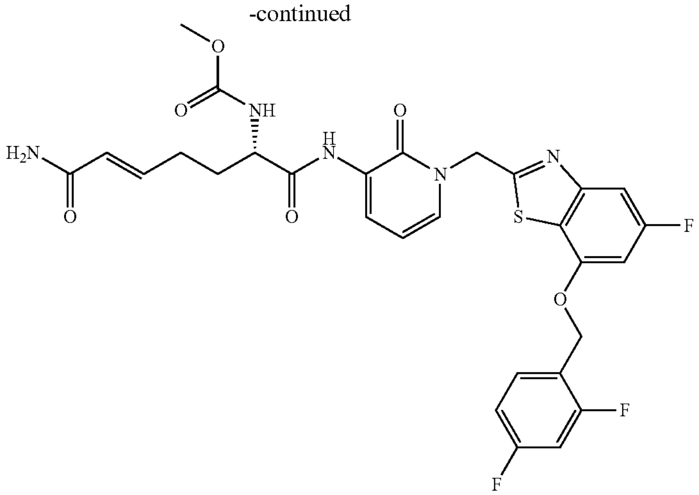

354

To a solution of 3-amino-1-((7-((2,4-difluorobenzyl)oxy)-5-fluorobenzo[d] thiazol-2-yl)methyl)pyridin-2(1H)-one (180 mg, 0.431 mmol) and (S,E)-7-amino-2-((methoxycarbonyl)amino)-7-oxohept-5-enoic acid (199 mg, 0.862 mmol) in DMF (2 mL) were added HATU (394 mg, 1.03 mmol) and DIEA (334 mg, 2.59 mmol, 0.452 mL) at 0° C. The mixture was stirred at 30° C. for 2 hours. The mixture was diluted with water (30 mL) and extracted with ethyl acetate (30 mL×3). The combined organic layers were washed with brine (80 mL×3), dried over anhydrous $Na_2SO_4$, filtered and concentrated in vacuum to give (S,E)-methyl (7-amino-1-((1-((7-((2,4-difluorobenzyl)oxy)-5-fluorobenzo[d]thiazol-2-yl)methyl)-2-oxo-1,2-dihydropyridin-3-yl)amino)-1,7-dioxohept-5-en-2-yl)carbamate (Compound 354) (54.7 mg, 20% yield) as a white solid after purification by silica gel chromatography and prep-HPLC. LCMS m/z 630.2 $(M+1)^+$. $^1H$ NMR (400 MHz, DMSO-$d_6$) δ 9.34 (s, 1H), 8.26 (dd, J=7.6, 1.6 Hz, 1H), 7.80-7.58 (m, 3H), 7.49 (dd, J=9.6, 2.4 Hz, 1H), 7.42-7.22 (m, 3H), 7.19-7.11 (m, 1H), 6.89 (s, 1H), 6.66-6.51 (m, 1H), 6.38 (t, J=7.2 Hz, 1H), 5.90-5.78 (m, 1H), 5.65-5.51 (m, 2H), 5.33 (s, 2H), 4.28-4.11 (m, 1H), 3.54 (s, 3H), 2.23-2.09 (m, 2H), 1.91-1.76 (m, 1H), 1.75-1.58 (m, 1H).

The following compounds were prepared according to the procedures described in Example 56 using the appropriate intermediates.

| Compound | Structure | LCMS Data |
|---|---|---|
| 355 | 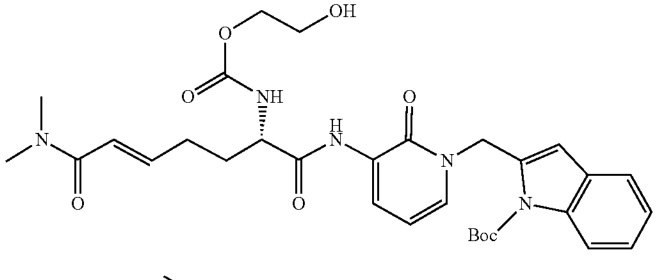 | LCMS m/z 658.2 $(M + 1)^+$ |
| 356 | 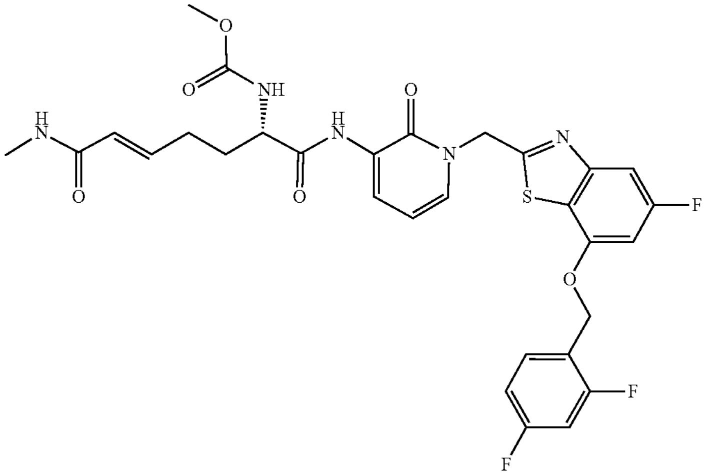 [SMILES: CNC(=O)/C=C/CC[C@H](NC(=O)OC)C(=O)Nc1cccn(Cc2nc3cc(F)cc(OCc4ccc(F)cc4F)c3s2)c1=O] | LCMS m/z 644.2 $(M + 1)^+$ |

The Synthesis of Intermediate I-525

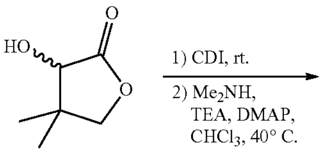

I-517

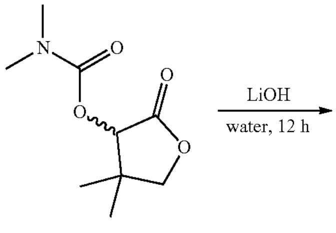

I-518

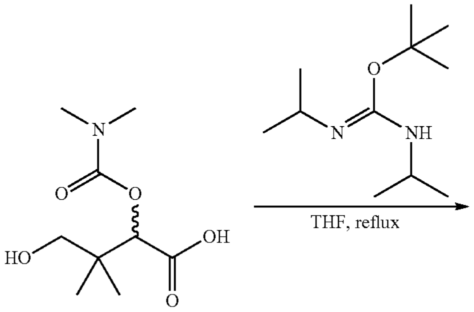

I-519

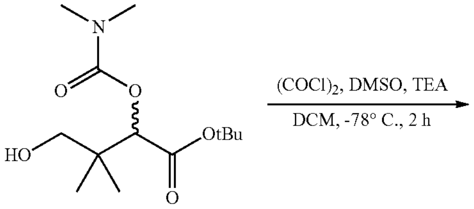

I-520

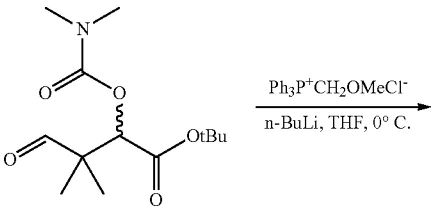

I-521

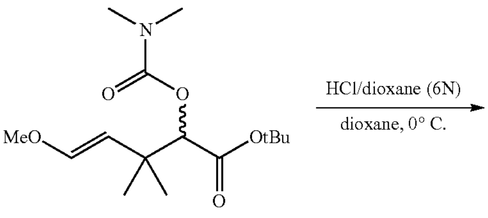

I-522

-continued

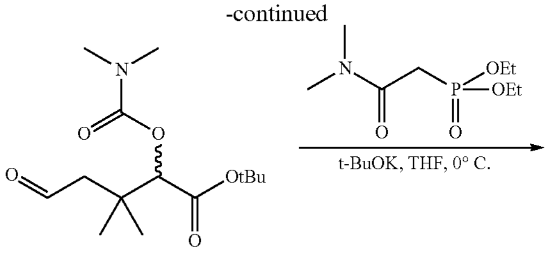

I-523

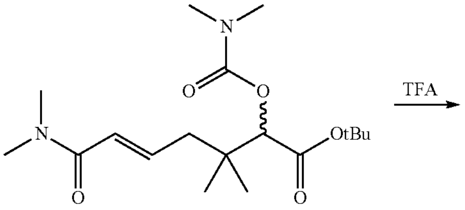

I-524

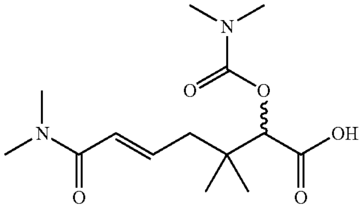

I-525

A mixture of 3-hydroxy-4,4-dimethyl-tetrahydrofuran-2-one (25 g, 192.10 mmol), CDI (37.38 g, 230.52 mmol) in $CHCl_3$ (250 mL) was stirred at 20° C. for 1.5 hr, then N-methylmethanamine (23.50 g, 288.15 mmol, 26.40 mL, HCl) and TEA (58.32 g, 576.30 mmol, 80.21 mL) and DMAP (2.35 g, 19.21 mmol) was added and then the mixture was stirred at 40° C. for 1 hr. The reaction mixture was diluted with sat. $NH_4Cl$ solution 500 mL. The organic phase ($CHCl_3$) was collected and washed with brine (200 mL), dried over anhydrous $Na_2SO_4$ while the water phase was extracted with EtOAc 200 mL (100 mL×2). The combined organic phase (EtOAc) was washed with brine (100 mL), then dried over anhydrous $Na_2SO_4$, filtered and concentrated under reduced pressure to give an oil. The residue was purified by column chromatography to give (4,4-dimethyl-2-oxo-tetrahydrofuran-3-yl) N,N-dimethylcarbamate (I-518) (86.4 g) as a white solid.

A mixture of (4,4-dimethyl-2-oxo-tetrahydrofuran-3-yl) N,N-dimethylcarbamate (86.4 g, 429.38 mmol), $LiOH{\cdot}H_2O$ (36.04 g, 858.76 mmol) in water (500 mL) was stirred at 20° C. for 12 hr. The reaction mixture was washed with DCM 400 mL (200 mL×2). The water phase was adjusted to pH~1 by 12 N HCl solution and extracted with EtOAc 1000 mL (200 mL×5). The combined organic phase was concentrated under reduced pressure to give 2-(dimethylcarbamoyloxy)-4-hydroxy-3,3-dimethyl-butanoic acid (I-519) (50 g) as a light yellow oil.

To a solution of 2-(dimethylcarbamoyloxy)-4-hydroxy-3,3-dimethyl-butanoic acid (20 g, 91.23 mmol) in THF (200 mL) was added 2-tert-butyl-1,3-diisopropyl-isourea (49.34 g, 246.31 mmol). The mixture was stirred at 60° C. for 3 h under $N_2$ atmosphere. The reaction mixture was filtered and concentrated under reduced pressure to give a residue. The residue was purified by column chromatography to give tert-butyl 2-(dimethylcarbamoyloxy)-4-hydroxy-3,3-dimethyl-butanoate (I-520) (10 g, 40% yield) as a light yellow liquid.

A solution of $(COCl)_2$ (10.60 g, 83.53 mmol, 7.31 mL) was added dropwise to a solution of DMSO (13.05 g, 167.07 mmol, 13.05 mL) in dry DCM (100 mL) under an atmosphere of argon at −65° C. The mixture was stirred at the same temperature for 30 mins. Then dropwise added tert-butyl2-(dimethylcarbamoyloxy)-4-hydroxy-3,3-dimethyl-butanoate (10 g, 36.32 mmol) in DCM (20 mL). The reaction mixture was stirred at −65° C. for 30 mins. Subsequently, TEA (32.34 g, 319.60 mmol, 44.49 mL) was added dropwise to the reaction mixture followed by stirring for 1 h at −65° C. The reaction mixture was diluted with sat. $NH_4Cl$ solution (200 mL) and extracted with DCM 100 mL (50 mL×2). The combined organic phase was washed with brine (100 mL), dried over anhydrous $Na_2SO_4$, filtered and concentrated under reduced pressure to give an oil. The residue was purified by column chromatography to give tert-butyl 2-(dimethylcarbamoyloxy)-3,3-dimethyl-4-oxo-butanoate (I-521) (6.8 g, 69% yield) as a yellow oil.

A mixture of methoxymethyl(triphenyl)phosphonium; chloride (12.79 g, 37.32 mmol) in THF (35 mL) was added n-BuLi (2.5 M, 12.44 mL) at 0° C. The mixture was stirred at 0° C. for 0.5 hr. tert-Butyl 2-(dimethylcarbamoyloxy)-3,3-dimethyl-4-oxo-butanoate (3.4 g, 12.44 mmol) was added. The mixture was stirred at 0° C. for 0.5 hr under $N_2$ atmosphere. The reaction was added to cold sat. $NH_4Cl$ solution (100 mL) and then extracted with EtOAc (50 mL×2). The combined organic phase were dried over anhydrous $Na_2SO_4$, filtered and concentrated under reduced pressure to give an oil. The residue was purified by column chromatography to give tert-butyl (E)-2-(dimethylcarbamoyloxy)-5-methoxy-3,3-dimethyl-pent-4-enoate and tert-butyl (Z)-2-(dimethylcarbamoyloxy)-5-methoxy-3,3-dimethyl-pent-4-enoate (I-522) (4.5 g) as a yellow oil.

To a mixture of tert-butyl (E)-2-(dimethylcarbamoyloxy)-5-methoxy-3,3-dimethyl-pent-4-enoate (1 g, 3.32 mmol), tert-butyl (Z)-2-(dimethylcarbamoyloxy)-5-methoxy-3,3-dimethyl-pent-4-enoate (1.00 g, 3.32 mmol) in (HCl/dioxane (10 mL, 6M) and dioxane (2 mL)) was added water (478.21 mg, 26.54 mmol, 478.21 uL) at 0° C. The mixture was stirred at 0° C. for 1 hr. To the reaction was added cold sat. $NaHCO_3$ solution (10 mL) and then extracted with EtOAc 10 mL (5 mL×2). The combined organic phase were dried over anhydrous $Na_2SO_4$, filtered and concentrated under reduced pressure. The residue was purified by column chromatography to give tert-butyl 2-(dimethylcarbamoyloxy)-3,3-dimethyl-5-oxo-pentanoate (I-523) (0.35 g, 37% yield) as a yellow oil.

To a mixture of 2-diethoxyphosphoryl-N,N-dimethyl-acetamide (466.06 mg, 2.09 mmol) in THF (4 mL) was added t-BuOK (234.30 mg, 2.09 mmol) at 0° C. The mixture was stirred at 0° C. for 0.5 hr. tert-Butyl 2-(dimethylcarbamoyloxy)-3,3-dimethyl-5-oxo-pentanoate (0.3 g, 1.04 mmol) was added, and then the mixture was stirred at 0° C. for 0.5 hr. The mixture was stirred at 25° C. for 11 h. The reaction mixture was diluted with sat. $NH_4Cl$ solution (20 mL) and extracted with EtOAc (6 mL×2). The combined organic phase was washed with brine (15 mL), dried over anhydrous $Na_2SO_4$, filtered and concentrated under reduced pressure. The residue was purified by prep-HPLC and SFC to give tert-butyl (E)-7-(dimethylamino)-2-(dimethylcarbamoyloxy)-3,3-dimethyl-7-oxo-hept-5-enoate (I-524) (380 mg) as an off-white gum.

To a solution of tert-butyl (E)-7-(dimethylamino)-2-(dimethylcarbamoyloxy)-3,3-dimethyl-7-oxo-hept-5-enoate (0.38 g, 1.07 mmol) in DCM (3 mL) was added TFA (3.65 g, 31.98 mmol, 2.37 mL). The mixture was stirred at 25° C. for 1.5 hr. The reaction mixture was concentrated under reduced pressure to give an oil. The residue was purified by prep-HPLC (TFA) to give (E)-7-(dimethylamino)-2-(dimethylcarbamoyloxy)-3,3-dimethyl-7-oxo-hept-5-enoic acid (I-525) (0.14 g, 44% yield) as a colorless oil.

Example 58

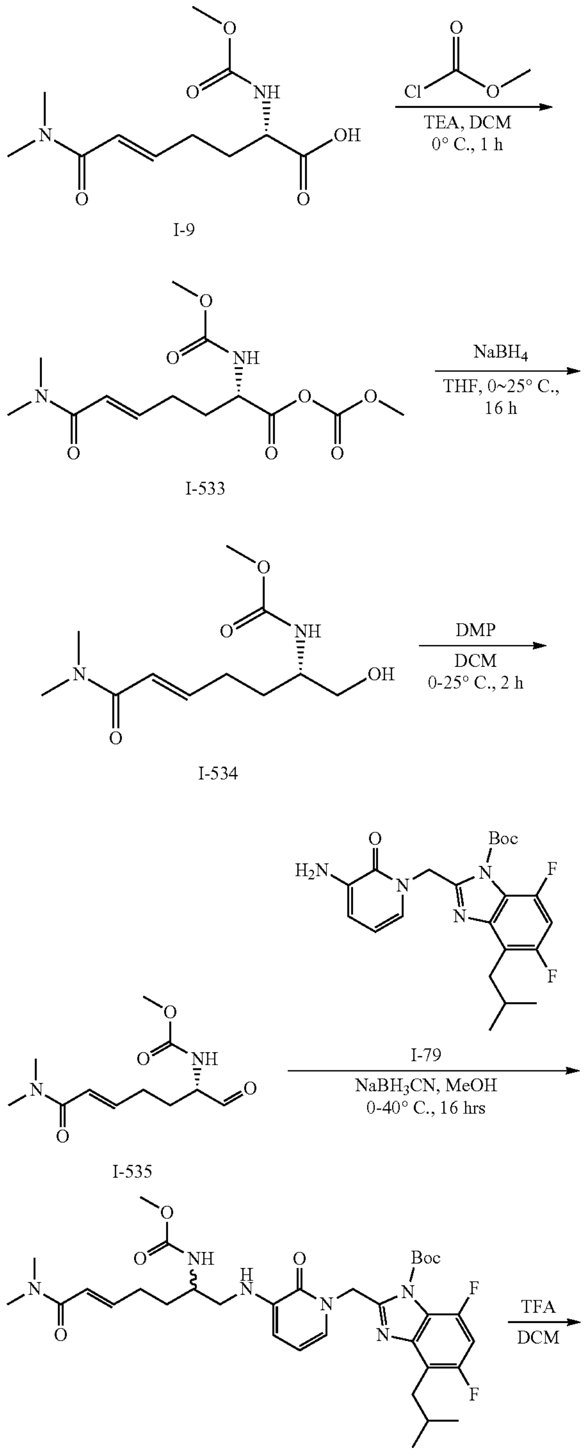

I-9

I-533

I-534

I-535

I-536

-continued

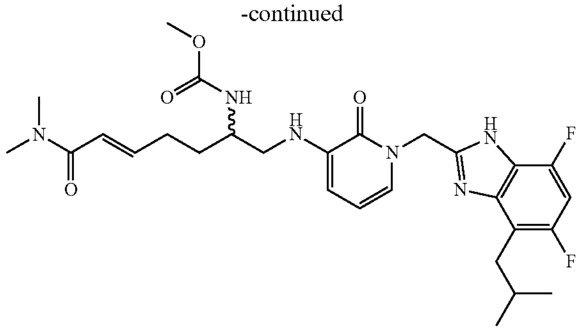

394

To a solution of (E,2S)-7-(dimethylamino)-2-(methoxycarbonylamino)-7-oxo-hept-5-enoic acid (1 g, 3.87 mmol, 1 eq) in DCM (10 mL) was added TEA (1.18 g, 11.62 mmol, 1.62 mL, 3 eq) and methyl carbonochloridate (548.83 mg, 5.81 mmol, 449.86 uL, 1.5 eq) at 0° C. The mixture was stirred at 0° C. for 1 hr. The reaction mixture was partitioned between water (20 mL) and dichloromethane (20 mL). The organic phase was separated, washed with brine (20 mL), dried over anhydrous $Na_2SO_4$, filtered and concentrated under reduced pressure to give methoxycarbonyl (E,2S)-7-(dimethylamino)-2-(methoxycarbonylamino)-7-oxo-hept-5-enoate (I-533) (910 mg) which was used in the next step without further purification as a yellow oil.

To a solution of methoxycarbonyl (E,2S)-7-(dimethylamino)-2-(methoxycarbonylamino)-7-oxo-hept-5-enoate (910 mg, 2.88 mmol, 1 eq) in THF (10 mL) was added $NaBH_4$ (544.21 mg, 14.38 mmol, 5 eq) at 0° C. The mixture was stirred at 25° C. for 16 h. The reaction mixture was partitioned between sat. $NH_4Cl$ (20 mL) and ethyl acetate (20 mL). The organic phase was separated, washed with brine (20 mL), dried over anhydrous $Na_2SO_4$, filtered and concentrated under reduced pressure to give a residue. The residue was purified by prep-TLC to give N-[(E,1S)-6-(dimethylamino)-1-(hydroxymethyl)-6-oxo-hex-4-enyl]carbamate (I-534) (220 mg, 31% yield) as a yellow oil. LCMS: $[M+1]^+$=245.2.

To a solution of methyl N-[(E,1S)-6-(dimethylamino)-1-(hydroxymethyl)-6-oxo-hex-4-enyl]carbamate (200 mg, 818.71 umol, 1 eq) in DCM (2 mL) was added DMP (208.35 mg, 491.23 umol, 152.08 uL, 0.6 eq) at 0° C. The mixture was stirred for 0.5 hr at the same temperature. Additional DMP (208.35 mg, 491.23 umol, 152.08 uL, 0.6 eq) was added at 0° C., and the reaction mixture was stirred at 25° C. for 1.5 h. The reaction mixture was filtered and concentrated under reduced pressure to remove the solvent to afford oil. The crude product methyl N-[(E,1S)-6-(dimethylamino)-1-formyl-6-oxo-hex-4-enyl]carbamate (I-535) (200 mg) was used in the next step without further purification as a yellow oil. LCMS: $[M+1]^+$=243.2

A mixture of methyl N-[(E,1S)-6-(dimethylamino)-1-formyl-6-oxo-hex-4-enyl]carbamate (67.23 mg, 277.48 umol), tert-butyl 2-[(3-amino-2-oxo-1-pyridyl)methyl]-5,7-difluoro-4-isobutyl-benzimidazole-1-carboxylate (0.08 g, 184.99 umol), AcOH (5.55 mg, 92.49 umol, 5.29 uL) in MeOH (2 mL) was stirred at 40° C. for 1 hour, then $NaBH_3CN$ (23.25 mg, 369.97 umol) was added at 20° C. and then the mixture was stirred at 20° C. for 11 hours. The reaction mixture was diluted with water 10 mL and then extracted with EtOAc (8 mL×2). The combined organic layers were washed with brine 10 mL, dried over $Na_2SO_4$, filtered and the filtrate was concentrated to give the residue. The residue was purified by prep-TLC and prep-HPLC to give tert-butyl 2-[[3-[[(E)-7-(dimethylamino)-2-(methoxycarbonylamino)-7-oxo-hept-5-enyl]amino]-2-oxo-1-pyridyl]methyl]-5,7-difluoro-4-isobutyl-benzimidazole-1-carboxylate (I-536) (38 mg, 27% yield) as a brown gum. LCMS m/z 659.4 $(M+1)^+$.

A mixture of tert-butyl 2-[[3-[[(E)-7-(dimethylamino)-2-(methoxycarbonylamino)-7-oxo-hept-5-enyl]amino]-2-oxo-1-pyridyl]methyl]-5,7-difluoro-4-isobutyl-benzimidazole-1-carboxylate (35 mg, 45.16 umol) in TFA (0.5 mL) and DCM (2 mL) was stirred at 20° C. for 1 hr. The reaction mixture was poured into sat. $NaHCO_3$ (10 mL) and extracted with DCM (8 mL×2). The combined organic layers were washed with brine (10 mL), dried over anhydrous $Na_2SO_4$, filtered and concentrated under reduced pressure to give methyl N-[(E)-1-[[[1-[(5,7-difluoro-4-isobutyl-1H-benzimidazol-2-yl)methyl]-2-oxo-3-pyridyl]amino]methyl]-6-(dimethylamino)-6-oxo-hex-4-enyl]carbamate (Compound 394) (23.6 mg, 92% yield) as a green solid. LCMS m/z 559.3 $(M+1)^+$. $^1H$ NMR (400 MHz, DMSO-$d_6$) δ 12.96 (br s, 1H) 7.16 (br d, J=8.44 Hz, 1H) 7.04 (br d, J=5.87 Hz, 1H) 6.95 (t, J=10.82 Hz, 1H) 6.56-6.65 (m, 1H) 6.31-6.40 (m, 2H) 6.19 (t, J=7.03 Hz, 1H) 5.49 (br t, J=5.56 Hz, 1H) 5.27-5.36 (m, 2H) 3.64 (brd, J=3.67 Hz, 1H) 3.51 (s, 3H) 3.00-3.12 (m, 2H) 2.98 (s, 3H) 2.83 (s, 3H) 2.69 (br d, J=7.21 Hz, 2H) 2.11-2.28 (m, 2H) 1.92 (dt, J=13.42, 6.68 Hz, 1H) 1.49-1.69 (m, 2H) 0.83-0.92 (m, 6H).

The Synthesis of Intermediate I-544

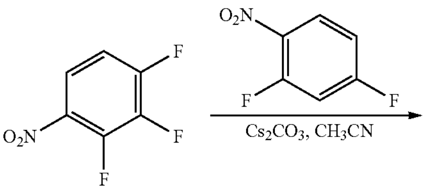

I-537

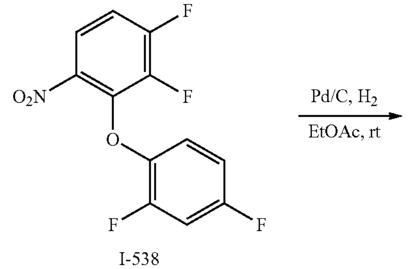

I-538

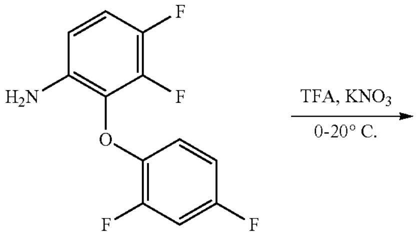

I-539

-continued

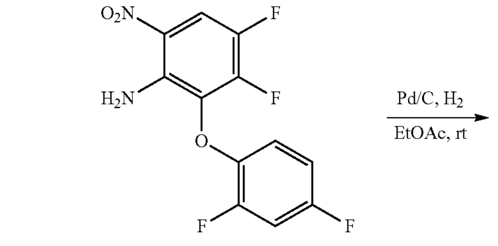

I-540

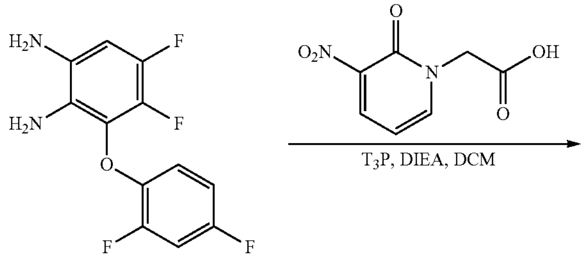

I-541

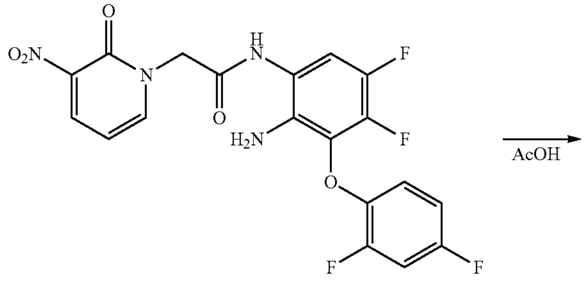

I-542

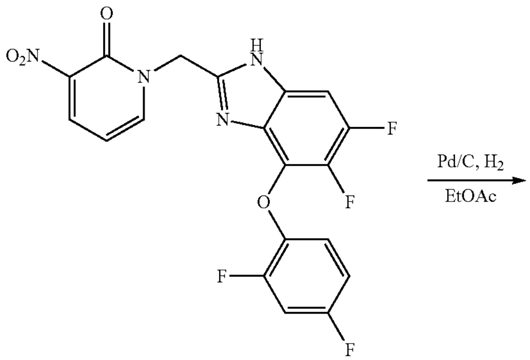

I-543

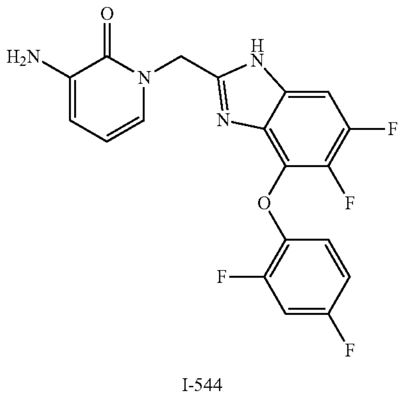

I-544

To a mixture of 1,2,3-trifluoro-4-nitro-benzene (5 g, 28.24 mmol, 3.25 mL) in MeCN (100 mL) was added $Cs_2CO_3$ (18.40 g, 56.47 mmol) and 2,4-difluorophenol (3.67 g, 28.24 mmol), then the mixture was stirred at 15° C. for 16 h. The mixture was filtered and the filtrate was concentrated to give the crude product 3-(2,4-difluorophenoxy)-1,2-difluoro-4-nitro-benzene (I-538) (8.0 g) as a red oil.

To a solution of 3-(2,4-difluorophenoxy)-1,2-difluoro-4-nitro-benzene (8 g, 27.86 mmol) in EtOAc (80 mL) was added Pd/C (3 g, 27.86 mmol, 10% purity). The suspension was degassed under vacuum and purged with $H_2$ several times. The mixture was stirred under $H_2$ (15 psi) at 20° C. for 0.5 hours. The mixture was filtered and the filtrate was concentrated to give 2-(2,4-difluorophenoxy)-3,4-difluoro-aniline (I-539) (7.1 g) as a brown oil which was used in the next step without further purification. LCMS m/z 258.1 $(M+1)^+$.

To a solution of 2-(2,4-difluorophenoxy)-3,4-difluoro-aniline (3.5 g, 13.61 mmol) in TFA (35 mL) was added $KNO_3$ (1.65 g, 16.33 mmol) at 0° C. The mixture was stirred at 20° C. for 1 hr. The reaction mixture was poured into cold sat. aq. $NaHCO_3$ (300 mL), and extracted with ethyl acetate (100 mL*3). The combined organic phase was washed with brine (100 mL*2), dried with anhydrous $Na_2SO_4$, filtered and concentrated in vacuum. The residue was purified by column chromatography to give 2-(2,4-difluorophenoxy)-3,4-difluoro-6-nitro-aniline (I-540) (6 g, 73% yield) as a yellow solid. $^1H$ NMR (400 MHz, $CDCl_3$) δ 7.73-7.91 (m, 1H) 6.81-6.96 (m, 2H) 6.74 (dddd, J=9.11, 7.61, 2.84, 1.71 Hz, 1H) 6.30 (br s, 2H).

To a solution of 2-(2,4-difluorophenoxy)-3,4-difluoro-6-nitro-aniline (2 g, 6.62 mmol) in EtOAc (20 mL) was added Pd/C (0.6 g, 10% purity). The suspension was degassed under vacuum and purged with $H_2$ several times. The mixture was stirred under $H_2$ (15 psi) at 20° C. for 0.5 hours. The mixture was filtered and the filtrate was concentrated to give 3-(2,4-difluorophenoxy)-4,5-difluoro-benzene-1,2-diamine (I-541) (1.5 g) as a white solid.

To a solution of 3-(2,4-difluorophenoxy)-4,5-difluoro-benzene-1,2-diamine (500 mg, 1.84 mmol) and 2-(3-nitro-2-oxo-1-pyridyl)acetic acid (545.93 mg, 2.76 mmol) in DCM (5 mL) was added $T_3P$ (1.40 g, 2.20 mmol, 1.31 mL, 50% purity) and DIEA (474.80 mg, 3.67 mmol, 639.89 uL). The mixture was stirred at 20° C. for 12 hr. The reaction mixture was concentrated under reduced pressure to give a N-[2-amino-3-(2,4-difluorophenoxy)-4,5-difluoro-phenyl]-2-(3-nitro-2-oxo-1-pyridyl)acetamide (I-542) (3 g) as a brown oil. LCMS m/z 453.1 $(M+1)^+$.

A mixture of N-[2-amino-3-(2,4-difluorophenoxy)-4,5-difluoro-phenyl]-2-(3-nitro-2-oxo-1-pyridyl)acetamide (2.8 g, 6.19 mmol) in AcOH (30 mL) was stirred at 80° C. for 1 hr. Water (20 mL) was added to the mixture and 1-[[4-(2,4-difluorophenoxy)-5,6-difluoro-1H-benzimidazol-2-yl]methyl]-3-nitro-pyridin-2-one (I-543) (800 mg, 30% yield) obtained as a white solid was collected by filtration.

To a solution of 1-[[4-(2,4-difluorophenoxy)-5,6-difluoro-1H-benzimidazol-2-yl]methyl]-3-nitro-pyridin-2-one (100 mg, 230.26 umol) in EtOAc (1 mL) was added Pd/C (30 mg, 10% purity) under $N_2$. The suspension was degassed under vacuum and purged with $H_2$ several times. The mixture was stirred under $H_2$ (15 psi) at 20° C. for 0.5 hours. The reaction mixture was filtered and the filtrate was concentrated to give 3-amino-1-[[4-(2,4-difluorophenoxy)-5,6-difluoro-1H-benzimidazol-2-yl]methyl]pyridin-2-one (I-544) (100 mg) as a white solid which was used in the next step without further purification. LCMS m/z 405.1 $(M+1)^+$.

The following intermediates were prepared according to the procedures described for the synthesis of I-544 using the appropriate reagents.
| Compound | Structure | LCMS Data |
|---|---|---|
| I-557 | 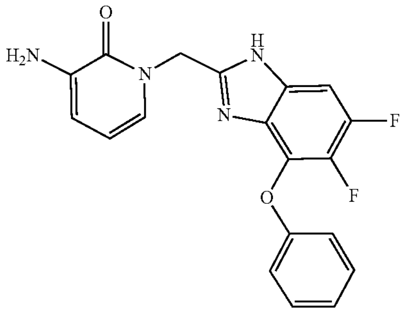 [SMILES: Nc1cccn(Cc2nc3c(Oc4ccccc4)c(F)c(F)cc3[nH]2)c1=O] | LCMS m/z 369.1 $(M+1)^+$ |
| I-558 | 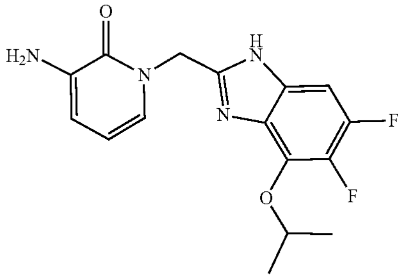 [SMILES: CC(C)Oc1c(F)c(F)cc2[nH]c(Cn3cccc(N)c3=O)nc12] | LCMS m/z 335.1 $(M+1)^+$ |
| I-559 | 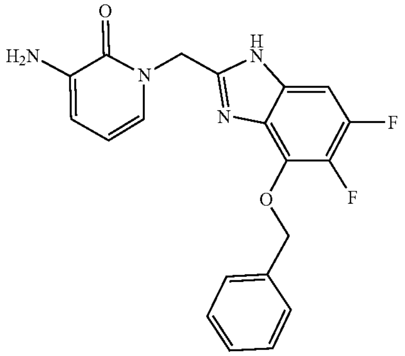 [SMILES: Nc1cccn(Cc2nc3c(OCc4ccccc4)c(F)c(F)cc3[nH]2)c1=O] | LCMS m/z 383.1 $(M+1)^+$ |
| I-560 | 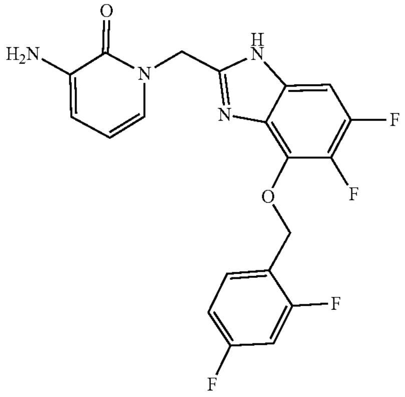 [SMILES: Nc1cccn(Cc2nc3c(OCc4ccc(F)cc4F)c(F)c(F)cc3[nH]2)c1=O] | LCMS m/z 419.1 $(M+1)^+$ |

Example 59

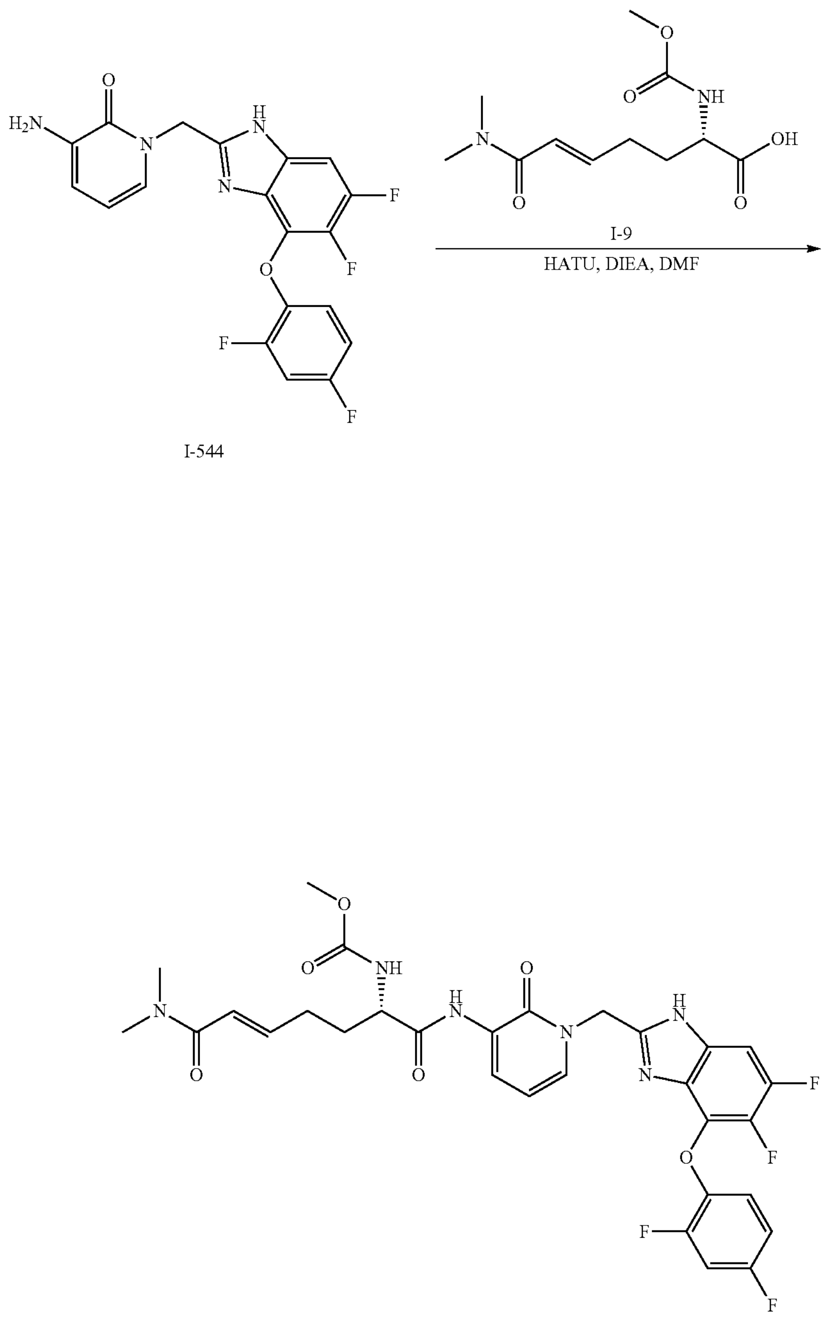

To a solution of 3-amino-1-[[4-(2,4-difluorophenoxy)-5,6-difluoro-1H-benzimidazol-2-yl]methyl]pyridin-2-one (100 mg, 247.33 umol) and (E,2S)-7-(dimethylamino)-2-(methoxycarbonylamino)-7-oxo-hept-5-enoic acid (63.88 mg, 247.33 umol) in DMF (1 mL) was added HATU (141.06 mg, 371.00 umol) and DIEA (63.93 mg, 494.66 umol, 86.16 uL). The mixture was stirred at 40° C. for 0.5 hr. The reaction mixture was filtered. The filtrate was purified by prep-HPLC to give methyl N-[(E,1S)-1-[[1-[[4-(2,4-difluorophenoxy)-5,6-difluoro-1H-benzimidazol-2-yl] methyl]-2-oxo-3-pyridyl] carbamoyl]-6-(dimethylamino)-6-oxo-hex-4-enyl]carbamate (Compound 411) (23.9 mg, 15% yield) as a white solid. LCMS m/z 645.2 $(M+1)^+$. $^1H$ NMR (400 MHz, DMSO-$d_6$) δ12.87 (br s, 1H) 9.24 (s, 1H) 8.18-8.28 (m, 1H) 7.73 (br d, J=7.58 Hz, 1H) 7.49 (br s, 3H) 6.87-7.01 (m, 2H) 6.54-6.65 (m, 1H) 6.28-6.41 (m, 2H) 5.33 (s, 2H) 4.13-4.22 (m, 1H) 3.54 (s, 3H) 2.98 (s, 3H) 2.83 (s, 3H) 2.14-2.31 (m, 2H) 1.88 (br d, J=6.85 Hz, 1H) 1.65-1.78 (m, 1H).

The following compounds were prepared according to the procedures described for the synthesis of Example 59 using the appropriate intermediates.

| Compound | Structure | LCMS Data |
| --- | --- | --- |
| 409 | 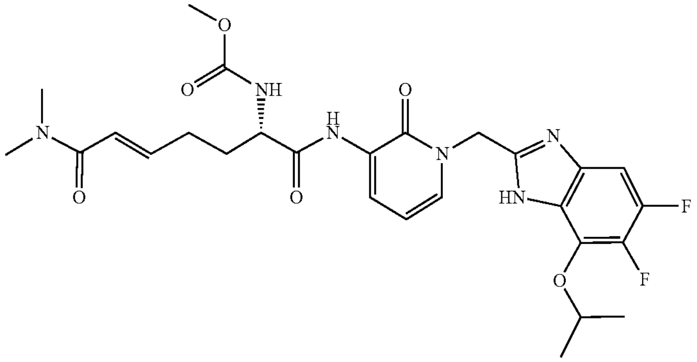 [SMILES: COC(=O)N[C@@H](CC/C=C/C(=O)N(C)C)C(=O)Nc1cccn(Cc2nc3cc(F)c(F)c(OC(C)C)c3[nH]2)c1=O] | LCMS m/z 575.3 (M + 1)$^+$ |
| 416 | 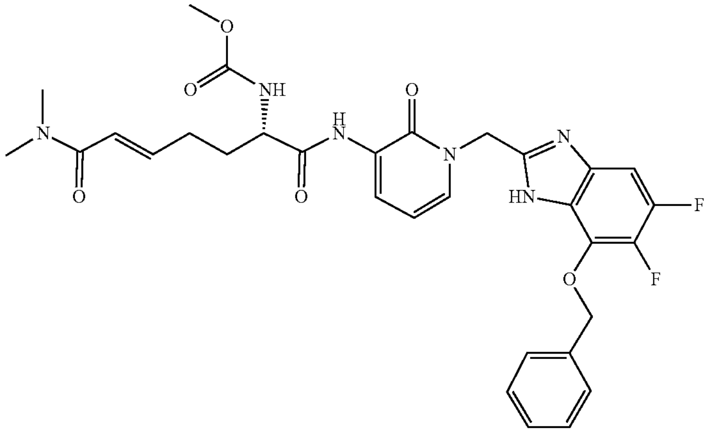 [SMILES: COC(=O)N[C@@H](CC/C=C/C(=O)N(C)C)C(=O)Nc1cccn(Cc2nc3cc(F)c(F)c(OCc4ccccc4)c3[nH]2)c1=O] | LCMS m/z 622.2 (M + 1)$^+$ |
| 417 | 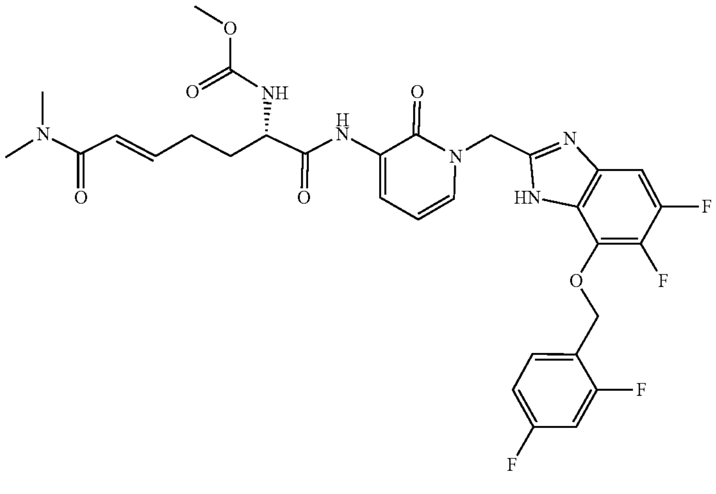 [SMILES: COC(=O)N[C@@H](CC/C=C/C(=O)N(C)C)C(=O)Nc1cccn(Cc2nc3cc(F)c(F)c(OCc4ccc(F)cc4F)c3[nH]2)c1=O] | LCMS m/z 659.2 (M + 1)$^+$ |

-continued
| Compound | Structure | LCMS Data |
|---|---|---|
| 420 | 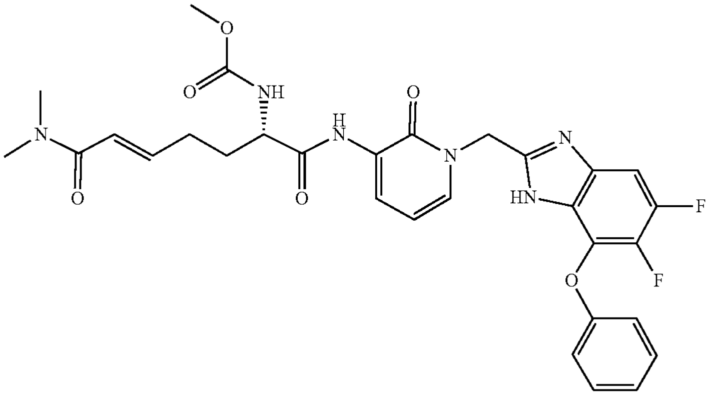 [SMILES: COC(=O)N[C@@H](CC/C=C/C(=O)N(C)C)C(=O)Nc1cccn(Cc2nc3cc(F)c(F)c(Oc4ccccc4)c3[nH]2)c1=O] | LCMS: $[M + 1]^+ = 609.2$ |
| 445 | 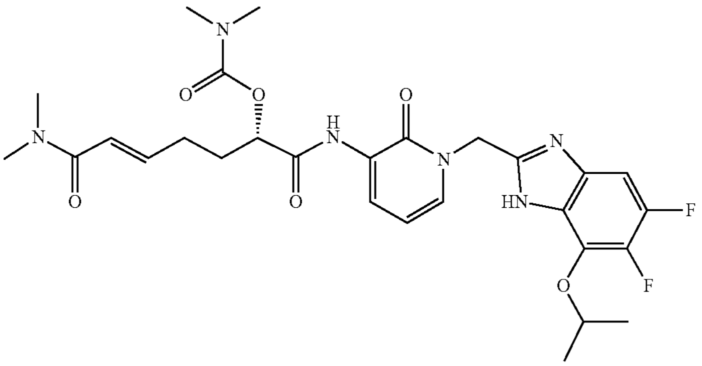 [SMILES: CC(C)Oc1c(F)c(F)cc2nc(Cn3cccc(NC(=O)[C@H](CC/C=C/C(=O)N(C)C)OC(=O)N(C)C)c3=O)[nH]c12] | LCMS m/z 589.3 $(M + 1)^+$ |
| 449 | 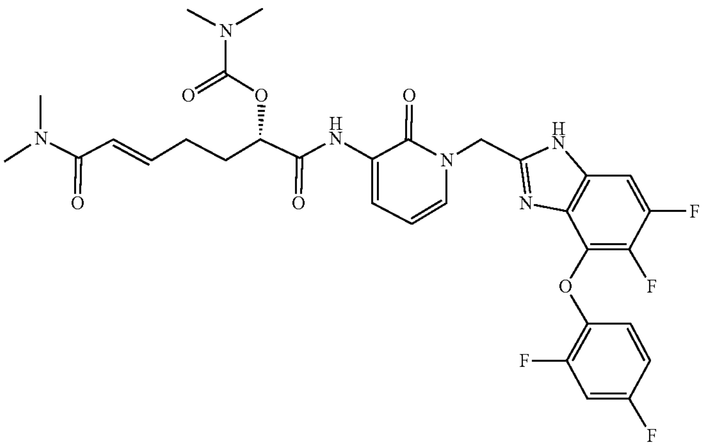 [SMILES: CN(C)C(=O)/C=C/CC[C@H](OC(=O)N(C)C)C(=O)Nc1cccn(Cc2nc3c(Oc4ccc(F)cc4F)c(F)c(F)cc3[nH]2)c1=O] | LCMS m/z 659.3 $(M + 1)^+$ |

-continued
| Compound | Structure | LCMS Data |
|---|---|---|
| 458 | 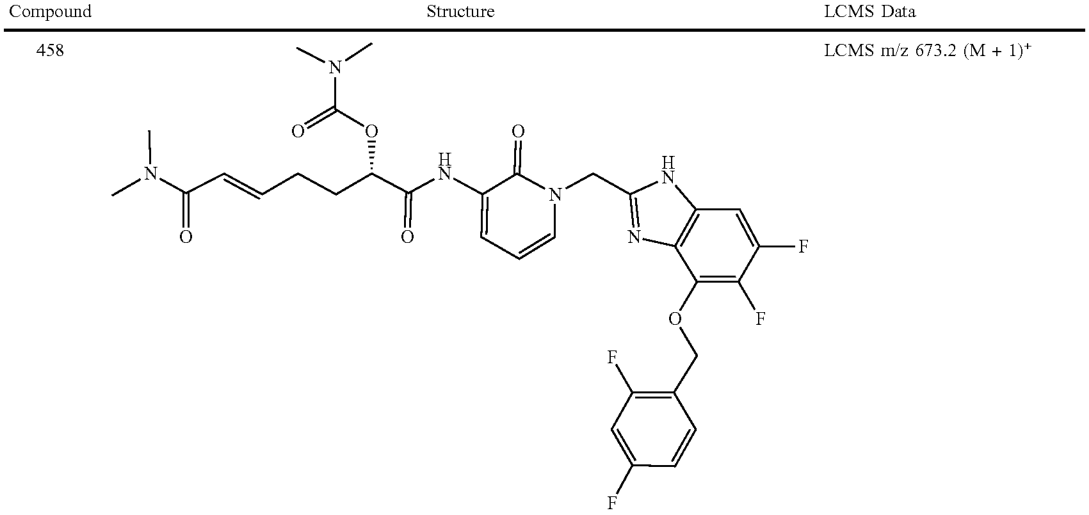 | LCMS m/z 673.2 (M + 1)$^+$ |
Example 60
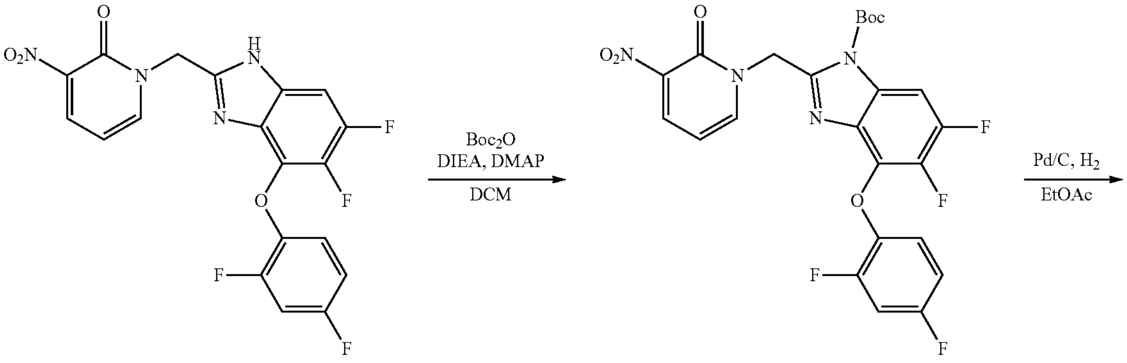
I-543
I-545
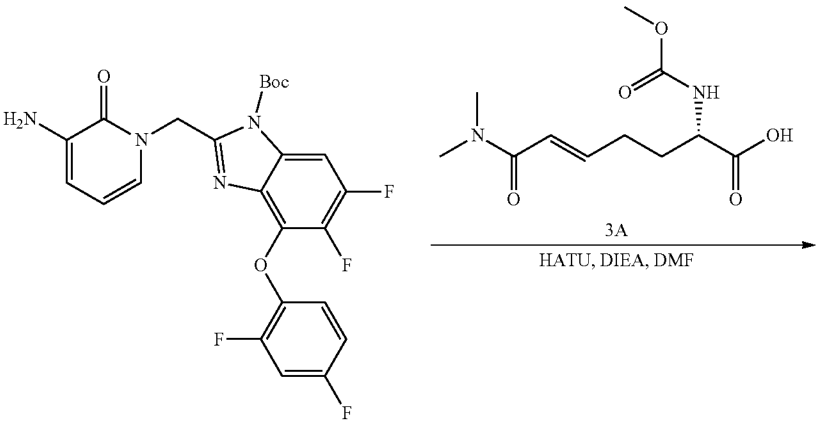
I-546

-continued

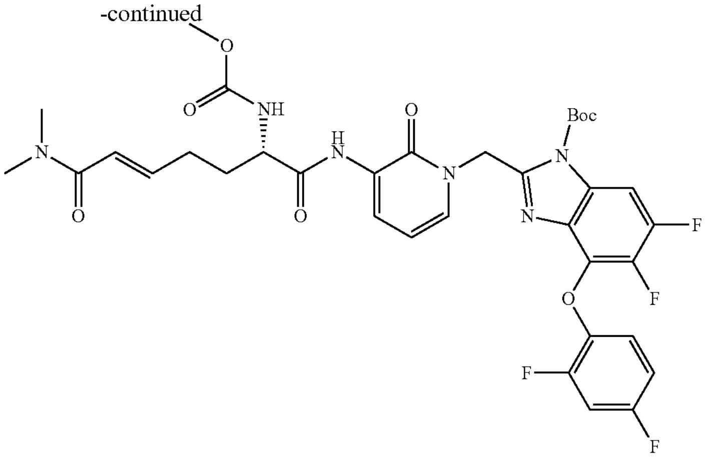

410

To a solution of 1-[[4-(2,4-difluorophenoxy)-5,6-difluoro-1H-benzimidazol-2-yl]methyl]-3-nitro-pyridin-2-one (100 mg, 230.26 umol) and tert-butoxycarbonyl tert-butyl carbonate (60.30 mg, 276.31 umol, 63.48 uL) in DCM (0.5 mL) was added DIEA (59.52 mg, 460.51 umol, 80.21 uL) and DMAP (2.81 mg, 23.03 umol). The mixture was stirred at 20° C. for 0.5 hr. The reaction mixture was added saturated $NH_4Cl$ solution (5 mL), and extracted with ethyl acetate (3 mL*3). The combined organic phase was washed with brine (5 mL*2), dried with anhydrous $Na_2SO_4$, filtered and concentrated in vacuum. The residue was purified by prep-TLC to give tert-butyl 4-(2,4-difluorophenoxy)-5,6-difluoro-2-[(3-nitro-2-oxo-1-pyridyl)methyl]benzimidazole-1-carboxylate (I-545) (70 mg, 57% yield) as a yellow solid. LCMS m/z 535.3 $(M+1)^+$.

To a solution of tert-butyl 4-(2,4-difluorophenoxy)-5,6-difluoro-2-[(3-nitro-2-oxo-1-pyridyl)methyl]benzimidazole-1-carboxylate (70 mg, 130.98 umol) in EtOAc (0.5 mL) was added Pd/C (10 mg, 10% purity) under $N_2$. The suspension was degassed under vacuum and purged with $H_2$ several times. The mixture was stirred under $H_2$ (15 psi) at 20° C. for 10 min. The reaction mixture was filtered and the filtrate was concentrated to give tert-butyl 2-[(3-amino-2-oxo-1-pyridyl)methyl]-4-(2,4-difluorophenoxy)-5,6-difluoro-benzimidazole-1-carboxylate (I-546) (50 mg) as a white solid which was used in the next step without further purification. LCMS m/z 527.0 $(M+23)^+$.

The following intermediates were prepared according to the procedures described for the synthesis of I-546 using the appropriate reagents.

| Compound | Structure | LCMS Data |
| --- | --- | --- |
| I-561 | 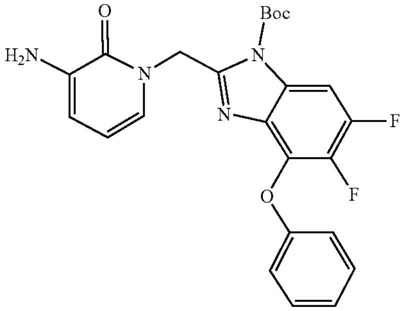 [SMILES: CC(C)(C)OC(=O)n1c(Cn2cccc(N)c2=O)nc2c(Oc3ccccc3)c(F)c(F)cc21] | LCMS m/z 469.1 $(M + 1)^+$ |
| I-562 | 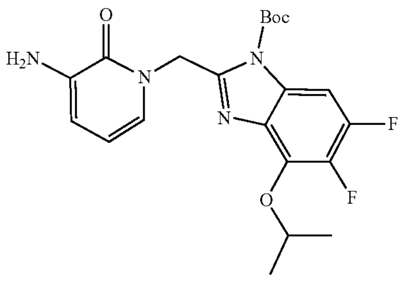 [SMILES: CC(C)Oc1c(F)c(F)cc2c1nc(Cn1cccc(N)c1=O)n2C(=O)OC(C)(C)C] | LCMS m/z 435.1 $(M + 1)^+$ |

-continued

| Compound | Structure | LCMS Data |
|---|---|---|
| I-563 | 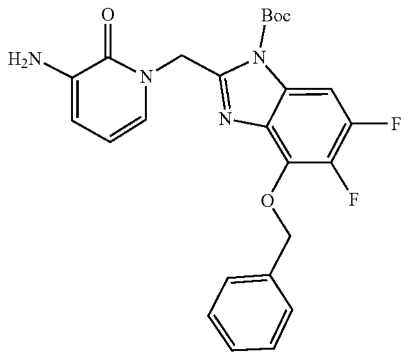 [SMILES: CC(C)(C)OC(=O)n1c(Cn2cccc(N)c2=O)nc2c(OCc3ccccc3)c(F)c(F)cc21] | LCMS m/z 483.1 (M + 1)$^+$ |
| I-564 | 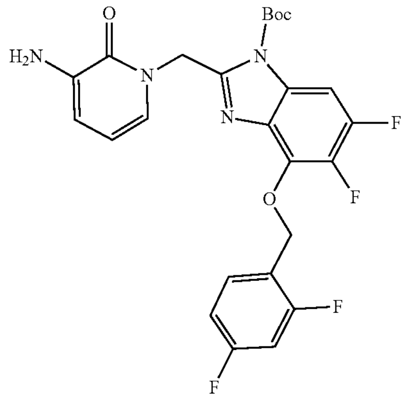 [SMILES: CC(C)(C)OC(=O)n1c(Cn2cccc(N)c2=O)nc2c(OCc3ccc(F)cc3F)c(F)c(F)cc21] | LCMS m/z 519.1 (M + 1)$^+$ |

A mixture of tert-butyl 2-[(3-amino-2-oxo-1-pyridyl)methyl]-4-(2,4-difluorophenoxy)-5,6-difluoro-benzimidazole-1-carboxylate (50 mg, 99.12 umol), (E,2S)-7-(dimethylamino)-2-(methoxycarbonylamino)-7-oxo-hept-5-enoic acid (25.60 mg, 99.12 umol), HATU (56.53 mg, 148.68 umol) and DIEA (25.62 mg, 198.24 umol, 34.53 uL) in DMF (1 mL) and then the mixture was stirred at 40° C. for 1 hr. The reaction mixture was filtered and concentrated. The residue was purified by prep-HPLC to give tert-butyl 4-(2,4-difluorophenoxy)-2-[[3-[[(E,2S)-7-(dimethylamino)-2-(methoxycarbonylamino)-7-oxo-hept-5-enoyl]amino]-2-oxo-1-pyridyl]methyl]-5,6-difluoro-benzimidazole-1-carboxylate (Compound 410) (14.8 mg, 19% yield) as a white solid. LCMS m/z 645.2 (M+1)$^+$. $^1$H NMR (400 MHz, DMSO-$d_6$) δ 9.18 (s, 1H) 8.24 (br d, J=7.02 Hz, 1H) 7.80 (br d, J=8.33 Hz, 1H) 7.66-7.75 (m, 1H) 7.28 (br d, J=6.58 Hz, 1H) 7.11 (br d, J=9.65 Hz, 2H) 6.79 (br s, 1H) 6.55-6.68 (m, 1H) 6.39 (br d, J=14.91 Hz, 1H) 6.22 (t, J=7.02 Hz, 1H) 5.50 (s, 2H) 4.18 (br s, 1H) 3.55 (s, 3H) 2.99 (s, 3H) 2.84 (s, 3H) 2.25 (br d, J=7.02 Hz, 2H) 1.72-2.00 (m, 2H) 1.69 (s, 9H).

following compounds were prepared according to the procedures described for the synthesis of Example 60 using the appropriate intermediates.

| Compound | Structure | LCMS Data |
|---|---|---|
| 408 | 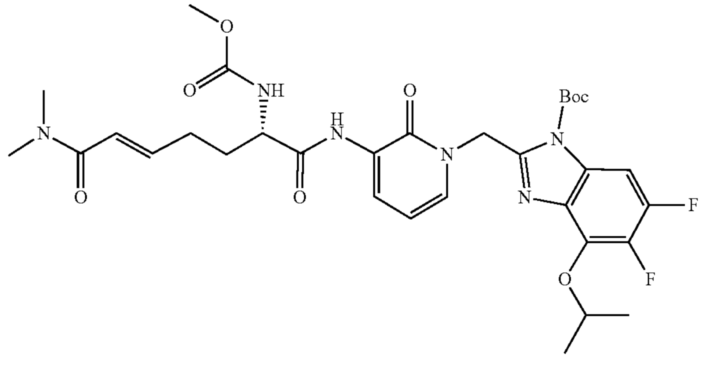 [SMILES: COC(=O)N[C@@H](CC/C=C/C(=O)N(C)C)C(=O)Nc1cccn(Cc2nc3c(OC(C)C)c(F)c(F)cc3n2C(=O)OC(C)(C)C)c1=O] | LCMS m/z 675.3 (M + 1)$^+$ |

-continued
| Compound | Structure | LCMS Data |
| --- | --- | --- |
| 412 | 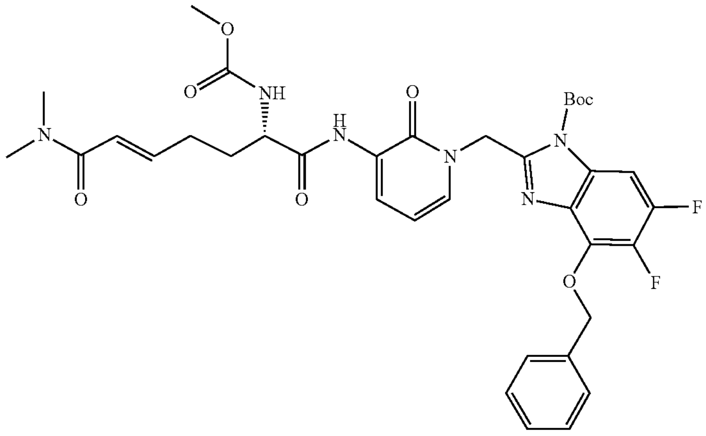 [SMILES: COC(=O)N[C@@H](CC/C=C/C(=O)N(C)C)C(=O)Nc1cccn(Cc2nc3c(OCc4ccccc4)c(F)c(F)cc3n2C(=O)OC(C)(C)C)c1=O] | LCMS m/z 723.3 $(M + 1)^+$ |
| 418 | 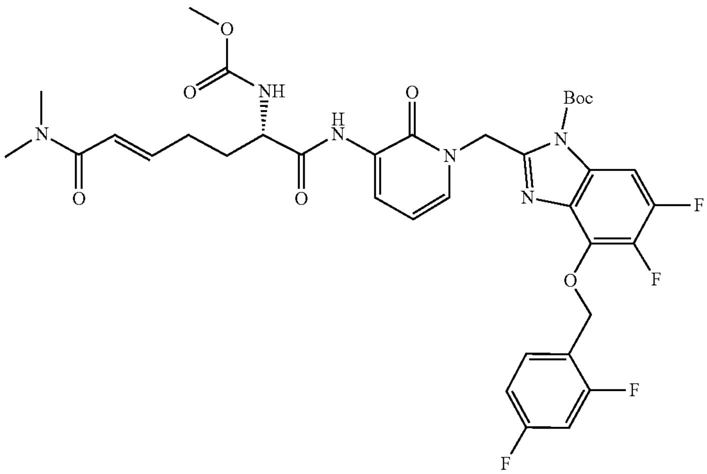 [SMILES: COC(=O)N[C@@H](CC/C=C/C(=O)N(C)C)C(=O)Nc1cccn(Cc2nc3c(OCc4ccc(F)cc4F)c(F)c(F)cc3n2C(=O)OC(C)(C)C)c1=O] | LCMS m/z 758.2 $(M + 1)^+$ |
| 429 | 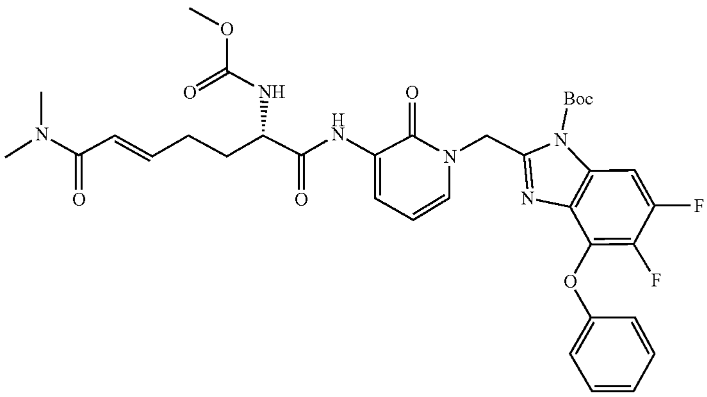 [SMILES: COC(=O)N[C@@H](CC/C=C/C(=O)N(C)C)C(=O)Nc1cccn(Cc2nc3c(Oc4ccccc4)c(F)c(F)cc3n2C(=O)OC(C)(C)C)c1=O] | LCMS m/z 709.3 $(M + 1)^+$ |

-continued
| Compound | Structure | LCMS Data |
|---|---|---|
| 454 | 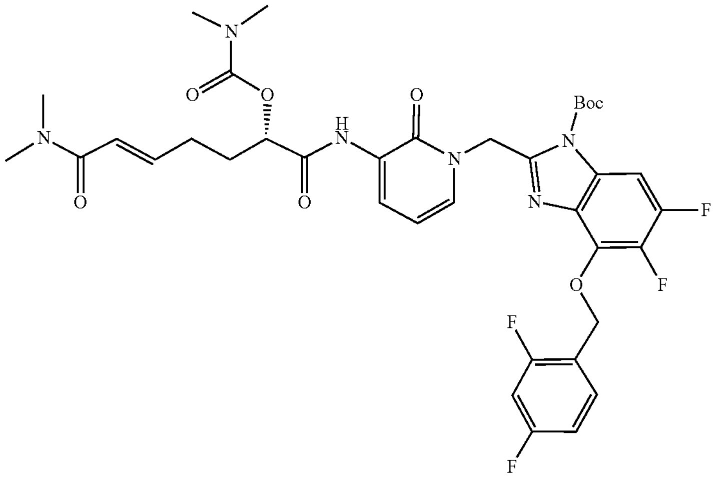 [SMILES: CN(C)C(=O)/C=C/CC[C@H](OC(=O)N(C)C)C(=O)Nc1cccn(Cc2nc3c(OCc4ccc(F)cc4F)c(F)c(F)cc3n2C(=O)OC(C)(C)C)c1=O] | LCMS m/z 773.2 (M + 1)$^+$ |
The Synthesis of Intermediate I-556:0
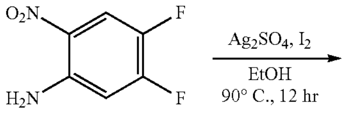
I-547
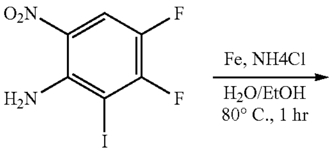
I-548
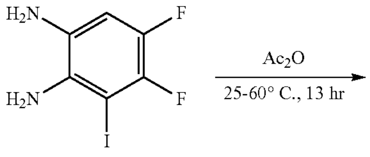
I-549
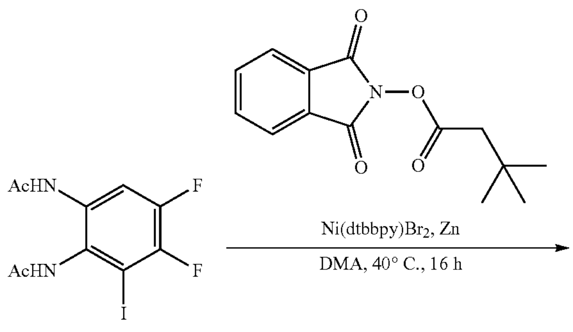
I-550
-continued
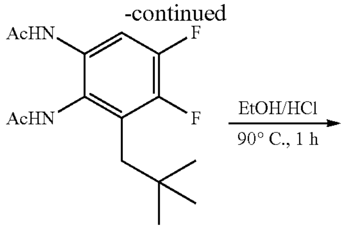
I-551
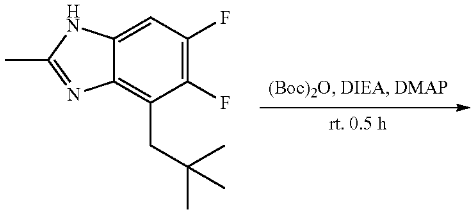
I-552
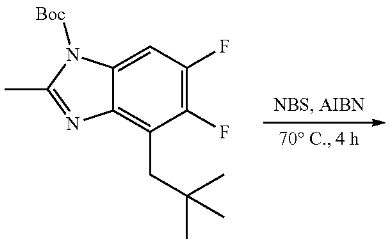
I-553
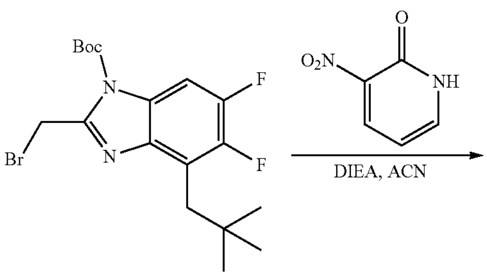
I-554

-continued

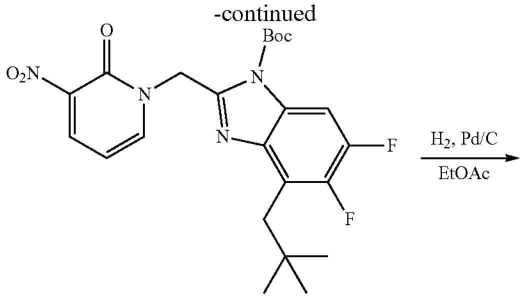

I-555

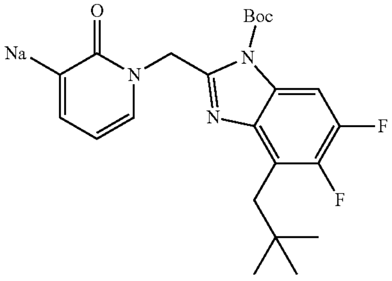

I-556

4,5-Difluoro-2-nitro-aniline (5 g, 28.72 mmol, 1 eq) was added in one portion to $I_2$ (21.87 g, 86.16 mmol, 17.35 mL, 3 eq) dissolved in EtOH (50 mL) followed by $Ag_2SO_4$ (22.39 g, 71.80 mmol, 12.17 mL, 2.5 eq). The mixture was heated to 90° C. and stirred for 12 hr. The reaction mixture was filtered and concentrated under reduced pressure to give a residue. The residue was purified by column chromatography to give 4-difluoro-2-iodo-6-nitro-aniline (I-548) (15 g, 87% yield) as a yellow solid.

To a solution of 3,4-difluoro-2-iodo-6-nitro-aniline (7.45 g, 24.83 mmol, 1 eq) in $H_2O$ (20 mL) and EtOH (100 mL) was added Fe (6.93 g, 124.17 mmol, 5 eq) and $NH_4Cl$ (13.28 g, 248.33 mmol, 8.68 mL, 10 eq) under $N_2$ at 25° C. The mixture was warmed and stirred at 80° C. for 1 hr. The reaction mixture was filtered and concentrated under reduced pressure to remove EtOH, then diluted with water (50 mL) and extracted with EtOAc 100 mL (50 mL×2). The combined organic layers were washed with brine (50 mL), dried over $Na_2SO_4$, filtered and concentrated under reduced pressure to give 5-difluoro-3-iodo-benzene-1,2-diamine (I-549) (14 g) as a brown oil. LCMS m/z 271.0 $(M+1)^+$.

A mixture of 4,5-difluoro-3-iodo-benzene-1,2-diamine (13.9 g, 51.48 mmol, 1 eq) in $Ac_2O$ (30 mL) was stirred at 25° C. for 1 hr and then the mixture was stirred at 60° C. for 12 hr. The reaction mixture was poured into ice water (100 mL). The mixture was filtered and concentrated under reduced pressure to give N-(2-acetamido-4,5-difluoro-3-iodo-phenyl)acetamide (I-550) (12.5 g) as a yellow solid. LCMS m/z 355.1 $(M+1)^+$.

To a solution of N-(2-acetamido-4,5-difluoro-3-iodo-phenyl)acetamide (7 g, 19.77 mmol, 1 eq), (1,3-dioxoisoindolin-2-yl) 3,3-dimethylbutanoate (7.75 g, 29.65 mmol, 1.5 eq), and Zn (2.59 g, 39.54 mmol, 2 eq) in DMA (42 mL) was added (dtbbpy)NiBr (4.81 g, 9.88 mmol, 0.5 eq) at 20° C., then the reaction was stirred at 40° C. for 12 h. The reaction mixture was poured into water 50 mL and extracted with EtOAc (25 mL×2). The combined organic layers were washed with brine (15 mL*2), dried over Na2SO4, filtered and concentrated under reduced pressure to give a residue. The residue was purified by column chromatography to give a residue. The residue was purified by prep-TLC to give N-[2-acetamido-3-(2,2-dimethylpropyl)-4,5-difluoro-phenyl]acetamide (I-551) (330 mg, 5% yield) as a white solid. $^1H$ NMR (400 MHz, $CD_3OD$) δ 0.94 (d, J=0.98 Hz, 9H) 2.16 (d, J=6.97 Hz, 6H) 2.64 (d, J=2.69 Hz, 2H) 7.53 (dd, J=11.74, 8.31 Hz, 1H).

A solution of N-[2-acetamido-3-(2,2-dimethylpropyl)-4,5-difluoro-phenyl]acetamide (330 mg, 1.11 mmol, 1 eq) and HCl (6 M, 5 mL, 27.12 eq) in EtOH (5 mL) was stirred at 90° C. for 1 h. The mixture was concentrated in vacuum to give a solid. To the solid was added sat. aq. $NaHCO_3$ to pH=7 and the mixture was extracted with EtOAc (10 mL*2), washed with brine (5 mL*2), dried over $Na_2SO_4$, and concentrated in vacuum to give 4-(2,2-dimethylpropyl)-5,6-difluoro-2-methyl-1H-benzimidazole (I-552) (320 mg) as a yellow solid. LCMS m/z 238.9 $(M+1)^+$.

To a solution of 4-(2,2-dimethylpropyl)-5,6-difluoro-2-methyl-1H-benzimidazole (320 mg, 1.34 mmol, 1 eq), DIEA (347.13 mg, 2.69 mmol, 467.84 uL, 2 eq) and DMAP (16.41 mg, 134.30 umol, 0.1 eq) in DCM (5 mL) was added $Boc_2O$ (381.04 mg, 1.75 mmol, 401.09 uL, 1.3 eq) at 0° C. The reaction mixture was stirred at 20° C. for 0.5 h and then concentrated. The residue was purified by column chromatography to give tert-butyl 4-(2,2-dimethylpropyl)-5,6-difluoro-2-methyl-benzimidazole-1-carboxylate (I-553) (360 mg, 79% yield) as a yellow solid. LCMS m/z 282.9 $(M+1)^+$.

To a solution of tert-butyl 4-(2,2-dimethylpropyl)-5,6-difluoro-2-methyl-benzimidazole-1-carboxylate (360 mg, 1.06 mmol, 1 eq) in $CCl_4$ (10 mL) was added AIBN (40.18 mg, 244.69 umol, 0.23 eq) and NBS (189.35 mg, 1.06 mmol, 1 eq) at 20° C. The reaction mixture was stirred at 70° C. for 2 h. The mixture was concentrated in vacuum to give tert-butyl 2-(bromomethyl)-4-(2,2-dimethylpropyl)-5,6-difluoro-benzimidazole-1-carboxylate (I-554) (710 mg) as a yellow oil.

A solution of tert-butyl 2-(bromomethyl)-4-(2,2-dimethylpropyl)-5,6-difluoro-benzimidazole-1-carboxylate (710 mg, 1.70 mmol, 1 eq), 3-nitro-1H-pyridin-2-one (286.04 mg, 2.04 mmol, 1.2 eq), and DIEA (329.85 mg, 2.55 mmol, 444.54 uL, 1.5 eq) in ACN (5 mL) was stirred at 20° C. for 2 h. The reaction mixture was concentrated and the residue was purified by column chromatography to give tert-butyl 4-(2,2-dimethylpropyl)-5,6-difluoro-2-[(3-nitro-2-oxo-1-pyridyl)methyl]benzimidazole-1-carboxylate (I-555) (460 mg, 57% yield) as a yellow oil. LCMS m/z 376.9 $(M+1-100)^+$.

A solution of tert-butyl 4-(2,2-dimethylpropyl)-5,6-difluoro-2-[(3-nitro-2-oxo-1-pyridyl)methyl]benzimidazole-1-carboxylate (300 mg, 629.63 umol, 1 eq) and Pd/C (260 mg, 10% purity) in EtOAc (10 mL) was stirred at 20° C. for 1 h under $H_2$ (15 psi). The mixture was concentrated in vacuum and the filtrate was concentrated in vacuum to give tert-butyl 2-[(3-amino-2-oxo-1-pyridyl)methyl]-4-(2,2-dimethylpropyl)-5,6-difluoro-benzimidazole-1-carboxylate (I-556) (270 mg) as a yellow solid. LCMS m/z 447.0 $(M+1)^+$.

Example 61

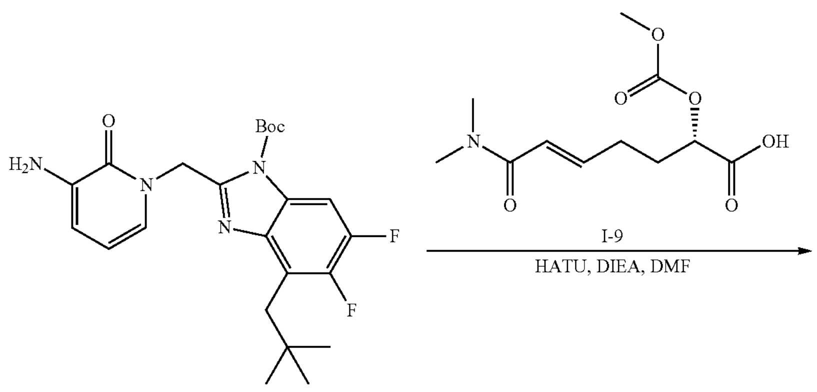

I-556

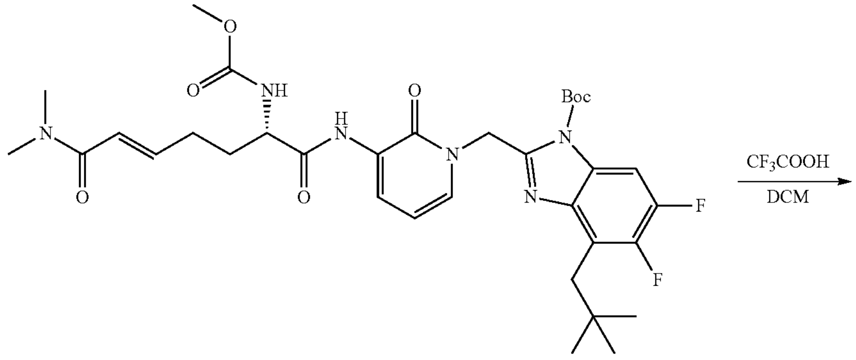

461

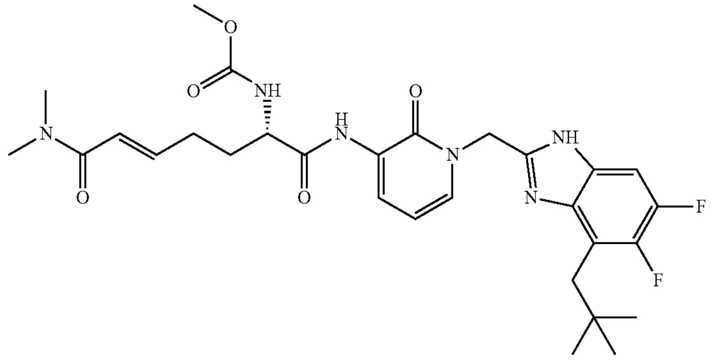

467

To a solution of tert-butyl 2-[(3-amino-2-oxo-1-pyridyl) methyl]-4-(2,2-dimethylpropyl)-5,6-difluoro-benzimidazole-1-carboxylate (40 mg, 89.59 umol, 1 eq), (E,2S)-7-(dimethylamino)-2-(methoxycarbonylamino)-7-oxo-hept-5-enoic acid (23.14 mg, 89.59 umol, 1 eq) and DIEA (57.89 mg, 447.95 umol, 78.02 uL, 5 eq) in DMF (1 mL) was added HATU (68.13 mg, 179.18 umol, 2 eq) at 20° C., then the reaction was stirred at 20° C. for 12 h. The reaction mixture was poured into water 10 mL and extracted with EtOAc 10 mL (5 mL×2). The combined organic layers were washed with brine 5 mL (5 mL×1), dried over $Na_2SO_4$, filtered and concentrated under reduced pressure to give a residue. The residue was purified by prep-TLC and prep-HPLC to give tert-butyl 2-[[3-[[(E,2S)-7-(dimethylamino)-2-(methoxycarbonylamino)-7-oxo-hept-5-enoyl]amino]-2-oxo-1-pyridyl] methyl]-4-(2,2-dimethylpropyl)-5,6-difluoro-benzimidazole-1-carboxylate (Compound 461) (3.1 mg, 5% yield) as a white solid. LCMS m/z 687.3 $(M+1)^+$. $^1H$ NMR (400 MHz, DMSO-$d_6$) δ 0.68 (s, 9H) 1.64 (s, 10H) 1.80 (br s, 1H) 2.09-2.22 (m, 2H) 2.57-2.67 (m, 2H) 2.78 (s, 3H) 2.93 (s, 3H) 3.47 (s, 3H) 4.10 (br s, 1H) 5.55 (s, 2H) 6.23-6.36 (m, 2H) 6.48-6.62 (m, 1H) 7.41 (dd, J=6.91, 1.65 Hz, 1H) 7.57-7.75 (m, 2H) 8.22 (dd, J=7.40, 1.65 Hz, 1H) 9.12 (s, 1H).

A solution of tert-butyl 2-[[3-[[(E,2S)-7-(dimethylamino)-2-(methoxycarbonylamino)-7-oxo-hept-5-enoyl] amino]-2-oxo-1-pyridyl]methyl]-4-(2,2-dimethylpropyl)-5,6-difluoro-benzimidazole-1-carboxylate (300 mg, 436.84 umol, 1 eq) and $CF_3COOH$ (924 mg, 8.10 mmol, 600 uL, 18.55 eq) in DCM (2.4 mL) was stirred at 20° C. for 0.5 h. The mixture was concentrated in vacuum to give oil. The oil was purified by prep-HPLC to give methyl N-[(E,1S)-6-(dimethylamino)-1-[[1-[[4-(2,2-dimethylpropyl)-5,6-difluoro-1H-benzimidazol-2-yl]methyl]-2-oxo-3-pyridyl]carbamoyl]-6-oxo-hex-4-enyl]carbamate (Compound 467) (74.3 mg, 29% yield) as a white solid. LCMS m/z 587.3 $(M+1)^+$. $^1$HNMR (400 MHz, DMSO-$d_6$) δ 0.93 (s, 9H) 1.64-1.78 (m, 1H) 1.87 (br d, J=6.72 Hz, 1H) 2.16-2.30 (m, 2H) 2.84 (s, 5H) 2.99 (s, 3H) 3.54 (s, 3H) 4.10-4.23 (m, 1H) 5.40 (s, 2H) 6.30-6.44 (m, 2H) 6.53-6.68 (m, 1H) 7.38-7.49 (m, 1H) 7.52-7.60 (m, 1H) 7.74 (br d, J=7.58 Hz, 1H) 8.26 (dd, J=7.34, 1.22 Hz, 1H) 9.26 (s, 1H).

The following compounds were prepared according to the procedures described for the synthesis of Example 61 using the appropriate intermediates.

-continued

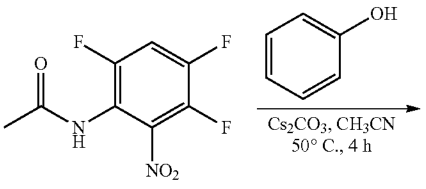

I-568

| Compound | Structure | LCMS Data |
|---|---|---|
| 488 | 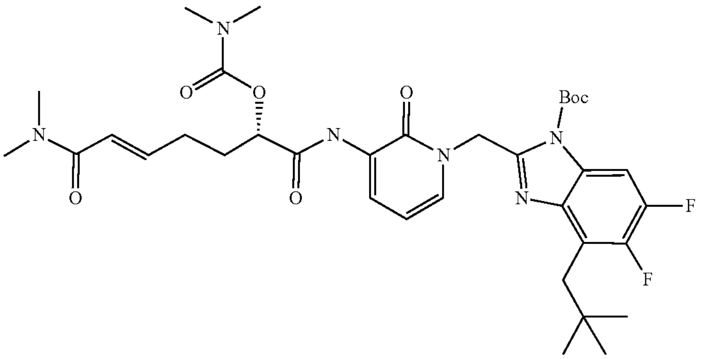 | LCMS m/z 701.3 $(M + 1)^+$ |
| 465 | 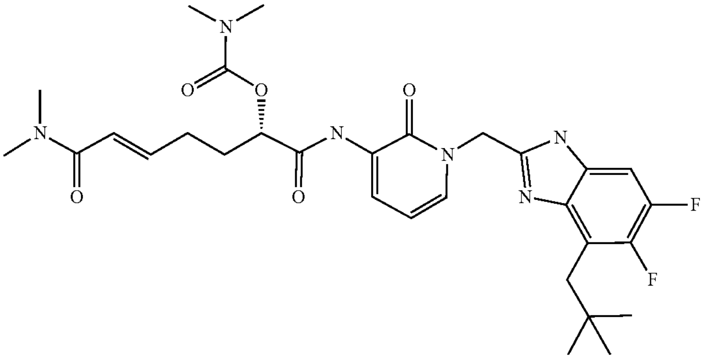 | LCMS m/z 601.3 $(M + 1)^+$ |

The Synthesis of Intermediate I-575

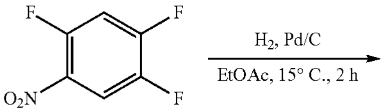

I-565

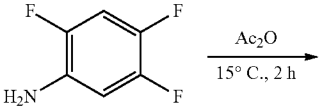

I-566

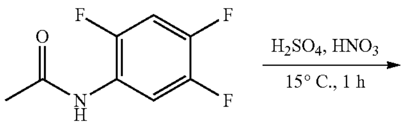

I-567

-continued

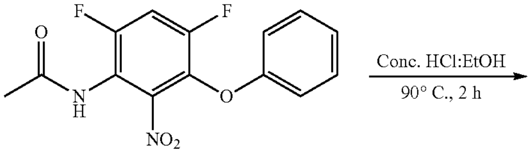

I-569

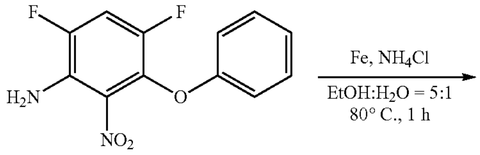

I-570

-continued

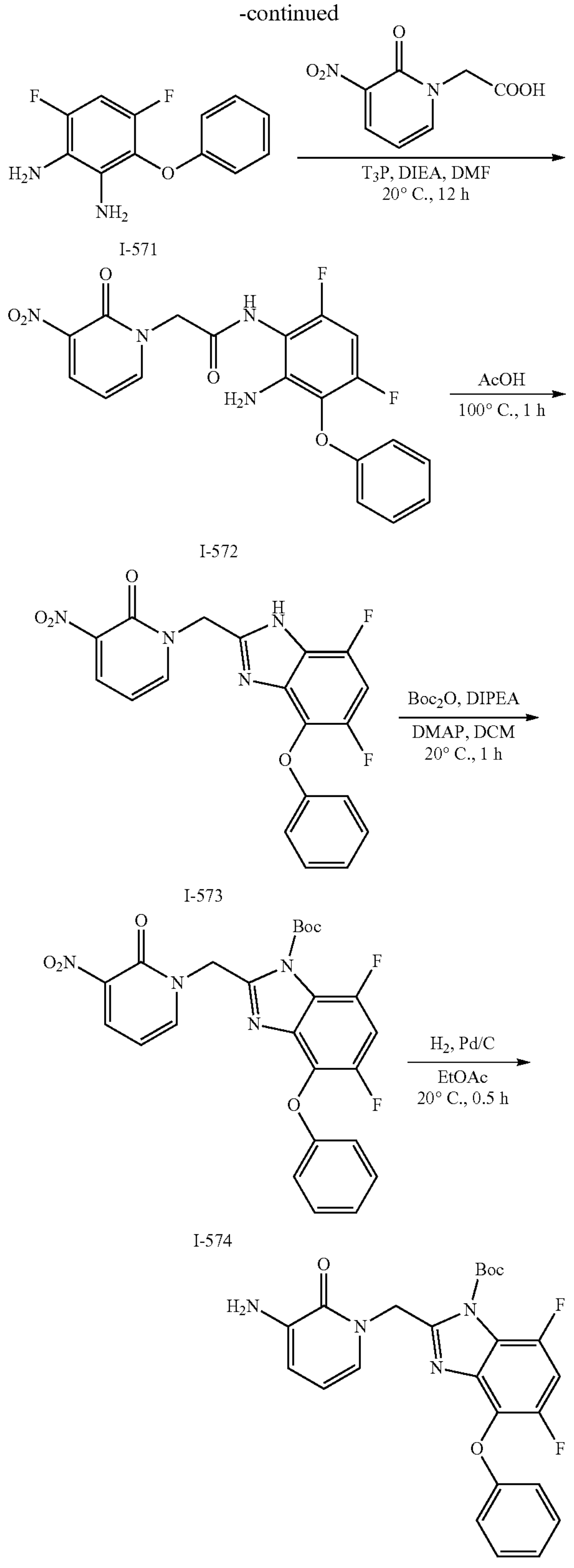

I-571

I-572

I-573

I-574

I-575

To a solution of 1,2,4-trifluoro-5-nitro-benzene (23 g, 130 mmol, 15 mL, 1 eq) in MeOH (250 mL) was added Pd/C (10 g, 10% purity) under $N_2$. The suspension was degassed under vacuum and purged with $H_2$ several times. The mixture was stirred under $H_2$ (15 psi) at 15° C. for 13 hour. The mixture was filtered and concentrated under reduced pressure to give 2,4,5-trifluoroaniline (I-566) (18 g, 122 mmol, 94.2% yield) as a brown oil which was used in the next step without further purification.

A solution of 2,4,5-trifluoroaniline (18 g, 122 mmol, 12 mL, 1 eq) in $Ac_2O$ (100 mL) was stirred at 15° C. for 1 hr. The precipitate was filtered to give a white solid. The crude product N-(2,4,5-trifluorophenyl)acetamide (I-567) (21 g) was used in the next step without further purification as a white solid.

To a solution of N-(2,4,5-trifluorophenyl)acetamide (10 g, 53 mmol, 1 eq) in $H_2SO_4$ (100 mL) was added $HNO_3$ (3.33 g, 53 mmol, 2.4 mL, 1 eq) at 0° C. The mixture was stirred at 0° C. for 1 hr. Poured the reaction mixture to ice, then the mixture was extracted with EtOAc (200 mL). The organic layer was washed with sat. $NaHCO_3$ (500 mL) and brine (250 mL), dried over $Na_2SO_4$ and concentrated to give a crude product. The crude N-(3,4,6-trifluoro-2-nitro-phenyl) acetamide (I-568) (7.2 g, 30.7 mmol, 58% yield) was used in the next step without further purification as a yellow solid.

A mixture of N-(3,4,6-trifluoro-2-nitro-phenyl)acetamide (1 g, 4.3 mmol, 1 eq), phenol (442 mg, 4.70 mmol, 413 Ul, 1.1 eq) and $Cs_2CO_3$ (2.09 g, 6.41 mmol, 1.5 eq) in $CH_3CN$ (10 mL) was stirred at 55° C. for 4 h. Water (5 mL) was added to the mixture. The mixture was extracted with EtOAc (10 mL). The combined organic layer was washed with brine (10 mL), dried over $Na_2SO_4$ and filtered. The filtrate was concentrated under reduced pressure to give a residue. The residue was purified by column to give N-(4,6-difluoro-2-nitro-3-phenoxy-phenyl) acetamide (I-569) (0.95 g, 72% yield) as a white solid. LCMS m/z 307.9 $(M+1)^+$.

A solution of N-(4,6-difluoro-2-nitro-3-phenoxy-phenyl) acetamide (0.95 g, 3.08 mmol, 1 eq) in HCl (12M) (5 mL) and EtOH (5 mL) was heated to 90° C. for 2 h. The mixture was concentrated to remove EtOH, then extracted with EtOAc (10 mL). The organic layer was washed with sat. $NaHCO_3$ (20 mL), dried over $Na_2SO_4$ and filtered. The filtrate was concentrated under reduced pressure to give 4,6-difluoro-2-nitro-3-phenoxy-aniline (I-570) (0.715 g, 87% yield) was used in the next step without further purification as a yellow solid. $^1H$ NMR (400 MHz, $CDCl_3$) δ 7.28-7.36 (m, 2H) 7.06-7.19 (m, 2H) 6.94 (d, J=8.60 Hz, 2H) 5.12 (s, 2H).

A mixture of 4,6-difluoro-2-nitro-3-phenoxy-aniline (0.7 g, 2.63 mmol, 1 eq), Fe(734 mg, 13.2 mmol, 5 eq) and $NH_4Cl$ (1.41 g, 26.3 mmol, 919 Ul, 10 eq) in $EtOH/H_2O$ (5:1) (10 mL) was heated to 80° C. for 1 h. The mixture was filtered and the filtrate was concentrated to give 4,6-difluoro-3-phenoxy-benzene-1,2-diamine (I-571) (0.61 g) which was used in the next step without further purification as a brown solid.

To a mixture of 4,6-difluoro-3-phenoxy-benzene-1,2-diamine (0.61 g, 2.58 mmol, 1 eq), 2-(3-nitro-2-oxo-1-pyridyl) acetic acid (563 mg, 2.84 mmol, 1.1 eq) and DIPEA (667 mg, 5.16 mmol, 900 Ul, 2 eq) in DCM (6 mL) was added $T_3P$ (2.46 g, 3.87 mmol, 2.30 mL, 50% purity, 1.5 eq) at 20° C. The mixture was stirred at 20° C. for 12 h. The mixture was concentrated to give a crude product. The crude product N-(2-amino-4,6-difluoro-3-phenoxy-phenyl)-2-(3-nitro-2-oxo-1-pyridyl)acetamide (I-572) (1.08 g) was used in the next step without further purification as a brown solid. LCMS m/z 417.0 $(M+1)^+$.

A solution of N-(2-amino-4,6-difluoro-3-phenoxy-phenyl)-2-(3-nitro-2-oxo-1-pyridyl) acetamide (1.08 g, 2.6 mmol, 1 eq) in HOAc (10 mL) was heated to 100° C. for 1 h. The mixture was concentrated to give a crude product. The crude residue was diluted in EtOAc (50 mL) and washed with sat. $NaHCO_3$ (10 mL*3). The organic layer was dried over $Na_2SO_4$ and concentrated to give 1-[(5,7-difluoro-4-phenoxy-1H-benzimidazol-2-yl)methyl]-3-nitro-pyridin-2-one (I-573) (450 mg) as a yellow solid. LCMS m/z 399.0 $(M+1)^+$.

To a solution of 1-[(5,7-difluoro-4-phenoxy-1H-benzimidazol-2-yl)methyl]-3-nitro-pyridin-2-one (0.08 g, 201 umol, 1 eq), DIPEA (51.9 mg, 402 umol, 70 Ul, 2 eq), DMAP (2.5 mg, 20 umol, 0.1 eq) in DCM (1 mL) was added $Boc_2O$ (52.6 mg, 241 umol, 55 Ul, 1.2 eq) at 20° C. under $N_2$. The mixture was stirred at 20° C. for 1 hour. The mixture was concentrated to give a crude product at 20° C. under reduced pressure. The residue was purified by prep-TLC to give tert-butyl 5,7-difluoro-2-[(3-nitro-2-oxo-1-pyridyl)methyl]-4-phenoxy-benzimidazole-1-carboxylate (I-574) (0.08 g, 161 umol, 79.9% yield) as a white solid.

To a solution of tert-butyl 5,7-difluoro-2-[(3-nitro-2-oxo-1-pyridyl)methyl]-4-phenoxy-benzimidazole-1-carboxylate (80 mg, 161 umol, 1 eq) in EtOAc (2 mL) was added Pd/C (50 mg, 10% purity) under $N_2$. The suspension was degassed under vacuum and purged with $H_2$ several times. The mixture was stirred under $H_2$ (15 psi) at 20° C. for 0.5 hours. The mixture was filtered and the filtrate was concentrated to give tert-butyl [(3-amino-2-oxo-1-pyridyl)methyl]-5,7-difluoro-4-phenoxy-benzimidazole-1-carboxylate (I-575) (53 mg) as a brown solid.

The following intermediates were prepared according to the procedures described for the synthesis of I-575 using the appropriate reagents.

| Compound | Structure | LCMS Data |
|---|---|---|
| I-576 | 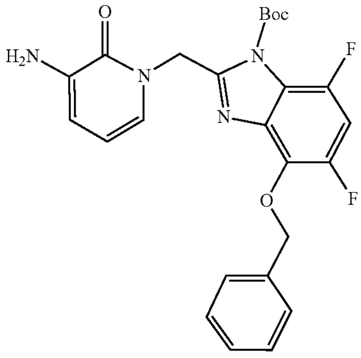 [SMILES: CC(C)(C)OC(=O)n1c(Cn2cccc(N)c2=O)nc2c(OCc3ccccc3)c(F)cc(F)c21] | LCMS m/z 483.2 $(M + 1)^+$ |
| I-577 | 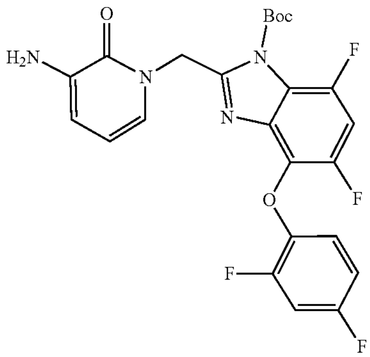 [SMILES: CC(C)(C)OC(=O)n1c(Cn2cccc(N)c2=O)nc2c(Oc3ccc(F)cc3F)c(F)cc(F)c21] | LCMS m/z 505.2 $(M + 1)^+$ |

Example 62

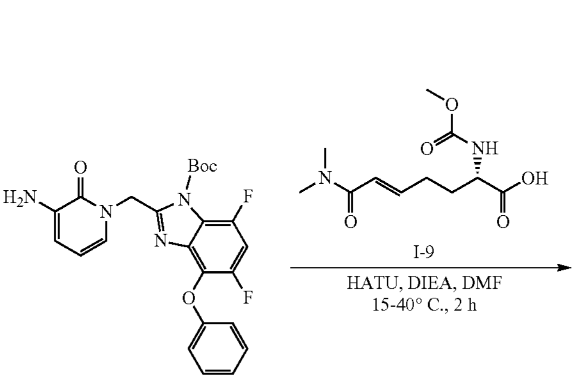

I-575

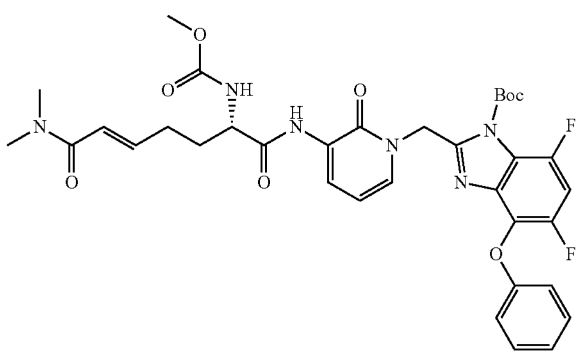

413

HATU (64.5 mg, 170 umol, 1.5 eq) was added to a mixture of tert-butyl 2-[(3-amino-2-oxo-1-pyridyl)methyl]-5,7-difluoro-4-phenoxy-benzimidazole-1-carboxylate (53 mg, 113 umol, 1 eq), (E,2S)-7-(dimethylamino)-2-(methoxycarbonylamino)-7-oxo-hept-5-enoic acid (31 mg, 119 umol, 1.05 eq) and DIPEA (29 mg, 226 umol, 2 eq) in DMF (1 mL) at 15° C. Then the mixture was heated to 40° C. and stirred for 2 h. The mixture was extracted with EtOAc (10 mL×2). The combined organic layers were washed with brine (20 mL), dried over $Na_2SO_4$ and filtered. The filtrate was concentrated under reduced pressure to give a residue. The residue was purified by prep-HPLC to give tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-phenoxy-benzimidazole-1-carboxylate (Compound 413) (5.8 mg, 7% yield) as a white solid. LCMS m/z 709.3 $(M+1)^+$. $^1H$ NMR (400 MHz, DMSO-$d_6$) δ 9.12-9.29 (m, 1H) 8.14-8.32 (m, 1H) 7.72 (brs, 1H) 7.39-7.60 (m, 2H) 7.17-7.35 (m, 2H) 6.97-7.08 (m, 1H) 6.79-6.90 (m, 2H) 6.54-6.66 (m, 1H) 6.21-6.42 (m, 2H) 5.46-5.57 (m, 1H) 5.28 (s, 1H) 4.16 (br s, 1H) 3.53 (s, 3H) 2.97 (s, 3H) 2.82 (s, 3H) 2.15-2.30 (m, 2H) 1.69-1.94 (m, 2H) 1.65 (s, 4H) 1.34-1.42 (m, 5H).

The following compound was prepared according to the procedures described for the synthesis of Example 62 using the appropriate intermediates.

| Compound | Structure | LCMS Data |
|---|---|---|
| 407 | 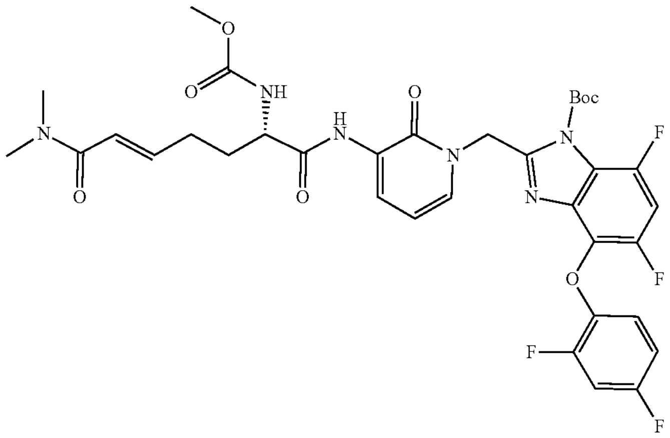 [SMILES: COC(=O)N[C@@H](CC/C=C/C(=O)N(C)C)C(=O)Nc1cccn(Cc2nc3c(Oc4ccc(F)cc4F)c(F)cc(F)c3n2C(=O)OC(C)(C)C)c1=O] | LCMS m/z 645.3 (M + 1-100)$^+$ |

Example 63

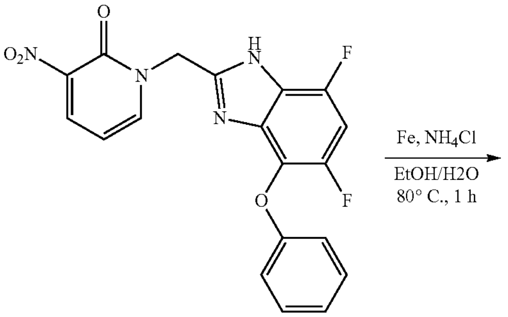

I-573

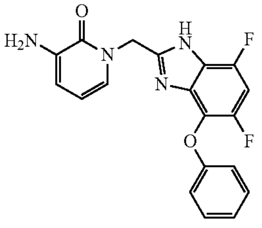

I-578

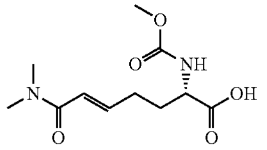

I-9

HATU, DIEA, DMF
15-40° C., 2 h

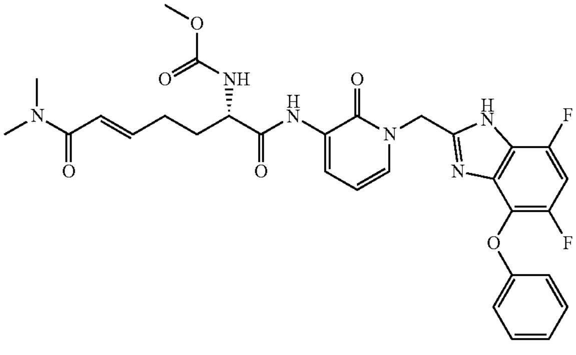

434

To a solution of 1-[(5,7-difluoro-4-phenoxy-1H-benzimidazol-2-yl)methyl]-3-nitro-pyridine-2-one (0.2 g, 502.11 umol, 1 eq) in EtOH/H2O (5:1) (2 mL) was added Fe (140 mg, 2.51 mmol, 5 eq), $NH_4Cl$ (269 mg, 5.02 mmol, 10 eq) under $N_2$. The mixture was stirred at 80° C. for 1 hour. The mixture was filtered and filtrate was concentrated to give 3-amino-1-((5,7-difluoro-4-phenoxy-1H-benzo[d]imidazol-2-yl)methyl)pyridin-2(1H)-one (I-578) (185 mg) was used in the next step without further purification as a brown solid. LCMS m/z 368.9 (M+1)$^+$.

The following intermediates were prepared according to the procedures described for the synthesis of I-578 using the appropriate reagents.

| Compound | Structure | LCMS Data |
|---|---|---|
| I-579 | 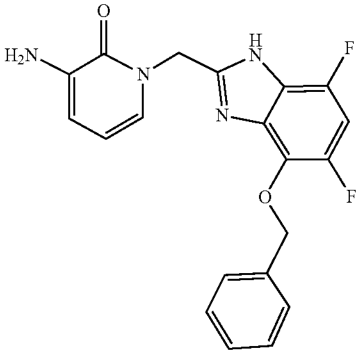 [SMILES: Nc1cccn(Cc2nc3c(OCc4ccccc4)c(F)cc(F)c3[nH]2)c1=O] | LCMS m/z 383.2 (M + 1)$^+$ |
| I-580 | 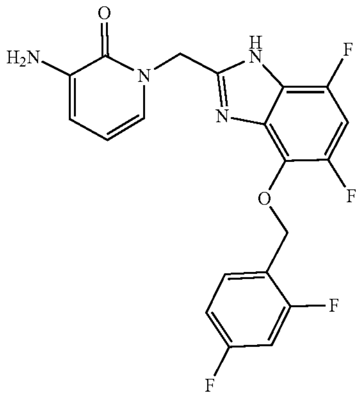 [SMILES: Nc1cccn(Cc2nc3c(OCc4ccc(F)cc4F)c(F)cc(F)c3[nH]2)c1=O] | LCMS m/z 419.2 (M + 1)$^+$ |

-continued

| Compound | Structure | LCMS Data |
|---|---|---|
| I-581 | 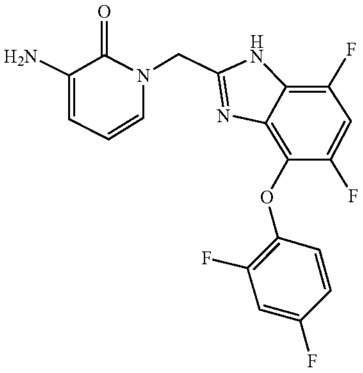 [SMILES: Nc1cccn(Cc2nc3c(Oc4ccc(F)cc4F)c(F)cc(F)c3[nH]2)c1=O] | LCMS m/z 405.2 (M + 1)$^+$ |
| I-582 | 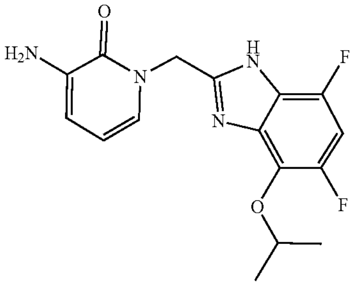 [SMILES: CC(C)Oc1c(F)cc(F)c2[nH]c(Cn3cccc(N)c3=O)nc12] | LCMS m/z 335.2 (M + 1)$^+$ |

HATU (286 mg, 753 umol, 1.5 eq) was added to a mixture of 3-amino-1-[(5,7-difluoro-4-phenoxy-1H-benzimidazol-2-yl)methyl]pyridine-2-one (185 mg, 502 umol, 1 eq), (E,2S)-7-(dimethylamino)-2-(methoxycarbonylamino)-7-oxo-hept-5-enoic acid (143 mg, 552 umol, 1.1 eq) and DIPEA (130 mg, 1.00 mmol, 2 eq) in DMF (5 mL) at 15° C. The mixture was heated to 40° C. and stirred for 2 h. The mixture was filtered the filtrate was purified by prep-HPLC to give methyl N-[(E,1S)-1-[[1-[(5,7-difluoro-4-phenoxy-1H-benzimidazol-2-yl)methyl]-2-oxo-3-pyridyl]carbamoyl]-6-(dimethylamino)-6-oxo-hex-4-enyl]carbamate (Compound 434) (101.2 mg, 33% yield) as a white solid. LCMS m/z 609.3 $(M+1)^+$. $^1H$ NMR (400 MHz, DMSO-$d_6$) δ 9.25 (s, 1H) 8.25 (br d, J=6.11 Hz, 1H) 7.72 (br d, J=7.70 Hz, 1H) 7.56 (br d, J=6.85 Hz, 1H) 7.20-7.41 (m, 3H) 7.08 (br t, J=7.27 Hz, 1H) 6.92 (br d, J=8.07 Hz, 2H) 6.53-6.66 (m, 1H) 6.30-6.43 (m, 2H) 5.36 (s, 2H) 4.17 (br s, 1H) 3.54 (s, 3H) 2.99 (s, 3H) 2.84 (s, 3H) 2.17-2.31 (m, 2H) 1.64-1.93 (m, 2H).

The following compounds were prepared according to the procedures described for the synthesis of Example 63 using the appropriate intermediates.

| Compound | Structure | LCMS Data |
|---|---|---|
| 433 | 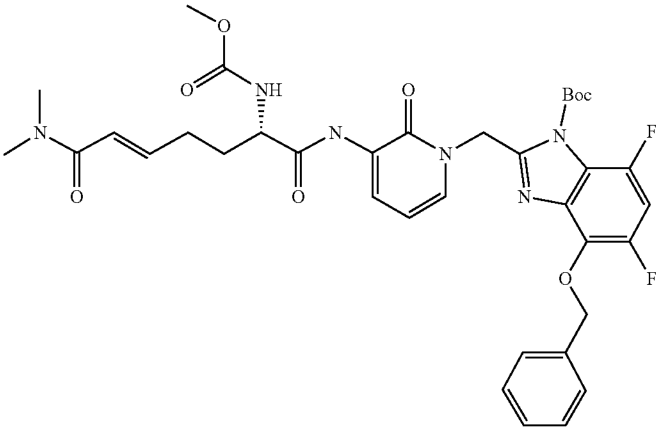 | LCMS m/z 723.3 (M + 1)$^+$ |
| 432 | 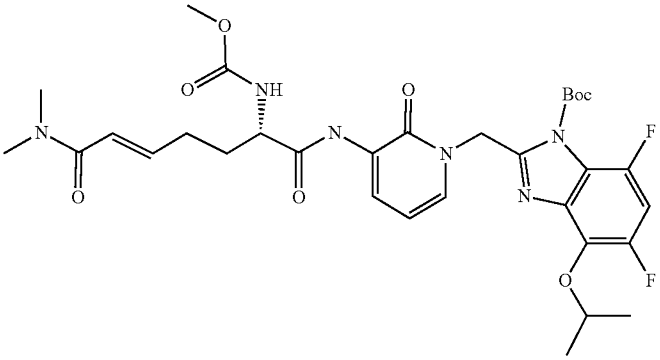 | LCMS m/z 575.2 (M + 1)$^+$ |

-continued
| Compound | Structure | LCMS Data |
|---|---|---|
| 437 | 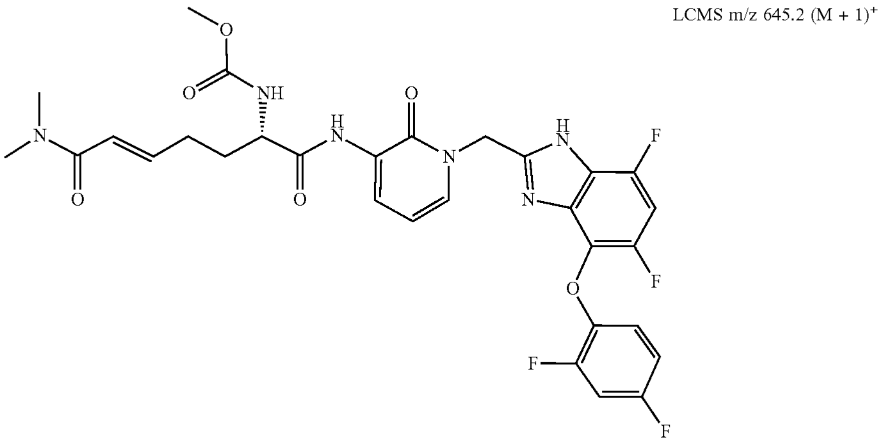 | LCMS m/z 645.2 $(M + 1)^+$ |
| 438 | 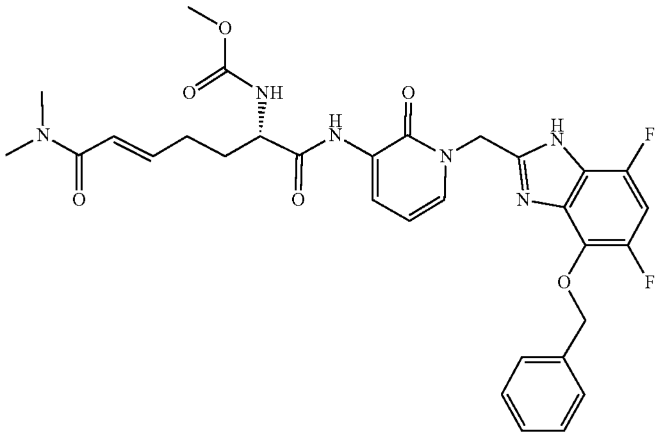 [SMILES: COC(=O)N[C@@H](CC/C=C/C(=O)N(C)C)C(=O)Nc1cccn(Cc2nc3c(OCc4ccccc4)c(F)cc(F)c3[nH]2)c1=O] | LCMS m/z 623.2 $(M + 1)^+$ |
| 439 | 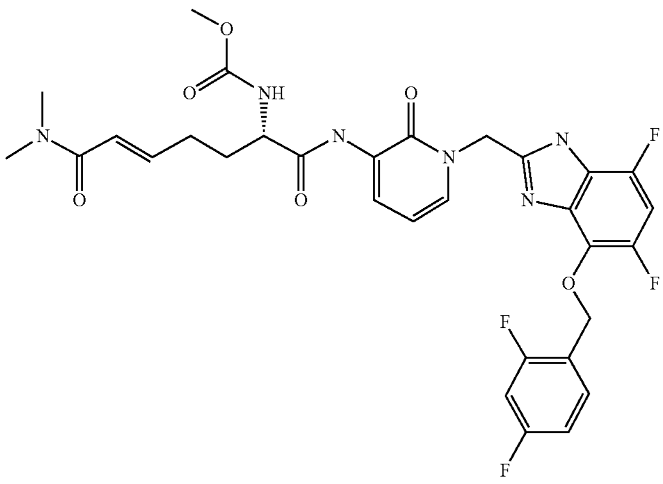 | LCMS m/z 659.3 $(M + 1)^+$ |

-continued
| Compound | Structure | LCMS Data |
|---|---|---|
| 453 | 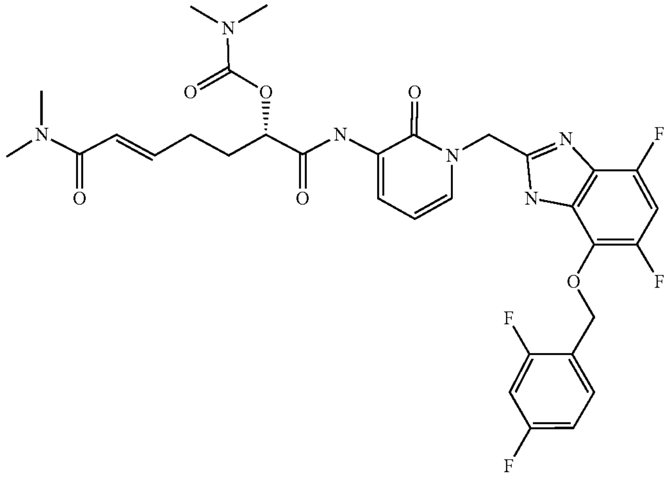 | LCMS m/z 673.2 $(M + 1)^+$ |
The Synthesis of Intermediate I-603
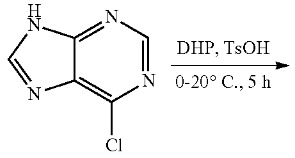
I-595
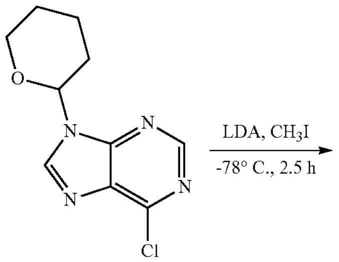
I-596
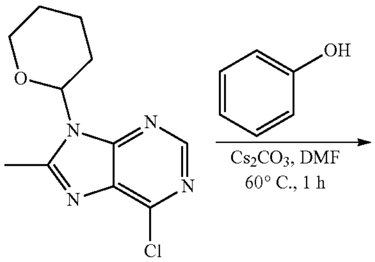
I-597
-continued
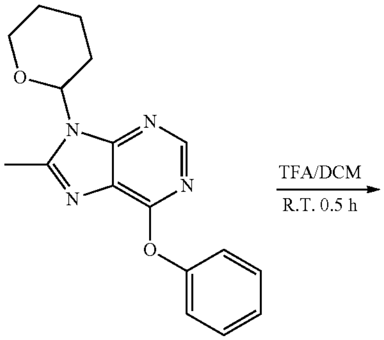
I-598
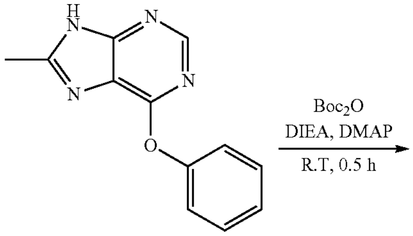
I-599
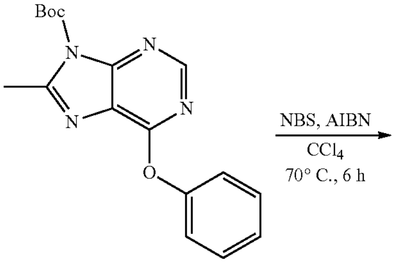
I-600

-continued

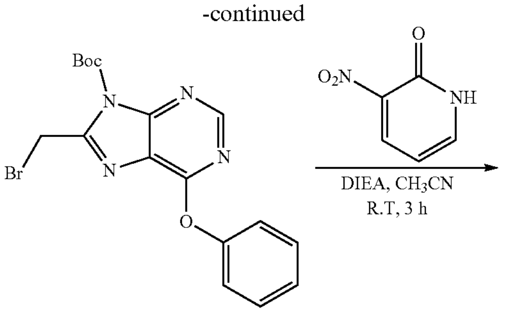

I-601

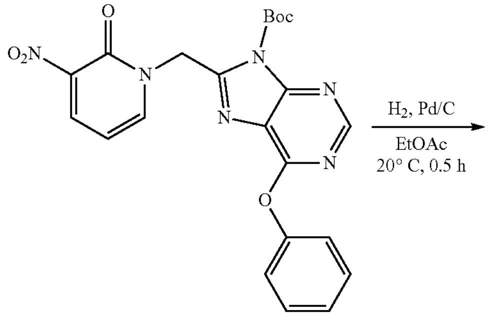

I-602

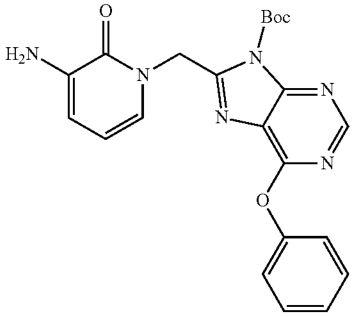

I-603

DHP (4.79 g, 56.9 mmol, 5.2 mL, 1.1 eq) was added to a mixture of 6-chloro-9H-purine (8 g, 51.7 mmol, 1 eq) and TsOH·$H_2O$ (984 mg, 5.18 mmol, 0.1 eq) in $CHCl_3$ (80 mL) at 0° C. dropwise. The mixture was stirred at 20° C. for 5 h. Water (100 mL) was added to the mixture and the mixture was extracted with DCM (100 mL×2). The combined organic layers were washed with brine (100 mL), dried over $Na_2SO_4$ and filtered. The filtrate was concentrated under reduced pressure to give a residue. The residue was stirred in petroleum ether (100 mL) for 2 h, the precipitate was filtered and dried to give 6-chloro-9-tetrahydropyran-2-yl-purine (I-596) (11.3 g, 92% yield) as a yellow solid. $^1H$ NMR (400 MHz, $CDCl_3$) δ 8.75 (s, 1H) 8.34 (s, 1H) 5.79 (dd, J=10.36, 2.43 Hz, 1H) 4.13-4.25 (m, 1H) 3.73-3.84 (m, 1H) 2.00-2.21 (m, 3H) 1.65-1.87 (m, 3H).

To a solution of 6-chloro-9-tetrahydropyran-2-yl-purine (3 g, 12.6 mmol, 1 eq) in THF (30 mL) was added LDA (2 M, 8.8 mL, 1.40 eq) at −78° C. dropwise. The mixture was stirred at −78° C. for 0.5 h, then $CH_3I$ (17.8 g, 126 mmol, 7.8 mL, 10 eq) was added to the mixture and stirred for another 2 h. The reaction was quenched with sat. $NH_4Cl$ (20 mL). The mixture was extracted with EtOAc (30 mL). The combined organic layers were washed with brine (20 mL), dried over $Na_2SO_4$ and filtered. The filtrate was concentrated under reduced pressure to give 6-chloro-8-methyl-9-tetrahydropyran-2-yl-purine (I-597) (3.5 g) was used in the next step without further purification as a red oil. $^1H$ NMR (400 MHz, $CDCl_3$) δ 8.68 (s, 1H) 5.78 (dd, J=10.36, 2.43 Hz, 1H) 4.20-4.24 (m, 1H) 3.72-3.78 (m, 1H) 2.82 (s, 3H) 2.49-2.54 (m, 1H) 2.12-2.14 (m, 1H) 1.92-1.95 (m, 1H) 1.76-1.81 (m, 2H) 1.66-1.68 (m, 1H).

A mixture of 6-chloro-8-methyl-9-tetrahydropyran-2-yl-purine (1 g, 3.96 mmol, 1 eq), phenol (447 mg, 4.75 mmol, 1.2 eq) and $Cs_2CO_3$ (2.58 g, 7.91 mmol, 2 eq) in DMF (10 mL) was stirred at 60° C. for 1 h. Water (10 mL) was added to the mixture. The mixture was extracted with EtOAc (10 mL). The combined organic layers were washed with brine (10 mL), dried over $Na_2SO_4$ and filtered. The filtrate was concentrated under reduced pressure to give a residue. The crude product 8-methyl-6-phenoxy-9-tetrahydropyran-2-yl-purine (I-598) (1.2 g) was used in the next step without further purification as a red oil. $^1H$ NMR (400 MHz, $CDCl_3$) δ 7.39-7.47 (m, 2H) 7.23-7.28 (m, 3H) 5.77 (dd, J=11.25, 2.43 Hz, 1H) 4.20 (dd, J=10.47, 3.20 Hz, 1H) 3.69-3.78 (m, 1H) 2.78 (s, 3H) 2.44-2.57 (m, 1H) 2.09-2.11 (m, 1H) 1.90-1.93 (m, 1H) 1.74-1.82 (m, 2H) 1.63-1.65 (m, 1H).

TFA (8.08 g, 70.9 mmol, 5.3 mL, 20 eq) was added to a solution of 8-methyl-6-phenoxy-9-tetrahydropyran-2-yl-purine (1.1 g, 3.54 mmol, 1 eq) in DCM (10 mL) at 20° C. and stirred for 0.5 h. To the mixture was added sat. $NaHCO_3$ until pH=7. The mixture was extracted with DCM (20 mL*3) and the organic layers were concentrated to give 8-methyl-6-phenoxy-9H-purine (I-599) (0.61 g) as a yellow oil which was used in the next step without further purification.

To a mixture of 8-methyl-6-phenoxy-9H-purine (0.61 g, 2.70 mmol, 1 eq), DIPEA (697 mg, 5.39 mmol, 2 eq) and DMAP (33 mg, 270 umol, 0.1 eq) in DCM (10 mL) was added $Boc_2O$ (706 mg, 3.24 mmol, 1.2 eq) at 20° C., the mixture was stirred at 20° C. for 20 min. The mixture was concentrated. The residue was purified by column chromatography to give tert-butyl 8-methyl-6-phenoxy-purine-9-carboxylate (I-600) (0.46 g, 1.41 mmol, 52% yield) as a white solid. $^1H$ NMR (400 MHz, $CD_3OD$) δ 8.34 (s, 1H) 7.33-7.41 (m, 2H) 7.13-7.24 (m, 3H) 2.74 (s, 3H) 1.62 (s, 9H).

AIBN (34 mg, 207 umol, 0.25 eq) and NBS (162 mg, 91 umol, 1.1 eq) was added to a solution of tert-butyl 8-methyl-6-phenoxy-purine-9-carboxylate (270 mg, 827 umol, 1 eq) in $CCl_4$ (1 mL) at 70° C. under $N_2$. The reaction was stirred at 70° C. for another 3 h. Water (2 mL) was added to the mixture and the mixture was extracted with DCM (5 mL×2). The combined organic layers were dried over $Na_2SO_4$ and filtered. The filtrate was concentrated under reduced pressure to give tert-butyl 8-(bromomethyl)-6-phenoxy-purine-9-carboxylate (I-601) (335 mg) which was used in the next step without further purification as a yellow solid.

A mixture of tert-butyl 8-(bromomethyl)-6-phenoxy-purine-9-carboxylate (335 mg, 827 umol, 1 eq), 3-nitro-1H-pyridin-2-one (139 mg, 992 umol, 1.2 eq) and DIPEA (213 mg, 1.65 mmol, 2 eq) in $CH_3CN$ (1 mL) was stirred at 20° C. for 3 h. The mixture was concentrated to give a crude product. The residue was purified by column chromatography to give tert-butyl 8-[(3-nitro-2-oxo-1-pyridyl)methyl]-6-phenoxy-purine-9-carboxylate (I-602) (163 mg, 43% yield) as a yellow solid.

To a solution of tert-butyl 8-[(3-nitro-2-oxo-1-pyridyl) methyl]-6-phenoxy-purine-9-carboxylate (150 mg, 323 umol, 1 eq) in EtOAc (5 mL) was added Pd/C (50 mg, 10% purity) under $N_2$. The suspension was degassed under vacuum and purged with $H_2$ several times. The mixture was stirred under $H_2$ (15 psi) at 20° C. for 0.5 hours. The mixture was filtered and the filtrate was concentrated to give tert-butyl 8-[(3-amino-2-oxo-1-pyridyl)methyl]-6-phenoxy-purine-9-carboxylate (I-603) (130 mg, 79% yield) was used in the next step without further purification as a yellow solid. LCMS m/z 435.0 $(M+1)^+$.

The following intermediates were prepared according to the procedures described for the synthesis of I-603 using the appropriate reagents.

| Compound | Structure | LCMS Data |
|---|---|---|
| I-604 | 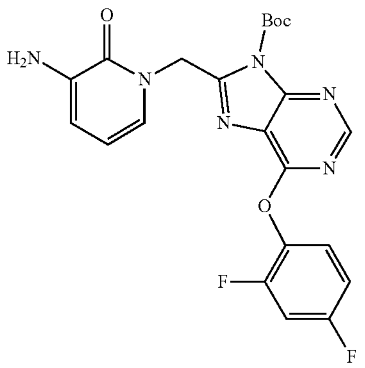 [SMILES: CC(C)(C)OC(=O)n1c(Cn2cccc(N)c2=O)nc2c(Oc3ccc(F)cc3F)ncnc21] | LCMS m/z 471.2 $(M + 1)^+$ |
| I-605 | 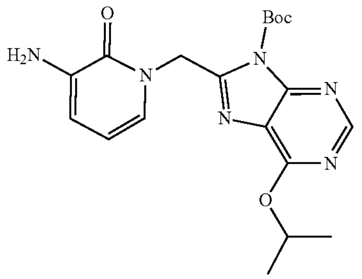 [SMILES: CC(C)Oc1ncnc2c1nc(Cn1cccc(N)c1=O)n2C(=O)OC(C)(C)C] | LCMS m/z 401.2 $(M + 1)^+$ |
| I-606 | 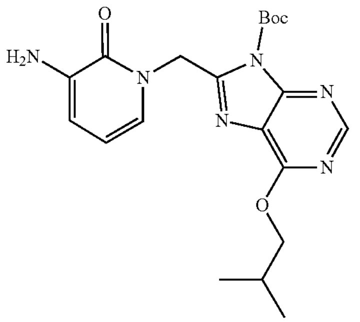 [SMILES: CC(C)COc1ncnc2c1nc(Cn1cccc(N)c1=O)n2C(=O)OC(C)(C)C] | LCMS m/z 415.2 $(M + 1)^+$ |

Example 64

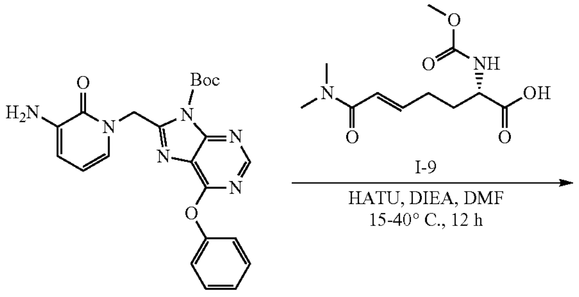

I-603

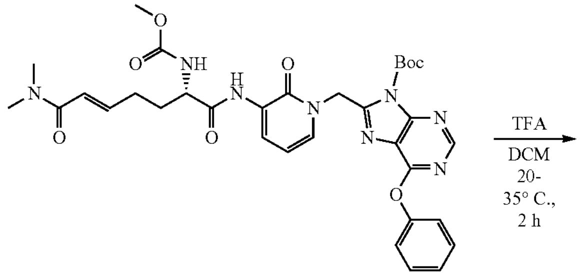

I-607

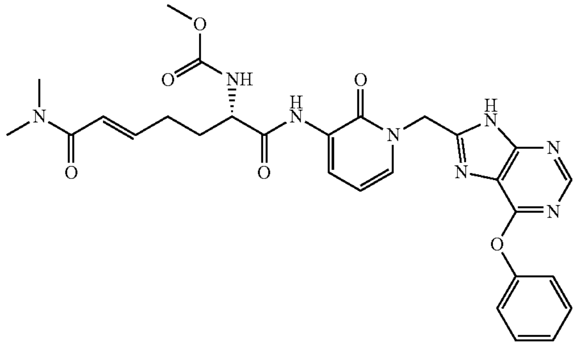

430

HATU (131 mg, 345 umol, 1.5 eq) was added to a mixture of tert-butyl 8-[(3-amino-2-oxo-1-pyridyl)methyl]-6-phenoxy-purine-9-carboxylate (100 mg, 230 umol, 1 eq), (E,2S)-7-(dimethylamino)-2-(methoxycarbonylamino)-7-oxo-hept-5-enoic acid (62.4 mg, 242 umol, 1.05 eq) and DIPEA (59.5 mg, 460 umol, 2 eq) in DMF (2 mL) at 15° C. The mixture was heated to 40° C. and stirred for 12 h. The mixture was extracted with EtOAc (10 mL×2). The combined organic layers were washed with brine (20 mL), dried over $Na_2SO_4$ and filtered. The filtrate was concentrated under reduced pressure to give tert-butyl 8-[[3-[[(E,2S)-7-(dimethylamino)-2-(methoxycarbonylamino)-7-oxo-hept-5-enoyl]amino]-2-oxo-1-pyridyl]methyl]-6-phenoxy-purine-9-carboxylate (I-607) (155 mg) was used in the next step without further purification as a yellow solid. LCMS m/z 675.3 $(M+1)^+$.

TFA (524 mg, 4.59 mmol, 20 eq) was added to a mixture of tert-butyl 8-[[3-[[(E,2S)-7-(dimethylamino)-2-(methoxycarbonylamino)-7-oxo-hept-5-enoyl]amino]-2-oxo-1-pyridyl]methyl]-6-phenoxy-purine-9-carboxylate (155 mg, 230 umol, 1 eq) in DCM (3 mL) at 20° C. and stirred for 2 h. The mixture was concentrated to give a crude product.

The residue was purified by prep-HPLC to give methyl N-[(E,1S)-6-(dimethylamino)-6-oxo-1-[[2-oxo-1-[(6-phenoxy-9H-purin-8-yl)methyl]-3-pyridyl]carbamoyl]hex-4-enyl]carbamate (Compound 607) (35.1 mg, 27% yield) as a white solid. LCMS m/z 575.2 $(M+1)^+$. $^1H$ NMR (400 MHz, DMSO-$d_6$) δ 9.27 (s, 1H) 8.38 (s, 1H) 8.27-8.29 (m, 1H) 7.62-7.74 (m, 1H) 7.61-7.62 (m, 1H) 7.44-7.48 (m, 2H) 7.26-7.31 (m, 3H) 6.59-6.62 (m, 1H) 6.36-6.41 (m, 2H) 5.46 (s, 2H) 4.16-4.21 (m, 1H) 3.55 (s, 3H) 2.99 (s, 3H) 2.80 (s, 3H) 2.20-2.27 (m, 2H) 1.71-1.89 (m, 2H).

The following compounds were prepared according to the procedures described for the synthesis of Example 64 using the appropriate intermediates.

| Compound | Structure | LCMS Data |
|---|---|---|
| 435 | 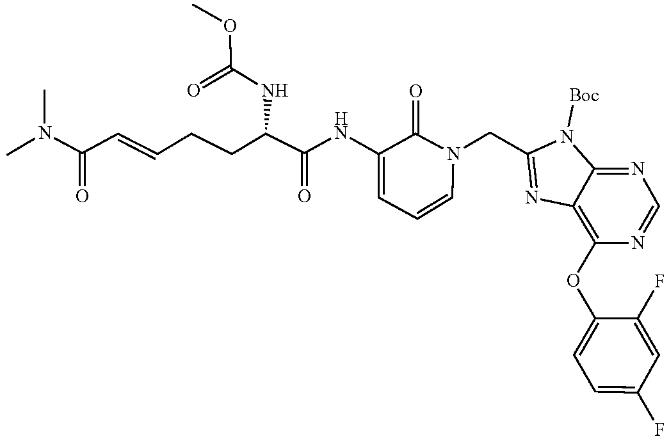 [SMILES: COC(=O)N[C@@H](CC/C=C/C(=O)N(C)C)C(=O)Nc1cccn(Cc2nc3c(Oc4ccc(F)cc4F)ncnc3n2C(=O)OC(C)(C)C)c1=O] | LCMS m/z 611.3 $(M + 1\text{-}100)^+$ |
| 436 | 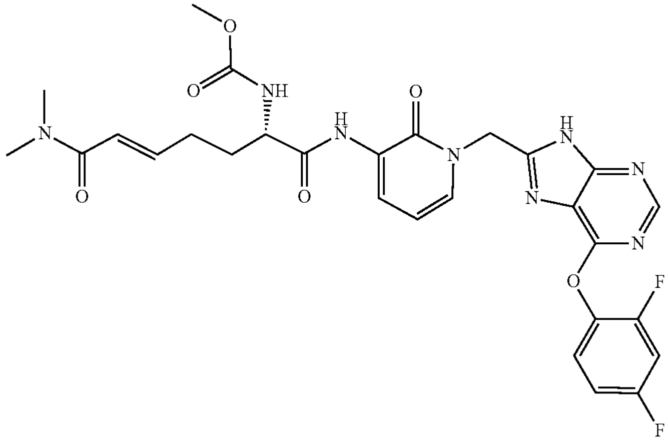 [SMILES: COC(=O)N[C@@H](CC/C=C/C(=O)N(C)C)C(=O)Nc1cccn(Cc2nc3c(Oc4ccc(F)cc4F)ncnc3[nH]2)c1=O] | LCMS m/z 611.3 $(M + 1)^+$ |
| 440 | 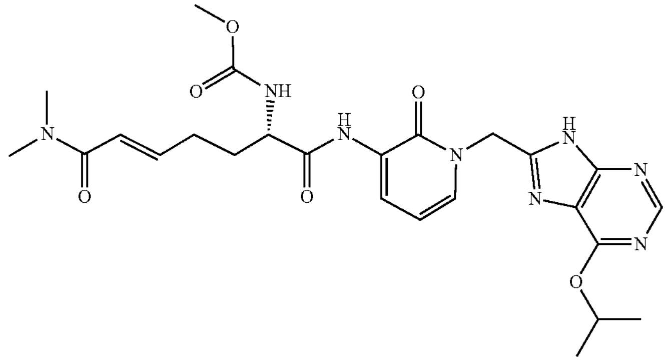 [SMILES: COC(=O)N[C@@H](CC/C=C/C(=O)N(C)C)C(=O)Nc1cccn(Cc2nc3c(OC(C)C)ncnc3[nH]2)c1=O] | LCMS m/z 541.3 $(M + 1)^+$ |

-continued
| Compound | Structure | LCMS Data |
| --- | --- | --- |
| 452 | 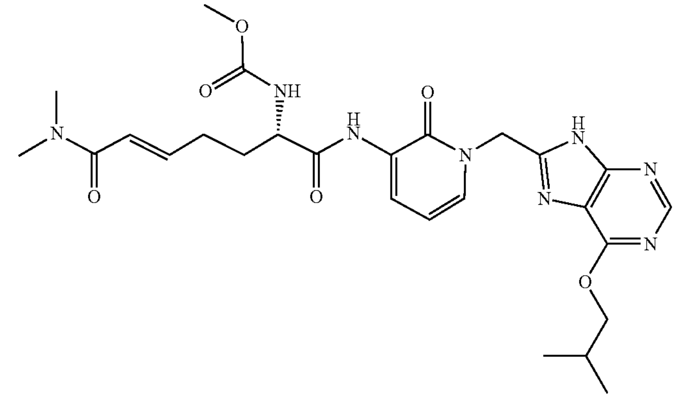 [SMILES: COC(=O)N[C@@H](CC/C=C/C(=O)N(C)C)C(=O)Nc1cccn(Cc2nc3c(OCC(C)C)ncnc3[nH]2)c1=O] | LCMS m/z 554.2 $(M + 1)^+$ |
The Synthesis of Intermediate I-615
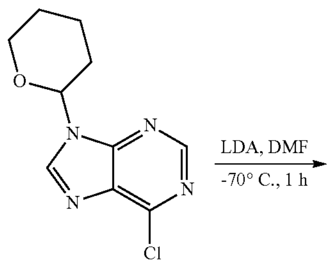
I-596
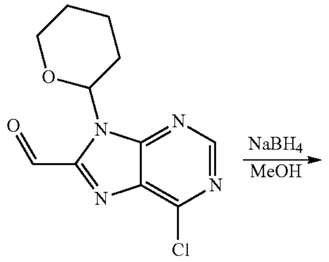
I-608
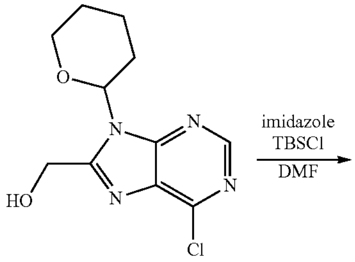
I-609
-continued
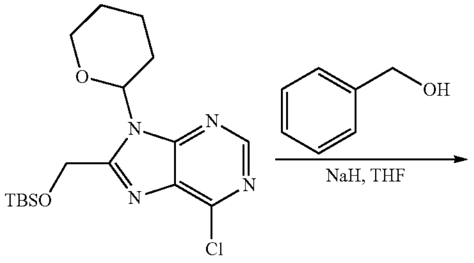
I-610
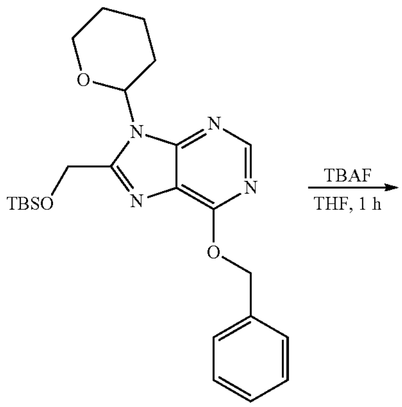
I-611

-continued

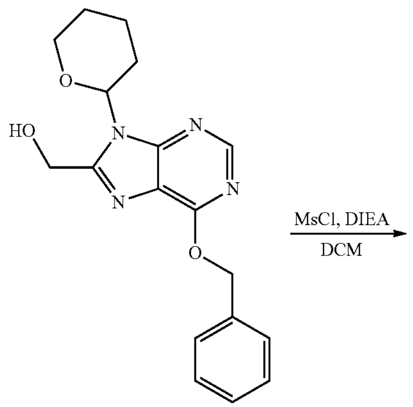

I-612

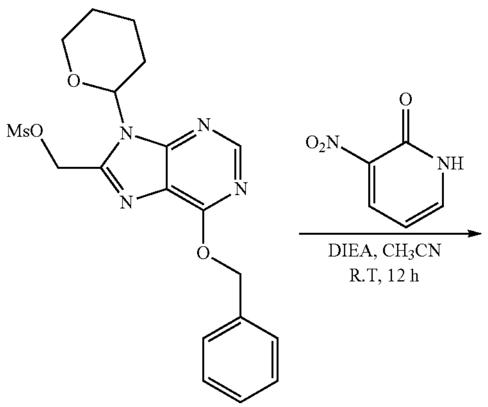

I-613

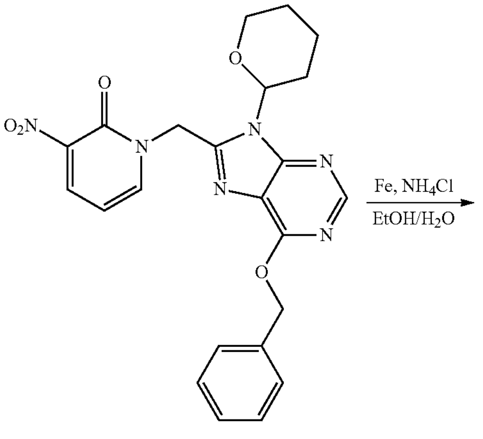

I-614

-continued

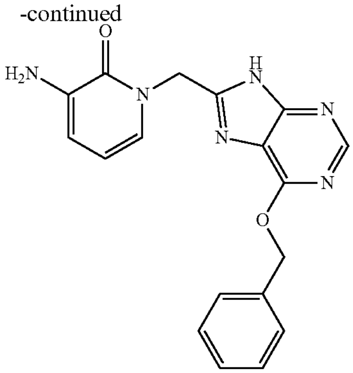

I-615

To a solution of 6-chloro-9-tetrahydropyran-2-yl-purine (1 g, 4.19 mmol, 1 eq) in THF (10 mL) was added LDA (2 M, 3.14 mL, 1.5 eq) at −70° C., and the reaction mixture was stirred at −70° C. for 0.5 hr. Then DMF (918.75 mg, 12.57 mmol, 967.11 uL, 3 eq) was added at −70° C., and the mixture was stirred at −70° C. for additional 0.5 hr. The reaction mixture was quenched by addition water 10 mL at 0° C., and then diluted with ethyl acetate 10 mL and extracted with ethyl acetate 10 mL (10 mL×1). The combined organic layers were washed with brine (10 mL×2), dried over anhydrous $Na_2SO_4$, filtered and concentrated under reduced pressure to give an oil. The oil was purified by column chromatography to give 6-chloro-9-tetrahydropyran-2-yl-purine-8-carbaldehyde (I-608) (900 mg) as a yellow oil. LCMS m/z 183.0 $(M-84+1)^+$.

To a solution of 6-chloro-9-tetrahydropyran-2-yl-purine-8-carbaldehyde (900 mg, 3.37 mmol, 1 eq) in MeOH (10 mL) was added $NaBH_4$ (255.35 mg, 6.75 mmol, 2 eq) at 0° C. The mixture was stirred at 15° C. for 0.5 hr. The reaction mixture was quenched by addition water (5 mL) at 0° C., and then diluted with ethyl acetate (5 mL) and extracted with ethyl acetate (5 mL×1). The combined organic layers were washed with brine (5 mL), dried over anhydrous $Na_2SO_4$, filtered and concentrated under reduced pressure to give (6-chloro-9-tetrahydropyran-2-yl-purin-8-yl)methanol (I-609) (880 mg) was used in the next step without further purification as a light yellow solid. LCMS m/z 185.0 $(M-84+1)^+$.

To a solution of (6-chloro-9-tetrahydropyran-2-yl-purin-8-yl)methanol (830 mg, 3.09 mmol, 1 eq) in DMF (10 mL) was added imidazole (420.58 mg, 6.18 mmol, 2 eq) and TBSCl (558.69 mg, 3.71 mmol, 454.22 uL, 1.2 eq) at 15° C. The mixture was stirred at 15° C. for 0.5 hr. The reaction mixture was partitioned between water (10 mL) and ethyl acetate (10 mL). The organic phase was separated, washed with brine (10 mL), dried over anhydrous $Na_2SO_4$, filtered and concentrated under reduced pressure to give a residue. The residue was purified by column chromatography to give tert-butyl-[(6-chloro-9-tetrahydropyran-2-yl-purin-8-yl)methoxy]-dimethyl-silane (I-610) (300 mg, 25% yield) as a light yellow oil. LCMS m/z 383.0 $(M+1)^+$.

To a solution of phenylmethanol (211.78 mg, 1.96 mmol, 203.63 uL, 3 eq) in THF (3 mL) was added NaH (52.22 mg, 1.31 mmol, 60% purity, 2 eq) at 0° C. The mixture was stirred at 15° C. for 0.5 hr. Then tert-butyl-[(6-chloro-9-tetrahydropyran-2-yl-purin-8-yl)methoxy]-dimethyl-silane (250 mg, 652.81 umol, 1 eq) was added, and the result reaction mixture was stirred at 15° C. for 0.5 hr. The reaction mixture was quenched by addition water 5 mL at 0° C., and then diluted with ethyl acetate 5 mL and extracted with ethyl acetate 5 mL (5 mL×1). The combined organic layers were washed with brine 5 mL (5 mL×1), dried over anhydrous $Na_2SO_4$, filtered and concentrated under reduced pressure to give an oil. The oil was purified by prep-TLC to give (6-benzyloxy-9-tetrahydropyran-2-yl-purin-8-yl)methoxy-tert-butyl-dimethylsilane (I-611) (240 mg, 527.89 umol, 81% yield) as a colorless oil. LCMS m/z 455.1 $(M+1)^+$.

To a solution of (6-benzyloxy-9-tetrahydropyran-2-yl-purin-8-yl)methoxy-tert-butyl-dimethylsilane (230 mg, 505.90 umol, 1 eq) in THF (3 mL) was added TBAF (1 M, 1.01 mL, 2 eq) at 15° C. The mixture was stirred at 15° C. for 1 hr. The reaction mixture was concentrated under reduced pressure to remove the solvent to afford a yellow oil. The oil was purified by column chromatography to give (6-benzyloxy-9-tetrahydropyran-2-yl-purin-8-yl)methanol (I-612) (130 mg, 76% yield) as a colorless oil. LCMS m/z 341.1 $(M+1)^+$.

To a solution of (6-benzyloxy-9-tetrahydropyran-2-yl-purin-8-yl)methanol (130 mg, 381.93 umol, 1 eq) in DCM (2 mL) was added DIEA (148.09 mg, 1.15 mmol, 199.58 uL, 3 eq) and MsCl (87.50 mg, 763.86 umol, 59.12 uL, 2 eq) at 0° C. The mixture was stirred at 15° C. for 1 hr. The reaction mixture was partitioned between water (2 mL) and dichloromethane (2 mL). The organic phase was separated, washed with brine (2 mL), dried over anhydrous $Na_2SO_4$, filtered and concentrated under reduced pressure to give (6-benzyloxy-9-tetrahydropyran-2-yl-purin-8-yl)methyl methanesulfonate (I-613) (180 mg) which was used in the next step without further purification as an orange oil.

To a solution of 3-nitro-1H-pyridin-2-one (60.26 mg, 430.14 umol, 1 eq) in ACN (2 mL) was added DIEA (111.19 mg, 860.28 umol, 149.85 uL, 2 eq) and (6-benzyloxy-9-tetrahydropyran-2-yl-purin-8-yl)methyl methanesulfonate (180 mg, 430.14 umol, 1 eq) at 0° C. The mixture was stirred at 15° C. for 12 h. The reaction mixture was concentrated under reduced pressure to remove the solvent to afford a brown oil. The oil was purified by prep-TLC to give 1-[(6-benzyloxy-9-tetrahydropyran-2-yl-purin-8-yl)methyl]-3-nitro-pyridin-2-one (I-614) (70 mg, 35% yield) as a light yellow solid. LCMS m/z 463.0 $(M+1)^+$.

To a solution of 1-[(6-benzyloxy-9-tetrahydropyran-2-yl-purin-8-yl)methyl]-3-nitro-pyridin-2-one (65 mg, 140.55 umol, 1 eq) in EtOH (1 mL) and $H_2O$ (0.2 mL) was added Fe (39.25 mg, 702.77 umol, 5 eq) and $NH_4Cl$ (75.18 mg, 1.41 mmol, 49.14 uL, 10 eq) at 15° C. The mixture was stirred at 90° C. for 0.5 hr. The reaction mixture was filtered and concentrated under reduced pressure to remove the solvent to afford 3-amino-1-[(6-benzyloxy-9H-purin-8-yl)methyl]pyridine-2-one (I-615) (50 mg) was used in the next step without further purification as a yellow solid. LCMS m/z 349.0 $(M+1)^+$.

The following intermediate was prepared according to the procedures described for the synthesis of I-615 using the appropriate reagents.

| Compound | Structure | LCMS Data |
| --- | --- | --- |
| I-616 | 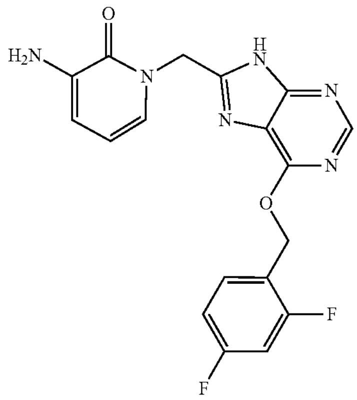 [SMILES: Nc1cccn(Cc2nc3c(OCc4ccc(F)cc4F)ncnc3[nH]2)c1=O] | LCMS m/z 385.2 $(M+1)^+$ |

Example 65

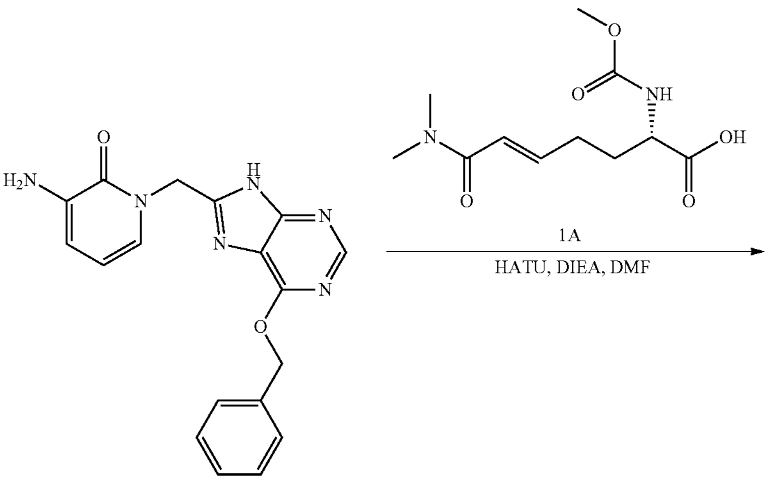

I-615

-continued

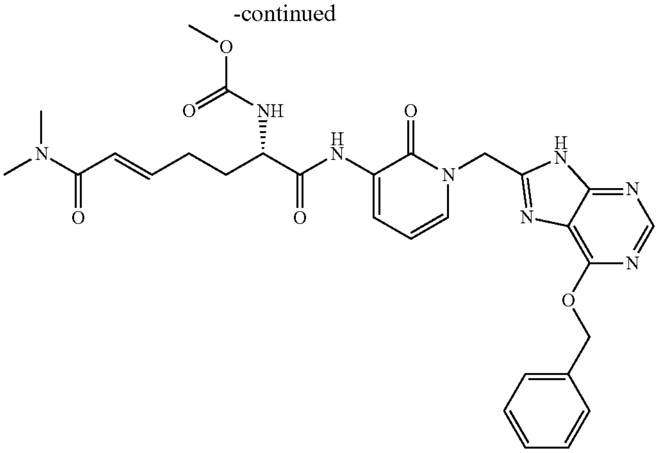

462

To a solution of 3-amino-1-[(6-benzyloxy-9H-purin-8-yl)methyl]pyridin-2-one (45 mg, 129.18 umol, 1 eq) and (E,2S)-7-(dimethylamino)-2-(methoxycarbonylamino)-7-oxo-hept-5-enoic acid (33.36 mg, 129.18 umol, 1 eq) in DMF (1 mL) was added HATU (58.94 mg, 155.01 umol, 1.2 eq) and DIEA (33.39 mg, 258.35 umol, 45.00 uL, 2 eq) at 15° C. The mixture was stirred at 15° C. for 12 h. The reaction mixture was filtered and concentrated. The residue was purified by prep-HPLC to give methyl N-[(E,1S)-1-[[1-[(6-benzyloxy-9H-purin-8-yl)methyl]-2-oxo-3-pyridyl]carbamoyl]-6-(dimethylamino)-6-oxo-hex-4-enyl]carbamate (Compound 462) (18.7 mg, 22% yield) as an orange solid. LCMS m/z 589.2 $(M+1)^+$. $^1H$ NMR (400 MHz, DMSO-$d_6$) δ 9.23 (s, 1H), 8.47 (s, 1H), 8.22 (dd, J=1.4, 7.4 Hz, 1H), 7.71 (br d, J=7.7 Hz, 1H), 7.54 (dd, J=1.7, 6.9 Hz, 1H), 7.47 (br d, J=6.8 Hz, 2H), 7.42-7.26 (m, 4H), 6.64-6.49 (m, 1H), 6.40-6.28 (m, 2H), 5.55 (s, 2H), 5.37 (s, 2H), 4.20-4.10 (m, 1H), 3.52 (s, 3H), 2.96 (s, 3H), 2.81 (s, 3H), 2.28-2.13 (m, 2H), 1.91-1.61 (m, 2H).

The following compounds were prepared according to the procedures described for the synthesis of Example 65 using the appropriate intermediates.

| Compound | Structure | LCMS Data |
| --- | --- | --- |
| 476 | 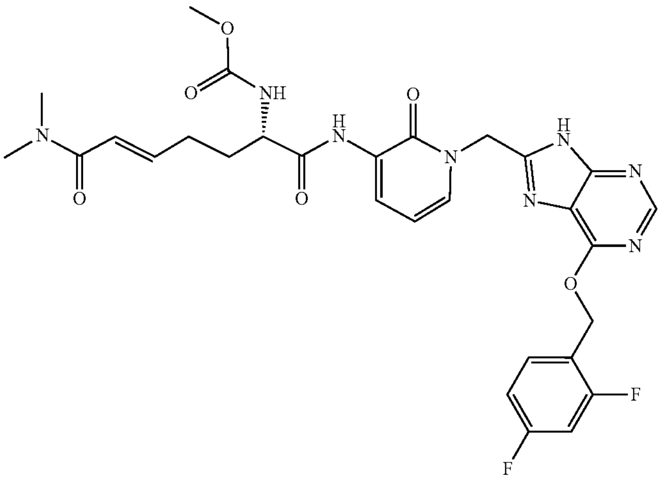 [SMILES: COC(=O)N[C@@H](CC/C=C/C(=O)N(C)C)C(=O)Nc1cccn(Cc2nc3c(OCc4ccc(F)cc4F)ncnc3[nH]2)c1=O] | LCMS m/z 625.2 $(M + 1)^+$ |

-continued

| Compound | Structure | LCMS Data |
| --- | --- | --- |
| 477 | 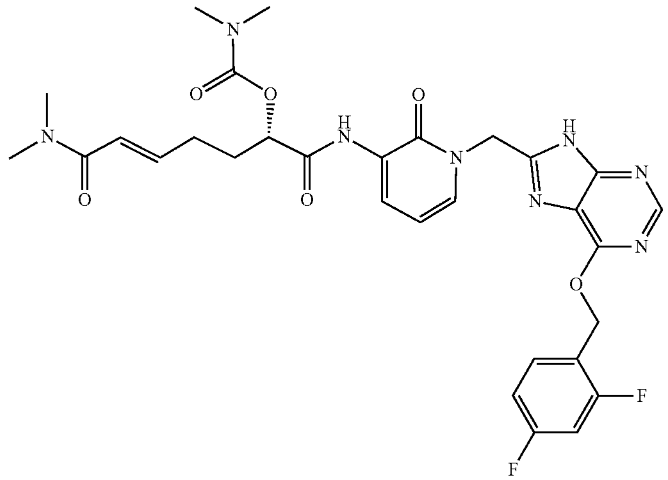 [SMILES: CN(C)C(=O)/C=C/CC[C@H](OC(=O)N(C)C)C(=O)Nc1cccn(Cc2nc3c(OCc4ccc(F)cc4F)ncnc3[nH]2)c1=O] | LCMS m/z 639.2 $(M + 1)^+$ |

The Synthesis of Intermediate I-621

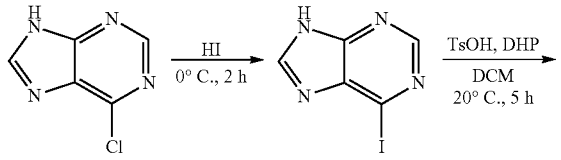

I-595 I-617

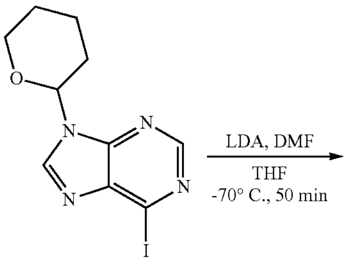

I-618

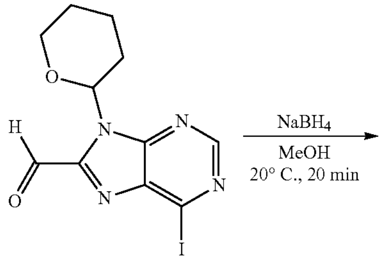

I-619

-continued

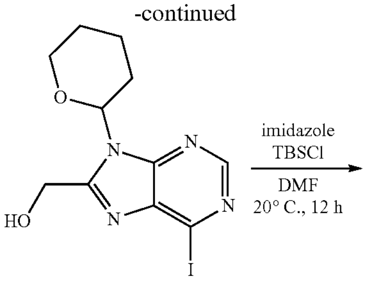

I-620

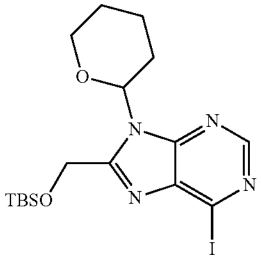

I-621

To HI (47%) (150 mL) in an ice-bath was added 6-chloro-9H-purine (20 g, 129 mmol, 1 eq) slowly with stirring at 0° C. The mixture was stirred at 0° C. for 2 hours. The mixture was warmed to 20° C. and stirred for another 2 h. The mixture was filtered. The filter cake was suspended in 100 mL of cold water and adjusted to pH 7 by the addition of $NH_3 \cdot H_2O$. The precipitate was filtered, washed with cold water (50 mL) and dried in vacuum to give 6-iodo-9H-purine (I-617) (23 g, 72% yield) as a yellow solid. $^1H$ NMR (400 MHz, DMSO-$d_6$) δ 13.85 (br s, 1H) 8.64 (s, 1H) 8.59 (s, 1H).

DHP (6.84 g, 81.3 mmol, 2 eq) was added to a mixture of 6-iodo-9H-purine (10 g, 40.7 mmol, 1 eq) and $TsOH \cdot H_2O$ (773 mg, 4.06 mmol, 0.1 eq) in DCM (150 mL) at 0° C. dropwise. The mixture was stirred at 20° C. for 5 h. Water (100 mL) was added to the mixture and the mixture was extracted with DCM (100 mL×2). The combined organic layers were washed with brine (100 mL), dried over $Na_2SO_4$ and filtered. The filtrate was concentrated under reduced pressure to give a residue. The residue was purified by column chromatography to give 6-iodo-9-tetrahydropyran-2-yl-purine (I-618) (11 g, 31.5 mmol, 78% yield) as a yellow solid. $^1$H NMR (400 MHz, $CDCl_3$) δ 8.62 (s, 1H) 8.38 (s, 1H) 5.75 (dd, J=10.4, 2.4 Hz, 1H) 4.16-4.19 (m, 1H) 3.74-3.84 (m, 1H) 2.03-2.21 (m, 3H) 1.68-1.79 (m, 3H).

n-BuLi (2.5 M, 13.6 mL, 1.25 eq) was added dropwise to a solution of diisopropylamine (3.59 g, 35.4 mmol, 5.01 mL, 1.3 eq) in THF (30 mL) at −70° C. under $N_2$. The mixture was stirred for 10 min. The mixture was added dropwise to a solution of 6-iodo-9-tetrahydropyran-2-yl-purine (9 g, 27.3 mmol, 1 eq) in THF (100 mL) at −70° C. under $N_2$ and stirred for 20 min. DMF (5.98 g, 81.8 mmol, 3 eq) was added to the mixture at −70° C. and stirred for 20 min. The reaction was quenched the reaction with sat. $NH_4Cl$ (100 mL). The mixture was extracted with EtOAc (100 mL×2). The combined organic layers were washed with brine (100 mL*2), dried over $Na_2SO_4$ and filtered. The filtrate was concentrated under reduced pressure to give 6-iodo-9-tetrahydropyran-2-yl-purine-8-carbaldehyde (I-619) (8.75 g) was used in the next step without further purification as a yellow solid.

$NaBH_4$ (1.39 g, 36.6 mmol, 1.5 eq) was added to a solution of 6-iodo-9-tetrahydropyran-2-yl-purine-8-carbaldehyde (8.75 g, 24.4 mmol, 1 eq) in MeOH (100 mL) at 0° C. The mixture was stirred at 20° C. for 20 min. The reaction was quenched with water (100 mL) and concentrated. The mixture was extracted with EtOAc (50 mL×2). The combined organic layers were washed with brine (50 mL), dried over $Na_2SO_4$ and filtered. The filtrate was concentrated under reduced pressure to give (6-iodo-9-tetrahydropyran-2-yl-purin-8-yl)methanol (I-620) (8.54 g) which was used in the next step without further purification as a yellow solid.

TBSCl (4.29 g, 28.5 mmol, 1.2 eq) was added to a mixture of (6-iodo-9-tetrahydropyran-2-yl-purin-8-yl)methanol (8.54 g, 23.7 mmol, 1 eq) and imidazole (2.42 g, 35.6 mmol, 1.5 eq) in DMF (100 mL) at 20° C. The mixture was stirred at 20° C. for 12 h. Water (100 mL) was added and the mixture was extracted with EtOAc (100 mL×2). The combined organic layers were washed with brine (100 mL*2), dried over $Na_2SO_4$ and filtered. The filtrate was concentrated under reduced pressure to give a residue. The residue was purified by column chromatography to give tert-butyl-[(6-iodo-9-tetrahydropyran-2-yl-purin-8-yl)methoxy]-dimethyl-silane (I-621) (4.5 g, 37% yield) as a light yellow oil. LCMS m/z 475.0 (M+1)$^+$.

The Synthesis of Intermediate I-626

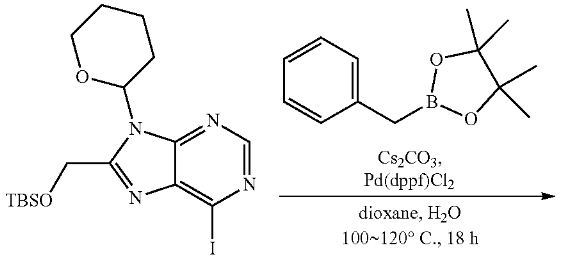

I-621

-continued

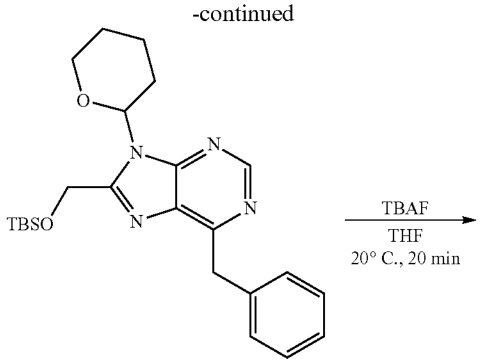

I-622

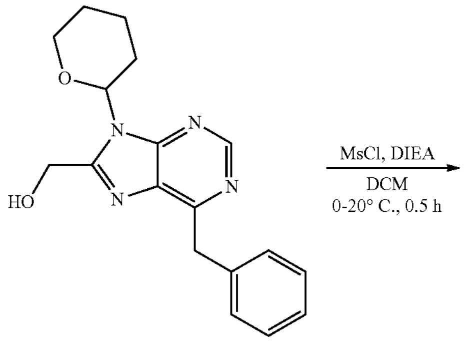

I-623

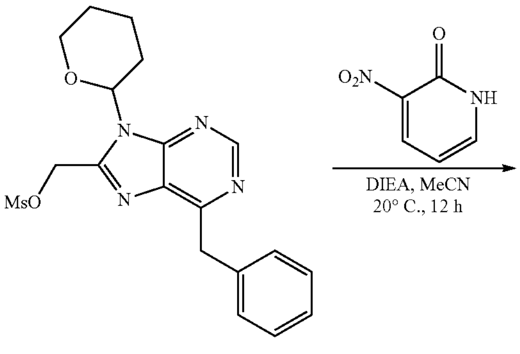

I-624

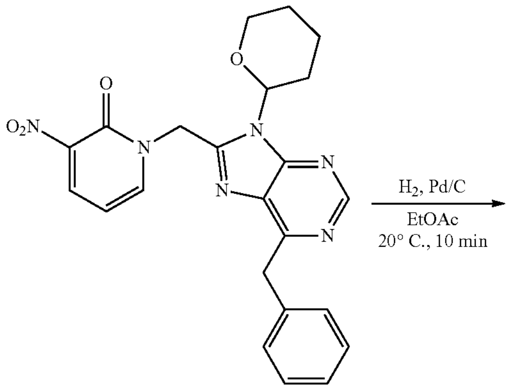

I-625

-continued

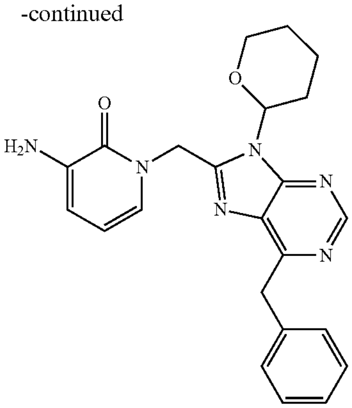

I-626

Pd(dppf)$Cl_2$ (77.1 mg, 105 umol, 0.05 eq) was added to a mixture of tert-butyl-[(6-iodo-9-tetrahydropyran-2-yl-purin-8-yl)methoxy]-dimethylsilane (1 g, 2.11 mmol, 1 eq), 2-benzyl-4,4,5,5-tetramethyl-1,3,2-dioxaborolane (598 mg, 2.74 mmol, 1.3 eq) and $Cs_2CO_3$ (1.37 g, 4.22 mmol, 2 eq) in dioxane/$H_2O$ (10:1) (15 mL) under $N_2$. The mixture was stirred at 100° C. for 18 h. The mixture was filtered and the filtrate was concentrated to give a crude product. The residue was purified by column chromatography to give (6-benzyl-9-tetrahydropyran-2-yl-purin-8-yl)methoxy-tert-butyl-dimethylsilane (I-622) (170 mg, 16% yield) as a yellow oil. LCMS m/z 439.1 $(M+1)^+$.

TBAF (1 M, 775 uL, 2 eq) was added to a solution of (6-benzyl-9-tetrahydropyran-2-yl-purin-8-yl)methoxy-tert-butyl-dimethylsilane (170 mg, 388 umol, 1 eq) in THF (3 mL) at 20° C. and stirred for 20 min. Brine (5 mL) was added to the mixture and the mixture was extracted with EtOAc (5 mL×2). The combined organic layers were washed with brine (10 mL), dried over $Na_2SO_4$ and filtered. The filtrate was concentrated under reduced pressure to give (6-benzyl-9-tetrahydropyran-2-yl-purin-8-yl)methanol (I-623) (90 mg) which was used in the next step without further purification as a yellow oil.

MsCl (38.1 mg, 333 umol, 1.2 eq) was added to a mixture of (6-benzyl-9-tetrahydropyran-2-yl-purin-8-yl)methanol (90 mg, 277 umol, 1 eq) and DIPEA (71.7 mg, 555 umol, 2 eq) in DCM (2 mL) at 0° C. The reaction mixture was stirred at 20° C. for 0.5 h. The reaction mixture was quenched the reaction with water (5 mL), extracted with DCM (5 mL*2), dried over $Na_2SO_4$ and filtered. The filtrate was concentrated under reduced pressure to give (6-benzyl-9-tetrahydropyran-2-yl-purin-8-yl)methyl methanesulfonate (I-624) (111 mg) which was used in the next step without further purification as a yellow oil.

A mixture of (6-benzyl-9-tetrahydropyran-2-yl-purin-8-yl)methyl methanesulfonate (111 mg, 276 umol, 1 eq), 3-nitro-1H-pyridin-2-one (46.4 mg, 331 umol, 1.2 eq) and DIPEA (71.3 mg, 552 umol, 2 eq) in $CH_3CN$ (3 mL) was stirred at 20° C. for 12 h. The mixture was concentrated to give a crude product. The residue was purified by prep-TLC to give 1-[(6-benzyl-9-tetrahydropyran-2-yl-purin-8-yl)methyl]-3-nitro-pyridin-2-one (I-625) (60 mg, 49% yield) as a yellow oil. LCMS m/z 447.1 $(M+1)^+$.

To a solution of 1-[(6-benzyl-9-tetrahydropyran-2-yl-purin-8-yl)methyl]-3-nitro-pyridin-2-one (60 mg, 134 umol, 1 eq) in EtOAc (2 mL) was added Pd/C (30 mg, 10% purity) under $N_2$. The suspension was degassed under vacuum and purged with $H_2$ several times. The mixture was stirred under $H_2$ (15 psi) at 20° C. for 10 min. The mixture was filtered and the filtrate was concentrated to give 3-amino-1-[(6-benzyl-9-tetrahydropyran-2-yl-purin-8-yl)methyl]pyridin-2-one (I-626) (40 mg, 69% yield) as a white solid. LCMS m/z 417.1 $(M+1)^+$.

The following intermediates were prepared according to the procedures described for the synthesis of I-626 using the appropriate reagents.

| Compound | Structure | LCMS Data |
|---|---|---|
| I-627 | 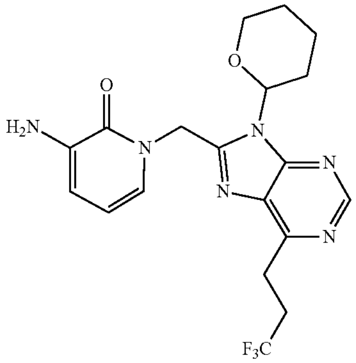 [SMILES: Nc1cccn(Cc2nc3c(CCC(F)(F)F)ncnc3n2C2CCCCO2)c1=O] | LCMS m/z 423.1 $(M + 1)^+$ |
| I-628 | 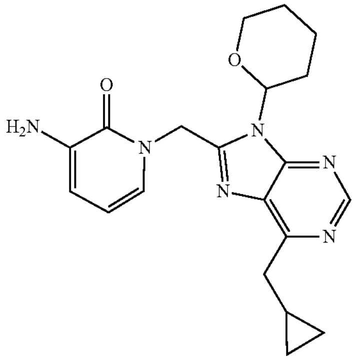 [SMILES: Nc1cccn(Cc2nc3c(CC4CC4)ncnc3n2C2CCCCO2)c1=O] | LCMS m/z 380.2 $(M + 1)^+$ |

Example 66

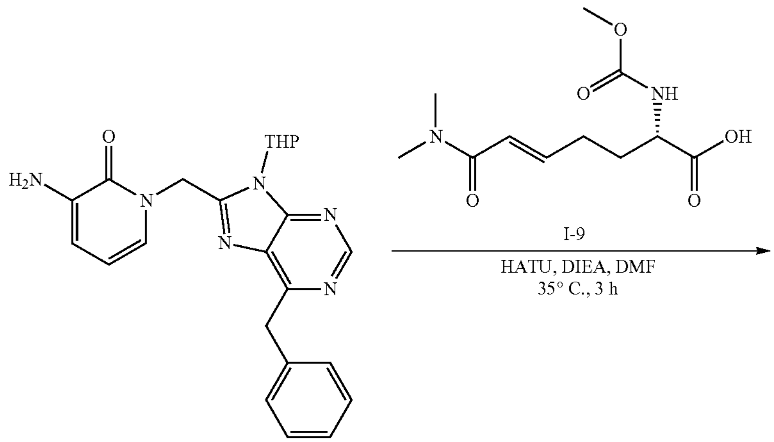

I-626

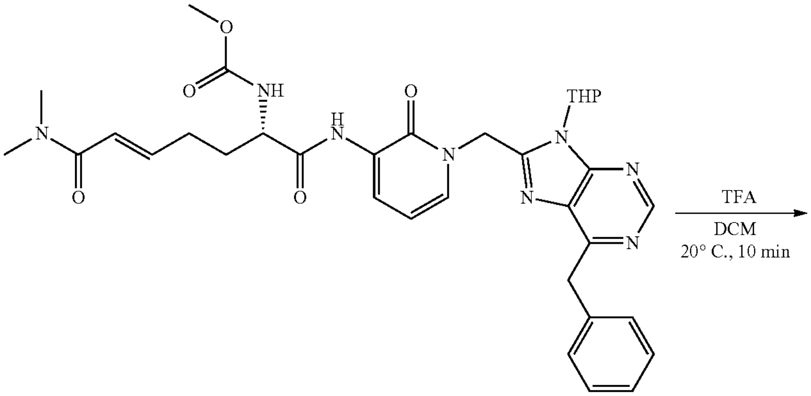

I-629

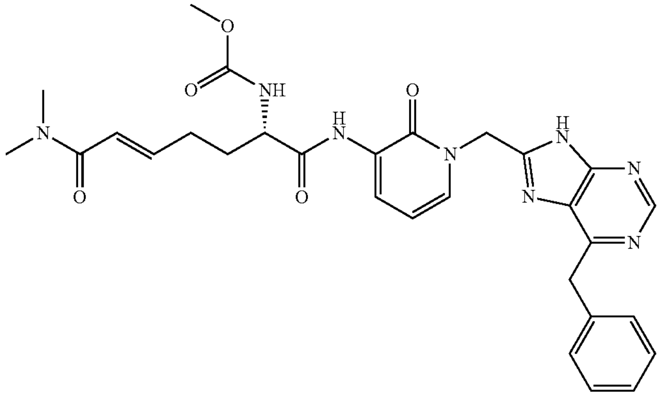

466

HATU (54.8 mg, 144 umol, 1.5 eq) was added to a mixture of 3-amino-1-[(6-benzyl-9-tetrahydropyran-2-yl-purin-8-yl)methyl]pyridin-2-one (40 mg, 96.0 umol, 1 eq), (E,2S)-7-(dimethylamino)-2-(methoxycarbonylamino)-7-oxo-hept-5-enoic acid (27.3 mg, 106 umol, 1.1 eq) and DIPEA (24.8 mg, 192 umol, 2 eq) in DMF (1 mL). The mixture was stirred at 35° C. for 3 h. Water (3 mL) was added to the mixture and the mixture was extracted with EtOAc (5 mL×3). The combined organic layers were washed with brine (10 mL), dried over $Na_2SO_4$ and filtered. The filtrate was concentrated under reduced pressure to give methyl N-[(E,1S)-1-[[1-[(6-benzyl-9-tetrahydropyran-2-yl-purin-8-yl)methyl]-2-oxo-3-pyridyl]carbamoyl]-6-(dimethylamino)-6-oxo-hex-4-enyl]carbamate (I-629) (60 mg) which was used in the next step without further purification as a brown oil. LCMS m/z 657.3 $(M+1)^+$.

TFA (208 mg, 1.83 mmol, 20 eq) was added to a solution of methyl N-[(E,1S)-1-[[1-[(6-benzyl-9-tetrahydropyran-2-yl-purin-8-yl)methyl]-2-oxo-3-pyridyl]carbamoyl]-6-(dimethylamino)-6-oxo-hex-4-enyl]carbamate (60 mg, 91.4 umol, 1 eq) in DCM (1 mL) at 20° C. The mixture was stirred for 10 min. The mixture was concentrated to give a crude product which was purified by prep-HPLC to give methyl N-[(E,1S)-1-[[1-[(6-benzyl-9H-purin-8-yl)methyl]-2-oxo-3-pyridyl]carbamoyl]-6-(dimethylamino)-6-oxo-hex-4-enyl]carbamate (Compound 466) (18.6 mg, 33% yield) as a white solid. LCMS m/z 573.2 $(M+1)^+$. $^1H$ NMR (400 MHz, DMSO-$d_6$) δ 9.24 (s, 1H) 8.73 (s, 1H) 8.26 (dd, J=7.39, 1.65 Hz, 1H) 8.11 (s, 1H) 7.69 (br d, J=7.94 Hz, 1H) 7.59 (dd, J=6.95, 1.65 Hz, 1H) 7.27-7.31 (m, 2H) 7.22 (t, J=7.39 Hz, 2H) 7.12-7.18 (m, 1H) 6.52-6.63 (m, 1H) 6.29-6.41 (m, 2H) 5.45 (s, 2H) 4.31 (s, 2H) 4.11-4.19 (m, 1H) 3.50-3.54 (m, 3H) 2.95 (s, 3H) 2.78-2.84 (m, 3H) 2.12-2.27 (m, 2H) 1.84 (br d, J=7.28 Hz, 1H) 1.62-1.75 (m, 1H).
The following compounds were prepared according to the procedures described for the synthesis of Example 66 using the appropriate intermediates.
| Compound | Structure | LCMS Data |
|---|---|---|
| 470 | 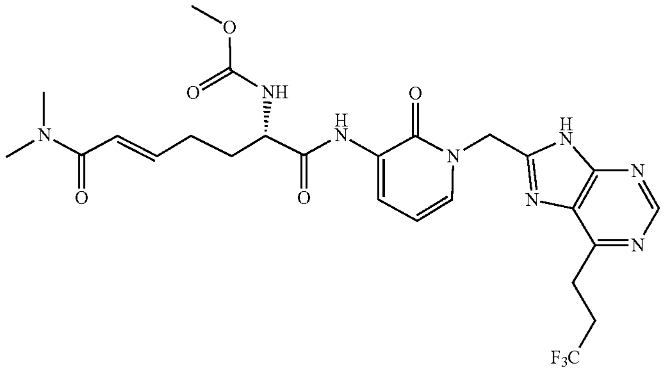 | LCMS m/z 579.2 $(M + 1)^+$ |
| 478 | 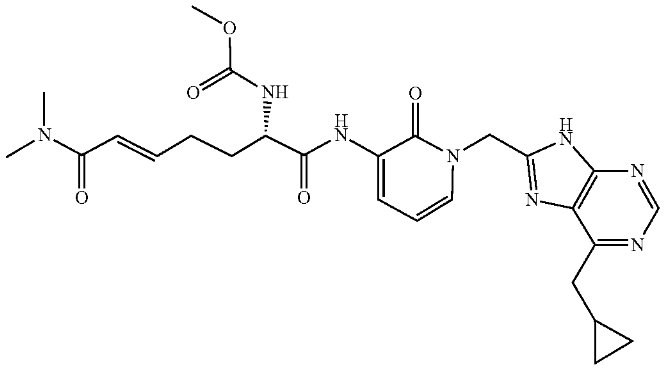 [SMILES: COC(=O)N[C@@H](CC/C=C/C(=O)N(C)C)C(=O)Nc1cccn(Cc2nc3c(CC4CC4)ncnc3[nH]2)c1=O] | LCMS m/z 537.2 $(M + 1)^+$ |
| 484 | 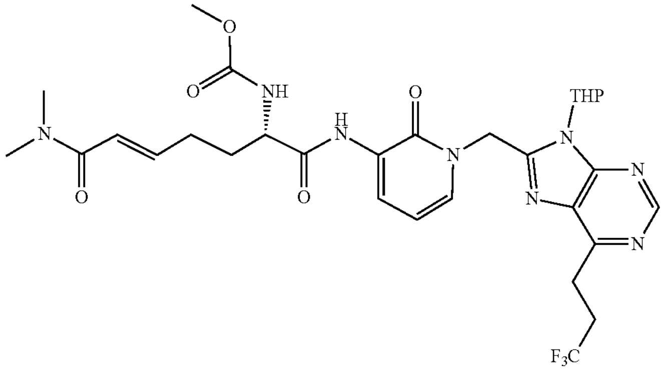 | LCMS m/z 663.2 $(M + 1)^+$ |

-continued
| Compound | Structure | LCMS Data |
| --- | --- | --- |
| 485 | 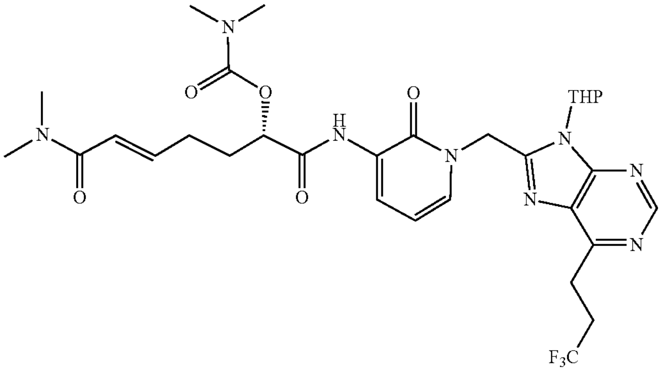 | LCMS m/z 677.2 $(M + 1)^+$ |
| 486 | 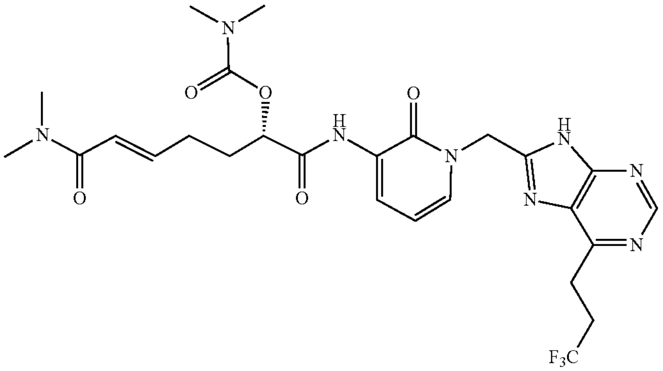 [SMILES: CN(C)C(=O)/C=C/CC[C@H](OC(=O)N(C)C)C(=O)Nc1cccn(Cc2nc3c(CCC(F)(F)F)ncnc3[nH]2)c1=O] | LCMS m/z 593.2 $(M+ 1)^+$ |
| 495 | 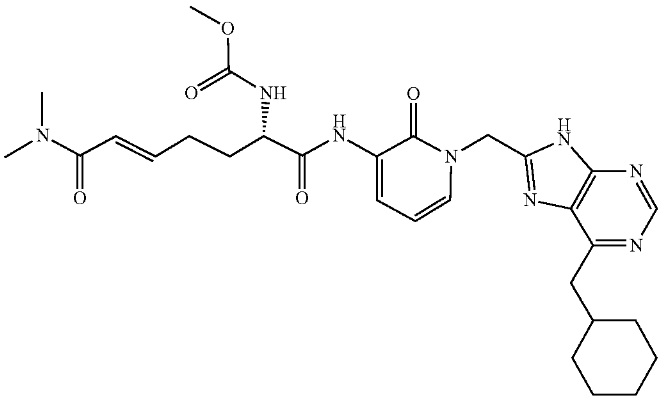 [SMILES: COC(=O)N[C@@H](CC/C=C/C(=O)N(C)C)C(=O)Nc1cccn(Cc2nc3c(CC4CCCCC4)ncnc3[nH]2)c1=O] | LCMS m/z 579.3 $(M + 1)^+$ |
| 496 | 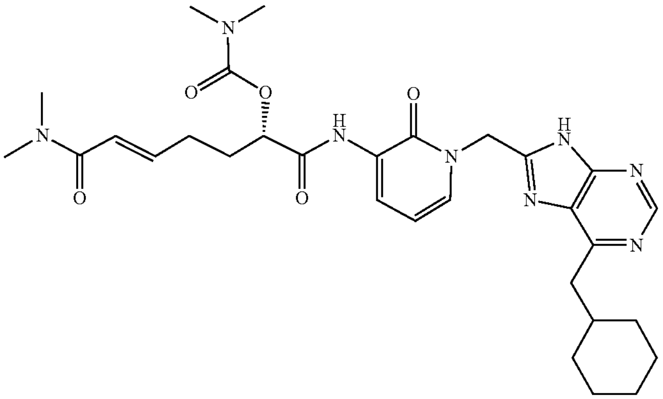 [SMILES: CN(C)C(=O)/C=C/CC[C@H](OC(=O)N(C)C)C(=O)Nc1cccn(Cc2nc3c(CC4CCCCC4)ncnc3[nH]2)c1=O] | LCMS m/z 593.3 $(M + 1)^+$ |

-continued
| Compound | Structure | LCMS Data |
| --- | --- | --- |
| 499 | 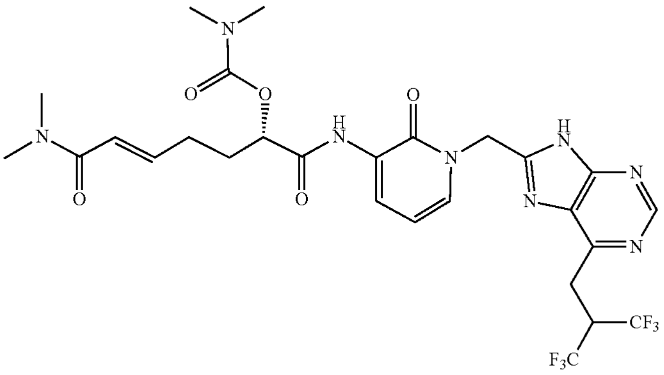 [SMILES: CN(C)C(=O)/C=C/CC[C@H](OC(=O)N(C)C)C(=O)Nc1cccn(Cc2nc3c(CC(C(F)(F)F)C(F)(F)F)ncnc3[nH]2)c1=O] | LCMS m/z 661.2 $(M + 1)^+$ |
The Synthesis of Intermediate I-634
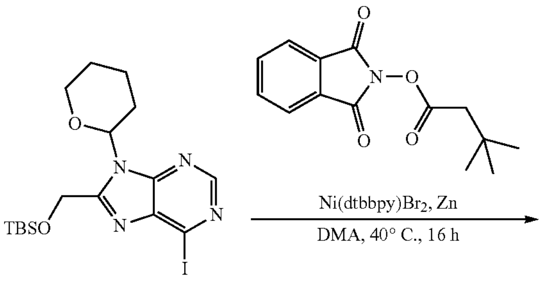
I-621
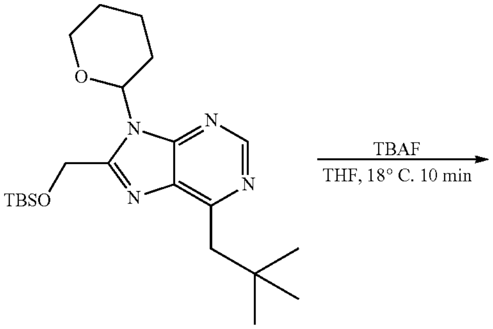
I-630
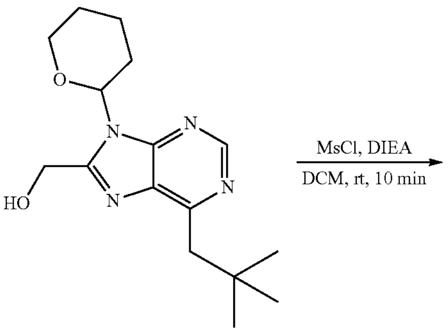
I-631
-continued
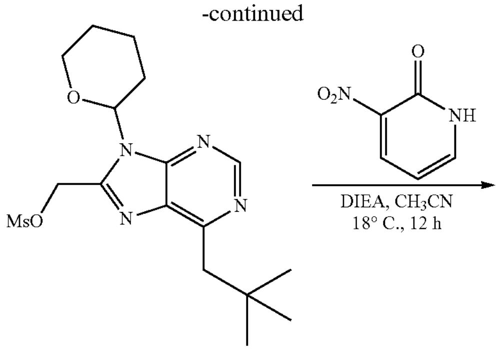
I-632
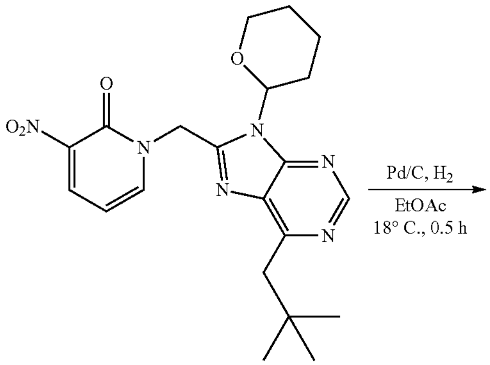
I-633

-continued

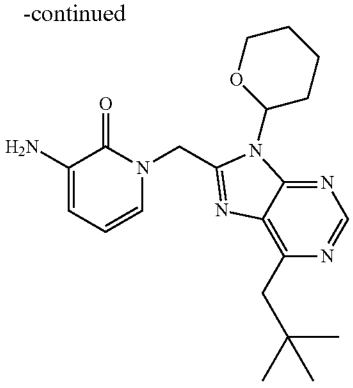

I-634

To a solution of (1,3-dioxoisoindolin-2-yl) 3,3-dimethylbutanoate (660.88 mg, 2.53 mmol, 1.2 eq), tert-butyl-[(6-iodo-9-tetrahydropyran-2-yl-purin-8-yl)methoxy]-dimethyl-silane (1 g, 2.11 mmol, 1 eq) and Zn (275.67 mg, 4.22 mmol, 2 eq) in DMA (4 mL) was added (dtbbpy)NiBr (153.95 mg, 316.18 umol, 0.15 eq) at 20° C. The reaction was stirred at 40° C. for 12 h. The mixture was poured into water (2 mL) and filtered, the filtrate was extracted with EtOAc (3 mL*2), washed with brine (2 mL), dried by $Na_2SO_4$, and concentrated in vacuum to give a residue. The residue was purified by prep-TLC to give 8-(((tert-butyldimethylsilyl)oxy)methyl)-6-neopentyl-9-(tetrahydro-2H-pyran-2-yl)-9H-purine (I-630) (0.56 g, 32% yield) as a white solid.

A solution of 8-(((tert-butyldimethylsilyl)oxy)methyl)-6-neopentyl-9-(tetrahydro-2H-pyran-2-yl)-9H-purine (560 mg, 1.34 mmol, 1 eq) and TBAF (1 M, 668.82 uL, 0.5 eq) in THF (5 mL) was stirred at 18° C. for 0.5 h. The mixture was concentrated in vacuum to give an oil which was purified by column chromatography to give [6-(2,2-dimethylpropyl)-9-tetrahydropyran-2-yl-purin-8-yl]methanol (I-631) (360 mg) as a colorless oil.

A solution of N-[5-amino-6-[(E)-2-cyclopropylvinyl]pyrimidin-4-yl]-2-(3-nitro-2-oxo-1-pyridyl)acetamide (780 mg, 2.19 mmol, 1 eq) in AcOH (20 mL) was stirred at 120° C. for 12 h. The mixture was concentrated in vacuum to give an oil which was purified by prep-HPLC to give 1-[[6-[(E)-2-cyclopropylvinyl]-9H-purin-8-yl]methyl]-3-nitro-pyridin-2-one (I-632) (440 mg, 59% yield) as a brown solid.

A solution of [6-(2,2-dimethylpropyl)-9-tetrahydropyran-2-yl-purin-8-yl]methyl methanesulfonate (500 mg, 1.31 mmol, 1 eq), 3-nitro-1H-pyridin-2-one (183.53 mg, 1.31 mmol, 1 eq), and DIEA (203.17 mg, 1.57 mmol, 273.81 uL, 1.2 eq) in ACN (5 mL) was stirred at 18° C. for 2 h. The reaction mixture was poured into water (20 mL) and extracted with EtOAc (10 mL×2). The combined organic layers were washed with brine (10 mL), dried over Na2SO4, filtered and concentrated under reduced pressure to give a residue. The residue was purified by column chromatography to give 1-[[6-(2,2-dimethylpropyl)-9-tetrahydropyran-2-yl-purin-8-yl]methyl]-3-nitro-pyridin-2-one (I-633) (210 mg, 38% yield) as a yellow oil. LCMS m/z 427.2 $(M+1)^+$.

A solution of 1-[[6-(2,2-dimethylpropyl)-9-tetrahydropyran-2-yl-purin-8-yl]methyl]-3-nitro-pyridin-2-one (210 mg, 492.42 umol, 1 eq) and Pd/C (0.2 g, 10% purity) in EtOAc (5 mL) was stirred at 18° C. under H2 15 psi for 5 min. The mixture was filtered and the filtrate was concentrated in vacuum to give 3-amino-1-[[6-(2,2-dimethylpropyl)-9-tetrahydropyran-2-yl-purin-8-yl]methyl]pyridin-2-one (I-634) (0.23 g) as a green oil which was used in the next step.

Example 67

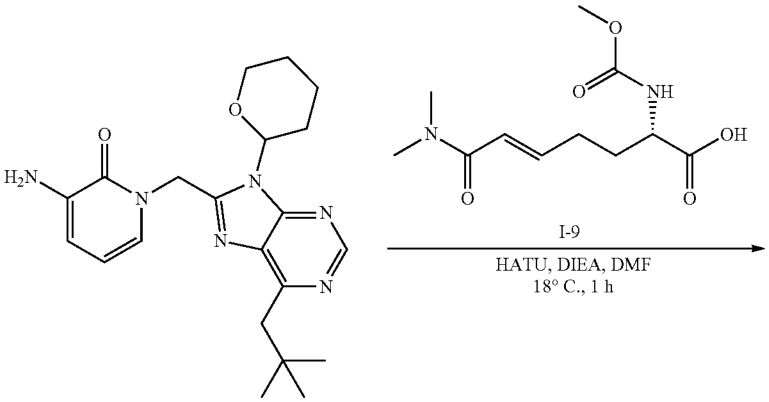

I-634

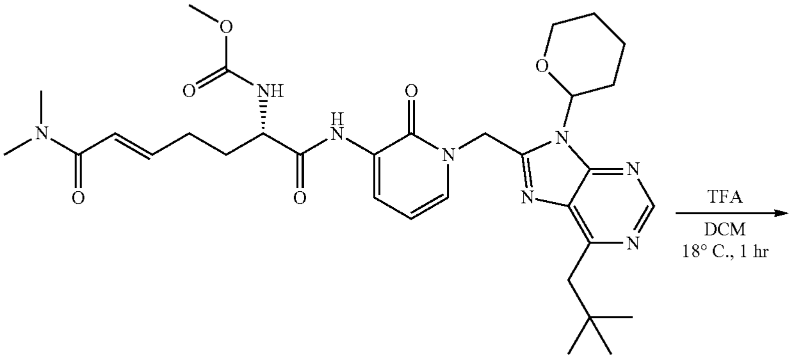

I-635

-continued

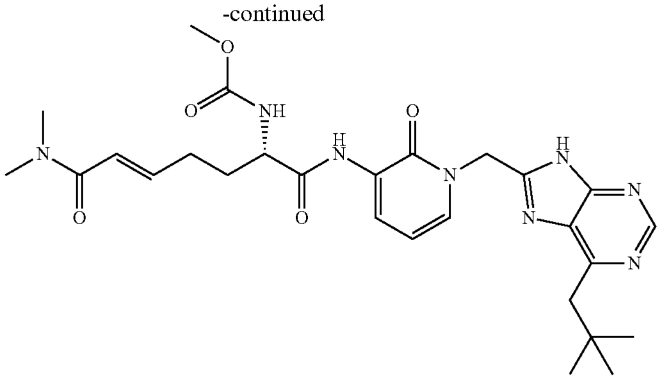

468

To a solution of 3-amino-1-[[6-(2,2-dimethylpropyl)-9-tetrahydropyran-2-yl-purin-8-yl] methyl]pyridin-2-one (110 mg, 277.44 umol, 1 eq), (E,2S)-7-(dimethylamino)-2-(methoxycarbonylamino)-7-oxo-hept-5-enoic acid (85.98 mg, 332.93 umol, 1.2 eq), and DIEA (71.71 mg, 554.88 umol, 96.65 uL, 2 eq) in DMF (1 mL) was added HATU (126.59 mg, 332.93 umol, 1.2 eq) at 18° C. The reaction was stirred at 40° C. for 1 h. The reaction mixture was poured into water 5 mL and extracted with EtOAc (4 mL×2). The combined organic layers were washed with brine (4 mL), dried over $Na_2SO_4$, filtered and concentrated under reduced pressure to give methyl N-[(E,1S)-6-(dimethylamino)-1-[[1-[[6-(2,2-dimethylpropyl)-9-tetrahydropyran-2-yl-purin-8-yl]methyl]-2-oxo-3-pyridyl]carbamoyl]-6-oxo-hex-4-enyl] carbamate (I-635) (250 mg) as a black oil.

A solution of methyl N-[(E,1S)-6-(dimethylamino)-1-[[1-[[6-(2,2-dimethylpropyl)-9-tetrahydropyran-2-yl-purin-8-yl]methyl]-2-oxo-3-pyridyl]carbamoyl]-6-oxo-hex-4-enyl] carbamate (250 mg, 392.62 umol, 1 eq) and $CF_3COOH$ (525 mg, 8.74 mmol, 500 uL, 22.27 eq) in DCM (2 mL) was stirred at 18° C. for 0.5 h. The mixture was concentrated in vacuum to give an oil which was purified by prep-HPLC to give methyl N-[(E,1S)-6-(dimethylamino)-1-[[1-[[6-(2,2-dimethylpropyl)-9H-purin-8-yl]methyl]-2-oxo-3-pyridyl]carbamoyl]-6-oxo-hex-4-enyl]carbamate (Compound 468) (101.2 mg, 46% yield) as a white solid. LCMS m/z 553.1 $(M+1)^+$. $^1H$ NMR (400 MHz, DMSO-$d_6$) δ 0.88-1.04 (m, 9H) 1.62-1.79 (m, 1H) 1.87 (br d, J=6.72 Hz, 1H) 2.15-2.31 (m, 2H) 2.84 (s, 3H) 2.90 (s, 2H) 2.99 (s, 3H) 3.54 (s, 3H) 4.13-4.23 (m, 1H) 5.46 (br d, J=18.46 Hz, 2H) 6.29-6.43 (m, 2H) 6.53-6.70 (m, 1H) 7.51-7.66 (m, 1H) 7.72 (br s, 1H) 8.27 (br t, J=7.34 Hz, 1H) 8.62-8.90 (m, 1H) 9.26 (s, 1H) 13.16-13.57 (m, 1H).

The following compounds were prepared according to the procedures described for the synthesis of Example 67 using the appropriate intermediates.

| Compound | Structure | LCMS Data |
|---|---|---|
| 469 | 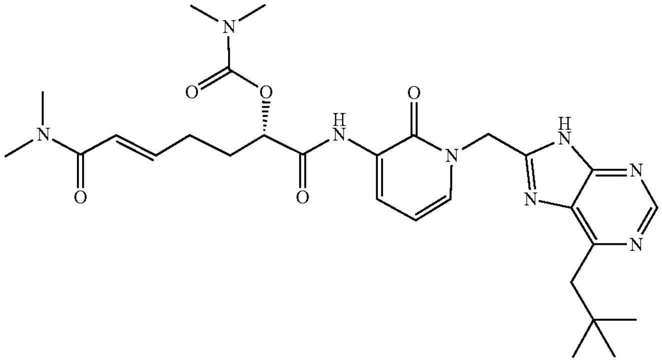 [SMILES: CN(C)C(=O)/C=C/CC[C@H](OC(=O)N(C)C)C(=O)Nc1cccn(Cc2nc3c(CC(C)(C)C)ncnc3[nH]2)c1=O] | LCMS m/z 567.3 $(M + 1)^+$ |

-continued
| Compound | Structure | LCMS Data |
|---|---|---|
| 492 | 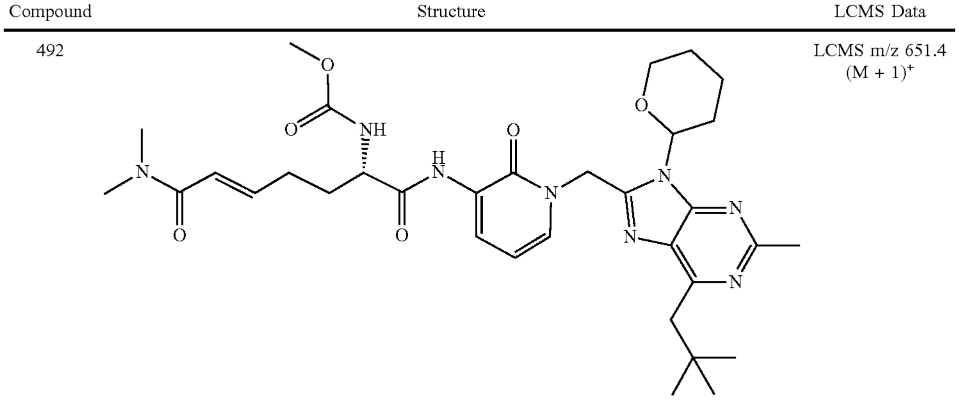 | LCMS m/z 651.4 (M + 1)$^+$ |
| 493 | 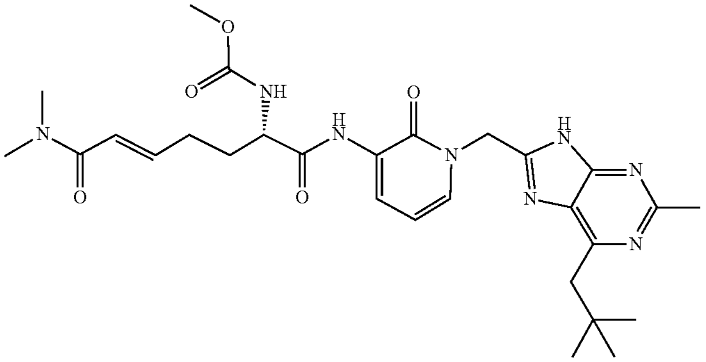 | LCMS m/z 567.3 (M + 1)$^+$ |
| 494 | 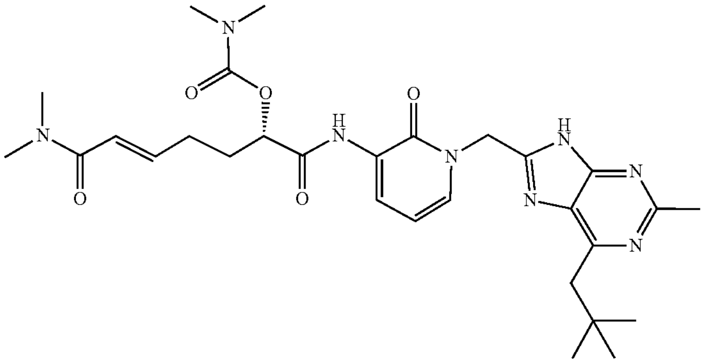 | LCMS m/z 581.3 (M + 1)$^+$ |
The Synthesis of Intermediate I-641
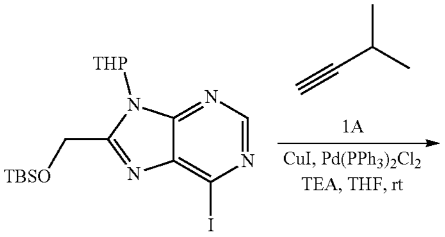
I-621
-continued
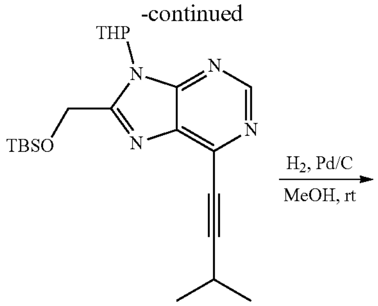
I-636

-continued

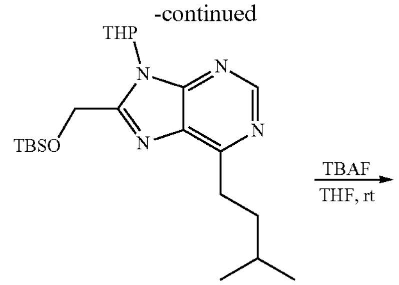

I-637

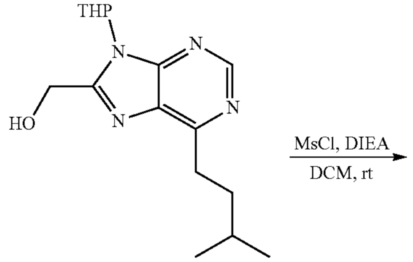

I-638

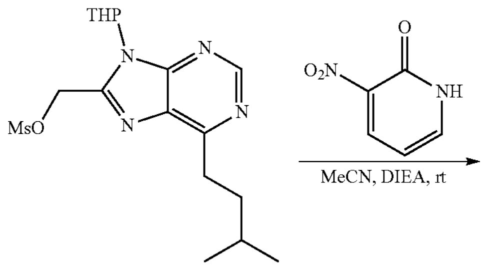

I-639

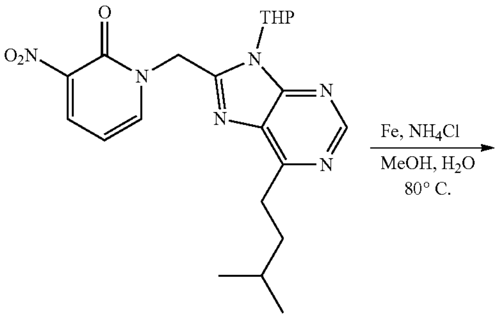

I-640

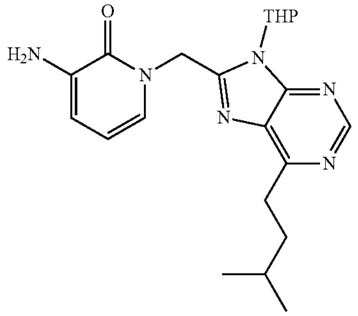

I-641

To a solution of tert-butyl-[(6-iodo-9-tetrahydropyran-2-yl-purin-8-yl)methoxy]-dimethylsilane (800 mg, 1.69 mmol) in THF (10 mL) was added CuI (80.29 mg, 421.58 umol) and $Et_3N$ (511.91 mg, 5.06 mmol, 704.14 uL), $Pd(PPh_3)_2Cl_2$ (118.36 mg, 168.63 umol), and 3-methylbut-1-yne (287.16 mg, 4.22 mmol, 431.18 uL). The mixture was stirred at 20° C. for 1 hr under $N_2$. The mixture was poured into water (10 mL) and the aqueous phase was extracted with ethyl acetate (5 mL*3). The combined organic phase was concentrated in vacuum. The residue was purified by column chromatography to give tert-butyl-dimethyl-[[6-(3-methylbut-1-ynyl)-9-tetrahydropyran-2-yl-purin-8-yl] methoxy]silane (I-636) (800 mg) as a yellow oil. LCMS m/z 415.0 $(M+1)^+$.

To a solution of tert-butyl-dimethyl-[[6-(3-methylbut-1-ynyl)-9-tetrahydropyran-2-yl-purin-8-yl]methoxy]silane (800 mg, 1.93 mmol) in EtOAc (15 mL) was added Pd/C (300 mg, 10% purity). The suspension was degassed under vacuum and purged with $H_2$ several times. The mixture was stirred under $H_2$ (15 psi) at 20° C. for 12 hours. The reaction mixture was filtered and the filtrate was concentrated to give tert-butyl-[(6-isopentyl-9-tetrahydropyran-2-yl-purin-8-yl) methoxy]-dimethylsilane (I-637) (700 mg) as a yellow oil. LCMS m/z 419.1 $(M+1)^+$.

To a solution of tert-butyl-[(6-isopentyl-9-tetrahydropyran-2-yl-purin-8-yl) methoxy]-dimethyl-silane (700 mg, 1.67 mmol) in THF (10 mL) was added TBAF (1 M, 2.01 mL). The mixture was stirred at 18° C. for 1 hr. The reaction mixture was concentrated under reduced pressure to remove THF. The residue was diluted with $H_2O$ (5 mL) and extracted with EtOAc (5 mL×3). The combined organic layers were concentrated under reduced pressure to give (6-isopentyl-9-tetrahydropyran-2-yl-purin-8-yl) methanol (I-638) (600 mg) as a yellow oil. $^1H$ NMR (400 MHz, $CDCl_3$) δ 8.74 (s, 1H), 5.83 (dd, J=2.6, 11.1 Hz, 1H), 5.00-4.82 (m, 2H), 4.20-4.08 (m, 1H), 3.69 (dt, J=2.6, 11.7 Hz, 1H), 3.11-3.04 (m, 2H), 2.20-2.10 (m, 1H), 1.99 (br d, J=9.5 Hz, 1H), 1.90 (br d, J=13.1 Hz, 1H), 1.75-1.62 (m, 5H), 1.62-1.53 (m, 2H), 0.89 (d, J=6.5 Hz, 6H).

To a solution of (6-isopentyl-9-tetrahydropyran-2-yl-purin-8-yl)methanol (550 mg, 1.81 mmol) in DCM (4 mL) was added DIPEA (700.59 mg, 5.42 mmol, 944.20 uL). MsCl (310.48 mg, 2.71 mmol, 209.78 uL) was dropwise at 18° C. The mixture was stirred at 18° C. for 1 hr. The mixture was poured into water (5 mL) and organic phase was concentrated in vacuum at 20° C. to give (6-isopentyl-9-tetrahydropyran-2-yl-purin-8-yl)methyl methanesulfonate (I-639) (680 mg) as a yellow oil.

To a solution of 3-nitro-1H-pyridin-2-one (273.98 mg, 1.96 mmol) in MeCN (12 mL) was added DIPEA (459.55 mg, 3.56 mmol, 619.34 uL) and (6-isopentyl-9-tetrahydropyran-2-yl-purin-8-yl)methyl methanesulfonate (680 mg, 1.78 mmol) at 0° C., the mixture was stirred at 18° C. for 12 hr. The mixture was poured into water (5 mL). The aqueous phase was extracted with ethyl acetate (5 mL*3) and the combined organic phase was concentrated in vacuum. The residue was purified by column chromatography to give 1-[(6-isopentyl-9-tetrahydropyran-2-yl-purin-8-yl)methyl]-3-nitro-pyridin-2-one (I-640) (400 mg) as a yellow oil. LCMS m/z 449.0 $(M+23)^+$.

To a solution of 1-[(6-isopentyl-9-tetrahydropyran-2-yl-purin-8-yl)methyl]-3-nitro-pyridin-2-one (200 mg, 468.97 umol) in MeOH (2 mL) and $H_2O$ (0.5 mL) was added Fe (340.46 mg, 6.10 mmol) and $NH_4Cl$ (326.12 mg, 6.10 mmol, 213.15 uL). The mixture was stirred at 80° C. for 1 hour. The reaction mixture was filtered and the filtrate was concentrated. The residue was poured into water (2 mL) and the aqueous phase was extracted with DCM (2 mL*3). The combined organic phase was concentrated in vacuum to give 3-amino-1-[(6-isopentyl-9-tetrahydropyran-2-yl-purin-8-yl)

methyl]pyridin-2-one (I-641) (157 mg) as a black brown solid. LCMS m/z 397.4 $(M+1)^+$.
The following intermediates were prepared according to the procedures described for the synthesis of I-641 using the appropriate reagents.
| Compound | Structure | LCMS Data |
| --- | --- | --- |
| I-642 | 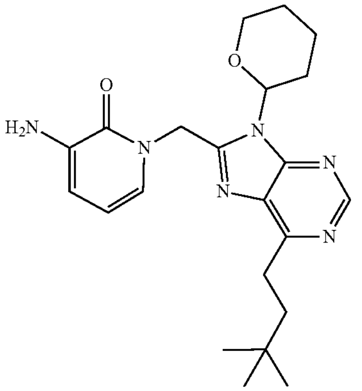 [SMILES: CC(C)(C)CCc1ncnc2c1nc(Cn1cccc(N)c1=O)n2C1CCCCO1] | LCMS m/z 411.2 $(M + 1)^+$ |
-continued
| Compound | Structure | LCMS Data |
| --- | --- | --- |
| I-643 | 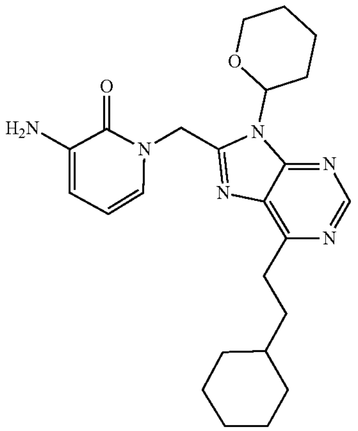 [SMILES: Nc1cccn(Cc2nc3c(CCC4CCCCC4)ncnc3n2C2CCCCO2)c1=O] | LCMS m/z 437.2 $(M + 1)^+$ |
Example 68
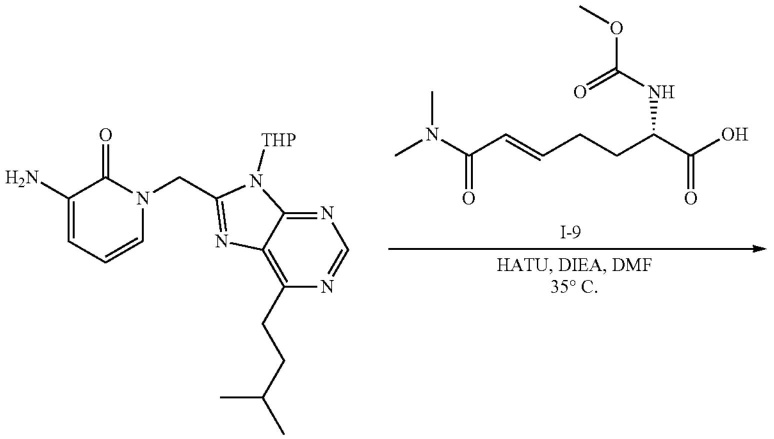
I-9
I-641
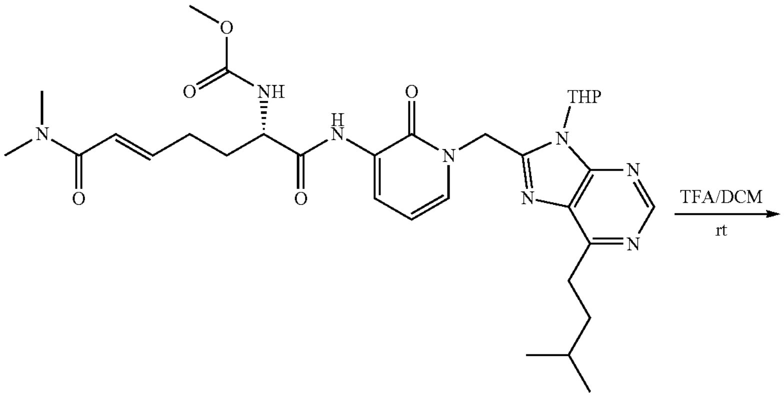
I-644

-continued

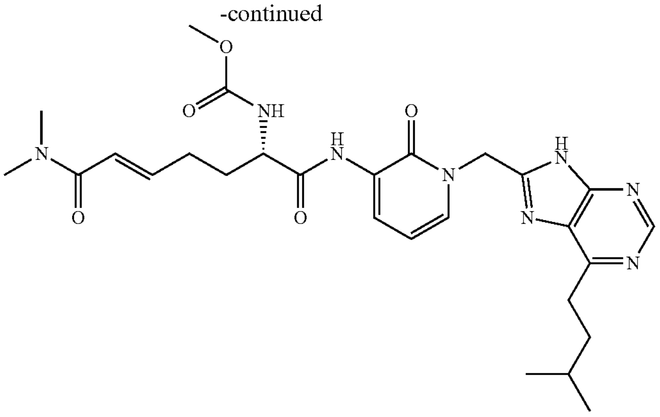

471

To a solution of 3-amino-1-[(6-isopentyl-9-tetrahydropyran-2-yl-purin-8-yl) methyl]pyridin-2-one (157 mg, 395.98 umol) in DMF (0.5 mL) was added (E,2S)-7-(dimethylamino)-2-(methoxycarbonylamino)-7-oxo-hept-5-enoic acid (122.72 mg, 475.18 umol) and DIPEA (102.36 mg, 791.96 umol, 137.95 uL) and HATU (225.85 mg, 593.97 umol). The mixture was stirred at 35° C. for 12 hr. The mixture was poured into water (4 mL). The aqueous phase was extracted with DCM (5 mL*2). The combined organic phase was washed with brine (5 mL*3), dried with anhydrous $Na_2SO_4$, filtered and concentrated in vacuum to give methyl N-[(E,1S)-6-(dimethylamino)-1-[[1-[(6-isopentyl-9-tetrahydropyran-2-yl-purin-8-yl) methyl]-2-oxo-3-pyridyl] carbamoyl]-6-oxo-hex-4-enyl]carbamate (I-644) (180 mg) as a black brown oil. LCMS m/z 637.1 $(M+1)^+$.

To a solution of methyl N-[(E,1S)-6-(dimethylamino)-1-[[1-[(6-isopentyl-9-tetrahydropyran-2-yl-purin-8-yl) methyl]-2-oxo-3-pyridyl]carbamoyl]-6-oxo-hex-4-enyl]carbamate (173 mg, 271.70 umol) in DCM (1.5 mL) was added TFA (464.69 mg, 4.08 mmol, 301.75 uL). The mixture was stirred at 18° C. for 0.5 hr. The mixture was poured into sat. $NaHCO_3$ solution (5 mL). The combined organic phase was washed with brine (3 mL*2), dried with anhydrous $Na_2SO_4$, filtered and concentrated in vacuum. The residue was purified by prep-HPLC to afford methyl (S,E)-(7-(dimethylamino)-1-((1-((6-isopentyl-9H-purin-8-yl)methyl)-2-oxo-1,2-dihydropyridin-3-yl)amino)-1,7-dioxohept-5-en-2-yl) carbamate (Compound 471) (51.1 mg, 33% yield) as a white solid. $^1H$ NMR (400 MHz, DMSO-$d_6$) δ 13.50 (br s, 1H), 9.27 (s, 1H), 8.74 (s, 1H), 8.28 (d, J=7.3 Hz, 1H), 7.73 (br d, J=7.7 Hz, 1H), 7.60 (br d, J=7.0 Hz, 1H), 6.65-6.54 (m, 1H), 6.44-6.31 (m, 2H), 5.45 (s, 2H), 4.18 (br s, 1H), 3.54 (s, 3H), 3.03-2.95 (m, 5H), 2.84 (s, 3H), 2.30-2.13 (m, 2H), 1.87 (br d, J=7.7 Hz, 1H), 1.76-1.63 (m, 3H), 1.56 (br s, 1H), 0.91 (br d, J=6.1 Hz, 6H). LCMS m/z 553.2 $(M+1)^+$.

The following compounds were prepared according to the procedures described for the synthesis of Example 68 using the appropriate intermediates.

| Compound | Structure | LCMS Data |
| --- | --- | --- |
| 456 | 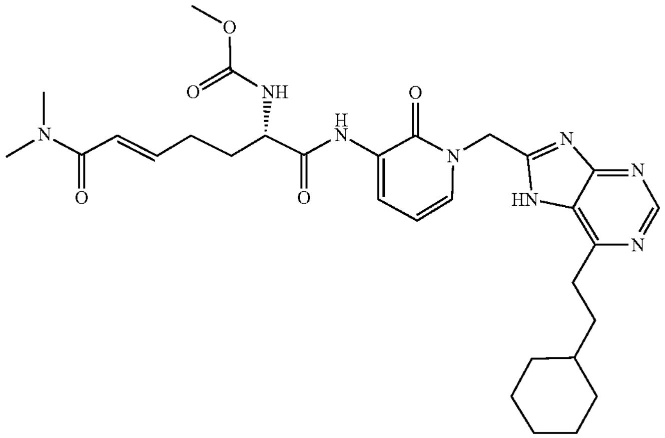 [SMILES: COC(=O)N[C@@H](CC/C=C/C(=O)N(C)C)C(=O)Nc1cccn(Cc2nc3ncnc(CCC4CCCCC4)c3[nH]2)c1=O] | LCMS m/z 593.3 $(M + 1)^+$ |

-continued
| Compound | Structure | LCMS Data |
|---|---|---|
| 472 | 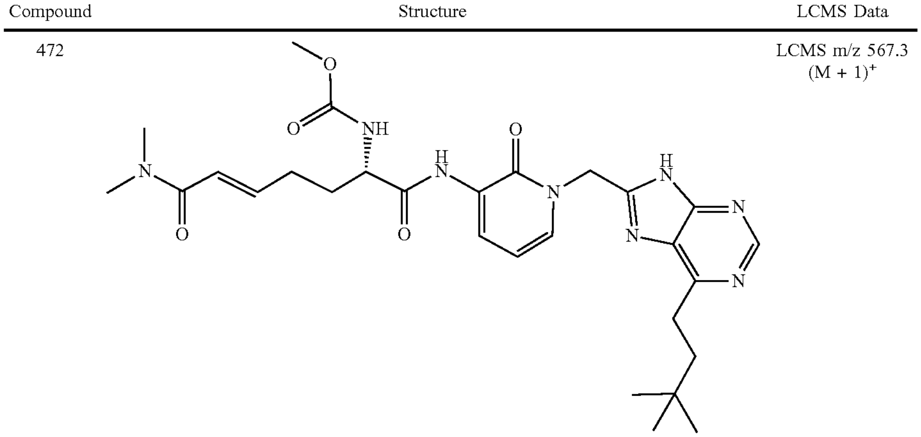 | LCMS m/z 567.3 $(M + 1)^+$ |
| 473 | 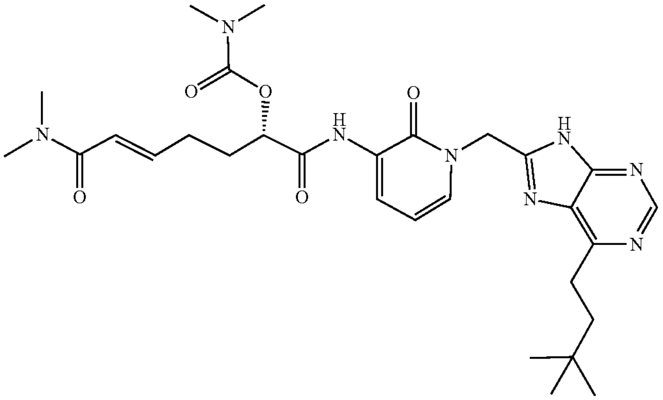 [SMILES: CN(C)C(=O)/C=C/CC[C@H](OC(=O)N(C)C)C(=O)Nc1cccn(Cc2nc3c(CCC(C)(C)C)ncnc3[nH]2)c1=O] | LCMS m/z 581.3 $(M + 1)^+$ |
| 475 | 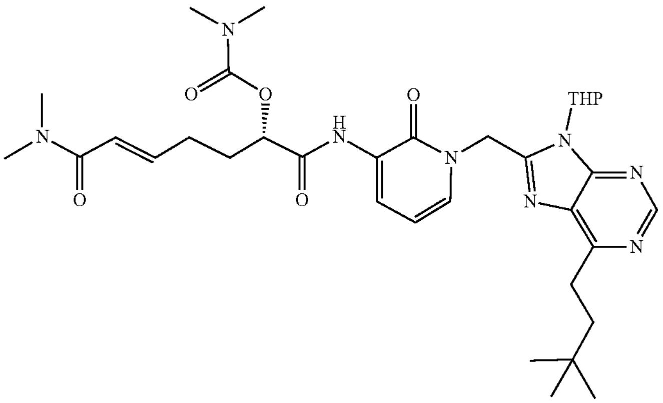 | LCMS m/z 665.4 $(M + 1)^+$ |
| 481 | 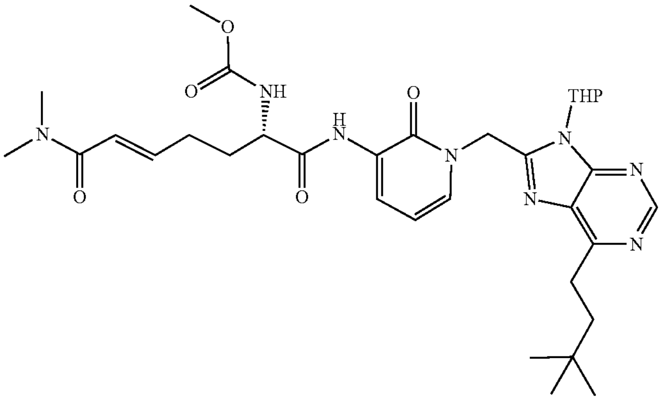 | LCMS m/z 651.4 $(M + 1)^+$ |

-continued
| Compound | Structure | LCMS Data |
|---|---|---|
| 482 | 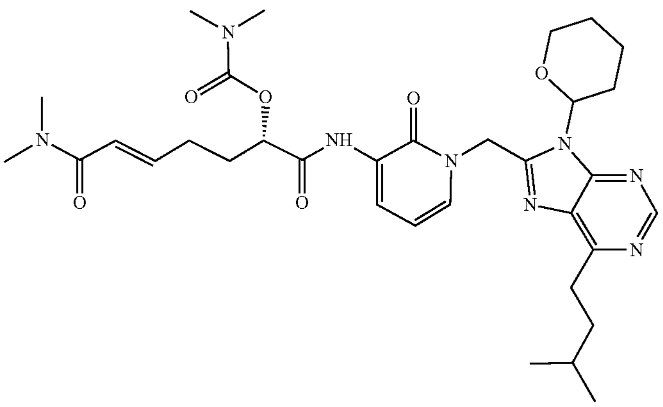 [SMILES: CC(C)CCc1ncnc2c1nc(Cn1cccc(NC(=O)[C@H](CC/C=C/C(=O)N(C)C)OC(=O)N(C)C)c1=O)n2C1CCCCO1] | LCMS m/z 651.4 (M + 1)+ |
| 483 | 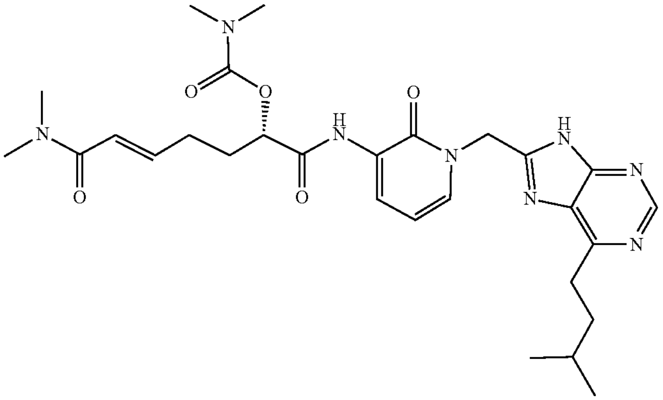 [SMILES: CC(C)CCc1ncnc2[nH]c(Cn3cccc(NC(=O)[C@H](CC/C=C/C(=O)N(C)C)OC(=O)N(C)C)c3=O)nc12] | LCMS m/z 567.3 (M + 1)+ |
The Synthesis of Intermediate I-655
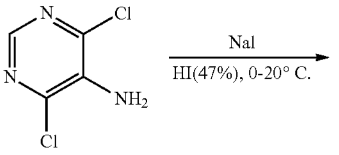
I-645
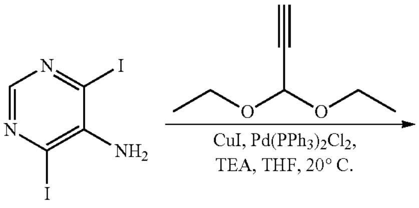
I-646
-continued
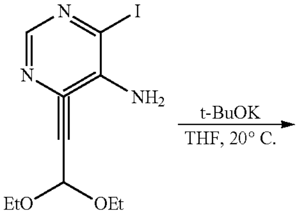
I-647
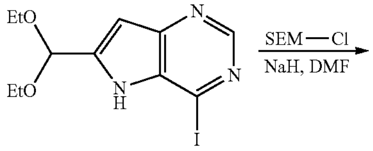
I-648
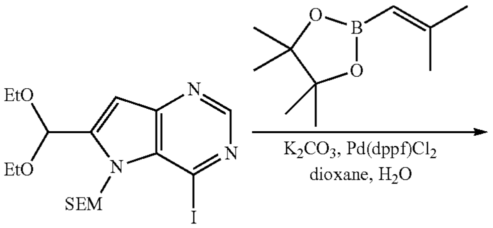
I-649

-continued

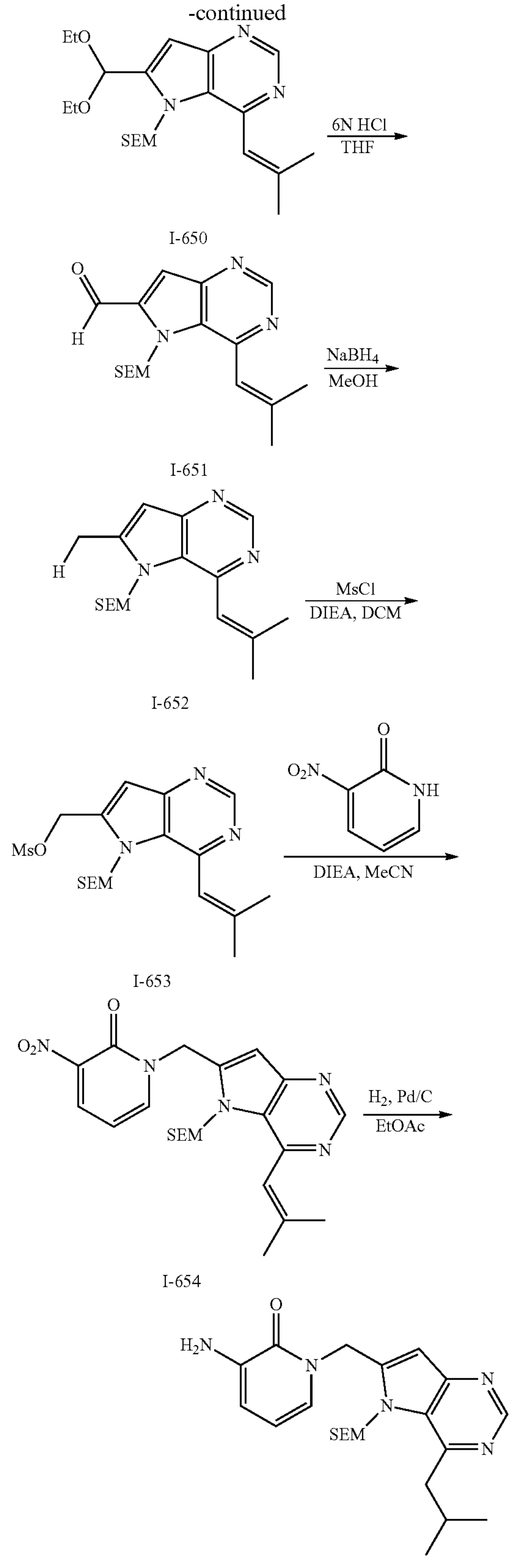

I-650

I-651

I-652

I-653

I-654

I-655

4,6Dichloropyrimidin-5-amine (5 g, 30.49 mmol) was added in one portion to HI (47%) (60 mL) at 0° C., followed by NaI (22.85 g, 152.45 mmol) at 0° C. The mixture was stirred at 20° C. for 12 hours. The reaction mixture was poured into water 100 mL and extracted with DCM (50 mL×2). The combined organic phase was washed with sat. $NaHCO_3$ (40 mL), sat. $Na_2S_2O_3$ (40 mL) and brine (40 mL), dried over $Na_2SO_4$ and filtered. The filtrate was concentrated under reduced pressure to give 4,6-diiodopyrimidin-5-amine (I-646) (5.8 g, 55% yield) as a yellow solid.

A mixture of 4,6-diiodopyrimidin-5-amine (3.8 g, 10.95 mmol), 3,3-diethoxyprop-1-yne (1.54 g, 12.05 mmol, 1.73 mL), CuI (521.56 mg, 2.74 mmol), $Pd(PPh_3)_2Cl_2$ (768.88 mg, 1.10 mmol) and TEA (5.54 g, 54.77 mmol, 7.62 mL) in THF (45 mL) was degassed and purged with $N_2$ for 3 times, and then the mixture was stirred at 20° C. for 12 hr under $N_2$ atmosphere. The reaction mixture was concentrated under reduced pressure to give a residue. The residue was purified by flash silica gel chromatography to give 4-(3,3-diethoxy-prop-1-ynyl)-6-iodo-pyrimidin-5-amine (I-647) (1.8 g) as a yellow oil.

A mixture of 4-(3,3-diethoxyprop-1-ynyl)-6-iodo-pyrimidin-5-amine (1.8 g, 5.19 mmol) in THF (20 mL) was added t-BuOK (727.28 mg, 6.48 mmol) at 0° C. The mixture was stirred at 20° C. for 1.5 hours. The reaction mixture was diluted with sat. $NH_4Cl$ (30 mL) and extracted with EtOAc (20 mL×2). The combined organic layers were washed with brine (30 mL), dried over $Na_2SO_4$ and filtered. The filtrate was concentrated under reduced pressure to give 6-(diethoxymethyl)-4-iodo-5H-pyrrolo[3,2-d]pyrimidine (I-648) (1.7 g, 94% yield) as a brown solid.

A mixture of 6-(diethoxymethyl)-4-iodo-5H-pyrrolo[3,2-d]pyrimidine (1.7 g, 4.90 mmol) in DMF (20 mL) was added NaH (254.64 mg, 6.37 mmol, 60% purity) at 0° C., and then the mixture was stirred at 0° C. for 0.5 hour, then SEM-Cl (1.06 g, 6.37 mmol, 1.13 mL) was added at 0° C., and then the mixture was stirred at 20° C. for 1 hr. The reaction mixture was poured into sat. $NH_4Cl$ (40 mL) and extracted with EtOAc (15 mL×2). The combined organic layers were washed with brine (30 mL), dried over $Na_2SO_4$ and filtered. The filtrate was concentrated under reduced pressure to give a residue. The residue was purified by column chromatography to give 2-[[6-(diethoxymethyl)-4-iodo-pyrrolo[3,2-d]pyrimidin-5-yl]methoxy]ethyl-trimethyl-silane (I-649) (1.2 g, 2.51 mmol, 51.33% yield) as a yellow oil.

A mixture of 2-[[6-(diethoxymethyl)-4-iodo-pyrrolo[3,2-d]pyrimidin-5-yl]methoxy]ethyl-trimethyl-silane (0.7 g, 1.47 mmol), 4,4,5,5-tetramethyl-2-(2-methylprop-1-enyl)-1,3,2-dioxaborolane (400.43 mg, 2.20 mmol), $K_2CO_3$ (405.29 mg, 2.93 mmol), $Pd(dppf)Cl_2$ (107.29 mg, 146.62 umol) in dioxane (8 mL) and $H_2O$ (1.6 mL) was degassed and purged with $N_2$ for 3 times. The mixture was stirred at 100° C. for 12 hours under $N_2$ atmosphere. To the reaction mixture was added sat. $NH_4Cl$ (20 mL). The reaction mixture was extracted with EtOAc (10 mL×2). The combined organic layers were washed with brine (20 mL), dried over $Na_2SO_4$ and filtered. The filtrate was concentrated under reduced pressure to give a residue. The residue was purified by column chromatography to give 2-[[6-(diethoxymethyl)-4-(2-methylprop-1-enyl)pyrrolo[3,2-d]pyrimidin-5-yl]methoxy]ethyl-trimethylsilane (I-650) (0.29 g, 49% yield) as a yellow oil.

A mixture of 2-[[6-(diethoxymethyl)-4-(2-methylprop-1-enyl)pyrrolo[3,2-d]pyrimidin-5-yl]methoxy]ethyl-trimethyl-silane (0.29 g, 714.98 umol) in THF (2 mL) was added HCl (2 mL, 6N) at 45° C. The mixture was stirred at 45° C. for 1.5 hr. To the reaction mixture was added NaOH (solid) at 0° C. until the pH~8. The mixture was diluted with water (10 mL) and extracted with EtOAc (8 mL×2). The combined organic layers were washed with brine (10 mL), dried over $Na_2SO_4$ and filtered. The filtrate was concentrated under reduced pressure to give 4-(2-methylprop-1-enyl)-5-(2-trimethylsilylethoxymethyl)pyrrolo[3,2-d] pyrimidine-6-carbaldehyde (I-651) (0.16 g) as a brown oil.

A mixture of 4-(2-methylprop-1-enyl)-5-(2-trimethylsilylethoxymethyl)pyrrolo[3,2-d] pyrimidine-6-carbaldehyde (0.16 g, 482.68 umol) in MeOH (2 mL) was added $NaBH_4$ (36.52 mg, 965.36 umol) at 0° C. The mixture was stirred at 20° C. for 2 hr. To the reaction mixture was added water (5 mL) to quench $NaBH_4$, and then the mixture was concentrated under reduced pressure to remove MeOH. The aqueous phase was extracted with EtOAc (4 mL×2). The combined organic layers were dried over $Na_2SO_4$ and filtered. The filtrate was concentrated under reduced pressure to give a residue which was purified by prep-TLC to give [4-(2-methylprop-1-enyl)-5-(2-trimethylsilylethoxymethyl)pyrrolo[3,2-d]pyrimidin-6-yl]methanol (I-652) (0.04 g, 119.94 umol, 25% yield) as a yellow oil.

A mixture of [4-(2-methylprop-1-enyl)-5-(2-trimethylsilylethoxymethyl)pyrrolo[3,2-d] pyrimidin-6-yl]methanol (0.04 g, 119.94 umol), DIEA (46.50 mg, 359.82 umol, 62.67 uL) in DCM (1 mL) was added MsCl (27.48 mg, 239.88 umol, 18.57 uL) at 0° C. The mixture was stirred at 0° C. for 1 hr. The reaction mixture was diluted with sat. $NH_4Cl$ solution (3 mL) and extracted with DCM (2 mL×2). The combined organic phase were dried over anhydrous $Na_2SO_4$, filtered and concentrated under reduced pressure to give [4-(2-methylprop-1-enyl)-5-(2-trimethylsilylethoxymethyl)pyrrolo[3,2-d]pyrimidin-6-yl]methyl methanesulfonate (I-653) (0.065 g) as a brown oil.

A mixture of 3-nitro-1H-pyridin-2-one (22.12 mg, 157.92 umol), DIEA (40.82 mg, 315.85 umol, 55.02 uL) in ACN (1 mL) was added a solution of [4-(2-methylprop-1-enyl)-5-(2-trimethylsilylethoxymethyl)pyrrolo[3,2-d]pyrimidin-6-yl]methyl methanesulfonate (0.065 g, 157.92 umol) in ACN (1 mL) at 0° C., and then the mixture was stirred at 20° C. for 12 hr. The reaction mixture was concentrated under reduced pressure to give an oil which was purified by prep-TLC to give 1-[[4-(2-methylprop-1-enyl)-5-(2-trimethylsilylethoxymethyl)pyrrolo[3,2-d]pyrimidin-6-yl]methyl]-3-nitro-pyridin-2-one (I-654) (0.05 g) as a yellow oil. LCMS m/z 458.3 $(M+1)^+$.

A mixture of 1-[[4-(2-methylprop-1-enyl)-5-(2-trimethylsilylethoxymethyl)pyrrolo[3,2-d] pyrimidin-6-yl]methyl]-3-nitro-pyridin-2-one (0.05 g, 109.75 umol), Pd/C (0.05 g, 10% purity) in EtOAc (10 mL) was degassed and purged with $H_2$ for 3 times, and then the mixture was stirred at 20° C. for 1 hr under $H_2$ atmosphere (15 psi). The reaction mixture was filtered and the filtrate was concentrated under reduced pressure to give 3-amino-1-[[4-isobutyl-5-(2-trimethylsilylethoxymethyl)pyrrolo[3,2-d]pyrimidin-6-yl] methyl]pyridin-2-one (I-655) (0.047 g) as a green oil. LCMS m/z 428.4 $(M+1)^+$.

The following intermediate was prepared according to the procedures described for the synthesis of I-655 using the appropriate reagents.

| Compound | Structure | LCMS Data |
| --- | --- | --- |
| I-656 | 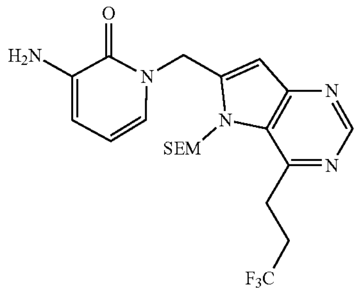 [SMILES: C[Si](C)(C)CCOCn1c(Cn2cccc(N)c2=O)cc2ncnc(CCC(F)(F)F)c21] | LCMS m/z 468.3 $(M + 1)^+$ |

Example 69

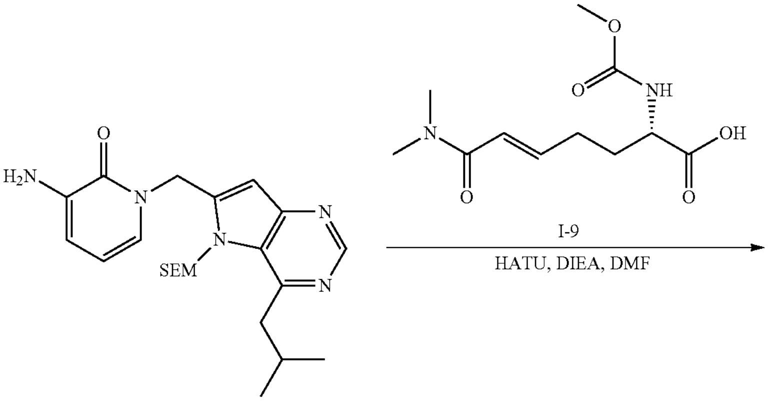

I-655

-continued

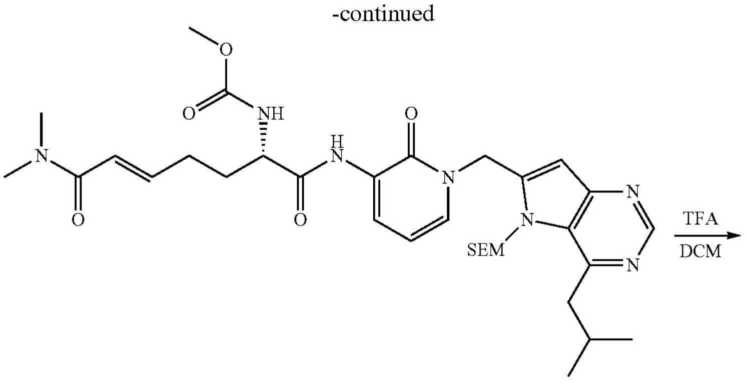

I-657

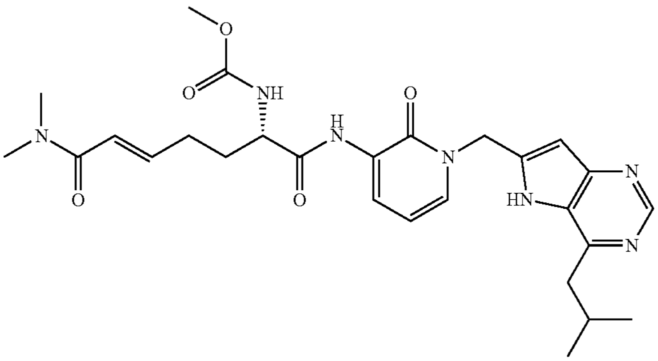

459

A mixture of 3-amino-1-[[4-isobutyl-5-(2-trimethylsilylethoxymethyl)pyrrolo[3,2-d] pyrimidin-6-yl]methyl]pyridin-2-one (0.047 g, 109.91 umol), (E,2S)-7-(dimethylamino)-2-(methoxycarbonylamino)-7-oxo-hept-5-enoic acid (34.06 mg, 131.89 umol), and DIEA (28.41 mg, 219.82 umol, 38.29 uL) in DMF (1.5 mL) was added HATU (50.15 mg, 131.89 umol) at 30° C. The mixture was stirred at 30° C. for 12 hr. The reaction mixture was poured into water (15 mL) and extracted with EtOAc (8 mL×3). The combined organic layers were washed with brine (15 mL) and concentrated under reduced pressure to give a residue. The residue was purified by prep-TLC to give methyl N-[(E,1S)-6-(dimethylamino)-1-[[1-[[4-isobutyl-5-(2-trimethylsilylethoxymethyl)pyrrolo[3,2-d]pyrimidin-6-yl]methyl]-2-oxo-3-pyridyl]carbamoyl]-6-oxo-hex-4-enyl]carbamate (I-657) (40 mg, 54% yield) as a yellow oil. LCMS m/z 668.5 $(M+1)^+$.

A mixture of methyl N-[(E,1S)-6-(dimethylamino)-1-[[1-[[4-isobutyl-5-(2-trimethylsilylethoxymethyl)pyrrolo[3,2-d] pyrimidin-6-yl]methyl]-2-oxo-3-pyridyl]carbamoyl]-6-oxo-hex-4-enyl]carbamate (35 mg, 52.41 umol) in DCM (1.5 mL) and TFA (1.5 mL), and then the mixture was stirred at 35° C. for 2 hr. The reaction mixture was poured into sat. $NaHCO_3$ aq. (10 mL) and extracted with DCM (8 mL×2). The combined organic layers were washed with brine 10 mL, dried over anhydrous $Na_2SO_4$, filtered and concentrated under reduced pressure to give the crude product. The crude product was purified by prep-HPLC to give methyl N-[(E, 1S)-6-(dimethylamino)-1-[[1-[(4-isobutyl-5H-pyrrolo[3,2-d]pyrimidin-6-yl)methyl]-2-oxo-3-pyridyl] carbamoyl]-6-oxo-hex-4-enyl]carbamate (Compound 459) (13.9 mg, 49% yield) as a white solid. $^1$H NMR (400 MHz, DMSO-$d_6$) δ12.08 (br s, 1H) 9.32 (s, 1H) 8.69 (s, 1H) 8.26 (dd, J=7.34, 1.34 Hz, 1H) 7.75 (br d, J=7.70 Hz, 1H) 7.55 (br d, J=5.50 Hz, 1H) 6.57-6.66 (m, 1H) 6.34-6.43 (m, 2H) 6.30 (s, 1H) 5.41 (s, 2H) 4.15-4.25 (m, 1H) 3.56 (s, 3H) 2.99 (s, 3H) 2.88 (d, J=7.34 Hz, 2H) 2.84 (s, 3H) 2.17-2.33 (m, 3H) 1.67-1.94 (m, 2H) 0.93 (d, J=6.60 Hz, 6H). LCMS m/z 538.3 $(M+1)^+$.

The following compounds were prepared according to the procedures described for the synthesis of Example 69 using the appropriate intermediates.

| Compound | Structure | LCMS Data |
|---|---|---|
| 474 | 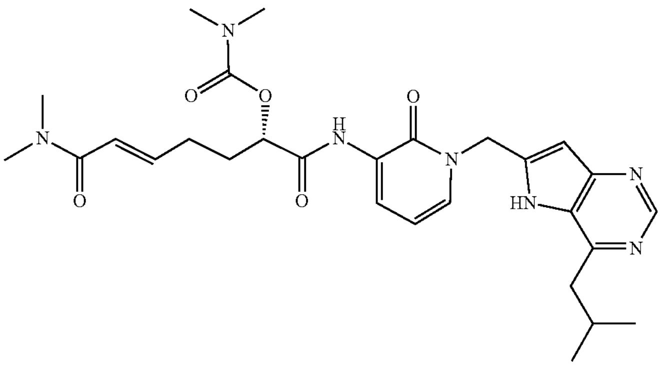 [SMILES: CC(C)Cc1ncnc2cc(Cn3cccc(NC(=O)[C@H](CC/C=C/C(=O)N(C)C)OC(=O)N(C)C)c3=O)[nH]c12] | LCMS m/z 552.2 (M + 1)$^+$ |
| 490 | 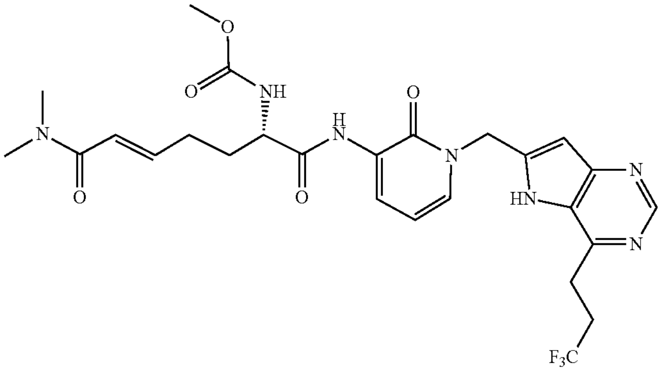 | LCMS m/z 578.2 (M + 1)$^+$ |
| 491 | 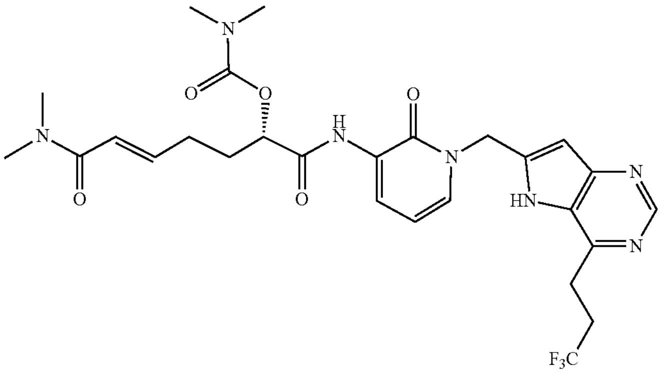 [SMILES: CN(C)C(=O)/C=C/CC[C@H](OC(=O)N(C)C)C(=O)Nc1cccn(Cc2cc3ncnc(CCC(F)(F)F)c3[nH]2)c1=O] | LCMS m/z 592.3 (M + 1)$^+$ |
| 497 | 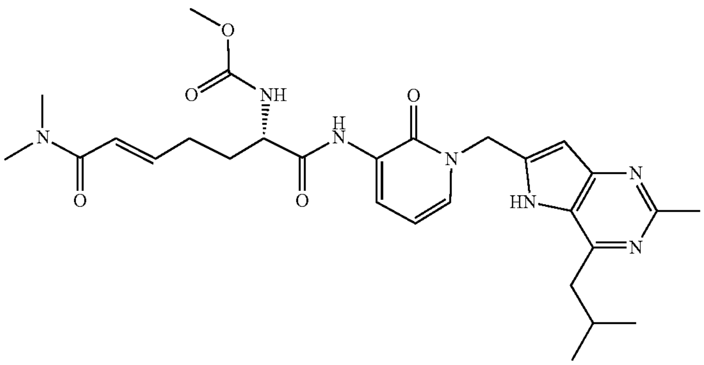 | LCMS m/z 552.3 (M + 1)$^+$ |

-continued
| Compound | Structure | LCMS Data |
|---|---|---|
| 498 | 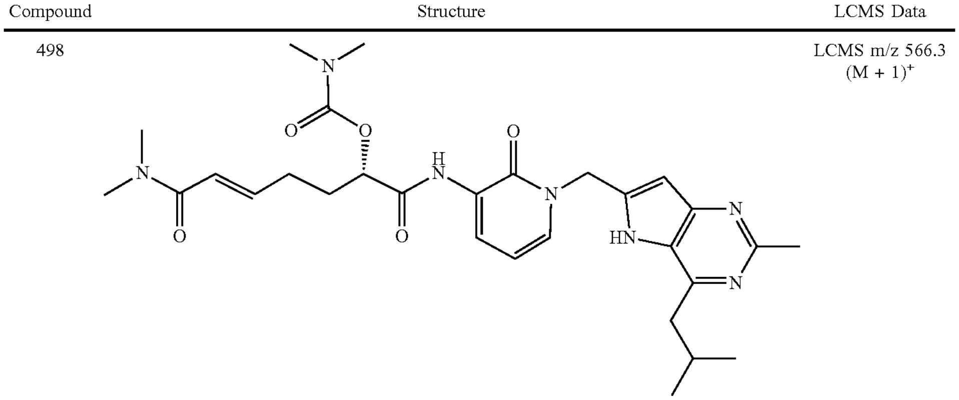 | LCMS m/z 566.3 $(M + 1)^+$ |
Synthesis of Intermediate I-671
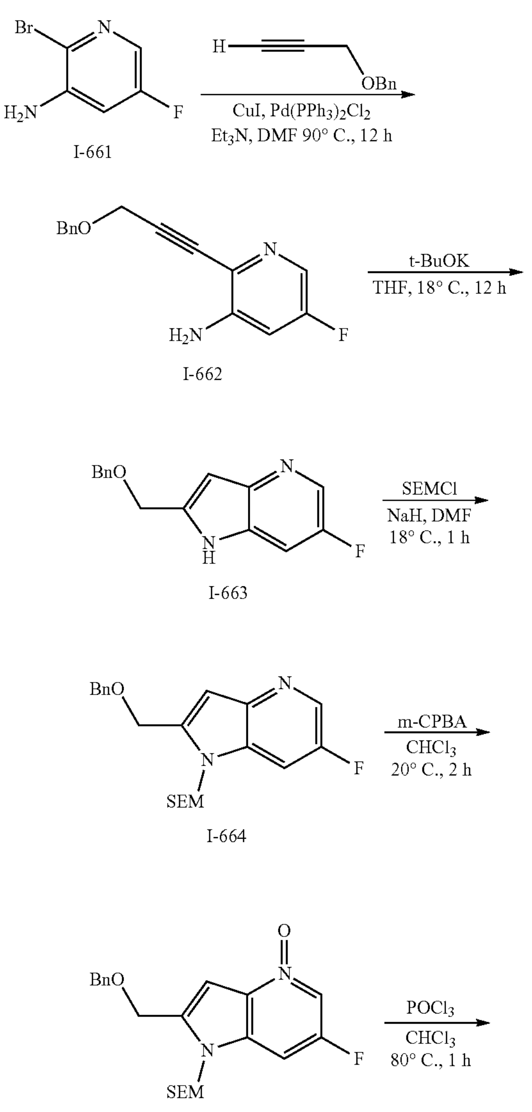
I-661
I-662
I-663
I-664
I-665
-continued
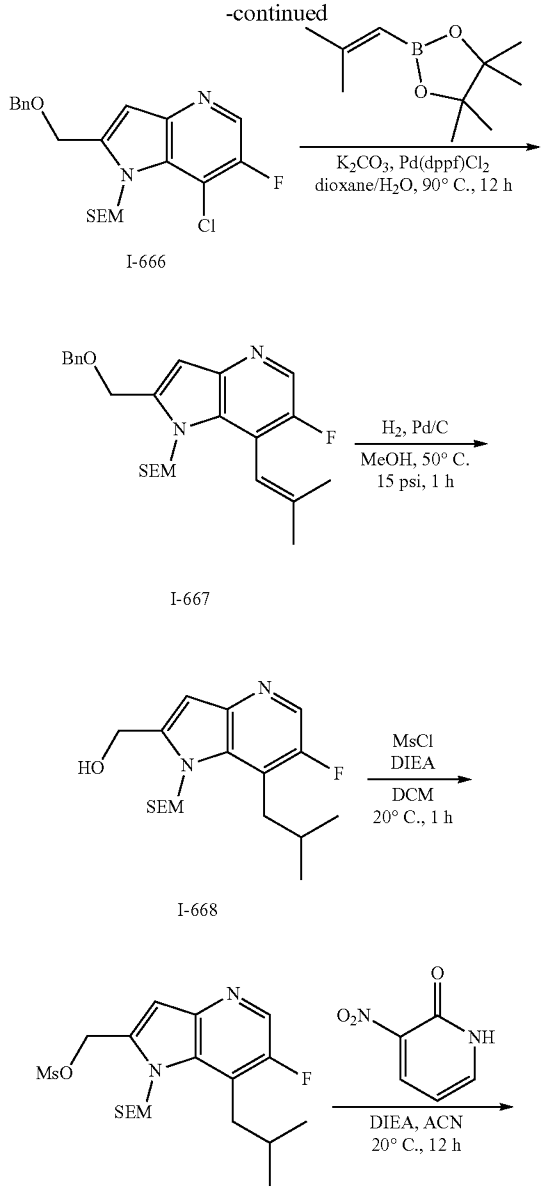
I-666
I-667
I-668
I-669

-continued

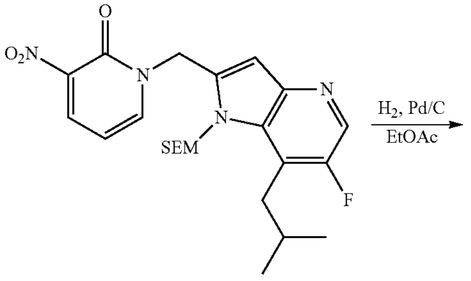

I-670

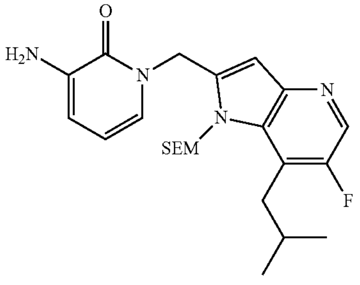

I-671

To a solution of 2-bromo-5-fluoro-pyridin-3-amine (5.6 g, 29.32 mmol, 1 eq), prop-2-ynoxymethylbenzene (6.43 g, 43.98 mmol, 58.39 uL, 1.5 eq), CuI (1.40 g, 7.33 mmol, 0.25 eq), and TEA (10.38 g, 102.62 mmol, 14.28 mL, 3.5 eq) in DMF (60 mL) was added dichloropalladiumtriphenylphosphane (2.06 g, 2.93 mmol, 0.1 eq) at 18° C. The reaction was stirred at 18° C. for 12 h. The reaction mixture was poured into water 60 mL and extracted with EtOAc 60 mL (30 mL*2). The combined organic layers were washed with brine (30 mL), dried over $Na_2SO_4$, filtered, and concentrated under reduced pressure to give a residue. The residue was purified by column chromatography ($SiO_2$) to give 2-(3-benzyloxyprop-1-ynyl)-5-fluoro-pyridin-3-amine (I-662) (4.24 g, 56% yield) as a brown oil. LCMS m/z 257 $(M+1)^+$.

To a solution of 2-(3-benzyloxyprop-1-ynyl)-5-fluoro-pyridin-3-amine (4.24 g, 16.54 mmol, 1 eq) in THF (50 mL) was added t-BuOK (2.23 g, 19.85 mmol, 1.2 eq) at 0° C., then the reaction was stirred at 20° C. for 3 h. The reaction mixture was poured into water 60 mL and extracted with EtOAc 60 mL (30 mL*2). The combined organic layers were washed with brine 30 mL (30 mL*1), dried over $Na_2SO_4$, filtered, and concentrated under reduced pressure to give a residue. The residue was purified by column chromatography ($SiO_2$) to give 2-(benzyloxymethyl)-6-fluoro-1H-pyrrolo[3,2-b]pyridine (I-663) (3 g, 71% yield) as a yellow solid. LCMS m/z 256.8 $(M+1)^+$.

To a solution of 2-(benzyloxymethyl)-6-fluoro-1H-pyrrolo[3,2-b]pyridine (3 g, 11.03 mmol, 1 eq) in DMF (30 mL) was added NaH (661.57 mg, 16.54 mmol, 60% purity, 1.5 eq) at 0° C. The solution was stirred at 0° C. for 0.5 h and then SEM-Cl (2.21 g, 13.23 mmol, 2.34 mL, 1.2 eq) was added to the solution at 0° C. The solution was stirred at 0° C. for 0.5 h. The reaction mixture was poured into water 60 mL and extracted with EtOAc 60 mL (30 mL*2). The combined organic layers were washed with brine 30 mL (30 mL*1), dried over $Na_2SO_4$, filtered and concentrated under reduced pressure to give a residue. The residue was purified by column chromatography ($SiO_2$) to give 2-[[2-(benzyloxymethyl)-6-fluoro-pyrrolo[3,2-b]pyridin-1-yl]methoxy]ethyl-trimethyl-silane (I-664) (2.5 g, 59% yield) as a yellow oil. LCMS m/z 387.4 $(M+1)^+$.

To a solution of 2-[[2-(benzyloxymethyl)-6-fluoro-pyrrolo[3,2-b]pyridin-1-yl]methoxy]ethyl-trimethyl-silane (2.5 g, 6.47 mmol, 1 eq) in $CHCl_3$ (25 mL) was added m-CPBA (2.09 g, 9.70 mmol, 80% purity, 1.5 eq) at 0° C. The reaction was stirred at 20° C. for 2 h. The reaction mixture was poured into sat. aq. $Na_2SO_3$ (30 mL) and sat. aq. $NaHCO_3$ (30 mL), and then extracted with EtOAc (30 mL*2). The combined organic layers were washed with brine (20 mL*1), dried over $Na_2SO_4$, filtered and concentrated under reduced pressure to give 2-[[2-(benzyloxymethyl)-6-fluoro-4-oxido-pyrrolo[3,2-b]pyridin-4-ium-1-yl]methoxy]ethyl-trimethyl-silane (I-665) (3 g) as a yellow oil which was used directly in the next step.

To a solution of 2-[[2-(benzyloxymethyl)-6-fluoro-4-oxido-pyrrolo[3,2-b]pyridin-4-ium-1-yl]methoxy]ethyl-trimethyl-silane (0.1 g, 248.43 umol, 1 eq) in $CHCl_3$ (1 mL) was added $POCl_3$ (495.00 mg, 3.23 mmol, 0.3 mL, 12.99 eq) at 80° C. The reaction was stirred at 80° C. for 0.5 h. The reaction mixture was quenched with ice water (20 mL) at 0° C., and then adjusted by sat. aq. $NaHCO_3$ to pH=7, and extracted with EtOAc (25 mL*2). The combined organic layers were washed with brine (20 mL*2), dried over $Na_2SO_4$, filtered, and concentrated under reduced pressure to give a residue. The residue was purified by flash silica gel chromatography to give 2-[[2-(benzyloxymethyl)-7-chloro-6-fluoro-pyrrolo[3,2-b]pyridin-1-yl]methoxy]ethyl-trimethyl-silane (I-666) (0.78 g, 25% yield) as a green oil.

To a solution of 2-[[2-(benzyloxymethyl)-7-chloro-6-fluoro-pyrrolo[3,2-b]pyridin-1-yl]methoxy]ethyl-trimethyl-silane (780 mg, 1.85 mmol, 1 eq), 4,4,5,5-tetramethyl-2-(2-methylprop-1-enyl)-1,3,2-dioxaborolane (404.81 mg, 2.22 mmol, 1.2 eq), and $K_2CO_3$ (768.21 mg, 5.56 mmol, 3 eq) in dioxane (8 mL) and $H_2O$ (1.6 mL) was added Pd(dppf)$Cl_2 \cdot CH_2Cl_2$ (181.57 mg, 222.34 umol, 0.12 eq). The mixture was stirred at 110° C. under $N_2$ for 12 h.

The reaction mixture was concentrated under reduced pressure to give a residue. The residue was purified by flash silica gel chromatography to give 2-[[2-(benzyloxymethyl)-6-fluoro-7-(2-methylprop-1-enyl)pyrrolo[3,2-b]pyridin-1-yl]methoxy]ethyl-trimethyl-silane (I-667) (550 mg, 67% yield) as a yellow oil. LCMS m/z 441.4 $(M+1)^+$.

A solution of 2-[[2-(benzyloxymethyl)-6-fluoro-7-(2-methylprop-1-enyl)pyrrolo[3,2-b]pyridin-1-yl]methoxy]ethyl-trimethyl-silane (550 mg, 1.25 mmol, 1 eq) and Pd/C (550 mg, 10% purity) in MeOH (10 mL) was stirred at 50° C. under $H_2$ (15 psi) for 2 h. The mixture was filtered and the filtrate was concentrated in vacuum to give crude [6-fluoro-7-isobutyl-1-(2-trimethylsilylethoxymethyl)pyrrolo[3,2-b]pyridin-2-yl]methanol (I-668) (460 mg) as a yellow oil. LCMS m/z 352.9 $(M+1)^+$.

To a solution of [6-fluoro-7-isobutyl-1-(2-trimethylsilylethoxymethyl)pyrrolo[3,2-b]pyridin-2-yl]methanol (0.25 g, 709.18 umol, 1 eq) and DIEA (183.31 mg, 1.42 mmol, 247.05 uL, 2 eq) in DCM (2 mL) was added MsCl (121.86 mg, 1.06 mmol, 82.33 uL, 1.5 eq) dropwise at 0° C. The reaction was stirred at 0° C. for 1 h. The reaction mixture was poured into water 5 mL and extracted with DCM (10 mL*2). The combined organic layers were washed with brine (10 mL*1), dried over $Na_2SO_4$, filtered, and concentrated under reduced pressure to give crude [6-fluoro-7-isobutyl-1-(2-trimethylsilylethoxymethyl)pyrrolo[3,2-b]pyridin-2-yl]methyl methanesulfonate (I-669) (750 mg) as a black oil.

A solution of 3-nitro-1H-pyridin-2-one (292.81 mg, 2.09 mmol, 1.2 eq), [6-fluoro-7-isobutyl-1-(2-trimethylsilylethoxymethyl)pyrrolo[3,2-b]pyridin-2-yl]methylmethanesulfonate (750 mg, 1.74 mmol, 1 eq), and DIEA (337.66 mg, 2.61 mmol, 455.07 uL, 1.5 eq) in ACN (7 mL) was stirred at 30° C. for 12 h. The reaction mixture was poured into water (40 mL), and extracted with EtOAc (20 mL*2). The combined organic layers were washed with brine (10 mL*2), dried over $Na_2SO_4$, filtered, and concentrated under reduced pressure to give a residue. The residue was purified by column chromatography ($SiO_2$) to give 1-[[6-fluoro-7-isobutyl-1-(2-trimethylsilylethoxymethyl)pyrrolo[3,2-b]pyridin-2-yl]methyl]-3-nitro-pyridin-2-one (I-670) (0.36 g, 44% yield) as a black oil. LCMS m/z 475.0 (M+1)+.

To solution of 1-[[6-fluoro-7-isobutyl-1-(2-trimethylsilylethoxymethyl)pyrrolo[3,2-b]pyridin-2-yl]methyl]-3-nitro-pyridin-2-one (0.36 g, 758.53 umol, 1 eq) and Pd/C (200 mg, 10% purity) in EtOAc (5 mL) was stirred at 20° C. for 0.5 h under $H_2$ (15 psi). The mixture was filtered and the filtrate was concentrated in vacuum to give 3-amino-1-[[6-fluoro-7-isobutyl-1-(2-trimethylsilylethoxymethyl)pyrrolo[3,2-b]pyridin-2-yl]methyl]pyridin-2-one (I-671) (0.36 g) as a green oil. LCMS m/z 445.0 (M+1)+.

Example 70

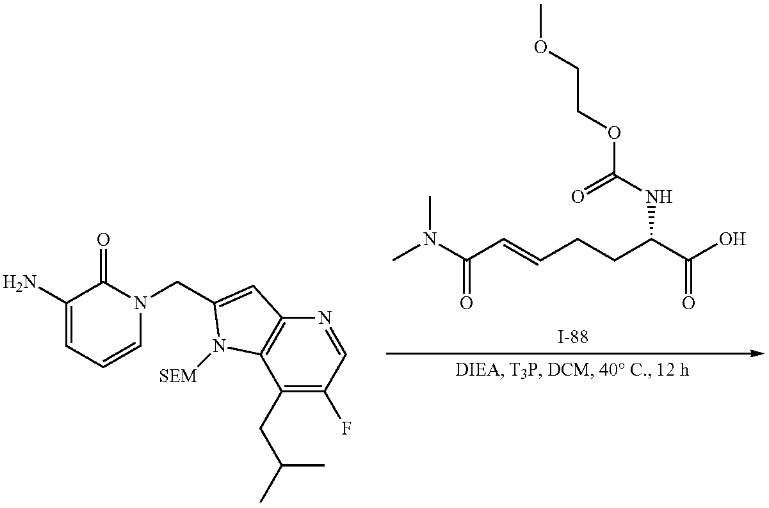

I-671

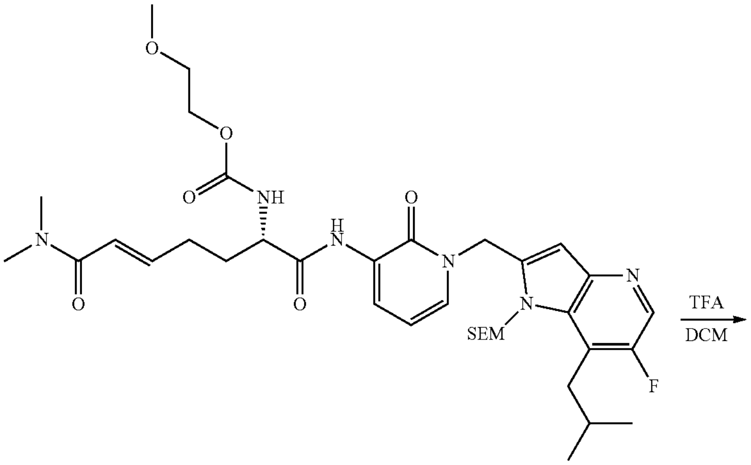

I-675

-continued

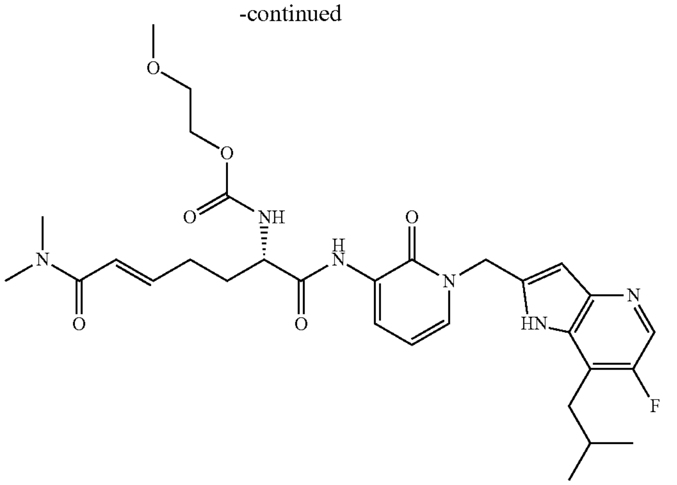

527

A solution of 3-amino-1-[[6-fluoro-7-isobutyl-1-(2-trimethylsilylethoxymethyl) pyrrolo[3,2-b]pyridin-2-yl]methyl] pyridin-2-one (80 mg, 180 umol, 1 eq), (E,2S)-7-(dimethylamino)-2-(2-methoxyethoxycarbonylamino)-7-oxo-hept-5-enoic acid (109 mg, 360 umol, 2 eq), DIEA (233 mg, 1.80 mmol, 10 eq), and $T_3P$ (573 mg, 900 umol, 50% purity, 5 eq) in DCM (3 mL) was stirred at 30° C. for 12 h. Sat. aq. $NaHCO_3$ (5 mL) was added to the mixture, and the mixture was extracted with DCM (5 mL*3). The organic layer was concentrated under reduced pressure to give 2-methoxyethyl N-[(E,1S)-6-(dimethylamino)-1-[[1-[[6-fluoro-7-isobutyl-1-(2-trimethylsilylethoxymethyl)pyrrolo[3,2-b]pyridin-2-yl]methyl]-2-oxo-3-pyridyl]carbamoyl]-6-oxo-hex-4-enyl] carbamate (I-675) (131 mg) as a brown oil which was used in the next step without further purification. LCMS m/z 729.4 $(M+1)^+$.

TFA (1.54 g, 13.5 mmol, 1 mL) was added to a solution of 2-methoxyethyl N-[(E,1S)-6-(dimethylamino)-1-[[1-[[6-fluoro-7-isobutyl-1-(2-trimethylsilylethoxymethyl)pyrrolo [3,2-b]pyridin-2-yl]methyl]-2-oxo-3-pyridyl]carbamoyl]-6-oxo-hex-4-enyl]carbamate (131 mg, 180 umol, 1 eq) in DCM (2 mL) at 25° C. and stirred for 12.5 h. The mixture was concentrated to remove DCM, then dissolved in MeOH (2 mL) and basified to pH 7 with $NaHCO_3$. KOAc (35.3 mg, 359 umol, 2 eq) was added to the mixture and stirred at 25° C. for 1 h. The mixture was concentrated to give a residue. The residue was purified by prep-HPLC to give 2-methoxyethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate (Compound 527) (37.4 mg, 34% yield) as a white solid. LCMS m/z 599.4 $(M+1)^+$. $^1H$ NMR (400 MHz, DMSO-$d_6$) δ 11.56 (s, 1H) 9.31 (s, 1H) 8.16-8.30 (m, 2H) 7.85 (br d, J=7.6 Hz, 1H) 7.48 (br d, J=5.4 Hz, 1H) 6.55-6.68 (m, 1H) 6.28-6.43 (m, 3H) 5.33 (s, 2H) 4.14-4.23 (m, 1H) 4.08 (br d, J=2.8 Hz, 2H) 3.50 (br t, J=4.4 Hz, 2H) 3.25 (s, 3H) 2.99 (s, 3H) 2.83 (s, 3H) 2.77 (br d, J=7.2 Hz, 2H) 2.17-2.30 (m, 2H) 2.01 (dt, J=13.6, 6.8 Hz, 1H) 1.66-1.92 (m, 2H) 0.91 (d, J=6.4 Hz, 6H).

The following compounds were prepared according to the procedures described for the synthesis of Example 70 using the appropriate intermediates.

| Compound | Structure | LCMS Data |
| --- | --- | --- |
| 500 | 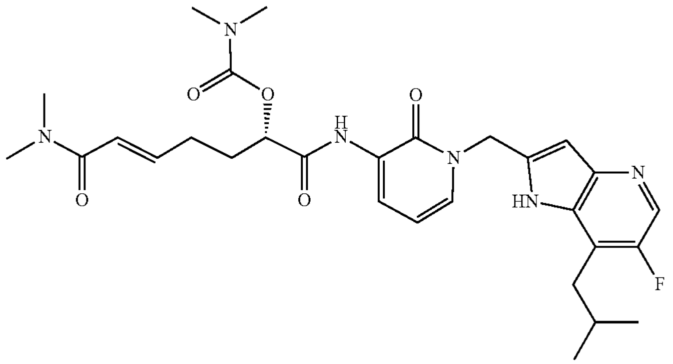 [SMILES: CC(C)Cc1c(F)cnc2cc(Cn3cccc(NC(=O)[C@H](CC/C=C/C(=O)N(C)C)OC(=O)N(C)C)c3=O)[nH]c12] | LCMS m/z 569.4 $(M + 1)^+$ |

-continued

| Compound | Structure | LCMS Data |
|---|---|---|
| 520 | 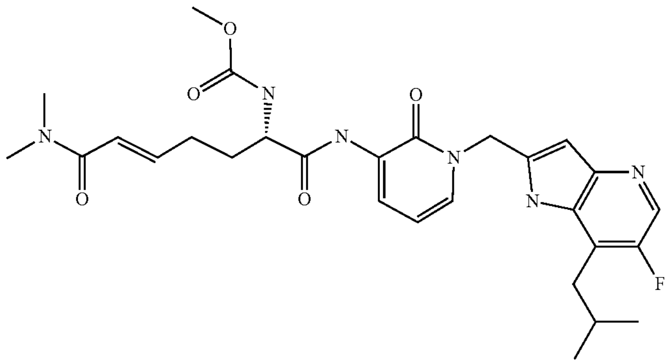 [SMILES: COC(=O)N[C@@H](CC/C=C/C(=O)N(C)C)C(=O)Nc1cccn(Cc2cc3ncc(F)c(CC(C)C)c3[nH]2)c1=O] | LCMS m/z 554.6 $(M+1)^+$ |
| 521 | 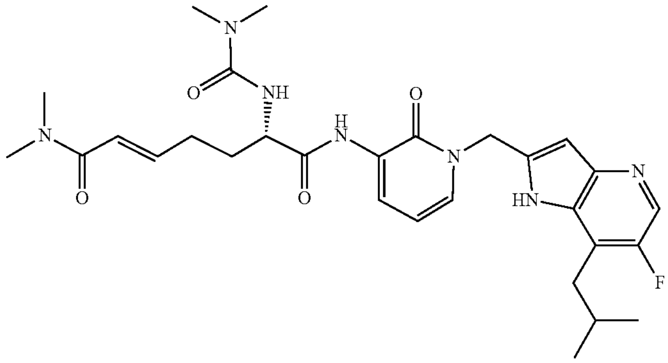 [SMILES: CC(C)Cc1c(F)cnc2cc(Cn3cccc(NC(=O)[C@H](CC/C=C/C(=O)N(C)C)NC(=O)N(C)C)c3=O)[nH]c12] | LCMS m/z 568.3 $(M+1)^+$ |

The Synthesis of Intermediate I-676

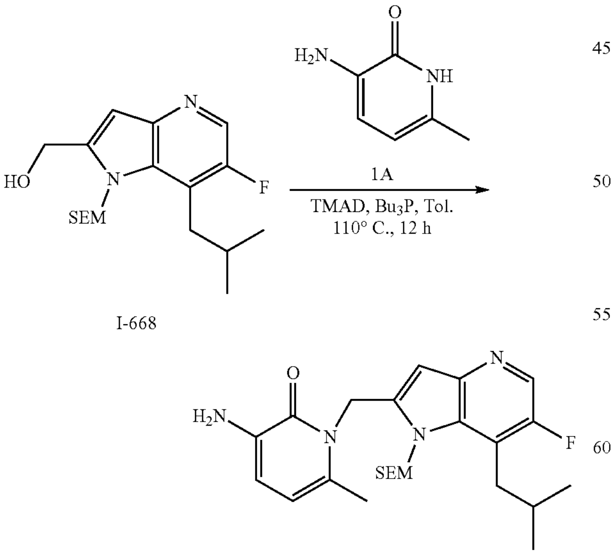

I-668

I-676

To the mixture of [6-fluoro-7-isobutyl-1-(2-trimethylsilylethoxymethyl)pyrrolo[3,2-b]pyridin-2-yl]methanol (500 mg, 1.42 mmol), 3-amino-6-methyl-1H-pyridin-2-one (352.15 mg, 2.84 mmol), and tributylphosphane (573.93 mg, 2.84 mmol, 699.91 uL) in toluene (10 mL) was added TMAD (488.46 mg, 2.84 mmol) at 0° C. The reaction mixture was stirred at 110° C. for 12 hours under $N_2$. The reaction was concentrated in vacuum. The residue was purified by column chromatography ($SiO_2$) and then was purified by prep-HPLC to give 3-amino-1-[[6-fluoro-7-isobutyl-1-(2-trimethylsilylethoxymethyl)pyrrolo[3,2-b]pyridin-2-yl]methyl]-6-methyl-pyridin-2-one (I-676) (0.11 g, 239.84 umol, 16.91% yield) as a yellow oil.

The following intermediate was prepared according to the procedures described for the synthesis of I-676 using the appropriate reagents.

| Compound | Structure | LCMS Data |
| --- | --- | --- |
| I-677 | 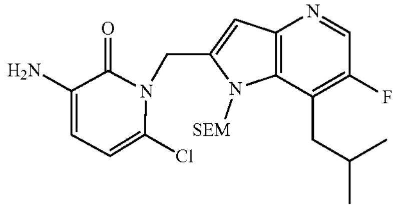 [SMILES: CC(C)Cc1c(F)cnc2cc(Cn3c(Cl)ccc(N)c3=O)n(COCC[Si](C)(C)C)c12] | LCMS m/z 479.4 $(M + H)^+$ |

Example 71

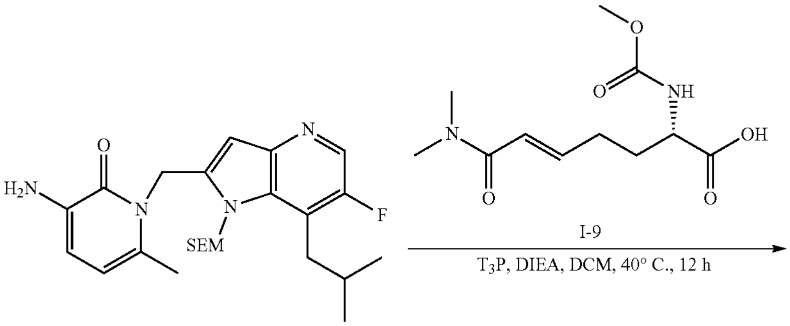

I-676

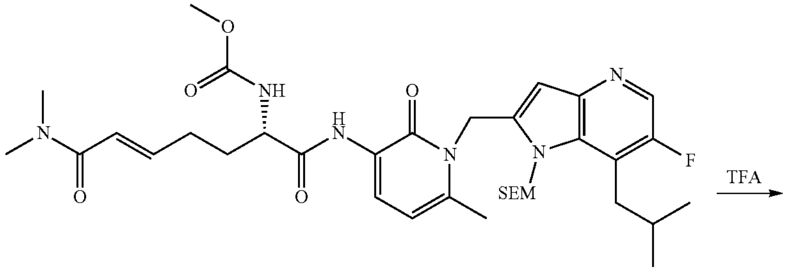

I-678

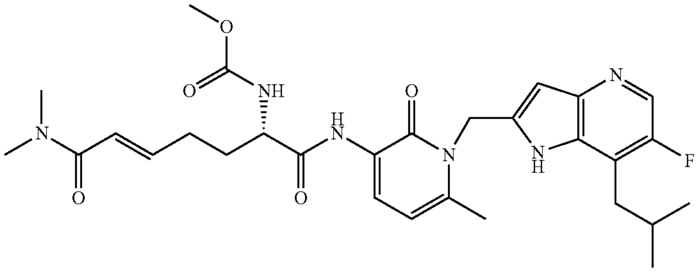

553

To the mixture of 3-amino-1-[[6-fluoro-7-isobutyl-1-(2-trimethylsilylethoxymethyl)pyrrolo [3,2-b]pyridin-2-yl] methyl]-6-methyl-pyridin-2-one (45 mg, 98.12 umol), (E,2S)-7-(dimethylamino)-2-(methoxycarbonylamino)-7-oxo-hept-5-enoic acid (32.94 mg, 127.55 umol) and DIEA (25.36 mg, 196.23 umol, 34.18 uL) in DCM (2 mL) was added $T_3P$ (124.87 mg, 196.23 umol, 116.70 uL, 50% purity) (in EtOAc), and then the mixture was stirred at 40° C. for 12 hours. The mixture was added saturated $NH_4Cl$ (10 mL) and extracted with DCM (3 mL*3). The combined organic phase was washed with brine (10 mL*1), dried with anhydrous $Na_2SO_4$, filtered and concentrated in vacuum to give methyl N-[(E,1S)-6-(dimethylamino)-1-[[1-[[6-fluoro-7-isobutyl-1-(2-trimethylsilylethoxymethyl)pyrrolo[3,2-b]pyridin-2-yl]methyl]-6-methyl-2-oxo-3-pyridyl]carbamoyl]-6-oxo-hex-4-enyl]carbamate (I-678) (80 mg) as light yellow oil.

The mixture of methyl N-[(E,1S)-6-(dimethylamino)-1-[[1-[[6-fluoro-7-isobutyl-1-(2-trimethylsilylethoxymethyl) pyrrolo[3,2-b]pyridin-2-yl]methyl]-6-methyl-2-oxo-3-pyridyl]carbamoyl]-6-oxo-hex-4-enyl]carbamate (80 mg, 114.47 umol) in TFA (2 mL) was stirred at 30° C. for 1.5 hours. The reaction mixture was dried by flowing $N_2$, then added MeOH (2 mL), adjusted by $NaHCO_3$ (solid) to pH~7, then added KOAc (22.47 mg, 228.93 umol) to the mixture, and stirred at 40° C. for 2 hours. The reaction mixture was filtered. The filtrate was purified by prep-HPLC to give methyl N-[(E,1S)-6-(dimethylamino)-1-[[1-[(6-fluoro-7-isobutyl-1H-pyrrolo[3,2-b]pyridin-2-yl)methyl]-6-methyl-2-oxo-3-pyridyl]carbamoyl]-6-oxo-hex-4-enyl]carbamate (Compound 553) (29.0 mg, 40% yield) as a light yellow solid. LCMS m/z 569.3 (M+1) LCMS m/z 569.3 $(M+1)^+$. $^1H$ NMR (400 MHz, DMSO-$d_6$) δ 11.61 (br s, 1H) 9.23 (br s, 1H) 8.12-8.23 (m, 2H) 7.75 (br d, J=7.28 Hz, 1H) 6.55-6.66 (m, 1H) 6.38 (br d, J=15.21 Hz, 1H) 6.25 (br d, J=7.50 Hz, 1H) 5.95 (br s, 1H) 5.45 (br s, 2H) 4.18 (br s, 1H) 3.55 (br s, 3H) 2.99 (s, 3H) 2.75-2.88 (m, 5H) 2.37 (br s, 3H) 2.23 (br d, J=6.17 Hz, 2H) 1.98-2.09 (m, 1H) 1.65-1.94 (m, 2H) 0.93 (br d, J=5.95 Hz, 6H).

The following compounds were prepared according to the procedures described for the synthesis of Example 71 using the appropriate intermediates.

| Compound | Structure | Characterization Data |
|---|---|---|
| 564 | 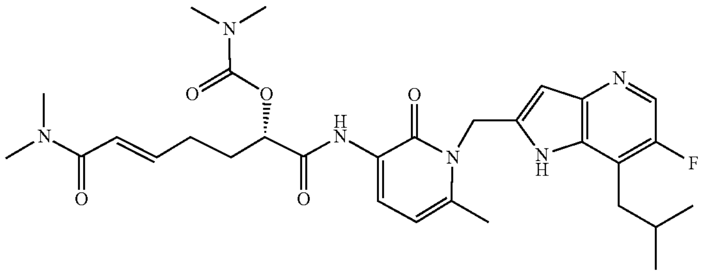 [SMILES: Cc1ccc(NC(=O)[C@H](CC/C=C/C(=O)N(C)C)OC(=O)N(C)C)c(=O)n1Cc1cc2ncc(F)c(CC(C)C)c2[nH]1] | LCMS m/z 583.4 $(M + 1)^+$ |
| 554 | 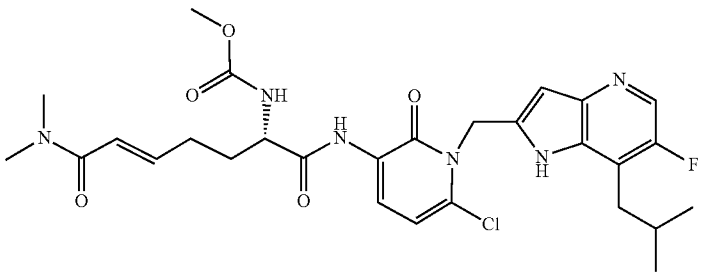 [SMILES: COC(=O)N[C@@H](CC/C=C/C(=O)N(C)C)C(=O)Nc1ccc(Cl)n(Cc2cc3ncc(F)c(CC(C)C)c3[nH]2)c1=O] | LCMS m/z 589.2 $(M + 1)^+$ |
| 563 | 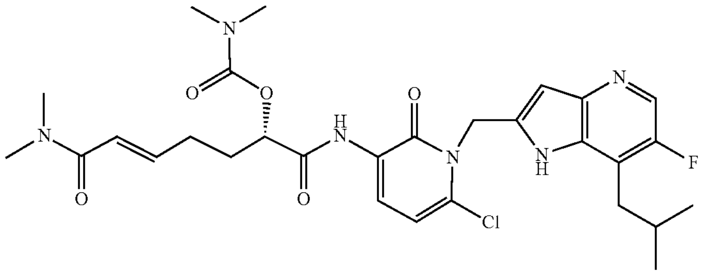 [SMILES: CC(C)Cc1c(F)cnc2cc(Cn3c(Cl)ccc(NC(=O)[C@H](CC/C=C/C(=O)N(C)C)OC(=O)N(C)C)c3=O)[nH]c12] | LCMS m/z 603.2 $(M + 1)^+$ |

Example 72
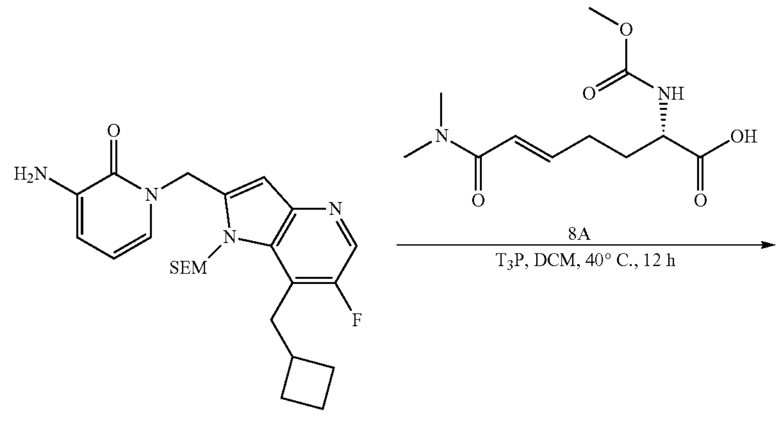
I-685
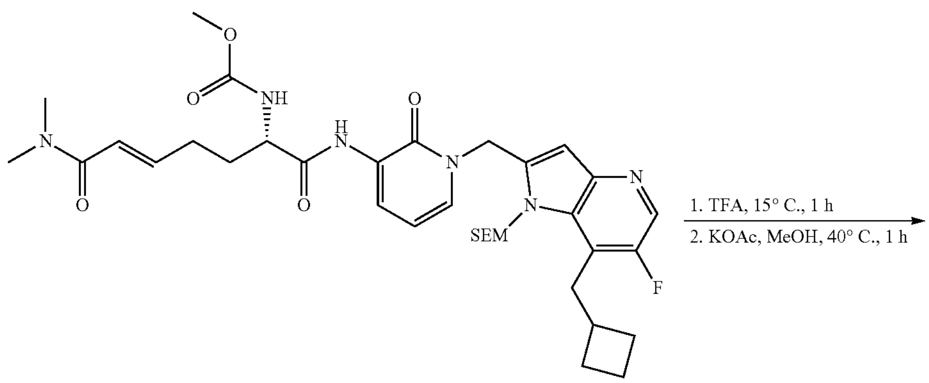
I-686
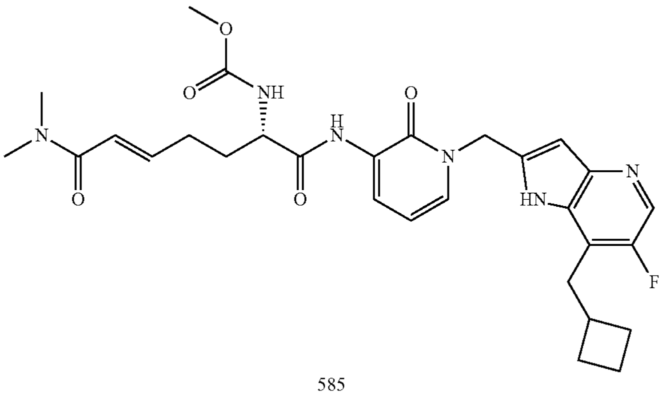
585
Compound 585 was prepared according to the procedures for Examples 70 and 71 using the appropriate intermediates. LCMS m/z 567.2 $(M+1)^+$. $^1H$ NMR (400 MHz, DMSO-$d_6$) δ 11.61 (s, 1H), 9.32 (s, 1H), 8.28-8.14 (m, 2H), 7.76 (br d, J=7.7 Hz, 1H), 7.51-7.44 (m, 1H), 6.67-6.52 (m, 1H), 6.41-6.27 (m, 3H), 5.32 (s, 2H), 4.24-4.13 (m, 1H), 3.55 (s, 3H), 2.98 (s, 5H), 2.82 (s, 3H), 2.70-2.58 (m, 1H), 2.23 (td, J=7.2, 14.2 Hz, 2H), 1.95-1.68 (m, 8H).
The following compound was prepared according to the procedures described in Example 72 using the appropriate intermediates.

| Compound | Structure | Characterization Data |
| --- | --- | --- |
| 588 | 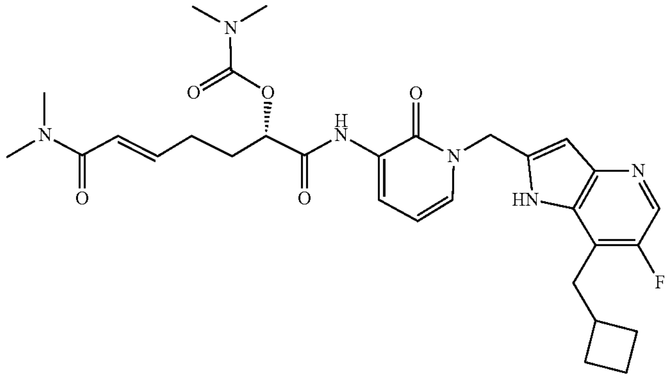 [SMILES: CN(C)C(=O)/C=C/CC[C@H](OC(=O)N(C)C)C(=O)Nc1cccn(Cc2cc3ncc(F)c(CC4CCC4)c3[nH]2)c1=O] | LCMS m/z 581.4 $(M + 1)^+$ |

Synthesis of Intermediate I-692

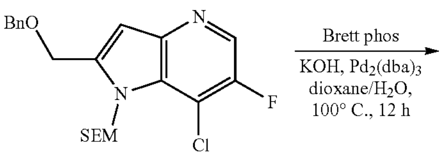

I-666

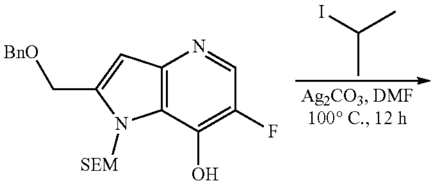

I-687

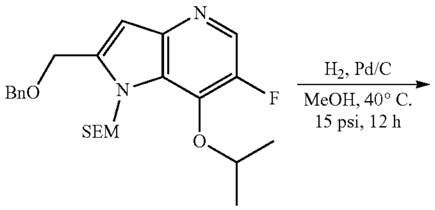

I-688

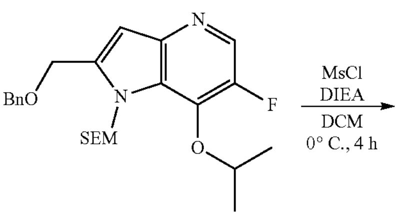

I-689

-continued

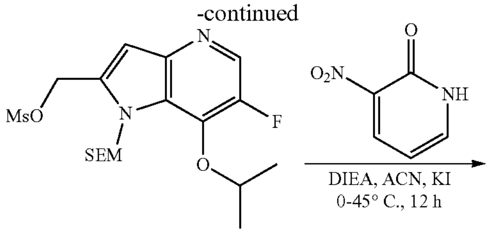

I-690

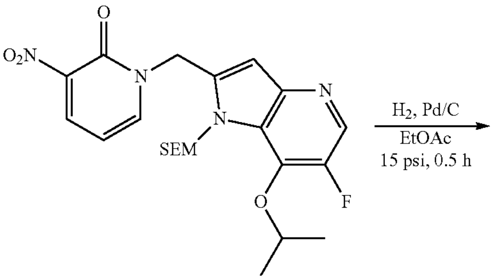

I-691

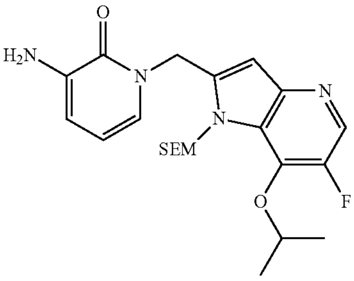

I-692

A mixture of 2-[[2-(benzyloxymethyl)-7-chloro-6-fluoro-pyrrolo[3,2-b]pyridin-1-yl]methoxy]ethyl-trimethyl-silane (0.1 g, 237.54 umol, 1 eq), dicyclohexyl-[2-(2,4,6-triisopropylphenyl)phenyl]phosphane (13.59 mg, 28.50 umol, 0.12 eq), KOH (39.98 mg, 712.62 umol, 3 eq) in dioxane (1 mL) and $H_2O$ (1 mL), then $Pd_2(dba)_3$ (6.53 mg, 7.13 umol, 0.03 eq) was added under $N_2$, then the mixture was degassed and purged with $N_2$ for 3 times, and then the mixture was stirred at 100° C. for 12 hr under $N_2$ atmosphere. The reaction mixture was filtered and the filtrate was concentrated under reduced pressure to give a residue. The residue was purified by column chromatography ($SiO_2$) to give 2-(benzyloxymethyl)-6-fluoro-1-(2-trimethylsilylethoxymethyl)pyrrolo[3,2-b]pyridin-7-ol (I-687) (60 mg) as a yellow solid.

To a solution of 2-(benzyloxymethyl)-6-fluoro-1-(2-trimethylsilylethoxymethyl)pyrrolo[3,2-b]pyridin-7-ol (0.8 g, 1.99 mmol, 1 eq) and 2-iodopropane (506.76 mg, 2.98 mmol, 298.10 uL, 1.5 eq) in DMF (10 mL) was added $Ag_2CO_3$ (1.10 g, 3.97 mmol, 180.27 uL, 2 eq). The mixture was stirred at 100° C. for 12 hr. The reaction mixture was diluted with water 20 mL and extracted with EtOAc 30 mL. The combined organic layers were washed with brine 20 mL, dried over, filtered and concentrated under reduced pressure to give a residue. The residue was purified by column chromatography ($SiO_2$) to give 2-[[2-(benzyloxymethyl)-6-fluoro-7-isopropoxy-pyrrolo [3,2-b]pyridin-1-yl] methoxy] ethyl-trimethyl-silane (I-688) (570 mg) as a yellow oil.

To a solution of 2-[[2-(benzyloxymethyl)-6-fluoro-7-isopropoxy-pyrrolo[3,2-b]pyridin-1-yl]methoxy]ethyl-trimethyl-silane (520 mg, 1.17 mmol, 1 eq) in MeOH (20 mL) was added Pd/C (500 mg, 10% purity). The suspension was degassed and purged with $H_2$ for 3 times. The mixture was stirred under $H_2$ (15 Psi) at 40° C. for 12 hr. The reaction mixture was filtered and the filtrate was concentrated under reduced pressure to give (6-fluoro-7-isopropoxy-1-((2-(trimethylsilyl)ethoxy)methyl)-1H-pyrrolo[3,2-b]pyridin-2-yl)methanol (I-689) (300 mg) as a light yellow solid.

To a solution of [6-fluoro-7-isopropoxy-1-(2-trimethylsilylethoxymethyl)pyrrolo[3,2-b]pyridin-2-yl]methanol (300 mg, 846.28 umol, 1 eq) and DIEA (218.75 mg, 1.69 mmol, 294.81 uL, 2 eq) in DCM (5 mL) was added MsCl (145.41 mg, 1.27 mmol, 98.25 uL, 1.5 eq) drop wise at 0° C. The mixture was stirred at 0° C. for 7 hr. The mixture was poured into water 10 mL, and then extracted by DCM 20 mL. The combined organic layers were washed with brine 20 mL, dried over $Na_2SO_4$, then filtered and filtrate was concentrated under reduced pressure to give [6-fluoro-7-isopropoxy-1-(2-trimethylsilylethoxymethyl)pyrrolo[3,2-b] pyridin-2-yl]methyl methanesulfonate (I-690) (400 mg) as a yellow oil.

To a solution of 3-nitro-1H-pyridin-2-one (129.54 mg, 924.68 umol, 1 eq) and DIEA (179.26 mg, 1.39 mmol, 241.59 uL, 1.5 eq) and KI (15.35 mg, 92.47 umol, 0.1 eq) in MeCN (3 mL) was added[6-fluoro-7-isopropoxy-1-(2-trimethylsilylethoxymethyl)pyrrolo[3,2-b]pyridin-2-yl]methyl methanesulfonate (400 mg, 924.68 umol, 1 eq) in MeCN (2 mL) at 0° C. The mixture was stirred at 45° C. for 12 hr. The reaction mixture was diluted with water 25 mL and extracted with EtOAc 40 mL. The combined organic layers were washed with brine 30 mL, dried over $Na_2SO_4$, filtered and the filtrate was concentrated under reduced pressure to give a residue. The residue was purified by prep-TLC ($SiO_2$) to give 1-[[6-fluoro-7-isopropoxy-1-(2-trimethylsilylethoxymethyl)pyrrolo[3,2-b] pyridin-2-yl]methyl]-3-nitro-pyridin-2-one (I-691) (150 mg) as a yellow solid.

To a solution of 1-[[6-fluoro-7-isopropoxy-1-(2-trimethylsilylethoxymethyl)pyrrolo[3,2-b]pyridin-2-yl]methyl]-3-nitro-pyridin-2-one (150 mg, 314.75 umol, 1 eq) in EtOAc (20 mL) was added Pd/C (150 mg, 10% purity). The suspension was degassed and purged with $H_2$ for 3 times. The mixture was stirred under $H_2$ (15 Psi) at 30° C. for 0.5 hr. The reaction mixture was filtered and the filtrate was concentrated under reduced pressure to give 3-amino-1-[[6-fluoro-7-isopropoxy-1-(2-trimethylsilylethoxymethyl)pyrrolo[3,2-b]pyridin-2-yl]methyl]pyridin-2-one (I-692) (140 mg) as a yellow solid.

The following intermediates were prepared according to the procedures described for the synthesis of I-692 using the appropriate reagents.

| Compound | Structure | Characterization Data |
|---|---|---|
| I-693 | 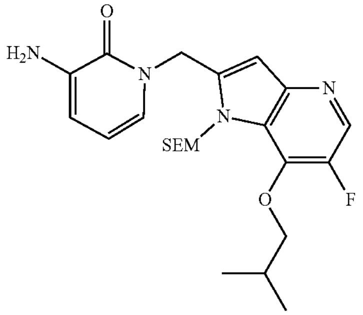 [SMILES: CC(C)COc1c(F)cnc2cc(Cn3cccc(N)c3=O)n(COCC[Si](C)(C)C)c12] | LCMS m/z 461.2 (M + 1)+ |
| I-694 | 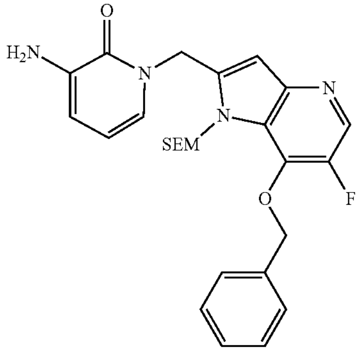 [SMILES: C[Si](C)(C)CCOCn1c(Cn2cccc(N)c2=O)cc2ncc(F)c(OCc3ccccc3)c21] | LCMS m/z 494.2 (M + 1)+ |

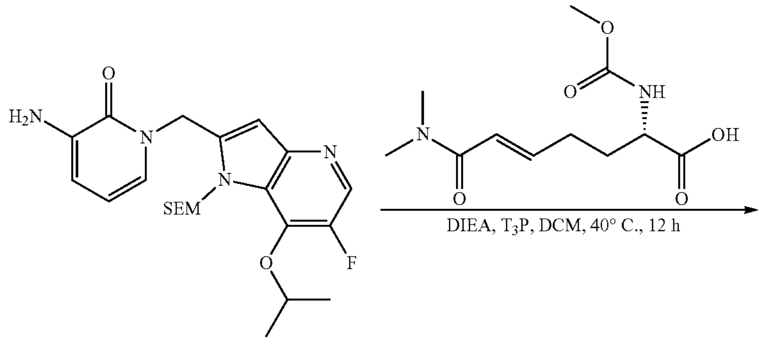

I-692

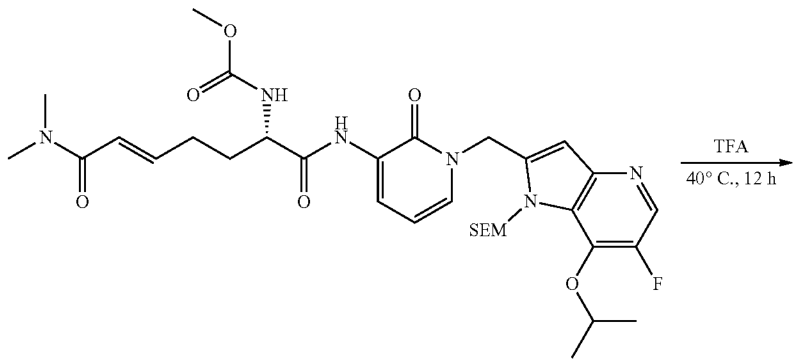

I-695

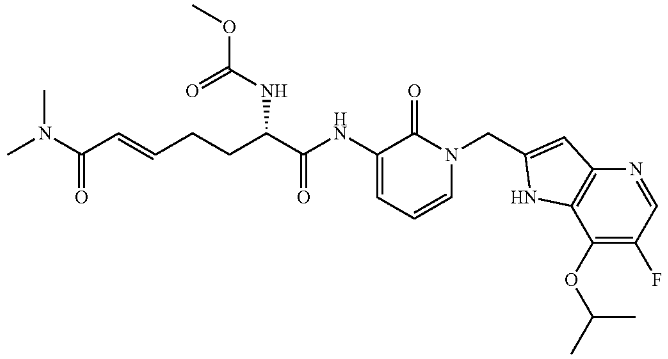

544

Compound 544 was prepared according to the procedures for Example 71 using the appropriate intermediates. LCMS m/z 557.6 $(M+1)^+$. $^1H$ NMR (400 MHz, DMSO-$d_6$) δ 11.58 (br s, 1H), 9.29 (s, 1H), 8.20 (br d, J=5.7 Hz, 2H), 7.73 (br d, J=8.2 Hz, 1H), 7.48 (br d, J=6.8 Hz, 1H), 6.58 (td, J=7.0, 14.4 Hz, 1H), 6.38-6.26 (m, 3H), 5.28 (s, 2H), 4.85-4.79 (m, 1H), 4.17 (br s, 1H), 3.53 (s, 3H), 2.97 (s, 3H), 2.81 (s, 3H), 2.21 (br d, J=7.3 Hz, 2H), 1.88-1.66 (m, 2H), 1.32 (br d, J=6.0 Hz, 6H).

The following compounds were prepared according to the procedures described for the synthesis of Examples 72 and 73 using the appropriate intermediates.

| Compound | Structure | Characterization Data |
|---|---|---|
| 549 | 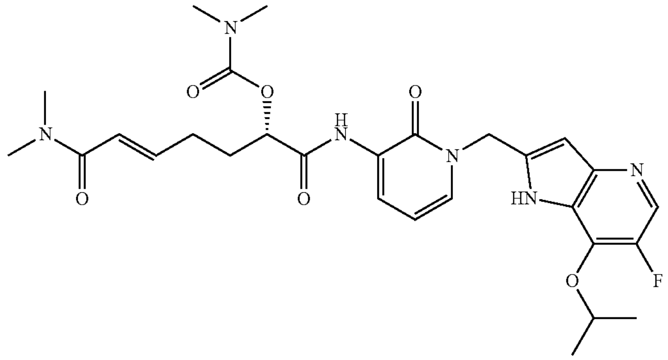 [SMILES: CC(C)Oc1c(F)cnc2cc(Cn3cccc(NC(=O)[C@H](CC/C=C/C(=O)N(C)C)OC(=O)N(C)C)c3=O)[nH]c12] | LCMS m/z 571.6 $(M + 1)^+$ |
| 538 | 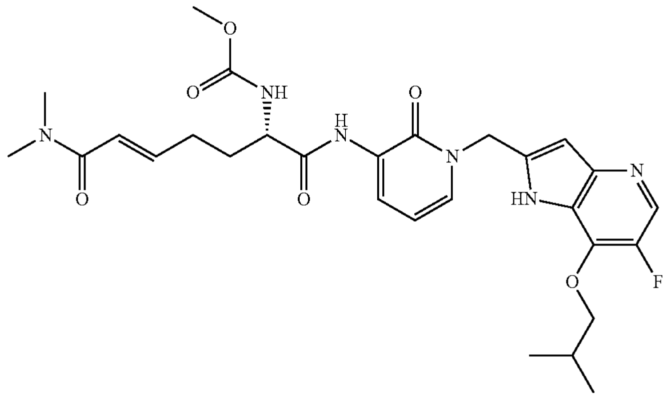 [SMILES: COC(=O)N[C@@H](CC/C=C/C(=O)N(C)C)C(=O)Nc1cccn(Cc2cc3ncc(F)c(OCC(C)C)c3[nH]2)c1=O] | LCMS m/z 571.2 $(M + 1)^+$ |
| 551 | 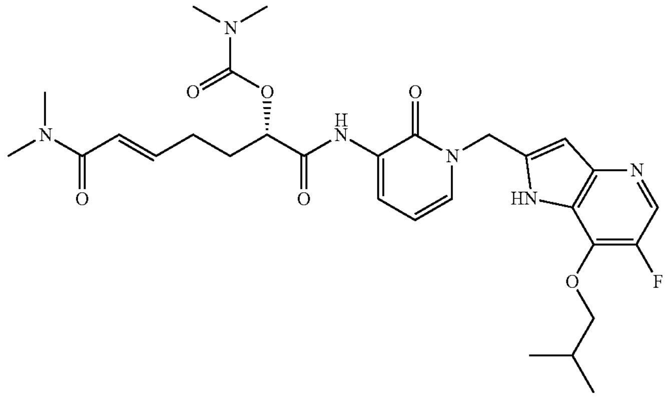 [SMILES: CC(C)COc1c(F)cnc2cc(Cn3cccc(NC(=O)[C@H](CC/C=C/C(=O)N(C)C)OC(=O)N(C)C)c3=O)[nH]c12] | LCMS m/z 585.3 $(M + 1)^+$ |
| 548 | 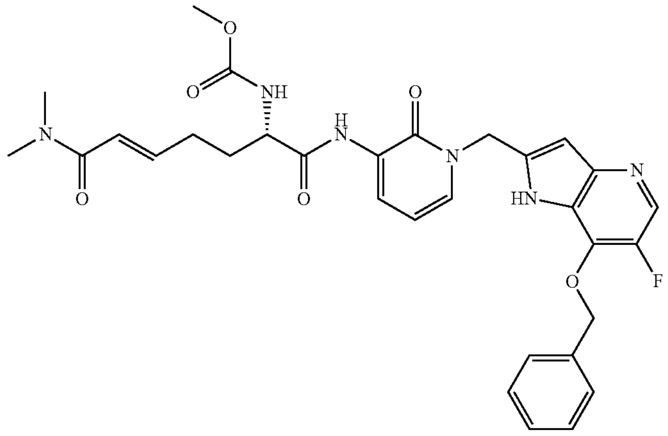 [SMILES: COC(=O)N[C@@H](CC/C=C/C(=O)N(C)C)C(=O)Nc1cccn(Cc2cc3ncc(F)c(OCc4ccccc4)c3[nH]2)c1=O] | LCMS m/z 605.2 $(M + 1)^+$ |

-continued

| Compound | Structure | Characterization Data |
| --- | --- | --- |
| 550 | 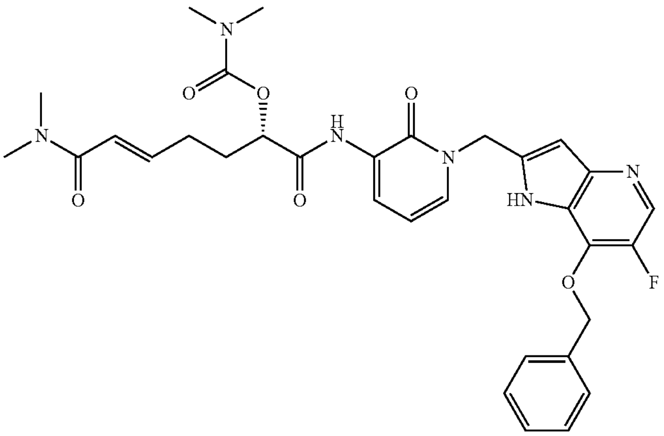 [SMILES: CN(C)C(=O)/C=C/CC[C@H](OC(=O)N(C)C)C(=O)Nc1cccn(Cc2cc3ncc(F)c(OCc4ccccc4)c3[nH]2)c1=O] | LCMS m/z 619.2 (M + 1)$^+$ |

Example 74

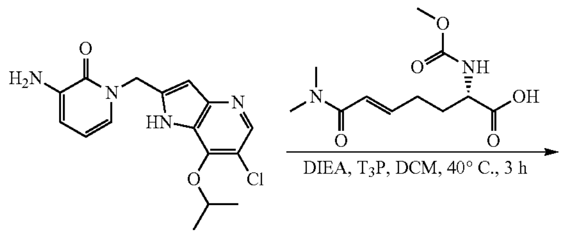

I-703

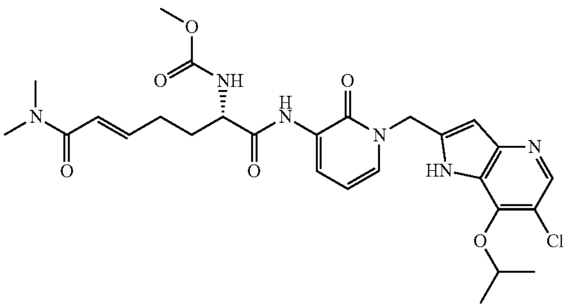

536

To a solution of 3-amino-1-[(6-chloro-7-isobutyl-1H-pyrrolo[3,2-b]pyridin-2-yl)methyl]pyridin-2-one (54 mg, 163.24 umol, 1 eq), (E,2S)-7-(dimethylamino)-2-(methoxycarbonylamino)-7-oxo-hept-5-enoic acid (42.16 mg, 163.24 umol, 1 eq) and DIEA (63.29 mg, 489.71 umol, 85.30 uL, 3 eq) in DCM (2 mL) was added $T_3P$ (311.63 mg, 489.71 umol, 291.24 uL, 50% purity, 3 eq) (50% in EtOAc) and the mixture was stirred at 40° C. for 3 h. The mixture was concentrated in vacuum to give oil. The oil was purified by prep-HPLC to give methyl N-[(E,1S)-1-[[1-[(6-chloro-7-isobutyl-1H-pyrrolo[3,2-b]pyridin-2-yl)methyl]-2-oxo-3-pyridyl]carbamoyl]-6-(dimethylamino)-6-oxo-hex-4-enyl] carbamate (31.5 mg, 34% yield) as a white solid. LCMS m/z 571.1 (M+1)$^+$. $^1$H NMR (400 MHz, DMSO-$d_6$) δ 0.93 (d, J=6.60 Hz, 6H) 1.64-1.81 (m, 1H) 1.89 (br d, J=6.97 Hz, 1H) 2.09 (dt, J=13.36, 6.83 Hz, 1H) 2.18-2.32 (m, 2H) 2.79-2.94 (m, 5H) 3.00 (s, 3H) 3.56 (s, 3H) 4.15-4.27 (m, 1H) 5.36 (br s, 2H) 6.26-6.46 (m, 3H) 6.57-6.70 (m, 1H) 7.52 (br s, 1H) 7.76 (br d, J=7.83 Hz, 1H) 8.19-8.29 (m, 2H) 9.33 (s, 1H) 11.64 (br s, 1H).

The following compounds were prepared according to the procedures described in Example 74 using the appropriate intermediates.

| Compound | Structure | Characterization Data |
| --- | --- | --- |
| 539 | 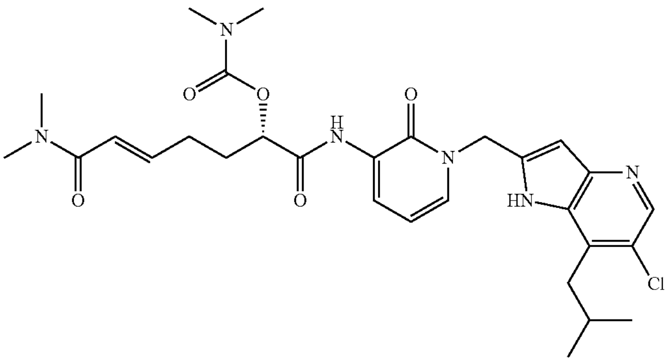 [SMILES: CC(C)Cc1c(Cl)cnc2cc(Cn3cccc(NC(=O)[C@H](CC/C=C/C(=O)N(C)C)OC(=O)N(C)C)c3=O)[nH]c12] | LCMS m/z 584.9 (M + 1)$^+$ |

-continued
| Compound | Structure | Characterization Data |
| --- | --- | --- |
| 537 | 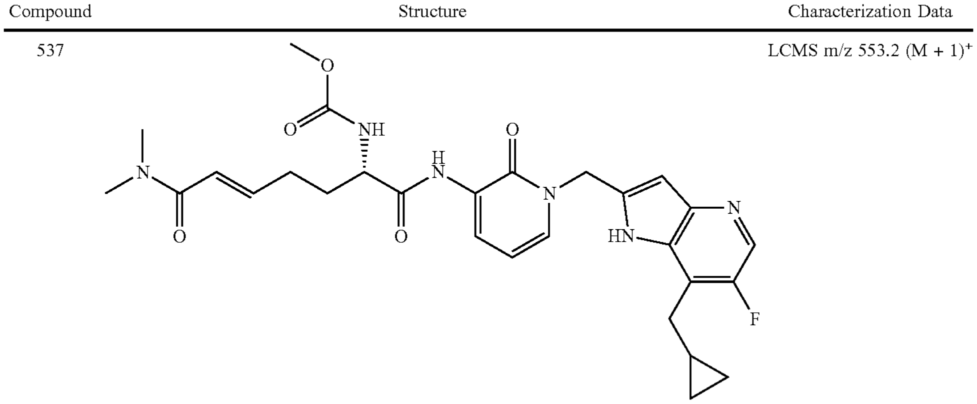 | LCMS m/z 553.2 $(M + 1)^+$ |
Example 75
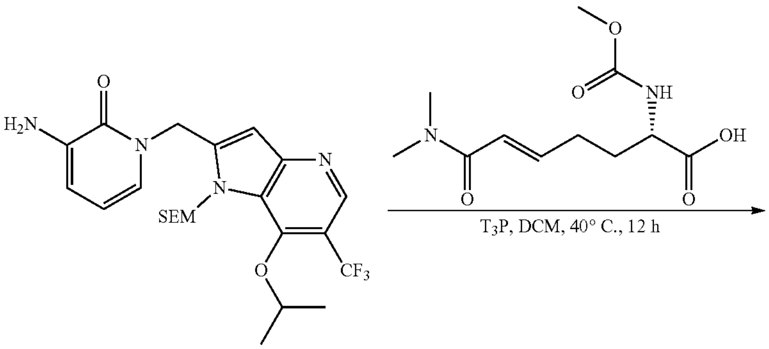
I-717
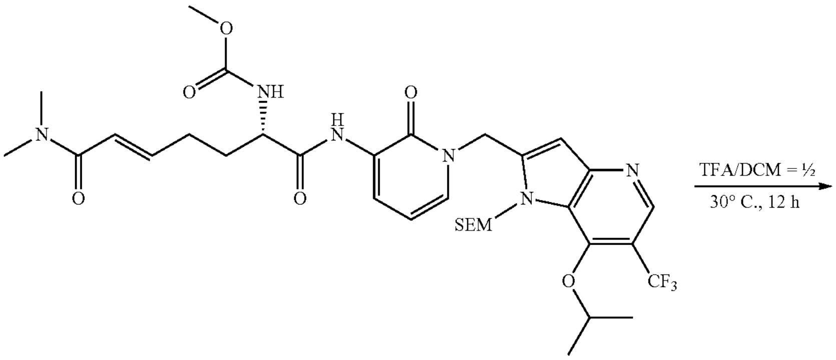
I-718

-continued
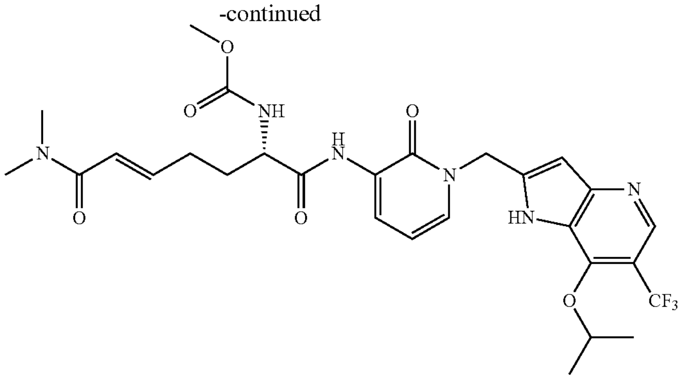
581
Compound 581 was prepared according to the procedures for Example 71 using the appropriate intermediates. LCMS m/z 605.3 $(M+1)^+$. $^1H$ NMR (400 MHz, DMSO-$d_6$) δ 0.87 (d, J=6.39 Hz, 6H) 1.71 (br s, 1H) 1.86 (br s, 1H) 2.05-2.14 (m, 1H) 2.22 (dt, J=14.55, 7.28 Hz, 2H) 2.81 (s, 3H) 2.92 (br d, J=7.06 Hz, 2H) 2.97 (s, 3H) 3.53 (s, 3H) 4.10-4.24 (m, 1H) 5.39 (s, 2H) 6.26-6.40 (m, 3H) 6.50-6.67 (m, 1H) 7.52 (d, J=5.51 Hz, 1H) 7.74 (brd, J=7.50 Hz, 1H) 8.18-8.30 (m, 1H) 8.18-8.30 (m, 1H) 8.18-8.30 (m, 1H) 8.51 (s, 1H) 9.31 (s, 1H) 11.87 (s, 1H).
Example 76
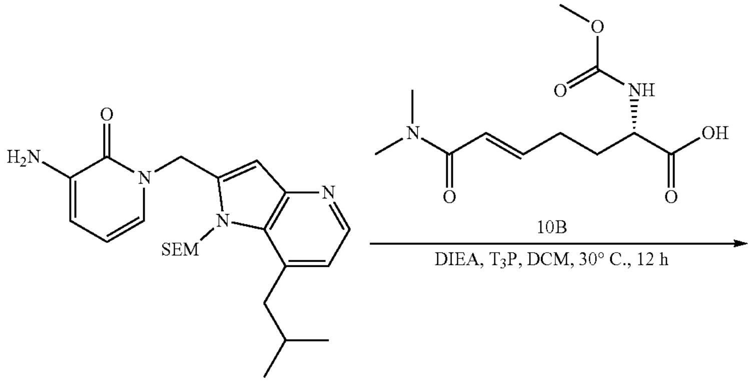
I-728
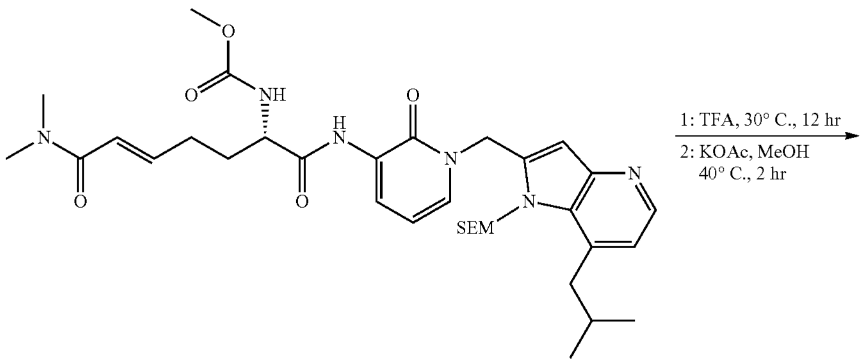
I-730

-continued

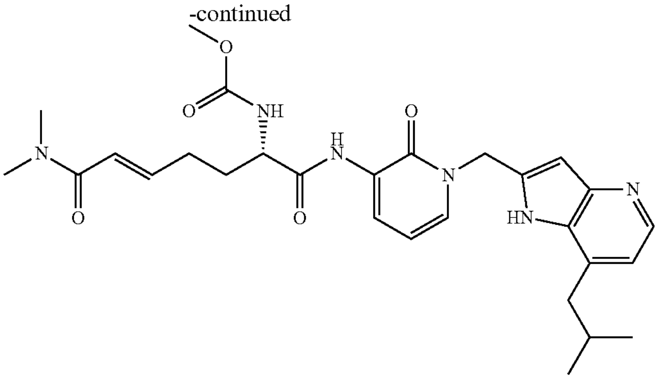

506

Compound 506 was prepared according to the procedures for Example 71 using the appropriate intermediates. LCMS m/z 537.3 $(M+1)^+$. $^1H$ NMR (400 MHz, DMSO-$d_6$) δ 11.49 (br s, 1H) 9.32 (s, 1H) 8.21-8.26 (m, 2H) 8.17 (d, J=4.63 Hz, 1H) 7.77 (br d, J=7.50 Hz, 1H) 7.54 (d, J=6.61 Hz, 1H) 6.87 (d, J=4.85 Hz, 1H) 6.56-6.65 (m, 1H) 6.27-6.41 (m, 3H) 5.35 (s, 2H) 4.15-4.23 (m, 1H) 3.56 (s, 3H) 2.99 (s, 3H) 2.83 (s, 3H) 2.71 (d, J=7.28 Hz, 2H) 2.24 (dt, J=14.55, 7.28 Hz, 2H) 2.02 (dt, J=13.62, 6.75 Hz, 1H) 1.66-1.93 (m, 1H) 1.64-1.91 (m, 1H) 0.90 (d, J=6.62 Hz, 6H).

The following compounds were prepared according to the procedures described in Example 76 using the appropriate intermediates.

| Compound | Structure | Characterization Data |
|---|---|---|
| 503 | 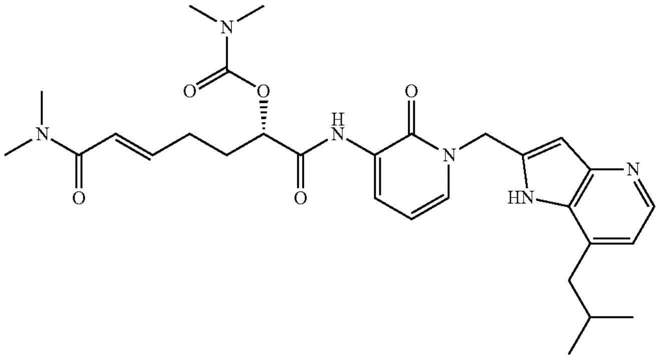 [SMILES: CC(C)Cc1ccnc2cc(Cn3cccc(NC(=O)[C@H](CC/C=C/C(=O)N(C)C)OC(=O)N(C)C)c3=O)[nH]c12] | LCMS m/z 551.3 $(M + 1)^+$ |
| 505 | 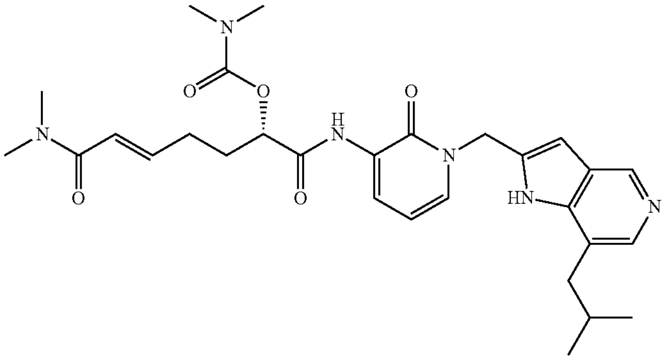 [SMILES: CC(C)Cc1cncc2cc(Cn3cccc(NC(=O)[C@H](CC/C=C/C(=O)N(C)C)OC(=O)N(C)C)c3=O)[nH]c12] | LCMS m/z 551.2 $(M + 1)^+$ |

-continued
| Compound | Structure | Characterization Data |
| --- | --- | --- |
| 509 | 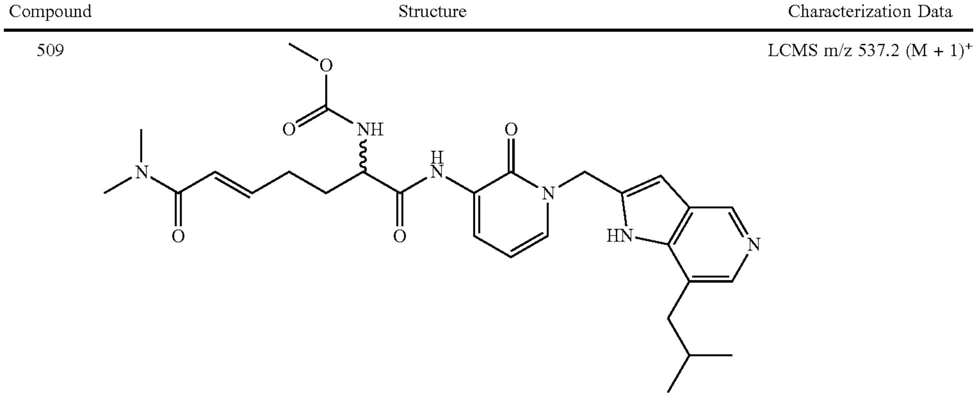 | LCMS m/z 537.2 $(M + 1)^+$ |
Example 77
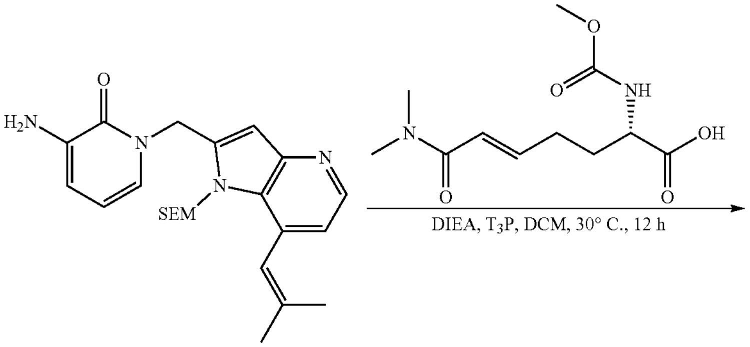
I-731
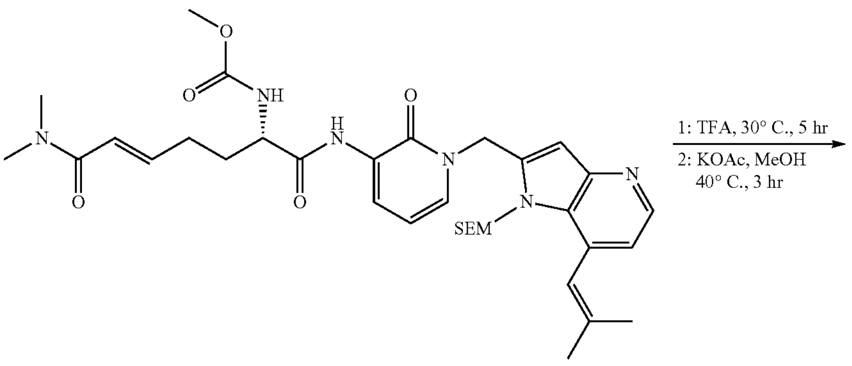
I-733

-continued

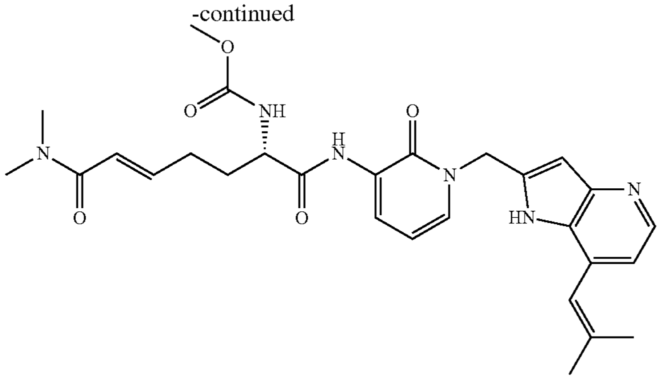

513

Compound 513 was prepared according to the procedures for Example 71 using the appropriate intermediates. LCMS m/z 535.3 $(M+1)^+$. $^1H$ NMR (400 MHz, DMSO-$d_6$) δ 11.39 (br s, 1H) 9.32 (s, 1H) 8.16-8.28 (m, 3H) 7.77 (br d, J=7.70 Hz, 1H) 7.51 (br d, J=5.62 Hz, 1H) 6.94 (d, J=4.89 Hz, 1H) 6.56-6.67 (m, 1H) 6.52 (s, 1H) 6.29-6.42 (m, 3H) 5.33 (s, 2H) 4.14-4.24 (m, 1H) 3.52-3.59 (m, 3H) 2.97-3.02 (m, 3H) 2.82-2.86 (m, 3H) 2.24 (dt, J=14.00, 6.94 Hz, 2H) 1.99 (s, 3H) 1.86 (s, 3H) 1.57-1.81 (m, 2H).

The following compounds were prepared according to the procedures described in Example 77 using the appropriate intermediates.

| Compound | Structure | Characterization Data |
|---|---|---|
| 511 | 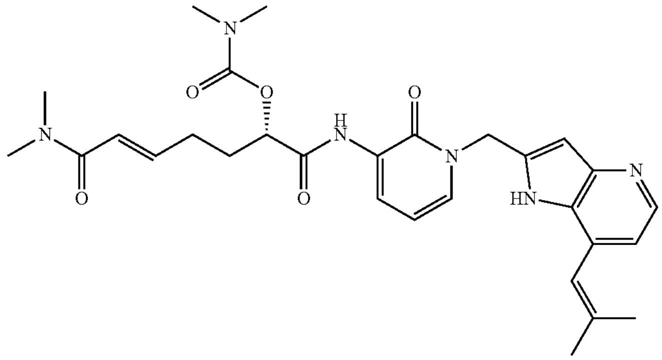 [SMILES: CC(C)=Cc1ccnc2cc(Cn3cccc(NC(=O)[C@H](CC/C=C/C(=O)N(C)C)OC(=O)N(C)C)c3=O)[nH]c12] | LCMS m/z 549.3 (M + 1)$^+$ |
| 530 | 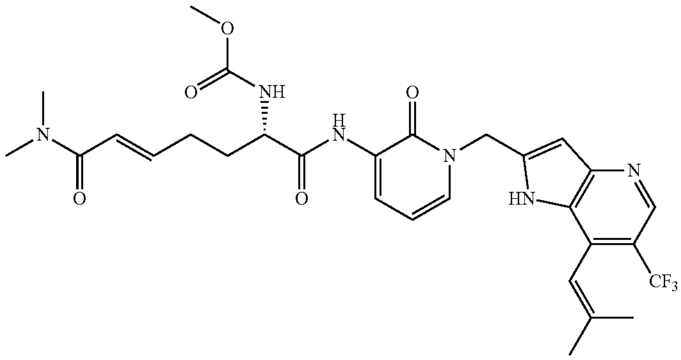 [SMILES: COC(=O)N[C@@H](CC/C=C/C(=O)N(C)C)C(=O)Nc1cccn(Cc2cc3ncc(C(F)(F)F)c(C=C(C)C)c3[nH]2)c1=O] | LCMS m/z 603.3 (M + 1)$^+$ |

Synthesis of Intermediate I-739
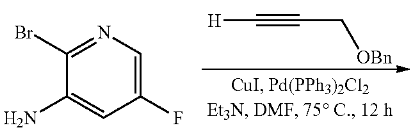
I-661
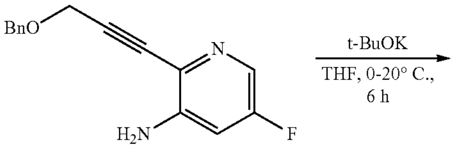
I-662
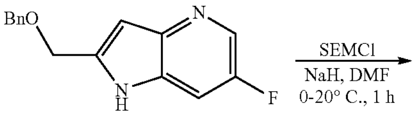
I-663
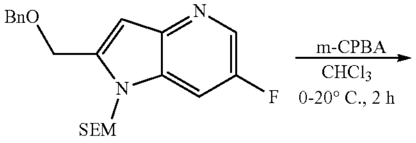
I-664
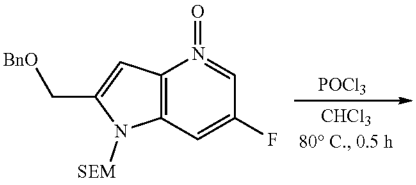
I-665
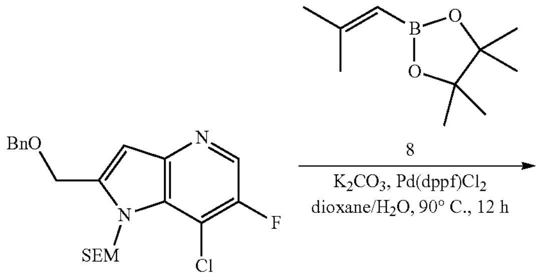
I-666
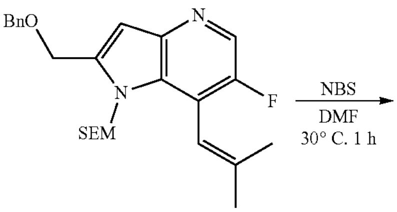
I-667
-continued
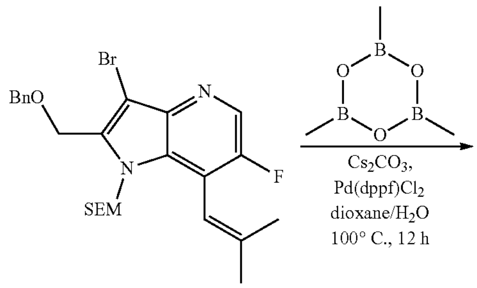
I-734
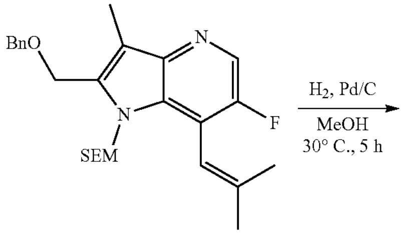
I-735
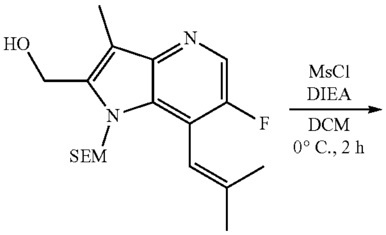
I-736
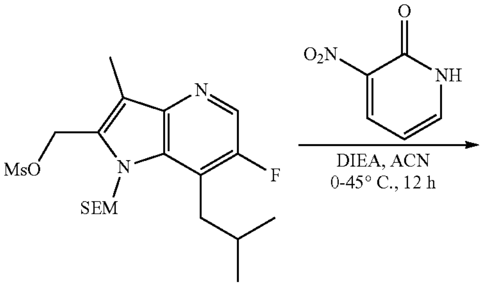
I-737
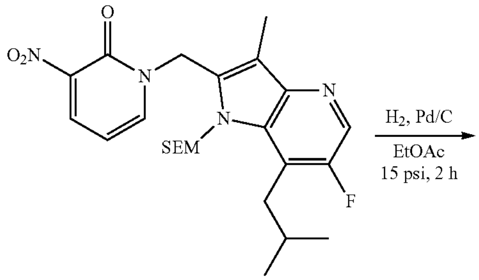
I-738

-continued

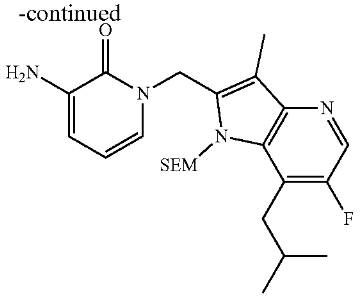

I-739

To a solution of 2-bromo-5-fluoro-pyridin-3-amine (5 g, 26.18 mmol, 1 eq), prop-2-ynoxymethylbenzene (5.74 g, 39.27 mmol, 1.5 eq) CuI (1.25 g, 6.54 mmol, 0.25 eq) and TEA (9.27 g, 91.62 mmol, 12.75 mL, 3.5 eq) in DMF (50 mL) was degassed and purged with $N_2$ for 3 times. Then $Pd(PPh_3)_2Cl_2$ (1.84 g, 2.62 mmol, 0.1 eq) was added at 20° C., then the mixture was degassed and purged with $N_2$ for 3 times. The mixture was stirred at 75° C. for 12 hr under $N_2$. 2 batches was work up together. The mixture was filtered and the filtrate was diluted with water 300 mL and extracted with EtOAC 400 mL. The combined organic layers were washed with brine 400 mL, dried over $Na_2SO_4$, filtered and concentrated under reduced pressure to give a residue. The residue was purified by flash silica gel chromatography to give 2-(3-benzyloxyprop-1-ynyl)-5-fluoro-pyridin-3-amine (I-662) (10.81 g) as a yellow solid. $^1H$ NMR (400 MHz, $CDCl_3$) δ 7.78 (d, J=2.4 Hz, 1H), 7.33-7.23 (m, 6H), 7.19 (s, 1H), 6.65 (dd, J=2.4, 9.8 Hz, 1H), 4.61 (s, 2H), 4.41 (s, 2H), 4.28 (br s, 1H), 4.32-4.21 (m, 1H).

To a solution of 2-(3-benzyloxyprop-1-ynyl)-5-fluoro-pyridin-3-amine (5.5 g, 21.46 mmol, 1 eq) in THF (60 mL) was added t-BuOK (3.61 g, 32.19 mmol, 1.5 eq) at 0° C. The mixture was stirred at 20° C. for 6 hr. The 2 batches were work up together. The reaction mixture was diluted with sat. $NH_4Cl$ solution 100 mL and extracted with EtOAc 300 mL. The combined organic layers were washed with brine 200 mL, dried over $Na_2SO_4$, filtered and concentrated under reduced pressure to give a residue. The crude product was triturated with EtOAc (50 mL) at 20° C. for 30 min. Then the mixture was filtered and the filter cake was concentrated under reduced pressure to give a yellow solid. 2-(benzyloxymethyl)-6-fluoro-1H-pyrrolo[3,2-b]pyridine (I-663) (8.5 g) was obtained as a yellow solid. $^1H$ NMR (400 MHz, $CDCl_3$) δ 8.47 (br s, 1H), 7.33-7.24 (m, 6H), 6.53 (br s, 1H), 4.66 (s, 2H), 4.51 (s, 2H).

To a solution of 2-(benzyloxymethyl)-6-fluoro-1H-pyrrolo[3,2-b]pyridine (11 g, 42.92 mmol, 1 eq) in DMF (100 mL) was added NaH (2.58 g, 64.38 mmol, 60% purity, 1.5 eq) at 0° C. for several portion, the mixture was stirred at 0° C. for 0.5 hr. Then SEM-Cl (8.59 g, 51.51 mmol, 9.12 mL, 1.2 eq) was added to the solution at 0° C. The mixture was stirred at 20° C. for 0.5 hr. The reaction mixture was poured into sat. $NH_4Cl$ solution (200 mL) and extracted by EtOAc (300 mL). The combined organic layers were washed with brine 200 mL, dried over $Na_2SO_4$, filtered and concentrated under reduced pressure to give a residue. The residue was purified by column chromatography ($SiO_2$) to give 2-[[2-(benzyloxymethyl)-6-fluoro-pyrrolo[3,2-b]pyridin-1-yl]methoxy]ethyl-trimethyl-silane (I-664) (11 g) as a brown oil. LCMS m/z 387.3 $(M+1)^+$.

To a solution of 2-[[2-(benzyloxymethyl)-6-fluoro-pyrrolo[3,2-b]pyridin-1-yl]methoxy]ethyl-trimethyl-silane (5.25 g, 13.58 mmol, 1 eq) in $CHCl_3$ (60 mL) was added m-CPBA (4.39 g, 20.37 mmol, 80% purity, 1.5 eq) at 0° C. The mixture was stirred at 20° C. for 2 hr. Two batches was work up together. The mixture was poured into sat. $Na_2SO_3$ solution 200 mL, then extracted with EtOAc 300 mL. The combined organic layers were washed with brine 200 mL, dried over $Na_2SO_4$, filtered and concentrated under reduced pressure to give a residue. The residue was purified by column chromatography ($SiO_2$) to give 2-[[2-(benzyloxymethyl)-6-fluoro-4-oxido-pyrrolo[3,2-b]pyridin-4-ium-1-yl]methoxy]ethyl-trimethyl-silane (I-665) (8.78 g) as a brown oil. $^1H$ NMR (400 MHz, $CDCl_3$) δ 8.23 (dd, J=1.8, 5.2 Hz, 1H), 7.47-7.36 (m, 5H), 7.35-7.29 (m, 1H), 7.34-7.29 (m, 1H), 6.98 (s, 1H), 5.58 (s, 2H), 4.76 (s, 2H), 4.61 (s, 2H), 3.56-3.46 (m, 2H), 0.97-0.87 (m, 2H), 0.04–-0.05 (m, 9H).

To a solution of 2-[[2-(benzyloxymethyl)-6-fluoro-4-oxido-pyrrolo[3,2-b]pyridin-4-ium-1-yl]methoxy]ethyl-trimethyl-silane (3 g, 7.45 mmol, 1 eq) in $CHCl_3$ (30 mL) was added $POCl_3$ (9.90 g, 64.57 mmol, 6.00 mL, 8.66 eq) at 80° C. The mixture was stirred at 80° C. for 0.5 hr. Two batches were work up together. The reaction was poured into ice water 100 mL to quench $POCl_3$, then adjusted by sat. $NaHCO_3$ to pH~7, then extracted by EtOAc 200 mL. The combined organic layers were washed with brine 100 mL, dried over $Na_2SO_4$, filtered and concentrated under reduced pressure to give a residue. The residue was purified by column chromatography ($SiO_2$) to give 2-[[2-(benzyloxymethyl)-7-chloro-6-fluoro-pyrrolo[3,2-b]pyridin-1-yl]methoxy]ethyl-trimethyl-silane (I-666) (2.57 g) as a yellow oil.

To a solution of 2-[[2-(benzyloxymethyl)-7-chloro-6-fluoro-pyrrolo[3,2-b]pyridin-1-yl]methoxy]ethyl-trimethyl-silane (2.9 g, 6.89 mmol, 1 eq) and 4,4,5,5-tetramethyl-2-(2-methylprop-1-enyl)-1,3,2-dioxaborolane (1.51 g, 8.27 mmol, 1.2 eq) in dioxane (30 mL) and $H_2O$ (6 mL) was added $K_2CO_3$ (2.86 g, 20.67 mmol, 3 eq) and $Pd(dppf)Cl_2$ (604.86 mg, 826.64 umol, 0.12 eq), was degassed and purged with $N_2$ for 3 times, and then the mixture was stirred at 90° C. for 12 hr under $N_2$ atmosphere. The reaction mixture was filtered then diluted with water 100 mL and extracted with EtOAc 200 mL. The combined organic layers were washed with brine 100 mL, dried over $Na_2SO_4$, filtered and concentrated under reduced pressure to give a residue. The residue was purified by flash silica gel chromatography to give 2-[[2-(benzyloxymethyl)-6-fluoro-7-(2-methylprop-1-enyl)pyrrolo[3,2-b]pyridin-1-yl]methoxy]ethyl-trimethyl-silane (I-667) (2 g) as a yellow oil.

To a solution of 2-[[2-(benzyloxymethyl)-6-fluoro-7-(2-methylprop-1-enyl)pyrrolo[3,2-b]pyridin-1-yl]methoxy]ethyl-trimethyl-silane (0.3 g, 680.85 umol, 1 eq) in DMF (5 mL) was added NBS (133.30 mg, 748.94 umol, 1.1 eq). The mixture was stirred at 30° C. for 1 hr. The reaction mixture was diluted with water 15 mL and extracted with EtOAc 20 mL. The combined organic layers were washed with brine 20 mL, dried over $Na_2SO_4$, filtered and the filtrate was concentrated under reduced pressure to give 2-[[2-(benzyloxymethyl)-3-bromo-6-fluoro-7-(2-methylprop-1-enyl)pyrrolo[3,2-b]pyridin-1-yl]methoxy]ethyl-trimethyl-silane (I-734) (400 mg) as a yellow oil. LCMS m/z 519.2 $(M+1)^+$.

A mixture of 2-[[2-(benzyloxymethyl)-3-bromo-6-fluoro-7-(2-methylprop-1-enyl)pyrrolo[3,2-b]pyridin-1-yl]methoxy]ethyl-trimethyl-silane (400 mg, 769.94 umol, 1 eq), 2,4,6-trimethyl-1,3,5,2,4,6-trioxatriborinane (231.97 mg, 923.93 umol, 258.32 uL, 1.2 eq) (50% purity), $Cs_2CO_3$ (501.72 mg, 1.54 mmol, 2 eq) and $Pd(dppf)Cl_2$ (56.34 mg, 76.99 umol, 0.1 eq) in dioxane (6 mL) and $H_2O$ (1.2 mL) was degassed and purged with $N_2$ for 3 times, and then the mixture was stirred at 100° C. for 12 hr under $N_2$ atmosphere. Then 2,4,6-trimethyl-1,3,5,2,4,6-trioxatriborinane (231.97 mg, 923.93 umol, 258.32 uL, 1.2 eq) was added, the mixture was stirred at 100° C. for another 12 hr. The reaction mixture was filtered and then diluted with water 25 mL and extracted with EtOAc 50 mL. The combined organic layers were washed with brine 30 mL, dried over $Na_2SO_4$, filtered and concentrated under reduced pressure to give a residue. The residue was purified by prep-TLC ($SiO_2$) to give 2-[[2-(benzyloxymethyl)-6-fluoro-3-methyl-7-(2-methylprop-1-enyl)pyrrolo[3,2-b]pyridin-1-yl]methoxy]ethyl-trimethyl-silane (I-735) (200 mg) as a yellow oil. LCMS m/z 455.2 $(M+1)^+$.

To a solution of 2-[[2-(benzyloxymethyl)-6-fluoro-3-methyl-7-(2-methylprop-1-enyl)pyrrolo[3,2-b]pyridin-1-yl]methoxy]ethyl-trimethyl-silane (200 mg, 439.90 umol, 1 eq) in MeOH (20 mL) was added Pd/C (200 mg, 10% purity). The suspension was degassed and purged with $H_2$ for 3 times. The mixture was stirred under $H_2$ (15 Psi.) at 30° C. for 5 hr. The reaction mixture was filtered and the filtrate was concentrated under reduced pressure to give [6-fluoro-7-isobutyl-3-methyl-1-(2-trimethylsilylethoxymethyl)pyrrolo[3,2-b]pyridin-2-yl]methanol (I-736) (200 mg) as a colorless oil. LCMS m/z 367.2 $(M+1)^+$.

To a solution of [6-fluoro-7-isobutyl-3-methyl-1-(2-trimethylsilylethoxymethyl)pyrrolo[3,2-b]pyridin-2-yl]methanol (200 mg, 545.64 umol, 1 eq) and DIEA (141.04 mg, 1.09 mmol, 190.08 uL, 2 eq) in DCM (5 mL) was added MsCl (93.75 mg, 818.45 umol, 63.35 uL, 1.5 eq) dropwised at 0° C. The mixture was stirred at 0° C. for 2 hr. The mixture was poured into water 20 mL, then extracted by DCM 25 mL. The combined organic layers were washed with brine 25 mL, dried over $Na_2SO_4$, filtered and the filtrate was concentrated under reduced pressure to give[6-fluoro-7-isobutyl-3-methyl-1-(2-trimethylsilylethoxymethyl)pyrrolo[3,2-b]pyridin-2-yl]methylmethanesulfonate (I-737) (250 mg) as a yellow oil. LCMS m/z 381.4 $(M+1)^+$.

To a solution of 3-nitro-1H-pyridin-2-one (78.77 mg, 562.26 umol, 1 eq) and DIEA (109.00 mg, 843.39 umol, 146.90 uL, 1.5 eq) in MeCN (4 mL) was added[6-fluoro-7-isobutyl-3-methyl-1-(2-trimethylsilylethoxymethyl)pyrrolo[3,2-b]pyridin-2-yl]methyl methanesulfonate (250 mg, 562.26 umol, 1 eq) in MeCN (3 mL) at 0° C. The mixture was stirred at 45° C. for 24 hr. The reaction mixture was diluted with water 20 mL and extracted with EtOAc 30 mL. The combined organic layers were washed with brine 20 mL, dried over $Na_2SO_4$, filtered and the filtrate was concentrated under reduced pressure to give a residue. The residue was purified by prep-TLC ($SiO_2$) to give 1-[[6-fluoro-7-isobutyl-3-methyl-1-(2-trimethylsilylethoxymethyl)pyrrolo[3,2-b]pyridin-2-yl]methyl]-3-nitro-pyridin-2-one (I-738) (60 mg) as a yellow solid. LCMS m/z 489.3 $(M+1)^+$.

To a solution of 1-[[6-fluoro-7-isobutyl-3-methyl-1-(2-trimethylsilylethoxymethyl)pyrrolo[3,2-b]pyridin-2-yl]methyl]-3-nitro-pyridin-2-one (130 mg, 266.05 umol, 1 eq) in EtOAc (20 mL) was added Pd/C (150 mg, 10% purity). The suspension was degassed and purged with $H_2$ for 3 times. The mixture was stirred under $H_2$ (15 Psi) at 30° C. for 2 hr. The reaction mixture was filtered and the filtrate was concentrated under reduced pressure to give 3-amino-1-[[6-fluoro-7-isobutyl-3-methyl-1-(2-trimethylsilylethoxymethyl)pyrrolo[3,2-b]pyridin-2-yl]methyl]pyridin-2-one (I-739) (150 mg) as a yellow oil. LCMS m/z 459.4 $(M+1)^+$.

Example 78

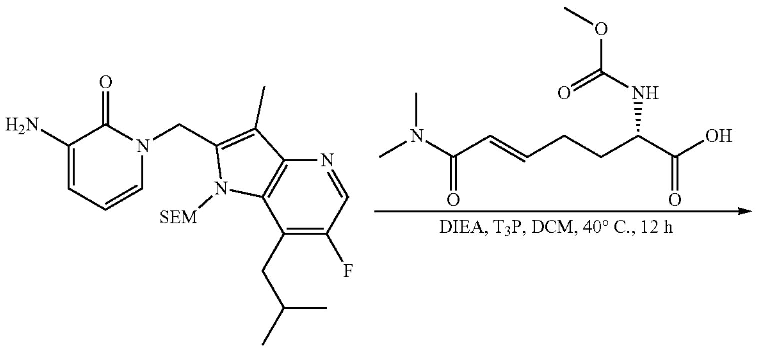

I-739

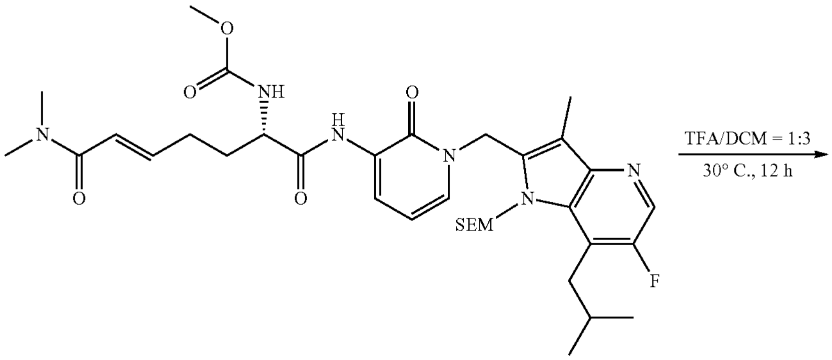

I-740

-continued

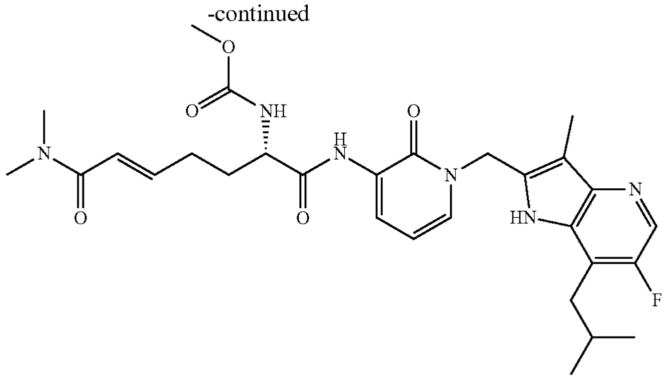

531

A mixture of 3-amino-1-[[6-fluoro-7-isobutyl-3-methyl-1-(2-trimethylsilylethoxymethyl)pyrrolo[3,2-b]pyridin-2-yl]methyl]pyridin-2-one (I-739) (75 mg, 163.53 umol, 1 eq), (E,2S)-7-(dimethylamino)-2-(methoxycarbonylamino)-7-oxo-hept-5-enoic acid (I-9) (42.23 mg, 163.53 umol, 1 eq), $T_3P$ (135.28 mg, 212.58 umol, 126.43 uL, 50% purity, 1.3 eq) and DIEA (31.70 mg, 245.29 umol, 42.72 uL, 1.5 eq) in DCM (3 mL) and then the mixture was stirred at 40° C. for 12 hr. The mixture was poured into water 10 mL, then extracted with DCM 20 mL. The combined organic layers were washed with brine 20 mL, dried over $Na_2SO_4$, filtered and concentrated under reduced pressure to give methylN-[(E,1S)-6-(dimethylamino)-1-[[1-[[6-fluoro-7-isobutyl-3-methyl-1-(2-trimethylsilylethoxymethyl)pyrrolo[3,2-b]pyridin-2-yl]methyl]-2-oxo-3-pyridyl]carbamoyl]-6-oxo-hex-4-enyl]carbamate (I-740) (100 mg) as a brown oil.

To a solution of methyl N-[(E,1S)-6-(dimethylamino)-1-[[1-[[6-fluoro-7-isobutyl-3-methyl-1-(2-trimethylsilylethoxymethyl)pyrrolo[3,2-b]pyridin-2-yl]methyl]-2-oxo-3-pyridyl]carbamoyl]-6-oxo-hex-4-enyl]carbamate (100 mg, 143.08 umol, 1 eq) in DCM (3 mL) was added TFA (1 mL). The mixture was stirred at 30° C. for 12 hr. The mixture was poured into sat. $NaHCO_3$ solution to adjust pH~7, then diluted with water 20 mL and extracted with DCM (25 mL). The combined organic layers were washed with brine 15 mL, dried over $Na_2SO_4$, filtered and concentrated under reduced pressure to give a residue. The residue was purified by prep-HPLC to give methyl N-[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl]carbamate (Compound 531) (15.5 mg, 18% yield) as a light yellow solid. LCMS m/z 568.6 $(M+1)^+$. $^1H$ NMR (400 MHz, DMSO-$d_6$) δ 11.20 (s, 1H), 9.32 (s, 1H), 8.21-8.16 (m, 2H), 7.74 (br d, J=7.9 Hz, 1H), 7.37 (br d, J=5.5 Hz, 1H), 6.64-6.55 (m, 1H), 6.36 (d, J=15.2 Hz, 1H), 6.28 (t, J=7.2 Hz, 1H), 5.31 (s, 2H), 4.17 (br s, 1H), 3.55 (s, 3H), 2.97 (s, 3H), 2.82 (s, 3H), 2.74 (d, J=7.5 Hz, 2H), 2.26-2.18 (m, 5H), 2.02-1.93 (m, 1H), 1.91-1.64 (m, 2H), 0.88 (d, J=6.4 Hz, 6H).

Example 79

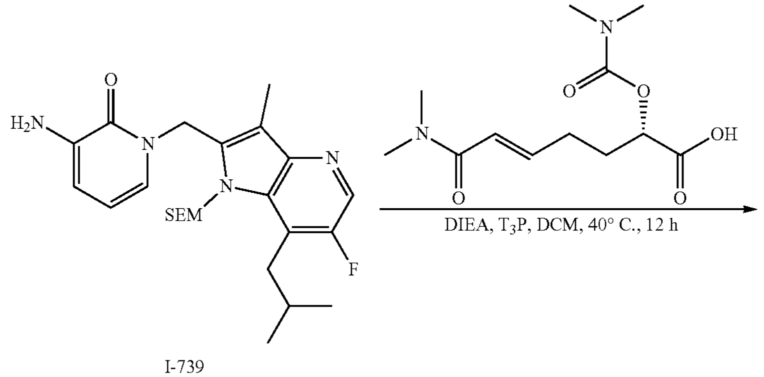

I-739

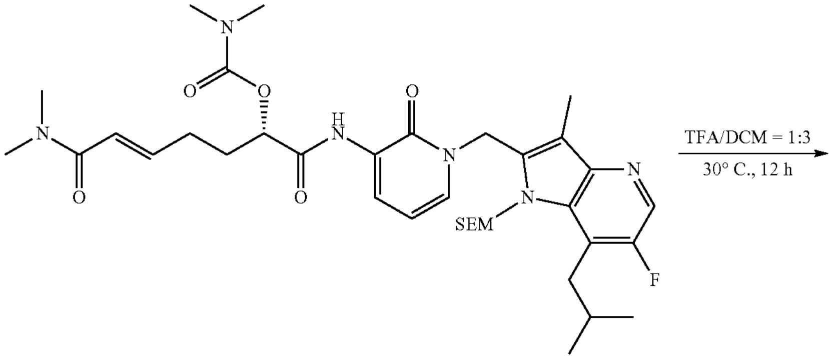

I-741

-continued

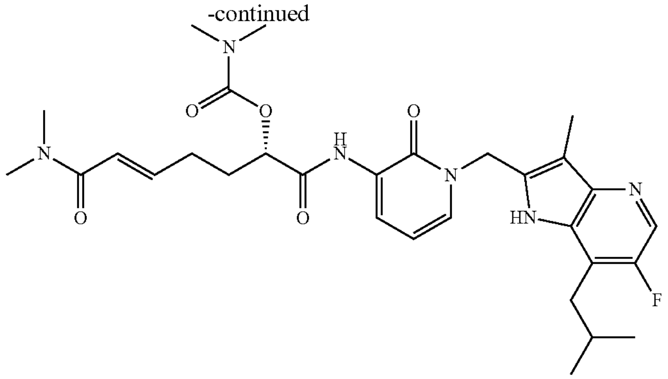

532

A mixture of 3-amino-1-[[6-fluoro-7-isobutyl-3-methyl-1-(2-trimethylsilylethoxymethyl)pyrrolo[3,2-b]pyridin-2-yl]methyl]pyridin-2-one (75 mg, 163.53 umol, 1 eq), (E,2S)-7-(dimethylamino)-2-(dimethylcarbamoyloxy)-7-oxo-hept-5-enoic acid (44.53 mg, 163.53 umol, 1 eq), $T_3P$ (135.28 mg, 212.59 umol, 126.43 uL, 50% purity, 1.3 eq) and DIEA (31.70 mg, 245.30 umol, 42.72 uL, 1.5 eq) in DCM (3 mL) and then the mixture was stirred at 40° C. for 20 hr. The mixture was poured into water 10 mL, and then extracted with DCM 20 mL. The combined organic layers were washed with brine 20 mL, dried over $Na_2SO_4$, filtered and concentrated under reduced pressure to give [(E,1S)-6-(dimethylamino)-1-[[1-[[6-fluoro-7-isobutyl-3-methyl-1-(2-trimethylsilylethoxymethyl)pyrrolo[3,2-b]pyridin-2-yl]methyl]-2-oxo-3-pyridyl]carbamoyl]-6-oxo-hex-4-enyl]N,N-dimethylcarbamate (I-741) (100 mg) as a brown oil. LCMS m/z 713.4 $(M+1)^+$.

To a solution of [(E,1S)-6-(dimethylamino)-1-[[1-[[6-fluoro-7-isobutyl-3-methyl-1-(2-trimethylsilylethoxymethyl)pyrrolo[3,2-b]pyridin-2-yl]methyl]-2-oxo-3-pyridyl]carbamoyl]-6-oxo-hex-4-enyl] N,N-dimethylcarbamate (100 mg, 140.27 umol, 1 eq) in DCM (3 mL) was added TFA (1 mL). The mixture was stirred at 30° C. for 17 hr. The mixture was poured into sat. $NaHCO_3$ solution to adjust pH~7, then diluted with water 20 mL and extracted with DCM 25 mL. The combined organic layers were washed with brine 15 mL, dried over $Na_2SO_4$, filtered and concentrated under reduced pressure to give a residue. The residue was purified by prep-HPLC to give [(E,1S)-6-(dimethylamino)-1-[[1-[(6-fluoro-7-isobutyl-3-methyl-TH-pyrrolo[3,2-b]pyridin-2-yl)methyl]-2-oxo-3-pyridyl]carbamoyl]-6-oxo-hex-4-enyl] N,N-dimethylcarbamate (Compound 532) (14.2 mg, 17% yield) as a white solid. LCMS m/z 582.6 $(M+1)^+$. $^1H$ NMR (400 MHz, DMSO-$d_6$) δ 11.18 (s, 1H), 9.37 (s, 1H), 8.21-8.15 (m, 2H), 7.36 (dd, J=1.7, 6.9 Hz, 1H), 6.67-6.59 (m, 1H), 6.38 (d, J=15.2 Hz, 1H), 6.28 (t, J=7.2 Hz, 1H), 5.31 (s, 2H), 5.09 (dd, J=4.5, 7.6 Hz, 1H), 2.96 (s, 6H), 2.81 (s, 6H), 2.73 (br d, J=7.3 Hz, 2H), 2.29-2.23 (m, 5H), 2.05 (s, 1H), 2.00-1.88 (m, 3H), 0.88 (d, J=6.6 Hz, 5H).

Example 80

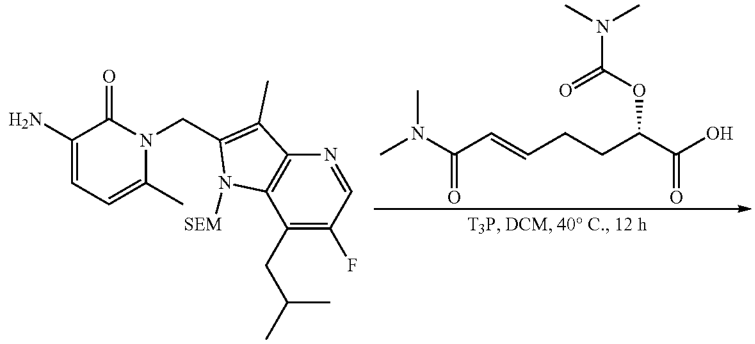

I-742

-continued

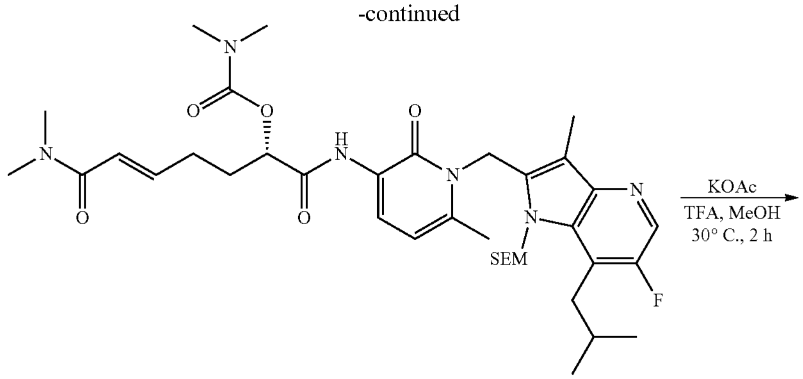

I-743

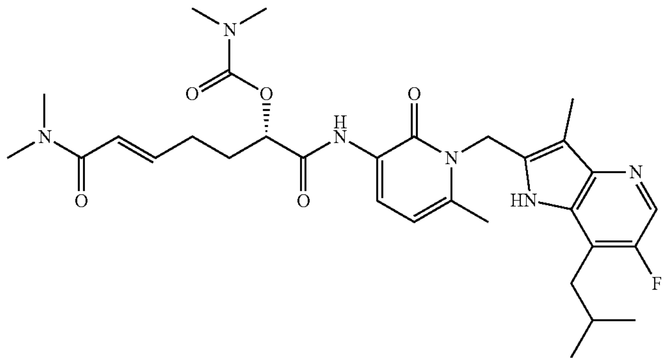

593

Compound 593 was prepared according to the procedures for Example 71 using the appropriate intermediates. LCMS m/z 597.6 $(M+1)^+$. $^1H$ NMR (400 MHz, DMSO-$d_6$) δ 10.98 (s, 1H), 9.33 (s, 1H), 8.19 (d, J=2.1 Hz, 1H), 8.16 (d, J=7.6 Hz, 1H), 6.70-6.63 (m, 1H), 6.41 (d, J=15.2 Hz, 1H), 6.23 (d, J=7.9 Hz, 1H), 5.53 (s, 2H), 5.12 (dd, J=4.5, 7.7 Hz, 1H), 3.01-2.98 (m, 6H), 2.84 (s, 6H), 2.78 (br d, J=7.2 Hz, 2H), 2.35-2.30 (m, 2H), 2.28 (s, 3H), 2.03-1.97 (m, 2H), 1.96 (s, 4H), 0.90 (d, J=6.6 Hz, 6H).

The following compound was prepared according to the procedures described in Example 80 using the appropriate intermediates.

| Compound | Structure | Characterization Data |
|---|---|---|
| 592 | 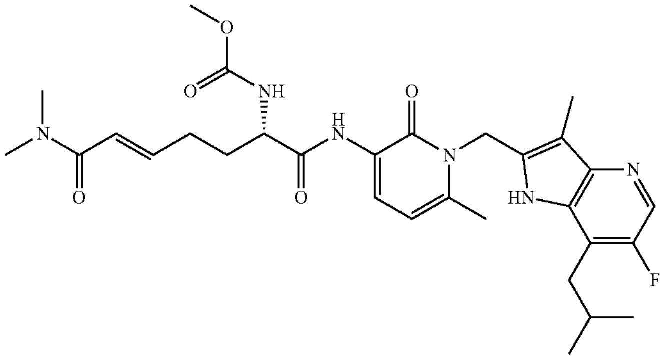 [SMILES: COC(=O)N[C@@H](CC/C=C/C(=O)N(C)C)C(=O)Nc1ccc(C)n(Cc2[nH]c3c(CC(C)C)c(F)cnc3c2C)c1=O] | LCMS m/z 583.6 $(M + 1)^+$ |

Example 81

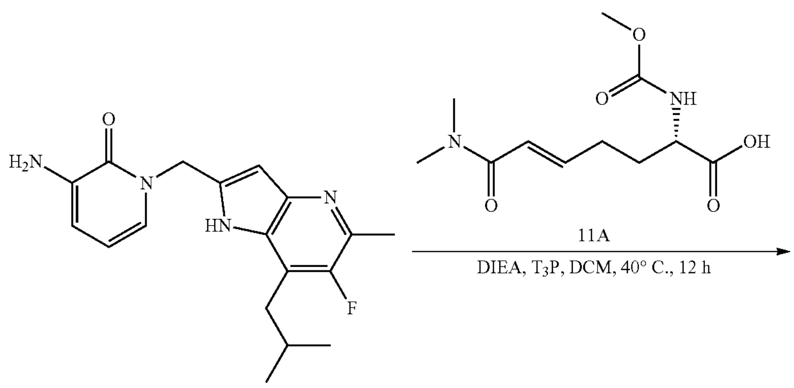

I-753

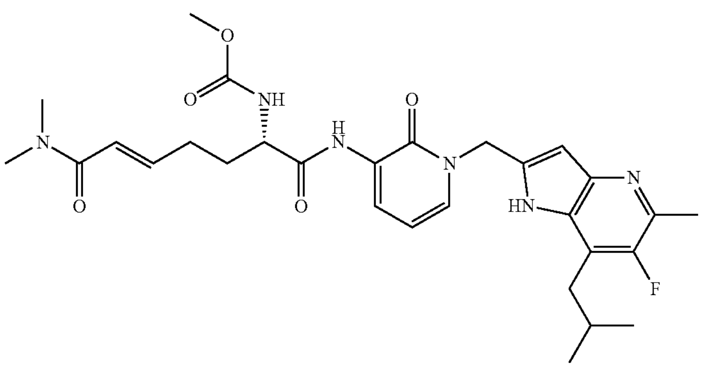

541

Compound 541 was prepared according to the procedures for Example 80 using the appropriate intermediates. LCMS m/z 569.3 $(M+1)^+$. $^1H$ NMR (400 MHz, DMSO-$d_6$) δ 11.40 (br s, 1H) 9.32 (s, 1H) 8.23 (d, J=6.39 Hz, 1H) 8.13 (s, 1H) 7.76 (br d, J=7.72 Hz, 1 H) 7.46 (br d, J=6.17 Hz, 1H) 6.57-6.65 (m, 1H) 6.29-6.42 (m, 2H) 6.25 (s, 1H) 5.31 (br s, 2H) 4.14-4.24 (m, 1H) 3.56 (s, 3H) 2.95-3.03 (m, 3H) 2.83 (s, 3H) 2.74 (br d, J=7.28 Hz, 2H) 2.43 (d, J=3.31 Hz, 3H) 2.24 (dt, J=14.06, 6.75 Hz, 2H) 1.99 (dt, J=13.51, 6.81 Hz, 1H) 1.66-1.93 (m, 2H) 0.91 (d, J=6.62 Hz, 6H).

The following compound was prepared according to the procedures described in Example 81 using the appropriate intermediates.

| Compound | Structure | Characterization Data |
| --- | --- | --- |
| 546 | 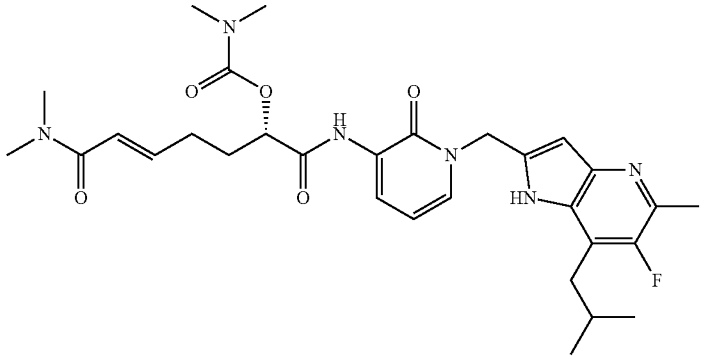 | LCMS m/z 292.1 $(m/2 + 1)^+$ |

Synthesis of Intermediate I-759

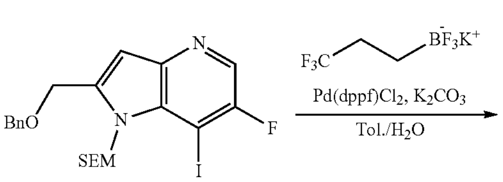

I-754

-continued

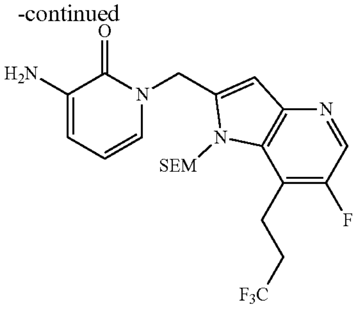

I-759

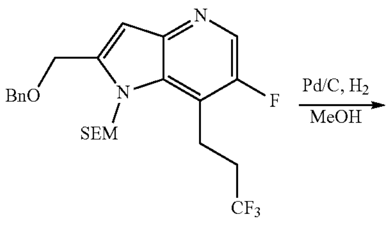

I-755

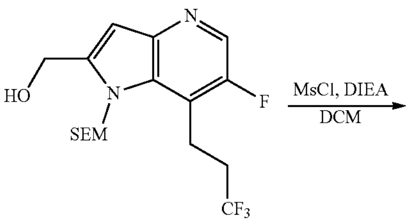

I-756

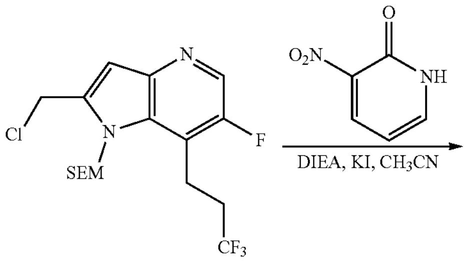

I-757

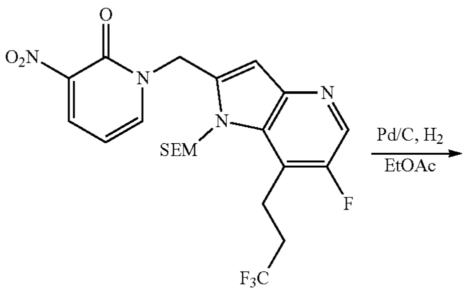

I-758

$Pd(dppf)Cl_2$ (42.8 mg, 58.5 umol, 0.1 eq) was added to a mixture of 2-[[2-(benzyloxymethyl)-6-fluoro-7-iodo-pyrrolo[3,2-b]pyridin-1-yl]methoxy]ethyl-trimethyl-silane (0.3 g, 585 umol, 1 eq), potassium hydride;trifluoro (3,3,3-trifluoropropyl)boron (167 mg, 820 umol, 1.4 eq) and $K_2CO_3$ (162 mg, 1.17 mmol, 2 eq) in Tol./$H_2O$ (10:1) (5 mL) under $N_2$. Then the mixture was heated to 100° C. for 12 h. Three reactions were combined and worked up together. The mixture was filtered and the filtrate was extracted between EtOAc (30 mL) and water (30 mL), the organic layer was concentrated to give a crude product. The residue was purified by column ($SiO_2$) to give 2-[[2-(benzyloxymethyl)-6-fluoro-7-(3,3,3-trifluoropropyl)pyrrolo[3,2-b]pyridine-1-yl]methoxy]ethyl-trimethyl-silane (I-755) (828 mg, 1.61 mmol, 92% yield) as a yellow oil.

To a solution of 2-[[2-(benzyloxymethyl)-6-fluoro-7-(3,3,3-trifluoropropyl)pyrrolo [3,2-b]pyridin-1-yl]methoxy] ethyl-trimethyl-silane (800 mg, 1.66 mmol, 1 eq) in MeOH (30 mL) was added Pd/C (300 mg, 10% purity) under $N_2$. The suspension was degassed under vacuum and purged with $H_2$ several times. The mixture was stirred under $H_2$ (15 psi) at 50° C. for 12 hours. The mixture was filtered and the filtrate was concentrated to give [6-fluoro-7-(3,3,3-trifluoropropyl)-1-(2-trimethylsilylethoxymethyl)pyrrol[3,2-b]pyridin-2-yl]methanol (I-756) (676 mg) as a yellow solid.

MsCl (587 mg, 5.12 mmol, 3 eq) was added to a mixture of [6-fluoro-7-(3,3,3-trifluoropropyl)-1-(2-trimethylsilylethoxymethyl)pyrrolo[3,2-b]pyridin-2-yl]methanol (670 mg, 1.71 mmol, 1 eq) and DIEA (882 mg, 6.83 mmol, 4 eq) in DCM (10 mL) at 0° C., then stirred at 25° C. for 0.5 h. Water (10 mL) was added to the mixture. The mixture was extracted with DCM (10 mL×2). The combined organic layers were washed with brine (10 mL), dried over $Na_2SO_4$ and filtered. The filtrate was concentrated under reduced pressure to give a residue. The crude product 2-[[2-(chloromethyl)-6-fluoro-7-(3,3,3-trifluoropropyl)pyrrolo[3,2-b]pyridin-1-yl]methoxy] ethyl-trimethyl-silane (I-757) (701 mg) was used into the next step without further purification as a yellow oil.

To a mixture of 3-nitro-1H-pyridin-2-one (262 mg, 1.87 mmol, 1.1 eq), KI (282 mg, 1.70 mmol, 1 eq) and DIEA (329 mg, 2.55 mmol, 1.5 eq) in $CH_3CN$ (10 mL) was added 2-[[2-(chloromethyl)-6-fluoro-7-(3,3,3-trifluoropropyl)pyrrolo[3,2-b]pyridine-1-yl]methoxy]ethyl-trimethyl-silane (700 mg, 1.70 mmol, 1 eq) at 25° C. Then the mixture was stirred at 40° C. for 12 h. The mixture was concentrated to give a crude product. The residue was purified by column chromatography (SiO2) to give 1-[[6-fluoro-7-(3,3,3-trifluoropropyl)-1-(2-trimethylsilylethoxymethyl)pyrrolo[3,2-b]pyridin-2-yl]methyl]-3-nitro-pyridin-2-one (I-758) (590 mg, 1.15 mmol, 67.5% yield) as a yellow oil. $^1$H NMR (400 MHz, DMSO-$d_6$) δ 8.44-8.50 (m, 1H) 8.36-8.41 (m, 1H)

8.15-8.20 (m, 1H) 6.67-6.72 (m, 1H) 6.47-6.54 (m, 1H) 5.49-5.60 (m, 4H) 3.49 (br t, J=8.05 Hz, 2H) 3.20-3.27 (m, 2H) 2.64-2.75 (m, 2H) 0.71-0.80 (m, 2H) −0.07 (s, 9H)

To a solution of 1-[[6-fluoro-7-(3,3,3-trifluoropropyl)-1-(2-trimethylsilylethoxymethyl) pyrrolo[3,2-b]pyridin-2-yl] methyl]-3-nitro-pyridin-2-one (300 mg, 583 umol, 1 eq) in EtOAc (10 mL) was added Pd/C (100 mg, 10% purity) under $N_2$. The suspension was degassed under vacuum and purged with $H_2$ several times. The mixture was stirred under $H_2$ (15 psi) at 25° C. for 0.5 hours. The mixture was filtered and the filtrate was concentrated to give 3-amino-1-[[6-fluoro-7-(3,3-trifluoropropyl)-1-(2-trimethylsilyl ethoxymethyl)pyrrolo[3,2-b]pyridin-2-yl]methyl]pyridin-2-one (I-759) (280 mg) as a yellow oil.

Example 82

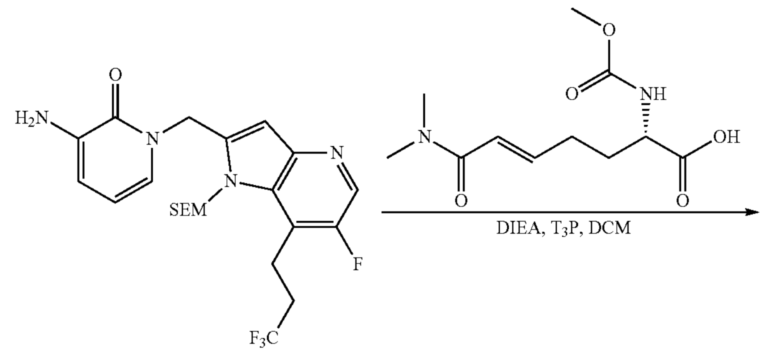

I-759

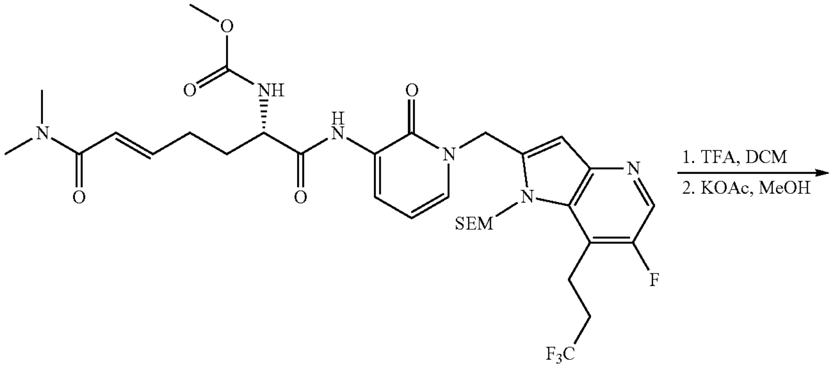

I-760

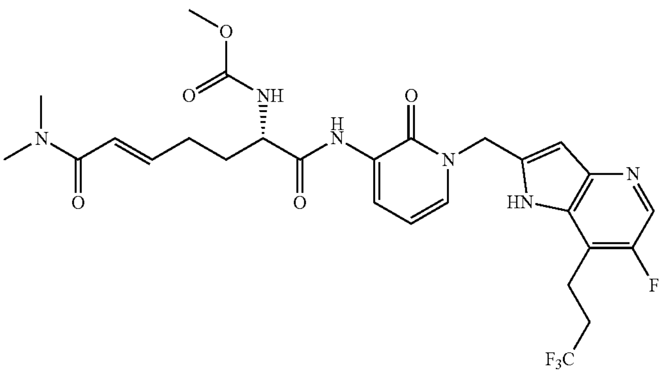

540

Compound 540 was prepared according to the procedures for Example 71 using the appropriate intermediates. LCMS m/z 595.2 $(M+1)^+$. $^1H$ NMR (400 MHz, DMSO-$d_6$) δ 11.78 (br s, 1H) 9.33 (s, 1H) 8.21-8.28 (m, 2H) 7.77 (br d, J=7.6 Hz, 1H) 7.51 (dd, J=6.8, 1.54 Hz, 1H) 6.56-6.67 (m, 1H) 6.31-6.42 (m, 3H) 5.35 (s, 2H) 4.13-4.25 (m, 1H) 3.56 (s, 3H) 3.10-3.21 (m, 2H) 3.00 (s, 3H) 2.84 (s, 3H) 2.66 (dt, J=10.8, 8.0 Hz, 2H) 2.25 (dt, J=14.4, 7.2 Hz, 2H) 1.82-1.95 (m, 1H) 1.65-1.79 (m, 1H).

The following compound was prepared according to the procedures described for the synthesis of Example 82 using the appropriate intermediates.

-continued

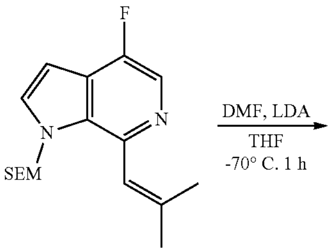

I-764

| Compound | Structure | Characterization Data |
|---|---|---|
| 542 | 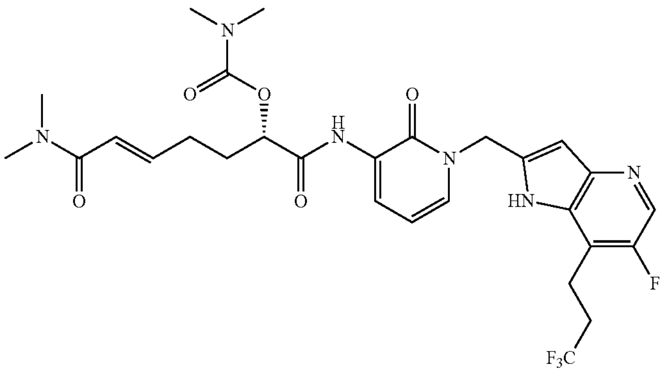 [SMILES: CN(C)C(=O)/C=C/CC[C@H](OC(=O)N(C)C)C(=O)Nc1cccn(Cc2cc3ncc(F)c(CCC(F)(F)F)c3[nH]2)c1=O] | LCMS m/z 609.2 $(M+1)^+$ |

Synthetic of Intermediate I-770

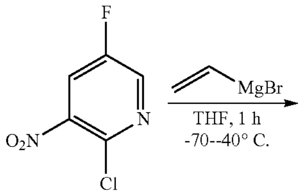

I-761

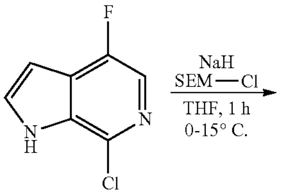

I-762

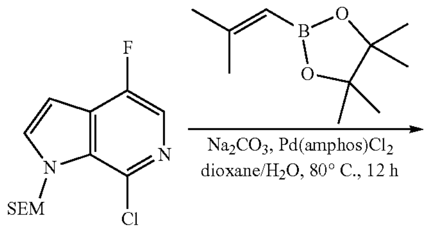

I-763

-continued

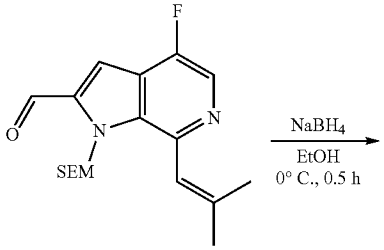

I-765

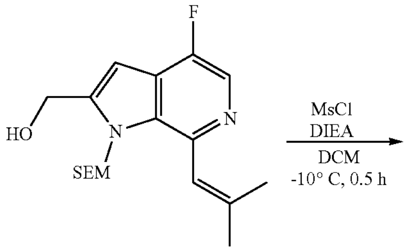

I-766

-continued

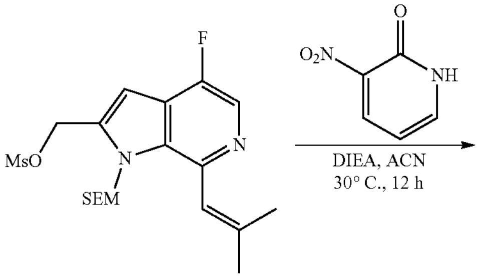

I-767

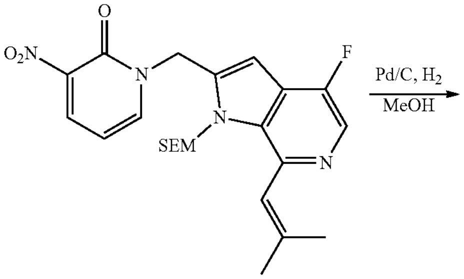

I-768

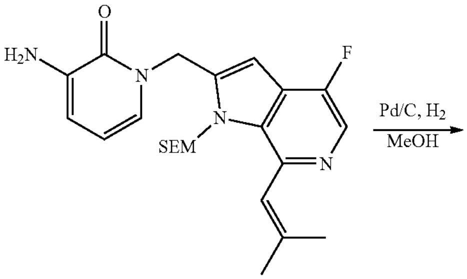

I-769

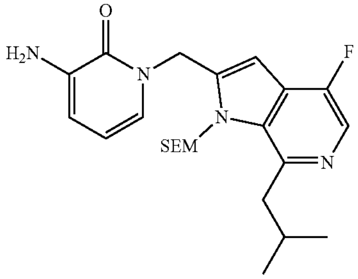

I-770

Two reactions were carried out in parallel: To a solution of 2-chloro-5-fluoro-3-nitro-pyridine (5 g, 28.32 mmol, 1 eq) in THF (50 mL) was added bromo(vinyl)magnesium (1 M, 90.63 mL, 3.2 eq) at −78° C. The mixture was stirred at −40° C. for 1 hr. Two reactions were combined for work-up. The reaction mixture was partitioned between sat. $NH_4Cl$ (aq) 100 mL and ethyl acetate 100 mL. The organic phase was separated, washed with brine 100 mL (100 mL*1), dried over anhydrous $Na_2SO_4$, filtered and concentrated under reduced pressure to give a residue. The residue was purified by column chromatography ($SiO_2$) to give 7-chloro-4-fluoro-1H-pyrrolo[2,3-c]pyridine (I-762) (5.6 g, 58% yield) as a yellow solid. LCMS m/z 171.2 $(M+1)^+$.

To a solution of 7-chloro-4-fluoro-1H-pyrrolo[2,3-c]pyridine (5.6 g, 32.83 mmol, 1 eq) in DMF (60 mL) was added NaH (1.97 g, 49.25 mmol, 60% purity, 1.5 eq) at 0° C. The mixture was stirred at 0° C. for 0.5 hr. Then SEM-Cl (7.12 g, 42.68 mmol, 7.55 mL, 1.3 eq) was added dropwise, and the result reaction mixture was allowed to stir at 20° C. for 0.5 hr. The reaction mixture was quenched by addition sat. $NH_4Cl$ (aq) 50 mL at 0° C., and then diluted with ethyl acetate 50 mL and extracted with ethyl acetate 50 mL (50 mL*1). The combined organic layers were washed with brine 50 mL (50 mL*1), dried over anhydrous $Na_2SO_4$, filtered and concentrated under reduced pressure to give a residue. The residue was purified by column chromatography ($SiO_2$) to give 2-[(7-chloro-4-fluoro-pyrrolo[2,3-c]pyridin-1-yl)methoxy]ethyl-trimethyl-silane (I-763) (3.6 g, 36% yield) as a yellow oil. LCMS m/z 301.1 $(M+1)^+$.

A mixture of 2-[(7-chloro-4-fluoro-pyrrolo[2,3-c]pyridin-1-yl)methoxy]ethyl-trimethyl-silane (3.6 g, 11.97 mmol, 1 eq), 4,4,5,5-tetramethyl-2-(2-methylprop-1-enyl)-1,3,2-dioxaborolane (2.40 g, 13.16 mmol, 1.1 eq), $Na_2CO_3$ (2.54 g, 23.93 mmol, 2 eq), 4-ditert-butylphosphanyl-N,N-dimethyl-aniline;dichloropalladium (847.34 mg, 1.20 mmol, 847.34 uL, 0.1 eq) in dioxane (40 mL) and $H_2O$ (4 mL) was degassed and purged with $N_2$ for 3 times, and then the mixture was stirred at 90° C. for 12 hrs under $N_2$ atmosphere. The reaction mixture was concentrated under reduced pressure to remove the solvent to afford black oil. The oil was purified by column chromatography ($SiO_2$) to give 2-[[4-fluoro-7-(2-methylprop-1-enyl)pyrrolo[2,3-c]pyridin-1-yl]methoxy]ethyl-trimethyl-silane (I-764) (2.2 g, 57% yield) as a yellow oil. LCMS m/z 321.1 $(M+1)^+$.

To a solution of 2-[[4-fluoro-7-(2-methylprop-1-enyl)pyrrolo[2,3-c]pyridin-1-yl]methoxy]ethyl-trimethyl-silane (2.2 g, 6.86 mmol, 1 eq) in THF (25 mL) was added LDA (2 M, 5.15 mL, 1.5 eq) at −70° C. The mixture was stirred at −70° C. for 0.5 hr. Then DMF (1.51 g, 20.59 mmol, 1.58 mL, 3 eq) was added at −70° C., and the result reaction mixture was stirred at −70° C. for additional 0.5 hr. The reaction mixture was quenched by addition sat. $NH_4Cl$ (aq) 20 mL at 0° C., and then diluted with ethyl acetate 20 mL and extracted with ethyl acetate 20 mL (20 mL*1). The combined organic layers were washed with brine 20 mL (20 mL*1), dried over anhydrous $Na_2SO_4$, filtered and concentrated under reduced pressure to give a residue. The residue was purified by column chromatography ($SiO_2$) to give 4-fluoro-7-(2-methylprop-1-enyl)-1-(2-trimethylsilylethoxymethyl)pyrrolo[2,3-c]pyridine-2-carbaldehyde (I-765) (350 mg, 1.00 mmol, 14.57% yield) as a yellow oil. LCMS m/z 349.1 $(M+1)^+$.

To a solution of 4-fluoro-7-(2-methylprop-1-enyl)-1-(2-trimethylsilylethoxymethyl) pyrrolo[2,3-c]pyridine-2-carbaldehyde (350 mg, 1.00 mmol, 1 eq) in MeOH (4 mL) was added $NaBH_4$ (57.00 mg, 1.51 mmol, 1.5 eq) at 0° C. The mixture was stirred at 20° C. for 0.5 hr. The reaction mixture was quenched by addition sat. $NH_4Cl$ (aq) 5 mL at 0° C., and then diluted with ethyl acetate 5 mL and extracted with ethyl acetate 5 mL (5 mL*1). The combined organic layers were washed with brine 5 mL (5 mL*1), dried over anhydrous $Na_2SO_4$, filtered and concentrated under reduced pressure to give a residue. The residue was purified by prep-TLC ($SiO_2$) to give [4-fluoro-7-(2-methylprop-1-enyl)-1-(2-trimethylsilylethoxymethyl) pyrrolo[2,3-c]pyridin-2-yl]methanol (I-766) (150 mg, 43% yield) was obtained as colorless oil. LCMS m/z 350.9 $(M+1)^+$.

To a solution of [4-fluoro-7-(2-methylprop-1-enyl)-1-(2-trimethylsilylethoxymethyl)pyrrolo[2,3-c]pyridin-2-yl] methanol (340 mg, 970.04 umol, 1 eq) in DCM (4 mL) was added MsCl (166.68 mg, 1.46 mmol, 112.62 uL, 1.5 eq) and DIEA (250.74 mg, 1.94 mmol, 337.93 uL, 2 eq) at −10° C. The mixture was stirred at −10° C. for 0.5 hr. The reaction mixture was quenched by addition sat. $NH_4Cl$ (aq) 5 mL at 0° C., and then diluted with dichloromethane 5 mL and extracted with dichloromethane 5 mL (5 mL*1). The combined organic layers were washed with brine 5 mL (5 mL*1), dried over anhydrous $Na_2SO_4$, filtered and concentrated under reduced pressure to give a residue. The crude product [4-fluoro-7-(2-methylprop-1-enyl)-1-(2-trimethylsilylethoxymethyl)pyrrolo[2,3-c]pyridin-2-yl]methyl methanesulfonate (I-767) (420 mg) was used into the next step without further purification as brown oil. LCMS m/z 429.1 $(M+1)^+$.

To a solution of 3-nitro-1H-pyridin-2-one (164.75 mg, 1.18 mmol, 1.2 eq) in MeCN (5 mL) was added DIEA (189.98 mg, 1.47 mmol, 256.03 uL, 1.5 eq) and [4-fluoro-7-(2-methylprop-1-enyl)-1-(2-trimethylsilylethoxymethyl)pyrrolo[2,3-c]pyridin-2-yl]methyl methanesulfonate (420 mg, 979.95 umol, 1 eq) at 20° C. The mixture was stirred at 20° C. for 12 hrs. The organic phase was separated, washed with brine 10 mL (10 mL*1), dried over anhydrous $Na_2SO_4$, filtered and concentrated under reduced pressure to give a residue. The residue was purified by prep-TLC ($SiO_2$) to give 1-[[4-fluoro-7-(2-methylprop-1-enyl)-1-(2-trimethylsilylethoxymethyl)pyrrolo[2,3-c]pyridin-2-yl]methyl]-3-nitro-pyridin-2-one (I-768) (280 mg, 592.49 umol, 60.46% yield) as a light yellow oil. LCMS m/z 473.3 $(M+1)^+$.

To a solution of 1-[[4-fluoro-7-(2-methylprop-1-enyl)-1-(2-trimethylsilylethoxy methyl)pyrrolo[2,3-c]pyridin-2-yl]methyl]-3-nitro-pyridin-2-one (250 mg, 529.01 umol, 1 eq) in MeOH (5 mL) was added Pd/C (20 mg, 529.01 umol, 10% purity, 1.00 eq) under $N_2$. The suspension was degassed under vacuum and purged with $H_2$ several times. The mixture was stirred under $H_2$ (15 psi) at 15° C. for 1 hr. The reaction mixture was filtered and the filtrate was concentrated under reduced pressure to remove the solvent to afford the crude product 3-amino-1-[[4-fluoro-7-(2-methylprop-1-enyl)-1-(2-trimethylsilylethoxymethyl)pyrrolo[2,3-c]pyridin-2-yl]methyl]pyridin-2-one (I-769) (220 mg) was used into the next step without further purification as light yellow oil. LCMS m/z 443.3 $(M+1)^+$.

To a solution of 3-amino-1-[[4-fluoro-7-(2-methylprop-1-enyl)-1-(2-trimethylsilylethoxymethyl)pyrrolo[2,3-c]pyridin-2-yl]methyl]pyridin-2-one (190 mg, 429.28 umol, 1 eq) in MeOH (5 mL) was added Pd/C (20 mg, 10% purity) under $N_2$. The suspension was degassed under vacuum and purged with $H_2$ several times. The mixture was stirred under $H_2$ (15 psi) at 20° C. for 2 hrs. The reaction mixture was filtered and the filtrate was concentrated under reduced pressure to remove the solvent to afford light yellow oil. The crude product 3-amino-1-[[4-fluoro-7-isobutyl-1-(2-trimethylsilylethoxymethyl)pyrrolo[2,3-c]pyridin-2-yl]methyl]pyridin-2-one (I-770) (160 mg) was used into the next step without further purification as light yellow oil. LCMS m/z 445.2 $(M+1)^+$.

The following intermediate was prepared according to the procedures described for the synthesis of I-770 using the appropriate reagents.

| Compound | Structure | Characterization Data |
| --- | --- | --- |
| I-771 | 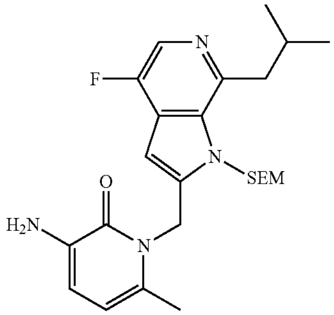 | LCMS m/z 464.2 $(M + 1)^+$ |

Example 83

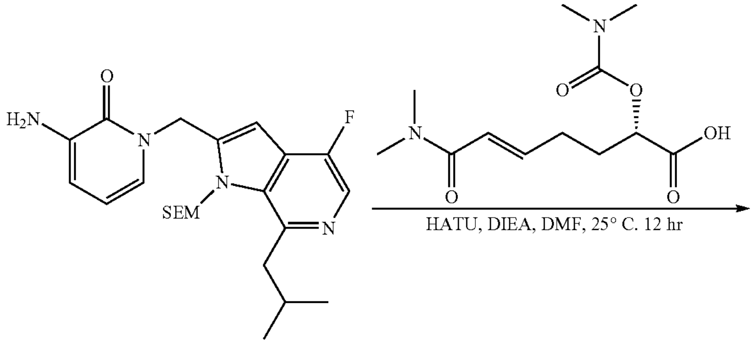

I-770

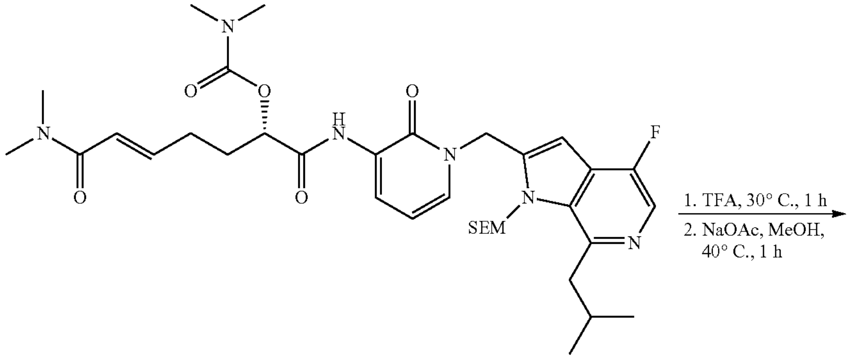

I-772

-continued

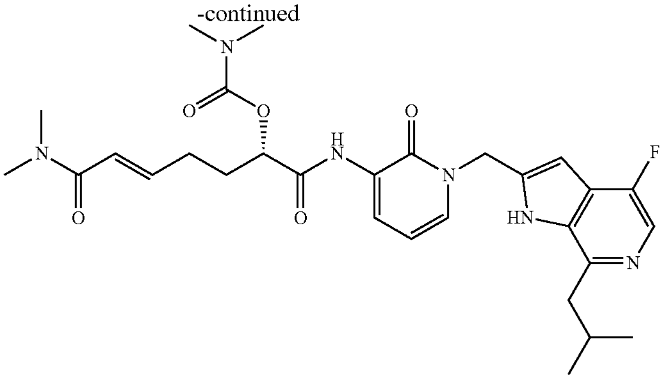

507

Compound 507 was prepared according to the procedures for Example 71 using the appropriate intermediates. LCMS m/z 569.2 $(M+1)^+$. $^1H$ NMR (400 MHz, DMSO-$d_6$) δ 11.94 (br s, 1H), 9.33 (br s, 1H), 8.21 (br d, J=7.3 Hz, 1H), 7.90 (br s, 1H), 7.52 (br d, J=6.8 Hz, 1H), 6.69-6.56 (m, 1H), 6.44-6.23 (m, 3H), 5.35 (br s, 2H), 5.08 (br d, J=4.4 Hz, 1H), 2.95 (br s, 6H), 2.86-2.73 (m, 8H), 2.33-2.11 (m, 3H), 1.92 (br s, 2H), 0.91-0.86 (m, 6H).

The following compounds were prepared according to the procedures described in Example 83 using the appropriate intermediates.

| Compound | Structure | Characterization Data |
|---|---|---|
| 508 | 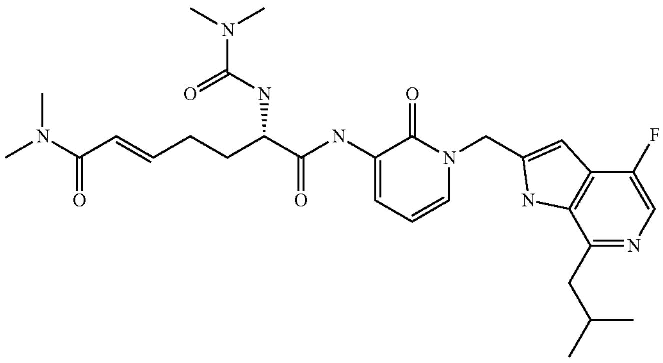 [SMILES: CC(C)Cc1ncc(F)c2cc(Cn3cccc(NC(=O)[C@H](CC/C=C/C(=O)N(C)C)NC(=O)N(C)C)c3=O)[nH]c12] | LCMS m/z 584.9 $(M + 1)^+$ |
| 518 | 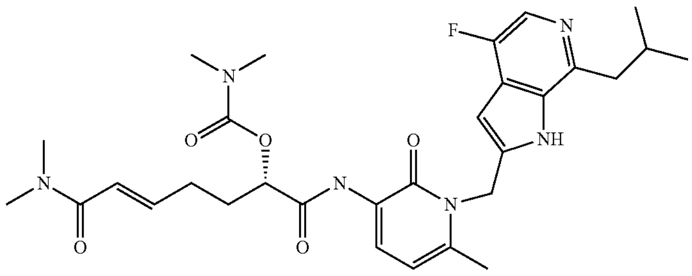 [SMILES: Cc1ccc(NC(=O)[C@H](CC/C=C/C(=O)N(C)C)OC(=O)N(C)C)c(=O)n1Cc1cc2c(F)cnc(CC(C)C)c2[nH]1] | LCMS m/z 583.2 (M + 1) |
| 519 | 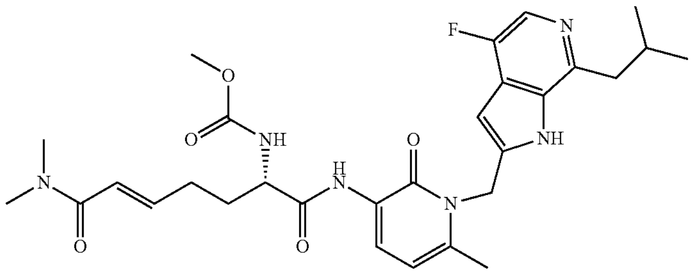 [SMILES: COC(=O)N[C@@H](CC/C=C/C(=O)N(C)C)C(=O)Nc1ccc(C)n(Cc2cc3c(F)cnc(CC(C)C)c3[nH]2)c1=O] | LCMS m/z 569.2 (M + 1) |

Example 84

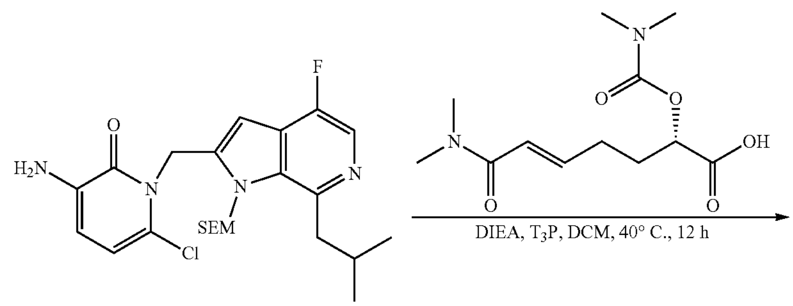

I-776

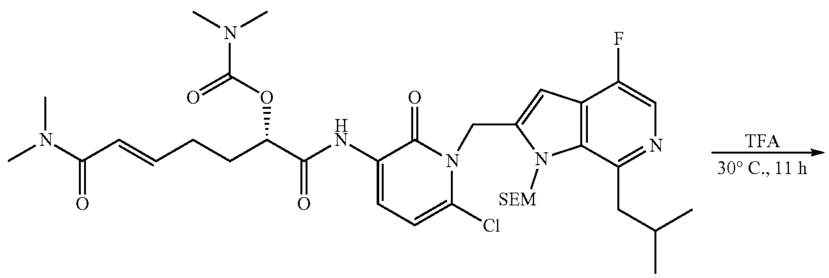

I-777

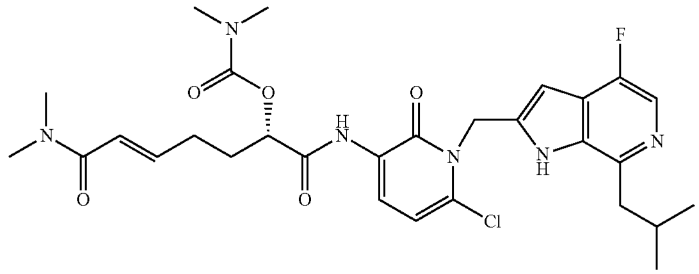

533

Compound 533 was prepared according to the procedures for Example 71 using the appropriate intermediates. LCMS m/z 603.2 $(M+1)^+$. $^1$HNMR (400 MHz, DMSO-$d_6$) δ 12.06 (br s, 1H) 9.42 (s, 1H) 8.25 (d, J=8.07 Hz, 1H) 7.87-7.95 (m, 1H) 6.58-6.71 (m, 2H) 6.40 (br d, J=15.16 Hz, 1H) 6.11 (s, 1H) 5.62 (s, 2H) 5.12 (dd, J=7.52, 4.46 Hz, 1H) 2.92-3.01 (m, 6H) 2.78-2.88 (m, 8H) 2.29 (q, J=6.85 Hz, 2H) 2.13-2.24 (m, 1H) 1.85-2.03 (m, 2H) 0.91 (d, J=6.60 Hz, 6H).

The following compound was prepared according to the procedures described in Example 84 using the appropriate intermediates.

| Compound | Structure | Characterization Data |
| --- | --- | --- |
| 534 | 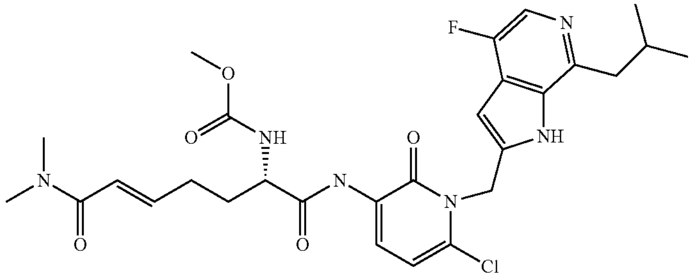 [SMILES: COC(=O)N[C@@H](CC/C=C/C(=O)N(C)C)C(=O)Nc1ccc(Cl)n(Cc2cc3c(F)cnc(CC(C)C)c3[nH]2)c1=O] | LCMS m/z 589.2 $(M + 1)^+$ |

Synthesis of Intermediate I-778

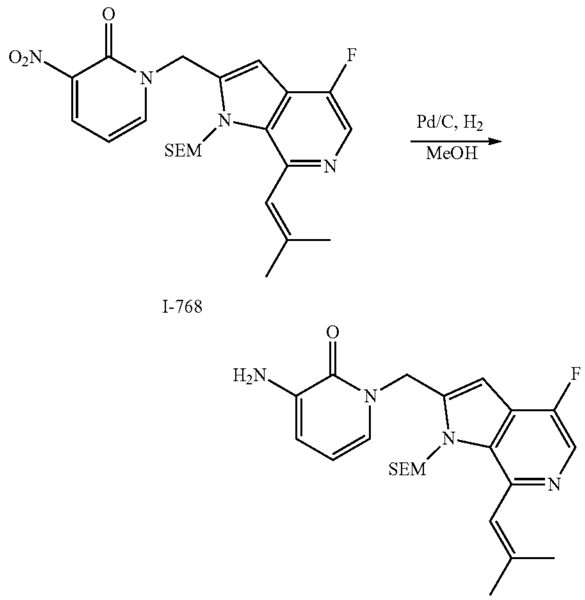

I-768

I-778

To a solution of 1-[[4-fluoro-7-(2-methylprop-1-enyl)-1-(2-trimethylsilylethoxy methyl)pyrrolo[2,3-c]pyridin-2-yl] methyl]-3-nitro-pyridin-2-one (I-768) (250 mg, 529.01 umol, 1 eq) in MeOH (5 mL) was added Pd/C (20 mg, 529.01 umol, 10% purity, 1.00 eq) under $N_2$. The suspension was degassed under vacuum and purged with $H_2$ several times. The mixture was stirred under $H_2$ (15 psi) at 15° C. for 1 hr. The reaction mixture was filtered and the filtrate was concentrated under reduced pressure to remove the solvent to afford the crude product 3-amino-1-[[4-fluoro-7-(2-methylprop-1-enyl)-1-(2-trimethylsilylethoxymethyl)pyrrolo[2,3-c]pyridin-2-yl]methyl]pyridin-2-one (I-778)) (220 mg) was used into the next step without further purification as light yellow oil. LCMS m/z 443.3 $(M+1)^+$.

Example 85

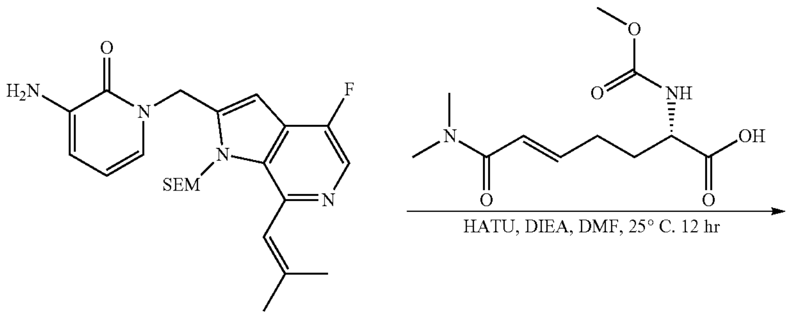

I-778

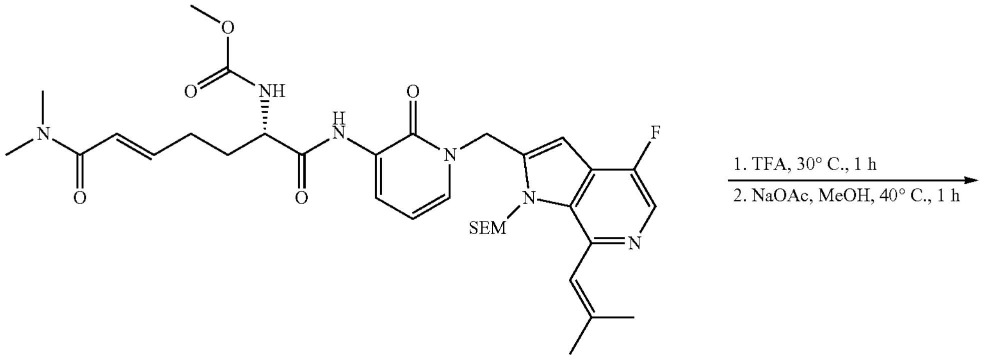

I-779

-continued

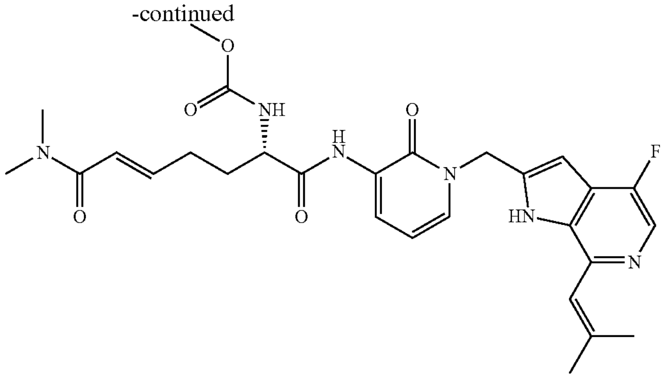

501

Compound 501 was prepared according to the procedures for Example 71 using the appropriate intermediates. LCMS m/z 553.3 $(M+1)^+$. $^1H$ NMR (400 MHz, DMSO-$d_6$) δ 11.97 (br s, 1H), 9.30 (s, 1H), 8.22 (d, J=6.0 Hz, 1H), 7.97 (d, J=1.3 Hz, 1H), 7.73 (br d, J=7.7 Hz, 1H), 7.55-7.46 (m, 1H), 6.67-6.51 (m, 2H), 6.40-6.26 (m, 3H), 5.34 (s, 2H), 4.17 (br s, 1H), 3.54 (s, 3H), 2.97 (s, 3H), 2.81 (s, 3H), 2.30-2.16 (m, 2H), 2.12 (s, 3H), 1.97 (s, 3H), 1.91-1.64 (m, 2H).

The following compound was prepared according to the procedures described in Example 85 using the appropriate intermediates.

| Compound | Structure | Characterization Data |
| --- | --- | --- |
| 502 | 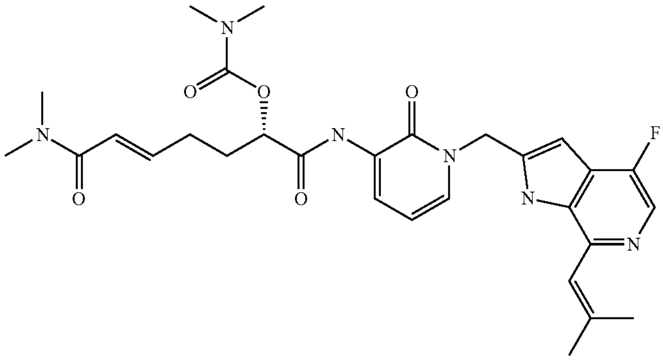 [SMILES: CC(C)=Cc1ncc(F)c2cc(Cn3cccc(NC(=O)[C@H](CC/C=C/C(=O)N(C)C)OC(=O)N(C)C)c3=O)[nH]c12] | LCMS m/z 567.3 (M + 1)$^+$ |

Example 86

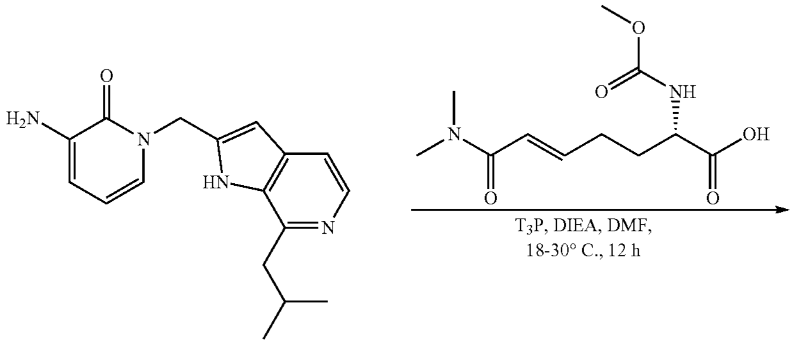

-continued

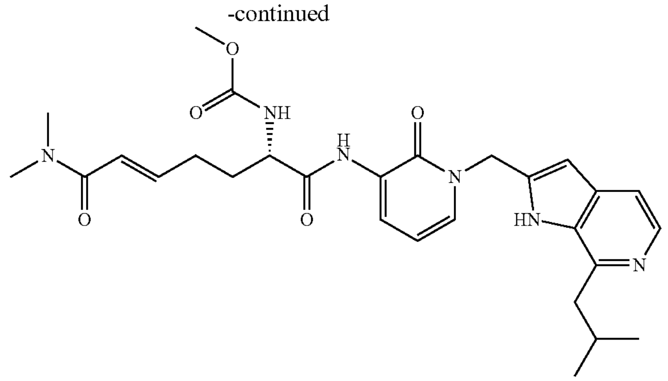

512

$T_3P$ (172 mg, 270 umol, 50% purity, 2 eq) was added to a solution of 3-amino-1-[(7-isobutyl-1H-pyrrolo[2,3-c]pyridin-2-yl)methyl]pyridin-2-one (40 mg, 135 umol, 1 eq), (E,2S)-7-(dimethylamino)-2-(methoxycarbonylamino)-7-oxo-hept-5-enoic acid (41.8 mg, 162 umol, 1.2 eq) and DIEA (34.9 mg, 270 umol, 2 eq) in DCM (2 mL) at 18° C. Then the mixture was stirred at 30° C. for 12 h. The mixture was concentrated to give a crude product. The residue was purified by prep-HPLC to give methyl N-[(E,1S)-6-(dimethylamino)-1-[[1-[(7-isobutyl-1H-pyrrolo[2,3-c]pyridin-2-yl)methyl]-2-oxo-3-pyridyl]carbamoyl]-6-oxo-hex-4-enyl] carbamate (Compound 512) (17.1 mg, 22% yield) as a white solid. LCMS m/z 537.3 $(M+1)^+$. $^1H$ NMR (400 MHz, DMSO-$d_6$) δ 11.58 (br s, 1H) 9.31 (s, 1H) 8.24 (dd, J=7.2, 1.8 Hz, 1H) 7.97 (d, J=5.6 Hz, 1H) 7.75 (br d, J=7.2 Hz, 1H) 7.52 (dd, J=6.8, 1.8 Hz, 1H) 7.26 (d, J=5.6 Hz, 1H) 6.56-6.65 (m, 1H) 6.31-6.42 (m, 2H) 6.19 (s, 1H) 5.35 (s, 2H) 4.14-4.24 (m, 1H) 3.56 (s, 3H) 2.99 (s, 3H) 2.78-2.89 (m, 5H) 2.19-2.28 (m, 3H) 1.75-1.89 (m, 1H) 1.71-1.75 (m, 1H) 0.91 (d, J=6.6 Hz, 6H).

The following compound was prepared according to the procedures described in Example 86 using the appropriate intermediates.

Synthesis of Intermediate I-801

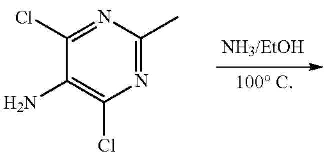

1-790

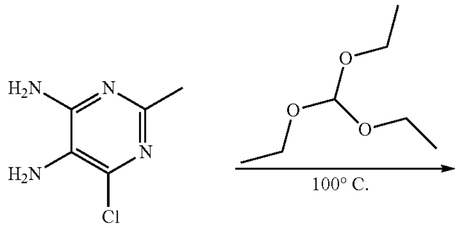

1-791

| Compound | Structure | Characterization Data |
| --- | --- | --- |
| 515 | 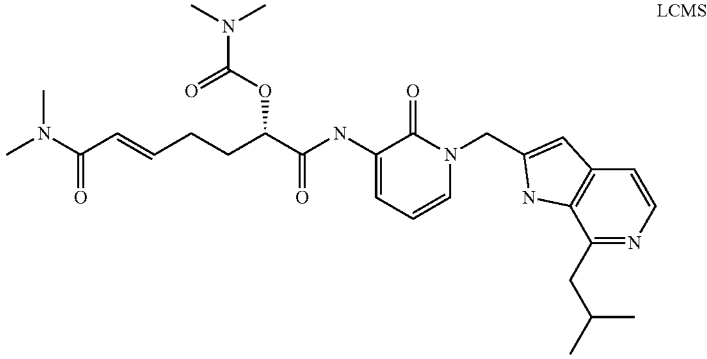 | LCMS m/z 551.3 $(M + 1)^+$ |

-continued

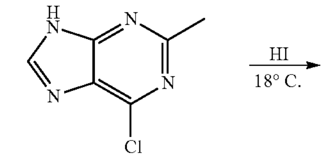

I-792

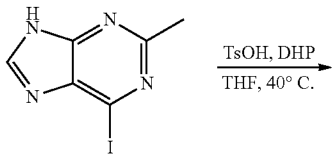

I-793

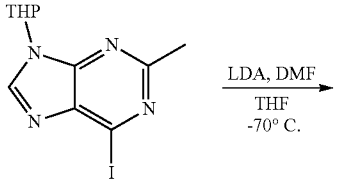

I-794

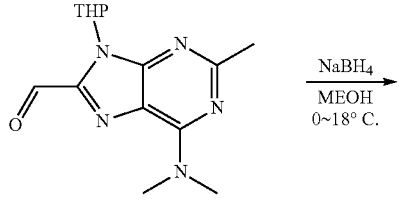

I-795

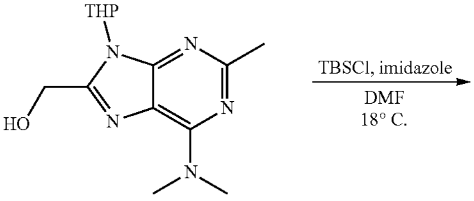

I-796

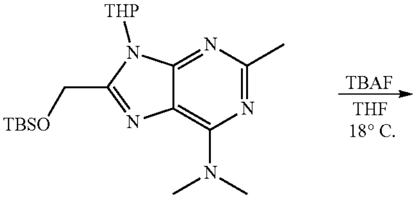

I-797

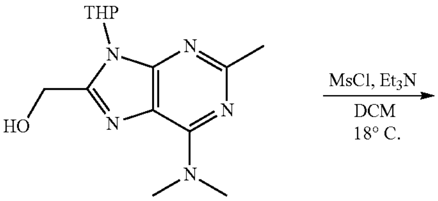

I-798

-continued

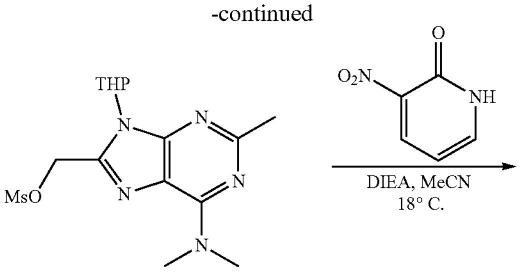

I-799

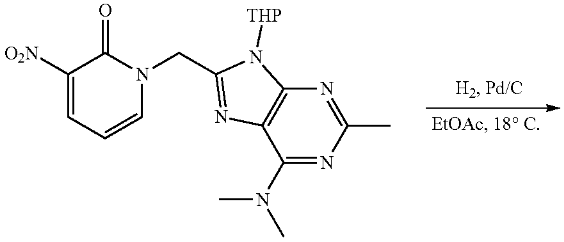

I-800

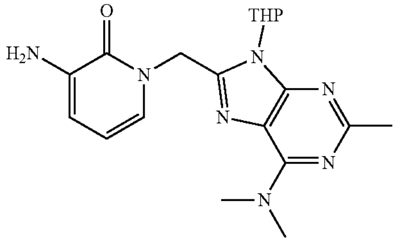

I-801

$NH_3$ (g) was bubbled into EtOH (60 mL) at −40° C. for 0.5 h (15 Psi). Then 4,6-dichloro-2-methyl-pyrimidin-5-amine (5 g, 28.09 mmol, 1 eq) was added at 18° C., and the result reaction mixture was stirred at 120° C. for 13.5 hr (15 Psi). The reaction mixture was concentrated under reduced pressure to remove EtOH. Compound 6-chloro-2-methyl-pyrimidine-4, 5-diamine (I-791) (5.8 g) was obtained as a yellow solid. LCMS m/z 158.8 $(M+1)^+$.

A mixture of 6-chloro-2-methyl-pyrimidine-4,5-diamine (4.8 g, 30.27 mmol, 1 eq), diethoxymethoxyethane (13.46 g, 90.80 mmol, 15.10 mL, 3 eq), and then the mixture was stirred at 100° C. for 4 hr. The reaction mixture was filter and the filter cake was obtained, filtrate was diluted with water 5 mL extracted with EtOAc 15 mL (5 mL*3). The combined organic layers were dried over $Na_2SO_4$, filtered and concentrated under reduced pressure to give a residue, combined with filter cake, compound 6-chloro-2-methyl-9H-purine (I-792) (5.3 g) was obtained as a yellow solid. LCMS m/z 168.8 $(M+1)^+$.

A solution of 6-chloro-2-methyl-9H-purine (4.1 g, 24.32 mmol, 1 eq) in HI (15 mL) (purity 47%) the mixture was stirred at 18° C. for 0.2 hr. The reaction mixture was filter and filter cake 6-iodo-2-methyl-9H-purine (I-793) (5.3 g) was obtained as a yellow solid. LCMS m/z 260.8 $(M+1)^+$.

To a solution of 6-iodo-2-methyl-9H-purine (2.4 g, 9.23 mmol, 1 eq) in THF (25 mL) was added TsOH·$H_2O$ (175.56 mg, 922.95 umol, 0.1 eq) and DHP (1.55 g, 18.46 mmol, 1.69 mL, 2 eq) at 18° C. The mixture was stirred at 40° C. for 12 hr. The reaction mixture was concentrated under reduced pressure to give a residue. The residue was purified by silica gel chromatography ($SiO_2$) to give 6-iodo-2-methyl-9-tetrahydropyran-2-yl-purine (I-794) (1.3 g, 41% yield) as a yellow oil. LCMS m/z 345.0 $(M+1)^+$. $^1$H NMR (400 MHz, $CDCl_3$) δ 8.19 (s, 1H), 5.68 (dd, J=2.2, 10.6 Hz, 1H), 4.15-4.08 (m, 1H), 3.72 (dt, J=2.6, 11.7 Hz, 1H), 2.73 (s, 3H), 2.09-1.94 (m, 3H), 1.77-1.60 (m, 3H).

To a solution of 6-iodo-2-methyl-9-tetrahydropyran-2-yl-purine (1.2 g, 3.49 mmol, 1 eq) in THF (15 mL) was added dropwise LDA (2 M, 2.62 mL, 1.5 eq) at −70° C. under $N_2$. After addition, the mixture was stirred at this temperature (−70° C.) for 20 min, and then DMF (764.60 mg, 10.46 mmol, 804.84 uL, 3 eq) was added to the reaction mixture at −70° C. under $N_2$, The resulting mixture was stirred at −70° C. for 20 min. Quenched the reaction with water 5 mL at 0° C., then added 15% NaOH solution (5 mL) and extracted with EtOAc (10 ml*3), the combined organic layers were washed with brine (15 ml), dried over with anhydrous $Na_2SO_4$ and concentrated to give a crude product. 1.7 g of the mixture 6-iodo-2-methyl-9-tetrahydropyran-2-yl-purine-8-carbaldehyde (crude) and 6-(dimethylamino)-2-methyl-9-tetrahydropyran-2-yl-purine-8-carbaldehyde (I-795) (crude) was obtained as a yellow oil.

To a solution of 6-iodo-2-methyl-9-tetrahydropyran-2-yl-purine-8-carbaldehyde (4.57 mmol, 1 eq) and 6-(dimethylamino)-2-methyl-9-tetrahydropyran-2-yl-purine-8-carbaldehyde (4.57 mmol, 1 eq) (1.7 g crude) in MeOH (10 mL) was added $NaBH_4$ (207.38 mg, 5.48 mmol, 1.2 eq) at 0° C. The mixture was stirred at 18° C. for 0.5 hr. The mixture was poured into water (5 mL). The aqueous phase was extracted with ethyl acetate (5 mL*5). The combined organic phase was washed with brine (10 mL), dried with anhydrous $Na_2SO_4$, filtered and concentrated in vacuum. 0.9 g of the mixture (6-iodo-2-methyl-9-tetrahydropyran-2-yl-purin-8-yl)methanol and [6-(dimethylamino)-2-methyl-9-tetrahydropyran-2-yl-purin-8-yl]methanol (I-796) was obtained as a yellow oil. LCMS m/z 291.9 $(M+1)^+$.

To a solution of (6-iodo-2-methyl-9-tetrahydropyran-2-yl-purin-8-yl)methanol (2.41 mmol, 1 eq) and [6-(dimethylamino)-2-methyl-9-tetrahydropyran-2-yl-purin-8-yl]methanol (2.41 mmol, 1 eq) (0.9 g) in DMF (10 mL) was added tert-butyl-chloro-dimethyl-silane (544.86 mg, 3.62 mmol, 442.98 uL, 1.5 eq) and imidazole (410.16 mg, 6.03 mmol, 2.5 eq). The mixture was stirred at 18° C. for 12 hr. The mixture was poured into water (10 mL). The aqueous phase was extracted with ethyl acetate (15 mL*3). The combined organic phase was washed with brine (10 mL*2), dried with anhydrous $Na_2SO_4$, filtered and concentrated in vacuum. The residue was purified by column chromatography ($SiO_2$) to give 8-[[tert-butyl(dimethyl)silyl]oxymethyl]-N,N,2-trimethyl-9-tetrahydropyran-2-yl-purin-6-amine (I-797) (320 mg) as a white solid. $^1$H NMR (400 MHz, $CDCl_3$) δ 5.72 (dd, J=2.3, 11.1 Hz, 1H), 4.93-4.89 (m, 1H), 4.80-4.76 (m, 1H), 3.73-3.56 (m, 2H), 3.40 (br s, 6H), 2.46 (s, 3H), 1.77-1.68 (m, 3H), 1.64-1.51 (m, 3H), 0.82 (s, 9H), 0.05-0.01 (m, 6H).

To a solution of 8-[[tert-butyl(dimethyl)silyl]oxymethyl]-N,N,2-trimethyl-9-tetrahydropyran-2-yl-purin-6-amine (0.32 g, 788.94 umol, 1 eq) in THF (5 mL) was added TBAF (1 M, 946.73 uL, 1.2 eq) at 18° C., the mixture was stirred at 18° C. for 0.5 hr. The reaction mixture was concentrated under reduced pressure to remove THF. The residue was diluted with $H_2O$ (5 mL) and extracted with EtOAc (5 mL*3). The combined organic layers were concentrated under reduced pressure to give a residue. Compound [6-(dimethylamino)-2-methyl-9-tetrahydropyran-2-yl-purin-8-yl]methanol (I-798) (240 mg) was obtained as a yellow oil. LCMS m/z 292.2 $(M+1)^+$.

To a solution of [6-(dimethylamino)-2-methyl-9-tetrahydropyran-2-yl-purin-8-yl]methanol (220 mg, 755.11 umol, 1 eq) in DCM (5 mL) was added DIPEA (292.77 mg, 2.27 mmol, 394.57 uL, 3 eq) and MsCl (129.75 mg, 1.13 mmol, 87.67 uL, 1.5 eq) at 0° C. The mixture was stirred at 18° C. for 1 h. The residue was poured into water (3 mL). The aqueous phase was extracted with DCM (3 mL*2). The combined organic phase was washed with brine (3 mL), dried with anhydrous $Na_2SO_4$, filtered and filtrate evaporation solvent. Compound 8-(chloromethyl)-N,N,2-trimethyl-9-tetrahydropyran-2-yl-purin-6-amine (I-799) (290 mg) was obtained as a yellow solid. LCMS m/z 310.1 $(M+1)^+$.

To a solution of 8-(chloromethyl)-N,N,2-trimethyl-9-tetrahydropyran-2-yl-purin-6-amine (290 mg, 936.11 umol, 1 eq) in $CH_3CN$ (5.0 mL) was added DIPEA (241.97 mg, 1.87 mmol, 326.11 uL, 2 eq) and 3-nitro-1H-pyridin-2-one (144.26 mg, 1.03 mmol, 1.1 eq) at 18° C. The mixture was stirred at 18° C. for 16 hr. The mixture was poured into water (5 mL). The reaction mixture was concentrated under reduced pressure to remove $CH_3CN$. The aqueous phase was extracted with ethyl acetate (8 mL*3) and the combined organic phase was concentrated in vacuum. The residue was purified by prep-TLC to give 1-[[6-(dimethylamino)-2-methyl-9-tetrahydropyran-2-yl-purin-8-yl]methyl]-3-nitro-pyridin-2-one (I-800) (130 mg) as a yellow solid. LCMS m/z 414.0 $(M+1)^+$.

To a solution of 1-[[6-(dimethylamino)-2-methyl-9-tetrahydropyran-2-yl-purin-8-yl]methyl]-3-nitro-pyridin-2-one (80 mg, 193.50 umol, 1 eq) in EtOAc (5 mL) was added Pd/C (40 mg, 10% purity) at 18° C. The suspension was degassed under vacuum and purged with $H_2$ several times. The mixture was stirred under $H_2$ (15 psi) at 18° C. for 2 h. The reaction mixture was filtered and the filtrate was concentrated. Compound 3-amino-1-[[6-(dimethylamino)-2-methyl-9-tetrahydropyran-2-yl-purin-8-yl]methyl]pyridin-2-one (I-801) (40 mg) was obtained as colorless oil. LCMS m/z 384.0 $(M+1)^+$.

Example 87

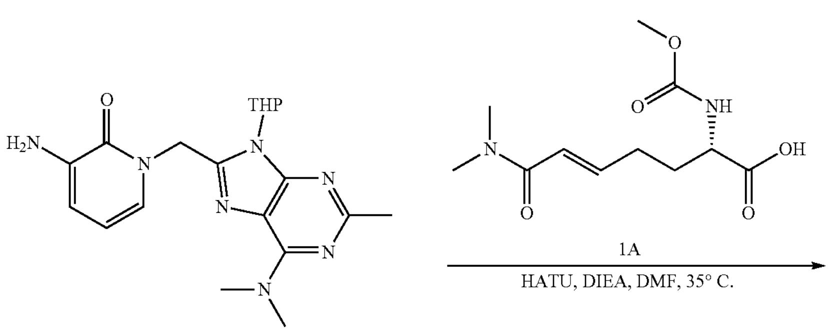

I-801

-continued
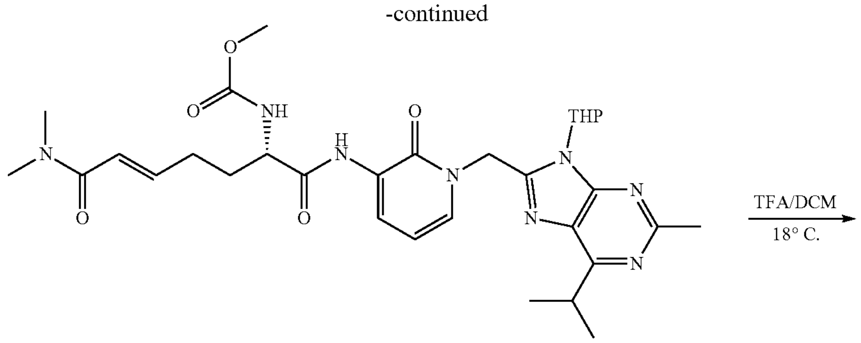
I-802
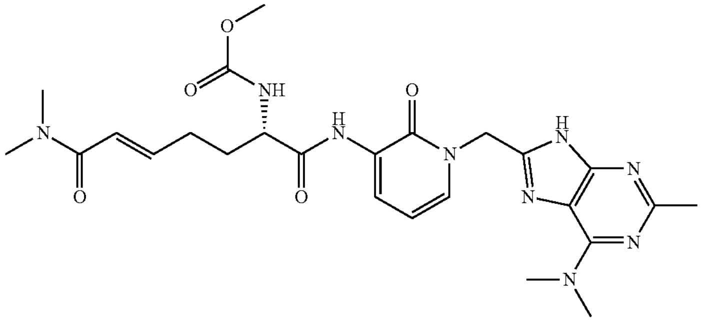
504
Compound 504 was prepared according to the procedures for Example 68 using the appropriate intermediates. LCMS m/z 540.2 $(M+1)^+$. $^1H$ NMR (400 MHz, DMSO-$d_6$) δ 9.26 (s, 1H), 8.24 (br d, J=6.2 Hz, 1H), 7.74 (br d, J=7.3 Hz, 1H), 7.61-7.48 (m, 1H), 6.65-6.56 (m, 1H), 6.44-6.32 (m, 2H), 5.36 (br s, 2H), 4.18 (br s, 1H), 3.55 (s, 3H), 3.36-3.33 (m, 6H), 2.99 (s, 3H), 2.84 (s, 3H), 2.43 (br s, 3H), 2.30-2.17 (m, 2H), 1.88 (br d, J=7.0 Hz, 1H), 1.79-1.62 (m, 1H).
Synthesis of Intermediate I-806
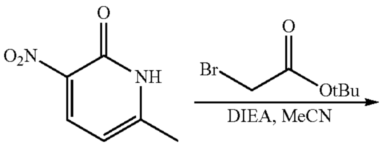
I-803
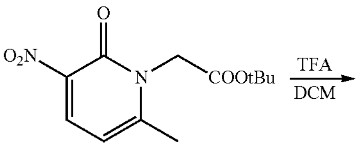
I-804
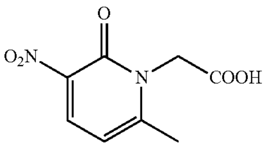
I-805
-continued
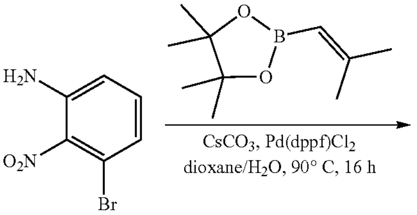
I-58
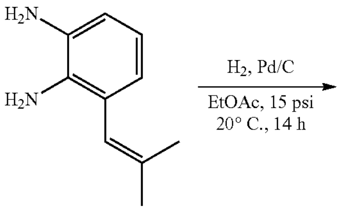
I-59
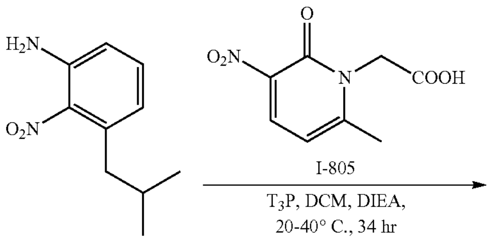
I-60

-continued

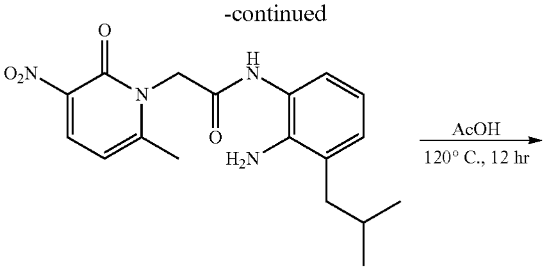

I-923

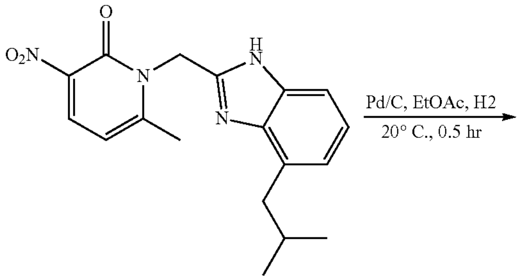

I-924

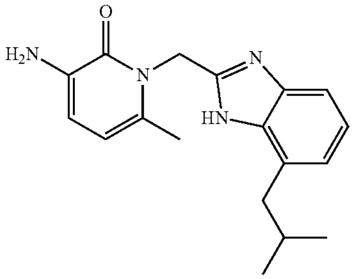

I-806

To a solution of 6-methyl-3-nitro-1H-pyridin-2-one (2 g, 12.98 mmol, 1 eq) and DIEA (3.35 g, 25.95 mmol, 4.52 mL, 2 eq) in MeCN (20 mL) was added tert-butyl 2-bromoacetate (3.04 g, 15.57 mmol, 2.30 mL, 1.2 eq) at 20° C., then the reaction was stirred at 20° C. for 12 h. The mixture was concentrated to give the crude product. The crude product was purified by column chromatography ($SiO_2$) to give tert-butyl 2-(6-methyl-3-nitro-2-oxo-1-pyridyl)acetate (I-804) (2.55 g, 9.51 mmol, 73.25% yield) as a yellow solid.

To a solution of tert-butyl 2-(6-methyl-3-nitro-2-oxo-1-pyridyl)acetate (2.55 g, 9.51 mmol, 1 eq) in DCM (30 mL) was added $CF_3COOH$ (23.10 g, 202.59 mmol, 15 mL, 21.31 eq) at 0° C., then the reaction was stirred at 20° C. for 1 h. The mixture was concentrated in vacuum to give 2-(6-methyl-3-nitro-2-oxo-1-pyridyl)acetic acid (I-805) (1.95 g) as a yellow solid.

A solution of 2-(6-methyl-3-nitro-2-oxo-1-pyridyl)acetic acid (I-805) (465.02 mg, 2.19 mmol, 0.9 eq), 3-isobutylbenzene-1,2-diamine (I-60) (0.4 g, 2.44 mmol, 1 eq), DIEA (629.49 mg, 4.87 mmol, 848.37 uL, 2 eq), and $T_3P$ (2.32 g, 3.65 mmol, 2.17 mL, 50% purity, 1.5 eq) in DCM (10 mL) was stirred at 30° C. for 2 h. The mixture was concentrated in vacuum to give N-(2-amino-3-isobutyl-phenyl)-2-(6-methyl-3-nitro-2-oxo-1-pyridyl)acetamide (I-923) (1 g) as a brown solid which was used directly in the next step. LCMS m/z 358.9 $(M+1)^+$.

A solution of N-(2-amino-3-isobutyl-phenyl)-2-(6-methyl-3-nitro-2-oxo-1-pyridyl)acetamide (1 g, 2.79 mmol, 1 eq) in AcOH (20 mL) was stirred at 120° C. for 12 h. The mixture was concentrated in vacuum to give oil. The oil was purified by prep-HPLC to give 1-[(4-isobutyl-1H-benzimidazol-2-yl)methyl]-6-methyl-3-nitro-pyridin-2-one (I-924) (600 mg, 63% yield) as a yellow solid. LCMS m/z 340.8 $(M+1)^+$.

A solution of 1-[(4-isobutyl-1H-benzimidazol-2-yl)methyl]-6-methyl-3-nitro-pyridin-2-one (300 mg, 881.38 umol, 1 eq) and Pd/C (100 mg, 10% purity) in EtOAc (30 mL) was stirred at 20° C. under $H_2$ (15 psi) for 0.5 h. The mixture was filtered and the filtrate was concentrated in vacuum to 3-amino-1-[(4-isobutyl-1H-benzimidazol-2-yl)methyl]-6-methyl-pyridin-2-one (I-806) (200 mg) as a white solid which was used directly in the next step. LCMS m/z 310.9 $(M+1)^+$.

Example 88

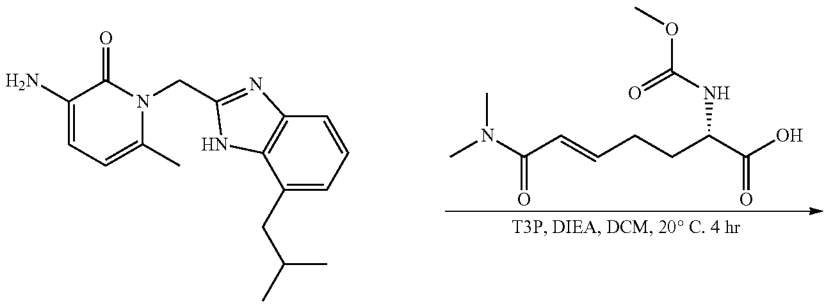

I-806

-continued

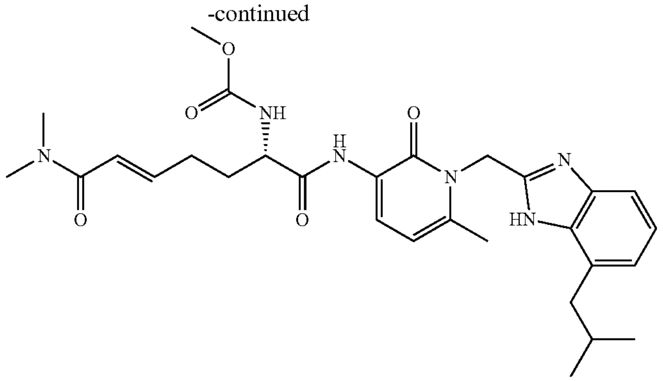

510

To a solution of 3-amino-1-[(4-isobutyl-1H-benzimidazol-2-yl)methyl]-6-methyl-pyridin-2-one (I-806) (100 mg, 322.17 umol, 1 eq), (E,2S)-7-(dimethylamino)-2-(methoxycarbonylamino)-7-oxo-hept-5-enoic acid (I-9) (91.53 mg, 354.39 umol, 1.1 eq) and DIEA (62.46 mg, 483.26 umol, 84.17 uL, 1.5 eq) in DCM (2 mL) was added $T_3P$ (246.02 mg, 386.61 umol, 229.93 uL, 50% purity, 1.2 eq) (EtOAc solution) and the solution was stirred at 20° C. for 4 h. The mixture was concentrated in vacuum to give an oil. The oil was purified by prep-HPLC to give methyl N-[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl]carbamate (Compound 510) (79.5 mg, 44% yield) as a white solid. LCMS m/z 550.8 $(M+1)^+$. $^1H$ NMR (400 MHz, DMSO-$d_6$) δ 0.78-0.99 (m, 5H) 0.78-0.99 (m, 1H) 1.64-1.94 (m, 2H) 1.95-2.14 (m, 1H) 2.15-2.31 (m, 2H) 2.44 (s, 3H) 2.67-2.78 (m, 2H) 2.84 (s, 3H) 2.89-3.05 (m, 3H) 3.55 (br d, J=6.97 Hz, 3H) 4.15 (br s, 1H) 5.50 (br d, J=6.60 Hz, 2H) 6.25 (d, J=7.70 Hz, 1H) 6.37 (br d, J=15.16 Hz, 1H) 6.55-6.68 (m, 1H) 6.86-6.96 (m, 1H) 7.00-7.12 (m, 1H) 7.21-7.37 (m, 1H) 7.65-7.83 (m, 1H) 8.17 (brd, J=7.46 Hz, 1H) 9.04-9.24 (m, 1H) 12.13-12.57 (m, 1H).

Example 89

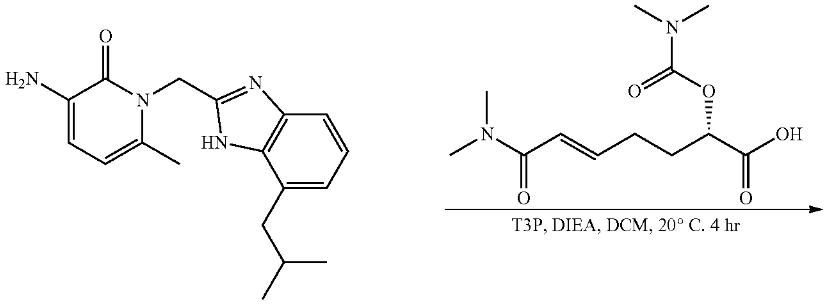

I-806

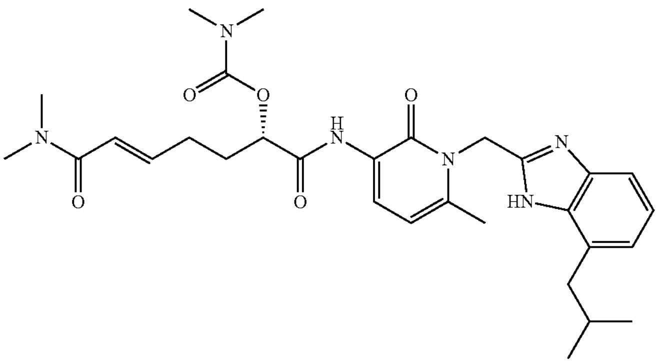

514

To a solution of 3-amino-1-[(4-isobutyl-1H-benzimidazol-2-yl)methyl]-6-methyl-pyridin-2-one (I-806) (100 mg, 322.17 umol, 1 eq), (E,2S)-7-(dimethylamino)-2-(dimethylcarbamoyloxy)-7-oxo-hept-5-enoic acid (I-37) (96.50 mg, 354.39 umol, 1.1 eq) and DIEA (62.46 mg, 483.26 umol, 84.17 uL, 1.5 eq) in DCM (2 mL) was added $T_3P$ (246.02 mg, 386.60 umol, 229.93 uL, 50% purity, 1.2 eq) (EtOAc solution) and the solution was stirred at 20° C. for 4 h. The mixture was concentrated in vacuum to give oil. The oil was purified by prep-HPLC to give [(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl] N,N-dimethylcarbamate (Compound 514) (97.5 mg, 51% yield) as a white solid. LCMS m/z 564.9 $(M+1)^+$. $^1H$ NMR (400 MHz, DMSO-$d_6$) δ 0.83-0.95 (m, 6H) 1.84-2.16 (m, 3H) 2.22-2.36 (m, 2H) 2.44 (br d, J=3.18 Hz, 3H) 2.68-2.77 (m, 2H) 2.78-3.07 (m, 12H) 5.09 (ddd, J=11.37, 7.09, 4.65 Hz, 1H) 5.51 (br d, J=8.19 Hz, 2H) 6.26 (d, J=7.70 Hz, 1H) 6.35-6.45 (m, 1H) 6.57-6.71 (m, 1H) 6.87-6.97 (m, 1H) 6.99-7.11 (m, 1H) 7.23-7.37 (m, 1H) 8.11-8.21 (m, 1H) 9.11-9.25 (m, 1H) 12.15-12.55 (m, 1H).

Example 90

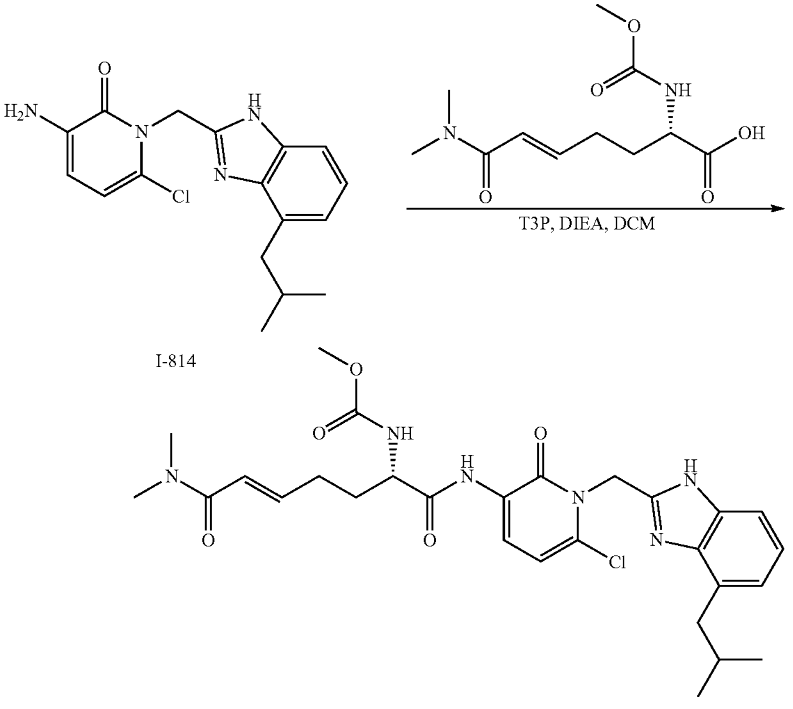

I-814

522

Compound 522 was prepared according to the procedures for Example 88 using the appropriate intermediates. LCMS m/z 571.2 $(M+1)^+$. $^1H$ NMR (400 MHz, DMSO-$d_6$) δ 0.87-0.95 (m, 6H) 1.68-1.79 (m, 1H) 1.83-1.94 (m, 1H) 2.02 (br s, 1H) 2.19-2.32 (m, 2H) 2.72 (brd, J=7.28 Hz, 2H) 2.84 (s, 3H) 3.00 (s, 3H) 3.49-3.65 (m, 3H) 4.17-4.31 (m, 1H) 5.64 (s, 2H) 6.38 (d, J=15.21 Hz, 1H) 6.56-6.67 (m, 2H) 6.90-7.09 (m, 2H) 7.26-7.44 (m, 2H) 7.73 (br d, J=7.50 Hz, 1H) 8.27 (d, J=8.16 Hz, 1H) 9.36 (s, 1H).

The following compound was prepared according to the procedures described in Example 90 using the appropriate intermediates.

| Compound | Structure | Characterization Data |
| --- | --- | --- |
| 526 | 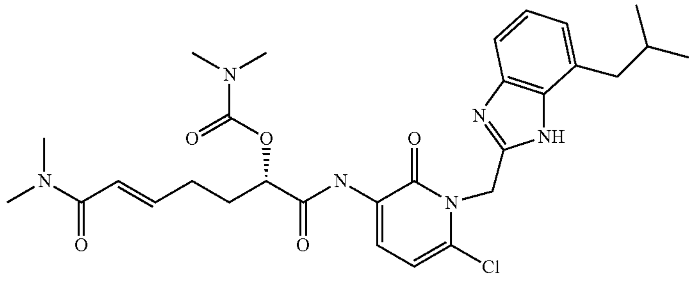 [SMILES: CC(C)Cc1cccc2nc(Cn3c(Cl)ccc(NC(=O)[C@H](CC/C=C/C(=O)N(C)C)OC(=O)N(C)C)c3=O)[nH]c12] | LCMS m/z 585.2 $(M + 1)^+$. |

Synthesis of Intermediate I-826
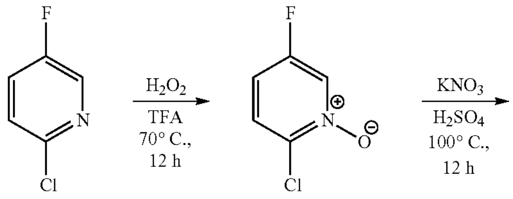
I-815 I-816
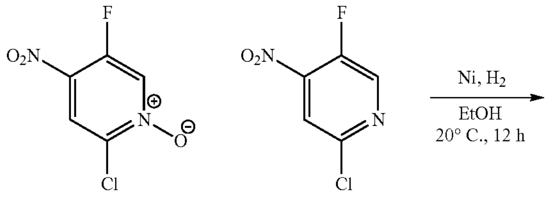
I-817 I-818
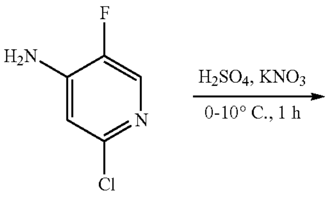
I-819
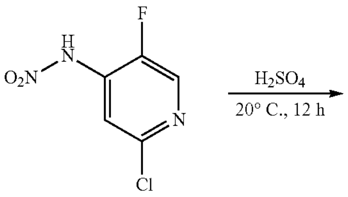
I-820
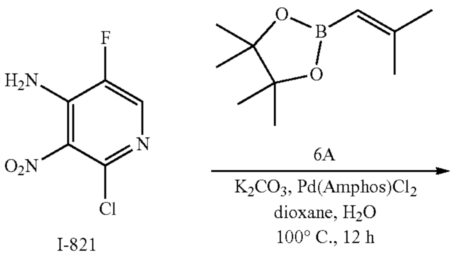
I-821
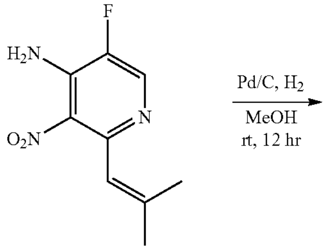
I-822
-continued
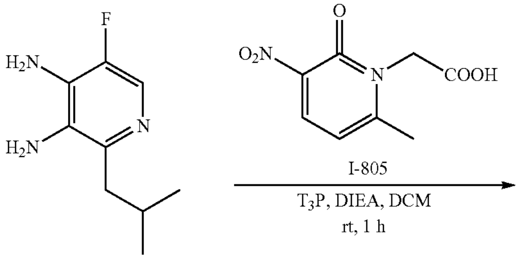
I-823
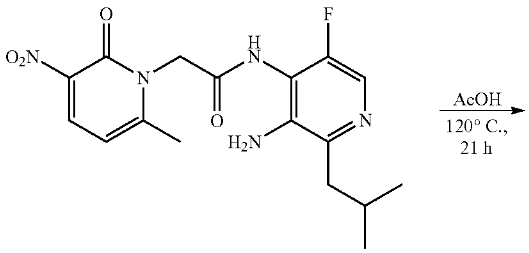
I-824
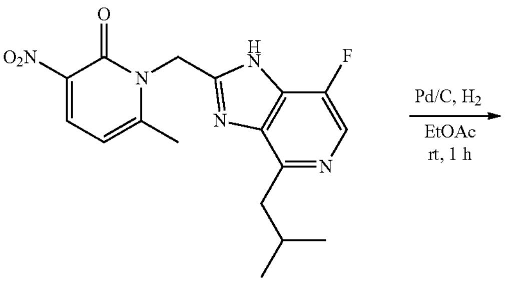
I-825
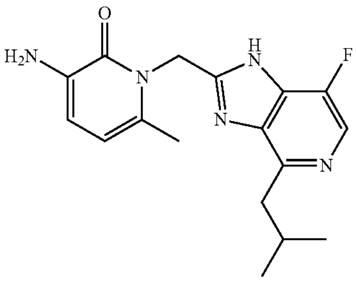
I-826
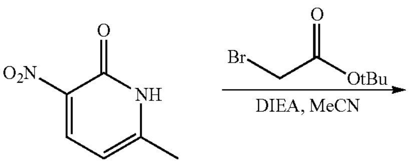
I-803
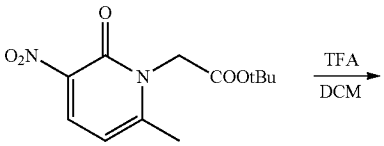
I-804

-continued

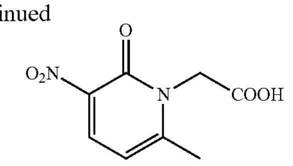

I-805

To a mixture of 2-chloro-5-fluoro-pyridine (50 g, 380.13 mmol, 1 eq) in TFA (400 mL) was added $H_2O_2$ (230.89 g, 1.90 mol, 195.67 mL, 28% purity, 5 eq) slowly under nitrogen at 70° C. The reaction mixture was stirred at 70° C. for 16 hrs. The mixture was concentrated to remove most of the TFA then the residue was poured into ice-water (500 mL), then basified by NaOH (solid) till pH=7, extracted with DCM (1000 mL*3). The organic layer was dried over $Na_2SO_4$, concentrated to give the crude product. 2-chloro-5-fluoro-1-oxido-pyridin-1-ium (I-816) (46 g, 82% yield) was obtained as a yellow solid. $^1H$ NMR (400 MHz, $CDCl_3$) δ 6.99 (ddd, J=9.17, 6.48, 2.57 Hz, 1H) 7.41 (dd, J=9.17, 6.48 Hz, 1H) 8.24 (dd, J=4.03, 2.69 Hz, 1H).

To a mixture of 2-chloro-5-fluoro-1-oxido-pyridin-1-ium (36 g, 244.01 mmol, 1 eq) in $H_2SO_4$ (200 mL) was added $KNO_3$ (98.68 g, 976.04 mmol, 4 eq) at 0° C. Then the mixture was heated to 100° C. for 12 hrs under $N_2$. The mixture was poured into ice-water (1000 mL), extracted with EtOAc (300 mL*3). The organic layer was dried over $Na_2SO_4$, concentrated to give the crude product. The crude product was purified by column chromatography on silica gel to give 2-chloro-5-fluoro-4-nitro-1-oxido-pyridinium (I-817) (8 g, 41.55 mmol, 17.03% yield) was obtained as a yellow solid which was confirmed by 1H-NMR. $^1H$ NMR (400 MHz, $CDCl_3$) δ 7.86 (d, J=5.07 Hz, 1H) 8.53 (d, J=1.76 Hz, 1H). 2-chloro-5-fluoro-4-nitro-pyridine (I-818) (8.1 g, 45.88 mmol, 18.80% yield) was obtained as a yellow oil which was confirmed by $^1H$-NMR. $^1H$ NMR (400 MHz, $CDCl_3$) δ 8.32 (d, J=8.16 Hz, 1H) 8.43 (d, J=5.51 Hz, 1H)

To a mixture of 2-chloro-5-fluoro-4-nitro-pyridine (I-818) (8.1 g, 45.88 mmol, 1 eq) in EtOH (150 mL) was added Ni (5 g) then the mixture was stirred at 20° C. for 4 hrs under $H_2$ (40 Psi). The reaction mixture was filtered and the filtrate was concentrated to give the crude product. 2-chloro-5-fluoro-pyridin-4-amine (I-819) (6.2 g) was obtained as a white solid. $^1H$ NMR (400 MHz, $CD_3OD$) δ 6.71 (d, J=6.84 Hz, 1H) 7.80 (d, J=3.53 Hz, 1H).

Alternatively, to a mixture of 2-chloro-5-fluoro-4-nitro-1-oxido-pyridin-1-ium (I-817) (8 g, 41.55 mmol, 1 eq) in EtOH (150 mL) was added Ni (5 g) then the mixture was stirred at 20° C. for 3 hrs under $H_2$ (40 Psi). The reaction mixture was filtered and the filtrate was concentrated to give the crude product. 2-chloro-5-fluoro-pyridin-4-amine (I-819) (5 g, 34.12 mmol, 82.11% yield) was obtained as a yellow solid. $^1H$ NMR (400 MHz, $CD_3OD$) δ 6.71 (d, J=6.84 Hz, 1H) 7.80 (d, J=3.53 Hz, 1H).

2-chloro-5-fluoro-pyridin-4-amine (6.5 g, 44.35 mmol, 1 eq) was added to concentrated $H_2SO_4$ (70 mL) at 0-5° C., then $KNO_3$ (8.97 g, 88.71 mmol, 2 eq) was added by portions to the above mixture during a period of 30 mins while the internal temperature was maintained below 5° C. The reaction mixture was stirred at 0-5° C. for 1 hr and at 20° C. for 30 mins. The two parallel mixtures were combined and poured into ice 400 g, extracted with DCM (100 mL*5). The organic layer was dried over $Na_2SO_4$, concentrated to give the crude product. N-(2-chloro-5-fluoro-4-pyridyl)nitramide (I-820) (13 g) was obtained as a yellow solid which was confirmed by $^1H$-NMR. $^1H$ NMR (400 MHz, $CDCl_3$) δ 7.97 (d, J=5.29 Hz, 1H) 8.26 (d, J=1.54 Hz, 1H).

The mixture of N-(2-chloro-5-fluoro-4-pyridyl)nitramide (13 g, 67.87 mmol, 1 eq) in concentrated H2SO4 (100 mL) was stirred at 20° C. for 12 hr. The mixture was added to ice (2000 g) and extracted with EtOAc (100 mL*3). The organic layer was washed with sat. $NaHCO_3$ (aq. 100 mL*2), then dried over $Na_2SO_4$, and concentrated to give 2-chloro-5-fluoro-3-nitro-pyridin-4-amine (I-821) (10 g) as a yellow solid. $^1H$ NMR (400 MHz, $CDCl_3$) δ 5.80 (br s, 2H) 8.00 (d, J=1.32 Hz, 1H).

To a mixture of 2-chloro-5-fluoro-3-nitro-pyridin-4-amine (7 g, 36.54 mmol, 1 eq) and 4,4,5,5-tetramethyl-2-(2-methylprop-1-enyl)-1,3,2-dioxaborolane (6.72 g, 36.91 mmol, 1.01 eq) in dioxane (100 mL) and $H_2O$ (10 mL) was added $K_2CO_3$ (10.10 g, 73.09 mmol, 2 eq) and 4-ditert-butylphosphanyl-N,N-dimethyl-aniline;dichloropalladium (1.29 g, 1.83 mmol, 1.29 mL, 0.05 eq). Then the mixture was stirred at 100° C. for 12 hrs under $N_2$. The mixture was concentrated to give the crude product. The crude product was purified by column chromatography on silica gel to give 5-fluoro-2-(2-methylprop-1-enyl)-3-nitro-pyridin-4-amine (I-822) (7.2 g, 34.09 mmol, 93.29% yield) as a red oil. $^1H$ NMR (400 MHz, $CDCl_3$) δ 1.85 (s, 3H) 1.93 (s, 3H) 5.85 (br s, 2H) 6.39 (br d, J=1.10 Hz, 1H) 8.24 (d, J=1.54 Hz, 1H).

To a mixture of 5-fluoro-2-(2-methylprop-1-enyl)-3-nitro-pyridin-4-amine (7.2 g, 34.09 mmol, 1 eq) in MeOH (150 mL) was added Pd/C (5 g, 10% purity) and then the mixture was stirred at 20° C. for 36 hrs under $H_2$ (15 Psi). The mixture was filtered and the filtrate was concentrated to give the crude product 5-fluoro-2-isobutyl-pyridine-3,4-diamine (I-823) (7 g) as a yellow oil.

To a mixture of 5-fluoro-2-isobutyl-pyridine-3,4-diamine (I-823) (90 mg, 491.20 umol, 1 eq) and 2-(6-methyl-3-nitro-2-oxo-1-pyridyl)acetic acid (I-805) (93.79 mg, 442.08 umol, 0.9 eq) in DCM (10 mL) was added DIEA (126.96 mg, 982.40 umol, 171.11 uL, 2 eq) and $T_3P$ (406.35 mg, 638.56 umol, 379.77 uL, 50% purity, 1.3 eq) at 20° C. Then the mixture was stirred at 20° C. for 1 hr. The mixture was concentrated to give N-(3-amino-5-fluoro-2-isobutyl-4-pyridyl)-2-(6-methyl-3-nitro-2-oxo-1-pyridyl)acetamide (I-824) (200 mg) as a black oil.

The mixture of N-(3-amino-5-fluoro-2-isobutyl-4-pyridyl)-2-(6-methyl-3-nitro-2-oxo-1-pyridyl)acetamide (200 mg, 529.99 umol, 1 eq) in AcOH (5 mL) was heated to 120° C. and stirred at 120° C. for 21 hrs. The mixture was concentrated to give the crude product. The crude product was purified by prep-HPLC to give 1-[(7-fluoro-4-isobutyl-1H-imidazo[4,5-c]pyridin-2-yl)methyl]-6-methyl-3-nitro-pyridin-2-one (I-825) (120 mg, 63% yield) as a yellow solid.

To a mixture of 1-[(7-fluoro-4-isobutyl-1H-imidazo[4,5-c]pyridin-2-yl)methyl]-6-methyl-3-nitro-pyridin-2-one (120 mg, 333.93 umol, 1 eq) in EtOAc (5 mL) was added Pd/C (100 mg, 10% purity) then the mixture was stirred at 20° C. for 1 hr under $H_2$ (15 Psi). The mixture was filtered and the filtrate was concentrated to give 3-amino-1-[(7-fluoro-4-isobutyl-1H-Imidazo[4,5-c]pyridine-2-yl)methyl]-6-methyl-pyridin-2-one (I-826) (100 mg) was obtained as a yellow oil. LCMS m/z 315.9 $(M+1)^+$.

Example 91

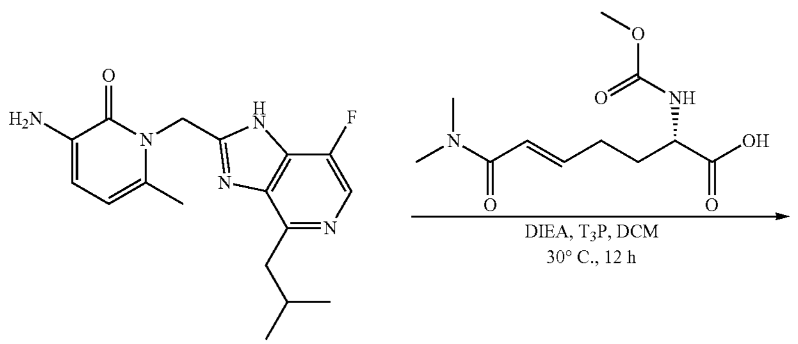

I-826

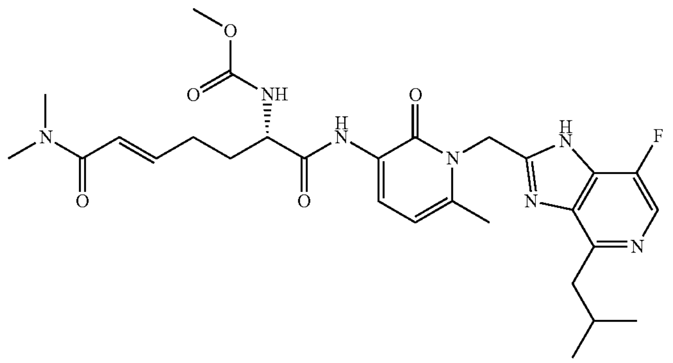

516

To a mixture of 3-amino-1-[(7-fluoro-4-isobutyl-1H-imidazo[4,5-c]pyridin-2-yl)methyl]-6-methyl-pyridin-2-one (I-826) (100 mg, 303.61 umol, 1 eq) in DCM (3 mL) was added DIEA (117.72 mg, 910.83 umol, 158.65 uL, 3 eq), (E,2S)-7-(dimethylamino)-2-(methoxycarbonylamino)-7-oxo-hept-5-enoic acid (I-9) (78.41 mg, 303.61 umol, 1 eq) and $T_3P$ (289.81 mg, 455.41 umol, 270.85 uL, 50% purity, 1.5 eq) at 30° C. Then the mixture was stirred at 30° C. for 12 hrs. The mixture was concentrated to give the crude product. The crude product was purified by prep-HPLC to give methyl-N-[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl]carbamate (Compound 516) (56.8 mg, 32% yield) as a white solid $^1H$ NMR (400 MHz, DMSO-$d_6$) δ 0.88 (br d, J=5.73 Hz, 6H) 1.63-1.75 (m, 1H) 1.86 (br d, J=7.06 Hz, 1H) 2.12-2.25 (m, 3H) 2.41 (s, 3H) 2.79-2.86 (m, 5H) 2.96 (s, 3H) 3.52 (s, 3H) 4.09-4.18 (m, 1H) 5.51 (s, 2H) 6.25 (d, J=7.72 Hz, 1H) 6.35 (d, J=15.21 Hz, 1H) 6.52-6.63 (m, 1H) 7.68 (br d, J=7.50 Hz, 1H) 8.12 (d, J=1.76 Hz, 1H) 8.15 (d, J=7.50 Hz, 1H) 9.13 (s, 1H) 13.35 (br s, 1H). LCMS m/z 570.2 $(M+1)^+$.

Example 92

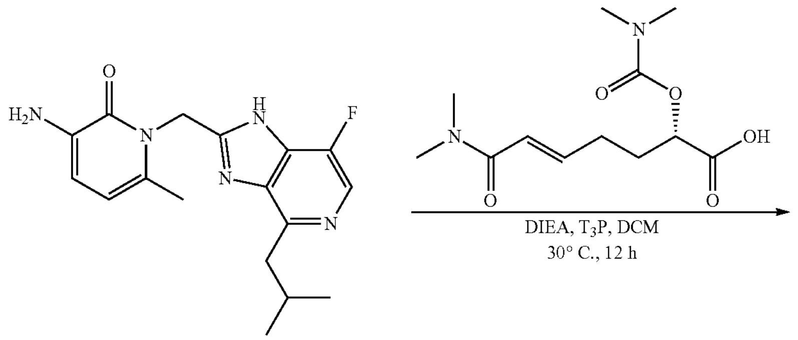

I-826

-continued

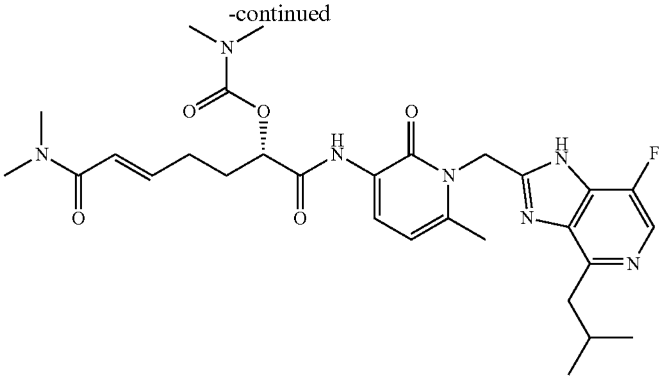

517

To a mixture of 3-amino-1-[(7-fluoro-4-isobutyl-1H-imidazo[4,5-c]pyridin-2-yl)methyl]-6-methyl-pyridin-2-one (I-826) (70 mg, 212.53 umol, 1 eq) in DCM (3 mL) was added DIEA (82.40 mg, 637.58 umol, 111.05 uL, 3 eq), (E,2S)-7-(dimethylamino)-2-(dimethylcarbamoyloxy)-7-oxo-hept-5-enoic acid (I-37) (57.87 mg, 212.53 umol, 1 eq) and $T_3P$ (202.86 mg, 318.79 umol, 189.59 uL, 50% purity, 1.5 eq) at 20° C. After addition, the mixture was stirred at 20° C. for 2 hrs. The mixture was concentrated to give the crude product. The crude product was purified by prep-HPLC to give [(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl] N,N-dimethylcarbamate (Compound 517) (45.8 mg, 36% yield) as a white solid. LCMS m/z 584.2 $(M+1)^+$. $^1H$ NMR (400 MHz, DMSO-$d_6$) δ 0.88 (brd, J=5.07 Hz, 6H) 1.84-1.99 (m, 2H) 2.11-2.28 (m, 3H) 2.41 (s, 3H) 2.76-2.88 (m, 8H) 2.89-3.01 (m, 6H) 5.05 (dd, J=7.39, 4.74 Hz, 1H) 5.52 (s, 2H) 6.27 (d, J=7.72 Hz, 1H) 6.36 (d, J=15.21 Hz, 1H) 6.54-6.68 (m, 1H) 8.07-8.18 (m, 2H) 9.15 (s, 1H) 13.37 (br s, 1H)

The following compound was prepared according to the procedures described in Example 92 using the appropriate intermediates.

| Compound | Structure | Characterization Data |
| --- | --- | --- |
| 561 | 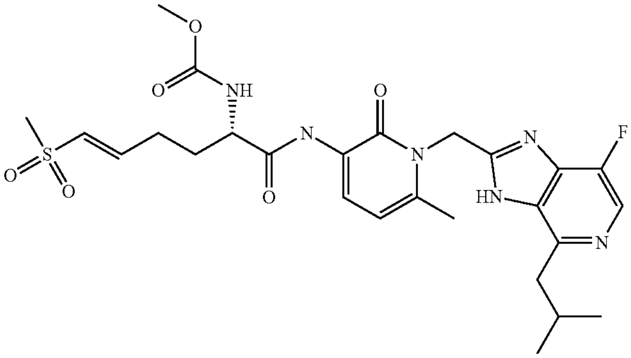 [SMILES: COC(=O)N[C@@H](CC/C=C/S(C)(=O)=O)C(=O)Nc1ccc(C)n(Cc2nc3c(F)cnc(CC(C)C)c3[nH]2)c1=O] | LCMS m/z 577.2 (M + 1)$^+$ |

Synthesis of Intermediate I-829

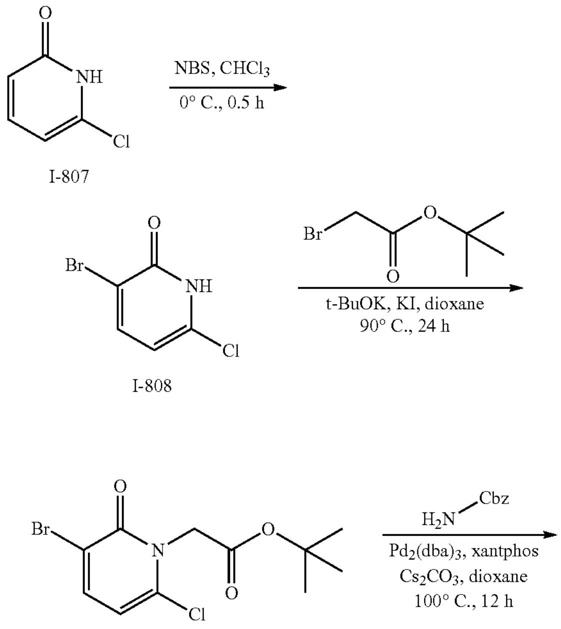

I-807

I-808

I-809

-continued

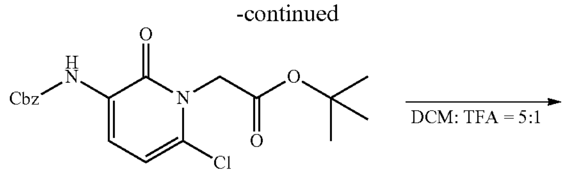

I-810

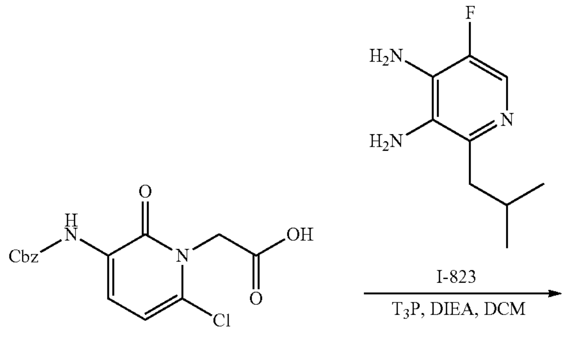

I-811

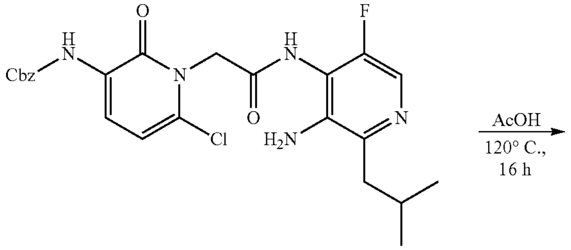

I-827

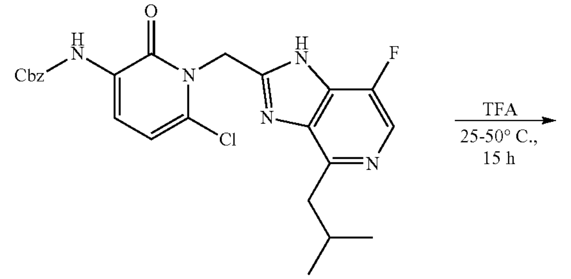

I-828

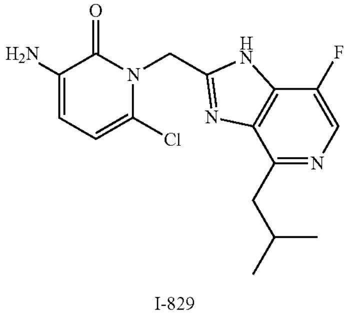 [SMILES: CC(C)Cc1ncc(F)c2[nH]c(Cn3c(Cl)ccc(N)c3=O)nc12]

I-829

A mixture of 6-chloro-1H-pyridin-2-one (20 g, 154.39 mmol) in $CHCl_3$ (250 mL) was added NBS (27.48 g, 154.39 mmol) at 0° C. and the mixture was stirred at 0° C. for 0.5 hr. The reaction mixture was concentrated under reduced pressure to give a residue. The residue was purified by prep-HPLC to give 3-bromo-6-chloro-1H-pyridin-2-one (I-808) (3.25 g, 10% yield) as a green solid. LCMS m/z 210.0 $(M+1)^+$.

A mixture of 3-bromo-6-chloro-1H-pyridin-2-one (2.75 g, 13.19 mmol), tert-butyl 2-bromoacetate (6.43 g, 32.98 mmol, 4.87 mL), t-BuOK (2.22 g, 19.79 mmol), KI (219.01 mg, 1.32 mmol) in dioxane (30 mL) was stirred at 90° C. for 24 hrs. The mixture was concentrated under reduced pressure to remove dioxane, the residue was added sat. $NH_4Cl$ aq. 50 mL, then extracted with EtOAc (30 mL*2), the combined organic phase was washed with brine 50 mL, then dried over $Na_2SO_4$, filtered and concentrated under reduced pressure to give a residue. The residue was purified by flash silica gel chromatography to give tert-butyl 2-(3-bromo-6-chloro-2-oxo-1-pyridyl)acetate (I-809) (3 g, 9.30 mmol, 70.49% yield) as a yellow oil.

A mixture of tert-butyl 2-(3-bromo-6-chloro-2-oxo-1-pyridyl)acetate (3.32 g, 10.29 mmol), benzyl carbamate (1.56 g, 10.29 mmol), $Cs_2CO_3$ (6.71 g, 20.58 mmol), Xantphos (357.31 mg, 617.52 umol) and $Pd_2(dba)_3$ (282.74 mg, 308.76 umol) in dioxane (40 mL) was degassed and purged with $N_2$ for 3 times, and then the mixture was stirred at 100° C. for 12 hrs under $N_2$ atmosphere. The reaction mixture was concentrated under reduced pressure to give a residue. The residue was purified by column chromatography ($SiO_2$) to give tert-butyl 2-[3-(benzyloxycarbonylamino)-6-chloro-2-oxo-1-pyridyl]acetate (I-810) (1.6 g, 40% yield) as a light yellow solid. LCMS m/z 415.2 $(M+23)^+$.

To a solution of tert-butyl 2-[3-(benzyloxycarbonylamino)-6-chloro-2-oxo-1-pyridyl]acetate (0.9 g, 2.29 mmol) in DCM (10 mL) was added TFA (2 mL) at 0° C. The mixture was stirred at 25° C. for 3.5 hrs. The reaction mixture was concentrated under reduced pressure to give 2-[3-(benzyloxycarbonylamino)-6-chloro-2-oxo-1-pyridyl] acetic acid (I-811) (0.9 g) as a yellow solid. LCMS m/z 336.7 $(M+1)^+$.

A mixture of 2-[3-(benzyloxycarbonylamino)-6-chloro-2-oxo-1-pyridyl]acetic acid (I-811) (0.5 g, 1.48 mmol), 5-fluoro-2-isobutyl-pyridine-3,4-diamine (I-823) (272.07 mg, 1.48 mmol), DIEA (1.92 g, 14.85 mmol, 2.59 mL) in DCM (8 mL) was added $T_3P$ (2.36 g, 3.71 mmol, 2.21 mL, 50% purity) at 0° C. and then the mixture was stirred at 25° C. for 12 hrs. The mixture was added water 0.1 mL and then concentrated in vacuum to give benzyl N-[1-[2-[(3-amino-5-fluoro-2-isobutyl-4-pyridyl)amino]-2-oxo-ethyl]-6-chloro-2-oxo-3-pyridyl]carbamate (I-827) (2 g) as a yellow oil. LCMS m/z 502.2 $(M+1)^+$.

A mixture of benzyl N-[1-[2-[(3-amino-5-fluoro-2-isobutyl-4-pyridyl)amino]-2-oxo-ethyl]-6-chloro-2-oxo-3-pyridyl]carbamate (2 g, 3.98 mmol) in AcOH (22 mL) was stirred at 130° C. for 29.5 hours. The mixture was concentrated in vacuum to give oil. The residue was purified by prep-HPLC to give benzyl N-[6-chloro-1-[(7-fluoro-4-isobutyl-1H-imidazo[4,5-c]pyridin-2-yl)methyl]-2-oxo-3-pyridyl]carbamate (I-828) (250 mg, 13% yield) as an orange solid. LCMS m/z 484.1 $(M+1)^+$.

A mixture of benzyl N-[6-chloro-1-[(7-fluoro-4-isobutyl-1H-imidazo[4,5-c]pyridin-2-yl)methyl]-2-oxo-3-pyridyl] carbamate (250 mg, 516.61 umol) in TFA (4.5 mL) was stirred at 25° C. for 23 hour. The reaction was poured into ice sat. $NaHCO_3$ aq. 20 mL, then the mixture was added NaOH (solid) until the pH~8, the mixture was extracted with DCM (10 mL*2), the combined organic phase was washed with brine 15 mL, then dried over $Na_2SO_4$, filtered and filtrate was concentrated under reduced pressure to give a 3-amino-6-chloro-1-[(7-fluoro-4-isobutyl-1H-imidazo[4,5-c]pyridin-2-yl)methyl]pyridin-2-one (I-829) (240 mg) as a green gum. LCMS m/z 350.1 $(M+1)^+$.

Example 93

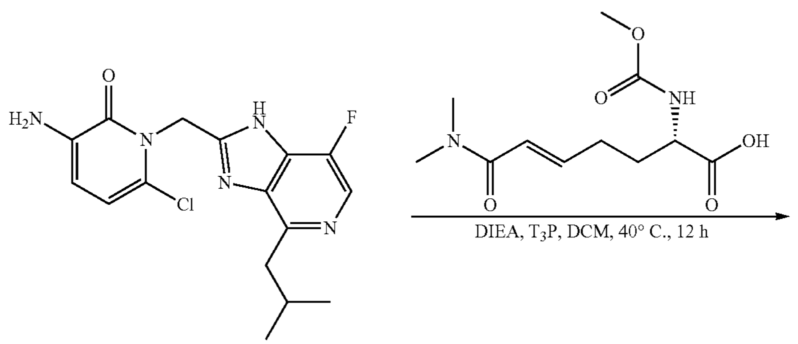

I-829

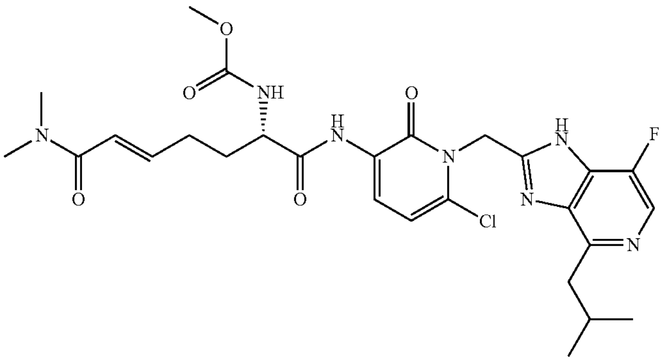

523

A mixture of 3-amino-6-chloro-1-[(7-fluoro-4-isobutyl-1H-imidazo[4,5-c]pyridin-2-yl)methyl]pyridin-2-one (I-829) (120 mg, 343.06 umol), (E,2S)-7-(dimethylamino)-2-(methoxycarbonylamino)-7-oxo-hept-5-enoic acid (I-9) (88.60 mg, 343.06 umol), DIEA (88.68 mg, 686.13 umol, 119.51 uL) in DCM (3 mL) was added $T_3P$ (654.94 mg, 1.03 mmol, 612.09 uL, 50% purity) at 25° C., and then the mixture was stirred at 40° C. for 12 hr. The reaction mixture was concentrated under reduced pressure to give an oil. The residue was purified by prep-HPLC to give methyl N-[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]carbamate (Compound 523) (48.6 mg, 23.29% yield) as a white solid. LCMS m/z 590.2 $(M+1)^+$. $^1H$ NMR (400 MHz, DMSO-$d_6$) δ 13.35-13.60 (m, 1H) 9.37 (br s, 1H) 8.28 (d, J=8.07 Hz, 1H) 8.16 (br s, 1H) 7.71 (br d, J=7.70 Hz, 1H) 6.57-6.67 (m, 2H) 6.38 (d, J=15.04 Hz, 1H) 5.70 (s, 2H) 4.25 (br s, 1H) 3.55 (s, 3H) 3.00 (s, 3H) 2.83-2.88 (m, 5H) 2.23 (dq, J=15.24, 7.51 Hz, 3H) 1.68-1.92 (m, 2H) 0.91 (br d, J=5.99 Hz, 6H).

Example 94

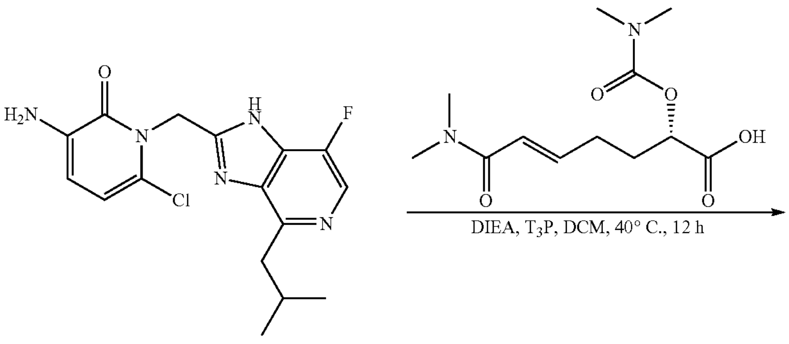

I-829

-continued

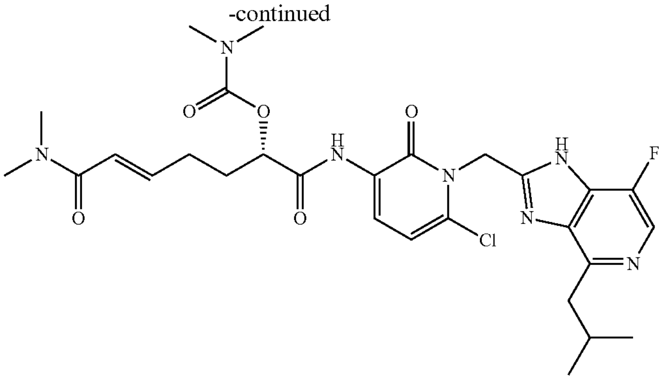

524

A mixture of 3-amino-6-chloro-1-[(7-fluoro-4-isobutyl-1H-imidazo[4,5-c]pyridin-2-yl)methyl]pyridin-2-one (I-829) (120 mg, 343.06 umol), (E,2S)-7-(dimethylamino)-2-(dimethylcarbamoyloxy)-7-oxo-hept-5-enoic acid (I-37) (93.41 mg, 343.06 umol), DIEA (88.68 mg, 686.12 umol, 119.51 uL) in DCM (3 mL) was added $T_3P$ (654.94 mg, 1.03 mmol, 612.09 uL, 50% purity) at 25° C., and then the mixture was stirred at 40° C. for 12 hrs. The reaction mixture was concentrated under reduced pressure to give an oil. The residue was purified by prep-HPLC to give [(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]N,N-dimethylcarbamate (Compound 524) (45.6 mg, 21% yield) as a white solid. LCMS m/z 604.2 $(M+1)^+$. $^1H$ NMR (400 MHz, DMSO-$d_6$) δ 13.36-13.56 (m, 1H) 9.38-9.48 (m, 1H) 8.26 (d, J=8.19 Hz, 1H) 8.12-8.20 (m, 1H) 6.61-6.71 (m, 2H) 6.40 (d, J=15.04 Hz, 1H) 5.70 (s, 2H) 5.11 (br dd, J=7.15, 4.58 Hz, 1H) 2.90-3.01 (m, 6H) 2.78-2.89 (m, 8H) 2.12-2.36 (m, 3H) 1.88-2.01 (m, 2H) 0.83-0.94 (m, 6H).

Synthesis of Intermediate I-834

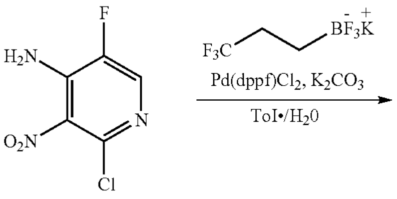

I-821

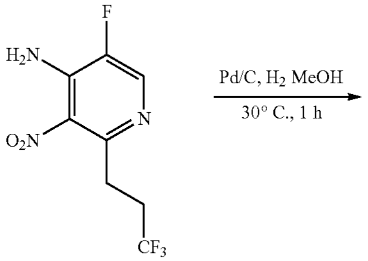

I-830

-continued

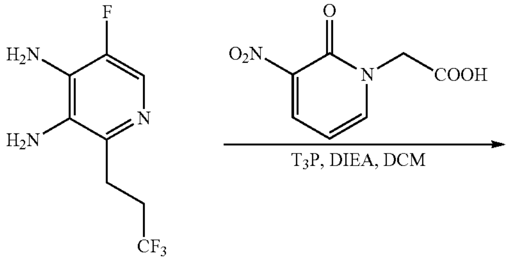

I-831

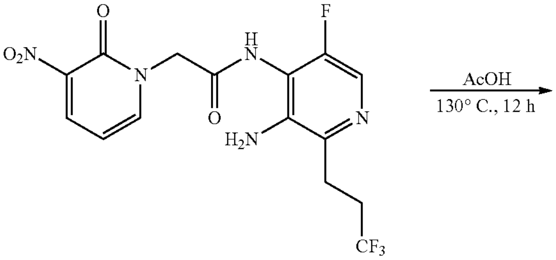

I-832

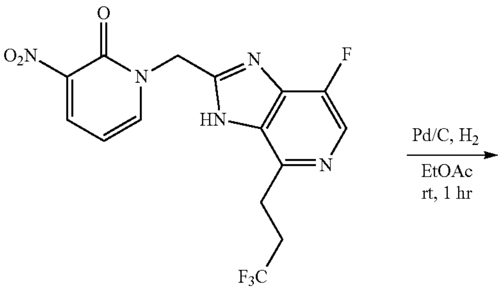

I-833

-continued

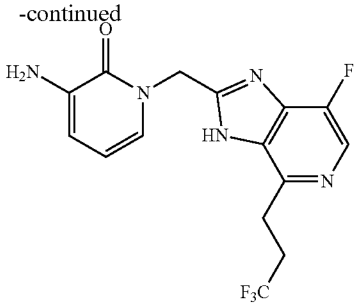

I-834

Two reactions were carried out in parallel: Pd(dppf) $Cl_2 \cdot CH_2Cl_2$ (59.7 mg, 73.1 umol, 0.1 eq) was added to a mixture of 2-chloro-5-fluoro-3-nitro-pyridin-4-amine (140 mg, 731 umol, 1 eq), potassium hydride;trifluoro(3,3,3-trifluoropropyl)boron (209 mg, 1.02 mmol, 1.4 eq) and $K_2CO_3$ (252 mg, 1.83 mmol, 2.5 eq) in toluene/$H_2O$ (10:1) (4 mL) under $N_2$. Then the mixture was heated to 110° C. for 12 h. Two reactions were combined and worked up together. The mixture was filtered and the filtrate was extracted between EtOAc (30 mL) and water (30 mL), the organic layer was concentrated to give a crude product. The residue was purified by column ($SiO_2$) to give 5-fluoro-3-nitro-2-(3,3,3-trifluoropropyl)pyridin-4-amine (I-830) (340 mg, 1.34 mmol, 91.9% yield) as a yellow oil.

To a solution of 5-fluoro-3-nitro-2-(3,3,3-trifluoropropyl) pyridin-4-amine (0.63 g, 2.49 mmol, 1 eq) in EtOAc (30 mL) was added Pd/C (200 mg, 10% purity) under $N_2$. The suspension was degassed under vacuum and purged with $H_2$ several times. The mixture was stirred under $H_2$ (15 psi) at 25° C. for 20 min. The reaction mixture was filtered and the filtrate was concentrated. The crude product 5-fluoro-2-(3,3,3-trifluoropropyl)pyridine-3,4-diamine (I-831) (560 mg) was used into the next step without further purification as a yellow solid.

$T_3P$ (556 mg, 874 umol, 50% purity, 1.5 eq) was added to a solution of 5-fluoro-2-(3,3,3-trifluoropropyl)pyridine-3,4-diamine (130 mg, 583 umol, 1 eq) and 2-(3-nitro-2-oxo-1-pyridyl)acetic acid (150 mg, 757 umol, 1.3 eq) in DCM (3 mL) at 25° C., then the mixture was stirred at 40° C. for 12 h. Sat. $NaHCO_3$ (10 mL) was added to the mixture, the mixture was extracted with EtOAc (30 mL*2), The combined organic layers were washed with brine (20 mL), dried over $Na_2SO_4$ and filtered. The filtrate was concentrated under reduced pressure to give a residue. The crude product N-[3-amino-5-fluoro-2-(3,3,3-trifluoropropyl)-4-pyridyl]-2-(3-nitro-2-oxo-1-pyridyl)acetamide (I-832) (235 mg) was used into the next step without further purification as a yellow solid. LCMS m/z 404.0 $(M+1)^+$.

A solution of N-[3-amino-5-fluoro-2-(3,3,3-trifluoropropyl)-4-pyridyl]-2-(3-nitro-2-oxo-1-pyridyl)acetamide (230 mg, 570 umol, 1 eq) in HOAc (3 mL) was heated to 120° C. for 12 h. The mixture was concentrated to remove HOAc. Sat. $NaHCO_3$ (30 mL) was added to the mixture, the mixture was extracted with EtOAc (30 mL*2). The combined organic layers were washed with brine (20 mL), dried over $Na_2SO_4$ and filtered. The filtrate was concentrated under reduced pressure to give 1-[[7-fluoro-4-(3,3,3-trifluoropropyl)-3H-imidazo[4,5-c]pyridine-2-yl]methyl]-3-nitro-pyridin-2-one (I-833) (191 mg) as a white solid. LCMS m/z 386.0 $(M+1)^+$.

To a solution of 1-[[7-fluoro-4-(3,3,3-trifluoropropyl)-3H-imidazo[4,5-c]pyridin-2-yl] methyl]-3-nitro-pyridin-2-one (190 mg, 493 umol, 1 eq) in EtOAc (20 mL) was added Pd/C (100 mg, 10% purity) under $N_2$. The suspension was degassed under vacuum and purged with $H_2$ several times. The mixture was stirred under $H_2$ (15 psi) at 25° C. for 15 min. The mixture was filtered and the filtrate was concentrated to give 3-amino-1-[[7-fluoro-4-(3,3,3-trifluoropropyl)-3H-imidazo[4,5-c]pyridin-2-yl]methyl]pyridin-2-one (I-834) (144 mg) as a white solid. LCMS m/z 356.0 $(M+1)^+$.

The following intermediate was prepared according to the procedures described for the synthesis of I-834 using the appropriate reagents.

| Compound | Structure | Characterization Data |
| --- | --- | --- |
| I-835 | 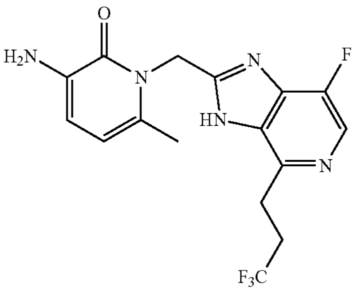 [SMILES: Cc1ccc(N)c(=O)n1Cc1nc2c(F)cnc(CCC(F)(F)F)c2[nH]1] | LCMS m/z 370.2 $(M + H)^+$ |

Example 95

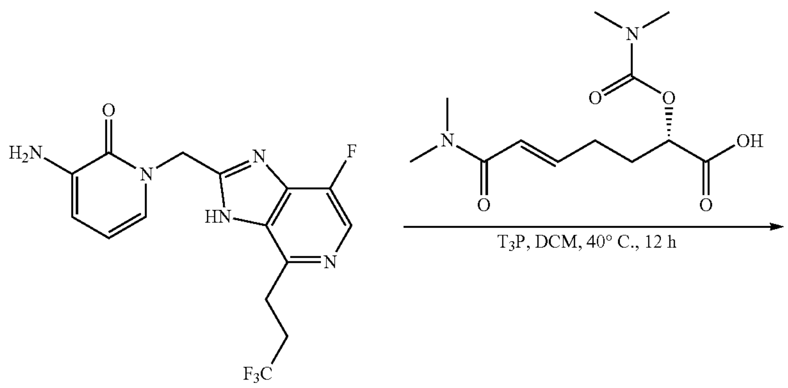

I-834

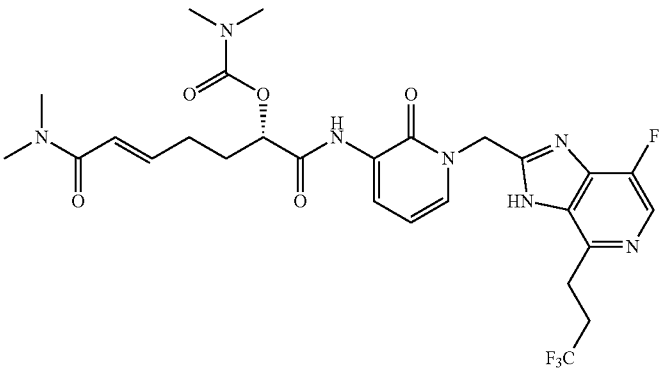

552

Compound 552 was prepared according to the procedures for Example 70 using the appropriate intermediates. LCMS m/z 610.2 $(M+1)^+$. $^1H$ NMR (400 MHz, DMSO-$d_6$) δ 9.30 (s, 1H) 8.14-8.33 (m, 2H) 7.62 (dd, J=6.95, 1.65 Hz, 1H) 6.55-6.71 (m, 1H) 6.32-6.45 (m, 2H) 5.48 (s, 2H) 5.07 (dd, J=7.50, 4.63 Hz, 1H) 3.23-3.28 (m, 2H) 2.89-3.01 (m, 6H) 2.74-2.88 (m, 8H) 2.27 (q, J=6.76 Hz, 2H) 1.85-2.00 (m, 2H).

The following compounds were prepared according to the procedures described for the synthesis of Example 95 using the appropriate intermediates.

| Compound | Structure | Characterization Data |
| --- | --- | --- |
| 556 | 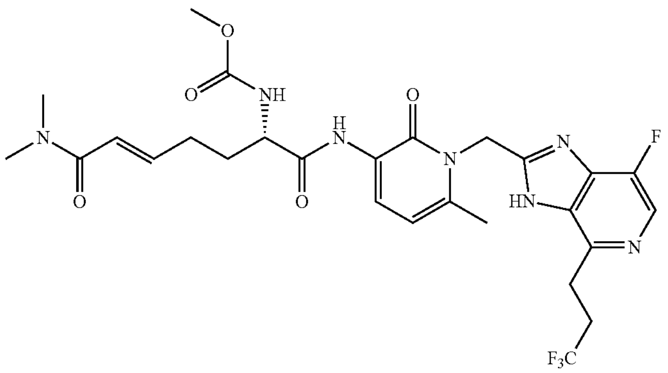 [SMILES: COC(=O)N[C@@H](CC/C=C/C(=O)N(C)C)C(=O)Nc1ccc(C)n(Cc2nc3c(F)cnc(CCC(F)(F)F)c3[nH]2)c1=O] | LCMS m/z 610.2 $(M + 1)^+$ |

-continued

| Compound | Structure | Characterization Data |
| --- | --- | --- |
| 557 | 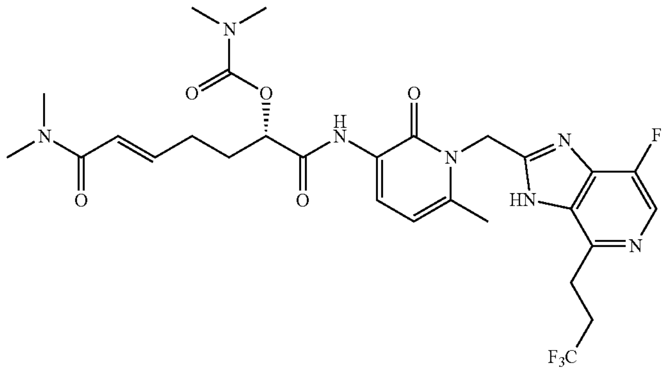 [SMILES: Cc1ccc(NC(=O)[C@H](CC/C=C/C(=O)N(C)C)OC(=O)N(C)C)c(=O)n1Cc1nc2c(F)cnc(CCC(F)(F)F)c2[nH]1] | LCMS m/z 624.2 $(M + 1)^+$ |

Example 96

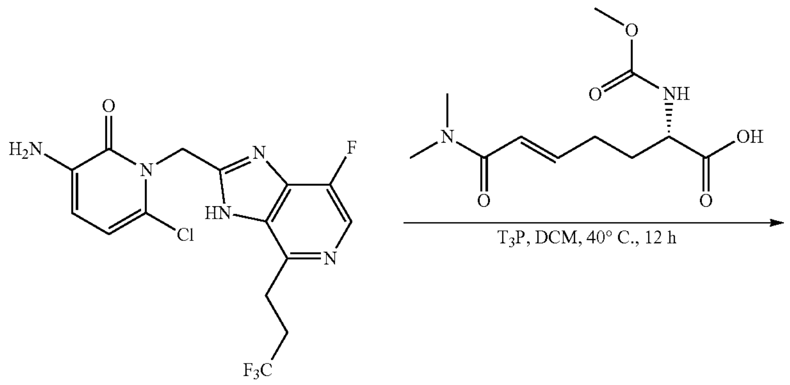

I-838

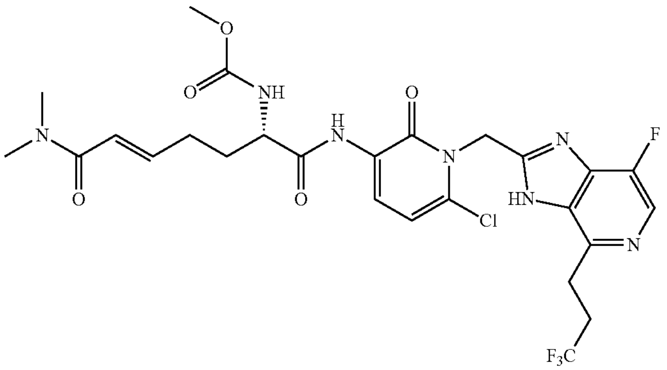

555

Compound 555 was prepared according to the procedures for Example 95 using the appropriate intermediates. LCMS m/z 630.2 $(M+1)^+$. $^1$H NMR (400 MHz, DMSO-$d_6$) δ 13.37-13.75 (m, 1H) 9.38 (s, 1H) 8.27 (d, J=7.94 Hz, 1H) 8.19 (d, J=2.20 Hz, 1H) 7.72 (br d, J=7.72 Hz, 1H) 6.55-6.69 (m, 2H) 6.37 (d, J=15.21 Hz, 1H) 5.70 (s, 2H) 4.18-4.29 (m, 1H) 3.54 (s, 3H) 3.21-3.28 (m, 2H) 2.99 (s, 3H) 2.75-2.88 (m, 5H) 2.14-2.30 (m, 2H) 1.81-1.93 (m, 1H) 1.64-1.79 (m, 1H).

The following compound was prepared according to the procedures described for the synthesis of Example 96 using the appropriate intermediates.

| Compound | Structure | Characterization Data |
| --- | --- | --- |
| 562 | 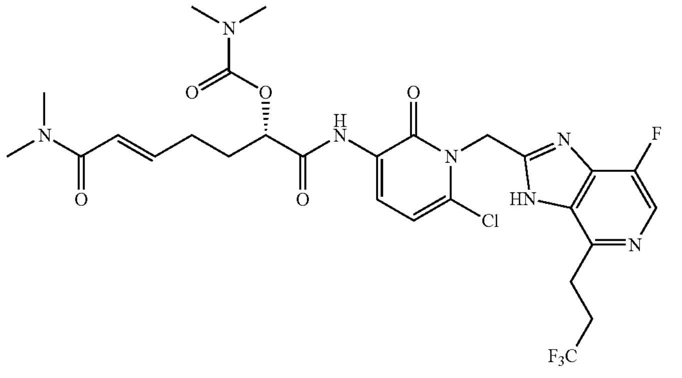 | LCMS m/z 644.2 $(M + 1)^+$ |

Example 97

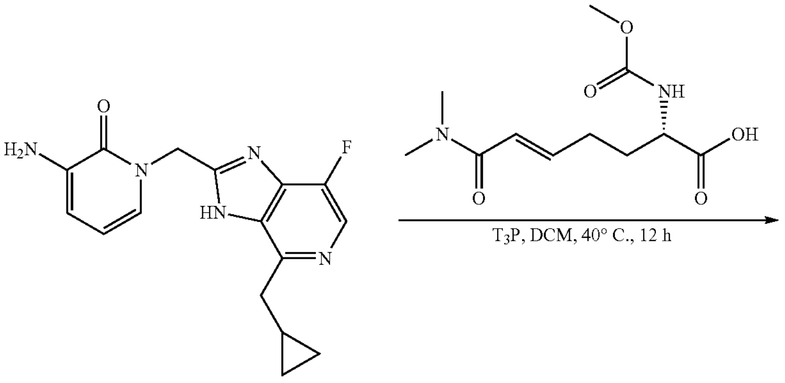

I-844

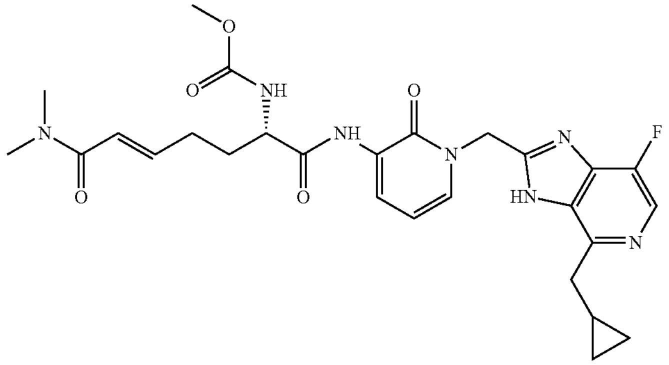

578

Compound 578 was prepared according to the procedures for Example 88 using the appropriate intermediates. LCMS m/z 554.3 $(M+1)^+$. $^1H$ NMR (400 MHz, DMSO-$d_6$) δ 13.42 (br s, 1H), 9.27 (s, 1H), 8.27 (d, J=7.3 Hz, 1H), 8.15 (d, J=2.0 Hz, 1H), 7.73 (br d, J=7.7 Hz, 1H), 7.61 (br d, J=6.6 Hz, 1H), 6.64-6.55 (m, 1H), 6.41-6.33 (m, 2H), 5.45 (s, 2H), 4.22-4.14 (m, 1H), 3.53 (s, 3H), 2.98 (s, 3H), 2.89 (d, J=7.1 Hz, 2H), 2.83 (s, 3H), 2.22 (q, J=7.5, 14.8 Hz, 2H), 1.93-1.81 (m, 1H), 1.78-1.64 (m, 1H), 1.26-1.12 (m, 1H), 0.42 (br d, J=7.5 Hz, 2H), 0.25 (br d, J=4.4 Hz, 2H).

The following compounds were prepared according to the procedures described in Example 97 using the appropriate intermediates.

| Compound | Structure | Characterization Data |
|---|---|---|
| 579 | 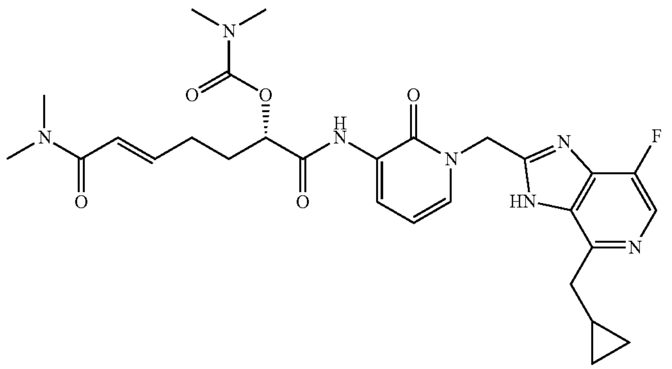 [SMILES: CN(C)C(=O)/C=C/CC[C@H](OC(=O)N(C)C)C(=O)Nc1cccn(Cc2nc3c(F)cnc(CC4CC4)c3[nH]2)c1=O] | LCMS m/z 568.3 (M + 1)$^+$ |
| 596 | 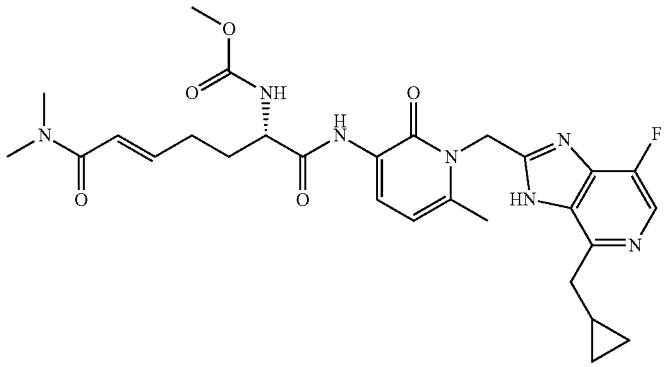 [SMILES: COC(=O)N[C@@H](CC/C=C/C(=O)N(C)C)C(=O)Nc1ccc(C)n(Cc2nc3c(F)cnc(CC4CC4)c3[nH]2)c1=O] | LCMS m/z 568.2 (M + 1)$^+$ |
| 597 | 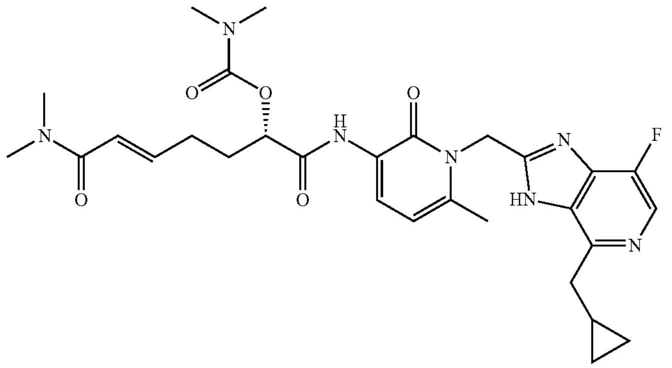 [SMILES: Cc1ccc(NC(=O)[C@H](CC/C=C/C(=O)N(C)C)OC(=O)N(C)C)c(=O)n1Cc1nc2c(F)cnc(CC3CC3)c2[nH]1] | LCMS m/z 582.2 (M + 1)$^+$ |
| 594 | 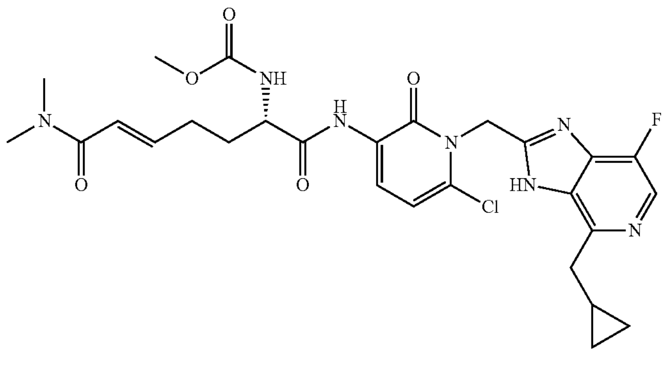 [SMILES: COC(=O)N[C@@H](CC/C=C/C(=O)N(C)C)C(=O)Nc1ccc(Cl)n(Cc2nc3c(F)cnc(CC4CC4)c3[nH]2)c1=O] | LCMS m/z 588.3(M + 1)$^+$ |

-continued

| Compound | Structure | Characterization Data |
| --- | --- | --- |
| 595 | 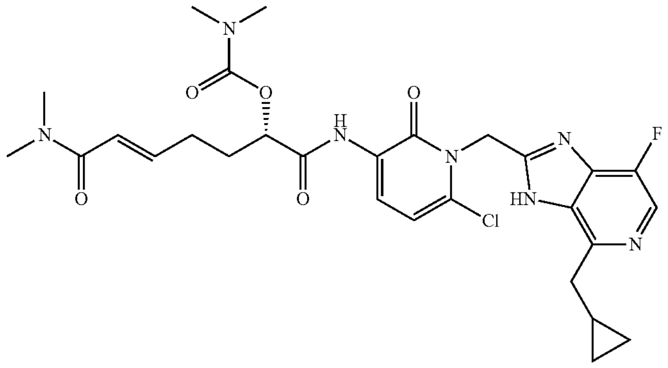 [SMILES: CN(C)C(=O)/C=C/CC[C@H](OC(=O)N(C)C)C(=O)Nc1ccc(Cl)n(Cc2nc3c(F)cnc(CC4CC4)c3[nH]2)c1=O] | LCMS m/z 602.3 $(M + 1)^+$ |

Synthesis of Intermediate I-853

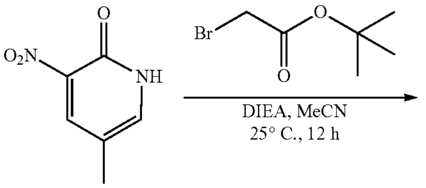

I-848

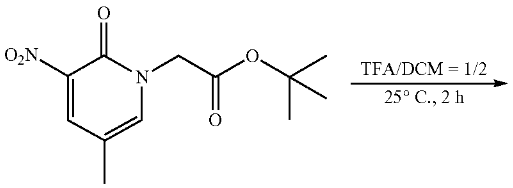

I-849

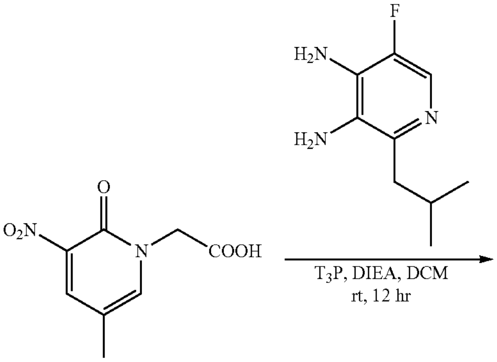

I-850

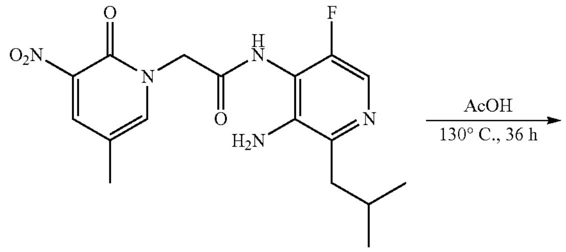

I-851

-continued

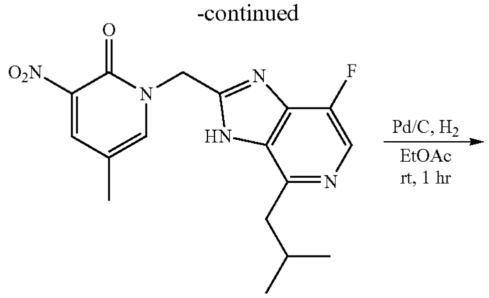

I-852

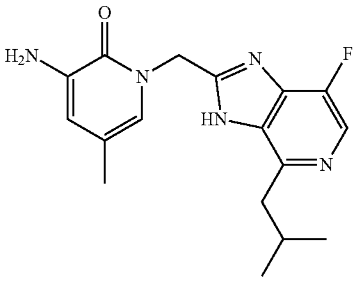

I-853

To a solution of 5-methyl-3-nitro-1H-pyridin-2-one (1 g, 6.49 mmol) in ACN (15 mL) was added DIEA (1.68 g, 12.98 mmol, 2.26 mL) and tert-butyl 2-bromoacetate (2.53 g, 12.98 mmol, 1.92 mL) at 0° C. The mixture was stirred at 25° C. for 12 hr. The reaction mixture was concentrated to give a residue. The residue was purified by column chromatography ($SiO_2$) to give tert-butyl 2-(5-methyl-3-nitro-2-oxo-1-pyridyl)acetate (I-849) (1.53 g, 88% yield) as a yellow solid. LCMS m/z 269.2 $(M+1)^+$.

A mixture of tert-butyl 2-(5-methyl-3-nitro-2-oxo-1-pyridyl)acetate (1.6 g, 5.96 mmol) in DCM (12 mL) was added TFA (6 mL) at 0° C., and then the mixture was stirred at 25° C. for 2 hr. The reaction mixture was concentrated under reduced pressure to remove DCM. The residue was dilute with (Petroleum ether/Ethyl acetate=10:1) 30 mL and then the mixture was stirred at 25° C. for 10 min. Then the mixture was filtered and the filter cake was concentrated under reduced pressure to give a yellow solid. Compound 2-(5-methyl-3-nitro-2-oxo-1-pyridyl)acetic acid (I-850) (1.3 g) was obtained as a yellow solid. LCMS m/z 213.1 $(M+1)^+$.

To a solution of 2-(5-methyl-3-nitro-2-oxo-1-pyridyl)acetic acid (0.3 g, 1.41 mmol) and 5-fluoro-2-isobutyl-pyridine- 3,4-diamine (297.95 mg, 1.63 mmol) in DCM (6 mL) was added DIEA (365.51 mg, 2.83 mmol, 492.60 uL) and $T_3P$ (1.35 g, 2.12 mmol, 1.26 mL, 50% purity) at 0° C. The mixture was stirred at 40° C. for 12 hr. The mixture was concentrated under reduced pressure to give crude N-(3-amino-5-fluoro-2-isobutyl-4-pyridyl)-2-(5-methyl-3-nitro-2-oxo-1-pyridyl)acetamide (I-851) (2.1 g) was obtained as a yellow oil. LCMS m/z 378.2 $(M+1)^+$.

To a solvent of AcOH (20 mL) was added N-(3-amino-5-fluoro-2-isobutyl-4-pyridyl)-2-(5-methyl-3-nitro-2-oxo-1-pyridyl)acetamide (2.1 g, 5.56 mmol) at 25° C. Then the mixture was stirred at 130° C. for 36 hr. The mixture was concentrated under reduced pressure to give a residue. The residue was purified by prep-HPLC to give 1-[(7-fluoro-4-isobutyl-3H-imidazo[4,5-c]pyridin-2-yl)methyl]-5-methyl-3-nitro-pyridin-2-one (I-852) (200 mg, 10% yield) as a yellow solid. LCMS m/z 360.2 $(M+1)^+$.

A mixture of 1-[(7-fluoro-4-isobutyl-3H-imidazo[4,5-c]pyridin-2-yl)methyl]-5-methyl-3-nitro-pyridin-2-one (180 mg, 500.90 umol), Pd/C (0.14 g, 10% purity) in EtOAc (15 mL) was degassed and purged with $H_2$ for 3 times, and then the mixture was stirred at 25° C. for 1 hr under $H_2$ atmosphere (15 Psi). The mixture was filtered and the filtrate was concentrated to give the Crude Product. Compound 3-amino-1-[(7-fluoro-4-isobutyl-3H-imidazo[4,5-c]pyridin-2-yl)methyl]-5-methyl-pyridin-2-one (I-853) (200 mg) was obtained as a yellow oil. LCMS m/z 330.2 $(M+1)^+$.

The following intermediates were prepared according to the procedures described for the synthesis of I-853 using the appropriate reagents.

| Compound | Structure | Characterization Data |
|---|---|---|
| I-854 | 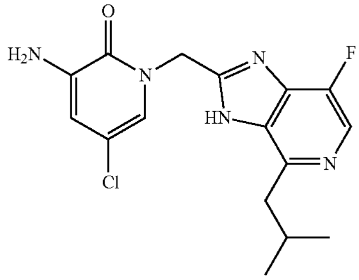 [SMILES: CC(C)Cc1ncc(F)c2nc(Cn3cc(Cl)cc(N)c3=O)[nH]c12] | LCMS m/z 350.2 $(M + H)^+$ |
| I-855 | 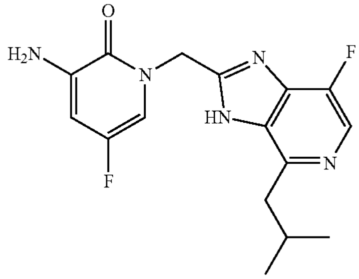 [SMILES: CC(C)Cc1ncc(F)c2nc(Cn3cc(F)cc(N)c3=O)[nH]c12] | LCMS m/z 334.2 $(M + H)^+$ |

Example 98

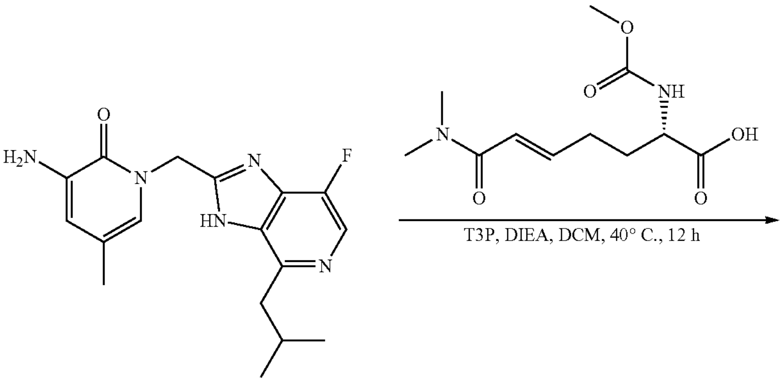

I-853

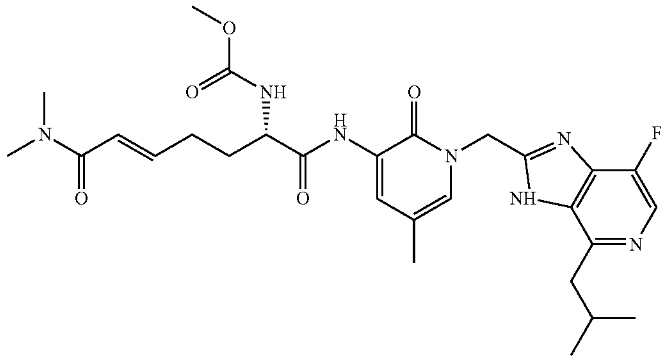

To a solution of (E,2S)-7-(dimethylamino)-2-(methoxycarbonylamino)-7-oxo-hept-5-enoic acid (86.25 mg, 333.97 umol) and 3-amino-1-[(7-fluoro-4-isobutyl-3H-imidazo[4,5-c]pyridin-2-yl)methyl]-5-methyl-pyridin-2-one (100 mg, 303.61 umol) in DCM (3 mL) was added DIEA (58.86 mg, 455.41 umol, 79.32 uL) and $T_3P$ (289.81 mg, 455.41 umol, 270.85 uL, 50% purity) at 25° C. Then the mixture was stirred at 40° C. for 12 hr. The mixture was concentrated under reduced pressure to give a residue. The residue was purified by prep-HPLC to give methyl N-[(E,1S)-6-(dimethylamino)-1-[[1-[(7-fluoro-4-isobutyl-3H-imidazo[4,5-c]pyridin-2-yl)methyl]-5-methyl-2-oxo-3-pyridyl]carbamoyl]-6-oxo-hex-4-enyl]carbamate (42.3 mg, 24% yield) as white solid. LCMS m/z 570.4 $(M+1)^+$. $^1H$ NMR (400 MHz, DMSO-$d_6$) δ 13.30-13.44 (m, 1H) 9.19 (s, 1H) 8.17 (d, J=2.19 Hz, 1H) 8.18 (s, 1H) 7.66 (s, 1H) 7.33-7.42 (m, 1H) 6.53-6.62 (m, 1H) 6.30-6.39 (m, 1H) 5.41 (s, 2H) 4.09-4.19 (m, 1H) 3.45-3.55 (m, 3H) 2.94-2.97 (m, 3H) 2.83-2.87 (m, 2H) 2.80-2.83 (m, 3H) 2.14-2.25 (m, 3H) 2.08 (s, 3H) 1.66-1.87 (m, 2H) 0.87 (br d, J=5.70 Hz, 6H).

The following compounds were prepared according to the procedures described in Example 98 using the appropriate intermediates.

| Compound | Structure | Characterization Data |
|---|---|---|
| 559 | 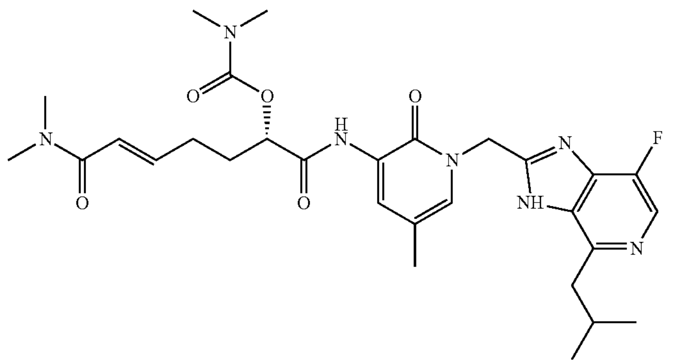 [SMILES: Cc1cc(NC(=O)[C@H](CC/C=C/C(=O)N(C)C)OC(=O)N(C)C)c(=O)n(Cc2nc3c(F)cnc(CC(C)C)c3[nH]2)c1] | LCMS m/z 584.4 $(M + 1)^+$ |
| 574 | 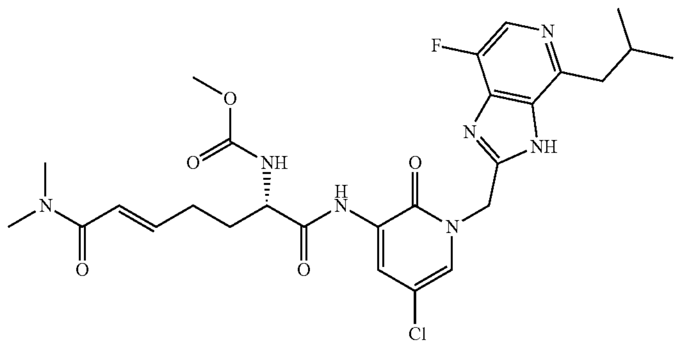 | LCMS m/z 590.2 $(M + 1)^+$ |
| 586 | 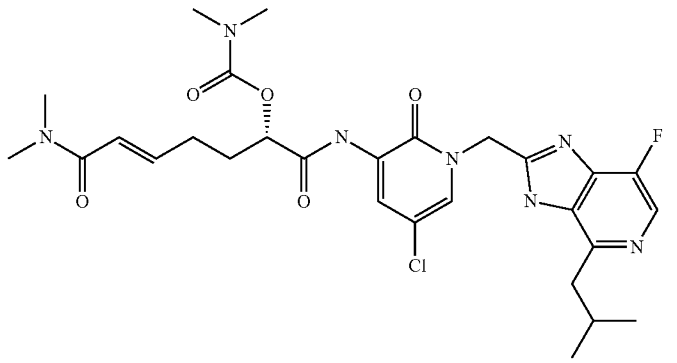 [SMILES: CC(C)Cc1ncc(F)c2nc(Cn3cc(Cl)cc(NC(=O)[C@H](CC/C=C/C(=O)N(C)C)OC(=O)N(C)C)c3=O)[nH]c12] | LCMS m/z 604.3 $(M + 1)^+$ |

-continued

| Compound | Structure | Characterization Data |
|---|---|---|
| 575 | 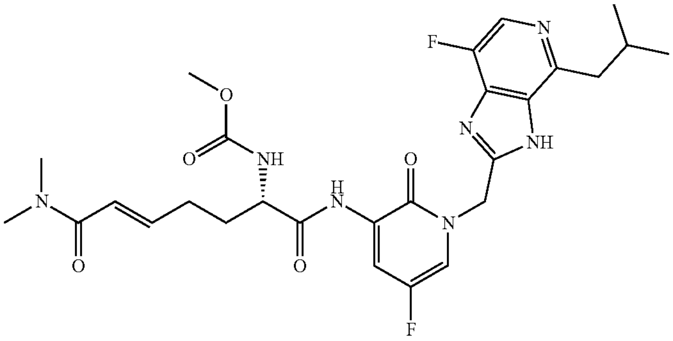 [SMILES: COC(=O)N[C@@H](CC/C=C/C(=O)N(C)C)C(=O)Nc1cc(F)cn(Cc2nc3c(F)cnc(CC(C)C)c3[nH]2)c1=O] | LCMS m/z 574.2 (M + 1)$^+$ |
| 587 | 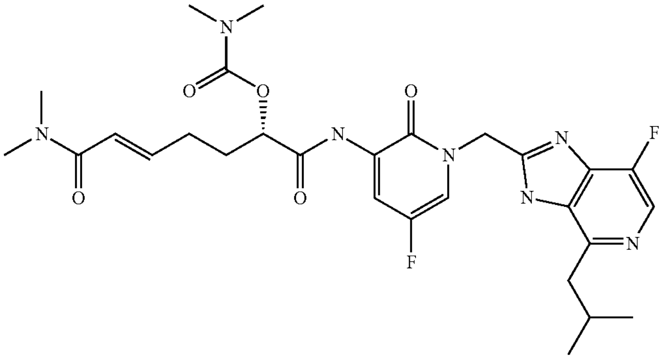 | LCMS m/z 588.3 (M + 1)$^+$ |

The following intermediates were prepared according to the procedures described for the synthesis of I-65 using the appropriate reagents.

| Compound | Structure | Characterization Data |
|---|---|---|
| I-863 | 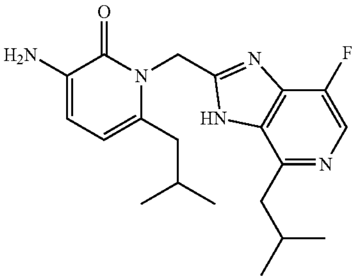 [SMILES: CC(C)Cc1ncc(F)c2nc(Cn3c(CC(C)C)ccc(N)c3=O)[nH]c12] | LCMS m/z 372.3 (M + H)$^+$ |
| I-864 | 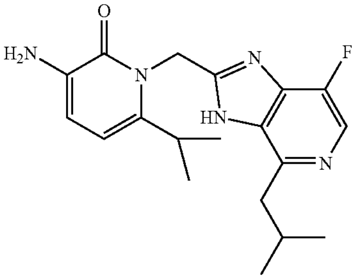 [SMILES: CC(C)Cc1ncc(F)c2nc(Cn3c(C(C)C)ccc(N)c3=O)[nH]c12] | LCMS m/z 358.2 (M + H)$^+$ |

-continued

| Compound | Structure | Characterization Data |
|---|---|---|
| I-865 | 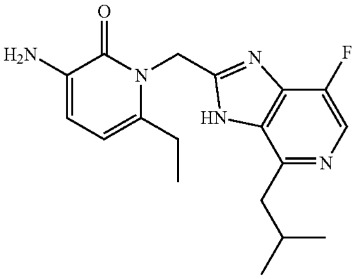 [SMILES: CCc1ccc(N)c(=O)n1Cc1nc2c(F)cnc(CC(C)C)c2[nH]1] | LCMS m/z 344.2 (M + H)$^+$ |
| I-866 | 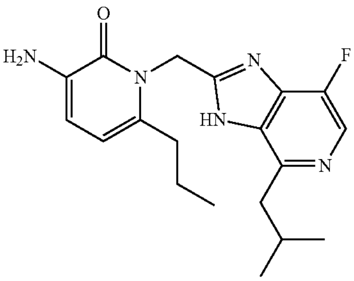 [SMILES: CCCc1ccc(N)c(=O)n1Cc1nc2c(F)cnc(CC(C)C)c2[nH]1] | LCMS m/z 358.2 (M + H)$^+$ |

-continued

| Compound | Structure | Characterization Data |
|---|---|---|
| I-867 | 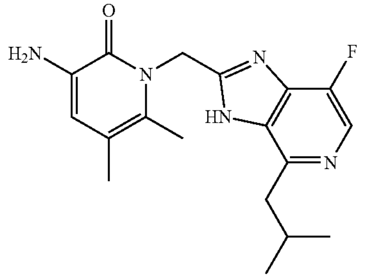 [SMILES: Cc1cc(N)c(=O)n(Cc2nc3c(F)cnc(CC(C)C)c3[nH]2)c1C] | LCMS m/z 344.2 (M + H)$^+$ |

Example 99

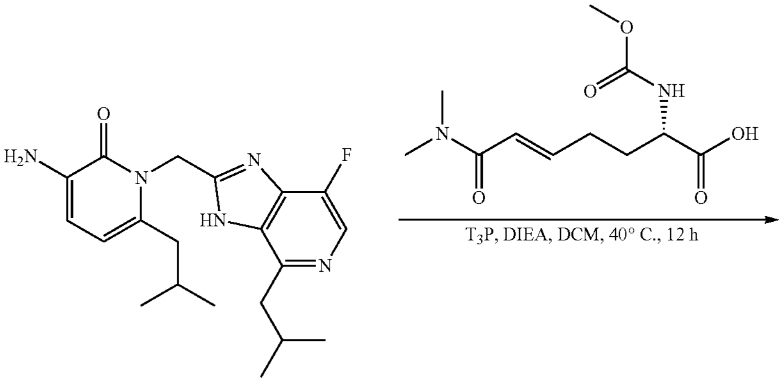

I-863

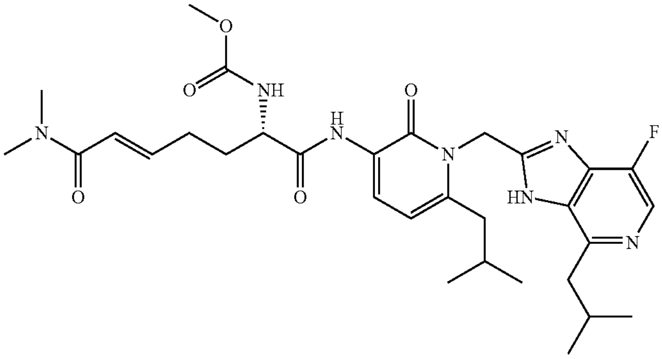

565

Compound 565 was prepared according to the procedures for Example 98 using the appropriate intermediates. LCMS m/z 612.4 (M+1)$^+$. H NMR (400 MHz, DMSO-$d_6$) δ 13.33-13.54 (m, 1H) 9.17 (br s, 1H) 8.18 (d, J=7.72 Hz, 1H) 8.09-8.15 (m, 1H) 7.69 (br d, J=7.50 Hz, 1H) 6.53-6.62 (m, 1H) 6.34 (d, J=14.99 Hz, 1H) 6.22 (d, J=7.72 Hz, 1H) 5.46 (brs, 2H) 4.09-4.17 (m, 1H) 3.51 (s, 3H) 2.96 (s, 3H) 2.79-2.86 (m, 5H) 2.58 (brd, J=6.84 Hz, 2H) 2.10-2.27 (m, 3H) 1.85 (br dd, J=13.12, 6.73 Hz, 2H) 1.62-1.73 (m, 1H) 0.79-0.91 (m, 12H).

The following compounds were prepared according to the procedures described in Example 99 using the appropriate intermediates.

| Compound | Structure | Characterization Data |
|---|---|---|
| 566 | 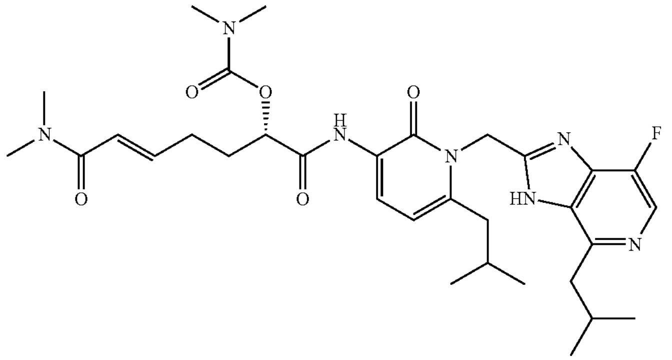 [SMILES: CC(C)Cc1ncc(F)c2nc(Cn3c(CC(C)C)ccc(NC(=O)[C@H](CC/C=C/C(=O)N(C)C)OC(=O)N(C)C)c3=O)[nH]c12] | LCMS m/z 626.4 (M + 1)+ |
| 569 | 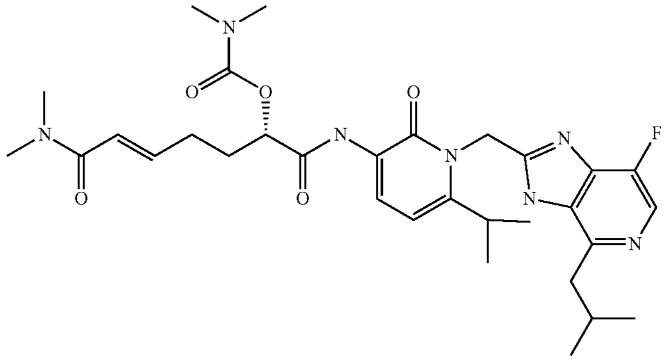 | LCMS m/z 582.2 (M + 1)+ |
| 573 | 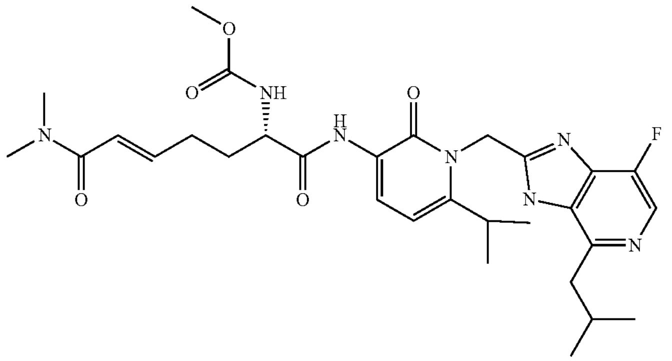 [SMILES: COC(=O)N[C@@H](CC/C=C/C(=O)N(C)C)C(=O)Nc1ccc(C(C)C)n(Cc2nc3c(F)cnc(CC(C)C)c3[nH]2)c1=O] | LCMS m/z 598.3 (M + 1)+ |
| 572 | 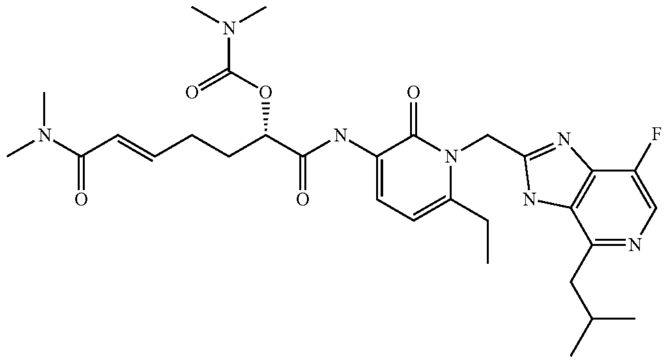 [SMILES: CCc1ccc(NC(=O)[C@H](CC/C=C/C(=O)N(C)C)OC(=O)N(C)C)c(=O)n1Cc1nc2c(F)cnc(CC(C)C)c2[nH]1] | LCMS m/z 598.4 (M + 1)+ |

-continued
| Compound | Structure | Characterization Data |
| --- | --- | --- |
| 571 | 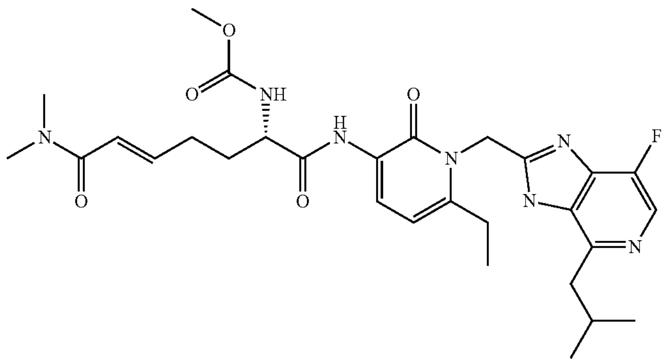 [SMILES: CCc1ccc(NC(=O)[C@H](CC/C=C/C(=O)N(C)C)NC(=O)OC)c(=O)n1Cc1nc2c(F)cnc(CC(C)C)c2[nH]1] | LCMS m/z 584.3 $(M + 1)^+$ |
| 582 | 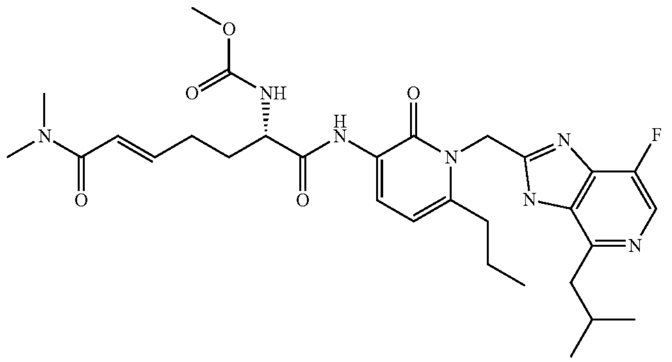 [SMILES: CCCc1ccc(NC(=O)[C@H](CC/C=C/C(=O)N(C)C)NC(=O)OC)c(=O)n1Cc1nc2c(F)cnc(CC(C)C)c2[nH]1] | LCMS m/z 598.3 $(M + 1)^+$ |
| 598 | 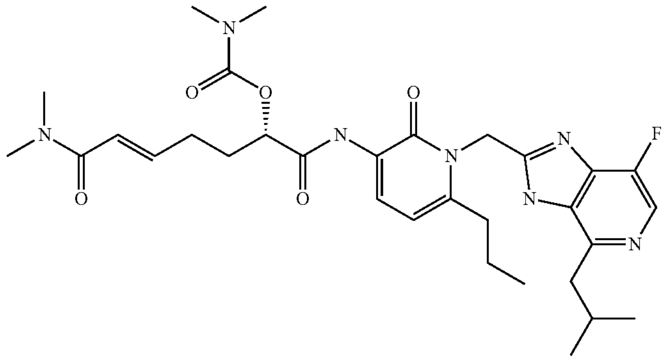 [SMILES: CCCc1ccc(NC(=O)[C@H](CC/C=C/C(=O)N(C)C)OC(=O)N(C)C)c(=O)n1Cc1nc2c(F)cnc(CC(C)C)c2[nH]1] | LCMS m/z 612.3 $(M + 1)^+$ |
| 568 | 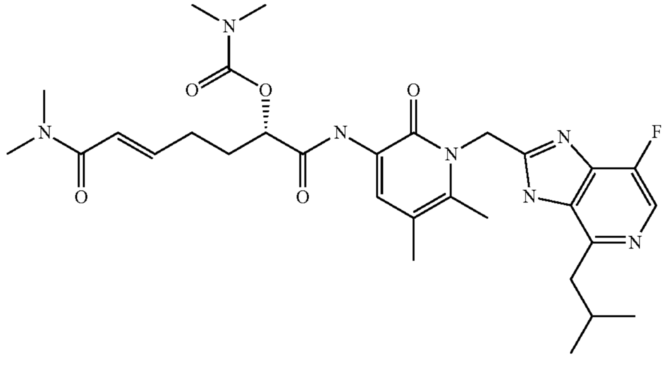 [SMILES: Cc1cc(NC(=O)[C@H](CC/C=C/C(=O)N(C)C)OC(=O)N(C)C)c(=O)n(Cc2nc3c(F)cnc(CC(C)C)c3[nH]2)c1C] | LCMS m/z 598.1 $(M + 1)^+$ |

-continued

| Compound | Structure | Characterization Data |
|---|---|---|
| 570 | 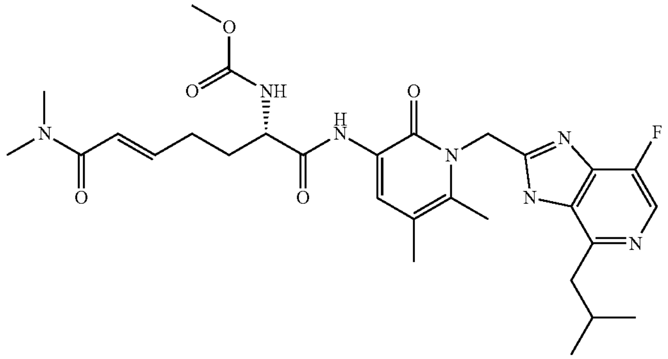 [SMILES: COC(=O)N[C@@H](CC/C=C/C(=O)N(C)C)C(=O)Nc1cc(C)c(C)n(Cc2nc3c(F)cnc(CC(C)C)c3[nH]2)c1=O] | LCMS m/z 584.3 $(M + 1)^+$ |

Synthesis of Intermediate I-874

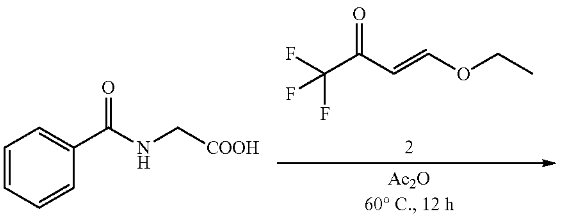

I-868

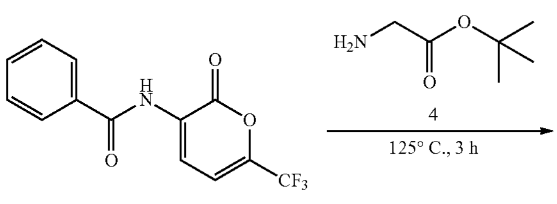

I-869

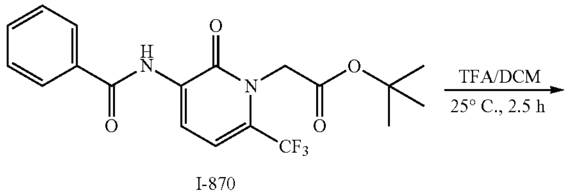

I-870

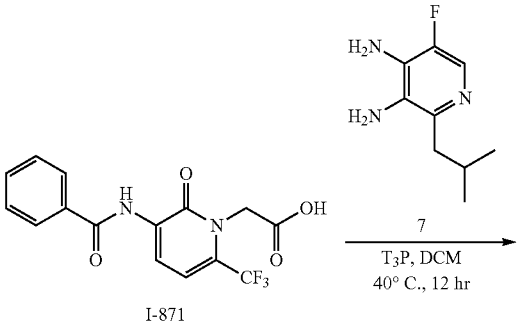

I-871

-continued

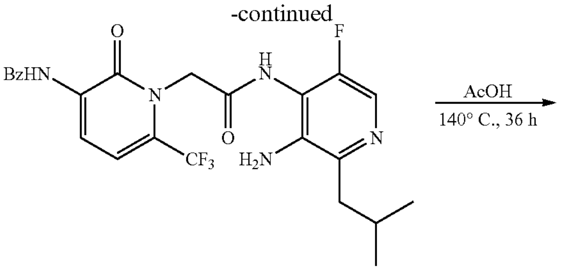

I-872

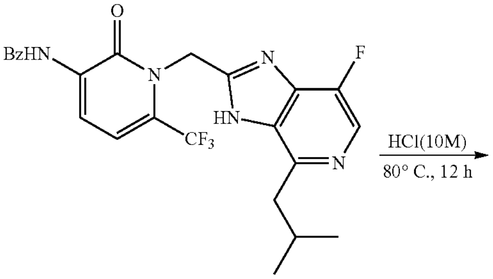

I-873

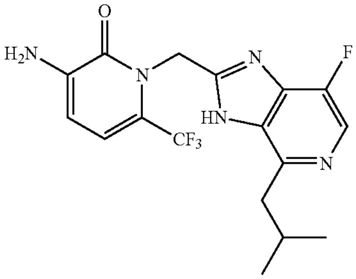

I-874

A solution of 2-benzamidoacetic acid (10 g, 55.8 mmol, 1 eq) and (E)-4-ethoxy-1,1,1-trifluoro-but-3-en-2-one (8.91 g, 53.0 mmol, 7.55 mL, 0.95 eq) in $Ac_2O$ (100 mL) was heated to 60° C. for 14 h. The mixture was concentrated to remove $Ac_2O$. Then sat. $NaHCO_3$ (200 mL) was added to the mixture. The mixture was extracted with EtOAc (200 mL×2). The combined organic layers were washed with brine (200 mL), dried over $Na_2SO_4$ and filtered. The filtrate was concentrated under reduced pressure to give a residue. The residue was purified by column chromatography ($SiO_2$)

to give N-[2-oxo-6-(trifluoromethyl)pyran-3-yl]benzamide (I-869) (4.76 g, 30% yield) as a yellow solid.

A mixture of N-[2-oxo-6-(trifluoromethyl)pyran-3-yl]benzamide (4.76 g, 16.8 mmol, 1 eq) and tert-butyl 2-aminoacetate (11.0 g, 84.0 mmol, 5 eq) was heated to 125° C. for 12 h. sat. $NH_4Cl$ (100 mL) was added to the mixture and then the mixture was extracted with EtOAc (100 mL×2). The combined organic layers were washed with brine (100 mL), dried over $Na_2SO_4$ and filtered. The filtrate was concentrated under reduced pressure to give a residue. The residue was purified by column chromatography ($SiO_2$) to give tert-butyl 2-[3-benzamido-2-oxo-6-(trifluoromethyl)-1-pyridyl]acetate (I-870) (2.9 g, 44% yield) as a white solid. LCMS m/z 397.1 $(M+1)^+$.

TFA (6.16 g, 54.0 mmol, 4 mL, 21.4 eq) was added to a solution of tert-butyl 2-[3-benzamido-2-oxo-6-(trifluoromethyl)-1-pyridyl]acetate (1 g, 2.52 mmol, 1 eq) in DCM (8 mL) at 25° C. The mixture was stirred for 2.5 h. The mixture was concentrated to remove TFA and DCM to give a solid. The solid was triturated in PE (10 mL), filtered and the solid was dried to give 2-[3-benzamido-2-oxo-6-(trifluoromethyl)-1-pyridyl]acetic acid (I-871) (810 mg) as a white solid. LCMS m/z 340.9 $(M+1)^+$.

$T_3P$ (1.56 g, 2.46 mmol, 1.46 mL, 50% purity, 1.5 eq) was added to a solution of 5-fluoro-2-isobutyl-pyridine-3,4-diamine (300 mg, 1.64 mmol, 1 eq) and 2-[3-benzamido-2-oxo-6-(trifluoromethyl)-1-pyridyl]acetic acid (557 mg, 1.64 mmol, 1 eq) in DCM (3 mL) at 25° C. Then the mixture was stirred at 40° C. for 12 h. sat. $NaHCO_3$ (10 mL) was added to the mixture with white solid precipitated, filtered and the filter cake were dried to give a crude product. The crude product N-[1-[2-[(3-amino-5-fluoro-2-isobutyl-4-pyridyl)amino]-2-oxo-ethyl]-2-oxo-6-(trifluoromethyl)-3-pyridyl]benzamide (I-872) (1 g) was used into the next step without further purification as a white solid. LCMS m/z 506.2 $(M+1)^+$.

A solution of N-[1-[2-[(3-amino-5-fluoro-2-isobutyl-4-pyridyl)amino]-2-oxo-ethyl]-2-oxo-6-(trifluoromethyl)-3-pyridyl]benzamide (700 mg, 1.38 mmol, 1 eq) in HOAc (7 mL) was heated to 140° C. for 36 h. The mixture was stirred at 140° C. for another 24 h. The mixture was concentrated to remove HOAc, then sat. $NaHCO_3$ (50 mL) was added to the mixture, and extracted with EtOAc (40 mL*2), the organic layer was washed with brine (40 mL), dried over $Na_2SO_4$, and concentrated to give N-[1-[(7-fluoro-4-isobutyl-3H-imidazo[4,5-c]pyridin-2-yl)methyl]-2-oxo-6-(trifluoromethyl)-3-pyridyl]benzamide (I-873) (500 mg) as a brown solid. LCMS m/z 488.1 $(M+1)^+$.

The following intermediate was prepared according to the procedures described for the synthesis of I-873 using the appropriate reagents.

| Compound | Structure | Characterization Data |
|---|---|---|
| I-875 | 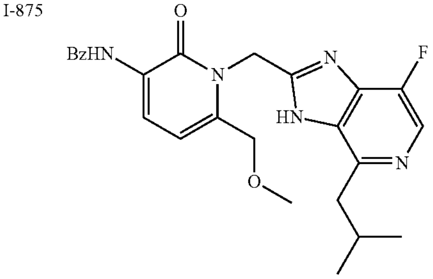 | LCMS m/z 464.2 $(M + H)^+$ |

A solution of N-[1-[(7-fluoro-4-isobutyl-3H-imidazo[4,5-c]pyridin-2-yl)methyl]-2-oxo-6-(trifluoromethyl)-3-pyridyl]benzamide (500 mg, 1.03 mmol, 1 eq) in HCl (10M) (10 mL) was heated to 90° C. for 5 h. The mixture was concentrated to remove HCl, then $NaHCO_3$ (50 mL) was added to the mixture. The mixture was extracted with EtOAc (30 mL×2). The combined organic layers were washed with brine (20 mL), dried over $Na_2SO_4$ and filtered. The filtrate was concentrated under reduced pressure to give 3-amino-1-[(7-fluoro-4-isobutyl-3H-imidazo[4,5-c]pyridin-2-yl)methyl]-6-(trifluoromethyl)pyridin-2-one (I-874) (383 mg) as a brown solid. LCMS m/z 384.0 $(M+1)^+$.

Example 100

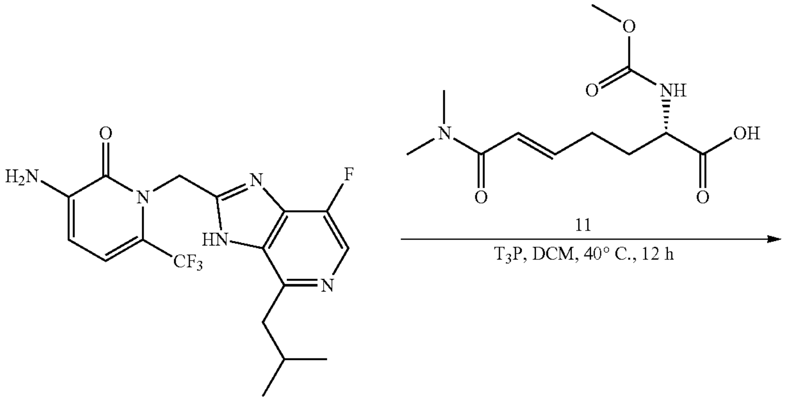

I-874

-continued

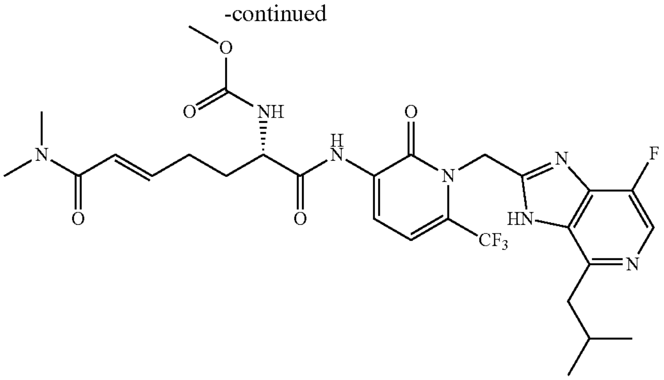

576

Compound 576 was prepared according to the procedures for Example 70 using the appropriate intermediates. $^{1}H$ NMR (400 MHz, DMSO-$d_6$) δ 13.24-13.43 (m, 1H) 9.67 (s, 1H) 8.35 (d, J=7.95 Hz, 1H) 8.10-8.20 (m, 1H) 7.66-7.77 (m, 1H) 7.12 (d, J=8.07 Hz, 1H) 6.53-6.67 (m, 1H) 6.36 (d, J=15.04 Hz, 1H) 5.50 (br s, 2H) 4.23-4.35 (m, 1H) 3.53 (s, 3H) 2.98 (s, 3H) 2.75-2.89 (m, 5H) 2.13-2.30 (m, 3H) 1.67-1.90 (m, 2H) 1.32-1.32 (m, 1H) 0.77-0.96 (m, 6H). LCMS m/z 624.3 $(M+1)^+$.

The following compound was prepared according to the procedures described in Example 100 using the appropriate intermediates.

| Compound | Structure | Characterization Data |
|---|---|---|
| 577 | 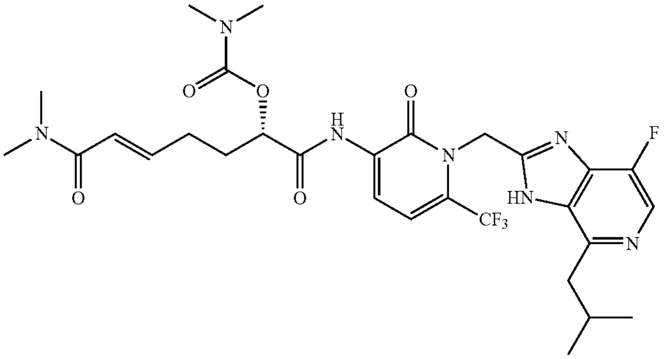 | LCMS m/z 638.3 $(M + 1)^+$ |

Example 101

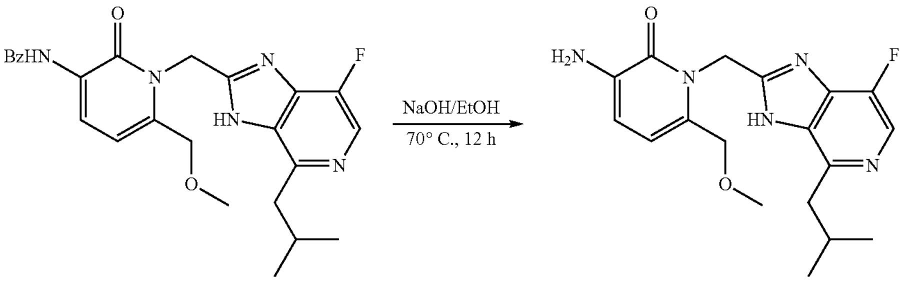

I-875 I-876

-continued

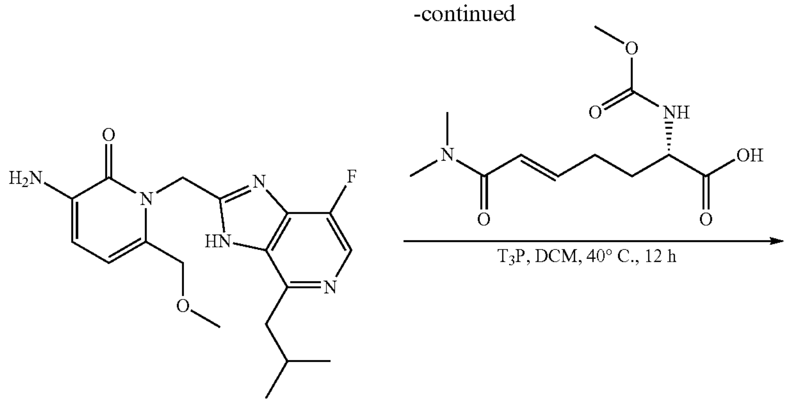

I-876

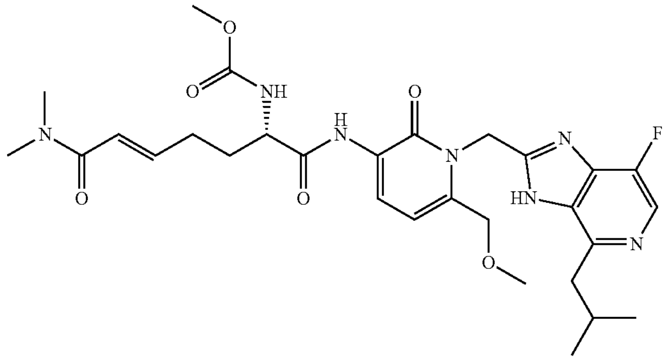

599

To a solution of N-[1-[(7-fluoro-4-isobutyl-3H-imidazo [4,5-c]pyridin-2-yl) methyl]-6-(methoxymethyl)-2-oxo-3-pyridyl]benzamide (215 mg, 463.86 umol) in EtOH (5 mL) was added NaOH (55.66 mg, 1.39 mmol) at 25° C. The mixture was stirred at 80° C. for 12 hr. To the reaction was added NaOH (37.11 mg), then the mixture was stirred at 80° C. for 24 h. The reaction was concentrated to give the residue. The residue was purified by prep-TLC ($SiO_2$) to give 3-amino-1-[(7-fluoro-4-isobutyl-3H-imidazo[4,5-c] pyridin-2-yl)methyl]-6-(methoxymethyl)pyridin-2-one (I-876) (170 mg) as a green solid. LCMS m/z 360.2 $(M+1)^+$.

Compound 599 was prepared according to the procedures for Example 70 using the appropriate intermediates. LCMS m/z 600.3 $(M+1)^+$. 1H NMR (400 MHz, DMSO-$d_6$) δ 13.26-13.44 (m, 1H) 9.29 (s, 1H) 8.24 (d, J=7.46 Hz, 1H) 8.12 (br s, 1H) 7.71 (br d, J=6.11 Hz, 1H) 6.55-6.64 (m, 1H) 6.48 (br d, J=7.58 Hz, 1H) 6.36 (d, J=15.04 Hz, 1H) 5.53 (br s, 2H) 4.47 (s, 2H) 4.15-4.22 (m, 1H) 3.53 (s, 3H) 3.24 (br s, 3H) 2.98 (s, 3H) 2.81-2.87 (m, 5H) 2.22 (dq, J=14.92, 7.38 Hz, 3H) 1.82-1.92 (m, 1H) 1.66-1.76 (m, 1H) 0.91 (br d, J=5.62 Hz, 6H).

Example 102

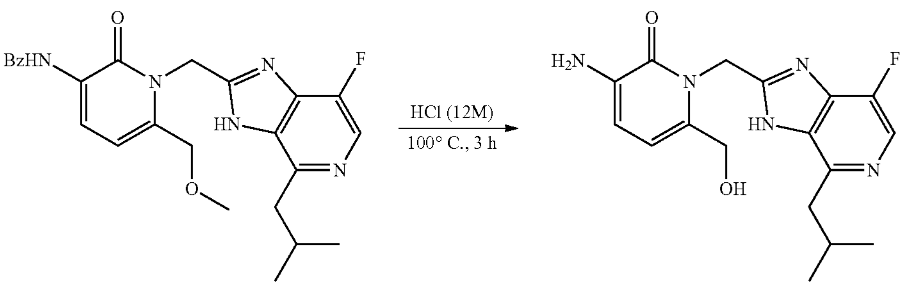

I-875 I-877

-continued

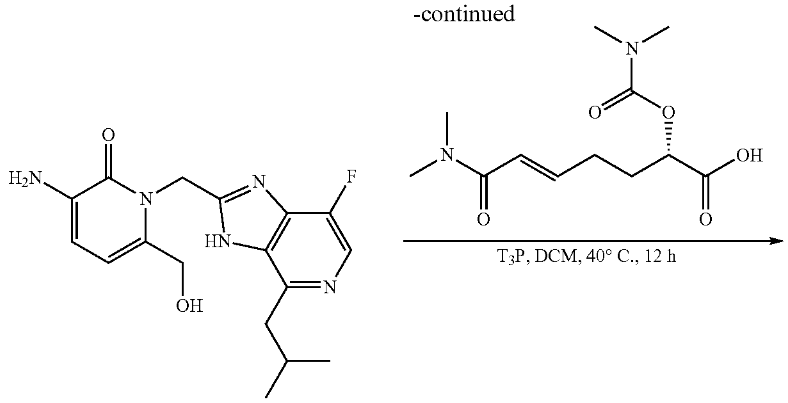

I-877

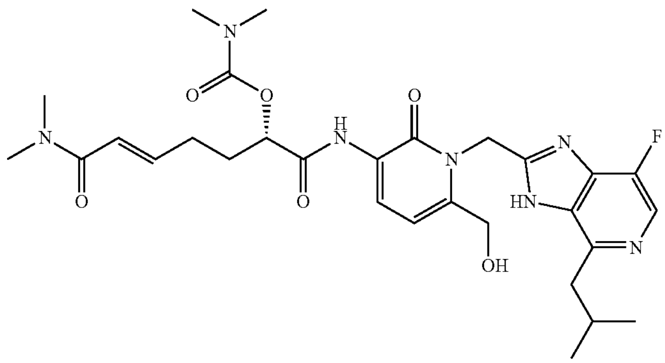

591

Compound 591 was prepared according to the procedures for Example 100 using the appropriate intermediates. LCMS m/z 528.3 $(M+1)^+$. $^1H$ NMR (400 MHz, DMSO-$d_6$) δ 9.44 (d, J=3.91 Hz, 1H) 8.22-8.31 (m, 2H) 6.60-6.73 (m, 2H) 6.40 (d, J=15.04 Hz, 1H) 5.69 (s, 1H) 5.61 (s, 1H) 5.45 (d, J=5.99 Hz, 2H) 5.10-5.17 (m, 1H) 3.09 (d, J=7.09 Hz, 1H) 2.95-3.03 (m, 6H) 2.93 (d, J=7.46 Hz, 1H) 2.78-2.87 (m, 6H) 2.09-2.34 (m, 3H) 1.88-2.01 (m, 2H) 0.86-0.97 (m, 6H).

The following compound was prepared according to the procedures described in Example 102 using the appropriate intermediates.

| Compound | Structure | Characterization Data |
|---|---|---|
| 580 | 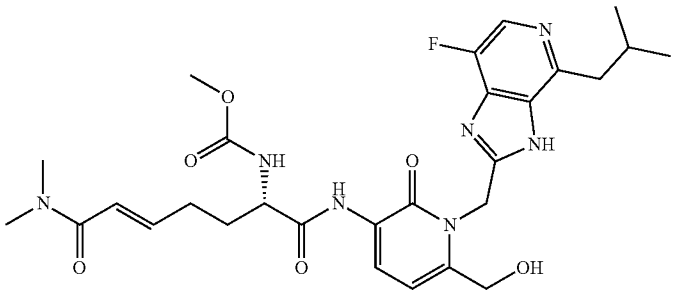 | LCMS m/z 549.3 $(M + 1)^+$ |

Example 103

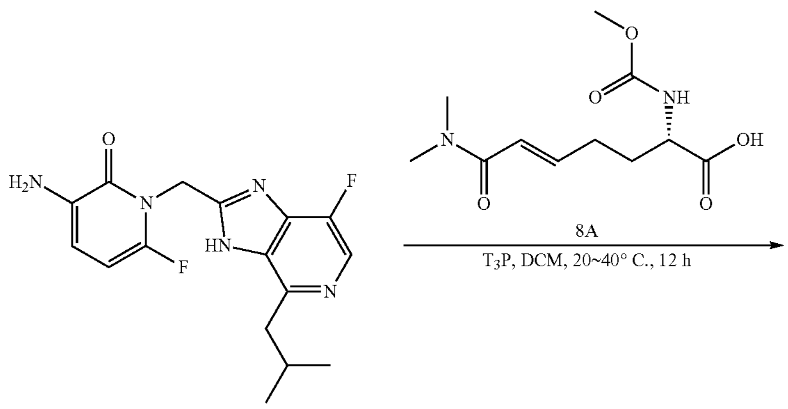

I-885

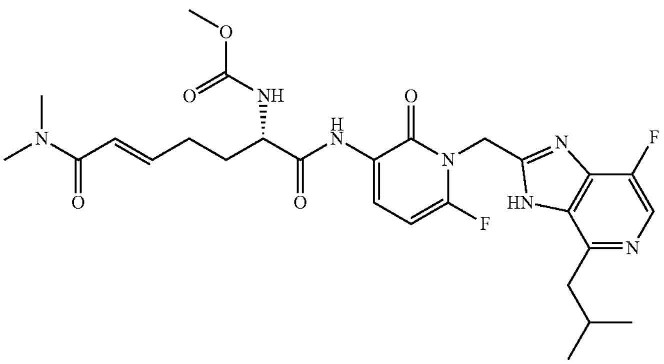

589

Compound 589 was prepared according to the procedures for Example 70 using the appropriate intermediates. LCMS m/z 574.2 $(M+1)^+$. H NMR (400 MHz, DMSO-$d_6$) δ 13.48 (br s, 1H) 9.27 (s, 1H) 8.32 (t, J=8.25 Hz, 1H) 8.13-8.18 (m, 1H) 7.68 (br d, J=7.82 Hz, 1H) 6.56-6.66 (m, 1H) 6.38 (d, J=15.16 Hz, 1H) 6.29 (dd, J=8.38, 5.32 Hz, 1H) 5.54 (d, J=1.47 Hz, 2H) 4.22 (br d, J=3.55 Hz, 1H) 3.55 (s, 3H) 2.99 (s, 3H) 2.81-2.89 (m, 5H) 2.22 (dt, J=15.34, 7.73 Hz, 3H) 1.87 (br d, J=7.58 Hz, 1H) 1.67-1.77 (m, 1H) 0.85-0.93 (m, 1H) 0.85-0.93 (m, 1H) 0.90 (br d, J=5.87 Hz, 4H).

The following compound was prepared according to the procedures described in Example 103 using the appropriate intermediates.

| Compound | Structure | Characterization Data |
| --- | --- | --- |
| 590 | 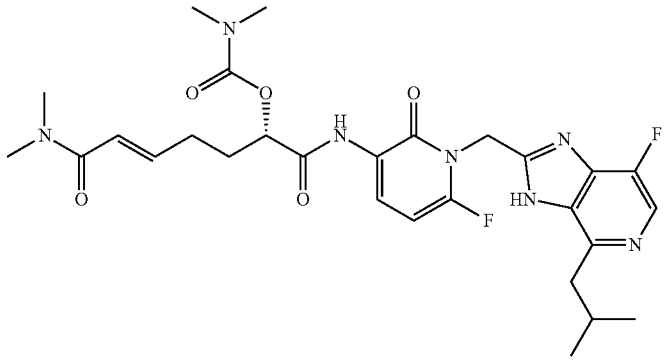 [SMILES: CC(C)Cc1ncc(F)c2nc(Cn3c(F)ccc(NC(=O)[C@H](CC/C=C/C(=O)N(C)C)OC(=O)N(C)C)c3=O)[nH]c12] | 1H NMR (400 MHz, DMSO-$d_6$) δ 13.45 (br s, 1 H) 9.30 (s, 1 H) 8.31 (t, J = 8.25 Hz, 1 H) 8.16 (s, 1 H) 6.60-6.69 (m, 1 H) 6.40 (d, J = 15.04 Hz, 1 H) 6.30 (dd, J = 8.31, 5.38 Hz, 1 H) 5.55 (s, 2 H) 5.09 (dd, J = 7.46, 4.65 Hz, 1 H) 2.91-3.01 (m, 6 H) 2.80-2.88 (m, 8 H) 2.29 (q, J = 7.17 Hz, 2 H) 2.20 (br s, 1 H) 1.88-1.99 (m, 2 H) 0.89 (br s, 6H)<br>LCMS m/z 588.2 (M + 1) |

Example 104

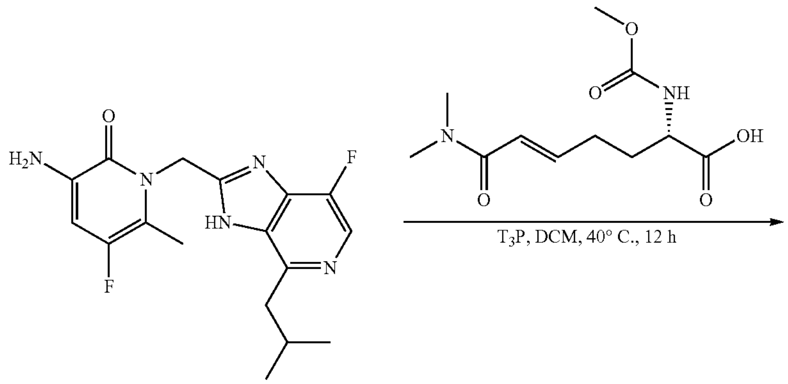

I-896

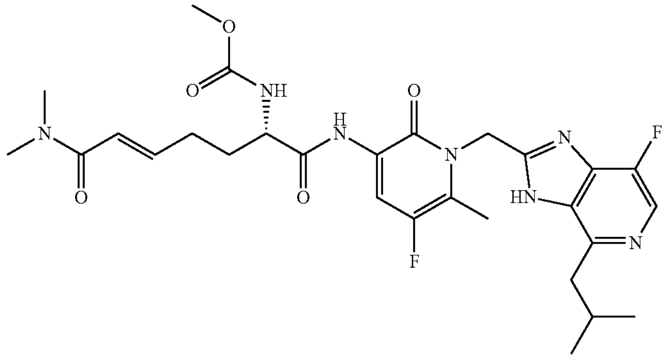

583

Compound 583 was prepared according to the procedures for Example 70 using the appropriate intermediates. LCMS m/z 588.3 $(M+1)^+$. H NMR (400 MHz, DMSO-$d_6$) δ 13.42 (br s, 1H), 9.43 (s, 1H), 8.31 (d, J=10.6 Hz, 1H), 8.15 (br d, J=1.6 Hz, 1H), 7.72 (br d, J=7.2 Hz, 1H), 6.67-6.51 (m, 1H), 6.37 (br d, J=15.0 Hz, 1H), 5.55 (s, 2H), 4.23 (br s, 1H), 3.54 (s, 3H), 2.98 (s, 3H), 2.90-2.79 (m, 5H), 2.38 (br s, 3H), 2.23 (br dd, J=6.8, 13.5 Hz, 3H), 1.94-1.65 (m, 2H), 0.90 (br d, J=6.4 Hz, 6H).

The following compound was prepared according to the procedures described in Example 104 using the appropriate intermediates.

| Compound | Structure | Characterization Data |
| --- | --- | --- |
| 584 | 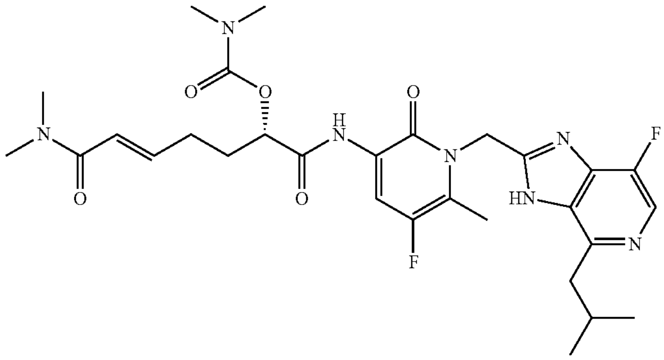 [SMILES: Cc1c(F)cc(NC(=O)[C@H](CC/C=C/C(=O)N(C)C)OC(=O)N(C)C)c(=O)n1Cc1nc2c(F)cnc(CC(C)C)c2[nH]1] | LCMS m/z 602.2 $(M + 1)^+$ |

Example 105

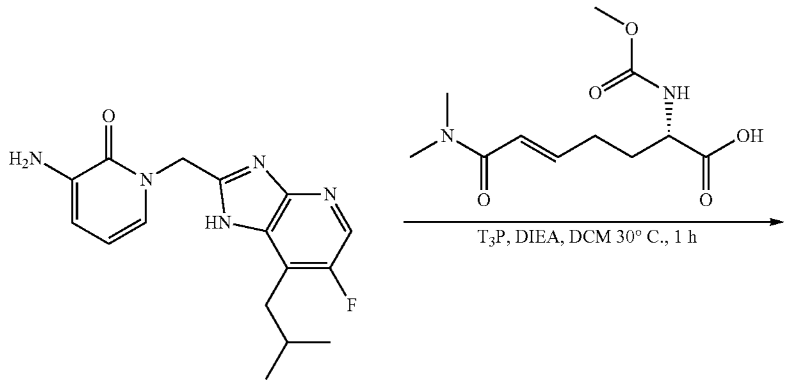

I-905

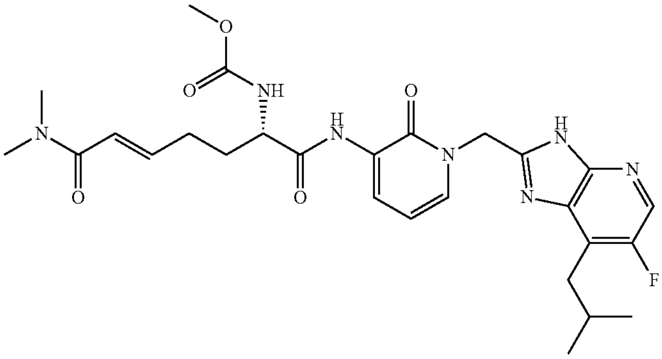

525

Compound 525 was prepared according to the procedures for Example 98 using the appropriate intermediates. LCMS m/z 556.2 $(M+1)^+$. $^1H$ NMR (400 MHz, DMSO-$d_6$) δ 0.90 (br d, J=5.26 Hz, 6H) 1.65-1.79 (m, 1H) 1.80-1.96 (m, 1H) 1.99-2.13 (m, 1H) 2.16-2.35 (m, 2H) 2.73-2.88 (m, 5H) 2.99 (s, 3H) 3.54 (s, 3H) 4.09-4.29 (m, 1H) 5.42 (br s, 2H) 6.32-6.45 (m, 2H) 6.54-6.67 (m, 1H) 7.59 (br s, 1H) 7.73 (br d, J=7.82 Hz, 1H) 8.19-8.33 (m, 2H) 9.27 (s, 1H).

The following compounds were prepared according to the procedures described for the synthesis of Example 105 using the appropriate intermediates.

| Compound | Structure | Characterization Data |
| --- | --- | --- |
| 535 | 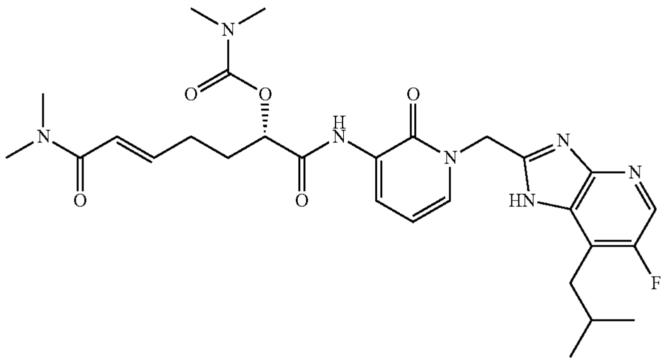 [SMILES: CC(C)Cc1c(F)cnc2nc(Cn3cccc(NC(=O)[C@H](CC/C=C/C(=O)N(C)C)OC(=O)N(C)C)c3=O)[nH]c12] | LCMS m/z 569.9 $(M + 1)^+$ |

-continued
| Compound | Structure | Characterization Data |
| --- | --- | --- |
| 528 | 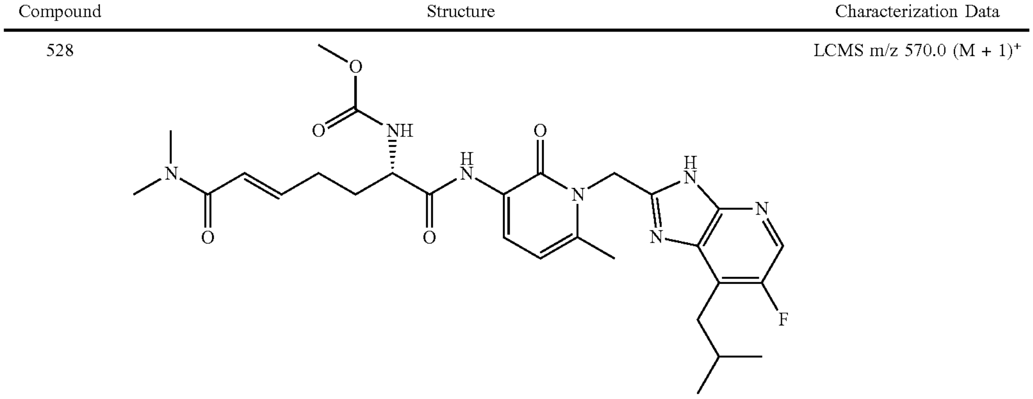 | LCMS m/z 570.0 $(M + 1)^+$ |
| 529 | 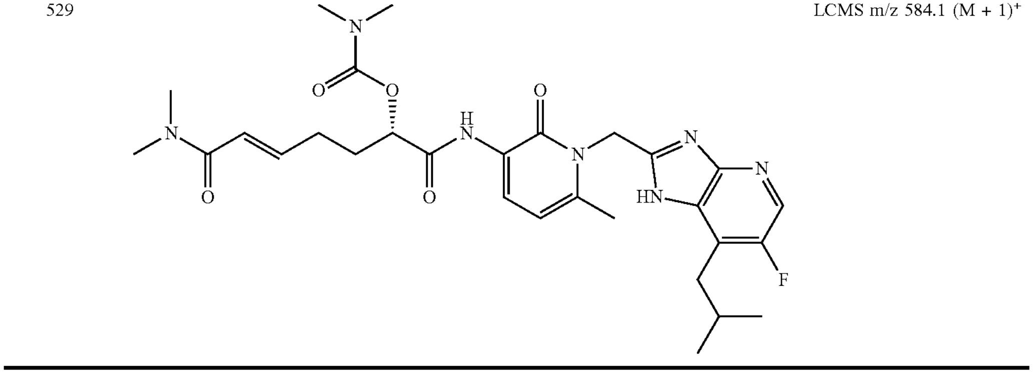 | LCMS m/z 584.1 $(M + 1)^+$ |
Example 106
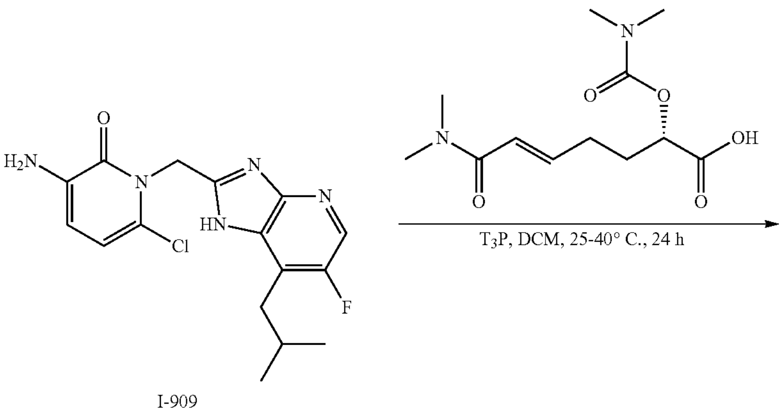
I-909

-continued

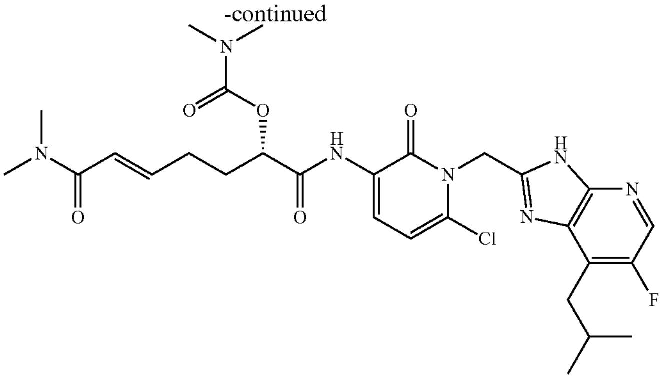

560

Compound 560 was prepared according to the procedures for Example 70 using the appropriate intermediates. H NMR (400 MHz, DMSO-$d_6$) δ 0.85 (br s, 6H) 1.83-2.10 (m, 3H) 2.21-2.35 (m, 2H) 2.71-2.84 (m, 8H) 2.87-3.01 (m, 6H) 5.09 (dd, J=7.50, 4.63 Hz, 1H) 5.63 (s, 2H) 6.37 (d, J=14.99 Hz, 1H) 6.57-6.67 (m, 2H) 8.22 (br d, J=8.16 Hz, 2H) 9.41 (br s, 1H) 12.89-13.33 (m, 1H). LCMS m/z 604.2 $(M+1)^+$.

The following compound was prepared according to the procedures described in Example 106 using the appropriate intermediates.

| Compound | Structure | Characterization Data |
|---|---|---|
| 545 | 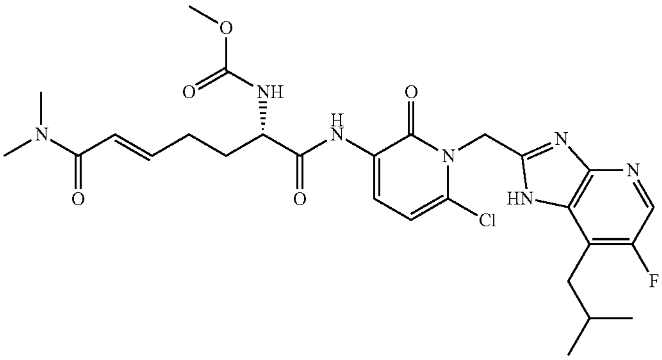 [SMILES: COC(=O)N[C@@H](CC/C=C/C(=O)N(C)C)C(=O)Nc1ccc(Cl)n(Cc2nc3ncc(F)c(CC(C)C)c3[nH]2)c1=O] | LCMS m/z 590.2 $(M + 1)^+$ |

Example 107

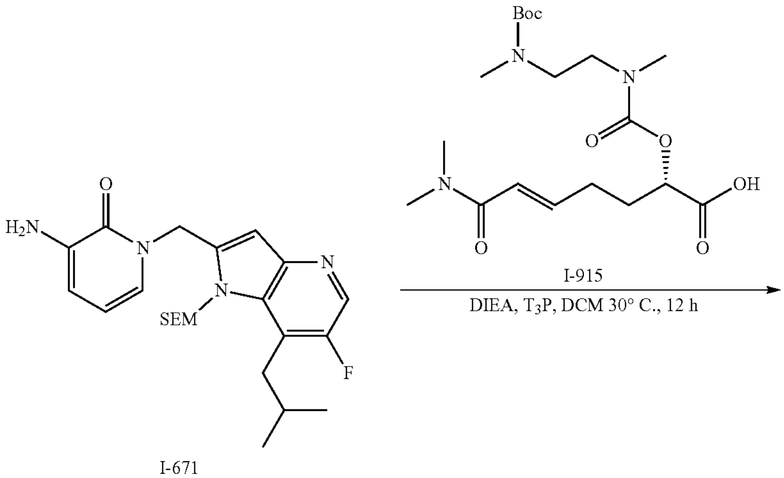

I-671

-continued

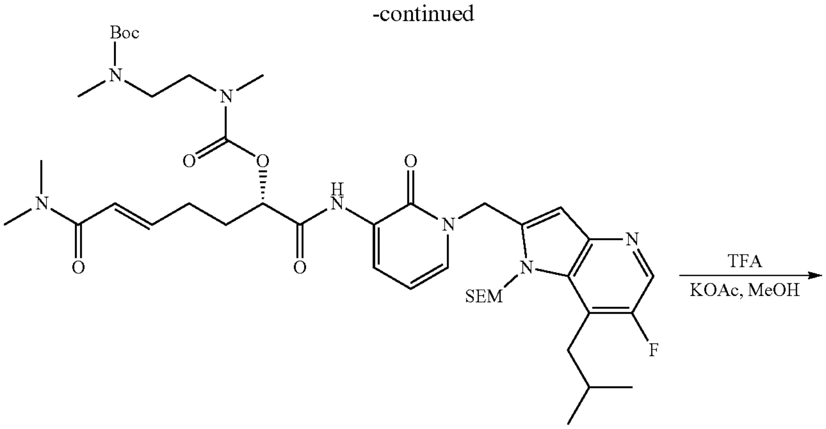

I-916

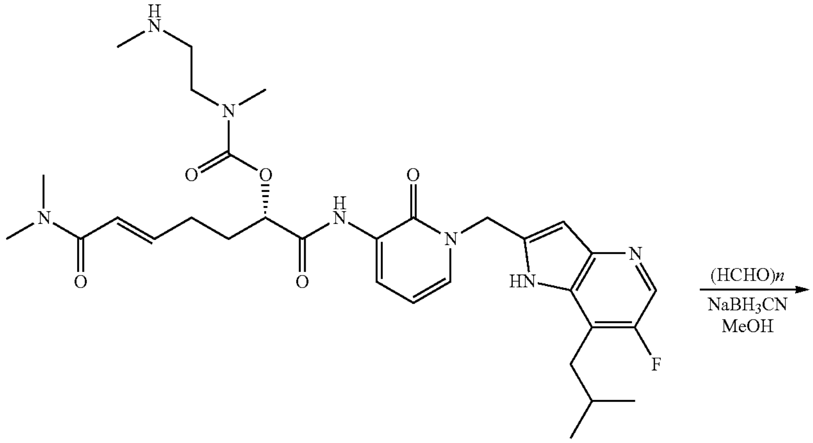

I-917

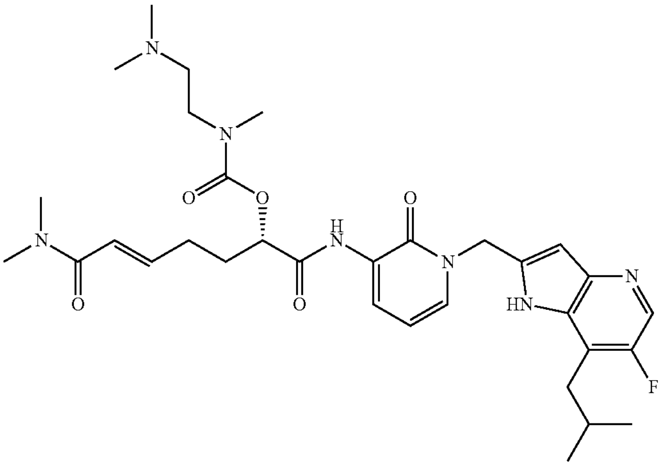

543

A solution of 3-amino-1-[[6-fluoro-7-isobutyl-1-(2-trimethylsilylethoxymethyl) pyrrolo[3,2-b]pyridin-2-yl]methyl] pyridin-2-one (150 mg, 337 umol, 1 eq), (E,2S)-2-[2-[tert-butoxycarbonyl(methyl)amino]ethyl-methyl-carbamoyl] oxy-7-(dimethylamino)-7-oxo-hept-5-enoic acid (168 mg, 405 umol, 1.2 eq), DIEA (349 mg, 2.70 mmol, 8 eq) and $T_3P$ (859 mg, 1.35 mmol, 50% purity, 4 eq) in DCM (3 mL) was stirred at 30° C. for 36 h. Water (10 mL) was added to the mixture. The mixture was extracted with EtOAc (10 mL×3). The combined organic layers were washed with brine (20 mL), dried over $Na_2SO_4$ and filtered. The filtrate was concentrated under reduced pressure to give 327 mg crude product. The residue was purified by prep-TLC ($SiO_2$) to give [(E,1S)-6-(dimethylamino)-1-[[1-[[6-fluoro-7-isobutyl-1-(2-trimethylsilylethoxymethyl)pyrrolo[3,2-b] pyridin-2-yl]methyl]-2-oxo-3-pyridyl]carbamoyl]-6-oxo-hex-4-enyl]N-[2-[tert-butoxycarbonyl(methyl)amino] ethyl]-N-methyl-carbamate (I-916) (180 mg, 63% yield) as a yellow oil. LCMS m/z 842.4 $(M+1)^+$.

A solution of [(E,1S)-6-(dimethylamino)-1-[[1-[[6-fluoro-7-isobutyl-1-(2-trimethylsilylethoxymethyl)pyrrolo [3,2-b]pyridin-2-yl]methyl]-2-oxo-3-pyridyl]carbamoyl]-6- oxo-hex-4-enyl]N-[2-[tert-butoxycarbonyl(methyl)amino] ethyl]-N-methyl-carbamate (160 mg, 190 umol, 1 eq) in TFA (2 mL) was stirred at 25° C. for 0.5 h. The mixture was concentrated to remove TFA. The residue was dissolved in MeOH (3 mL) adjusted to pH 7 by adding $NaHCO_3$. Then KOAc (37.3 mg, 380 umol, 2 eq) was added to the mixture, and stirred for 1 h. The mixture was filtered and the filtrate was concentrated to give [(E,1S)-6-(dimethylamino)-1-[[1-[(6-fluoro-7-isobutyl-1H-pyrrolo[3,2-b]pyridin-2-yl) methyl]-2-oxo-3-pyridyl]carbamoyl]-6-oxo-hex-4-enyl]N-methyl-N-[2-(methylamino)ethyl]carbamate (I-917) (180 mg) as a yellow oil. LCMS m/z 612.1 $(M+1)^+$.

A solution of [(E,1S)-6-(dimethylamino)-1-[[1-[(6-fluoro-7-isobutyl-1H-pyrrolo [3,2-b]pyridin-2-yl)methyl]-2-oxo-3-pyridyl]carbamoyl]-6-oxo-hex-4-enyl]N-methyl-N-[2-(methylamino)ethyl]carbamate (100 mg, 163 umol, 1 eq) and paraformaldehyde (30 mg, 16.3 umol) in MeOH (4 mL) was stirred at 25° C. for 13 h. The reaction mixture was quenched by addition $H_2O$ (5 mL) and concentrated in vacuum to remove most of MeOH. Then the mixture was extracted with EtOAc (4 mL*3) and the combined organic layer was washed with brine (5 mL), dried over $Na_2SO_4$ and concentrated in vacuum to give a residue. The residue was purified by prep-HPLC to give [(E,1S)-6-(dimethylamino)-1-[[1-[(6-fluoro-7-isobutyl-1H-pyrrolo[3,2-b]pyridin-2-yl) methyl]-2-oxo-3-pyridyl]carbamoyl]-6-oxo-hex-4-enyl]N-[2-(dimethylamino)ethyl]-N-methyl-carbamate (Compound 543) (15.5 mg, 14.1% yield) as a light yellow oil. LCMS m/z 626.4 $(M+1)^+$. $^1H$ NMR (400 MHz, DMSO-$d_6$) δ 11.58 (br s, 1H) 9.36 (br d, J=8.8 Hz, 1H) 8.21 (br d, J=2.0 Hz, 2H) 7.51 (dd, J=6.8, 1.2 Hz, 1H) 6.59-6.70 (m, 1H) 6.26-6.44 (m, 3H) 5.34 (s, 2H) 5.11 (br s, 1H) 3.50 (br s, 3H) 2.97 (s, 5H) 2.71-2.87 (m, 7H) 2.26-2.34 (m, 2H) 2.17 (brd, J=16.8 Hz, 6H) 1.88-2.04 (m, 3H) 0.91 (d, J=6.4 Hz, 6H).

Example 108

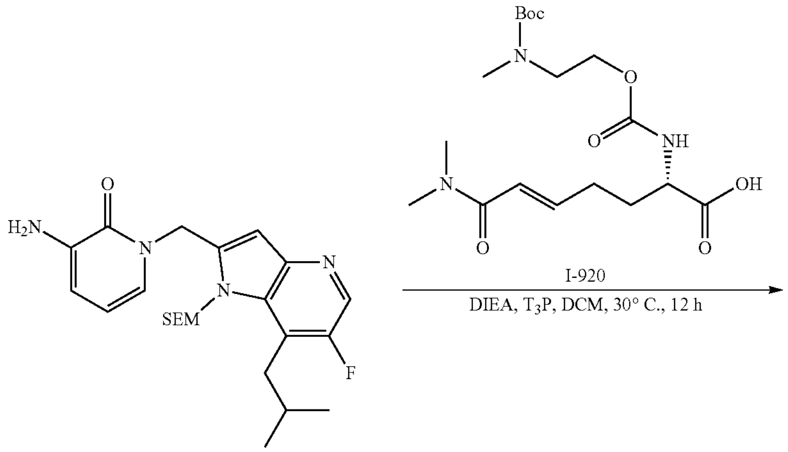

I-920

I-671

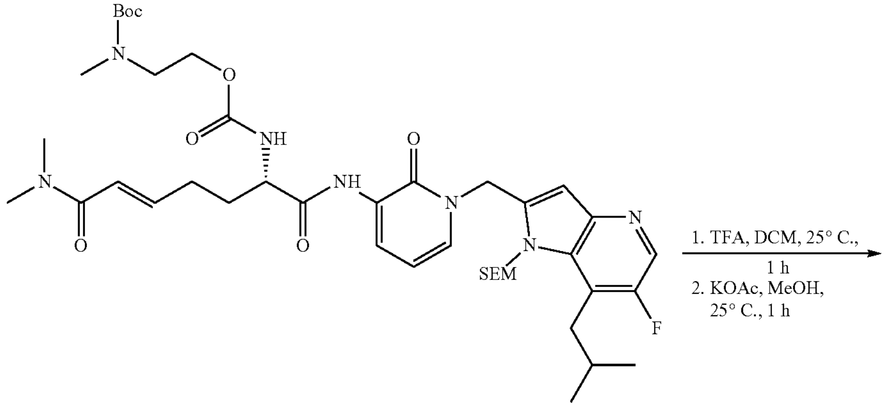

I-921

-continued

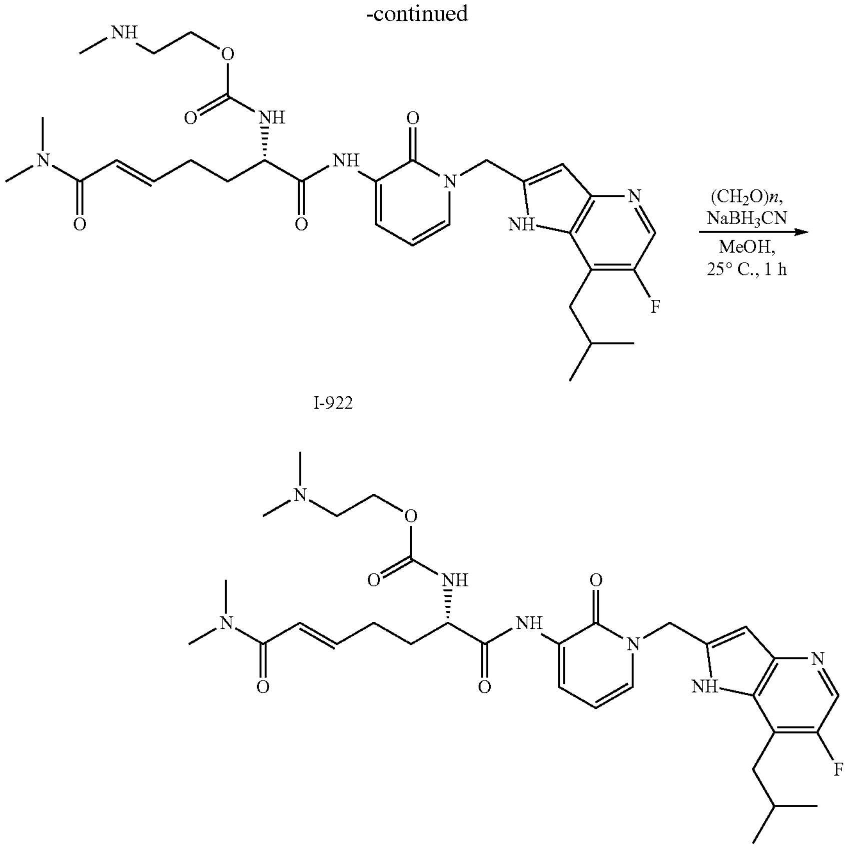

I-922

547

To a solution of (E,2S)-2-[2-[tert-butoxycarbonyl(methyl)amino]ethoxycarbonyl amino]-7-(dimethylamino)-7-oxo-hept-5-enoic acid (198.64 mg, 494.81 umol, 1 eq) and 3-amino-1-[[6-fluoro-7-isobutyl-1-(2-trimethylsilylethoxymethyl)pyrrolo[3,2-b]pyridin-2-yl]methyl]pyridin-2-one (220 mg, 494.81 umol, 1 eq) in DCM (3 mL) was added $T_3P$ (629.75 mg, 989.62 umol, 588.55 uL, 50% purity, 2 eq) and DIEA (191.85 mg, 1.48 mmol, 258.55 uL, 3 eq) at 25° C. The mixture was stirred at 25° C. for 24 hrs. The reaction mixture was partitioned between water 5 mL and ethyl acetate 5 mL. The organic phase was separated, washed with brine 5 mL (5 mL*1), dried over anhydrous $Na_2SO_4$, filtered and concentrated under reduced pressure to give a residue. The residue was purified by prep-TLC ($SiO_2$) to give tert-butyl N-[2-[[(E,1S)-6-(dimethylamino)-1-[[1-[[6-fluoro-7-isobutyl-1-(2-trimethylsilylethoxymethyl)pyrrolo[3,2-b]pyridin-2-yl]methyl]-2-oxo-3-pyridyl]carbamoyl]-6-oxo-hex-4-enyl]carbamoyloxy]ethyl]-N-methyl-carbamate (I-921) (240 mg, 59% yield) as a brown oil. LCMS m/z 828.5 $(M+1)^+$.

A mixture of tert-butyl N-[2-[[(E,1S)-6-(dimethylamino)-1-[[1-[[6-fluoro-7-isobutyl-1-(2-trimethylsilylethoxymethyl)pyrrolo[3,2-b]pyridin-2-yl]methyl]-2-oxo-3-pyridyl]carbamoyl]-6-oxo-hex-4-enyl]carbamoyloxy]ethyl]-N-methyl-carbamate (140 mg, 169.07 umol, 1 eq) in TFA (1 mL) was stirred at 25° C. for 1 hr. Then the reaction mixture was concentrated, and then dissolved in MeOH (1 mL), KOAc (16.59 mg, 169.07 umol, 1 eq) was added, and the result reaction mixture was stirred at 40° C. for 1 hr. The reaction mixture was filtered and the filtrate was concentrated under reduced pressure to remove the solvent to afford a brown residue. The crude product 2-(methylamino)ethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate (I-922) (100 mg) was used into the next step without further purification as a brown oil. LCMS m/z 598.4 $(M+1)^+$.

To a solution of 2-(methylamino)ethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate (100 mg, 167.31 umol, 1 eq) in MeOH (1 mL) was added $(HCHO)_n$ (20 mg, 200.78 umol) at 25° C. The mixture was stirred at 25° C. for 0.5 hr. Then $NaBH_3CN$ (52.57 mg, 836.57 umol, 5 eq) was added at 25° C., the result reaction mixture was stirred at 25° C. for additional 11.5 hrs. The reaction mixture was filtered and purified by prep-HPLC to give 2-(dimethylamino)ethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate (Compound 547) (33.1 mg, 32% yield) as a yellow solid. LCMS m/z 612.3 $(M+1)^+$. $^1H$ NMR (400 MHz, DMSO-$d_6$) δ 11.55 (s, 1H), 9.30 (s, 1H), 8.25-8.18 (m, 2H), 7.79 (br d, J=7.6 Hz, 1H), 7.49 (br d, J=6.5 Hz, 1H), 6.68-6.53 (m, 1H), 6.41-6.25 (m, 3H), 5.32 (s, 2H), 4.22-4.13 (m, 1H), 4.08-4.01 (m, 2H), 2.99 (s, 3H), 2.83 (s, 3H), 2.76 (br d, J=7.5 Hz, 2H), 2.30-2.07 (m, 9H), 2.01 (dt, J=6.8, 13.7 Hz, 2H), 1.91-1.67 (m, 2H), 0.91 (d, J=6.5 Hz, 6H).

The following compounds was prepared according to the procedures described in the previous examples using the appropriate intermediates.

| Compound | Structure | Characterization Data |
| --- | --- | --- |
| 600 | 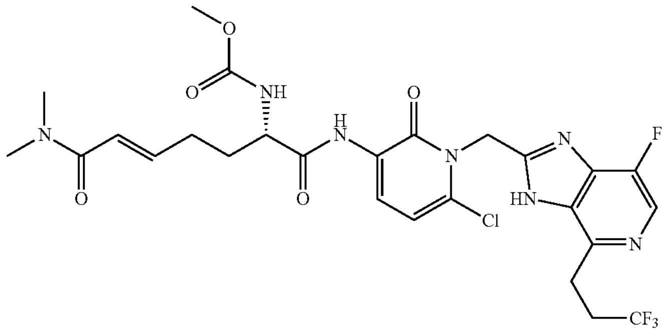 [SMILES: COC(=O)N[C@@H](CC/C=C/C(=O)N(C)C)C(=O)Nc1ccc(Cl)n(Cc2nc3c(F)cnc(CCC(F)(F)F)c3[nH]2)c1=O] | LCMS m/z 630.2 $(M + 1)^+$ |
| 601 | 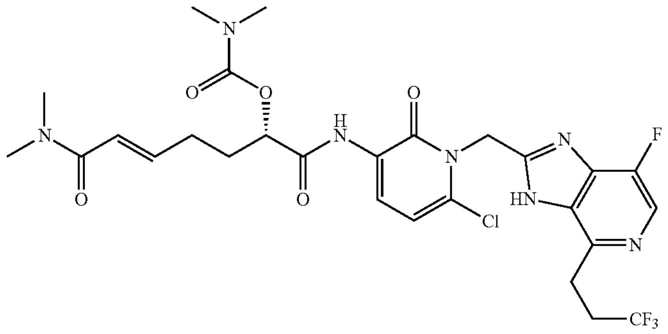 [SMILES: CN(C)C(=O)/C=C/CC[C@H](OC(=O)N(C)C)C(=O)Nc1ccc(Cl)n(Cc2nc3c(F)cnc(CCC(F)(F)F)c3[nH]2)c1=O] | LCMS m/z 644.2 $(M + 1)^+$ |
| 602 | 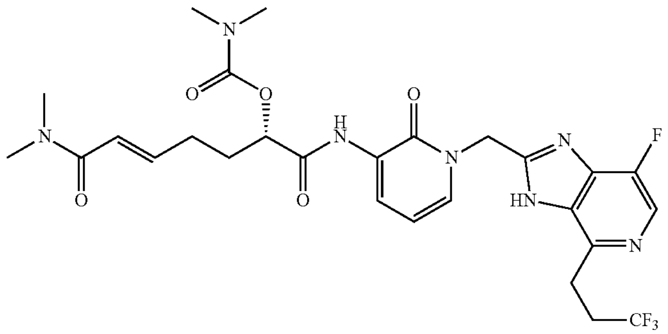 [SMILES: CN(C)C(=O)/C=C/CC[C@H](OC(=O)N(C)C)C(=O)Nc1cccn(Cc2nc3c(F)cnc(CCC(F)(F)F)c3[nH]2)c1=O] | LCMS m/z 610.3 $(M + 1)^+$ |
| 603 | 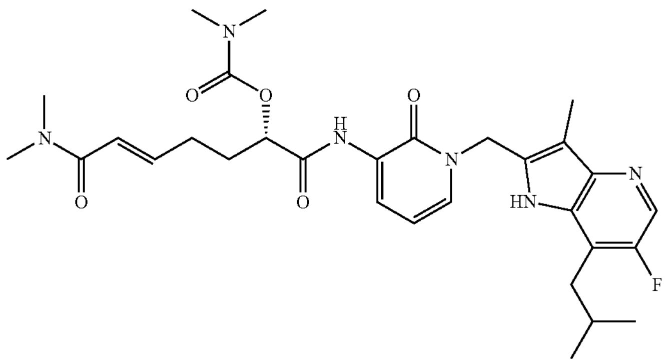 [SMILES: Cc1c(Cn2cccc(NC(=O)[C@H](CC/C=C/C(=O)N(C)C)OC(=O)N(C)C)c2=O)[nH]c2c(CC(C)C)c(F)cnc12] | LCMS m/z 583.2 $(M + 1)^+$ |

-continued
| Compound | Structure | Characterization Data |
| --- | --- | --- |
| 604 | 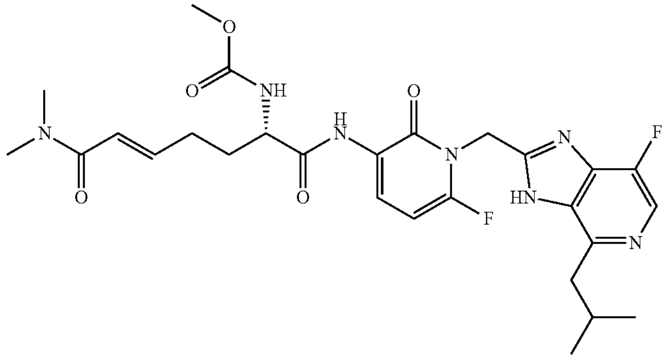 | LCMS m/z 574.2 $(M + 1)^+$ |
| 605 | 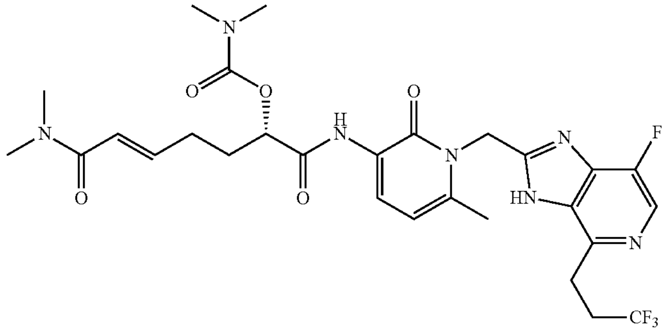 [SMILES: Cc1ccc(NC(=O)[C@H](CC/C=C/C(=O)N(C)C)OC(=O)N(C)C)c(=O)n1Cc1nc2c(F)cnc(CCC(F)(F)F)c2[nH]1] | LCMS m/z 624.2 $(M + 1)^+$ |
| 606 | 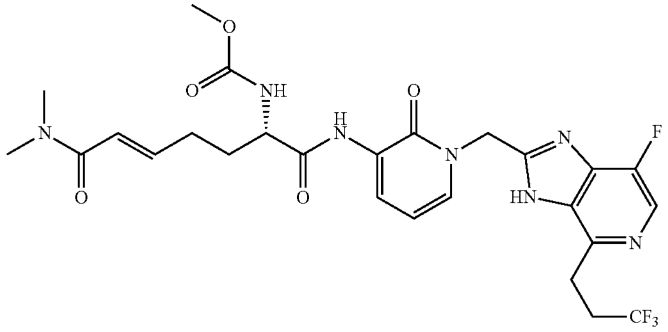 | LCMS m/z 596.3 $(M + 1)^+$ |
| 607 | 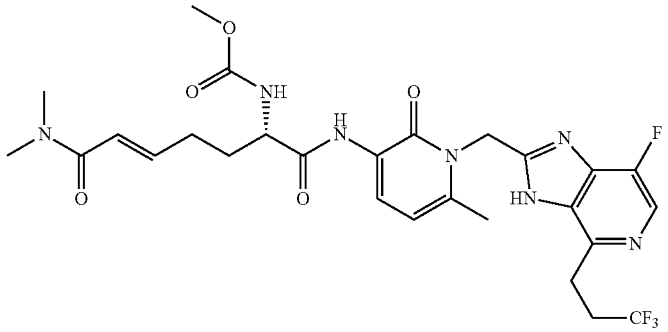 [SMILES: COC(=O)N[C@@H](CC/C=C/C(=O)N(C)C)C(=O)Nc1ccc(C)n(Cc2nc3c(F)cnc(CCC(F)(F)F)c3[nH]2)c1=O] | LCMS m/z 610.2 $(M + 1)^+$ |

-continued
| Compound | Structure | Characterization Data |
|---|---|---|
| 608 | 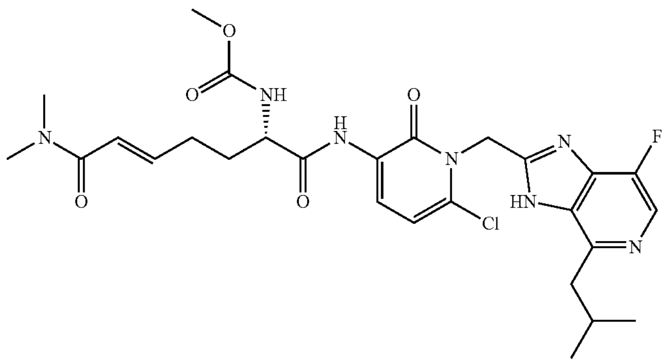 [SMILES: COC(=O)N[C@@H](CC/C=C/C(=O)N(C)C)C(=O)Nc1ccc(Cl)n(Cc2nc3c(F)cnc(CC(C)C)c3[nH]2)c1=O] | LCMS m/z 590.2 (M + 1)+ |
| 609 | 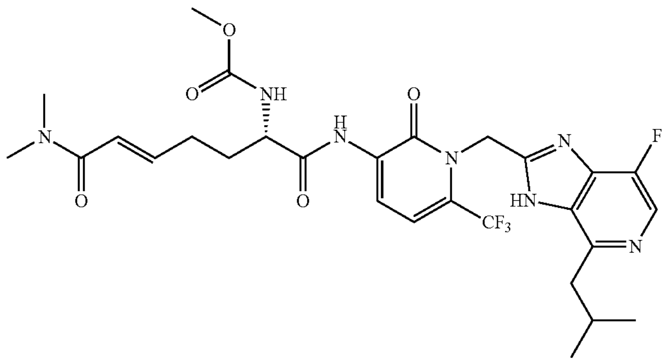 [SMILES: COC(=O)N[C@@H](CC/C=C/C(=O)N(C)C)C(=O)Nc1ccc(C(F)(F)F)n(Cc2nc3c(F)cnc(CC(C)C)c3[nH]2)c1=O] | LCMS m/z 624.3 (M + 1)+ |
| 610 | 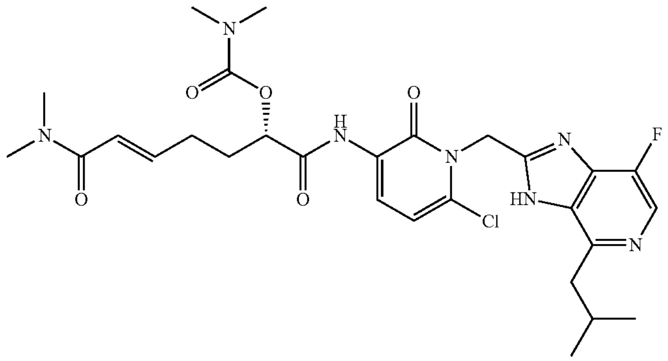 | LCMS m/z 604.2 (M + 1)+ |
| 611 | 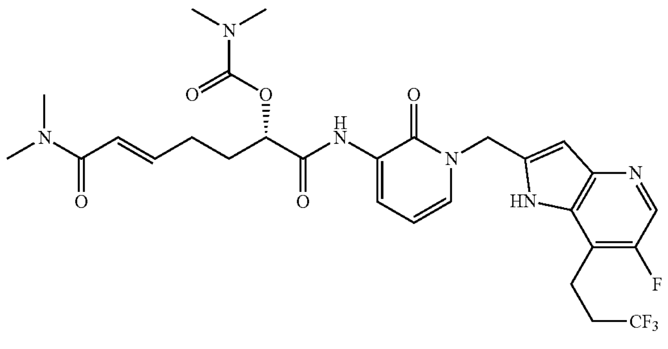 [SMILES: CN(C)C(=O)/C=C/CC[C@H](OC(=O)N(C)C)C(=O)Nc1cccn(Cc2cc3ncc(F)c(CCC(F)(F)F)c3[nH]2)c1=O] | LCMS m/z 609.2 (M + 1)+ |

-continued

| Compound | Structure | Characterization Data |
|---|---|---|
| 612 | 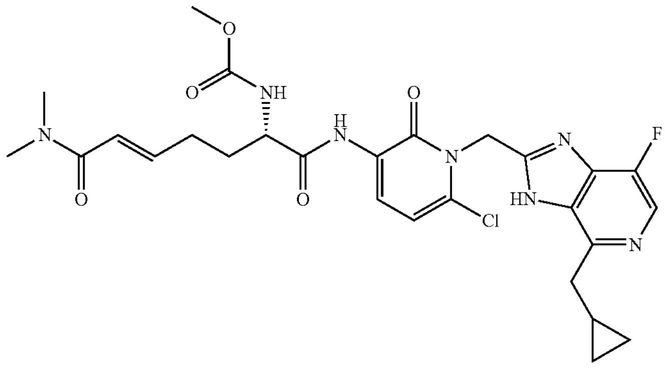 | LCMS m/z 588.3 $(M + 1)^+$ |
| 613 | 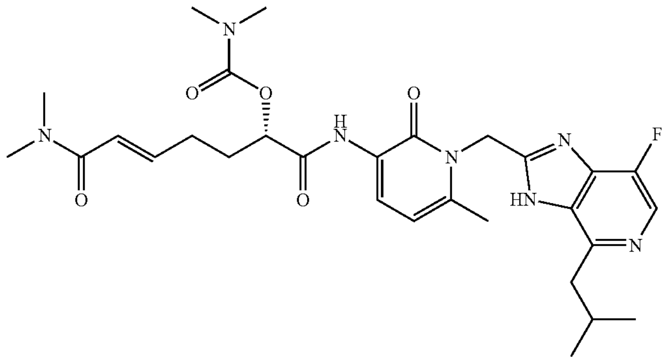 | LCMS m/z 584.3 $(M + 1)^+$ |
| 614 | 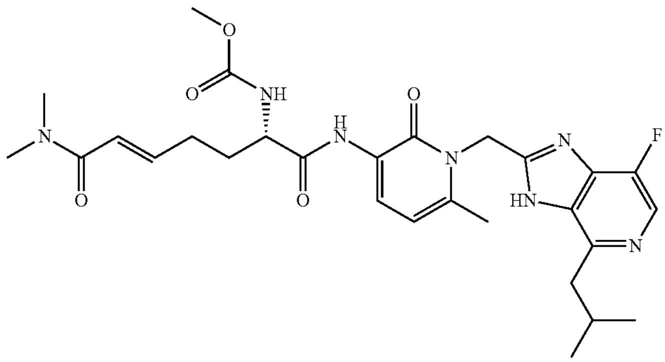 [SMILES: COC(=O)N[C@@H](CC/C=C/C(=O)N(C)C)C(=O)Nc1ccc(C)n(Cc2nc3c(F)cnc(CC(C)C)c3[nH]2)c1=O] | LCMS m/z 570.2 $(M + 1)^+$ |

Biological Evaluation

Example 1A: Transglutaminase (TG) Inhibitor Assay

The assay relies on the ability of active TG to crosslink amine donor groups, such as lysine found in proteins or peptides or other free amines present in small molecule substrates, onto specific protein glutamine sites (amine acceptor). Using the fluorescent amine donor, dansyl cadaverine (DSC), and the multiple glutamine bearing amine acceptor N,N-dimethylated casein (NMC), TG activity was measured via the change in fluorescence of cross-linked DSC into NMC over time. The ability of test compounds to block the formation of these crosslinks at various compound concentrations provides a measurement of TG inhibitor performance.

Distribute test compounds across 96 well plate in an 8 point titration at 5 µL/well and 20× desired final concentration.

At timer=0 min, starting from a 1.12× concentration of TG in reaction buffer, add TG to plate at 90 µL/well (also include no TG controls=1.12× buffer only).

At timer=10 min or 30 min, starting from 20× final concentration of TG substrates NMC and DSC, add substrates at 5 µL/well.

At timer=90 min, measure fluorescence of all wells in a plate reader.

Export raw data and analyze to determine $IC_{50}$ of each compound tested.

The IC50 data for the test compounds is shown in Table 1.

TABLE 1

| Compd | TG2 $IC_{50}$ |
|---|---|
| 1 | A |
| 2 | A |

TABLE 1-continued

| Compd | TG2 $IC_{50}$ |
|---|---|
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | B |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | B |
| 46 | A |
| 47 | B |
| 48 | B |
| 49 | A |
| 50 | A |
| 51 | B |
| 52 | B |
| 53 | B |
| 54 | B |
| 55 | B |
| 57 | A |
| 58 | A |
| 59 | B |
| 60 | A |
| 61 | A |
| 62 | B |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |

TABLE 1-continued

| Compd | TG2 $IC_{50}$ |
|---|---|
| 82 | B |
| 83 | B |
| 84 | A |
| 85 | A |
| 86 | A |
| 87 | A |
| 88 | A |
| 89 | A |
| 90 | A |
| 91 | A |
| 92 | A |
| 93 | B |
| 94 | A |
| 95 | A |
| 96 | A |
| 97 | A |
| 98 | A |
| 99 | A |
| 100 | C |
| 101 | B |
| 102 | A |
| 103 | A |
| 104 | A |
| 105 | A |
| 106 | A |
| 107 | A |
| 108 | A |
| 109 | A |
| 110 | A |
| 111 | B |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | B |
| 149 | A |
| 150 | A |
| 151 | A |
| 152 | A |
| 153 | B |
| 154 | A |
| 155 | A |
| 156 | A |
| 157 | A |
| 158 | A |
| 159 | A |

TABLE 1-continued

| Compd | TG2 $IC_{50}$ |
|---|---|
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | C |
| 174 | C |
| 175 | B |
| 176 | B |
| 177 | B |
| 178 | C |
| 179 | B |
| 180 | C |
| 181 | B |
| 182 | B |
| 183 | C |
| 184 | B |
| 185 | B |
| 186 | B |
| 187 | B |
| 188 | B |
| 189 | B |
| 190 | B |
| 191 | C |
| 192 | C |
| 193 | B |
| 194 | B |
| 195 | B |
| 196 | B |
| 197 | B |
| 198 | B |
| 199 | B |
| 200 | B |
| 201 | B |
| 202 | B |
| 203 | B |
| 204 | B |
| 205 | B |
| 206 | B |
| 207 | B |
| 208 | B |
| 209 | A |
| 210 | C |
| 211 | B |
| 212 | B |
| 213 | A |
| 214 | B |
| 215 | B |
| 216 | B |
| 217 | A |
| 218 | A |
| 219 | A |
| 220 | B |
| 221 | B |
| 222 | A |
| 223 | B |
| 224 | A |
| 225 | B |
| 226 | C |
| 227 | A |
| 228 | A |
| 229 | A |
| 230 | A |
| 231 | A |
| 232 | A |
| 233 | A |
| 234 | A |
| 235 | B |
| 236 | A |
| 237 | A |

TABLE 1-continued

| Compd | TG2 $IC_{50}$ |
|---|---|
| 238 | A |
| 239 | B |
| 240 | A |
| 241 | A |
| 242 | B |
| 243 | A |
| 244 | C |
| 245 | A |
| 246 | A |
| 247 | B |
| 248 | A |
| 249 | C |
| 250 | A |
| 251 | B |
| 252 | A |
| 253 | C |
| 254 | A |
| 255 | A |
| 256 | B |
| 257 | A |
| 258 | A |
| 259 | A |
| 260 | A |
| 261 | A |
| 262 | A |
| 263 | B |
| 264 | B |
| 265 | A |
| 266 | A |
| 267 | A |
| 268 | B |
| 269 | B |
| 270 | A |
| 271 | A |
| 272 | B |
| 273 | A |
| 274 | A |
| 275 | A |
| 276 | B |
| 277 | A |
| 278 | A |
| 279 | A |
| 280 | B |
| 281 | A |
| 282 | B |
| 285 | C |
| 286 | B |
| 287 | B |
| 288 | A |
| 289 | B |
| 290 | A |
| 291 | B |
| 292 | A |
| 293 | B |
| 294 | A |
| 295 | A |
| 296 | C |
| 297 | B |
| 298 | A |
| 299 | A |
| 300 | C |
| 301 | A |
| 302 | B |
| 303 | C |
| 304 | B |
| 305 | A |
| 307 | B |
| 308 | A |
| 309 | A |
| 310 | C |
| 311 | A |
| 312 | A |
| 313 | B |
| 314 | A |
| 315 | B |
| 316 | B |
| 317 | A |
| 318 | A |

TABLE 1-continued

| Compd | TG2 $IC_{50}$ |
|---|---|
| 319 | A |
| 320 | A |
| 321 | A |
| 322 | A |
| 323 | A |
| 325 | A |
| 326 | A |
| 327 | A |
| 328 | A |
| 329 | B |
| 330 | A |
| 331 | A |
| 332 | B |
| 333 | A |
| 334 | B |
| 335 | B |
| 336 | B |
| 337 | B |
| 338 | B |
| 339 | B |
| 340 | B |
| 341 | B |
| 342 | A |
| 343 | B |
| 344 | A |
| 345 | A |
| 346 | A |
| 347 | A |
| 348 | A |
| 349 | B |
| 350 | A |
| 351 | B |
| 352 | C |
| 353 | A |
| 354 | A |
| 355 | A |
| 356 | A |
| 357 | A |
| 358 | A |
| 359 | A |
| 360 | B |
| 361 | A |
| 362 | A |
| 363 | A |
| 364 | A |
| 365 | A |
| 366 | A |
| 367 | A |
| 368 | A |
| 369 | A |
| 370 | A |
| 371 | A |
| 372 | A |
| 373 | A |
| 374 | B |
| 375 | A |
| 376 | B |
| 377 | A |
| 378 | A |
| 379 | A |
| 380 | A |
| 381 | A |
| 382 | B |
| 383 | A |
| 384 | C |
| 385 | A |
| 386 | B |
| 387 | B |
| 388 | A |
| 389 | A |
| 390 | A |
| 391 | A |
| 393 | B |
| 394 | B |
| 396 | C |
| 397 | B |
| 398 | A |
| 399 | A |

TABLE 1-continued

| Compd | TG2 $IC_{50}$ |
|---|---|
| 400 | A |
| 401 | A |
| 402 | A |
| 403 | A |
| 404 | A |
| 405 | A |
| 406 | A |
| 407 | A |
| 408 | B |
| 409 | A |
| 410 | A |
| 411 | B |
| 412 | A |
| 413 | B |
| 414 | A |
| 416 | A |
| 417 | A |
| 418 | B |
| 419 | B |
| 420 | B |
| 421 | A |
| 422 | B |
| 423 | A |
| 424 | A |
| 425 | A |
| 426 | B |
| 427 | B |
| 428 | B |
| 429 | B |
| 430 | B |
| 431 | A |
| 432 | A |
| 433 | B |
| 434 | A |
| 435 | B |
| 436 | B |
| 437 | A |
| 438 | A |
| 439 | A |
| 440 | B |
| 441 | A |
| 442 | A |
| 443 | A |
| 444 | B |
| 445 | B |
| 446 | A |
| 447 | A |
| 448 | A |
| 449 | B |
| 450 | A |
| 451 | A |
| 452 | B |
| 453 | A |
| 454 | A |
| 455 | A |
| 456 | A |
| 457 | B |
| 458 | A |
| 459 | A |
| 460 | A |
| 461 | A |
| 462 | B |
| 463 | A |
| 464 | A |
| 465 | A |
| 466 | A |
| 467 | A |
| 468 | A |
| 469 | A |
| 470 | A |
| 471 | A |
| 472 | A |
| 473 | A |
| 474 | A |
| 475 | B |
| 476 | A |
| 477 | B |
| 478 | A |

TABLE 1-continued

| Compd | TG2 $IC_{50}$ |
|---|---|
| 479 | A |
| 480 | A |
| 481 | A |
| 482 | B |
| 483 | A |
| 484 | B |
| 485 | B |
| 486 | A |
| 487 | A |
| 488 | A |
| 489 | A |
| 490 | A |
| 491 | A |
| 492 | A |
| 493 | A |
| 494 | A |
| 495 | A |
| 496 | A |
| 497 | A |
| 498 | A |
| 499 | B |
| 500 | A |
| 501 | A |
| 502 | A |
| 503 | A |
| 504 | B |
| 505 | A |
| 506 | A |
| 507 | A |
| 508 | A |
| 509 | A |
| 510 | A |
| 511 | A |
| 512 | A |
| 513 | A |
| 514 | A |
| 515 | A |
| 516 | A |
| 517 | A |
| 518 | A |
| 519 | A |
| 520 | A |
| 521 | A |
| 522 | A |
| 523 | A |
| 524 | A |
| 525 | A |
| 526 | A |
| 527 | A |
| 528 | A |
| 529 | A |
| 530 | A |
| 531 | A |
| 532 | A |
| 533 | A |
| 534 | A |
| 535 | A |
| 536 | A |
| 537 | A |
| 538 | A |
| 539 | A |
| 540 | A |
| 541 | A |
| 542 | A |
| 543 | B |
| 544 | A |
| 545 | A |
| 546 | A |
| 547 | A |
| 548 | A |
| 549 | B |
| 550 | A |
| 551 | A |
| 552 | A |
| 553 | A |
| 554 | A |
| 555 | A |
| 556 | A |

TABLE 1-continued

| Compd | TG2 $IC_{50}$ |
|---|---|
| 557 | A |
| 558 | A |
| 559 | A |
| 560 | A |
| 561 | A |
| 562 | A |
| 563 | A |
| 564 | A |
| 565 | A |
| 566 | A |
| 568 | A |
| 569 | A |
| 570 | A |
| 571 | A |
| 572 | A |
| 573 | A |
| 574 | A |
| 575 | A |
| 576 | A |
| 577 | A |
| 578 | A |
| 579 | A |
| 580 | B |
| 581 | A |
| 582 | A |
| 583 | A |
| 584 | A |
| 585 | A |
| 586 | A |
| 587 | A |
| 588 | A |
| 589 | A |
| 590 | A |
| 591 | B |
| 592 | A |
| 593 | A |
| 594 | A |
| 595 | A |
| 596 | A |
| 597 | A |
| 598 | A |
| 599 | A |
| 600 | A |
| 601 | A |
| 602 | A |
| 603 | A |
| 604 | A |
| 605 | A |
| 606 | A |
| 607 | A |
| 608 | A |
| 609 | A |
| 610 | A |
| 611 | A |
| 612 | A |
| 613 | A |
| 614 | A |

A: $IC_{50} < 0.5$ μM;
B: 0.5 μM $\leq IC_{50} \leq$ 5 μM;
C: 5 μM $< IC_{50} <$ 100 μM

The invention claimed is:

1. A compound according to Formula (I) or a pharmaceutically acceptable salt thereof:

(I)

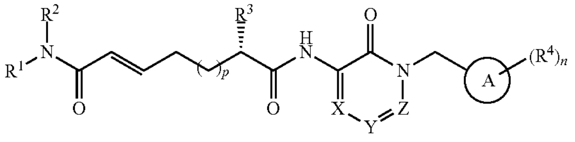

wherein:

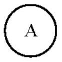

is a 9-membered bicyclic heteroaryl ring;

X, Y, and Z are selected from $=C(R^{11})-$ or $=N-$, wherein at least two of X, Y, and Z are $=C(R^{11})-$;

$R^1$ and $R^2$ are independently selected from H or optionally substituted alkyl; or $R^1$ and $R^2$, together with the nitrogen to which they are attached, form an optionally substituted 3-, 4-, 5- or 6-membered heterocycloalkyl ring;

$R^3$ is $-N(H)C(O)OR^5$, $-OC(O)NR^6R^7$, $-N(H)C(O)NR^6R^7$, or $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, optionally substituted alkyl, optionally substituted alkenyl, optionally substituted alkynyl, optionally substituted cycloalkyl, optionally substituted phenyl, or optionally substituted heteroaryl;

$R^5$ is selected from optionally substituted alkyl, optionally substituted heterocycloalkyl, optionally substituted phenyl, or optionally substituted heteroaryl;

$R^6$ and $R^7$ are independently selected from H or optionally substituted alkyl; or $R^6$ and $R^7$, together with the nitrogen to which they are attached, form an optionally substituted 5- or 6-membered heterocycloalkyl ring;

$R^8$ is selected from optionally substituted alkyl, optionally substituted cycloalkyl, optionally substituted phenyl, optionally substituted heterocycloalkyl, or optionally substituted heteroaryl;

each $R^9$ is independently selected from optionally substituted alkyl, optionally substituted cycloalkyl, optionally substituted phenyl, or optionally substituted heteroaryl;

each $R^{10}$ is independently selected from H, optionally substituted alkyl, optionally substituted cycloalkyl, optionally substituted phenyl, or optionally substituted heteroaryl;

each $R^{11}$ is independently selected from H, halogen, or optionally substituted alkyl;

n is 0, 1, 2, 3, or 4; and p is 0, 1, or 2.

2. A compound according to Formula (II) or a pharmaceutically acceptable salt thereof:

(II)

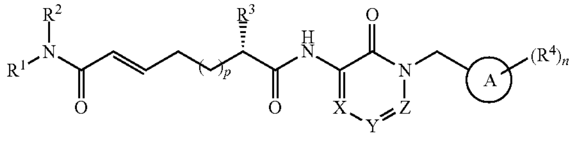

wherein:

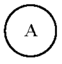

is a 9-membered bicyclic heteroaryl ring;

X, Y, and Z are selected from $=C(R^{11})-$ or $=N-$, wherein at least two of X, Y, and Z are $=C(R^{11})-$;

$R^1$ and $R^2$ are independently selected from H, $C_{1-6}$alkyl, and $-C_{1-6}$alkyl-OH; or $R^1$ or $R^2$, together with the nitrogen to which they are attached, form a 3-, 4-, 5- or 6-membered heterocycloalkyl ring optionally substituted with one or two groups independently selected from halogen or $C_{1-6}$alkyl;

$R^3$ is selected from $-N(H)C(O)OR^5$, $-OC(O)NR^6R^7$, $-N(H)C(O)NR^6R^7$, or $-N(H)C(O)R^8$;

each $R^4$ is independently selected from halogen, $-CN$, $-OR^9$, $-SR^9$, $-N(R^{10})_2$, $-S(O)R^9$, $-S(O)_2R^9$, $-NHS(O)_2R^9$, $-S(O)_2N(R^{10})_2$, $-C(O)R^9$, $-C(O)OR^9$, $-OC(O)R^9$, $-C(O)N(R^{10})_2$, $-OC(O)N(R^{10})_2$, $-NR^{10}C(O)N(R^{10})_2$, $-NR^{10}C(O)R^9$, $-NR^{10}C(O)OR^9$, $C_{1-10}$alkyl, $C_{1-10}$alkyl-OH, $C_{1-10}$alkyl-$OR^9$, $C_{2-10}$alkenyl, $C_{2-10}$alkynyl, $C_{1-10}$haloalkyl, $C_{1-10}$haloalkyl-OH, $C_{2-10}$haloalkenyl, $C_{3-12}$cycloalkyl, $-C_{1-6}$alkyl-$C_{3-12}$cycloalkyl, $-C_{2-6}$alkenyl-$C_{3-12}$cycloalkyl, phenyl, $-C_{1-6}$alkyl-phenyl, $-C_{2-6}$alkenyl-phenyl, $C_{2-9}$heterocycloalkyl, or $C_{2-9}$heteroaryl, wherein phenyl, $-C_{1-6}$alkyl-phenyl, $-C_{2-6}$alkenyl-phenyl, $C_{2-9}$heterocycloalkyl, and $C_{2-9}$heteroaryl are optionally substituted with one, two, or three groups independently selected from halogen or $C_{1-6}$alkyl;

$R^5$ is selected from $C_{1-6}$alkyl, $-C_{1-6}$alkyl-OH, $-C_{1-6}$alkyl-O$-C_{1-6}$alkyl, $-C_{1-6}$alkyl-O$-C(O)C_{1-6}$alkyl, $C_{2-9}$heterocycloalkyl, $-C_{1-6}$alkyl-$C_{2-9}$heterocycloalkyl, phenyl, $C_{1-6}$alkyl-phenyl, or $C_{2-9}$heteroaryl, wherein $C_{2-9}$heterocycloalkyl, $-C_{1-6}$alkyl-$C_{2-9}$heterocycloalkyl, phenyl, $-C_{1-6}$alkyl-phenyl, and $C_{2-9}$heteroaryl are optionally substituted with one or two groups independently selected from halogen or $C_{1-6}$alkyl;

$R^6$ and $R^7$ are independently selected from H, $C_{1-6}$alkyl, $-C_{1-6}$alkyl-OH, $-C_{1-6}$alkyl-O$-C_{1-6}$alkyl, or $-C_{1-6}$alkyl-$N(C_{1-6}$alkyl$)_2$; or $R^6$ and $R^7$, together with the nitrogen to which they are attached, form a 5- or 6-membered heterocycloalkyl ring optionally substituted with one or two groups independently selected from halogen or $C_{1-6}$alkyl;

$R^8$ is selected from $C_{1-6}$alkyl, $C_{1-6}$haloalkyl, $-C_{1-6}$alkyl-OH, $-C_{1-6}$alkyl-O$-C_{1-6}$alkyl, $C_{3-6}$cycloalkyl, phenyl, $C_{2-9}$heterocycloalkyl, or $C_{2-9}$heteroaryl, wherein $C_{3-6}$cycloalkyl, phenyl, $C_{2-9}$heterocycloalkyl, and $C_{2-9}$heteroaryl are optionally substituted with one or two groups independently selected from halogen or $C_{1-6}$alkyl;

each $R^9$ is independently selected from $C_{1-10}$ alkyl, $C_{1-10}$haloalkyl, $C_{3-12}$cycloalkyl, $-C_{1-6}$alkyl-$C_{3-12}$cycloalkyl, phenyl, $-C_{1-6}$alkyl-phenyl, or $C_{2-9}$heteroaryl, wherein phenyl, $-C_{1-6}$alkyl-phenyl, and $C_{2-9}$heteroaryl are optionally substituted with one or two groups independently selected from halogen or $C_{1-6}$alkyl;

each $R^{10}$ is independently selected from H, $C_{1-10}$alkyl, $C_{1-10}$haloalkyl, $C_{3-12}$cycloalkyl, $-C_{1-6}$alkyl-$C_{3-12}$cycloalkyl, phenyl, $-C_{1-6}$alkyl-phenyl, or $C_{2-9}$heteroaryl, wherein phenyl, $-C_{1-6}$alkyl-phenyl, and $C_{2-9}$heteroaryl are optionally substituted with one or two groups independently selected from halogen or $C_{1-6}$alkyl;

each $R^{11}$ is independently selected from H, halogen, $C_{1-6}$alkyl, or $C_{1-6}$haloalkyl;

n is 0, 1, 2, 3, or 4; and p is 0, 1, or 2.

3. The compound or pharmaceutically acceptable salt thereof according to claim 1, wherein X, Y, and Z are each $=C(R^{11})—$.

4. The compound or pharmaceutically acceptable salt thereof according to claim 3, wherein X and Y are each $=C(H)—$; and Z is $=C(CH)—$, $=C(CH_3)—$, or $=C(Cl)—$.

5. The compound or pharmaceutically acceptable salt thereof according to claim 4, wherein X, Y, and Z are each $=C(H)—$.

6. The compound or pharmaceutically acceptable salt thereof according to claim 1, wherein

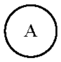

is selected from benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, or triazolopyrazinyl.

7. The compound or pharmaceutically acceptable salt thereof according to claim 6, wherein

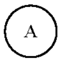

is selected from benzimidazolyl, imidazopyridinyl, purinyl, indoly, pyrrolopyridinyl, pyrrolopyrimidinyl, benzoxazolyl, or benzothiazolyl.

8. The compound or pharmaceutically acceptable salt thereof according to claim 7, wherein

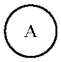

is selected from

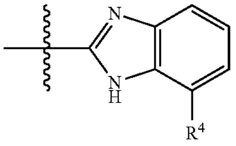

,

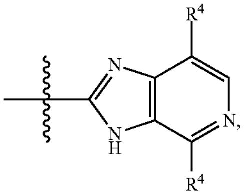

and

-continued

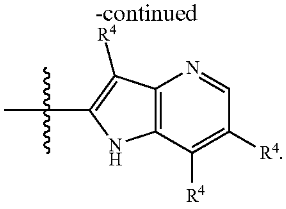

9. The compound or pharmaceutically acceptable salt thereof according to claim 8, wherein $R^4$ is independently selected from halogen or optionally substituted alkyl.

10. The compound or pharmaceutically acceptable salt thereof according to claim 9, wherein $R^4$ is independently selected from chloro, fluoro, methyl, ethyl, butyl, or isobutyl.

11. The compound or pharmaceutically acceptable salt thereof according to claim 1, wherein $R^1$ and $R^2$ are each $C_{1-6}$alkyl.

12. The compound or pharmaceutically acceptable salt thereof according to claim 11, wherein $R^1$ and $R^2$ are each $—CH_3$.

13. The compound or pharmaceutically acceptable salt thereof according to claim 1, wherein $R^3$ is selected from $—N(H)C(O)OR^5$ or $—OC(O)NR^6R^7$; $R^5$ is $C_{1-6}$alkyl; and $R^6$ and $R^7$ are independently selected from H or $C_{1-6}$alkyl.

14. The compound or pharmaceutically acceptable salt thereof according to claim 1, wherein:

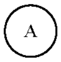

is benzimidazolyl, imidazopyridinyl, purinyl, indoly, pyrrolopyridinyl, pyrrolopyrimidinyl, benzoxazolyl, benzothiazolyl, imidazopyrazinyl, imidazopyridazinyl, pyrrolopyrazinyl, pyrrolopyridazinyl, oxazolopyridinyl, oxazolopyrimidinyl, oxazolopyrazinyl, oxazolopyridazinyl, benzofuranyl, furopyridinyl, furopyrimidinyl, furopyrazinyl, furopyridazinyl, thiazolopyridinyl, thiazolopyrimidinyl, thiazolopyrazinyl, thiazolopyridazinyl, benzothiophenyl, thienopyridinyl, thienopyrimidinyl, thienopyrazinyl, thienopyridazinyl, indolizinyl, pyrrolotriazinyl, imidazotriazinyl, triazolopyridinyl, triazolopyridazinyl, triazolopyrimidinyl, or triazolopyrazinyl;

X, Y, and Z are $=C(R^{11})—$;

$R^1$ and $R^2$ are independently selected from H or $C_{1-6}$alkyl, $R^3$ is selected from $—N(H)C(O)OR^5$ or $—OC(O)NR^6R^7$;

each $R^4$ is independently selected from halogen or $C_{1-10}$alkyl;

$R^5$ is $C_{1-6}$alkyl;

$R^6$ and $R^7$ are independently selected from H or $C_{1-6}$alkyl;

each $R^{11}$ is independently selected from H, halogen, or $C_{1-6}$alkyl;

n is 0, 1, 2, 3, or 4; and p is 0, 1, or 2.

15. The compound or pharmaceutically acceptable salt thereof according to claim 1, wherein:

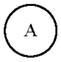

is benzimidazolyl, imidazopyridinyl, purinyl, indoly, pyrrolopyridinyl, pyrrolopyrimidinyl, benzoxazolyl, or benzothiazolyl;

X, Y, and Z are $=C(R^{11})-$;

$R^1$ and $R^2$ are independently selected from H or $C_{1-6}$alkyl, $R^3$ is selected from $-N(H)C(O)OR^5$ or $-OC(O)NR^6R^7$;

each $R^4$ is independently selected from halogen or $C_{1-10}$alkyl;

$R^5$ is $C_{1-6}$alkyl;

$R^6$ and $R^7$ are independently selected from H or $C_{1-6}$alkyl;

each $R^{11}$ is independently selected from H, halogen, or $C_{1-6}$alkyl;

n is 1, 2, or 3; and p is 1.

16. The compound or pharmaceutically acceptable salt thereof according to claim 1 wherein the compound is:

tert-butyl 2-[[3-[[(E,2S)-7-(dimethylamino)-2-(methoxycarbonylamino)-7-oxo-hept-5-enoyl]amino]-2-oxo-1-pyridyl]methyl]-4-isobutyl-benzimidazole-1-carboxylate;

methyl N-[(E,1S)-6-(dimethylamino)-1-[[1-[(4-isobutyl-1H-benzimidazol-2-yl)methyl]-2-oxo-3-pyridyl]carbamoyl]-6-oxo-hex-4-enyl]carbamate;

tert-butyl (S,E)-2-((3-(7-amino-2-(((benzyloxy)carbonyl)amino)-7-oxohept-5-enamido)-2-oxopyridin-1(2H)-yl)methyl)-4-isobutyl-1H-benzo[d]imidazole-1-carboxylate;

benzyl (S,E)-(7-amino-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-4-isobutyl-1H-benzo[d]imidazole-1-carboxylate;

methyl (S,E)-(7-amino-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-2-((3-(2-(((benzyloxy)carbonyl)amino)-7-(dimethylamino)-7-oxohept-5-enamido)-2-oxopyridin-1(2H)-yl)methyl)-4-isobutyl-1H-benzo[d]imidazole-1-carboxylate;

benzyl (S,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl 2-((3-((2S,E)-7-amino-7-oxo-2-((((tetrahydrofuran-3-yl)oxy)carbonyl)amino)hept-5-enamido)-2-oxopyridin-1(2H)-yl)methyl)-4-isobutyl-1H-benzo[d]imidazole-1-carboxylate;

(tetrahydrofuran-3-yl)methyl ((S,E)-7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tetrahydrofuran-3-yl ((S,E)-7-amino-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl 2-((3-((2S,E)-7-amino-7-oxo-2-((((tetrahydrofuran-3-yl)methoxy)carbonyl)amino)hept-5-enamido)-2-oxopyridin-1(2H)-yl)methyl)-4-isobutyl-1H-benzo[d]imidazole-1-carboxylate;

(tetrahydrofuran-3-yl)methyl ((S,E)-7-amino-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

2-hydroxyethyl (S,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-4-isobutyl-2-((3-(2-((methoxycarbonyl)amino)-7-(methylamino)-7-oxohept-5-enamido)-2-oxopyridin-1(2H)-yl)methyl)-1H-benzo[d]imidazole-1-carboxylate;

methyl (S,E)-(1-((1-((4-isobutyl-1H-benzo[d]imidazol-2-yl)methyl)-2-oxo-1,2-dihydropyridin-3-yl)amino)-7-(methylamino)-1,7-dioxohept-5-en-2-yl)carbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-4-isobutyl-1H-benzo[d]imidazole-1-carboxylate;

(S,E)-7-(dimethylamino)-1-((1-((7-isobutyl-1H-benzo[d]imidazol-2-yl)methyl)-2-oxo-1,2-dihydropyridin-3-yl)amino)-1,7-dioxohept-5-en-2-yl dimethylcarbamate;

(S,E)-1-((1-((5,6-difluoro-7-isobutyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-4-isobutyl-1H-benzo[d]imidazole-1-carboxylate;

methyl (S,E)-(1-((1-((5,6-difluoro-7-isobutyl-1H-benzo[d]imidazol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-isobutyl-1H-benzo[d]imidazole-1-carboxylate;

(S,E)-7-(dimethylamino)-1-((1-((5-fluoro-7-isobutyl-1H-benzo[d]imidazol-2-yl)methyl)-2-oxo-1,2-dihydropyridin-3-yl)amino)-1,7-dioxohept-5-en-2-yl dimethylcarbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-6-fluoro-4-isobutyl-1H-benzo[d]imidazole-1-carboxylate;

methyl (S,E)-(7-(dimethylamino)-1-((1-((6-fluoro-4-isobutyl-1H-benzo[d]imidazol-2-yl)methyl)-2-oxo-1,2-dihydropyridin-3-yl)amino)-1,7-dioxohept-5-en-2-yl)carbamate;

(S,E)-6-(3,3-dimethylureido)-N7-(1-((5-fluoro-7-isobutyl-1H-benzo[d]imidazol-2-yl)methyl)-2-oxo-1,2-dihydropyridin-3-yl)-N1,N1-dimethylhept-2-enediamide;

tert-butyl (S,E)-2-((3-(7-(dimethylamino)-2-(3,3-dimethylureido)-7-oxohept-5-enamido)-2-oxopyridin-1(2H)-yl)methyl)-6-fluoro-4-isobutyl-1H-benzo[d]imidazole-1-carboxylate;

methyl (R,E)-(7-(dimethylamino)-1-((1-((4-isobutyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-2-((3-(7-(dimethylamino)-2-(3,3-dimethylureido)-7-oxohept-5-enamido)-2-oxopyridin-1(2H)-yl)methyl)-4-isobutyl-1H-benzo[d]imidazole-1-carboxylate;

(S,E)-6-(3,3-dimethylureido)-N7-(1-((4-isobutyl-1H-benzo[d]imidazol-2-yl)methyl)-2-oxo-1,2-dihydropyridin-3-yl)-N1,N1-dimethylhept-2-enediamide;

tert-butyl (S,E)-2-((3-(7-(dimethylamino)-2-(3-(2-methoxyethyl)-3-methylureido)-7-oxohept-5-enamido)-2-oxopyridin-1(2H)-yl)methyl)-6-fluoro-4-isobutyl-1H-benzo[d]imidazole-1-carboxylate;

(S,E)-N7-(1-((5-fluoro-7-isobutyl-1H-benzo[d]imidazol-2-yl)methyl)-2-oxo-1,2-dihydropyridin-3-yl)-6-(3-(2-methoxyethyl)-3-methylureido)-N1,N1-dimethylhept-2-enediamide;

tert-butyl (S,E)-2-((3-(7-(dimethylamino)-2-((methoxycarbonyl)amino)-7-oxohept-5-enamido)-2-oxopyridin-1(2H)-yl)methyl)-4-isobutyl-1H-imidazo[4,5-c]pyridine-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-7-isobutyl-3H-imidazo[4,5-b]pyridine-3-carboxylate;

methyl (S,E)-(7-(dimethylamino)-1-((1-((7-isobutyl-3H-imidazo[4,5-b]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((4-isobutyl-1H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((6-isobutyl-2-methyl-9H-purin-8-yl)methyl)-2-oxo-1,2-dihydropyridin-3-yl)amino)-1,7-dioxohept-5-en-2-yl)carbamate;

tert-butyl (S,E)-8-((3-(7-(dimethylamino)-2-((methoxycarbonyl)amino)-7-oxohept-5-enamido)-2-oxopyridin-1(2H)-yl)methyl)-6-isobutyl-2-methyl-9H-purine-9-carboxylate;

methyl (S,E)-(1-((1-((6-(2-cyclopropylethyl)-9H-purin-8-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1,7-dioxo-1-((2-oxo-1-((6-pentyl-9H-purin-8-yl)methyl)-1,2-dihydropyridin-3-yl)amino)hept-5-en-2-yl)carbamate;

methyl N-[(E,1S)-6-(dimethylamino)-1-[[1-[[6-(2-methylprop-1-enyl)-9H-purin-8-yl]methyl]-2-oxo-3-pyridyl]carbamoyl]-6-oxo-hex-4-enyl]carbamate;

methyl (S,E)-(7-(dimethylamino)-1-((1-((6-isobutyl-9H-purin-8-yl)methyl)-2-oxo-1,2-dihydropyridin-3-yl)amino)-1,7-dioxohept-5-en-2-yl)carbamate;

(S,E)-7-(dimethylamino)-1-((1-((6-(2-methylprop-1-en-1-yl)-9H-purin-8-yl)methyl)-2-oxo-1,2-dihydropyridin-3-yl)amino)-1,7-dioxohept-5-en-2-yl dimethylcarbamate;

(S,E)-7-(dimethylamino)-1-((1-((6-isobutyl-9H-purin-8-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((7-(2-methylprop-1-en-1-yl)-3H-imidazo[4,5-b]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(1-((1-((6-cyclohexyl-9H-purin-8-yl)methyl)-2-oxo-1,2-dihydropyridin-3-yl)amino)-7-(dimethylamino)-1,7-dioxohept-5-en-2-yl)carbamate;

(S,E)-1-((1-((6-cyclohexyl-9H-purin-8-yl)methyl)-2-oxo-1,2-dihydropyridin-3-yl)amino)-7-(dimethylamino)-1,7-dioxohept-5-en-2-yl dimethylcarbamate;

methyl (S,E)-(7-(dimethylamino)-1-((1-((7-fluoro-4-isobutyl-1H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((2-methyl-6-(2-methylprop-1-en-1-yl)-9H-purin-8-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-(2-methylprop-1-en-1-yl)-3H-imidazo[4,5-c]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((7-fluoro-4-isobutyl-1H-imidazo[4,5-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate;

methyl ((S,E)-7-(dimethylamino)-1,7-dioxo-1-((2-oxo-1-((6-((E)-styryl)-9H-purin-8-yl)methyl)-1,2-dihydropyridin-3-yl)amino)hept-5-en-2-yl)carbamate;

methyl (S,E)-(7-(dimethylamino)-1-((1-((7-isobutyl-3H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((4-isobutyl-6-methyl-1H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((6-methyl-4-(2-methylprop-1-en-1-yl)-1H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1,7-dioxo-1-((2-oxo-1-((6-phenethyl-7H-purin-8-yl)methyl)-1,2-dihydropyridin-3-yl)amino)hept-5-en-2-yl)carbamate;

(S,E)-7-(dimethylamino)-1,7-dioxo-1-((2-oxo-1-((6-phenethyl-9H-purin-8-yl)methyl)-1,2-dihydropyridin-3-yl)amino)hept-5-en-2-yl dimethylcarbamate;

(S,E)-7-(dimethylamino)-1-((1-((7-(2-methylprop-1-en-1-yl)-3H-imidazo[4,5-c]pyridin-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((7-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate;

methyl ((S,E)-1-((1-((6-((E)-2-cyclopropylvinyl)-9H-purin-8-yl)methyl)-2-oxo-1,2-dihydropyridin-3-yl)amino)-7-(dimethylamino)-1,7-dioxohept-5-en-2-yl)carbamate;

tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-isobutyl-benzimidazole-1-carboxylate;

methyl N-[(E,1S)-1-[[1-[(5,7-difluoro-4-isobutyl-1H-benzimidazol-2-yl)methyl]-2-oxo-3-pyridyl]carbamoyl]-6-(dimethylamino)-6-oxo-hex-4-enyl]carbamate;

(S,E)-tert-butyl 2-((3-(2-((tert-butoxycarbonyl)amino)-7-(dimethylamino)-7-oxohept-5-enamido)-2-oxopyridin-1(2H)-yl)methyl)-4-isobutyl-1H-benzo[d]imidazole-1-carboxylate;

(S,E)-N7-(1-((4-isobutyl-1H-benzo[d]imidazol-2-yl)methyl)-2-oxo-1,2-dihydropyridin-3-yl)-N1,N1-dimethyl-6-(oxazole-5-carboxamido)hept-2-enediamide;

(S,E)-N7-(1-((4-isobutyl-1H-benzo[d]imidazol-2-yl)methyl)-2-oxo-1,2-dihydropyridin-3-yl)-N1,N1-dimethyl-6-(pyrimidine-2-carboxamido)hept-2-enediamide;

(S,E)-6-(2-fluorobenzamido)-N7-(1-((4-isobutyl-1H-benzo[d]imidazol-2-yl)methyl)-2-oxo-1,2-dihydropyridin-3-yl)-N1,N1-dimethylhept-2-enediamide;

(S,E)-N7-(1-((4-isobutyl-1H-benzo[d]imidazol-2-yl)methyl)-2-oxo-1,2-dihydropyridin-3-yl)-N1,N1-dimethyl-6-(oxazole-2-carboxamido)hept-2-enediamide;

(S,E)-N7-(1-((4-isobutyl-1H-benzo[d]imidazol-2-yl)methyl)-2-oxo-1,2-dihydropyridin-3-yl)-N1,N1-dimethyl-6-(1-methyl-1H-imidazole-5-carboxamido)hept-2-enediamide;

(S,E)-N7-(1-((4-isobutyl-1H-benzo[d]imidazol-2-yl)methyl)-2-oxo-1,2-dihydropyridin-3-yl)-N1,N1-dimethyl-6-(1-methyl-1H-imidazole-2-carboxamido)hept-2-enediamide;

(S,E)-N7-(1-((4-isobutyl-1H-benzo[d]imidazol-2-yl)methyl)-2-oxo-1,2-dihydropyridin-3-yl)-N1,N1-dimethyl-6-(picolinamido)hept-2-enediamide;

(S,E)-N7-(1-((4-isobutyl-1H-benzo[d]imidazol-2-yl)methyl)-2-oxo-1,2-dihydropyridin-3-yl)-6-(3-methoxypropanamido)-N1,N1-dimethylhept-2-enediamide;

(S,E)-N7-(1-((7-isobutyl-1H-benzo[d]imidazol-2-yl)methyl)-2-oxo-1,2-dihydropyridin-3-yl)-6-(2-methoxyacetamido)-N1,N1-dimethylhept-2-enediamide;

(6S,E)-N7-(1-((7-isobutyl-1H-benzo[d]imidazol-2-yl)methyl)-2-oxo-1,2-dihydropyridin-3-yl)-N1,N1-dimethyl-6-(tetrahydrofuran-2-carboxamido)hept-2-enediamide;

(S,E)-tert-butyl 2-((3-(7-amino-2-(((2-methoxyethoxy)carbonyl)amino)-7-oxohept-5-enamido)-2-oxopyridin-1(2H)-yl)methyl)-1H-benzo[d]imidazole-1-carboxylate;

(S,E)-2-methoxyethyl (1-((1-((1H-benzo[d]imidazol-2-yl)methyl)-2-oxo-1,2-dihydropyridin-3-yl)amino)-7-amino-1,7-dioxohept-5-en-2-yl)carbamate;

methyl (S,E)-(1-((1-((1H-benzo[d]imidazol-2-yl)methyl)-2-oxo-1,2-dihydropyridin-3-yl)amino)-7-amino-1,7-dioxohept-5-en-2-yl)carbamate;

methyl (S,E)-(1-((1-((1H-benzo[d]imidazol-2-yl)methyl)-2-oxo-1,2-dihydropyridin-3-yl)amino)-7-(dimethylamino)-1,7-dioxohept-5-en-2-yl)carbamate;

benzyl (S,E)-(1-((1-((1H-benzo[d]imidazol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(2-((tert-butoxycarbonyl)amino)-7-(dimethylamino)-7-oxohept-5-enamido)-2-oxopyridin-1(2H)-yl)methyl)-1H-benzo[d]imidazole-1-carboxylate;

tert-butyl (S,E)-2-((3-(2-((methoxycarbonyl)amino)-7-(methylamino)-7-oxohept-5-enamido)-2-oxopyridin-1(2H)-yl)methyl)-1H-benzo[d]imidazole-1-carboxylate;

methyl (S,E)-(1-((1-((1H-benzo[d]imidazol-2-yl)methyl)-2-oxo-1,2-dihydropyridin-3-yl)amino)-7-(methylamino)-1,7-dioxohept-5-en-2-yl)carbamate;

methyl (S,E)-(7-(dimethylamino)-1-((1-((5-fluoro-1H-benzo[d]imidazol-2-yl)methyl)-2-oxo-1,2-dihydropyridin-3-yl)amino)-1,7-dioxohept-5-en-2-yl)carbamate;

(S,E)-1-((1-((5,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate;

methyl (S,E)-(1-((1-((5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

(R,E)-7-(dimethylamino)-1-((1-((5-fluoro-1H-benzo[d]imidazol-2-yl)methyl)-2-oxo-1,2-dihydropyridin-3-yl)amino)-1,7-dioxohept-5-en-2-yl-3,3-$d_2$ dimethylcarbamate;

(S,E)-7-(dimethylamino)-1-((1-((5-fluoro-1H-benzo[d]imidazol-2-yl)methyl)-2-oxo-1,2-dihydropyridin-3-yl)amino)-1,7-dioxohept-5-en-2-yl-3,3-$d_2$ dimethylcarbamate;

(S,E)-2-hydroxyethyl(1-((1-((1H-benzo[d]imidazol-2-yl)methyl)-2-oxo-1,2-dihydropyridin-3-yl)amino)-7-amino-1,7-dioxohept-5-en-2-yl)carbamate;

(S)-2-((((S,E)-1-((1-((1H-benzo[d]imidazol-2-yl)methyl)-2-oxo-1,2-dihydropyridin-3-yl)amino)-7-amino-1,7-dioxohept-5-en-2-yl)carbamoyl)oxy)ethyl2-((S)-2-amino-3-methylbutanamido)-3-methylbutanoate;

(S,E)-N7-(1-((1H-benzo[d]imidazol-2-yl)methyl)-2-oxo-1,2-dihydropyridin-3-yl)-6-(2-hydroxyacetamido)-N1,N1-dimethylhept-2-enediamide;

(E,6S)—N'-[1-(1H-benzimidazol-2-ylmethyl)-2-oxo-3-pyridyl]-6-(3-hydroxypropanoylamino)-N,N-dimethyl-hept-2-enediamide;

(S,E)-N7-(1-((1H-benzo[d]imidazol-2-yl)methyl)-2-oxo-1,2-dihydropyridin-3-yl)-6-(4-hydroxybutanamido)-N1,N1-dimethylhept-2-enediamide;

(S,E)-methyl(1-((1-((1H-benzol[d]imidazol-2-yl)methyl)-2-oxo-1,2-dihydropyridin-3-yl)amino)-7-((2-hydroxyethyl)amino)-1,7-dioxohept-5-en-2-yl)carbamate;

(S,E)-methyl (7-(dimethylamino)-1-((1-((6-fluoro-4-neopentyl-1H-benzo[d]imidazol-2-yl)methyl)-2-oxo-1,2-dihydropyridin-3-yl)amino)-1,7-dioxohept-5-en-2-yl)carbamate;

methyl (S,E)-(1-((1-((6-fluoro-4-neopentyl-1H-benzo[d]imidazol-2-yl)methyl)-2-oxo-1,2-dihydropyridin-3-yl)amino)-1,7-dioxo-7-(pyrrolidin-1-yl)hept-5-en-2-yl)carbamate;

(S,E)-7-(dimethylamino)-1-((1-((5-fluoro-7-neopentyl-1H-benzo[d]imidazol-2-yl)methyl)-2-oxo-1,2-dihydropyridin-3-yl)amino)-1,7-dioxohept-5-en-2-yl dimethylcarbamate;

2-methoxyethyl (S,E)-(7-(dimethylamino)-1-((1-((6-fluoro-4-neopentyl-1H-benzo[d]imidazol-2-yl)methyl)-2-oxo-1,2-dihydropyridin-3-yl)amino)-1,7-dioxohept-5-en-2-yl)carbamate;

(S,E)-7-(dimethylamino)-1-((1-((5-fluoro-7-neopentyl-1H-benzo[d]imidazol-2-yl)methyl)-2-oxo-1,2-dihydropyridin-3-yl)amino)-1,7-dioxohept-5-en-2-yl (2-methoxyethyl)(methyl)carbamate;

(S,E)-1-((1-((5-fluoro-7-neopentyl-1H-benzo[d]imidazol-2-yl)methyl)-2-oxo-1,2-dihydropyridin-3-yl)amino)-1,7-dioxo-7-(pyrrolidin-1-yl)hept-5-en-2-yl dimethylcarbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-6-methoxy-4-neopentyl-1H-benzo[d]imidazole-1-carboxylate;

(S,E)-7-(dimethylamino)-1-((1-((6-methoxy-4-neopentyl-1H-benzo[d]imidazol-2-yl)methyl)-2-oxo-1,2-dihydropyridin-3-yl)amino)-1,7-dioxohept-5-en-2-yl dimethylcarbamate;

tert-butyl (S,E)-2-((3-(7-amino-2-((methoxycarbonyl)amino)-7-oxohept-5-enamido)-2-oxopyridin-1(2H)-yl)methyl)-4-neopentyl-1H-benzo[d]imidazole-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-4-neopentyl-1H-benzo[d]imidazole-1-carboxylate;

methyl (S,E)-(7-amino-1-((1-((7-neopentyl-1H-benzo[d]imidazol-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-neopentyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-2-((3-(7-(dimethylamino)-7-oxo-2-((((tetrahydro-2H-pyran-4-yl)methoxy)carbonyl)amino)hept-5-enamido)-2-oxopyridin-1(2H)-yl)methyl)-4-neopentyl-1H-benzol[d]imidazole-1-carboxylate;

(tetrahydro-2H-pyran-4-yl)methyl (S,E)-(7-(dimethylamino)-1-((1-((7-neopentyl-1H-benzo[d]imidazol-2-yl)methyl)-2-oxo-1,2-dihydropyridin-3-yl)amino)-1,7-dioxohept-5-en-2-yl)carbamate;

tetrahydrofuran-3-yl ((S,E)-7-(dimethylamino)-1-((1-((4-neopentyl-1H-benzo[d]imidazol-2-yl)methyl)-2-oxo-1,2-dihydropyridin-3-yl)amino)-1,7-dioxohept-5-en-2-yl)carbamate;

tert-butyl 2-((3-((2S,E)-7-amino-7-oxo-2-((((tetrahydrofuran-3-yl)oxy)carbonyl)amino)hept-5-enamido)-2-oxopyridin-1(2H)-yl)methyl)-4-neopentyl-1H-benzo[d]imidazole-1-carboxylate;

tetrahydrofuran-3-yl ((S,E)-7-amino-1-((1-((4-neopentyl-1H-benzo[d]imidazol-2-yl)methyl)-2-oxo-1,2-dihydropyridin-3-yl)amino)-1,7-dioxohept-5-en-2-yl)carbamate;

tert-butyl (S,E)-2-((3-(7-amino-7-oxo-2-((((tetrahydro-2H-pyran-4-yl)methoxy)carbonyl)amino)hept-5-enamido)-2-oxopyridin-1(2H)-yl)methyl)-4-neopentyl-1H-benzo [d]imidazole-1-carboxylate;

(tetrahydro-2H-pyran-4-yl)methyl (S,E)-(7-amino-1-((1-((4-neopentyl-1H-benzo[d]imidazol-2-yl)methyl)-2-oxo-1,2-dihydropyridin-3-yl)amino)-1,7-dioxohept-5-en-2-yl)carbamate;

(S,E)-7-(dimethylamino)-1-((1-((7-fluoro-4-neopentyl-1H-benzo[d]imidazol-2-yl)methyl)-2-oxo-1,2-dihydropyridin-3-yl)amino)-1,7-dioxohept-5-en-2-yl dimethylcarbamate;

tert-butyl (S,E)-2-((3-(7-(dimethylamino)-2-((methoxycarbonyl)amino)-7-oxohept-5-enamido)-2-oxopyridin-1(2H)-yl)methyl)-5,7-difluoro-4-neopentyl-1H-benzo[d]imidazole-1-carboxylate;

methyl (S,E)-(1-((1-((5,7-difluoro-4-neopentyl-1H-benzo[d]imidazol-2-yl)methyl)-2-oxo-1,2-dihydropyridin-3-yl)amino)-7-(dimethylamino)-1,7-dioxohept-5-en-2-yl)carbamate;

[(E,1S)-6-(dimethylamino)-1-[[1-[[4-(2,2-dimethylpropyl)-6-fluoro-1-methyl-benzimidazol-2-yl]methyl]-2-oxo-3-pyridyl]carbamoyl]-6-oxo-hex-4-enyl] N,N-dimethylcarbamate;

2-methoxyethyl (S,E)-(7-(dimethylamino)-1-((1-((6-fluoro-1-methyl-4-neopentyl-1H-benzo[d]imidazol-2-yl)methyl)-2-oxo-1,2-dihydropyridin-3-yl)amino)-1,7-dioxohept-5-en-2-yl)carbamate;

tert-butyl 2-[[5-[[(E,2S)-7-(dimethylamino)-2-(dimethylcarbamoyloxy)-7-oxo-hept-5-enoyl]amino]-6-oxo-pyridazin-1-yl]methyl]-4-(2,2-dimethylpropyl)-6-fluoro-benzimidazole-1-carboxylate;

[(E,1S)-6-(dimethylamino)-1-[[2-[[7-(2,2-dimethylpropyl)-5-fluoro-1H-benzimidazol-2-yl]methyl]-3-oxo-pyridazin-4-yl]carbamoyl]-6-oxo-hex-4-enyl] N,N-dimethylcarbamate TFA salt;

tert-butyl (S,E)-2-((3-(7-(dimethylamino)-2-((dimethylcarbamoyl)oxy)-7-oxohept-5-enamido)-2-oxopyrazin-1(2H)-yl)methyl)-6-fluoro-4-neopentyl-1H-benzo[d]imidazole-1-carboxylate;

(S,E)-7-(dimethylamino)-1-((1-((5-fluoro-7-neopentyl-1H-benzo[d]imidazol-2-yl)methyl)-6-oxo-1,6-dihydropyrimidin-5-yl)amino)-1,7-dioxohept-5-en-2-yl dimethylcarbamate;

tert-butyl 2-[[3-[[(E,2S)-7-(dimethylamino)-2-(methoxycarbonylamino)-7-oxo-hept-5-enoyl]amino]-2-oxo-1-pyridyl]methyl]-6-fluoro-4-(3,3,3-trifluoropropyl)benzimidazole-1-carboxylate;

methyl N-[(E,1S)-6-(dimethylamino)-1-[[1-[[5-fluoro-7-(3,3,3-trifluoropropyl)-1H-benzimidazol-2-yl]methyl]-2-oxo-3-pyridyl]carbamoyl]-6-oxo-hex-4-enyl]carbamate;

methyl (S,E)-(7-amino-1,7-dioxo-1-((2-oxo-1-((4-(3,3,3-trifluoropropyl)-1H-benzo[d]imidazol-2-yl)methyl)-1,2-dihydropyridin-3-yl)amino)hept-5-en-2-yl)carbamate;

methyl (S,E)-(7-(dimethylamino)-1,7-dioxo-1-((2-oxo-1-((4-(3,3,3-trifluoropropyl)-1H-benzo[d]imidazol-2-yl)methyl)-1,2-dihydropyridin-3-yl)amino)hept-5-en-2-yl)carbamate;

(S,E)-7-(dimethylamino)-1-((1-((5-fluoro-7-(3,3,3-trifluoropropyl)-1H-benzo[d]imidazol-2-yl)methyl)-2-oxo-1,2-dihydropyridin-3-yl)amino)-1,7-dioxohept-5-en-2-yl dimethylcarbamate;

tert-butyl (S,E)-6-fluoro-2-((3-(2-((methoxycarbonyl)amino)-7-oxo-7-(pyrrolidin-1-yl)hept-5-enamido)-2-oxopyridin-1(2H)-yl)methyl)-4-(3,3,3-trifluoropropyl)-1H-benzo[d]imidazole-1-carboxylate;

methyl (S,E)-(1-((1-((6-fluoro-4-(3,3,3-trifluoropropyl)-1H-benzo[d]imidazol-2-yl)methyl)-2-oxo-1,2-dihydropyridin-3-yl)amino)-1,7-dioxo-7-(pyrrolidin-1-yl)hept-5-en-2-yl)carbamate;

tert-butyl (S,E)-2-((3-(2-((dimethylcarbamoyl)oxy)-7-(methylamino)-7-oxohept-5-enamido)-2-oxopyridin-1(2H)-yl)methyl)-5-fluoro-7-(3,3,3-trifluoropropyl)-1H-benzo[d]imidazole-1-carboxylate;

(S,E)-1-((1-((5-fluoro-7-(3,3,3-trifluoropropyl)-1H-benzo[d]imidazol-2-yl)methyl)-2-oxo-1,2-dihydropyridin-3-yl)amino)-7-(methylamino)-1,7-dioxohept-5-en-2-yl dimethylcarbamate;

methyl (S,E)-(1-((1-((4,6-difluoro-7-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-5,7-difluoro-4-(3,3,3-trifluoropropyl)-1H-benzo[d]imidazole-1-carboxylate;

(S,E)-1-((1-((4,6-difluoro-7-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-(3,3,3-trifluoropropyl)-1H-benzo [d]imidazole-1-carboxylate;

methyl (S,E)-(1-((1-((5,6-difluoro-4-(3,3,3-trifluoropropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

[(E,1S)-6-(dimethylamino)-1-[[1-[[6-fluoro-1-methyl-4-(3,3,3-trifluoropropyl)benzimidazol-2-yl]methyl]-2-oxo-3-pyridyl]carbamoyl]-6-oxo-hex-4-enyl] N,N-dimethylcarbamate;

2-methoxyethyl (S,E)-(7-(dimethylamino)-1-((1-((6-fluoro-1-methyl-4-(3,3,3-trifluoropropyl)-1H-benzo[d]imidazol-2-yl)methyl)-2-oxo-1,2-dihydropyridin-3-yl)amino)-1,7-dioxohept-5-en-2-yl)carbamate;

tert-butyl 2-[[5-[[(E,2S)-7-(dimethylamino)-2-(methoxycarbonylamino)-7-oxo-hept-5-enoyl]amino]-6-oxo-pyrimidin-1-yl]methyl]-6-fluoro-4-(3,3,3-trifluoropropyl)benzimidazole-1-carboxylate;

methyl N-[(E,1S)-6-(dimethylamino)-1-[[1-[[5-fluoro-7-(3,3,3-trifluoropropyl)-1H-benzimidazol-2-yl]methyl]-6-oxo-pyrimidin-5-yl]carbamoyl]-6-oxo-hex-4-enyl]carbamate;

methyl (S,E)-(1-((1-((5-fluoro-7-(3,3,3-trifluoropropyl)-1H-benzo[d]imidazol-2-yl)methyl)-6-oxo-1,6-dihydropyrimidin-5-yl)amino)-7-(methylamino)-1,7-dioxohept-5-en-2-yl)carbamate;

tert-butyl (S,E)-6-fluoro-2-((5-(2-((methoxycarbonyl)amino)-7-(methylamino)-7-oxohept-5-enamido)-6-oxopyrimidin-1(6H)-yl)methyl)-4-(3,3,3-trifluoropropyl)-1H-benzo[d]imidazole-1-carboxylate;

tert-butyl 4-(cyclopropylmethyl)-2-[[3-[[(E,2S)-7-(dimethylamino)-2-(methoxycarbonylamino)-7-oxo-hept-5-enoyl]amino]-2-oxo-1-pyridyl]methyl]-6-fluoro-benzimidazole-1-carboxylate;

methyl N-[(E,1S)-1-[[1-[[4-(cyclopropylmethyl)-6-fluoro-1H-benzimidazol-2-yl]methyl]-2-oxo-3-pyridyl]carbamoyl]-6-(dimethylamino)-6-oxo-hex-4-enyl]carbamate;

tert-butyl (S,E)-4-(cyclopropylmethyl)-2-((3-(7-(dimethylamino)-2-((methoxycarbonyl)amino)-7-oxohept-5-enamido)-2-oxopyridin-1(2H)-yl)methyl)-1H-benzo[d]imidazole-1-carboxylate;

methyl (S,E)-(1-((1-((4-(cyclopropylmethyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-4-(cyclopropylmethyl)-1H-benzo[d]imidazole-1-carboxylate;

methyl (S,E)-(7-amino-1-((1-((4-(cyclopropylmethyl)-1H-benzo[d]imidazol-2-yl)methyl)-2-oxo-1,2-dihydropyridin-3-yl)amino)-1,7-dioxohept-5-en-2-yl)carbamate;

(S,E)-methyl (1-((1-((4-(2,4-difluorophenoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-(dimethylamino)-2-((methoxycarbonyl)amino)-7-oxohept-5-enamido)-2-oxopyridin-1(2H)-yl)methyl)-4-phenoxy-1H-benzo[d]imidazole-1-carboxylate;

methyl (S,E)-(7-(dimethylamino)-1,7-dioxo-1-((2-oxo-1-((7-phenoxy-1H-benzo[d]imidazol-2-yl)methyl)-1,2-dihydropyridin-3-yl)amino)hept-5-en-2-yl)carbamate;

methyl (S,E)-(7-amino-1,7-dioxo-1-((2-oxo-1-((4-phenoxy-1H-benzo[d]imidazol-2-yl)methyl)-1,2-dihydropyridin-3-yl)amino)hept-5-en-2-yl)carbamate;

methyl (S,E)-(1-((1-((6-(2,4-difluorophenoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-methyl(1-((1-((7-((2,4-difluorobenzyl)oxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

benzyl (S,E)-(7-amino-1-((1-((4-isopropoxy-1H-benzo[d]imidazol-2-yl)methyl)-2-oxo-1,2-dihydropyridin-3-yl)amino)-1,7-dioxohept-5-en-2-yl)carbamate;

methyl (S,E)-(1-((1-((7-(benzyloxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

benzyl (S,E)-(7-(dimethylamino)-1-((1-((7-isobutoxy-1-methyl-1H-benzo[d]imidazol-2-yl)methyl)-2-oxo-1,2-dihydropyridin-3-yl)amino)-1,7-dioxohept-5-en-2-yl)carbamate;

methyl (S,E)-(7-amino-1-((1-((7-isobutoxy-1H-benzo[d]imidazol-2-yl)methyl)-2-oxo-1,2-dihydropyridin-3-yl)amino)-1,7-dioxohept-5-en-2-yl)carbamate;

methyl (S,E)-(7-amino-1-((1-((7-(benzyloxy)-1H-benzo[d]imidazol-2-yl)methyl)-2-oxo-1,2-dihydropyridin-3-yl)amino)-1,7-dioxohept-5-en-2-yl)carbamate;

methyl (S,E)-(7-amino-1-((1-((4-isopropoxy-1H-benzo[d]imidazol-2-yl)methyl)-2-oxo-1,2-dihydropyridin-3-yl)amino)-1,7-dioxohept-5-en-2-yl)carbamate;

methyl (S,E)-(7-amino-1-((1-((7-(cyclopropylmethoxy)-1H-benzo[d]imidazol-2-yl)methyl)-2-oxo-1,2-dihydropyridin-3-yl)amino)-1,7-dioxohept-5-en-2-yl)carbamate;

methyl (S,E)-(1-((1-((6-((2,4-difluorobenzyl)oxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((4-(2,2-difluoroethoxy)-6-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(7-amino-1-((1-((4-(2,2-difluoroethoxy)-6-fluoro-1H-benzo[d]imidazol-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((6-fluoro-4-(2,2,2-trifluoroethoxy)-1H-benzo[d]imidazol-2-yl)methyl)-2-oxo-1,2-dihydropyridin-3-yl)amino)-1,7-dioxohept-5-en-2-yl)carbamate;

methyl (S,E)-(7-amino-1-((1-((6-fluoro-4-(2,2,2-trifluoroethoxy)-1H-benzo[d]imidazol-2-yl)methyl)-2-oxo-1,2-dihydropyridin-3-yl)amino)-1,7-dioxohept-5-en-2-yl)carbamate;

methyl (S,E)-(1-((1-((7-((2,4-difluorobenzyl)oxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((4-((2,4-difluorobenzyl)oxy)-6-fluoro-1H-benzo[d]imidazol-2-yl)methyl)-2-oxo-1,2-dihydropyridin-3-yl)amino)-7-(methylamino)-1,7-dioxohept-5-en-2-yl)carbamate;

methyl (S,E)-(7-amino-1-((1-((7-((2,4-difluorobenzyl)oxy)-5-fluoro-1H-benzo[d]imidazol-2-yl)methyl)-2-oxo-1,2-dihydropyridin-3-yl)amino)-1,7-dioxohept-5-en-2-yl)carbamate;

2-methoxyethyl (S,E)-(1-((1-((7-((2,4-difluorobenzyl)oxy)-5-fluoro-1H-benzo[d]imidazol-2-yl)methyl)-2- oxo-1,2-dihydropyridin-3-yl)amino)-7-(dimethyl-amino)-1,7-dioxohept-5-en-2-yl)carbamate;

(S,E)-1-((1-((7-((2,4-difluorobenzyl)oxy)-5-fluoro-1H-benzo[d]imidazol-2-yl)methyl)-2-oxo-1,2-dihydro-pyridin-3-yl)amino)-7-(dimethylamino)-1,7-dioxo-hept-5-en-2-yl dimethylcarbamate;

(S,E)-1-((1-((7-((2,4-difluorobenzyl)oxy)-5-fluoro-1H-benzo[d]imidazol-2-yl)methyl)-2-oxo-1,2-dihydro-pyridin-3-yl)amino)-7-(dimethylamino)-1,7-dioxo-hept-5-en-2-yl (2-methoxyethyl)(methyl)carbamate;

methyl (S,E)-(1-((1-((7-(cyclopropylmethoxy)-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-methyl (7-(dimethyl-amino)-1-((1-((5-fluoro-7-(1,1,2,2-tetrafluoroethoxy)-1H-benzo[d]imidazol-2-yl)methyl)-2-oxo-1,2-dihydropyridin-3-yl)amino)-1,7-dioxohept-5-en-2-yl)carbamate;

(S,E)-N7-(1-((7-(2,4-difluorophenoxy)-1H-benzo[d]imidazol-2-yl)methyl)-2-oxo-1,2-dihydropyridin-3-yl)-N1,N1-dimethyl-6-(oxazole-2-carboxamido)hept-2-enediamide;

(S,E)-N7-(1-((7-(2,4-difluorophenoxy)-1H-benzo[d]imidazol-2-yl)methyl)-2-oxo-1,2-dihydropyridin-3-yl)-6-(2-methoxyacetamido)-N1,N1-dimethylhept-2-enediamide;

(S,E)-N7-(1-((7-(2,4-difluorophenoxy)-1H-benzo[d]imidazol-2-yl)methyl)-2-oxo-1,2-dihydropyridin-3-yl)-N1,N1-dimethyl-6-(1-methyl-1H-imidazole-5-carboxamido)hept-2-enediamide;

(S,E)-N7-(1-((4-((2,4-difluorobenzyl)oxy)-1H-benzo[d]imidazol-2-yl)methyl)-2-oxo-1,2-dihydropyridin-3-yl)-N1,N1-dimethyl-6-(oxazole-2-carboxamido)hept-2-enediamide;

(S,E)-N7-(1-((7-((2,4-difluorobenzyl)oxy)-1H-benzo[d]imidazol-2-yl)methyl)-2-oxo-1,2-dihydropyridin-3-yl)-6-(2-methoxyacetamido)-N1,N1-dimethylhept-2-enediamide;

(S,E)-N7-(1-((4-((2,4-difluorobenzyl)oxy)-1H-benzo[d]imidazol-2-yl)methyl)-2-oxo-1,2-dihydropyridin-3-yl)-N1,N1-dimethyl-6-(1-methyl-1H-imidazole-2-carboxamido)hept-2-enediamide;

(S,E)-N7-(1-((7-((2,4-difluorobenzyl)oxy)-1H-benzo[d]imidazol-2-yl)methyl)-2-oxo-1,2-dihydropyridin-3-yl)-6-(4,4-difluorocyclohexane-1-carboxamido)-N1,N1-dimethylhept-2-enediamide;

(S,E)-N7-(1-((7-((2,4-difluorobenzyl)oxy)-5-fluoro-1H-benzo[d]imidazol-2-yl)methyl)-2-oxo-1,2-dihydro-pyridin-3-yl)-6-(2-methoxyacetamido)hept-2-enediamide;

(S,E)-N7-(1-((7-((2,4-difluorobenzyl)oxy)-5-fluoro-1H-benzo[d]imidazol-2-yl)methyl)-2-oxo-1,2-dihydro-pyridin-3-yl)-6-(5-fluoropicolinamido)hept-2-enediamide;

(S,E)-N7-(1-((4-((2,4-difluorobenzyl)oxy)-6-fluoro-1H-benzo[d]imidazol-2-yl)methyl)-2-oxo-1,2-dihydro-pyridin-3-yl)-6-(2-methoxyacetamido)-N1,N1-dimethylhept-2-enediamide;

(S,E)-N7-(1-((4-((2,4-difluorobenzyl)oxy)-6-fluoro-1H-benzo[d]imidazol-2-yl)methyl)-2-oxo-1,2-dihydro-pyridin-3-yl)-6-(5-fluoropicolinamido)-N1,N1-dimethylhept-2-enediamide;

methyl N-[(E,1S)-1-[[1-[[4-[(2,4-difluorophenoxy)methyl]-1H-benzimidazol-2-yl]methyl]-2-oxo-3-pyridyl]carbamoyl]-6-(dimethylamino)-6-oxo-hex-4-enyl]carbamate;

methyl (S,E)-(7-(dimethylamino)-1-((1-((4-(isopropoxymethyl)-1H-benzo[d]imidazol-2-yl)methyl)-2-oxo-1,2-dihydropyridin-3-yl)amino)-1,7-dioxohept-5-en-2-yl)carbamate;

(S,E)-tert-butyl 2-((3-(7-(dimethylamino)-2-((methoxycarbonyl)amino)-7-oxohept-5-enamido)-2-oxopyridin-1(2H)-yl)methyl)-4-(3,3,3-trifluoro-2-(trifluoromethyl)propyl)-1H-benzo [d]imidazole-1-carboxylate;

(S,E)-methyl(7-(dimethylamino)-1,7-dioxo-1-((2-oxo-1-((4-(3,3,3-trifluoro-2-(trifluoromethyl)propyl)-1H-benzo[d]imidazol-2-yl)methyl)-1,2-dihydropyridin-3-yl)amino)hept-5-en-2-yl)carbamate;

methyl (S,E)-(7-amino-1,7-dioxo-1-((2-oxo-1-((4-(3,3,3-trifluoro-2-(trifluoromethyl)propyl)-1H-benzo[d]imidazol-2-yl)methyl)-1,2-dihydropyridin-3-yl)amino)hept-5-en-2-yl)carbamate;

methyl ((2S,E)-7-(dimethylamino)-1-((1-((4-(1-hydroxy-2-methylpropyl)-1H-benzo [d]imidazol-2-yl)methyl)-2-oxo-1,2-dihydropyridin-3-yl)amino)-1,7-dioxohept-5-en-2-yl)carbamate;

methyl ((2S,E)-7-amino-1-((1-((4-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-(dimethylamino)-1-((1-((7-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-(dimethylamino)-1-((1-((7-(1-hydroxy-2-methylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-(dimethylamino)-1-((1-((7-(1-fluoro-2-methylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-amino-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate;

tert-butyl ((2S,E)-7-(dimethylamino)-1-((1-((7-(1-hydroxy-2,2-dimethylpropyl)-1H-benzo[d]imidazol-2-yl)methyl)-2-oxo-1,2-dihydropyridin-3-yl)amino)-1,7-dioxohept-5-en-2-yl)carbamate;

(6S,E)-N7-(1-((7-(1-hydroxy-2,2-dimethylpropyl)-1H-benzo[d]imidazol-2-yl)methyl)-2-oxo-1,2-dihydro-pyridin-3-yl)-N1,N1-dimethyl-6-(oxazole-2-carboxamido)hept-2-enediamide;

(S,E)-methyl (7-(dimethylamino)-1,7-dioxo-1-((2-oxo-1-((7-pivaloyl-1H-benzo[d]imidazol-2-yl)methyl)-1,2-dihydropyridin-3-yl)amino)hept-5-en-2-yl)carbamate;

methyl ((2S,E)-7-(dimethylamino)-1-((1-((7-(1-fluoro-2,2-dimethylpropyl)-1H-benzo[d]imidazol-2-yl)methyl)-2-oxo-1,2-dihydropyridin-3-yl)amino)-1,7-dioxohept-5-en-2-yl)carbamate;

methyl ((2S,E)-7-amino-1-((1-((4-(1-fluoro-2,2-dimethylpropyl)-1H-benzo[d]imidazol-2-yl)methyl)-2-oxo-1,2-dihydropyridin-3-yl)amino)-1,7-dioxohept-5-en-2-yl)carbamate;

(S,E)-methyl(1-((1-((4-(1,1-difluoro-2-hydroxy-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-methyl (1-((1-((4-(1,1-difluoro-2-methylpropyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(7-amino-1-((1-((4-(1,1-difluoro-2-methylpropyl)-1H-benzo[d]imidazol-2-yl)methyl)-2-oxo-1,2-dihydropyridin-3-yl)amino)-1,7-dioxohept-5-en-2-yl)carbamate;

methyl (S,E)-(1-((1-((4-(1,1-difluoro-2-methylallyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(7-amino-1-((1-((4-(1,1-difluoro-2-methylallyl)-1H-benzo[d]imidazol-2-yl)methyl)-2-oxo-1,2-dihydropyridin-3-yl)amino)-1,7-dioxohept-5-en-2-yl)carbamate;

(S,E)-methyl (1-((1-((7-(tert-butoxy)-5-fluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(7-amino-1-((1-((7-(tert-butoxy)-5-fluoro-1H-benzo[d]imidazol-2-yl)methyl)-2-oxo-1,2-dihydropyridin-3-yl)amino)-1,7-dioxohept-5-en-2-yl)carbamate;

[(E,1S)-6-(dimethylamino)-1-[[1-[(5-fluoro-1-methyl-benzimidazol-2-yl)methyl]-2-oxo-3-pyridyl]carbamoyl]-6-oxo-hex-4-enyl] N,N-dimethylcarbamate;

methyl N-[(E,1S)-6-(dimethylamino)-1-[[1-[(5-fluoro-1-methyl-benzimidazol-2-yl) methyl]-6-oxo-pyrimidin-5-yl]carbamoyl]-6-oxo-hex-4-enyl]carbamate;

(S,E)-1-((1-((5,6-difluoro-1-isopentyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-1-((1-((1-(cyclopropylmethyl)-5-fluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-7-(dimethylamino)-1-((1-((5-fluoro-1-neopentyl-1H-benzo[d]imidazol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((1-ethyl-5-fluoro-1H-benzo[d]imidazol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((5-fluoro-1-isobutyl-1H-benzo[d]imidazol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((5-fluoro-1-(3,3,3-trifluoropropyl)-1H-benzo[d]imidazol-2-yl)methyl)-2-oxo-1,2-dihydropyridin-3-yl)amino)-1,7-dioxohept-5-en-2-yl dimethylcarbamate;

(S,E)-1-((1-((1-(2-cyclopropylethyl)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((1-((1-(2-cyclopropylethyl)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-1-((1-((1-benzyl-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl dimethylcarbamate;

(S,E)-1-((1-((1-(2,4-difluorobenzyl)-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl dimethylcarbamate;

methyl (S,E)-(1-((1-((1-(2,4-difluorobenzyl)-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl)carbamate;

(S,E)-7-(dimethylamino)-1-((1-((5-fluoro-1-neopentyl-1H-benzo[d]imidazol-2-yl)methyl)-6-oxo-1,6-dihydropyrimidin-5-yl)amino)-1,7-dioxohept-5-en-2-yl dimethylcarbamate;

methyl (S,E)-(1-((1-((5,6-difluoro-1-(2-isopropoxyethyl)-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((5-fluoro-1-(4-fluorobenzyl)-1H-benzo[d]imidazol-2-yl)methyl)-6-oxo-1,6-dihydropyrimidin-5-yl)amino)-1,7-dioxohept-5-en-2-yl)carbamate;

methyl (S,E)-(1-((1-((1-(cyclopropylmethyl)-5-fluoro-1H-benzo[d]imidazol-2-yl)methyl)-6-oxo-1,6-dihydropyrimidin-5-yl)amino)-7-(dimethylamino)-1,7-dioxohept-5-en-2-yl)carbamate;

methyl (S,E)-(7-(dimethylamino)-1-((1-((5-fluoro-1-isobutyl-1H-benzo[d]imidazol-2-yl)methyl)-6-oxo-1,6-dihydropyrimidin-5-yl)amino)-1,7-dioxohept-5-en-2-yl)carbamate;

(S,E)-7-(dimethylamino)-1-((1-((1-ethyl-5-fluoro-1H-benzo[d]imidazol-2-yl)methyl)-6-oxo-1,6-dihydropyrimidin-5-yl)amino)-1,7-dioxohept-5-en-2-yl dimethylcarbamate;

(S,E)-7-(dimethylamino)-1-((1-((5-fluoro-1-methyl-1H-benzo[d]imidazol-2-yl)methyl)-6-oxo-1,6-dihydropyrimidin-5-yl)amino)-1,7-dioxohept-5-en-2-yl dimethylcarbamate;

ethyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-benzimidazole-1-carboxylate;

cyclopropylmethyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-benzimidazole-1-carboxylate;

methyl (S,E)-2-((3-(7-(dimethylamino)-2-((dimethylcarbamoyl)oxy)-7-oxohept-5-enamido)-2-oxopyridin-1(2H)-yl)methyl)-5-fluoro-1H-benzo[d]imidazole-1-carboxylate;

ethyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-1H-benzo [d]imidazole-1-carboxylate;

cyclopropylmethyl (S,E)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate;

ethyl (S,E)-2-((3-(7-(dimethylamino)-2-((methoxycarbonyl)amino)-7-oxohept-5-enamido)-2-oxopyridin-1(2H)-yl)methyl)-5,6-difluoro-1H-benzo [d]imidazole-1-carboxylate;

cyclopropylmethyl (S,E)-2-((3-(7-(dimethylamino)-2-((methoxycarbonyl)amino)-7-oxohept-5-enamido)-2-oxopyridin-1(2H)-yl)methyl)-5-fluoro-1H-benzo[d]imidazole-1-carboxylate;

ethyl (S,E)-2-((3-(7-(dimethylamino)-2-((methoxycarbonyl)amino)-7-oxohept-5-enamido)-2-oxopyridin-1(2H)-yl)methyl)-5-fluoro-1H-benzo [d]imidazole-1-carboxylate;

methyl 2-[[5-[[(E,2S)-7-(dimethylamino)-2-(methoxycarbonylamino)-7-oxo-hept-5-enoyl]amino]-6-oxo-pyrimidin-1-yl]methyl]-5-fluoro-benzimidazole-1-carboxylate;

[(E,1S)-1-[[1-[(1-benzyl-6-fluoro-benzimidazol-2-yl)methyl]-2-oxo-3-pyridyl]carbamoyl]-6-(dimethylamino)-6-oxo-hex-4-enyl] N,N-dimethylcarbamate;

[(E,1S)-1-[[1-[(1-benzyl-5-fluoro-benzimidazol-2-yl)methyl]-2-oxo-3-pyridyl]carbamoyl]-6-(dimethylamino)-6-oxo-hex-4-enyl] N,N-dimethylcarbamate;

(S,E)-1-((1-((1-(2,4-difluorobenzyl)-5-fluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-1-((1-((1-(2,4-difluorobenzyl)-6-fluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-7-(dimethylamino)-1-((1-((5-fluoro-1-(4-fluorobenzyl)-1H-benzo[d]imidazol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((6-fluoro-1-(4-fluorobenzyl)-1H-benzo[d]imidazol-2-yl)methyl)-2-oxo-1,2-dihydropyridin-3-yl)amino)-1,7-dioxohept-5-en-2-yl dimethylcarbamate;

(S,E)-methyl (7-(dimethylamino)-1-((1-((5-fluoro-1H-indol-2-yl)methyl)-2-oxo-1,2-dihydropyridin-3-yl)amino)-1,7-dioxohept-5-en-2-yl)carbamate;

tert-butyl (S,E)-5-fluoro-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate;

tert-butyl (S,E)-5-fluoro-2-((3-(2-(((2-hydroxyethoxy)carbonyl)amino)-7-oxo-7-(pyrrolidin-1-yl)hept-5-enamido)-2-oxopyridin-1(2H)-yl)methyl)-1H-indole-1-carboxylate;

2-hydroxyethyl (S,E)-(1-((1-((5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate;

methyl (S,E)-(7-amino-1-((1-((5-fluoro-1H-indol-2-yl)methyl)-2-oxo-1,2-dihydropyridin-3-yl)amino)-1,7-dioxohept-5-en-2-yl)carbamate;

methyl (S,E)-(1-((1-((5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate;

(S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl (2-methoxyethyl)(methyl)carbamate;

(S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl pyrrolidine-1-carboxylate;

tert-butyl (S,E)-2-((3-(7-amino-2-((dimethylcarbamoyl)oxy)-7-oxohept-5-enamido)-2-oxopyridin-1(2H)-yl)methyl)-5-fluoro-1H-indole-1-carboxylate;

(S,E)-7-amino-1-((1-((5-fluoro-1H-indol-2-yl)methyl)-2-oxo-1,2-dihydropyridin-3-yl)amino)-1,7-dioxohept-5-en-2-yl dimethylcarbamate;

tert-butyl (S,E)-2-((3-(2-((bis(2-methoxyethyl)carbamoyl)oxy)-7-(dimethylamino)-7-oxohept-5-enamido)-2-oxopyridin-1(2H)-yl)methyl)-5-fluoro-1H-indole-1-carboxylate;

(S,E)-7-(dimethylamino)-1-((1-((5-fluoro-1H-indol-2-yl)methyl)-2-oxo-1,2-dihydropyridin-3-yl)amino)-1,7-dioxohept-5-en-2-yl bis(2-methoxyethyl)carbamate;

benzyl (S,E)-2-((3-(7-(dimethylamino)-2-((dimethylcarbamoyl)oxy)-7-oxohept-5-enamido)-2-oxopyridin-1(2H)-yl)methyl)-5-fluoro-1H-indole-1-carboxylate;

(E)-7-(dimethylamino)-1-((1-((5-fluoro-1H-indol-2-yl)methyl)-2-oxo-1,2-dihydropyridin-3-yl)amino)-1,7-dioxohept-5-en-2-yl-3,3-$d_2$ dimethylcarbamate;

tert-butyl (E)-2-((3-(7-(dimethylamino)-2-((dimethylcarbamoyl)oxy)-7-oxohept-5-enamido-3,3-d2)-2-oxopyridin-1(2H)-yl)methyl)-5-fluoro-1H-indole-1-carboxylate;

tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-5-fluoro-indole-1-carboxylate;

[(E,1S)-6-(dimethylamino)-1-[[4-[(5-fluoro-1H-indol-2-yl)methyl]-3-oxo-pyrazin-2-yl]carbamoyl]-6-oxo-hex-4-enyl]N,N-dimethylcarbamate;

(S,E)-7-(dimethylamino)-1-((1-((5-fluoro-1H-indol-2-yl)methyl)-6-oxo-1,6-dihydropyrimidin-5-yl)amino)-1,7-dioxohept-5-en-2-yl dimethylcarbamate;

(S,E)-tert-butyl 2-((3-(7-(dimethylamino)-2-((methoxycarbonyl)amino)-7-oxohept-5-enamido)-2-oxopyridin-1(2H)-yl)methyl)-4-isobutyl-1H-indole-1-carboxylate;

(S,E)-methyl (7-(dimethylamino)-1-((1-((4-isobutyl-1H-indol-2-yl)methyl)-2-oxo-1,2-dihydropyridin-3-yl)amino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-4-isobutyl-1H-indole-1-carboxylate;

methyl (S,E)-(7-amino-1-((1-((4-isobutyl-1H-indol-2-yl)methyl)-2-oxo-1,2-dihydropyridin-3-yl)amino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-7-isobutyl-1H-indole-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-7-isobutyl-1H-indole-1-carboxylate;

methyl (S,E)-(7-amino-1-((1-((7-isobutyl-1H-indol-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamate;

(S,E)-7-(dimethylamino)-1-((1-((7-isobutyl-1H-indol-2-yl)methyl)-2-oxo-1,2-dihydropyridin-3-yl)amino)-1,7-dioxohept-5-en-2-yl dimethylcarbamate;

tert-butyl (S,E)-2-((3-(7-(dimethylamino)-2-((methylcarbamoyl)oxy)-7-oxohept-5-enamido)-2-oxopyridin-1(2H)-yl)methyl)-7-isobutyl-1H-indole-1-carboxylate;

(S,E)-7-(dimethylamino)-1-((1-((7-isobutyl-1H-indol-2-yl)methyl)-2-oxo-1,2-dihydropyridin-3-yl)amino)-1,7-dioxohept-5-en-2-yl methylcarbamate;

(S,E)-1-((1-((7-isobutyl-1H-indol-2-yl)methyl)-2-oxo-1,2-dihydropyridin-3-yl)amino)-7-(methylamino)-1,7-dioxohept-5-en-2-yl dimethylcarbamate;

tert-butyl (S,E)-2-((3-(7-(dimethylamino)-7-oxo-2-((pyrrolidine-1-carbonyl)oxy)hept-5-enamido)-2-oxopyridin-1(2H)-yl)methyl)-7-isobutyl-1H-indole-1-carboxylate;

(S,E)-7-(dimethylamino)-1-((1-((7-isobutyl-1H-indol-2-yl)methyl)-2-oxo-1,2-dihydropyridin-3-yl)amino)-1,7-dioxohept-5-en-2-yl pyrrolidine-1-carboxylate;

tert-butyl (S,E)-7-isobutyl-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate;

methyl (S,E)-(1-((1-((7-isobutyl-1H-indol-2-yl)methyl)-2-oxo-1,2-dihydropyridin-3-yl)amino)-1,7-dioxo-7-(pyrrolidin-1-yl)hept-5-en-2-yl)carbamate;

(E)-7-(dimethylamino)-1-((1-((7-isobutyl-1H-indol-2-yl)methyl)-2-oxo-1,2-dihydropyridin-3-yl)amino)-1,7-dioxohept-5-en-2-yl-3,3-$d_2$ dimethylcarbamate;

tert-butyl (E)-2-((3-(7-(dimethylamino)-2-((dimethylcarbamoyl)oxy)-7-oxohept-5-enamido-3,3-$d_2$)-2-oxopyridin-1(2H)-yl)methyl)-7-isobutyl-1H-indole-1-carboxylate;

(S,E)-2-(((7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamoyl)oxy)ethyl acetate;

(S,E)-tert-butyl 2-((3-(7-(dimethylamino)-2-(((2-hydroxyethoxy)carbonyl)amino)-7-oxohept-5-enamido)-2-oxopyridin-1(2H)-yl)methyl)-7-isobutyl-1H-indole-1-carboxylate;

(S,E)-2-hydroxyethyl (7-(dimethylamino)-1-((1-((7-isobutyl-1H-indol-2-yl)methyl)-2-oxo-1,2-dihydropyridin-3-yl)amino)-1,7-dioxohept-5-en-2-yl)carbamate;

tert-butyl (S,E)-2-((3-(2-(((2-hydroxyethoxy)carbonyl)amino)-7-oxo-7-(pyrrolidin-1-yl)hept-5-enamido)-2-oxopyridin-1(2H)-yl)methyl)-7-isobutyl-1H-indole-1-carboxylate;

2-hydroxyethyl (S,E)-(1-((1-((7-isobutyl-1H-indol-2-yl)methyl)-2-oxo-1,2-dihydropyridin-3-yl)amino)-1,7-dioxo-7-(pyrrolidin-1-yl)hept-5-en-2-yl)carbamate;

(S,E)-N7-(1-((7-((2,4-difluorobenzyl)oxy)-1H-indol-2-yl)methyl)-2-oxo-1,2-dihydropyridin-3-yl)-6-(4,4-difluorocyclohexanecarboxamido)-N1,N1-dimethylhept-2-enediamide;

tert-butyl (S,E)-(1-((1-((7-((2,4-difluorobenzyl)oxy)-1H-indol-2-yl)methyl)-2-oxo-1,2-dihydropyridin-3-yl)amino)-7-(dimethylamino)-1,7-dioxohept-5-en-2-yl)carbamate;

(S,E)-N7-(1-((7-((2,4-difluorobenzyl)oxy)-1H-indol-2-yl)methyl)-2-oxo-1,2-dihydropyridin-3-yl)-N1,N1-dimethyl-6-(oxazole-2-carboxamido)hept-2-enediamide;

(S,E)-N7-(1-((7-((2,4-difluorobenzyl)oxy)-1H-indol-2-yl)methyl)-2-oxo-1,2-dihydropyridin-3-yl)-6-(2-methoxyacetamido)-N1,N1-dimethylhept-2-enediamide;

(S,E)-N7-(1-((7-((2,4-difluorobenzyl)oxy)-1H-indol-2-yl)methyl)-2-oxo-1,2-dihydropyridin-3-yl)-N1,N1-dimethyl-6-(3,3,3-trifluoropropanamido)hept-2-enediamide;

(S,E)-N7-(1-((7-((2,4-difluorobenzyl)oxy)-1H-indol-2-yl)methyl)-2-oxo-1,2-dihydropyridin-3-yl)-6-(2-fluorobenzamido)-N1,N1-dimethylhept-2-enediamide;

methyl (S,E)-(1-((1-((7-((2,4-difluorobenzyl)oxy)-1H-indol-2-yl)methyl)-2-oxo-1,2-dihydropyridin-3-yl)amino)-7-(dimethylamino)-1,7-dioxohept-5-en-2-yl)carbamate;

tert-butyl (S,E)-7-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-1H-indole-1-carboxylate;

tert-butyl (S,E)-2-((3-(7-amino-2-((tert-butoxycarbonyl)amino)-7-oxohept-5-enamido)-2-oxopyridin-1(2H)-yl)methyl)-7-((2,4-difluorobenzyl)oxy)-1H-indole-1-carboxylate;

tert-butyl (S,E)-2-((3-(7-amino-2-((methoxycarbonyl)amino)-7-oxohept-5-enamido)-2-oxopyridin-1(2H)-yl)methyl)-7-((2,4-difluorobenzyl)oxy)-1H-indole-1-carboxylate;

(S,E)-N7-(1-((7-((2,4-difluorobenzyl)oxy)-1H-indol-2-yl)methyl)-2-oxo-1,2-dihydropyridin-3-yl)-6-(2-fluorobenzamido)hept-2-enediamide;

methyl (S,E)-(7-amino-1-((1-((7-(2,2-difluoroethoxy)-1H-indol-2-yl)methyl)-2-oxo-1,2-dihydropyridin-3-yl)amino)-1,7-dioxohept-5-en-2-yl)carbamate;

methyl (S,E)-(1-((1-((7-(2,2-difluoroethoxy)-1H-indol-2-yl)methyl)-2-oxo-1,2-dihydropyridin-3-yl)amino)-7-(dimethylamino)-1,7-dioxohept-5-en-2-yl)carbamate;

tert-butyl (S,E)-7-(2,2-difluoroethoxy)-2-((3-(7-(dimethylamino)-2-((methoxycarbonyl)amino)-7-oxohept-5-enamido)-2-oxopyridin-1(2H)-yl)methyl)-1H-indole-1-carboxylate;

methyl (S,E)-(7-amino-1-((1-((7-((2,4-difluorobenzyl)oxy)-1H-indol-2-yl)methyl)-2-oxo-1,2-dihydropyridin-3-yl)amino)-1,7-dioxohept-5-en-2-yl)carbamate;

(S,E)-N7-(1-((7-((2,4-difluorobenzyl)oxy)-1H-indol-2-yl)methyl)-2-oxo-1,2-dihydropyridin-3-yl)-6-(2-methoxyacetamido)hept-2-enediamide;

(S,E)-tert-butyl 7-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate;

(S,E)-methyl (1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-7-((2,4-difluorobenzyl)oxy)-5-fluoro-1H-indole-1-carboxylate;

methyl (S,E)-(7-amino-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl)carbamate;

tert-butyl (S,E)-7-(2,2-difluoroethoxy)-2-((3-(7-(dimethylamino)-2-((methoxycarbonyl)amino)-7-oxohept-5-enamido)-2-oxopyridin-1(2H)-yl)methyl)-5-fluoro-1H-indole-1-carboxylate;

methyl (S,E)-(1-((1-((7-(2,2-difluoroethoxy)-5-fluoro-1H-indol-2-yl)methyl)-2-oxo-1,2-dihydropyridin-3-yl)amino)-7-(dimethylamino)-1,7-dioxohept-5-en-2-yl)carbamate;

tert-butyl (S,E)-2-((3-(7-amino-2-((methoxycarbonyl)amino)-7-oxohept-5-enamido)-2-oxopyridin-1(2H)-yl)methyl)-7-(2,2-difluoroethoxy)-5-fluoro-1H-indole-1-carboxylate;

methyl (S,E)-(7-amino-1-((1-((7-(2,2-difluoroethoxy)-5-fluoro-1H-indol-2-yl)methyl)-2-oxo-1,2-dihydropyridin-3-yl)amino)-1,7-dioxohept-5-en-2-yl)carbamate;

tert-butyl (S,E)-7-((2,4-difluorobenzyl)oxy)-5-fluoro-2-((3-(2-((methoxycarbonyl)amino)-7-(methylamino)-7-oxohept-5-enamido)-2-oxopyridin-1(2H)-yl)methyl)-1H-indole-1-carboxylate;

methyl (S,E)-(1-((1-((7-((2,4-difluorobenzyl)oxy)-5-fluoro-1H-indol-2-yl)methyl)-2-oxo-1,2-dihydropyridin-3-yl)amino)-7-(methylamino)-1,7-dioxohept-5-en-2-yl)carbamate;

tert-butyl (S,E)-7-((2,4-difluorobenzyl)oxy)-2-((3-(7-(dimethylamino)-2-(((2-methoxyethoxy)carbonyl)amino)-7-oxohept-5-enamido)-2-oxopyridin-1(2H)-yl)methyl)-5-fluoro-1H-indole-1-carboxylate;

tert-butyl (S,E)-7-((2,4-difluorobenzyl)oxy)-5-fluoro-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate;

methyl (S,E)-(1-((1-((7-((2,4-difluorobenzyl)oxy)-5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate;

tert-butyl (S,E)-2-((3-(7-(dimethylamino)-2-((methoxycarbonyl)amino)-7-oxohept-5-enamido)-2-oxopyridin-1(2H)-yl)methyl)-5-fluoro-7-isobutyl-1H-indole-1-carboxylate;

methyl (S,E)-(7-(dimethylamino)-1-((1-((5-fluoro-7-isobutyl-1H-indol-2-yl)methyl)-2-oxo-1,2-dihydropyridin-3-yl)amino)-1,7-dioxohept-5-en-2-yl)carbamate;

2-hydroxyethyl (S,E)-(1-((1-((7-((2,4-difluorobenzyl)oxy)-5-fluoro-1H-indol-2-yl)methyl)-2-oxo-1,2-dihydropyridin-3-yl)amino)-1,7-dioxo-7-(pyrrolidin-1-yl)hept-5-en-2-yl)carbamate;

(S,E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate;

tert-butyl (S,E)-7-((2,4-difluorobenzyl)oxy)-2-((3-(7-(dimethylamino)-2-(((2-methoxyethyl)(methyl)carbamoyl)oxy)-7-oxohept-5-enamido)-2-oxopyridin-1(2H)-yl)methyl)-5-fluoro-1H-indole-1-carboxylate;

(S,E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl (2-methoxyethyl)(methyl)carbamate;

tert-butyl (S,E)-7-((2,4-difluorobenzyl)oxy)-2-((3-(7-(dimethylamino)-7-oxo-2-((pyrrolidine-1-carbonyl)oxy)hept-5-enamido)-2-oxopyridin-1(2H)-yl)methyl)-5-fluoro-1H-indole-1-carboxylate;

(S,E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl pyrrolidine-1-carboxylate;

2-methoxyethyl (S,E)-(1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl)carbamate;

tert-butyl (S,E)-7-((2,4-difluorobenzyl)oxy)-2-((3-(2-((dimethylcarbamoyl)oxy)-7-oxo-7-(pyrrolidin-1-yl)hept-5-enamido)-2-oxopyridin-1(2H)-yl)methyl)-5-fluoro-1H-indole-1-carboxylate;

(S,E)-1-((1-((7-((2,4-difluorobenzyl)oxy)-5-fluoro-1H-indol-2-yl)methyl)-2-oxo-1,2-dihydropyridin-3-yl)amino)-1,7-dioxo-7-(pyrrolidin-1-yl)hept-5-en-2-yl dimethylcarbamate;

(S,E)-7-amino-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl dimethylcarbamate;

methyl (S,E)-(1-((1-((5-fluoro-7-isobutyl-1H-indol-2-yl)methyl)-2-oxo-1,2-dihydropyridin-3-yl)amino)-1,7-dioxo-7-(pyrrolidin-1-yl)hept-5-en-2-yl)carbamate;

tert-butyl (S,E)-5-fluoro-7-isobutyl-2-((3-(2-((methoxycarbonyl)amino)-7-oxo-7-(pyrrolidin-1-yl)hept-5-enamido)-2-oxopyridin-1(2H)-yl)methyl)-1H-indole-1-carboxylate;

methyl (S,E)-(7-(bis(methyl-$d_3$)amino)-1-((1-((7-((2,4-difluorobenzyl)oxy)-5-fluoro-1H-indol-2-yl)methyl)-2-oxo-1,2-dihydropyridin-3-yl)amino)-1,7-dioxohept-5-en-2-yl)carbamate;

tert-butyl (S,E)-2-((3-(7-(bis(methyl-$d_3$)amino)-2-((methoxycarbonyl)amino)-7-oxohept-5-enamido)-2-oxopyridin-1(2H)-yl)methyl)-7-((2,4-difluorobenzyl)oxy)-5-fluoro-1H-indole-1-carboxylate;

tert-butyl (E)-7-((2,4-difluorobenzyl)oxy)-2-((3-(7-(dimethylamino)-2-((dimethylcarbamoyl)oxy)-7-oxohept-5-enamido-3,3-d2)-2-oxopyridin-1(2H)-yl)methyl)-5-fluoro-1H-indole-1-carboxylate;

(E)-1-((1-((7-((2,4-difluorobenzyl)oxy)-5-fluoro-1H-indol-2-yl)methyl)-2-oxo-1,2-dihydropyridin-3-yl)amino)-7-(dimethylamino)-1,7-dioxohept-5-en-2-yl-3,3-$d_2$ dimethylcarbamate;

tert-butyl (E)-2-((3-(7-(dimethylamino)-2-((dimethylcarbamoyl)oxy)-7-oxohept-5-enamido-3,3-d2)-2-oxopyridin-1(2H)-yl)methyl)-5-fluoro-7-isobutyl-1H-indole-1-carboxylate;

(E)-7-(dimethylamino)-1-((1-((5-fluoro-7-isobutyl-1H-indol-2-yl)methyl)-2-oxo-1,2-dihydropyridin-3-yl)amino)-1,7-dioxohept-5-en-2-yl-3,3-$d_2$ dimethylcarbamate;

[(E,1S)-6-(dimethylamino)-1-[[1-[[5-fluoro-7-(3,3,3-trifluoropropyl)-1H-indol-2-yl]methyl]-2-oxo-3-pyridyl]carbamoyl]-6-oxo-hex-4-enyl] N,N-dimethylcarbamate;

tert-butyl (S,E)-5-fluoro-2-((3-(2-((methoxycarbonyl)amino)-7-oxo-7-(pyrrolidin-1-yl)hept-5-enamido)-2-oxopyridin-1(2H)-yl)methyl)-7-(3,3,3-trifluoropropyl)-1H-indole-1-carboxylate;

methyl (S,E)-(1-((1-((5-fluoro-7-(3,3,3-trifluoropropyl)-1H-indol-2-yl)methyl)-2-oxo-1,2-dihydropyridin-3-yl)amino)-1,7-dioxo-7-(pyrrolidin-1-yl)hept-5-en-2-yl)carbamate;

methyl (S,E)-(7-(dimethylamino)-1-((1-((5-fluoro-7-(3,3,3-trifluoropropyl)-1H-indol-2-yl)methyl)-2-oxo-1,2-dihydropyridin-3-yl)amino)-1,7-dioxohept-5-en-2-yl)carbamate;

tert-butyl (S,E)-2-((3-(7-(dimethylamino)-2-((methoxycarbonyl)amino)-7-oxohept-5-enamido)-2-oxopyridin-1(2H)-yl)methyl)-5-fluoro-7-(3,3,3-trifluoropropyl)-1H-indole-1-carboxylate;

(S,E)-7-(dimethylamino)-1-((1-((5-fluoro-7-(trifluoromethyl)-1H-indol-2-yl)methyl)-2-oxo-1,2-dihydropyridin-3-yl)amino)-1,7-dioxohept-5-en-2-yl dimethylcarbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-5-fluoro-7-(trifluoromethyl)-1H-indole-1-carboxylate;

tert-butyl (S,E)-2-((3-(2-((dimethylcarbamoyl)oxy)-7-(methylamino)-7-oxohept-5-enamido)-2-oxopyridin-1(2H)-yl)methyl)-5-fluoro-7-(3,3,3-trifluoropropyl)-1H-indole-1-carboxylate;

(S,E)-1-((1-((5-fluoro-7-(3,3,3-trifluoropropyl)-1H-indol-2-yl)methyl)-2-oxo-1,2-dihydropyridin-3-yl)amino)-7-(methylamino)-1,7-dioxohept-5-en-2-yl dimethylcarbamate;

tert-butyl 2-[[3-[[(E,2S)-7-(dimethylamino)-7-oxo-2-(pyrrolidine-1-carbonyloxy)hept-5-enoyl]amino]-2-oxo-1-pyridyl]methyl]-7-(2,2-dimethylpropyl)-5-fluoro-indole-1-carboxylate;

[(E,1S)-6-(dimethylamino)-1-[[1-[[7-(2,2-dimethylpropyl)-5-fluoro-1H-indol-2-yl]methyl]-2-oxo-3-pyridyl]carbamoyl]-6-oxo-hex-4-enyl] pyrrolidine-1-carboxylate;

2-methoxyethyl (S,E)-(7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl)carbamate;

(S,E)-7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl dimethylcarbamate;

methyl (S,E)-(1-((1-((5-fluoro-7-neopentyl-1H-indol-2-yl)methyl)-2-oxo-1,2-dihydropyridin-3-yl)amino)-1,7-dioxo-7-(pyrrolidin-1-yl)hept-5-en-2-yl)carbamate;

(S,E)-7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl (2-methoxyethyl)(methyl)carbamate;

(S,E)-1-((1-((5-fluoro-7-neopentyl-1H-indol-2-yl)methyl)-2-oxo-1,2-dihydropyridin-3-yl)amino)-1,7-dioxo-7-(pyrrolidin-1-yl)hept-5-en-2-yl pyrrolidine-1-carboxylate;

methyl (S,E)-(7-(dimethylamino)-1-((1-((5-fluoro-7-neopentyl-1H-indol-2-yl)methyl)-2-oxo-1,2-dihydropyridin-3-yl)amino)-1,7-dioxohept-5-en-2-yl)carbamate;

tert-butyl 2-[[3-[[(E,2S)-7-(dimethylamino)-2-(dimethylcarbamoyloxy)-7-oxo-hept-5-enoyl]amino]-2-oxo-pyrazin-1-yl]methyl]-7-(2,2-dimethylpropyl)-5-fluoro-indole-1-carboxylate;

[(E,1S)-6-(dimethylamino)-1-[[4-[[7-(2,2-dimethylpropyl)-5-fluoro-1H-indol-2-yl]methyl]-3-oxo-pyrazin-2-yl]carbamoyl]-6-oxo-hex-4-enyl] N,N-dimethylcarbamate;

tert-butyl (S,E)-2-((5-(7-(dimethylamino)-2-((dimethylcarbamoyl)oxy)-7-oxohept-5-enamido)-6-oxopyrimidin-1(6H)-yl)methyl)-5-fluoro-7-neopentyl-1H-indole-1-carboxylate;

(S,E)-7-(dimethylamino)-1-((1-((5-fluoro-7-neopentyl-1H-indol-2-yl)methyl)-6-oxo-1,6-dihydropyrimidin-5-yl)amino)-1,7-dioxohept-5-en-2-yl dimethylcarbamate;

tert-butyl (S,E)-2-((3-(7-(dimethylamino)-2-((dimethylcarbamoyl)oxy)-7-oxohept-5-enamido)-2-oxopyrazin-1(2H)-yl)methyl)-5-fluoro-7-(3,3,3-trifluoropropyl)-1H-indole-1-carboxylate;

tert-butyl (S,E)-2-((5-(7-(dimethylamino)-2-((dimethylcarbamoyl)oxy)-7-oxohept-5-enamido)-6-oxopyrimidin-1(6H)-yl)methyl)-5-fluoro-7-(3,3,3-trifluoropropyl)-1H-indole-1-carboxylate;

(S,E)-7-(dimethylamino)-1-((1-((5-fluoro-7-(3,3,3-trifluoropropyl)-1H-indol-2-yl)methyl)-6-oxo-1,6-dihydropyrimidin-5-yl)amino)-1,7-dioxohept-5-en-2-yl dimethylcarbamate;

tert-butyl (S,E)-2-((5-(2-((dimethylcarbamoyl)oxy)-7-(methylamino)-7-oxohept-5-enamido)-6-oxopyrimidin-1(6H)-yl)methyl)-5-fluoro-7-(3,3,3-trifluoropropyl)-1H-indole-1-carboxylate;

(S,E)-1-((1-((5-fluoro-7-(3,3,3-trifluoropropyl)-1H-indol-2-yl)methyl)-6-oxo-1,6-dihydropyrimidin-5-yl)amino)-7-(methylamino)-1,7-dioxohept-5-en-2-yl dimethylcarbamate;

[(E,1S)-6-(dimethylamino)-1-[[1-[(5-fluoro-1-isobutyl-indol-2-yl) methyl]-6-oxo-pyrimidin-5-yl]carbamoyl]-6-oxo-hex-4-enyl]N,N-dimethylcarbamate;

(S,E)-1-((1-((1-benzyl-5-fluoro-1H-indol-2-yl)methyl)-2-oxo-1,2-dihydropyridin-3-yl)amino)-7-(dimethylamino)-1,7-dioxohept-5-en-2-yl dimethylcarbamate;

(S,E)-1-((1-((1-(cyclopropylmethyl)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate;

(S,E)-7-(dimethylamino)-1-((1-((5-fluoro-1-methyl-1H-indol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((5-fluoro-1-(4-fluorobenzyl)-1H-indol-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((1-ethyl-5-fluoro-1H-indol-2-yl)methyl)-2-oxo-1,2-dihydropyridin-3-yl)amino)-1,7-dioxohept-5-en-2-yl dimethylcarbamate;

(S,E)-1-((1-((1-(2,4-difluorobenzyl)-5-fluoro-1H-indol-2-yl)methyl)-2-oxo-1,2-dihydropyridin-3-yl)amino)-7-(dimethylamino)-1,7-dioxohept-5-en-2-yl dimethylcarbamate;

methyl 2-[[3-[[(E,2S)-7-(dimethylamino)-2-(dimethylcarbamoyloxy)-7-oxo-hept-5-enoyl]amino]-2-oxo-1-pyridyl]methyl]-5-fluoro-indole-1-carboxylate;

2,4-difluorobenzyl (S,E)-2-((3-(7-(dimethylamino)-2-((dimethylcarbamoyl)oxy)-7-oxohept-5-enamido)-2-oxopyridin-1(2H)-yl)methyl)-5-fluoro-1H-indole-1-carboxylate;

[(E,1S)-6-(dimethylamino)-1-[[4-[(5-fluoro-1-isobutyl-indol-2-yl)methyl]-3-oxo-pyrazin-2-yl]carbamoyl]-6-oxo-hex-4-enyl] N,N-dimethylcarbamate;

(S,E)-7-(dimethylamino)-1-((4-((1-ethyl-5-fluoro-1H-indol-2-yl)methyl)-3-oxo-3,4-dihydropyrazin-2-yl)amino)-1,7-dioxohept-5-en-2-yl dimethylcarbamate;

(S,E)-1-((4-((1-benzyl-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate;

(S,E)-1-((4-((1-(cyclopropylmethyl)-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate;

(S,E)-7-(dimethylamino)-1-((4-((5-fluoro-1-(4-fluorobenzyl)-1H-indol-2-yl)methyl)-3-oxo-3,4-dihydropyrazin-2-yl)amino)-1,7-dioxohept-5-en-2-yl dimethylcarbamate;

(S,E)-7-(dimethylamino)-1-((1-((5-fluoro-1-isobutyl-1H-indol-2-yl)methyl)-6-oxo-1,6-dihydropyrimidin-5-yl)amino)-1,7-dioxohept-5-en-2-yl dimethylcarbamate;

(S,E)-1-((4-((1-(2,4-difluorobenzyl)-5-fluoro-1H-indol-2-yl)methyl)-3-oxo-3,4-dihydropyrazin-2-yl)amino)-7-(dimethylamino)-1,7-dioxohept-5-en-2-yl dimethylcarbamate;

[(E,1S)-6-(dimethylamino)-1-[[1-[(5-fluoro-1-methyl-indol-2-yl)methyl]-2-oxo-3-pyridyl]carbamoyl]-6-oxo-hex-4-enyl]-N—[2-[tert-butoxycarbonyl(methyl)amino]ethyl]-N-methyl-carbamate;

[(E,1S)-6-(dimethylamino)-1-[[1-[(5-fluoro-1-methyl-indol-2-yl)methyl]-2-oxo-3-pyridyl]carbamoyl]-6-oxo-hex-4-enyl]-N—[2-(dimethylamino)ethyl]-N-methyl-carbamate;

(S,E)-tert-butyl 7-((3-(7-amino-2-((methoxycarbonyl)amino)-7-oxohept-5-enamido)-2-oxopyridin-1(2H)-yl)methyl)-1H-indole-1-carboxylate;

(S,E)-methyl (7-(dimethylamino)-1-((1-((7-isobutylbenzo[d]oxazol-2-yl)methyl)-2-oxo-1,2-dihydropyridin-3-yl)amino)-1,7-dioxohept-5-en-2-yl)carbamate;

methyl (S,E)-(7-amino-1-((1-((7-isobutylbenzo[d]oxazol-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((4-isobutylbenzo[d]oxazol-2-yl)methyl)-2-oxo-1,2-dihydropyridin-3-yl)amino)-1,7-dioxohept-5-en-2-yl)carbamate;

methyl (S,E)-(7-amino-1-((1-((4-isobutylbenzo[d]oxazol-2-yl)methyl)-2-oxo-1,2-dihydropyridin-3-yl)amino)-1,7-dioxohept-5-en-2-yl)carbamate;

2-hydroxyethyl (S,E)-(7-(dimethylamino)-1-((1-((7-isobutylbenzo[d]oxazol-2-yl)methyl)-2-oxo-1,2-dihydropyridin-3-yl)amino)-1,7-dioxohept-5-en-2-yl)carbamate;

(S,E)-methyl (7-(dimethylamino)-1-((1-((7-isobutylbenzo[d]thiazol-2-yl)methyl)-2-oxo-1,2-dihydropyridin-3-yl)amino)-1,7-dioxohept-5-en-2-yl)carbamate;

methyl (S,E)-(7-amino-1-((1-((7-isobutylbenzo[d]thiazol-2-yl)methyl)-2-oxo-1,2-dihydropyridin-3-yl)amino)-1,7-dioxohept-5-en-2-yl)carbamate;

2-hydroxyethyl (S,E)-(7-(dimethylamino)-1-((1-((7-isobutylbenzo[d]thiazol-2-yl)methyl)-2-oxo-1,2-dihydropyridin-3-yl)amino)-1,7-dioxohept-5-en-2-yl)carbamate;

(S,E)-tert-butyl (1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate;

(S,E)-N7-(1-((7-((2,4-difluorobenzyl)oxy)benzo[d]thiazol-2-yl)methyl)-2-oxo-1,2-dihydropyridin-3-yl)-N1,N1-dimethyl-6-(oxazole-2-carboxamido)hept-2-enediamide;

(S,E)-N7-(1-((7-((2,4-difluorobenzyl)oxy)benzo[d]thiazol-2-yl)methyl)-2-oxo-1,2-dihydropyridin-3-yl)-6-(4,4-difluorocyclohexane-1-carboxamido)-N1,N1-dimethylhept-2-enediamide;

(S,E)-N7-(1-((7-((2,4-difluorobenzyl)oxy)benzo[d]thiazol-2-yl)methyl)-2-oxo-1,2-dihydropyridin-3-yl)-6-(2-fluorobenzamido)-N1,N1-dimethylhept-2-enediamide;

methyl (S,E)-(7-amino-1-((1-((7-((2,4-difluorobenzyl)oxy)benzo[d]thiazol-2-yl)methyl)-2-oxo-1,2-dihydropyridin-3-yl)amino)-1,7-dioxohept-5-en-2-yl)carbamate;

methyl (S,E)-(1-((1-((7-((2,4-difluorobenzyl)oxy)benzo[d]thiazol-2-yl)methyl)-2-oxo-1,2-dihydropyridin-3-yl)amino)-7-(dimethylamino)-1,7-dioxohept-5-en-2-yl)carbamate;

(S,E)-N7-(1-((7-((2,4-difluorobenzyl)oxy)benzo[d]thiazol-2-yl)methyl)-2-oxo-1,2-dihydropyridin-3-yl)-6-(2-methoxyacetamido)-N1,N1-dimethylhept-2-enediamide;

methyl (S,E)-(7-amino-1-((1-((7-(2,2-difluoroethoxy)benzo[d]thiazol-2-yl)methyl)-2-oxo-1,2-dihydropyridin-3-yl)amino)-1,7-dioxohept-5-en-2-yl)carbamate;

methyl (S,E)-(1-((1-((7-(2,2-difluoroethoxy)benzo[d]thiazol-2-yl)methyl)-2-oxo-1,2-dihydropyridin-3-yl)amino)-7-(dimethylamino)-1,7-dioxohept-5-en-2-yl)carbamate;

methyl (S,E)-(7-amino-1,7-dioxo-1-((2-oxo-1-((7-(1,1,2,2-tetrafluoroethoxy)benzo[d]thiazol-2-yl)methyl)-1,2-dihydropyridin-3-yl)amino)hept-5-en-2-yl)carbamate;

methyl (S,E)-(7-(dimethylamino)-1,7-dioxo-1-((2-oxo-1-((7-(1,1,2,2-tetrafluoroethoxy)benzo[d]thiazol-2-yl)methyl)-1,2-dihydropyridin-3-yl)amino)hept-5-en-2-yl)carbamate;

methyl (S,E)-(7-(dimethylamino)-1,7-dioxo-1-((2-oxo-1-((7-(2,2,2-trifluoroethoxy)benzo[d]thiazol-2-yl)methyl)-1,2-dihydropyridin-3-yl)amino)hept-5-en-2-yl)carbamate;

methyl (S,E)-(7-amino-1,7-dioxo-1-((2-oxo-1-((7-(2,2,2-trifluoroethoxy)benzo[d]thiazol-2-yl)methyl)-1,2-dihydropyridin-3-yl)amino)hept-5-en-2-yl)carbamate;

tert-butyl (S,E)-(7-amino-1-((1-((7-((2,4-difluorobenzyl)oxy)benzo[d]thiazol-2-yl)methyl)-2-oxo-1,2-dihydropyridin-3-yl)amino)-1,7-dioxohept-5-en-2-yl)carbamate;

(S,E)-N7-(1-((7-((2,4-difluorobenzyl)oxy)benzo[d]thiazol-2-yl)methyl)-2-oxo-1,2-dihydropyridin-3-yl)-6-(2-methoxyacetamido)hept-2-enediamide;

(S,E)-N7-(1-((7-((2,4-difluorobenzyl)oxy)benzo[d]thiazol-2-yl)methyl)-2-oxo-1,2-dihydropyridin-3-yl)-6-(2-fluorobenzamido)hept-2-enediamide;

(S,E)-methyl(7-(dimethylamino)-1-((1-((5-fluorobenzo[d]thiazol-2-yl)methyl)-2-oxo-1,2-dihydropyridin-3-yl)amino)-1,7-dioxohept-5-en-2-yl)carbamate;

methyl (S,E)-(7-amino-1-((1-((5-fluorobenzo[d]thiazol-2-yl)methyl)-2-oxo-1,2-dihydropyridin-3-yl)amino)-1,7-dioxohept-5-en-2-yl)carbamate;

methyl (S,E)-(1-((1-((5-fluorobenzo[d]thiazol-2-yl)methyl)-2-oxo-1,2-dihydropyridin-3-yl)amino)-1,7-dioxo-7-(pyrrolidin-1-yl)hept-5-en-2-yl)carbamate;

methyl (S,E)-methyl (1-((1-((7-((2,4-difluorophenoxy)methyl)benzo[d]thiazol-2-yl)methyl)-2-oxo-1,2-dihydropyridin-3-yl)amino)-7-(dimethylamino)-1,7-dioxohept-5-en-2-yl)carbamate;

(S,E)-2-hydroxyethyl (1-((1-(benzo[d]thiazol-2-ylmethyl)-2-oxo-1,2-dihydropyridin-3-yl)amino)-7-(dimethylamino)-1,7-dioxohept-5-en-2-yl)carbamate;

tert-butyl (S,E)-2-((3-(7-(dimethylamino)-2-(((2-hydroxyethoxy)carbonyl)amino)-7-oxohept-5-enamido)-2-oxopyridin-1(2H)-yl)methyl)-1H-indole-1-carboxylate;

2-hydroxyethyl (S,E)-(7-amino-1-((1-(benzo[d]oxazol-2-ylmethyl)-2-oxo-1,2-dihydropyridin-3-yl)amino)-1,7-dioxohept-5-en-2-yl)carbamate;

2-hydroxyethyl (S,E)-(7-amino-1-((1-(benzo[d]thiazol-2-ylmethyl)-2-oxo-1,2-dihydropyridin-3-yl)amino)-1,7-dioxohept-5-en-2-yl)carbamate;

2-hydroxyethyl (S,E)-(1-((1-((1H-indol-2-yl)methyl)-2-oxo-1,2-dihydropyridin-3-yl)amino)-7-amino-1,7-dioxohept-5-en-2-yl)carbamate;

tert-butyl (S,E)-2-((3-(7-amino-2-(((2-hydroxyethoxy)carbonyl)amino)-7-oxohept-5-enamido)-2-oxopyridin-1(2H)-yl)methyl)-1H-indole-1-carboxylate;

(S,E)-methyl (7-amino-1-((1-((7-((2,4-difluorobenzyl)oxy)-5-fluorobenzo[d]thiazol-2-yl)methyl)-2-oxo-1,2-dihydropyridin-3-yl)amino)-1,7-dioxohept-5-en-2-yl)carbamate;

tert-butyl (S,E)-2-((3-(7-(dimethylamino)-2-(((2-hydroxyethoxy)carbonyl)amino)-7-oxohept-5-enamido)-2-oxopyridin-1(2H)-yl)methyl)-1H-indole-1-carboxylate;

methyl (S,E)-(1-((1-((7-((2,4-difluorobenzyl)oxy)-5-fluorobenzo[d]thiazol-2-yl)methyl)-2-oxo-1,2-dihydropyridin-3-yl)amino)-7-(methylamino)-1,7-dioxohept-5-en-2-yl)carbamate;

methyl N-[(E)-1-[[[1-[(5,7-difluoro-4-isobutyl-1H-benzimidazol-2-yl)methyl]-2-oxo-3-pyridyl]amino]methyl]-6-(dimethylamino)-6-oxo-hex-4-enyl]carbamate;

methyl N-[(E,1S)-1-[[1-[[4-(2,4-difluorophenoxy)-5,6-difluoro-1H-benzimidazol-2-yl]methyl]-2-oxo-3-pyridyl]carbamoyl]-6-(dimethylamino)-6-oxo-hex-4-enyl]carbamate;

methyl (S,E)-(1-((1-((5,6-difluoro-7-isopropoxy-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((7-(benzyloxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((7-((2,4-difluorobenzyl)oxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((5,6-difluoro-7-phenoxy-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-1-((1-((5,6-difluoro-7-isopropoxy-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-1-((1-((4-(2,4-difluorophenoxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

(S,E)-1-((1-((4-((2,4-difluorobenzyl)oxy)-5,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

tert-butyl 4-(2,4-difluorophenoxy)-2-[[3-[[(E,2S)-7-(dimethylamino)-2-(methoxycarbonylamino)-7-oxo-hept-5-enoyl]amino]-2-oxo-1-pyridyl]methyl]-5,6-difluoro-benzimidazole-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-isopropoxy-1H-benzo[d]imidazole-1-carboxylate;

tert-butyl (S,E)-4-(benzyloxy)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate;

tert-butyl (S,E)-4-((2,4-difluorobenzyl)oxy)-2-((3-(7-(dimethylamino)-2-((methoxycarbonyl)amino)-7-oxohept-5-enamido)-2-oxopyridin-1(2H)-yl)methyl)-5,6-difluoro-1H-benzo[d]imidazole-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-5,6-difluoro-4-phenoxy-1H-benzo[d]imidazole-1-carboxylate;

tert-butyl (S,E)-4-((2,4-difluorobenzyl)oxy)-2-((3-(7-(dimethylamino)-2-((dimethylcarbamoyl)oxy)-7-oxohept-5-enamido)-2-oxopyridin-1(2H)-yl)methyl)-5,6-difluoro-1H-benzo[d]imidazole-1-carboxylate;

tert-butyl 2-[[3-[[(E,2S)-7-(dimethylamino)-2-(methoxycarbonylamino)-7-oxo-hept-5-enoyl]amino]-2-oxo-1-pyridyl]methyl]-4-(2,2-dimethylpropyl)-5,6-difluoro-benzimidazole-1-carboxylate;

methyl N-[(E,1S)-6-(dimethylamino)-1-[[1-[[4-(2,2-dimethylpropyl)-5,6-difluoro-1H-benzimidazol-2-yl]methyl]-2-oxo-3-pyridyl]carbamoyl]-6-oxo-hex-4-enyl]carbamate;

tert-butyl (S,E)-2-((3-(7-(dimethylamino)-2-((dimethylcarbamoyl)oxy)-7-oxohept-5-enamido)-2-oxopyridin-1(2H)-yl)methyl)-5,6-difluoro-4-neopentyl-1H-benzo[d]imidazole-1-carboxylate;

(S,E)-1-((1-((5,6-difluoro-4-neopentyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

tert-butyl 2-[[3-[[(E,2S)-7-(dimethylamino)-2-(methoxycarbonylamino)-7-oxo-hept-5-enoyl]amino]-2-oxo-1-pyridyl]methyl]-5,7-difluoro-4-phenoxy-benzimidazole-1-carboxylate;

tert-butyl (S,E)-4-(2,4-difluorophenoxy)-2-((3-(7-(dimethylamino)-2-((methoxycarbonyl)amino)-7-oxohept-5-enamido)-2-oxopyridin-1(2H)-yl)methyl)-5,7-difluoro-1H-benzo[d]imidazole-1-carboxylate;

methyl N-[(E,1S)-1-[[1-[(5,7-difluoro-4-phenoxy-1H-benzimidazol-2-yl)methyl]-2-oxo-3-pyridyl]carbamoyl]-6-(dimethylamino)-6-oxo-hex-4-enyl]carbamate;

tert-butyl (S,E)-4-(benzyloxy)-2-((3-(7-(dimethylamino)-2-((methoxycarbonyl)amino)-7-oxohept-5-enamido)-2-oxopyridin-1(2H)-yl)methyl)-5,7-difluoro-1H-benzo[d]imidazole-1-carboxylate;

tert-butyl (S,E)-2-((3-(7-(dimethylamino)-2-((methoxycarbonyl)amino)-7-oxohept-5-enamido)-2-oxopyridin-1(2H)-yl)methyl)-5,7-difluoro-4-isopropoxy-1H-benzo[d]imidazole-1-carboxylate;

methyl (S,E)-(1-((1-((4-(2,4-difluorophenoxy)-5,7-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((4-(benzyloxy)-5,7-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

methyl (S,E)-(1-((1-((4-((2,4-difluorobenzyl)oxy)-5,7-difluoro-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-1-((1-((7-((2,4-difluorobenzyl)oxy)-4,6-difluoro-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

methyl N-[(E,1S)-6-(dimethylamino)-6-oxo-1-[[2-oxo-1-[(6-phenoxy-9H-purin-8-yl)methyl]-3-pyridyl]carbamoyl]hex-4-enyl]carbamate;

tert-butyl (S,E)-6-(2,4-difluorophenoxy)-8-((3-(7-(dimethylamino)-2-((methoxycarbonyl)amino)-7-oxohept-5-enamido)-2-oxopyridin-1(2H)-yl)methyl)-9H-purine-9-carboxylate;

methyl (S,E)-(1-((1-((6-(2,4-difluorophenoxy)-9H-purin-8-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((6-isopropoxy-9H-purin-8-yl)methyl)-2-oxo-1,2-dihydropyridin-3-yl)amino)-1,7-dioxohept-5-en-2-yl)carbamate;

methyl (S,E)-(7-(dimethylamino)-1-((1-((6-isobutoxy-9H-purin-8-yl)methyl)-2-oxo-1,2-dihydropyridin-3-yl)amino)-1,7-dioxohept-5-en-2-yl)carbamate;

methyl N-[(E,1S)-1-[[1-[(6-benzyloxy-9H-purin-8-yl)methyl]-2-oxo-3-pyridyl]carbamoyl]-6-(dimethylamino)-6-oxo-hex-4-enyl]carbamate;

methyl (S,E)-(1-((1-((6-((2,4-difluorobenzyl)oxy)-9H-purin-8-yl)methyl)-2-oxo-1,2-dihydropyridin-3-yl)amino)-7-(dimethylamino)-1,7-dioxohept-5-en-2-yl)carbamate;

(S,E)-1-((1-((6-((2,4-difluorobenzyl)oxy)-9H-purin-8-yl)methyl)-2-oxo-1,2-dihydropyridin-3-yl)amino)-7-(dimethylamino)-1,7-dioxohept-5-en-2-yl dimethylcarbamate;

methyl N-[(E,1S)-1-[[1-[(6-benzyl-9H-purin-8-yl)methyl]-2-oxo-3-pyridyl]carbamoyl]-6-(dimethylamino)-6-oxo-hex-4-enyl]carbamate;

methyl (S,E)-(7-(dimethylamino)-1,7-dioxo-1-((2-oxo-1-((6-(3,3,3-trifluoropropyl)-9H-purin-8-yl)methyl)-1,2-dihydropyridin-3-yl)amino)hept-5-en-2-yl)carbamate;

methyl (S,E)-(1-((1-((6-(cyclopropylmethyl)-9H-purin-8-yl)methyl)-2-oxo-1,2-dihydropyridin-3-yl)amino)-7-(dimethylamino)-1,7-dioxohept-5-en-2-yl)carbamate;

methyl ((2S,E)-7-(dimethylamino)-1,7-dioxo-1-((2-oxo-1-((9-(tetrahydro-2H-pyran-2-yl)-6-(3,3,3-trifluoropropyl)-9H-purin-8-yl)methyl)-1,2-dihydropyridin-3-yl)amino)hept-5-en-2-yl)carbamate;

(2S,E)-7-(dimethylamino)-1,7-dioxo-1-((2-oxo-1-((9-(tetrahydro-2H-pyran-2-yl)-6-(3,3,3-trifluoropropyl)-9H-purin-8-yl)methyl)-1,2-dihydropyridin-3-yl)amino)hept-5-en-2-yl dimethylcarbamate;

(S,E)-7-(dimethylamino)-1,7-dioxo-1-((2-oxo-1-((6-(3,3,3-trifluoropropyl)-9H-purin-8-yl)methyl)-1,2-dihydropyridin-3-yl)amino)hept-5-en-2-yl dimethylcarbamate;

methyl N-[(E,1S)-6-(dimethylamino)-1-[[1-[[6-(2,2-dimethylpropyl)-9H-purin-8-yl]methyl]-2-oxo-3-pyridyl]carbamoyl]-6-oxo-hex-4-enyl]carbamate;

(S,E)-7-(dimethylamino)-1-((1-((6-neopentyl-9H-purin-8-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-isopentyl-9H-purin-8-yl)methyl)-2-oxo-1,2-dihydropyridin-3-yl)amino)-1,7-dioxohept-5-en-2-yl)carbamate;

methyl (S,E)-(1-((1-((6-(2-cyclohexylethyl)-7H-purin-8-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((6-(3,3-dimethylbutyl)-9H-purin-8-yl)methyl)-2-oxo-1,2-dihydropyridin-3-yl)amino)-1,7-dioxohept-5-en-2-yl)carbamate;

(S,E)-7-(dimethylamino)-1-((1-((6-(3,3-dimethylbutyl)-9H-purin-8-yl)methyl)-2-oxo-1,2-dihydropyridin-3-yl)amino)-1,7-dioxohept-5-en-2-yl dimethylcarbamate;

(2S,E)-7-(dimethylamino)-1-((1-((6-(3,3-dimethylbutyl)-9-(tetrahydro-2H-pyran-2-yl)-9H-purin-8-yl)methyl)-2-oxo-1,2-dihydropyridin-3-yl)amino)-1,7-dioxohept-5-en-2-yl dimethylcarbamate;

methyl ((2S,E)-7-(dimethylamino)-1-((1-((6-(3,3-dimethylbutyl)-9-(tetrahydro-2H-pyran-2-yl)-9H-purin-8-yl)methyl)-2-oxo-1,2-dihydropyridin-3-yl)amino)-1,7-dioxohept-5-en-2-yl)carbamate;

(2S,E)-7-(dimethylamino)-1-((1-((6-isopentyl-9-(tetrahydro-2H-pyran-2-yl)-9H-purin-8-yl)methyl)-2-oxo-1,2-dihydropyridin-3-yl)amino)-1,7-dioxohept-5-en-2-yl dimethylcarbamate;

(S,E)-7-(dimethylamino)-1-((1-((6-isopentyl-9H-purin-8-yl)methyl)-2-oxo-1,2-dihydropyridin-3-yl)amino)-1,7-dioxohept-5-en-2-yl dimethylcarbamate;

methyl N-[(E,1S)-6-(dimethylamino)-1-[[1-[(4-isobutyl-5H-pyrrolo[3,2-d]pyrimidin-6-yl)methyl]-2-oxo-3-pyridyl]carbamoyl]-6-oxo-hex-4-enyl]carbamate;

(S,E)-7-(dimethylamino)-1-((1-((4-isobutyl-5H-pyrrolo[3,2-d]pyrimidin-6-yl)methyl)-2-oxo-1,2-dihydropyridin-3-yl)amino)-1,7-dioxohept-5-en-2-yl dimethylcarbamate;

methyl (S,E)-(7-(dimethylamino)-1,7-dioxo-1-((2-oxo-1-((4-(3,3,3-trifluoropropyl)-5H-pyrrolo[3,2-d]pyrimidin-6-yl)methyl)-1,2-dihydropyridin-3-yl)amino)hept-5-en-2-yl)carbamate;

(S,E)-7-(dimethylamino)-1,7-dioxo-1-((2-oxo-1-((4-(3,3,3-trifluoropropyl)-5H-pyrrolo[3,2-d]pyrimidin-6-yl)methyl)-1,2-dihydropyridin-3-yl)amino)hept-5-en-2-yl dimethylcarbamate;

methyl ((2S,E)-7-(dimethylamino)-1-((1-((2-methyl-6-neopentyl-9-(tetrahydro-2H-pyran-2-yl)-9H-purin-8-yl)methyl)-2-oxo-1,2-dihydropyridin-3-yl)amino)-1,7-dioxohept-5-en-2-yl)carbamate;

methyl (S,E)-(7-(dimethylamino)-1-((1-((2-methyl-6-neopentyl-9H-purin-8-yl)methyl)-2-oxo-1,2-dihydropyridin-3-yl)amino)-1,7-dioxohept-5-en-2-yl)carbamate;

(S,E)-7-(dimethylamino)-1-((1-((2-methyl-6-neopentyl-9H-purin-8-yl)methyl)-2-oxo-1,2-dihydropyridin-3-yl)amino)-1,7-dioxohept-5-en-2-yl dimethylcarbamate;

methyl (S,E)-(1-((1-((6-(cyclohexylmethyl)-9H-purin-8-yl)methyl)-2-oxo-1,2-dihydropyridin-3-yl)amino)-7-(dimethylamino)-1,7-dioxohept-5-en-2-yl)carbamate;

(S,E)-1-((1-((6-(cyclohexylmethyl)-9H-purin-8-yl)methyl)-2-oxo-1,2-dihydropyridin-3-yl)amino)-7-(dimethylamino)-1,7-dioxohept-5-en-2-yl dimethylcarbamate;

methyl (S,E)-(7-(dimethylamino)-1-((1-((4-isobutyl-2-methyl-5H-pyrrolo[3,2-d]pyrimidin-6-yl)methyl)-2-oxo-1,2-dihydropyridin-3-yl)amino)-1,7-dioxohept-5-en-2-yl)carbamate;

(S,E)-7-(dimethylamino)-1-((1-((4-isobutyl-2-methyl-5H-pyrrolo[3,2-d]pyrimidin-6-yl)methyl)-2-oxo-1,2-dihydropyridin-3-yl)amino)-1,7-dioxohept-5-en-2-yl dimethylcarbamate;

(S,E)-7-(dimethylamino)-1,7-dioxo-1-((2-oxo-1-((6-(3,3,3-trifluoro-2-(trifluoromethyl)propyl)-9H-purin-8-yl)methyl)-1,2-dihydropyridin-3-yl)amino)hept-5-en-2-yl dimethylcarbamate;

2-methoxyethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate;

(S,E)-7-(dimethylamino)-1-((1-((6-fluoro-7-isobutyl-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-isobutyl-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-6-(3,3-dimethylureido)-N7-(1-((6-fluoro-7-isobutyl-1H-pyrrolo[3,2-b]pyridin-2-yl)methyl)-2-oxo-1,2-dihydropyridin-3-yl)-N1,N1-dimethylhept-2-enediamide;

methyl N-[(E,1S)-6-(dimethylamino)-1-[[1-[(6-fluoro-7-isobutyl-1H-pyrrolo[3,2-b]pyridin-2-yl)methyl]-6-methyl-2-oxo-3-pyridyl]carbamoyl]-6-oxo-hex-4-enyl]carbamate;

(S,E)-7-(dimethylamino)-1-((1-((6-fluoro-7-isobutyl-1H-pyrrolo[3,2-b]pyridin-2-yl)methyl)-6-methyl-2-oxo-1,2-dihydropyridin-3-yl)amino)-1,7-dioxohept-5-en-2-yl dimethylcarbamate;

methyl (S,E)-(1-((6-chloro-1-((6-fluoro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate;

(S,E)-1-((6-chloro-1-((6-fluoro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((1-((7-(cyclobutylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate;

(S,E)-1-((1-((7-(cyclobutylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(7-(dimethylamino)-1-((1-((6-fluoro-7-isopropoxy-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((6-fluoro-7-isopropoxy-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-isobutoxy-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((6-fluoro-7-isobutoxy-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(1-((1-((7-(benzyloxy)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate;

(S,E)-1-((1-((7-(benzyloxy)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate;

methyl N-[(E,1S)-1-[[1-[(6-chloro-7-isobutyl-1H-pyrrolo[3,2-b]pyridin-2-yl)methyl]-2-oxo-3-pyridyl]carbamoyl]-6-(dimethylamino)-6-oxo-hex-4-enyl]carbamate;

(S,E)-1-((1-((6-chloro-7-isobutyl-1H-pyrrolo[3,2-b]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((1-((7-(cyclopropylmethyl)-6-fluoro-1H-pyrrolo[3,2-b]pyridin-2-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((7-isobutyl-6-(trifluoromethyl)-1H-pyrrolo[3,2-b]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-isobutyl-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((7-isobutyl-1H-pyrrolo[3,2-b]pyridin-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((7-isobutyl-1H-pyrrolo[3,2-c]pyridin-2-yl)methyl)-2-oxo-1,2-dihydropyridin-3-yl)amino)-1,7-dioxohept-5-en-2-yl dimethylcarbamate;

methyl (E)-(7-(dimethylamino)-1-((1-((7-isobutyl-1H-pyrrolo[3,2-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-(2-methylprop-1-en-1-yl)-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((7-(2-methylprop-1-en-1-yl)-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((7-(2-methylprop-1-en-1-yl)-6-(trifluoromethyl)-1H-pyrrolo[3,2-b]pyridin-2-yl)methyl)-2-oxo-1,2-dihydropyridin-3-yl)amino)-1,7-dioxohept-5-en-2-yl)carbamate;

methyl N-[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl]carbamate;

(S,E)-7-(dimethylamino)-1-((1-((6-fluoro-7-isobutyl-3-methyl-1H-pyrrolo[3,2-b]pyridin-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((6-fluoro-7-isobutyl-3-methyl-1H-pyrrolo[3,2-b]pyridin-2-yl)methyl)-6-methyl-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-isobutyl-3-methyl-1H-pyrrolo[3,2-b]pyridin-2-yl)methyl)-6-methyl-2-oxo-1,2-dihydropyridin-3-yl)amino)-1,7-dioxohept-5-en-2-yl)carbamate;

methyl (S,E)-(7-(dimethylamino)-1-((1-((6-fluoro-7-isobutyl-5-methyl-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((6-fluoro-7-isobutyl-5-methyl-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((4-fluoro-7-isobutyl-1H-pyrrolo[2,3-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((4-fluoro-7-isobutyl-1H-pyrrolo[2,3-c]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((4-fluoro-7-isobutyl-1H-pyrrolo[2,3-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(7-(dimethylamino)-1-((1-((4-fluoro-7-isobutyl-1H-pyrrolo[2,3-c]pyridin-2-yl)methyl)-6-methyl-2-oxo-1,2-dihydropyridin-3-yl)amino)-1,7-dioxohept-5-en-2-yl)carbamate;

(S,E)-1-((6-chloro-1-((4-fluoro-7-isobutyl-1H-pyrrolo[2,3-c]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((6-chloro-1-((4-fluoro-7-isobutyl-1H-pyrrolo[2,3-c]pyridin-2-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((4-fluoro-7-(2-methylprop-1-en-1-yl)-1H-pyrrolo[2,3-c]pyridin-2-yl)

methyl)-2-oxo-1,2-dihydropyridin-3-yl)amino)-1,7-dioxohept-5-en-2-yl)carbamate;

(S,E)-7-(dimethylamino)-1-((1-((4-fluoro-7-(2-methylprop-1-en-1-yl)-1H-pyrrolo[2,3-c]pyridin-2-yl)methyl)-2-oxo-1,2-dihydropyridin-3-yl)amino)-1,7-dioxohept-5-en-2-yl dimethylcarbamate;

methyl N-[(E,1S)-6-(dimethylamino)-1-[[1-[(7-isobutyl-1H-pyrrolo[2,3-c]pyridin-2-yl)methyl]-2-oxo-3-pyridyl]carbamoyl]-6-oxo-hex-4-enyl]carbamate;

(S,E)-7-(dimethylamino)-1-((1-((7-isobutyl-1H-pyrrolo[2,3-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-(dimethylamino)-2-methyl-9H-purin-8-yl)methyl)-2-oxo-1,2-dihydropyridin-3-yl)amino)-1,7-dioxohept-5-en-2-yl)carbamate;

methyl N-[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl]carbamate;

(S,E)-7-(dimethylamino)-1-((1-((7-isobutyl-1H-benzo[d]imidazol-2-yl)methyl)-6-methyl-2-oxo-1,2-dihydropyridin-3-yl)amino)-1,7-dioxohept-5-en-2-yl dimethylcarbamate;

methyl (S,E)-(1-((6-chloro-1-((4-isobutyl-1H-benzo[d]imidazol-2-yl)methyl)-2-oxo-1,2-dihydropyridin-3-yl)amino)-7-(dimethylamino)-1,7-dioxohept-5-en-2-yl)carbamate;

(S,E)-1-((6-chloro-1-((7-isobutyl-1H-benzo[d]imidazol-2-yl)methyl)-2-oxo-1,2-dihydropyridin-3-yl)amino)-7-(dimethylamino)-1,7-dioxohept-5-en-2-yl dimethylcarbamate;

methyl-N-[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl]carbamate;

(S,E)-7-(dimethylamino)-1-((1-((7-fluoro-4-isobutyl-1H-imidazo[4,5-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(1-((1-((7-fluoro-4-isobutyl-3H-imidazo[4,5-c]pyridin-2-yl)methyl)-6-methyl-2-oxo-1,2-dihydropyridin-3-yl)amino)-6-(methylsulfonyl)-1-oxohex-5-en-2-yl)carbamate;

methyl N-[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]carbamate;

[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl] N,N-dimethylcarbamate;

(S,E)-7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl)carbamate;

(S,E)-7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-1-((1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((1-((4-(cyclopropylmethyl)-7-fluoro-3H-imidazo[4,5-c]pyridin-2-yl)methyl)-6-methyl-2-oxo-1,2-dihydropyridin-3-yl)amino)-7-(dimethylamino)-1,7-dioxohept-5-en-2-yl)carbamate;

(S,E)-1-((1-((4-(cyclopropylmethyl)-7-fluoro-3H-imidazo[4,5-c]pyridin-2-yl)methyl)-6-methyl-2-oxo-1,2-dihydropyridin-3-yl)amino)-7-(dimethylamino)-1,7-dioxohept-5-en-2-yl dimethylcarbamate;

methyl (S,E)-(1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

methyl N-[(E,1S)-6-(dimethylamino)-1-[[1-[(7-fluoro-4-isobutyl-3H-imidazo[4,5-c]pyridin-2-yl)methyl]-5-methyl-2-oxo-3-pyridyl]carbamoyl]-6-oxo-hex-4-enyl]carbamate;

(S,E)-7-(dimethylamino)-1-((1-((7-fluoro-4-isobutyl-3H-imidazo[4,5-c]pyridin-2-yl)methyl)-5-methyl-2-oxo-1,2-dihydropyridin-3-yl)amino)-1,7-dioxohept-5-en-2-yl dimethylcarbamate;

methyl (S,E)-(1-((5-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-1-((5-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(7-(dimethylamino)-1-((5-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate;

(S,E)-7-(dimethylamino)-1-((5-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-6-isobutyl-2-oxo-1,2-dihydropyridin-3-yl)amino)-1,7-dioxohept-5-en-2-yl)carbamate;

(S,E)-7-(dimethylamino)-1-((1-((7-fluoro-4-isobutyl-3H-imidazo[4,5-c]pyridin-2-yl)methyl)-6-isobutyl-2-oxo-1,2-dihydropyridin-3-yl)amino)-1,7-dioxohept-5-en-2-yl dimethylcarbamate;

(S,E)-7-(dimethylamino)-1-((1-((7-fluoro-4-isobutyl-3H-imidazo[4,5-c]pyridin-2-yl)methyl)-6-isopropyl-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-6-isopropyl-2-oxo-1,2-dihydropyridin-3-yl)amino)-1,7-dioxohept-5-en-2-yl)carbamate;

(S,E)-7-(dimethylamino)-1-((6-ethyl-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((6-ethyl-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-fluoro-4-isobutyl-3H-imidazo[4,5-c]pyridin-2-yl)methyl)-2-oxo-6-propyl-1,2-dihydropyridin-3-yl)amino)-1,7-dioxohept-5-en-2-yl)carbamate;

(S,E)-7-(dimethylamino)-1-((1-((7-fluoro-4-isobutyl-3H-imidazo[4,5-c]pyridin-2-yl)methyl)-2-oxo-6-propyl-1,2-dihydropyridin-3-yl)amino)-1,7-dioxohept-5-en-2-yl dimethylcarbamate;

(S,E)-7-(dimethylamino)-1-((1-((7-fluoro-4-isobutyl-3H-imidazo[4,5-c]pyridin-2-yl)methyl)-5,6-dimethyl-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-5,6-dimethyl-2-oxo-1,2-dihydropyridin-3-yl)amino)-1,7-dioxohept-5-en-2-yl)carbamate;

methyl (S,E)-(7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-1,7-dioxohept-5-en-2-yl)carbamate;

(S,E)-7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-6-(methoxymethyl)-2-oxo-1,2-dihydropyridin-3-yl)amino)-1,7-dioxohept-5-en-2-yl)carbamate;

(S,E)-7-(dimethylamino)-1-((1-((7-fluoro-4-isobutyl-3H-imidazo[4,5-c]pyridin-2-yl)methyl)-6-(hydroxymethyl)-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-6-(hydroxymethyl)-2-oxo-1,2-dihydropyridin-3-yl)amino)-1,7-dioxohept-5-en-2-yl)carbamate;

methyl (S,E)-(7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate;

(S,E)-7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((5-fluoro-1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl)carbamate;

(S,E)-7-(dimethylamino)-1-((5-fluoro-1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-isobutyl-3H-imidazo[4,5-b]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((6-fluoro-7-isobutyl-1H-imidazo[4,5-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((1-((6-fluoro-7-isobutyl-3H-imidazo[4,5-b]pyridin-2-yl)methyl)-6-methyl-2-oxo-1,2-dihydropyridin-3-yl)amino)-1,7-dioxohept-5-en-2-yl)carbamate;

(S,E)-7-(dimethylamino)-1-((1-((6-fluoro-7-isobutyl-1H-imidazo[4,5-b]pyridin-2-yl)methyl)-6-methyl-2-oxo-1,2-dihydropyridin-3-yl)amino)-1,7-dioxohept-5-en-2-yl dimethylcarbamate;

(S,E)-1-((6-chloro-1-((6-fluoro-7-isobutyl-3H-imidazo[4,5-b]pyridin-2-yl)methyl)-2-oxo-1,2-dihydropyridin-3-yl)amino)-7-(dimethylamino)-1,7-dioxohept-5-en-2-yl dimethylcarbamate;

methyl (S,E)-(1-((6-chloro-1-((6-fluoro-7-isobutyl-1H-imidazo[4,5-b]pyridin-2-yl)methyl)-2-oxo-1,2-dihydropyridin-3-yl)amino)-7-(dimethylamino)-1,7-dioxohept-5-en-2-yl)carbamate;

[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]N—[2-(dimethylamino)ethyl]-N-methyl-carbamate;

2-(dimethylamino)ethyl N-[(E,1S)-6-(dimethylamino)-1-[[1-[(6-fluoro-7-isobutyl-1H-pyrrolo[3,2-b]pyridin-2-yl)methyl]-2-oxo-3-pyridyl]carbamoyl]-6-oxo-hex-4-enyl]carbamate;

methyl (S,E)-(1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-1-((6-chloro-1-((7-fluoro-4-(3,3,3-trifluoropropyl)-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

(S,E)-7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl dimethylcarbamate;

(S,E)-7-(dimethylamino)-1-((1-((6-fluoro-7-isobutyl-3-methyl-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(7-(dimethylamino)-1-((6-fluoro-1-((7-fluoro-4-isobutyl-3H-imidazo[4,5-c]pyridin-2-yl)methyl)-2-oxo-1,2-dihydropyridin-3-yl)amino)-1,7-dioxohept-5-en-2-yl)carbamate;

(S,E)-7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-(3,3,3-trifluoropropyl)-3H-imidazo[4,5-c]pyridin-2-yl)methyl)-2-oxo-1,2-dihydropyridin-3-yl)amino)-1,7-dioxohept-5-en-2-yl)carbamate;

methyl (S,E)-(7-(dimethylamino)-1-((1-((7-fluoro-4-(3,3,3-trifluoropropyl)-3H-imidazo[4,5-c]pyridin-2-yl)methyl)-6-methyl-2-oxo-1,2-dihydropyridin-3-yl)amino)-1,7-dioxohept-5-en-2-yl)carbamate;

methyl (S,E)-(1-((6-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

methyl (S,E)-(7-(dimethylamino)-1-((1-((7-fluoro-4-isobutyl-3H-imidazo[4,5-c]pyridin-2-yl)methyl)-2-oxo-6-(trifluoromethyl)-1,2-dihydropyridin-3-yl)amino)-1,7-dioxohept-5-en-2-yl)carbamate;

(S,E)-1-((6-chloro-1-((7-fluoro-4-isobutyl-3H-imidazo[4,5-c]pyridin-2-yl)methyl)-2-oxo-1,2-dihydropyridin-3-yl)amino)-7-(dimethylamino)-1,7-dioxohept-5-en-2-yl dimethylcarbamate;

(S,E)-7-(dimethylamino)-1-((1-((6-fluoro-7-(3,3,3-trifluoropropyl)-1H-pyrrolo[3,2-b]pyridin-2-yl)methyl)-2-oxo-1,2-dihydropyridin-3-yl)amino)-1,7-dioxohept-5-en-2-yl dimethylcarbamate;

methyl (S,E)-(1-((6-chloro-1-((4-(cyclopropylmethyl)-7-fluoro-3H-imidazo[4,5-c]pyridin-2-yl)methyl)-2-oxo-1,2-dihydropyridin-3-yl)amino)-7-(dimethylamino)-1,7-dioxohept-5-en-2-yl)carbamate;

(S,E)-7-(dimethylamino)-1-((1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl dimethylcarbamate;

methyl (S,E)-(7-(dimethylamino)-1-((1-((7-fluoro-4-isobutyl-3H-imidazo[4,5-c]pyridin-2-yl)methyl)-6-methyl-2-oxo-1,2-dihydropyridin-3-yl)amino)-1,7-dioxohept-5-en-2-yl)carbamate;

[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl] N,N-dimethylcarbamate;

[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl] N,N-dimethylcarbamate; or

[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl] N,N-dimethylcarbamate;

or a pharmaceutically acceptable salt thereof.

17. The compound or pharmaceutically acceptable salt thereof according to claim 1 wherein the compound is:

methyl N-[(E,1S)-6-(dimethylamino)-1-[[1-[(4-isobutyl-1H-benzimidazol-2-yl)methyl]-2-oxo-3-pyridyl]carbamoyl]-6-oxo-hex-4-enyl]carbamate;

methyl N-[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl]carbamate;

[(E,1S)-6-(dimethylamino)-1-[[1-[(4-isobutyl-1H-benzimidazol-2-yl)methyl]-6-methyl-2-oxo-3-pyridyl]carbamoyl]-6-oxo-hex-4-enyl] N,N-dimethylcarbamate;

methyl N-[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl]carbamate;

[(E,1S)-1-[[6-chloro-1-[(7-fluoro-4-isobutyl-1H-imidazo[4,5-c]pyridin-2-yl)methyl]-2-oxo-3-pyridyl]carbamoyl]-6-(dimethylamino)-6-oxo-hex-4-enyl] N,N-dimethylcarbamate;

methyl-N-[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl]carbamate;

[(E,1S)-6-(dimethylamino)-1-[[1-[(7-fluoro-4-isobutyl-1H-imidazo[4,5-c]pyridin-2-yl)methyl]-6-methyl-2-oxo-3-pyridyl]carbamoyl]-6-oxo-hex-4-enyl] N,N-dimethylcarbamate;

methyl N-[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl]carbamate; or

[(E,1S)-6-(dimethylamino)-1-[[1-[(6-fluoro-7-isobutyl-3-methyl-1H-pyrrolo[3,2-b]pyridin-2-yl)methyl]-2-oxo-3-pyridyl]carbamoyl]-6-oxo-hex-4-enyl] N,N-dimethylcarbamate;

or a pharmaceutically acceptable salt thereof.

18. The compound or pharmaceutically acceptable salt thereof according to claim 1 wherein the compound is:

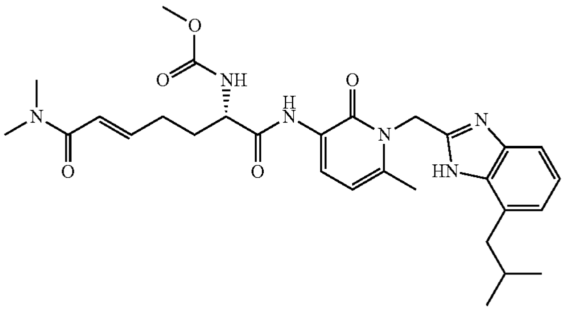

;

or a pharmaceutically acceptable salt thereof.

19. The compound or pharmaceutically acceptable salt thereof according to claim 1 wherein the compound is:

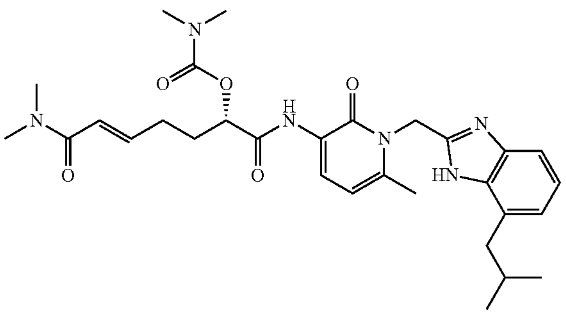

;

or a pharmaceutically acceptable salt thereof.

20. The compound or pharmaceutically acceptable salt thereof according to claim 1 wherein the compound is:

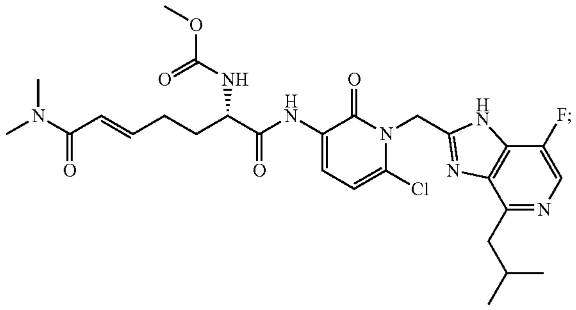 [SMILES: COC(=O)N[C@@H](CC/C=C/C(=O)N(C)C)C(=O)Nc1ccc(Cl)n(Cc2nc3c(CC(C)C)ncc(F)c3[nH]2)c1=O]

;

or a pharmaceutically acceptable salt thereof.

21. The compound or pharmaceutically acceptable salt thereof according to claim 1 wherein the compound is:

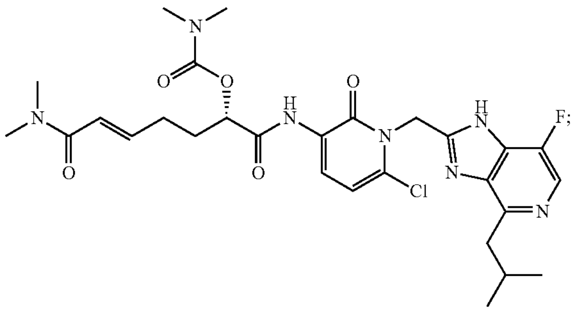 [SMILES: CC(C)Cc1ncc(F)c2[nH]c(Cn3c(Cl)ccc(NC(=O)[C@H](CC/C=C/C(=O)N(C)C)OC(=O)N(C)C)c3=O)nc12]

or a pharmaceutically acceptable salt thereof.

22. The compound or pharmaceutically acceptable salt thereof according to claim 1 wherein the compound is:

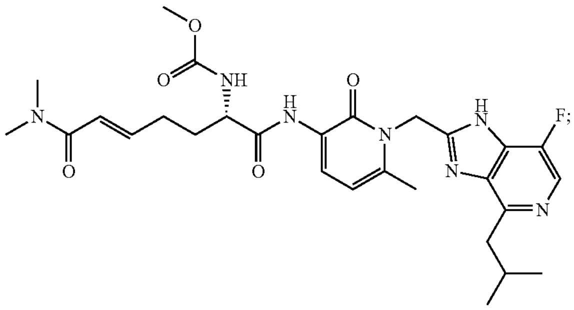 [SMILES: COC(=O)N[C@@H](CC/C=C/C(=O)N(C)C)C(=O)Nc1ccc(C)n(Cc2nc3c(CC(C)C)ncc(F)c3[nH]2)c1=O]

or a pharmaceutically acceptable salt thereof.

23. The compound or pharmaceutically acceptable salt thereof according to claim 1 wherein the compound is:

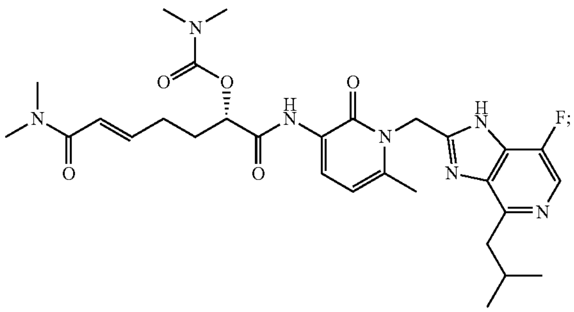 [SMILES: Cc1ccc(NC(=O)[C@H](CC/C=C/C(=O)N(C)C)OC(=O)N(C)C)c(=O)n1Cc1nc2c(CC(C)C)ncc(F)c2[nH]1]

or a pharmaceutically acceptable salt thereof.

24. The compound or pharmaceutically acceptable salt thereof according to claim 1 wherein the compound is:

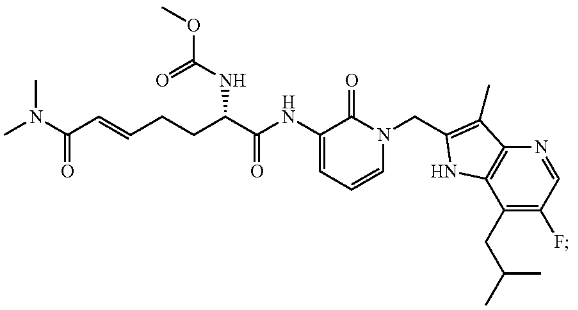 [SMILES: COC(=O)N[C@@H](CC/C=C/C(=O)N(C)C)C(=O)Nc1cccn(Cc2[nH]c3c(CC(C)C)c(F)cnc3c2C)c1=O]

or a pharmaceutically acceptable salt thereof.

25. The compound or pharmaceutically acceptable salt thereof according to claim 1 wherein the compound is:

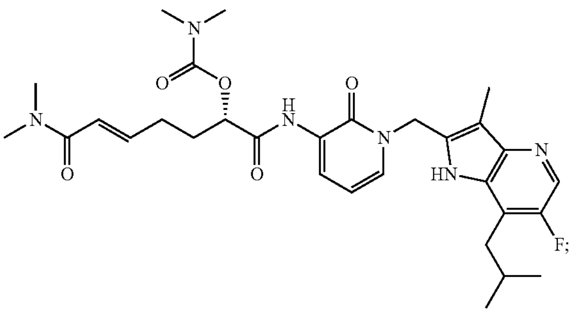 [SMILES: Cc1c(Cn2cccc(NC(=O)[C@H](CC/C=C/C(=O)N(C)C)OC(=O)N(C)C)c2=O)[nH]c2c(CC(C)C)c(F)cnc12]

or a pharmaceutically acceptable salt thereof.

26. A pharmaceutical composition comprising the compound or pharmaceutically acceptable salt thereof according to claim 1 and a pharmaceutically acceptable excipient.

27. A method of treating a patient having a transglutaminase 2 mediated disease or disorder comprising administering to the patient a therapeutically effective amount of the compound or pharmaceutically acceptable salt thereof according to claim 1, wherein the transglutaminase 2 mediated disease or disorder is selected from the group consisting of celiac disease, kidney fibrosis, idiopathic pulmonary fibrosis, and liver fibrosis.

* * * * *